(12) United States Patent
Moras et al.

(10) Patent No.: US 7,279,325 B2
(45) Date of Patent: Oct. 9, 2007

(54) METHOD FOR IDENTIFYING ANTAGONIST COMPOUNDS OF THE ESTROGEN-RELATED RECEPTOR 3 (ERR3) BY USING THE X-RAY STRUCTURAL COORDINATES OF THE LIGAND BINDING DOMAIN

(75) Inventors: Dino Moras, Lampertheim (FR); Jean-Paul Renaud, Ostwald (FR); Holger Greschik, Stasbourg (FR); Jean-Marie Wurtz, Drusenheim (FR)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 434 days.

(21) Appl. No.: 10/355,218

(22) Filed: Jan. 31, 2003

(65) Prior Publication Data

US 2004/0009558 A1    Jan. 15, 2004

Related U.S. Application Data

(60) Provisional application No. 60/352,551, filed on Jan. 31, 2002.

(51) Int. Cl.
*C12N 15/00* (2006.01)
*C12N 5/00* (2006.01)
*C07K 14/00* (2006.01)

(52) U.S. Cl. ................ 435/320.1; 435/325; 530/350

(58) Field of Classification Search ............. 435/320.1
See application file for complete search history.

(56) References Cited

U.S. PATENT DOCUMENTS 5,579,250 A * 11/1996 Balaji et al. .................. 702/19
5,642,292 A *  6/1997 Itai et al. ..................... 702/27

FOREIGN PATENT DOCUMENTS

WO    WO98/56812    12/1998
WO    WO 00/26365    5/2000

OTHER PUBLICATIONS

Coward, P. et al. P. Natl. Acad. Sci. USA., vol. 98., pp. 8880-8884, 2001.*
Rollerova et al. Intracellular Estrogen Receptors, Their Characterization and Function (Review). Endocrine Regulations. 2000. vol. 34, pp. 203-218.*

Bohm et al. The Computer Program LUDI: A New Method for the de novo Design of Enzyme Inhibitors. Journal of Computer-Aided Molecular Design. 1992. vol. 6, pp. 61-78.*
Goodsell et al. Automated Docking of Flexible Ligands: Applications of AutoDock. Journal of Molecular Recognition. 1996. vol. 9, pp. 1-5.*
Dean, P.M., Recent Advances in Drug Design Methods: Where Will They Lead? BioEssays, 1994. vol. 16, No. 9, pp. 683-687.*
Shiau, Andrew et al.: "The Structural Basis of Estrogen Receptor/Coactivator Recognition and the Antagonism of This Interaction by Tamoxifen",Cell, vol. 95, No. 7, Dec. 23, 1998, pp. 927-937, XP-002248698.
Ashley, C.W. Pike, "A structural biologist's view of the oestrogen receptor", Journal of Steroid Biochemistry and Molecular Biology, vol. 74, No. 5, 2000, pp. 261-268, XP-002248699.
Tanenbaum, David M. et al.: "Crystallographic comparison of the estrogen and progesterone receptor's ligand binding domains", Proceedings of the National Academy of Science, vol. 95, May 1998, pp. 5998-6003, XP-002222196.
Lewis, David F.V. et al.: "Molecular Modelling of the Human Estrogen Receptor and Ligand Interactions Based on Site-directed Mutagenesis and Amino Acid Sequence Homology", Journal of Steroid Biochemistry and Molecular Biology, vol. 52, No. 1, 1995, pp. 55-65, XP-002248700.
Wurtz, Jean-Marie et at.: "Three-Dimensional Models of Estrogen Receptor Ligand Binding Domain Complexes, Based on Related Crystal Structures and Mutational and Structure-Activity Relationship Data", Journal of Medicinal Chemistry, vol. 41, No. 11, May 1998, pp. 1803-1814, XP-002200987.
Gangloff, M. et al.: "Crystal Structure of a Mutant hERα Ligand-binding Domain Reveals Key Structural Features for the Mechanism of Partial Agonism", Journal of Biological Chemistry, vol. 276, No. 18, May 4, 2001, pp. 15059-15065, XP-002248701.
Brzozowski, Andrzej M. et al.: "Molecular basis of agonism and antagonism in the oestrogen receptor", vol. 389, No. 6652, 1997, pp. 753-758, XP-002248702.
Norris, John D. et al.: Peptide Antagonists of the Human Estrogen Receptor, Science, vol. 285, No. 5428, Jul. 30, 1999, pp. 744-746, XP-002248703.
Greschik, Holger et al.: "Structural and Functional Evidence for Ligand-Independent Transcriptional Activation by the Estrogen-Related Receptor 3", Molecular Cell, vol. 9, No. 2, Feb. 2002, pp. 303-313, XP-002248704.

* cited by examiner

*Primary Examiner*—Kathleen Kerr Bragdon
*Assistant Examiner*—Suzanne M. Noakes
(74) *Attorney, Agent, or Firm*—Young & Thompson

(57) ABSTRACT

The present invention relates to the identification of novel biologically active compounds having an agonist or an antagonist effect on the transcriptional-activating activity of the Estrogen-Related Receptor 3 (ERR3).

8 Claims, 11 Drawing Sheets

METHOD FOR IDENTIFYING ANTAGONIST COMPOUNDS OF THE ESTROGEN-RELATED RECEPTOR 3 (ERR3) BY USING THE X-RAY STRUCTURAL COORDINATES OF THE LIGAND BINDING DOMAIN

CROSS REFERENCE TO RELATED APPLICATIONS

This application claims priority and benefit to U.S. Provisional Application No. 60/352,551, filed Jan. 31, 2002, the contents of which are hereby incorporated by reference in its entirety.

FIELD OF THE INVENTION

The present invention relates to the identification of novel biologically-active compounds having an agonist or an antagonist effect on the transcriptional-activating activity of the Estrogen-Related Receptor 3 (ERR3).

For this purpose, the invention discloses a peptide fragment comprising the Ligand Binding Domain (LBD) of the Estrogen-Related Receptor 3 (ERR3) which, when fused to a protein containing a DNA-binding domain, is functionally active and activates the transcription of a suitable reporter DNA construct.

The invention also provides for means for producing the peptide fragment above.

According to the present invention, the peptide fragment above is used, eventually as a fusion protein, in methods for the screening of compounds which are agonists or antagonists for the Estrogen-Related Receptor 3 (ERR3).

This invention is also directed to the LBD of the Estrogen-Related Receptor 3 (ERR3) under the form of a crystallised molecule or a crystallised molecular complex of specified structural coordinates.

According to the invention, the crystallised molecule or molecular complex above is used to design or select compounds which are agonists or antagonists for the Estrogen-Related Receptor 3 (ERR3).

This invention also provides for mutants of the peptide fragment comprising the LBD of the Estrogen-Related Receptor 3 (ERR3), as well as with methods for producing said mutants.

BACKGROUND OF THE INVENTION

The Estrogen-Related Receptor 3 (ERR3), also termed Estrogen-Related Receptor gamma (ERRγ), belong to the family of estrogen-related receptors, for which no natural ligand has yet been identified. Estrogen-related receptors belong themselves to the family of the Nuclear Receptors (NRs).

Orphan members of the nuclear receptor (NR) superfamily were initially identified by their high homology with the steroid or retinoid receptors and hypothesized to be ligand-regulated despite the lack of a known ligand (Willy et al., 1998; Giguere, 1999)). Meanwhile, for some of them, e.g. the peroxisome proliferator-activated receptors (PPARs), the constitutive androstane receptors (CARs), the pregnane X receptor (PXR), and recently the estrogen-related receptors (ERRs), synthetic or natural ligands have been identified (Kliewer et al., 1999; Tzameli et al., 2001; Tremblay et al., 2001; Coward et al., 2001).

To date, the family of estrogen-related receptors (ERRs) include three receptors, namely ERR1, ERR2 and ERR3.

As constitutive androstane receptors (CARs) and retinoid-related orphan receptors (RORs), ERRs constitutively activate transcription in eukaryotic cells (Hong et al., 1999; Xie et al., 1999; Chen et al., 2001).

ERR3 is the first orphan receptor identified because of its constitutive interaction with transcriptional activators. ERR1 and ERR2 were formerly identified by simply screening cDNA libraries for clones with homology with nuclear receptors.

The genes encoding ERRs exhibits a high degree of DNA sequence homology to the estrogen receptor (ER) and shows a considerable level of amino acid sequence identity with ER in both the DNA-binding domain (DBD) and the Ligand Binding Domain (LBD) (Giguere et al., 1988; Heard et al., 2000; Hong et al., 1999).

ERRs, including ERR3, can bind to functional estrogen response elements (EREs) in ER target genes such as lactoferrin (Yang et al., 1996) and aromatase (Yang et al., 1998), which shows that there exists a possible overlap between ERRs biology, and particularly ERR3 biology, and ER biology.

Several lines of evidence suggest that ERRs, including ERR3, are hormone-regulated. First, Vanacker et al. (1999) have observed that fetal calf serum contains a factor or factors that can stimulate ERRα basal activity by 12-fold. Second, Yang and Chen (1999) have reported that micromolar concentrations of the pesticides toxaphene and chlordane decrease ERRα basal activity.

Further, Coward et al. (2001) have reported that the estrogen diethylstilbestrol (DES) and the antiestrogens tamoxifen (TAM) and 4-hydroxytamoxifen (4-OHT) bind to ERR3 with submicromolar affinities and that 4-OHT repressed transactivation mediated by ERR3.

Also, Tremblay et al. (2001) have shown that DES interacts with both ERRα (ERR1), ERRβ (ERR2), and ERRγ (ERR3) to suppress coactivator binding and transcription from a reporter gene, and that the synthetic estrogen controls the differentiation of trophoblast cells in culture and in utero.

It has also been shown that ERR3 binds as a homodimer to direct repeats (DR) of the nuclear receptor half-site "5'-AGGTCA-3'", to extended half-sites, and to the inverted estrogen response element.

Also, Hong et al. (1999) have reported that ERR3 binds specifically to an estrogen response element and activates reporter genes controlled by estrogen response elements, both in yeast and mammalian cells. According to these authors, expression of ERR3 in adult mouse is restricted; highest expression was observed in heart, kidney and brain. Further, in the mouse embryo, no ERR3 expression was observed at day 7, and highest expression occurred around the 11-15 day stages. These authors believe that ERR3 would have a unique role in development.

There is a need in the art to identify compounds which behave as agonists or antagonists of ERRs in order to provide to the public biologically active compounds exerting an enhancement or in contrast a decrease in the transcriptional-activating activity of ERRs, for example in pathologies wherein a dysfunction in the level of ERRs biological activity is detected or measured.

Such ERR3 agonist or, more likely, antagonist compounds would be biologically-active compounds useful in modulating the estrogenic response on:
fertility,
birth control,
bone remodeling,
breast cancer,
prostate cancer.

SUMMARY OF THE INVENTION

Now, the present invention provides for technical means useful for performing various methods for the screening of compounds which behave as ligands, particularly as antagonists, as regards the transcriptional-activating activity of ERRs and especially ERR3.

A first object of the invention consists of a peptide fragment that encompasses the ligand-binding domain (LBD) of the estrogen-related receptor 3 (ERR3) of SEQ ID NO: 1 (SEQ ID NO: 1 encoded for by SEQ ID NO: 3), which peptide fragment mimicks, when fused to a polypeptide containing a DNA-binding domain, the transcriptional-activating activity of the estrogen-related receptor 3 (ERR3) of SEQ ID NO: 1, wherein said peptide fragment has an amino acid chain of up to 267 amino acids in length and wherein said peptide fragment comprises the amino acid sequence starting at the Prolyl amino acid residue in position 229 and ending at the Valyl amino acid residue in position 458.

The present invention also relates to transcriptionally-active fusion polypeptides comprising the peptide fragment above as well as protein complexes comprising said peptide fragment or said fusion polypeptides, including dimeric protein complexes.

The invention is also directed to nucleic acids encoding said peptide fragment and said fusion polypeptides, expression cassettes and recombinant vectors containing said nucleic acids, and also host cells which are transformed with said nucleic acids, said expression cassettes or said recombinant vectors.

This invention also relates to a crystallised peptide fragment above, to a crystallised dimeric protein complex above and to a crystallised Ligand Binding Domain (LBD) of ERR3 of SEQ ID NO: 1.

Another object of the invention consists of methods for the screening of ligand compounds of the LBD of ERR3, particularly compounds which are agonists or antagonists in respect to ERR3, and especially compounds which are antagonists in respect to ERR3, and wherein said methods make use, respectively, of the peptide fragment, the protein complexes, including the dimeric protein complexes, as well as the crystallised protein complexes which are disclosed above.

The present invention is also directed to peptides which consist of mutants of the peptide fragment containing the LBP of ERR3 described above, as well as to nucleic acids encoding said mutant peptide fragments.

General Definitions of Relevant Terms

In accordance with the present invention there may be employed conventional molecular biology, microbiology, and recombinant DNA techniques within the skill of the art. Such techniques are explained fully in the literature. See, e.g., Sambrook et al., 1989; Glover, 1985; Gait, 1984; Hames and Higgins, 1985; Hames and Higgins, 1984; Freshney, 1986; Perbal, 1984; and F. Ausubel et al., 1994.

Every polypeptide or nucleic acid used according to the invention is preferably under an isolated or a purified form.

An "isolated" nucleic acid or protein consists of a biological material (nucleic acid or protein) which has been removed from its original environment (the environment in which it is naturally present).

For example, a polynucleotide present in the natural state in a plant or an animal is not isolated. The same polynucleotide separated from the adjacent nucleic acids in which it is naturally inserted in the genome of the plant or animal is considered as being "isolated".

Such a polynucleotide may be included in a vector and/or such a polynucleotide may be included in a composition and remains nevertheless in the isolated state because of the fact that the vector or the composition does not constitute its natural environment.

The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

For the purposes of the present description, the expression "nucleotide sequence" may be used to designate either a polynucleotide or a nucleic acid. The expression "nucleotide sequence" covers the genetic material itself and is therefore not restricted to the information relating to its sequence.

The terms "nucleic acid", "polynucleotide", "oligonucleotide" or "nucleotide sequence" cover RNA, DNA, gDNA or cDNA sequences or alternatively RNA/DNA hybrid sequences of more than one nucleotide, either in the single-stranded form or in the duplex, double-stranded form.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence or coding sequence.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

"Regulatory region" means a nucleic acid sequence which regulates the expression of a nucleic acid. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

DESCRIPTION OF THE FIGURES

FIG. 1:

FIG. 1(B) represents the alignment of the LBD sequences of human ERR1, (SEQ ID NO: 9) ERR2 (SEQ ID NO: 8) and ERRE3 (SEQ ID NO: 1), respectively.

FIG. 2:

FIG. 3:

DETAILED DESCRIPTION OF THE INVENTION

Figure 1A:
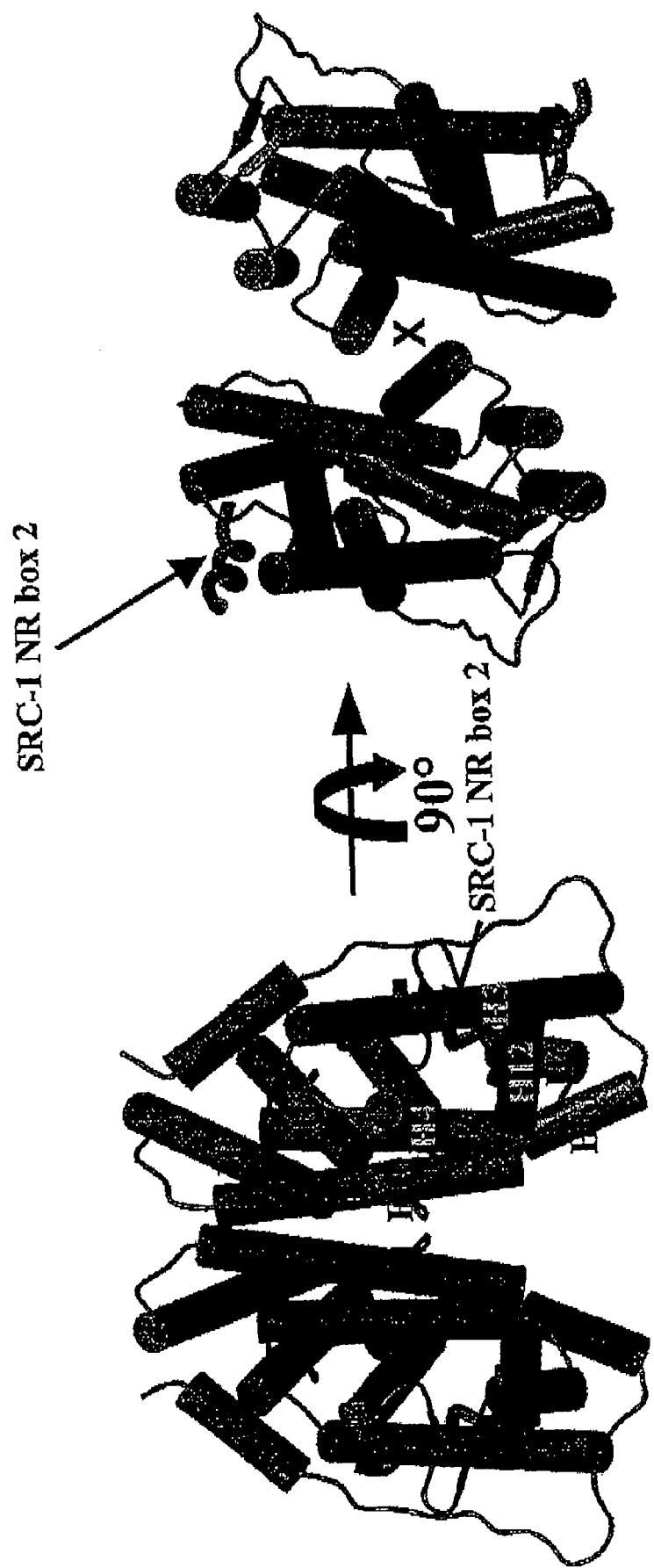
FIG. 1(A) shows spatial representations of a homodimer the Ligand Binding Domain (LBD) of ERR3 which is bound to the SRC-1 coactivator peptide, respectively in two orientations.

It has been shown according to the invention that a peptide fragment encompassing the ligand-binding domain (LBD) of the estrogen-related receptor 3 (ERR3), when said peptide fragment is fused to a protein which contains a DNA-binding domain, leads to a fusion polypeptide which mimicks the transcriptionally-activating activity of the complete ERR3 protein.

The inventors have crystallised the Ligand Binding Domain (LBD) of the ERR3 receptor in complex with a coactivator SRC-1 peptide wherein, in said protein complex, the ERR3 LBD adopts its transcriptionally active conformation in the absence of any ligand, demonstrating that ERR3 is a constitutive activator of transcription. Further, the inventors have crystallised the ERR3 LBD in complex with diethylstilbestrol (DES), a ligand that was shown to deactivate ERR3. In this complex, the binding of the ligand displaces helix 12 of the ERR3 LBD, precluding the transcriptionally active conformation of the receptor observed in the absence of ligand and thereby deactivating the receptor.

By allowing the use of either (i) the structure of the ERR3 LBD in complex with the coactivator SRC-1 peptide or (ii) the structure of the ERR3 LBD in complex with the antagonist DES, this invention provides for methods for the design of high affinity, high-specificity ligands, particularly agonist (using (i)) or, more likely, antagonist (using (ii)) compounds in respect to ERR3, wherein the positively screened compounds among the designed candidate ligands should be useful as therapeutical active substances, especially for patients who are affected with physiological states or disorders caused by the regulation or a dysfunction in the transcriptional activity of ERR3, such as fertility dysfunction, or regulation, birth control, bone remodelling, breast cancer and prostate cancer.

Peptides and Proteins of the Invention, Nucleic Acids Encoding Them, and Screening Methods Using Them A first object of the invention consists of a peptide fragment encompassing the ligand-binding domain (LBD) of the estrogen-related receptor 3 (ERR3) of SEQ ID NO: 1 that mimics, when fused to a polypeptide containing a DNA-binding domain, the ligand dependence of the transcriptional activity of (ERR3), wherein said peptide fragment has an amino acid chain of up to 267 amino acids in length and wherein said peptide fragment comprises the amino acid sequence starting at the Prolyl amino acid residue in position 229 and ending at the Valyl amino acid residue in position 458 of the amino acid sequence SEQ ID NO: 1.

Preferably, the peptide fragment above has an amino acid length of up to 267, 253, 239, or 235 consecutive amino acids of SEQ ID NO: 1 and ends at the Valyl amino acid residue in position 458 of the amino acid sequence SEQ ID NO: 1.

Most preferably, the peptide fragment above consists of the amino acid sequence starting at the Prolyl amino acid residue in position 229 and ending at the Valyl amino acid residue in position 458 of the amino acid sequence SEQ ID NO: 1.

The transcriptional-activating activity of the peptide fragment described above is easily assayed by the one skilled in the art, preferably by fusing said peptide fragment with a protein containing a known DNA-binding domain and by assaying the biological activity of the fusion polypeptide thus obtained in a cell host previously transformed with a reporter DNA construct, wherein said DNA construct comprises (i) at least one nucleic acid sequence which specifically binds to the DNA-binding domain of said fusion polypeptide and (ii) an open reading frame (which may be also termed a "coding sequence") operably linked to a promoter sequence which is functional in said transformed cell host, as it is disclosed in the Examples.

The protein containing the DNA-binding domain can be selected from the group of proteins consisting of:
(i) the suitable proteins disclosed in the DNA-binding protein collection freely available at the Web site of the NDB (On-line address http://ndbserver.rutgers.edu/structure-finder/dnabind/)
(ii) Helix-Turn-Helix type proteins consisting of the prokaryotic proteins *E. coli* Catabolite activator protein (CAP), *E. coli* trp repressor, Lambda phage repressor & Cro, 434 phage repressor & Cro; eukaryotic proteins Yeast a-MAT, *Drosophila* Engrailed, *Drosophila* Even-skipped, Human Oct-1 POUs, Mouse c-Myb, Mouse HNF-3/forkhead and Yeast heat shock regulatory protein
(iii) Zinc bearing proteins consisting of the eukaryotic proteins *Drosophila* Tramtrack, Mouse Zif268, Yeast ADR1, Rat Glucocorticoid receptor DNA-binding domain (DBD), Chicken GATA-1 DBD, Yeast GAL4, Yeast PPR1 and Human Elongation transcription factor;
(iv) Leucine-zipper coled-coil motif proteins consisting of Yeast GCN4, Human/Mouse MyoD and Mouse Max; and
(v) Beta sheet recognition motif proteins consisting of *E. coli* Met J repressor and Yeast TATA binding protein.

In a preferred embodiment, the protein containing a DNA-binding domain consists of the well known yeast Gal4 protein.

Advantageously, the reporter DNA construct contains more than one nucleic acid sequence which binds to the DNA-binding domain-containing protein.

Preferably, said reporter DNA-construct contains from 1 to 10 and most preferably 1, 2, 3, 4 or 5 nucleic acid sequences which bind to the DNA-binding domain-containing protein.

Illustratively, the examples herein disclose a fusion polypeptide comprising the LBD of ERR3 fused to the Gal4 protein, which is used in the assays with cell hosts transformed with a reporter DNA-construct containing five copies of the nucleic acid sequence which binds to the Gal4 protein upstream of a thymidine kinase promoter sequence.

The reporter DNA construct also comprises an open reading frame (a "coding region") which encodes a detectable protein. The detectable protein may be of any kind, since it can be detected, for example, through the use of antibodies, including monoclonal antibodies, that specifically bind thereto.

Preferably, the detectable protein is detected through enzyme, fluorescence or luminescence assays.

For enzyme assays, detectable proteins such as chloramphenicol acetyl transferase are preferred.

For fluorescence assays, detectable proteins such as GFP (Green Fluorescent Protein) or YFP (Yellow Fluorescent Protein) are preferred.

For luminescence assays, detectable proteins such as luciferase are preferred.

Illustratively, the examples herein disclose reporter DNA-constructs which contain an open reading frame encoding luciferase.

Further, the reporter DNA construct contains a promoter sequence which is functional in the cell host which has been transformed therewith, for example an eukaryotic promoter in a transformed eukaryotic cell host, a mammalian promoter in a transformed mammalian cell host and a human promoter in a human cell host.

Illustratively, the examples herein disclose reporter DNA-constructs which contain a thymidine kinase promoter sequence.

Most preferably, the transformed cell host consists of a transformed mammalian cell host and thus the promoter sequence most preferably consists of a mammalian promoter.

Illustratively, the examples herein disclose the use of transformed mammalian cells such as COS-1 cells, which originate from *Cercopithecus aethiops* (African green monkey), BHK cells, which originate from *Mesocricetus auratus* (hamster, Syrian golden) and the murine neuroblastoma cell line, clone NB2A (Neuro2A; CCL-131; American Cell Type Culture Collection, Bethesda, Md., USA).

A further object of the invention consists of a fusion polypeptide consisting of the peptide fragment comprising the Ligand Binding Domain (LBD) of ERR3 from amino acid 229 to amino acid 458 of SEQ ID NO: 1 which peptide fragment is fused to a polypeptide containing a DNA-binding domain such as disclosed above.

Said fusion polypeptide is preferably obtained from a nucleic acid construct encoding it. For preparing a nucleic acid construct encoding said fusion polypeptide, the nucleic acid encoding peptide fragment comprising the Ligand Binding Domain (LBD) of ERR3 from amino acid 229 to amino acid 458 of SEQ ID NO: 1 is preferably inserted at a cloning site of a recipient vector which already contains an open reading frame encoding the polypeptide containing a DNA-binding domain located close to said cloning site, so as to obtain a recombinant vector which encodes the fusion polypeptide, the region encoding said fusion polypeptide being operably linked to a functional promoter sequence within said recombinant vector.

Illustratively, the examples herein disclose inserting the nucleic acid encoding peptide fragment comprising the Ligand Binding Domain (LBD) of ERR3 from amino acid 229 to amino acid 458 of SEQ ID NO: 1 within the pCMX-Gal4 recipient vector.

For obtaining a nucleic acid encoding a peptide fragment comprising the Ligand Binding Domain (LBD) of ERR3 from amino acid 229 to amino acid 458 of SEQ ID NO: 1 the one skilled in the art can perform a nucleic acid amplification method, such as a PCR method, with a suitable pair of nucleic acid primers, starting from a cDNA clone encoding the full length ERR3 receptor.

Most preferred primers are respectively the nucleic acid primer of SEQ ID NO: 5 and the nucleic acid primer of SEQ ID NO: 6.

As an illustrative example, the cDNA clone containing the peptide fragment comprising the Ligand Binding Domain (LBD) of ERR3 from amino acid 229 to amino acid 458 of SEQ ID NO: 1 consists of that disclosed by Chen et al. (1999), Nagase et al. (1998), Eudy et al. (1998) or Hong et al. (1999).

It has been found according to the invention that the Ligand Binding Domain (LBD) of the ERR3 receptor may be obtained in the transcriptionally active conformational state when said LBD peptide fragment forms a protein complex with an amino acid portion of SEQ ID NO: 2 which comprises the Receptor Interaction Domain (RID) of the SRC-1 coactivator starting from the amino acid residue in position 614 to the amino acid residue in position 764 of SEQ ID NO: 2, or alternatively with a SRC-1 coactivator peptide from amino acid 686 to amino acid 704 of SEQ ID NO: 2.

Another object of the invention consists of a protein complex between (i) a protein comprising the peptide fragment comprising the Ligand Binding Domain of ERR3 as defined above and (ii) the SRC-1 coactivator peptide of SEQ ID NO: 2 or a peptide fragment thereof comprising the Receptor Interaction Domain (RID) of SRC-1, wherein said protein complex, when the peptide fragment of claim 1 is fused to a polypeptide containing a DNA-binding domain, mimicks the transcriptional-activating activity of the estrogen-related receptor 3 (ERR3) of SEQ ID NO: 1.

In a first preferred embodiment of the protein complex above, the peptide fragment comprising the RID of the SRC-1 coactivator peptide has up to 200 consecutive amino acids of SEQ ID NO: 2 and comprises the RID amino acid sequence starting from the amino acid in position 614 and ending at the amino acid in position 764 of SEQ ID NO: 2.

Preferably, said peptide fragment has up to 180, 175, 160, 155, 154, 153, 152, or 151 consecutive amino acids of SEQ ID NO: 2 and comprises the RID amino acid sequence starting from the amino acid in position 614 and ending at the amino acid in position 764 of SEQ ID NO: 2.

In a second preferred embodiment of the protein complex above, the peptide fragment comprising the RID of the SRC-1 coactivator peptide has up to 30 consecutive amino acids of SEQ ID NO: 2 and comprises the RID amino acid sequence starting from the amino acid in position 686 and ending at the amino acid in position 700 of SEQ ID NO: 2.

Preferably, according to this second preferred embodiment, said peptide fragment has up to 25, 20, 19, 18, 17, 16 or 15 consecutive amino acids of SEQ ID NO: 2 and comprises the RID amino acid sequence starting from the amino acid in position 686 and ending at the amino acid in position 700 of SEQ ID NO: 2.

For obtaining the SRC-1 coactivator peptide or a peptide fragment comprising the RID amino acid sequence thereof, the one skilled in the art may (i) transform cell hosts, namely prokaryotic or eukaryotic host cells, such as E. coli or mammalian cell hosts, respectively, with a nucleic acid comprising an open reading frame encoding the SRC-1 coactivator peptide, or the peptide fragment thereof comprising the RID amino acid sequence, wherein said nucleic acid also comprises a promoter sequence which is functional in said cell host, (ii) culture the transformed cell hosts in an appropriate culture medium so as to allow said transform host cells to express the SRC-1 coactivator peptide, or the peptide fragment thereof comprising the RID amino acid sequence thereof, then (iii) collect the SRC-1 coactivator peptide, or the peptide fragment thereof comprising the RID amino acid sequence thereof, in the cell culture supernatant or the cell lysate and then preferably (iv) purify said protein from the culture supernatant or from the cell lysate.

The one skilled in the art may prepare the nucleic acid encoding the SRC1 coactivator peptide, or the peptide fragment of interest comprising the RID sequence thereof, by performing a nucleic acid amplification reaction from the SRC-1 cDNA sequence of SEQ ID NO: 4.

Most preferably, for performing the nucleic acid amplification, such as a PCR reaction, the one skilled in the art will use a suitable pair of nucleic acid primers.

In preferred embodiments, the open reading frame above encodes the peptide of interest under the form of a fusion with a peptide "tag", said peptide tag being used for the purification step on a separation column such as an immunoaffinity purification column or a separation column containing Nickel or Cobalt ions.

Preferably, said peptide tag is selected from the group consisting of a poly-histidine, for example [His]$_6$, (SEQ ID NO: 7) and GST, as disclosed in the examples herein.

Illustratively, for producing a peptide fragment comprising the RID amino acid sequence of the SRC-1 coactivator peptide, the one skilled in the art may use the recombinant vector pGEX-4T1 commercialised by the Amersham Company, wherein has been inserted a nucleic acid sequence encoding the peptide fragment consisting of the amino acid sequence starting from the amino acid in position 614 and ending at the amino acid in position 764 of SEQ ID NO: 2 as disclosed in the examples herein.

For preparing a protein complex between (i) a protein comprising the peptide fragment comprising the Ligand Binding Domain of ERR3 as defined above and (ii) a SRC-1 fragment of SEQ ID NO: 2 comprising the Receptor Interaction Domain (RID) or a SRC-1 coactivator peptide wherein said protein complex, when the peptide fragment of claim 1 is fused to a polypeptide containing a DNA-binding domain, mimicks the transcriptional-activating activity of the estrogen-related receptor 3 (ERR3) of SEQ ID NO: 1, the one skilled in the art preferably mix the purified protein (i) with a molar excess of the purified peptide fragment (ii). Most preferably the purified peptide fragment (ii) is mixed with the purified protein (i) in a 3-molar excess.

In a particular embodiment of the protein complex above, the purified protein (i) consists of the peptide fragment that mimicks, when fused to a polypeptide containing a DNA-binding domain, the transcriptional-activating activity of the estrogen-related receptor 3 (ERR3) of SEQ ID NO: 1, wherein said peptide fragment has an amino acid chain of up to 267 amino acids in length and wherein said peptide fragment comprises the amino acid sequence starting at the Prolyl amino acid residue in position 229 and ending at the Valyl amino acid residue in position 458 of the amino acid sequence SEQ ID NO: 1, wherein said peptide fragment is fused to a polypeptide containing a DNA-binding domain, as described previously in the present specification.

According to the particular embodiment above, the polypeptide containing a DNA-binding domain consists of the Gal4 protein.

In a first preferred embodiment of the protein complex above, the SRC-1 coactivator peptide fragment comprises the amino acid sequence starting from the amino acid residue in position 614 and ending at the amino acid residue in position 764 of the amino acid sequence SEQ ID NO: 2.

In a second preferred embodiment of the protein complex above, the SRC-1 coactivator peptide fragment consists of the amino acid sequence starting from the amino acid residue in position 686 and ending at the amino acid residue in position 700 of the amino acid sequence SEQ ID NO: 2.

It is known in the art that the ERR3 receptor which is naturally expressed in human cells is present within said cells under the form of a homodimer protein complex.

Now, according to the invention, it has been produced protein complexes comprising, or alternatively consisting of, a homodimer between two peptide fragments comprising the Ligand Binding Domain of the ERR3 receptor, wherein, eventually, each peptide fragment monomer forms itself a protein complex with the SRC-1 coactivator RID fragment or with a short peptide thereof, as described above.

It has surprisingly been shown, according to the invention, that, in the crystal structure of the dimeric protein complex, the Ligand Binding Domain (LBD) of ERR3 is found in the transcriptionally-active conformation in the absence of any ligand and that this structure thus reveals the biologically-active conformation of the Ligand Binding Pocket (LBP).

The present invention is also directed to a nucleic acid encoding the peptide fragment comprising the Ligand Binding Domain of the ERR3 receptor, as described above.

The invention also relates to a nucleic acid encoding a fusion polypeptide consisting of the peptide fragment comprising the Ligand Binding Domain of the ERR3 receptor which is fused to a polypeptide containing a DNA-binding domain, as described above.

Most preferably, the polypeptide containing a DNA-binding domain consists of the Gal4 protein.

The invention also relates to an expression cassette comprising (i) a nucleic acid encoding the peptide fragment comprising the full-length ERR3 receptor or a nucleic acid encoding a fusion polypeptide consisting of the peptide fragment comprising the Ligand Binding Domain of the ERR3 receptor which is fused to a polypeptide containing a DNA-binding domain; and (ii) a regulatory polynucleotide sequence, preferably a promoter sequence, to which said nucleic acid is operably linked.

In a most preferred embodiment of the expression cassette above, said regulatory polynucleotide, preferably said promoter sequence, is functionally-active in eukaryotic cells, preferably in mammalian cells and most preferably in human cells.

Illustrative examples of expression cassettes according to the invention are provided in the examples, including the expression cassettes which are comprised in the recombinant vectors, PCMX and pCMX-Gal4.

Another object of the invention consists of a recombinant vector comprising a nucleic acid as defined above or an expression cassette as defined above.

Another object of the invention consists of a cell host which is transformed with a recombinant vector containing an expression cassette as defined above.

Taking advantage of the showing according to the invention that a peptide fragment of the ERR3 receptor comprising the Ligand Binding Domain (LBD) thereof, possesses its transcriptional-activating activity, the inventors have performed a method for the screening of ligand compounds, particularly agonist or antagonist compounds, and especially antagonist compounds, wherein said screening method make use of said peptide fragment of ERR3 which comprises the LBD thereof under the form of a fusion polypeptide with a polypeptide containing a DNA-binding domain.

Thus, another object of the invention consists of a method for the screening of compounds which are agonists or antagonists of the transcriptional-activating activity of the estrogen-related receptor 3 (ERR3) of SEQ ID NO: 1, wherein said method comprises the steps of:

a) incubating a culture of transformed cell hosts, wherein said transformed cell hosts express a fusion polypeptides as defined above and wherein said transformed cell hosts comprise a reporter polynucleotide comprising (i) at least one nucleic acid sequence which is recognised by the DNA-binding domain contained within said fusion polypeptide and (ii) an open reading frame encoding a detectable protein, with a candidate compound to be assayed;

b) measuring the amount of the detectable protein which is produced by said transformed cell hosts;

c) comparing the amount of the detectable protein measured at step b) with the amount of the detectable protein which is produced by a control culture of said transformed cell hosts wherein step a) is performed without said candidate substance;

d) selecting, respectively:
   (i) candidate compounds which inhibit the detectable protein production, which consist of antagonist compounds of the estrogen-related receptor 3 (ERR3) of SEQ ID NO: 1; and
   (ii) candidate compounds which enhance the detectable protein production, which consist of agonist compounds of the estrogen-related receptor 3 (ERR3) of SEQ ID NO: 1.

In a first preferred embodiment of the screening method above, the detectable protein consists of the luciferase protein.

Specific embodiments of the various products used for performing the screening method above have already been described previously within the present specification.

Most preferably, the polypeptide containing the DNA-binding domain which is included in the fusion polypeptide used at step a) of the screening method consists of the Gal4 protein.

Most preferably, the nucleic acid sequence which is recognised by the DNA-binding domain of the fusion polypeptide above consists of the nucleic acid sequence onto which specifically binds the Gal4 protein, which nucleic acid sequence is disclosed by Giniger et al. (1985).

The amount of detectable protein is measured by any appropriate detecting device, taking into account that the signal to be detected is a colour signal, a fluorescence signal or a luminescence signal.

When luciferase is used as the detectable protein, the measure of the amount of luciferase which is produced is most preferably performed as described by Greiner et al. (1996).

According to the invention, other methods for the screening of ligand compounds, particularly agonist compounds or antagonist compound, and especially antagonist compounds, for the ERR3 receptor are described hereunder, which takes advantage that the LBD of ERR3 exhibits a transcriptionally-active conformation in the absence of any ligand.

For this purpose, the inventors have performed a crystallisation of a peptide fragment comprising the LBD of the ERR3 receptor, including a crystallisation of said peptide fragment under the form of a protein complex with an SRC-1 peptide fragment comprising the RID sequence, and especially a short SRC-1 peptide fragment thereof, as already disclosed in the present specification.

Crystallised ERR3 Peptide Fragments and Methods Using Them.

Another object of the invention consists of a crystallised ERR3 peptide fragment, wherein said peptide fragment has an amino acid chain of up to 267 amino acids in length and wherein said peptide fragment comprises the amino acid sequence starting at the Prolyl amino acid residue in position 229 and ending at the Valyl amino acid residue in position 458 of the amino acid sequence SEQ ID NO: 1.

A further object of the invention consists of a crystallised ERR3 peptide fragment, wherein said peptide fragment consists of the amino acid sequence starting at the Prolyl amino acid residue in position 229 and ending at the Valyl amino acid residue in position 458 of the amino acid sequence SEQ ID NO: 1.

In a first preferred embodiment, the ERR3 peptide fragment above is crystallised under the form of a protein complex with an SRC-1 coactivator peptide comprising the amino acid sequence starting from the amino acid in position 686 and ending at the amino acid in position 700 of SEQ ID NO: 2.

In a second preferred embodiment, the ERR3 peptide fragment above is crystallised under the form of a protein complex with an SRC-1 coactivator peptide fragment of up to 30 consecutive amino acids of SEQ ID NO: 2 comprising the RID amino acid sequence starting from the amino acid in position 686 and ending at the amino acid in position 700 of SEQ ID NO: 2.

A further object of the invention consists of a crystallised protein complex between (i) a protein comprising the peptide fragment according to claim 1 and (ii) the SRC-1 coactivator peptide of SEQ ID NO: 2 or a peptide fragment thereof comprising the Receptor Interaction Domain (RID) of SRC-1, wherein said protein complex, when the peptide fragment of claim 1 is fused to a polypeptide containing a DNA-binding domain, mimicks the transcriptional-activating activity of the estrogen-related receptor 3 (ERR3) of SEQ ID NO: 1.

A still further object of the invention consists of a crystallised protein complex between (i) the peptide fragment of the ERR3 receptor of SEQ ID NO: 1 that is defined above and (ii) a peptide fragment of the SRC-1 coactivator peptide of SEQ ID NO: 2 comprising the Receptor Interaction Domain (RID) thereof.

Preferably, in the crystallised protein complex above, the peptide fragment (ii) consists of the Receptor Interaction Domain (RID) of the SRC-1 protein.

In a preferred embodiment of the crystallised protein complex above, two protein complexes form together a dimeric protein complex.

The preparation of a protein complex between said ERR3 peptide fragment and said SRC-1 peptide fragment has previously been disclosed in the present specification and is further detailed in the examples.

For performing crystallisation of the ERR3 peptide fragment, including the embodiment wherein said peptide fragment is under the form of a protein complex with an SRC-1 peptide fragment, the one skilled in the art will preferably use the conventional hanging-drop vapour-diffusion method which is extensively described by Ducruix and Giegé (1999), this technique being further detailed in the examples herein.

Preferably crystals are made with the hanging drop methods. Regulated temperature control is desirable to improve crystal stability and quality. Temperatures between 4 and 25° C. are generally used and it is often preferable to test crystallization over a range of temperatures. It is preferable to use crystallization temperatures from 18° C. to 25° C., more preferably 20 to 23° C., and most preferably 22° C.

As an illustrative example, crystals grow within a few days at 4° C. with a reservoir of 100 mM Tris.HCl pH 8.0, 1.5 mM ammonium sulfate and 15% glycerol.

It has been found, according to the invention, that the crystallised protein complexes above belong to the space group $P4_32_12$ (a=b=83.317 Å and c=240.610 Å), with one homodimer (of protein complex ERR3 peptide fragment/SRC-1 peptide fragment) per asymmetric unit and a solvent content of 60%.

Preferably, before analysis, crystals are cryoprotected, for example in 100 mM Tris.HCl pH 8.0, 1.5 mM ammonium sulfate, 15% glycerol and 10% ethylene glycol and then flash frozen in liquid ethane at liquid nitrogen temperature.

As mentioned above, it has been prepared, according to the invention, a crystallised protein complex wherein, for each molecule of protein complex included in the crystal, two molecules of protein complex form together a dimeric, and more specifically a homodimeric, protein complex.

Using a grown crystal complex of the present invention, X-ray diffraction data can be collected by a variety of means in order to obtain the atomic coordinates of the molecules in the crystallised complex. With the aid of specifically designed computer software, such crystallographic data can be used to generate a three dimensional structure of the molecules in the complex. Various methods used to generate and refine a three dimensional structure of a molecular structure are well known to the thos skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

For analysis, the crystallised protein complex of the invention has been subjected to an X-ray diffraction step and X-ray diffraction data, specifically to 2.7 Å resolution, and reflections were measured within 15-2.7 Å. The X-ray data thus obtained were integrated and scaled using the HKL software package which is described by Otwinowski et al. (1997).

The Cartesian coordinates which define one and every structural conformation feature of the homodimeric protein complex [2×(ERR3 peptide fragment/SRC-1 peptide fragment)] of the invention are listed in Table 1.

In Table 1:
first column designates the nature of the information given in the corresponding line;
second column represents a single increment numbering of the lines of Table 1;
third column refers to a specific atom of the considered amino acid;
fourth column designates the specific amino acid of the peptide fragment which is considered;
fifth column refers to the peptide chain to which a specific amino acid belongs;
sixth column specifies the amino acid position of the amino acid which is considered, as regards the numbering of the amino acid sequence of the complete ERR3 receptor of sequence SEQ ID NO: 1;
seventh, eighth and ninth columns specify the Cartesian coordinates of the atom which is considered along, respectively, the x, y and z axis;
tenth column specifies the occupancy of the considered position by the considered atom;
eleventh column specifies the B factor characterizing the thermal motion of the considered atom;
twelfth column refers to the peptide chain to which a specific amino acid belongs;

Also, the Cartesian coordinates which define one and every structural conformation feature of a complex between (i) the homodimeric protein complex [2×(ERR3 peptide fragment/SRC-1 peptide fragment)] and (ii) the diethylstilbestrol molecule are listed in Table 2.

In Table 2:
first column designates the nature of the information given in the corresponding line;
second column represents a single increment numbering of the lines of Table 1;
third column refers to a specific atom of the considered amino acid;
fourth column designates the specific amino acid of the peptide fragment which is considered;
fifth column refers to the peptide chain to which a specific amino acid belongs;
sixth column specifies the amino acid position of the amino acid which is considered, as regards the numbering of the amino acid sequence of the complete ERR3 receptor of sequence SEQ ID NO: 1;
seventh, eighth and ninth columns specify the Cartesian coordinates of the atom which is considered along, respectively, the x, y and z axis;
tenth column specifies the occupancy of the considered position by the considered atom;
eleventh column specifies the B factor characterizing the thermal motion of the considered atom;
twelfth column refers to the peptide chain to which a specific amino acid belongs;

As used herein, "structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modelling. Various software programs allow for the graphical representation of a set of structural coordinates of the present invention may be modified from the original sets provided in Table 1 by mathematical manipulation, such as by inversion or integer additions or substratctions. As such, it is recognised that the structural coordinates of the present invention are relative, and are in no way specifically limited by the actual x, y, z coordinates in Table 1.

As used herein, "Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in the same structural coordinates within the stated root mean square deviation.

It will be obvious to the one skilled in the art that the numbering of the amino acid residues of the various chains of the crystallised protein complex defined herein may be different than set forth herein, and lay contain certain conservative amino acid substitutions that yield the same three-dimensional structures as those defined in Table 1 herein. Corresponding amino acids and conservative substitutions are easily identified by visual inspection of the relevant amino acid sequences or by using commercially available homology software programs, such as MODELLER (MSI, San Diego, Calif., USA).

As used herein, "conservative substitutions" are those amino acid substitutions which are functionally equivalent to the substituted amino acid residue, either by way of having similar polarity, steric arrangement, or by belonging to the same class as the substituted residue (e.g. hydrophobic, acidic or basic), and includes substitutions having an inconsequential effect on the three dimensional structure of the crystallised protein complex of the invention with respect to the use of said structures for the identification of ligand compounds which interact with the LBP of the ERR3 receptor, more particularly, agonist or antagonist compounds, and more specifically antagonist compounds of the ERR3 receptor, for molecular replacement analyses and/or for homology modelling.

According to one specific embodiment of the crystallised protein complex of the invention, each of the protein complex (ERR3 peptide fragment/SRC-1 peptide fragment) of the dimeric, specifically homodimeric, protein complex [2×(ERR3 peptide fragment/SRC-1 peptide fragment)] comprises the Ligand Binding Domain (LBD) of the estrogen-related receptor 3 (ERR3) of SEQ ID NO: 1 and wherein each dimeric protein complex delineates a contact area of 1245 Å$^3$ and a Ligand Binding Pocket (LBP) with a cavity volume of 220 Å$^3$.

As shown in the examples, the various amino acid residues from the LBD of the ERR3 receptor that delineate the inner space area of said Ligand Binding Pocket have been determined, using the structural coordinates of the crystallised protein complex which are set forth in Table 1.

Thus, the crystallised LBD of the ERR3 receptor, and more specifically the inner space area of said Ligand Binding Pocket, can also be defined exclusively as respect to the various amino acid residues which are involved in delineating it.

Another object of the invention consists of a crystallised Ligand Binding Domain (LBD) of the estrogen-related receptor 3 (ERR3) of SEQ ID NO: 1 wherein said Ligand Binding Pocket (LBP) comprises the relative structural coordinates of amino acid residues LEU268, CYS269, L271, ALA272, GLU275, TRP305, LEU309, ILE310, VAL313, ARG316, VAL313, TYR326, LEU342, LEU345, N346, I349, ALA431, VAL432, HIS434, PHE435, PHE450 and LEU454 according to Table 1 for chain A or chain B The present invention is also directed to a crystal complex between the Ligand Binding Domain (LBD) of the estrogen-related receptor 3 (ERR3) of SEQ ID NO: 1, wherein said LBD is complexed with one diethylstilbestrol molecule. The complete structural coordinates of the crystallised complex between the ERR3 LBD and diethylstilbestrol are set forth in Table 2.

The availability, according to the present invention, of the whole structural coordinates of the homodimeric protein complex described above, and specifically of the structural coordinates of the various amino acid residues which are involved for forming the Ligand Binding Pocket of the ERR3 receptor, allows the one skilled in the art to generate models of docking compounds of a known chemical structure within said Ligand Binding Pocket and select those compounds that are potential or actual agonist compounds or antagonist comppounds in respect to the trancriptional-activating activity of the ERR3 receptor.

More particularly, according to the invention, a compound which will behave as an antagonist compound in respect to the transcriptional-activating activity of the ERR3 receptor consists of a compound that, when docked in the LBP of the ERR3 receptor, induces steric constraints onto one or several chemical groups, including lateral chains, of one or several of the amino acid residues which are involved in delineating the inner space area of the LBP of the ERR3 receptor, as it is shown in the examples and in the figures herein.

An illustrative example of such an antagonist compound consists of diethylstilbestrol, which complexes with the ERR3 LBD as shown in the examples and in Table 2.

On another hand, according to the invention, a compound which will behave as an agonist compound in respect to the transcriptional-activating activity of the ERR3 receptor consists of a compound that, when docked in the LBP of the ERR3 receptor, interacts with one or several chemical groups of the amino acid residues which are involved in forming the LBP of the ERR3 receptor, for example through the generation of hydrogen bonds or through interaction via Van der Waals bounds or also through electrostatic interactions, wherein the various electronic bounds which are generated, between atoms of the amino acid residues of the LBP of the ERR3 receptor and the ligand compound tested, will stabilise the spatial conformation of the transcriptionally-active form of the LBP and thus will stabilise or enhance the transcriptional-activating activity of the complete ERR3 receptor.

In another aspect, the present invention is directed to a method for identifying a ligand compound, more particularly an agonist or an antagonist compound, and more specifically an antagonist compound, that interacts with the LBP of the ERR3 receptor.

Another object of the invention consists of a method for selecting a compound that fits in the Ligand Binding Pocket (LBP) of the estrogen-related receptor 3 (ERR3) of SEQ ID NO: 1 wherein said method comprises the steps of:
a) generating a three-dimensional model of an ERR3 LBD dimer using the relative structural coordinates according to Table 1, and
b) employing said three-dimensional model to design or select a compound, from a serial of compounds, that interacts with said ERR3 LBD.

According to the screening method above, the selected compound interacts with the LBP of the ERR3 receptor and induces a stabilisation of the LBD, or in contrast induces a deformation of the LBD and, consequently, should exhibit a biological activity of an agonist compound or of an antagonist compound, respectively, in respect to the transcriptional-activating activity of the ERR3 receptor.

In order to further precise the class of compounds to which the selected ligand belongs, step b) may further comprise specific sub-steps wherein it is determined whether the compound, which has been primarily selected for its ability to interact with the LBD of the ERR3 receptor, further induces stabilisation or, in contrast, steric constraints onto chemical groups belonging to the amino acid residues involved in the LBP so as to stabilise the spatial conformation of the LBP and may enhance the transcriptional-activating activity of the ERR3 receptor or, in contrast, cause a change in the spatial conformation of the LBP that reduces or even blocks the transcriptional-activating activity of the ERR3 receptor.

For example, it has been shown, according to the invention, that estradiol (E2), diethylstilbestrol (DES) and 4-hydroxytamoxifen (4-OHT) all cause steric constraints onto chemical groups belonging to the amino acid residues involved in the LBP so as to cause a change in the spatial conformation of the LBP that reduces or even blocks the transcriptional-activating activity of the ERR3 receptor.

When docked within the LBP of ERR3 defined by the structural coordinates as set forth in Table1, estradiol is shown to induce a steric clash by causing a steric constraint on the lateral aromatic group of the amino acid residue PHE435, thus inducing spatial conformation changes in the ERR3 LBP, leading to an inactive LBP spatial conformation. The same generation of steric constraint on the lateral aromatic group of the amino acid residue PHE435 has also been observed after docking of diethylstilbestrol (DES) and 4-hydroxytamoxifen (4-OHT), as it is shown in the examples.

In order to further characterise the biological activity of the compound which has been positively selected by performing steps (a) and (b) of the screening method above, it may be required to assay for the actual biological activity of said positively selected compound, in respect to the transcriptional-activating activity of the ERR3 receptor, or in respect to a fusion polypeptide which is previously described in the present specification, which fusion polypeptide comprises the ERR3 Ligand Binding Domain (LBD) and mimics the transcriptional-activating activity of the complete ERR3 receptor.

According to a first aspect, a further biological assay using said positively selected compound will confirm that said candidate compound which causes steric constraints within the ERR3 LBP effectively reduces or blocks the transcriptional-activating activity of the ERR3 receptor, or of the fusion polypeptide which mimics the transcriptional-activating activity of the complete ERR3 receptor.

According to a second aspect, a further biological assay using said positively selected compound will confirm that said candidate compound, which interacts without causing defavourable steric constraints within the ERR3 LBP effectively enhances the transcriptional-activating activity of the ERR3 receptor, or of the fusion polypeptide which mimics the transcriptional-activating activity of the complete ERR3 receptor.

Thus, in a further embodiment, the screening method above, said method further comprises the steps of:
c) obtaining the compound designed or selected at step b); and
d) contacting the compound obtained at step c) with a protein containing the peptide fragment of claim 1 in order to determine the effect the compound has on transcriptional-activating activity of the estrogen-related receptor 3 (ERR3) of SEQ ID NO: 1.

In a most preferred embodiment, step d) of the screening method above consists of performing the screening method which has been previously described in detail in the present specification, which screening method makes use cell hosts transformed with a reporter DNA construct encoding a detectable protein and wherein the level of the biological activity of the LBD of the ERR3 receptor is determined through the measure of the amount of said detectable protein which is produced by said transformed cell hosts.

In a preferred embodiment of said screening method, in step d), the compound which has been selected in step b) is used as the candidate agonist or antagonist compound in step a) of the biological screening method which is used in step d).

According to a first aspect of the screening method above, the candidate ligand compound, more particularly the candidate agonist or antagonist compound, is selected from a library of compounds previously synthesised.

According to a second aspect of the screening method above, the candidate ligand compound, more particularly the candidate agonist or antagonist compound, is selected from compounds, the chemical structure of which is defined in a database, for example an electronic database. According to a third embodiment of the screening method above, the candidate ligand compound, more particularly the candidate agonist or antagonist compound, is conceived de novo, by taking into account the spatial conformation stabilisation or, in contrast, the spatial conformation changes, that chemical group(s) of said compound may cause, when docked within the LBP of the ERR3 receptor. Indeed, after its de novo conception, and if positively selected, said candidate ligand compound, more particularly said candidate agonist compound or said candidate antagonist compound, can be actually chemically synthesised. According to a fourth embodiment of the screening method above, the candidate ligand compound, more particularly the candidate antagonist compound, is selected from the group consisting of estradiol (E2), diethylstilbestrol (DES) and 4-hydroxytamoxifen (4-OHT).

In a further aspect, a ligand compound which has been positively selected by performing the screening method above is mixed or brought into contact, in a molar excess, with the homodimeric LBD alone of the invention and then the resulting complex is crystallised. The resulting crystal thus obtained is then subjected to x-ray diffraction or NMR analysis and the x-ray diffraction data or the NMR data are appropriately mathematically manipulated so as to generate a spatial model of the association between the ligand compound and the protein complex, wherein the various interactions of the ligand compound with the chemical groups of the amino acid residues involved in forming the LPB of the ERR3 receptor are visualised.

Illustratively, it has been prepared according to the invention a crystallised complex between (i) the LBD of ERR3 and (ii) diethylstilbestrol (DES) and the structural coordinates of this complex resulting from the X-ray diffraction data are represented in Table 2.

Alternatively, the preformed crystallised protein complex of the invention is soaked in the presence of the ligand compound to be tested, preferably in a molecular excess of said candidate ligand, thereby forming a protein/ligand complex and obviating the need to crystallise each complex formed between the protein complex of the invention and each of the ligand compounds which are assayed.

For selecting suitable ligand compounds, at step a) of the screening method above, it is made use of computational methods which are well known from the one skilled in the art.

Generally, computational methods for designing an ERR3 LBP ligand compound determines which amino acid or which amino acids of the LBP interact with a chemical moiety (at least one) of the ligand compound using a three dimensional model of the crystallised protein complex of the invention, the structural coordinates of which are set forth in Table 1.

Alternatively, computational methods for designing an ERR3 LBP ligand compound determines which amino acid or which amino acids of the LBP interact with a chemical moiety (at least one) of the ligand compound using a three dimensional model of the crystallised protein complex of the invention with diethylstilbestrol, the structural coordinates of which are set forth in Table 2.

These computational methods are particularly useful in designing an antagonist compound or a partial agonist compound to the ERR3 receptor, wherein said antagonist compound or said partial agonist compound has an extended chemical moiety that prevents any one of a number of ligand-induced molecular events that alters the receptor's biological activity on the regulation of gene expression, such as preventing the normal coordination of the activation domain observed for a naturally occurring ligand compound or other ligand compounds that mimic naturally occurring ligand compound, such as an agonist.

The three-dimensional structure of the liganded ERR3 receptor will greatly aid in the development of new ERR3 synthetic ligands. In addition, ERR3 is overall well suited to modern methods including three dimensional structure elucidation and combinatorial chemistry such as those disclosed in the European patent No. EP 335 628 and the U.S. Pat. No. 5,463,564, which are incorporated herein by reference. Computer programs that use crystallographic data when practising the present invention will enable the rational design of ligand to ERR3 receptor.

Programs such as RASMOL can be used with the atomic coordinates from crystals generated by practicing the invention or used to practice the invention by generating three dimensional models and/or determining the structures involved in ligand binding. Computer program such as INSIGHT and GRASP allow further manipulation and the ability to introduce new structures. In addition, high throughput binding and bioactivity assays can be devised using purified recombinant protein and modern reporter gene transcription assays described herein and known in the art in order to refine the activity of a CDL.

Generally, the computational method of designing a ERR3 synthetic ligand comprises two steps:

1) determining which amino acid or amino acids of ERR3-LBP interacts with a first chemical moiety (at least one) of the ligand using a three dimensional model of a crystallized protein comprising an ERR3-LPB with a bound ligand; and 2) selecting a chemical modification (at least one) of the first chemical moiety to produce a second chemical moiety with a structure to either increase or decrease an interaction between the interacting amino acid and the second chemical moiety compared to the interaction between the interacting amino acid and the first chemical moiety.

As shown herein, interacting amino acids form contacts with the ligand and the center of the atoms of the interacting amino acids are usually 2 to 4 angstroms away from the center of the atoms of the ligand. Generally these distances are determined by computer as discussed herein and as it is decribed by Mc Ree (1993), however distances can be determined manually once the three dimensional model is made. Also, Robert Esnouf has described how performing stereochemical figures of three dimensional models using for instance the program Bobscript. The program is on the website for the Division of Structural Biology, Oxford University.

More commonly, the atoms of the ligand and the atoms of interacting amino acids are 3 to 4 angstroms apart. The invention can be practiced by repeating step 1 and 2 above to refine the fit of the ligand to the LBP and to determine a better ligand, such as an agonist. The three dimensional model of ERR3 can be represented in two dimensions to determine which amino acids contact the ligand and to select a position on the ligand for chemical modification and changing the interaction with a particular amino acid compared to that before chemical modification. The chemical modification may be made using a computer, manually using a two dimensional representation of the three dimensional model or by chemically synthesizing the ligand. The ligand can also interact with distant amino acids after chemical modification of the ligand to create a new ligand. Distant amino acids are generally not in contact with the ligand before chemical modification. A chemical modification can change the structure of the ligand to make a new ligand that interacts with a distant amino acid usually at least 4.5 angstroms away from the ligand, preferably wherein said first chemical moiety is 6 to 12 angstroms away from a distant amino acid. Often distant amino acids will not line the surface of the binding activity for the ligand, they are too far away from the ligand to be part of a pocket or binding cavity. The interaction between a LBP amino acid and an atom of an LBP ligand can be made by any force or attraction described in nature. Usually the interaction between the atom of the amino acid and the ligand will be the result of a hydrogen bonding interaction, charge interaction, hydrophobic effect, van der Waals interaction or dipole interaction. In the case of the hydrophobic effect it is recognized that is not a per se interaction between the amino acid and ligand, but rather the usual result, in part, of the repulsion of water or other hydrophilic group from a hydrophobic surface. Reducing or enhancing the interaction of the LBD and a ligand can be measured by calculating or testing binding energies, computationally or using thermodynamic or kinetic methods as known in the art.

Chemical modifications will often enhance or reduce interactions of an atom of a LBD amino acid and an atom of the ligand. Steric hindrance will be a common means of changing the interaction of the LBD cavity with the activation domain.

However, as will be understood by those of skill in the art upon this disclosure, other structure based design methods can be used. Various computational structure based design methods have been disclosed in the art.

For example, a number computer modeling systems are available in which the sequence of the ERR3-LBP structure (i.e., atomic coordinates of ERR3-LBP and/or the atomic coordinates of the ligand binding site, the bond and dihedral angles, and distances between atoms in the active site such as provided in Tables 1 or 2 can be input. This computer system then generates the structural details of the site in which a potential ERR3-LBP ligand compound binds so that complementary structural details of the potential modulators can be determined. Design in these modelling systems is generally based upon the compound being capable of physically and structurally associating with ERR3-LBP. In addition, the compound must be able to assume a conformation that allows it to associate with ERR3-LBP. Some modelling systems estimate the potential inhibitory or binding effect of a potential ROR modulator prior to actual synthesis and testing.

Methods for screening chemical entities or fragments for their ability to associate with ERR3-LBP are also well known. Often these methods begin by visual inspection of the active site on the computer screen. Selected fragments or chemical entities are then positioned with the ERR3-LBP. Docking is accomplished using software such as QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, P. J.J. Med. Chem. 1985 28: 849-857), AUTODOCK (Goodsell, D. S. and Olsen, A. J. Proteins, Structure, Functions, and Genetics 1990 8: 195-202), and DOCK (Kunts et al. J. Mol. Biol. 1982 161:269-288).

Upon selection of preferred chemical entities or fragments, their relationship to each other and ERR3-LBP can be visualized and then assembled into a single potential modulator. Programs useful in assembing the individual chemical entities include, but are not limited to, CAVEAT (Bartlett et al. Molecular Recognition in Chemical and Biological Problems Special Publication, Royal Chem. Soc. 78, 00. 182-196 (1989)) and 3D Database systems (Martin, Y. C. J. Med. Chem. 1992 35:2145-2154).

Alternatively, compounds may be designed de novo using either an empty active site or optionaly including some portion of a known inhibitor. Methods of this type of design include, but are not limited to LUDI (Bohm H-J, J. Comp. Aid. Molec. Design 1992 6:61-78) and LeapFrog (Tripos Associates, St. Louis Mo.).

For "fitting" or "docking" a ligand compound to the LBP of the ERR3 receptor, starting from the structural coordinates of the protein complex of the invention which are set forth in Table 1, or alternatively starting from the structural coordinates of the protein complex with diethylstilbestrol which are set forth in Table 2, the one skilled in the art may use known techniques such as those reviewed by Sheridan et al. (1987), Goodford (1984), Beddell (1985), Hol (1986), Verlinde et al. (1994) and Blundell et al. (1987).

Fitting or docking a ligand compound to the LBP of the ERR3 receptor, starting from the structural coordinates of the protein complex of the invention which are set forth in Table 1, can also be performed using software such as QUANTA and SYBYL, following by energy minimisation and molecular dynamics with standard molecular mechanic force fields such as CHARMM and AMBER. Examples of computer programs which assist in the selection of chemical fragment or chemical entities useful in the present invention include, but are not limited to, GRID (Goodford, P. J.J. Med. Chem. 1985 28: 849-857), AUTODOCK (Goodsell, D. S. and Olsen, A. J. Proteins, Structure, Functions, and Genetics 1990 8: 195-202), and DOCK (Kunts et al. J. Mol. Biol. 1982 161:269-288).

Upon selection of preferred chemical entities or fragments, their relationship to each other and ERR3-LBP can be visualised and then assembled into a single potential modulator. Programs useful in assembing the individual chemical entities include, but are not limited to CAVEAT (Bartlett et al. Molecular Recognition in Chemical and Biological Problems Special Publication, Royal Chem. Soc. 78, 00. 182-196 (1989) and 3D Database systems (Martin, Y. C. J. Med. Chem. 1992 35:2145-2154).

Alternatively, compounds may be designed de novo using either an empty active site or optionally including some portion of a known inhibitor. Methods of this type of design include, but are not limited to LUDI (Bohm H-J, J. Comp. Aid. Molec. Design 1992 6:61-78) and LeapFrog (Tripos Associates, St. Louis Mo.).

Most preferably, according to the invention, the structure determination of a crystallised protein complex, whether free of a ligand compound or under the form of a complex with a ligand compound, is performed by molecular replacement using AmoRe, as described by Navaza et al. (1994) and the homodimer of the hERα LBD/GRIP1 NR box complex described by Shiau et al. (1998) as the search model.

Most preferably, the structure is refined at 2.7 Å resolution using CNS described by Brunger et al. (1998), with 21641 significant unique reflections (90.1% completeness).

Most preferably, manual adjustments and rebuilding of the model are performed using the program O described by Jones et al. (1991). The final model ($R_{cryst}$=23.3%, $R_{free}$=26.7% (test set: 5% of the reflections)Protein Data Bank code 1KV6) containing 31 added water molecules is validated using PROCHECK described by Laskowski et al. (1993).

Most preferably, the probe-occupied volume of the LBP of the ERR3 receptor is calculated with VOIDOO described by Kleywegt et al. (1994).

Some ligands such as diethylstilbestrol (DES) and 4-hydroxytamoxifen (4OHT) have been reported to deactivate ERRs. We solved the crystal structure of an ERR3 LBD/coactivator peptide complex and, based on this structure, our docking studies have suggested a mechanism for receptor deactivation upon ligand binding and the mechanism was confirmed by the crystal structure of the ERR3 LBD/DES complex. DES binds to and inactivates all three ERRs, so it cannot be used as an isotype-specific antagonist since all isotypes would be deactivated, leading to a superposition of all three isotype-specific transcriptional modulations. On the other hand, 4OHT binds both ERR2 and ERR3, though it appears to inactive only ERR3 in cell-based assays. Anyhow, there is a need for ligands that clearly bind specifically to only one of the three ERR isotypes, resulting in the specific deactivation (or alternatively in the specific super-activation) of the said isotype.

The crystal structure of the ERR3 LBD/DES complex and the homology models of the ERR1 LBD and the ERR2 LBD together constitute the starting point for the design of high-affinity, isotype-specific antagonists.

According to the present invention, a method, which can be implemented via a computer-based system, is provided for the identification or design of ligands which bind specifically to one of the three ERR isotypes. A computer-based system implementing the present invention includes a data-storage means for storing data corresponding to the crystal structure of the ERR3 LBD or to homology models of the ERR1 and ERR2 LBDs, and a data analysing means such as a computer program for analysing data stored in the data-storage means for identifying or designing ligands capable of binding to the LBD of one of the ERR isotypes.

The crystal structure of the err3 LBD in the unliganded, active (agonist-like)conformation can be obtained as described above. The crystal structure of the ERR3 LBD in the liganded, inactive (antagonist-like) conformation can also be obtained as described above, when using the structural coordinates that are reported in Tables 1 or 2. Homology models of the ERR1 and ERR2 LBDs in the unliganded, active (agonist-like) and in the liganded, inactive (antagonist-like) conformations can be obtained by the one skilled in the art from the corresponding ERR3 LBD structure and the sequence alignment provided in FIG. 1B by using commercially available homology software programs such as MODELLER (Accelrys, San Diego, Calif., USA; Sanchez R. and Sali A (2000) "Comparative protein structure modelling. Introduction and practical examples with Modeller", Methds Mol. Biol. 143:97-129).

Use of a computer program has two main goals: complex prediction and virtual screening.

Complex Prediction

In the first approach (complex prediction), one starts from a small molecule selected on the basis of a visual examination of the ligand-binding pocket as revealed by X-ray crystallography or predicted from homology modelling. Indeed, the knowledge of the ligand-binding pocket gives indications about the size, the shape, and putative anchoring groups of the ligand. Once a suitable candidate is selected, its molecular model can be built thanks to modules of programs such as the QUANTA Molecular Modeling Package (Accelrys, San Diego, Calif., USA). Then the putative ligand is docked manually in the ligand-binding pocket by the one skilled in the art to evaluate its suitability as a candidate ligand, based on:

the absence of steric clashes with atoms from the protein residues forming the ligand-binding pocket (showing the physical possibility to be accommodated in the pocket), the possibility to form favourable interactions with atoms from the pocket such as salt bridges, hydrogen bonds, or van der Waals contacts (showing the potential for a high affinity for the receptor).

This procedure can be referred to as "manual" design.

In an improved procedure, the position of the manually docked ligand in the ligand-binding pocket is optimised through the use of an energy minimization algorithm such as the one provided in CNS (Brunger, A. T. et al. (1998) "Crystallography and NMR system (CNS): A new software system for macromolecular structure determination" Acta Cryst. D54: 905-921). In an even further improved procedure, docking programs are used to predict the geometry of the protein-ligand complex and estimates the binding affinity. Programs that perform flexible protein-ligand docking include GOLD (Jones et al. (1995) J. Mol. Biol. 245:43-53), FlexX (Rarey, M. et al. (1995) "Time-efficient docking of flexible ligands into active sites of proteins" Proc. Int. Conf. Intell. Syst. Mol. Biol. 3:300-308, AAAI Press, Menlo Park, Calif., USA), and Dock (Ewing, T. J. A. and Kuntz, I. D. (1997) "Critical evaluation of search algorithms for automated molecular docking and database screening" J. Comput. Chem. 18:1175-1189). The SuperStar program (Verdonk, M. L. et al. (1999) "A knowledge-based approach for identifying interaction sites in proteins" J. Mol. Biol. 289; 1093-1108) is used for the prediction of favourable interaction sites in proteins.

Virtual Screening

In the second approach (virtual screening), a more advanced procedure, the computer program is used to search a whole small-molecule database (see for instance: Makino, S. and Kuntz, I. D. (1997) "Automated flexible ligand docking method and its application for database search" J. Comp. Chem. 18:1812-1825).

Once a ligand has been selected on the basis of its predicted binding to the receptor through docking studies as described above, it can be validated according to any of the methods below:

a) Detecting of the direct binding of the ligand to the receptor, that can be demonstrated by electrospray ionisation mass spectrometry (ESI MS) under non-denaturing conditions, a technique allowing the detection of non-covalent complexes (Loo, J. A., (1997) "Studying noncovalent protein complexes by electrospray ionisation mass spectrometry" Mass Spectrom, Rev. 16:1-23);

b) Measuring the transcription-activating activity of the different ERR isotypes in the presence of the candidate ligand, that can be performed according to Greschik et al. (2002), Tremblay et al. (2001) or Coward et al. (2001).

Thus, from above, assays are known and available for determining whether a ligand identified or designed according to the present invention either agonizes or antagonizes ERR transcriptional activity. High-affinity, high-specificity ligands found in this way can then be used for in vivo assays aiming at the characterization of the regulatory pathways controlled by a given ERR isotype. Additional assays can be carried out in parallel to study the effect of the selected ligands on the transcription-activating activity of ERs (ERα and ERβ) in order to unravel potential cross-talk mechanisms between ERs and ERRs.

Finally, from above, assays are available for determining whether these ligands may be useful therapeutically.

The present invention further relates to a method for selecting a compound that interacts with the Ligand Binding Domain (LBD) of the estrogen-related receptor 3 (ERR3) of SEQ ID NO: 1, wherein said method consists in:

a) selecting or designing a candidate agonist or antagonist compound for the estrogen-related receptor 3 (ERR3) of SEQ ID NO: 1 by performing computer fitting analysis of the candidate agonist or antagonist compound with the three-dimensional structure of the Ligand Binding Domain (LBD) of said ERR3 receptor that is disclosed in the present specification.

The selection or the design of said candidate agonist or antagonist compound is carried out by one of the methods which are extensively described above.

Thus, in a further embodiment, the screening method above, said method further comprises the steps of:

b) obtaining the compound designed or selected at step b); and c) contacting the compound obtained at step c) with a protein containing the peptide fragment as defined herein in order to determine the effect the compound has on transcriptional-activating activity of the estrogen-related receptor 3 (ERR3) of SEQ ID NO: 1.

In a preferred embodiment of said screening method, in step c), the compound which has been selected in step a) is used as the candidate agonist or antagonist compound in step a) of the biological screening method which is used in step c).

According to a first aspect of the screening method above, the candidate ligand compound, more particularly the candidate agonist or antagonist compound, is selected from a library of compounds previously synthesised.

According to a second aspect of the screening method above, the candidate ligand compound, more particularly the candidate agonist or antagonist compound, is selected from compounds, the chemical structure of which is defined in a database, for example an electronic database.

According to a third embodiment of the screening method above, the candidate ligand compound, more particularly the candidate agonist or antagonist compound, is conceived de novo, by taking into account the spatial conformation stabilisation or, in contrast, the spatial conformation changes, that chemical group(s) of said compound may cause, when docked within the LBP of the ERR3 receptor. Indeed, after its de novo conception, and if positively selected, said candidate ligand compound, more particularly said candidate agonist compound or said candidate antagonist compound, can be actually chemically synthesised. According to a fourth embodiment of the screening method above, the candidate ligand compound, more particularly the candidate antagonist compound, is selected from the group consisting of estradiol (E2), diethylstilbestrol (DES) and 4-hydroxytamoxifen (4-OHT).

Another object of the present invention consists of a method for selecting an antagonist compound for the transcriptional-activating activity of the estrogen-related receptor 3 (ERR3) of SEQ ID NO: 1, wherein said method comprises the steps of:

a) generating a three-dimensional model of an ERR3 LBP dimer using the relative structural coordinates of amino acid residues LEU268, ALA272, GLU275, LEU309, ILE310, ARG316, VAL313, LEU345, HIS434, PHE435, LEU454 and PHE450 according to Table 1 for chain A±a root mean square deviation from the backbone atoms of said amino acids of not more than 1.5 Å; and b) performing, for each candidate compound, a computer fitting analysis of said candidate antagonist compound with three-dimensional model generated at step a); and c) selecting, as an antagonist compound, every candidate compound having a chemical structure inducing a steric constraint with PHE435 or LEU345 amino acid residues of the the estrogen-related receptor 3 (ERR3) Ligand Binding Pocket (LBP).

Thus, in a further embodiment, the screening method above, said method further comprises the steps of:

c) obtaining the compound designed or selected at step b); and d) contacting the compound obtained at step c) with a protein containing the peptide fragment of claim 1 in order to determine the effect the compound has on transcriptional-activating activity of the estrogen-related receptor 3 (ERR3) of SEQ ID NO: 1.

In a preferred embodiment of said screening method, in step d), the compound which has been selected in step b) is used as the candidate agonist or antagonist compound in step a) of the biological screening method which is used in step d).

According to a first aspect of the screening method above, the candidate ligand compound, more particularly the candidate agonist or antagonist compound, is selected from a library of compounds previously synthesised.

According to a second aspect of the screening method above, the candidate ligand compound, more particularly the candidate agonist or antagonist compound, is selected from compounds, the chemical structure of which is defined in a database, for example an electronic database.

According to a third embodiment of the screening method above, the candidate ligand compound, more particularly the candidate agonist or antagonist compound, is conceived de novo, by taking into account the spatial conformation stabilisation or, in contrast, the spatial conformation changes, that chemical group(s) of said compound may cause, when docked within the LBP of the ERR3 receptor. Indeed, after its de novo conception, and if positively selected, said candidate ligand compound, more particularly said candidate agonist compound or said candidate antagonist compound, can be actually chemically synthesised. According to a fourth embodiment of the screening method above, the candidate ligand compound, more particularly the candidate antagonist compound, is selected from the group consisting of estradiol (E2), diethylstilbestrol (DES) and 4-hydroxytamoxifen (4-OHT).

The present invention further relates to a crystallised complex between
(i) a complex comprising (i1) the peptide fragment of the ERR3 receptor that is described in the present specification and (i2) a peptide fragment of the SRC-1 coactivator peptide of SEQ ID NO: 2 comprising the Receptor Interaction Domain (RID) thereof; and
(ii) a ligand of the the estrogen-related receptor 3 (ERR3) Ligand Binding Pocket (LBP).

Preferably, within the crystallised complex described above, said ligand consists of an antagonist compound of the estrogen-related receptor 3 (ERR3) of SEQ ID NO: 1.

Preferably, within the crystallised complex described above, said ligand is selected from the group consisting of estradiol (E2), diethylstilbestrol (DES) and 4-hydroxytamoxifen (4-OHT).

The present invention is also directed to a molecular complex model comprising:
(i) the estrogen-related receptor 3 (ERR3) Ligand binding Pocket (LBP) defined by the structural coordinates of amino acid residues LEU268, ALA272, GLU275, LEU309, ILE310, ARG316, VAL313, LEU345, HIS434, PHE435, LEU454 and PHE450 according to Table 1 for chain A±a root mean square deviation from the backbone atoms of said amino acids of not more than 1.5 Å; and
(ii) a ligand for said estrogen-related receptor 3 (ERR3), Ligand binding Pocket (LBP).

According to a first preferred embodiment, said ligand consists of an antagonist compound for the estrogen-related receptor 3 (ERR3) of SEQ ID NO: 1.

According to a second preferred embodiment, said ligand is selected from the group consisting of estradiol (E2), diethylstilbestrol (DES) and 4-hydroxytamoxifen (4-OHT).

In a most preferred embodiment wherein said ligand consists of diethylstilbestrol (DES), the crystallised complex above is defined by the structural coordinates that are set forth in Table 2, which crystallised complex also forms part of the present invention.

For deeper analysis of the interaction between the protein complex of the invention and ligand compounds, notably estradiol (E2), diethylstilbestrol (DES) and 4-hydroxytamoxifen (4-OHT), it has been prepared protein mutants of the LBP of the ERR3 receptor, which are used herein to eventually confirm the ligand interaction results obtained with the wild type LBP of the ERR3 receptor.

These protein mutants are also part of the present invention. Thus, another object of the invention consists of a mutant of the peptide fragment of claim 1, wherein, based on the amino acid residue numbering of SEQ ID NO: 1, said mutant is selected from the group of mutants consisting of:
1) the mutant "PHE435LEU";
2) the mutant "ALA272PHE";
3) the mutant "ALA272LEU"; and
4) the mutant "LEU3451LE; PHE435LEU; PHE450LEU".

The invention is also directed to a nucleic acid which encodes a mutant as described above.

According to a preferred embodiment of said nucleic acid, the open reading frame encoding the mutant is operably linked to a regulatory polynucleotide.

This invention further relates to a recombinant vector comprising, inserted therein, the nucleic acid which is described above.

Another object of the invention consists of a cell host which is transformed with a nucleic acid or a recombinant vector described above.

The present invention is also directed to a machine-readable data storage medium, comprising a data storage material encoded with machine-readable data, wherein said machine-readable data consist of the X-ray structural coordinate data of the Ligand Binding Pocket (LBP) of the estrogen-related receptor 3 (ERR3) according to Table 1.

This invention is also directed to a machine-readable data storage medium, comprising a data storage material encoded with machine-readable data which, when using a machine programmed with instructions for using said data, displays a graphical three-dimensional representation of a crystal of the Ligand Binding Pocket (LBP) of the estrogen-related receptor 3 (ERR3).

The present invention is also directed to a machine-readable data storage medium, comprising a data storage material encoded with machine-readable data, wherein said machine-readable data consist of the X-ray structural coordinate data of the Ligand Binding Pocket (LBP) of the estrogen-related receptor 3 (ERR3) containing one diethylstilbestrol (DES) molecule according to Table 2.

This invention is also directed to a machine-readable data storage medium, comprising a data storage material encoded with machine-readable data which, when using a machine programmed with instructions for using said data, displays a graphical three-dimensional representation of a crystal of the Ligand Binding Pocket (LBP) of the estrogen-related receptor 3 (ERR3) containing one diethylstilbestrol (DES) molecule according to Table 2.

The present invention is also directed to a machine-readable data storage medium, comprising a data storage material encoded with machine-readable data, wherein said machine-readable data consist of the X-ray structural coordinate data of the Ligand Binding Pocket (LBP) of the estrogen-related receptor 3 (ERR3) that is complexed with one diethylstilbestrol molecule (DES) according to Table 2.

This invention is also directed to a machine-readable data storage medium, comprising a data storage material encoded with machine-readable data which, when using a machine programmed with instructions for using said data, displays a graphical three-dimensional representation of a crystal of the Ligand Binding Pocket (LBP) of the estrogen-related receptor 3 (ERR3) that is complexed with one diethylstilbestrol molecule (DES).

The present invention is further illustrated by the following example.

EXAMPLE

A. Material and Methods
A.1. Construction of Recombinant Plasmids
cDNA fragments encoding wt or mutant ERR3 LBDs (residues 229 to 458, human and murine receptor are identical) were generated by PCR and cloned into the vectors pET-15b (Novagen) and pCMX-Gal4. The full length ERR3 cDNA was cloned into the vector pCMX. The RID of hSRC-1 (amino acids 614-764) was cloned by PCR into the vector pGEX-4T1 (Pharmacia).

A.2 Protein Purification, Crystallization, Data Collection and Processing.
The His-tagged ERR3 LBD was expressed in *E. coli* BL21(DE3), purified to more than 95% purity and homogeneity by cobalt affinity chromatography (TALON, Clontech) and gel filtration (HiLoad 16/60 Superdex 200 column, Pharmacia), and concentrated to 10 mg/ml. Cocrystallisation with a 3-molar excess of hSRC-1 peptide (686-700 from SEQ ID NO: 2) was carried out with the hanging-drop vapor-diffusion method (2 ml LBD/peptide solution+2 ml reservoir solution against 500 ml reservoir solution). The Hampton Research Crystal Screen 2 allowed to find preliminary crystallization conditions. In the refined conditions, crystals grow within a few days at 4° C. to a size of ~400×200×200 mm with a reservoir of 100 mM Tris.HCl pH 8.0, 1.5 M ammonium sulfate, and 15% glycerol. Crystals belong to the space group $P4_32_12$ (a=b=83.317 Å and c=240.610 Å) with one homodimer per asymmetric unit and a solvent content of 60%. Crystals were cryoprotected in 100 mM Tris.HCl pH 8.0, 1.5 M ammonium sulfate, 15% glycerol, and 10% ethylene glycol and flash frozen in liquid ethane at liquid nitrogen temperature. X-ray diffraction data to 2.7 Å resolution were collected at the ID14-1 beam line at the ESRF in Grenoble, France. 333,079 reflections were measured within the 15-2.7 Å resolution range, resulting in a final set of 23306 independent reflections (96.7% completeness, $R_{sym}$=4.9% [14.8% for the last shell (2.81-2.70 Å)]. The data were integrated and scaled using the HKL package (Otwinoski et al., 1997). The estimated overall B-factor from the Wilson plot is 71 Å$^2$.

ERR3-LBD DES Complex
Crystallization conditions
    100 mM Tris/HCl (pH 8.0)
    100 mM NaAc
    18% PEG 3350
Data collection at ESRF ID14-1 (1 data set)

| | |
|---|---|
| resolution | 25.0–2.25 (2.33–2.25) |
| total reflections | 299040 |
| unique reflections | 49240 |
| multiplicity | 6.1 |
| Rsym | 3.9% (10.3%) |
| completeness | 99.2 (100%) |
| I/σ | 14.9 (4.3) |

Space Group $P2_1$ (2 homodimers/asymmetric unit) a=71.999/b=77.457/c=95.770/β=97.549

A.3. Structure Determination and Refinement

The structure of the ERR3 LBD was solved by molecular replacement using AmoRe (Navaza et al., 1994) and the homodimer of the hERα LBD/GRIP1 NR box complex (Shiau et al., 1998) as search model. The structure was refined at 2.7 Å resolution using CNS (Brünger et al., 1998), with 21641 significant unique reflections (901% completeness). Manual adjustments and rebuilding of the model were performed using the program O (Jones et al., 1991). The final model ($R_{cryst}$=23.3%, $R_{free}$=26.7% (test set: 5% of the reflections)Protein Data Bank code 1KV6) containing 31 added water molecules was validated using PROCHECK (Laskowski et al., 1993). It exhibits a good geometry with no Ramachandran outliers. The high average B value can be explained by the few crystal contacts, notably for the B subunit. Accordingly, a few side chains in connecting loops are not visible. The probe-occupied volume of the putative ligand-binding pocket was calculated with VOIDOO (Kleywegt et al., 1994).

A.4. Homology Modeling and Ligand Docking Studies.

The homology models of the human ERR1 and ERR2 LBDs were generated with Modeller (Sali et al., 1993) using the ERR3 crystal structure as template and following a standard procedure. Ligands were positioned manually in the pocket.

A.5. In Vitro Protein-Protein Interaction Assay.

The His-tagged wt or mutant ERR3 LBDs, the GST-tagged SRC-1 RID, and GST were expressed in *E. coli* BL21(DE3) and partially purified by affinity chromatography using TALON (Clontech) or Glutathione Sepharose 4B (Pharmacia), respectively. The purity of all proteins was checked by SDS-PAGE and estimated to be about 90%. After purification the proteins were dialyzed in assay buffer (20 mM Tris.HCl pH 8.0, 200 mM NaCl), and concentrated. For the protein-protein interaction assays 2 mg (about 70 pmol) of His-tagged wt or mutant ERR3 LBD were mixed with 4 mg (about 100 pmol) of GST-tagged SRC-1 RID or 4 mg of GST and incubated on ice for 10 mins. Assays were performed in the absence or presence of ligand [$10^{-4}$M DES, $10^{-4}$M 4-OHT, or $10^{-4}$M E2 (Sigma)] in buffer containing 20 mM Tris.HCl pH 8.0, 200 mM NaCl. Protein complexes were resolved on native polyacrylamide gradient gels (8%-25%) using the Phast System (Pharmacia).

A.6. ESI-MS Analysis.

Wt or mutant ERR3 LBD samples (about 3.7 mmol) were dialyzed against 100 mM ammonium acetate buffer (pH 6.5) and incubated for 15 min on ice with a 1.7 molar excess of E2. Prior to ESI-MS analysis samples were diluted two-fold with ammonium acetate buffer (50 mM, pH 6.5) to a final concentration of about 50 mM and continuously injected into the electrospray (ESI) ion source of a Q-TOF2 mass spectrometer (Micromass, Manchester, UK) at a flow rate of 6 µl/min. To prevent dissociation of the ligand in the gas phase during the ionization/desorption process the cone voltage was optimized to 20 V. Mass data were acquired in the positive ion mode on a mass range of 1000-5000 m/z. The instrument was calibrated with multiply charged ions produced by horse heart myoglobine diluted to 2 pmol/µl in a 1:1 water-acetonitrile mixture (v/v) acidified with 1% formic acid.

A.7. Cell Culture and Transient Transfection Experiments.

COS-1 and BHK cells were cultured in DMEM supplemented with 5% FCS, penicillin, streptomycin, and glutamine. Neuro2A cells were cultured in EMEM supplemented with 10% FCS, penicillin, streptomycin, glutamine, and non-essential amino acids. Transient transfection assays were carried out in 24-well plates ($0.5 \times 10^5$ cells per well for COS-1 and Neuro2A cells, $0.25 \times 10^5$ cells per well for BHK cells) using the standard calcium phosphate coprecipitation technique as described in Greiner et al. (Greiner et al., 1996). Cells were transfected with 250 ng of Gal4(5×)-TATA-LUC, Gal4(3×)-TK-LUC, or ERE(2×)-TK-LUC reporter plasmid and 50 ng per well of pCMX-Gal4-ERR3 or pCMX-ERR3 expression plasmid. The empty plasmids pCMX-Gal4 and pCMX served as control. Experiments were carried out in the absence or presence of $10^{-5}$M DES, $10^{-6}$M 4-OHT, or $10^{-5}$M E2 (Sigma). Luciferase activity was assayed as described in Greiner et al. (1996). All experiments were repeated at least three times.

B. Results

B.1. The Crystal Structure of the ERR3 LBD Reveals a Transcriptionally Active Conformation in the Absence of Ligand.

The structure was solved by molecular replacement using the homodimer of the hERα LBD/GRIP1 NR box complex (Shiau et al., 1998) as search model. The asymmetric unit contains one ERR3 LBD homodimer, each subunit being complexed to a peptide containing the second LXXLL motif of the RID of SRC-1 (SRC-1 NR box 2, amino acids 686-700) (FIG. 1A).

In FIG. 1A, the ERR3 LBD forms a homodimer with a dimer interface similar to that of ERα. The ERR3 LBD adopts a transcriptionally active conformation with a SRC-1 NR box 2 peptide bound in an α-helical conformation. The peptide interacts with the ERR3 LBD as previously observed for other LBD-coactivator peptide complexes.

The ERR3 LBD adopts the canonical three-layered "α-helical sandwich" structure (Wurtz et al., 1996) and superimposes well with the E2-bound hERα LBD (Brzozowski et al., 1997) with a root mean square deviation of 1.05 Å over 197 Cα atoms using a 2.5 Å cut-off. Major differences in the length of α-helices are limited to regions where hERα displays insertions with respect to ERR3, e.g. at the N-termini of H9 and H10 (FIG. 1B).

Figure 1B:
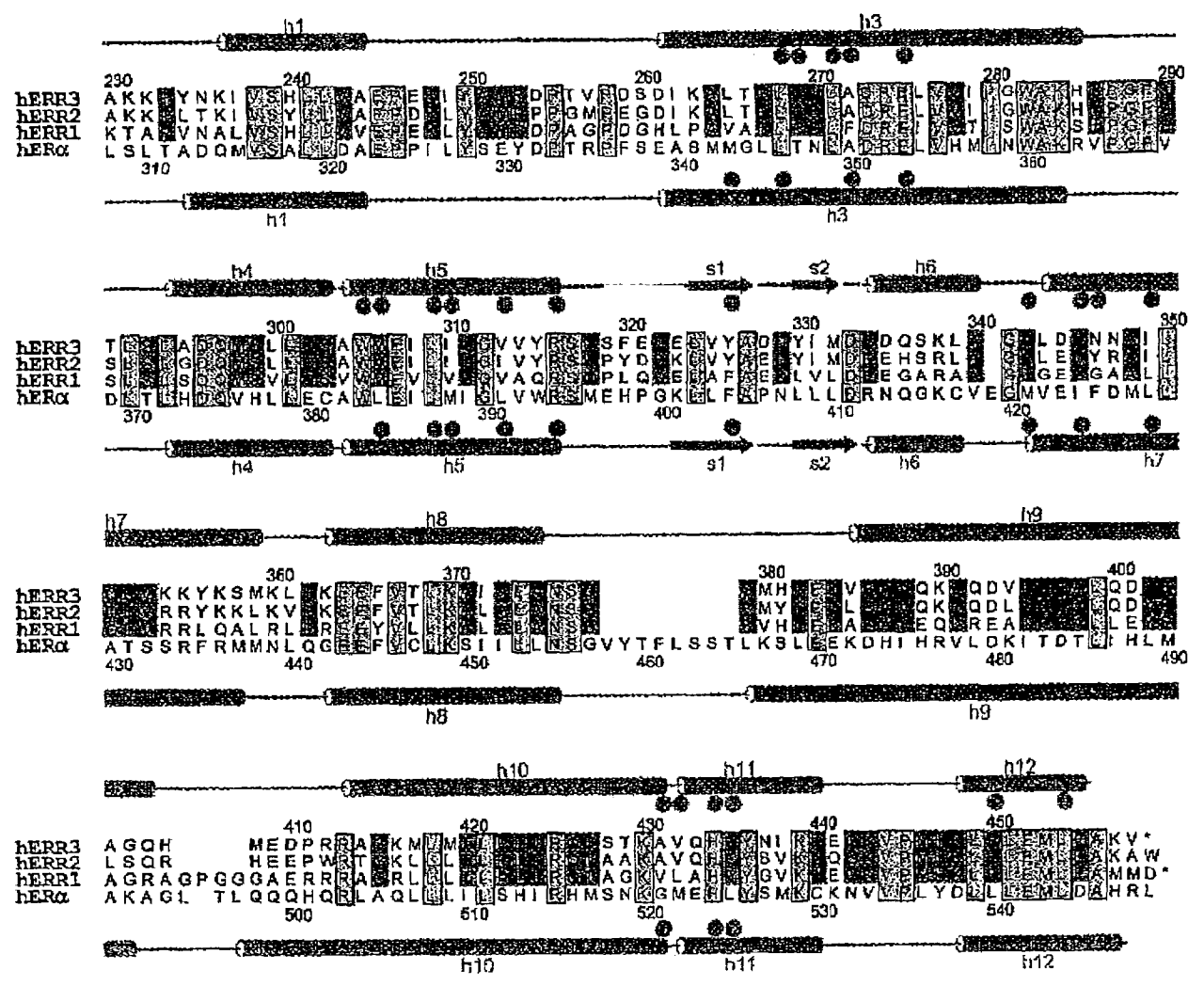

The FIG. 1B represents the alignment of the LBD sequences of human ERR1, 2, and 3, and human ERα. Amino acid residues conserved between all four receptors are marked light gray in closed boxes, residues conserved only in all ERR family members are marked dark gray. Secondary structure elements of the LBDs of hERR3 and hERα are shown above and below the amino acid sequence alignment, respectively. Amino acid numbering is given for hERR3 and hERα. To obtain the residue numbering of hERR1 and hERR2, one has to add the following offset to the hERR3 residue numbering: +56 and −25, respectively. (Note the insertion in ERR1 between H9 and H10.) Dots above and below the alignment mark the residues that line the ligand-binding cavities of hERR3 and hERα, respectively. SwissProt accession numbers are: O75454 (hERR3), P11474 (hERR1), O95718 (hERR2), and P03372 (hERα).

The dimerization mode of the ERR3 LBD is similar to that of the hERα LBD, with a contact area of 1245 Å$^3$ per molecule. Since the residues that form the dimer interface in ERR3 are mostly conserved in ERR1 and ERR2, the LBDs of these receptors may homodimerize in a similar manner. Homodimer formation of the purified LBDs of ERR3 and ERR1 is also observed during gel filtration and by mass spectrometry (FIG. 5), in agreement with the reported homodimeric binding of ERRs to DNA (Petersson et al., 1996; Vanacker et al., 1999b).

In the crystal, the ERR3 LBD adopts the typical transcriptionally active conformation of agonist-bound NRs. The SRC-1 coactivator peptide is bound in a position previously observed for e.g. the LBDs of hPPARγ and hERα (Nolte et al., 1998; Shiau et al., 1998). However, in the present structure the putative ERR3 ligand-binding pocket contains no ligand (FIG. 2A) as revealed by the lack of any significant electron density.

Figure 2A:
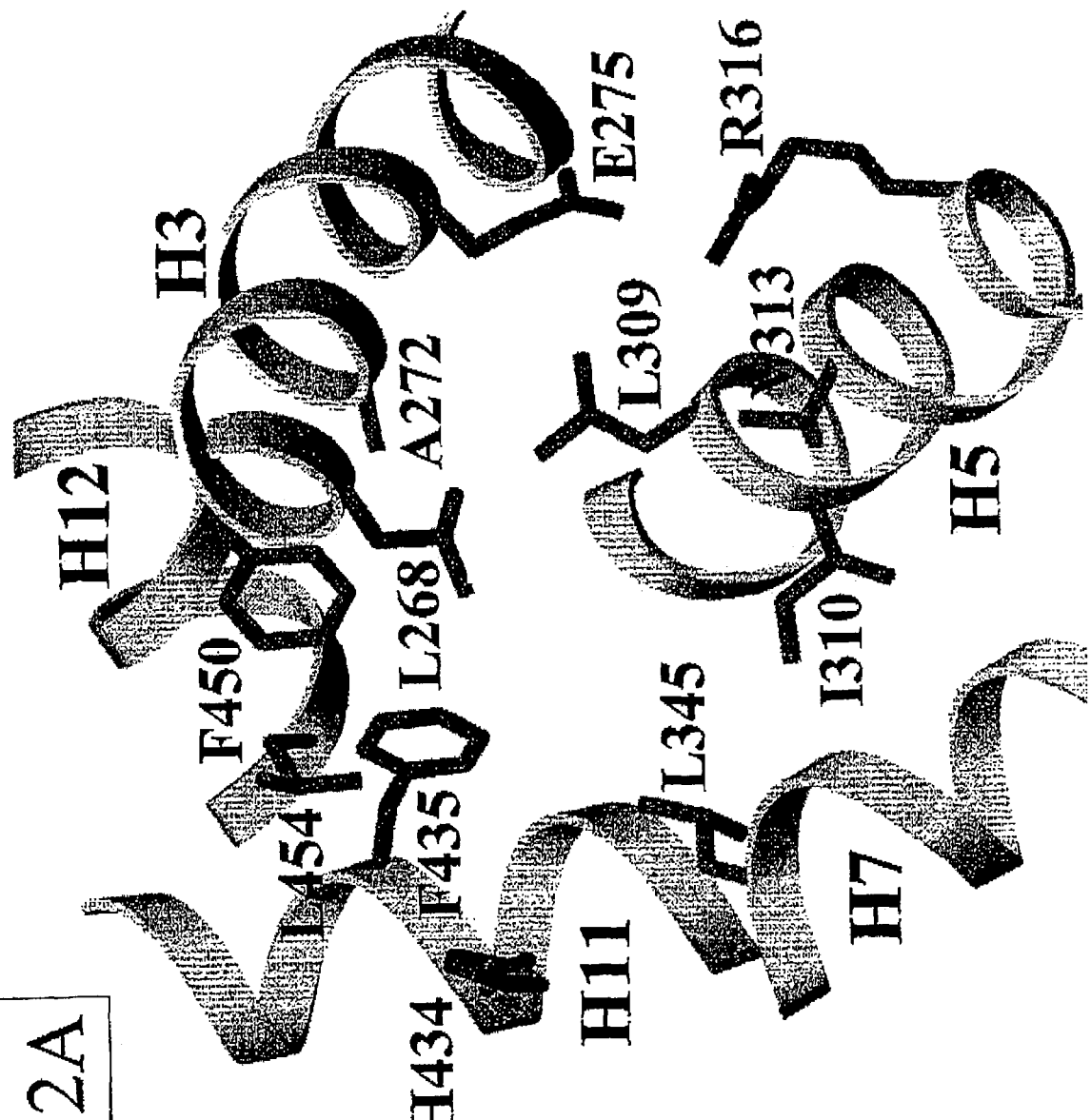
FIG. 2(A) shows a schematic representation of the ligand-binding pocket of the ERR3 LBD.
Figure 2B:
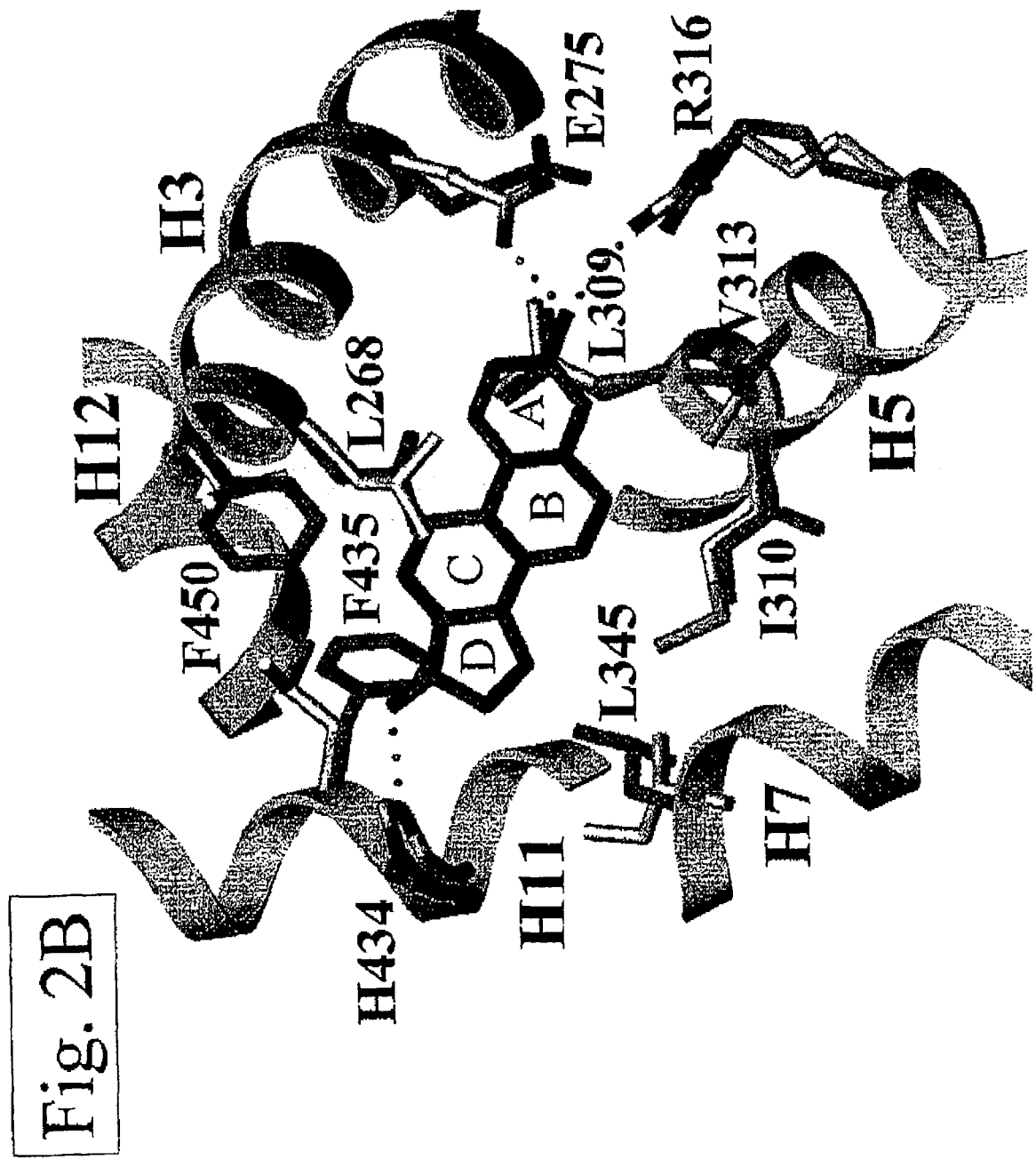
FIG. 2(B) shows a schematic representation of the ligand-binding pocket of the ERR3 LBD with docked estradiol (E2) resulting from the superposition of the hERα LBD/E2 complex over the ERR3 LBD.

FIG. 2A is a schematic representation of the ligand-binding pocket of the ERR3 LBD. Residues are indicated following the one-letter code. In the crystal structure, the positions of all the side chains that line the ligand-binding pocket are well-defined with the exception of that of E275 which exhibits high temperature factors. FIG. 2B is a view as in FIG. 2A with E2 docked into the empty ligand-binding cavity of ERR3. The position of E2 results from the superposition of the ERR3 LBD and the ERα LBD/E2 complex. Steric interference with the D-ring of E2 is mainly due to the presence of F435 (L525 in hERα) and L345 (I424 in hERα) in ERR3. To actual knowledge this is the first crystal structure in which an agonist LBD conformation with a bound coactivator peptide is adopted in the absence of any ligand. Nevertheless the LBD exhibits a putative ligand-binding pocket delimited by 22 amino acids (FIGS. 1B and 2). With the exception of the E275 side chain, the electron density is well defined for all residues that line the ligand-binding pocket. The cavity volume (220 Å$^3$) is the smallest observed so far, the next smallest pockets being those of the rat androgen receptor (~340 Å$^3$) and hERα (~400 Å$^3$) (PBD IDs: 1I37 and 1 ERE, respectively).

The empty ERR3 ligand-binding pocket is formed by hydrophobic and a few polar (Y326, N346, H434) or charged (E275, R316) residues. The two charged residues and the histidine are well conserved among all ERR and ER family members (FIG. 1B). In the hERα/E2 complex, the corresponding E353 and R394 form a hydrogen bonding network which anchors the 3-OH group of the A-ring of E2, while the corresponding H524 forms a hydrogen bond with the 17β-OH group of the D-ring. Therefore, the loosely defined position of the E275 side chain in ERR3 adds further evidence that no ligand is bound.

B.2. Docking of Ligands into the Ligand-Binding Pocket of ERRs.

Modeling of E2 into the empty ERR3 ligand-binding pocket after superposition of the ERR3 and ERα LBDs shows that, due to the high conservation of the surrounding residues, the A-ring including the 3-OH function fits the ERR3 pocket (FIG. 2B) However, a steric clash between the D-ring of E2 and L345 (in H7) or F435 (in H11) would preclude E2 binding to the ERR3 LBD in the active conformation. Due to the constraints imposed by these residues, putative agonists that could further stabilize the active ERR3 LBD conformation would have less than half the size of an E2 molecule (A- and B-ring only).

As for E2, a steric clash with F435 in H11 would also preclude the binding of the previously reported ERR antagonists DES and 4-OHT to the ERR3 LBD in the active conformation. However, assuming a different rotamer for the side chain of F435 and an antagonist position of H12 to avoid steric contacts with F435, DES and 4-OHT could be fitted into the ERR3 cavity (FIGS. 3B-C) with conformations observed in the crystal structures of their respective complexes with the hERα LBD (Shiau et al., 1998).

More particularly, the FIG. 3 is a docking of E2, DES, and 4-OHT into the Ligand-Binding Pocket of ERR3 and ERR1. Important residues are indicated following the one-letter code.

Figure 3A:
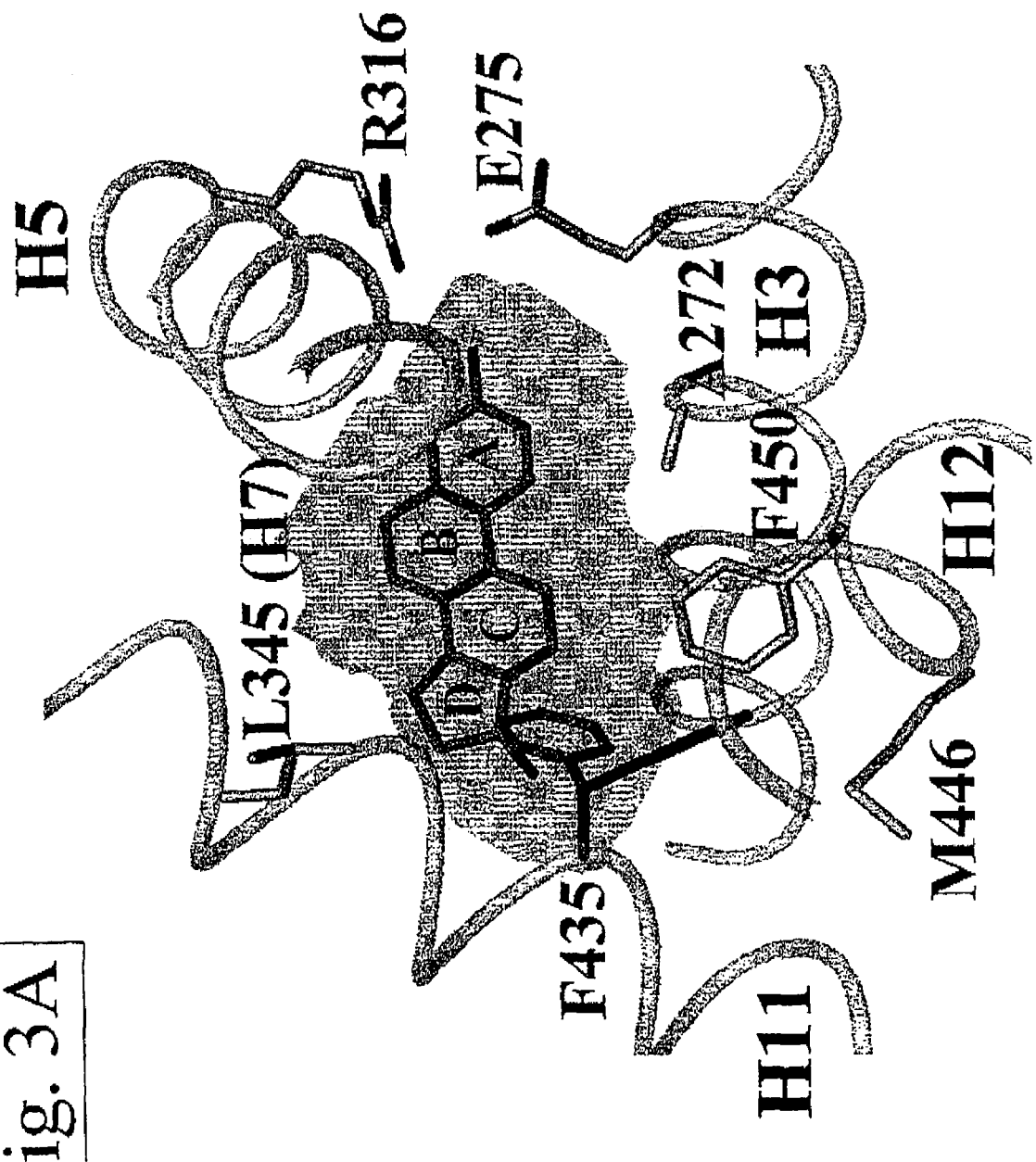
FIG. 3(A) shows a schematic representation of the ligand-binding pocket of the ERR3 LBD with estradiol (E2) into the enlarged ligand-binding pocket with a distinct rotamer of the side chain of PHE435.

In the FIG. 3A, E2 is positioned within the enlarged ERR3 ligand-binding pocket obtained upon moving the side chain of F435 in H11 from its position observed in the crystal structure (marked gray) to the position which induces an antagonist LBD conformation (marked black). The "activation helix" (H12) is still depicted in the agonist position observed in the crystal structure, but would have to move into an antagonist position to avoid a steric clash with the new rotamer of F435. Despite the conformational change of F435, E2 would still not significantly bind to ERR3 due to steric interference with L345 in H7.

Figure 3B:
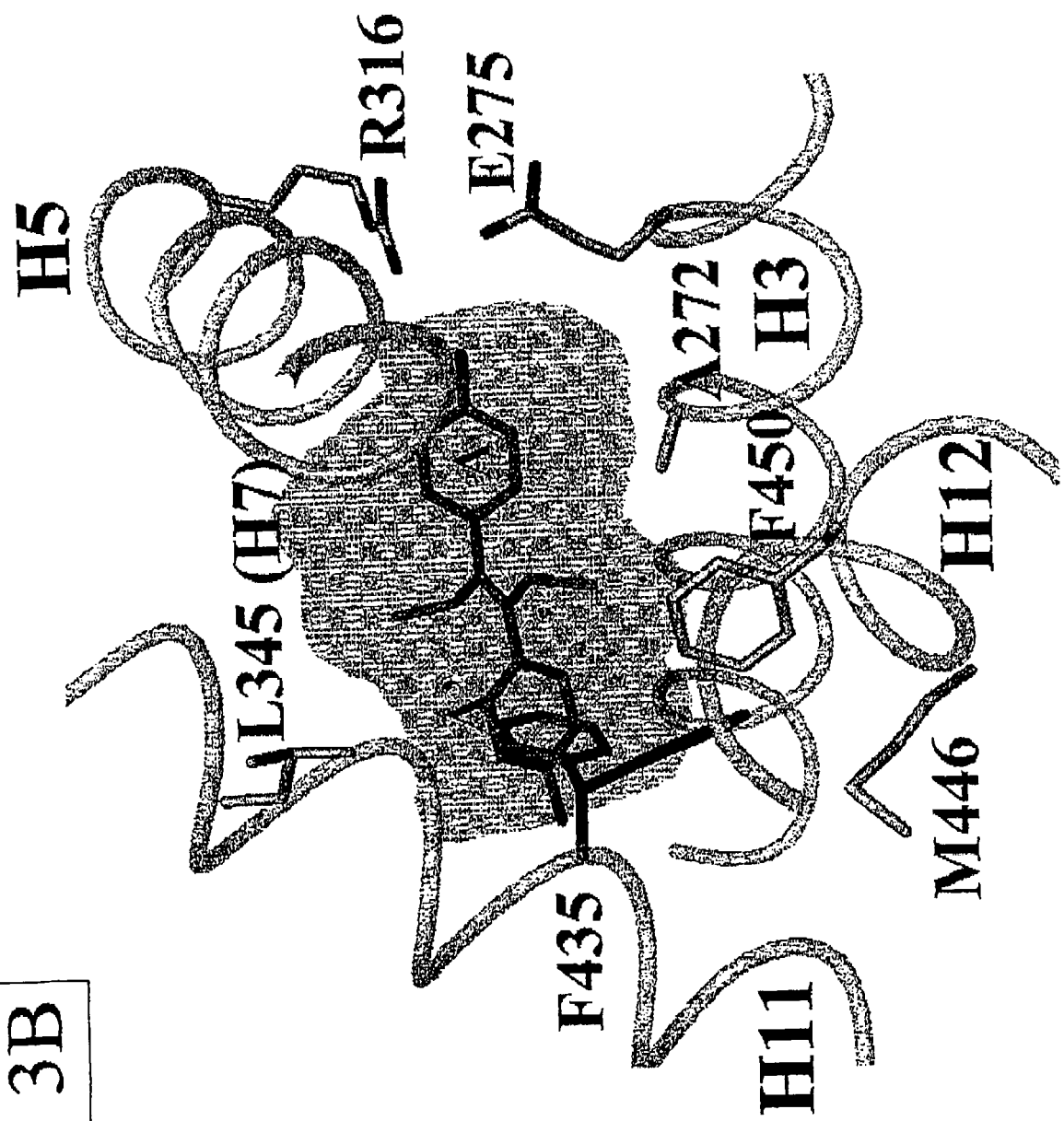
FIGS. 3(B) and 3(C) show schematic representations of DES and 4-OHT, respectively, into the enlarged ligand-binding pocket with a distinct rotamer of the side chain of PHE435.
Figure 3C:
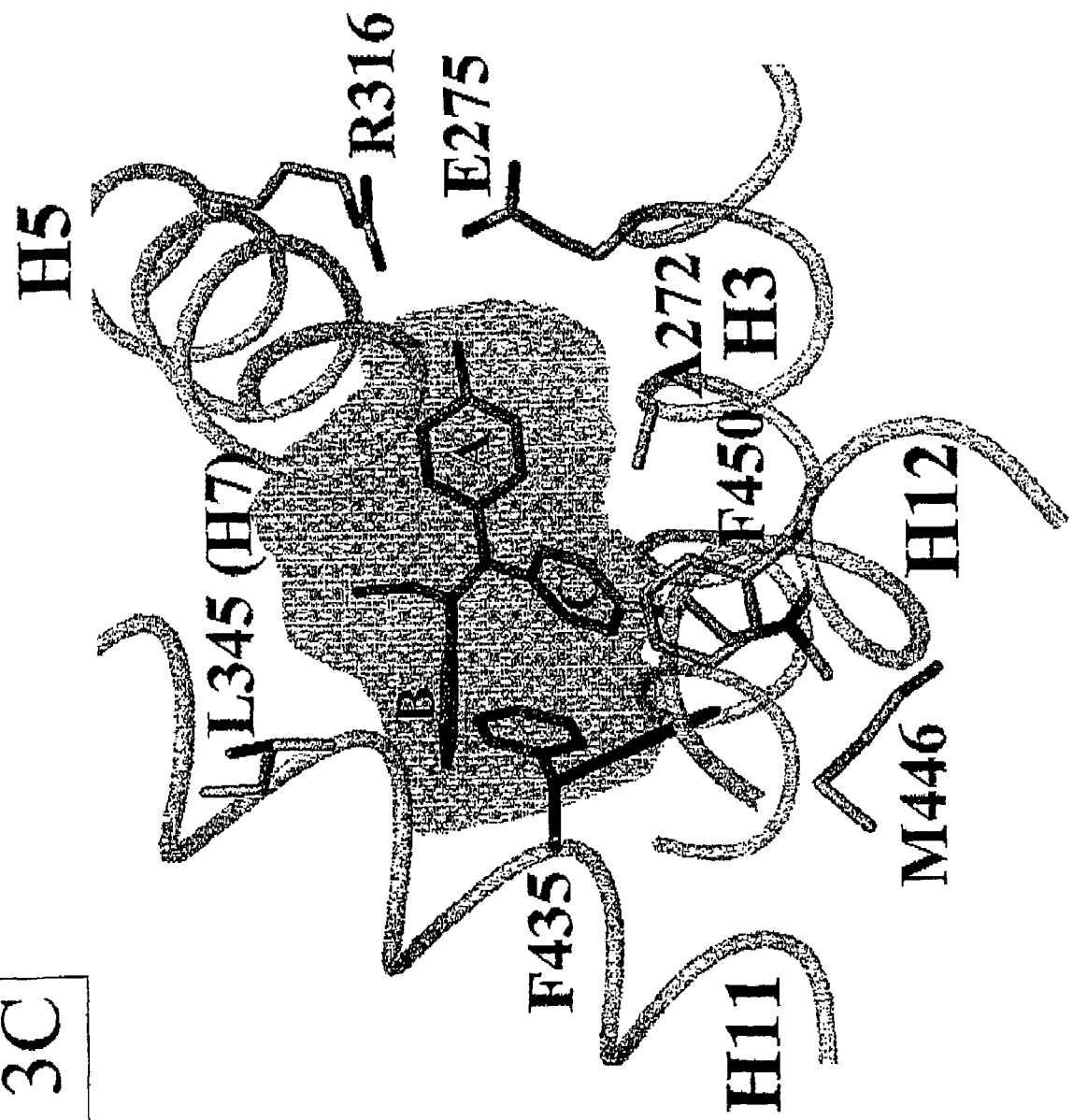

FIGS. 3B and 3C are docking of DES and 4-OHT, respectively, into the enlarged ligand-binding pocket of ERR3. The antagonist action of DES mainly results from the conformational changes of F435 and subsequently H12 induced upon ligand binding. In comparison, the side chain containing the C-ring of 4-OHT also contributes to the antagonist action of this ligand due to steric interference with H12.

Figure 3D:
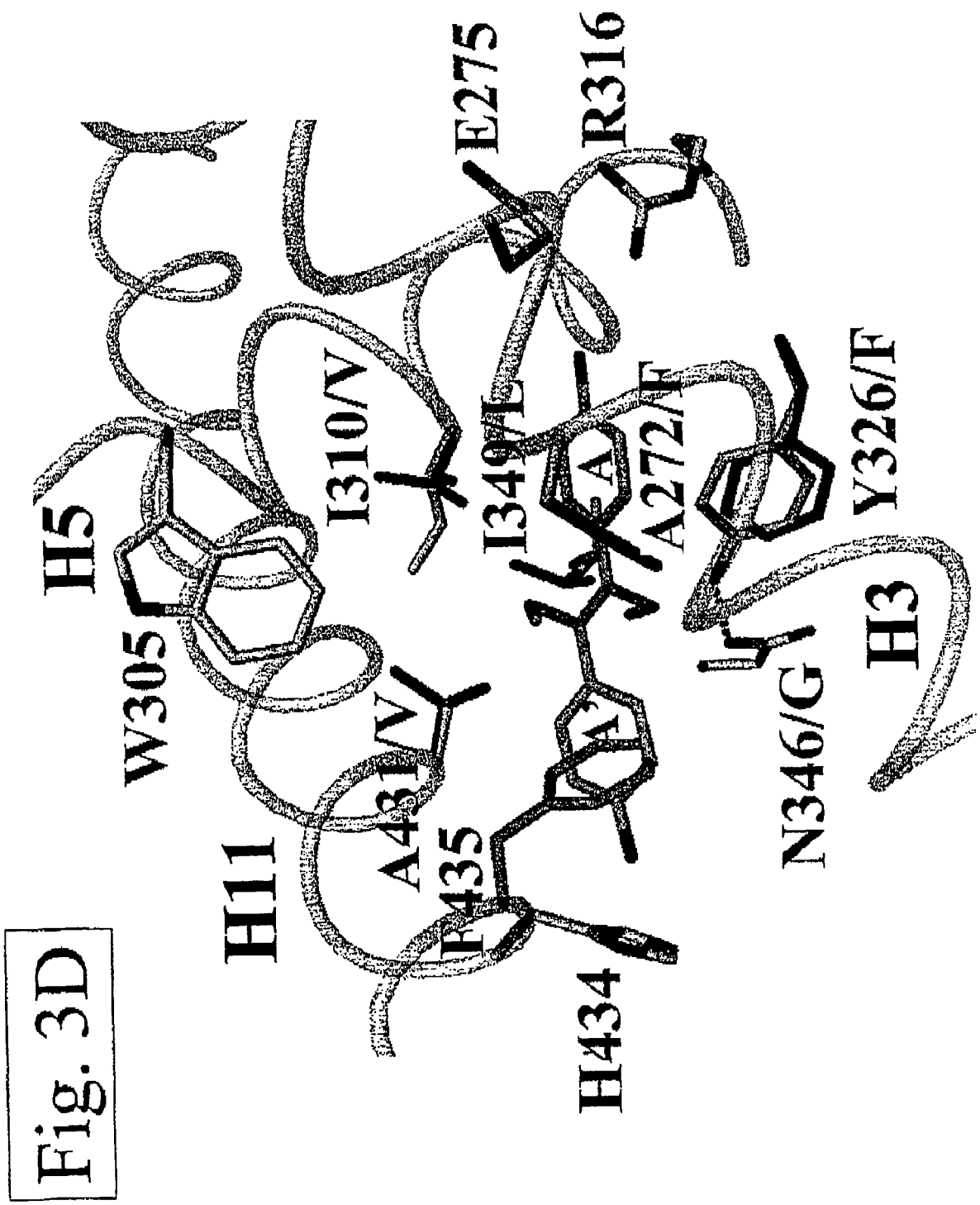
FIG. 3(D) shows a comparison of the ligand-binding cavities of ERR3 (experimental) and ERR1 (modeled).

FIG. 3D is a comparison of the ligand-binding cavities of ERR3 and ERR1. F435 in H11 ( ) is conserved between ERR1 and ERR3 and interferes with the positioning of DES (marked aromatic cycle A'). Residues of ERR1 that account for isotype-specific differences in the ligand-binding pocket are indicated after the slash (/) in the residue name. Most importantly, A272 is replaced by phenylalanine which in the given conformation fills the cavity. Therefore, multiple conformational changes are required to accommodate ligands such as DES in ERR1.

The induced conformational change of F435 appears to be crucial for DES acting as an antagonist on ERR3 while being an ER agonist. In comparison, flipping of F435 and protrusion of the side chain of 4-OHT containing the C-ring from the ERR3 ligand-binding pocket together define the antagonist action of 4-OHT. By contrast, conformational changes of F435 and H12 would not be sufficient for a proper binding of E2 because of steric interference with L345 in H7. Attempts to find a more favourable side chain conformation for L345 (which is an isoleucine residue in ER) only resulted in a maximal distance of about 2.3 Å to the D-ring of E2. As this leucine residue is conserved in all three isotypes, our explanation holds for all ERRs.

The high conservation between the ligand-binding cavities of ERR2 and ERR3, with only two changes (V313 to isoleucine and N346 to tyrosine), suggests that both receptors can bind very similar ligands. While the isoleucine residue in ERR2 replacing V313 in ERR3 should not significantly alter ligand binding, the exchange of N346 for tyrosine appears to be more significant. In ERR3, N346 forms a hydrogen bond with Y326 which is most likely disrupted in ERR2. In ERR2, where two tyrosine residues are found in the corresponding positions, the situation may be similar to ERα where two phenylalanines are involved in hydrophobic interactions.

A lower level of conservation is observed between the cavities of ERR1 and ERR3 (7 amino acid differences) or ERR1 and ERR2 (8 amino acid differences) (FIG. 1B). Interestingly, in ERR1 a glycine and a phenylalanine replace N346 and Y326 of ERR3, respectively. The presence of a glycine opens the ERR1 cavity at one end and possibly allows a more flexible adaptation to the binding of ligands in this region. The major difference, however, is the phenylalanine in ERR1 which replaces A272 in ERR3 (A247 in ERR2 and A350 in ERα). This phenylalanine has been found to be crucial for the constitutive activity of ERR1 (Chen S. et al., 2001). Modeling of the ERR1 LBD based on the ERR3 crystal structure shows that the presence of this phenylalanine strongly modifies the size and shape of the pocket (FIG. 3D). The most populated phenylalanine rotamer found in the rotamer database (53% population) (Dunbrack et al., 1997) fits the ERR1 pocket without interfering with an agonist LBD conformation. However, this phenylalanine conformation would not permit the binding of DES to ERR1. The second most populated phenylalanine rotamer (33% population) would allow the binding of DES but would clash with F450 in H12, W305 in H4, and L309 in H5 (ERR3 numbering). Therefore, DES binding to ERR1 requires a structural adaptation leading to an antagonist LBD conformation. In contrast, no phenylalanine conformation could circumvent a steric clash with the side chain containing the C-ring of 4-OHT, explaining why 4-OHT does not bind ERR1 (Coward et al., 2001).

B.3. The Transcriptionally Active ERR3 LBD Conformation is Ligand-Independent in Vitro.

Figure 4:
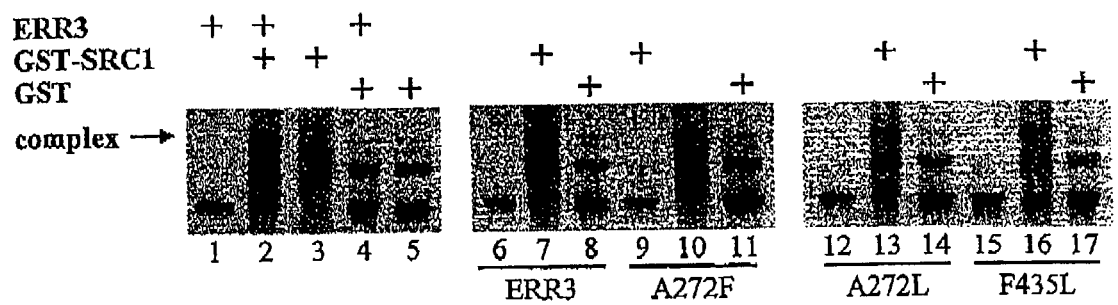
FIG. 4: represents in vitro interaction between wild-type or mutant LBDs of ERR3 and the RID of SRC-1 wherein (A) 2 mg (about 70 pmol) of partially purified His-tagged ERR3 LBD were preincubated for 10 min on ice with 4 mg (about 100 pmol) of GST-tagged SRC-1 RID or GST in the absence or (B) and (C) in the presence of 10-4M 4-OHT or $10^{-4}$M DES.
Figure 4:
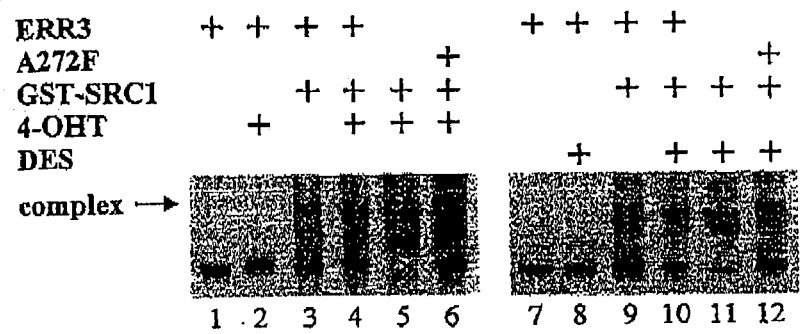
Figure 4:
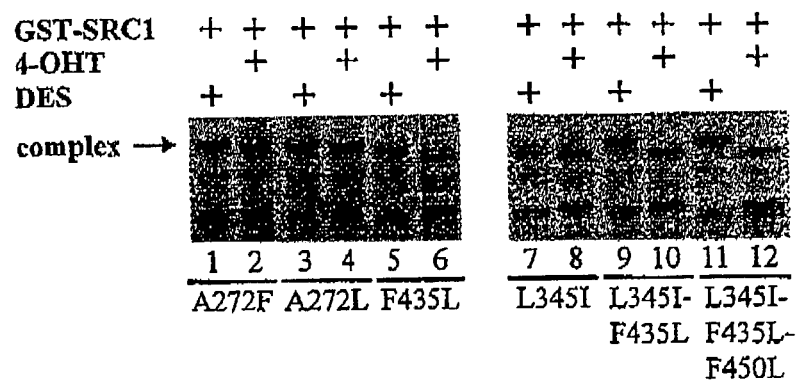

In order to confirm that the agonist conformation of the ERR3 LBD is ligand-independent in vitro and in vivo, it has been generated mutant ERR3 LBDs in which the ligand-binding pocket is either filled up or significantly enlarged and tested wt and mutant receptors in functional assays. In vitro interaction assays with the RID (amino acids 617-764) of the coactivator SRC-1 has first been performed. Hexa-histidine (His)-tagged ERR3, LBD and GST-tagged SRC-1 RID were partially purified by affinity chromatography, the proteins were mixed, and complex formation was monitored on native polyacrylamide gels. More particularly, FIG. 4 represents in vitro interaction between wild-type or mutant LBDs of ERR3 and the RID of SRC-1 wherein (A) 2 mg (about 70 pmol) of partially purified His-tagged ERR3 LBD were preincubated for 10 min on ice with 4 mg (about 100 pmol) of GST-tagged SRC-1 RID or GST in the absence or (B) and (C) in the presence of $10^{-4}$M 4-OHT or $10^{-4}$M DES. Complexes were separated on native polyacrylamide gradient gels.

The ERR3 LBD forms a specific complex with GST-SRC-1 RID but not with GST (FIG. 4A, lanes 1-5), supporting the idea that the active LBD conformation can also be adopted in solution, in agreement with results from other groups (Hong H et al., 1999; Tremblay et al., 2001; Coward et al., 2001).

To block the ligand-binding cavity of the ERR3, LBD A272 has been mutated to phenylalanine (as found in ERR1) or leucine (A272F and A272L mutants). In addition, the ligand-binding pocket of ERR3 has been enlarged by either mutating F435 to leucine or by introducing a triple point mutation (L345I-F435L-F450L) which creates an "ERα-like" ligand-binding pocket. To convert partially the ERR3 ligand-binding pocket to that of ERα, the mutants L345I and L345I-F435L have also been included. All mutants formed specific complexes with GST-SRC-1 RID comparable to the wt receptor (FIG. 4A, lanes 6 to 17; FIG. 4C, lanes 7 to 12), suggesting that the interaction with SRC-1 is independent from the binding of a fortuitous ligand from E. coli.

Next, it has been tested whether 4-OHT or DES could disrupt the ERR3/SRC-1 complexes. The migration of the ERR3 LBD on native gels is retarded upon incubation with 4-OHT indicating a significant conformational change (FIG. 4B, lanes 1 and 2). Furthermore, the complex between the wt LBD and GST-SRC-1 RID is specifically disrupted by 4-OHT (FIG. 4B, lanes 3 to 5), while no effect is observed on the complex between GST-SRC-1 RID and the mutants A272F or A272L in which the ligand-binding cavity is filled up (FIG. 4B, lane 6; FIG. 4C, lanes 2 and 4). In contrast, the ERR3(F435L)/GST-SRC-1 RID complex is still disrupted by 4-OHT, showing that the mutation does not significantly influence the antagonist action of this ligand (FIG. 4C, lane 6). As 4-OHT, DES blocks the interaction of ERR3 with GST-SRC-1 RID (FIG. 4B, lanes 7-11). Noticeably, the conformational change of the ERR3 LBD induced by 4-OHT is more dramatic than that induced by DES, probably due to the presence of the long side chain of 4-OHT. Interestingly however, with the exception of the mutant L345I which behaves as wt ERR3, none of the other mutant ERR3/GST-SRC-1 RID complexes is disrupted by DES (FIG. 4C, lanes 1, 3, 5, 9, and 11). For the A272F and A272L mutants, the most probable explanation is that the binding of DES is further reduced due to the introduction of a bulky side chain. With respect to ERR1 for which DES acts as a full antagonist at a concentration of $10^{-4}$M despite the presence of the bulky phenylalanine residue (Tremblay et al., 2001), this result suggests that the single A272F mutation is not sufficient to generate an "ERR1-like" ligand-binding pocket. Concerning the mutants that contain a F435L mutation (F435L, L345I-F435L, and L345I-F435L-F450L), the modeling studies suggested that the presence of F435 in H11 is crucial for the antagonist action of DES on ERR3. Indeed, replacement of F435 by leucine abolishes the antagonist effect of DES on the ERR3 LBD in vitro. In contrast, due to the presence of its long side chain, 4-OHT still acts as an antagonist on the F435L, L345I-F435L, and L345I-F435L-F450L mutants.

B.4. The Activity of ERR3 is Ligand-Independent in Vivo.

Finally, it has been asked whether ERR3 could activate transcription independently of a putative endogenous ligand The wt and mutant ERR3 LBDs were fused to the DNA-binding domain of Gal4, and Gal4-ERR3 fusion proteins were tested for their potential to activate transcription in transient transfection assays using synthetic reporters in eukaryotic cell lines.

Gal4-ERR3 robustly activates transcription in COS-1 cells from a Gal4(5×)-TATA-LUC reporter plasmid that contains five Gal4 binding sites in front of a minimal promoter and a luciferase (LUC) reporter (FIG. 5A).

Figure 5:
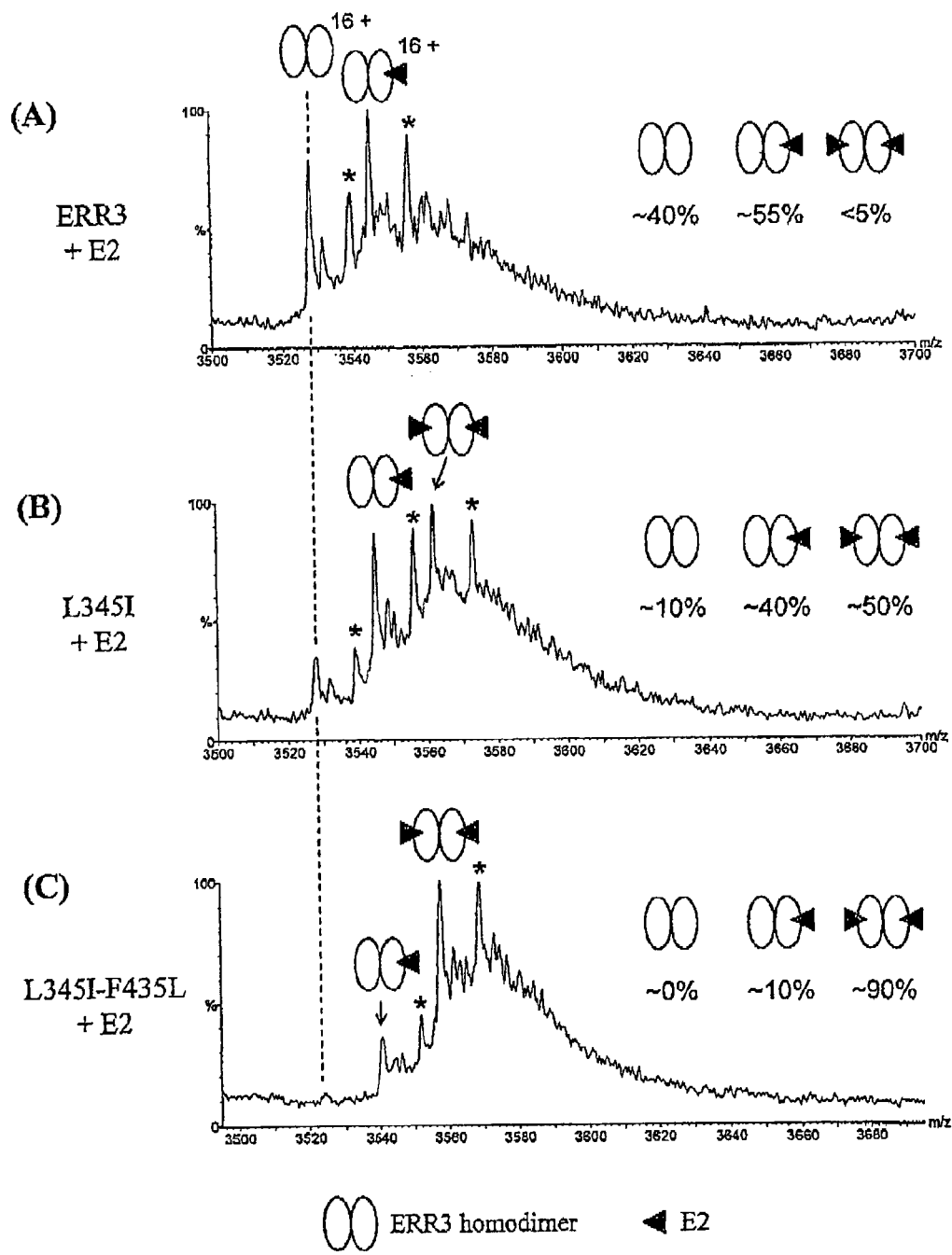
FIG. 5: represents the mass spectrometry analysis of estradiol binding to wild-type and mutant ERR3 LBDs, wherein 3.7 nmol of wild-type ERR3 LBD (A) or the mutants L345I (B) or L345I-F435L (C) were incubated for 15 min on ice with a 1.7 molar excess of E2. Samples were diluted two-fold with ammonium acetate (50 mM, pH 6.5) to a final concentration of about 50 μM and continuously injected into the electrospray (ESI) ion source of a Q-TOF2 mass spectrometer (Micromass, Manchester, UK) at a flow rate of 6 μl/min. Mass spectra were collected at a cone voltage of 20 Volts. Mass data were acquired in the positive ion mode on a mass range of 1000-5000 m/z. The spectrum of the mutant L345I-F435L was aligned with those of the wild-type LBD and the mutant L345I to compensate for the difference in mass. The relative abundance of unliganded or E2-bound species is indicated above the spectra.
Figure 6:
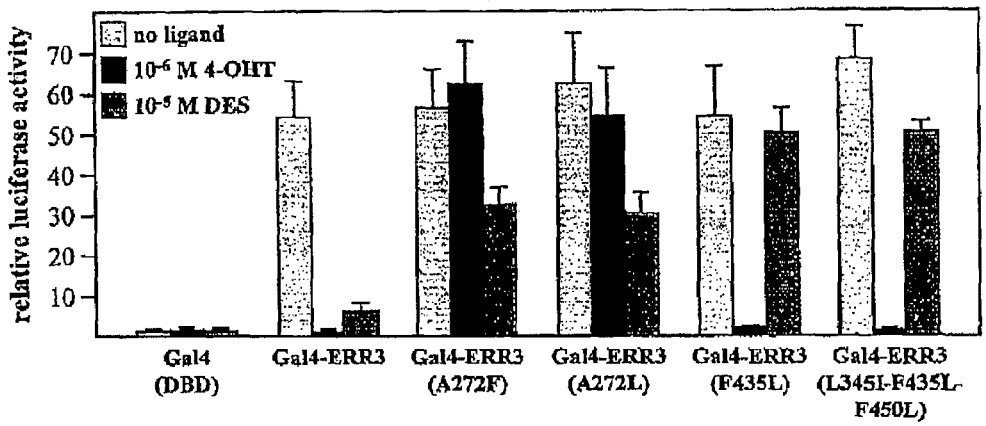
FIG. 6: represents the transcriptional activities of wild-type and mutant ERR3 fusion proteins in transient transfection assays, wherein (A) COS-1 cells were transfected in 24-well plates with 250 ng per well of Gal4(5×)-TATA-LUC reporter and 50 ng of wt or mutant pCMX-Gal4-ERR3 expression plasmid. Experiments were performed in the absence or presence of $10^{-6}$M 4-OHT or $10^{-5}$M DES. (B) Experiments were performed as described in (A) using 250 ng per well of Gal4(3×)-TK-LUC reporter plasmid and 50 ng of wt or mutant Gal4-ERR3 expression plasmid. (C) Experiments were performed as described in (A) in the absence or presence of $10^{-5}$M E2. FIGS. A to C represent an average of three independent experiments. The activity of the Gal4 DBD control was set to one.
Figure 6:
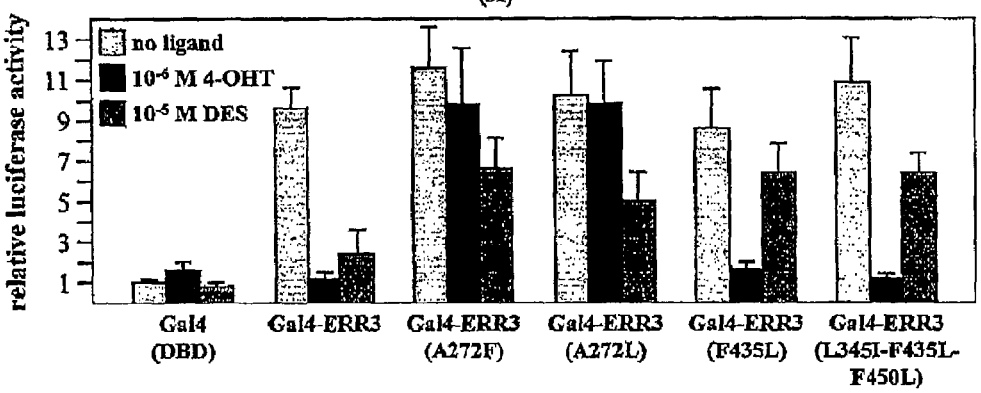
Figure 6:
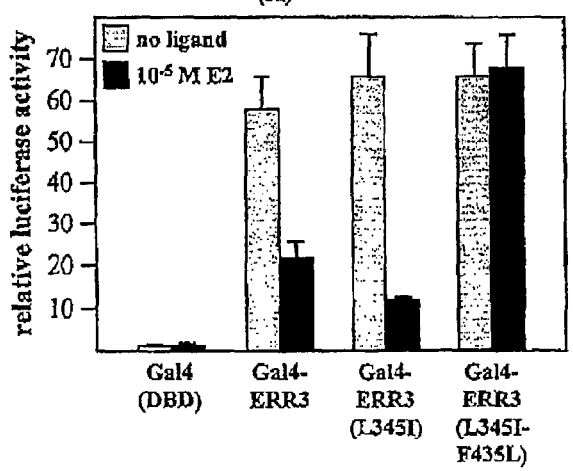

More particularly, the FIG. 5 represents the transcriptional activities of wild-type and mutant ERR3 fusion proteins in transient transfection assays, wherein (A) COS-1 cells were transfected in 24-well plates with 250 ng per well of Gal4(5×)-TATA-LUC reporter and 50 ng of wt or mutant pCMX-Gal4-ERR3 expression plasmid. The empty plasmid pCMX-Gal4 served as control. Experiments were performed in the absence or presence of $10^{-6}$M 4-OHT or $10^{-5}$M DES. (B) Experiments were performed as described in (A) using 250 ng of Gal4(3×)-TK-LUC reporter plasmid and 50 ng of wt or mutant Gal4-ERR3 expression plasmid. FIGS. 5A and 5B represent an average of three independent experiments.

As expected, the activity of Gal4-ERR3 can be blocked efficiently by $10^{-6}$M 4-OHT and partially by $10^{-5}$M DES. The lower antagonist activity of DES compared to 4-OHT can in part be explained by its observed reduced binding to ERRs (Coward et al., 2001). In addition, DES may be less efficient in the displacement of coactivator complexes since in reported in vitro experiments, DES induces a less dramatic conformational change of the ERR3 LBD than 4-OHT (FIG. 4B). Importantly, the Gal4-ERR3(A272F) and Gal4-ERR3(A272L) mutants, in which the ligand-binding pocket is filled up, display the same activity as the wt receptor (FIG. 5A). Less expected is the observation that Gal4-ERR3 (F345L) and Gal4-ERR3(L345I-F435L-F450L) that contain an enlarged ligand-binding cavity also constitutively activate transcription as the wt receptor. The triple point mutation L345I-F435L-F450L generates a ligand-binding cavity which is supposedly similar in size and shape to that of ERα. Therefore, assuming that no fortuitous ligand binds to and stabilizes the mutant protein, the size of the ligand-binding pocket is apparently not the major determinant for the constitutive activity of ERR3. Importantly, as suggested by presently reported in vitro results, none of the mutants is efficiently inactivated by DES, while 4-OHT antagonizes the transcriptional activity of Gal4-ERR3(F435L) and Gal4-ERR3(L345I-F435L-F450L) but not of Gal4-ERR3(A272F) or Gal4-ERR3(A272L).

Comparable results were also obtained in COS-1 cells when a Gal4(3×)-TK-LUC reporter plasmid was used, in which three Gal4 binding sites are placed in front of the thymidine kinase (TK) promoter (FIG. 5B). The activity of Gal4-ERR3 and Gal4-ERR3 mutants was also found to be ligand-independent in Neuro2A cells using both reporter plasmids and in BHK cells using the Gal4(5×)-TATA-LUC reporter, although the overall level of activation was lower in this cell line. Interestingly, neither 4-OHT nor DES repress the constitutive activity of Gal4-ERR3 below basal levels of the TK promoter (FIG. 5B). Similarly, in the presence of 4-OHT, full length ERR3 does not actively repress transcription of the TK promoter when tested with a ERE(2×)-TK-LUC reporter plasmid. These results indicate that ERR3 does not actively recruit corepressors when bound to 4-OHT. This observation is in contrast to findings for ERα which has been reported to recruit corepressors in the presence of 4-OHT (Klinge et al., 2000). In the case of ERα the NTD appears to be involved in the 4-OHT-dependent recruitment of corepressors. Since the N-termini of ERRs and ERs are not conserved, the potential to recruit corepressors may be a distinctive feature of both subfamilies.

B.5. Constitutive Activity of Orphan Nuclear Receptors.

Several orphan receptors such as CARs, RORs, and ERRs have been reported to possess constitutive activating activity in cell-based transcription assays (Giguere et al., 1994; Choi et al., 1997; Hong H et al., 1999; Xie et al., 1999; Chen S et al., 2001). Nevertheless, until now the question whether this apparent constitutive activity results from the binding of endogenous ligands or represents an inherent (ligand-independent) property has not been convincingly addressed. For CARs and ERRs the in vitro interaction of E. coli-expressed receptor LBDs with p160 coactivators was regarded as sufficient evidence for their ligand-independence (Forman et al., 1998; Hong H et al., 1999; Xie et al., 1999). This view has recently been challenged by the finding that NRs can bind fortuitous ligands such as fatty acids or phospholipids from the expression host (Billas et al., 2000; Bourguet et al., 2000; Stehlin et al., 2001). Since these fortuitous ligands can stabilize an antagonist as well as an agonist LBD conformation, it is clear that no convincing evidence for ligand-independent constitutive activity of a nuclear receptor has been presented to date. This idea may be exemplified by the crystal structure of the RORβ LBD, in which a transcriptionally active LBD conformation is stabilized by a fortuitous fatty acid ligand. RORβ mutants in which the ligand-binding pocket is blocked no longer activate transcription in eukaryotic cells, suggesting that RORs are rather ligand-regulated than constitutive orphan receptors (Stehlin et al., 2001). Site-directed mutagenesis has also been applied to modify the ligand-binding cavity of mouse CAR (mCAR) (Tzameli et al., 2000). Interestingly, a double-point mutation of residues in H3 blocks the antagonist effect of androstanol and the agonist effect of 1,4-bis[2-(3,5dichloropyridyloxy)] benzene (TCPOBOP) both in vitro and in vivo without affecting the apparent constitutive activity of the receptor. However, both mutations enlarge rather than efficiently block the ligand-binding cavity of mCAR. Taken into account that mCAR may be activated by different agonists, it cannot be ruled out that the apparent constitutive activity of the double-point mutant results from the binding of an endogenous ligand. Finally, it needs to be clarified whether the observed difference in the interaction between human and murine CAR with p160 coactivators is a consequence of the binding of a fortuitous ligand.

Several lines of evidence presented in this study strongly suggest that ERRs, unlike RORs (and possibly unlike CARs), are ligand-independent activators of transcription. First, the ERR3 LBD adopts in the crystal a transcriptionally active conformation in the absence of any ligand. Second, the small ERR3 ligand-binding pocket can be filled up or significantly enlarged to the size of the ERα pocket without affecting the transcriptionally active conformation in vitro or the transcriptional properties of Gal-ERR3 fusion proteins in vivo. The conclusions drawn for ERR3 are most likely also valid for ERR2 due to the high degree of conservation of their ligand-binding cavities. Differences appear to exist with ERR1: it has been reported (Chen S et al., 2001) that mutation of F328 (corresponding to A272 in ERR3) to alanine results in a receptor that is no longer constitutively active but can be activated by toxaphene.

B.6. Do ERRs Have Natural Ligands?

While there is no apparent need for an ERR3 agonist, molecules with about half the size of E2 could potentially bind to the LBD in the active conformation. Small size ligands (benzoate derivatives) have been reported to bind to and activate the benzoate X receptor (BXR) (Blumberg et al., 1998). However, in contrast to ERR3 the in vitro interaction with SRC-1 and the transcriptional activity of BXR in vivo clearly depend on the presence of these ligands. Since a small putative ERR agonist would probably bind to the receptor with the same low affinity as benzoates to BXR, the inventors currently favor the idea that natural agonists do not play a significant role in ERR signaling. In addition, due to the differences observed in the ligand-binding cavities, a putative ERR1 agonist would most probably differ from one for ERR2/ERR3. In contrast, a natural antagonist could possibly bind to all three ERRs; however, the inventors cannot currently predict the structure of such a molecule.

The design of isotype-specific ligands for all three receptors would substantially enhance the identification of ERR target genes by reverse endocrinology methods. More particularly without limitation an application of the present invention is a tool for the structure-aided design of isotype-specific modulators for estrogen-related receptors and also a method for identifying a compound that modulates binding of a coactivator to estrogen-related receptors. 4-OHT already represents the prototype of a selective antagonist because it binds to ERR2 and ERR3 but not to ERR1 and appears to selectively block the transcriptional activity of ERR3 (Coward et al., 2001). The ERR3 crystal structure suggests that the change of N346 in ERR3 to tyrosine in ERR2 can be further exploited to design high affinity ligands which act selectively on ERR2 or more efficiently on ERR3. In addition, assuming that natural ERR antagonists exist, the mutants A272F and A272L could also contribute to the elucidation of ERR3 function, as they may represent "real" constitutive receptors.

B.7. Concluding Remarks

The reported results strongly suggest that ERRs activate transcription in the absence of ligand and may be inactivated by endogenous ligands instead. Nevertheless, isotype- and cell type-specific differences in the activation potential of ERRs have been observed and the activity of ERR1 may depend on the presence of an unknown serum component. Therefore, additional mechanisms of regulation of ERR transcriptional activity most likely exist. These mechanisms could include a regulatory function of the NTD, specific modification such as phosphorylation of receptor domains and/or association with a subset of tissue-restricted coregulators in vivo.

Until now, the majority of the physiological effects of steroid hormones has been attributed to the binding to "classical" steroid receptors. Cross-talk between ERRs and ERs, for example, has been attributed mainly to the competition for binding sites at certain promoters (Vanacker et al., 1999b). However, if endogenous steroids turn out to be inactivating ligands for ERRs, there may be a more complicated interplay between "classical" steroid and "orphan" receptors which has been underestimated to date. A detailed comparison of the LBDs of steroid receptors and ERRs will allow to more specifically pursue this issue, and in that respect isotype-specific ERR ligands will constitute very powerful tools of investigation and will eventually be used in clinics as modulators of estrogenic treatments.

The crystallographic structure of the ligand-binding domain (LBD) of the orphan nuclear receptor ERR3 in complex with a SRC-1 peptide presented here yielded the picture at atomic resolution of the ligand-binding pocket (LBP) in the transcriptionally active state. In other cases, this information is crucial since it opens the way to the rational design of high-affinity, isotype-specific agonists. But in the present case, the structure demonstrated that the active conformation (allowing to recruit coactivators) was obtained in the absence of any ligand, in good agreement with published reports showing that ERRs are apparently constitutively active (they activate transcription without any added ligand). However, this structure may be useful in the design of molecules that could bind to the LBP in the active state, stabilizing it even further. However, the small size of such putative agonists (due to the small size of the LBP in this conformation) should prevent them from exhibiting very high affinities.

On the other hand, docking studies suggested a mechanism for receptor deactivation upon ligand binding. The structure of a complex between the ERR3 LBD and diethylstilbestrol (DES), a known ERR antagonist, also presented here, allowed to confirm the mechanism that we proposed and now constitutes an experimental starting point for the design of high-affinity, isotype-specific antagonists.

Indeed, as DES binds all ERRs, this molecule cannot be used as an antagonist against one of the 3 isotypes since the 2 others would be also deactivated, leading to unwanted side-effects. Ideally, one should try to design, on the basis of the experimental structure of ERR3 and of homology models of ERR1 and ERR2, high-affinity ligands that bind specifically to one isotype. Such ligands would constitute unique tools to characterize ERR isotype-specific regulatory pathways and associated pathologies, and to investigate crosstalks between ERs and ERRs. For instance, DES is an ER agonist and 4-OHT an ER antagonist but both deactivate ERR3. This could help to elucidate up-to-now unexplained phenomena and unwanted side-effects occuring upon therapeutic use of these molecules.

TABLE 1

ATOMIC COORDINATES OF THE ERR3 LBD/SRC-1 NR BOX 2 PEPTIDE COMPLEX (PDB CODE 1KV6)

REMARK: THE STRUCTURE IS A HOMODIMER OF THE COMPLEX
CHAIN A: ERR3 LBD FIRST MONOMER
CHAIN B: ERR3 LBD SECOND MONOMER
CHAIN C: SRC-1 NR BOX 2 PEPTIDE FIRST MONOMER
CHAIN D: SRC-1 NR BOX 2 PEPTIDE SECOND MONOMER
CRYST1   83.317   83.317   240.610   90.00   90.00   90.00   P   43   21   2   1

TABLE 1-continued

ATOMIC COORDINATES OF THE ERR3 LBD/SRC-1 NR
BOX 2 PEPTIDE COMPLEX (PDB CODE 1KV6)

| | | | | | | | | | | |
|---|---|---|---|---|---|---|---|---|---|---|
| ORIGX1 | | 1.000000 | | 0.000000 | | 0.000000 | 0.00000 | | | |
| ORIGX2 | | 0.000000 | | 1.000000 | | 0.000000 | 0.00000 | | | |
| ORIGX3 | | 0.000000 | | 0.000000 | | 1.000000 | 0.00000 | | | |
| SCALE1 | | 0.012002 | | 0.000000 | | 0.000000 | 0.00000 | | | |
| SCALE2 | | 0.000000 | | 0.012002 | | 0.000000 | 0.00000 | | | |
| SCALE3 | | 0.000000 | | 0.000000 | | 0.004156 | 0.00000 | | | |
| ATOM | 1 | CB | ASN | A | 235 | 15.312 | 18.748 | 7.244 | 1.00 | 59.07 A |
| ATOM | 2 | CG | ASN | A | 235 | 16.333 | 19.916 | 7.099 | 1.00 | 60.77 A |
| ATOM | 3 | OD1 | ASN | A | 235 | 16.604 | 20.646 | 8.060 | 1.00 | 60.13 A |
| ATOM | 4 | ND2 | ASN | A | 235 | 16.904 | 20.072 | 5.899 | 1.00 | 59.13 A |
| ATOM | 5 | C | ASN | A | 235 | 16.405 | 18.041 | 9.410 | 1.00 | 57.22 A |
| ATOM | 6 | O | ASN | A | 235 | 15.652 | 18.551 | 10.246 | 1.00 | 57.97 A |
| ATOM | 7 | N | ASN | A | 235 | 14.848 | 16.481 | 8.138 | 1.00 | 56.76 A |
| ATOM | 8 | CA | ASN | A | 235 | 15.874 | 17.558 | 8.043 | 1.00 | 57.12 A |
| ATOM | 9 | N | LYS | A | 236 | 17.714 | 17.883 | 9.632 | 1.00 | 56.49 A |
| ATOM | 10 | CA | LYS | A | 236 | 18.341 | 18.290 | 10.890 | 1.00 | 56.54 A |
| ATOM | 11 | CB | LYS | A | 236 | 19.854 | 18.129 | 10.821 | 1.00 | 57.66 A |
| ATOM | 12 | CG | LYS | A | 236 | 20.355 | 16.773 | 11.176 | 1.00 | 62.16 A |
| ATOM | 13 | CD | LYS | A | 236 | 19.957 | 15.747 | 10.146 | 1.00 | 64.62 A |
| ATOM | 14 | CE | LYS | A | 236 | 20.740 | 14.448 | 10.371 | 1.00 | 66.56 A |
| ATOM | 15 | NZ | LYS | A | 236 | 22.192 | 14.577 | 10.016 | 1.00 | 66.44 A |
| ATOM | 16 | C | LYS | A | 236 | 18.042 | 19.689 | 11.425 | 1.00 | 55.98 A |
| ATOM | 17 | O | LYS | A | 236 | 17.692 | 19.818 | 12.598 | 1.00 | 56.14 A |
| ATOM | 18 | N | ILE | A | 237 | 18.208 | 20.728 | 10.608 | 1.00 | 53.79 A |
| ATOM | 19 | CA | ILE | A | 237 | 17.950 | 22.080 | 11.097 | 1.00 | 53.72 A |
| ATOM | 20 | CB | ILE | A | 237 | 18.200 | 23.197 | 10.019 | 1.00 | 55.34 A |
| ATOM | 21 | CG2 | ILE | A | 237 | 18.107 | 24.587 | 10.673 | 1.00 | 53.62 A |
| ATOM | 22 | CG1 | ILE | A | 237 | 19.532 | 22.981 | 9.286 | 1.00 | 54.65 A |
| ATOM | 23 | CD1 | ILE | A | 237 | 20.730 | 23.206 | 10.064 | 1.00 | 54.08 A |
| ATOM | 24 | C | ILE | A | 237 | 16.485 | 22.208 | 11.523 | 1.00 | 52.35 A |
| ATOM | 25 | O | ILE | A | 237 | 16.184 | 22.698 | 12.606 | 1.00 | 52.94 A |
| ATOM | 26 | N | VAL | A | 238 | 15.576 | 21.777 | 10.676 | 1.00 | 50.53 A |
| ATOM | 27 | CA | VAL | A | 238 | 14.170 | 21.895 | 11.002 | 1.00 | 53.00 A |
| ATOM | 28 | CB | VAL | A | 238 | 13.306 | 21.412 | 9.816 | 1.00 | 51.84 A |
| ATOM | 29 | CG1 | VAL | A | 238 | 11.826 | 21.503 | 10.162 | 1.00 | 51.85 A |
| ATOM | 30 | CG2 | VAL | A | 238 | 13.616 | 22.264 | 8.579 | 1.00 | 48.46 A |
| ATOM | 31 | C | VAL | A | 238 | 13.800 | 21.166 | 12.310 | 1.00 | 54.66 A |
| ATOM | 32 | O | VAL | A | 238 | 13.025 | 21.689 | 13.106 | 1.00 | 56.25 A |
| ATOM | 33 | N | SER | A | 239 | 14.353 | 19.972 | 12.512 | 1.00 | 55.21 A |
| ATOM | 34 | CA | SER | A | 239 | 14.099 | 19.213 | 13.737 | 1.00 | 55.91 A |
| ATOM | 35 | CB | SER | A | 239 | 14.851 | 17.885 | 13.710 | 1.00 | 57.16 A |
| ATOM | 36 | OG | SER | A | 239 | 14.345 | 17.014 | 12.719 | 1.00 | 59.92 A |
| ATOM | 37 | C | SER | A | 239 | 14.604 | 20.007 | 14.940 | 1.00 | 55.90 A |
| ATOM | 38 | O | SER | A | 239 | 13.951 | 20.104 | 15.983 | 1.00 | 58.30 A |
| ATOM | 39 | N | HIS | A | 240 | 15.794 | 20.568 | 14.781 | 1.00 | 55.71 A |
| ATOM | 40 | CA | HIS | A | 240 | 16.422 | 21.344 | 15.824 | 1.00 | 53.89 A |
| ATOM | 41 | CB | HIS | A | 240 | 17.798 | 21.749 | 15.398 | 1.00 | 52.64 A |
| ATOM | 42 | CG | HIS | A | 240 | 18.575 | 22.382 | 16.490 | 1.00 | 52.76 A |
| ATOM | 43 | CD2 | HIS | A | 240 | 19.088 | 23.625 | 16.614 | 1.00 | 52.33 A |
| ATOM | 44 | ND1 | HIS | A | 240 | 18.884 | 21.715 | 17.654 | 1.00 | 54.18 A |
| ATOM | 45 | CE1 | HIS | A | 240 | 19.552 | 22.528 | 18.456 | 1.00 | 54.93 A |
| ATOM | 46 | NE2 | HIS | A | 240 | 19.690 | 23.693 | 17.848 | 1.00 | 54.64 A |
| ATOM | 47 | C | HIS | A | 240 | 15.657 | 22.590 | 16.172 | 1.00 | 53.72 A |
| ATOM | 48 | O | HIS | A | 240 | 15.573 | 22.949 | 17.339 | 1.00 | 54.27 A |
| ATOM | 49 | N | LEU | A | 241 | 15.124 | 23.259 | 15.156 | 1.00 | 53.50 A |
| ATOM | 50 | CA | LEU | A | 241 | 14.362 | 24.484 | 15.377 | 1.00 | 54.72 A |
| ATOM | 51 | CB | LEU | A | 241 | 14.095 | 25.233 | 14.050 | 1.00 | 54.44 A |
| ATOM | 52 | CG | LEU | A | 241 | 15.273 | 25.741 | 13.197 | 1.00 | 55.27 A |
| ATOM | 53 | CD1 | LEU | A | 241 | 14.754 | 26.441 | 11.939 | 1.00 | 52.00 A |
| ATOM | 54 | CD2 | LEU | A | 241 | 16.128 | 26.690 | 14.038 | 1.00 | 55.29 A |
| ATOM | 55 | C | LEU | A | 241 | 13.041 | 24.115 | 16.052 | 1.00 | 55.36 A |
| ATOM | 56 | O | LEU | A | 241 | 12.469 | 24.911 | 16.818 | 1.00 | 54.24 A |
| ATOM | 57 | N | LEU | A | 242 | 12.569 | 22.903 | 15.902 | 1.00 | 55.02 A |
| ATOM | 58 | CA | LEU | A | 242 | 11.333 | 22.444 | 16.351 | 1.00 | 55.35 A |
| ATOM | 59 | CB | LEU | A | 242 | 10.875 | 21.171 | 15.664 | 1.00 | 54.51 A |
| ATOM | 60 | CG | LEU | A | 242 | 9.982 | 21.387 | 14.440 | 1.00 | 54.68 A |
| ATOM | 61 | CD1 | LEU | A | 242 | 9.646 | 20.061 | 13.858 | 1.00 | 52.51 A |
| ATOM | 62 | CD2 | LEU | A | 242 | 8.706 | 22.139 | 14.820 | 1.00 | 52.83 A |
| ATOM | 63 | C | LEU | A | 242 | 11.523 | 22.228 | 17.849 | 1.00 | 56.92 A |
| ATOM | 64 | O | LEU | A | 242 | 10.640 | 22.521 | 18.650 | 1.00 | 59.47 A |
| ATOM | 65 | N | VAL | A | 243 | 12.678 | 21.736 | 18.252 | 1.00 | 56.84 A |
| ATOM | 66 | CA | VAL | A | 243 | 12.885 | 21.553 | 19.671 | 1.00 | 56.87 A |
| ATOM | 67 | CB | VAL | A | 243 | 14.031 | 20.608 | 19.949 | 1.00 | 55.71 A |
| ATOM | 68 | CG1 | VAL | A | 243 | 14.382 | 20.648 | 21.407 | 1.00 | 52.76 A |
| ATOM | 69 | CG2 | VAL | A | 243 | 13.651 | 19.231 | 19.530 | 1.00 | 52.66 A |
| ATOM | 70 | C | VAL | A | 243 | 13.187 | 22.882 | 20.336 | 1.00 | 58.37 A |

TABLE 1-continued

ATOMIC COORDINATES OF THE ERR3 LBD/SRC-1 NR
BOX 2 PEPTIDE COMPLEX (PDB CODE 1KV6)

| ATOM | 71 | O | VAL | A | 243 | 12.733 | 23.147 | 21.437 | 1.00 | 60.44 | A |
|---|---|---|---|---|---|---|---|---|---|---|---|
| ATOM | 72 | N | ALA | A | 244 | 13.980 | 23.714 | 19.683 | 1.00 | 60.03 | A |
| ATOM | 73 | CA | ALA | A | 244 | 14.320 | 25.021 | 20.238 | 1.00 | 60.41 | A |
| ATOM | 74 | CB | ALA | A | 244 | 15.333 | 25.718 | 19.315 | 1.00 | 60.55 | A |
| ATOM | 75 | C | ALA | A | 244 | 13.083 | 25.925 | 20.450 | 1.00 | 61.17 | A |
| ATOM | 76 | O | ALA | A | 244 | 13.170 | 26.951 | 21.124 | 1.00 | 59.86 | A |
| ATOM | 77 | N | GLU | A | 245 | 11.945 | 25.542 | 19.878 | 1.00 | 62.24 | A |
| ATOM | 78 | CA | GLU | A | 245 | 10.723 | 26.323 | 20.000 | 1.00 | 65.17 | A |
| ATOM | 79 | CB | GLU | A | 245 | 9.623 | 25.670 | 19.137 | 1.00 | 65.72 | A |
| ATOM | 80 | CG | GLU | A | 245 | 8.318 | 26.459 | 19.021 | 1.00 | 70.67 | A |
| ATOM | 81 | CD | GLU | A | 245 | 8.464 | 27.886 | 18.434 | 1.00 | 73.34 | A |
| ATOM | 82 | OE1 | GLU | A | 245 | 7.473 | 28.646 | 18.486 | 1.00 | 74.22 | A |
| ATOM | 83 | OE2 | GLU | A | 245 | 9.542 | 28.259 | 17.911 | 1.00 | 78.05 | A |
| ATOM | 84 | C | GLU | A | 245 | 10.274 | 26.470 | 21.479 | 1.00 | 67.15 | A |
| ATOM | 85 | O | GLU | A | 245 | 9.831 | 25.498 | 22.113 | 1.00 | 68.35 | A |
| ATOM | 86 | N | PRO | A | 246 | 10.367 | 27.694 | 22.046 | 1.00 | 67.71 | A |
| ATOM | 87 | CD | PRO | A | 246 | 10.613 | 28.944 | 21.313 | 1.00 | 66.10 | A |
| ATOM | 88 | CA | PRO | A | 246 | 9.989 | 27.998 | 23.439 | 1.00 | 68.70 | A |
| ATOM | 89 | CB | PRO | A | 246 | 10.199 | 29.506 | 23.521 | 1.00 | 67.18 | A |
| ATOM | 90 | CG | PRO | A | 246 | 9.867 | 29.943 | 22.144 | 1.00 | 65.58 | A |
| ATOM | 91 | C | PRO | A | 246 | 8.578 | 27.601 | 23.920 | 1.00 | 69.96 | A |
| ATOM | 92 | O | PRO | A | 246 | 7.688 | 27.292 | 23.112 | 1.00 | 69.21 | A |
| ATOM | 93 | N | GLU | A | 247 | 8.390 | 27.628 | 25.245 | 1.00 | 71.29 | A |
| ATOM | 94 | CA | GLU | A | 247 | 7.091 | 27.302 | 25.860 | 1.00 | 73.79 | A |
| ATOM | 95 | CB | GLU | A | 247 | 7.276 | 26.909 | 27.343 | 1.00 | 77.55 | A |
| ATOM | 96 | CG | GLU | A | 247 | 8.305 | 25.769 | 27.618 | 1.00 | 83.68 | A |
| ATOM | 97 | CD | GLU | A | 247 | 8.108 | 24.514 | 26.735 | 1.00 | 87.35 | A |
| ATOM | 98 | OE1 | GLU | A | 247 | 6.941 | 24.226 | 26.359 | 1.00 | 89.66 | A |
| ATOM | 99 | OE2 | GLU | A | 247 | 9.113 | 23.811 | 26.426 | 1.00 | 88.64 | A |
| ATOM | 100 | C | GLU | A | 247 | 6.098 | 28.485 | 25.760 | 1.00 | 71.38 | A |
| ATOM | 101 | O | GLU | A | 247 | 6.511 | 29.635 | 25.543 | 1.00 | 70.24 | A |
| ATOM | 102 | N | LYS | A | 248 | 4.800 | 28.221 | 25.909 | 1.00 | 69.13 | A |
| ATOM | 103 | CA | LYS | A | 248 | 3.830 | 29.319 | 25.823 | 1.00 | 67.92 | A |
| ATOM | 104 | CB | LYS | A | 248 | 2.413 | 28.829 | 26.109 | 1.00 | 67.73 | A |
| ATOM | 105 | CG | LYS | A | 248 | 1.879 | 27.717 | 25.225 | 1.00 | 68.95 | A |
| ATOM | 106 | CD | LYS | A | 248 | 0.527 | 27.261 | 25.787 | 1.00 | 72.08 | A |
| ATOM | 107 | CE | LYS | A | 248 | −0.073 | 26.038 | 25.088 | 1.00 | 73.61 | A |
| ATOM | 108 | NZ | LYS | A | 248 | −0.598 | 26.383 | 23.731 | 1.00 | 74.82 | A |
| ATOM | 109 | C | LYS | A | 248 | 4.163 | 30.424 | 26.837 | 1.00 | 67.50 | A |
| ATOM | 110 | O | LYS | A | 248 | 4.615 | 30.141 | 27.965 | 1.00 | 68.04 | A |
| ATOM | 111 | N | ILE | A | 249 | 3.962 | 31.677 | 26.430 | 1.00 | 65.90 | A |
| ATOM | 112 | CA | ILE | A | 249 | 4.187 | 32.839 | 27.294 | 1.00 | 64.66 | A |
| ATOM | 113 | CB | ILE | A | 249 | 5.168 | 33.836 | 26.618 | 1.00 | 64.14 | A |
| ATOM | 114 | CG2 | ILE | A | 249 | 4.944 | 35.267 | 27.101 | 1.00 | 64.40 | A |
| ATOM | 115 | CG1 | ILE | A | 249 | 6.592 | 33.442 | 26.950 | 1.00 | 64.86 | A |
| ATOM | 116 | CD1 | ILE | A | 249 | 7.602 | 34.174 | 26.101 | 1.00 | 66.26 | A |
| ATOM | 117 | C | ILE | A | 249 | 2.807 | 33.487 | 27.544 | 1.00 | 64.54 | A |
| ATOM | 118 | O | ILE | A | 249 | 1.965 | 33.531 | 26.638 | 1.00 | 62.67 | A |
| ATOM | 119 | N | TYR | A | 250 | 2.563 | 33.979 | 28.765 | 1.00 | 64.51 | A |
| ATOM | 120 | CA | TYR | A | 250 | 1.249 | 34.570 | 29.058 | 1.00 | 63.79 | A |
| ATOM | 121 | CB | TYR | A | 250 | 0.666 | 33.888 | 30.282 | 1.00 | 63.54 | A |
| ATOM | 122 | CG | TYR | A | 250 | 0.382 | 32.428 | 30.018 | 1.00 | 62.98 | A |
| ATOM | 123 | CD1 | TYR | A | 250 | 1.386 | 31.460 | 30.186 | 1.00 | 62.57 | A |
| ATOM | 124 | CE1 | TYR | A | 250 | 1.139 | 30.113 | 29.918 | 1.00 | 62.94 | A |
| ATOM | 125 | CD2 | TYR | A | 250 | −0.882 | 32.017 | 29.568 | 1.00 | 61.77 | A |
| ATOM | 126 | CE2 | TYR | A | 250 | −1.145 | 30.681 | 29.292 | 1.00 | 63.29 | A |
| ATOM | 127 | CZ | TYR | A | 250 | −0.128 | 29.735 | 29.470 | 1.00 | 64.61 | A |
| ATOM | 128 | OH | TYR | A | 250 | −0.396 | 28.415 | 29.212 | 1.00 | 67.72 | A |
| ATOM | 129 | C | TYR | A | 250 | 1.088 | 36.082 | 29.185 | 1.00 | 62.80 | A |
| ATOM | 130 | O | TYR | A | 250 | 1.974 | 36.771 | 29.692 | 1.00 | 60.47 | A |
| ATOM | 131 | N | ALA | A | 251 | −0.058 | 36.578 | 28.707 | 1.00 | 63.46 | A |
| ATOM | 132 | CA | ALA | A | 251 | −0.393 | 38.009 | 28.734 | 1.00 | 65.79 | A |
| ATOM | 133 | CB | ALA | A | 251 | −1.623 | 38.277 | 27.898 | 1.00 | 63.61 | A |
| ATOM | 134 | C | ALA | A | 251 | −0.624 | 38.461 | 30.170 | 1.00 | 68.72 | A |
| ATOM | 135 | O | ALA | A | 251 | −0.078 | 39.498 | 30.588 | 1.00 | 71.50 | A |
| ATOM | 136 | N | MET | A | 252 | −1.444 | 37.695 | 30.909 | 1.00 | 69.55 | A |
| ATOM | 137 | CA | MET | A | 252 | −1.738 | 37.942 | 32.325 | 1.00 | 68.97 | A |
| ATOM | 138 | CB | MET | A | 252 | −0.479 | 37.730 | 33.176 | 1.00 | 68.94 | A |
| ATOM | 139 | CG | MET | A | 252 | 0.133 | 36.362 | 33.120 | 1.00 | 70.51 | A |
| ATOM | 140 | SD | MET | A | 252 | 1.373 | 36.201 | 34.442 | 1.00 | 77.25 | A |
| ATOM | 141 | CE | MET | A | 252 | 2.970 | 36.495 | 33.589 | 1.00 | 72.94 | A |
| ATOM | 142 | C | MET | A | 252 | −2.308 | 39.312 | 32.683 | 1.00 | 68.90 | A |
| ATOM | 143 | O | MET | A | 252 | −1.847 | 39.955 | 33.621 | 1.00 | 68.71 | A |
| ATOM | 144 | N | PRO | A | 253 | −3.312 | 39.781 | 31.953 | 1.00 | 69.65 | A |
| ATOM | 145 | CD | PRO | A | 253 | −4.090 | 39.104 | 30.903 | 1.00 | 68.88 | A |
| ATOM | 146 | CA | PRO | A | 253 | −3.878 | 41.102 | 32.287 | 1.00 | 71.43 | A |

TABLE 1-continued

ATOMIC COORDINATES OF THE ERR3 LBD/SRC-1 NR
BOX 2 PEPTIDE COMPLEX (PDB CODE 1KV6)

| ATOM | 147 | CB | PRO | A | 253 | -4.919 | 41.309 | 31.201 | 1.00 | 70.06 | A |
|---|---|---|---|---|---|---|---|---|---|---|---|
| ATOM | 148 | CG | PRO | A | 253 | -5.396 | 39.876 | 30.946 | 1.00 | 69.75 | A |
| ATOM | 149 | C | PRO | A | 253 | -4.518 | 41.092 | 33.679 | 1.00 | 73.71 | A |
| ATOM | 150 | O | PRO | A | 253 | -5.236 | 40.144 | 34.025 | 1.00 | 74.82 | A |
| ATOM | 151 | N | ASP | A | 254 | -4.271 | 42.134 | 34.475 | 1.00 | 75.86 | A |
| ATOM | 152 | CA | ASP | A | 254 | -4.848 | 42.202 | 35.829 | 1.00 | 77.53 | A |
| ATOM | 153 | CB | ASP | A | 254 | -4.444 | 43.495 | 36.541 | 1.00 | 76.10 | A |
| ATOM | 154 | CG | ASP | A | 254 | -4.484 | 43.355 | 38.057 | 1.00 | 77.28 | A |
| ATOM | 155 | OD1 | ASP | A | 254 | -5.349 | 42.593 | 38.563 | 1.00 | 77.32 | A |
| ATOM | 156 | OD2 | ASP | A | 254 | -3.652 | 44.005 | 38.742 | 1.00 | 76.51 | A |
| ATOM | 157 | C | ASP | A | 254 | -6.383 | 42.131 | 35.785 | 1.00 | 79.07 | A |
| ATOM | 158 | O | ASP | A | 254 | -7.031 | 42.880 | 35.052 | 1.00 | 80.20 | A |
| ATOM | 159 | N | PRO | A | 255 | -6.986 | 41.223 | 36.566 | 1.00 | 79.86 | A |
| ATOM | 160 | CD | PRO | A | 255 | -6.409 | 40.050 | 37.234 | 1.00 | 80.20 | A |
| ATOM | 161 | CA | PRO | A | 255 | -8.448 | 41.140 | 36.541 | 1.00 | 80.43 | A |
| ATOM | 162 | CB | PRO | A | 255 | -8.731 | 39.749 | 37.095 | 1.00 | 80.08 | A |
| ATOM | 163 | CG | PRO | A | 255 | -7.422 | 38.996 | 36.876 | 1.00 | 80.85 | A |
| ATOM | 164 | C | PRO | A | 255 | -9.036 | 42.229 | 37.426 | 1.00 | 82.04 | A |
| ATOM | 165 | O | PRO | A | 255 | -10.163 | 42.696 | 37.204 | 1.00 | 81.95 | A |
| ATOM | 166 | N | THR | A | 256 | -8.254 | 42.633 | 38.430 | 1.00 | 82.74 | A |
| ATOM | 167 | CA | THR | A | 256 | -8.674 | 43.665 | 39.374 | 1.00 | 83.01 | A |
| ATOM | 168 | CB | THR | A | 256 | -7.680 | 43.787 | 40.579 | 1.00 | 81.57 | A |
| ATOM | 169 | OG1 | THR | A | 256 | -6.565 | 44.632 | 40.231 | 1.00 | 80.60 | A |
| ATOM | 170 | CG2 | THR | A | 256 | -7.192 | 42.404 | 41.002 | 1.00 | 78.48 | A |
| ATOM | 171 | C | THR | A | 256 | -8.838 | 45.039 | 38.707 | 1.00 | 84.70 | A |
| ATOM | 172 | O | THR | A | 256 | -9.756 | 45.792 | 39.062 | 1.00 | 85.06 | A |
| ATOM | 173 | N | VAL | A | 257 | -7.963 | 45.341 | 37.739 | 1.00 | 85.79 | A |
| ATOM | 174 | CA | VAL | A | 257 | -7.974 | 46.612 | 37.009 | 1.00 | 86.66 | A |
| ATOM | 175 | CB | VAL | A | 257 | -6.633 | 46.856 | 36.327 | 1.00 | 84.22 | A |
| ATOM | 176 | CG1 | VAL | A | 257 | -6.654 | 48.199 | 35.627 | 1.00 | 82.14 | A |
| ATOM | 177 | CG2 | VAL | A | 257 | -5.523 | 46.768 | 37.342 | 1.00 | 82.68 | A |
| ATOM | 178 | C | VAL | A | 257 | -9.058 | 46.653 | 35.927 | 1.00 | 89.56 | A |
| ATOM | 179 | O | VAL | A | 257 | -9.160 | 45.736 | 35.109 | 1.00 | 89.21 | A |
| ATOM | 180 | N | PRO | A | 258 | -9.875 | 47.729 | 35.895 | 1.00 | 92.07 | A |
| ATOM | 181 | CD | PRO | A | 258 | -9.997 | 48.797 | 36.904 | 1.00 | 92.44 | A |
| ATOM | 182 | CA | PRO | A | 258 | -10.944 | 47.839 | 34.883 | 1.00 | 93.42 | A |
| ATOM | 183 | CB | PRO | A | 258 | -11.797 | 49.009 | 35.396 | 1.00 | 93.24 | A |
| ATOM | 184 | CG | PRO | A | 258 | -11.491 | 49.050 | 36.893 | 1.00 | 93.36 | A |
| ATOM | 185 | C | PRO | A | 258 | -10.434 | 48.068 | 33.446 | 1.00 | 94.59 | A |
| ATOM | 186 | O | PRO | A | 258 | -9.519 | 48.877 | 33.215 | 1.00 | 94.66 | A |
| ATOM | 187 | N | ASP | A | 259 | -11.037 | 47.359 | 32.491 | 1.00 | 95.39 | A |
| ATOM | 188 | CA | ASP | A | 259 | -10.648 | 47.466 | 31.092 | 1.00 | 95.87 | A |
| ATOM | 189 | CB | ASP | A | 259 | -11.527 | 46.573 | 30.227 | 1.00 | 96.90 | A |
| ATOM | 190 | CG | ASP | A | 259 | -11.168 | 45.111 | 30.363 | 1.00 | 99.11 | A |
| ATOM | 191 | OD1 | ASP | A | 259 | -9.956 | 44.802 | 30.473 | 1.00 | 99.68 | A |
| ATOM | 192 | OD2 | ASP | A | 259 | -12.091 | 44.267 | 30.343 | 1.00 | 99.82 | A |
| ATOM | 193 | C | ASP | A | 259 | -10.658 | 48.872 | 30.514 | 1.00 | 95.76 | A |
| ATOM | 194 | O | ASP | A | 259 | -11.643 | 49.603 | 30.636 | 1.00 | 95.94 | A |
| ATOM | 195 | N | SER | A | 260 | -9.542 | 49.227 | 29.876 | 1.00 | 95.70 | A |
| ATOM | 196 | CA | SER | A | 260 | -9.351 | 50.528 | 29.232 | 1.00 | 94.44 | A |
| ATOM | 197 | CB | SER | A | 260 | -8.751 | 51.541 | 30.208 | 1.00 | 93.04 | A |
| ATOM | 198 | OG | SER | A | 260 | -7.337 | 51.445 | 30.247 | 1.00 | 89.82 | A |
| ATOM | 199 | C | SER | A | 260 | -8.359 | 50.322 | 28.098 | 1.00 | 94.58 | A |
| ATOM | 200 | O | SER | A | 260 | -7.842 | 49.213 | 27.904 | 1.00 | 94.69 | A |
| ATOM | 201 | N | ASP | A | 261 | -8.078 | 51.390 | 27.362 | 1.00 | 94.15 | A |
| ATOM | 202 | CA | ASP | A | 261 | -7.122 | 51.289 | 26.275 | 1.00 | 93.64 | A |
| ATOM | 203 | CB | ASP | A | 261 | -7.271 | 52.459 | 25.286 | 1.00 | 95.25 | A |
| ATOM | 204 | CG | ASP | A | 261 | -7.316 | 53.814 | 25.971 | 1.00 | 97.92 | A |
| ATOM | 205 | OD1 | ASP | A | 261 | -8.238 | 54.047 | 26.794 | 1.00 | 98.70 | A |
| ATOM | 206 | OD2 | ASP | A | 261 | -6.430 | 54.652 | 25.674 | 1.00 | 98.82 | A |
| ATOM | 207 | C | ASP | A | 261 | -5.694 | 51.215 | 26.811 | 1.00 | 91.83 | A |
| ATOM | 208 | O | ASP | A | 261 | -4.836 | 50.584 | 26.198 | 1.00 | 91.72 | A |
| ATOM | 209 | N | ILE | A | 262 | -5.434 | 51.841 | 27.955 | 1.00 | 89.95 | A |
| ATOM | 210 | CA | ILE | A | 262 | -4.086 | 51.792 | 28.518 | 1.00 | 88.10 | A |
| ATOM | 211 | CB | ILE | A | 262 | -3.837 | 52.907 | 29.590 | 1.00 | 88.10 | A |
| ATOM | 212 | CG2 | ILE | A | 262 | -2.478 | 52.697 | 30.264 | 1.00 | 86.59 | A |
| ATOM | 213 | CG1 | ILE | A | 262 | -3.798 | 54.290 | 28.926 | 1.00 | 87.71 | A |
| ATOM | 214 | CD1 | ILE | A | 262 | -5.095 | 54.710 | 28.274 | 1.00 | 87.96 | A |
| ATOM | 215 | C | ILE | A | 262 | -3.851 | 50.423 | 29.143 | 1.00 | 86.53 | A |
| ATOM | 216 | O | ILE | A | 262 | -2.721 | 49.942 | 29.187 | 1.00 | 85.77 | A |
| ATOM | 217 | N | LYS | A | 263 | -4.922 | 49.790 | 29.615 | 1.00 | 85.96 | A |
| ATOM | 218 | CA | LYS | A | 263 | -4.800 | 48.464 | 30.217 | 1.00 | 84.74 | A |
| ATOM | 219 | CB | LYS | A | 263 | -6.167 | 47.941 | 30.660 | 1.00 | 84.03 | A |
| ATOM | 220 | CG | LYS | A | 263 | -6.083 | 46.646 | 31.461 | 1.00 | 83.73 | A |
| ATOM | 221 | CD | LYS | A | 263 | -7.434 | 46.295 | 32.063 | 1.00 | 83.36 | A |
| ATOM | 222 | CE | LYS | A | 263 | -7.374 | 45.035 | 32.912 | 1.00 | 82.26 | A |

TABLE 1-continued

ATOMIC COORDINATES OF THE ERR3 LBD/SRC-1 NR
BOX 2 PEPTIDE COMPLEX (PDB CODE 1KV6)

| ATOM | 223 | NZ  | LYS | A | 263 | −7.198  | 43.800 | 32.114 | 1.00 | 82.61 | A |
|------|-----|-----|-----|---|-----|---------|--------|--------|------|-------|---|
| ATOM | 224 | C   | LYS | A | 263 | −4.215  | 47.548 | 29.145 | 1.00 | 84.28 | A |
| ATOM | 225 | O   | LYS | A | 263 | −3.097  | 47.040 | 29.287 | 1.00 | 83.83 | A |
| ATOM | 226 | N   | ALA | A | 264 | −4.978  | 47.380 | 28.065 | 1.00 | 82.41 | A |
| ATOM | 227 | CA  | ALA | A | 264 | −4.581  | 46.554 | 26.937 | 1.00 | 81.65 | A |
| ATOM | 228 | CB  | ALA | A | 264 | −5.611  | 46.688 | 25.830 | 1.00 | 80.15 | A |
| ATOM | 229 | C   | ALA | A | 264 | −3.182  | 46.906 | 26.402 | 1.00 | 81.63 | A |
| ATOM | 230 | O   | ALA | A | 264 | −2.307  | 46.041 | 26.259 | 1.00 | 81.57 | A |
| ATOM | 231 | N   | LEU | A | 265 | −2.965  | 48.177 | 26.102 | 1.00 | 81.66 | A |
| ATOM | 232 | CA  | LEU | A | 265 | −1.673  | 48.594 | 25.580 | 1.00 | 81.51 | A |
| ATOM | 233 | CB  | LEU | A | 265 | −1.702  | 50.076 | 25.199 | 1.00 | 82.51 | A |
| ATOM | 234 | CG  | LEU | A | 265 | −1.804  | 50.357 | 23.686 | 1.00 | 83.42 | A |
| ATOM | 235 | CD1 | LEU | A | 265 | −2.737  | 49.386 | 22.960 | 1.00 | 83.32 | A |
| ATOM | 236 | CD2 | LEU | A | 265 | −2.308  | 51.768 | 23.514 | 1.00 | 84.57 | A |
| ATOM | 237 | C   | LEU | A | 265 | −0.534  | 48.317 | 26.533 | 1.00 | 80.65 | A |
| ATOM | 238 | O   | LEU | A | 265 | 0.587   | 48.045 | 26.091 | 1.00 | 80.06 | A |
| ATOM | 239 | N   | THR | A | 266 | −0.804  | 48.376 | 27.834 | 1.00 | 80.23 | A |
| ATOM | 240 | CA  | THR | A | 266 | 0.259   | 48.099 | 28.795 | 1.00 | 79.91 | A |
| ATOM | 241 | CB  | THR | A | 266 | −0.023  | 48.676 | 30.222 | 1.00 | 81.28 | A |
| ATOM | 242 | OG1 | THR | A | 266 | −0.333  | 50.073 | 30.134 | 1.00 | 83.03 | A |
| ATOM | 243 | CG2 | THR | A | 266 | 1.233   | 48.544 | 31.112 | 1.00 | 81.31 | A |
| ATOM | 244 | C   | THR | A | 266 | 0.464   | 46.595 | 28.895 | 1.00 | 77.54 | A |
| ATOM | 245 | O   | THR | A | 266 | 1.600   | 46.131 | 29.045 | 1.00 | 78.28 | A |
| ATOM | 246 | N   | THR | A | 267 | −0.625  | 45.834 | 28.808 | 1.00 | 73.97 | A |
| ATOM | 247 | CA  | THR | A | 267 | −0.537  | 44.371 | 28.879 | 1.00 | 71.08 | A |
| ATOM | 248 | CB  | THR | A | 267 | −1.945  | 43.724 | 28.778 | 1.00 | 69.96 | A |
| ATOM | 249 | OG1 | THR | A | 267 | −2.693  | 44.042 | 29.947 | 1.00 | 69.09 | A |
| ATOM | 250 | CG2 | THR | A | 267 | −1.858  | 42.236 | 28.677 | 1.00 | 68.69 | A |
| ATOM | 251 | C   | THR | A | 267 | 0.327   | 43.878 | 27.716 | 1.00 | 70.64 | A |
| ATOM | 252 | O   | THR | A | 267 | 1.266   | 43.088 | 27.897 | 1.00 | 68.87 | A |
| ATOM | 253 | N   | LEU | A | 268 | −0.001  | 44.375 | 26.524 | 1.00 | 69.89 | A |
| ATOM | 254 | CA  | LEU | A | 268 | 0.709   | 44.016 | 25.320 | 1.00 | 68.49 | A |
| ATOM | 255 | CB  | LEU | A | 268 | 0.089   | 44.705 | 24.125 | 1.00 | 67.34 | A |
| ATOM | 256 | CG  | LEU | A | 268 | −0.716  | 43.871 | 23.137 | 1.00 | 66.00 | A |
| ATOM | 257 | CD1 | LEU | A | 268 | −1.565  | 42.855 | 23.817 | 1.00 | 66.75 | A |
| ATOM | 258 | CD2 | LEU | A | 268 | −1.579  | 44.814 | 22.366 | 1.00 | 67.37 | A |
| ATOM | 259 | C   | LEU | A | 268 | 2.161   | 44.383 | 25.412 | 1.00 | 69.72 | A |
| ATOM | 260 | O   | LEU | A | 268 | 3.012   | 43.571 | 25.080 | 1.00 | 70.25 | A |
| ATOM | 261 | N   | CYS | A | 269 | 2.463   | 45.594 | 25.867 | 1.00 | 71.06 | A |
| ATOM | 262 | CA  | CYS | A | 269 | 3.861   | 46.005 | 25.957 | 1.00 | 73.43 | A |
| ATOM | 263 | CB  | CYS | A | 269 | 3.971   | 47.479 | 26.328 | 1.00 | 74.37 | A |
| ATOM | 264 | SG  | CYS | A | 269 | 3.519   | 48.544 | 24.981 | 1.00 | 81.77 | A |
| ATOM | 265 | C   | CYS | A | 269 | 4.647   | 45.177 | 26.948 | 1.00 | 73.66 | A |
| ATOM | 266 | O   | CYS | A | 269 | 5.864   | 45.088 | 26.852 | 1.00 | 73.70 | A |
| ATOM | 267 | N   | ASP | A | 270 | 3.946   | 44.584 | 27.912 | 1.00 | 74.34 | A |
| ATOM | 268 | CA  | ASP | A | 270 | 4.571   | 43.746 | 28.941 | 1.00 | 74.35 | A |
| ATOM | 269 | CB  | ASP | A | 270 | 3.651   | 43.691 | 30.176 | 1.00 | 78.20 | A |
| ATOM | 270 | CG  | ASP | A | 270 | 4.145   | 42.726 | 31.265 | 1.00 | 81.61 | A |
| ATOM | 271 | OD1 | ASP | A | 270 | 5.212   | 43.005 | 31.894 | 1.00 | 82.47 | A |
| ATOM | 272 | OD2 | ASP | A | 270 | 3.444   | 41.695 | 31.483 | 1.00 | 82.33 | A |
| ATOM | 273 | C   | ASP | A | 270 | 4.783   | 42.340 | 28.349 | 1.00 | 72.62 | A |
| ATOM | 274 | O   | ASP | A | 270 | 5.771   | 41.655 | 28.662 | 1.00 | 72.51 | A |
| ATOM | 275 | N   | LEU | A | 271 | 3.845   | 41.928 | 27.494 | 1.00 | 68.61 | A |
| ATOM | 276 | CA  | LEU | A | 271 | 3.929   | 40.634 | 26.838 | 1.00 | 65.61 | A |
| ATOM | 277 | CB  | LEU | A | 271 | 2.747   | 40.417 | 25.891 | 1.00 | 60.72 | A |
| ATOM | 278 | CG  | LEU | A | 271 | 2.030   | 39.065 | 25.916 | 1.00 | 56.86 | A |
| ATOM | 279 | CD1 | LEU | A | 271 | 1.107   | 38.996 | 24.710 | 1.00 | 53.79 | A |
| ATOM | 280 | CD2 | LEU | A | 271 | 3.021   | 37.928 | 25.929 | 1.00 | 53.89 | A |
| ATOM | 281 | C   | LEU | A | 271 | 5.197   | 40.644 | 26.014 | 1.00 | 66.52 | A |
| ATOM | 282 | O   | LEU | A | 271 | 5.983   | 39.680 | 26.026 | 1.00 | 66.33 | A |
| ATOM | 283 | N   | ALA | A | 272 | 5.381   | 41.763 | 25.308 | 1.00 | 66.70 | A |
| ATOM | 284 | CA  | ALA | A | 272 | 6.507   | 41.968 | 24.412 | 1.00 | 65.75 | A |
| ATOM | 285 | CB  | ALA | A | 272 | 6.280   | 43.189 | 23.606 | 1.00 | 64.22 | A |
| ATOM | 286 | C   | ALA | A | 272 | 7.868   | 42.029 | 25.086 | 1.00 | 66.89 | A |
| ATOM | 287 | O   | ALA | A | 272 | 8.865   | 41.601 | 24.503 | 1.00 | 66.83 | A |
| ATOM | 288 | N   | ASP | A | 273 | 7.936   | 42.552 | 26.303 | 1.00 | 68.27 | A |
| ATOM | 289 | CA  | ASP | A | 273 | 9.230   | 42.609 | 26.956 | 1.00 | 70.43 | A |
| ATOM | 290 | CB  | ASP | A | 273 | 9.210   | 43.510 | 28.206 | 1.00 | 73.27 | A |
| ATOM | 291 | CG  | ASP | A | 273 | 10.627  | 44.015 | 28.597 | 1.00 | 77.47 | A |
| ATOM | 292 | OD1 | ASP | A | 273 | 11.160  | 44.885 | 27.849 | 1.00 | 78.97 | A |
| ATOM | 293 | OD2 | ASP | A | 273 | 11.208  | 43.543 | 29.628 | 1.00 | 77.85 | A |
| ATOM | 294 | C   | ASP | A | 273 | 9.615   | 41.187 | 27.357 | 1.00 | 70.51 | A |
| ATOM | 295 | O   | ASP | A | 273 | 10.774  | 40.781 | 27.234 | 1.00 | 70.54 | A |
| ATOM | 296 | N   | ARG | A | 274 | 8.632   | 40.425 | 27.827 | 1.00 | 69.99 | A |
| ATOM | 297 | CA  | ARG | A | 274 | 8.898   | 39.060 | 28.250 | 1.00 | 69.51 | A |
| ATOM | 298 | CB  | ARG | A | 274 | 7.727   | 38.542 | 29.095 | 1.00 | 68.43 | A |

TABLE 1-continued

ATOMIC COORDINATES OF THE ERR3 LBD/SRC-1 NR
BOX 2 PEPTIDE COMPLEX (PDB CODE 1KV6)

| ATOM | 299 | CG | ARG | A | 274 | 7.713 | 39.195 | 30.483 | 1.00 | 67.61 | A |
|---|---|---|---|---|---|---|---|---|---|---|---|
| ATOM | 300 | CD | ARG | A | 274 | 6.651 | 38.667 | 31.427 | 1.00 | 66.93 | A |
| ATOM | 301 | NE | ARG | A | 274 | 5.345 | 39.243 | 31.143 | 1.00 | 66.13 | A |
| ATOM | 302 | CZ | ARG | A | 274 | 4.309 | 38.550 | 30.678 | 1.00 | 65.70 | A |
| ATOM | 303 | NH1 | ARG | A | 274 | 4.420 | 37.245 | 30.444 | 1.00 | 62.80 | A |
| ATOM | 304 | NH2 | ARG | A | 274 | 3.158 | 39.172 | 30.440 | 1.00 | 64.52 | A |
| ATOM | 305 | C | ARG | A | 274 | 9.199 | 38.182 | 27.044 | 1.00 | 69.96 | A |
| ATOM | 306 | O | ARG | A | 274 | 10.094 | 37.338 | 27.090 | 1.00 | 69.89 | A |
| ATOM | 307 | N | GLU | A | 275 | 8.460 | 38.420 | 25.962 | 1.00 | 70.77 | A |
| ATOM | 308 | CA | GLU | A | 275 | 8.633 | 37.712 | 24.698 | 1.00 | 70.98 | A |
| ATOM | 309 | CB | GLU | A | 275 | 7.569 | 38.183 | 23.720 | 1.00 | 73.45 | A |
| ATOM | 310 | CG | GLU | A | 275 | 6.533 | 37.144 | 23.402 | 1.00 | 79.42 | A |
| ATOM | 311 | CD | GLU | A | 275 | 6.983 | 36.210 | 22.283 | 1.00 | 84.66 | A |
| ATOM | 312 | OE1 | GLU | A | 275 | 8.049 | 35.553 | 22.418 | 1.00 | 85.86 | A |
| ATOM | 313 | OE2 | GLU | A | 275 | 6.265 | 36.129 | 21.252 | 1.00 | 89.27 | A |
| ATOM | 314 | C | GLU | A | 275 | 10.033 | 37.985 | 24.120 | 1.00 | 70.34 | A |
| ATOM | 315 | O | GLU | A | 275 | 10.732 | 37.058 | 23.688 | 1.00 | 68.56 | A |
| ATOM | 316 | N | LEU | A | 276 | 10.434 | 39.259 | 24.127 | 1.00 | 68.90 | A |
| ATOM | 317 | CA | LEU | A | 276 | 11.738 | 39.650 | 23.611 | 1.00 | 68.10 | A |
| ATOM | 318 | CB | LEU | A | 276 | 11.941 | 41.169 | 23.715 | 1.00 | 68.13 | A |
| ATOM | 319 | CG | LEU | A | 276 | 11.275 | 42.096 | 22.685 | 1.00 | 68.37 | A |
| ATOM | 320 | CD1 | LEU | A | 276 | 11.433 | 43.545 | 23.098 | 1.00 | 67.94 | A |
| ATOM | 321 | CD2 | LEU | A | 276 | 11.889 | 41.895 | 21.336 | 1.00 | 67.33 | A |
| ATOM | 322 | C | LEU | A | 276 | 12.860 | 38.930 | 24.351 | 1.00 | 67.64 | A |
| ATOM | 323 | O | LEU | A | 276 | 13.884 | 38.582 | 23.747 | 1.00 | 68.77 | A |
| ATOM | 324 | N | VAL | A | 277 | 12.668 | 38.699 | 25.649 | 1.00 | 66.23 | A |
| ATOM | 325 | CA | VAL | A | 277 | 13.681 | 38.015 | 26.465 | 1.00 | 65.00 | A |
| ATOM | 326 | CB | VAL | A | 277 | 13.267 | 37.912 | 27.983 | 1.00 | 64.82 | A |
| ATOM | 327 | CG1 | VAL | A | 277 | 14.398 | 37.292 | 28.810 | 1.00 | 60.45 | A |
| ATOM | 328 | CG2 | VAL | A | 277 | 12.913 | 39.285 | 28.530 | 1.00 | 63.67 | A |
| ATOM | 329 | C | VAL | A | 277 | 13.864 | 36.600 | 25.928 | 1.00 | 64.52 | A |
| ATOM | 330 | O | VAL | A | 277 | 14.985 | 36.133 | 25.748 | 1.00 | 64.44 | A |
| ATOM | 331 | N | VAL | A | 278 | 12.745 | 35.926 | 25.690 | 1.00 | 63.71 | A |
| ATOM | 332 | CA | VAL | A | 278 | 12.735 | 34.571 | 25.154 | 1.00 | 62.81 | A |
| ATOM | 333 | CB | VAL | A | 278 | 11.302 | 34.054 | 25.130 | 1.00 | 61.64 | A |
| ATOM | 334 | CG1 | VAL | A | 278 | 11.196 | 32.786 | 24.302 | 1.00 | 58.72 | A |
| ATOM | 335 | CG2 | VAL | A | 278 | 10.860 | 33.840 | 26.543 | 1.00 | 59.43 | A |
| ATOM | 336 | C | VAL | A | 278 | 13.317 | 34.524 | 23.735 | 1.00 | 63.39 | A |
| ATOM | 337 | O | VAL | A | 278 | 14.115 | 33.630 | 23.408 | 1.00 | 61.80 | A |
| ATOM | 338 | N | ILE | A | 279 | 12.914 | 35.496 | 22.909 | 1.00 | 63.13 | A |
| ATOM | 339 | CA | ILE | A | 279 | 13.383 | 35.590 | 21.535 | 1.00 | 63.08 | A |
| ATOM | 340 | CB | ILE | A | 279 | 12.892 | 36.854 | 20.814 | 1.00 | 63.21 | A |
| ATOM | 341 | CG2 | ILE | A | 279 | 13.415 | 36.851 | 19.394 | 1.00 | 62.96 | A |
| ATOM | 342 | CG1 | ILE | A | 279 | 11.363 | 36.926 | 20.816 | 1.00 | 64.72 | A |
| ATOM | 343 | CD1 | ILE | A | 279 | 10.795 | 38.059 | 19.997 | 1.00 | 63.47 | A |
| ATOM | 344 | C | ILE | A | 279 | 14.886 | 35.629 | 21.478 | 1.00 | 64.03 | A |
| ATOM | 345 | O | ILE | A | 279 | 15.464 | 35.025 | 20.603 | 1.00 | 65.67 | A |
| ATOM | 346 | N | ILE | A | 280 | 15.522 | 36.347 | 22.397 | 1.00 | 63.71 | A |
| ATOM | 347 | CA | ILE | A | 280 | 16.977 | 36.445 | 22.412 | 1.00 | 64.30 | A |
| ATOM | 348 | CB | ILE | A | 280 | 17.438 | 37.530 | 23.381 | 1.00 | 64.72 | A |
| ATOM | 349 | CG2 | ILE | A | 280 | 18.947 | 37.456 | 23.580 | 1.00 | 63.55 | A |
| ATOM | 350 | CG1 | ILE | A | 280 | 17.010 | 38.894 | 22.852 | 1.00 | 63.89 | A |
| ATOM | 351 | CD1 | ILE | A | 280 | 17.428 | 39.987 | 23.759 | 1.00 | 64.05 | A |
| ATOM | 352 | C | ILE | A | 280 | 17.682 | 35.143 | 22.785 | 1.00 | 65.51 | A |
| ATOM | 353 | O | ILE | A | 280 | 18.761 | 34.852 | 22.289 | 1.00 | 66.28 | A |
| ATOM | 354 | N | GLY | A | 281 | 17.083 | 34.364 | 23.670 | 1.00 | 66.11 | A |
| ATOM | 355 | CA | GLY | A | 281 | 17.697 | 33.107 | 24.059 | 1.00 | 66.25 | A |
| ATOM | 356 | C | GLY | A | 281 | 17.446 | 32.007 | 23.032 | 1.00 | 66.97 | A |
| ATOM | 357 | O | GLY | A | 281 | 18.193 | 31.008 | 22.961 | 1.00 | 68.09 | A |
| ATOM | 358 | N | TRP | A | 282 | 16.379 | 32.180 | 22.251 | 1.00 | 64.74 | A |
| ATOM | 359 | CA | TRP | A | 282 | 16.029 | 31.241 | 21.195 | 1.00 | 63.27 | A |
| ATOM | 360 | CB | TRP | A | 282 | 14.587 | 31.489 | 20.750 | 1.00 | 63.18 | A |
| ATOM | 361 | CG | TRP | A | 282 | 14.249 | 30.949 | 19.422 | 1.00 | 61.48 | A |
| ATOM | 362 | CD2 | TRP | A | 282 | 14.162 | 31.686 | 18.195 | 1.00 | 62.66 | A |
| ATOM | 363 | CE2 | TRP | A | 282 | 13.825 | 30.761 | 17.176 | 1.00 | 61.07 | A |
| ATOM | 364 | CE3 | TRP | A | 282 | 14.346 | 33.033 | 17.854 | 1.00 | 61.83 | A |
| ATOM | 365 | CD1 | TRP | A | 282 | 13.966 | 29.661 | 19.115 | 1.00 | 62.73 | A |
| ATOM | 366 | NE1 | TRP | A | 282 | 13.705 | 29.534 | 17.767 | 1.00 | 63.20 | A |
| ATOM | 367 | CZ2 | TRP | A | 282 | 13.659 | 31.136 | 15.846 | 1.00 | 59.90 | A |
| ATOM | 368 | CZ3 | TRP | A | 282 | 14.179 | 33.405 | 16.522 | 1.00 | 61.57 | A |
| ATOM | 369 | CH2 | TRP | A | 282 | 13.844 | 32.450 | 15.534 | 1.00 | 59.87 | A |
| ATOM | 370 | C | TRP | A | 282 | 16.987 | 31.449 | 20.013 | 1.00 | 62.99 | A |
| ATOM | 371 | O | TRP | A | 282 | 17.480 | 30.482 | 19.434 | 1.00 | 63.19 | A |
| ATOM | 372 | N | ALA | A | 283 | 17.260 | 32.704 | 19.665 | 1.00 | 60.71 | A |
| ATOM | 373 | CA | ALA | A | 283 | 18.163 | 32.990 | 18.558 | 1.00 | 60.63 | A |
| ATOM | 374 | CB | ALA | A | 283 | 18.350 | 34.497 | 18.403 | 1.00 | 60.19 | A |

TABLE 1-continued

ATOMIC COORDINATES OF THE ERR3 LBD/SRC-1 NR
BOX 2 PEPTIDE COMPLEX (PDB CODE 1KV6)

| ATOM | 375 | C | ALA | A | 283 | 19.513 | 32.313 | 18.775 | 1.00 | 60.13 | A |
|---|---|---|---|---|---|---|---|---|---|---|---|
| ATOM | 376 | O | ALA | A | 283 | 20.236 | 32.026 | 17.837 | 1.00 | 60.61 | A |
| ATOM | 377 | N | LYS | A | 284 | 19.851 | 32.055 | 20.023 | 1.00 | 61.43 | A |
| ATOM | 378 | CA | LYS | A | 284 | 21.113 | 31.411 | 20.340 | 1.00 | 61.95 | A |
| ATOM | 379 | CB | LYS | A | 284 | 21.362 | 31.470 | 21.858 | 1.00 | 60.92 | A |
| ATOM | 380 | CG | LYS | A | 284 | 9999.000 | 9999.000 | 9999.000 | 1.00 | 0.00 | A |
| ATOM | 381 | CD | LYS | A | 284 | 9999.000 | 9999.000 | 9999.000 | 1.00 | 0.00 | A |
| ATOM | 382 | CE | LYS | A | 284 | 9999.000 | 9999.000 | 9999.000 | 1.00 | 0.00 | A |
| ATOM | 383 | NZ | LYS | A | 284 | 9999.000 | 9999.000 | 9999.000 | 1.00 | 0.00 | A |
| ATOM | 384 | C | LYS | A | 284 | 21.124 | 29.966 | 19.837 | 1.00 | 62.39 | A |
| ATOM | 385 | O | LYS | A | 284 | 22.194 | 29.397 | 19.655 | 1.00 | 62.70 | A |
| ATOM | 386 | N | HIS | A | 285 | 19.945 | 29.384 | 19.605 | 1.00 | 62.31 | A |
| ATOM | 387 | CA | HIS | A | 285 | 19.852 | 28.005 | 19.103 | 1.00 | 63.83 | A |
| ATOM | 388 | CB | HIS | A | 285 | 18.626 | 27.247 | 19.625 | 1.00 | 66.79 | A |
| ATOM | 389 | CG | HIS | A | 285 | 18.649 | 27.007 | 21.094 | 1.00 | 70.20 | A |
| ATOM | 390 | CD2 | HIS | A | 285 | 17.759 | 27.328 | 22.065 | 1.00 | 71.50 | A |
| ATOM | 391 | ND1 | HIS | A | 285 | 19.733 | 26.448 | 21.732 | 1.00 | 71.27 | A |
| ATOM | 392 | CE1 | HIS | A | 285 | 19.516 | 26.445 | 23.035 | 1.00 | 71.54 | A |
| ATOM | 393 | NE2 | HIS | A | 285 | 18.326 | 26.973 | 23.263 | 1.00 | 72.31 | A |
| ATOM | 394 | C | HIS | A | 285 | 19.769 | 27.892 | 17.602 | 1.00 | 63.11 | A |
| ATOM | 395 | O | HIS | A | 285 | 19.676 | 26.784 | 17.103 | 1.00 | 63.62 | A |
| ATOM | 396 | N | ILE | A | 286 | 19.757 | 29.007 | 16.879 | 1.00 | 62.08 | A |
| ATOM | 397 | CA | ILE | A | 286 | 19.687 | 28.941 | 15.430 | 1.00 | 60.30 | A |
| ATOM | 398 | CB | ILE | A | 286 | 19.245 | 30.273 | 14.865 | 1.00 | 59.15 | A |
| ATOM | 399 | CG2 | ILE | A | 286 | 19.407 | 30.296 | 13.363 | 1.00 | 58.35 | A |
| ATOM | 400 | CG1 | ILE | A | 286 | 17.787 | 30.508 | 15.243 | 1.00 | 58.88 | A |
| ATOM | 401 | CD1 | ILE | A | 286 | 17.318 | 31.910 | 14.923 | 1.00 | 59.61 | A |
| ATOM | 402 | C | ILE | A | 286 | 21.078 | 28.569 | 14.933 | 1.00 | 61.04 | A |
| ATOM | 403 | O | ILE | A | 286 | 22.021 | 29.320 | 15.110 | 1.00 | 60.98 | A |
| ATOM | 404 | N | PRO | A | 287 | 21.215 | 27.389 | 14.306 | 1.00 | 61.38 | A |
| ATOM | 405 | CD | PRO | A | 287 | 20.129 | 26.537 | 13.782 | 1.00 | 60.85 | A |
| ATOM | 406 | CA | PRO | A | 287 | 22.503 | 26.924 | 13.800 | 1.00 | 62.14 | A |
| ATOM | 407 | CB | PRO | A | 287 | 22.113 | 25.790 | 12.842 | 1.00 | 61.94 | A |
| ATOM | 408 | CG | PRO | A | 287 | 20.857 | 25.273 | 13.432 | 1.00 | 60.88 | A |
| ATOM | 409 | C | PRO | A | 287 | 23.286 | 28.016 | 13.103 | 1.00 | 62.86 | A |
| ATOM | 410 | O | PRO | A | 287 | 22.808 | 28.599 | 12.117 | 1.00 | 62.28 | A |
| ATOM | 411 | N | GLY | A | 288 | 24.482 | 28.280 | 13.637 | 1.00 | 63.83 | A |
| ATOM | 412 | CA | GLY | A | 288 | 25.389 | 29.277 | 13.081 | 1.00 | 64.80 | A |
| ATOM | 413 | C | GLY | A | 288 | 25.196 | 30.755 | 13.372 | 1.00 | 65.64 | A |
| ATOM | 414 | O | GLY | A | 288 | 25.947 | 31.562 | 12.852 | 1.00 | 67.01 | A |
| ATOM | 415 | N | PHE | A | 289 | 24.191 | 31.115 | 14.171 | 1.00 | 67.26 | A |
| ATOM | 416 | CA | PHE | A | 289 | 23.911 | 32.509 | 14.535 | 1.00 | 67.39 | A |
| ATOM | 417 | CB | PHE | A | 289 | 22.537 | 32.620 | 15.181 | 1.00 | 64.47 | A |
| ATOM | 418 | CG | PHE | A | 289 | 22.213 | 33.997 | 15.696 | 1.00 | 62.78 | A |
| ATOM | 419 | CD1 | PHE | A | 289 | 21.721 | 34.975 | 14.845 | 1.00 | 63.23 | A |
| ATOM | 420 | CD2 | PHE | A | 289 | 22.310 | 34.285 | 17.039 | 1.00 | 62.24 | A |
| ATOM | 421 | CE1 | PHE | A | 289 | 21.314 | 36.219 | 15.330 | 1.00 | 61.66 | A |
| ATOM | 422 | CE2 | PHE | A | 289 | 21.909 | 35.526 | 17.536 | 1.00 | 62.60 | A |
| ATOM | 423 | CZ | PHE | A | 289 | 21.407 | 36.489 | 16.678 | 1.00 | 61.95 | A |
| ATOM | 424 | C | PHE | A | 289 | 24.935 | 32.957 | 15.556 | 1.00 | 69.38 | A |
| ATOM | 425 | O | PHE | A | 289 | 25.661 | 33.914 | 15.343 | 1.00 | 69.16 | A |
| ATOM | 426 | N | SER | A | 290 | 24.979 | 32.244 | 16.671 | 1.00 | 71.40 | A |
| ATOM | 427 | CA | SER | A | 290 | 25.902 | 32.566 | 17.755 | 1.00 | 75.33 | A |
| ATOM | 428 | CB | SER | A | 290 | 25.758 | 31.572 | 18.910 | 1.00 | 75.22 | A |
| ATOM | 429 | OG | SER | A | 290 | 26.311 | 30.330 | 18.517 | 1.00 | 80.14 | A |
| ATOM | 430 | C | SER | A | 290 | 27.383 | 32.628 | 17.361 | 1.00 | 76.29 | A |
| ATOM | 431 | O | SER | A | 290 | 28.210 | 33.064 | 18.176 | 1.00 | 77.25 | A |
| ATOM | 432 | N | THR | A | 291 | 27.733 | 32.191 | 16.151 | 1.00 | 76.26 | A |
| ATOM | 433 | CA | THR | A | 291 | 29.133 | 32.271 | 15.753 | 1.00 | 76.96 | A |
| ATOM | 434 | CB | THR | A | 291 | 29.540 | 31.130 | 14.785 | 1.00 | 77.51 | A |
| ATOM | 435 | OG1 | THR | A | 291 | 28.680 | 31.130 | 13.636 | 1.00 | 79.16 | A |
| ATOM | 436 | CG2 | THR | A | 291 | 29.462 | 29.770 | 15.503 | 1.00 | 76.41 | A |
| ATOM | 437 | C | THR | A | 291 | 29.424 | 33.640 | 15.133 | 1.00 | 76.56 | A |
| ATOM | 438 | O | THR | A | 291 | 30.575 | 33.996 | 14.886 | 1.00 | 76.43 | A |
| ATOM | 439 | N | LEU | A | 292 | 28.373 | 34.414 | 14.880 | 1.00 | 76.05 | A |
| ATOM | 440 | CA | LEU | A | 292 | 28.564 | 35.756 | 14.347 | 1.00 | 76.09 | A |
| ATOM | 441 | CB | LEU | A | 292 | 27.229 | 36.379 | 13.913 | 1.00 | 72.44 | A |
| ATOM | 442 | CG | LEU | A | 292 | 26.435 | 35.739 | 12.776 | 1.00 | 70.12 | A |
| ATOM | 443 | CD1 | LEU | A | 292 | 25.073 | 36.407 | 12.658 | 1.00 | 66.47 | A |
| ATOM | 444 | CD2 | LEU | A | 292 | 27.213 | 35.881 | 11.482 | 1.00 | 67.74 | A |
| ATOM | 445 | C | LEU | A | 292 | 29.150 | 36.577 | 15.508 | 1.00 | 77.84 | A |
| ATOM | 446 | O | LEU | A | 292 | 29.310 | 36.078 | 16.638 | 1.00 | 78.01 | A |
| ATOM | 447 | N | SER | A | 293 | 29.481 | 37.832 | 15.230 | 1.00 | 78.62 | A |
| ATOM | 448 | CA | SER | A | 293 | 30.016 | 38.698 | 16.267 | 1.00 | 78.46 | A |
| ATOM | 449 | CB | SER | A | 293 | 30.741 | 39.900 | 15.653 | 1.00 | 78.20 | A |
| ATOM | 450 | OG | SER | A | 293 | 29.868 | 40.727 | 14.901 | 1.00 | 78.53 | A |

TABLE 1-continued

ATOMIC COORDINATES OF THE ERR3 LBD/SRC-1 NR
BOX 2 PEPTIDE COMPLEX (PDB CODE 1KV6)

| ATOM | 451 | C   | SER | A | 293 | 28.819 | 39.169 | 17.086 | 1.00 | 78.64 | A |
|------|-----|-----|-----|---|-----|--------|--------|--------|------|-------|---|
| ATOM | 452 | O   | SER | A | 293 | 27.658 | 38.957 | 16.695 | 1.00 | 77.84 | A |
| ATOM | 453 | N   | LEU | A | 294 | 29.109 | 39.802 | 18.217 | 1.00 | 78.74 | A |
| ATOM | 454 | CA  | LEU | A | 294 | 28.064 | 40.290 | 19.098 | 1.00 | 79.75 | A |
| ATOM | 455 | CB  | LEU | A | 294 | 28.680 | 40.716 | 20.429 | 1.00 | 81.07 | A |
| ATOM | 456 | CG  | LEU | A | 294 | 27.877 | 40.398 | 21.692 | 1.00 | 83.41 | A |
| ATOM | 457 | CD1 | LEU | A | 294 | 27.533 | 38.890 | 21.765 | 1.00 | 82.73 | A |
| ATOM | 458 | CD2 | LEU | A | 294 | 28.706 | 40.816 | 22.892 | 1.00 | 83.15 | A |
| ATOM | 459 | C   | LEU | A | 294 | 27.390 | 41.469 | 18.416 | 1.00 | 79.62 | A |
| ATOM | 460 | O   | LEU | A | 294 | 26.199 | 41.755 | 18.619 | 1.00 | 80.65 | A |
| ATOM | 461 | N   | ALA | A | 295 | 28.176 | 42.153 | 17.595 | 1.00 | 78.42 | A |
| ATOM | 462 | CA  | ALA | A | 295 | 27.686 | 43.293 | 16.847 | 1.00 | 76.81 | A |
| ATOM | 463 | CB  | ALA | A | 295 | 28.847 | 43.962 | 16.101 | 1.00 | 75.52 | A |
| ATOM | 464 | C   | ALA | A | 295 | 26.636 | 42.789 | 15.862 | 1.00 | 75.23 | A |
| ATOM | 465 | O   | ALA | A | 295 | 25.527 | 43.329 | 15.798 | 1.00 | 74.78 | A |
| ATOM | 466 | N   | ASP | A | 296 | 26.997 | 41.743 | 15.113 | 1.00 | 73.72 | A |
| ATOM | 467 | CA  | ASP | A | 296 | 26.110 | 41.139 | 14.108 | 1.00 | 72.73 | A |
| ATOM | 468 | CB  | ASP | A | 296 | 26.859 | 40.043 | 13.342 | 1.00 | 73.28 | A |
| ATOM | 469 | CG  | ASP | A | 296 | 27.992 | 40.607 | 12.434 | 1.00 | 74.61 | A |
| ATOM | 470 | OD1 | ASP | A | 296 | 28.902 | 39.813 | 12.047 | 1.00 | 74.98 | A |
| ATOM | 471 | OD2 | ASP | A | 296 | 27.959 | 41.824 | 12.105 | 1.00 | 72.52 | A |
| ATOM | 472 | C   | ASP | A | 296 | 24.852 | 40.582 | 14.771 | 1.00 | 71.20 | A |
| ATOM | 473 | O   | ASP | A | 296 | 23.734 | 41.007 | 14.452 | 1.00 | 70.06 | A |
| ATOM | 474 | N   | GLN | A | 297 | 25.038 | 39.664 | 15.720 | 1.00 | 69.12 | A |
| ATOM | 475 | CA  | GLN | A | 297 | 23.915 | 39.089 | 16.445 | 1.00 | 67.44 | A |
| ATOM | 476 | CB  | GLN | A | 297 | 24.397 | 38.319 | 17.667 | 1.00 | 64.88 | A |
| ATOM | 477 | CG  | GLN | A | 297 | 25.291 | 37.154 | 17.349 | 1.00 | 63.05 | A |
| ATOM | 478 | CD  | GLN | A | 297 | 25.607 | 36.326 | 18.582 | 1.00 | 63.39 | A |
| ATOM | 479 | OE1 | GLN | A | 297 | 24.761 | 36.167 | 19.455 | 1.00 | 63.11 | A |
| ATOM | 480 | NE2 | GLN | A | 297 | 26.826 | 35.779 | 18.653 | 1.00 | 61.91 | A |
| ATOM | 481 | C   | GLN | A | 297 | 22.928 | 40.168 | 16.892 | 1.00 | 68.68 | A |
| ATOM | 482 | O   | GLN | A | 297 | 21.716 | 39.959 | 16.846 | 1.00 | 70.45 | A |
| ATOM | 483 | N   | MET | A | 298 | 23.439 | 41.320 | 17.318 | 1.00 | 68.85 | A |
| ATOM | 484 | CA  | MET | A | 298 | 22.580 | 42.403 | 17.779 | 1.00 | 68.76 | A |
| ATOM | 485 | CB  | MET | A | 298 | 23.365 | 43.357 | 18.656 | 1.00 | 70.67 | A |
| ATOM | 486 | CG  | MET | A | 298 | 23.760 | 42.770 | 19.964 | 1.00 | 74.85 | A |
| ATOM | 487 | SD  | MET | A | 298 | 24.381 | 44.008 | 21.128 | 1.00 | 79.56 | A |
| ATOM | 488 | CE  | MET | A | 298 | 26.165 | 43.993 | 20.686 | 1.00 | 79.58 | A |
| ATOM | 489 | C   | MET | A | 298 | 21.961 | 43.192 | 16.645 | 1.00 | 67.78 | A |
| ATOM | 490 | O   | MET | A | 298 | 20.842 | 43.704 | 16.764 | 1.00 | 67.07 | A |
| ATOM | 491 | N   | SER | A | 299 | 22.687 | 43.302 | 15.546 | 1.00 | 66.20 | A |
| ATOM | 492 | CA  | SER | A | 299 | 22.167 | 44.046 | 14.411 | 1.00 | 67.41 | A |
| ATOM | 493 | CB  | SER | A | 299 | 23.237 | 44.212 | 13.302 | 1.00 | 68.25 | A |
| ATOM | 494 | OG  | SER | A | 299 | 24.476 | 44.688 | 13.803 | 1.00 | 68.08 | A |
| ATOM | 495 | C   | SER | A | 299 | 20.963 | 43.312 | 13.826 | 1.00 | 66.81 | A |
| ATOM | 496 | O   | SER | A | 299 | 19.948 | 43.941 | 13.458 | 1.00 | 68.77 | A |
| ATOM | 497 | N   | LEU | A | 300 | 21.090 | 41.982 | 13.718 | 1.00 | 64.55 | A |
| ATOM | 498 | CA  | LEU | A | 300 | 20.019 | 41.160 | 13.172 | 1.00 | 60.83 | A |
| ATOM | 499 | CB  | LEU | A | 300 | 20.464 | 39.716 | 13.057 | 1.00 | 57.57 | A |
| ATOM | 500 | CG  | LEU | A | 300 | 21.593 | 39.517 | 12.041 | 1.00 | 55.65 | A |
| ATOM | 501 | CD1 | LEU | A | 300 | 21.797 | 38.037 | 11.787 | 1.00 | 52.47 | A |
| ATOM | 502 | CD2 | LEU | A | 300 | 21.260 | 40.262 | 10.737 | 1.00 | 56.35 | A |
| ATOM | 503 | C   | LEU | A | 300 | 18.824 | 41.265 | 14.077 | 1.00 | 60.60 | A |
| ATOM | 504 | O   | LEU | A | 300 | 17.730 | 41.637 | 13.636 | 1.00 | 59.33 | A |
| ATOM | 505 | N   | LEU | A | 301 | 19.069 | 40.982 | 15.356 | 1.00 | 60.24 | A |
| ATOM | 506 | CA  | LEU | A | 301 | 18.037 | 41.026 | 16.375 | 1.00 | 61.50 | A |
| ATOM | 507 | CB  | LEU | A | 301 | 18.602 | 40.663 | 17.741 | 1.00 | 58.13 | A |
| ATOM | 508 | CG  | LEU | A | 301 | 18.572 | 39.144 | 17.973 | 1.00 | 57.40 | A |
| ATOM | 509 | CD1 | LEU | A | 301 | 19.199 | 38.756 | 19.285 | 1.00 | 56.79 | A |
| ATOM | 510 | CD2 | LEU | A | 301 | 17.136 | 38.680 | 17.956 | 1.00 | 58.19 | A |
| ATOM | 511 | C   | LEU | A | 301 | 17.280 | 42.331 | 16.465 | 1.00 | 64.37 | A |
| ATOM | 512 | O   | LEU | A | 301 | 16.040 | 42.330 | 16.393 | 1.00 | 64.07 | A |
| ATOM | 513 | N   | GLN | A | 302 | 17.974 | 43.462 | 16.600 | 1.00 | 68.77 | A |
| ATOM | 514 | CA  | GLN | A | 302 | 17.193 | 44.698 | 16.710 | 1.00 | 71.50 | A |
| ATOM | 515 | CB  | GLN | A | 302 | 17.974 | 45.880 | 17.345 | 1.00 | 73.70 | A |
| ATOM | 516 | CG  | GLN | A | 302 | 19.348 | 46.245 | 16.844 | 1.00 | 76.75 | A |
| ATOM | 517 | CD  | GLN | A | 302 | 20.227 | 46.790 | 17.994 | 1.00 | 78.75 | A |
| ATOM | 518 | OE1 | GLN | A | 302 | 19.727 | 47.134 | 19.080 | 1.00 | 77.82 | A |
| ATOM | 519 | NE2 | GLN | A | 302 | 21.539 | 46.865 | 17.754 | 1.00 | 79.14 | A |
| ATOM | 520 | C   | GLN | A | 302 | 16.535 | 45.082 | 15.415 | 1.00 | 70.47 | A |
| ATOM | 521 | O   | GLN | A | 302 | 15.630 | 45.911 | 15.377 | 1.00 | 71.90 | A |
| ATOM | 522 | N   | SER | A | 303 | 16.940 | 44.426 | 14.348 | 1.00 | 69.77 | A |
| ATOM | 523 | CA  | SER | A | 303 | 16.303 | 44.717 | 13.092 | 1.00 | 68.12 | A |
| ATOM | 524 | CB  | SER | A | 303 | 17.343 | 44.703 | 11.979 | 1.00 | 67.21 | A |
| ATOM | 525 | OG  | SER | A | 303 | 16.922 | 45.563 | 10.938 | 1.00 | 67.67 | A |
| ATOM | 526 | C   | SER | A | 303 | 15.120 | 43.759 | 12.769 | 1.00 | 66.59 | A |

TABLE 1-continued

ATOMIC COORDINATES OF THE ERR3 LBD/SRC-1 NR BOX 2 PEPTIDE COMPLEX (PDB CODE 1KV6)

| ATOM | 527 | O | SER | A | 303 | 14.254 | 44.100 | 11.954 | 1.00 | 66.33 | A |
|---|---|---|---|---|---|---|---|---|---|---|---|
| ATOM | 528 | N | ALA | A | 304 | 15.048 | 42.599 | 13.427 | 1.00 | 64.52 | A |
| ATOM | 529 | CA | ALA | A | 304 | 13.986 | 41.639 | 13.123 | 1.00 | 63.63 | A |
| ATOM | 530 | CB | ALA | A | 304 | 14.599 | 40.351 | 12.683 | 1.00 | 62.43 | A |
| ATOM | 531 | C | ALA | A | 304 | 12.990 | 41.331 | 14.208 | 1.00 | 62.75 | A |
| ATOM | 532 | O | ALA | A | 304 | 11.972 | 40.714 | 13.926 | 1.00 | 61.95 | A |
| ATOM | 533 | N | TRP | A | 305 | 13.283 | 41.751 | 15.440 | 1.00 | 63.83 | A |
| ATOM | 534 | CA | TRP | A | 305 | 12.435 | 41.426 | 16.573 | 1.00 | 64.16 | A |
| ATOM | 535 | CB | TRP | A | 305 | 12.850 | 42.182 | 17.868 | 1.00 | 67.15 | A |
| ATOM | 536 | CG | TRP | A | 305 | 12.669 | 43.655 | 17.840 | 1.00 | 70.97 | A |
| ATOM | 537 | CD2 | TRP | A | 305 | 11.538 | 44.409 | 18.332 | 1.00 | 72.98 | A |
| ATOM | 538 | CE2 | TRP | A | 305 | 11.706 | 45.741 | 17.897 | 1.00 | 72.91 | A |
| ATOM | 539 | CE3 | TRP | A | 305 | 10.400 | 44.088 | 19.090 | 1.00 | 74.06 | A |
| ATOM | 540 | CD1 | TRP | A | 305 | 13.450 | 44.542 | 17.178 | 1.00 | 72.98 | A |
| ATOM | 541 | NE1 | TRP | A | 305 | 12.882 | 45.789 | 17.196 | 1.00 | 73.41 | A |
| ATOM | 542 | CZ2 | TRP | A | 305 | 10.772 | 46.759 | 18.181 | 1.00 | 72.53 | A |
| ATOM | 543 | CZ3 | TRP | A | 305 | 9.463 | 45.112 | 19.375 | 1.00 | 73.61 | A |
| ATOM | 544 | CH2 | TRP | A | 305 | 9.663 | 46.423 | 18.919 | 1.00 | 72.96 | A |
| ATOM | 545 | C | TRP | A | 305 | 10.958 | 41.567 | 16.340 | 1.00 | 64.22 | A |
| ATOM | 546 | O | TRP | A | 305 | 10.209 | 40.716 | 16.785 | 1.00 | 65.68 | A |
| ATOM | 547 | N | MET | A | 306 | 10.502 | 42.591 | 15.640 | 1.00 | 63.67 | A |
| ATOM | 548 | CA | MET | A | 306 | 9.058 | 42.695 | 15.467 | 1.00 | 63.79 | A |
| ATOM | 549 | CB | MET | A | 306 | 8.678 | 44.109 | 15.044 | 1.00 | 63.69 | A |
| ATOM | 550 | CG | MET | A | 306 | 7.203 | 44.438 | 15.185 | 1.00 | 61.81 | A |
| ATOM | 551 | SD | MET | A | 306 | 6.684 | 44.509 | 16.895 | 1.00 | 64.14 | A |
| ATOM | 552 | CE | MET | A | 306 | 5.008 | 44.035 | 16.739 | 1.00 | 64.96 | A |
| ATOM | 553 | C | MET | A | 306 | 8.501 | 41.680 | 14.462 | 1.00 | 64.53 | A |
| ATOM | 554 | O | MET | A | 306 | 7.323 | 41.322 | 14.485 | 1.00 | 64.63 | A |
| ATOM | 555 | N | GLU | A | 307 | 9.348 | 41.198 | 13.573 | 1.00 | 66.22 | A |
| ATOM | 556 | CA | GLU | A | 307 | 8.894 | 40.232 | 12.589 | 1.00 | 66.96 | A |
| ATOM | 557 | CB | GLU | A | 307 | 9.892 | 40.177 | 11.427 | 1.00 | 68.74 | A |
| ATOM | 558 | CG | GLU | A | 307 | 9.534 | 41.159 | 10.311 | 1.00 | 74.24 | A |
| ATOM | 559 | CD | GLU | A | 307 | 10.604 | 41.276 | 9.234 | 1.00 | 78.09 | A |
| ATOM | 560 | OE1 | GLU | A | 307 | 11.592 | 42.012 | 9.461 | 1.00 | 79.91 | A |
| ATOM | 561 | OE2 | GLU | A | 307 | 10.459 | 40.630 | 8.164 | 1.00 | 80.05 | A |
| ATOM | 562 | C | GLU | A | 307 | 8.718 | 38.882 | 13.285 | 1.00 | 65.45 | A |
| ATOM | 563 | O | GLU | A | 307 | 7.772 | 38.144 | 13.007 | 1.00 | 65.08 | A |
| ATOM | 564 | N | ILE | A | 308 | 9.620 | 38.590 | 14.214 | 1.00 | 63.49 | A |
| ATOM | 565 | CA | ILE | A | 308 | 9.559 | 37.369 | 15.000 | 1.00 | 62.48 | A |
| ATOM | 566 | CB | ILE | A | 308 | 10.833 | 37.190 | 15.779 | 1.00 | 62.97 | A |
| ATOM | 567 | CG2 | ILE | A | 308 | 10.731 | 35.964 | 16.625 | 1.00 | 62.80 | A |
| ATOM | 568 | CG1 | ILE | A | 308 | 12.018 | 37.079 | 14.817 | 1.00 | 63.44 | A |
| ATOM | 569 | CD1 | ILE | A | 308 | 13.362 | 36.942 | 15.556 | 1.00 | 63.39 | A |
| ATOM | 570 | C | ILE | A | 308 | 8.365 | 37.401 | 15.980 | 1.00 | 62.14 | A |
| ATOM | 571 | O | ILE | A | 308 | 7.781 | 36.357 | 16.301 | 1.00 | 63.70 | A |
| ATOM | 572 | N | LEU | A | 309 | 7.999 | 38.587 | 16.464 | 1.00 | 60.45 | A |
| ATOM | 573 | CA | LEU | A | 309 | 6.847 | 38.704 | 17.350 | 1.00 | 58.71 | A |
| ATOM | 574 | CB | LEU | A | 309 | 6.815 | 40.046 | 18.066 | 1.00 | 58.26 | A |
| ATOM | 575 | CG | LEU | A | 309 | 7.833 | 40.283 | 19.187 | 1.00 | 58.08 | A |
| ATOM | 576 | CD1 | LEU | A | 309 | 7.555 | 41.647 | 19.832 | 1.00 | 56.97 | A |
| ATOM | 577 | CD2 | LEU | A | 309 | 7.757 | 39.172 | 20.225 | 1.00 | 55.84 | A |
| ATOM | 578 | C | LEU | A | 309 | 5.555 | 38.546 | 16.572 | 1.00 | 58.40 | A |
| ATOM | 579 | O | LEU | A | 309 | 4.693 | 37.793 | 16.980 | 1.00 | 59.76 | A |
| ATOM | 580 | N | ILE | A | 310 | 5.409 | 39.253 | 15.455 | 1.00 | 58.06 | A |
| ATOM | 581 | CA | ILE | A | 310 | 4.189 | 39.144 | 14.658 | 1.00 | 57.41 | A |
| ATOM | 582 | CB | ILE | A | 310 | 4.165 | 40.238 | 13.542 | 1.00 | 56.82 | A |
| ATOM | 583 | CG2 | ILE | A | 310 | 2.985 | 40.003 | 12.555 | 1.00 | 53.96 | A |
| ATOM | 584 | CG1 | ILE | A | 310 | 4.001 | 41.609 | 14.222 | 1.00 | 57.81 | A |
| ATOM | 585 | CD1 | ILE | A | 310 | 4.278 | 42.819 | 13.360 | 1.00 | 59.08 | A |
| ATOM | 586 | C | ILE | A | 310 | 3.969 | 37.735 | 14.070 | 1.00 | 57.83 | A |
| ATOM | 587 | O | ILE | A | 310 | 2.837 | 37.235 | 14.008 | 1.00 | 58.22 | A |
| ATOM | 588 | N | LEU | A | 311 | 5.056 | 37.098 | 13.647 | 1.00 | 56.57 | A |
| ATOM | 589 | CA | LEU | A | 311 | 4.972 | 35.762 | 13.092 | 1.00 | 55.22 | A |
| ATOM | 590 | CB | LEU | A | 311 | 6.364 | 35.260 | 12.726 | 1.00 | 53.11 | A |
| ATOM | 591 | CG | LEU | A | 311 | 6.718 | 35.126 | 11.251 | 1.00 | 51.92 | A |
| ATOM | 592 | CD1 | LEU | A | 311 | 7.877 | 34.135 | 11.148 | 1.00 | 51.71 | A |
| ATOM | 593 | CD2 | LEU | A | 311 | 5.514 | 34.650 | 10.452 | 1.00 | 48.31 | A |
| ATOM | 594 | C | LEU | A | 311 | 4.366 | 34.854 | 14.152 | 1.00 | 55.90 | A |
| ATOM | 595 | O | LEU | A | 311 | 3.586 | 33.943 | 13.851 | 1.00 | 53.82 | A |
| ATOM | 596 | N | GLY | A | 312 | 4.755 | 35.117 | 15.398 | 1.00 | 56.72 | A |
| ATOM | 597 | CA | GLY | A | 312 | 4.265 | 34.344 | 16.523 | 1.00 | 56.94 | A |
| ATOM | 598 | C | GLY | A | 312 | 2.771 | 34.529 | 16.730 | 1.00 | 56.51 | A |
| ATOM | 599 | O | GLY | A | 312 | 2.033 | 33.551 | 16.940 | 1.00 | 55.82 | A |
| ATOM | 600 | N | VAL | A | 313 | 2.322 | 35.780 | 16.670 | 1.00 | 55.06 | A |
| ATOM | 601 | CA | VAL | A | 313 | 0.908 | 36.065 | 16.834 | 1.00 | 54.81 | A |
| ATOM | 602 | CB | VAL | A | 313 | 0.617 | 37.541 | 16.787 | 1.00 | 53.66 | A |

TABLE 1-continued

ATOMIC COORDINATES OF THE ERR3 LBD/SRC-1 NR
BOX 2 PEPTIDE COMPLEX (PDB CODE 1KV6)

| ATOM | 603 | CG1 | VAL | A | 313 | −0.918 | 37.759 | 16.731 | 1.00 | 55.47 | A |
|---|---|---|---|---|---|---|---|---|---|---|---|
| ATOM | 604 | CG2 | VAL | A | 313 | 1.227 | 38.213 | 17.991 | 1.00 | 50.80 | A |
| ATOM | 605 | C | VAL | A | 313 | 0.147 | 35.424 | 15.696 | 1.00 | 56.19 | A |
| ATOM | 606 | O | VAL | A | 313 | −0.867 | 34.757 | 15.902 | 1.00 | 57.15 | A |
| ATOM | 607 | N | VAL | A | 314 | 0.654 | 35.629 | 14.489 | 1.00 | 56.51 | A |
| ATOM | 608 | CA | VAL | A | 314 | 0.035 | 35.084 | 13.306 | 1.00 | 55.40 | A |
| ATOM | 609 | CB | VAL | A | 314 | 0.839 | 35.530 | 12.060 | 1.00 | 53.68 | A |
| ATOM | 610 | CG1 | VAL | A | 314 | 0.681 | 34.543 | 10.903 | 1.00 | 53.46 | A |
| ATOM | 611 | CG2 | VAL | A | 314 | 0.340 | 36.886 | 11.632 | 1.00 | 52.47 | A |
| ATOM | 612 | C | VAL | A | 314 | −0.120 | 33.564 | 13.373 | 1.00 | 57.15 | A |
| ATOM | 613 | O | VAL | A | 314 | −1.201 | 33.043 | 13.101 | 1.00 | 58.81 | A |
| ATOM | 614 | N | TYR | A | 315 | 0.935 | 32.848 | 13.748 | 1.00 | 57.24 | A |
| ATOM | 615 | CA | TYR | A | 315 | 0.853 | 31.396 | 13.806 | 1.00 | 58.18 | A |
| ATOM | 616 | CB | TYR | A | 315 | 2.194 | 30.788 | 14.214 | 1.00 | 59.71 | A |
| ATOM | 617 | CG | TYR | A | 315 | 2.152 | 29.290 | 14.136 | 1.00 | 62.49 | A |
| ATOM | 618 | CD1 | TYR | A | 315 | 1.987 | 28.512 | 15.284 | 1.00 | 62.64 | A |
| ATOM | 619 | CE1 | TYR | A | 315 | 1.813 | 27.111 | 15.196 | 1.00 | 63.56 | A |
| ATOM | 620 | CD2 | TYR | A | 315 | 2.150 | 28.643 | 12.891 | 1.00 | 62.80 | A |
| ATOM | 621 | CE2 | TYR | A | 315 | 1.971 | 27.248 | 12.788 | 1.00 | 63.67 | A |
| ATOM | 622 | CZ | TYR | A | 315 | 1.802 | 26.493 | 13.951 | 1.00 | 64.08 | A |
| ATOM | 623 | OH | TYR | A | 315 | 1.609 | 25.138 | 13.851 | 1.00 | 64.85 | A |
| ATOM | 624 | C | TYR | A | 315 | −0.223 | 30.916 | 14.774 | 1.00 | 59.10 | A |
| ATOM | 625 | O | TYR | A | 315 | −1.064 | 30.099 | 14.440 | 1.00 | 59.38 | A |
| ATOM | 626 | N | ARG | A | 316 | −0.182 | 31.435 | 15.989 | 1.00 | 60.90 | A |
| ATOM | 627 | CA | ARG | A | 316 | −1.149 | 31.084 | 17.021 | 1.00 | 60.44 | A |
| ATOM | 628 | CB | ARG | A | 316 | −0.844 | 31.880 | 18.305 | 1.00 | 58.51 | A |
| ATOM | 629 | CG | ARG | A | 316 | 0.489 | 31.543 | 18.962 | 1.00 | 55.32 | A |
| ATOM | 630 | CD | ARG | A | 316 | 0.600 | 32.214 | 20.334 | 1.00 | 56.41 | A |
| ATOM | 631 | NE | ARG | A | 316 | 0.872 | 33.648 | 20.291 | 1.00 | 56.39 | A |
| ATOM | 632 | CZ | ARG | A | 316 | 2.093 | 34.177 | 20.164 | 1.00 | 57.68 | A |
| ATOM | 633 | NH1 | ARG | A | 316 | 3.178 | 33.396 | 20.071 | 1.00 | 55.80 | A |
| ATOM | 634 | NH2 | ARG | A | 316 | 2.233 | 35.498 | 20.117 | 1.00 | 57.49 | A |
| ATOM | 635 | C | ARG | A | 316 | −2.602 | 31.343 | 16.584 | 1.00 | 62.19 | A |
| ATOM | 636 | O | ARG | A | 316 | −3.528 | 30.668 | 17.057 | 1.00 | 62.19 | A |
| ATOM | 637 | N | SER | A | 317 | −2.797 | 32.299 | 15.676 | 1.00 | 62.37 | A |
| ATOM | 638 | CA | SER | A | 317 | −4.135 | 32.658 | 15.226 | 1.00 | 62.97 | A |
| ATOM | 639 | CB | SER | A | 317 | −4.184 | 34.140 | 14.898 | 1.00 | 61.55 | A |
| ATOM | 640 | OG | SER | A | 317 | −3.712 | 34.896 | 15.989 | 1.00 | 61.97 | A |
| ATOM | 641 | C | SER | A | 317 | −4.641 | 31.882 | 14.034 | 1.00 | 64.20 | A |
| ATOM | 642 | O | SER | A | 317 | −5.778 | 32.062 | 13.623 | 1.00 | 64.65 | A |
| ATOM | 643 | N | LEU | A | 318 | −3.806 | 31.010 | 13.492 | 1.00 | 65.73 | A |
| ATOM | 644 | CA | LEU | A | 318 | −4.178 | 30.250 | 12.322 | 1.00 | 67.74 | A |
| ATOM | 645 | CB | LEU | A | 318 | −3.090 | 29.226 | 12.028 | 1.00 | 64.94 | A |
| ATOM | 646 | CG | LEU | A | 318 | −2.225 | 29.523 | 10.797 | 1.00 | 61.39 | A |
| ATOM | 647 | CD1 | LEU | A | 318 | −2.279 | 30.983 | 10.450 | 1.00 | 61.93 | A |
| ATOM | 648 | CD2 | LEU | A | 318 | −0.794 | 29.066 | 11.066 | 1.00 | 60.24 | A |
| ATOM | 649 | C | LEU | A | 318 | −5.545 | 29.582 | 12.411 | 1.00 | 71.35 | A |
| ATOM | 650 | O | LEU | A | 318 | −6.297 | 29.520 | 11.423 | 1.00 | 72.17 | A |
| ATOM | 651 | N | SER | A | 319 | −5.896 | 29.104 | 13.596 | 1.00 | 74.62 | A |
| ATOM | 652 | CA | SER | A | 319 | −7.181 | 28.431 | 13.756 | 1.00 | 76.65 | A |
| ATOM | 653 | CB | SER | A | 319 | −7.008 | 27.247 | 14.701 | 1.00 | 76.40 | A |
| ATOM | 654 | OG | SER | A | 319 | −6.524 | 27.708 | 15.943 | 1.00 | 79.08 | A |
| ATOM | 655 | C | SER | A | 319 | −8.353 | 29.303 | 14.238 | 1.00 | 77.74 | A |
| ATOM | 656 | O | SER | A | 319 | −9.361 | 28.771 | 14.707 | 1.00 | 79.01 | A |
| ATOM | 657 | N | PHE | A | 320 | −8.243 | 30.623 | 14.121 | 1.00 | 77.70 | A |
| ATOM | 658 | CA | PHE | A | 320 | −9.328 | 31.488 | 14.560 | 1.00 | 78.57 | A |
| ATOM | 659 | CB | PHE | A | 320 | −8.839 | 32.394 | 15.685 | 1.00 | 77.43 | A |
| ATOM | 660 | CG | PHE | A | 320 | −8.541 | 31.663 | 16.962 | 1.00 | 76.53 | A |
| ATOM | 661 | CD1 | PHE | A | 320 | −9.277 | 31.909 | 18.112 | 1.00 | 76.52 | A |
| ATOM | 662 | CD2 | PHE | A | 320 | −7.516 | 30.728 | 17.022 | 1.00 | 77.20 | A |
| ATOM | 663 | CE1 | PHE | A | 320 | −8.988 | 31.228 | 19.307 | 1.00 | 76.81 | A |
| ATOM | 664 | CE2 | PHE | A | 320 | −7.219 | 30.038 | 18.216 | 1.00 | 77.00 | A |
| ATOM | 665 | CZ | PHE | A | 320 | −7.955 | 30.291 | 19.355 | 1.00 | 75.93 | A |
| ATOM | 666 | C | PHE | A | 320 | −9.891 | 32.329 | 13.417 | 1.00 | 80.55 | A |
| ATOM | 667 | O | PHE | A | 320 | −9.282 | 32.427 | 12.356 | 1.00 | 81.93 | A |
| ATOM | 668 | N | GLU | A | 321 | −11.061 | 32.927 | 13.617 | 1.00 | 81.64 | A |
| ATOM | 669 | CA | GLU | A | 321 | −11.652 | 33.767 | 12.580 | 1.00 | 83.22 | A |
| ATOM | 670 | CB | GLU | A | 321 | −13.105 | 33.362 | 12.279 | 1.00 | 86.19 | A |
| ATOM | 671 | CG | GLU | A | 321 | −13.319 | 32.676 | 10.913 | 1.00 | 89.49 | A |
| ATOM | 672 | CD | GLU | A | 321 | −12.579 | 31.331 | 10.791 | 1.00 | 92.23 | A |
| ATOM | 673 | OE1 | GLU | A | 321 | −12.197 | 30.962 | 9.636 | 1.00 | 92.36 | A |
| ATOM | 674 | OE2 | GLU | A | 321 | −12.389 | 30.651 | 11.847 | 1.00 | 91.90 | A |
| ATOM | 675 | C | GLU | A | 321 | −11.622 | 35.194 | 13.068 | 1.00 | 82.98 | A |
| ATOM | 676 | O | GLU | A | 321 | −12.222 | 35.511 | 14.072 | 1.00 | 82.48 | A |
| ATOM | 677 | N | ASP | A | 322 | −10.886 | 36.040 | 12.360 | 1.00 | 83.69 | A |
| ATOM | 678 | CA | ASP | A | 322 | −10.763 | 37.460 | 12.682 | 1.00 | 83.62 | A |

TABLE 1-continued

ATOMIC COORDINATES OF THE ERR3 LBD/SRC-1 NR
BOX 2 PEPTIDE COMPLEX (PDB CODE 1KV6)

| ATOM | 679 | CB  | ASP | A | 322 | -12.037 | 38.190 | 12.266 | 1.00 | 85.92 | A |
|------|-----|-----|-----|---|-----|---------|--------|--------|------|-------|---|
| ATOM | 680 | CG  | ASP | A | 322 | -12.432 | 37.852 | 10.852 | 1.00 | 88.76 | A |
| ATOM | 681 | OD1 | ASP | A | 322 | -12.940 | 36.721 | 10.649 | 1.00 | 90.52 | A |
| ATOM | 682 | OD2 | ASP | A | 322 | -12.206 | 38.696 | 9.945  | 1.00 | 90.23 | A |
| ATOM | 683 | C   | ASP | A | 322 | -10.405 | 37.805 | 14.116 | 1.00 | 81.64 | A |
| ATOM | 684 | O   | ASP | A | 322 | -10.840 | 38.834 | 14.645 | 1.00 | 80.07 | A |
| ATOM | 685 | N   | GLU | A | 323 | -9.604  | 36.941 | 14.730 | 1.00 | 79.85 | A |
| ATOM | 686 | CA  | GLU | A | 323 | -9.143  | 37.152 | 16.090 | 1.00 | 78.32 | A |
| ATOM | 687 | CB  | GLU | A | 323 | -9.763  | 36.125 | 17.046 | 1.00 | 81.39 | A |
| ATOM | 688 | CG  | GLU | A | 323 | -11.208 | 36.400 | 17.468 | 1.00 | 86.05 | A |
| ATOM | 689 | CD  | GLU | A | 323 | -11.706 | 35.453 | 18.582 | 1.00 | 90.29 | A |
| ATOM | 690 | OE1 | GLU | A | 323 | -11.673 | 34.207 | 18.381 | 1.00 | 91.61 | A |
| ATOM | 691 | OE2 | GLU | A | 323 | -12.137 | 35.957 | 19.659 | 1.00 | 90.98 | A |
| ATOM | 692 | C   | GLU | A | 323 | -7.635  | 36.985 | 16.067 | 1.00 | 74.90 | A |
| ATOM | 693 | O   | GLU | A | 323 | -7.097  | 36.295 | 15.222 | 1.00 | 75.62 | A |
| ATOM | 694 | N   | LEU | A | 324 | -6.949  | 37.621 | 16.995 | 1.00 | 71.01 | A |
| ATOM | 695 | CA  | LEU | A | 324 | -5.501  | 37.522 | 17.045 | 1.00 | 68.09 | A |
| ATOM | 696 | CB  | LEU | A | 324 | -4.853  | 38.903 | 16.868 | 1.00 | 67.19 | A |
| ATOM | 697 | CG  | LEU | A | 324 | -4.928  | 39.614 | 15.516 | 1.00 | 65.89 | A |
| ATOM | 698 | CD1 | LEU | A | 324 | -4.305  | 40.962 | 15.681 | 1.00 | 66.79 | A |
| ATOM | 699 | CD2 | LEU | A | 324 | -4.210  | 38.836 | 14.426 | 1.00 | 65.72 | A |
| ATOM | 700 | C   | LEU | A | 324 | -5.106  | 36.955 | 18.384 | 1.00 | 66.67 | A |
| ATOM | 701 | O   | LEU | A | 324 | -5.461  | 37.507 | 19.419 | 1.00 | 67.77 | A |
| ATOM | 702 | N   | VAL | A | 325 | -4.360  | 35.865 | 18.384 | 1.00 | 63.79 | A |
| ATOM | 703 | CA  | VAL | A | 325 | -3.967  | 35.282 | 19.641 | 1.00 | 62.26 | A |
| ATOM | 704 | CB  | VAL | A | 325 | -4.079  | 33.749 | 19.561 | 1.00 | 61.58 | A |
| ATOM | 705 | CG1 | VAL | A | 325 | -3.678  | 33.105 | 20.877 | 1.00 | 58.51 | A |
| ATOM | 706 | CG2 | VAL | A | 325 | -5.503  | 33.375 | 19.193 | 1.00 | 60.18 | A |
| ATOM | 707 | C   | VAL | A | 325 | -2.568  | 35.728 | 20.101 | 1.00 | 63.83 | A |
| ATOM | 708 | O   | VAL | A | 325 | -1.549  | 35.068 | 19.847 | 1.00 | 64.04 | A |
| ATOM | 709 | N   | TYR | A | 326 | -2.525  | 36.866 | 20.777 | 1.00 | 63.04 | A |
| ATOM | 710 | CA  | TYR | A | 326 | -1.277  | 37.370 | 21.311 | 1.00 | 65.12 | A |
| ATOM | 711 | CB  | TYR | A | 326 | -1.509  | 38.713 | 21.980 | 1.00 | 66.36 | A |
| ATOM | 712 | CG  | TYR | A | 326 | -1.579  | 39.831 | 20.990 | 1.00 | 68.39 | A |
| ATOM | 713 | CD1 | TYR | A | 326 | -0.417  | 40.349 | 20.456 | 1.00 | 69.30 | A |
| ATOM | 714 | CE1 | TYR | A | 326 | -0.450  | 41.349 | 19.488 | 1.00 | 72.51 | A |
| ATOM | 715 | CD2 | TYR | A | 326 | -2.806  | 40.336 | 20.538 | 1.00 | 69.27 | A |
| ATOM | 716 | CE2 | TYR | A | 326 | -2.858  | 41.334 | 19.566 | 1.00 | 70.89 | A |
| ATOM | 717 | CZ  | TYR | A | 326 | -1.660  | 41.846 | 19.042 | 1.00 | 72.85 | A |
| ATOM | 718 | OH  | TYR | A | 326 | -1.627  | 42.871 | 18.106 | 1.00 | 74.05 | A |
| ATOM | 719 | C   | TYR | A | 326 | -0.779  | 36.360 | 22.327 | 1.00 | 65.88 | A |
| ATOM | 720 | O   | TYR | A | 326 | 0.411   | 36.089 | 22.412 | 1.00 | 65.47 | A |
| ATOM | 721 | N   | ALA | A | 327 | -1.714  | 35.805 | 23.091 | 1.00 | 67.60 | A |
| ATOM | 722 | CA  | ALA | A | 327 | -1.439  | 34.784 | 24.110 | 1.00 | 69.74 | A |
| ATOM | 723 | CB  | ALA | A | 327 | -1.029  | 35.459 | 25.426 | 1.00 | 68.43 | A |
| ATOM | 724 | C   | ALA | A | 327 | -2.713  | 33.912 | 24.292 | 1.00 | 71.11 | A |
| ATOM | 725 | O   | ALA | A | 327 | -3.800  | 34.309 | 23.869 | 1.00 | 70.62 | A |
| ATOM | 726 | N   | ASP | A | 328 | -2.605  | 32.727 | 24.892 | 1.00 | 73.88 | A |
| ATOM | 727 | CA  | ASP | A | 328 | -3.812  | 31.898 | 25.051 | 1.00 | 75.48 | A |
| ATOM | 728 | CB  | ASP | A | 328 | -3.489  | 30.549 | 25.704 | 1.00 | 75.09 | A |
| ATOM | 729 | CG  | ASP | A | 328 | -2.763  | 29.585 | 24.765 | 1.00 | 76.94 | A |
| ATOM | 730 | OD1 | ASP | A | 328 | -2.834  | 29.755 | 23.521 | 1.00 | 76.79 | A |
| ATOM | 731 | OD2 | ASP | A | 328 | -2.130  | 28.631 | 25.276 | 1.00 | 77.74 | A |
| ATOM | 732 | C   | ASP | A | 328 | -4.836  | 32.634 | 25.907 | 1.00 | 76.46 | A |
| ATOM | 733 | O   | ASP | A | 328 | -6.051  | 32.562 | 25.672 | 1.00 | 76.79 | A |
| ATOM | 734 | N   | ASP | A | 329 | -4.316  | 33.358 | 26.890 | 1.00 | 77.42 | A |
| ATOM | 735 | CA  | ASP | A | 329 | -5.122  | 34.135 | 27.822 | 1.00 | 79.26 | A |
| ATOM | 736 | CB  | ASP | A | 329 | -4.410  | 34.183 | 29.176 | 1.00 | 79.69 | A |
| ATOM | 737 | CG  | ASP | A | 329 | -3.132  | 34.998 | 29.130 | 1.00 | 79.80 | A |
| ATOM | 738 | OD1 | ASP | A | 329 | -2.511  | 35.213 | 30.187 | 1.00 | 81.28 | A |
| ATOM | 739 | OD2 | ASP | A | 329 | -2.744  | 35.427 | 28.029 | 1.00 | 80.35 | A |
| ATOM | 740 | C   | ASP | A | 329 | -5.423  | 35.587 | 27.358 | 1.00 | 80.23 | A |
| ATOM | 741 | O   | ASP | A | 329 | -5.930  | 36.407 | 28.138 | 1.00 | 80.34 | A |
| ATOM | 742 | N   | TYR | A | 330 | -5.098  | 35.903 | 26.106 | 1.00 | 80.37 | A |
| ATOM | 743 | CA  | TYR | A | 330 | -5.340  | 37.232 | 25.574 | 1.00 | 80.26 | A |
| ATOM | 744 | CB  | TYR | A | 330 | -4.140  | 38.130 | 25.867 | 1.00 | 82.41 | A |
| ATOM | 745 | CG  | TYR | A | 330 | -4.502  | 39.602 | 25.980 | 1.00 | 85.41 | A |
| ATOM | 746 | CD1 | TYR | A | 330 | -5.076  | 40.281 | 24.916 | 1.00 | 87.46 | A |
| ATOM | 747 | CE1 | TYR | A | 330 | -5.403  | 41.633 | 25.008 | 1.00 | 89.06 | A |
| ATOM | 748 | CD2 | TYR | A | 330 | -4.269  | 40.315 | 27.150 | 1.00 | 86.66 | A |
| ATOM | 749 | CE2 | TYR | A | 330 | -4.596  | 41.665 | 27.247 | 1.00 | 88.87 | A |
| ATOM | 750 | CZ  | TYR | A | 330 | -5.162  | 42.311 | 26.171 | 1.00 | 88.93 | A |
| ATOM | 751 | OH  | TYR | A | 330 | -5.494  | 43.635 | 26.255 | 1.00 | 90.37 | A |
| ATOM | 752 | C   | TYR | A | 330 | -5.603  | 37.173 | 24.071 | 1.00 | 79.60 | A |
| ATOM | 753 | O   | TYR | A | 330 | -4.678  | 37.215 | 23.282 | 1.00 | 79.59 | A |
| ATOM | 754 | N   | ILE | A | 331 | -6.873  | 37.086 | 23.686 | 1.00 | 79.12 | A |

TABLE 1-continued

ATOMIC COORDINATES OF THE ERR3 LBD/SRC-1 NR
BOX 2 PEPTIDE COMPLEX (PDB CODE 1KV6)

| ATOM | 755 | CA | ILE | A | 331 | −7.268 | 37.004 | 22.284 | 1.00 | 78.50 | A |
|---|---|---|---|---|---|---|---|---|---|---|---|
| ATOM | 756 | CB | ILE | A | 331 | −8.087 | 35.722 | 22.026 | 1.00 | 75.76 | A |
| ATOM | 757 | CG2 | ILE | A | 331 | −8.547 | 35.662 | 20.593 | 1.00 | 72.84 | A |
| ATOM | 758 | CG1 | ILE | A | 331 | −7.254 | 34.496 | 22.378 | 1.00 | 73.29 | A |
| ATOM | 759 | CD1 | ILE | A | 331 | −8.043 | 33.254 | 22.374 | 1.00 | 70.68 | A |
| ATOM | 760 | C | ILE | A | 331 | −8.139 | 38.207 | 21.941 | 1.00 | 81.83 | A |
| ATOM | 761 | O | ILE | A | 331 | −9.146 | 38.451 | 22.602 | 1.00 | 83.18 | A |
| ATOM | 762 | N | MET | A | 332 | −7.760 | 38.952 | 20.903 | 1.00 | 84.89 | A |
| ATOM | 763 | CA | MET | A | 332 | −8.512 | 40.139 | 20.481 | 1.00 | 87.24 | A |
| ATOM | 764 | CB | MET | A | 332 | −7.565 | 41.307 | 20.226 | 1.00 | 86.89 | A |
| ATOM | 765 | CG | MET | A | 332 | −6.802 | 41.752 | 21.433 | 1.00 | 87.54 | A |
| ATOM | 766 | SD | MET | A | 332 | −6.155 | 43.383 | 21.135 | 1.00 | 90.17 | A |
| ATOM | 767 | CE | MET | A | 332 | −4.546 | 43.264 | 21.942 | 1.00 | 89.24 | A |
| ATOM | 768 | C | MET | A | 332 | −9.385 | 39.992 | 19.247 | 1.00 | 89.23 | A |
| ATOM | 769 | O | MET | A | 332 | −8.949 | 39.491 | 18.221 | 1.00 | 89.53 | A |
| ATOM | 770 | N | ASP | A | 333 | −10.628 | 40.433 | 19.351 | 1.00 | 92.28 | A |
| ATOM | 771 | CA | ASP | A | 333 | −11.517 | 40.404 | 18.201 | 1.00 | 95.34 | A |
| ATOM | 772 | CB | ASP | A | 333 | −12.916 | 39.902 | 18.569 | 1.00 | 98.05 | A |
| ATOM | 773 | CG | ASP | A | 333 | −13.500 | 40.610 | 19.784 | 1.00 | 100.47 | A |
| ATOM | 774 | OD1 | ASP | A | 333 | −13.394 | 41.860 | 19.875 | 1.00 | 100.16 | A |
| ATOM | 775 | OD2 | ASP | A | 333 | −14.075 | 39.900 | 20.645 | 1.00 | 101.96 | A |
| ATOM | 776 | C | ASP | A | 333 | −11.573 | 41.858 | 17.774 | 1.00 | 96.13 | A |
| ATOM | 777 | O | ASP | A | 333 | −10.859 | 42.683 | 18.338 | 1.00 | 95.06 | A |
| ATOM | 778 | N | GLU | A | 334 | −12.412 | 42.184 | 16.800 | 1.00 | 98.26 | A |
| ATOM | 779 | CA | GLU | A | 334 | −12.488 | 43.561 | 16.328 | 1.00 | 101.10 | A |
| ATOM | 780 | CB | GLU | A | 334 | −13.524 | 43.682 | 15.218 | 1.00 | 103.47 | A |
| ATOM | 781 | CG | GLU | A | 334 | −13.095 | 43.032 | 13.910 | 1.00 | 107.34 | A |
| ATOM | 782 | CD | GLU | A | 334 | −14.200 | 43.039 | 12.854 | 1.00 | 109.32 | A |
| ATOM | 783 | OE1 | GLU | A | 334 | −14.844 | 44.113 | 12.673 | 1.00 | 109.07 | A |
| ATOM | 784 | OE2 | GLU | A | 334 | −14.406 | 41.972 | 12.205 | 1.00 | 109.53 | A |
| ATOM | 785 | C | GLU | A | 334 | −12.781 | 44.594 | 17.401 | 1.00 | 102.00 | A |
| ATOM | 786 | O | GLU | A | 334 | −11.986 | 45.516 | 17.612 | 1.00 | 101.45 | A |
| ATOM | 787 | N | ASP | A | 335 | −13.926 | 44.437 | 18.066 | 1.00 | 103.80 | A |
| ATOM | 788 | CA | ASP | A | 335 | −14.377 | 45.353 | 19.126 | 1.00 | 104.87 | A |
| ATOM | 789 | CB | ASP | A | 335 | −15.503 | 44.716 | 19.955 | 1.00 | 106.04 | A |
| ATOM | 790 | CG | ASP | A | 335 | −16.542 | 44.004 | 19.098 | 1.00 | 107.68 | A |
| ATOM | 791 | OD1 | ASP | A | 335 | −16.157 | 43.125 | 18.283 | 1.00 | 108.31 | A |
| ATOM | 792 | OD2 | ASP | A | 335 | −17.747 | 44.309 | 19.253 | 1.00 | 108.00 | A |
| ATOM | 793 | C | ASP | A | 335 | −13.235 | 45.718 | 20.069 | 1.00 | 105.03 | A |
| ATOM | 794 | O | ASP | A | 335 | −13.015 | 46.895 | 20.360 | 1.00 | 105.20 | A |
| ATOM | 795 | N | GLN | A | 336 | −12.520 | 44.697 | 20.541 | 1.00 | 104.91 | A |
| ATOM | 796 | CA | GLN | A | 336 | −11.408 | 44.889 | 21.463 | 1.00 | 105.03 | A |
| ATOM | 797 | CB | GLN | A | 336 | −10.849 | 43.538 | 21.916 | 1.00 | 105.65 | A |
| ATOM | 798 | CG | GLN | A | 336 | −11.819 | 42.645 | 22.653 | 1.00 | 106.56 | A |
| ATOM | 799 | CD | GLN | A | 336 | −11.140 | 41.388 | 23.180 | 1.00 | 108.21 | A |
| ATOM | 800 | OE1 | GLN | A | 336 | −11.654 | 40.277 | 23.009 | 1.00 | 108.81 | A |
| ATOM | 801 | NE2 | GLN | A | 336 | −9.977 | 41.556 | 23.826 | 1.00 | 108.26 | A |
| ATOM | 802 | C | GLN | A | 336 | −10.271 | 45.713 | 20.859 | 1.00 | 105.03 | A |
| ATOM | 803 | O | GLN | A | 336 | −9.780 | 46.662 | 21.480 | 1.00 | 105.36 | A |
| ATOM | 804 | N | SER | A | 337 | −9.847 | 45.347 | 19.652 | 1.00 | 104.45 | A |
| ATOM | 805 | CA | SER | A | 337 | −8.755 | 46.053 | 19.007 | 1.00 | 103.21 | A |
| ATOM | 806 | CB | SER | A | 337 | −8.364 | 45.354 | 17.699 | 1.00 | 102.83 | A |
| ATOM | 807 | OG | SER | A | 337 | −9.450 | 45.317 | 16.802 | 1.00 | 104.05 | A |
| ATOM | 808 | C | SER | A | 337 | −9.088 | 47.526 | 18.774 | 1.00 | 102.45 | A |
| ATOM | 809 | O | SER | A | 337 | −8.186 | 48.366 | 18.788 | 1.00 | 102.63 | A |
| ATOM | 810 | N | LYS | A | 338 | −10.363 | 47.856 | 18.570 | 1.00 | 101.35 | A |
| ATOM | 811 | CA | LYS | A | 338 | −10.728 | 49.267 | 18.378 | 1.00 | 100.69 | A |
| ATOM | 812 | CB | LYS | A | 338 | −12.210 | 49.423 | 18.015 | 1.00 | 100.38 | A |
| ATOM | 813 | CG | LYS | A | 338 | −12.642 | 48.746 | 16.732 | 1.00 | 101.27 | A |
| ATOM | 814 | CD | LYS | A | 338 | −14.157 | 48.873 | 16.530 | 1.00 | 101.58 | A |
| ATOM | 815 | CE | LYS | A | 338 | −14.662 | 47.952 | 15.417 | 1.00 | 100.90 | A |
| ATOM | 816 | NZ | LYS | A | 338 | −16.136 | 48.028 | 15.274 | 1.00 | 99.71 | A |
| ATOM | 817 | C | LYS | A | 338 | −10.457 | 50.030 | 19.685 | 1.00 | 100.11 | A |
| ATOM | 818 | O | LYS | A | 338 | −9.870 | 51.122 | 19.666 | 1.00 | 99.95 | A |
| ATOM | 819 | N | LEU | A | 339 | −10.884 | 49.431 | 20.807 | 1.00 | 98.57 | A |
| ATOM | 820 | CA | LEU | A | 339 | −10.724 | 50.000 | 22.149 | 1.00 | 97.18 | A |
| ATOM | 821 | CB | LEU | A | 339 | −11.408 | 49.119 | 23.189 | 1.00 | 97.31 | A |
| ATOM | 822 | CG | LEU | A | 339 | −12.670 | 48.389 | 22.742 | 1.00 | 98.67 | A |
| ATOM | 823 | CD1 | LEU | A | 339 | −13.310 | 47.700 | 23.949 | 1.00 | 98.40 | A |
| ATOM | 824 | CD2 | LEU | A | 339 | −13.642 | 49.369 | 22.092 | 1.00 | 99.07 | A |
| ATOM | 825 | C | LEU | A | 339 | −9.268 | 50.187 | 22.563 | 1.00 | 96.49 | A |
| ATOM | 826 | O | LEU | A | 339 | −8.976 | 50.885 | 23.536 | 1.00 | 96.16 | A |
| ATOM | 827 | N | ALA | A | 340 | −8.359 | 49.539 | 21.844 | 1.00 | 95.31 | A |
| ATOM | 828 | CA | ALA | A | 340 | −6.938 | 49.656 | 22.128 | 1.00 | 94.03 | A |
| ATOM | 829 | CB | ALA | A | 340 | −6.275 | 48.280 | 22.093 | 1.00 | 94.24 | A |
| ATOM | 830 | C | ALA | A | 340 | −6.363 | 50.549 | 21.047 | 1.00 | 93.46 | A |

TABLE 1-continued

ATOMIC COORDINATES OF THE ERR3 LBD/SRC-1 NR
BOX 2 PEPTIDE COMPLEX (PDB CODE 1KV6)

| ATOM | 831 | O | ALA | A | 340 | −5.183 | 50.907 | 21.084 | 1.00 | 92.67 | A |
|------|-----|-----|-----|---|-----|--------|--------|--------|------|-------|---|
| ATOM | 832 | N | GLY | A | 341 | −7.226 | 50.895 | 20.087 | 1.00 | 93.52 | A |
| ATOM | 833 | CA | GLY | A | 341 | −6.846 | 51.746 | 18.968 | 1.00 | 93.62 | A |
| ATOM | 834 | C | GLY | A | 341 | −5.818 | 51.078 | 18.076 | 1.00 | 93.43 | A |
| ATOM | 835 | O | GLY | A | 341 | −4.906 | 51.721 | 17.558 | 1.00 | 92.73 | A |
| ATOM | 836 | N | LEU | A | 342 | −5.973 | 49.773 | 17.898 | 1.00 | 93.46 | A |
| ATOM | 837 | CA | LEU | A | 342 | −5.049 | 48.992 | 17.092 | 1.00 | 93.49 | A |
| ATOM | 838 | CB | LEU | A | 342 | −4.328 | 47.953 | 17.969 | 1.00 | 92.22 | A |
| ATOM | 839 | CG | LEU | A | 342 | −3.435 | 48.417 | 19.132 | 1.00 | 91.90 | A |
| ATOM | 840 | CD1 | LEU | A | 342 | −3.132 | 47.211 | 20.015 | 1.00 | 91.94 | A |
| ATOM | 841 | CD2 | LEU | A | 342 | −2.150 | 49.090 | 18.620 | 1.00 | 89.83 | A |
| ATOM | 842 | C | LEU | A | 342 | −5.826 | 48.280 | 16.000 | 1.00 | 94.10 | A |
| ATOM | 843 | O | LEU | A | 342 | −5.464 | 47.178 | 15.587 | 1.00 | 95.55 | A |
| ATOM | 844 | N | LEU | A | 343 | −6.893 | 48.906 | 15.524 | 1.00 | 93.63 | A |
| ATOM | 845 | CA | LEU | A | 343 | −7.703 | 48.285 | 14.487 | 1.00 | 92.52 | A |
| ATOM | 846 | CB | LEU | A | 343 | −8.937 | 49.128 | 14.217 | 1.00 | 91.69 | A |
| ATOM | 847 | CG | LEU | A | 343 | −9.945 | 48.453 | 13.297 | 1.00 | 91.92 | A |
| ATOM | 848 | CD1 | LEU | A | 343 | −10.601 | 47.239 | 13.978 | 1.00 | 90.80 | A |
| ATOM | 849 | CD2 | LEU | A | 343 | −10.974 | 49.502 | 12.913 | 1.00 | 92.10 | A |
| ATOM | 850 | C | LEU | A | 343 | −6.923 | 48.094 | 13.192 | 1.00 | 91.78 | A |
| ATOM | 851 | O | LEU | A | 343 | −6.991 | 47.040 | 12.554 | 1.00 | 92.18 | A |
| ATOM | 852 | N | ASP | A | 344 | −6.175 | 49.116 | 12.808 | 1.00 | 90.95 | A |
| ATOM | 853 | CA | ASP | A | 344 | −5.399 | 49.038 | 11.584 | 1.00 | 90.58 | A |
| ATOM | 854 | CB | ASP | A | 344 | −4.797 | 50.407 | 11.266 | 1.00 | 92.67 | A |
| ATOM | 855 | CG | ASP | A | 344 | −5.867 | 51.485 | 11.082 | 1.00 | 94.47 | A |
| ATOM | 856 | OD1 | ASP | A | 344 | −6.675 | 51.385 | 10.121 | 1.00 | 94.12 | A |
| ATOM | 857 | OD2 | ASP | A | 344 | −5.898 | 52.428 | 11.909 | 1.00 | 95.76 | A |
| ATOM | 858 | C | ASP | A | 344 | −4.306 | 47.975 | 11.676 | 1.00 | 89.39 | A |
| ATOM | 859 | O | ASP | A | 344 | −4.314 | 47.011 | 10.905 | 1.00 | 89.00 | A |
| ATOM | 860 | N | LEU | A | 345 | −3.384 | 48.149 | 12.632 | 1.00 | 87.49 | A |
| ATOM | 861 | CA | LEU | A | 345 | −2.267 | 47.226 | 12.850 | 1.00 | 84.28 | A |
| ATOM | 862 | CB | LEU | A | 345 | −1.589 | 47.519 | 14.171 | 1.00 | 83.04 | A |
| ATOM | 863 | CG | LEU | A | 345 | −0.083 | 47.310 | 14.160 | 1.00 | 83.03 | A |
| ATOM | 864 | CD1 | LEU | A | 345 | 0.351 | 47.101 | 15.587 | 1.00 | 82.07 | A |
| ATOM | 865 | CD2 | LEU | A | 345 | 0.312 | 46.139 | 13.301 | 1.00 | 82.85 | A |
| ATOM | 866 | C | LEU | A | 345 | −2.753 | 45.791 | 12.881 | 1.00 | 83.41 | A |
| ATOM | 867 | O | LEU | A | 345 | −2.179 | 44.913 | 12.247 | 1.00 | 83.63 | A |
| ATOM | 868 | N | ASN | A | 346 | −3.819 | 45.562 | 13.635 | 1.00 | 81.96 | A |
| ATOM | 869 | CA | ASN | A | 346 | −4.401 | 44.241 | 13.759 | 1.00 | 80.35 | A |
| ATOM | 870 | CB | ASN | A | 346 | −5.476 | 44.253 | 14.844 | 1.00 | 80.00 | A |
| ATOM | 871 | CG | ASN | A | 346 | −4.928 | 43.857 | 16.198 | 1.00 | 79.94 | A |
| ATOM | 872 | OD1 | ASN | A | 346 | −3.745 | 44.065 | 16.485 | 1.00 | 77.74 | A |
| ATOM | 873 | ND2 | ASN | A | 346 | −5.790 | 43.282 | 17.044 | 1.00 | 80.93 | A |
| ATOM | 874 | C | ASN | A | 346 | −4.977 | 43.732 | 12.449 | 1.00 | 79.70 | A |
| ATOM | 875 | O | ASN | A | 346 | −4.824 | 42.554 | 12.123 | 1.00 | 78.97 | A |
| ATOM | 876 | N | ASN | A | 347 | −5.640 | 44.603 | 11.695 | 1.00 | 79.81 | A |
| ATOM | 877 | CA | ASN | A | 347 | −6.204 | 44.182 | 10.409 | 1.00 | 80.26 | A |
| ATOM | 878 | CB | ASN | A | 347 | −7.032 | 45.296 | 9.796 | 1.00 | 81.32 | A |
| ATOM | 879 | CG | ASN | A | 347 | −8.453 | 45.251 | 10.245 | 1.00 | 83.25 | A |
| ATOM | 880 | OD1 | ASN | A | 347 | −9.176 | 46.230 | 10.125 | 1.00 | 85.53 | A |
| ATOM | 881 | ND2 | ASN | A | 347 | −8.879 | 44.098 | 10.761 | 1.00 | 83.78 | A |
| ATOM | 882 | C | ASN | A | 347 | −5.137 | 43.748 | 9.412 | 1.00 | 79.37 | A |
| ATOM | 883 | O | ASN | A | 347 | −5.379 | 42.857 | 8.578 | 1.00 | 78.32 | A |
| ATOM | 884 | N | ALA | A | 348 | −3.974 | 44.402 | 9.506 | 1.00 | 78.63 | A |
| ATOM | 885 | CA | ALA | A | 348 | −2.824 | 44.111 | 8.657 | 1.00 | 78.03 | A |
| ATOM | 886 | CB | ALA | A | 348 | −1.704 | 45.142 | 8.881 | 1.00 | 76.68 | A |
| ATOM | 887 | C | ALA | A | 348 | −2.345 | 42.733 | 9.061 | 1.00 | 76.76 | A |
| ATOM | 888 | O | ALA | A | 348 | −2.067 | 41.883 | 8.210 | 1.00 | 77.32 | A |
| ATOM | 889 | N | ILE | A | 349 | −2.269 | 42.521 | 10.373 | 1.00 | 74.84 | A |
| ATOM | 890 | CA | ILE | A | 349 | −1.827 | 41.248 | 10.912 | 1.00 | 72.93 | A |
| ATOM | 891 | CB | ILE | A | 349 | −1.635 | 41.333 | 12.443 | 1.00 | 71.39 | A |
| ATOM | 892 | CG2 | ILE | A | 349 | −1.228 | 40.000 | 12.999 | 1.00 | 70.11 | A |
| ATOM | 893 | CG1 | ILE | A | 349 | −0.560 | 42.384 | 12.745 | 1.00 | 70.95 | A |
| ATOM | 894 | CD1 | ILE | A | 349 | −0.036 | 42.391 | 14.175 | 1.00 | 70.34 | A |
| ATOM | 895 | C | ILE | A | 349 | −2.782 | 40.114 | 10.532 | 1.00 | 72.28 | A |
| ATOM | 896 | O | ILE | A | 349 | −2.335 | 38.986 | 10.387 | 1.00 | 74.41 | A |
| ATOM | 897 | N | LEU | A | 350 | −4.075 | 40.398 | 10.341 | 1.00 | 71.23 | A |
| ATOM | 898 | CA | LEU | A | 350 | −5.036 | 39.352 | 9.956 | 1.00 | 69.46 | A |
| ATOM | 899 | CB | LEU | A | 350 | −6.465 | 39.775 | 10.272 | 1.00 | 68.76 | A |
| ATOM | 900 | CG | LEU | A | 350 | −6.925 | 39.642 | 11.719 | 1.00 | 68.42 | A |
| ATOM | 901 | CD1 | LEU | A | 350 | −8.415 | 39.920 | 11.771 | 1.00 | 67.60 | A |
| ATOM | 902 | CD2 | LEU | A | 350 | −6.631 | 38.233 | 12.235 | 1.00 | 68.44 | A |
| ATOM | 903 | C | LEU | A | 350 | −4.929 | 39.020 | 8.473 | 1.00 | 68.36 | A |
| ATOM | 904 | O | LEU | A | 350 | −5.411 | 37.989 | 8.012 | 1.00 | 66.35 | A |
| ATOM | 905 | N | GLN | A | 351 | −4.290 | 39.918 | 7.736 | 1.00 | 69.29 | A |
| ATOM | 906 | CA | GLN | A | 351 | −4.067 | 39.761 | 6.297 | 1.00 | 70.22 | A |

TABLE 1-continued

ATOMIC COORDINATES OF THE ERR3 LBD/SRC-1 NR
BOX 2 PEPTIDE COMPLEX (PDB CODE 1KV6)

| | | | | | | | | | | | |
|---|---|---|---|---|---|---|---|---|---|---|---|
| ATOM | 907 | CB | GLN | A | 351 | −3.505 | 41.064 | 5.757 | 1.00 | 71.95 | A |
| ATOM | 908 | CG | GLN | A | 351 | −3.956 | 41.419 | 4.378 | 1.00 | 77.89 | A |
| ATOM | 909 | CD | GLN | A | 351 | −3.214 | 42.645 | 3.843 | 1.00 | 80.09 | A |
| ATOM | 910 | OE1 | GLN | A | 351 | −3.252 | 43.739 | 4.435 | 1.00 | 80.03 | A |
| ATOM | 911 | NE2 | GLN | A | 351 | −2.533 | 42.462 | 2.724 | 1.00 | 80.20 | A |
| ATOM | 912 | C | GLN | A | 351 | −3.032 | 38.627 | 6.162 | 1.00 | 69.90 | A |
| ATOM | 913 | O | GLN | A | 351 | −3.184 | 37.672 | 5.370 | 1.00 | 69.52 | A |
| ATOM | 914 | N | LEU | A | 352 | −1.976 | 38.763 | 6.961 | 1.00 | 68.21 | A |
| ATOM | 915 | CA | LEU | A | 352 | −0.924 | 37.790 | 7.039 | 1.00 | 65.77 | A |
| ATOM | 916 | CB | LEU | A | 352 | 0.077 | 38.203 | 8.095 | 1.00 | 64.36 | A |
| ATOM | 917 | CG | LEU | A | 352 | 1.418 | 38.684 | 7.564 | 1.00 | 64.54 | A |
| ATOM | 918 | CD1 | LEU | A | 352 | 2.246 | 39.135 | 8.756 | 1.00 | 63.42 | A |
| ATOM | 919 | CD2 | LEU | A | 352 | 2.116 | 37.576 | 6.746 | 1.00 | 60.81 | A |
| ATOM | 920 | C | LEU | A | 352 | −1.564 | 36.490 | 7.450 | 1.00 | 65.42 | A |
| ATOM | 921 | O | LEU | A | 352 | −1.252 | 35.448 | 6.894 | 1.00 | 67.31 | A |
| ATOM | 922 | N | VAL | A | 353 | −2.457 | 36.552 | 8.433 | 1.00 | 65.32 | A |
| ATOM | 923 | CA | VAL | A | 353 | −3.131 | 35.360 | 8.936 | 1.00 | 65.72 | A |
| ATOM | 924 | CB | VAL | A | 353 | −4.205 | 35.692 | 10.018 | 1.00 | 64.56 | A |
| ATOM | 925 | CG1 | VAL | A | 353 | −5.019 | 34.456 | 10.345 | 1.00 | 64.31 | A |
| ATOM | 926 | CG2 | VAL | A | 353 | −3.533 | 36.152 | 11.292 | 1.00 | 62.53 | A |
| ATOM | 927 | C | VAL | A | 353 | −3.790 | 34.634 | 7.792 | 1.00 | 67.21 | A |
| ATOM | 928 | O | VAL | A | 353 | −3.523 | 33.454 | 7.566 | 1.00 | 67.65 | A |
| ATOM | 929 | N | LYS | A | 354 | −4.630 | 35.353 | 7.059 | 1.00 | 68.44 | A |
| ATOM | 930 | CA | LYS | A | 354 | −5.345 | 34.789 | 5.929 | 1.00 | 71.18 | A |
| ATOM | 931 | CB | LYS | A | 354 | −6.140 | 35.884 | 5.226 | 1.00 | 74.29 | A |
| ATOM | 932 | CG | LYS | A | 354 | −7.096 | 35.384 | 4.151 | 1.00 | 79.06 | A |
| ATOM | 933 | CD | LYS | A | 354 | −7.795 | 36.594 | 3.493 | 1.00 | 85.28 | A |
| ATOM | 934 | CE | LYS | A | 354 | −8.758 | 36.201 | 2.340 | 1.00 | 88.99 | A |
| ATOM | 935 | NZ | LYS | A | 354 | −9.557 | 37.362 | 1.804 | 1.00 | 90.11 | A |
| ATOM | 936 | C | LYS | A | 354 | −4.466 | 34.064 | 4.908 | 1.00 | 70.88 | A |
| ATOM | 937 | O | LYS | A | 354 | −4.817 | 32.961 | 4.466 | 1.00 | 71.36 | A |
| ATOM | 938 | N | LYS | A | 355 | −3.344 | 34.668 | 4.523 | 1.00 | 69.23 | A |
| ATOM | 939 | CA | LYS | A | 355 | −2.461 | 34.046 | 3.546 | 1.00 | 68.86 | A |
| ATOM | 940 | CB | LYS | A | 355 | −1.254 | 34.954 | 3.221 | 1.00 | 71.71 | A |
| ATOM | 941 | CG | LYS | A | 355 | −0.965 | 35.158 | 1.715 | 1.00 | 75.30 | A |
| ATOM | 942 | CD | LYS | A | 355 | −0.376 | 33.906 | 1.022 | 1.00 | 77.00 | A |
| ATOM | 943 | CE | LYS | A | 355 | −0.626 | 33.887 | −0.507 | 1.00 | 79.33 | A |
| ATOM | 944 | NZ | LYS | A | 355 | −0.383 | 35.203 | −1.204 | 1.00 | 79.81 | A |
| ATOM | 945 | C | LYS | A | 355 | −1.964 | 32.702 | 4.035 | 1.00 | 68.40 | A |
| ATOM | 946 | O | LYS | A | 355 | −2.014 | 31.727 | 3.291 | 1.00 | 68.30 | A |
| ATOM | 947 | N | TYR | A | 356 | −1.491 | 32.642 | 5.281 | 1.00 | 67.35 | A |
| ATOM | 948 | CA | TYR | A | 356 | −0.956 | 31.395 | 5.843 | 1.00 | 66.83 | A |
| ATOM | 949 | CB | TYR | A | 356 | −0.203 | 31.683 | 7.131 | 1.00 | 65.84 | A |
| ATOM | 950 | CG | TYR | A | 356 | 1.101 | 32.394 | 6.925 | 1.00 | 65.80 | A |
| ATOM | 951 | CD1 | TYR | A | 356 | 2.101 | 31.826 | 6.135 | 1.00 | 64.94 | A |
| ATOM | 952 | CE1 | TYR | A | 356 | 3.338 | 32.448 | 5.987 | 1.00 | 64.16 | A |
| ATOM | 953 | CD2 | TYR | A | 356 | 1.366 | 33.616 | 7.567 | 1.00 | 65.69 | A |
| ATOM | 954 | CE2 | TYR | A | 356 | 2.607 | 34.247 | 7.433 | 1.00 | 64.91 | A |
| ATOM | 955 | CZ | TYR | A | 356 | 3.591 | 33.655 | 6.637 | 1.00 | 65.35 | A |
| ATOM | 956 | OH | TYR | A | 356 | 4.829 | 34.247 | 6.479 | 1.00 | 63.67 | A |
| ATOM | 957 | C | TYR | A | 356 | −2.023 | 30.349 | 6.118 | 1.00 | 67.30 | A |
| ATOM | 958 | O | TYR | A | 356 | −1.787 | 29.134 | 6.015 | 1.00 | 67.12 | A |
| ATOM | 959 | N | LYS | A | 357 | −3.189 | 30.846 | 6.508 | 1.00 | 67.52 | A |
| ATOM | 960 | CA | LYS | A | 357 | −4.356 | 30.025 | 6.778 | 1.00 | 68.39 | A |
| ATOM | 961 | CB | LYS | A | 357 | −5.510 | 30.962 | 7.108 | 1.00 | 69.44 | A |
| ATOM | 962 | CG | LYS | A | 357 | −6.351 | 30.583 | 8.280 | 1.00 | 70.83 | A |
| ATOM | 963 | CD | LYS | A | 357 | −7.312 | 31.707 | 8.510 | 1.00 | 72.20 | A |
| ATOM | 964 | CE | LYS | A | 357 | −8.307 | 31.399 | 9.601 | 1.00 | 72.86 | A |
| ATOM | 965 | NZ | LYS | A | 357 | −9.149 | 32.617 | 9.739 | 1.00 | 73.10 | A |
| ATOM | 966 | C | LYS | A | 357 | −4.620 | 29.321 | 5.442 | 1.00 | 68.47 | A |
| ATOM | 967 | O | LYS | A | 357 | −4.777 | 28.107 | 5.353 | 1.00 | 68.33 | A |
| ATOM | 968 | N | SER | A | 358 | −4.626 | 30.146 | 4.406 | 1.00 | 68.55 | A |
| ATOM | 969 | CA | SER | A | 358 | −4.853 | 29.752 | 3.025 | 1.00 | 68.62 | A |
| ATOM | 970 | CB | SER | A | 358 | −4.828 | 31.014 | 2.153 | 1.00 | 68.78 | A |
| ATOM | 971 | OG | SER | A | 358 | −5.144 | 30.722 | 0.813 | 1.00 | 71.80 | A |
| ATOM | 972 | C | SER | A | 358 | −3.877 | 28.717 | 2.466 | 1.00 | 67.41 | A |
| ATOM | 973 | O | SER | A | 358 | −4.258 | 27.912 | 1.629 | 1.00 | 65.77 | A |
| ATOM | 974 | N | MET | A | 359 | −2.627 | 28.762 | 2.917 | 1.00 | 68.49 | A |
| ATOM | 975 | CA | MET | A | 359 | −1.590 | 27.831 | 2.470 | 1.00 | 69.17 | A |
| ATOM | 976 | CB | MET | A | 359 | −0.226 | 28.507 | 2.385 | 1.00 | 70.74 | A |
| ATOM | 977 | CG | MET | A | 359 | −0.185 | 29.752 | 1.565 | 1.00 | 73.78 | A |
| ATOM | 978 | SD | MET | A | 359 | 1.412 | 30.573 | 1.764 | 1.00 | 77.64 | A |
| ATOM | 979 | CE | MET | A | 359 | 2.315 | 29.745 | 0.453 | 1.00 | 75.33 | A |
| ATOM | 980 | C | MET | A | 359 | −1.442 | 26.690 | 3.449 | 1.00 | 68.60 | A |
| ATOM | 981 | O | MET | A | 359 | −0.643 | 25.778 | 3.208 | 1.00 | 68.13 | A |
| ATOM | 982 | N | LYS | A | 360 | −2.179 | 26.762 | 4.560 | 1.00 | 67.70 | A |

TABLE 1-continued

ATOMIC COORDINATES OF THE ERR3 LBD/SRC-1 NR
BOX 2 PEPTIDE COMPLEX (PDB CODE 1KV6)

| ATOM | 983 | CA | LYS | A | 360 | −2.121 | 25.740 | 5.601 | 1.00 | 67.55 | A |
|---|---|---|---|---|---|---|---|---|---|---|---|
| ATOM | 984 | CB | LYS | A | 360 | −2.600 | 24.400 | 5.054 | 1.00 | 67.90 | A |
| ATOM | 985 | CG | LYS | A | 360 | −3.949 | 24.498 | 4.409 | 1.00 | 70.27 | A |
| ATOM | 986 | CD | LYS | A | 360 | −4.402 | 23.147 | 3.918 | 1.00 | 74.10 | A |
| ATOM | 987 | CE | LYS | A | 360 | −5.701 | 23.242 | 3.134 | 1.00 | 75.99 | A |
| ATOM | 988 | NZ | LYS | A | 360 | −5.914 | 21.999 | 2.333 | 1.00 | 77.58 | A |
| ATOM | 989 | C | LYS | A | 360 | −0.698 | 25.602 | 6.126 | 1.00 | 66.55 | A |
| ATOM | 990 | O | LYS | A | 360 | −0.120 | 24.510 | 6.116 | 1.00 | 67.25 | A |
| ATOM | 991 | N | LEU | A | 361 | −0.150 | 26.725 | 6.580 | 1.00 | 64.18 | A |
| ATOM | 992 | CA | LEU | A | 361 | 1.198 | 26.804 | 7.108 | 1.00 | 62.02 | A |
| ATOM | 993 | CB | LEU | A | 361 | 1.443 | 28.248 | 7.577 | 1.00 | 61.04 | A |
| ATOM | 994 | CG | LEU | A | 361 | 2.807 | 28.484 | 8.214 | 1.00 | 59.67 | A |
| ATOM | 995 | CD1 | LEU | A | 361 | 3.821 | 28.554 | 7.086 | 1.00 | 59.57 | A |
| ATOM | 996 | CD2 | LEU | A | 361 | 2.828 | 29.711 | 9.065 | 1.00 | 56.46 | A |
| ATOM | 997 | C | LEU | A | 361 | 1.430 | 25.828 | 8.272 | 1.00 | 61.53 | A |
| ATOM | 998 | O | LEU | A | 361 | 0.792 | 25.950 | 9.296 | 1.00 | 62.65 | A |
| ATOM | 999 | N | GLU | A | 362 | 2.360 | 24.889 | 8.136 | 1.00 | 61.45 | A |
| ATOM | 1000 | CA | GLU | A | 362 | 2.658 | 23.929 | 9.203 | 1.00 | 62.58 | A |
| ATOM | 1001 | CB | GLU | A | 362 | 3.139 | 22.631 | 8.592 | 1.00 | 65.59 | A |
| ATOM | 1002 | CG | GLU | A | 362 | 2.298 | 22.192 | 7.411 | 1.00 | 71.42 | A |
| ATOM | 1003 | CD | GLU | A | 362 | 2.978 | 21.102 | 6.603 | 1.00 | 75.17 | A |
| ATOM | 1004 | OE1 | GLU | A | 362 | 4.238 | 21.066 | 6.637 | 1.00 | 75.31 | A |
| ATOM | 1005 | OE2 | GLU | A | 362 | 2.258 | 20.306 | 5.934 | 1.00 | 76.55 | A |
| ATOM | 1006 | C | GLU | A | 362 | 3.712 | 24.413 | 10.213 | 1.00 | 63.37 | A |
| ATOM | 1007 | O | GLU | A | 362 | 4.527 | 25.296 | 9.902 | 1.00 | 63.88 | A |
| ATOM | 1008 | N | LYS | A | 363 | 3.716 | 23.816 | 11.413 | 1.00 | 62.38 | A |
| ATOM | 1009 | CA | LYS | A | 363 | 4.666 | 24.207 | 12.458 | 1.00 | 60.81 | A |
| ATOM | 1010 | CB | LYS | A | 363 | 4.559 | 23.281 | 13.682 | 1.00 | 60.73 | A |
| ATOM | 1011 | CG | LYS | A | 363 | 5.162 | 23.873 | 14.978 | 1.00 | 65.24 | A |
| ATOM | 1012 | CD | LYS | A | 363 | 5.533 | 22.801 | 16.025 | 1.00 | 69.35 | A |
| ATOM | 1013 | CE | LYS | A | 363 | 5.789 | 23.373 | 17.454 | 1.00 | 73.15 | A |
| ATOM | 1014 | NZ | LYS | A | 363 | 6.670 | 22.486 | 18.320 | 1.00 | 74.11 | A |
| ATOM | 1015 | C | LYS | A | 363 | 6.118 | 24.203 | 11.959 | 1.00 | 59.74 | A |
| ATOM | 1016 | O | LYS | A | 363 | 6.913 | 25.074 | 12.344 | 1.00 | 58.74 | A |
| ATOM | 1017 | N | GLU | A | 364 | 6.463 | 23.221 | 11.129 | 1.00 | 59.22 | A |
| ATOM | 1018 | CA | GLU | A | 364 | 7.821 | 23.102 | 10.564 | 1.00 | 61.22 | A |
| ATOM | 1019 | CB | GLU | A | 364 | 7.965 | 21.822 | 9.719 | 1.00 | 62.53 | A |
| ATOM | 1020 | CG | GLU | A | 364 | 7.882 | 20.546 | 10.500 | 1.00 | 66.88 | A |
| ATOM | 1021 | CD | GLU | A | 364 | 6.450 | 20.126 | 10.823 | 1.00 | 69.27 | A |
| ATOM | 1022 | OE1 | GLU | A | 364 | 6.288 | 18.955 | 11.233 | 1.00 | 71.66 | A |
| ATOM | 1023 | OE2 | GLU | A | 364 | 5.494 | 20.933 | 10.675 | 1.00 | 69.75 | A |
| ATOM | 1024 | C | GLU | A | 364 | 8.231 | 24.287 | 9.674 | 1.00 | 58.52 | A |
| ATOM | 1025 | O | GLU | A | 364 | 9.403 | 24.662 | 9.615 | 1.00 | 56.41 | A |
| ATOM | 1026 | N | GLU | A | 365 | 7.245 | 24.847 | 8.986 | 1.00 | 56.75 | A |
| ATOM | 1027 | CA | GLU | A | 365 | 7.450 | 25.957 | 8.087 | 1.00 | 56.34 | A |
| ATOM | 1028 | CB | GLU | A | 365 | 6.336 | 25.957 | 7.036 | 1.00 | 56.01 | A |
| ATOM | 1029 | CG | GLU | A | 365 | 6.377 | 24.680 | 6.178 | 1.00 | 55.43 | A |
| ATOM | 1030 | CD | GLU | A | 365 | 5.215 | 24.544 | 5.261 | 1.00 | 57.95 | A |
| ATOM | 1031 | OE1 | GLU | A | 365 | 4.095 | 24.866 | 5.702 | 1.00 | 61.52 | A |
| ATOM | 1032 | OE2 | GLU | A | 365 | 5.410 | 24.118 | 4.106 | 1.00 | 59.29 | A |
| ATOM | 1033 | C | GLU | A | 365 | 7.506 | 27.252 | 8.867 | 1.00 | 55.52 | A |
| ATOM | 1034 | O | GLU | A | 365 | 8.185 | 28.185 | 8.462 | 1.00 | 58.50 | A |
| ATOM | 1035 | N | PHE | A | 366 | 6.816 | 27.295 | 9.991 | 1.00 | 53.60 | A |
| ATOM | 1036 | CA | PHE | A | 366 | 6.801 | 28.463 | 10.862 | 1.00 | 52.29 | A |
| ATOM | 1037 | CB | PHE | A | 366 | 5.694 | 28.274 | 11.898 | 1.00 | 51.27 | A |
| ATOM | 1038 | CG | PHE | A | 366 | 5.794 | 29.167 | 13.098 | 1.00 | 50.86 | A |
| ATOM | 1039 | CD1 | PHE | A | 366 | 5.461 | 30.524 | 13.011 | 1.00 | 50.69 | A |
| ATOM | 1040 | CD2 | PHE | A | 366 | 6.205 | 28.632 | 14.343 | 1.00 | 48.59 | A |
| ATOM | 1041 | CE1 | PHE | A | 366 | 5.528 | 31.340 | 14.157 | 1.00 | 51.21 | A |
| ATOM | 1042 | CE2 | PHE | A | 366 | 6.283 | 29.428 | 15.498 | 1.00 | 47.53 | A |
| ATOM | 1043 | CZ | PHE | A | 366 | 5.947 | 30.788 | 15.412 | 1.00 | 50.07 | A |
| ATOM | 1044 | C | PHE | A | 366 | 8.166 | 28.694 | 11.551 | 1.00 | 53.04 | A |
| ATOM | 1045 | O | PHE | A | 366 | 8.726 | 29.792 | 11.503 | 1.00 | 51.91 | A |
| ATOM | 1046 | N | VAL | A | 367 | 8.710 | 27.659 | 12.182 | 1.00 | 53.28 | A |
| ATOM | 1047 | CA | VAL | A | 367 | 9.995 | 27.804 | 12.845 | 1.00 | 52.59 | A |
| ATOM | 1048 | CB | VAL | A | 367 | 10.361 | 26.545 | 13.641 | 1.00 | 50.44 | A |
| ATOM | 1049 | CG1 | VAL | A | 367 | 9.375 | 26.355 | 14.759 | 1.00 | 50.91 | A |
| ATOM | 1050 | CG2 | VAL | A | 367 | 10.396 | 25.346 | 12.730 | 1.00 | 49.38 | A |
| ATOM | 1051 | C | VAL | A | 367 | 11.112 | 28.130 | 11.852 | 1.00 | 54.14 | A |
| ATOM | 1052 | O | VAL | A | 367 | 11.996 | 28.930 | 12.152 | 1.00 | 53.92 | A |
| ATOM | 1053 | N | THR | A | 368 | 11.075 | 27.516 | 10.673 | 1.00 | 55.63 | A |
| ATOM | 1054 | CA | THR | A | 368 | 12.097 | 27.772 | 9.656 | 1.00 | 57.88 | A |
| ATOM | 1055 | CB | THR | A | 368 | 11.976 | 26.742 | 8.527 | 1.00 | 56.77 | A |
| ATOM | 1056 | OG1 | THR | A | 368 | 12.326 | 25.456 | 9.052 | 1.00 | 58.90 | A |
| ATOM | 1057 | CG2 | THR | A | 368 | 12.901 | 27.069 | 7.390 | 1.00 | 54.50 | A |
| ATOM | 1058 | C | THR | A | 368 | 11.980 | 29.202 | 9.102 | 1.00 | 58.13 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1059 | O | THR | A | 368 | 12.963 | 29.912 | 8.909 | 1.00 | 57.22 | A |
|---|---|---|---|---|---|---|---|---|---|---|---|
| ATOM | 1060 | N | LEU | A | 369 | 10.744 | 29.604 | 8.874 | 1.00 | 58.07 | A |
| ATOM | 1061 | CA | LEU | A | 369 | 10.424 | 30.917 | 8.378 | 1.00 | 57.62 | A |
| ATOM | 1062 | CB | LEU | A | 369 | 8.931 | 30.982 | 8.175 | 1.00 | 58.33 | A |
| ATOM | 1063 | CG | LEU | A | 369 | 8.534 | 31.778 | 6.952 | 1.00 | 60.75 | A |
| ATOM | 1064 | CD1 | LEU | A | 369 | 9.423 | 31.353 | 5.740 | 1.00 | 60.19 | A |
| ATOM | 1065 | CD2 | LEU | A | 369 | 7.024 | 31.582 | 6.715 | 1.00 | 61.63 | A |
| ATOM | 1066 | C | LEU | A | 369 | 10.855 | 31.995 | 9.367 | 1.00 | 56.72 | A |
| ATOM | 1067 | O | LEU | A | 369 | 11.240 | 33.082 | 8.996 | 1.00 | 56.20 | A |
| ATOM | 1068 | N | LYS | A | 370 | 10.769 | 31.683 | 10.641 | 1.00 | 55.51 | A |
| ATOM | 1069 | CA | LYS | A | 370 | 11.135 | 32.626 | 11.679 | 1.00 | 55.48 | A |
| ATOM | 1070 | CB | LYS | A | 370 | 10.617 | 32.056 | 12.984 | 1.00 | 52.77 | A |
| ATOM | 1071 | CG | LYS | A | 370 | 10.583 | 32.969 | 14.126 | 1.00 | 54.32 | A |
| ATOM | 1072 | CD | LYS | A | 370 | 9.292 | 32.781 | 14.971 | 1.00 | 53.92 | A |
| ATOM | 1073 | CE | LYS | A | 370 | 9.118 | 31.382 | 15.571 | 1.00 | 54.65 | A |
| ATOM | 1074 | NZ | LYS | A | 370 | 10.082 | 30.975 | 16.634 | 1.00 | 60.98 | A |
| ATOM | 1075 | C | LYS | A | 370 | 12.686 | 32.825 | 11.672 | 1.00 | 57.39 | A |
| ATOM | 1076 | O | LYS | A | 370 | 13.200 | 33.953 | 11.721 | 1.00 | 58.33 | A |
| ATOM | 1077 | N | ALA | A | 371 | 13.431 | 31.729 | 11.590 | 1.00 | 56.19 | A |
| ATOM | 1078 | CA | ALA | A | 371 | 14.876 | 31.822 | 11.560 | 1.00 | 54.36 | A |
| ATOM | 1079 | CB | ALA | A | 371 | 15.504 | 30.416 | 11.573 | 1.00 | 52.94 | A |
| ATOM | 1080 | C | ALA | A | 371 | 15.283 | 32.595 | 10.290 | 1.00 | 54.97 | A |
| ATOM | 1081 | O | ALA | A | 371 | 16.207 | 33.410 | 10.313 | 1.00 | 54.32 | A |
| ATOM | 1082 | N | ILE | A | 372 | 14.593 | 32.335 | 9.184 | 1.00 | 53.91 | A |
| ATOM | 1083 | CA | ILE | A | 372 | 14.896 | 33.023 | 7.948 | 1.00 | 52.85 | A |
| ATOM | 1084 | CB | ILE | A | 372 | 14.131 | 32.400 | 6.770 | 1.00 | 51.46 | A |
| ATOM | 1085 | CG2 | ILE | A | 372 | 14.167 | 33.331 | 5.561 | 1.00 | 48.11 | A |
| ATOM | 1086 | CG1 | ILE | A | 372 | 14.740 | 31.018 | 6.444 | 1.00 | 50.97 | A |
| ATOM | 1087 | CD1 | ILE | A | 372 | 13.879 | 30.143 | 5.517 | 1.00 | 49.75 | A |
| ATOM | 1088 | C | ILE | A | 372 | 14.579 | 34.518 | 8.055 | 1.00 | 54.45 | A |
| ATOM | 1089 | O | ILE | A | 372 | 15.309 | 35.338 | 7.515 | 1.00 | 53.92 | A |
| ATOM | 1090 | N | ALA | A | 373 | 13.498 | 34.890 | 8.737 | 1.00 | 54.64 | A |
| ATOM | 1091 | CA | ALA | A | 373 | 13.211 | 36.302 | 8.863 | 1.00 | 56.45 | A |
| ATOM | 1092 | CB | ALA | A | 373 | 11.867 | 36.523 | 9.509 | 1.00 | 53.48 | A |
| ATOM | 1093 | C | ALA | A | 373 | 14.347 | 36.966 | 9.699 | 1.00 | 59.04 | A |
| ATOM | 1094 | O | ALA | A | 373 | 14.719 | 38.123 | 9.452 | 1.00 | 60.03 | A |
| ATOM | 1095 | N | LEU | A | 374 | 14.906 | 36.245 | 10.671 | 1.00 | 57.70 | A |
| ATOM | 1096 | CA | LEU | A | 374 | 15.992 | 36.802 | 11.455 | 1.00 | 56.84 | A |
| ATOM | 1097 | CB | LEU | A | 374 | 16.333 | 35.894 | 12.663 | 1.00 | 57.80 | A |
| ATOM | 1098 | CG | LEU | A | 374 | 17.388 | 36.456 | 13.644 | 1.00 | 58.44 | A |
| ATOM | 1099 | CD1 | LEU | A | 374 | 16.978 | 37.854 | 14.105 | 1.00 | 58.18 | A |
| ATOM | 1100 | CD2 | LEU | A | 374 | 17.551 | 35.532 | 14.831 | 1.00 | 58.85 | A |
| ATOM | 1101 | C | LEU | A | 374 | 17.237 | 36.974 | 10.567 | 1.00 | 56.93 | A |
| ATOM | 1102 | O | LEU | A | 374 | 17.870 | 38.026 | 10.575 | 1.00 | 58.16 | A |
| ATOM | 1103 | N | ALA | A | 375 | 17.599 | 35.962 | 9.791 | 1.00 | 56.53 | A |
| ATOM | 1104 | CA | ALA | A | 375 | 18.793 | 36.085 | 8.962 | 1.00 | 57.60 | A |
| ATOM | 1105 | CB | ALA | A | 375 | 19.180 | 34.706 | 8.419 | 1.00 | 56.96 | A |
| ATOM | 1106 | C | ALA | A | 375 | 18.688 | 37.128 | 7.814 | 1.00 | 58.17 | A |
| ATOM | 1107 | O | ALA | A | 375 | 19.642 | 37.841 | 7.523 | 1.00 | 58.28 | A |
| ATOM | 1108 | N | ASN | A | 376 | 17.513 | 37.219 | 7.204 | 1.00 | 59.69 | A |
| ATOM | 1109 | CA | ASN | A | 376 | 17.201 | 38.115 | 6.093 | 1.00 | 59.89 | A |
| ATOM | 1110 | CB | ASN | A | 376 | 16.231 | 37.372 | 5.172 | 1.00 | 60.01 | A |
| ATOM | 1111 | CG | ASN | A | 376 | 16.139 | 37.965 | 3.767 | 1.00 | 61.81 | A |
| ATOM | 1112 | OD1 | ASN | A | 376 | 17.129 | 37.988 | 3.028 | 1.00 | 63.55 | A |
| ATOM | 1113 | ND2 | ASN | A | 376 | 14.939 | 38.408 | 3.375 | 1.00 | 59.07 | A |
| ATOM | 1114 | C | ASN | A | 376 | 16.544 | 39.410 | 6.614 | 1.00 | 61.91 | A |
| ATOM | 1115 | O | ASN | A | 376 | 15.615 | 39.939 | 5.995 | 1.00 | 61.50 | A |
| ATOM | 1116 | N | SER | A | 377 | 17.024 | 39.917 | 7.747 | 1.00 | 65.05 | A |
| ATOM | 1117 | CA | SER | A | 377 | 16.458 | 41.136 | 8.355 | 1.00 | 68.73 | A |
| ATOM | 1118 | CB | SER | A | 377 | 16.905 | 41.266 | 9.813 | 1.00 | 67.87 | A |
| ATOM | 1119 | OG | SER | A | 377 | 18.312 | 41.482 | 9.885 | 1.00 | 71.92 | A |
| ATOM | 1120 | C | SER | A | 377 | 16.811 | 42.439 | 7.619 | 1.00 | 70.59 | A |
| ATOM | 1121 | O | SER | A | 377 | 16.138 | 43.464 | 7.821 | 1.00 | 69.95 | A |
| ATOM | 1122 | N | ASP | A | 378 | 17.874 | 42.397 | 6.804 | 1.00 | 72.67 | A |
| ATOM | 1123 | CA | ASP | A | 378 | 18.337 | 43.539 | 6.008 | 1.00 | 74.78 | A |
| ATOM | 1124 | CB | ASP | A | 378 | 17.211 | 44.054 | 5.111 | 1.00 | 74.85 | A |
| ATOM | 1125 | CG | ASP | A | 378 | 16.922 | 43.135 | 3.953 | 1.00 | 75.59 | A |
| ATOM | 1126 | OD1 | ASP | A | 378 | 16.042 | 42.267 | 4.065 | 1.00 | 78.38 | A |
| ATOM | 1127 | OD2 | ASP | A | 378 | 17.583 | 43.265 | 2.914 | 1.00 | 77.74 | A |
| ATOM | 1128 | C | ASP | A | 378 | 18.921 | 44.714 | 6.795 | 1.00 | 77.04 | A |
| ATOM | 1129 | O | ASP | A | 378 | 18.760 | 45.874 | 6.409 | 1.00 | 74.83 | A |
| ATOM | 1130 | N | SER | A | 379 | 19.595 | 44.399 | 7.905 | 1.00 | 80.17 | A |
| ATOM | 1131 | CA | SER | A | 379 | 20.253 | 45.395 | 8.762 | 1.00 | 82.03 | A |
| ATOM | 1132 | CB | SER | A | 379 | 20.848 | 44.710 | 10.007 | 1.00 | 82.29 | A |
| ATOM | 1133 | OG | SER | A | 379 | 21.516 | 45.632 | 10.866 | 1.00 | 84.11 | A |
| ATOM | 1134 | C | SER | A | 379 | 21.375 | 46.108 | 7.997 | 1.00 | 83.48 | A |

TABLE 1-continued

ATOMIC COORDINATES OF THE ERR3 LBD/SRC-1 NR BOX 2 PEPTIDE COMPLEX (PDB CODE 1KV6)

| ATOM | 1135 | O | SER | A | 379 | 22.067 | 45.508 | 7.157 | 1.00 | 83.05 | A |
|---|---|---|---|---|---|---|---|---|---|---|---|
| ATOM | 1136 | N | MET | A | 380 | 21.562 | 47.387 | 8.309 | 1.00 | 85.10 | A |
| ATOM | 1137 | CA | MET | A | 380 | 22.593 | 48.186 | 7.655 | 1.00 | 86.07 | A |
| ATOM | 1138 | CB | MET | A | 380 | 22.234 | 49.656 | 7.754 | 1.00 | 87.57 | A |
| ATOM | 1139 | CG | MET | A | 380 | 20.761 | 49.926 | 7.544 | 1.00 | 90.64 | A |
| ATOM | 1140 | SD | MET | A | 380 | 20.407 | 51.703 | 7.336 | 1.00 | 95.58 | A |
| ATOM | 1141 | CE | MET | A | 380 | 20.564 | 51.916 | 5.368 | 1.00 | 92.53 | A |
| ATOM | 1142 | C | MET | A | 380 | 23.972 | 47.986 | 8.260 | 1.00 | 84.97 | A |
| ATOM | 1143 | O | MET | A | 380 | 24.946 | 47.777 | 7.547 | 1.00 | 85.25 | A |
| ATOM | 1144 | N | HIS | A | 381 | 24.031 | 48.029 | 9.582 | 1.00 | 83.97 | A |
| ATOM | 1145 | CA | HIS | A | 381 | 25.283 | 47.923 | 10.311 | 1.00 | 84.80 | A |
| ATOM | 1146 | CB | HIS | A | 381 | 25.102 | 48.548 | 11.700 | 1.00 | 87.90 | A |
| ATOM | 1147 | CG | HIS | A | 381 | 24.151 | 49.701 | 11.705 | 1.00 | 91.17 | A |
| ATOM | 1148 | CD2 | HIS | A | 381 | 24.363 | 51.032 | 11.565 | 1.00 | 91.67 | A |
| ATOM | 1149 | ND1 | HIS | A | 381 | 22.781 | 49.532 | 11.720 | 1.00 | 92.60 | A |
| ATOM | 1150 | CE1 | HIS | A | 381 | 22.191 | 50.707 | 11.582 | 1.00 | 92.84 | A |
| ATOM | 1151 | NE2 | HIS | A | 381 | 23.128 | 51.634 | 11.485 | 1.00 | 92.63 | A |
| ATOM | 1152 | C | HIS | A | 381 | 25.891 | 46.544 | 10.454 | 1.00 | 83.73 | A |
| ATOM | 1153 | O | HIS | A | 381 | 26.424 | 46.210 | 11.518 | 1.00 | 84.39 | A |
| ATOM | 1154 | N | ILE | A | 382 | 25.854 | 45.748 | 9.393 | 1.00 | 81.51 | A |
| ATOM | 1155 | CA | ILE | A | 382 | 26.423 | 44.408 | 9.484 | 1.00 | 80.27 | A |
| ATOM | 1156 | CB | ILE | A | 382 | 25.501 | 43.364 | 8.692 | 1.00 | 80.12 | A |
| ATOM | 1157 | CG2 | ILE | A | 382 | 24.713 | 44.082 | 7.581 | 1.00 | 80.64 | A |
| ATOM | 1158 | CG1 | ILE | A | 382 | 26.326 | 42.180 | 8.172 | 1.00 | 78.59 | A |
| ATOM | 1159 | CD1 | ILE | A | 382 | 26.950 | 41.330 | 9.249 | 1.00 | 77.52 | A |
| ATOM | 1160 | C | ILE | A | 382 | 27.922 | 44.334 | 9.088 | 1.00 | 79.72 | A |
| ATOM | 1161 | O | ILE | A | 382 | 28.340 | 44.835 | 8.043 | 1.00 | 78.25 | A |
| ATOM | 1162 | N | GLU | A | 383 | 28.718 | 43.720 | 9.969 | 1.00 | 79.92 | A |
| ATOM | 1163 | CA | GLU | A | 383 | 30.162 | 43.546 | 9.786 | 1.00 | 79.35 | A |
| ATOM | 1164 | CB | GLU | A | 383 | 30.842 | 43.165 | 11.112 | 1.00 | 81.46 | A |
| ATOM | 1165 | CG | GLU | A | 383 | 30.804 | 44.241 | 12.223 | 1.00 | 84.02 | A |
| ATOM | 1166 | CD | GLU | A | 383 | 31.407 | 43.752 | 13.560 | 1.00 | 85.55 | A |
| ATOM | 1167 | OE1 | GLU | A | 383 | 31.905 | 42.590 | 13.614 | 1.00 | 84.45 | A |
| ATOM | 1168 | OE2 | GLU | A | 383 | 31.379 | 44.536 | 14.546 | 1.00 | 85.14 | A |
| ATOM | 1169 | C | GLU | A | 383 | 30.507 | 42.479 | 8.759 | 1.00 | 78.23 | A |
| ATOM | 1170 | O | GLU | A | 383 | 30.889 | 42.800 | 7.645 | 1.00 | 79.30 | A |
| ATOM | 1171 | N | ASP | A | 384 | 30.391 | 41.208 | 9.135 | 1.00 | 76.17 | A |
| ATOM | 1172 | CA | ASP | A | 384 | 30.711 | 40.114 | 8.211 | 1.00 | 74.80 | A |
| ATOM | 1173 | CB | ASP | A | 384 | 31.169 | 38.869 | 8.996 | 1.00 | 73.01 | A |
| ATOM | 1174 | CG | ASP | A | 384 | 31.808 | 37.797 | 8.098 | 1.00 | 72.53 | A |
| ATOM | 1175 | OD1 | ASP | A | 384 | 31.683 | 37.870 | 6.837 | 1.00 | 70.31 | A |
| ATOM | 1176 | OD2 | ASP | A | 384 | 32.435 | 36.873 | 8.673 | 1.00 | 71.60 | A |
| ATOM | 1177 | C | ASP | A | 384 | 29.509 | 39.753 | 7.320 | 1.00 | 74.56 | A |
| ATOM | 1178 | O | ASP | A | 384 | 28.725 | 38.850 | 7.642 | 1.00 | 74.75 | A |
| ATOM | 1179 | N | VAL | A | 385 | 29.381 | 40.457 | 6.198 | 1.00 | 73.02 | A |
| ATOM | 1180 | CA | VAL | A | 385 | 28.289 | 40.246 | 5.251 | 1.00 | 71.89 | A |
| ATOM | 1181 | CB | VAL | A | 385 | 28.431 | 41.249 | 4.076 | 1.00 | 72.35 | A |
| ATOM | 1182 | CG1 | VAL | A | 385 | 27.395 | 40.990 | 3.007 | 1.00 | 70.92 | A |
| ATOM | 1183 | CG2 | VAL | A | 385 | 28.281 | 42.675 | 4.608 | 1.00 | 71.87 | A |
| ATOM | 1184 | C | VAL | A | 385 | 28.201 | 38.809 | 4.716 | 1.00 | 71.43 | A |
| ATOM | 1185 | O | VAL | A | 385 | 27.113 | 38.247 | 4.594 | 1.00 | 68.57 | A |
| ATOM | 1186 | N | GLU | A | 386 | 29.355 | 38.222 | 4.416 | 1.00 | 72.67 | A |
| ATOM | 1187 | CA | GLU | A | 386 | 29.435 | 36.863 | 3.894 | 1.00 | 73.74 | A |
| ATOM | 1188 | CB | GLU | A | 386 | 30.863 | 36.547 | 3.426 | 1.00 | 78.68 | A |
| ATOM | 1189 | CG | GLU | A | 386 | 31.378 | 37.472 | 2.287 | 1.00 | 86.14 | A |
| ATOM | 1190 | CD | GLU | A | 386 | 32.479 | 36.832 | 1.400 | 1.00 | 90.91 | A |
| ATOM | 1191 | OE1 | GLU | A | 386 | 32.913 | 37.506 | 0.422 | 1.00 | 92.79 | A |
| ATOM | 1192 | OE2 | GLU | A | 386 | 32.900 | 35.666 | 1.674 | 1.00 | 93.36 | A |
| ATOM | 1193 | C | GLU | A | 386 | 29.004 | 35.828 | 4.915 | 1.00 | 71.59 | A |
| ATOM | 1194 | O | GLU | A | 386 | 28.467 | 34.776 | 4.564 | 1.00 | 71.25 | A |
| ATOM | 1195 | N | ALA | A | 387 | 29.242 | 36.129 | 6.181 | 1.00 | 69.86 | A |
| ATOM | 1196 | CA | ALA | A | 387 | 28.860 | 35.221 | 7.262 | 1.00 | 68.56 | A |
| ATOM | 1197 | CB | ALA | A | 387 | 29.454 | 35.694 | 8.576 | 1.00 | 67.70 | A |
| ATOM | 1198 | C | ALA | A | 387 | 27.329 | 35.118 | 7.388 | 1.00 | 67.39 | A |
| ATOM | 1199 | O | ALA | A | 387 | 26.794 | 34.021 | 7.594 | 1.00 | 65.69 | A |
| ATOM | 1200 | N | VAL | A | 388 | 26.654 | 36.269 | 7.283 | 1.00 | 66.02 | A |
| ATOM | 1201 | CA | VAL | A | 388 | 25.196 | 36.350 | 7.353 | 1.00 | 65.98 | A |
| ATOM | 1202 | CB | VAL | A | 388 | 24.698 | 37.801 | 7.482 | 1.00 | 65.01 | A |
| ATOM | 1203 | CG1 | VAL | A | 388 | 23.192 | 37.819 | 7.371 | 1.00 | 65.25 | A |
| ATOM | 1204 | CG2 | VAL | A | 388 | 25.116 | 38.390 | 8.801 | 1.00 | 65.60 | A |
| ATOM | 1205 | C | VAL | A | 388 | 24.545 | 35.758 | 6.094 | 1.00 | 66.13 | A |
| ATOM | 1206 | O | VAL | A | 388 | 23.497 | 35.125 | 6.160 | 1.00 | 66.28 | A |
| ATOM | 1207 | N | GLN | A | 389 | 25.167 | 35.993 | 4.947 | 1.00 | 66.04 | A |
| ATOM | 1208 | CA | GLN | A | 389 | 24.660 | 35.473 | 3.701 | 1.00 | 64.39 | A |
| ATOM | 1209 | CB | GLN | A | 389 | 25.487 | 36.007 | 2.538 | 1.00 | 65.80 | A |
| ATOM | 1210 | CG | GLN | A | 389 | 25.117 | 35.392 | 1.211 | 1.00 | 67.62 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1211 | CD  | GLN | A | 389 | 23.694 | 35.729 | 0.801  | 1.00 | 71.80 | A |
|------|------|-----|-----|---|-----|--------|--------|--------|------|-------|---|
| ATOM | 1212 | OE1 | GLN | A | 389 | 23.340 | 36.918 | 0.659  | 1.00 | 72.59 | A |
| ATOM | 1213 | NE2 | GLN | A | 389 | 22.863 | 34.690 | 0.605  | 1.00 | 71.53 | A |
| ATOM | 1214 | C   | GLN | A | 389 | 24.772 | 33.969 | 3.765  | 1.00 | 63.18 | A |
| ATOM | 1215 | O   | GLN | A | 389 | 23.981 | 33.273 | 3.185  | 1.00 | 61.89 | A |
| ATOM | 1216 | N   | LYS | A | 390 | 25.763 | 33.475 | 4.491  | 1.00 | 63.06 | A |
| ATOM | 1217 | CA  | LYS | A | 390 | 25.981 | 32.048 | 4.617  | 1.00 | 63.58 | A |
| ATOM | 1218 | CB  | LYS | A | 390 | 27.397 | 31.825 | 5.159  | 1.00 | 67.36 | A |
| ATOM | 1219 | CG  | LYS | A | 390 | 28.067 | 30.496 | 4.804  | 1.00 | 70.06 | A |
| ATOM | 1220 | CD  | LYS | A | 390 | 27.735 | 29.365 | 5.803  | 1.00 | 78.54 | A |
| ATOM | 1221 | CE  | LYS | A | 390 | 28.197 | 29.635 | 7.286  | 1.00 | 80.29 | A |
| ATOM | 1222 | NZ  | LYS | A | 390 | 28.231 | 28.388 | 8.153  | 1.00 | 81.03 | A |
| ATOM | 1223 | C   | LYS | A | 390 | 24.911 | 31.482 | 5.551  | 1.00 | 63.28 | A |
| ATOM | 1224 | O   | LYS | A | 390 | 24.499 | 30.333 | 5.417  | 1.00 | 63.31 | A |
| ATOM | 1225 | N   | LEU | A | 391 | 24.453 | 32.307 | 6.490  | 1.00 | 63.29 | A |
| ATOM | 1226 | CA  | LEU | A | 391 | 23.411 | 31.907 | 7.432  | 1.00 | 63.34 | A |
| ATOM | 1227 | CB  | LEU | A | 391 | 23.300 | 32.899 | 8.595  | 1.00 | 63.17 | A |
| ATOM | 1228 | CG  | LEU | A | 391 | 22.087 | 32.660 | 9.516  | 1.00 | 64.30 | A |
| ATOM | 1229 | CD1 | LEU | A | 391 | 22.383 | 31.453 | 10.360 | 1.00 | 66.23 | A |
| ATOM | 1230 | CD2 | LEU | A | 391 | 21.801 | 33.847 | 10.411 | 1.00 | 64.78 | A |
| ATOM | 1231 | C   | LEU | A | 391 | 22.064 | 31.860 | 6.706  | 1.00 | 63.22 | A |
| ATOM | 1232 | O   | LEU | A | 391 | 21.222 | 31.012 | 6.992  | 1.00 | 64.89 | A |
| ATOM | 1233 | N   | GLN | A | 392 | 21.849 | 32.778 | 5.779  | 1.00 | 60.65 | A |
| ATOM | 1234 | CA  | GLN | A | 392 | 20.595 | 32.774 | 5.063  | 1.00 | 60.20 | A |
| ATOM | 1235 | CB  | GLN | A | 392 | 20.458 | 34.016 | 4.201  | 1.00 | 58.87 | A |
| ATOM | 1236 | CG  | GLN | A | 392 | 20.527 | 35.304 | 4.975  | 1.00 | 61.64 | A |
| ATOM | 1237 | CD  | GLN | A | 392 | 20.699 | 36.515 | 4.077  | 1.00 | 63.77 | A |
| ATOM | 1238 | OE1 | GLN | A | 392 | 20.940 | 37.619 | 4.554  | 1.00 | 62.71 | A |
| ATOM | 1239 | NE2 | GLN | A | 392 | 20.572 | 36.309 | 2.766  | 1.00 | 65.13 | A |
| ATOM | 1240 | C   | GLN | A | 392 | 20.541 | 31.545 | 4.191  | 1.00 | 59.87 | A |
| ATOM | 1241 | O   | GLN | A | 392 | 19.479 | 30.967 | 3.981  | 1.00 | 59.06 | A |
| ATOM | 1242 | N   | ASP | A | 393 | 21.698 | 31.103 | 3.726  | 1.00 | 59.42 | A |
| ATOM | 1243 | CA  | ASP | A | 393 | 21.698 | 29.979 | 2.839  | 1.00 | 58.77 | A |
| ATOM | 1244 | CB  | ASP | A | 393 | 22.949 | 30.020 | 1.962  | 1.00 | 61.91 | A |
| ATOM | 1245 | CG  | ASP | A | 393 | 22.988 | 31.289 | 1.037  | 1.00 | 68.27 | A |
| ATOM | 1246 | OD1 | ASP | A | 393 | 21.997 | 32.069 | 0.993  | 1.00 | 73.42 | A |
| ATOM | 1247 | OD2 | ASP | A | 393 | 23.998 | 31.530 | 0.335  | 1.00 | 67.34 | A |
| ATOM | 1248 | C   | ASP | A | 393 | 21.475 | 28.624 | 3.493  | 1.00 | 58.59 | A |
| ATOM | 1249 | O   | ASP | A | 393 | 20.809 | 27.782 | 2.893  | 1.00 | 57.71 | A |
| ATOM | 1250 | N   | VAL | A | 394 | 21.963 | 28.400 | 4.721  | 1.00 | 57.81 | A |
| ATOM | 1251 | CA  | VAL | A | 394 | 21.744 | 27.085 | 5.356  | 1.00 | 57.31 | A |
| ATOM | 1252 | CB  | VAL | A | 394 | 22.646 | 26.815 | 6.617  | 1.00 | 57.99 | A |
| ATOM | 1253 | CG1 | VAL | A | 394 | 24.079 | 27.235 | 6.335  | 1.00 | 59.76 | A |
| ATOM | 1254 | CG2 | VAL | A | 394 | 22.115 | 27.496 | 7.816  | 1.00 | 58.38 | A |
| ATOM | 1255 | C   | VAL | A | 394 | 20.279 | 26.936 | 5.741  | 1.00 | 57.02 | A |
| ATOM | 1256 | O   | VAL | A | 394 | 19.700 | 25.850 | 5.582  | 1.00 | 56.54 | A |
| ATOM | 1257 | N   | LEU | A | 395 | 19.687 | 28.043 | 6.206  | 1.00 | 56.13 | A |
| ATOM | 1258 | CA  | LEU | A | 395 | 18.278 | 28.090 | 6.601  | 1.00 | 55.38 | A |
| ATOM | 1259 | CB  | LEU | A | 395 | 17.949 | 29.417 | 7.305  | 1.00 | 56.15 | A |
| ATOM | 1260 | CG  | LEU | A | 395 | 18.637 | 29.801 | 8.627  | 1.00 | 54.22 | A |
| ATOM | 1261 | CD1 | LEU | A | 395 | 17.933 | 31.022 | 9.227  | 1.00 | 53.48 | A |
| ATOM | 1262 | CD2 | LEU | A | 395 | 18.584 | 28.635 | 9.592  | 1.00 | 53.94 | A |
| ATOM | 1263 | C   | LEU | A | 395 | 17.399 | 27.952 | 5.365  | 1.00 | 54.43 | A |
| ATOM | 1264 | O   | LEU | A | 395 | 16.376 | 27.269 | 5.389  | 1.00 | 53.82 | A |
| ATOM | 1265 | N   | HIS | A | 396 | 17.806 | 28.608 | 4.280  | 1.00 | 53.62 | A |
| ATOM | 1266 | CA  | HIS | A | 396 | 17.062 | 28.532 | 3.037  | 1.00 | 53.53 | A |
| ATOM | 1267 | CB  | HIS | A | 396 | 17.725 | 29.422 | 1.995  | 1.00 | 53.06 | A |
| ATOM | 1268 | CG  | HIS | A | 396 | 16.986 | 29.513 | 0.693  | 1.00 | 53.10 | A |
| ATOM | 1269 | CD2 | HIS | A | 396 | 15.874 | 28.886 | 0.241  | 1.00 | 54.50 | A |
| ATOM | 1270 | ND1 | HIS | A | 396 | 17.433 | 30.286 | −0.354 | 1.00 | 54.28 | A |
| ATOM | 1271 | CE1 | HIS | A | 396 | 16.634 | 30.127 | −1.399 | 1.00 | 53.19 | A |
| ATOM | 1272 | NE2 | HIS | A | 396 | 15.680 | 29.280 | −1.067 | 1.00 | 52.65 | A |
| ATOM | 1273 | C   | HIS | A | 396 | 17.030 | 27.077 | 2.557  | 1.00 | 55.30 | A |
| ATOM | 1274 | O   | HIS | A | 396 | 15.968 | 26.576 | 2.203  | 1.00 | 55.71 | A |
| ATOM | 1275 | N   | GLU | A | 397 | 18.193 | 26.410 | 2.552  | 1.00 | 55.83 | A |
| ATOM | 1276 | CA  | GLU | A | 397 | 18.318 | 25.028 | 2.105  | 1.00 | 56.16 | A |
| ATOM | 1277 | CB  | GLU | A | 397 | 19.780 | 24.598 | 2.091  | 1.00 | 56.00 | A |
| ATOM | 1278 | CG  | GLU | A | 397 | 19.994 | 23.144 | 1.742  | 1.00 | 58.01 | A |
| ATOM | 1279 | CD  | GLU | A | 397 | 21.473 | 22.711 | 1.876  | 1.00 | 62.50 | A |
| ATOM | 1280 | OE1 | GLU | A | 397 | 22.327 | 23.560 | 2.251  | 1.00 | 60.38 | A |
| ATOM | 1281 | OE2 | GLU | A | 397 | 21.783 | 21.513 | 1.607  | 1.00 | 63.81 | A |
| ATOM | 1282 | C   | GLU | A | 397 | 17.540 | 24.089 | 3.004  | 1.00 | 57.78 | A |
| ATOM | 1283 | O   | GLU | A | 397 | 17.085 | 23.020 | 2.570  | 1.00 | 58.21 | A |
| ATOM | 1284 | N   | ALA | A | 398 | 17.398 | 24.477 | 4.267  | 1.00 | 56.61 | A |
| ATOM | 1285 | CA  | ALA | A | 398 | 16.660 | 23.662 | 5.214  | 1.00 | 55.17 | A |
| ATOM | 1286 | CB  | ALA | A | 398 | 16.892 | 24.173 | 6.607  | 1.00 | 54.66 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1287 | C   | ALA | A | 398 | 15.163 | 23.692 | 4.882  | 1.00 | 55.89 | A |
|------|------|-----|-----|---|-----|--------|--------|--------|------|-------|---|
| ATOM | 1288 | O   | ALA | A | 398 | 14.482 | 22.667 | 4.959  | 1.00 | 56.14 | A |
| ATOM | 1289 | N   | LEU | A | 399 | 14.660 | 24.872 | 4.531  | 1.00 | 54.87 | A |
| ATOM | 1290 | CA  | LEU | A | 399 | 13.274 | 25.029 | 4.174  | 1.00 | 54.62 | A |
| ATOM | 1291 | CB  | LEU | A | 399 | 12.958 | 26.501 | 4.025  | 1.00 | 55.17 | A |
| ATOM | 1292 | CG  | LEU | A | 399 | 11.738 | 26.839 | 3.165  | 1.00 | 54.58 | A |
| ATOM | 1293 | CD1 | LEU | A | 399 | 10.476 | 26.639 | 3.971  | 1.00 | 51.89 | A |
| ATOM | 1294 | CD2 | LEU | A | 399 | 11.851 | 28.275 | 2.665  | 1.00 | 53.93 | A |
| ATOM | 1295 | C   | LEU | A | 399 | 13.020 | 24.338 | 2.853  | 1.00 | 56.67 | A |
| ATOM | 1296 | O   | LEU | A | 399 | 11.991 | 23.723 | 2.638  | 1.00 | 58.46 | A |
| ATOM | 1297 | N   | GLN | A | 400 | 13.973 | 24.467 | 1.952  | 1.00 | 59.04 | A |
| ATOM | 1298 | CA  | GLN | A | 400 | 13.894 | 23.891 | 0.615  | 1.00 | 61.14 | A |
| ATOM | 1299 | CB  | GLN | A | 400 | 15.129 | 24.361 | -0.176 | 1.00 | 62.39 | A |
| ATOM | 1300 | CG  | GLN | A | 400 | 15.288 | 23.914 | -1.617 | 1.00 | 68.23 | A |
| ATOM | 1301 | CD  | GLN | A | 400 | 16.569 | 24.525 | -2.300 | 1.00 | 70.96 | A |
| ATOM | 1302 | OE1 | GLN | A | 400 | 17.727 | 24.121 | -2.028 | 1.00 | 70.08 | A |
| ATOM | 1303 | NE2 | GLN | A | 400 | 16.345 | 25.507 | -3.177 | 1.00 | 73.22 | A |
| ATOM | 1304 | C   | GLN | A | 400 | 13.806 | 22.371 | 0.731  | 1.00 | 61.03 | A |
| ATOM | 1305 | O   | GLN | A | 400 | 13.012 | 21.766 | 0.015  | 1.00 | 60.24 | A |
| ATOM | 1306 | N   | ASP | A | 401 | 14.605 | 21.767 | 1.627  | 1.00 | 59.65 | A |
| ATOM | 1307 | CA  | ASP | A | 401 | 14.590 | 20.310 | 1.842  | 1.00 | 60.31 | A |
| ATOM | 1308 | CB  | ASP | A | 401 | 15.621 | 19.859 | 2.861  | 1.00 | 62.88 | A |
| ATOM | 1309 | CG  | ASP | A | 401 | 17.014 | 19.809 | 2.294  | 1.00 | 68.11 | A |
| ATOM | 1310 | OD1 | ASP | A | 401 | 17.911 | 19.180 | 2.929  | 1.00 | 70.11 | A |
| ATOM | 1311 | OD2 | ASP | A | 401 | 17.220 | 20.413 | 1.210  | 1.00 | 74.32 | A |
| ATOM | 1312 | C   | ASP | A | 401 | 13.250 | 19.863 | 2.374  | 1.00 | 60.50 | A |
| ATOM | 1313 | O   | ASP | A | 401 | 12.669 | 18.889 | 1.890  | 1.00 | 62.92 | A |
| ATOM | 1314 | N   | TYR | A | 402 | 12.759 | 20.572 | 3.383  | 1.00 | 58.19 | A |
| ATOM | 1315 | CA  | TYR | A | 402 | 11.484 | 20.258 | 3.972  | 1.00 | 56.62 | A |
| ATOM | 1316 | CB  | TYR | A | 402 | 11.097 | 21.289 | 5.014  | 1.00 | 57.93 | A |
| ATOM | 1317 | CG  | TYR | A | 402 | 9.781  | 20.929 | 5.662  | 1.00 | 59.66 | A |
| ATOM | 1318 | CD1 | TYR | A | 402 | 9.707  | 19.903 | 6.620  | 1.00 | 59.82 | A |
| ATOM | 1319 | CE1 | TYR | A | 402 | 8.480  | 19.501 | 7.143  | 1.00 | 59.78 | A |
| ATOM | 1320 | CD2 | TYR | A | 402 | 8.589  | 21.546 | 5.254  | 1.00 | 59.44 | A |
| ATOM | 1321 | CE2 | TYR | A | 402 | 7.354  | 21.145 | 5.771  | 1.00 | 59.25 | A |
| ATOM | 1322 | CZ  | TYR | A | 402 | 7.312  | 20.123 | 6.707  | 1.00 | 59.71 | A |
| ATOM | 1323 | OH  | TYR | A | 402 | 6.095  | 19.689 | 7.149  | 1.00 | 60.35 | A |
| ATOM | 1324 | C   | TYR | A | 402 | 10.381 | 20.192 | 2.937  | 1.00 | 56.13 | A |
| ATOM | 1325 | O   | TYR | A | 402 | 9.722  | 19.179 | 2.827  | 1.00 | 56.88 | A |
| ATOM | 1326 | N   | GLU | A | 403 | 10.171 | 21.267 | 2.189  | 1.00 | 55.99 | A |
| ATOM | 1327 | CA  | GLU | A | 403 | 9.132  | 21.293 | 1.166  | 1.00 | 56.74 | A |
| ATOM | 1328 | CB  | GLU | A | 403 | 9.084  | 22.674 | 0.536  | 1.00 | 56.04 | A |
| ATOM | 1329 | CG  | GLU | A | 403 | 9.057  | 23.787 | 1.534  | 1.00 | 55.71 | A |
| ATOM | 1330 | CD  | GLU | A | 403 | 7.726  | 23.916 | 2.179  | 1.00 | 55.26 | A |
| ATOM | 1331 | OE1 | GLU | A | 403 | 6.771  | 23.406 | 1.578  | 1.00 | 55.31 | A |
| ATOM | 1332 | OE2 | GLU | A | 403 | 7.619  | 24.530 | 3.263  | 1.00 | 57.01 | A |
| ATOM | 1333 | C   | GLU | A | 403 | 9.348  | 20.251 | 0.066  | 1.00 | 58.37 | A |
| ATOM | 1334 | O   | GLU | A | 403 | 8.419  | 19.789 | -0.584 | 1.00 | 58.14 | A |
| ATOM | 1335 | N   | ALA | A | 404 | 10.590 | 19.894 | -0.169 | 1.00 | 61.29 | A |
| ATOM | 1336 | CA  | ALA | A | 404 | 10.855 | 18.909 | -1.199 | 1.00 | 64.91 | A |
| ATOM | 1337 | CB  | ALA | A | 404 | 12.323 | 18.912 | -1.549 | 1.00 | 62.53 | A |
| ATOM | 1338 | C   | ALA | A | 404 | 10.438 | 17.524 | -0.707 | 1.00 | 67.30 | A |
| ATOM | 1339 | O   | ALA | A | 404 | 9.846  | 16.754 | -1.451 | 1.00 | 69.81 | A |
| ATOM | 1340 | N   | GLY | A | 405 | 10.752 | 17.207 | 0.544  | 1.00 | 68.33 | A |
| ATOM | 1341 | CA  | GLY | A | 405 | 10.394 | 15.906 | 1.067  | 1.00 | 68.87 | A |
| ATOM | 1342 | C   | GLY | A | 405 | 8.974  | 15.819 | 1.575  | 1.00 | 69.83 | A |
| ATOM | 1343 | O   | GLY | A | 405 | 8.363  | 14.780 | 1.522  | 1.00 | 71.96 | A |
| ATOM | 1344 | N   | GLN | A | 406 | 8.424  | 16.918 | 2.051  | 1.00 | 70.29 | A |
| ATOM | 1345 | CA  | GLN | A | 406 | 7.082  | 16.902 | 2.574  | 1.00 | 69.92 | A |
| ATOM | 1346 | CB  | GLN | A | 406 | 7.052  | 17.731 | 3.839  | 1.00 | 72.83 | A |
| ATOM | 1347 | CG  | GLN | A | 406 | 7.056  | 16.911 | 5.094  | 1.00 | 78.47 | A |
| ATOM | 1348 | CD  | GLN | A | 406 | 5.721  | 16.215 | 5.310  | 1.00 | 80.83 | A |
| ATOM | 1349 | OE1 | GLN | A | 406 | 4.661  | 16.868 | 5.380  | 1.00 | 80.81 | A |
| ATOM | 1350 | NE2 | GLN | A | 406 | 5.761  | 14.884 | 5.411  | 1.00 | 82.14 | A |
| ATOM | 1351 | C   | GLN | A | 406 | 5.974  | 17.382 | 1.664  | 1.00 | 69.63 | A |
| ATOM | 1352 | O   | GLN | A | 406 | 4.835  | 17.054 | 1.901  | 1.00 | 68.87 | A |
| ATOM | 1353 | N   | HIS | A | 407 | 6.276  | 18.165 | 0.636  | 1.00 | 70.71 | A |
| ATOM | 1354 | CA  | HIS | A | 407 | 5.207  | 18.693 | -0.209 | 1.00 | 72.14 | A |
| ATOM | 1355 | CB  | HIS | A | 407 | 4.975  | 20.172 | 0.103  | 1.00 | 71.63 | A |
| ATOM | 1356 | CG  | HIS | A | 407 | 4.420  | 20.418 | 1.473  | 1.00 | 73.42 | A |
| ATOM | 1357 | CD2 | HIS | A | 407 | 5.037  | 20.651 | 2.660  | 1.00 | 73.70 | A |
| ATOM | 1358 | ND1 | HIS | A | 407 | 3.069  | 20.410 | 1.741  | 1.00 | 73.86 | A |
| ATOM | 1359 | CE1 | HIS | A | 407 | 2.879  | 20.630 | 3.032  | 1.00 | 74.92 | A |
| ATOM | 1360 | NE2 | HIS | A | 407 | 4.057  | 20.778 | 3.612  | 1.00 | 73.35 | A |
| ATOM | 1361 | C   | HIS | A | 407 | 5.415  | 18.523 | -1.693 | 1.00 | 74.10 | A |
| ATOM | 1362 | O   | HIS | A | 407 | 5.143  | 19.428 | -2.472 | 1.00 | 74.41 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1363 | N | MET | A | 408 | 5.875 | 17.338 | −2.073 | 1.00 | 77.74 | A |
|---|---|---|---|---|---|---|---|---|---|---|---|
| ATOM | 1364 | CA | MET | A | 408 | 6.129 | 16.975 | −3.462 | 1.00 | 80.35 | A |
| ATOM | 1365 | CB | MET | A | 408 | 6.312 | 15.465 | −3.525 | 1.00 | 85.35 | A |
| ATOM | 1366 | CG | MET | A | 408 | 7.271 | 14.981 | −4.586 | 1.00 | 94.46 | A |
| ATOM | 1367 | SD | MET | A | 408 | 8.015 | 13.369 | −4.073 | 1.00 | 105.56 | A |
| ATOM | 1368 | CE | MET | A | 408 | 9.781 | 13.826 | −3.640 | 1.00 | 101.77 | A |
| ATOM | 1369 | C | MET | A | 408 | 5.050 | 17.436 | −4.465 | 1.00 | 78.88 | A |
| ATOM | 1370 | O | MET | A | 408 | 5.360 | 17.707 | −5.614 | 1.00 | 79.55 | A |
| ATOM | 1371 | N | GLU | A | 409 | 3.791 | 17.549 | −4.047 | 1.00 | 78.03 | A |
| ATOM | 1372 | CA | GLU | A | 409 | 2.754 | 17.987 | −4.984 | 1.00 | 77.54 | A |
| ATOM | 1373 | CB | GLU | A | 409 | 1.341 | 17.850 | −4.427 | 1.00 | 78.75 | A |
| ATOM | 1374 | CG | GLU | A | 409 | 1.200 | 17.113 | −3.128 | 1.00 | 82.92 | A |
| ATOM | 1375 | CD | GLU | A | 409 | 1.713 | 17.901 | −1.937 | 1.00 | 84.27 | A |
| ATOM | 1376 | OE1 | GLU | A | 409 | 1.154 | 18.989 | −1.611 | 1.00 | 81.89 | A |
| ATOM | 1377 | OE2 | GLU | A | 409 | 2.685 | 17.400 | −1.321 | 1.00 | 86.41 | A |
| ATOM | 1378 | C | GLU | A | 409 | 2.916 | 19.435 | −5.378 | 1.00 | 76.82 | A |
| ATOM | 1379 | O | GLU | A | 409 | 2.468 | 19.818 | −6.454 | 1.00 | 78.03 | A |
| ATOM | 1380 | N | ASP | A | 410 | 3.488 | 20.257 | −4.495 | 1.00 | 74.22 | A |
| ATOM | 1381 | CA | ASP | A | 410 | 3.695 | 21.663 | −4.818 | 1.00 | 70.56 | A |
| ATOM | 1382 | CB | ASP | A | 410 | 3.022 | 22.604 | −3.836 | 1.00 | 70.15 | A |
| ATOM | 1383 | CG | ASP | A | 410 | 2.998 | 24.027 | −4.355 | 1.00 | 69.32 | A |
| ATOM | 1384 | OD1 | ASP | A | 410 | 3.603 | 24.244 | −5.427 | 1.00 | 65.66 | A |
| ATOM | 1385 | OD2 | ASP | A | 410 | 2.383 | 24.913 | −3.716 | 1.00 | 70.65 | A |
| ATOM | 1386 | C | ASP | A | 410 | 5.164 | 21.954 | −4.818 | 1.00 | 68.48 | A |
| ATOM | 1387 | O | ASP | A | 410 | 5.737 | 22.357 | −3.802 | 1.00 | 68.00 | A |
| ATOM | 1388 | N | PRO | A | 411 | 5.797 | 21.755 | −5.974 | 1.00 | 66.88 | A |
| ATOM | 1389 | CD | PRO | A | 411 | 5.064 | 21.443 | −7.213 | 1.00 | 66.19 | A |
| ATOM | 1390 | CA | PRO | A | 411 | 7.219 | 21.953 | −6.254 | 1.00 | 65.33 | A |
| ATOM | 1391 | CB | PRO | A | 411 | 7.337 | 21.477 | −7.696 | 1.00 | 65.59 | A |
| ATOM | 1392 | CG | PRO | A | 411 | 6.017 | 21.889 | −8.267 | 1.00 | 66.52 | A |
| ATOM | 1393 | C | PRO | A | 411 | 7.634 | 23.405 | −6.082 | 1.00 | 63.07 | A |
| ATOM | 1394 | O | PRO | A | 411 | 8.802 | 23.718 | −6.022 | 1.00 | 64.46 | A |
| ATOM | 1395 | N | ARG | A | 412 | 6.640 | 24.269 | −5.960 | 1.00 | 61.90 | A |
| ATOM | 1396 | CA | ARG | A | 412 | 6.810 | 25.711 | −5.814 | 1.00 | 59.99 | A |
| ATOM | 1397 | CB | ARG | A | 412 | 5.949 | 26.366 | −6.886 | 1.00 | 63.32 | A |
| ATOM | 1398 | CG | ARG | A | 412 | 6.581 | 27.478 | −7.673 | 1.00 | 68.55 | A |
| ATOM | 1399 | CD | ARG | A | 412 | 5.784 | 27.707 | −8.941 | 1.00 | 71.60 | A |
| ATOM | 1400 | NE | ARG | A | 412 | 5.970 | 26.585 | −9.850 | 1.00 | 73.93 | A |
| ATOM | 1401 | CZ | ARG | A | 412 | 4.989 | 26.038 | −10.548 | 1.00 | 74.36 | A |
| ATOM | 1402 | NH1 | ARG | A | 412 | 3.751 | 26.521 | −10.437 | 1.00 | 73.75 | A |
| ATOM | 1403 | NH2 | ARG | A | 412 | 5.256 | 24.994 | −11.323 | 1.00 | 75.18 | A |
| ATOM | 1404 | C | ARG | A | 412 | 6.380 | 26.246 | −4.433 | 1.00 | 57.13 | A |
| ATOM | 1405 | O | ARG | A | 412 | 6.038 | 27.411 | −4.302 | 1.00 | 56.12 | A |
| ATOM | 1406 | N | ARG | A | 413 | 6.414 | 25.411 | −3.403 | 1.00 | 55.66 | A |
| ATOM | 1407 | CA | ARG | A | 413 | 5.951 | 25.851 | −2.103 | 1.00 | 53.16 | A |
| ATOM | 1408 | CB | ARG | A | 413 | 5.379 | 24.654 | −1.318 | 1.00 | 52.10 | A |
| ATOM | 1409 | CG | ARG | A | 413 | 4.624 | 25.021 | −0.026 | 1.00 | 48.21 | A |
| ATOM | 1410 | CD | ARG | A | 413 | 3.972 | 23.800 | 0.541 | 1.00 | 55.00 | A |
| ATOM | 1411 | NE | ARG | A | 413 | 3.473 | 23.926 | 1.913 | 1.00 | 58.53 | A |
| ATOM | 1412 | CZ | ARG | A | 413 | 2.285 | 24.427 | 2.258 | 1.00 | 57.98 | A |
| ATOM | 1413 | NH1 | ARG | A | 413 | 1.440 | 24.871 | 1.335 | 1.00 | 56.54 | A |
| ATOM | 1414 | NH2 | ARG | A | 413 | 1.940 | 24.470 | 3.536 | 1.00 | 57.29 | A |
| ATOM | 1415 | C | ARG | A | 413 | 6.989 | 26.601 | −1.303 | 1.00 | 51.29 | A |
| ATOM | 1416 | O | ARG | A | 413 | 6.656 | 27.561 | −0.591 | 1.00 | 51.16 | A |
| ATOM | 1417 | N | ALA | A | 414 | 8.242 | 26.191 | −1.402 | 1.00 | 51.10 | A |
| ATOM | 1418 | CA | ALA | A | 414 | 9.295 | 26.936 | −0.684 | 1.00 | 51.82 | A |
| ATOM | 1419 | CB | ALA | A | 414 | 10.680 | 26.337 | −0.999 | 1.00 | 48.16 | A |
| ATOM | 1420 | C | ALA | A | 414 | 9.228 | 28.443 | −1.101 | 1.00 | 51.53 | A |
| ATOM | 1421 | O | ALA | A | 414 | 9.272 | 29.347 | −0.263 | 1.00 | 49.84 | A |
| ATOM | 1422 | N | GLY | A | 415 | 9.070 | 28.684 | −2.410 | 1.00 | 51.62 | A |
| ATOM | 1423 | CA | GLY | A | 415 | 8.980 | 30.035 | −2.927 | 1.00 | 52.60 | A |
| ATOM | 1424 | C | GLY | A | 415 | 7.747 | 30.789 | −2.475 | 1.00 | 55.38 | A |
| ATOM | 1425 | O | GLY | A | 415 | 7.826 | 31.974 | −2.163 | 1.00 | 55.65 | A |
| ATOM | 1426 | N | LYS | A | 416 | 6.601 | 30.116 | −2.445 | 1.00 | 55.36 | A |
| ATOM | 1427 | CA | LYS | A | 416 | 5.384 | 30.769 | −2.012 | 1.00 | 53.95 | A |
| ATOM | 1428 | CB | LYS | A | 416 | 4.216 | 29.822 | −2.119 | 1.00 | 55.47 | A |
| ATOM | 1429 | CG | LYS | A | 416 | 3.748 | 29.605 | −3.549 | 1.00 | 56.15 | A |
| ATOM | 1430 | CD | LYS | A | 416 | 2.538 | 28.695 | −3.605 | 1.00 | 58.00 | A |
| ATOM | 1431 | CE | LYS | A | 416 | 2.253 | 28.268 | −5.041 | 1.00 | 61.67 | A |
| ATOM | 1432 | NZ | LYS | A | 416 | 1.016 | 27.424 | −5.140 | 1.00 | 62.20 | A |
| ATOM | 1433 | C | LYS | A | 416 | 5.564 | 31.222 | −0.585 | 1.00 | 55.25 | A |
| ATOM | 1434 | O | LYS | A | 416 | 4.999 | 32.261 | −0.161 | 1.00 | 52.35 | A |
| ATOM | 1435 | N | MET | A | 417 | 6.359 | 30.443 | 0.160 | 1.00 | 56.07 | A |
| ATOM | 1436 | CA | MET | A | 417 | 6.641 | 30.776 | 1.556 | 1.00 | 57.09 | A |
| ATOM | 1437 | CB | MET | A | 417 | 7.360 | 29.623 | 2.269 | 1.00 | 60.48 | A |
| ATOM | 1438 | CG | MET | A | 417 | 6.501 | 28.412 | 2.632 | 1.00 | 64.23 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1439 | SD | MET | A | 417 | 5.129 | 28.913 | 3.681 | 1.00 | 71.21 | A |
|---|---|---|---|---|---|---|---|---|---|---|---|
| ATOM | 1440 | CE | MET | A | 417 | 3.804 | 28.043 | 3.013 | 1.00 | 69.38 | A |
| ATOM | 1441 | C | MET | A | 417 | 7.499 | 32.049 | 1.610 | 1.00 | 55.91 | A |
| ATOM | 1442 | O | MET | A | 417 | 7.196 | 32.974 | 2.361 | 1.00 | 55.94 | A |
| ATOM | 1443 | N | LEU | A | 418 | 8.561 | 32.106 | 0.803 | 1.00 | 53.97 | A |
| ATOM | 1444 | CA | LEU | A | 418 | 9.429 | 33.274 | 0.789 | 1.00 | 51.95 | A |
| ATOM | 1445 | CB | LEU | A | 418 | 10.630 | 33.020 | −0.120 | 1.00 | 48.33 | A |
| ATOM | 1446 | CG | LEU | A | 418 | 11.451 | 31.776 | 0.284 | 1.00 | 49.78 | A |
| ATOM | 1447 | CD1 | LEU | A | 418 | 12.566 | 31.485 | −0.751 | 1.00 | 44.00 | A |
| ATOM | 1448 | CD2 | LEU | A | 418 | 12.047 | 31.962 | 1.711 | 1.00 | 47.60 | A |
| ATOM | 1449 | C | LEU | A | 418 | 8.629 | 34.501 | 0.329 | 1.00 | 52.38 | A |
| ATOM | 1450 | O | LEU | A | 418 | 8.792 | 35.608 | 0.862 | 1.00 | 55.45 | A |
| ATOM | 1451 | N | MET | A | 419 | 7.735 | 34.315 | −0.626 | 1.00 | 51.03 | A |
| ATOM | 1452 | CA | MET | A | 419 | 6.942 | 35.435 | −1.114 | 1.00 | 50.07 | A |
| ATOM | 1453 | CB | MET | A | 419 | 6.178 | 35.056 | −2.393 | 1.00 | 51.14 | A |
| ATOM | 1454 | CG | MET | A | 419 | 7.043 | 35.069 | −3.633 | 1.00 | 53.91 | A |
| ATOM | 1455 | SD | MET | A | 419 | 6.230 | 34.425 | −5.107 | 1.00 | 61.03 | A |
| ATOM | 1456 | CE | MET | A | 419 | 4.798 | 35.648 | −5.247 | 1.00 | 58.96 | A |
| ATOM | 1457 | C | MET | A | 419 | 5.998 | 36.058 | −0.087 | 1.00 | 48.27 | A |
| ATOM | 1458 | O | MET | A | 419 | 5.245 | 36.990 | −0.416 | 1.00 | 48.23 | A |
| ATOM | 1459 | N | THR | A | 420 | 6.028 | 35.565 | 1.145 | 1.00 | 47.48 | A |
| ATOM | 1460 | CA | THR | A | 420 | 5.185 | 36.187 | 2.173 | 1.00 | 47.79 | A |
| ATOM | 1461 | CB | THR | A | 420 | 4.392 | 35.173 | 3.034 | 1.00 | 46.89 | A |
| ATOM | 1462 | OG1 | THR | A | 420 | 5.301 | 34.284 | 3.684 | 1.00 | 47.67 | A |
| ATOM | 1463 | CG2 | THR | A | 420 | 3.412 | 34.388 | 2.186 | 1.00 | 47.13 | A |
| ATOM | 1464 | C | THR | A | 420 | 6.043 | 37.044 | 3.115 | 1.00 | 47.72 | A |
| ATOM | 1465 | O | THR | A | 420 | 5.518 | 37.829 | 3.895 | 1.00 | 49.54 | A |
| ATOM | 1466 | N | LEU | A | 421 | 7.362 | 36.890 | 3.036 | 1.00 | 47.59 | A |
| ATOM | 1467 | CA | LEU | A | 421 | 8.270 | 37.672 | 3.867 | 1.00 | 49.55 | A |
| ATOM | 1468 | CB | LEU | A | 421 | 9.723 | 37.240 | 3.617 | 1.00 | 47.80 | A |
| ATOM | 1469 | CG | LEU | A | 421 | 10.056 | 35.860 | 4.178 | 1.00 | 46.88 | A |
| ATOM | 1470 | CD1 | LEU | A | 421 | 11.405 | 35.458 | 3.754 | 1.00 | 45.95 | A |
| ATOM | 1471 | CD2 | LEU | A | 421 | 9.989 | 35.892 | 5.694 | 1.00 | 45.68 | A |
| ATOM | 1472 | C | LEU | A | 421 | 8.102 | 39.199 | 3.656 | 1.00 | 50.71 | A |
| ATOM | 1473 | O | LEU | A | 421 | 8.364 | 39.982 | 4.574 | 1.00 | 49.71 | A |
| ATOM | 1474 | N | PRO | A | 422 | 7.673 | 39.633 | 2.446 | 1.00 | 51.58 | A |
| ATOM | 1475 | CD | PRO | A | 422 | 7.579 | 38.823 | 1.214 | 1.00 | 53.02 | A |
| ATOM | 1476 | CA | PRO | A | 422 | 7.470 | 41.058 | 2.148 | 1.00 | 54.26 | A |
| ATOM | 1477 | CB | PRO | A | 422 | 7.165 | 41.061 | 0.647 | 1.00 | 55.57 | A |
| ATOM | 1478 | CG | PRO | A | 422 | 7.873 | 39.829 | 0.141 | 1.00 | 54.62 | A |
| ATOM | 1479 | C | PRO | A | 422 | 6.297 | 41.659 | 2.971 | 1.00 | 55.88 | A |
| ATOM | 1480 | O | PRO | A | 422 | 6.415 | 42.773 | 3.528 | 1.00 | 55.09 | A |
| ATOM | 1481 | N | LEU | A | 423 | 5.171 | 40.940 | 3.040 | 1.00 | 55.74 | A |
| ATOM | 1482 | CA | LEU | A | 423 | 4.033 | 41.427 | 3.821 | 1.00 | 58.04 | A |
| ATOM | 1483 | CB | LEU | A | 423 | 2.780 | 40.597 | 3.541 | 1.00 | 57.00 | A |
| ATOM | 1484 | CG | LEU | A | 423 | 1.539 | 41.097 | 4.279 | 1.00 | 55.46 | A |
| ATOM | 1485 | CD1 | LEU | A | 423 | 1.493 | 42.623 | 4.264 | 1.00 | 54.65 | A |
| ATOM | 1486 | CD2 | LEU | A | 423 | 0.312 | 40.523 | 3.637 | 1.00 | 54.60 | A |
| ATOM | 1487 | C | LEU | A | 423 | 4.352 | 41.395 | 5.336 | 1.00 | 60.01 | A |
| ATOM | 1488 | O | LEU | A | 423 | 3.794 | 42.167 | 6.149 | 1.00 | 61.31 | A |
| ATOM | 1489 | N | LEU | A | 424 | 5.264 | 40.509 | 5.719 | 1.00 | 58.93 | A |
| ATOM | 1490 | CA | LEU | A | 424 | 5.659 | 40.414 | 7.116 | 1.00 | 58.64 | A |
| ATOM | 1491 | CB | LEU | A | 424 | 6.432 | 39.107 | 7.335 | 1.00 | 53.62 | A |
| ATOM | 1492 | CG | LEU | A | 424 | 7.041 | 38.836 | 8.695 | 1.00 | 51.08 | A |
| ATOM | 1493 | CD1 | LEU | A | 424 | 5.944 | 38.901 | 9.733 | 1.00 | 50.17 | A |
| ATOM | 1494 | CD2 | LEU | A | 424 | 7.731 | 37.483 | 8.685 | 1.00 | 46.78 | A |
| ATOM | 1495 | C | LEU | A | 424 | 6.518 | 41.639 | 7.497 | 1.00 | 60.18 | A |
| ATOM | 1496 | O | LEU | A | 424 | 6.363 | 42.196 | 8.598 | 1.00 | 61.23 | A |
| ATOM | 1497 | N | ARG | A | 425 | 7.404 | 42.045 | 6.577 | 1.00 | 60.62 | A |
| ATOM | 1498 | CA | ARG | A | 425 | 8.318 | 43.177 | 6.772 | 1.00 | 61.40 | A |
| ATOM | 1499 | CB | ARG | A | 425 | 9.267 | 43.301 | 5.567 | 1.00 | 60.84 | A |
| ATOM | 1500 | CG | ARG | A | 425 | 10.272 | 44.457 | 5.612 | 1.00 | 56.45 | A |
| ATOM | 1501 | CD | ARG | A | 425 | 11.260 | 44.306 | 6.764 | 1.00 | 57.70 | A |
| ATOM | 1502 | NE | ARG | A | 425 | 12.129 | 43.139 | 6.620 | 1.00 | 56.25 | A |
| ATOM | 1503 | CZ | ARG | A | 425 | 13.184 | 43.046 | 5.807 | 1.00 | 57.08 | A |
| ATOM | 1504 | NH1 | ARG | A | 425 | 13.552 | 44.066 | 5.036 | 1.00 | 55.18 | A |
| ATOM | 1505 | NH2 | ARG | A | 425 | 13.880 | 41.912 | 5.764 | 1.00 | 56.21 | A |
| ATOM | 1506 | C | ARG | A | 425 | 7.532 | 44.470 | 6.923 | 1.00 | 62.61 | A |
| ATOM | 1507 | O | ARG | A | 425 | 7.808 | 45.299 | 7.804 | 1.00 | 62.55 | A |
| ATOM | 1508 | N | GLN | A | 426 | 6.537 | 44.611 | 6.056 | 1.00 | 63.51 | A |
| ATOM | 1509 | CA | GLN | A | 426 | 5.657 | 45.775 | 6.003 | 1.00 | 64.57 | A |
| ATOM | 1510 | CB | GLN | A | 426 | 4.739 | 45.618 | 4.807 | 1.00 | 64.70 | A |
| ATOM | 1511 | CG | GLN | A | 426 | 4.083 | 46.861 | 4.348 | 1.00 | 66.47 | A |
| ATOM | 1512 | CD | GLN | A | 426 | 2.935 | 46.542 | 3.428 | 1.00 | 68.27 | A |
| ATOM | 1513 | OE1 | GLN | A | 426 | 3.090 | 45.832 | 2.423 | 1.00 | 69.07 | A |
| ATOM | 1514 | NE2 | GLN | A | 426 | 1.758 | 47.051 | 3.768 | 1.00 | 70.61 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1515 | C | GLN | A | 426 | 4.825 | 45.965 | 7.272 | 1.00 | 65.31 | A |
|---|---|---|---|---|---|---|---|---|---|---|---|
| ATOM | 1516 | O | GLN | A | 426 | 4.826 | 47.045 | 7.871 | 1.00 | 66.01 | A |
| ATOM | 1517 | N | THR | A | 427 | 4.101 | 44.915 | 7.658 | 1.00 | 65.21 | A |
| ATOM | 1518 | CA | THR | A | 427 | 3.264 | 44.939 | 8.851 | 1.00 | 64.47 | A |
| ATOM | 1519 | CB | THR | A | 427 | 2.514 | 43.601 | 9.019 | 1.00 | 65.00 | A |
| ATOM | 1520 | OG1 | THR | A | 427 | 1.552 | 43.458 | 7.969 | 1.00 | 63.95 | A |
| ATOM | 1521 | CG2 | THR | A | 427 | 1.816 | 43.544 | 10.342 | 1.00 | 64.55 | A |
| ATOM | 1522 | C | THR | A | 427 | 4.180 | 45.153 | 10.036 | 1.00 | 64.41 | A |
| ATOM | 1523 | O | THR | A | 427 | 3.908 | 45.961 | 10.914 | 1.00 | 64.31 | A |
| ATOM | 1524 | N | SER | A | 428 | 5.275 | 44.419 | 10.064 | 1.00 | 65.16 | A |
| ATOM | 1525 | CA | SER | A | 428 | 6.209 | 44.581 | 11.143 | 1.00 | 67.00 | A |
| ATOM | 1526 | CB | SER | A | 428 | 7.410 | 43.667 | 10.946 | 1.00 | 67.40 | A |
| ATOM | 1527 | OG | SER | A | 428 | 8.480 | 44.126 | 11.758 | 1.00 | 68.30 | A |
| ATOM | 1528 | C | SER | A | 428 | 6.692 | 46.034 | 11.337 | 1.00 | 67.69 | A |
| ATOM | 1529 | O | SER | A | 428 | 6.614 | 46.544 | 12.444 | 1.00 | 67.44 | A |
| ATOM | 1530 | N | THR | A | 429 | 7.197 | 46.712 | 10.305 | 1.00 | 69.37 | A |
| ATOM | 1531 | CA | THR | A | 429 | 7.668 | 48.093 | 10.542 | 1.00 | 72.05 | A |
| ATOM | 1532 | CB | THR | A | 429 | 8.602 | 48.672 | 9.362 | 1.00 | 71.15 | A |
| ATOM | 1533 | OG1 | THR | A | 429 | 7.912 | 48.634 | 8.115 | 1.00 | 69.22 | A |
| ATOM | 1534 | CG2 | THR | A | 429 | 9.938 | 47.876 | 9.244 | 1.00 | 70.21 | A |
| ATOM | 1535 | C | THR | A | 429 | 6.489 | 49.060 | 10.847 | 1.00 | 73.05 | A |
| ATOM | 1536 | O | THR | A | 429 | 6.672 | 50.123 | 11.472 | 1.00 | 72.11 | A |
| ATOM | 1537 | N | LYS | A | 430 | 5.279 | 48.673 | 10.439 | 1.00 | 73.53 | A |
| ATOM | 1538 | CA | LYS | A | 430 | 4.108 | 49.493 | 10.723 | 1.00 | 75.01 | A |
| ATOM | 1539 | CB | LYS | A | 430 | 2.924 | 49.044 | 9.864 | 1.00 | 74.59 | A |
| ATOM | 1540 | CG | LYS | A | 430 | 1.839 | 50.098 | 9.675 | 1.00 | 74.97 | A |
| ATOM | 1541 | CD | LYS | A | 430 | 0.510 | 49.492 | 9.157 | 1.00 | 76.40 | A |
| ATOM | 1542 | CE | LYS | A | 430 | 0.663 | 48.571 | 7.917 | 1.00 | 78.63 | A |
| ATOM | 1543 | NZ | LYS | A | 430 | 0.790 | 49.229 | 6.574 | 1.00 | 77.41 | A |
| ATOM | 1544 | C | LYS | A | 430 | 3.790 | 49.333 | 12.227 | 1.00 | 76.15 | A |
| ATOM | 1545 | O | LYS | A | 430 | 3.303 | 50.265 | 12.871 | 1.00 | 78.15 | A |
| ATOM | 1546 | N | ALA | A | 431 | 4.073 | 48.158 | 12.789 | 1.00 | 75.59 | A |
| ATOM | 1547 | CA | ALA | A | 431 | 3.832 | 47.927 | 14.207 | 1.00 | 76.02 | A |
| ATOM | 1548 | CB | ALA | A | 431 | 3.850 | 46.444 | 14.513 | 1.00 | 73.82 | A |
| ATOM | 1549 | C | ALA | A | 431 | 4.896 | 48.647 | 15.039 | 1.00 | 77.15 | A |
| ATOM | 1550 | O | ALA | A | 431 | 4.592 | 49.219 | 16.076 | 1.00 | 78.04 | A |
| ATOM | 1551 | N | VAL | A | 432 | 6.143 | 48.636 | 14.585 | 1.00 | 78.58 | A |
| ATOM | 1552 | CA | VAL | A | 432 | 7.214 | 49.297 | 15.332 | 1.00 | 79.54 | A |
| ATOM | 1553 | CB | VAL | A | 432 | 8.588 | 49.019 | 14.729 | 1.00 | 77.88 | A |
| ATOM | 1554 | CG1 | VAL | A | 432 | 9.635 | 49.822 | 15.461 | 1.00 | 77.46 | A |
| ATOM | 1555 | CG2 | VAL | A | 432 | 8.907 | 47.550 | 14.846 | 1.00 | 77.47 | A |
| ATOM | 1556 | C | VAL | A | 432 | 7.042 | 50.795 | 15.381 | 1.00 | 80.71 | A |
| ATOM | 1557 | O | VAL | A | 432 | 7.393 | 51.440 | 16.361 | 1.00 | 80.33 | A |
| ATOM | 1558 | N | GLN | A | 433 | 6.512 | 51.349 | 14.306 | 1.00 | 83.15 | A |
| ATOM | 1559 | CA | GLN | A | 433 | 6.294 | 52.778 | 14.251 | 1.00 | 86.07 | A |
| ATOM | 1560 | CB | GLN | A | 433 | 5.959 | 53.219 | 12.811 | 1.00 | 88.43 | A |
| ATOM | 1561 | CG | GLN | A | 433 | 5.385 | 54.646 | 12.651 | 1.00 | 92.71 | A |
| ATOM | 1562 | CD | GLN | A | 433 | 6.269 | 55.819 | 13.187 | 1.00 | 94.89 | A |
| ATOM | 1563 | OE1 | GLN | A | 433 | 5.871 | 56.985 | 13.075 | 1.00 | 95.62 | A |
| ATOM | 1564 | NE2 | GLN | A | 433 | 7.444 | 55.513 | 13.762 | 1.00 | 95.69 | A |
| ATOM | 1565 | C | GLN | A | 433 | 5.173 | 53.133 | 15.207 | 1.00 | 86.58 | A |
| ATOM | 1566 | O | GLN | A | 433 | 5.365 | 53.962 | 16.089 | 1.00 | 87.04 | A |
| ATOM | 1567 | N | HIS | A | 434 | 4.020 | 52.486 | 15.049 | 1.00 | 87.81 | A |
| ATOM | 1568 | CA | HIS | A | 434 | 2.851 | 52.739 | 15.902 | 1.00 | 88.83 | A |
| ATOM | 1569 | CB | HIS | A | 434 | 1.777 | 51.700 | 15.636 | 1.00 | 90.08 | A |
| ATOM | 1570 | CG | HIS | A | 434 | 0.476 | 51.994 | 16.309 | 1.00 | 92.37 | A |
| ATOM | 1571 | CD2 | HIS | A | 434 | −0.800 | 51.890 | 15.867 | 1.00 | 93.22 | A |
| ATOM | 1572 | ND1 | HIS | A | 434 | 0.393 | 52.395 | 17.623 | 1.00 | 93.99 | A |
| ATOM | 1573 | CE1 | HIS | A | 434 | −0.879 | 52.523 | 17.966 | 1.00 | 94.08 | A |
| ATOM | 1574 | NE2 | HIS | A | 434 | −1.622 | 52.220 | 16.918 | 1.00 | 94.14 | A |
| ATOM | 1575 | C | HIS | A | 434 | 3.168 | 52.746 | 17.397 | 1.00 | 89.35 | A |
| ATOM | 1576 | O | HIS | A | 434 | 2.771 | 53.660 | 18.111 | 1.00 | 89.33 | A |
| ATOM | 1577 | N | PHE | A | 435 | 3.865 | 51.722 | 17.880 | 1.00 | 90.06 | A |
| ATOM | 1578 | CA | PHE | A | 435 | 4.213 | 51.667 | 19.295 | 1.00 | 91.14 | A |
| ATOM | 1579 | CB | PHE | A | 435 | 4.705 | 50.267 | 19.687 | 1.00 | 91.35 | A |
| ATOM | 1580 | CG | PHE | A | 435 | 3.596 | 49.311 | 19.945 | 1.00 | 91.00 | A |
| ATOM | 1581 | CD1 | PHE | A | 435 | 3.121 | 49.119 | 21.224 | 1.00 | 91.44 | A |
| ATOM | 1582 | CD2 | PHE | A | 435 | 2.965 | 48.665 | 18.886 | 1.00 | 91.46 | A |
| ATOM | 1583 | CE1 | PHE | A | 435 | 2.025 | 48.300 | 21.447 | 1.00 | 91.94 | A |
| ATOM | 1584 | CE2 | PHE | A | 435 | 1.869 | 47.842 | 19.095 | 1.00 | 91.10 | A |
| ATOM | 1585 | CZ | PHE | A | 435 | 1.398 | 47.660 | 20.376 | 1.00 | 92.09 | A |
| ATOM | 1586 | C | PHE | A | 435 | 5.240 | 52.711 | 19.693 | 1.00 | 91.49 | A |
| ATOM | 1587 | O | PHE | A | 435 | 5.308 | 53.099 | 20.858 | 1.00 | 91.67 | A |
| ATOM | 1588 | N | TYR | A | 436 | 6.052 | 53.164 | 18.746 | 1.00 | 91.90 | A |
| ATOM | 1589 | CA | TYR | A | 436 | 7.020 | 54.203 | 19.075 | 1.00 | 92.56 | A |
| ATOM | 1590 | CB | TYR | A | 436 | 7.906 | 54.518 | 17.874 | 1.00 | 92.60 | A |

TABLE 1-continued

ATOMIC COORDINATES OF THE ERR3 LBD/SRC-1 NR
BOX 2 PEPTIDE COMPLEX (PDB CODE 1KV6)

| ATOM | 1591 | CG  | TYR | A | 436 | 8.996  | 55.521 | 18.173 | 1.00 | 93.63  | A |
|------|------|-----|-----|---|-----|--------|--------|--------|------|--------|---|
| ATOM | 1592 | CD1 | TYR | A | 436 | 10.026 | 55.217 | 19.065 | 1.00 | 93.99  | A |
| ATOM | 1593 | CE1 | TYR | A | 436 | 11.042 | 56.132 | 19.344 | 1.00 | 94.55  | A |
| ATOM | 1594 | CD2 | TYR | A | 436 | 9.003  | 56.777 | 17.560 | 1.00 | 94.58  | A |
| ATOM | 1595 | CE2 | TYR | A | 436 | 10.015 | 57.705 | 17.833 | 1.00 | 94.79  | A |
| ATOM | 1596 | CZ  | TYR | A | 436 | 11.030 | 57.372 | 18.727 | 1.00 | 94.91  | A |
| ATOM | 1597 | OH  | TYR | A | 436 | 12.025 | 58.277 | 19.005 | 1.00 | 94.68  | A |
| ATOM | 1598 | C   | TYR | A | 436 | 6.209  | 55.453 | 19.471 | 1.00 | 92.73  | A |
| ATOM | 1599 | O   | TYR | A | 436 | 6.604  | 56.219 | 20.347 | 1.00 | 92.98  | A |
| ATOM | 1600 | N   | ASN | A | 437 | 5.062  | 55.639 | 18.827 | 1.00 | 92.21  | A |
| ATOM | 1601 | CA  | ASN | A | 437 | 4.198  | 56.770 | 19.119 | 1.00 | 92.68  | A |
| ATOM | 1602 | CB  | ASN | A | 437 | 3.119  | 56.898 | 18.046 | 1.00 | 92.15  | A |
| ATOM | 1603 | CG  | ASN | A | 437 | 3.696  | 57.177 | 16.676 | 1.00 | 92.39  | A |
| ATOM | 1604 | OD1 | ASN | A | 437 | 2.967  | 57.230 | 15.686 | 1.00 | 92.28  | A |
| ATOM | 1605 | ND2 | ASN | A | 437 | 5.015  | 57.356 | 16.610 | 1.00 | 92.46  | A |
| ATOM | 1606 | C   | ASN | A | 437 | 3.546  | 56.637 | 20.494 | 1.00 | 93.31  | A |
| ATOM | 1607 | O   | ASN | A | 437 | 3.270  | 57.634 | 21.152 | 1.00 | 94.67  | A |
| ATOM | 1608 | N   | ILE | A | 438 | 3.277  | 55.414 | 20.926 | 1.00 | 92.88  | A |
| ATOM | 1609 | CA  | ILE | A | 438 | 2.682  | 55.228 | 22.232 | 1.00 | 92.46  | A |
| ATOM | 1610 | CB  | ILE | A | 438 | 2.231  | 53.771 | 22.439 | 1.00 | 92.58  | A |
| ATOM | 1611 | CG2 | ILE | A | 438 | 1.702  | 53.593 | 23.849 | 1.00 | 92.06  | A |
| ATOM | 1612 | CG1 | ILE | A | 438 | 1.177  | 53.387 | 21.392 | 1.00 | 92.80  | A |
| ATOM | 1613 | CD1 | ILE | A | 438 | -0.083 | 54.244 | 21.408 | 1.00 | 93.45  | A |
| ATOM | 1614 | C   | ILE | A | 438 | 3.782  | 55.561 | 23.231 | 1.00 | 92.51  | A |
| ATOM | 1615 | O   | ILE | A | 438 | 3.518  | 55.999 | 24.363 | 1.00 | 93.48  | A |
| ATOM | 1616 | N   | LYS | A | 439 | 5.019  | 55.352 | 22.789 | 1.00 | 91.28  | A |
| ATOM | 1617 | CA  | LYS | A | 439 | 6.185  | 55.609 | 23.610 | 1.00 | 91.41  | A |
| ATOM | 1618 | CB  | LYS | A | 439 | 7.443  | 55.166 | 22.881 | 1.00 | 90.70  | A |
| ATOM | 1619 | CG  | LYS | A | 439 | 8.705  | 55.430 | 23.665 | 1.00 | 91.74  | A |
| ATOM | 1620 | CD  | LYS | A | 439 | 9.914  | 55.532 | 22.765 | 1.00 | 93.12  | A |
| ATOM | 1621 | CE  | LYS | A | 439 | 11.125 | 56.062 | 23.525 | 1.00 | 94.33  | A |
| ATOM | 1622 | NZ  | LYS | A | 439 | 12.324 | 56.140 | 22.639 | 1.00 | 95.30  | A |
| ATOM | 1623 | C   | LYS | A | 439 | 6.275  | 57.094 | 23.911 | 1.00 | 92.28  | A |
| ATOM | 1624 | O   | LYS | A | 439 | 6.388  | 57.511 | 25.070 | 1.00 | 91.96  | A |
| ATOM | 1625 | N   | LEU | A | 440 | 6.231  | 57.880 | 22.837 | 1.00 | 93.81  | A |
| ATOM | 1626 | CA  | LEU | A | 440 | 6.298  | 59.341 | 22.887 | 1.00 | 94.46  | A |
| ATOM | 1627 | CB  | LEU | A | 440 | 6.300  | 59.905 | 21.456 | 1.00 | 92.24  | A |
| ATOM | 1628 | CG  | LEU | A | 440 | 7.657  | 60.245 | 20.805 | 1.00 | 91.03  | A |
| ATOM | 1629 | CD1 | LEU | A | 440 | 8.831  | 59.489 | 21.438 | 1.00 | 89.28  | A |
| ATOM | 1630 | CD2 | LEU | A | 440 | 7.546  | 59.951 | 19.327 | 1.00 | 89.07  | A |
| ATOM | 1631 | C   | LEU | A | 440 | 5.150  | 59.940 | 23.699 | 1.00 | 96.01  | A |
| ATOM | 1632 | O   | LEU | A | 440 | 5.387  | 60.743 | 24.601 | 1.00 | 96.36  | A |
| ATOM | 1633 | N   | GLU | A | 441 | 3.914  | 59.542 | 23.394 | 1.00 | 97.43  | A |
| ATOM | 1634 | CA  | GLU | A | 441 | 2.743  | 60.044 | 24.121 | 1.00 | 98.88  | A |
| ATOM | 1635 | CB  | GLU | A | 441 | 1.456  | 59.481 | 23.504 | 1.00 | 99.83  | A |
| ATOM | 1636 | CG  | GLU | A | 441 | 1.202  | 59.925 | 22.065 | 1.00 | 101.94 | A |
| ATOM | 1637 | CD  | GLU | A | 441 | 0.248  | 58.990 | 21.333 | 1.00 | 103.79 | A |
| ATOM | 1638 | OE1 | GLU | A | 441 | -0.854 | 58.744 | 21.871 | 1.00 | 104.69 | A |
| ATOM | 1639 | OE2 | GLU | A | 441 | 0.599  | 58.501 | 20.228 | 1.00 | 103.40 | A |
| ATOM | 1640 | C   | GLU | A | 441 | 2.776  | 59.729 | 25.631 | 1.00 | 98.96  | A |
| ATOM | 1641 | O   | GLU | A | 441 | 1.815  | 60.006 | 26.347 | 1.00 | 99.83  | A |
| ATOM | 1642 | N   | GLY | A | 442 | 3.880  | 59.151 | 26.102 | 1.00 | 98.67  | A |
| ATOM | 1643 | CA  | GLY | A | 442 | 4.043  | 58.819 | 27.511 | 1.00 | 97.72  | A |
| ATOM | 1644 | C   | GLY | A | 442 | 2.880  | 58.209 | 28.278 | 1.00 | 97.41  | A |
| ATOM | 1645 | O   | GLY | A | 442 | 3.036  | 57.848 | 29.439 | 1.00 | 97.14  | A |
| ATOM | 1646 | N   | LYS | A | 443 | 1.724  | 58.056 | 27.649 | 1.00 | 97.34  | A |
| ATOM | 1647 | CA  | LYS | A | 443 | 0.576  | 57.506 | 28.348 | 1.00 | 97.69  | A |
| ATOM | 1648 | CB  | LYS | A | 443 | -0.711 | 57.892 | 27.612 | 1.00 | 98.65  | A |
| ATOM | 1649 | CG  | LYS | A | 443 | -1.086 | 59.358 | 27.786 | 1.00 | 99.99  | A |
| ATOM | 1650 | CD  | LYS | A | 443 | -2.553 | 59.615 | 27.434 | 1.00 | 100.89 | A |
| ATOM | 1651 | CE  | LYS | A | 443 | -2.966 | 61.028 | 27.845 | 1.00 | 101.33 | A |
| ATOM | 1652 | NZ  | LYS | A | 443 | -2.746 | 61.271 | 29.308 | 1.00 | 100.35 | A |
| ATOM | 1653 | C   | LYS | A | 443 | 0.576  | 55.996 | 28.641 | 1.00 | 97.68  | A |
| ATOM | 1654 | O   | LYS | A | 443 | -0.366 | 55.494 | 29.275 | 1.00 | 98.39  | A |
| ATOM | 1655 | N   | VAL | A | 444 | 1.603  | 55.271 | 28.183 | 1.00 | 96.63  | A |
| ATOM | 1656 | CA  | VAL | A | 444 | 1.704  | 53.820 | 28.438 | 1.00 | 94.23  | A |
| ATOM | 1657 | CB  | VAL | A | 444 | 1.363  | 52.956 | 27.180 | 1.00 | 93.44  | A |
| ATOM | 1658 | CG1 | VAL | A | 444 | 1.830  | 51.520 | 27.388 | 1.00 | 92.48  | A |
| ATOM | 1659 | CG2 | VAL | A | 444 | -0.139 | 52.942 | 26.940 | 1.00 | 92.36  | A |
| ATOM | 1660 | C   | VAL | A | 444 | 3.094  | 53.415 | 28.923 | 1.00 | 92.93  | A |
| ATOM | 1661 | O   | VAL | A | 444 | 4.083  | 53.554 | 28.200 | 1.00 | 93.33  | A |
| ATOM | 1662 | N   | PRO | A | 445 | 3.181  | 52.902 | 30.157 | 1.00 | 91.39  | A |
| ATOM | 1663 | CD  | PRO | A | 445 | 2.042  | 52.665 | 31.063 | 1.00 | 91.48  | A |
| ATOM | 1664 | CA  | PRO | A | 445 | 4.441  | 52.464 | 30.769 | 1.00 | 89.72  | A |
| ATOM | 1665 | CB  | PRO | A | 445 | 4.045  | 52.207 | 32.215 | 1.00 | 90.53  | A |
| ATOM | 1666 | CG  | PRO | A | 445 | 2.632  | 51.701 | 32.070 | 1.00 | 91.38  | A |

TABLE 1-continued

ATOMIC COORDINATES OF THE ERR3 LBD/SRC-1 NR
BOX 2 PEPTIDE COMPLEX (PDB CODE 1KV6)

| | | | | | | | | | | |
|---|---|---|---|---|---|---|---|---|---|---|
| ATOM | 1667 | C | PRO | A | 445 | 4.958 | 51.214 | 30.078 | 1.00 | 87.79 | A |
| ATOM | 1668 | O | PRO | A | 445 | 4.190 | 50.291 | 29.803 | 1.00 | 88.92 | A |
| ATOM | 1669 | N | MET | A | 446 | 6.259 | 51.183 | 29.814 | 1.00 | 85.17 | A |
| ATOM | 1670 | CA | MET | A | 446 | 6.889 | 50.064 | 29.123 | 1.00 | 82.49 | A |
| ATOM | 1671 | CB | MET | A | 446 | 7.184 | 50.468 | 27.681 | 1.00 | 80.97 | A |
| ATOM | 1672 | CG | MET | A | 446 | 6.074 | 51.304 | 27.077 | 1.00 | 79.70 | A |
| ATOM | 1673 | SD | MET | A | 446 | 6.510 | 52.032 | 25.502 | 1.00 | 80.79 | A |
| ATOM | 1674 | CE | MET | A | 446 | 4.891 | 51.957 | 24.631 | 1.00 | 79.34 | A |
| ATOM | 1675 | C | MET | A | 446 | 8.183 | 49.679 | 29.806 | 1.00 | 81.99 | A |
| ATOM | 1676 | O | MET | A | 446 | 8.873 | 50.531 | 30.354 | 1.00 | 81.91 | A |
| ATOM | 1677 | N | HIS | A | 447 | 8.536 | 48.405 | 29.768 | 1.00 | 81.71 | A |
| ATOM | 1678 | CA | HIS | A | 447 | 9.767 | 48.002 | 30.417 | 1.00 | 81.65 | A |
| ATOM | 1679 | CB | HIS | A | 447 | 9.785 | 46.513 | 30.709 | 1.00 | 82.67 | A |
| ATOM | 1680 | CG | HIS | A | 447 | 8.875 | 46.113 | 31.822 | 1.00 | 82.27 | A |
| ATOM | 1681 | CD2 | HIS | A | 447 | 9.131 | 45.811 | 33.113 | 1.00 | 81.82 | A |
| ATOM | 1682 | ND1 | HIS | A | 447 | 7.513 | 45.980 | 31.657 | 1.00 | 82.62 | A |
| ATOM | 1683 | CE1 | HIS | A | 447 | 6.965 | 45.609 | 32.797 | 1.00 | 82.50 | A |
| ATOM | 1684 | NE2 | HIS | A | 447 | 7.926 | 45.502 | 33.697 | 1.00 | 83.87 | A |
| ATOM | 1685 | C | HIS | A | 447 | 10.971 | 48.374 | 29.596 | 1.00 | 81.72 | A |
| ATOM | 1686 | O | HIS | A | 447 | 10.845 | 48.904 | 28.496 | 1.00 | 81.29 | A |
| ATOM | 1687 | N | LYS | A | 448 | 12.143 | 48.074 | 30.132 | 1.00 | 81.27 | A |
| ATOM | 1688 | CA | LYS | A | 448 | 13.378 | 48.456 | 29.478 | 1.00 | 81.28 | A |
| ATOM | 1689 | CB | LYS | A | 448 | 14.553 | 48.290 | 30.472 | 1.00 | 81.46 | A |
| ATOM | 1690 | CG | LYS | A | 448 | 9999.000 | 9999.000 | 9999.000 | 1.00 | 0.00 | A |
| ATOM | 1691 | CD | LYS | A | 448 | 9999.000 | 9999.000 | 9999.000 | 1.00 | 0.00 | A |
| ATOM | 1692 | CE | LYS | A | 448 | 9999.000 | 9999.000 | 9999.000 | 1.00 | 0.00 | A |
| ATOM | 1693 | NZ | LYS | A | 448 | 9999.000 | 9999.000 | 9999.000 | 1.00 | 0.00 | A |
| ATOM | 1694 | C | LYS | A | 448 | 13.720 | 47.800 | 28.144 | 1.00 | 80.32 | A |
| ATOM | 1695 | O | LYS | A | 448 | 14.113 | 48.500 | 27.205 | 1.00 | 80.35 | A |
| ATOM | 1696 | N | LEU | A | 449 | 13.583 | 46.475 | 28.059 | 1.00 | 78.48 | A |
| ATOM | 1697 | CA | LEU | A | 449 | 13.931 | 45.770 | 26.832 | 1.00 | 76.37 | A |
| ATOM | 1698 | CB | LEU | A | 449 | 13.788 | 44.260 | 26.993 | 1.00 | 74.99 | A |
| ATOM | 1699 | CG | LEU | A | 449 | 15.013 | 43.443 | 26.575 | 1.00 | 74.14 | A |
| ATOM | 1700 | CD1 | LEU | A | 449 | 14.542 | 42.053 | 26.223 | 1.00 | 74.11 | A |
| ATOM | 1701 | CD2 | LEU | A | 449 | 15.734 | 44.065 | 25.391 | 1.00 | 73.06 | A |
| ATOM | 1702 | C | LEU | A | 449 | 13.088 | 46.221 | 25.666 | 1.00 | 75.50 | A |
| ATOM | 1703 | O | LEU | A | 449 | 13.630 | 46.558 | 24.631 | 1.00 | 74.82 | A |
| ATOM | 1704 | N | PHE | A | 450 | 11.768 | 46.226 | 25.835 | 1.00 | 74.84 | A |
| ATOM | 1705 | CA | PHE | A | 450 | 10.857 | 46.650 | 24.772 | 1.00 | 75.72 | A |
| ATOM | 1706 | CB | PHE | A | 450 | 9.389 | 46.596 | 25.260 | 1.00 | 71.93 | A |
| ATOM | 1707 | CG | PHE | A | 450 | 8.367 | 47.029 | 24.217 | 1.00 | 69.13 | A |
| ATOM | 1708 | CD1 | PHE | A | 450 | 8.113 | 46.245 | 23.083 | 1.00 | 68.10 | A |
| ATOM | 1709 | CD2 | PHE | A | 450 | 7.606 | 48.187 | 24.402 | 1.00 | 67.70 | A |
| ATOM | 1710 | CE1 | PHE | A | 450 | 7.101 | 46.613 | 22.154 | 1.00 | 67.32 | A |
| ATOM | 1711 | CE2 | PHE | A | 450 | 6.594 | 48.558 | 23.477 | 1.00 | 67.37 | A |
| ATOM | 1712 | CZ | PHE | A | 450 | 6.341 | 47.772 | 22.359 | 1.00 | 67.04 | A |
| ATOM | 1713 | C | PHE | A | 450 | 11.209 | 48.071 | 24.308 | 1.00 | 77.62 | A |
| ATOM | 1714 | O | PHE | A | 450 | 11.171 | 48.373 | 23.108 | 1.00 | 78.65 | A |
| ATOM | 1715 | N | LEU | A | 451 | 11.559 | 48.930 | 25.269 | 1.00 | 79.06 | A |
| ATOM | 1716 | CA | LEU | A | 451 | 11.918 | 50.333 | 25.010 | 1.00 | 79.04 | A |
| ATOM | 1717 | CB | LEU | A | 451 | 12.041 | 51.093 | 26.346 | 1.00 | 77.99 | A |
| ATOM | 1718 | CG | LEU | A | 451 | 10.985 | 52.143 | 26.733 | 1.00 | 75.75 | A |
| ATOM | 1719 | CD1 | LEU | A | 451 | 9.713 | 52.055 | 25.889 | 1.00 | 75.75 | A |
| ATOM | 1720 | CD2 | LEU | A | 451 | 10.676 | 51.949 | 28.181 | 1.00 | 74.30 | A |
| ATOM | 1721 | C | LEU | A | 451 | 13.222 | 50.428 | 24.228 | 1.00 | 79.36 | A |
| ATOM | 1722 | O | LEU | A | 451 | 13.333 | 51.204 | 23.284 | 1.00 | 78.33 | A |
| ATOM | 1723 | N | GLU | A | 452 | 14.195 | 49.619 | 24.634 | 1.00 | 80.74 | A |
| ATOM | 1724 | CA | GLU | A | 452 | 15.494 | 49.573 | 23.978 | 1.00 | 82.39 | A |
| ATOM | 1725 | CB | GLU | A | 452 | 16.412 | 48.587 | 24.693 | 1.00 | 84.34 | A |
| ATOM | 1726 | CG | GLU | A | 452 | 17.877 | 48.802 | 24.362 | 1.00 | 87.46 | A |
| ATOM | 1727 | CD | GLU | A | 452 | 18.752 | 47.675 | 24.845 | 1.00 | 89.80 | A |
| ATOM | 1728 | OE1 | GLU | A | 452 | 18.924 | 46.713 | 24.063 | 1.00 | 91.49 | A |
| ATOM | 1729 | OE2 | GLU | A | 452 | 19.253 | 47.747 | 25.999 | 1.00 | 90.15 | A |
| ATOM | 1730 | C | GLU | A | 452 | 15.381 | 49.156 | 22.511 | 1.00 | 81.90 | A |
| ATOM | 1731 | O | GLU | A | 452 | 16.027 | 49.742 | 21.639 | 1.00 | 81.10 | A |
| ATOM | 1732 | N | MET | A | 453 | 14.581 | 48.121 | 22.254 | 1.00 | 82.06 | A |
| ATOM | 1733 | CA | MET | A | 453 | 14.380 | 47.630 | 20.896 | 1.00 | 82.44 | A |
| ATOM | 1734 | CB | MET | A | 453 | 13.604 | 46.310 | 20.872 | 1.00 | 80.08 | A |
| ATOM | 1735 | CG | MET | A | 453 | 14.299 | 45.155 | 21.546 | 1.00 | 79.00 | A |
| ATOM | 1736 | SD | MET | A | 453 | 15.849 | 44.753 | 20.776 | 1.00 | 79.60 | A |
| ATOM | 1737 | CE | MET | A | 453 | 16.985 | 45.346 | 21.984 | 1.00 | 79.94 | A |
| ATOM | 1738 | C | MET | A | 453 | 13.573 | 48.675 | 20.168 | 1.00 | 83.26 | A |
| ATOM | 1739 | O | MET | A | 453 | 13.866 | 49.018 | 19.027 | 1.00 | 82.96 | A |
| ATOM | 1740 | N | LEU | A | 454 | 12.550 | 49.190 | 20.840 | 1.00 | 85.13 | A |
| ATOM | 1741 | CA | LEU | A | 454 | 11.690 | 50.196 | 20.229 | 1.00 | 86.91 | A |
| ATOM | 1742 | CB | LEU | A | 454 | 10.559 | 50.587 | 21.175 | 1.00 | 86.61 | A |

TABLE 1-continued

ATOMIC COORDINATES OF THE ERR3 LBD/SRC-1 NR
BOX 2 PEPTIDE COMPLEX (PDB CODE 1KV6)

| | | | | | | | | | | |
|---|---|---|---|---|---|---|---|---|---|---|
| ATOM | 1743 | CG | LEU | A | 454 | 9.370 | 51.154 | 20.413 | 1.00 | 87.12 | A |
| ATOM | 1744 | CD1 | LEU | A | 454 | 9.024 | 50.205 | 19.243 | 1.00 | 85.97 | A |
| ATOM | 1745 | CD2 | LEU | A | 454 | 8.186 | 51.325 | 21.369 | 1.00 | 86.87 | A |
| ATOM | 1746 | C | LEU | A | 454 | 12.502 | 51.425 | 19.830 | 1.00 | 88.24 | A |
| ATOM | 1747 | O | LEU | A | 454 | 12.099 | 52.163 | 18.926 | 1.00 | 88.93 | A |
| ATOM | 1748 | N | GLU | A | 455 | 13.639 | 51.634 | 20.509 | 1.00 | 89.13 | A |
| ATOM | 1749 | CA | GLU | A | 455 | 14.557 | 52.744 | 20.213 | 1.00 | 89.23 | A |
| ATOM | 1750 | CB | GLU | A | 455 | 15.429 | 53.068 | 21.423 | 1.00 | 88.07 | A |
| ATOM | 1751 | CG | GLU | A | 455 | 9999.000 | 9999.000 | 9999.000 | 1.00 | 0.00 | A |
| ATOM | 1752 | CD | GLU | A | 455 | 9999.000 | 9999.000 | 9999.000 | 1.00 | 0.00 | A |
| ATOM | 1753 | OE1 | GLU | A | 455 | 9999.000 | 9999.000 | 9999.000 | 1.00 | 0.00 | A |
| ATOM | 1754 | OE2 | GLU | A | 455 | 9999.000 | 9999.000 | 9999.000 | 1.00 | 0.00 | A |
| ATOM | 1755 | C | GLU | A | 455 | 15.427 | 52.259 | 19.053 | 1.00 | 89.37 | A |
| ATOM | 1756 | O | GLU | A | 455 | 14.972 | 52.247 | 17.912 | 1.00 | 90.21 | A |
| ATOM | 1757 | N | ALA | A | 456 | 16.657 | 51.840 | 19.349 | 1.00 | 89.45 | A |
| ATOM | 1758 | CA | ALA | A | 456 | 17.601 | 51.321 | 18.344 | 1.00 | 89.77 | A |
| ATOM | 1759 | CB | ALA | A | 456 | 17.627 | 49.771 | 18.421 | 1.00 | 88.36 | A |
| ATOM | 1760 | C | ALA | A | 456 | 17.416 | 51.785 | 16.866 | 1.00 | 90.06 | A |
| ATOM | 1761 | O | ALA | A | 456 | 18.318 | 52.502 | 16.334 | 1.00 | 89.88 | A |
| ATOM | 1762 | OXT | ALA | A | 456 | 16.383 | 51.434 | 16.238 | 1.00 | 89.69 | A |
| TER | | | | | | | | | | | |
| ATOM | 1763 | CB | ASN | B | 235 | 11.236 | 30.211 | −19.929 | 1.00 | 74.99 | B |
| ATOM | 1764 | CG | ASN | B | 235 | 9.945 | 30.626 | −19.253 | 1.00 | 76.57 | B |
| ATOM | 1765 | OD1 | ASN | B | 235 | 9.632 | 31.814 | −19.163 | 1.00 | 76.17 | B |
| ATOM | 1766 | ND2 | ASN | B | 235 | 9.169 | 29.645 | −18.799 | 1.00 | 78.63 | B |
| ATOM | 1767 | C | ASN | B | 235 | 10.235 | 31.315 | −21.989 | 1.00 | 72.20 | B |
| ATOM | 1768 | O | ASN | B | 235 | 10.664 | 32.475 | −21.984 | 1.00 | 72.19 | B |
| ATOM | 1769 | N | ASN | B | 235 | 12.477 | 30.059 | −22.118 | 1.00 | 72.77 | B |
| ATOM | 1770 | CA | ASN | B | 235 | 11.102 | 30.140 | −21.469 | 1.00 | 73.81 | B |
| ATOM | 1771 | N | LYS | B | 236 | 9.012 | 31.000 | −22.417 | 1.00 | 70.74 | B |
| ATOM | 1772 | CA | LYS | B | 236 | 8.088 | 31.990 | −22.995 | 1.00 | 69.72 | B |
| ATOM | 1773 | CB | LYS | B | 236 | 6.716 | 31.351 | −23.302 | 1.00 | 72.45 | B |
| ATOM | 1774 | CG | LYS | B | 236 | 6.761 | 29.961 | −23.918 | 1.00 | 77.34 | B |
| ATOM | 1775 | CD | LYS | B | 236 | 7.286 | 28.923 | −22.884 | 1.00 | 80.84 | B |
| ATOM | 1776 | CE | LYS | B | 236 | 7.443 | 27.507 | −23.485 | 1.00 | 83.06 | B |
| ATOM | 1777 | NZ | LYS | B | 236 | 8.101 | 26.563 | −22.521 | 1.00 | 83.68 | B |
| ATOM | 1778 | C | LYS | B | 236 | 7.845 | 33.292 | −22.211 | 1.00 | 67.47 | B |
| ATOM | 1779 | O | LYS | B | 236 | 8.012 | 34.373 | −22.762 | 1.00 | 66.25 | B |
| ATOM | 1780 | N | ILE | B | 237 | 7.439 | 33.184 | −20.944 | 1.00 | 64.70 | B |
| ATOM | 1781 | CA | ILE | B | 237 | 7.161 | 34.354 | −20.140 | 1.00 | 61.49 | B |
| ATOM | 1782 | CB | ILE | B | 237 | 6.692 | 33.971 | −18.721 | 1.00 | 59.81 | B |
| ATOM | 1783 | CG2 | ILE | B | 237 | 6.336 | 35.248 | −17.925 | 1.00 | 57.25 | B |
| ATOM | 1784 | CG1 | ILE | B | 237 | 5.537 | 32.983 | −18.802 | 1.00 | 57.95 | B |
| ATOM | 1785 | CD1 | ILE | B | 237 | 4.239 | 33.560 | −19.335 | 1.00 | 58.17 | B |
| ATOM | 1786 | C | ILE | B | 237 | 8.371 | 35.259 | −19.994 | 1.00 | 61.55 | B |
| ATOM | 1787 | O | ILE | B | 237 | 8.246 | 36.483 | −20.009 | 1.00 | 61.66 | B |
| ATOM | 1788 | N | VAL | B | 238 | 9.542 | 34.668 | −19.829 | 1.00 | 61.23 | B |
| ATOM | 1789 | CA | VAL | B | 238 | 10.723 | 35.481 | −19.646 | 1.00 | 62.53 | B |
| ATOM | 1790 | CB | VAL | B | 238 | 11.944 | 34.627 | −19.185 | 1.00 | 62.94 | B |
| ATOM | 1791 | CG1 | VAL | B | 238 | 13.182 | 35.504 | −19.086 | 1.00 | 64.02 | B |
| ATOM | 1792 | CG2 | VAL | B | 238 | 11.676 | 34.022 | −17.814 | 1.00 | 59.44 | B |
| ATOM | 1793 | C | VAL | B | 238 | 11.041 | 36.250 | −20.926 | 1.00 | 63.71 | B |
| ATOM | 1794 | O | VAL | B | 238 | 11.413 | 37.432 | −20.866 | 1.00 | 64.38 | B |
| ATOM | 1795 | N | SER | B | 239 | 10.884 | 35.587 | −22.078 | 1.00 | 63.92 | B |
| ATOM | 1796 | CA | SER | B | 239 | 11.131 | 36.225 | −23.375 | 1.00 | 62.83 | B |
| ATOM | 1797 | CB | SER | B | 239 | 10.879 | 35.259 | −24.511 | 1.00 | 61.81 | B |
| ATOM | 1798 | OG | SER | B | 239 | 11.923 | 34.327 | −24.579 | 1.00 | 63.42 | B |
| ATOM | 1799 | C | SER | B | 239 | 10.195 | 37.398 | −23.543 | 1.00 | 63.30 | B |
| ATOM | 1800 | O | SER | B | 239 | 10.630 | 38.533 | −23.750 | 1.00 | 64.11 | B |
| ATOM | 1801 | N | HIS | B | 240 | 8.902 | 37.096 | −23.467 | 1.00 | 62.78 | B |
| ATOM | 1802 | CA | HIS | B | 240 | 7.844 | 38.076 | −23.574 | 1.00 | 62.81 | B |
| ATOM | 1803 | CB | HIS | B | 240 | 6.556 | 37.407 | −23.155 | 1.00 | 62.77 | B |
| ATOM | 1804 | CG | HIS | B | 240 | 5.352 | 38.259 | −23.316 | 1.00 | 65.44 | B |
| ATOM | 1805 | CD2 | HIS | B | 240 | 5.067 | 39.501 | −22.855 | 1.00 | 66.95 | B |
| ATOM | 1806 | ND1 | HIS | B | 240 | 4.238 | 37.835 | −24.006 | 1.00 | 66.90 | B |
| ATOM | 1807 | CE1 | HIS | B | 240 | 3.316 | 38.785 | −23.962 | 1.00 | 68.62 | B |
| ATOM | 1808 | NE2 | HIS | B | 240 | 3.793 | 39.804 | −23.269 | 1.00 | 67.63 | B |
| ATOM | 1809 | C | HIS | B | 240 | 8.158 | 39.302 | −22.701 | 1.00 | 64.14 | B |
| ATOM | 1810 | O | HIS | B | 240 | 8.040 | 40.444 | −23.157 | 1.00 | 65.15 | B |
| ATOM | 1811 | N | LEU | B | 241 | 8.590 | 39.068 | −21.461 | 1.00 | 64.05 | B |
| ATOM | 1812 | CA | LEU | B | 241 | 8.934 | 40.157 | −20.550 | 1.00 | 63.04 | B |
| ATOM | 1813 | CB | LEU | B | 241 | 9.152 | 39.602 | −19.151 | 1.00 | 62.37 | B |
| ATOM | 1814 | CG | LEU | B | 241 | 7.912 | 39.193 | −18.341 | 1.00 | 62.65 | B |
| ATOM | 1815 | CD1 | LEU | B | 241 | 8.361 | 38.829 | −16.937 | 1.00 | 62.17 | B |
| ATOM | 1816 | CD2 | LEU | B | 241 | 6.893 | 40.329 | −18.271 | 1.00 | 61.03 | B |
| ATOM | 1817 | C | LEU | B | 241 | 10.143 | 41.028 | −20.965 | 1.00 | 63.72 | B |

TABLE 1-continued

ATOMIC COORDINATES OF THE ERR3 LBD/SRC-1 NR
BOX 2 PEPTIDE COMPLEX (PDB CODE 1KV6)

| ATOM | 1818 | O | LEU | B | 241 | 10.169 | 42.223 | −20.672 | 1.00 | 66.44 | B |
|---|---|---|---|---|---|---|---|---|---|---|---|
| ATOM | 1819 | N | LEU | B | 242 | 11.143 | 40.443 | −21.618 | 1.00 | 61.47 | B |
| ATOM | 1820 | CA | LEU | B | 242 | 12.324 | 41.180 | −22.096 | 1.00 | 59.68 | B |
| ATOM | 1821 | CB | LEU | B | 242 | 13.284 | 40.251 | −22.839 | 1.00 | 55.26 | B |
| ATOM | 1822 | CG | LEU | B | 242 | 14.568 | 39.723 | −22.231 | 1.00 | 53.83 | B |
| ATOM | 1823 | CD1 | LEU | B | 242 | 15.000 | 40.539 | −20.968 | 1.00 | 52.38 | B |
| ATOM | 1824 | CD2 | LEU | B | 242 | 14.350 | 38.263 | −21.972 | 1.00 | 53.80 | B |
| ATOM | 1825 | C | LEU | B | 242 | 11.863 | 42.169 | −23.137 | 1.00 | 61.00 | B |
| ATOM | 1826 | O | LEU | B | 242 | 12.183 | 43.369 | −23.126 | 1.00 | 61.85 | B |
| ATOM | 1827 | N | VAL | B | 243 | 11.146 | 41.593 | −24.083 | 1.00 | 61.33 | B |
| ATOM | 1828 | CA | VAL | B | 243 | 10.585 | 42.285 | −25.207 | 1.00 | 59.80 | B |
| ATOM | 1829 | CB | VAL | B | 243 | 9.876 | 41.258 | −26.086 | 1.00 | 57.45 | B |
| ATOM | 1830 | CG1 | VAL | B | 243 | 8.595 | 41.802 | −26.621 | 1.00 | 57.61 | B |
| ATOM | 1831 | CG2 | VAL | B | 243 | 10.802 | 40.833 | −27.157 | 1.00 | 52.99 | B |
| ATOM | 1832 | C | VAL | B | 243 | 9.635 | 43.411 | −24.819 | 1.00 | 61.03 | B |
| ATOM | 1833 | O | VAL | B | 243 | 9.527 | 44.406 | −25.556 | 1.00 | 61.89 | B |
| ATOM | 1834 | N | ALA | B | 244 | 8.969 | 43.274 | −23.668 | 1.00 | 60.78 | B |
| ATOM | 1835 | CA | ALA | B | 244 | 7.999 | 44.280 | −23.235 | 1.00 | 60.73 | B |
| ATOM | 1836 | CB | ALA | B | 244 | 6.903 | 43.627 | −22.430 | 1.00 | 58.55 | B |
| ATOM | 1837 | C | ALA | B | 244 | 8.583 | 45.446 | −22.468 | 1.00 | 63.11 | B |
| ATOM | 1838 | O | ALA | B | 244 | 7.890 | 46.427 | −22.225 | 1.00 | 62.36 | B |
| ATOM | 1839 | N | GLU | B | 245 | 9.860 | 45.359 | −22.097 | 1.00 | 68.32 | B |
| ATOM | 1840 | CA | GLU | B | 245 | 10.524 | 46.446 | −21.361 | 1.00 | 73.71 | B |
| ATOM | 1841 | CB | GLU | B | 245 | 12.011 | 46.173 | −21.184 | 1.00 | 72.74 | B |
| ATOM | 1842 | CG | GLU | B | 245 | 12.322 | 45.416 | −19.932 | 1.00 | 73.28 | B |
| ATOM | 1843 | CD | GLU | B | 245 | 11.863 | 46.146 | −18.671 | 1.00 | 75.37 | B |
| ATOM | 1844 | OE1 | GLU | B | 245 | 12.425 | 47.230 | −18.338 | 1.00 | 72.44 | B |
| ATOM | 1845 | OE2 | GLU | B | 245 | 10.934 | 45.619 | −18.004 | 1.00 | 75.66 | B |
| ATOM | 1846 | C | GLU | B | 245 | 10.363 | 47.790 | −22.038 | 1.00 | 77.99 | B |
| ATOM | 1847 | O | GLU | B | 245 | 10.680 | 47.956 | −23.216 | 1.00 | 78.24 | B |
| ATOM | 1848 | N | PRO | B | 246 | 9.853 | 48.779 | −21.304 | 1.00 | 82.69 | B |
| ATOM | 1849 | CD | PRO | B | 246 | 9.344 | 48.852 | −19.923 | 1.00 | 83.36 | B |
| ATOM | 1850 | CA | PRO | B | 246 | 9.711 | 50.059 | −21.989 | 1.00 | 86.50 | B |
| ATOM | 1851 | CB | PRO | B | 246 | 8.785 | 50.841 | −21.059 | 1.00 | 86.00 | B |
| ATOM | 1852 | CG | PRO | B | 246 | 9.230 | 50.351 | −19.701 | 1.00 | 85.10 | B |
| ATOM | 1853 | C | PRO | B | 246 | 11.073 | 50.731 | −22.207 | 1.00 | 89.79 | B |
| ATOM | 1854 | O | PRO | B | 246 | 12.022 | 50.546 | −21.432 | 1.00 | 89.34 | B |
| ATOM | 1855 | N | GLU | B | 247 | 11.141 | 51.482 | −23.304 | 1.00 | 93.78 | B |
| ATOM | 1856 | CA | GLU | B | 247 | 12.313 | 52.247 | −23.750 | 1.00 | 97.02 | B |
| ATOM | 1857 | CB | GLU | B | 247 | 11.951 | 52.965 | −25.066 | 1.00 | 98.87 | B |
| ATOM | 1858 | CG | GLU | B | 247 | 10.394 | 53.149 | −25.345 | 1.00 | 100.92 | B |
| ATOM | 1859 | CD | GLU | B | 247 | 9.545 | 53.649 | −24.134 | 1.00 | 101.68 | B |
| ATOM | 1860 | OE1 | GLU | B | 247 | 8.736 | 52.845 | −23.601 | 1.00 | 100.54 | B |
| ATOM | 1861 | OE2 | GLU | B | 247 | 9.680 | 54.836 | −23.720 | 1.00 | 102.52 | B |
| ATOM | 1862 | C | GLU | B | 247 | 12.825 | 53.280 | −22.721 | 1.00 | 97.90 | B |
| ATOM | 1863 | O | GLU | B | 247 | 12.046 | 53.825 | −21.917 | 1.00 | 98.54 | B |
| ATOM | 1864 | N | LYS | B | 248 | 14.126 | 53.562 | −22.770 | 1.00 | 98.31 | B |
| ATOM | 1865 | CA | LYS | B | 248 | 14.746 | 54.514 | −21.849 | 1.00 | 99.81 | B |
| ATOM | 1866 | CB | LYS | B | 248 | 16.212 | 54.718 | −22.250 | 1.00 | 98.79 | B |
| ATOM | 1867 | CG | LYS | B | 248 | 17.086 | 55.329 | −21.176 | 1.00 | 98.15 | B |
| ATOM | 1868 | CD | LYS | B | 248 | 18.532 | 55.502 | −21.660 | 1.00 | 98.37 | B |
| ATOM | 1869 | CE | LYS | B | 248 | 19.265 | 54.169 | −21.902 | 1.00 | 97.63 | B |
| ATOM | 1870 | NZ | LYS | B | 248 | 18.779 | 53.441 | −23.110 | 1.00 | 95.91 | B |
| ATOM | 1871 | C | LYS | B | 248 | 14.010 | 55.876 | −21.772 | 1.00 | 101.66 | B |
| ATOM | 1872 | O | LYS | B | 248 | 13.139 | 56.198 | −22.601 | 1.00 | 102.00 | B |
| ATOM | 1873 | N | ILE | B | 249 | 14.355 | 56.665 | −20.757 | 1.00 | 103.02 | B |
| ATOM | 1874 | CA | ILE | B | 249 | 13.737 | 57.971 | −20.560 | 1.00 | 104.18 | B |
| ATOM | 1875 | CB | ILE | B | 249 | 12.436 | 57.851 | −19.724 | 1.00 | 104.29 | B |
| ATOM | 1876 | CG2 | ILE | B | 249 | 11.934 | 59.223 | −19.319 | 1.00 | 104.31 | B |
| ATOM | 1877 | CG1 | ILE | B | 249 | 11.361 | 57.138 | −20.547 | 1.00 | 104.55 | B |
| ATOM | 1878 | CD1 | ILE | B | 249 | 10.110 | 56.812 | −19.759 | 1.00 | 105.29 | B |
| ATOM | 1879 | C | ILE | B | 249 | 14.716 | 58.933 | −19.887 | 1.00 | 105.08 | B |
| ATOM | 1880 | O | ILE | B | 249 | 15.536 | 58.533 | −19.047 | 1.00 | 103.30 | B |
| ATOM | 1881 | N | TYR | B | 250 | 14.623 | 60.205 | −20.278 | 1.00 | 106.83 | B |
| ATOM | 1882 | CA | TYR | B | 250 | 15.509 | 61.233 | −19.752 | 1.00 | 107.89 | B |
| ATOM | 1883 | CB | TYR | B | 250 | 16.181 | 61.951 | −20.922 | 1.00 | 107.19 | B |
| ATOM | 1884 | CG | TYR | B | 250 | 16.864 | 60.971 | −21.843 | 1.00 | 107.81 | B |
| ATOM | 1885 | CD1 | TYR | B | 250 | 16.122 | 60.230 | −22.770 | 1.00 | 107.61 | B |
| ATOM | 1886 | CE1 | TYR | B | 250 | 16.718 | 59.213 | −23.533 | 1.00 | 108.46 | B |
| ATOM | 1887 | CD2 | TYR | B | 250 | 18.232 | 60.682 | −21.703 | 1.00 | 108.22 | B |
| ATOM | 1888 | CE2 | TYR | B | 250 | 18.845 | 59.665 | −22.459 | 1.00 | 108.25 | B |
| ATOM | 1889 | CZ | TYR | B | 250 | 18.077 | 58.930 | −23.368 | 1.00 | 108.91 | B |
| ATOM | 1890 | OH | TYR | B | 250 | 18.644 | 57.889 | −24.078 | 1.00 | 108.88 | B |
| ATOM | 1891 | C | TYR | B | 250 | 14.832 | 62.222 | −18.802 | 1.00 | 108.83 | B |
| ATOM | 1892 | O | TYR | B | 250 | 13.644 | 62.537 | −18.947 | 1.00 | 107.75 | B |
| ATOM | 1893 | N | ALA | B | 251 | 15.606 | 62.677 | −17.814 | 1.00 | 110.43 | B |

TABLE 1-continued

ATOMIC COORDINATES OF THE ERR3 LBD/SRC-1 NR BOX 2 PEPTIDE COMPLEX (PDB CODE 1KV6)

| ATOM | 1894 | CA  | ALA | B | 251 | 15.142   | 63.625   | −16.804  | 1.00 | 112.59 | B |
|------|------|-----|-----|---|-----|----------|----------|----------|------|--------|---|
| ATOM | 1895 | CB  | ALA | B | 251 | 16.125   | 63.662   | −15.626  | 1.00 | 111.09 | B |
| ATOM | 1896 | C   | ALA | B | 251 | 15.013   | 65.014   | −17.415  | 1.00 | 114.53 | B |
| ATOM | 1897 | O   | ALA | B | 251 | 14.010   | 65.711   | −17.198  | 1.00 | 114.93 | B |
| ATOM | 1898 | N   | MET | B | 252 | 16.037   | 65.390   | −18.188  | 1.00 | 116.30 | B |
| ATOM | 1899 | CA  | MET | B | 252 | 16.107   | 66.686   | −18.844  | 1.00 | 117.65 | B |
| ATOM | 1900 | CB  | MET | B | 252 | 14.966   | 66.849   | −19.845  | 1.00 | 117.33 | B |
| ATOM | 1901 | CG  | MET | B | 252 | 14.898   | 65.766   | −20.895  | 1.00 | 117.43 | B |
| ATOM | 1902 | SD  | MET | B | 252 | 13.565   | 66.070   | −22.086  | 1.00 | 118.33 | B |
| ATOM | 1903 | CE  | MET | B | 252 | 12.090   | 66.403   | −20.955  | 1.00 | 116.87 | B |
| ATOM | 1904 | C   | MET | B | 252 | 16.007   | 67.763   | −17.771  | 1.00 | 119.44 | B |
| ATOM | 1905 | O   | MET | B | 252 | 15.051   | 68.563   | −17.762  | 1.00 | 119.28 | B |
| ATOM | 1906 | N   | PRO | B | 253 | 16.980   | 67.789   | −16.833  | 1.00 | 120.72 | B |
| ATOM | 1907 | CD  | PRO | B | 253 | 18.256   | 67.047   | −16.773  | 1.00 | 120.12 | B |
| ATOM | 1908 | CA  | PRO | B | 253 | 16.911   | 68.817   | −15.789  | 1.00 | 122.32 | B |
| ATOM | 1909 | CB  | PRO | B | 253 | 18.230   | 68.627   | −15.024  | 1.00 | 121.19 | B |
| ATOM | 1910 | CG  | PRO | B | 253 | 19.152   | 68.007   | −16.042  | 1.00 | 120.20 | B |
| ATOM | 1911 | C   | PRO | B | 253 | 16.796   | 70.181   | −16.479  | 1.00 | 124.51 | B |
| ATOM | 1912 | O   | PRO | B | 253 | 17.075   | 70.288   | −17.675  | 1.00 | 124.86 | B |
| ATOM | 1913 | N   | ASP | B | 254 | 16.373   | 71.217   | −15.761  | 1.00 | 126.66 | B |
| ATOM | 1914 | CA  | ASP | B | 254 | 16.257   | 72.530   | −16.402  | 1.00 | 128.71 | B |
| ATOM | 1915 | CB  | ASP | B | 254 | 14.965   | 73.229   | −15.958  | 1.00 | 128.63 | B |
| ATOM | 1916 | CG  | ASP | B | 254 | 14.327   | 74.024   | −17.085  | 1.00 | 128.57 | B |
| ATOM | 1917 | OD1 | ASP | B | 254 | 14.994   | 74.938   | −17.617  | 1.00 | 128.71 | B |
| ATOM | 1918 | OD2 | ASP | B | 254 | 13.165   | 73.726   | −17.447  | 1.00 | 127.98 | B |
| ATOM | 1919 | C   | ASP | B | 254 | 17.477   | 73.444   | −16.145  | 1.00 | 129.66 | B |
| ATOM | 1920 | O   | ASP | B | 254 | 17.892   | 73.638   | −14.993  | 1.00 | 129.97 | B |
| ATOM | 1921 | N   | PRO | B | 255 | 18.071   | 74.008   | −17.224  | 1.00 | 130.05 | B |
| ATOM | 1922 | CD  | PRO | B | 255 | 17.716   | 73.752   | −18.637  | 1.00 | 129.57 | B |
| ATOM | 1923 | CA  | PRO | B | 255 | 19.241   | 74.897   | −17.131  | 1.00 | 130.43 | B |
| ATOM | 1924 | CB  | PRO | B | 255 | 19.788   | 74.876   | −18.556  | 1.00 | 130.02 | B |
| ATOM | 1925 | CG  | PRO | B | 255 | 18.535   | 74.786   | −19.379  | 1.00 | 129.76 | B |
| ATOM | 1926 | C   | PRO | B | 255 | 18.909   | 76.321   | −16.634  | 1.00 | 130.99 | B |
| ATOM | 1927 | O   | PRO | B | 255 | 19.805   | 77.125   | −16.348  | 1.00 | 130.58 | B |
| ATOM | 1928 | N   | THR | B | 256 | 17.611   | 76.606   | −16.523  | 1.00 | 131.41 | B |
| ATOM | 1929 | CA  | THR | B | 256 | 17.101   | 77.901   | −16.062  | 1.00 | 131.42 | B |
| ATOM | 1930 | CB  | THR | B | 256 | 15.638   | 78.120   | −16.582  | 1.00 | 131.29 | B |
| ATOM | 1931 | OG1 | THR | B | 256 | 15.645   | 78.178   | −18.016  | 1.00 | 130.39 | B |
| ATOM | 1932 | CG2 | THR | B | 256 | 15.033   | 79.411   | −16.029  | 1.00 | 130.73 | B |
| ATOM | 1933 | C   | THR | B | 256 | 17.136   | 78.042   | −14.521  | 1.00 | 131.66 | B |
| ATOM | 1934 | O   | THR | B | 256 | 16.977   | 79.148   | −13.988  | 1.00 | 132.03 | B |
| ATOM | 1935 | N   | VAL | B | 257 | 17.347   | 76.925   | −13.817  | 1.00 | 131.44 | B |
| ATOM | 1936 | CA  | VAL | B | 257 | 17.423   | 76.912   | −12.346  | 1.00 | 130.70 | B |
| ATOM | 1937 | CB  | VAL | B | 257 | 16.387   | 75.926   | −11.738  | 1.00 | 130.18 | B |
| ATOM | 1938 | CG1 | VAL | B | 257 | 16.246   | 76.169   | −10.230  | 1.00 | 129.03 | B |
| ATOM | 1939 | CG2 | VAL | B | 257 | 15.048   | 76.058   | −12.463  | 1.00 | 129.33 | B |
| ATOM | 1940 | C   | VAL | B | 257 | 18.828   | 76.458   | −11.907  | 1.00 | 130.68 | B |
| ATOM | 1941 | O   | VAL | B | 257 | 19.472   | 75.673   | −12.608  | 1.00 | 130.71 | B |
| ATOM | 1942 | N   | PRO | B | 258 | 19.331   | 76.964   | −10.759  | 1.00 | 130.65 | B |
| ATOM | 1943 | CD  | PRO | B | 258 | 18.788   | 78.110   | −10.001  | 1.00 | 130.40 | B |
| ATOM | 1944 | CA  | PRO | B | 258 | 20.668   | 76.584   | −10.254  | 1.00 | 130.32 | B |
| ATOM | 1945 | CB  | PRO | B | 258 | 21.084   | 77.800   | −9.438   | 1.00 | 130.28 | B |
| ATOM | 1946 | CG  | PRO | B | 258 | 19.765   | 78.231   | −8.833   | 1.00 | 130.97 | B |
| ATOM | 1947 | C   | PRO | B | 258 | 20.593   | 75.317   | −9.389   | 1.00 | 129.78 | B |
| ATOM | 1948 | O   | PRO | B | 258 | 19.503   | 74.942   | −8.948   | 1.00 | 130.05 | B |
| ATOM | 1949 | N   | ASP | B | 259 | 21.737   | 74.673   | −9.142   | 1.00 | 128.71 | B |
| ATOM | 1950 | CA  | ASP | B | 259 | 21.786   | 73.446   | −8.331   | 1.00 | 127.84 | B |
| ATOM | 1951 | CB  | ASP | B | 259 | 23.246   | 72.999   | −8.135   | 1.00 | 127.15 | B |
| ATOM | 1952 | CG  | ASP | B | 259 | 9999.000 | 9999.000 | 9999.000 | 1.00 | 0.00   | B |
| ATOM | 1953 | OD1 | ASP | B | 259 | 9999.000 | 9999.000 | 9999.000 | 1.00 | 0.00   | B |
| ATOM | 1954 | OD2 | ASP | B | 259 | 9999.000 | 9999.000 | 9999.000 | 1.00 | 0.00   | B |
| ATOM | 1955 | C   | ASP | B | 259 | 21.092   | 73.593   | −6.961   | 1.00 | 127.16 | B |
| ATOM | 1956 | O   | ASP | B | 259 | 21.757   | 73.719   | −5.919   | 1.00 | 126.96 | B |
| ATOM | 1957 | N   | SER | B | 260 | 19.753   | 73.560   | −6.983   | 1.00 | 126.06 | B |
| ATOM | 1958 | CA  | SER | B | 260 | 18.908   | 73.691   | −5.785   | 1.00 | 124.10 | B |
| ATOM | 1959 | CB  | SER | B | 260 | 17.938   | 74.877   | −5.956   | 1.00 | 123.75 | B |
| ATOM | 1960 | OG  | SER | B | 260 | 9999.000 | 9999.000 | 9999.000 | 1.00 | 0.00   | B |
| ATOM | 1961 | C   | SER | B | 260 | 18.121   | 72.401   | −5.486   | 1.00 | 122.56 | B |
| ATOM | 1962 | O   | SER | B | 260 | 17.738   | 71.659   | −6.398   | 1.00 | 121.84 | B |
| ATOM | 1963 | N   | ASP | B | 261 | 17.885   | 72.147   | −4.201   | 1.00 | 120.83 | B |
| ATOM | 1964 | CA  | ASP | B | 261 | 17.169   | 70.952   | −3.776   | 1.00 | 119.48 | B |
| ATOM | 1965 | CB  | ASP | B | 261 | 17.155   | 70.843   | −2.242   | 1.00 | 120.20 | B |
| ATOM | 1966 | CG  | ASP | B | 261 | 16.331   | 71.939   | −1.568   | 1.00 | 121.00 | B |
| ATOM | 1967 | OD1 | ASP | B | 261 | 16.243   | 71.924   | −0.317   | 1.00 | 120.95 | B |
| ATOM | 1968 | OD2 | ASP | B | 261 | 15.773   | 72.813   | −2.271   | 1.00 | 121.19 | B |
| ATOM | 1969 | C   | ASP | B | 261 | 15.749   | 70.886   | −4.314   | 1.00 | 118.04 | B |

TABLE 1-continued

ATOMIC COORDINATES OF THE ERR3 LBD/SRC-1 NR
BOX 2 PEPTIDE COMPLEX (PDB CODE 1KV6)

| ATOM | 1970 | O   | ASP | B | 261 | 15.305 | 69.838 | −4.778  | 1.00 | 118.46 | B |
|------|------|-----|-----|---|-----|--------|--------|---------|------|--------|---|
| ATOM | 1971 | N   | ILE | B | 262 | 15.038 | 72.002 | −4.253  | 1.00 | 116.48 | B |
| ATOM | 1972 | CA  | ILE | B | 262 | 13.665 | 72.060 | −4.738  | 1.00 | 115.24 | B |
| ATOM | 1973 | CB  | ILE | B | 262 | 13.002 | 73.405 | −4.297  | 1.00 | 114.64 | B |
| ATOM | 1974 | CG2 | ILE | B | 262 | 14.015 | 74.534 | −4.383  | 1.00 | 115.09 | B |
| ATOM | 1975 | CG1 | ILE | B | 262 | 11.744 | 73.686 | −5.120  | 1.00 | 114.11 | B |
| ATOM | 1976 | CD1 | ILE | B | 262 | 10.656 | 72.685 | −4.927  | 1.00 | 113.42 | B |
| ATOM | 1977 | C   | ILE | B | 262 | 13.675 | 71.882 | −6.264  | 1.00 | 114.27 | B |
| ATOM | 1978 | O   | ILE | B | 262 | 12.682 | 71.470 | −6.876  | 1.00 | 113.48 | B |
| ATOM | 1979 | N   | LYS | B | 263 | 14.823 | 72.179 | −6.867  | 1.00 | 113.43 | B |
| ATOM | 1980 | CA  | LYS | B | 263 | 14.984 | 72.020 | −8.306  | 1.00 | 112.71 | B |
| ATOM | 1981 | CB  | LYS | B | 263 | 16.303 | 72.657 | −8.778  | 1.00 | 111.57 | B |
| ATOM | 1982 | CG  | LYS | B | 263 | 16.388 | 72.825 | −10.289 | 1.00 | 110.10 | B |
| ATOM | 1983 | CD  | LYS | B | 263 | 17.796 | 72.591 | −10.835 | 1.00 | 109.72 | B |
| ATOM | 1984 | CE  | LYS | B | 263 | 17.780 | 72.495 | −12.364 | 1.00 | 108.42 | B |
| ATOM | 1985 | NZ  | LYS | B | 263 | 19.091 | 72.084 | −12.942 | 1.00 | 107.69 | B |
| ATOM | 1986 | C   | LYS | B | 263 | 15.013 | 70.503 | −8.529  | 1.00 | 112.31 | B |
| ATOM | 1987 | O   | LYS | B | 263 | 14.158 | 69.949 | −9.225  | 1.00 | 111.36 | B |
| ATOM | 1988 | N   | ALA | B | 264 | 15.997 | 69.851 | −7.899  | 1.00 | 111.98 | B |
| ATOM | 1989 | CA  | ALA | B | 264 | 16.183 | 68.400 | −7.966  | 1.00 | 111.37 | B |
| ATOM | 1990 | CB  | ALA | B | 264 | 17.238 | 67.956 | −6.945  | 1.00 | 110.14 | B |
| ATOM | 1991 | C   | ALA | B | 264 | 14.870 | 67.658 | −7.709  | 1.00 | 110.90 | B |
| ATOM | 1992 | O   | ALA | B | 264 | 14.334 | 67.012 | −8.606  | 1.00 | 111.09 | B |
| ATOM | 1993 | N   | LEU | B | 265 | 14.354 | 67.760 | −6.487  | 1.00 | 110.09 | B |
| ATOM | 1994 | CA  | LEU | B | 265 | 13.106 | 67.091 | −6.127  | 1.00 | 109.91 | B |
| ATOM | 1995 | CB  | LEU | B | 265 | 12.615 | 67.565 | −4.753  | 1.00 | 110.18 | B |
| ATOM | 1996 | CG  | LEU | B | 265 | 13.082 | 66.811 | −3.502  | 1.00 | 110.23 | B |
| ATOM | 1997 | CD1 | LEU | B | 265 | 14.605 | 66.858 | −3.361  | 1.00 | 110.12 | B |
| ATOM | 1998 | CD2 | LEU | B | 265 | 12.404 | 67.441 | −2.283  | 1.00 | 110.54 | B |
| ATOM | 1999 | C   | LEU | B | 265 | 11.961 | 67.230 | −7.139  | 1.00 | 109.44 | B |
| ATOM | 2000 | O   | LEU | B | 265 | 11.062 | 66.374 | −7.177  | 1.00 | 109.62 | B |
| ATOM | 2001 | N   | THR | B | 266 | 11.983 | 68.291 | −7.950  | 1.00 | 108.12 | B |
| ATOM | 2002 | CA  | THR | B | 266 | 10.925 | 68.499 | −8.945  | 1.00 | 106.33 | B |
| ATOM | 2003 | CB  | THR | B | 266 | 10.718 | 70.004 | −9.278  | 1.00 | 107.29 | B |
| ATOM | 2004 | OG1 | THR | B | 266 | 10.511 | 70.752 | −8.069  | 1.00 | 108.08 | B |
| ATOM | 2005 | CG2 | THR | B | 266 | 9.491  | 70.175 | −10.184 | 1.00 | 107.24 | B |
| ATOM | 2006 | C   | THR | B | 266 | 11.264 | 67.765 | −10.235 | 1.00 | 104.17 | B |
| ATOM | 2007 | O   | THR | B | 266 | 10.384 | 67.437 | −11.035 | 1.00 | 102.84 | B |
| ATOM | 2008 | N   | THR | B | 267 | 12.555 | 67.524 | −10.430 | 1.00 | 102.85 | B |
| ATOM | 2009 | CA  | THR | B | 267 | 13.028 | 66.818 | −11.615 | 1.00 | 102.22 | B |
| ATOM | 2010 | CB  | THR | B | 267 | 14.579 | 66.807 | −11.717 | 1.00 | 103.00 | B |
| ATOM | 2011 | OG1 | THR | B | 267 | 15.135 | 67.880 | −10.944 | 1.00 | 103.94 | B |
| ATOM | 2012 | CG2 | THR | B | 267 | 15.013 | 66.960 | −13.171 | 1.00 | 102.53 | B |
| ATOM | 2013 | C   | THR | B | 267 | 12.581 | 65.382 | −11.443 | 1.00 | 100.86 | B |
| ATOM | 2014 | O   | THR | B | 267 | 12.033 | 64.760 | −12.346 | 1.00 | 100.69 | B |
| ATOM | 2015 | N   | LEU | B | 268 | 12.831 | 64.868 | −10.248 | 1.00 | 99.56  | B |
| ATOM | 2016 | CA  | LEU | B | 268 | 12.481 | 63.512 | −9.909  | 1.00 | 97.34  | B |
| ATOM | 2017 | CB  | LEU | B | 268 | 13.113 | 63.160 | −8.560  | 1.00 | 94.39  | B |
| ATOM | 2018 | CG  | LEU | B | 268 | 14.614 | 62.793 | −8.657  | 1.00 | 93.05  | B |
| ATOM | 2019 | CD1 | LEU | B | 268 | 15.321 | 63.638 | −9.695  | 1.00 | 91.79  | B |
| ATOM | 2020 | CD2 | LEU | B | 268 | 15.291 | 62.959 | −7.304  | 1.00 | 92.06  | B |
| ATOM | 2021 | C   | LEU | B | 268 | 10.970 | 63.329 | −9.922  | 1.00 | 97.35  | B |
| ATOM | 2022 | O   | LEU | B | 268 | 10.478 | 62.384 | −10.524 | 1.00 | 97.84  | B |
| ATOM | 2023 | N   | CYS | B | 269 | 10.224 | 64.237 | −9.303  | 1.00 | 97.19  | B |
| ATOM | 2024 | CA  | CYS | B | 269 | 8.769  | 64.104 | −9.296  | 1.00 | 98.58  | B |
| ATOM | 2025 | CB  | CYS | B | 269 | 8.141  | 65.111 | −8.330  | 1.00 | 99.04  | B |
| ATOM | 2026 | SG  | CYS | B | 269 | 8.474  | 64.787 | −6.567  | 1.00 | 100.96 | B |
| ATOM | 2027 | C   | CYS | B | 269 | 8.192  | 64.295 | −10.697 | 1.00 | 99.53  | B |
| ATOM | 2028 | O   | CYS | B | 269 | 7.007  | 64.026 | −10.954 | 1.00 | 99.62  | B |
| ATOM | 2029 | N   | ASP | B | 270 | 9.044  | 64.775 | −11.598 | 1.00 | 100.62 | B |
| ATOM | 2030 | CA  | ASP | B | 270 | 8.673  | 64.995 | −13.000 | 1.00 | 101.05 | B |
| ATOM | 2031 | CB  | ASP | B | 270 | 9.470  | 66.200 | −13.568 | 1.00 | 104.20 | B |
| ATOM | 2032 | CG  | ASP | B | 270 | 9.652  | 66.153 | −15.106 | 1.00 | 106.48 | B |
| ATOM | 2033 | OD1 | ASP | B | 270 | 8.644  | 65.943 | −15.845 | 1.00 | 107.89 | B |
| ATOM | 2034 | OD2 | ASP | B | 270 | 10.819 | 66.340 | −15.564 | 1.00 | 106.68 | B |
| ATOM | 2035 | C   | ASP | B | 270 | 8.976  | 63.704 | −13.780 | 1.00 | 99.40  | B |
| ATOM | 2036 | O   | ASP | B | 270 | 8.103  | 63.167 | −14.494 | 1.00 | 98.56  | B |
| ATOM | 2037 | N   | LEU | B | 271 | 10.219 | 63.226 | −13.615 | 1.00 | 97.10  | B |
| ATOM | 2038 | CA  | LEU | B | 271 | 10.725 | 62.002 | −14.242 | 1.00 | 94.11  | B |
| ATOM | 2039 | CB  | LEU | B | 271 | 12.133 | 61.696 | −13.725 | 1.00 | 91.69  | B |
| ATOM | 2040 | CG  | LEU | B | 271 | 13.048 | 60.876 | −14.635 | 1.00 | 90.34  | B |
| ATOM | 2041 | CD1 | LEU | B | 271 | 14.270 | 60.447 | −13.853 | 1.00 | 89.99  | B |
| ATOM | 2042 | CD2 | LEU | B | 271 | 12.325 | 59.658 | −15.175 | 1.00 | 90.88  | B |
| ATOM | 2043 | C   | LEU | B | 271 | 9.782  | 60.874 | −13.840 | 1.00 | 93.33  | B |
| ATOM | 2044 | O   | LEU | B | 271 | 9.306  | 60.092 | −14.675 | 1.00 | 92.95  | B |
| ATOM | 2045 | N   | ALA | B | 272 | 9.512  | 60.821 | −12.542 | 1.00 | 91.95  | B |

TABLE 1-continued

ATOMIC COORDINATES OF THE ERR3 LBD/SRC-1 NR
BOX 2 PEPTIDE COMPLEX (PDB CODE 1KV6)

| ATOM | 2046 | CA | ALA | B | 272 | 8.629 | 59.829 | −11.978 | 1.00 | 91.22 | B |
|------|------|------|------|---|-----|--------|--------|---------|------|--------|---|
| ATOM | 2047 | CB | ALA | B | 272 | 8.518 | 60.043 | −10.487 | 1.00 | 91.14 | B |
| ATOM | 2048 | C | ALA | B | 272 | 7.242 | 59.854 | −12.612 | 1.00 | 90.98 | B |
| ATOM | 2049 | O | ALA | B | 272 | 6.678 | 58.800 | −12.895 | 1.00 | 90.62 | B |
| ATOM | 2050 | N | ASP | B | 273 | 6.685 | 61.040 | −12.838 | 1.00 | 90.51 | B |
| ATOM | 2051 | CA | ASP | B | 273 | 5.353 | 61.094 | −13.419 | 1.00 | 90.97 | B |
| ATOM | 2052 | CB | ASP | B | 273 | 4.791 | 62.523 | −13.404 | 1.00 | 92.15 | B |
| ATOM | 2053 | CG | ASP | B | 273 | 3.274 | 62.559 | −13.701 | 1.00 | 93.69 | B |
| ATOM | 2054 | OD1 | ASP | B | 273 | 2.488 | 62.219 | −12.786 | 1.00 | 93.84 | B |
| ATOM | 2055 | OD2 | ASP | B | 273 | 2.863 | 62.905 | −14.844 | 1.00 | 94.00 | B |
| ATOM | 2056 | C | ASP | B | 273 | 5.328 | 60.565 | −14.851 | 1.00 | 90.79 | B |
| ATOM | 2057 | O | ASP | B | 273 | 4.409 | 59.830 | −15.251 | 1.00 | 90.12 | B |
| ATOM | 2058 | N | ARG | B | 274 | 6.326 | 60.953 | −15.637 | 1.00 | 90.71 | B |
| ATOM | 2059 | CA | ARG | B | 274 | 6.369 | 60.504 | −17.024 | 1.00 | 91.07 | B |
| ATOM | 2060 | CB | ARG | B | 274 | 7.414 | 61.303 | −17.823 | 1.00 | 90.22 | B |
| ATOM | 2061 | CG | ARG | B | 274 | 6.951 | 62.749 | −18.128 | 1.00 | 88.07 | B |
| ATOM | 2062 | CD | ARG | B | 274 | 7.988 | 63.598 | −18.865 | 1.00 | 84.23 | B |
| ATOM | 2063 | NE | ARG | B | 274 | 9.202 | 63.809 | −18.080 | 1.00 | 81.43 | B |
| ATOM | 2064 | CZ | ARG | B | 274 | 10.390 | 63.288 | −18.381 | 1.00 | 80.29 | B |
| ATOM | 2065 | NH1 | ARG | B | 274 | 10.528 | 62.515 | −19.460 | 1.00 | 78.91 | B |
| ATOM | 2066 | NH2 | ARG | B | 274 | 11.442 | 63.542 | −17.603 | 1.00 | 79.05 | B |
| ATOM | 2067 | C | ARG | B | 274 | 6.668 | 59.020 | −17.012 | 1.00 | 91.26 | B |
| ATOM | 2068 | O | ARG | B | 274 | 6.184 | 58.261 | −17.853 | 1.00 | 91.44 | B |
| ATOM | 2069 | N | GLU | B | 275 | 7.443 | 58.616 | −16.015 | 1.00 | 91.63 | B |
| ATOM | 2070 | CA | GLU | B | 275 | 7.793 | 57.224 | −15.839 | 1.00 | 91.91 | B |
| ATOM | 2071 | CB | GLU | B | 275 | 8.782 | 57.085 | −14.680 | 1.00 | 94.64 | B |
| ATOM | 2072 | CG | GLU | B | 275 | 10.085 | 56.352 | −15.017 | 1.00 | 98.85 | B |
| ATOM | 2073 | CD | GLU | B | 275 | 9.855 | 54.903 | −15.483 | 1.00 | 102.59 | B |
| ATOM | 2074 | OE1 | GLU | B | 275 | 10.796 | 54.057 | −15.349 | 1.00 | 104.82 | B |
| ATOM | 2075 | OE2 | GLU | B | 275 | 8.736 | 54.618 | −15.992 | 1.00 | 103.22 | B |
| ATOM | 2076 | C | GLU | B | 275 | 6.520 | 56.409 | −15.554 | 1.00 | 90.29 | B |
| ATOM | 2077 | O | GLU | B | 275 | 6.303 | 55.369 | −16.172 | 1.00 | 90.86 | B |
| ATOM | 2078 | N | LEU | B | 276 | 5.668 | 56.891 | −14.648 | 1.00 | 88.35 | B |
| ATOM | 2079 | CA | LEU | B | 276 | 4.438 | 56.177 | −14.288 | 1.00 | 86.89 | B |
| ATOM | 2080 | CB | LEU | B | 276 | 3.665 | 56.944 | −13.197 | 1.00 | 86.79 | B |
| ATOM | 2081 | CG | LEU | B | 276 | 4.356 | 57.147 | −11.829 | 1.00 | 87.35 | B |
| ATOM | 2082 | CD1 | LEU | B | 276 | 3.400 | 57.843 | −10.865 | 1.00 | 87.24 | B |
| ATOM | 2083 | CD2 | LEU | B | 276 | 4.799 | 55.816 | −11.229 | 1.00 | 86.30 | B |
| ATOM | 2084 | C | LEU | B | 276 | 3.491 | 55.826 | −15.451 | 1.00 | 85.90 | B |
| ATOM | 2085 | O | LEU | B | 276 | 2.823 | 54.779 | −15.420 | 1.00 | 85.96 | B |
| ATOM | 2086 | N | VAL | B | 277 | 3.436 | 56.682 | −16.474 | 1.00 | 84.02 | B |
| ATOM | 2087 | CA | VAL | B | 277 | 2.574 | 56.437 | −17.645 | 1.00 | 81.40 | B |
| ATOM | 2088 | CB | VAL | B | 277 | 2.425 | 57.711 | −18.512 | 1.00 | 81.57 | B |
| ATOM | 2089 | CG1 | VAL | B | 277 | 1.371 | 57.489 | −19.614 | 1.00 | 78.67 | B |
| ATOM | 2090 | CG2 | VAL | B | 277 | 2.055 | 58.886 | −17.618 | 1.00 | 81.66 | B |
| ATOM | 2091 | C | VAL | B | 277 | 3.191 | 55.330 | −18.499 | 1.00 | 79.30 | B |
| ATOM | 2092 | O | VAL | B | 277 | 2.500 | 54.497 | −19.097 | 1.00 | 77.66 | B |
| ATOM | 2093 | N | VAL | B | 278 | 4.513 | 55.356 | −18.551 | 1.00 | 77.65 | B |
| ATOM | 2094 | CA | VAL | B | 278 | 5.279 | 54.352 | −19.269 | 1.00 | 76.89 | B |
| ATOM | 2095 | CB | VAL | B | 278 | 6.810 | 54.680 | −19.186 | 1.00 | 77.26 | B |
| ATOM | 2096 | CG1 | VAL | B | 278 | 7.638 | 53.394 | −19.131 | 1.00 | 78.12 | B |
| ATOM | 2097 | CG2 | VAL | B | 278 | 7.220 | 55.540 | −20.386 | 1.00 | 77.00 | B |
| ATOM | 2098 | C | VAL | B | 278 | 4.987 | 53.005 | −18.591 | 1.00 | 75.52 | B |
| ATOM | 2099 | O | VAL | B | 278 | 4.722 | 52.000 | −19.264 | 1.00 | 72.74 | B |
| ATOM | 2100 | N | ILE | B | 279 | 5.022 | 53.021 | −17.250 | 1.00 | 74.86 | B |
| ATOM | 2101 | CA | ILE | B | 279 | 4.790 | 51.840 | −16.433 | 1.00 | 73.89 | B |
| ATOM | 2102 | CB | ILE | B | 279 | 5.097 | 52.132 | −14.969 | 1.00 | 72.41 | B |
| ATOM | 2103 | CG2 | ILE | B | 279 | 4.385 | 51.120 | −14.084 | 1.00 | 73.15 | B |
| ATOM | 2104 | CG1 | ILE | B | 279 | 6.615 | 52.101 | −14.749 | 1.00 | 71.02 | B |
| ATOM | 2105 | CD1 | ILE | B | 279 | 7.042 | 52.225 | −13.272 | 1.00 | 69.27 | B |
| ATOM | 2106 | C | ILE | B | 279 | 3.391 | 51.235 | −16.560 | 1.00 | 75.07 | B |
| ATOM | 2107 | O | ILE | B | 279 | 3.243 | 50.002 | −16.598 | 1.00 | 73.94 | B |
| ATOM | 2108 | N | ILE | B | 280 | 2.373 | 52.093 | −16.629 | 1.00 | 75.47 | B |
| ATOM | 2109 | CA | ILE | B | 280 | 0.997 | 51.632 | −16.779 | 1.00 | 75.41 | B |
| ATOM | 2110 | CB | ILE | B | 280 | 0.039 | 52.798 | −16.652 | 1.00 | 74.31 | B |
| ATOM | 2111 | CG2 | ILE | B | 280 | −1.385 | 52.324 | −16.786 | 1.00 | 72.99 | B |
| ATOM | 2112 | CG1 | ILE | B | 280 | 0.268 | 53.480 | −15.312 | 1.00 | 74.39 | B |
| ATOM | 2113 | CD1 | ILE | B | 280 | −0.674 | 54.639 | −15.035 | 1.00 | 75.32 | B |
| ATOM | 2114 | C | ILE | B | 280 | 0.807 | 50.967 | −18.151 | 1.00 | 77.24 | B |
| ATOM | 2115 | O | ILE | B | 280 | −0.080 | 50.121 | −18.333 | 1.00 | 77.66 | B |
| ATOM | 2116 | N | GLY | B | 281 | 1.636 | 51.366 | −19.119 | 1.00 | 77.84 | B |
| ATOM | 2117 | CA | GLY | B | 281 | 1.560 | 50.779 | −20.444 | 1.00 | 77.33 | B |
| ATOM | 2118 | C | GLY | B | 281 | 2.217 | 49.417 | −20.375 | 1.00 | 77.96 | B |
| ATOM | 2119 | O | GLY | B | 281 | 1.671 | 48.418 | −20.870 | 1.00 | 78.80 | B |
| ATOM | 2120 | N | TRP | B | 282 | 3.395 | 49.385 | −19.755 | 1.00 | 77.51 | B |
| ATOM | 2121 | CA | TRP | B | 282 | 4.136 | 48.148 | −19.551 | 1.00 | 77.65 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2122 | CB | TRP | B | 282 | 5.319 | 48.402 | −18.624 | 1.00 | 79.04 | B |
|------|------|------|------|---|-----|--------|--------|---------|------|-------|---|
| ATOM | 2123 | CG | TRP | B | 282 | 6.012 | 47.146 | −18.218 | 1.00 | 82.64 | B |
| ATOM | 2124 | CD2 | TRP | B | 282 | 6.020 | 46.554 | −16.916 | 1.00 | 83.75 | B |
| ATOM | 2125 | CE2 | TRP | B | 282 | 6.787 | 45.363 | −17.000 | 1.00 | 84.34 | B |
| ATOM | 2126 | CE3 | TRP | B | 282 | 5.451 | 46.909 | −15.683 | 1.00 | 84.74 | B |
| ATOM | 2127 | CD1 | TRP | B | 282 | 6.752 | 46.313 | −19.020 | 1.00 | 83.65 | B |
| ATOM | 2128 | NE1 | TRP | B | 282 | 7.220 | 45.241 | −18.296 | 1.00 | 84.09 | B |
| ATOM | 2129 | CZ2 | TRP | B | 282 | 7.003 | 44.527 | −15.897 | 1.00 | 84.43 | B |
| ATOM | 2130 | CZ3 | TRP | B | 282 | 5.664 | 46.078 | −14.584 | 1.00 | 84.53 | B |
| ATOM | 2131 | CH2 | TRP | B | 282 | 6.435 | 44.901 | −14.700 | 1.00 | 85.08 | B |
| ATOM | 2132 | C | TRP | B | 282 | 3.224 | 47.086 | −18.912 | 1.00 | 77.11 | B |
| ATOM | 2133 | O | TRP | B | 282 | 2.984 | 46.019 | −19.476 | 1.00 | 76.74 | B |
| ATOM | 2134 | N | ALA | B | 283 | 2.709 | 47.397 | −17.727 | 1.00 | 76.51 | B |
| ATOM | 2135 | CA | ALA | B | 283 | 1.830 | 46.484 | −16.998 | 1.00 | 75.62 | B |
| ATOM | 2136 | CB | ALA | B | 283 | 1.081 | 47.241 | −15.902 | 1.00 | 76.17 | B |
| ATOM | 2137 | C | ALA | B | 283 | 0.831 | 45.726 | −17.854 | 1.00 | 74.91 | B |
| ATOM | 2138 | O | ALA | B | 283 | 0.600 | 44.548 | −17.628 | 1.00 | 73.89 | B |
| ATOM | 2139 | N | LYS | B | 284 | 0.240 | 46.393 | −18.836 | 1.00 | 75.23 | B |
| ATOM | 2140 | CA | LYS | B | 284 | −0.752 | 45.730 | −19.667 | 1.00 | 75.74 | B |
| ATOM | 2141 | CB | LYS | B | 284 | −1.439 | 46.746 | −20.575 | 1.00 | 74.92 | B |
| ATOM | 2142 | CG | LYS | B | 284 | −2.120 | 47.857 | −19.751 | 1.00 | 78.13 | B |
| ATOM | 2143 | CD | LYS | B | 284 | −3.320 | 48.524 | −20.458 | 1.00 | 80.38 | B |
| ATOM | 2144 | CE | LYS | B | 284 | −4.432 | 47.505 | −20.882 | 1.00 | 82.86 | B |
| ATOM | 2145 | NZ | LYS | B | 284 | −5.043 | 46.670 | −19.770 | 1.00 | 81.68 | B |
| ATOM | 2146 | C | LYS | B | 284 | −0.177 | 44.569 | −20.460 | 1.00 | 75.72 | B |
| ATOM | 2147 | O | LYS | B | 284 | −0.903 | 43.633 | −20.804 | 1.00 | 75.22 | B |
| ATOM | 2148 | N | HIS | B | 285 | 1.137 | 44.603 | −20.698 | 1.00 | 76.03 | B |
| ATOM | 2149 | CA | HIS | B | 285 | 1.820 | 43.552 | −21.475 | 1.00 | 75.93 | B |
| ATOM | 2150 | CB | HIS | B | 285 | 2.946 | 44.143 | −22.352 | 1.00 | 78.41 | B |
| ATOM | 2151 | CG | HIS | B | 285 | 2.451 | 44.982 | −23.494 | 1.00 | 79.85 | B |
| ATOM | 2152 | CD2 | HIS | B | 285 | 2.415 | 46.328 | −23.663 | 1.00 | 80.52 | B |
| ATOM | 2153 | ND1 | HIS | B | 285 | 1.857 | 44.441 | −24.617 | 1.00 | 81.01 | B |
| ATOM | 2154 | CE1 | HIS | B | 285 | 1.476 | 45.417 | −25.425 | 1.00 | 81.27 | B |
| ATOM | 2155 | NE2 | HIS | B | 285 | 1.803 | 46.572 | −24.871 | 1.00 | 80.96 | B |
| ATOM | 2156 | C | HIS | B | 285 | 2.379 | 42.395 | −20.664 | 1.00 | 74.05 | B |
| ATOM | 2157 | O | HIS | B | 285 | 2.976 | 41.498 | −21.229 | 1.00 | 73.02 | B |
| ATOM | 2158 | N | ILE | B | 286 | 2.199 | 42.425 | −19.349 | 1.00 | 73.66 | B |
| ATOM | 2159 | CA | ILE | B | 286 | 2.640 | 41.331 | −18.489 | 1.00 | 73.37 | B |
| ATOM | 2160 | CB | ILE | B | 286 | 2.584 | 41.710 | −16.992 | 1.00 | 73.91 | B |
| ATOM | 2161 | CG2 | ILE | B | 286 | 2.858 | 40.484 | −16.130 | 1.00 | 72.23 | B |
| ATOM | 2162 | CG1 | ILE | B | 286 | 3.599 | 42.815 | −16.684 | 1.00 | 74.70 | B |
| ATOM | 2163 | CD1 | ILE | B | 286 | 3.383 | 43.471 | −15.308 | 1.00 | 74.60 | B |
| ATOM | 2164 | C | ILE | B | 286 | 1.640 | 40.200 | −18.721 | 1.00 | 73.53 | B |
| ATOM | 2165 | O | ILE | B | 286 | 0.425 | 40.386 | −18.533 | 1.00 | 74.33 | B |
| ATOM | 2166 | N | PRO | B | 287 | 2.130 | 39.015 | −19.137 | 1.00 | 72.50 | B |
| ATOM | 2167 | CD | PRO | B | 287 | 3.548 | 38.622 | −19.255 | 1.00 | 71.24 | B |
| ATOM | 2168 | CA | PRO | B | 287 | 1.245 | 37.873 | −19.384 | 1.00 | 71.29 | B |
| ATOM | 2169 | CB | PRO | B | 287 | 2.202 | 36.691 | −19.428 | 1.00 | 71.38 | B |
| ATOM | 2170 | CG | PRO | B | 287 | 3.453 | 37.296 | −19.968 | 1.00 | 72.25 | B |
| ATOM | 2171 | C | PRO | B | 287 | 0.207 | 37.724 | −18.279 | 1.00 | 71.83 | B |
| ATOM | 2172 | O | PRO | B | 287 | 0.550 | 37.510 | −17.108 | 1.00 | 70.37 | B |
| ATOM | 2173 | N | GLY | B | 288 | −1.058 | 37.886 | −18.664 | 1.00 | 73.45 | B |
| ATOM | 2174 | CA | GLY | B | 288 | −2.172 | 37.743 | −17.740 | 1.00 | 73.81 | B |
| ATOM | 2175 | C | GLY | B | 288 | −2.688 | 38.942 | −16.964 | 1.00 | 74.30 | B |
| ATOM | 2176 | O | GLY | B | 288 | −3.841 | 38.937 | −16.552 | 1.00 | 74.21 | B |
| ATOM | 2177 | N | PHE | B | 289 | −1.871 | 39.961 | −16.739 | 1.00 | 74.97 | B |
| ATOM | 2178 | CA | PHE | B | 289 | −2.351 | 41.102 | −15.968 | 1.00 | 76.73 | B |
| ATOM | 2179 | CB | PHE | B | 289 | −1.258 | 42.153 | −15.867 | 1.00 | 74.06 | B |
| ATOM | 2180 | CG | PHE | B | 289 | −1.653 | 43.410 | −15.118 | 1.00 | 71.05 | B |
| ATOM | 2181 | CD1 | PHE | B | 289 | −1.247 | 43.607 | −13.801 | 1.00 | 69.69 | B |
| ATOM | 2182 | CD2 | PHE | B | 289 | −2.296 | 44.455 | −15.773 | 1.00 | 69.33 | B |
| ATOM | 2183 | CE1 | PHE | B | 289 | −1.455 | 44.830 | −13.167 | 1.00 | 70.45 | B |
| ATOM | 2184 | CE2 | PHE | B | 289 | −2.512 | 45.692 | −15.142 | 1.00 | 69.08 | B |
| ATOM | 2185 | CZ | PHE | B | 289 | −2.093 | 45.885 | −13.845 | 1.00 | 69.34 | B |
| ATOM | 2186 | C | PHE | B | 289 | −3.603 | 41.722 | −16.581 | 1.00 | 79.76 | B |
| ATOM | 2187 | O | PHE | B | 289 | −4.395 | 42.346 | −15.882 | 1.00 | 80.34 | B |
| ATOM | 2188 | N | SER | B | 290 | −3.792 | 41.546 | −17.883 | 1.00 | 83.26 | B |
| ATOM | 2189 | CA | SER | B | 290 | −4.959 | 42.134 | −18.542 | 1.00 | 86.01 | B |
| ATOM | 2190 | CB | SER | B | 290 | −4.720 | 42.257 | −20.047 | 1.00 | 85.82 | B |
| ATOM | 2191 | OG | SER | B | 290 | −3.672 | 43.179 | −20.303 | 1.00 | 88.41 | B |
| ATOM | 2192 | C | SER | B | 290 | −6.199 | 41.308 | −18.280 | 1.00 | 87.75 | B |
| ATOM | 2193 | O | SER | B | 290 | −7.321 | 41.799 | −18.397 | 1.00 | 89.05 | B |
| ATOM | 2194 | N | THR | B | 291 | −5.983 | 40.047 | −17.928 | 1.00 | 89.05 | B |
| ATOM | 2195 | CA | THR | B | 291 | −7.070 | 39.124 | −17.622 | 1.00 | 91.07 | B |
| ATOM | 2196 | CB | THR | B | 291 | −6.504 | 37.645 | −17.438 | 1.00 | 92.92 | B |
| ATOM | 2197 | OG1 | THR | B | 291 | −5.874 | 37.200 | −18.659 | 1.00 | 91.14 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2198 | CG2 | THR | B | 291 | −7.624 | 36.663 | −17.039 | 1.00 | 92.33 | B |
|---|---|---|---|---|---|---|---|---|---|---|---|
| ATOM | 2199 | C | THR | B | 291 | −7.811 | 39.585 | −16.333 | 1.00 | 91.40 | B |
| ATOM | 2200 | O | THR | B | 291 | −8.929 | 39.135 | −16.058 | 1.00 | 91.66 | B |
| ATOM | 2201 | N | LEU | B | 292 | −7.188 | 40.476 | −15.553 | 1.00 | 91.18 | B |
| ATOM | 2202 | CA | LEU | B | 292 | −7.797 | 40.991 | −14.313 | 1.00 | 90.93 | B |
| ATOM | 2203 | CB | LEU | B | 292 | −6.755 | 41.684 | −13.415 | 1.00 | 89.10 | B |
| ATOM | 2204 | CG | LEU | B | 292 | −5.555 | 40.880 | −12.927 | 1.00 | 87.77 | B |
| ATOM | 2205 | CD1 | LEU | B | 292 | −4.744 | 41.741 | −12.002 | 1.00 | 86.90 | B |
| ATOM | 2206 | CD2 | LEU | B | 292 | −6.012 | 39.612 | −12.235 | 1.00 | 86.57 | B |
| ATOM | 2207 | C | LEU | B | 292 | −8.900 | 42.001 | −14.609 | 1.00 | 91.44 | B |
| ATOM | 2208 | O | LEU | B | 292 | −9.289 | 42.190 | −15.759 | 1.00 | 91.27 | B |
| ATOM | 2209 | N | SER | B | 293 | −9.393 | 42.653 | −13.561 | 1.00 | 92.44 | B |
| ATOM | 2210 | CA | SER | B | 293 | −10.439 | 43.660 | −13.701 | 1.00 | 93.83 | B |
| ATOM | 2211 | CB | SER | B | 293 | −11.491 | 43.498 | −12.597 | 1.00 | 94.11 | B |
| ATOM | 2212 | OG | SER | B | 293 | −10.925 | 43.649 | −11.309 | 1.00 | 94.99 | B |
| ATOM | 2213 | C | SER | B | 293 | −9.772 | 45.021 | −13.599 | 1.00 | 94.36 | B |
| ATOM | 2214 | O | SER | B | 293 | −8.690 | 45.134 | −13.037 | 1.00 | 94.80 | B |
| ATOM | 2215 | N | LEU | B | 294 | −10.402 | 46.051 | −14.145 | 1.00 | 95.45 | B |
| ATOM | 2216 | CA | LEU | B | 294 | −9.813 | 47.388 | −14.097 | 1.00 | 96.63 | B |
| ATOM | 2217 | CB | LEU | B | 294 | −10.790 | 48.422 | −14.663 | 1.00 | 98.60 | B |
| ATOM | 2218 | CG | LEU | B | 294 | −11.551 | 48.067 | −15.958 | 1.00 | 101.49 | B |
| ATOM | 2219 | CD1 | LEU | B | 294 | −12.856 | 48.922 | −16.053 | 1.00 | 101.18 | B |
| ATOM | 2220 | CD2 | LEU | B | 294 | −10.622 | 48.259 | −17.196 | 1.00 | 101.03 | B |
| ATOM | 2221 | C | LEU | B | 294 | −9.495 | 47.747 | −12.651 | 1.00 | 96.40 | B |
| ATOM | 2222 | O | LEU | B | 294 | −8.559 | 48.497 | −12.365 | 1.00 | 96.35 | B |
| ATOM | 2223 | N | ALA | B | 295 | −10.285 | 47.202 | −11.736 | 1.00 | 96.24 | B |
| ATOM | 2224 | CA | ALA | B | 295 | −10.102 | 47.482 | −10.319 | 1.00 | 96.36 | B |
| ATOM | 2225 | CB | ALA | B | 295 | −11.330 | 47.044 | −9.548 | 1.00 | 97.32 | B |
| ATOM | 2226 | C | ALA | B | 295 | −8.866 | 46.779 | −9.777 | 1.00 | 96.02 | B |
| ATOM | 2227 | O | ALA | B | 295 | −7.965 | 47.429 | −9.229 | 1.00 | 95.51 | B |
| ATOM | 2228 | N | ASP | B | 296 | −8.845 | 45.451 | −9.919 | 1.00 | 95.11 | B |
| ATOM | 2229 | CA | ASP | B | 296 | −7.719 | 44.640 | −9.467 | 1.00 | 93.66 | B |
| ATOM | 2230 | CB | ASP | B | 296 | −7.869 | 43.191 | −9.964 | 1.00 | 94.70 | B |
| ATOM | 2231 | CG | ASP | B | 296 | −8.823 | 42.361 | −9.095 | 1.00 | 96.65 | B |
| ATOM | 2232 | OD1 | ASP | B | 296 | −9.048 | 41.161 | −9.420 | 1.00 | 97.11 | B |
| ATOM | 2233 | OD2 | ASP | B | 296 | −9.336 | 42.910 | −8.087 | 1.00 | 96.77 | B |
| ATOM | 2234 | C | ASP | B | 296 | −6.433 | 45.253 | −10.018 | 1.00 | 91.86 | B |
| ATOM | 2235 | O | ASP | B | 296 | −5.465 | 45.482 | −9.281 | 1.00 | 91.47 | B |
| ATOM | 2236 | N | GLN | B | 297 | −6.449 | 45.533 | −11.316 | 1.00 | 89.74 | B |
| ATOM | 2237 | CA | GLN | B | 297 | −5.312 | 46.124 | −11.989 | 1.00 | 87.52 | B |
| ATOM | 2238 | CB | GLN | B | 297 | −5.656 | 46.402 | −13.442 | 1.00 | 86.23 | B |
| ATOM | 2239 | CG | GLN | B | 297 | −5.644 | 45.155 | −14.289 | 1.00 | 84.52 | B |
| ATOM | 2240 | CD | GLN | B | 297 | −6.030 | 45.430 | −15.724 | 1.00 | 83.91 | B |
| ATOM | 2241 | OE1 | GLN | B | 297 | −5.627 | 46.441 | −16.307 | 1.00 | 83.05 | B |
| ATOM | 2242 | NE2 | GLN | B | 297 | −6.804 | 44.523 | −16.310 | 1.00 | 84.48 | B |
| ATOM | 2243 | C | GLN | B | 297 | −4.859 | 47.396 | −11.314 | 1.00 | 87.35 | B |
| ATOM | 2244 | O | GLN | B | 297 | −3.663 | 47.595 | −11.137 | 1.00 | 88.13 | B |
| ATOM | 2245 | N | MET | B | 298 | −5.808 | 48.253 | −10.938 | 1.00 | 86.88 | B |
| ATOM | 2246 | CA | MET | B | 298 | −5.485 | 49.509 | −10.267 | 1.00 | 86.76 | B |
| ATOM | 2247 | CB | MET | B | 298 | −6.704 | 50.423 | −10.204 | 1.00 | 87.83 | B |
| ATOM | 2248 | CG | MET | B | 298 | −7.069 | 51.075 | −11.515 | 1.00 | 89.16 | B |
| ATOM | 2249 | SD | MET | B | 298 | −8.439 | 52.256 | −11.326 | 1.00 | 89.65 | B |
| ATOM | 2250 | CE | MET | B | 298 | −9.848 | 51.095 | −11.248 | 1.00 | 89.26 | B |
| ATOM | 2251 | C | MET | B | 298 | −4.967 | 49.274 | −8.855 | 1.00 | 86.31 | B |
| ATOM | 2252 | O | MET | B | 298 | −4.045 | 49.959 | −8.407 | 1.00 | 85.37 | B |
| ATOM | 2253 | N | SER | B | 299 | −5.571 | 48.310 | −8.158 | 1.00 | 86.63 | B |
| ATOM | 2254 | CA | SER | B | 299 | −5.171 | 47.959 | −6.794 | 1.00 | 86.07 | B |
| ATOM | 2255 | CB | SER | B | 299 | −6.054 | 46.835 | −6.247 | 1.00 | 86.60 | B |
| ATOM | 2256 | OG | SER | B | 299 | −7.418 | 47.227 | −6.160 | 1.00 | 86.87 | B |
| ATOM | 2257 | C | SER | B | 299 | −3.712 | 47.513 | −6.817 | 1.00 | 85.94 | B |
| ATOM | 2258 | O | SER | B | 299 | −2.893 | 48.022 | −6.049 | 1.00 | 86.52 | B |
| ATOM | 2259 | N | LEU | B | 300 | −3.383 | 46.573 | −7.703 | 1.00 | 84.93 | B |
| ATOM | 2260 | CA | LEU | B | 300 | −2.002 | 46.105 | −7.828 | 1.00 | 83.54 | B |
| ATOM | 2261 | CB | LEU | B | 300 | −1.896 | 45.011 | −8.898 | 1.00 | 82.91 | B |
| ATOM | 2262 | CG | LEU | B | 300 | −2.644 | 43.689 | −8.662 | 1.00 | 82.81 | B |
| ATOM | 2263 | CD1 | LEU | B | 300 | −2.134 | 42.617 | −9.600 | 1.00 | 80.77 | B |
| ATOM | 2264 | CD2 | LEU | B | 300 | −2.432 | 43.237 | −7.240 | 1.00 | 83.61 | B |
| ATOM | 2265 | C | LEU | B | 300 | −1.050 | 47.267 | −8.177 | 1.00 | 83.18 | B |
| ATOM | 2266 | O | LEU | B | 300 | −0.082 | 47.522 | −7.466 | 1.00 | 83.45 | B |
| ATOM | 2267 | N | LEU | B | 301 | −1.336 | 47.979 | −9.263 | 1.00 | 83.12 | B |
| ATOM | 2268 | CA | LEU | B | 301 | −0.504 | 49.098 | −9.705 | 1.00 | 82.38 | B |
| ATOM | 2269 | CB | LEU | B | 301 | −1.061 | 49.693 | −11.004 | 1.00 | 82.22 | B |
| ATOM | 2270 | CG | LEU | B | 301 | −0.550 | 49.055 | −12.295 | 1.00 | 82.79 | B |
| ATOM | 2271 | CD1 | LEU | B | 301 | −1.267 | 49.650 | −13.501 | 1.00 | 82.23 | B |
| ATOM | 2272 | CD2 | LEU | B | 301 | 0.965 | 49.279 | −12.378 | 1.00 | 82.24 | B |
| ATOM | 2273 | C | LEU | B | 301 | −0.310 | 50.220 | −8.689 | 1.00 | 82.47 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2274 | O   | LEU | B | 301 | 0.787  | 50.771 | -8.567  | 1.00 | 81.24 | B |
|------|------|-----|-----|---|-----|--------|--------|---------|------|-------|---|
| ATOM | 2275 | N   | GLN | B | 302 | -1.359 | 50.584 | -7.964  | 1.00 | 83.08 | B |
| ATOM | 2276 | CA  | GLN | B | 302 | -1.181 | 51.661 | -7.007  | 1.00 | 83.06 | B |
| ATOM | 2277 | CB  | GLN | B | 302 | -2.468 | 52.460 | -6.843  | 1.00 | 83.67 | B |
| ATOM | 2278 | CG  | GLN | B | 302 | -3.677 | 51.680 | -6.488  | 1.00 | 85.55 | B |
| ATOM | 2279 | CD  | GLN | B | 302 | -4.913 | 52.526 | -6.671  | 1.00 | 87.56 | B |
| ATOM | 2280 | OE1 | GLN | B | 302 | -4.879 | 53.737 | -6.432  | 1.00 | 88.72 | B |
| ATOM | 2281 | NE2 | GLN | B | 302 | -6.016 | 51.901 | -7.095  | 1.00 | 87.92 | B |
| ATOM | 2282 | C   | GLN | B | 302 | -0.660 | 51.158 | -5.680  | 1.00 | 81.65 | B |
| ATOM | 2283 | O   | GLN | B | 302 | -0.456 | 51.913 | -4.733  | 1.00 | 79.78 | B |
| ATOM | 2284 | N   | SER | B | 303 | -0.411 | 49.862 | -5.629  | 1.00 | 80.86 | B |
| ATOM | 2285 | CA  | SER | B | 303 | 0.138  | 49.293 | -4.434  | 1.00 | 80.25 | B |
| ATOM | 2286 | CB  | SER | B | 303 | -0.570 | 47.983 | -4.099  | 1.00 | 81.02 | B |
| ATOM | 2287 | OG  | SER | B | 303 | -0.781 | 47.872 | -2.697  | 1.00 | 82.20 | B |
| ATOM | 2288 | C   | SER | B | 303 | 1.621  | 49.047 | -4.687  | 1.00 | 79.62 | B |
| ATOM | 2289 | O   | SER | B | 303 | 2.439  | 49.176 | -3.787  | 1.00 | 79.93 | B |
| ATOM | 2290 | N   | ALA | B | 304 | 1.983  | 48.741 | -5.926  | 1.00 | 79.82 | B |
| ATOM | 2291 | CA  | ALA | B | 304 | 3.376  | 48.429 | -6.229  | 1.00 | 79.77 | B |
| ATOM | 2292 | CB  | ALA | B | 304 | 3.450  | 47.035 | -6.862  | 1.00 | 79.12 | B |
| ATOM | 2293 | C   | ALA | B | 304 | 4.180  | 49.404 | -7.073  | 1.00 | 79.92 | B |
| ATOM | 2294 | O   | ALA | B | 304 | 5.399  | 49.256 | -7.145  | 1.00 | 80.83 | B |
| ATOM | 2295 | N   | TRP | B | 305 | 3.529  | 50.395 | -7.686  | 1.00 | 79.31 | B |
| ATOM | 2296 | CA  | TRP | B | 305 | 4.215  | 51.358 | -8.556  | 1.00 | 78.68 | B |
| ATOM | 2297 | CB  | TRP | B | 305 | 3.299  | 52.535 | -8.905  | 1.00 | 80.92 | B |
| ATOM | 2298 | CG  | TRP | B | 305 | 2.930  | 53.443 | -7.755  | 1.00 | 82.97 | B |
| ATOM | 2299 | CD2 | TRP | B | 305 | 3.630  | 54.629 | -7.320  | 1.00 | 83.69 | B |
| ATOM | 2300 | CE2 | TRP | B | 305 | 2.899  | 55.177 | -6.239  | 1.00 | 84.35 | B |
| ATOM | 2301 | CE3 | TRP | B | 305 | 4.804  | 55.282 | -7.743  | 1.00 | 84.22 | B |
| ATOM | 2302 | CD1 | TRP | B | 305 | 1.836  | 53.322 | -6.930  | 1.00 | 82.91 | B |
| ATOM | 2303 | NE1 | TRP | B | 305 | 1.814  | 54.360 | -6.020  | 1.00 | 83.03 | B |
| ATOM | 2304 | CZ2 | TRP | B | 305 | 3.300  | 56.348 | -5.577  | 1.00 | 84.04 | B |
| ATOM | 2305 | CZ3 | TRP | B | 305 | 5.201  | 56.437 | -7.086  | 1.00 | 84.60 | B |
| ATOM | 2306 | CH2 | TRP | B | 305 | 4.449  | 56.961 | -6.015  | 1.00 | 85.03 | B |
| ATOM | 2307 | C   | TRP | B | 305 | 5.567  | 51.923 | -8.112  | 1.00 | 78.08 | B |
| ATOM | 2308 | O   | TRP | B | 305 | 6.445  | 52.125 | -8.954  | 1.00 | 76.80 | B |
| ATOM | 2309 | N   | MET | B | 306 | 5.740  | 52.185 | -6.818  | 1.00 | 77.66 | B |
| ATOM | 2310 | CA  | MET | B | 306 | 6.992  | 52.726 | -6.315  | 1.00 | 78.46 | B |
| ATOM | 2311 | CB  | MET | B | 306 | 6.749  | 53.379 | -4.966  | 1.00 | 80.67 | B |
| ATOM | 2312 | CG  | MET | B | 306 | 7.984  | 54.043 | -4.345  | 1.00 | 81.83 | B |
| ATOM | 2313 | SD  | MET | B | 306 | 8.386  | 55.600 | -5.173  | 1.00 | 85.04 | B |
| ATOM | 2314 | CE  | MET | B | 306 | 10.179 | 55.435 | -5.448  | 1.00 | 81.75 | B |
| ATOM | 2315 | C   | MET | B | 306 | 8.110  | 51.678 | -6.194  | 1.00 | 79.24 | B |
| ATOM | 2316 | O   | MET | B | 306 | 9.298  | 52.018 | -6.194  | 1.00 | 78.13 | B |
| ATOM | 2317 | N   | GLU | B | 307 | 7.732  | 50.404 | -6.059  | 1.00 | 80.16 | B |
| ATOM | 2318 | CA  | GLU | B | 307 | 8.716  | 49.314 | -5.978  | 1.00 | 80.27 | B |
| ATOM | 2319 | CB  | GLU | B | 307 | 8.025  | 48.007 | -5.553  | 1.00 | 82.51 | B |
| ATOM | 2320 | CG  | GLU | B | 307 | 8.219  | 47.645 | -4.078  | 1.00 | 86.64 | B |
| ATOM | 2321 | CD  | GLU | B | 307 | 7.178  | 46.651 | -3.522  | 1.00 | 89.22 | B |
| ATOM | 2322 | OE1 | GLU | B | 307 | 6.003  | 47.054 | -3.363  | 1.00 | 91.75 | B |
| ATOM | 2323 | OE2 | GLU | B | 307 | 7.527  | 45.473 | -3.235  | 1.00 | 89.99 | B |
| ATOM | 2324 | C   | GLU | B | 307 | 9.308  | 49.181 | -7.385  | 1.00 | 78.58 | B |
| ATOM | 2325 | O   | GLU | B | 307 | 10.516 | 49.000 | -7.562  | 1.00 | 77.00 | B |
| ATOM | 2326 | N   | ILE | B | 308 | 8.427  | 49.304 | -8.376  | 1.00 | 77.33 | B |
| ATOM | 2327 | CA  | ILE | B | 308 | 8.770  | 49.225 | -9.802  | 1.00 | 77.63 | B |
| ATOM | 2328 | CB  | ILE | B | 308 | 7.479  | 49.112 | -10.646 | 1.00 | 76.99 | B |
| ATOM | 2329 | CG2 | ILE | B | 308 | 7.802  | 49.032 | -12.102 | 1.00 | 76.91 | B |
| ATOM | 2330 | CG1 | ILE | B | 308 | 6.716  | 47.847 | -10.257 | 1.00 | 76.77 | B |
| ATOM | 2331 | CD1 | ILE | B | 308 | 5.313  | 47.828 | -10.785 | 1.00 | 77.51 | B |
| ATOM | 2332 | C   | ILE | B | 308 | 9.626  | 50.416 | -10.306 | 1.00 | 78.17 | B |
| ATOM | 2333 | O   | ILE | B | 308 | 10.377 | 50.275 | -11.283 | 1.00 | 79.57 | B |
| ATOM | 2334 | N   | LEU | B | 309 | 9.512  | 51.581 | -9.660  | 1.00 | 76.64 | B |
| ATOM | 2335 | CA  | LEU | B | 309 | 10.323 | 52.733 | -10.038 | 1.00 | 74.95 | B |
| ATOM | 2336 | CB  | LEU | B | 309 | 9.773  | 54.037 | -9.459  | 1.00 | 74.86 | B |
| ATOM | 2337 | CG  | LEU | B | 309 | 8.490  | 54.634 | -10.026 | 1.00 | 76.18 | B |
| ATOM | 2338 | CD1 | LEU | B | 309 | 8.313  | 56.027 | -9.457  | 1.00 | 74.50 | B |
| ATOM | 2339 | CD2 | LEU | B | 309 | 8.543  | 54.664 | -11.535 | 1.00 | 75.89 | B |
| ATOM | 2340 | C   | LEU | B | 309 | 11.725 | 52.537 | -9.483  | 1.00 | 74.46 | B |
| ATOM | 2341 | O   | LEU | B | 309 | 12.730 | 52.822 | -10.143 | 1.00 | 75.60 | B |
| ATOM | 2342 | N   | ILE | B | 310 | 11.779 | 52.063 | -8.247  | 1.00 | 73.51 | B |
| ATOM | 2343 | CA  | ILE | B | 310 | 13.031 | 51.833 | -7.562  | 1.00 | 72.14 | B |
| ATOM | 2344 | CB  | ILE | B | 310 | 12.742 | 51.538 | -6.092  | 1.00 | 71.69 | B |
| ATOM | 2345 | CG2 | ILE | B | 310 | 14.055 | 51.293 | -5.317  | 1.00 | 71.22 | B |
| ATOM | 2346 | CG1 | ILE | B | 310 | 11.943 | 52.716 | -5.522  | 1.00 | 72.63 | B |
| ATOM | 2347 | CD1 | ILE | B | 310 | 11.332 | 52.494 | -4.144  | 1.00 | 74.15 | B |
| ATOM | 2348 | C   | ILE | B | 310 | 13.818 | 50.696 | -8.199  | 1.00 | 72.74 | B |
| ATOM | 2349 | O   | ILE | B | 310 | 15.056 | 50.719 | -8.237  | 1.00 | 71.33 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2350 | N   | LEU | B | 311 | 13.093 | 49.700 | −8.705  | 1.00 | 73.38 | B |
|------|------|-----|-----|---|-----|--------|--------|---------|------|-------|---|
| ATOM | 2351 | CA  | LEU | B | 311 | 13.739 | 48.554 | −9.329  | 1.00 | 74.66 | B |
| ATOM | 2352 | CB  | LEU | B | 311 | 12.702 | 47.479 | −9.705  | 1.00 | 75.67 | B |
| ATOM | 2353 | CG  | LEU | B | 311 | 12.670 | 46.265 | −8.756  | 1.00 | 76.06 | B |
| ATOM | 2354 | CD1 | LEU | B | 311 | 11.693 | 45.239 | −9.288  | 1.00 | 77.57 | B |
| ATOM | 2355 | CD2 | LEU | B | 311 | 14.061 | 45.647 | −8.611  | 1.00 | 74.76 | B |
| ATOM | 2356 | C   | LEU | B | 311 | 14.499 | 49.032 | −10.554 | 1.00 | 73.89 | B |
| ATOM | 2357 | O   | LEU | B | 311 | 15.647 | 48.634 | −10.783 | 1.00 | 72.33 | B |
| ATOM | 2358 | N   | GLY | B | 312 | 13.839 | 49.883 | −11.333 | 1.00 | 73.26 | B |
| ATOM | 2359 | CA  | GLY | B | 312 | 14.456 | 50.471 | −12.513 | 1.00 | 72.74 | B |
| ATOM | 2360 | C   | GLY | B | 312 | 15.703 | 51.254 | −12.109 | 1.00 | 72.49 | B |
| ATOM | 2361 | O   | GLY | B | 312 | 16.770 | 51.094 | −12.710 | 1.00 | 72.96 | B |
| ATOM | 2362 | N   | VAL | B | 313 | 15.602 | 52.092 | −11.080 | 1.00 | 71.10 | B |
| ATOM | 2363 | CA  | VAL | B | 313 | 16.774 | 52.848 | −10.669 | 1.00 | 70.04 | B |
| ATOM | 2364 | CB  | VAL | B | 313 | 16.477 | 53.762 | −9.460  | 1.00 | 69.94 | B |
| ATOM | 2365 | CG1 | VAL | B | 313 | 17.765 | 54.358 | −8.908  | 1.00 | 68.47 | B |
| ATOM | 2366 | CG2 | VAL | B | 313 | 15.519 | 54.840 | −9.875  | 1.00 | 68.83 | B |
| ATOM | 2367 | C   | VAL | B | 313 | 17.866 | 51.868 | −10.297 | 1.00 | 69.47 | B |
| ATOM | 2368 | O   | VAL | B | 313 | 19.001 | 52.015 | −10.715 | 1.00 | 71.35 | B |
| ATOM | 2369 | N   | VAL | B | 314 | 17.511 | 50.844 | −9.538  | 1.00 | 68.74 | B |
| ATOM | 2370 | CA  | VAL | B | 314 | 18.496 | 49.860 | −9.089  | 1.00 | 67.56 | B |
| ATOM | 2371 | CB  | VAL | B | 314 | 17.856 | 48.816 | −8.143  | 1.00 | 67.07 | B |
| ATOM | 2372 | CG1 | VAL | B | 314 | 18.887 | 47.730 | −7.828  | 1.00 | 66.84 | B |
| ATOM | 2373 | CG2 | VAL | B | 314 | 17.348 | 49.486 | −6.853  | 1.00 | 66.15 | B |
| ATOM | 2374 | C   | VAL | B | 314 | 19.188 | 49.097 | −10.219 | 1.00 | 66.53 | B |
| ATOM | 2375 | O   | VAL | B | 314 | 20.400 | 48.860 | −10.191 | 1.00 | 65.02 | B |
| ATOM | 2376 | N   | TYR | B | 315 | 18.412 | 48.703 | −11.211 | 1.00 | 66.25 | B |
| ATOM | 2377 | CA  | TYR | B | 315 | 18.990 | 47.959 | −12.298 | 1.00 | 66.97 | B |
| ATOM | 2378 | CB  | TYR | B | 315 | 17.905 | 47.378 | −13.209 | 1.00 | 65.21 | B |
| ATOM | 2379 | CG  | TYR | B | 315 | 18.521 | 46.398 | −14.165 | 1.00 | 66.65 | B |
| ATOM | 2380 | CD1 | TYR | B | 315 | 18.433 | 46.581 | −15.547 | 1.00 | 66.97 | B |
| ATOM | 2381 | CE1 | TYR | B | 315 | 19.090 | 45.722 | −16.430 | 1.00 | 66.80 | B |
| ATOM | 2382 | CD2 | TYR | B | 315 | 19.282 | 45.315 | −13.680 | 1.00 | 67.57 | B |
| ATOM | 2383 | CE2 | TYR | B | 315 | 19.943 | 44.440 | −14.551 | 1.00 | 67.74 | B |
| ATOM | 2384 | CZ  | TYR | B | 315 | 19.839 | 44.653 | −15.925 | 1.00 | 68.42 | B |
| ATOM | 2385 | OH  | TYR | B | 315 | 20.468 | 43.790 | −16.791 | 1.00 | 69.50 | B |
| ATOM | 2386 | C   | TYR | B | 315 | 19.965 | 48.827 | −13.106 | 1.00 | 67.77 | B |
| ATOM | 2387 | O   | TYR | B | 315 | 21.018 | 48.333 | −13.554 | 1.00 | 68.93 | B |
| ATOM | 2388 | N   | ARG | B | 316 | 19.625 | 50.111 | −13.286 | 1.00 | 66.82 | B |
| ATOM | 2389 | CA  | ARG | B | 316 | 20.485 | 51.047 | −14.031 | 1.00 | 65.78 | B |
| ATOM | 2390 | CB  | ARG | B | 316 | 19.752 | 52.367 | −14.279 | 1.00 | 63.24 | B |
| ATOM | 2391 | CG  | ARG | B | 316 | 18.572 | 52.133 | −15.154 | 1.00 | 62.56 | B |
| ATOM | 2392 | CD  | ARG | B | 316 | 17.878 | 53.367 | −15.585 | 1.00 | 63.53 | B |
| ATOM | 2393 | NE  | ARG | B | 316 | 17.166 | 54.063 | −14.521 | 1.00 | 64.64 | B |
| ATOM | 2394 | CZ  | ARG | B | 316 | 15.839 | 54.096 | −14.436 | 1.00 | 66.36 | B |
| ATOM | 2395 | NH1 | ARG | B | 316 | 15.095 | 53.456 | −15.348 | 1.00 | 65.54 | B |
| ATOM | 2396 | NH2 | ARG | B | 316 | 15.256 | 54.802 | −13.469 | 1.00 | 65.48 | B |
| ATOM | 2397 | C   | ARG | B | 316 | 21.826 | 51.309 | −13.342 | 1.00 | 65.73 | B |
| ATOM | 2398 | O   | ARG | B | 316 | 22.852 | 51.444 | −14.023 | 1.00 | 65.87 | B |
| ATOM | 2399 | N   | SER | B | 317 | 21.818 | 51.316 | −12.008 | 1.00 | 64.49 | B |
| ATOM | 2400 | CA  | SER | B | 317 | 23.008 | 51.568 | −11.208 | 1.00 | 65.83 | B |
| ATOM | 2401 | CB  | SER | B | 317 | 22.586 | 52.167 | −9.869  | 1.00 | 63.97 | B |
| ATOM | 2402 | OG  | SER | B | 317 | 21.347 | 52.842 | −9.998  | 1.00 | 64.89 | B |
| ATOM | 2403 | C   | SER | B | 317 | 23.902 | 50.364 | −10.929 | 1.00 | 69.03 | B |
| ATOM | 2404 | O   | SER | B | 317 | 24.914 | 50.467 | −10.212 | 1.00 | 67.59 | B |
| ATOM | 2405 | N   | LEU | B | 318 | 23.535 | 49.213 | −11.475 | 1.00 | 72.95 | B |
| ATOM | 2406 | CA  | LEU | B | 318 | 24.307 | 48.012 | −11.201 | 1.00 | 76.77 | B |
| ATOM | 2407 | CB  | LEU | B | 318 | 23.643 | 46.824 | −11.897 | 1.00 | 75.73 | B |
| ATOM | 2408 | CG  | LEU | B | 318 | 22.868 | 45.868 | −10.975 | 1.00 | 74.25 | B |
| ATOM | 2409 | CD1 | LEU | B | 318 | 21.872 | 46.597 | −10.109 | 1.00 | 72.01 | B |
| ATOM | 2410 | CD2 | LEU | B | 318 | 22.173 | 44.850 | −11.839 | 1.00 | 74.40 | B |
| ATOM | 2411 | C   | LEU | B | 318 | 25.797 | 48.129 | −11.550 | 1.00 | 79.84 | B |
| ATOM | 2412 | O   | LEU | B | 318 | 26.660 | 47.623 | −10.830 | 1.00 | 80.24 | B |
| ATOM | 2413 | N   | SER | B | 319 | 26.095 | 48.821 | −12.640 | 1.00 | 83.24 | B |
| ATOM | 2414 | CA  | SER | B | 319 | 27.477 | 49.021 | −13.072 | 1.00 | 86.25 | B |
| ATOM | 2415 | CB  | SER | B | 319 | 27.486 | 49.222 | −14.585 | 1.00 | 85.82 | B |
| ATOM | 2416 | OG  | SER | B | 319 | 26.486 | 50.163 | −14.949 | 1.00 | 87.18 | B |
| ATOM | 2417 | C   | SER | B | 319 | 28.202 | 50.205 | −12.360 | 1.00 | 88.13 | B |
| ATOM | 2418 | O   | SER | B | 319 | 29.436 | 50.269 | −12.367 | 1.00 | 88.63 | B |
| ATOM | 2419 | N   | PHE | B | 320 | 27.446 | 51.121 | −11.744 | 1.00 | 89.71 | B |
| ATOM | 2420 | CA  | PHE | B | 320 | 28.022 | 52.270 | −11.026 | 1.00 | 91.10 | B |
| ATOM | 2421 | CB  | PHE | B | 320 | 27.099 | 53.483 | −11.116 | 1.00 | 89.73 | B |
| ATOM | 2422 | CG  | PHE | B | 320 | 26.808 | 53.895 | −12.511 | 1.00 | 89.88 | B |
| ATOM | 2423 | CD1 | PHE | B | 320 | 26.009 | 53.109 | −13.324 | 1.00 | 89.96 | B |
| ATOM | 2424 | CD2 | PHE | B | 320 | 27.380 | 55.035 | −13.042 | 1.00 | 89.88 | B |
| ATOM | 2425 | CE1 | PHE | B | 320 | 25.783 | 53.448 | −14.648 | 1.00 | 89.73 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2426 | CE2 | PHE | B | 320 | 27.160 | 55.383 | −14.364 | 1.00 | 89.58 | B |
|---|---|---|---|---|---|---|---|---|---|---|---|
| ATOM | 2427 | CZ | PHE | B | 320 | 26.359 | 54.584 | −15.169 | 1.00 | 89.38 | B |
| ATOM | 2428 | C | PHE | B | 320 | 28.333 | 52.000 | −9.555 | 1.00 | 93.49 | B |
| ATOM | 2429 | O | PHE | B | 320 | 27.727 | 51.126 | −8.915 | 1.00 | 94.57 | B |
| ATOM | 2430 | N | GLU | B | 321 | 29.278 | 52.776 | −9.030 | 1.00 | 95.32 | B |
| ATOM | 2431 | CA | GLU | B | 321 | 29.726 | 52.662 | −7.648 | 1.00 | 97.14 | B |
| ATOM | 2432 | CB | GLU | B | 321 | 31.248 | 52.655 | −7.596 | 1.00 | 98.04 | B |
| ATOM | 2433 | CG | GLU | B | 321 | 31.871 | 51.329 | −7.950 | 1.00 | 101.21 | B |
| ATOM | 2434 | CD | GLU | B | 321 | 32.435 | 50.632 | −6.726 | 1.00 | 104.02 | B |
| ATOM | 2435 | OE1 | GLU | B | 321 | 32.921 | 49.476 | −6.863 | 1.00 | 105.10 | B |
| ATOM | 2436 | OE2 | GLU | B | 321 | 32.392 | 51.249 | −5.629 | 1.00 | 104.05 | B |
| ATOM | 2437 | C | GLU | B | 321 | 29.211 | 53.785 | −6.760 | 1.00 | 97.58 | B |
| ATOM | 2438 | O | GLU | B | 321 | 29.514 | 54.954 | −6.990 | 1.00 | 98.26 | B |
| ATOM | 2439 | N | ASP | B | 322 | 28.421 | 53.415 | −5.753 | 1.00 | 97.82 | B |
| ATOM | 2440 | CA | ASP | B | 322 | 27.868 | 54.352 | −4.781 | 1.00 | 96.93 | B |
| ATOM | 2441 | CB | ASP | B | 322 | 29.014 | 54.864 | −3.906 | 1.00 | 99.42 | B |
| ATOM | 2442 | CG | ASP | B | 322 | 30.055 | 53.749 | −3.582 | 1.00 | 102.61 | B |
| ATOM | 2443 | OD1 | ASP | B | 322 | 29.744 | 52.831 | −2.775 | 1.00 | 102.86 | B |
| ATOM | 2444 | OD2 | ASP | B | 322 | 31.182 | 53.787 | −4.149 | 1.00 | 103.17 | B |
| ATOM | 2445 | C | ASP | B | 322 | 27.094 | 55.505 | −5.429 | 1.00 | 95.40 | B |
| ATOM | 2446 | O | ASP | B | 322 | 26.879 | 56.537 | −4.818 | 1.00 | 95.36 | B |
| ATOM | 2447 | N | GLU | B | 323 | 26.662 | 55.300 | −6.667 | 1.00 | 93.85 | B |
| ATOM | 2448 | CA | GLU | B | 323 | 25.905 | 56.292 | −7.416 | 1.00 | 92.83 | B |
| ATOM | 2449 | CB | GLU | B | 323 | 26.630 | 56.668 | −8.702 | 1.00 | 95.89 | B |
| ATOM | 2450 | CG | GLU | B | 323 | 27.850 | 57.546 | −8.584 | 1.00 | 98.56 | B |
| ATOM | 2451 | CD | GLU | B | 323 | 28.402 | 57.880 | −9.969 | 1.00 | 101.17 | B |
| ATOM | 2452 | OE1 | GLU | B | 323 | 28.916 | 56.959 | −10.654 | 1.00 | 101.44 | B |
| ATOM | 2453 | OE2 | GLU | B | 323 | 28.303 | 59.058 | −10.384 | 1.00 | 102.65 | B |
| ATOM | 2454 | C | GLU | B | 323 | 24.553 | 55.719 | −7.815 | 1.00 | 90.70 | B |
| ATOM | 2455 | O | GLU | B | 323 | 24.409 | 54.515 | −7.979 | 1.00 | 90.81 | B |
| ATOM | 2456 | N | LEU | B | 324 | 23.579 | 56.589 | −8.028 | 1.00 | 87.68 | B |
| ATOM | 2457 | CA | LEU | B | 324 | 22.255 | 56.132 | −8.383 | 1.00 | 86.47 | B |
| ATOM | 2458 | CB | LEU | B | 324 | 21.263 | 56.469 | −7.267 | 1.00 | 86.14 | B |
| ATOM | 2459 | CG | LEU | B | 324 | 21.058 | 55.498 | −6.104 | 1.00 | 84.72 | B |
| ATOM | 2460 | CD1 | LEU | B | 324 | 19.970 | 56.061 | −5.201 | 1.00 | 84.26 | B |
| ATOM | 2461 | CD2 | LEU | B | 324 | 20.654 | 54.127 | −6.635 | 1.00 | 83.43 | B |
| ATOM | 2462 | C | LEU | B | 324 | 21.709 | 56.670 | −9.685 | 1.00 | 85.91 | B |
| ATOM | 2463 | O | LEU | B | 324 | 21.105 | 57.733 | −9.717 | 1.00 | 85.60 | B |
| ATOM | 2464 | N | VAL | B | 325 | 21.879 | 55.897 | −10.745 | 1.00 | 85.35 | B |
| ATOM | 2465 | CA | VAL | B | 325 | 21.407 | 56.257 | −12.067 | 1.00 | 85.27 | B |
| ATOM | 2466 | CB | VAL | B | 325 | 21.866 | 55.181 | −13.060 | 1.00 | 84.62 | B |
| ATOM | 2467 | CG1 | VAL | B | 325 | 21.514 | 55.582 | −14.476 | 1.00 | 84.24 | B |
| ATOM | 2468 | CG2 | VAL | B | 325 | 23.375 | 54.956 | −12.898 | 1.00 | 83.60 | B |
| ATOM | 2469 | C | VAL | B | 325 | 19.887 | 56.460 | −12.190 | 1.00 | 86.83 | B |
| ATOM | 2470 | O | VAL | B | 325 | 19.207 | 55.687 | −12.868 | 1.00 | 88.12 | B |
| ATOM | 2471 | N | TYR | B | 326 | 19.356 | 57.506 | −11.552 | 1.00 | 88.51 | B |
| ATOM | 2472 | CA | TYR | B | 326 | 17.915 | 57.814 | −11.608 | 1.00 | 90.72 | B |
| ATOM | 2473 | CB | TYR | B | 326 | 17.629 | 59.112 | −10.873 | 1.00 | 89.55 | B |
| ATOM | 2474 | CG | TYR | B | 326 | 17.178 | 58.902 | −9.458 | 1.00 | 90.82 | B |
| ATOM | 2475 | CD1 | TYR | B | 326 | 15.830 | 58.637 | −9.168 | 1.00 | 91.61 | B |
| ATOM | 2476 | CE1 | TYR | B | 326 | 15.402 | 58.415 | −7.847 | 1.00 | 92.01 | B |
| ATOM | 2477 | CD2 | TYR | B | 326 | 18.095 | 58.942 | −8.400 | 1.00 | 90.70 | B |
| ATOM | 2478 | CE2 | TYR | B | 326 | 17.687 | 58.722 | −7.073 | 1.00 | 92.21 | B |
| ATOM | 2479 | CZ | TYR | B | 326 | 16.338 | 58.460 | −6.801 | 1.00 | 92.71 | B |
| ATOM | 2480 | OH | TYR | B | 326 | 15.937 | 58.256 | −5.493 | 1.00 | 91.22 | B |
| ATOM | 2481 | C | TYR | B | 326 | 17.405 | 57.927 | −13.046 | 1.00 | 92.61 | B |
| ATOM | 2482 | O | TYR | B | 326 | 16.251 | 57.626 | −13.359 | 1.00 | 92.44 | B |
| ATOM | 2483 | N | ALA | B | 327 | 18.292 | 58.387 | −13.913 | 1.00 | 95.19 | B |
| ATOM | 2484 | CA | ALA | B | 327 | 18.013 | 58.530 | −15.330 | 1.00 | 96.98 | B |
| ATOM | 2485 | CB | ALA | B | 327 | 17.193 | 59.775 | −15.599 | 1.00 | 96.10 | B |
| ATOM | 2486 | C | ALA | B | 327 | 19.387 | 58.623 | −15.976 | 1.00 | 98.38 | B |
| ATOM | 2487 | O | ALA | B | 327 | 20.397 | 58.836 | −15.284 | 1.00 | 97.56 | B |
| ATOM | 2488 | N | ASP | B | 328 | 19.435 | 58.439 | −17.291 | 1.00 | 100.64 | B |
| ATOM | 2489 | CA | ASP | B | 328 | 20.703 | 58.482 | −18.008 | 1.00 | 103.28 | B |
| ATOM | 2490 | CB | ASP | B | 328 | 20.461 | 58.109 | −19.472 | 1.00 | 104.99 | B |
| ATOM | 2491 | CG | ASP | B | 328 | 21.321 | 56.939 | −19.924 | 1.00 | 107.10 | B |
| ATOM | 2492 | OD1 | ASP | B | 328 | 21.878 | 56.230 | −19.041 | 1.00 | 106.30 | B |
| ATOM | 2493 | OD2 | ASP | B | 328 | 21.428 | 56.732 | −21.161 | 1.00 | 108.80 | B |
| ATOM | 2494 | C | ASP | B | 328 | 21.347 | 59.868 | −17.895 | 1.00 | 103.87 | B |
| ATOM | 2495 | O | ASP | B | 328 | 22.543 | 60.016 | −17.605 | 1.00 | 102.73 | B |
| ATOM | 2496 | N | ASP | B | 329 | 20.516 | 60.877 | −18.107 | 1.00 | 104.70 | B |
| ATOM | 2497 | CA | ASP | B | 329 | 20.933 | 62.257 | −18.046 | 1.00 | 105.88 | B |
| ATOM | 2498 | CB | ASP | B | 329 | 20.199 | 63.056 | −19.105 | 1.00 | 106.57 | B |
| ATOM | 2499 | CG | ASP | B | 329 | 18.719 | 63.210 | −18.791 | 1.00 | 107.77 | B |
| ATOM | 2500 | OD1 | ASP | B | 329 | 18.100 | 64.153 | −19.332 | 1.00 | 109.43 | B |
| ATOM | 2501 | OD2 | ASP | B | 329 | 18.173 | 62.399 | −18.009 | 1.00 | 107.04 | B |

TABLE 1-continued

ATOMIC COORDINATES OF THE ERR3 LBD/SRC-1 NR BOX 2 PEPTIDE COMPLEX (PDB CODE 1KV6)

| ATOM | 2502 | C | ASP | B | 329 | 20.603 | 62.857 | −16.689 | 1.00 | 107.14 | B |
|---|---|---|---|---|---|---|---|---|---|---|---|
| ATOM | 2503 | O | ASP | B | 329 | 20.186 | 64.018 | −16.614 | 1.00 | 107.83 | B |
| ATOM | 2504 | N | TYR | B | 330 | 20.752 | 62.071 | −15.622 | 1.00 | 108.01 | B |
| ATOM | 2505 | CA | TYR | B | 330 | 20.483 | 62.559 | −14.266 | 1.00 | 108.33 | B |
| ATOM | 2506 | CB | TYR | B | 330 | 19.023 | 63.032 | −14.112 | 1.00 | 109.78 | B |
| ATOM | 2507 | CG | TYR | B | 330 | 18.788 | 63.884 | −12.866 | 1.00 | 112.68 | B |
| ATOM | 2508 | CD1 | TYR | B | 330 | 17.538 | 64.459 | −12.610 | 1.00 | 113.71 | B |
| ATOM | 2509 | CE1 | TYR | B | 330 | 17.332 | 65.286 | −11.491 | 1.00 | 113.99 | B |
| ATOM | 2510 | CD2 | TYR | B | 330 | 19.836 | 64.155 | −11.957 | 1.00 | 113.88 | B |
| ATOM | 2511 | CE2 | TYR | B | 330 | 19.639 | 64.980 | −10.835 | 1.00 | 114.47 | B |
| ATOM | 2512 | CZ | TYR | B | 330 | 18.379 | 65.541 | −10.616 | 1.00 | 114.83 | B |
| ATOM | 2513 | OH | TYR | B | 330 | 18.162 | 66.367 | −9.539 | 1.00 | 116.17 | B |
| ATOM | 2514 | C | TYR | B | 330 | 20.793 | 61.540 | −13.173 | 1.00 | 107.42 | B |
| ATOM | 2515 | O | TYR | B | 330 | 19.888 | 60.998 | −12.545 | 1.00 | 107.09 | B |
| ATOM | 2516 | N | ILE | B | 331 | 22.075 | 61.293 | −12.944 | 1.00 | 106.62 | B |
| ATOM | 2517 | CA | ILE | B | 331 | 22.478 | 60.369 | −11.906 | 1.00 | 106.28 | B |
| ATOM | 2518 | CB | ILE | B | 331 | 23.647 | 59.491 | −12.375 | 1.00 | 103.88 | B |
| ATOM | 2519 | CG2 | ILE | B | 331 | 23.705 | 59.491 | −13.891 | 1.00 | 102.66 | B |
| ATOM | 2520 | CG1 | ILE | B | 331 | 24.958 | 59.979 | −11.788 | 1.00 | 102.33 | B |
| ATOM | 2521 | CD1 | ILE | B | 331 | 26.057 | 59.015 | −12.015 | 1.00 | 101.96 | B |
| ATOM | 2522 | C | ILE | B | 331 | 22.873 | 61.182 | −10.668 | 1.00 | 108.26 | B |
| ATOM | 2523 | O | ILE | B | 331 | 23.003 | 62.404 | −10.744 | 1.00 | 108.80 | B |
| ATOM | 2524 | N | MET | B | 332 | 23.033 | 60.506 | −9.528 | 1.00 | 110.38 | B |
| ATOM | 2525 | CA | MET | B | 332 | 23.415 | 61.148 | −8.263 | 1.00 | 111.35 | B |
| ATOM | 2526 | CB | MET | B | 332 | 22.244 | 61.145 | −7.277 | 1.00 | 110.70 | B |
| ATOM | 2527 | CG | MET | B | 332 | 21.101 | 62.046 | −7.694 | 1.00 | 111.25 | B |
| ATOM | 2528 | SD | MET | B | 332 | 19.700 | 62.020 | −6.549 | 1.00 | 112.44 | B |
| ATOM | 2529 | CE | MET | B | 332 | 18.289 | 62.206 | −7.682 | 1.00 | 110.60 | B |
| ATOM | 2530 | C | MET | B | 332 | 24.618 | 60.466 | −7.611 | 1.00 | 112.31 | B |
| ATOM | 2531 | O | MET | B | 332 | 25.234 | 59.565 | −8.183 | 1.00 | 113.06 | B |
| ATOM | 2532 | N | ASP | B | 333 | 24.962 | 60.932 | −6.420 | 1.00 | 113.21 | B |
| ATOM | 2533 | CA | ASP | B | 333 | 26.070 | 60.389 | −5.648 | 1.00 | 114.54 | B |
| ATOM | 2534 | CB | ASP | B | 333 | 27.439 | 60.849 | −6.194 | 1.00 | 114.83 | B |
| ATOM | 2535 | CG | ASP | B | 333 | 27.526 | 62.371 | −6.438 | 1.00 | 115.34 | B |
| ATOM | 2536 | OD1 | ASP | B | 333 | 27.236 | 63.172 | −5.518 | 1.00 | 115.09 | B |
| ATOM | 2537 | OD2 | ASP | B | 333 | 27.909 | 62.770 | −7.562 | 1.00 | 114.80 | B |
| ATOM | 2538 | C | ASP | B | 333 | 25.835 | 60.900 | −4.241 | 1.00 | 115.75 | B |
| ATOM | 2539 | O | ASP | B | 333 | 24.892 | 61.664 | −4.017 | 1.00 | 115.11 | B |
| ATOM | 2540 | N | GLU | B | 334 | 26.659 | 60.488 | −3.286 | 1.00 | 117.62 | B |
| ATOM | 2541 | CA | GLU | B | 334 | 26.434 | 60.941 | −1.924 | 1.00 | 120.12 | B |
| ATOM | 2542 | CB | GLU | B | 334 | 27.593 | 60.528 | −1.026 | 1.00 | 120.92 | B |
| ATOM | 2543 | CG | GLU | B | 334 | 27.467 | 59.059 | −0.640 | 1.00 | 123.55 | B |
| ATOM | 2544 | CD | GLU | B | 334 | 28.595 | 58.553 | 0.230 | 1.00 | 124.87 | B |
| ATOM | 2545 | OE1 | GLU | B | 334 | 28.821 | 59.138 | 1.320 | 1.00 | 124.62 | B |
| ATOM | 2546 | OE2 | GLU | B | 334 | 29.245 | 57.558 | −0.181 | 1.00 | 125.93 | B |
| ATOM | 2547 | C | GLU | B | 334 | 26.202 | 62.432 | −1.881 | 1.00 | 120.90 | B |
| ATOM | 2548 | O | GLU | B | 334 | 25.058 | 62.879 | −1.812 | 1.00 | 121.05 | B |
| ATOM | 2549 | N | ASP | B | 335 | 27.284 | 63.196 | −1.951 | 1.00 | 121.75 | B |
| ATOM | 2550 | CA | ASP | B | 335 | 27.221 | 64.654 | −1.935 | 1.00 | 122.05 | B |
| ATOM | 2551 | CB | ASP | B | 335 | 28.446 | 65.203 | −2.666 | 1.00 | 122.92 | B |
| ATOM | 2552 | CG | ASP | B | 335 | 29.741 | 64.635 | −2.118 | 1.00 | 124.26 | B |
| ATOM | 2553 | OD1 | ASP | B | 335 | 29.935 | 63.393 | −2.187 | 1.00 | 124.37 | B |
| ATOM | 2554 | OD2 | ASP | B | 335 | 30.560 | 65.430 | −1.607 | 1.00 | 125.09 | B |
| ATOM | 2555 | C | ASP | B | 335 | 25.928 | 65.213 | −2.550 | 1.00 | 121.81 | B |
| ATOM | 2556 | O | ASP | B | 335 | 25.177 | 65.933 | −1.886 | 1.00 | 121.32 | B |
| ATOM | 2557 | N | GLN | B | 336 | 25.664 | 64.866 | −3.810 | 1.00 | 121.78 | B |
| ATOM | 2558 | CA | GLN | B | 336 | 24.469 | 65.338 | −4.506 | 1.00 | 122.16 | B |
| ATOM | 2559 | CB | GLN | B | 336 | 24.438 | 64.804 | −5.946 | 1.00 | 122.35 | B |
| ATOM | 2560 | CG | GLN | B | 336 | 25.406 | 65.522 | −6.890 | 1.00 | 123.33 | B |
| ATOM | 2561 | CD | GLN | B | 336 | 25.374 | 64.993 | −8.321 | 1.00 | 123.81 | B |
| ATOM | 2562 | OE1 | GLN | B | 336 | 24.303 | 64.813 | −8.912 | 1.00 | 123.02 | B |
| ATOM | 2563 | NE2 | GLN | B | 336 | 26.557 | 64.759 | −8.891 | 1.00 | 124.13 | B |
| ATOM | 2564 | C | GLN | B | 336 | 23.177 | 64.969 | −3.790 | 1.00 | 122.31 | B |
| ATOM | 2565 | O | GLN | B | 336 | 22.419 | 65.844 | −3.384 | 1.00 | 121.53 | B |
| ATOM | 2566 | N | SER | B | 337 | 22.931 | 63.671 | −3.634 | 1.00 | 123.30 | B |
| ATOM | 2567 | CA | SER | B | 337 | 21.722 | 63.198 | −2.962 | 1.00 | 124.05 | B |
| ATOM | 2568 | CB | SER | B | 337 | 21.685 | 61.668 | −2.952 | 1.00 | 124.30 | B |
| ATOM | 2569 | OG | SER | B | 337 | 22.749 | 61.142 | −2.178 | 1.00 | 124.90 | B |
| ATOM | 2570 | C | SER | B | 337 | 21.599 | 63.720 | −1.525 | 1.00 | 124.21 | B |
| ATOM | 2571 | O | SER | B | 337 | 20.492 | 63.967 | −1.048 | 1.00 | 124.83 | B |
| ATOM | 2572 | N | LYS | B | 338 | 22.732 | 63.887 | −0.841 | 1.00 | 123.97 | B |
| ATOM | 2573 | CA | LYS | B | 338 | 22.744 | 64.375 | 0.544 | 1.00 | 122.89 | B |
| ATOM | 2574 | CB | LYS | B | 338 | 24.136 | 64.167 | 1.169 | 1.00 | 123.67 | B |
| ATOM | 2575 | CG | LYS | B | 338 | 24.548 | 62.682 | 1.120 | 1.00 | 126.28 | B |
| ATOM | 2576 | CD | LYS | B | 338 | 25.753 | 62.276 | 1.993 | 1.00 | 127.34 | B |
| ATOM | 2577 | CE | LYS | B | 338 | 25.881 | 60.728 | 2.040 | 1.00 | 126.97 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2578 | NZ | LYS | B | 338 | 26.941 | 60.227 | 2.966 | 1.00 | 127.03 | B |
|---|---|---|---|---|---|---|---|---|---|---|---|
| ATOM | 2579 | C | LYS | B | 338 | 22.326 | 65.837 | 0.604 | 1.00 | 121.46 | B |
| ATOM | 2580 | O | LYS | B | 338 | 21.804 | 66.304 | 1.611 | 1.00 | 121.30 | B |
| ATOM | 2581 | N | LEU | B | 339 | 22.542 | 66.553 | −0.490 | 1.00 | 119.67 | B |
| ATOM | 2582 | CA | LEU | B | 339 | 22.156 | 67.952 | −0.557 | 1.00 | 118.03 | B |
| ATOM | 2583 | CB | LEU | B | 339 | 23.045 | 68.698 | −1.573 | 1.00 | 118.81 | B |
| ATOM | 2584 | CG | LEU | B | 339 | 24.380 | 69.330 | −1.135 | 1.00 | 119.16 | B |
| ATOM | 2585 | CD1 | LEU | B | 339 | 25.239 | 68.330 | −0.362 | 1.00 | 119.45 | B |
| ATOM | 2586 | CD2 | LEU | B | 339 | 25.108 | 69.842 | −2.372 | 1.00 | 118.22 | B |
| ATOM | 2587 | C | LEU | B | 339 | 20.675 | 68.083 | −0.953 | 1.00 | 116.42 | B |
| ATOM | 2588 | O | LEU | B | 339 | 20.067 | 69.151 | −0.794 | 1.00 | 116.07 | B |
| ATOM | 2589 | N | ALA | B | 340 | 20.098 | 66.996 | −1.466 | 1.00 | 114.32 | B |
| ATOM | 2590 | CA | ALA | B | 340 | 18.702 | 67.007 | −1.900 | 1.00 | 111.70 | B |
| ATOM | 2591 | CB | ALA | B | 340 | 18.551 | 66.209 | −3.190 | 1.00 | 110.90 | B |
| ATOM | 2592 | C | ALA | B | 340 | 17.749 | 66.480 | −0.828 | 1.00 | 109.42 | B |
| ATOM | 2593 | O | ALA | B | 340 | 16.532 | 66.401 | −1.050 | 1.00 | 108.00 | B |
| ATOM | 2594 | N | GLY | B | 341 | 18.317 | 66.138 | 0.331 | 1.00 | 107.60 | B |
| ATOM | 2595 | CA | GLY | B | 341 | 17.531 | 65.633 | 1.453 | 1.00 | 106.32 | B |
| ATOM | 2596 | C | GLY | B | 341 | 17.053 | 64.197 | 1.289 | 1.00 | 105.05 | B |
| ATOM | 2597 | O | GLY | B | 341 | 15.949 | 63.837 | 1.711 | 1.00 | 104.32 | B |
| ATOM | 2598 | N | LEU | B | 342 | 17.906 | 63.380 | 0.675 | 1.00 | 103.66 | B |
| ATOM | 2599 | CA | LEU | B | 342 | 17.611 | 61.983 | 0.400 | 1.00 | 101.13 | B |
| ATOM | 2600 | CB | LEU | B | 342 | 17.241 | 61.806 | −1.079 | 1.00 | 98.67 | B |
| ATOM | 2601 | CG | LEU | B | 342 | 16.112 | 62.683 | −1.621 | 1.00 | 97.09 | B |
| ATOM | 2602 | CD1 | LEU | B | 342 | 16.001 | 62.527 | −3.130 | 1.00 | 96.06 | B |
| ATOM | 2603 | CD2 | LEU | B | 342 | 14.820 | 62.320 | −0.924 | 1.00 | 96.08 | B |
| ATOM | 2604 | C | LEU | B | 342 | 18.839 | 61.146 | 0.717 | 1.00 | 100.72 | B |
| ATOM | 2605 | O | LEU | B | 342 | 19.038 | 60.088 | 0.136 | 1.00 | 100.34 | B |
| ATOM | 2606 | N | LEU | B | 343 | 19.669 | 61.621 | 1.632 | 1.00 | 100.96 | B |
| ATOM | 2607 | CA | LEU | B | 343 | 20.860 | 60.872 | 1.989 | 1.00 | 101.81 | B |
| ATOM | 2608 | CB | LEU | B | 343 | 21.602 | 61.587 | 3.118 | 1.00 | 102.50 | B |
| ATOM | 2609 | CG | LEU | B | 343 | 22.976 | 61.076 | 3.577 | 1.00 | 103.45 | B |
| ATOM | 2610 | CD1 | LEU | B | 343 | 23.462 | 61.953 | 4.728 | 1.00 | 104.25 | B |
| ATOM | 2611 | CD2 | LEU | B | 343 | 22.912 | 59.638 | 4.047 | 1.00 | 104.67 | B |
| ATOM | 2612 | C | LEU | B | 343 | 20.474 | 59.451 | 2.429 | 1.00 | 101.94 | B |
| ATOM | 2613 | O | LEU | B | 343 | 21.015 | 58.468 | 1.921 | 1.00 | 102.44 | B |
| ATOM | 2614 | N | ASP | B | 344 | 19.530 | 59.349 | 3.365 | 1.00 | 101.77 | B |
| ATOM | 2615 | CA | ASP | B | 344 | 19.083 | 58.052 | 3.901 | 1.00 | 100.58 | B |
| ATOM | 2616 | CB | ASP | B | 344 | 18.300 | 58.269 | 5.212 | 1.00 | 102.09 | B |
| ATOM | 2617 | CG | ASP | B | 344 | 19.213 | 58.624 | 6.396 | 1.00 | 103.41 | B |
| ATOM | 2618 | OD1 | ASP | B | 344 | 20.408 | 58.930 | 6.152 | 1.00 | 103.60 | B |
| ATOM | 2619 | OD2 | ASP | B | 344 | 18.739 | 58.603 | 7.562 | 1.00 | 103.70 | B |
| ATOM | 2620 | C | ASP | B | 344 | 18.267 | 57.165 | 2.953 | 1.00 | 98.42 | B |
| ATOM | 2621 | O | ASP | B | 344 | 18.489 | 55.958 | 2.902 | 1.00 | 98.48 | B |
| ATOM | 2622 | N | LEU | B | 345 | 17.330 | 57.756 | 2.217 | 1.00 | 95.47 | B |
| ATOM | 2623 | CA | LEU | B | 345 | 16.501 | 56.999 | 1.286 | 1.00 | 92.21 | B |
| ATOM | 2624 | CB | LEU | B | 345 | 15.430 | 57.889 | 0.676 | 1.00 | 92.76 | B |
| ATOM | 2625 | CG | LEU | B | 345 | 14.811 | 57.353 | −0.618 | 1.00 | 93.75 | B |
| ATOM | 2626 | CD1 | LEU | B | 345 | 14.154 | 55.990 | −0.386 | 1.00 | 94.25 | B |
| ATOM | 2627 | CD2 | LEU | B | 345 | 13.798 | 58.364 | −1.125 | 1.00 | 94.01 | B |
| ATOM | 2628 | C | LEU | B | 345 | 17.303 | 56.377 | 0.164 | 1.00 | 90.22 | B |
| ATOM | 2629 | O | LEU | B | 345 | 17.109 | 55.217 | −0.175 | 1.00 | 90.13 | B |
| ATOM | 2630 | N | ASN | B | 346 | 18.190 | 57.160 | −0.426 | 1.00 | 88.65 | B |
| ATOM | 2631 | CA | ASN | B | 346 | 19.017 | 56.674 | −1.515 | 1.00 | 86.89 | B |
| ATOM | 2632 | CB | ASN | B | 346 | 19.608 | 57.848 | −2.297 | 1.00 | 87.94 | B |
| ATOM | 2633 | CG | ASN | B | 346 | 18.611 | 58.477 | −3.241 | 1.00 | 89.47 | B |
| ATOM | 2634 | OD1 | ASN | B | 346 | 18.937 | 59.400 | −3.984 | 1.00 | 91.29 | B |
| ATOM | 2635 | ND2 | ASN | B | 346 | 17.385 | 57.980 | −3.222 | 1.00 | 90.95 | B |
| ATOM | 2636 | C | ASN | B | 346 | 20.127 | 55.756 | −1.020 | 1.00 | 85.51 | B |
| ATOM | 2637 | O | ASN | B | 346 | 20.729 | 55.019 | −1.799 | 1.00 | 85.58 | B |
| ATOM | 2638 | N | ASN | B | 347 | 20.408 | 55.796 | 0.274 | 1.00 | 84.07 | B |
| ATOM | 2639 | CA | ASN | B | 347 | 21.439 | 54.926 | 0.825 | 1.00 | 83.90 | B |
| ATOM | 2640 | CB | ASN | B | 347 | 21.884 | 55.433 | 2.195 | 1.00 | 84.30 | B |
| ATOM | 2641 | CG | ASN | B | 347 | 23.150 | 56.279 | 2.121 | 1.00 | 85.81 | B |
| ATOM | 2642 | OD1 | ASN | B | 347 | 23.402 | 57.128 | 2.981 | 1.00 | 87.77 | B |
| ATOM | 2643 | ND2 | ASN | B | 347 | 23.963 | 56.038 | 1.100 | 1.00 | 85.90 | B |
| ATOM | 2644 | C | ASN | B | 347 | 20.853 | 53.525 | 0.940 | 1.00 | 82.88 | B |
| ATOM | 2645 | O | ASN | B | 347 | 21.559 | 52.515 | 0.864 | 1.00 | 81.94 | B |
| ATOM | 2646 | N | ALA | B | 348 | 19.540 | 53.484 | 1.124 | 1.00 | 81.66 | B |
| ATOM | 2647 | CA | ALA | B | 348 | 18.823 | 52.231 | 1.235 | 1.00 | 79.98 | B |
| ATOM | 2648 | CB | ALA | B | 348 | 17.435 | 52.478 | 1.780 | 1.00 | 80.29 | B |
| ATOM | 2649 | C | ALA | B | 348 | 18.751 | 51.644 | −0.172 | 1.00 | 78.67 | B |
| ATOM | 2650 | O | ALA | B | 348 | 18.973 | 50.449 | −0.364 | 1.00 | 79.15 | B |
| ATOM | 2651 | N | ILE | B | 349 | 18.442 | 52.490 | −1.149 | 1.00 | 76.39 | B |
| ATOM | 2652 | CA | ILE | B | 349 | 18.373 | 52.060 | −2.533 | 1.00 | 74.53 | B |
| ATOM | 2653 | CB | ILE | B | 349 | 17.914 | 53.197 | −3.450 | 1.00 | 72.82 | B |

TABLE 1-continued

ATOMIC COORDINATES OF THE ERR3 LBD/SRC-1 NR BOX 2 PEPTIDE COMPLEX (PDB CODE 1KV6)

| ATOM | 2654 | CG2 | ILE | B | 349 | 17.739 | 52.684 | −4.878 | 1.00 | 72.10 | B |
|---|---|---|---|---|---|---|---|---|---|---|---|
| ATOM | 2655 | CG1 | ILE | B | 349 | 16.584 | 53.744 | −2.951 | 1.00 | 72.34 | B |
| ATOM | 2656 | CD1 | ILE | B | 349 | 15.874 | 54.605 | −3.957 | 1.00 | 72.45 | B |
| ATOM | 2657 | C | ILE | B | 349 | 19.725 | 51.549 | −3.020 | 1.00 | 74.88 | B |
| ATOM | 2658 | O | ILE | B | 349 | 19.787 | 50.762 | −3.962 | 1.00 | 74.16 | B |
| ATOM | 2659 | N | LEU | B | 350 | 20.807 | 52.002 | −2.393 | 1.00 | 76.25 | B |
| ATOM | 2660 | CA | LEU | B | 350 | 22.147 | 51.538 | −2.775 | 1.00 | 78.24 | B |
| ATOM | 2661 | CB | LEU | B | 350 | 23.247 | 52.562 | −2.422 | 1.00 | 80.09 | B |
| ATOM | 2662 | CG | LEU | B | 350 | 23.723 | 53.665 | −3.389 | 1.00 | 80.93 | B |
| ATOM | 2663 | CD1 | LEU | B | 350 | 25.136 | 54.082 | −2.949 | 1.00 | 79.29 | B |
| ATOM | 2664 | CD2 | LEU | B | 350 | 23.750 | 53.177 | −4.837 | 1.00 | 78.51 | B |
| ATOM | 2665 | C | LEU | B | 350 | 22.431 | 50.238 | −2.040 | 1.00 | 78.06 | B |
| ATOM | 2666 | O | LEU | B | 350 | 23.420 | 49.542 | −2.313 | 1.00 | 78.07 | B |
| ATOM | 2667 | N | GLN | B | 351 | 21.564 | 49.938 | −1.082 | 1.00 | 77.97 | B |
| ATOM | 2668 | CA | GLN | B | 351 | 21.672 | 48.711 | −0.311 | 1.00 | 77.90 | B |
| ATOM | 2669 | CB | GLN | B | 351 | 20.790 | 48.810 | 0.929 | 1.00 | 78.31 | B |
| ATOM | 2670 | CG | GLN | B | 351 | 21.420 | 48.227 | 2.162 | 1.00 | 80.60 | B |
| ATOM | 2671 | CD | GLN | B | 351 | 20.521 | 48.360 | 3.371 | 1.00 | 82.25 | B |
| ATOM | 2672 | OE1 | GLN | B | 351 | 20.107 | 49.463 | 3.741 | 1.00 | 82.79 | B |
| ATOM | 2673 | NE2 | GLN | B | 351 | 20.210 | 47.233 | 3.994 | 1.00 | 83.72 | B |
| ATOM | 2674 | C | GLN | B | 351 | 21.190 | 47.597 | −1.265 | 1.00 | 77.19 | B |
| ATOM | 2675 | O | GLN | B | 351 | 21.832 | 46.547 | −1.380 | 1.00 | 75.79 | B |
| ATOM | 2676 | N | LEU | B | 352 | 20.072 | 47.859 | −1.957 | 1.00 | 75.76 | B |
| ATOM | 2677 | CA | LEU | B | 352 | 19.513 | 46.937 | −2.946 | 1.00 | 74.50 | B |
| ATOM | 2678 | CB | LEU | B | 352 | 18.282 | 47.547 | −3.622 | 1.00 | 74.24 | B |
| ATOM | 2679 | CG | LEU | B | 352 | 17.039 | 47.384 | −2.751 | 1.00 | 75.10 | B |
| ATOM | 2680 | CD1 | LEU | B | 352 | 15.862 | 48.229 | −3.243 | 1.00 | 75.59 | B |
| ATOM | 2681 | CD2 | LEU | B | 352 | 16.696 | 45.902 | −2.738 | 1.00 | 76.43 | B |
| ATOM | 2682 | C | LEU | B | 352 | 20.582 | 46.654 | −3.990 | 1.00 | 73.30 | B |
| ATOM | 2683 | O | LEU | B | 352 | 20.948 | 45.497 | −4.228 | 1.00 | 74.29 | B |
| ATOM | 2684 | N | VAL | B | 353 | 21.080 | 47.727 | −4.600 | 1.00 | 71.64 | B |
| ATOM | 2685 | CA | VAL | B | 353 | 22.126 | 47.652 | −5.615 | 1.00 | 68.84 | B |
| ATOM | 2686 | CB | VAL | B | 353 | 22.814 | 49.037 | −5.848 | 1.00 | 67.54 | B |
| ATOM | 2687 | CG1 | VAL | B | 353 | 24.000 | 48.879 | −6.842 | 1.00 | 62.14 | B |
| ATOM | 2688 | CG2 | VAL | B | 353 | 21.775 | 50.059 | −6.369 | 1.00 | 65.97 | B |
| ATOM | 2689 | C | VAL | B | 353 | 23.206 | 46.670 | −5.212 | 1.00 | 67.97 | B |
| ATOM | 2690 | O | VAL | B | 353 | 23.502 | 45.747 | −5.953 | 1.00 | 66.99 | B |
| ATOM | 2691 | N | LYS | B | 354 | 23.790 | 46.881 | −4.040 | 1.00 | 68.10 | B |
| ATOM | 2692 | CA | LYS | B | 354 | 24.860 | 46.022 | −3.548 | 1.00 | 68.80 | B |
| ATOM | 2693 | CB | LYS | B | 354 | 25.241 | 46.420 | −2.119 | 1.00 | 71.44 | B |
| ATOM | 2694 | CG | LYS | B | 354 | 26.422 | 45.628 | −1.569 | 1.00 | 74.22 | B |
| ATOM | 2695 | CD | LYS | B | 354 | 26.755 | 45.955 | −0.110 | 1.00 | 74.76 | B |
| ATOM | 2696 | CE | LYS | B | 354 | 27.850 | 45.015 | 0.376 | 1.00 | 76.39 | B |
| ATOM | 2697 | NZ | LYS | B | 354 | 28.302 | 45.275 | 1.772 | 1.00 | 79.57 | B |
| ATOM | 2698 | C | LYS | B | 354 | 24.524 | 44.537 | −3.584 | 1.00 | 68.27 | B |
| ATOM | 2699 | O | LYS | B | 354 | 25.368 | 43.711 | −3.958 | 1.00 | 66.54 | B |
| ATOM | 2700 | N | LYS | B | 355 | 23.294 | 44.199 | −3.199 | 1.00 | 67.88 | B |
| ATOM | 2701 | CA | LYS | B | 355 | 22.882 | 42.801 | −3.195 | 1.00 | 68.78 | B |
| ATOM | 2702 | CB | LYS | B | 355 | 21.518 | 42.621 | −2.508 | 1.00 | 72.37 | B |
| ATOM | 2703 | CG | LYS | B | 355 | 20.983 | 41.154 | −2.507 | 1.00 | 73.57 | B |
| ATOM | 2704 | CD | LYS | B | 355 | 21.601 | 40.274 | −1.412 | 1.00 | 74.86 | B |
| ATOM | 2705 | CE | LYS | B | 355 | 21.211 | 40.774 | 0.000 | 1.00 | 77.14 | B |
| ATOM | 2706 | NZ | LYS | B | 355 | 21.538 | 39.805 | 1.117 | 1.00 | 75.99 | B |
| ATOM | 2707 | C | LYS | B | 355 | 22.802 | 42.278 | −4.617 | 1.00 | 67.52 | B |
| ATOM | 2708 | O | LYS | B | 355 | 23.426 | 41.263 | −4.961 | 1.00 | 66.20 | B |
| ATOM | 2709 | N | TYR | B | 356 | 22.046 | 42.978 | −5.454 | 1.00 | 65.85 | B |
| ATOM | 2710 | CA | TYR | B | 356 | 21.917 | 42.545 | −6.833 | 1.00 | 65.75 | B |
| ATOM | 2711 | CB | TYR | B | 356 | 20.938 | 43.434 | −7.586 | 1.00 | 62.85 | B |
| ATOM | 2712 | CG | TYR | B | 356 | 19.512 | 43.273 | −7.138 | 1.00 | 63.28 | B |
| ATOM | 2713 | CD1 | TYR | B | 356 | 18.963 | 42.000 | −6.918 | 1.00 | 62.45 | B |
| ATOM | 2714 | CE1 | TYR | B | 356 | 17.625 | 41.857 | −6.571 | 1.00 | 64.32 | B |
| ATOM | 2715 | CD2 | TYR | B | 356 | 18.682 | 44.391 | −6.995 | 1.00 | 63.67 | B |
| ATOM | 2716 | CE2 | TYR | B | 356 | 17.347 | 44.262 | −6.653 | 1.00 | 63.03 | B |
| ATOM | 2717 | CZ | TYR | B | 356 | 16.824 | 43.001 | −6.446 | 1.00 | 64.05 | B |
| ATOM | 2718 | OH | TYR | B | 356 | 15.502 | 42.902 | −6.125 | 1.00 | 63.39 | B |
| ATOM | 2719 | C | TYR | B | 356 | 23.262 | 42.497 | −7.554 | 1.00 | 66.39 | B |
| ATOM | 2720 | O | TYR | B | 356 | 23.490 | 41.621 | −8.392 | 1.00 | 66.59 | B |
| ATOM | 2721 | N | LYS | B | 357 | 24.146 | 43.442 | −7.224 | 1.00 | 68.55 | B |
| ATOM | 2722 | CA | LYS | B | 357 | 25.489 | 43.518 | −7.818 | 1.00 | 68.58 | B |
| ATOM | 2723 | CB | LYS | B | 357 | 26.242 | 44.721 | −7.235 | 1.00 | 70.70 | B |
| ATOM | 2724 | CG | LYS | B | 357 | 26.731 | 45.775 | −8.236 | 1.00 | 73.63 | B |
| ATOM | 2725 | CD | LYS | B | 357 | 27.289 | 46.978 | −7.453 | 1.00 | 77.97 | B |
| ATOM | 2726 | CE | LYS | B | 357 | 28.212 | 47.887 | −8.282 | 1.00 | 79.23 | B |
| ATOM | 2727 | NZ | LYS | B | 357 | 28.961 | 48.822 | −7.380 | 1.00 | 80.00 | B |
| ATOM | 2728 | C | LYS | B | 357 | 26.228 | 42.233 | −7.453 | 1.00 | 66.84 | B |
| ATOM | 2729 | O | LYS | B | 357 | 26.812 | 41.553 | −8.283 | 1.00 | 62.96 | B |

TABLE 1-continued

ATOMIC COORDINATES OF THE ERR3 LBD/SRC-1 NR BOX 2 PEPTIDE COMPLEX (PDB CODE 1KV6)

| ATOM | 2730 | N   | SER | B | 358 | 26.168 | 41.921 | -6.171  | 1.00 | 67.94 | B |
|------|------|-----|-----|---|-----|--------|--------|---------|------|-------|---|
| ATOM | 2731 | CA  | SER | B | 358 | 26.813 | 40.757 | -5.621  | 1.00 | 69.00 | B |
| ATOM | 2732 | CB  | SER | B | 358 | 26.635 | 40.782 | -4.113  | 1.00 | 68.77 | B |
| ATOM | 2733 | OG  | SER | B | 358 | 27.429 | 39.773 | -3.534  | 1.00 | 70.56 | B |
| ATOM | 2734 | C   | SER | B | 358 | 26.253 | 39.456 | -6.193  | 1.00 | 70.68 | B |
| ATOM | 2735 | O   | SER | B | 358 | 26.937 | 38.420 | -6.209  | 1.00 | 70.06 | B |
| ATOM | 2736 | N   | MET | B | 359 | 25.002 | 39.505 | -6.654  | 1.00 | 71.06 | B |
| ATOM | 2737 | CA  | MET | B | 359 | 24.367 | 38.324 | -7.220  | 1.00 | 70.91 | B |
| ATOM | 2738 | CB  | MET | B | 359 | 22.864 | 38.356 | -6.975  | 1.00 | 70.81 | B |
| ATOM | 2739 | CG  | MET | B | 359 | 22.513 | 38.446 | -5.520  | 1.00 | 74.90 | B |
| ATOM | 2740 | SD  | MET | B | 359 | 20.759 | 38.246 | -5.229  | 1.00 | 75.59 | B |
| ATOM | 2741 | CE  | MET | B | 359 | 20.618 | 36.436 | -5.564  | 1.00 | 77.47 | B |
| ATOM | 2742 | C   | MET | B | 359 | 24.621 | 38.222 | -8.706  | 1.00 | 70.06 | B |
| ATOM | 2743 | O   | MET | B | 359 | 24.642 | 37.119 | -9.262  | 1.00 | 70.98 | B |
| ATOM | 2744 | N   | LYS | B | 360 | 24.813 | 39.384 | -9.330  | 1.00 | 68.96 | B |
| ATOM | 2745 | CA  | LYS | B | 360 | 25.044 | 39.516 | -10.763 | 1.00 | 67.61 | B |
| ATOM | 2746 | CB  | LYS | B | 360 | 26.065 | 38.499 | -11.256 | 1.00 | 71.03 | B |
| ATOM | 2747 | CG  | LYS | B | 360 | 27.477 | 38.804 | -10.794 | 1.00 | 74.94 | B |
| ATOM | 2748 | CD  | LYS | B | 360 | 28.407 | 37.736 | -11.274 | 1.00 | 79.55 | B |
| ATOM | 2749 | CE  | LYS | B | 360 | 29.780 | 37.932 | -10.673 | 1.00 | 83.88 | B |
| ATOM | 2750 | NZ  | LYS | B | 360 | 30.593 | 36.674 | -10.808 | 1.00 | 87.82 | B |
| ATOM | 2751 | C   | LYS | B | 360 | 23.726 | 39.356 | -11.461 | 1.00 | 64.82 | B |
| ATOM | 2752 | O   | LYS | B | 360 | 23.573 | 38.608 | -12.421 | 1.00 | 62.07 | B |
| ATOM | 2753 | N   | LEU | B | 361 | 22.771 | 40.085 | -10.923 | 1.00 | 63.73 | B |
| ATOM | 2754 | CA  | LEU | B | 361 | 21.433 | 40.120 | -11.433 | 1.00 | 64.73 | B |
| ATOM | 2755 | CB  | LEU | B | 361 | 20.736 | 41.352 | -10.869 | 1.00 | 63.61 | B |
| ATOM | 2756 | CG  | LEU | B | 361 | 19.276 | 41.519 | -11.289 | 1.00 | 64.00 | B |
| ATOM | 2757 | CD1 | LEU | B | 361 | 18.490 | 40.222 | -10.916 | 1.00 | 61.26 | B |
| ATOM | 2758 | CD2 | LEU | B | 361 | 18.689 | 42.808 | -10.636 | 1.00 | 63.25 | B |
| ATOM | 2759 | C   | LEU | B | 361 | 21.478 | 40.209 | -12.952 | 1.00 | 64.76 | B |
| ATOM | 2760 | O   | LEU | B | 361 | 22.314 | 40.908 | -13.497 | 1.00 | 67.70 | B |
| ATOM | 2761 | N   | GLU | B | 362 | 20.581 | 39.505 | -13.635 | 1.00 | 64.34 | B |
| ATOM | 2762 | CA  | GLU | B | 362 | 20.520 | 39.551 | -15.097 | 1.00 | 63.87 | B |
| ATOM | 2763 | CB  | GLU | B | 362 | 20.575 | 38.147 | -15.684 | 1.00 | 62.78 | B |
| ATOM | 2764 | CG  | GLU | B | 362 | 21.776 | 37.395 | -15.222 | 1.00 | 67.21 | B |
| ATOM | 2765 | CD  | GLU | B | 362 | 21.717 | 35.946 | -15.595 | 1.00 | 70.72 | B |
| ATOM | 2766 | OE1 | GLU | B | 362 | 20.622 | 35.359 | -15.494 | 1.00 | 72.37 | B |
| ATOM | 2767 | OE2 | GLU | B | 362 | 22.764 | 35.373 | -15.977 | 1.00 | 74.47 | B |
| ATOM | 2768 | C   | GLU | B | 362 | 19.247 | 40.267 | -15.548 | 1.00 | 63.75 | B |
| ATOM | 2769 | O   | GLU | B | 362 | 18.323 | 40.506 | -14.753 | 1.00 | 62.42 | B |
| ATOM | 2770 | N   | LYS | B | 363 | 19.204 | 40.636 | -16.824 | 1.00 | 64.58 | B |
| ATOM | 2771 | CA  | LYS | B | 363 | 18.043 | 41.347 | -17.327 | 1.00 | 64.79 | B |
| ATOM | 2772 | CB  | LYS | B | 363 | 18.319 | 41.849 | -18.755 | 1.00 | 66.89 | B |
| ATOM | 2773 | CG  | LYS | B | 363 | 17.617 | 43.160 | -19.153 | 1.00 | 69.66 | B |
| ATOM | 2774 | CD  | LYS | B | 363 | 17.678 | 43.347 | -20.683 | 1.00 | 74.90 | B |
| ATOM | 2775 | CE  | LYS | B | 363 | 16.793 | 44.516 | -21.231 | 1.00 | 76.79 | B |
| ATOM | 2776 | NZ  | LYS | B | 363 | 16.307 | 44.272 | -22.678 | 1.00 | 77.81 | B |
| ATOM | 2777 | C   | LYS | B | 363 | 16.838 | 40.400 | -17.272 | 1.00 | 63.79 | B |
| ATOM | 2778 | O   | LYS | B | 363 | 15.728 | 40.837 | -16.959 | 1.00 | 63.12 | B |
| ATOM | 2779 | N   | GLU | B | 364 | 17.077 | 39.115 | -17.565 | 1.00 | 64.00 | B |
| ATOM | 2780 | CA  | GLU | B | 364 | 16.050 | 38.061 | -17.543 | 1.00 | 65.58 | B |
| ATOM | 2781 | CB  | GLU | B | 364 | 16.627 | 36.673 | -17.871 | 1.00 | 68.36 | B |
| ATOM | 2782 | CG  | GLU | B | 364 | 17.077 | 36.477 | -19.303 | 1.00 | 71.75 | B |
| ATOM | 2783 | CD  | GLU | B | 364 | 18.432 | 37.118 | -19.572 | 1.00 | 74.90 | B |
| ATOM | 2784 | OE1 | GLU | B | 364 | 19.008 | 36.914 | -20.670 | 1.00 | 76.59 | B |
| ATOM | 2785 | OE2 | GLU | B | 364 | 18.934 | 37.826 | -18.675 | 1.00 | 76.80 | B |
| ATOM | 2786 | C   | GLU | B | 364 | 15.468 | 37.983 | -16.160 | 1.00 | 65.27 | B |
| ATOM | 2787 | O   | GLU | B | 364 | 14.250 | 37.880 | -15.974 | 1.00 | 65.87 | B |
| ATOM | 2788 | N   | GLU | B | 365 | 16.358 | 38.015 | -15.178 | 1.00 | 64.24 | B |
| ATOM | 2789 | CA  | GLU | B | 365 | 15.926 | 37.963 | -13.799 | 1.00 | 62.98 | B |
| ATOM | 2790 | CB  | GLU | B | 365 | 17.114 | 37.635 | -12.902 | 1.00 | 61.75 | B |
| ATOM | 2791 | CG  | GLU | B | 365 | 17.808 | 36.373 | -13.350 | 1.00 | 60.66 | B |
| ATOM | 2792 | CD  | GLU | B | 365 | 19.043 | 36.041 | -12.543 | 1.00 | 62.90 | B |
| ATOM | 2793 | OE1 | GLU | B | 365 | 19.899 | 36.923 | -12.353 | 1.00 | 64.47 | B |
| ATOM | 2794 | OE2 | GLU | B | 365 | 19.175 | 34.887 | -12.100 | 1.00 | 63.73 | B |
| ATOM | 2795 | C   | GLU | B | 365 | 15.263 | 39.280 | -13.403 | 1.00 | 63.02 | B |
| ATOM | 2796 | O   | GLU | B | 365 | 14.219 | 39.263 | -12.771 | 1.00 | 65.88 | B |
| ATOM | 2797 | N   | PHE | B | 366 | 15.829 | 40.417 | -13.805 | 1.00 | 62.03 | B |
| ATOM | 2798 | CA  | PHE | B | 366 | 15.257 | 41.715 | -13.453 | 1.00 | 61.38 | B |
| ATOM | 2799 | CB  | PHE | B | 366 | 16.133 | 42.837 | -14.009 | 1.00 | 63.01 | B |
| ATOM | 2800 | CG  | PHE | B | 366 | 15.457 | 44.193 | -14.031 | 1.00 | 61.90 | B |
| ATOM | 2801 | CD1 | PHE | B | 366 | 15.011 | 44.786 | -12.863 | 1.00 | 60.07 | B |
| ATOM | 2802 | CD2 | PHE | B | 366 | 15.229 | 44.853 | -15.236 | 1.00 | 62.56 | B |
| ATOM | 2803 | CE1 | PHE | B | 366 | 14.341 | 46.015 | -12.891 | 1.00 | 61.32 | B |
| ATOM | 2804 | CE2 | PHE | B | 366 | 14.555 | 46.089 | -15.264 | 1.00 | 62.69 | B |
| ATOM | 2805 | CZ  | PHE | B | 366 | 14.112 | 46.663 | -14.089 | 1.00 | 60.90 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2806 | C | PHE | B | 366 | 13.824 | 41.907 | −13.923 | 1.00 | 60.31 | B |
|---|---|---|---|---|---|---|---|---|---|---|---|
| ATOM | 2807 | O | PHE | B | 366 | 12.956 | 42.271 | −13.147 | 1.00 | 60.58 | B |
| ATOM | 2808 | N | VAL | B | 367 | 13.568 | 41.674 | −15.195 | 1.00 | 59.35 | B |
| ATOM | 2809 | CA | VAL | B | 367 | 12.211 | 41.849 | −15.696 | 1.00 | 60.63 | B |
| ATOM | 2810 | CB | VAL | B | 367 | 12.174 | 41.678 | −17.235 | 1.00 | 58.75 | B |
| ATOM | 2811 | CG1 | VAL | B | 367 | 13.118 | 42.651 | −17.857 | 1.00 | 57.43 | B |
| ATOM | 2812 | CG2 | VAL | B | 367 | 12.547 | 40.248 | −17.617 | 1.00 | 57.04 | B |
| ATOM | 2813 | C | VAL | B | 367 | 11.168 | 40.899 | −15.064 | 1.00 | 61.84 | B |
| ATOM | 2814 | O | VAL | B | 367 | 9.976 | 41.249 | −14.956 | 1.00 | 62.71 | B |
| ATOM | 2815 | N | THR | B | 368 | 11.605 | 39.695 | −14.680 | 1.00 | 62.08 | B |
| ATOM | 2816 | CA | THR | B | 368 | 10.711 | 38.711 | −14.048 | 1.00 | 61.53 | B |
| ATOM | 2817 | CB | THR | B | 368 | 11.296 | 37.297 | −14.086 | 1.00 | 60.61 | B |
| ATOM | 2818 | OG1 | THR | B | 368 | 11.552 | 36.934 | −15.439 | 1.00 | 59.16 | B |
| ATOM | 2819 | CG2 | THR | B | 368 | 10.318 | 36.314 | −13.525 | 1.00 | 57.65 | B |
| ATOM | 2820 | C | THR | B | 368 | 10.450 | 39.083 | −12.591 | 1.00 | 60.96 | B |
| ATOM | 2821 | O | THR | B | 368 | 9.347 | 38.918 | −12.078 | 1.00 | 61.52 | B |
| ATOM | 2822 | N | LEU | B | 369 | 11.470 | 39.592 | −11.931 | 1.00 | 59.54 | B |
| ATOM | 2823 | CA | LEU | B | 369 | 11.322 | 40.011 | −10.554 | 1.00 | 60.14 | B |
| ATOM | 2824 | CB | LEU | B | 369 | 12.664 | 40.421 | −10.006 | 1.00 | 59.67 | B |
| ATOM | 2825 | CG | LEU | B | 369 | 12.909 | 40.078 | −8.564 | 1.00 | 58.73 | B |
| ATOM | 2826 | CD1 | LEU | B | 369 | 12.755 | 38.566 | −8.384 | 1.00 | 60.09 | B |
| ATOM | 2827 | CD2 | LEU | B | 369 | 14.332 | 40.535 | −8.219 | 1.00 | 61.57 | B |
| ATOM | 2828 | C | LEU | B | 369 | 10.377 | 41.208 | −10.471 | 1.00 | 60.20 | B |
| ATOM | 2829 | O | LEU | B | 369 | 9.548 | 41.311 | −9.583 | 1.00 | 60.34 | B |
| ATOM | 2830 | N | LYS | B | 370 | 10.509 | 42.119 | −11.412 | 1.00 | 61.05 | B |
| ATOM | 2831 | CA | LYS | B | 370 | 9.680 | 43.317 | −11.442 | 1.00 | 61.75 | B |
| ATOM | 2832 | CB | LYS | B | 370 | 10.166 | 44.168 | −12.605 | 1.00 | 64.53 | B |
| ATOM | 2833 | CG | LYS | B | 370 | 9.715 | 45.594 | −12.634 | 1.00 | 69.37 | B |
| ATOM | 2834 | CD | LYS | B | 370 | 10.718 | 46.413 | −13.503 | 1.00 | 71.89 | B |
| ATOM | 2835 | CE | LYS | B | 370 | 10.719 | 46.013 | −14.994 | 1.00 | 73.13 | B |
| ATOM | 2836 | NZ | LYS | B | 370 | 9.672 | 46.746 | −15.816 | 1.00 | 74.52 | B |
| ATOM | 2837 | C | LYS | B | 370 | 8.188 | 42.957 | −11.576 | 1.00 | 60.81 | B |
| ATOM | 2838 | O | LYS | B | 370 | 7.343 | 43.557 | −10.928 | 1.00 | 59.69 | B |
| ATOM | 2839 | N | ALA | B | 371 | 7.878 | 41.969 | −12.417 | 1.00 | 59.94 | B |
| ATOM | 2840 | CA | ALA | B | 371 | 6.498 | 41.526 | −12.622 | 1.00 | 59.92 | B |
| ATOM | 2841 | CB | ALA | B | 371 | 6.434 | 40.604 | −13.821 | 1.00 | 60.78 | B |
| ATOM | 2842 | C | ALA | B | 371 | 5.989 | 40.801 | −11.359 | 1.00 | 59.19 | B |
| ATOM | 2843 | O | ALA | B | 371 | 4.856 | 40.998 | −10.897 | 1.00 | 58.40 | B |
| ATOM | 2844 | N | ILE | B | 372 | 6.841 | 39.943 | −10.818 | 1.00 | 58.03 | B |
| ATOM | 2845 | CA | ILE | B | 372 | 6.524 | 39.235 | −9.599 | 1.00 | 57.40 | B |
| ATOM | 2846 | CB | ILE | B | 372 | 7.692 | 38.316 | −9.226 | 1.00 | 56.30 | B |
| ATOM | 2847 | CG2 | ILE | B | 372 | 7.673 | 38.003 | −7.725 | 1.00 | 55.25 | B |
| ATOM | 2848 | CG1 | ILE | B | 372 | 7.662 | 37.093 | −10.136 | 1.00 | 56.03 | B |
| ATOM | 2849 | CD1 | ILE | B | 372 | 8.763 | 36.067 | −9.854 | 1.00 | 56.57 | B |
| ATOM | 2850 | C | ILE | B | 372 | 6.216 | 40.232 | −8.451 | 1.00 | 58.07 | B |
| ATOM | 2851 | O | ILE | B | 372 | 5.347 | 39.972 | −7.615 | 1.00 | 57.58 | B |
| ATOM | 2852 | N | ALA | B | 373 | 6.909 | 41.373 | −8.402 | 1.00 | 58.95 | B |
| ATOM | 2853 | CA | ALA | B | 373 | 6.655 | 42.349 | −7.340 | 1.00 | 58.77 | B |
| ATOM | 2854 | CB | ALA | B | 373 | 7.844 | 43.261 | −7.182 | 1.00 | 59.56 | B |
| ATOM | 2855 | C | ALA | B | 373 | 5.351 | 43.159 | −7.560 | 1.00 | 60.09 | B |
| ATOM | 2856 | O | ALA | B | 373 | 4.798 | 43.721 | −6.636 | 1.00 | 61.06 | B |
| ATOM | 2857 | N | LEU | B | 374 | 4.853 | 43.213 | −8.782 | 1.00 | 61.39 | B |
| ATOM | 2858 | CA | LEU | B | 374 | 3.605 | 43.906 | −9.022 | 1.00 | 62.83 | B |
| ATOM | 2859 | CB | LEU | B | 374 | 3.517 | 44.363 | −10.496 | 1.00 | 62.50 | B |
| ATOM | 2860 | CG | LEU | B | 374 | 2.160 | 44.933 | −10.981 | 1.00 | 62.76 | B |
| ATOM | 2861 | CD1 | LEU | B | 374 | 1.841 | 46.230 | −10.246 | 1.00 | 59.66 | B |
| ATOM | 2862 | CD2 | LEU | B | 374 | 2.185 | 45.174 | −12.491 | 1.00 | 61.68 | B |
| ATOM | 2863 | C | LEU | B | 374 | 2.475 | 42.894 | −8.686 | 1.00 | 63.87 | B |
| ATOM | 2864 | O | LEU | B | 374 | 1.456 | 43.245 | −8.078 | 1.00 | 65.17 | B |
| ATOM | 2865 | N | ALA | B | 375 | 2.650 | 41.641 | −9.086 | 1.00 | 63.31 | B |
| ATOM | 2866 | CA | ALA | B | 375 | 1.650 | 40.631 | −8.799 | 1.00 | 64.59 | B |
| ATOM | 2867 | CB | ALA | B | 375 | 1.963 | 39.376 | −9.604 | 1.00 | 64.98 | B |
| ATOM | 2868 | C | ALA | B | 375 | 1.589 | 40.293 | −7.290 | 1.00 | 65.95 | B |
| ATOM | 2869 | O | ALA | B | 375 | 0.527 | 39.962 | −6.752 | 1.00 | 64.57 | B |
| ATOM | 2870 | N | ASN | B | 376 | 2.734 | 40.389 | −6.619 | 1.00 | 66.19 | B |
| ATOM | 2871 | CA | ASN | B | 376 | 2.848 | 40.069 | −5.212 | 1.00 | 66.27 | B |
| ATOM | 2872 | CB | ASN | B | 376 | 4.146 | 39.286 | −5.031 | 1.00 | 67.51 | B |
| ATOM | 2873 | CG | ASN | B | 376 | 4.227 | 38.571 | −3.700 | 1.00 | 70.52 | B |
| ATOM | 2874 | OD1 | ASN | B | 376 | 3.276 | 37.916 | −3.271 | 1.00 | 73.73 | B |
| ATOM | 2875 | ND2 | ASN | B | 376 | 5.377 | 38.673 | −3.042 | 1.00 | 72.59 | B |
| ATOM | 2876 | C | ASN | B | 376 | 2.850 | 41.378 | −4.430 | 1.00 | 66.75 | B |
| ATOM | 2877 | O | ASN | B | 376 | 3.595 | 41.553 | −3.467 | 1.00 | 67.13 | B |
| ATOM | 2878 | N | SER | B | 377 | 1.980 | 42.288 | −4.841 | 1.00 | 67.46 | B |
| ATOM | 2879 | CA | SER | B | 377 | 1.891 | 43.613 | −4.239 | 1.00 | 70.44 | B |
| ATOM | 2880 | CB | SER | B | 377 | 1.133 | 44.558 | −5.182 | 1.00 | 69.82 | B |
| ATOM | 2881 | OG | SER | B | 377 | −0.196 | 44.115 | −5.392 | 1.00 | 68.83 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2882 | C | SER | B | 377 | 1.284 | 43.698 | −2.846 | 1.00 | 72.44 | B |
|---|---|---|---|---|---|---|---|---|---|---|---|
| ATOM | 2883 | O | SER | B | 377 | 1.557 | 44.651 | −2.102 | 1.00 | 73.22 | B |
| ATOM | 2884 | N | ASP | B | 378 | 0.461 | 42.720 | −2.486 | 1.00 | 75.09 | B |
| ATOM | 2885 | CA | ASP | B | 378 | −0.175 | 42.702 | −1.165 | 1.00 | 77.67 | B |
| ATOM | 2886 | CB | ASP | B | 378 | 0.874 | 42.706 | −0.037 | 1.00 | 79.18 | B |
| ATOM | 2887 | CG | ASP | B | 378 | 1.580 | 41.360 | 0.110 | 1.00 | 81.69 | B |
| ATOM | 2888 | OD1 | ASP | B | 378 | 2.810 | 41.271 | −0.119 | 1.00 | 82.90 | B |
| ATOM | 2889 | OD2 | ASP | B | 378 | 0.894 | 40.374 | 0.446 | 1.00 | 84.35 | B |
| ATOM | 2890 | C | ASP | B | 378 | −1.145 | 43.851 | −0.963 | 1.00 | 78.50 | B |
| ATOM | 2891 | O | ASP | B | 378 | −1.185 | 44.473 | 0.100 | 1.00 | 77.25 | B |
| ATOM | 2892 | N | SER | B | 379 | −1.921 | 44.136 | −1.999 | 1.00 | 80.13 | B |
| ATOM | 2893 | CA | SER | B | 379 | −2.922 | 45.185 | −1.904 | 1.00 | 83.12 | B |
| ATOM | 2894 | CB | SER | B | 379 | −3.529 | 45.494 | −3.275 | 1.00 | 81.77 | B |
| ATOM | 2895 | OG | SER | B | 379 | −4.363 | 46.630 | −3.192 | 1.00 | 77.85 | B |
| ATOM | 2896 | C | SER | B | 379 | −3.995 | 44.578 | −1.017 | 1.00 | 86.09 | B |
| ATOM | 2897 | O | SER | B | 379 | −4.230 | 43.367 | −1.093 | 1.00 | 86.46 | B |
| ATOM | 2898 | N | MET | B | 380 | −4.650 | 45.391 | −0.189 | 1.00 | 88.74 | B |
| ATOM | 2899 | CA | MET | B | 380 | −5.698 | 44.865 | 0.683 | 1.00 | 90.96 | B |
| ATOM | 2900 | CB | MET | B | 380 | −5.618 | 45.514 | 2.068 | 1.00 | 93.30 | B |
| ATOM | 2901 | CG | MET | B | 380 | −5.761 | 47.032 | 2.029 | 1.00 | 97.53 | B |
| ATOM | 2902 | SD | MET | B | 380 | −5.277 | 47.884 | 3.573 | 1.00 | 102.77 | B |
| ATOM | 2903 | CE | MET | B | 380 | −3.852 | 49.020 | 3.020 | 1.00 | 101.34 | B |
| ATOM | 2904 | C | MET | B | 380 | −7.093 | 45.073 | 0.116 | 1.00 | 90.92 | B |
| ATOM | 2905 | O | MET | B | 380 | −8.061 | 44.899 | 0.837 | 1.00 | 91.35 | B |
| ATOM | 2906 | N | HIS | B | 381 | −7.197 | 45.430 | −1.166 | 1.00 | 91.65 | B |
| ATOM | 2907 | CA | HIS | B | 381 | −8.503 | 45.680 | −1.795 | 1.00 | 92.35 | B |
| ATOM | 2908 | CB | HIS | B | 381 | −8.612 | 47.139 | −2.253 | 1.00 | 93.02 | B |
| ATOM | 2909 | CG | HIS | B | 381 | −8.273 | 48.152 | −1.202 | 1.00 | 94.34 | B |
| ATOM | 2910 | CD2 | HIS | B | 381 | −9.066 | 48.926 | −0.420 | 1.00 | 94.01 | B |
| ATOM | 2911 | ND1 | HIS | B | 381 | −6.976 | 48.520 | −0.912 | 1.00 | 95.61 | B |
| ATOM | 2912 | CE1 | HIS | B | 381 | −6.983 | 49.480 | −0.002 | 1.00 | 95.27 | B |
| ATOM | 2913 | NE2 | HIS | B | 381 | −8.238 | 49.746 | 0.312 | 1.00 | 94.70 | B |
| ATOM | 2914 | C | HIS | B | 381 | −8.837 | 44.797 | −3.005 | 1.00 | 92.47 | B |
| ATOM | 2915 | O | HIS | B | 381 | −9.796 | 45.060 | −3.737 | 1.00 | 92.11 | B |
| ATOM | 2916 | N | ILE | B | 382 | −8.059 | 43.755 | −3.230 | 1.00 | 92.95 | B |
| ATOM | 2917 | CA | ILE | B | 382 | −8.318 | 42.909 | −4.379 | 1.00 | 94.29 | B |
| ATOM | 2918 | CB | ILE | B | 382 | −7.248 | 41.824 | −4.519 | 1.00 | 94.78 | B |
| ATOM | 2919 | CG2 | ILE | B | 382 | −7.726 | 40.737 | −5.469 | 1.00 | 94.09 | B |
| ATOM | 2920 | CG1 | ILE | B | 382 | −5.949 | 42.457 | −5.021 | 1.00 | 95.34 | B |
| ATOM | 2921 | CD1 | ILE | B | 382 | −4.815 | 41.474 | −5.155 | 1.00 | 97.32 | B |
| ATOM | 2922 | C | ILE | B | 382 | −9.675 | 42.243 | −4.325 | 1.00 | 95.08 | B |
| ATOM | 2923 | O | ILE | B | 382 | −10.041 | 41.668 | −3.306 | 1.00 | 94.93 | B |
| ATOM | 2924 | N | GLU | B | 383 | −10.415 | 42.321 | −5.434 | 1.00 | 96.15 | B |
| ATOM | 2925 | CA | GLU | B | 383 | −11.744 | 41.701 | −5.538 | 1.00 | 95.96 | B |
| ATOM | 2926 | CB | GLU | B | 383 | −12.512 | 42.238 | −6.747 | 1.00 | 96.51 | B |
| ATOM | 2927 | CG | GLU | B | 383 | −12.496 | 43.743 | −6.932 | 1.00 | 98.15 | B |
| ATOM | 2928 | CD | GLU | B | 383 | −13.290 | 44.157 | −8.171 | 1.00 | 99.96 | B |
| ATOM | 2929 | OE1 | GLU | B | 383 | −13.302 | 43.385 | −9.168 | 1.00 | 100.59 | B |
| ATOM | 2930 | OE2 | GLU | B | 383 | −13.895 | 45.253 | −8.153 | 1.00 | 100.16 | B |
| ATOM | 2931 | C | GLU | B | 383 | −11.552 | 40.196 | −5.720 | 1.00 | 95.50 | B |
| ATOM | 2932 | O | GLU | B | 383 | −11.939 | 39.398 | −4.860 | 1.00 | 95.39 | B |
| ATOM | 2933 | N | ASP | B | 384 | −10.958 | 39.824 | −6.855 | 1.00 | 94.86 | B |
| ATOM | 2934 | CA | ASP | B | 384 | −10.682 | 38.428 | −7.163 | 1.00 | 93.28 | B |
| ATOM | 2935 | CB | ASP | B | 384 | −10.740 | 38.167 | −8.668 | 1.00 | 93.49 | B |
| ATOM | 2936 | CG | ASP | B | 384 | −10.540 | 36.696 | −8.999 | 1.00 | 94.52 | B |
| ATOM | 2937 | OD1 | ASP | B | 384 | −9.893 | 36.004 | −8.174 | 1.00 | 95.89 | B |
| ATOM | 2938 | OD2 | ASP | B | 384 | −11.012 | 36.231 | −10.065 | 1.00 | 93.45 | B |
| ATOM | 2939 | C | ASP | B | 384 | −9.288 | 38.091 | −6.648 | 1.00 | 92.04 | B |
| ATOM | 2940 | O | ASP | B | 384 | −8.289 | 38.580 | −7.165 | 1.00 | 92.22 | B |
| ATOM | 2941 | N | VAL | B | 385 | −9.228 | 37.249 | −5.629 | 1.00 | 91.51 | B |
| ATOM | 2942 | CA | VAL | B | 385 | −7.959 | 36.869 | −5.035 | 1.00 | 90.82 | B |
| ATOM | 2943 | CB | VAL | B | 385 | −8.114 | 36.655 | −3.516 | 1.00 | 90.78 | B |
| ATOM | 2944 | CG1 | VAL | B | 385 | −6.971 | 35.826 | −2.987 | 1.00 | 90.93 | B |
| ATOM | 2945 | CG2 | VAL | B | 385 | −8.141 | 38.002 | −2.798 | 1.00 | 91.16 | B |
| ATOM | 2946 | C | VAL | B | 385 | −7.376 | 35.618 | −5.668 | 1.00 | 90.33 | B |
| ATOM | 2947 | O | VAL | B | 385 | −6.158 | 35.447 | −5.714 | 1.00 | 91.07 | B |
| ATOM | 2948 | N | GLU | B | 386 | −8.239 | 34.740 | −6.157 | 1.00 | 89.49 | B |
| ATOM | 2949 | CA | GLU | B | 386 | −7.766 | 33.522 | −6.781 | 1.00 | 88.98 | B |
| ATOM | 2950 | CB | GLU | B | 386 | −8.935 | 32.570 | −7.018 | 1.00 | 91.17 | B |
| ATOM | 2951 | CG | GLU | B | 386 | −9.690 | 32.218 | −5.742 | 1.00 | 95.86 | B |
| ATOM | 2952 | CD | GLU | B | 386 | −9.795 | 30.706 | −5.500 | 1.00 | 99.50 | B |
| ATOM | 2953 | OE1 | GLU | B | 386 | −10.207 | 30.315 | −4.368 | 1.00 | 100.65 | B |
| ATOM | 2954 | OE2 | GLU | B | 386 | −9.471 | 29.916 | −6.436 | 1.00 | 100.08 | B |
| ATOM | 2955 | C | GLU | B | 386 | −7.071 | 33.863 | −8.100 | 1.00 | 87.31 | B |
| ATOM | 2956 | O | GLU | B | 386 | −6.077 | 33.224 | −8.464 | 1.00 | 87.46 | B |
| ATOM | 2957 | N | ALA | B | 387 | −7.591 | 34.875 | −8.802 | 1.00 | 84.62 | B |

TABLE 1-continued

ATOMIC COORDINATES OF THE ERR3 LBD/SRC-1 NR
BOX 2 PEPTIDE COMPLEX (PDB CODE 1KV6)

| ATOM | 2958 | CA  | ALA | B | 387 | −7.033 | 35.326 | −10.083 | 1.00 | 82.22 | B |
|------|------|-----|-----|---|-----|--------|--------|---------|------|-------|---|
| ATOM | 2959 | CB  | ALA | B | 387 | −7.909 | 36.420 | −10.680 | 1.00 | 81.15 | B |
| ATOM | 2960 | C   | ALA | B | 387 | −5.618 | 35.865 | −9.889  | 1.00 | 81.17 | B |
| ATOM | 2961 | O   | ALA | B | 387 | −4.662 | 35.404 | −10.529 | 1.00 | 80.29 | B |
| ATOM | 2962 | N   | VAL | B | 388 | −5.512 | 36.850 | −8.997  | 1.00 | 78.62 | B |
| ATOM | 2963 | CA  | VAL | B | 388 | −4.248 | 37.476 | −8.686  | 1.00 | 76.19 | B |
| ATOM | 2964 | CB  | VAL | B | 388 | −4.399 | 38.566 | −7.616  | 1.00 | 74.57 | B |
| ATOM | 2965 | CG1 | VAL | B | 388 | −3.034 | 39.129 | −7.269  | 1.00 | 72.34 | B |
| ATOM | 2966 | CG2 | VAL | B | 388 | −5.330 | 39.658 | −8.111  | 1.00 | 71.92 | B |
| ATOM | 2967 | C   | VAL | B | 388 | −3.231 | 36.462 | −8.209  | 1.00 | 76.89 | B |
| ATOM | 2968 | O   | VAL | B | 388 | −2.047 | 36.640 | −8.457  | 1.00 | 77.30 | B |
| ATOM | 2969 | N   | GLN | B | 389 | −3.679 | 35.399 | −7.544  | 1.00 | 76.32 | B |
| ATOM | 2970 | CA  | GLN | B | 389 | −2.750 | 34.395 | −7.059  | 1.00 | 76.41 | B |
| ATOM | 2971 | CB  | GLN | B | 389 | −3.389 | 33.578 | −5.926  | 1.00 | 79.58 | B |
| ATOM | 2972 | CG  | GLN | B | 389 | −2.551 | 32.378 | −5.433  | 1.00 | 85.15 | B |
| ATOM | 2973 | CD  | GLN | B | 389 | −1.146 | 32.755 | −4.884  | 1.00 | 89.51 | B |
| ATOM | 2974 | OE1 | GLN | B | 389 | −1.028 | 33.531 | −3.918  | 1.00 | 92.16 | B |
| ATOM | 2975 | NE2 | GLN | B | 389 | −0.084 | 32.190 | −5.493  | 1.00 | 88.94 | B |
| ATOM | 2976 | C   | GLN | B | 389 | −2.283 | 33.505 | −8.219  | 1.00 | 75.24 | B |
| ATOM | 2977 | O   | GLN | B | 389 | −1.287 | 32.775 | −8.107  | 1.00 | 73.77 | B |
| ATOM | 2978 | N   | LYS | B | 390 | −2.986 | 33.566 | −9.345  | 1.00 | 74.08 | B |
| ATOM | 2979 | CA  | LYS | B | 390 | −2.556 | 32.769 | −10.493 | 1.00 | 74.31 | B |
| ATOM | 2980 | CB  | LYS | B | 390 | −3.744 | 32.387 | −11.383 | 1.00 | 74.88 | B |
| ATOM | 2981 | CG  | LYS | B | 390 | −3.640 | 30.982 | −11.996 | 1.00 | 75.36 | B |
| ATOM | 2982 | CD  | LYS | B | 390 | −3.343 | 31.014 | −13.487 | 1.00 | 77.27 | B |
| ATOM | 2983 | CE  | LYS | B | 390 | −4.534 | 31.538 | −14.316 | 1.00 | 79.51 | B |
| ATOM | 2984 | NZ  | LYS | B | 390 | −4.126 | 31.926 | −15.726 | 1.00 | 80.64 | B |
| ATOM | 2985 | C   | LYS | B | 390 | −1.545 | 33.618 | −11.275 | 1.00 | 73.82 | B |
| ATOM | 2986 | O   | LYS | B | 390 | −0.611 | 33.097 | −11.891 | 1.00 | 73.58 | B |
| ATOM | 2987 | N   | LEU | B | 391 | −1.742 | 34.934 | −11.237 | 1.00 | 71.97 | B |
| ATOM | 2988 | CA  | LEU | B | 391 | −0.840 | 35.853 | −11.902 | 1.00 | 69.18 | B |
| ATOM | 2989 | CB  | LEU | B | 391 | −1.260 | 37.297 | −11.673 | 1.00 | 68.05 | B |
| ATOM | 2990 | CG  | LEU | B | 391 | −0.395 | 38.284 | −12.451 | 1.00 | 66.29 | B |
| ATOM | 2991 | CD1 | LEU | B | 391 | −0.366 | 37.898 | −13.929 | 1.00 | 63.66 | B |
| ATOM | 2992 | CD2 | LEU | B | 391 | −0.947 | 39.670 | −12.251 | 1.00 | 62.35 | B |
| ATOM | 2993 | C   | LEU | B | 391 | 0.514  | 35.628 | −11.283 | 1.00 | 69.00 | B |
| ATOM | 2994 | O   | LEU | B | 391 | 1.505  | 35.519 | −11.978 | 1.00 | 69.94 | B |
| ATOM | 2995 | N   | GLN | B | 392 | 0.539  | 35.547 | −9.965  | 1.00 | 68.61 | B |
| ATOM | 2996 | CA  | GLN | B | 392 | 1.762  | 35.292 | −9.245  | 1.00 | 69.12 | B |
| ATOM | 2997 | CB  | GLN | B | 392 | 1.521  | 35.316 | −7.753  | 1.00 | 69.07 | B |
| ATOM | 2998 | CG  | GLN | B | 392 | 0.968  | 36.605 | −7.213  | 1.00 | 68.76 | B |
| ATOM | 2999 | CD  | GLN | B | 392 | 0.640  | 36.481 | −5.749  | 1.00 | 69.69 | B |
| ATOM | 3000 | OE1 | GLN | B | 392 | −0.019 | 37.342 | −5.171  | 1.00 | 69.90 | B |
| ATOM | 3001 | NE2 | GLN | B | 392 | 1.105  | 35.390 | −5.130  | 1.00 | 71.45 | B |
| ATOM | 3002 | C   | GLN | B | 392 | 2.352  | 33.935 | −9.581  | 1.00 | 70.37 | B |
| ATOM | 3003 | O   | GLN | B | 392 | 3.559  | 33.821 | −9.758  | 1.00 | 71.73 | B |
| ATOM | 3004 | N   | ASP | B | 393 | 1.533  | 32.890 | −9.674  | 1.00 | 71.84 | B |
| ATOM | 3005 | CA  | ASP | B | 393 | 2.120  | 31.581 | −9.973  | 1.00 | 73.02 | B |
| ATOM | 3006 | CB  | ASP | B | 393 | 1.122  | 30.436 | −9.709  | 1.00 | 78.49 | B |
| ATOM | 3007 | CG  | ASP | B | 393 | 0.929  | 30.155 | −8.192  | 1.00 | 85.96 | B |
| ATOM | 3008 | OD1 | ASP | B | 393 | 1.967  | 30.178 | −7.440  | 1.00 | 87.52 | B |
| ATOM | 3009 | OD2 | ASP | B | 393 | −0.248 | 29.908 | −7.757  | 1.00 | 87.34 | B |
| ATOM | 3010 | C   | ASP | B | 393 | 2.763  | 31.410 | −11.348 | 1.00 | 70.80 | B |
| ATOM | 3011 | O   | ASP | B | 393 | 3.724  | 30.652 | −11.456 | 1.00 | 70.60 | B |
| ATOM | 3012 | N   | VAL | B | 394 | 2.275  | 32.085 | −12.396 | 1.00 | 68.34 | B |
| ATOM | 3013 | CA  | VAL | B | 394 | 2.919  | 31.925 | −13.716 | 1.00 | 66.94 | B |
| ATOM | 3014 | CB  | VAL | B | 394 | 2.058  | 32.457 | −14.932 | 1.00 | 66.61 | B |
| ATOM | 3015 | CG1 | VAL | B | 394 | 0.928  | 31.508 | −15.218 | 1.00 | 67.85 | B |
| ATOM | 3016 | CG2 | VAL | B | 394 | 1.485  | 33.811 | −14.645 | 1.00 | 67.06 | B |
| ATOM | 3017 | C   | VAL | B | 394 | 4.260  | 32.639 | −13.710 | 1.00 | 64.62 | B |
| ATOM | 3018 | O   | VAL | B | 394 | 5.247  | 32.100 | −14.200 | 1.00 | 63.82 | B |
| ATOM | 3019 | N   | LEU | B | 395 | 4.295  | 33.832 | −13.117 | 1.00 | 62.34 | B |
| ATOM | 3020 | CA  | LEU | B | 395 | 5.517  | 34.625 | −13.023 | 1.00 | 60.12 | B |
| ATOM | 3021 | CB  | LEU | B | 395 | 5.216  | 35.979 | −12.391 | 1.00 | 57.16 | B |
| ATOM | 3022 | CG  | LEU | B | 395 | 4.199  | 36.838 | −13.158 | 1.00 | 56.33 | B |
| ATOM | 3023 | CD1 | LEU | B | 395 | 4.019  | 38.183 | −12.435 | 1.00 | 53.55 | B |
| ATOM | 3024 | CD2 | LEU | B | 395 | 4.661  | 37.049 | −14.600 | 1.00 | 54.09 | B |
| ATOM | 3025 | C   | LEU | B | 395 | 6.521  | 33.868 | −12.177 | 1.00 | 60.83 | B |
| ATOM | 3026 | O   | LEU | B | 395 | 7.701  | 33.731 | −12.543 | 1.00 | 60.11 | B |
| ATOM | 3027 | N   | HIS | B | 396 | 6.036  | 33.366 | −11.041 | 1.00 | 60.88 | B |
| ATOM | 3028 | CA  | HIS | B | 396 | 6.868  | 32.590 | −10.128 | 1.00 | 59.89 | B |
| ATOM | 3029 | CB  | HIS | B | 396 | 6.056  | 32.198 | −8.885  | 1.00 | 59.52 | B |
| ATOM | 3030 | CG  | HIS | B | 396 | 6.829  | 31.392 | −7.874  | 1.00 | 61.29 | B |
| ATOM | 3031 | CD2 | HIS | B | 396 | 8.161  | 31.261 | −7.659  | 1.00 | 61.61 | B |
| ATOM | 3032 | ND1 | HIS | B | 396 | 6.213  | 30.608 | −6.920  | 1.00 | 61.03 | B |
| ATOM | 3033 | CE1 | HIS | B | 396 | 7.132  | 30.033 | −6.164  | 1.00 | 61.07 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3034 | NE2 | HIS | B | 396 | 8.321 | 30.409 | −6.592 | 1.00 | 61.34 | B |
|------|------|-----|-----|---|-----|-------|--------|--------|------|-------|---|
| ATOM | 3035 | C | HIS | B | 396 | 7.413 | 31.337 | −10.841 | 1.00 | 59.67 | B |
| ATOM | 3036 | O | HIS | B | 396 | 8.589 | 31.027 | −10.731 | 1.00 | 59.09 | B |
| ATOM | 3037 | N | GLU | B | 397 | 6.575 | 30.619 | −11.583 | 1.00 | 60.75 | B |
| ATOM | 3038 | CA | GLU | B | 397 | 7.073 | 29.422 | −12.259 | 1.00 | 62.60 | B |
| ATOM | 3039 | CB | GLU | B | 397 | 5.936 | 28.590 | −12.879 | 1.00 | 66.02 | B |
| ATOM | 3040 | CG | GLU | B | 397 | 6.457 | 27.303 | −13.515 | 1.00 | 70.40 | B |
| ATOM | 3041 | CD | GLU | B | 397 | 5.442 | 26.590 | −14.424 | 1.00 | 76.21 | B |
| ATOM | 3042 | OE1 | GLU | B | 397 | 4.363 | 27.160 | −14.754 | 1.00 | 79.13 | B |
| ATOM | 3043 | OE2 | GLU | B | 397 | 5.745 | 25.435 | −14.823 | 1.00 | 78.92 | B |
| ATOM | 3044 | C | GLU | B | 397 | 8.080 | 29.788 | −13.342 | 1.00 | 60.25 | B |
| ATOM | 3045 | O | GLU | B | 397 | 8.995 | 29.007 | −13.630 | 1.00 | 58.64 | B |
| ATOM | 3046 | N | ALA | B | 398 | 7.885 | 30.963 | −13.953 | 1.00 | 58.07 | B |
| ATOM | 3047 | CA | ALA | B | 398 | 8.802 | 31.474 | −14.983 | 1.00 | 55.69 | B |
| ATOM | 3048 | CB | ALA | B | 398 | 8.241 | 32.738 | −15.605 | 1.00 | 53.69 | B |
| ATOM | 3049 | C | ALA | B | 398 | 10.178 | 31.760 | −14.334 | 1.00 | 54.77 | B |
| ATOM | 3050 | O | ALA | B | 398 | 11.209 | 31.378 | −14.877 | 1.00 | 53.94 | B |
| ATOM | 3051 | N | LEU | B | 399 | 10.191 | 32.410 | −13.173 | 1.00 | 52.80 | B |
| ATOM | 3052 | CA | LEU | B | 399 | 11.444 | 32.662 | −12.500 | 1.00 | 55.12 | B |
| ATOM | 3053 | CB | LEU | B | 399 | 11.217 | 33.433 | −11.186 | 1.00 | 54.24 | B |
| ATOM | 3054 | CG | LEU | B | 399 | 12.502 | 33.554 | −10.346 | 1.00 | 52.68 | B |
| ATOM | 3055 | CD1 | LEU | B | 399 | 13.617 | 34.167 | −11.169 | 1.00 | 52.58 | B |
| ATOM | 3056 | CD2 | LEU | B | 399 | 12.256 | 34.384 | −9.139 | 1.00 | 52.87 | B |
| ATOM | 3057 | C | LEU | B | 399 | 12.183 | 31.356 | −12.193 | 1.00 | 56.22 | B |
| ATOM | 3058 | O | LEU | B | 399 | 13.380 | 31.244 | −12.389 | 1.00 | 56.59 | B |
| ATOM | 3059 | N | GLN | B | 400 | 11.448 | 30.367 | −11.719 | 1.00 | 58.93 | B |
| ATOM | 3060 | CA | GLN | B | 400 | 11.993 | 29.062 | −11.342 | 1.00 | 62.84 | B |
| ATOM | 3061 | CB | GLN | B | 400 | 10.872 | 28.306 | −10.655 | 1.00 | 68.86 | B |
| ATOM | 3062 | CG | GLN | B | 400 | 11.237 | 27.398 | −9.514 | 1.00 | 77.63 | B |
| ATOM | 3063 | CD | GLN | B | 400 | 10.053 | 26.430 | −9.173 | 1.00 | 83.55 | B |
| ATOM | 3064 | OE1 | GLN | B | 400 | 9.432 | 25.800 | −10.079 | 1.00 | 86.26 | B |
| ATOM | 3065 | NE2 | GLN | B | 400 | 9.745 | 26.308 | −7.874 | 1.00 | 83.35 | B |
| ATOM | 3066 | C | GLN | B | 400 | 12.584 | 28.256 | −12.523 | 1.00 | 62.50 | B |
| ATOM | 3067 | O | GLN | B | 400 | 13.605 | 27.614 | −12.388 | 1.00 | 59.25 | B |
| ATOM | 3068 | N | ASP | B | 401 | 11.927 | 28.297 | −13.681 | 1.00 | 64.17 | B |
| ATOM | 3069 | CA | ASP | B | 401 | 12.398 | 27.610 | −14.894 | 1.00 | 64.11 | B |
| ATOM | 3070 | CB | ASP | B | 401 | 11.484 | 27.826 | −16.079 | 1.00 | 69.76 | B |
| ATOM | 3071 | CG | ASP | B | 401 | 10.407 | 26.821 | −16.170 | 1.00 | 76.23 | B |
| ATOM | 3072 | OD1 | ASP | B | 401 | 9.611 | 26.938 | −17.140 | 1.00 | 81.17 | B |
| ATOM | 3073 | OD2 | ASP | B | 401 | 10.356 | 25.929 | −15.280 | 1.00 | 79.96 | B |
| ATOM | 3074 | C | ASP | B | 401 | 13.668 | 28.234 | −15.327 | 1.00 | 62.00 | B |
| ATOM | 3075 | O | ASP | B | 401 | 14.690 | 27.567 | −15.460 | 1.00 | 60.88 | B |
| ATOM | 3076 | N | TYR | B | 402 | 13.561 | 29.533 | −15.611 | 1.00 | 60.01 | B |
| ATOM | 3077 | CA | TYR | B | 402 | 14.698 | 30.298 | −16.045 | 1.00 | 57.99 | B |
| ATOM | 3078 | CB | TYR | B | 402 | 14.434 | 31.783 | −15.951 | 1.00 | 58.64 | B |
| ATOM | 3079 | CG | TYR | B | 402 | 15.661 | 32.536 | −16.401 | 1.00 | 62.60 | B |
| ATOM | 3080 | CD1 | TYR | B | 402 | 16.072 | 32.491 | −17.732 | 1.00 | 61.81 | B |
| ATOM | 3081 | CE1 | TYR | B | 402 | 17.269 | 33.049 | −18.126 | 1.00 | 63.78 | B |
| ATOM | 3082 | CD2 | TYR | B | 402 | 16.494 | 33.183 | −15.476 | 1.00 | 61.95 | B |
| ATOM | 3083 | CE2 | TYR | B | 402 | 17.695 | 33.749 | −15.868 | 1.00 | 63.37 | B |
| ATOM | 3084 | CZ | TYR | B | 402 | 18.083 | 33.675 | −17.198 | 1.00 | 65.17 | B |
| ATOM | 3085 | OH | TYR | B | 402 | 19.306 | 34.189 | −17.603 | 1.00 | 66.40 | B |
| ATOM | 3086 | C | TYR | B | 402 | 15.857 | 29.937 | −15.148 | 1.00 | 56.32 | B |
| ATOM | 3087 | O | TYR | B | 402 | 16.900 | 29.489 | −15.608 | 1.00 | 54.92 | B |
| ATOM | 3088 | N | GLU | B | 403 | 15.646 | 30.086 | −13.854 | 1.00 | 54.97 | B |
| ATOM | 3089 | CA | GLU | B | 403 | 16.691 | 29.771 | −12.920 | 1.00 | 56.88 | B |
| ATOM | 3090 | CB | GLU | B | 403 | 16.230 | 30.059 | −11.498 | 1.00 | 56.60 | B |
| ATOM | 3091 | CG | GLU | B | 403 | 16.105 | 31.537 | −11.104 | 1.00 | 57.36 | B |
| ATOM | 3092 | CD | GLU | B | 403 | 17.261 | 32.391 | −11.577 | 1.00 | 56.72 | B |
| ATOM | 3093 | OE1 | GLU | B | 403 | 18.362 | 31.862 | −11.848 | 1.00 | 57.74 | B |
| ATOM | 3094 | OE2 | GLU | B | 403 | 17.065 | 33.610 | −11.667 | 1.00 | 57.75 | B |
| ATOM | 3095 | C | GLU | B | 403 | 17.213 | 28.346 | −12.986 | 1.00 | 57.28 | B |
| ATOM | 3096 | O | GLU | B | 403 | 18.404 | 28.116 | −12.879 | 1.00 | 59.24 | B |
| ATOM | 3097 | N | ALA | B | 404 | 16.341 | 27.374 | −13.157 | 1.00 | 58.49 | B |
| ATOM | 3098 | CA | ALA | B | 404 | 16.812 | 25.998 | −13.170 | 1.00 | 59.69 | B |
| ATOM | 3099 | CB | ALA | B | 404 | 15.664 | 25.045 | −12.960 | 1.00 | 60.42 | B |
| ATOM | 3100 | C | ALA | B | 404 | 17.539 | 25.652 | −14.442 | 1.00 | 61.17 | B |
| ATOM | 3101 | O | ALA | B | 404 | 18.380 | 24.753 | −14.452 | 1.00 | 63.60 | B |
| ATOM | 3102 | N | GLY | B | 405 | 17.211 | 26.358 | −15.517 | 1.00 | 61.40 | B |
| ATOM | 3103 | CA | GLY | B | 405 | 17.848 | 26.101 | −16.791 | 1.00 | 61.64 | B |
| ATOM | 3104 | C | GLY | B | 405 | 19.176 | 26.807 | −16.897 | 1.00 | 63.14 | B |
| ATOM | 3105 | O | GLY | B | 405 | 20.182 | 26.173 | −17.218 | 1.00 | 65.31 | B |
| ATOM | 3106 | N | GLN | B | 406 | 19.180 | 28.101 | −16.579 | 1.00 | 63.78 | B |
| ATOM | 3107 | CA | GLN | B | 406 | 20.358 | 28.964 | −16.637 | 1.00 | 64.94 | B |
| ATOM | 3108 | CB | GLN | B | 406 | 19.870 | 30.391 | −16.863 | 1.00 | 68.73 | B |
| ATOM | 3109 | CG | GLN | B | 406 | 19.798 | 30.787 | −18.319 | 1.00 | 73.98 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3110 | CD | GLN | B | 406 | 21.189 | 30.902 | −18.926 | 1.00 | 74.99 | B |
|---|---|---|---|---|---|---|---|---|---|---|---|
| ATOM | 3111 | OE1 | GLN | B | 406 | 22.076 | 31.583 | −18.378 | 1.00 | 75.63 | B |
| ATOM | 3112 | NE2 | GLN | B | 406 | 21.388 | 30.239 | −20.054 | 1.00 | 74.71 | B |
| ATOM | 3113 | C | GLN | B | 406 | 21.368 | 28.968 | −15.468 | 1.00 | 65.40 | B |
| ATOM | 3114 | O | GLN | B | 406 | 22.544 | 29.342 | −15.640 | 1.00 | 62.87 | B |
| ATOM | 3115 | N | HIS | B | 407 | 20.910 | 28.583 | −14.280 | 1.00 | 65.34 | B |
| ATOM | 3116 | CA | HIS | B | 407 | 21.775 | 28.590 | −13.123 | 1.00 | 65.60 | B |
| ATOM | 3117 | CB | HIS | B | 407 | 21.436 | 29.758 | −12.243 | 1.00 | 65.98 | B |
| ATOM | 3118 | CG | HIS | B | 407 | 21.744 | 31.069 | −12.871 | 1.00 | 68.94 | B |
| ATOM | 3119 | CD2 | HIS | B | 407 | 20.948 | 31.964 | −13.507 | 1.00 | 69.17 | B |
| ATOM | 3120 | ND1 | HIS | B | 407 | 23.026 | 31.570 | −12.942 | 1.00 | 69.11 | B |
| ATOM | 3121 | CE1 | HIS | B | 407 | 23.004 | 32.720 | −13.593 | 1.00 | 68.90 | B |
| ATOM | 3122 | NE2 | HIS | B | 407 | 21.756 | 32.981 | −13.946 | 1.00 | 68.54 | B |
| ATOM | 3123 | C | HIS | B | 407 | 21.701 | 27.350 | −12.310 | 1.00 | 66.47 | B |
| ATOM | 3124 | O | HIS | B | 407 | 21.578 | 27.414 | −11.095 | 1.00 | 66.67 | B |
| ATOM | 3125 | N | MET | B | 408 | 21.801 | 26.212 | −12.986 | 1.00 | 68.23 | B |
| ATOM | 3126 | CA | MET | B | 408 | 21.752 | 24.913 | −12.342 | 1.00 | 68.27 | B |
| ATOM | 3127 | CB | MET | B | 408 | 21.884 | 23.829 | −13.407 | 1.00 | 68.57 | B |
| ATOM | 3128 | CG | MET | B | 408 | 21.652 | 22.434 | −12.900 | 1.00 | 68.24 | B |
| ATOM | 3129 | SD | MET | B | 408 | 21.862 | 21.242 | −14.233 | 1.00 | 73.68 | B |
| ATOM | 3130 | CE | MET | B | 408 | 20.247 | 21.257 | −15.005 | 1.00 | 68.20 | B |
| ATOM | 3131 | C | MET | B | 408 | 22.811 | 24.716 | −11.233 | 1.00 | 69.65 | B |
| ATOM | 3132 | O | MET | B | 408 | 22.633 | 23.855 | −10.362 | 1.00 | 70.54 | B |
| ATOM | 3133 | N | GLU | B | 409 | 23.890 | 25.513 | −11.247 | 1.00 | 69.13 | B |
| ATOM | 3134 | CA | GLU | B | 409 | 24.952 | 25.393 | −10.246 | 1.00 | 67.56 | B |
| ATOM | 3135 | CB | GLU | B | 409 | 26.274 | 25.977 | −10.769 | 1.00 | 69.51 | B |
| ATOM | 3136 | CG | GLU | B | 409 | 26.312 | 27.500 | −10.892 | 1.00 | 74.03 | B |
| ATOM | 3137 | CD | GLU | B | 409 | 25.452 | 28.031 | −12.036 | 1.00 | 76.16 | B |
| ATOM | 3138 | OE1 | GLU | B | 409 | 25.299 | 29.284 | −12.133 | 1.00 | 77.83 | B |
| ATOM | 3139 | OE2 | GLU | B | 409 | 24.935 | 27.208 | −12.832 | 1.00 | 77.91 | B |
| ATOM | 3140 | C | GLU | B | 409 | 24.571 | 26.046 | −8.917 | 1.00 | 65.99 | B |
| ATOM | 3141 | O | GLU | B | 409 | 25.279 | 25.905 | −7.921 | 1.00 | 65.40 | B |
| ATOM | 3142 | N | ASP | B | 410 | 23.477 | 26.797 | −8.905 | 1.00 | 63.58 | B |
| ATOM | 3143 | CA | ASP | B | 410 | 23.006 | 27.370 | −7.655 | 1.00 | 62.74 | B |
| ATOM | 3144 | CB | ASP | B | 410 | 23.079 | 28.892 | −7.601 | 1.00 | 63.66 | B |
| ATOM | 3145 | CG | ASP | B | 410 | 22.610 | 29.449 | −6.240 | 1.00 | 65.88 | B |
| ATOM | 3146 | OD1 | ASP | B | 410 | 22.206 | 28.652 | −5.344 | 1.00 | 65.48 | B |
| ATOM | 3147 | OD2 | ASP | B | 410 | 22.648 | 30.687 | −6.063 | 1.00 | 68.34 | B |
| ATOM | 3148 | C | ASP | B | 410 | 21.567 | 26.947 | −7.584 | 1.00 | 61.12 | B |
| ATOM | 3149 | O | ASP | B | 410 | 20.673 | 27.637 | −8.072 | 1.00 | 62.31 | B |
| ATOM | 3150 | N | PRO | B | 411 | 21.320 | 25.790 | −6.976 | 1.00 | 60.20 | B |
| ATOM | 3151 | CD | PRO | B | 411 | 22.273 | 24.916 | −6.274 | 1.00 | 59.49 | B |
| ATOM | 3152 | CA | PRO | B | 411 | 19.958 | 25.273 | −6.855 | 1.00 | 59.40 | B |
| ATOM | 3153 | CB | PRO | B | 411 | 20.184 | 23.896 | −6.245 | 1.00 | 57.96 | B |
| ATOM | 3154 | CG | PRO | B | 411 | 21.361 | 24.130 | −5.372 | 1.00 | 57.06 | B |
| ATOM | 3155 | C | PRO | B | 411 | 19.031 | 26.166 | −6.020 | 1.00 | 56.86 | B |
| ATOM | 3156 | O | PRO | B | 411 | 17.839 | 25.916 | −5.956 | 1.00 | 56.92 | B |
| ATOM | 3157 | N | ARG | B | 412 | 19.583 | 27.217 | −5.409 | 1.00 | 55.39 | B |
| ATOM | 3158 | CA | ARG | B | 412 | 18.809 | 28.143 | −4.576 | 1.00 | 53.32 | B |
| ATOM | 3159 | CB | ARG | B | 412 | 19.396 | 28.176 | −3.169 | 1.00 | 53.17 | B |
| ATOM | 3160 | CG | ARG | B | 412 | 18.493 | 27.566 | −2.133 | 1.00 | 55.30 | B |
| ATOM | 3161 | CD | ARG | B | 412 | 19.276 | 27.039 | −0.969 | 1.00 | 56.94 | B |
| ATOM | 3162 | NE | ARG | B | 412 | 19.857 | 25.724 | −1.264 | 1.00 | 58.98 | B |
| ATOM | 3163 | CZ | ARG | B | 412 | 21.153 | 25.443 | −1.196 | 1.00 | 58.77 | B |
| ATOM | 3164 | NH1 | ARG | B | 412 | 22.026 | 26.390 | −0.851 | 1.00 | 58.52 | B |
| ATOM | 3165 | NH2 | ARG | B | 412 | 21.563 | 24.204 | −1.438 | 1.00 | 58.58 | B |
| ATOM | 3166 | C | ARG | B | 412 | 18.734 | 29.580 | −5.118 | 1.00 | 53.40 | B |
| ATOM | 3167 | O | ARG | B | 412 | 18.263 | 30.495 | −4.400 | 1.00 | 51.93 | B |
| ATOM | 3168 | N | ARG | B | 413 | 19.197 | 29.788 | −6.364 | 1.00 | 50.42 | B |
| ATOM | 3169 | CA | ARG | B | 413 | 19.161 | 31.109 | −6.956 | 1.00 | 49.83 | B |
| ATOM | 3170 | CB | ARG | B | 413 | 19.806 | 31.073 | −8.345 | 1.00 | 48.93 | B |
| ATOM | 3171 | CG | ARG | B | 413 | 19.993 | 32.469 | −8.942 | 1.00 | 49.52 | B |
| ATOM | 3172 | CD | ARG | B | 413 | 20.898 | 32.433 | −10.160 | 1.00 | 51.43 | B |
| ATOM | 3173 | NE | ARG | B | 413 | 21.104 | 33.760 | −10.755 | 1.00 | 51.00 | B |
| ATOM | 3174 | CZ | ARG | B | 413 | 21.959 | 34.659 | −10.285 | 1.00 | 51.05 | B |
| ATOM | 3175 | NH1 | ARG | B | 413 | 22.681 | 34.358 | −9.232 | 1.00 | 52.05 | B |
| ATOM | 3176 | NH2 | ARG | B | 413 | 22.076 | 35.856 | −10.843 | 1.00 | 51.54 | B |
| ATOM | 3177 | C | ARG | B | 413 | 17.764 | 31.801 | −7.023 | 1.00 | 49.72 | B |
| ATOM | 3178 | O | ARG | B | 413 | 17.640 | 33.004 | −6.708 | 1.00 | 47.39 | B |
| ATOM | 3179 | N | ALA | B | 414 | 16.721 | 31.075 | −7.431 | 1.00 | 48.51 | B |
| ATOM | 3180 | CA | ALA | B | 414 | 15.401 | 31.696 | −7.515 | 1.00 | 47.75 | B |
| ATOM | 3181 | CB | ALA | B | 414 | 14.385 | 30.701 | −8.074 | 1.00 | 46.77 | B |
| ATOM | 3182 | C | ALA | B | 414 | 14.960 | 32.197 | −6.141 | 1.00 | 48.20 | B |
| ATOM | 3183 | O | ALA | B | 414 | 14.386 | 33.280 | −6.017 | 1.00 | 48.91 | B |
| ATOM | 3184 | N | GLY | B | 415 | 15.245 | 31.404 | −5.107 | 1.00 | 49.60 | B |
| ATOM | 3185 | CA | GLY | B | 415 | 14.874 | 31.755 | −3.742 | 1.00 | 48.30 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3186 | C | GLY | B | 415 | 15.554 | 33.034 | −3.338 | 1.00 | 50.14 | B |
|---|---|---|---|---|---|---|---|---|---|---|---|
| ATOM | 3187 | O | GLY | B | 415 | 14.886 | 33.922 | −2.837 | 1.00 | 52.04 | B |
| ATOM | 3188 | N | LYS | B | 416 | 16.878 | 33.125 | −3.553 | 1.00 | 52.65 | B |
| ATOM | 3189 | CA | LYS | B | 416 | 17.673 | 34.325 | −3.251 | 1.00 | 52.07 | B |
| ATOM | 3190 | CB | LYS | B | 416 | 19.122 | 34.144 | −3.684 | 1.00 | 51.92 | B |
| ATOM | 3191 | CG | LYS | B | 416 | 19.899 | 33.313 | −2.746 | 1.00 | 54.89 | B |
| ATOM | 3192 | CD | LYS | B | 416 | 21.133 | 32.716 | −3.408 | 1.00 | 57.05 | B |
| ATOM | 3193 | CE | LYS | B | 416 | 21.679 | 31.578 | −2.535 | 1.00 | 59.51 | B |
| ATOM | 3194 | NZ | LYS | B | 416 | 22.963 | 31.069 | −3.062 | 1.00 | 63.90 | B |
| ATOM | 3195 | C | LYS | B | 416 | 17.098 | 35.547 | −3.943 | 1.00 | 52.28 | B |
| ATOM | 3196 | O | LYS | B | 416 | 17.124 | 36.631 | −3.383 | 1.00 | 53.40 | B |
| ATOM | 3197 | N | MET | B | 417 | 16.588 | 35.389 | −5.158 | 1.00 | 53.48 | B |
| ATOM | 3198 | CA | MET | B | 417 | 15.992 | 36.530 | −5.827 | 1.00 | 55.91 | B |
| ATOM | 3199 | CB | MET | B | 417 | 15.527 | 36.205 | −7.249 | 1.00 | 58.58 | B |
| ATOM | 3200 | CG | MET | B | 417 | 16.613 | 36.034 | −8.317 | 1.00 | 64.33 | B |
| ATOM | 3201 | SD | MET | B | 417 | 17.801 | 37.405 | −8.304 | 1.00 | 71.58 | B |
| ATOM | 3202 | CE | MET | B | 417 | 19.411 | 36.479 | −8.516 | 1.00 | 68.46 | B |
| ATOM | 3203 | C | MET | B | 417 | 14.767 | 36.932 | −5.040 | 1.00 | 55.85 | B |
| ATOM | 3204 | O | MET | B | 417 | 14.550 | 38.105 | −4.791 | 1.00 | 56.61 | B |
| ATOM | 3205 | N | LEU | B | 418 | 13.958 | 35.954 | −4.644 | 1.00 | 56.49 | B |
| ATOM | 3206 | CA | LEU | B | 418 | 12.727 | 36.255 | −3.921 | 1.00 | 57.78 | B |
| ATOM | 3207 | CB | LEU | B | 418 | 11.899 | 34.971 | −3.765 | 1.00 | 57.95 | B |
| ATOM | 3208 | CG | LEU | B | 418 | 11.367 | 34.374 | −5.076 | 1.00 | 58.01 | B |
| ATOM | 3209 | CD1 | LEU | B | 418 | 10.829 | 32.988 | −4.831 | 1.00 | 57.08 | B |
| ATOM | 3210 | CD2 | LEU | B | 418 | 10.288 | 35.273 | −5.635 | 1.00 | 56.32 | B |
| ATOM | 3211 | C | LEU | B | 418 | 12.944 | 36.936 | −2.570 | 1.00 | 57.35 | B |
| ATOM | 3212 | O | LEU | B | 418 | 12.154 | 37.825 | −2.160 | 1.00 | 55.10 | B |
| ATOM | 3213 | N | MET | B | 419 | 14.033 | 36.542 | −1.910 | 1.00 | 56.59 | B |
| ATOM | 3214 | CA | MET | B | 419 | 14.377 | 37.075 | −0.606 | 1.00 | 57.72 | B |
| ATOM | 3215 | CB | MET | B | 419 | 15.436 | 36.184 | 0.029 | 1.00 | 59.00 | B |
| ATOM | 3216 | CG | MET | B | 419 | 14.994 | 34.751 | 0.277 | 1.00 | 62.31 | B |
| ATOM | 3217 | SD | MET | B | 419 | 16.012 | 33.971 | 1.509 | 1.00 | 66.97 | B |
| ATOM | 3218 | CE | MET | B | 419 | 17.113 | 32.939 | 0.475 | 1.00 | 66.24 | B |
| ATOM | 3219 | C | MET | B | 419 | 14.828 | 38.546 | −0.565 | 1.00 | 57.79 | B |
| ATOM | 3220 | O | MET | B | 419 | 15.098 | 39.097 | 0.510 | 1.00 | 58.54 | B |
| ATOM | 3221 | N | THR | B | 420 | 14.903 | 39.182 | −1.729 | 1.00 | 57.77 | B |
| ATOM | 3222 | CA | THR | B | 420 | 15.290 | 40.581 | −1.830 | 1.00 | 57.06 | B |
| ATOM | 3223 | CB | THR | B | 420 | 16.205 | 40.818 | −3.066 | 1.00 | 55.93 | B |
| ATOM | 3224 | OG1 | THR | B | 420 | 15.429 | 40.758 | −4.267 | 1.00 | 54.69 | B |
| ATOM | 3225 | CG2 | THR | B | 420 | 17.325 | 39.744 | −3.137 | 1.00 | 56.88 | B |
| ATOM | 3226 | C | THR | B | 420 | 14.026 | 41.465 | −1.918 | 1.00 | 58.49 | B |
| ATOM | 3227 | O | THR | B | 420 | 14.103 | 42.690 | −1.763 | 1.00 | 59.69 | B |
| ATOM | 3228 | N | LEU | B | 421 | 12.865 | 40.840 | −2.145 | 1.00 | 57.93 | B |
| ATOM | 3229 | CA | LEU | B | 421 | 11.605 | 41.586 | −2.214 | 1.00 | 57.32 | B |
| ATOM | 3230 | CB | LEU | B | 421 | 10.457 | 40.690 | −2.632 | 1.00 | 52.96 | B |
| ATOM | 3231 | CG | LEU | B | 421 | 10.513 | 40.170 | −4.056 | 1.00 | 52.98 | B |
| ATOM | 3232 | CD1 | LEU | B | 421 | 9.264 | 39.375 | −4.298 | 1.00 | 53.15 | B |
| ATOM | 3233 | CD2 | LEU | B | 421 | 10.653 | 41.314 | −5.062 | 1.00 | 47.82 | B |
| ATOM | 3234 | C | LEU | B | 421 | 11.235 | 42.273 | −0.895 | 1.00 | 58.92 | B |
| ATOM | 3235 | O | LEU | B | 421 | 10.551 | 43.302 | −0.903 | 1.00 | 59.88 | B |
| ATOM | 3236 | N | PRO | B | 422 | 11.642 | 41.698 | 0.253 | 1.00 | 59.04 | B |
| ATOM | 3237 | CD | PRO | B | 422 | 12.227 | 40.366 | 0.486 | 1.00 | 59.20 | B |
| ATOM | 3238 | CA | PRO | B | 422 | 11.312 | 42.348 | 1.524 | 1.00 | 58.94 | B |
| ATOM | 3239 | CB | PRO | B | 422 | 11.852 | 41.369 | 2.593 | 1.00 | 58.82 | B |
| ATOM | 3240 | CG | PRO | B | 422 | 11.786 | 40.046 | 1.918 | 1.00 | 58.57 | B |
| ATOM | 3241 | C | PRO | B | 422 | 12.036 | 43.694 | 1.572 | 1.00 | 57.58 | B |
| ATOM | 3242 | O | PRO | B | 422 | 11.444 | 44.682 | 1.916 | 1.00 | 58.28 | B |
| ATOM | 3243 | N | LEU | B | 423 | 13.319 | 43.734 | 1.226 | 1.00 | 59.45 | B |
| ATOM | 3244 | CA | LEU | B | 423 | 14.059 | 45.008 | 1.243 | 1.00 | 59.65 | B |
| ATOM | 3245 | CB | LEU | B | 423 | 15.517 | 44.838 | 0.828 | 1.00 | 57.49 | B |
| ATOM | 3246 | CG | LEU | B | 423 | 16.342 | 46.117 | 1.034 | 1.00 | 54.26 | B |
| ATOM | 3247 | CD1 | LEU | B | 423 | 16.190 | 46.612 | 2.426 | 1.00 | 52.74 | B |
| ATOM | 3248 | CD2 | LEU | B | 423 | 17.810 | 45.819 | 0.765 | 1.00 | 52.84 | B |
| ATOM | 3249 | C | LEU | B | 423 | 13.445 | 46.040 | 0.324 | 1.00 | 60.36 | B |
| ATOM | 3250 | O | LEU | B | 423 | 13.418 | 47.207 | 0.653 | 1.00 | 61.76 | B |
| ATOM | 3251 | N | LEU | B | 424 | 12.964 | 45.584 | −0.834 | 1.00 | 61.42 | B |
| ATOM | 3252 | CA | LEU | B | 424 | 12.320 | 46.422 | −1.840 | 1.00 | 60.35 | B |
| ATOM | 3253 | CB | LEU | B | 424 | 11.938 | 45.591 | −3.071 | 1.00 | 57.94 | B |
| ATOM | 3254 | CG | LEU | B | 424 | 11.295 | 46.245 | −4.291 | 1.00 | 52.89 | B |
| ATOM | 3255 | CD1 | LEU | B | 424 | 12.299 | 47.100 | −4.947 | 1.00 | 56.55 | B |
| ATOM | 3256 | CD2 | LEU | B | 424 | 10.850 | 45.228 | −5.274 | 1.00 | 51.73 | B |
| ATOM | 3257 | C | LEU | B | 424 | 11.068 | 47.022 | −1.258 | 1.00 | 62.98 | B |
| ATOM | 3258 | O | LEU | B | 424 | 10.885 | 48.225 | −1.347 | 1.00 | 66.39 | B |
| ATOM | 3259 | N | ARG | B | 425 | 10.212 | 46.183 | −0.666 | 1.00 | 64.49 | B |
| ATOM | 3260 | CA | ARG | B | 425 | 8.949 | 46.630 | −0.080 | 1.00 | 64.89 | B |
| ATOM | 3261 | CB | ARG | B | 425 | 8.214 | 45.448 | 0.582 | 1.00 | 63.79 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3262 | CG | ARG | B | 425 | 6.939 | 45.818 | 1.412 | 1.00 | 60.65 | B |
|---|---|---|---|---|---|---|---|---|---|---|---|
| ATOM | 3263 | CD | ARG | B | 425 | 5.844 | 46.320 | 0.521 | 1.00 | 60.42 | B |
| ATOM | 3264 | NE | ARG | B | 425 | 5.556 | 45.380 | −0.567 | 1.00 | 62.25 | B |
| ATOM | 3265 | CZ | ARG | B | 425 | 4.860 | 44.253 | −0.424 | 1.00 | 61.79 | B |
| ATOM | 3266 | NH1 | ARG | B | 425 | 4.362 | 43.922 | 0.757 | 1.00 | 63.25 | B |
| ATOM | 3267 | NH2 | ARG | B | 425 | 4.690 | 43.437 | −1.451 | 1.00 | 62.46 | B |
| ATOM | 3268 | C | ARG | B | 425 | 9.193 | 47.712 | 0.962 | 1.00 | 66.26 | B |
| ATOM | 3269 | O | ARG | B | 425 | 8.436 | 48.683 | 1.058 | 1.00 | 64.60 | B |
| ATOM | 3270 | N | GLN | B | 426 | 10.253 | 47.515 | 1.738 | 1.00 | 67.57 | B |
| ATOM | 3271 | CA | GLN | B | 426 | 10.662 | 48.415 | 2.813 | 1.00 | 69.44 | B |
| ATOM | 3272 | CB | GLN | B | 426 | 11.842 | 47.781 | 3.563 | 1.00 | 67.85 | B |
| ATOM | 3273 | CG | GLN | B | 426 | 12.029 | 48.241 | 4.968 | 1.00 | 70.09 | B |
| ATOM | 3274 | CD | GLN | B | 426 | 13.447 | 47.994 | 5.457 | 1.00 | 72.76 | B |
| ATOM | 3275 | OE1 | GLN | B | 426 | 13.895 | 46.851 | 5.562 | 1.00 | 76.23 | B |
| ATOM | 3276 | NE2 | GLN | B | 426 | 14.168 | 49.069 | 5.755 | 1.00 | 74.17 | B |
| ATOM | 3277 | C | GLN | B | 426 | 11.062 | 49.795 | 2.257 | 1.00 | 71.52 | B |
| ATOM | 3278 | O | GLN | B | 426 | 10.544 | 50.843 | 2.694 | 1.00 | 71.93 | B |
| ATOM | 3279 | N | THR | B | 427 | 11.982 | 49.781 | 1.291 | 1.00 | 71.83 | B |
| ATOM | 3280 | CA | THR | B | 427 | 12.477 | 50.992 | 0.672 | 1.00 | 71.36 | B |
| ATOM | 3281 | CB | THR | B | 427 | 13.570 | 50.649 | −0.311 | 1.00 | 70.60 | B |
| ATOM | 3282 | OG1 | THR | B | 427 | 14.700 | 50.178 | 0.424 | 1.00 | 70.82 | B |
| ATOM | 3283 | CG2 | THR | B | 427 | 13.983 | 51.857 | −1.117 | 1.00 | 71.99 | B |
| ATOM | 3284 | C | THR | B | 427 | 11.340 | 51.683 | −0.033 | 1.00 | 72.15 | B |
| ATOM | 3285 | O | THR | B | 427 | 11.141 | 52.880 | 0.105 | 1.00 | 70.94 | B |
| ATOM | 3286 | N | SER | B | 428 | 10.581 | 50.910 | −0.787 | 1.00 | 73.75 | B |
| ATOM | 3287 | CA | SER | B | 428 | 9.446 | 51.440 | −1.523 | 1.00 | 76.43 | B |
| ATOM | 3288 | CB | SER | B | 428 | 8.690 | 50.287 | −2.188 | 1.00 | 76.27 | B |
| ATOM | 3289 | OG | SER | B | 428 | 7.329 | 50.628 | −2.404 | 1.00 | 77.15 | B |
| ATOM | 3290 | C | SER | B | 428 | 8.480 | 52.297 | −0.686 | 1.00 | 77.60 | B |
| ATOM | 3291 | O | SER | B | 428 | 8.074 | 53.379 | −1.118 | 1.00 | 77.58 | B |
| ATOM | 3292 | N | THR | B | 429 | 8.104 | 51.824 | 0.501 | 1.00 | 79.90 | B |
| ATOM | 3293 | CA | THR | B | 429 | 7.181 | 52.600 | 1.341 | 1.00 | 81.77 | B |
| ATOM | 3294 | CB | THR | B | 429 | 6.377 | 51.708 | 2.361 | 1.00 | 81.48 | B |
| ATOM | 3295 | OG1 | THR | B | 429 | 7.285 | 51.018 | 3.219 | 1.00 | 82.83 | B |
| ATOM | 3296 | CG2 | THR | B | 429 | 5.494 | 50.693 | 1.625 | 1.00 | 81.09 | B |
| ATOM | 3297 | C | THR | B | 429 | 7.905 | 53.731 | 2.093 | 1.00 | 81.72 | B |
| ATOM | 3298 | O | THR | B | 429 | 7.284 | 54.732 | 2.452 | 1.00 | 80.82 | B |
| ATOM | 3299 | N | LYS | B | 430 | 9.211 | 53.576 | 2.319 | 1.00 | 82.35 | B |
| ATOM | 3300 | CA | LYS | B | 430 | 9.989 | 54.630 | 2.983 | 1.00 | 83.27 | B |
| ATOM | 3301 | CB | LYS | B | 430 | 11.446 | 54.185 | 3.209 | 1.00 | 83.01 | B |
| ATOM | 3302 | CG | LYS | B | 430 | 12.245 | 55.072 | 4.171 | 1.00 | 84.91 | B |
| ATOM | 3303 | CD | LYS | B | 430 | 13.715 | 54.630 | 4.289 | 1.00 | 86.65 | B |
| ATOM | 3304 | CE | LYS | B | 430 | 13.882 | 53.101 | 4.581 | 1.00 | 89.31 | B |
| ATOM | 3305 | NZ | LYS | B | 430 | 13.375 | 52.586 | 5.927 | 1.00 | 89.46 | B |
| ATOM | 3306 | C | LYS | B | 430 | 9.956 | 55.879 | 2.070 | 1.00 | 83.95 | B |
| ATOM | 3307 | O | LYS | B | 430 | 9.798 | 57.017 | 2.542 | 1.00 | 83.82 | B |
| ATOM | 3308 | N | ALA | B | 431 | 10.089 | 55.646 | 0.763 | 1.00 | 83.59 | B |
| ATOM | 3309 | CA | ALA | B | 431 | 10.068 | 56.703 | −0.236 | 1.00 | 81.69 | B |
| ATOM | 3310 | CB | ALA | B | 431 | 10.512 | 56.162 | −1.572 | 1.00 | 81.22 | B |
| ATOM | 3311 | C | ALA | B | 431 | 8.664 | 57.267 | −0.347 | 1.00 | 81.34 | B |
| ATOM | 3312 | O | ALA | B | 431 | 8.463 | 58.448 | −0.162 | 1.00 | 81.84 | B |
| ATOM | 3313 | N | VAL | B | 432 | 7.682 | 56.430 | −0.636 | 1.00 | 80.90 | B |
| ATOM | 3314 | CA | VAL | B | 432 | 6.327 | 56.934 | −0.751 | 1.00 | 81.37 | B |
| ATOM | 3315 | CB | VAL | B | 432 | 5.330 | 55.797 | −0.920 | 1.00 | 79.93 | B |
| ATOM | 3316 | CG1 | VAL | B | 432 | 3.913 | 56.360 | −1.063 | 1.00 | 76.43 | B |
| ATOM | 3317 | CG2 | VAL | B | 432 | 5.717 | 54.965 | −2.119 | 1.00 | 79.22 | B |
| ATOM | 3318 | C | VAL | B | 432 | 5.889 | 57.770 | 0.452 | 1.00 | 84.11 | B |
| ATOM | 3319 | O | VAL | B | 432 | 5.161 | 58.754 | 0.301 | 1.00 | 84.32 | B |
| ATOM | 3320 | N | GLN | B | 433 | 6.314 | 57.374 | 1.649 | 1.00 | 86.96 | B |
| ATOM | 3321 | CA | GLN | B | 433 | 5.948 | 58.108 | 2.861 | 1.00 | 89.38 | B |
| ATOM | 3322 | CB | GLN | B | 433 | 6.328 | 57.318 | 4.114 | 1.00 | 88.54 | B |
| ATOM | 3323 | CG | GLN | B | 433 | 9999.000 | 9999.000 | 9999.000 | 1.00 | 0.00 | B |
| ATOM | 3324 | CD | GLN | B | 433 | 9999.000 | 9999.000 | 9999.000 | 1.00 | 0.00 | B |
| ATOM | 3325 | OE1 | GLN | B | 433 | 9999.000 | 9999.000 | 9999.000 | 1.00 | 0.00 | B |
| ATOM | 3326 | NE2 | GLN | B | 433 | 9999.000 | 9999.000 | 9999.000 | 1.00 | 0.00 | B |
| ATOM | 3327 | C | GLN | B | 433 | 6.670 | 59.440 | 2.853 | 1.00 | 91.36 | B |
| ATOM | 3328 | O | GLN | B | 433 | 6.098 | 60.452 | 3.252 | 1.00 | 91.76 | B |
| ATOM | 3329 | N | HIS | B | 434 | 7.922 | 59.425 | 2.391 | 1.00 | 93.52 | B |
| ATOM | 3330 | CA | HIS | B | 434 | 8.758 | 60.627 | 2.313 | 1.00 | 95.85 | B |
| ATOM | 3331 | CB | HIS | B | 434 | 10.201 | 60.251 | 1.999 | 1.00 | 97.94 | B |
| ATOM | 3332 | CG | HIS | B | 434 | 11.120 | 61.427 | 1.871 | 1.00 | 101.28 | B |
| ATOM | 3333 | CD2 | HIS | B | 434 | 10.932 | 62.651 | 1.326 | 1.00 | 102.00 | B |
| ATOM | 3334 | ND1 | HIS | B | 434 | 12.414 | 61.416 | 2.352 | 1.00 | 102.93 | B |
| ATOM | 3335 | CE1 | HIS | B | 434 | 12.979 | 62.584 | 2.115 | 1.00 | 103.32 | B |
| ATOM | 3336 | NE2 | HIS | B | 434 | 12.101 | 63.352 | 1.494 | 1.00 | 103.28 | B |
| ATOM | 3337 | C | HIS | B | 434 | 8.277 | 61.657 | 1.284 | 1.00 | 96.04 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3338 | O   | HIS | B | 434 | 8.133  | 62.845 | 1.598  | 1.00 | 95.94  | B |
| ---- | ---- | --- | --- | - | --- | ------ | ------ | ------ | ---- | ------ | - |
| ATOM | 3339 | N   | PHE | B | 435 | 8.069  | 61.226 | 0.047  | 1.00 | 95.58  | B |
| ATOM | 3340 | CA  | PHE | B | 435 | 7.596  | 62.137 | −0.967 | 1.00 | 95.21  | B |
| ATOM | 3341 | CB  | PHE | B | 435 | 7.706  | 61.537 | −2.355 | 1.00 | 92.77  | B |
| ATOM | 3342 | CG  | PHE | B | 435 | 9.072  | 61.621 | −2.912 | 1.00 | 91.34  | B |
| ATOM | 3343 | CD1 | PHE | B | 435 | 9.316  | 62.346 | −4.065 | 1.00 | 90.85  | B |
| ATOM | 3344 | CD2 | PHE | B | 435 | 10.125 | 60.986 | −2.275 | 1.00 | 90.61  | B |
| ATOM | 3345 | CE1 | PHE | B | 435 | 10.602 | 62.438 | −4.576 | 1.00 | 91.03  | B |
| ATOM | 3346 | CE2 | PHE | B | 435 | 11.416 | 61.065 | −2.770 | 1.00 | 90.20  | B |
| ATOM | 3347 | CZ  | PHE | B | 435 | 11.661 | 61.791 | −3.927 | 1.00 | 91.12  | B |
| ATOM | 3348 | C   | PHE | B | 435 | 6.178  | 62.479 | −0.692 | 1.00 | 96.45  | B |
| ATOM | 3349 | O   | PHE | B | 435 | 5.524  | 63.117 | −1.510 | 1.00 | 96.14  | B |
| ATOM | 3350 | N   | TYR | B | 436 | 5.662  | 62.024 | 0.444  | 1.00 | 98.90  | B |
| ATOM | 3351 | CA  | TYR | B | 436 | 4.290  | 62.384 | 0.783  | 1.00 | 101.85 | B |
| ATOM | 3352 | CB  | TYR | B | 436 | 3.557  | 61.255 | 1.465  | 1.00 | 101.39 | B |
| ATOM | 3353 | CG  | TYR | B | 436 | 2.108  | 61.633 | 1.653  | 1.00 | 101.94 | B |
| ATOM | 3354 | CD1 | TYR | B | 436 | 1.216  | 61.600 | 0.580  | 1.00 | 101.70 | B |
| ATOM | 3355 | CE1 | TYR | B | 436 | −0.118 | 61.975 | 0.736  | 1.00 | 102.44 | B |
| ATOM | 3356 | CD2 | TYR | B | 436 | 1.633  | 62.060 | 2.896  | 1.00 | 101.84 | B |
| ATOM | 3357 | CE2 | TYR | B | 436 | 0.301  | 62.442 | 3.069  | 1.00 | 102.04 | B |
| ATOM | 3358 | CZ  | TYR | B | 436 | −0.572 | 62.396 | 1.988  | 1.00 | 102.64 | B |
| ATOM | 3359 | OH  | TYR | B | 436 | −1.894 | 62.756 | 2.165  | 1.00 | 101.94 | B |
| ATOM | 3360 | C   | TYR | B | 436 | 4.360  | 63.577 | 1.710  | 1.00 | 103.54 | B |
| ATOM | 3361 | O   | TYR | B | 436 | 3.379  | 64.317 | 1.850  | 1.00 | 104.17 | B |
| ATOM | 3362 | N   | ASN | B | 437 | 5.507  | 63.725 | 2.369  | 1.00 | 105.10 | B |
| ATOM | 3363 | CA  | ASN | B | 437 | 5.743  | 64.882 | 3.242  | 1.00 | 107.02 | B |
| ATOM | 3364 | CB  | ASN | B | 437 | 7.026  | 64.727 | 4.031  | 1.00 | 106.87 | B |
| ATOM | 3365 | CG  | ASN | B | 437 | 6.985  | 63.566 | 4.991  | 1.00 | 106.49 | B |
| ATOM | 3366 | OD1 | ASN | B | 437 | 7.997  | 63.193 | 5.582  | 1.00 | 105.53 | B |
| ATOM | 3367 | ND2 | ASN | B | 437 | 5.782  | 63.002 | 5.180  | 1.00 | 106.20 | B |
| ATOM | 3368 | C   | ASN | B | 437 | 5.953  | 66.043 | 2.276  | 1.00 | 108.31 | B |
| ATOM | 3369 | O   | ASN | B | 437 | 5.341  | 67.105 | 2.394  | 1.00 | 108.19 | B |
| ATOM | 3370 | N   | ILE | B | 438 | 6.825  | 65.801 | 1.298  | 1.00 | 110.17 | B |
| ATOM | 3371 | CA  | ILE | B | 438 | 7.142  | 66.792 | 0.304  | 1.00 | 112.07 | B |
| ATOM | 3372 | CB  | ILE | B | 438 | 8.301  | 66.323 | −0.619 | 1.00 | 111.52 | B |
| ATOM | 3373 | CG2 | ILE | B | 438 | 8.986  | 67.515 | −1.230 | 1.00 | 110.84 | B |
| ATOM | 3374 | CG1 | ILE | B | 438 | 9.307  | 65.478 | 0.166  | 1.00 | 111.58 | B |
| ATOM | 3375 | CD1 | ILE | B | 438 | 9.980  | 66.188 | 1.326  | 1.00 | 111.11 | B |
| ATOM | 3376 | C   | ILE | B | 438 | 5.939  | 67.105 | −0.556 | 1.00 | 114.02 | B |
| ATOM | 3377 | O   | ILE | B | 438 | 6.003  | 67.986 | −1.392 | 1.00 | 114.75 | B |
| ATOM | 3378 | N   | LYS | B | 439 | 4.845  | 66.385 | −0.380 | 1.00 | 116.55 | B |
| ATOM | 3379 | CA  | LYS | B | 439 | 3.657  | 66.689 | −1.152 | 1.00 | 118.82 | B |
| ATOM | 3380 | CB  | LYS | B | 439 | 2.789  | 65.441 | −1.357 | 1.00 | 118.85 | B |
| ATOM | 3381 | CG  | LYS | B | 439 | 1.525  | 65.693 | −2.143 | 1.00 | 118.99 | B |
| ATOM | 3382 | CD  | LYS | B | 439 | 0.503  | 66.487 | −1.347 | 1.00 | 118.22 | B |
| ATOM | 3383 | CE  | LYS | B | 439 | −0.603 | 67.030 | −2.250 | 1.00 | 118.09 | B |
| ATOM | 3384 | NZ  | LYS | B | 439 | −1.414 | 65.957 | −2.927 | 1.00 | 117.18 | B |
| ATOM | 3385 | C   | LYS | B | 439 | 2.921  | 67.679 | −0.300 | 1.00 | 120.21 | B |
| ATOM | 3386 | O   | LYS | B | 439 | 2.681  | 68.818 | −0.692 | 1.00 | 120.59 | B |
| ATOM | 3387 | N   | LEU | B | 440 | 2.608  | 67.226 | 0.906  | 1.00 | 121.96 | B |
| ATOM | 3388 | CA  | LEU | B | 440 | 1.901  | 68.026 | 1.897  | 1.00 | 123.72 | B |
| ATOM | 3389 | CB  | LEU | B | 440 | 1.781  | 67.231 | 3.234  | 1.00 | 123.91 | B |
| ATOM | 3390 | CG  | LEU | B | 440 | 0.470  | 66.498 | 3.550  | 1.00 | 123.53 | B |
| ATOM | 3391 | CD1 | LEU | B | 440 | 0.056  | 65.599 | 2.400  | 1.00 | 122.08 | B |
| ATOM | 3392 | CD2 | LEU | B | 440 | 0.626  | 65.694 | 4.833  | 1.00 | 122.83 | B |
| ATOM | 3393 | C   | LEU | B | 440 | 2.553  | 69.390 | 2.142  | 1.00 | 124.50 | B |
| ATOM | 3394 | O   | LEU | B | 440 | 1.885  | 70.419 | 2.003  | 1.00 | 124.17 | B |
| ATOM | 3395 | N   | GLU | B | 441 | 3.841  | 69.404 | 2.473  | 1.00 | 125.72 | B |
| ATOM | 3396 | CA  | GLU | B | 441 | 4.541  | 70.663 | 2.730  | 1.00 | 126.09 | B |
| ATOM | 3397 | CB  | GLU | B | 441 | 6.057  | 70.431 | 2.734  | 1.00 | 125.92 | B |
| ATOM | 3398 | CG  | GLU | B | 441 | 6.759  | 70.943 | 1.511  | 1.00 | 126.91 | B |
| ATOM | 3399 | CD  | GLU | B | 441 | 8.250  | 70.669 | 1.518  | 1.00 | 127.93 | B |
| ATOM | 3400 | OE1 | GLU | B | 441 | 8.902  | 70.928 | 2.554  | 1.00 | 128.68 | B |
| ATOM | 3401 | OE2 | GLU | B | 441 | 8.764  | 70.181 | 0.483  | 1.00 | 127.75 | B |
| ATOM | 3402 | C   | GLU | B | 441 | 4.156  | 71.734 | 1.700  | 1.00 | 126.77 | B |
| ATOM | 3403 | O   | GLU | B | 441 | 3.862  | 72.877 | 2.053  | 1.00 | 127.47 | B |
| ATOM | 3404 | N   | GLY | B | 442 | 4.147  | 71.368 | 0.411  | 1.00 | 126.66 | B |
| ATOM | 3405 | CA  | GLY | B | 442 | 3.762  | 72.314 | −0.625 | 1.00 | 126.01 | B |
| ATOM | 3406 | C   | GLY | B | 442 | 4.847  | 73.031 | −1.427 | 1.00 | 125.85 | B |
| ATOM | 3407 | O   | GLY | B | 442 | 4.525  | 73.660 | −2.431 | 1.00 | 126.50 | B |
| ATOM | 3408 | N   | LYS | B | 443 | 6.102  | 72.947 | −1.002 | 1.00 | 125.09 | B |
| ATOM | 3409 | CA  | LYS | B | 443 | 7.207  | 73.623 | −1.707 | 1.00 | 123.59 | B |
| ATOM | 3410 | CB  | LYS | B | 443 | 8.418  | 73.749 | −0.791 | 1.00 | 123.94 | B |
| ATOM | 3411 | CG  | LYS | B | 443 | 8.360  | 74.891 | 0.188  | 1.00 | 124.23 | B |
| ATOM | 3412 | CD  | LYS | B | 443 | 9.605  | 74.885 | 1.043  | 1.00 | 124.81 | B |
| ATOM | 3413 | CE  | LYS | B | 443 | 9.514  | 75.882 | 2.174  | 1.00 | 124.68 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3414 | NZ | LYS | B | 443 | 10.587 | 75.610 | 3.155 | 1.00 | 124.14 | B |
|---|---|---|---|---|---|---|---|---|---|---|---|
| ATOM | 3415 | C | LYS | B | 443 | 7.672 | 73.014 | −3.037 | 1.00 | 122.53 | B |
| ATOM | 3416 | O | LYS | B | 443 | 8.457 | 73.637 | −3.736 | 1.00 | 122.25 | B |
| ATOM | 3417 | N | VAL | B | 444 | 7.245 | 71.790 | −3.367 | 1.00 | 121.26 | B |
| ATOM | 3418 | CA | VAL | B | 444 | 7.647 | 71.180 | −4.636 | 1.00 | 119.20 | B |
| ATOM | 3419 | CB | VAL | B | 444 | 8.410 | 69.845 | −4.438 | 1.00 | 118.51 | B |
| ATOM | 3420 | CG1 | VAL | B | 444 | 8.924 | 69.360 | −5.779 | 1.00 | 117.42 | B |
| ATOM | 3421 | CG2 | VAL | B | 444 | 9.577 | 70.025 | −3.469 | 1.00 | 118.35 | B |
| ATOM | 3422 | C | VAL | B | 444 | 6.432 | 70.922 | −5.528 | 1.00 | 118.25 | B |
| ATOM | 3423 | O | VAL | B | 444 | 5.384 | 70.449 | −5.063 | 1.00 | 118.25 | B |
| ATOM | 3424 | N | PRO | B | 445 | 6.548 | 71.275 | −6.823 | 1.00 | 116.84 | B |
| ATOM | 3425 | CD | PRO | B | 445 | 7.670 | 72.043 | −7.394 | 1.00 | 116.22 | B |
| ATOM | 3426 | CA | PRO | B | 445 | 5.474 | 71.103 | −7.810 | 1.00 | 115.97 | B |
| ATOM | 3427 | CB | PRO | B | 445 | 5.837 | 72.132 | −8.875 | 1.00 | 115.44 | B |
| ATOM | 3428 | CG | PRO | B | 445 | 7.338 | 72.080 | −8.868 | 1.00 | 115.52 | B |
| ATOM | 3429 | C | PRO | B | 445 | 5.397 | 69.663 | −8.361 | 1.00 | 115.48 | B |
| ATOM | 3430 | O | PRO | B | 445 | 6.414 | 69.094 | −8.785 | 1.00 | 116.10 | B |
| ATOM | 3431 | N | MET | B | 446 | 4.191 | 69.088 | −8.364 | 1.00 | 113.81 | B |
| ATOM | 3432 | CA | MET | B | 446 | 3.999 | 67.714 | −8.835 | 1.00 | 111.84 | B |
| ATOM | 3433 | CB | MET | B | 446 | 3.732 | 66.816 | −7.638 | 1.00 | 111.95 | B |
| ATOM | 3434 | CG | MET | B | 446 | 4.598 | 67.166 | −6.458 | 1.00 | 111.83 | B |
| ATOM | 3435 | SD | MET | B | 446 | 4.349 | 66.081 | −5.064 | 1.00 | 112.41 | B |
| ATOM | 3436 | CE | MET | B | 446 | 6.119 | 65.916 | −4.413 | 1.00 | 109.99 | B |
| ATOM | 3437 | C | MET | B | 446 | 2.857 | 67.587 | −9.838 | 1.00 | 110.52 | B |
| ATOM | 3438 | O | MET | B | 446 | 1.852 | 68.291 | −9.721 | 1.00 | 109.93 | B |
| ATOM | 3439 | N | HIS | B | 447 | 3.012 | 66.683 | −10.809 | 1.00 | 108.72 | B |
| ATOM | 3440 | CA | HIS | B | 447 | 2.000 | 66.486 | −11.847 | 1.00 | 107.23 | B |
| ATOM | 3441 | CB | HIS | B | 447 | 2.644 | 65.853 | −13.086 | 1.00 | 107.70 | B |
| ATOM | 3442 | CG | HIS | B | 447 | 3.779 | 66.656 | −13.668 | 1.00 | 108.25 | B |
| ATOM | 3443 | CD2 | HIS | B | 447 | 5.121 | 66.450 | −13.645 | 1.00 | 108.15 | B |
| ATOM | 3444 | ND1 | HIS | B | 447 | 3.587 | 67.819 | −14.386 | 1.00 | 107.73 | B |
| ATOM | 3445 | CE1 | HIS | B | 447 | 4.758 | 68.290 | −14.780 | 1.00 | 107.50 | B |
| ATOM | 3446 | NE2 | HIS | B | 447 | 5.705 | 67.478 | −14.344 | 1.00 | 107.34 | B |
| ATOM | 3447 | C | HIS | B | 447 | 0.808 | 65.657 | −11.353 | 1.00 | 106.27 | B |
| ATOM | 3448 | O | HIS | B | 447 | 0.823 | 65.147 | −10.237 | 1.00 | 105.78 | B |
| ATOM | 3449 | N | LYS | B | 448 | −0.218 | 65.520 | −12.191 | 1.00 | 105.40 | B |
| ATOM | 3450 | CA | LYS | B | 448 | −1.450 | 64.802 | −11.830 | 1.00 | 104.83 | B |
| ATOM | 3451 | CB | LYS | B | 448 | −2.510 | 65.042 | −12.900 | 1.00 | 104.49 | B |
| ATOM | 3452 | CG | LYS | B | 448 | 9999.000 | 9999.000 | 9999.000 | 1.00 | 0.00 | B |
| ATOM | 3453 | CD | LYS | B | 448 | 9999.000 | 9999.000 | 9999.000 | 1.00 | 0.00 | B |
| ATOM | 3454 | CE | LYS | B | 448 | 9999.000 | 9999.000 | 9999.000 | 1.00 | 0.00 | B |
| ATOM | 3455 | NZ | LYS | B | 448 | 9999.000 | 9999.000 | 9999.000 | 1.00 | 0.00 | B |
| ATOM | 3456 | C | LYS | B | 448 | −1.404 | 63.303 | −11.485 | 1.00 | 104.72 | B |
| ATOM | 3457 | O | LYS | B | 448 | −2.106 | 62.876 | −10.559 | 1.00 | 104.77 | B |
| ATOM | 3458 | N | LEU | B | 449 | −0.621 | 62.508 | −12.229 | 1.00 | 104.24 | B |
| ATOM | 3459 | CA | LEU | B | 449 | −0.499 | 61.060 | −11.972 | 1.00 | 102.96 | B |
| ATOM | 3460 | CB | LEU | B | 449 | 0.165 | 60.335 | −13.141 | 1.00 | 101.58 | B |
| ATOM | 3461 | CG | LEU | B | 449 | −0.671 | 59.301 | −13.897 | 1.00 | 101.08 | B |
| ATOM | 3462 | CD1 | LEU | B | 449 | 0.303 | 58.445 | −14.703 | 1.00 | 100.75 | B |
| ATOM | 3463 | CD2 | LEU | B | 449 | −1.516 | 58.433 | −12.950 | 1.00 | 99.81 | B |
| ATOM | 3464 | C | LEU | B | 449 | 0.320 | 60.766 | −10.720 | 1.00 | 102.93 | B |
| ATOM | 3465 | O | LEU | B | 449 | −0.113 | 60.007 | −9.858 | 1.00 | 102.81 | B |
| ATOM | 3466 | N | PHE | B | 450 | 1.503 | 61.368 | −10.632 | 1.00 | 102.61 | B |
| ATOM | 3467 | CA | PHE | B | 450 | 2.396 | 61.183 | −9.491 | 1.00 | 102.99 | B |
| ATOM | 3468 | CB | PHE | B | 450 | 3.666 | 62.003 | −9.677 | 1.00 | 102.56 | B |
| ATOM | 3469 | CG | PHE | B | 450 | 4.665 | 61.812 | −8.587 | 1.00 | 101.82 | B |
| ATOM | 3470 | CD1 | PHE | B | 450 | 5.379 | 60.627 | −8.486 | 1.00 | 101.69 | B |
| ATOM | 3471 | CD2 | PHE | B | 450 | 4.906 | 62.820 | −7.667 | 1.00 | 102.18 | B |
| ATOM | 3472 | CE1 | PHE | B | 450 | 6.333 | 60.449 | −7.485 | 1.00 | 101.61 | B |
| ATOM | 3473 | CE2 | PHE | B | 450 | 5.858 | 62.654 | −6.659 | 1.00 | 102.65 | B |
| ATOM | 3474 | CZ | PHE | B | 450 | 6.574 | 61.466 | −6.569 | 1.00 | 102.42 | B |
| ATOM | 3475 | C | PHE | B | 450 | 1.736 | 61.596 | −8.182 | 1.00 | 103.42 | B |
| ATOM | 3476 | O | PHE | B | 450 | 2.282 | 61.388 | −7.098 | 1.00 | 104.01 | B |
| ATOM | 3477 | N | LEU | B | 451 | 0.568 | 62.207 | −8.292 | 1.00 | 103.48 | B |
| ATOM | 3478 | CA | LEU | B | 451 | −0.174 | 62.640 | −7.128 | 1.00 | 103.34 | B |
| ATOM | 3479 | CB | LEU | B | 451 | −0.827 | 63.995 | −7.411 | 1.00 | 103.77 | B |
| ATOM | 3480 | CG | LEU | B | 451 | −0.061 | 65.230 | −6.924 | 1.00 | 103.86 | B |
| ATOM | 3481 | CD1 | LEU | B | 451 | 1.444 | 64.986 | −6.927 | 1.00 | 103.24 | B |
| ATOM | 3482 | CD2 | LEU | B | 451 | −0.449 | 66.406 | −7.801 | 1.00 | 103.25 | B |
| ATOM | 3483 | C | LEU | B | 451 | −1.222 | 61.581 | −6.845 | 1.00 | 103.29 | B |
| ATOM | 3484 | O | LEU | B | 451 | −1.257 | 60.991 | −5.762 | 1.00 | 103.08 | B |
| ATOM | 3485 | N | GLU | B | 452 | −2.065 | 61.333 | −7.839 | 1.00 | 103.15 | B |
| ATOM | 3486 | CA | GLU | B | 452 | −3.110 | 60.337 | −7.718 | 1.00 | 103.89 | B |
| ATOM | 3487 | CB | GLU | B | 452 | −3.712 | 60.069 | −9.080 | 1.00 | 104.16 | B |
| ATOM | 3488 | CG | GLU | B | 452 | −4.980 | 59.269 | −9.010 | 1.00 | 106.11 | B |
| ATOM | 3489 | CD | GLU | B | 452 | −5.399 | 58.794 | −10.369 | 1.00 | 107.53 | B |

TABLE 1-continued

ATOMIC COORDINATES OF THE ERR3 LBD/SRC-1 NR
BOX 2 PEPTIDE COMPLEX (PDB CODE 1KV6)

| ATOM | 3490 | OE1 | GLU | B | 452 | −4.894 | 57.734 | −10.800 | 1.00 | 109.17 | B |
|------|------|-----|-----|---|-----|--------|--------|---------|------|--------|---|
| ATOM | 3491 | OE2 | GLU | B | 452 | −6.214 | 59.492 | −11.015 | 1.00 | 108.20 | B |
| ATOM | 3492 | C | GLU | B | 452 | −2.563 | 59.025 | −7.144 | 1.00 | 104.35 | B |
| ATOM | 3493 | O | GLU | B | 452 | −3.293 | 58.267 | −6.489 | 1.00 | 103.76 | B |
| ATOM | 3494 | N | MET | B | 453 | −1.282 | 58.763 | −7.421 | 1.00 | 104.59 | B |
| ATOM | 3495 | CA | MET | B | 453 | −0.592 | 57.559 | −6.945 | 1.00 | 104.23 | B |
| ATOM | 3496 | CB | MET | B | 453 | 0.575 | 57.158 | −7.888 | 1.00 | 103.13 | B |
| ATOM | 3497 | CG | MET | B | 453 | 0.179 | 56.658 | −9.288 | 1.00 | 101.48 | B |
| ATOM | 3498 | SD | MET | B | 453 | −0.886 | 55.173 | −9.371 | 1.00 | 101.19 | B |
| ATOM | 3499 | CE | MET | B | 453 | −2.506 | 55.876 | −9.260 | 1.00 | 100.39 | B |
| ATOM | 3500 | C | MET | B | 453 | −0.045 | 57.817 | −5.538 | 1.00 | 104.10 | B |
| ATOM | 3501 | O | MET | B | 453 | −0.237 | 57.009 | −4.626 | 1.00 | 104.49 | B |
| ATOM | 3502 | N | LEU | B | 454 | 0.633 | 58.942 | −5.363 | 1.00 | 103.69 | B |
| ATOM | 3503 | CA | LEU | B | 454 | 1.195 | 59.286 | −4.069 | 1.00 | 104.19 | B |
| ATOM | 3504 | CB | LEU | B | 454 | 2.230 | 60.391 | −4.265 | 1.00 | 102.61 | B |
| ATOM | 3505 | CG | LEU | B | 454 | 2.973 | 60.980 | −3.074 | 1.00 | 101.55 | B |
| ATOM | 3506 | CD1 | LEU | B | 454 | 3.548 | 59.878 | −2.206 | 1.00 | 100.91 | B |
| ATOM | 3507 | CD2 | LEU | B | 454 | 4.061 | 61.888 | −3.602 | 1.00 | 101.10 | B |
| ATOM | 3508 | C | LEU | B | 454 | 0.103 | 59.720 | −3.072 | 1.00 | 105.26 | B |
| ATOM | 3509 | O | LEU | B | 454 | 0.328 | 60.582 | −2.229 | 1.00 | 106.50 | B |
| ATOM | 3510 | N | GLU | B | 455 | −1.074 | 59.111 | −3.163 | 1.00 | 105.53 | B |
| ATOM | 3511 | CA | GLU | B | 455 | −2.191 | 59.435 | −2.272 | 1.00 | 105.72 | B |
| ATOM | 3512 | CB | GLU | B | 455 | −2.638 | 60.886 | −2.511 | 1.00 | 105.01 | B |
| ATOM | 3513 | CG | GLU | B | 455 | 9999.000 | 9999.000 | 9999.000 | 1.00 | 0.00 | B |
| ATOM | 3514 | CD | GLU | B | 455 | 9999.000 | 9999.000 | 9999.000 | 1.00 | 0.00 | B |
| ATOM | 3515 | OE1 | GLU | B | 455 | 9999.000 | 9999.000 | 9999.000 | 1.00 | 0.00 | B |
| ATOM | 3516 | OE2 | GLU | B | 455 | 9999.000 | 9999.000 | 9999.000 | 1.00 | 0.00 | B |
| ATOM | 3517 | C | GLU | B | 455 | −3.354 | 58.471 | −2.556 | 1.00 | 106.53 | B |
| ATOM | 3518 | O | GLU | B | 455 | −4.369 | 58.876 | −3.138 | 1.00 | 106.76 | B |
| ATOM | 3519 | N | ALA | B | 456 | −3.219 | 57.203 | −2.150 | 1.00 | 106.36 | B |
| ATOM | 3520 | CA | ALA | B | 456 | −4.268 | 56.207 | −2.414 | 1.00 | 105.78 | B |
| ATOM | 3521 | CB | ALA | B | 456 | −3.919 | 55.403 | −3.674 | 1.00 | 104.63 | B |
| ATOM | 3522 | C | ALA | B | 456 | −4.533 | 55.259 | −1.246 | 1.00 | 105.53 | B |
| ATOM | 3523 | O | ALA | B | 456 | −5.680 | 54.758 | −1.140 | 1.00 | 105.38 | B |
| ATOM | 3524 | OXT | ALA | B | 456 | −3.587 | 55.017 | −0.468 | 1.00 | 105.15 | B |
| TER  |      |     |     |   |     |        |        |         |      |        |   |
| ATOM | 3525 | N | HIS | C | 687 | 21.415 | 49.025 | 23.055 | 1.00 | 91.78 | C |
| ATOM | 3526 | CA | HIS | C | 687 | 22.142 | 47.713 | 22.990 | 1.00 | 91.98 | C |
| ATOM | 3527 | CB | HIS | C | 687 | 23.384 | 47.851 | 22.069 | 1.00 | 91.45 | C |
| ATOM | 3528 | CG | HIS | C | 687 | 9999.000 | 9999.000 | 9999.000 | 1.00 | 0.00 | C |
| ATOM | 3529 | CD2 | HIS | C | 687 | 9999.000 | 9999.000 | 9999.000 | 1.00 | 0.00 | C |
| ATOM | 3530 | ND1 | HIS | C | 687 | 9999.000 | 9999.000 | 9999.000 | 1.00 | 0.00 | C |
| ATOM | 3531 | CE1 | HIS | C | 687 | 9999.000 | 9999.000 | 9999.000 | 1.00 | 0.00 | C |
| ATOM | 3532 | NE2 | HIS | C | 687 | 9999.000 | 9999.000 | 9999.000 | 1.00 | 0.00 | C |
| ATOM | 3533 | C | HIS | C | 687 | 22.566 | 47.173 | 24.381 | 1.00 | 91.62 | C |
| ATOM | 3534 | O | HIS | C | 687 | 22.878 | 45.984 | 24.514 | 1.00 | 92.23 | C |
| ATOM | 3535 | N | LYS | C | 688 | 22.565 | 48.037 | 25.403 | 1.00 | 90.01 | C |
| ATOM | 3536 | CA | LYS | C | 688 | 22.969 | 47.656 | 26.762 | 1.00 | 88.16 | C |
| ATOM | 3537 | CB | LYS | C | 688 | 22.684 | 48.805 | 27.739 | 1.00 | 88.05 | C |
| ATOM | 3538 | CG | LYS | C | 688 | 9999.000 | 9999.000 | 9999.000 | 1.00 | 0.00 | C |
| ATOM | 3539 | CD | LYS | C | 688 | 9999.000 | 9999.000 | 9999.000 | 1.00 | 0.00 | C |
| ATOM | 3540 | CE | LYS | C | 688 | 9999.000 | 9999.000 | 9999.000 | 1.00 | 0.00 | C |
| ATOM | 3541 | NZ | LYS | C | 688 | 9999.000 | 9999.000 | 9999.000 | 1.00 | 0.00 | C |
| ATOM | 3542 | C | LYS | C | 688 | 22.332 | 46.362 | 27.273 | 1.00 | 87.08 | C |
| ATOM | 3543 | O | LYS | C | 688 | 23.039 | 45.394 | 27.542 | 1.00 | 86.77 | C |
| ATOM | 3544 | N | ILE | C | 689 | 21.007 | 46.346 | 27.417 | 1.00 | 86.00 | C |
| ATOM | 3545 | CA | ILE | C | 689 | 20.306 | 45.153 | 27.897 | 1.00 | 84.97 | C |
| ATOM | 3546 | CB | ILE | C | 689 | 18.786 | 45.370 | 27.933 | 1.00 | 85.29 | C |
| ATOM | 3547 | CG2 | ILE | C | 689 | 18.125 | 44.286 | 28.776 | 1.00 | 83.75 | C |
| ATOM | 3548 | CG1 | ILE | C | 689 | 18.465 | 46.748 | 28.503 | 1.00 | 84.93 | C |
| ATOM | 3549 | CD1 | ILE | C | 689 | 17.001 | 47.140 | 28.321 | 1.00 | 85.84 | C |
| ATOM | 3550 | C | ILE | C | 689 | 20.578 | 43.981 | 26.949 | 1.00 | 84.35 | C |
| ATOM | 3551 | O | ILE | C | 689 | 21.129 | 42.953 | 27.346 | 1.00 | 83.04 | C |
| ATOM | 3552 | N | LEU | C | 690 | 20.182 | 44.159 | 25.691 | 1.00 | 83.70 | C |
| ATOM | 3553 | CA | LEU | C | 690 | 20.357 | 43.154 | 24.653 | 1.00 | 83.34 | C |
| ATOM | 3554 | CB | LEU | C | 690 | 20.131 | 43.786 | 23.290 | 1.00 | 82.48 | C |
| ATOM | 3555 | CG | LEU | C | 690 | 20.241 | 42.867 | 22.078 | 1.00 | 81.00 | C |
| ATOM | 3556 | CD1 | LEU | C | 690 | 18.967 | 42.089 | 21.943 | 1.00 | 80.96 | C |
| ATOM | 3557 | CD2 | LEU | C | 690 | 20.480 | 43.685 | 20.829 | 1.00 | 81.57 | C |
| ATOM | 3558 | C | LEU | C | 690 | 21.744 | 42.524 | 24.685 | 1.00 | 84.15 | C |
| ATOM | 3559 | O | LEU | C | 690 | 21.890 | 41.297 | 24.693 | 1.00 | 84.71 | C |
| ATOM | 3560 | N | HIS | C | 691 | 22.762 | 43.372 | 24.695 | 1.00 | 84.82 | C |
| ATOM | 3561 | CA | HIS | C | 691 | 24.141 | 42.918 | 24.712 | 1.00 | 85.64 | C |
| ATOM | 3562 | CB | HIS | C | 691 | 25.068 | 44.126 | 24.797 | 1.00 | 86.80 | C |
| ATOM | 3563 | CG | HIS | C | 691 | 26.515 | 43.766 | 24.897 | 1.00 | 88.65 | C |
| ATOM | 3564 | CD2 | HIS | C | 691 | 27.196 | 43.053 | 25.826 | 1.00 | 88.27 | C |

TABLE 1-continued

ATOMIC COORDINATES OF THE ERR3 LBD/SRC-1 NR
BOX 2 PEPTIDE COMPLEX (PDB CODE 1KV6)

| ATOM | 3565 | ND1 | HIS | C | 691 | 27.438 | 44.134 | 23.941 | 1.00 | 90.01 | C |
|---|---|---|---|---|---|---|---|---|---|---|---|
| ATOM | 3566 | CE1 | HIS | C | 691 | 28.625 | 43.661 | 24.277 | 1.00 | 89.76 | C |
| ATOM | 3567 | NE2 | HIS | C | 691 | 28.504 | 43.001 | 25.415 | 1.00 | 88.83 | C |
| ATOM | 3568 | C | HIS | C | 691 | 24.421 | 41.966 | 25.873 | 1.00 | 86.21 | C |
| ATOM | 3569 | O | HIS | C | 691 | 25.139 | 40.977 | 25.719 | 1.00 | 86.15 | C |
| ATOM | 3570 | N | ARG | C | 692 | 23.850 | 42.270 | 27.035 | 1.00 | 86.58 | C |
| ATOM | 3571 | CA | ARG | C | 692 | 24.051 | 41.456 | 28.228 | 1.00 | 86.66 | C |
| ATOM | 3572 | CB | ARG | C | 692 | 23.564 | 42.224 | 29.470 | 1.00 | 87.11 | C |
| ATOM | 3573 | CG | ARG | C | 692 | 23.830 | 41.515 | 30.814 | 1.00 | 86.89 | C |
| ATOM | 3574 | CD | ARG | C | 692 | 23.435 | 42.406 | 31.986 | 1.00 | 86.86 | C |
| ATOM | 3575 | NE | ARG | C | 692 | 21.985 | 42.502 | 32.157 | 1.00 | 86.84 | C |
| ATOM | 3576 | CZ | ARG | C | 692 | 21.318 | 43.642 | 32.340 | 1.00 | 87.03 | C |
| ATOM | 3577 | NH1 | ARG | C | 692 | 21.973 | 44.804 | 32.375 | 1.00 | 86.01 | C |
| ATOM | 3578 | NH2 | ARG | C | 692 | 19.994 | 43.616 | 32.495 | 1.00 | 84.75 | C |
| ATOM | 3579 | C | ARG | C | 692 | 23.341 | 40.103 | 28.140 | 1.00 | 86.68 | C |
| ATOM | 3580 | O | ARG | C | 692 | 23.907 | 39.068 | 28.510 | 1.00 | 86.80 | C |
| ATOM | 3581 | N | LEU | C | 693 | 22.099 | 40.123 | 27.660 | 1.00 | 86.72 | C |
| ATOM | 3582 | CA | LEU | C | 693 | 21.300 | 38.912 | 27.509 | 1.00 | 86.39 | C |
| ATOM | 3583 | CB | LEU | C | 693 | 19.915 | 39.283 | 26.992 | 1.00 | 86.23 | C |
| ATOM | 3584 | CG | LEU | C | 693 | 19.020 | 40.010 | 28.002 | 1.00 | 86.52 | C |
| ATOM | 3585 | CD1 | LEU | C | 693 | 17.986 | 40.871 | 27.292 | 1.00 | 86.94 | C |
| ATOM | 3586 | CD2 | LEU | C | 693 | 18.338 | 38.980 | 28.874 | 1.00 | 85.73 | C |
| ATOM | 3587 | C | LEU | C | 693 | 22.000 | 37.949 | 26.546 | 1.00 | 86.64 | C |
| ATOM | 3588 | O | LEU | C | 693 | 22.076 | 36.739 | 26.814 | 1.00 | 84.83 | C |
| ATOM | 3589 | N | LEU | C | 694 | 22.512 | 38.498 | 25.436 | 1.00 | 86.61 | C |
| ATOM | 3590 | CA | LEU | C | 694 | 23.245 | 37.712 | 24.437 | 1.00 | 87.49 | C |
| ATOM | 3591 | CB | LEU | C | 694 | 23.559 | 38.544 | 23.188 | 1.00 | 86.64 | C |
| ATOM | 3592 | CG | LEU | C | 694 | 22.445 | 38.844 | 22.187 | 1.00 | 85.85 | C |
| ATOM | 3593 | CD1 | LEU | C | 694 | 23.020 | 39.690 | 21.072 | 1.00 | 84.45 | C |
| ATOM | 3594 | CD2 | LEU | C | 694 | 21.855 | 37.550 | 21.641 | 1.00 | 84.78 | C |
| ATOM | 3595 | C | LEU | C | 694 | 24.563 | 37.219 | 25.019 | 1.00 | 87.84 | C |
| ATOM | 3596 | O | LEU | C | 694 | 24.930 | 36.050 | 24.879 | 1.00 | 87.15 | C |
| ATOM | 3597 | N | GLN | C | 695 | 25.275 | 38.121 | 25.677 | 1.00 | 88.88 | C |
| ATOM | 3598 | CA | GLN | C | 695 | 26.553 | 37.770 | 26.263 | 1.00 | 90.61 | C |
| ATOM | 3599 | CB | GLN | C | 695 | 27.219 | 39.031 | 26.804 | 1.00 | 90.86 | C |
| ATOM | 3600 | CG | GLN | C | 695 | 28.728 | 38.893 | 26.959 | 1.00 | 93.35 | C |
| ATOM | 3601 | CD | GLN | C | 695 | 29.455 | 40.219 | 26.879 | 1.00 | 94.61 | C |
| ATOM | 3602 | OE1 | GLN | C | 695 | 29.440 | 40.870 | 25.839 | 1.00 | 94.31 | C |
| ATOM | 3603 | NE2 | GLN | C | 695 | 30.099 | 40.626 | 27.982 | 1.00 | 95.49 | C |
| ATOM | 3604 | C | GLN | C | 695 | 26.470 | 36.675 | 27.342 | 1.00 | 91.30 | C |
| ATOM | 3605 | O | GLN | C | 695 | 27.321 | 35.770 | 27.391 | 1.00 | 90.95 | C |
| ATOM | 3606 | N | GLU | C | 696 | 25.443 | 36.741 | 28.190 | 1.00 | 92.76 | C |
| ATOM | 3607 | CA | GLU | C | 696 | 25.262 | 35.746 | 29.258 | 1.00 | 94.36 | C |
| ATOM | 3608 | CB | GLU | C | 696 | 24.728 | 36.425 | 30.531 | 1.00 | 94.68 | C |
| ATOM | 3609 | CG | GLU | C | 696 | 9999.000 | 9999.000 | 9999.000 | 1.00 | 0.00 | C |
| ATOM | 3610 | CD | GLU | C | 696 | 9999.000 | 9999.000 | 9999.000 | 1.00 | 0.00 | C |
| ATOM | 3611 | OE1 | GLU | C | 696 | 9999.000 | 9999.000 | 9999.000 | 1.00 | 0.00 | C |
| ATOM | 3612 | OE2 | GLU | C | 696 | 9999.000 | 9999.000 | 9999.000 | 1.00 | 0.00 | C |
| ATOM | 3613 | C | GLU | C | 696 | 24.321 | 34.611 | 28.844 | 1.00 | 94.49 | C |
| ATOM | 3614 | O | GLU | C | 696 | 24.765 | 33.757 | 28.039 | 1.00 | 94.54 | C |
| ATOM | 3615 | OXT | GLU | C | 696 | 23.160 | 34.601 | 29.326 | 1.00 | 94.03 | C |
| TER | | | | | | | | | | | |
| ATOM | 3616 | N | HIS | D | 687 | −7.771 | 58.169 | −8.351 | 1.00 | 115.70 | D |
| ATOM | 3617 | CA | HIS | D | 687 | −8.213 | 56.919 | −9.037 | 1.00 | 116.45 | D |
| ATOM | 3618 | CB | HIS | D | 687 | −9.198 | 56.172 | −8.130 | 1.00 | 115.80 | D |
| ATOM | 3619 | CG | HIS | D | 687 | 9999.000 | 9999.000 | 9999.000 | 1.00 | 0.00 | D |
| ATOM | 3620 | CD2 | HIS | D | 687 | 9999.000 | 9999.000 | 9999.000 | 1.00 | 0.00 | D |
| ATOM | 3621 | ND1 | HIS | D | 687 | 9999.000 | 9999.000 | 9999.000 | 1.00 | 0.00 | D |
| ATOM | 3622 | CE1 | HIS | D | 687 | 9999.000 | 9999.000 | 9999.000 | 1.00 | 0.00 | D |
| ATOM | 3623 | NE2 | HIS | D | 687 | 9999.000 | 9999.000 | 9999.000 | 1.00 | 0.00 | D |
| ATOM | 3624 | C | HIS | D | 687 | −8.832 | 57.127 | −10.445 | 1.00 | 116.50 | D |
| ATOM | 3625 | O | HIS | D | 687 | −9.360 | 56.178 | −11.039 | 1.00 | 116.67 | D |
| ATOM | 3626 | N | LYS | D | 688 | −8.754 | 58.349 | −10.984 | 1.00 | 116.60 | D |
| ATOM | 3627 | CA | LYS | D | 688 | −9.316 | 58.668 | −12.310 | 1.00 | 115.53 | D |
| ATOM | 3628 | CB | LYS | D | 688 | −9.987 | 60.042 | −12.267 | 1.00 | 115.01 | D |
| ATOM | 3629 | CG | LYS | D | 688 | 9999.000 | 9999.000 | 9999.000 | 1.00 | 0.00 | D |
| ATOM | 3630 | CD | LYS | D | 688 | 9999.000 | 9999.000 | 9999.000 | 1.00 | 0.00 | D |
| ATOM | 3631 | CE | LYS | D | 688 | 9999.000 | 9999.000 | 9999.000 | 1.00 | 0.00 | D |
| ATOM | 3632 | NZ | LYS | D | 688 | 9999.000 | 9999.000 | 9999.000 | 1.00 | 0.00 | D |
| ATOM | 3633 | C | LYS | D | 688 | −8.310 | 58.614 | −13.474 | 1.00 | 114.79 | D |
| ATOM | 3634 | O | LYS | D | 688 | −8.561 | 57.969 | −14.494 | 1.00 | 114.42 | D |
| ATOM | 3635 | N | ILE | D | 689 | −7.181 | 59.296 | −13.329 | 1.00 | 114.03 | D |
| ATOM | 3636 | CA | ILE | D | 689 | −6.164 | 59.301 | −14.374 | 1.00 | 113.75 | D |
| ATOM | 3637 | CB | ILE | D | 689 | −4.886 | 60.002 | −13.895 | 1.00 | 114.05 | D |
| ATOM | 3638 | CG2 | ILE | D | 689 | −3.984 | 60.296 | −15.088 | 1.00 | 113.34 | D |
| ATOM | 3639 | CG1 | ILE | D | 689 | −5.257 | 61.278 | −13.132 | 1.00 | 114.14 | D |

TABLE 1-continued

ATOMIC COORDINATES OF THE ERR3 LBD/SRC-1 NR
BOX 2 PEPTIDE COMPLEX (PDB CODE 1KV6)

| ATOM | 3640 | CD1 | ILE | D | 689 | −4.101 | 61.929 | −12.406 | 1.00 | 114.07 | D |
|---|---|---|---|---|---|---|---|---|---|---|---|
| ATOM | 3641 | C | ILE | D | 689 | −5.796 | 57.871 | −14.765 | 1.00 | 113.71 | D |
| ATOM | 3642 | O | ILE | D | 689 | −5.890 | 57.505 | −15.936 | 1.00 | 113.48 | D |
| ATOM | 3643 | N | LEU | D | 690 | −5.383 | 57.085 | −13.764 | 1.00 | 113.19 | D |
| ATOM | 3644 | CA | LEU | D | 690 | −4.977 | 55.686 | −13.919 | 1.00 | 112.08 | D |
| ATOM | 3645 | CB | LEU | D | 690 | −4.492 | 55.135 | −12.578 | 1.00 | 112.25 | D |
| ATOM | 3646 | CG | LEU | D | 690 | −4.357 | 53.610 | −12.480 | 1.00 | 111.67 | D |
| ATOM | 3647 | CD1 | LEU | D | 690 | −3.226 | 53.137 | −13.374 | 1.00 | 112.29 | D |
| ATOM | 3648 | CD2 | LEU | D | 690 | −4.106 | 53.196 | −11.041 | 1.00 | 111.41 | D |
| ATOM | 3649 | C | LEU | D | 690 | −6.069 | 54.768 | −14.465 | 1.00 | 112.01 | D |
| ATOM | 3650 | O | LEU | D | 690 | −5.770 | 53.709 | −15.023 | 1.00 | 111.55 | D |
| ATOM | 3651 | N | HIS | D | 691 | −7.329 | 55.161 | −14.288 | 1.00 | 111.89 | D |
| ATOM | 3652 | CA | HIS | D | 691 | −8.451 | 54.369 | −14.796 | 1.00 | 112.30 | D |
| ATOM | 3653 | CB | HIS | D | 691 | −9.768 | 54.800 | −14.126 | 1.00 | 113.16 | D |
| ATOM | 3654 | CG | HIS | D | 691 | −10.966 | 54.028 | −14.593 | 1.00 | 114.73 | D |
| ATOM | 3655 | CD2 | HIS | D | 691 | −12.023 | 54.397 | −15.357 | 1.00 | 115.58 | D |
| ATOM | 3656 | ND1 | HIS | D | 691 | −11.146 | 52.688 | −14.316 | 1.00 | 115.61 | D |
| ATOM | 3657 | CE1 | HIS | D | 691 | −12.259 | 52.263 | −14.891 | 1.00 | 115.44 | D |
| ATOM | 3658 | NE2 | HIS | D | 691 | −12.809 | 53.280 | −15.530 | 1.00 | 115.91 | D |
| ATOM | 3659 | C | HIS | D | 691 | −8.549 | 54.564 | −16.318 | 1.00 | 112.14 | D |
| ATOM | 3660 | O | HIS | D | 691 | −8.978 | 53.667 | −17.054 | 1.00 | 112.20 | D |
| ATOM | 3661 | N | ARG | D | 692 | −8.143 | 55.744 | −16.787 | 1.00 | 111.98 | D |
| ATOM | 3662 | CA | ARG | D | 692 | −8.180 | 56.044 | −18.217 | 1.00 | 110.99 | D |
| ATOM | 3663 | CB | ARG | D | 692 | −8.025 | 57.552 | −18.477 | 1.00 | 111.97 | D |
| ATOM | 3664 | CG | ARG | D | 692 | −8.126 | 57.888 | −19.965 | 1.00 | 113.01 | D |
| ATOM | 3665 | CD | ARG | D | 692 | −8.085 | 59.370 | −20.274 | 1.00 | 113.65 | D |
| ATOM | 3666 | NE | ARG | D | 692 | −6.784 | 59.988 | −20.025 | 1.00 | 114.10 | D |
| ATOM | 3667 | CZ | ARG | D | 692 | −6.508 | 60.748 | −18.968 | 1.00 | 114.81 | D |
| ATOM | 3668 | NH1 | ARG | D | 692 | −7.451 | 60.980 | −18.052 | 1.00 | 114.30 | D |
| ATOM | 3669 | NH2 | ARG | D | 692 | −5.295 | 61.292 | −18.839 | 1.00 | 114.26 | D |
| ATOM | 3670 | C | ARG | D | 692 | −7.078 | 55.291 | −18.952 | 1.00 | 109.41 | D |
| ATOM | 3671 | O | ARG | D | 692 | −7.361 | 54.508 | −19.864 | 1.00 | 108.70 | D |
| ATOM | 3672 | N | LEU | D | 693 | −5.830 | 55.537 | −18.551 | 1.00 | 107.62 | D |
| ATOM | 3673 | CA | LEU | D | 693 | −4.684 | 54.881 | −19.159 | 1.00 | 106.54 | D |
| ATOM | 3674 | CB | LEU | D | 693 | −3.413 | 55.180 | −18.374 | 1.00 | 106.05 | D |
| ATOM | 3675 | CG | LEU | D | 693 | −2.917 | 56.620 | −18.483 | 1.00 | 106.47 | D |
| ATOM | 3676 | CD1 | LEU | D | 693 | −3.929 | 57.539 | −17.829 | 1.00 | 107.02 | D |
| ATOM | 3677 | CD2 | LEU | D | 693 | −1.558 | 56.767 | −17.815 | 1.00 | 106.26 | D |
| ATOM | 3678 | C | LEU | D | 693 | −4.893 | 53.380 | −19.222 | 1.00 | 106.14 | D |
| ATOM | 3679 | O | LEU | D | 693 | −4.535 | 52.732 | −20.208 | 1.00 | 105.46 | D |
| ATOM | 3680 | N | LEU | D | 694 | −5.487 | 52.833 | −18.168 | 1.00 | 106.37 | D |
| ATOM | 3681 | CA | LEU | D | 694 | −5.747 | 51.400 | −18.084 | 1.00 | 107.17 | D |
| ATOM | 3682 | CB | LEU | D | 694 | −6.141 | 51.023 | −16.648 | 1.00 | 106.51 | D |
| ATOM | 3683 | CG | LEU | D | 694 | −5.017 | 50.774 | −15.638 | 1.00 | 105.77 | D |
| ATOM | 3684 | CD1 | LEU | D | 694 | −5.556 | 50.911 | −14.236 | 1.00 | 105.48 | D |
| ATOM | 3685 | CD2 | LEU | D | 694 | −4.425 | 49.387 | −15.860 | 1.00 | 104.87 | D |
| ATOM | 3686 | C | LEU | D | 694 | −6.839 | 50.964 | −19.050 | 1.00 | 107.94 | D |
| ATOM | 3687 | O | LEU | D | 694 | −6.825 | 49.844 | −19.568 | 1.00 | 107.86 | D |
| ATOM | 3688 | N | GLN | D | 695 | −7.780 | 51.863 | −19.296 | 1.00 | 109.19 | D |
| ATOM | 3689 | CA | GLN | D | 695 | −8.883 | 51.569 | −20.186 | 1.00 | 110.97 | D |
| ATOM | 3690 | CB | GLN | D | 695 | −9.981 | 52.592 | −19.972 | 1.00 | 111.97 | D |
| ATOM | 3691 | CG | GLN | D | 695 | −11.352 | 52.040 | −20.211 | 1.00 | 113.80 | D |
| ATOM | 3692 | CD | GLN | D | 695 | −12.402 | 52.992 | −19.718 | 1.00 | 115.26 | D |
| ATOM | 3693 | OE1 | GLN | D | 695 | −12.345 | 53.449 | −18.572 | 1.00 | 115.68 | D |
| ATOM | 3694 | NE2 | GLN | D | 695 | −13.371 | 53.307 | −20.572 | 1.00 | 115.58 | D |
| ATOM | 3695 | C | GLN | D | 695 | −8.469 | 51.532 | −21.660 | 1.00 | 111.43 | D |
| ATOM | 3696 | O | GLN | D | 695 | −9.227 | 51.058 | −22.511 | 1.00 | 111.32 | D |
| ATOM | 3697 | N | GLU | D | 696 | −7.265 | 52.026 | −21.953 | 1.00 | 111.99 | D |
| ATOM | 3698 | CA | GLU | D | 696 | −6.723 | 52.031 | −23.318 | 1.00 | 111.79 | D |
| ATOM | 3699 | CB | GLU | D | 696 | −5.267 | 52.514 | −23.309 | 1.00 | 111.18 | D |
| ATOM | 3700 | CG | GLU | D | 696 | −5.085 | 53.910 | −22.749 | 1.00 | 110.69 | D |
| ATOM | 3701 | CD | GLU | D | 696 | −5.973 | 54.939 | −23.426 | 1.00 | 110.64 | D |
| ATOM | 3702 | OE1 | GLU | D | 696 | −5.844 | 56.143 | −23.109 | 1.00 | 110.67 | D |
| ATOM | 3703 | OE2 | GLU | D | 696 | −6.801 | 54.545 | −24.273 | 1.00 | 110.20 | D |
| ATOM | 3704 | C | GLU | D | 696 | −6.794 | 50.650 | −23.992 | 1.00 | 112.13 | D |
| ATOM | 3705 | O | GLU | D | 696 | −7.463 | 50.487 | −25.027 | 1.00 | 112.03 | D |
| ATOM | 3706 | N | GLY | D | 697 | −6.099 | 49.664 | −23.417 | 1.00 | 111.34 | D |
| ATOM | 3707 | CA | GLY | D | 697 | −6.128 | 48.329 | −23.988 | 1.00 | 110.26 | D |
| ATOM | 3708 | C | GLY | D | 697 | −7.526 | 47.940 | −24.451 | 1.00 | 109.83 | D |
| ATOM | 3709 | O | GLY | D | 697 | −7.743 | 47.796 | −25.679 | 1.00 | 108.23 | D |
| ATOM | 3710 | OXT | GLY | D | 697 | −8.412 | 47.790 | −23.577 | 1.00 | 109.26 | D |
| TER | | | | | | | | | | | |
| ATOM | 3711 | OH2 | WAT | S | 1001 | 13.468 | 39.875 | 7.989 | 1.00 | 66.44 | S |
| ATOM | 3712 | OH2 | WAT | S | 1002 | 15.258 | 41.735 | 1.385 | 1.00 | 49.24 | S |
| ATOM | 3713 | OH2 | WAT | S | 1003 | 9.305 | 23.857 | −2.785 | 1.00 | 54.04 | S |
| ATOM | 3714 | OH2 | WAT | S | 1004 | 12.202 | 23.365 | −2.363 | 1.00 | 58.04 | S |

TABLE 1-continued

ATOMIC COORDINATES OF THE ERR3 LBD/SRC-1 NR BOX 2 PEPTIDE COMPLEX (PDB CODE 1KV6)

| ATOM | 3715 | OH2 | WAT | S | 1005 | 13.967 | 13.909 | 7.806 | 1.00 | 68.35 | S |
|---|---|---|---|---|---|---|---|---|---|---|---|
| ATOM | 3716 | OH2 | WAT | S | 1006 | 8.280 | 20.778 | −3.060 | 1.00 | 55.44 | S |
| ATOM | 3717 | OH2 | WAT | S | 1007 | 25.574 | 52.085 | −7.502 | 1.00 | 85.02 | S |
| ATOM | 3718 | OH2 | WAT | S | 1008 | 4.648 | 37.033 | 19.633 | 1.00 | 67.51 | S |
| ATOM | 3719 | OH2 | WAT | S | 1009 | 2.918 | 33.259 | −1.421 | 1.00 | 53.28 | S |
| ATOM | 3720 | OH2 | WAT | S | 1010 | 10.770 | 39.717 | 6.061 | 1.00 | 64.72 | S |
| ATOM | 3721 | OH2 | WAT | S | 1011 | 5.425 | 44.220 | −4.193 | 1.00 | 58.50 | S |
| ATOM | 3722 | OH2 | WAT | S | 1012 | 9.301 | 43.392 | −18.470 | 1.00 | 79.05 | S |
| ATOM | 3723 | OH2 | WAT | S | 1013 | 6.548 | 70.232 | −1.384 | 1.00 | 127.23 | S |
| ATOM | 3724 | OH2 | WAT | S | 1014 | −8.438 | 35.040 | 11.301 | 1.00 | 108.06 | S |
| ATOM | 3725 | OH2 | WAT | S | 1015 | 17.516 | 57.034 | −18.636 | 1.00 | 117.34 | S |
| ATOM | 3726 | OH2 | WAT | S | 1016 | 4.277 | 39.295 | 0.979 | 1.00 | 63.29 | S |
| ATOM | 3727 | OH2 | WAT | S | 1017 | 2.131 | 36.122 | −1.331 | 1.00 | 52.39 | S |
| ATOM | 3728 | OH2 | WAT | S | 1018 | 12.705 | 54.097 | −13.027 | 1.00 | 131.74 | S |
| ATOM | 3729 | OH2 | WAT | S | 1019 | 25.528 | 29.468 | −15.552 | 1.00 | 64.41 | S |
| ATOM | 3730 | OH2 | WAT | S | 1020 | 2.570 | 70.153 | −6.363 | 1.00 | 153.10 | S |
| ATOM | 3731 | OH2 | WAT | S | 1021 | −12.472 | 32.365 | 16.856 | 1.00 | 67.30 | S |
| ATOM | 3732 | OH2 | WAT | S | 1022 | 23.862 | 28.589 | −1.472 | 1.00 | 59.06 | S |
| ATOM | 3733 | OH2 | WAT | S | 1023 | 6.849 | 46.537 | 28.494 | 1.00 | 98.58 | S |
| ATOM | 3734 | OH2 | WAT | S | 1024 | −7.304 | 34.711 | 13.503 | 1.00 | 81.31 | S |
| ATOM | 3735 | OH2 | WAT | S | 1025 | 12.990 | 38.488 | 5.335 | 1.00 | 56.25 | S |
| ATOM | 3736 | OH2 | WAT | S | 1026 | 6.744 | 41.524 | −3.371 | 1.00 | 54.49 | S |
| ATOM | 3737 | OH2 | WAT | S | 1027 | 16.252 | 60.163 | 3.163 | 1.00 | 94.93 | S |
| ATOM | 3738 | OH2 | WAT | S | 1028 | 1.300 | 24.322 | −1.315 | 1.00 | 57.46 | S |
| ATOM | 3739 | OH2 | WAT | S | 1029 | 13.907 | 59.521 | 3.828 | 1.00 | 75.25 | S |
| ATOM | 3740 | OH2 | WAT | S | 1030 | 0.973 | 41.822 | −24.360 | 1.00 | 74.51 | S |
| ATOM | 3741 | OH2 | WAT | S | 1031 | 11.894 | 27.627 | 16.753 | 1.00 | 76.91 | S |
| END | | | | | | | | | | | |

TABLE 2

ATOMIC COORDINATES OF THE ERR3 LBD/ DIETHYLSTILBESTROL COMPLEX

REMARK Created by MOLEMAN V. 961218/7.2.5 at Fri Jan 10 11:15:51 2003 for greschik
REMARK MoleMan PDB file
REMARK coordinates from restrained individual B-factor refinement
REMARK refinement resolution: 25.0-2.25 A
REMARK starting r = 0.2638 free_r = 0.2706
REMARK final r = 0.2114 free_r = 0.2218
REMARK B rmsd for bonded mainchain atoms = 1.128 target = 1.5
REMARK B rmsd for bonded sidechain atoms = 2.009 target = 2.0
REMARK B rmsd for angle mainchain atoms = 1.888 target = 2.0
REMARK B rmsd for angle sidechain atoms = 3.024 target = 2.5
REMARK rweight = 0.1000 (with wa = 1.88781)
REMARK target = mlf steps = 50
REMARK sg = P2(1) a = 71.999 b = 77.457 c = 95.770 alpha = 90 beta = 97.549 gamma = 90
REMARK parameter file 1 CNS_TOPPAR: protein_rep.param
REMARK parameter file 2 des.par
REMARK parameter file 3 CNS_TOPPAR: water_rep.param
REMARK molecular structure file: 14_refmac.mtf
REMARK input coordinates: gen_14_refmac.pdb
REMARK reflection file = DES_NaAc_fin.cv
REMARK ncs = none
REMARK B-correction resolution: 6.0-2.25
REMARK initial B-factor correction applied to fobs:
REMARK B11 = 2.079 B22 = −9.865 B33 = 7.785
REMARK B12 = 0.000 B13 = 0.939 B23 = 0.000
REMARK B-factor correction applied to coordinate array B: −1.842
REMARK bulk solvent: density level = 0.353254 e/A^3, B-factor = 41.3961 A^2
REMARK reflections with |Fobs|/sigma_F < 3.0 rejected
REMARK reflections with |Fobs| > 10000 * rms(Fobs) rejected
REMARK theoretical total number of refl. in resol. range:     49668 (100.0%)
REMARK number of unobserved reflections (no entry or |F| = 0):    444 (0.9%)
REMARK number of reflections rejected:                         1310 (2.6%)
REMARK total number of reflections used:                      47914 (96.5%)
REMARK number of reflections in working set:                   45509 (91.6%)
REMARK number of reflections in test set:                       2405 (4.8%)
REMARK FILENAME = "/work/greschik/NaAc_DES/CNS/bref_1.pdb"
REMARK DATE: 10-Jan-03 11:08:14  created by user: greschik
REMARK VERSION: 1.1

TABLE 2-continued

ATOMIC COORDINATES OF THE ERR3 LBD/
DIETHYLSTILBESTROL COMPLEX

| CRYST1 | | 71.999 | 77.457 | 95.770 | 90.00 | 97.55 | 90.00 | P | 21 1 | |
|---|---|---|---|---|---|---|---|---|---|---|
| ORIGX1 | | 1.000000 | 0.000000 | 0.000000 | 0.00000 | | | | | |
| ORIGX2 | | 0.000000 | 1.000000 | 0.000000 | 0.00000 | | | | | |
| ORIGX3 | | 0.000000 | 0.000000 | 1.000000 | 0.00000 | | | | | |
| SCALE1 | | 0.013889 | 0.000000 | 0.001841 | 0.00000 | | | | | |
| SCALE2 | | 0.000000 | 0.012910 | 0.000000 | 0.00000 | | | | | |
| SCALE3 | | 0.000000 | 0.000000 | 0.010533 | 0.00000 | | | | | |
| ATOM | 1 | CB | TYR | A | 234 | 35.809 | 59.359 | 60.924 | 1.00 | 56.95 A |
| ATOM | 2 | CG | TYR | A | 234 | 36.156 | 58.017 | 60.425 | 1.00 | 58.69 A |
| ATOM | 3 | CD1 | TYR | A | 234 | 37.052 | 57.889 | 59.367 | 1.00 | 59.99 A |
| ATOM | 4 | CE1 | TYR | A | 234 | 37.339 | 56.713 | 58.803 | 1.00 | 59.98 A |
| ATOM | 5 | CD2 | TYR | A | 234 | 35.483 | 56.919 | 60.830 | 1.00 | 59.82 A |
| ATOM | 6 | CE2 | TYR | A | 234 | 35.773 | 55.690 | 60.251 | 1.00 | 61.21 A |
| ATOM | 7 | CZ | TYR | A | 234 | 36.728 | 55.640 | 59.232 | 1.00 | 60.77 A |
| ATOM | 8 | OH | TYR | A | 234 | 37.061 | 54.510 | 58.582 | 1.00 | 63.08 A |
| ATOM | 9 | C | TYR | A | 234 | 36.454 | 60.571 | 58.742 | 1.00 | 53.90 A |
| ATOM | 10 | O | TYR | A | 234 | 36.218 | 60.949 | 57.570 | 1.00 | 54.43 A |
| ATOM | 11 | N | TYR | A | 234 | 34.025 | 59.740 | 59.067 | 1.00 | 55.08 A |
| ATOM | 12 | CA | TYR | A | 234 | 35.317 | 60.284 | 59.751 | 1.00 | 55.55 A |
| ATOM | 13 | N | ASN | A | 235 | 37.665 | 60.511 | 59.252 | 1.00 | 51.67 A |
| ATOM | 14 | CA | ASN | A | 235 | 38.863 | 60.865 | 58.571 | 1.00 | 49.71 A |
| ATOM | 15 | CB | ASN | A | 235 | 40.023 | 60.303 | 59.443 | 1.00 | 49.47 A |
| ATOM | 16 | CG | ASN | A | 235 | 41.343 | 60.804 | 59.016 | 1.00 | 47.99 A |
| ATOM | 17 | OD1 | ASN | A | 235 | 41.918 | 60.343 | 58.015 | 1.00 | 46.89 A |
| ATOM | 18 | ND2 | ASN | A | 235 | 41.767 | 61.854 | 59.660 | 1.00 | 48.87 A |
| ATOM | 19 | C | ASN | A | 235 | 38.977 | 60.272 | 57.167 | 1.00 | 48.43 A |
| ATOM | 20 | O | ASN | A | 235 | 38.719 | 59.098 | 56.956 | 1.00 | 49.13 A |
| ATOM | 21 | N | LYS | A | 236 | 39.448 | 61.078 | 56.221 | 1.00 | 46.58 A |
| ATOM | 22 | CA | LYS | A | 236 | 39.578 | 60.624 | 54.877 | 1.00 | 44.96 A |
| ATOM | 23 | CB | LYS | A | 236 | 39.624 | 61.791 | 53.911 | 1.00 | 47.35 A |
| ATOM | 24 | CG | LYS | A | 236 | 40.619 | 62.891 | 54.218 | 1.00 | 53.90 A |
| ATOM | 25 | CD | LYS | A | 236 | 39.954 | 64.167 | 54.751 | 1.00 | 58.26 A |
| ATOM | 26 | CE | LYS | A | 236 | 39.422 | 64.021 | 56.176 | 1.00 | 59.80 A |
| ATOM | 27 | NZ | LYS | A | 236 | 38.796 | 65.280 | 56.668 | 1.00 | 61.93 A |
| ATOM | 28 | C | LYS | A | 236 | 40.871 | 59.764 | 54.721 | 1.00 | 41.59 A |
| ATOM | 29 | O | LYS | A | 236 | 40.872 | 58.859 | 53.938 | 1.00 | 38.97 A |
| ATOM | 30 | N | ILE | A | 237 | 41.939 | 60.084 | 55.428 | 1.00 | 37.47 A |
| ATOM | 31 | CA | ILE | A | 237 | 43.164 | 59.277 | 55.241 | 1.00 | 35.29 A |
| ATOM | 32 | CB | ILE | A | 237 | 44.280 | 59.710 | 56.116 | 1.00 | 35.92 A |
| ATOM | 33 | CG2 | ILE | A | 237 | 45.422 | 58.849 | 55.969 | 1.00 | 36.03 A |
| ATOM | 34 | CG1 | ILE | A | 237 | 44.643 | 61.176 | 55.859 | 1.00 | 37.89 A |
| ATOM | 35 | CD1 | ILE | A | 237 | 44.992 | 61.409 | 54.597 | 1.00 | 36.20 A |
| ATOM | 36 | C | ILE | A | 237 | 42.793 | 57.877 | 55.661 | 1.00 | 33.71 A |
| ATOM | 37 | O | ILE | A | 237 | 43.093 | 56.916 | 54.887 | 1.00 | 32.99 A |
| ATOM | 38 | N | VAL | A | 238 | 42.133 | 57.754 | 56.820 | 1.00 | 31.72 A |
| ATOM | 39 | CA | VAL | A | 238 | 41.797 | 56.437 | 57.379 | 1.00 | 31.36 A |
| ATOM | 40 | CB | VAL | A | 238 | 41.142 | 56.512 | 58.717 | 1.00 | 30.67 A |
| ATOM | 41 | CG1 | VAL | A | 238 | 40.751 | 55.077 | 59.237 | 1.00 | 29.03 A |
| ATOM | 42 | CG2 | VAL | A | 238 | 42.014 | 57.194 | 59.688 | 1.00 | 30.44 A |
| ATOM | 43 | C | VAL | A | 238 | 40.912 | 55.646 | 56.451 | 1.00 | 32.43 A |
| ATOM | 44 | O | VAL | A | 238 | 41.128 | 54.406 | 56.211 | 1.00 | 32.92 A |
| ATOM | 45 | N | SER | A | 239 | 39.869 | 56.280 | 55.907 | 1.00 | 33.39 A |
| ATOM | 46 | CA | SER | A | 239 | 38.975 | 55.531 | 55.026 | 1.00 | 34.93 A |
| ATOM | 47 | CB | SER | A | 239 | 37.814 | 56.437 | 54.670 | 1.00 | 39.57 A |
| ATOM | 48 | OG | SER | A | 239 | 38.301 | 57.594 | 53.976 | 1.00 | 49.19 A |
| ATOM | 49 | C | SER | A | 239 | 39.665 | 55.173 | 53.702 | 1.00 | 32.89 A |
| ATOM | 50 | O | SER | A | 239 | 39.448 | 54.130 | 53.112 | 1.00 | 33.31 A |
| ATOM | 51 | N | HIS | A | 240 | 40.543 | 56.024 | 53.239 | 1.00 | 31.28 A |
| ATOM | 52 | CA | HIS | A | 240 | 41.280 | 55.735 | 52.022 | 1.00 | 30.61 A |
| ATOM | 53 | CB | HIS | A | 240 | 42.117 | 56.892 | 51.648 | 1.00 | 30.25 A |
| ATOM | 54 | CG | HIS | A | 240 | 43.179 | 56.530 | 50.663 | 1.00 | 30.91 A |
| ATOM | 55 | CD2 | HIS | A | 240 | 44.483 | 56.244 | 50.838 | 1.00 | 29.61 A |
| ATOM | 56 | ND1 | HIS | A | 240 | 42.904 | 56.322 | 49.331 | 1.00 | 30.75 A |
| ATOM | 57 | CE1 | HIS | A | 240 | 44.013 | 55.938 | 48.726 | 1.00 | 29.30 A |
| ATOM | 58 | NE2 | HIS | A | 240 | 44.965 | 55.828 | 49.633 | 1.00 | 31.38 A |
| ATOM | 59 | C | HIS | A | 240 | 42.204 | 54.478 | 52.299 | 1.00 | 30.12 A |
| ATOM | 60 | O | HIS | A | 240 | 42.133 | 53.483 | 51.573 | 1.00 | 30.52 A |
| ATOM | 61 | N | LEU | A | 241 | 42.956 | 54.480 | 53.391 | 1.00 | 29.36 A |
| ATOM | 62 | CA | LEU | A | 241 | 43.784 | 53.237 | 53.776 | 1.00 | 29.25 A |
| ATOM | 63 | CB | LEU | A | 241 | 44.484 | 53.469 | 55.097 | 1.00 | 27.84 A |
| ATOM | 64 | CG | LEU | A | 241 | 45.564 | 54.558 | 54.954 | 1.00 | 28.81 A |
| ATOM | 65 | CD1 | LEU | A | 241 | 46.213 | 54.863 | 56.306 | 1.00 | 28.57 A |
| ATOM | 66 | CD2 | LEU | A | 241 | 46.613 | 53.986 | 53.955 | 1.00 | 27.72 A |
| ATOM | 67 | C | LEU | A | 241 | 42.978 | 51.990 | 53.849 | 1.00 | 29.20 A |
| ATOM | 68 | O | LEU | A | 241 | 43.448 | 50.915 | 53.474 | 1.00 | 29.59 A |
| ATOM | 69 | N | LEU | A | 242 | 41.709 | 52.041 | 54.265 | 1.00 | 30.65 A |

TABLE 2-continued

ATOMIC COORDINATES OF THE ERR3 LBD/
DIETHYLSTILBESTROL COMPLEX

| ATOM | 70 | CA | LEU | A | 242 | 40.862 | 50.797 | 54.330 | 1.00 | 32.15 | A |
|------|-----|-----|-----|---|-----|--------|--------|--------|------|-------|---|
| ATOM | 71 | CB | LEU | A | 242 | 39.483 | 50.982 | 54.965 | 1.00 | 31.67 | A |
| ATOM | 72 | CG | LEU | A | 242 | 39.430 | 51.250 | 56.446 | 1.00 | 34.12 | A |
| ATOM | 73 | CD1 | LEU | A | 242 | 38.006 | 51.702 | 56.808 | 1.00 | 30.87 | A |
| ATOM | 74 | CD2 | LEU | A | 242 | 39.770 | 49.966 | 57.224 | 1.00 | 31.89 | A |
| ATOM | 75 | C | LEU | A | 242 | 40.549 | 50.347 | 52.964 | 1.00 | 33.96 | A |
| ATOM | 76 | O | LEU | A | 242 | 40.452 | 49.182 | 52.671 | 1.00 | 34.22 | A |
| ATOM | 77 | N | VAL | A | 243 | 40.320 | 51.312 | 52.101 | 1.00 | 34.94 | A |
| ATOM | 78 | CA | VAL | A | 243 | 40.022 | 50.987 | 50.693 | 1.00 | 35.58 | A |
| ATOM | 79 | CB | VAL | A | 243 | 39.254 | 52.242 | 50.059 | 1.00 | 36.52 | A |
| ATOM | 80 | CG1 | VAL | A | 243 | 39.170 | 52.230 | 48.553 | 1.00 | 38.81 | A |
| ATOM | 81 | CG2 | VAL | A | 243 | 37.844 | 52.277 | 50.683 | 1.00 | 37.92 | A |
| ATOM | 82 | C | VAL | A | 243 | 41.303 | 50.559 | 49.978 | 1.00 | 35.82 | A |
| ATOM | 83 | O | VAL | A | 243 | 41.246 | 49.764 | 49.096 | 1.00 | 37.11 | A |
| ATOM | 84 | N | ALA | A | 244 | 42.471 | 51.014 | 50.407 | 1.00 | 35.41 | A |
| ATOM | 85 | CA | ALA | A | 244 | 43.728 | 50.557 | 49.865 | 1.00 | 35.24 | A |
| ATOM | 86 | CB | ALA | A | 244 | 44.835 | 51.597 | 50.269 | 1.00 | 36.27 | A |
| ATOM | 87 | C | ALA | A | 244 | 44.237 | 49.144 | 50.270 | 1.00 | 35.28 | A |
| ATOM | 88 | O | ALA | A | 244 | 45.210 | 48.651 | 49.716 | 1.00 | 35.20 | A |
| ATOM | 89 | N | GLU | A | 245 | 43.510 | 48.455 | 51.087 | 1.00 | 35.03 | A |
| ATOM | 90 | CA | GLU | A | 245 | 43.979 | 47.254 | 51.686 | 1.00 | 37.34 | A |
| ATOM | 91 | CB | GLU | A | 245 | 42.978 | 46.968 | 52.804 | 1.00 | 36.49 | A |
| ATOM | 92 | CG | GLU | A | 245 | 43.284 | 45.942 | 53.808 | 1.00 | 38.03 | A |
| ATOM | 93 | CD | GLU | A | 245 | 44.500 | 46.168 | 54.639 | 1.00 | 35.71 | A |
| ATOM | 94 | OE1 | GLU | A | 245 | 45.169 | 47.182 | 54.629 | 1.00 | 36.52 | A |
| ATOM | 95 | OE2 | GLU | A | 245 | 44.797 | 45.193 | 55.189 | 1.00 | 37.13 | A |
| ATOM | 96 | C | GLU | A | 245 | 44.072 | 46.143 | 50.649 | 1.00 | 37.60 | A |
| ATOM | 97 | O | GLU | A | 245 | 43.225 | 45.989 | 49.875 | 1.00 | 37.95 | A |
| ATOM | 98 | N | PRO | A | 246 | 45.122 | 45.332 | 50.618 | 1.00 | 38.34 | A |
| ATOM | 99 | CD | PRO | A | 246 | 46.150 | 45.122 | 51.607 | 1.00 | 37.77 | A |
| ATOM | 100 | CA | PRO | A | 246 | 45.313 | 44.363 | 49.526 | 1.00 | 39.07 | A |
| ATOM | 101 | CB | PRO | A | 246 | 46.687 | 43.771 | 49.855 | 1.00 | 38.14 | A |
| ATOM | 102 | CG | PRO | A | 246 | 47.242 | 44.781 | 50.722 | 1.00 | 37.71 | A |
| ATOM | 103 | C | PRO | A | 246 | 44.301 | 43.280 | 49.749 | 1.00 | 39.42 | A |
| ATOM | 104 | O | PRO | A | 246 | 43.931 | 43.123 | 50.903 | 1.00 | 38.97 | A |
| ATOM | 105 | N | GLU | A | 247 | 43.889 | 42.616 | 48.695 | 1.00 | 40.85 | A |
| ATOM | 106 | CA | GLU | A | 247 | 43.074 | 41.397 | 48.713 | 1.00 | 42.63 | A |
| ATOM | 107 | CB | GLU | A | 247 | 42.841 | 40.816 | 47.258 | 1.00 | 45.70 | A |
| ATOM | 108 | CG | GLU | A | 247 | 43.431 | 39.449 | 46.871 | 1.00 | 55.22 | A |
| ATOM | 109 | CD | GLU | A | 247 | 44.882 | 39.525 | 46.444 | 1.00 | 59.93 | A |
| ATOM | 110 | OE1 | GLU | A | 247 | 45.175 | 40.250 | 45.471 | 1.00 | 62.98 | A |
| ATOM | 111 | OE2 | GLU | A | 247 | 45.732 | 38.862 | 47.076 | 1.00 | 63.05 | A |
| ATOM | 112 | C | GLU | A | 247 | 43.823 | 40.353 | 49.466 | 1.00 | 41.06 | A |
| ATOM | 113 | O | GLU | A | 247 | 44.985 | 40.409 | 49.563 | 1.00 | 39.23 | A |
| ATOM | 114 | N | LYS | A | 248 | 43.112 | 39.309 | 49.807 | 1.00 | 41.29 | A |
| ATOM | 115 | CA | LYS | A | 248 | 43.620 | 38.170 | 50.589 | 1.00 | 41.44 | A |
| ATOM | 116 | CB | LYS | A | 248 | 42.471 | 37.222 | 50.956 | 1.00 | 41.06 | A |
| ATOM | 117 | CG | LYS | A | 248 | 41.565 | 37.868 | 52.063 | 1.00 | 41.69 | A |
| ATOM | 118 | CD | LYS | A | 248 | 40.133 | 37.225 | 52.102 | 1.00 | 42.45 | A |
| ATOM | 119 | CE | LYS | A | 248 | 39.679 | 36.961 | 53.591 | 1.00 | 43.07 | A |
| ATOM | 120 | NZ | LYS | A | 248 | 40.408 | 35.724 | 54.058 | 1.00 | 42.95 | A |
| ATOM | 121 | C | LYS | A | 248 | 44.634 | 37.449 | 49.780 | 1.00 | 42.19 | A |
| ATOM | 122 | O | LYS | A | 248 | 44.432 | 37.328 | 48.553 | 1.00 | 42.03 | A |
| ATOM | 123 | N | ILE | A | 249 | 45.696 | 36.938 | 50.450 | 1.00 | 41.91 | A |
| ATOM | 124 | CA | ILE | A | 249 | 46.764 | 36.172 | 49.793 | 1.00 | 41.05 | A |
| ATOM | 125 | CB | ILE | A | 249 | 48.140 | 36.869 | 49.815 | 1.00 | 40.08 | A |
| ATOM | 126 | CG2 | ILE | A | 249 | 49.175 | 36.246 | 49.511 | 0.00 | 40.45 | A |
| ATOM | 127 | CG1 | ILE | A | 249 | 47.982 | 38.342 | 49.364 | 1.00 | 40.49 | A |
| ATOM | 128 | CD1 | ILE | A | 249 | 49.197 | 39.250 | 49.593 | 1.00 | 39.97 | A |
| ATOM | 129 | C | ILE | A | 249 | 46.817 | 34.849 | 50.492 | 1.00 | 41.05 | A |
| ATOM | 130 | O | ILE | A | 249 | 46.629 | 34.712 | 51.734 | 1.00 | 40.59 | A |
| ATOM | 131 | N | TYR | A | 250 | 46.976 | 33.860 | 49.660 | 1.00 | 41.24 | A |
| ATOM | 132 | CA | TYR | A | 250 | 46.957 | 32.464 | 50.062 | 1.00 | 41.22 | A |
| ATOM | 133 | CB | TYR | A | 250 | 46.098 | 31.693 | 49.064 | 1.00 | 42.02 | A |
| ATOM | 134 | CG | TYR | A | 250 | 44.712 | 32.201 | 49.246 | 1.00 | 43.41 | A |
| ATOM | 135 | CD1 | TYR | A | 250 | 43.935 | 31.701 | 50.246 | 1.00 | 43.88 | A |
| ATOM | 136 | CE1 | TYR | A | 250 | 42.623 | 32.280 | 50.557 | 1.00 | 44.10 | A |
| ATOM | 137 | CD2 | TYR | A | 250 | 44.211 | 33.262 | 48.472 | 1.00 | 43.84 | A |
| ATOM | 138 | CE2 | TYR | A | 250 | 42.913 | 33.839 | 48.743 | 1.00 | 44.24 | A |
| ATOM | 139 | CZ | TYR | A | 250 | 42.145 | 33.306 | 49.779 | 1.00 | 45.02 | A |
| ATOM | 140 | OH | TYR | A | 250 | 40.897 | 33.760 | 50.061 | 1.00 | 45.97 | A |
| ATOM | 141 | C | TYR | A | 250 | 48.381 | 32.021 | 49.974 | 1.00 | 41.54 | A |
| ATOM | 142 | O | TYR | A | 250 | 49.142 | 32.463 | 49.058 | 1.00 | 41.56 | A |
| ATOM | 143 | N | ALA | A | 251 | 48.688 | 31.202 | 50.944 | 1.00 | 41.54 | A |
| ATOM | 144 | CA | ALA | A | 251 | 49.918 | 30.446 | 51.187 | 1.00 | 42.94 | A |
| ATOM | 145 | CB | ALA | A | 251 | 49.825 | 29.982 | 52.589 | 1.00 | 41.66 | A |

TABLE 2-continued

ATOMIC COORDINATES OF THE ERR3 LBD/
DIETHYLSTILBESTROL COMPLEX

| ATOM | 146 | C | ALA | A | 251 | 50.132 | 29.192 | 50.349 | 1.00 | 44.32 | A |
|---|---|---|---|---|---|---|---|---|---|---|---|
| ATOM | 147 | O | ALA | A | 251 | 51.226 | 28.917 | 49.907 | 1.00 | 43.63 | A |
| ATOM | 148 | N | MET | A | 252 | 49.091 | 28.376 | 50.219 | 1.00 | 46.74 | A |
| ATOM | 149 | CA | MET | A | 252 | 49.058 | 27.352 | 49.171 | 1.00 | 49.02 | A |
| ATOM | 150 | CB | MET | A | 252 | 49.465 | 27.927 | 47.841 | 1.00 | 50.89 | A |
| ATOM | 151 | CG | MET | A | 252 | 48.523 | 27.754 | 46.777 | 1.00 | 53.76 | A |
| ATOM | 152 | SD | MET | A | 252 | 48.093 | 29.263 | 46.094 | 1.00 | 56.77 | A |
| ATOM | 153 | CE | MET | A | 252 | 46.207 | 29.280 | 46.710 | 1.00 | 55.18 | A |
| ATOM | 154 | C | MET | A | 252 | 50.075 | 26.287 | 49.439 | 1.00 | 49.97 | A |
| ATOM | 155 | O | MET | A | 252 | 50.865 | 25.939 | 48.559 | 1.00 | 48.24 | A |
| ATOM | 156 | N | PRO | A | 253 | 50.049 | 25.764 | 50.643 | 1.00 | 51.85 | A |
| ATOM | 157 | CD | PRO | A | 253 | 48.962 | 25.945 | 51.633 | 1.00 | 51.36 | A |
| ATOM | 158 | CA | PRO | A | 253 | 51.019 | 24.743 | 51.002 | 1.00 | 54.61 | A |
| ATOM | 159 | CB | PRO | A | 253 | 50.645 | 24.416 | 52.470 | 1.00 | 53.68 | A |
| ATOM | 160 | CG | PRO | A | 253 | 49.087 | 24.779 | 52.619 | 1.00 | 52.32 | A |
| ATOM | 161 | C | PRO | A | 253 | 50.836 | 23.476 | 49.979 | 1.00 | 58.10 | A |
| ATOM | 162 | O | PRO | A | 253 | 49.732 | 23.298 | 49.417 | 1.00 | 58.19 | A |
| ATOM | 163 | N | ASP | A | 254 | 51.900 | 22.702 | 49.726 | 1.00 | 61.72 | A |
| ATOM | 164 | CA | ASP | A | 254 | 51.906 | 21.693 | 48.687 | 1.00 | 65.58 | A |
| ATOM | 165 | CB | ASP | A | 254 | 53.302 | 21.615 | 48.076 | 1.00 | 68.89 | A |
| ATOM | 166 | CG | ASP | A | 254 | 54.405 | 21.428 | 49.118 | 1.00 | 73.36 | A |
| ATOM | 167 | OD1 | ASP | A | 254 | 55.562 | 21.196 | 48.706 | 1.00 | 75.42 | A |
| ATOM | 168 | OD2 | ASP | A | 254 | 54.137 | 21.516 | 50.337 | 1.00 | 75.67 | A |
| ATOM | 169 | C | ASP | A | 254 | 51.495 | 20.342 | 49.264 | 1.00 | 66.60 | A |
| ATOM | 170 | O | ASP | A | 254 | 52.265 | 19.834 | 50.086 | 1.00 | 67.35 | A |
| ATOM | 171 | N | PRO | A | 255 | 50.317 | 19.784 | 48.876 | 1.00 | 67.24 | A |
| ATOM | 172 | CD | PRO | A | 255 | 49.211 | 20.491 | 48.191 | 1.00 | 67.11 | A |
| ATOM | 173 | CA | PRO | A | 255 | 49.925 | 18.333 | 49.030 | 1.00 | 68.06 | A |
| ATOM | 174 | CB | PRO | A | 255 | 48.966 | 17.937 | 48.625 | 0.00 | 67.74 | A |
| ATOM | 175 | CG | PRO | A | 255 | 47.885 | 19.665 | 48.627 | 1.00 | 67.43 | A |
| ATOM | 176 | C | PRO | A | 255 | 50.668 | 17.299 | 49.886 | 1.00 | 68.50 | A |
| ATOM | 177 | O | PRO | A | 255 | 51.616 | 16.736 | 49.346 | 1.00 | 69.51 | A |
| ATOM | 178 | N | PRO | A | 258 | 54.812 | 16.857 | 51.611 | 1.00 | 61.62 | A |
| ATOM | 179 | CD | PRO | A | 258 | 55.754 | 16.370 | 50.567 | 1.00 | 61.12 | A |
| ATOM | 180 | CA | PRO | A | 258 | 54.907 | 16.077 | 52.875 | 1.00 | 62.29 | A |
| ATOM | 181 | CB | PRO | A | 258 | 55.654 | 14.754 | 52.480 | 1.00 | 62.15 | A |
| ATOM | 182 | CG | PRO | A | 258 | 56.433 | 15.115 | 51.139 | 1.00 | 61.65 | A |
| ATOM | 183 | C | PRO | A | 258 | 55.614 | 16.828 | 54.029 | 1.00 | 62.65 | A |
| ATOM | 184 | O | PRO | A | 258 | 56.829 | 17.157 | 54.016 | 1.00 | 63.11 | A |
| ATOM | 185 | N | ASP | A | 259 | 54.793 | 17.063 | 55.037 | 1.00 | 62.64 | A |
| ATOM | 186 | CA | ASP | A | 259 | 55.144 | 17.787 | 56.216 | 1.00 | 62.81 | A |
| ATOM | 187 | CB | ASP | A | 259 | 54.156 | 17.446 | 57.307 | 1.00 | 63.65 | A |
| ATOM | 188 | CG | ASP | A | 259 | 52.986 | 18.410 | 57.338 | 1.00 | 65.16 | A |
| ATOM | 189 | OD1 | ASP | A | 259 | 52.539 | 18.873 | 56.248 | 1.00 | 65.60 | A |
| ATOM | 190 | OD2 | ASP | A | 259 | 52.463 | 18.801 | 58.415 | 1.00 | 65.22 | A |
| ATOM | 191 | C | ASP | A | 259 | 56.580 | 17.580 | 56.644 | 1.00 | 62.68 | A |
| ATOM | 192 | O | ASP | A | 259 | 56.988 | 16.440 | 56.919 | 1.00 | 63.56 | A |
| ATOM | 193 | N | SER | A | 260 | 57.364 | 18.700 | 56.609 | 1.00 | 62.08 | A |
| ATOM | 194 | CA | SER | A | 260 | 58.705 | 18.837 | 57.244 | 1.00 | 59.89 | A |
| ATOM | 195 | CB | SER | A | 260 | 59.545 | 18.354 | 56.249 | 0.00 | 60.52 | A |
| ATOM | 196 | OG | SER | A | 260 | 59.436 | 19.129 | 55.067 | 1.00 | 61.12 | A |
| ATOM | 197 | C | SER | A | 260 | 58.853 | 20.306 | 57.724 | 1.00 | 58.99 | A |
| ATOM | 198 | O | SER | A | 260 | 58.166 | 21.186 | 57.240 | 1.00 | 58.44 | A |
| ATOM | 199 | N | ASP | A | 261 | 59.752 | 20.574 | 58.663 | 1.00 | 57.62 | A |
| ATOM | 200 | CA | ASP | A | 261 | 60.066 | 21.928 | 58.952 | 1.00 | 56.08 | A |
| ATOM | 201 | CB | ASP | A | 261 | 61.168 | 22.101 | 60.047 | 1.00 | 56.46 | A |
| ATOM | 202 | CG | ASP | A | 261 | 62.415 | 21.209 | 59.838 | 1.00 | 57.48 | A |
| ATOM | 203 | OD1 | ASP | A | 261 | 62.677 | 20.680 | 58.729 | 1.00 | 58.52 | A |
| ATOM | 204 | OD2 | ASP | A | 261 | 63.215 | 21.018 | 60.780 | 1.00 | 58.77 | A |
| ATOM | 205 | C | ASP | A | 261 | 60.399 | 22.626 | 57.617 | 1.00 | 54.62 | A |
| ATOM | 206 | O | ASP | A | 261 | 59.950 | 23.795 | 57.364 | 1.00 | 54.16 | A |
| ATOM | 207 | N | ILE | A | 262 | 61.122 | 21.952 | 56.733 | 1.00 | 53.13 | A |
| ATOM | 208 | CA | ILE | A | 262 | 61.580 | 22.679 | 55.576 | 1.00 | 52.04 | A |
| ATOM | 209 | CB | ILE | A | 262 | 62.722 | 22.052 | 54.731 | 1.00 | 51.29 | A |
| ATOM | 210 | CG2 | ILE | A | 262 | 63.083 | 20.717 | 55.157 | 1.00 | 51.80 | A |
| ATOM | 211 | CG1 | ILE | A | 262 | 62.478 | 22.156 | 53.177 | 1.00 | 50.89 | A |
| ATOM | 212 | CD1 | ILE | A | 262 | 62.191 | 22.223 | 52.181 | 0.00 | 51.06 | A |
| ATOM | 213 | C | ILE | A | 262 | 60.338 | 23.060 | 54.737 | 1.00 | 51.82 | A |
| ATOM | 214 | O | ILE | A | 262 | 60.415 | 24.044 | 53.974 | 1.00 | 51.27 | A |
| ATOM | 215 | N | LYS | A | 263 | 59.230 | 22.287 | 54.868 | 1.00 | 50.67 | A |
| ATOM | 216 | CA | LYS | A | 263 | 58.034 | 22.621 | 54.142 | 1.00 | 50.57 | A |
| ATOM | 217 | CB | LYS | A | 263 | 57.017 | 21.501 | 54.081 | 1.00 | 50.48 | A |
| ATOM | 218 | CG | LYS | A | 263 | 55.683 | 21.834 | 53.248 | 1.00 | 52.41 | A |
| ATOM | 219 | CD | LYS | A | 263 | 54.840 | 20.513 | 53.046 | 1.00 | 54.40 | A |
| ATOM | 220 | CE | LYS | A | 263 | 53.308 | 20.587 | 53.100 | 1.00 | 54.56 | A |
| ATOM | 221 | NZ | LYS | A | 263 | 52.879 | 20.233 | 54.570 | 1.00 | 56.84 | A |

TABLE 2-continued

ATOMIC COORDINATES OF THE ERR3 LBD/
DIETHYLSTILBESTROL COMPLEX

| ATOM | 222 | C | LYS | A | 263 | 57.324 | 23.845 | 54.695 | 1.00 | 49.63 | A |
|---|---|---|---|---|---|---|---|---|---|---|---|
| ATOM | 223 | O | LYS | A | 263 | 56.866 | 24.667 | 53.891 | 1.00 | 49.75 | A |
| ATOM | 224 | N | ALA | A | 264 | 57.180 | 23.909 | 56.006 | 1.00 | 47.76 | A |
| ATOM | 225 | CA | ALA | A | 264 | 56.588 | 25.010 | 56.655 | 1.00 | 47.70 | A |
| ATOM | 226 | CB | ALA | A | 264 | 56.567 | 24.808 | 58.143 | 1.00 | 47.23 | A |
| ATOM | 227 | C | ALA | A | 264 | 57.365 | 26.299 | 56.245 | 1.00 | 48.44 | A |
| ATOM | 228 | O | ALA | A | 264 | 56.821 | 27.163 | 55.529 | 1.00 | 48.13 | A |
| ATOM | 229 | N | LEU | A | 265 | 58.665 | 26.300 | 56.509 | 1.00 | 47.75 | A |
| ATOM | 230 | CA | LEU | A | 265 | 59.469 | 27.418 | 56.323 | 1.00 | 47.66 | A |
| ATOM | 231 | CB | LEU | A | 265 | 60.838 | 27.051 | 56.869 | 1.00 | 48.33 | A |
| ATOM | 232 | CG | LEU | A | 265 | 60.923 | 26.814 | 58.397 | 1.00 | 48.45 | A |
| ATOM | 233 | CD1 | LEU | A | 265 | 62.351 | 26.300 | 58.712 | 1.00 | 48.11 | A |
| ATOM | 234 | CD2 | LEU | A | 265 | 60.631 | 28.097 | 59.172 | 1.00 | 48.58 | A |
| ATOM | 235 | C | LEU | A | 265 | 59.559 | 27.839 | 54.841 | 1.00 | 47.69 | A |
| ATOM | 236 | O | LEU | A | 265 | 59.451 | 29.008 | 54.431 | 1.00 | 46.66 | A |
| ATOM | 237 | N | THR | A | 266 | 59.811 | 26.880 | 54.013 | 1.00 | 46.55 | A |
| ATOM | 238 | CA | THR | A | 266 | 59.799 | 27.171 | 52.625 | 1.00 | 45.47 | A |
| ATOM | 239 | CB | THR | A | 266 | 59.894 | 25.823 | 51.841 | 1.00 | 45.33 | A |
| ATOM | 240 | OG1 | THR | A | 266 | 61.272 | 25.444 | 51.670 | 1.00 | 46.65 | A |
| ATOM | 241 | CG2 | THR | A | 266 | 59.408 | 25.974 | 50.516 | 1.00 | 44.40 | A |
| ATOM | 242 | C | THR | A | 266 | 58.468 | 27.864 | 52.300 | 1.00 | 44.75 | A |
| ATOM | 243 | O | THR | A | 266 | 58.418 | 28.723 | 51.414 | 1.00 | 44.71 | A |
| ATOM | 244 | N | THR | A | 267 | 57.379 | 27.381 | 52.878 | 1.00 | 43.24 | A |
| ATOM | 245 | CA | THR | A | 267 | 56.081 | 27.883 | 52.508 | 1.00 | 42.15 | A |
| ATOM | 246 | CB | THR | A | 267 | 54.954 | 27.083 | 53.146 | 1.00 | 43.13 | A |
| ATOM | 247 | OG1 | THR | A | 267 | 54.927 | 25.742 | 52.678 | 1.00 | 45.77 | A |
| ATOM | 248 | CG2 | THR | A | 267 | 53.551 | 27.609 | 52.687 | 1.00 | 44.18 | A |
| ATOM | 249 | C | THR | A | 267 | 55.820 | 29.336 | 53.025 | 1.00 | 40.00 | A |
| ATOM | 250 | O | THR | A | 267 | 55.058 | 30.062 | 52.406 | 1.00 | 39.23 | A |
| ATOM | 251 | N | LEU | A | 268 | 56.335 | 29.642 | 54.193 | 1.00 | 38.64 | A |
| ATOM | 252 | CA | LEU | A | 268 | 56.168 | 30.949 | 54.845 | 1.00 | 37.69 | A |
| ATOM | 253 | CB | LEU | A | 268 | 56.602 | 30.973 | 56.287 | 1.00 | 36.61 | A |
| ATOM | 254 | CG | LEU | A | 268 | 55.694 | 30.151 | 57.189 | 1.00 | 35.43 | A |
| ATOM | 255 | CD1 | LEU | A | 268 | 56.295 | 29.941 | 58.474 | 1.00 | 34.13 | A |
| ATOM | 256 | CD2 | LEU | A | 268 | 54.368 | 30.910 | 57.535 | 1.00 | 36.29 | A |
| ATOM | 257 | C | LEU | A | 268 | 57.006 | 31.883 | 54.070 | 1.00 | 37.69 | A |
| ATOM | 258 | O | LEU | A | 268 | 56.532 | 32.954 | 53.872 | 1.00 | 37.28 | A |
| ATOM | 259 | N | CYS | A | 269 | 58.154 | 31.429 | 53.530 | 1.00 | 36.78 | A |
| ATOM | 260 | CA | CYS | A | 269 | 59.055 | 32.265 | 52.769 | 1.00 | 37.32 | A |
| ATOM | 261 | CB | CYS | A | 269 | 60.444 | 31.626 | 52.535 | 1.00 | 38.23 | A |
| ATOM | 262 | SG | CYS | A | 269 | 61.448 | 31.689 | 54.056 | 1.00 | 43.20 | A |
| ATOM | 263 | C | CYS | A | 269 | 58.408 | 32.603 | 51.455 | 1.00 | 36.58 | A |
| ATOM | 264 | O | CYS | A | 269 | 58.493 | 33.726 | 50.978 | 1.00 | 35.27 | A |
| ATOM | 265 | N | ASP | A | 270 | 57.682 | 31.670 | 50.895 | 1.00 | 36.41 | A |
| ATOM | 266 | CA | ASP | A | 270 | 57.143 | 32.010 | 49.599 | 1.00 | 37.72 | A |
| ATOM | 267 | CB | ASP | A | 270 | 56.849 | 30.736 | 48.742 | 1.00 | 39.74 | A |
| ATOM | 268 | CG | ASP | A | 270 | 56.145 | 31.055 | 47.460 | 1.00 | 42.35 | A |
| ATOM | 269 | OD1 | ASP | A | 270 | 56.833 | 31.645 | 46.531 | 1.00 | 44.45 | A |
| ATOM | 270 | OD2 | ASP | A | 270 | 54.892 | 30.800 | 47.329 | 1.00 | 42.44 | A |
| ATOM | 271 | C | ASP | A | 270 | 55.872 | 32.863 | 49.778 | 1.00 | 36.66 | A |
| ATOM | 272 | O | ASP | A | 270 | 55.613 | 33.723 | 48.934 | 1.00 | 36.33 | A |
| ATOM | 273 | N | LEU | A | 271 | 55.110 | 32.646 | 50.841 | 1.00 | 34.66 | A |
| ATOM | 274 | CA | LEU | A | 271 | 54.026 | 33.584 | 51.207 | 1.00 | 34.89 | A |
| ATOM | 275 | CB | LEU | A | 271 | 53.281 | 33.072 | 52.469 | 1.00 | 34.55 | A |
| ATOM | 276 | CG | LEU | A | 271 | 52.394 | 34.076 | 53.144 | 1.00 | 34.80 | A |
| ATOM | 277 | CD1 | LEU | A | 271 | 51.254 | 34.413 | 52.274 | 1.00 | 35.45 | A |
| ATOM | 278 | CD2 | LEU | A | 271 | 51.874 | 33.425 | 54.331 | 1.00 | 33.08 | A |
| ATOM | 279 | C | LEU | A | 271 | 54.598 | 35.050 | 51.413 | 1.00 | 34.64 | A |
| ATOM | 280 | O | LEU | A | 271 | 54.232 | 36.041 | 50.708 | 1.00 | 33.37 | A |
| ATOM | 281 | N | ALA | A | 272 | 55.593 | 35.150 | 52.284 | 1.00 | 33.88 | A |
| ATOM | 282 | CA | ALA | A | 272 | 56.229 | 36.439 | 52.518 | 1.00 | 34.87 | A |
| ATOM | 283 | CB | ALA | A | 272 | 57.327 | 36.276 | 53.382 | 1.00 | 35.17 | A |
| ATOM | 284 | C | ALA | A | 272 | 56.671 | 37.073 | 51.219 | 1.00 | 35.48 | A |
| ATOM | 285 | O | ALA | A | 272 | 56.433 | 38.269 | 50.956 | 1.00 | 34.11 | A |
| ATOM | 286 | N | ASP | A | 273 | 57.227 | 36.271 | 50.320 | 1.00 | 36.18 | A |
| ATOM | 287 | CA | ASP | A | 273 | 57.740 | 36.886 | 49.089 | 1.00 | 38.12 | A |
| ATOM | 288 | CB | ASP | A | 273 | 58.389 | 35.879 | 48.199 | 1.00 | 43.00 | A |
| ATOM | 289 | CG | ASP | A | 273 | 59.834 | 36.215 | 47.967 | 1.00 | 48.09 | A |
| ATOM | 290 | OD1 | ASP | A | 273 | 60.721 | 35.644 | 48.655 | 1.00 | 50.71 | A |
| ATOM | 291 | OD2 | ASP | A | 273 | 60.178 | 37.059 | 47.145 | 1.00 | 51.51 | A |
| ATOM | 292 | C | ASP | A | 273 | 56.649 | 37.481 | 48.258 | 1.00 | 37.75 | A |
| ATOM | 293 | O | ASP | A | 273 | 56.767 | 38.576 | 47.785 | 1.00 | 37.06 | A |
| ATOM | 294 | N | ARG | A | 274 | 55.554 | 36.755 | 48.127 | 1.00 | 36.10 | A |
| ATOM | 295 | CA | ARG | A | 274 | 54.354 | 37.347 | 47.457 | 1.00 | 36.01 | A |
| ATOM | 296 | CB | ARG | A | 274 | 53.294 | 36.255 | 47.108 | 1.00 | 36.01 | A |
| ATOM | 297 | CG | ARG | A | 274 | 53.866 | 35.118 | 46.133 | 1.00 | 37.00 | A |

TABLE 2-continued

ATOMIC COORDINATES OF THE ERR3 LBD/
DIETHYLSTILBESTROL COMPLEX

| ATOM | 298 | CD | ARG | A | 274 | 52.836 | 33.912 | 45.748 | 1.00 | 37.14 | A |
|---|---|---|---|---|---|---|---|---|---|---|---|
| ATOM | 299 | NE | ARG | A | 274 | 52.797 | 32.917 | 46.841 | 1.00 | 36.51 | A |
| ATOM | 300 | CZ | ARG | A | 274 | 51.788 | 32.801 | 47.650 | 1.00 | 37.54 | A |
| ATOM | 301 | NH1 | ARG | A | 274 | 50.751 | 33.602 | 47.515 | 1.00 | 36.95 | A |
| ATOM | 302 | NH2 | ARG | A | 274 | 51.809 | 31.909 | 48.610 | 1.00 | 35.52 | A |
| ATOM | 303 | C | ARG | A | 274 | 53.714 | 38.514 | 48.234 | 1.00 | 34.57 | A |
| ATOM | 304 | O | ARG | A | 274 | 53.174 | 39.439 | 47.609 | 1.00 | 33.15 | A |
| ATOM | 305 | N | GLU | A | 275 | 53.783 | 38.503 | 49.582 | 1.00 | 34.07 | A |
| ATOM | 306 | CA | GLU | A | 275 | 53.291 | 39.697 | 50.366 | 1.00 | 33.38 | A |
| ATOM | 307 | CB | GLU | A | 275 | 53.282 | 39.495 | 51.886 | 1.00 | 33.27 | A |
| ATOM | 308 | CG | GLU | A | 275 | 52.321 | 38.347 | 52.250 | 1.00 | 34.22 | A |
| ATOM | 309 | CD | GLU | A | 275 | 52.075 | 38.145 | 53.714 | 1.00 | 36.05 | A |
| ATOM | 310 | OE1 | GLU | A | 275 | 51.415 | 39.024 | 54.280 | 1.00 | 36.76 | A |
| ATOM | 311 | OE2 | GLU | A | 275 | 52.535 | 37.134 | 54.277 | 1.00 | 35.76 | A |
| ATOM | 312 | C | GLU | A | 275 | 54.156 | 40.871 | 50.046 | 1.00 | 34.14 | A |
| ATOM | 313 | O | GLU | A | 275 | 53.649 | 41.947 | 49.931 | 1.00 | 33.11 | A |
| ATOM | 314 | N | LEU | A | 276 | 55.464 | 40.680 | 49.904 | 1.00 | 34.64 | A |
| ATOM | 315 | CA | LEU | A | 276 | 56.321 | 41.799 | 49.715 | 1.00 | 35.91 | A |
| ATOM | 316 | CB | LEU | A | 276 | 57.778 | 41.447 | 49.789 | 1.00 | 35.29 | A |
| ATOM | 317 | CG | LEU | A | 276 | 58.075 | 41.114 | 51.235 | 1.00 | 39.08 | A |
| ATOM | 318 | CD1 | LEU | A | 276 | 59.381 | 40.246 | 51.292 | 1.00 | 39.21 | A |
| ATOM | 319 | CD2 | LEU | A | 276 | 58.225 | 42.403 | 52.008 | 1.00 | 38.07 | A |
| ATOM | 320 | C | LEU | A | 276 | 56.119 | 42.431 | 48.410 | 1.00 | 36.66 | A |
| ATOM | 321 | O | LEU | A | 276 | 56.187 | 43.646 | 48.324 | 1.00 | 35.93 | A |
| ATOM | 322 | N | VAL | A | 277 | 55.941 | 41.611 | 47.395 | 1.00 | 37.07 | A |
| ATOM | 323 | CA | VAL | A | 277 | 55.508 | 42.120 | 46.088 | 1.00 | 38.04 | A |
| ATOM | 324 | CB | VAL | A | 277 | 55.055 | 41.010 | 45.168 | 1.00 | 38.04 | A |
| ATOM | 325 | CG1 | VAL | A | 277 | 54.574 | 41.620 | 43.830 | 1.00 | 38.73 | A |
| ATOM | 326 | CG2 | VAL | A | 277 | 56.068 | 40.113 | 44.993 | 0.00 | 38.21 | A |
| ATOM | 327 | C | VAL | A | 277 | 54.352 | 43.006 | 46.265 | 1.00 | 37.55 | A |
| ATOM | 328 | O | VAL | A | 277 | 54.404 | 44.189 | 45.925 | 1.00 | 38.37 | A |
| ATOM | 329 | N | VAL | A | 278 | 53.337 | 42.502 | 46.923 | 1.00 | 37.25 | A |
| ATOM | 330 | CA | VAL | A | 278 | 52.135 | 43.310 | 47.170 | 1.00 | 35.96 | A |
| ATOM | 331 | CB | VAL | A | 278 | 51.089 | 42.455 | 47.834 | 1.00 | 36.31 | A |
| ATOM | 332 | CG1 | VAL | A | 278 | 50.055 | 43.235 | 48.533 | 1.00 | 34.98 | A |
| ATOM | 333 | CG2 | VAL | A | 278 | 50.447 | 41.529 | 46.765 | 1.00 | 34.53 | A |
| ATOM | 334 | C | VAL | A | 278 | 52.402 | 44.624 | 47.974 | 1.00 | 36.10 | A |
| ATOM | 335 | O | VAL | A | 278 | 51.791 | 45.707 | 47.672 | 1.00 | 36.15 | A |
| ATOM | 336 | N | ILE | A | 279 | 53.264 | 44.552 | 48.998 | 1.00 | 34.75 | A |
| ATOM | 337 | CA | ILE | A | 279 | 53.562 | 45.697 | 49.823 | 1.00 | 34.71 | A |
| ATOM | 338 | CB | ILE | A | 279 | 54.494 | 45.321 | 50.923 | 1.00 | 34.66 | A |
| ATOM | 339 | CG2 | ILE | A | 279 | 55.090 | 46.574 | 51.654 | 1.00 | 32.38 | A |
| ATOM | 340 | CG1 | ILE | A | 279 | 53.741 | 44.654 | 52.039 | 1.00 | 34.55 | A |
| ATOM | 341 | CD1 | ILE | A | 279 | 54.692 | 44.187 | 53.185 | 1.00 | 38.70 | A |
| ATOM | 342 | C | ILE | A | 279 | 54.138 | 46.923 | 49.017 | 1.00 | 34.18 | A |
| ATOM | 343 | O | ILE | A | 279 | 53.877 | 48.046 | 49.291 | 1.00 | 34.31 | A |
| ATOM | 344 | N | ILE | A | 280 | 54.885 | 46.678 | 48.017 | 1.00 | 34.73 | A |
| ATOM | 345 | CA | ILE | A | 280 | 55.299 | 47.741 | 47.110 | 1.00 | 35.17 | A |
| ATOM | 346 | CB | ILE | A | 280 | 56.342 | 47.164 | 46.096 | 1.00 | 35.61 | A |
| ATOM | 347 | CG2 | ILE | A | 280 | 56.695 | 48.247 | 45.108 | 1.00 | 36.58 | A |
| ATOM | 348 | CG1 | ILE | A | 280 | 57.602 | 46.818 | 46.918 | 1.00 | 35.86 | A |
| ATOM | 349 | CD1 | ILE | A | 280 | 58.661 | 46.127 | 46.194 | 1.00 | 37.53 | A |
| ATOM | 350 | C | ILE | A | 280 | 54.152 | 48.456 | 46.443 | 1.00 | 34.16 | A |
| ATOM | 351 | O | ILE | A | 280 | 54.091 | 49.707 | 46.444 | 1.00 | 34.48 | A |
| ATOM | 352 | N | GLY | A | 281 | 53.201 | 47.712 | 45.924 | 1.00 | 33.11 | A |
| ATOM | 353 | CA | GLY | A | 281 | 52.052 | 48.372 | 45.298 | 1.00 | 31.39 | A |
| ATOM | 354 | C | GLY | A | 281 | 51.181 | 49.171 | 46.255 | 1.00 | 30.60 | A |
| ATOM | 355 | O | GLY | A | 281 | 50.673 | 50.315 | 45.963 | 1.00 | 30.09 | A |
| ATOM | 356 | N | TRP | A | 282 | 51.039 | 48.537 | 47.419 | 1.00 | 29.80 | A |
| ATOM | 357 | CA | TRP | A | 282 | 50.285 | 49.049 | 48.541 | 1.00 | 29.97 | A |
| ATOM | 358 | CB | TRP | A | 282 | 50.103 | 48.018 | 49.612 | 1.00 | 27.79 | A |
| ATOM | 359 | CG | TRP | A | 282 | 49.652 | 48.556 | 50.936 | 1.00 | 28.67 | A |
| ATOM | 360 | CD2 | TRP | A | 282 | 50.489 | 49.009 | 52.042 | 1.00 | 28.75 | A |
| ATOM | 361 | CE2 | TRP | A | 282 | 49.661 | 49.525 | 53.000 | 1.00 | 29.95 | A |
| ATOM | 362 | CE3 | TRP | A | 282 | 51.826 | 48.984 | 52.301 | 1.00 | 28.39 | A |
| ATOM | 363 | CD1 | TRP | A | 282 | 48.409 | 48.892 | 51.263 | 1.00 | 28.36 | A |
| ATOM | 364 | NE1 | TRP | A | 282 | 48.394 | 49.493 | 52.491 | 1.00 | 29.05 | A |
| ATOM | 365 | CZ2 | TRP | A | 282 | 50.115 | 49.953 | 54.214 | 1.00 | 30.53 | A |
| ATOM | 366 | CZ3 | TRP | A | 282 | 52.288 | 49.417 | 53.510 | 1.00 | 29.51 | A |
| ATOM | 367 | CH2 | TRP | A | 282 | 51.435 | 49.910 | 54.438 | 1.00 | 31.96 | A |
| ATOM | 368 | C | TRP | A | 282 | 50.902 | 50.352 | 49.019 | 1.00 | 30.25 | A |
| ATOM | 369 | O | TRP | A | 282 | 50.164 | 51.324 | 49.250 | 1.00 | 30.73 | A |
| ATOM | 370 | N | ALA | A | 283 | 52.213 | 50.478 | 49.053 | 1.00 | 28.86 | A |
| ATOM | 371 | CA | ALA | A | 283 | 52.781 | 51.705 | 49.574 | 1.00 | 29.59 | A |
| ATOM | 372 | CB | ALA | A | 283 | 54.211 | 51.574 | 49.781 | 1.00 | 29.22 | A |
| ATOM | 373 | C | ALA | A | 283 | 52.530 | 52.929 | 48.721 | 1.00 | 30.15 | A |

TABLE 2-continued

ATOMIC COORDINATES OF THE ERR3 LBD/
DIETHYLSTILBESTROL COMPLEX

| ATOM | 374 | O | ALA | A | 283 | 52.480 | 54.083 | 49.261 | 1.00 | 30.78 | A |
|---|---|---|---|---|---|---|---|---|---|---|---|
| ATOM | 375 | N | LYS | A | 284 | 52.495 | 52.745 | 47.439 | 1.00 | 30.33 | A |
| ATOM | 376 | CA | LYS | A | 284 | 52.068 | 53.831 | 46.530 | 1.00 | 32.33 | A |
| ATOM | 377 | CB | LYS | A | 284 | 51.876 | 53.246 | 45.125 | 1.00 | 32.92 | A |
| ATOM | 378 | CG | LYS | A | 284 | 53.177 | 52.842 | 44.367 | 1.00 | 35.85 | A |
| ATOM | 379 | CD | LYS | A | 284 | 52.734 | 52.054 | 43.078 | 1.00 | 38.26 | A |
| ATOM | 380 | CE | LYS | A | 284 | 53.782 | 51.075 | 42.569 | 1.00 | 41.47 | A |
| ATOM | 381 | NZ | LYS | A | 284 | 54.935 | 51.878 | 41.994 | 1.00 | 43.35 | A |
| ATOM | 382 | C | LYS | A | 284 | 50.716 | 54.570 | 46.920 | 1.00 | 32.02 | A |
| ATOM | 383 | O | LYS | A | 284 | 50.518 | 55.673 | 46.534 | 1.00 | 31.21 | A |
| ATOM | 384 | N | HIS | A | 285 | 49.812 | 53.835 | 47.578 | 1.00 | 31.10 | A |
| ATOM | 385 | CA | HIS | A | 285 | 48.492 | 54.299 | 47.969 | 1.00 | 32.00 | A |
| ATOM | 386 | CB | HIS | A | 285 | 47.528 | 53.141 | 48.073 | 1.00 | 30.73 | A |
| ATOM | 387 | CG | HIS | A | 285 | 47.226 | 52.465 | 46.763 | 1.00 | 33.35 | A |
| ATOM | 388 | CD2 | HIS | A | 285 | 47.980 | 51.683 | 45.952 | 1.00 | 33.09 | A |
| ATOM | 389 | ND1 | HIS | A | 285 | 45.951 | 52.491 | 46.201 | 1.00 | 34.32 | A |
| ATOM | 390 | CE1 | HIS | A | 285 | 45.960 | 51.806 | 45.070 | 1.00 | 35.37 | A |
| ATOM | 391 | NE2 | HIS | A | 285 | 47.176 | 51.327 | 44.875 | 1.00 | 36.07 | A |
| ATOM | 392 | C | HIS | A | 285 | 48.493 | 55.020 | 49.361 | 1.00 | 31.33 | A |
| ATOM | 393 | O | HIS | A | 285 | 47.497 | 55.555 | 49.791 | 1.00 | 30.89 | A |
| ATOM | 394 | N | ILE | A | 286 | 49.653 | 55.109 | 49.989 | 1.00 | 30.00 | A |
| ATOM | 395 | CA | ILE | A | 286 | 49.735 | 55.749 | 51.238 | 1.00 | 29.29 | A |
| ATOM | 396 | CB | ILE | A | 286 | 50.937 | 55.176 | 52.066 | 1.00 | 28.02 | A |
| ATOM | 397 | CG2 | ILE | A | 286 | 51.127 | 55.987 | 53.340 | 1.00 | 26.58 | A |
| ATOM | 398 | CG1 | ILE | A | 286 | 50.618 | 53.709 | 52.414 | 1.00 | 27.26 | A |
| ATOM | 399 | CD1 | ILE | A | 286 | 51.780 | 52.993 | 52.812 | 1.00 | 28.28 | A |
| ATOM | 400 | C | ILE | A | 286 | 49.938 | 57.231 | 50.967 | 1.00 | 29.64 | A |
| ATOM | 401 | O | ILE | A | 286 | 51.026 | 57.632 | 50.419 | 1.00 | 29.96 | A |
| ATOM | 402 | N | PRO | A | 287 | 49.002 | 58.037 | 51.476 | 1.00 | 31.05 | A |
| ATOM | 403 | CD | PRO | A | 287 | 47.825 | 57.590 | 52.201 | 1.00 | 30.50 | A |
| ATOM | 404 | CA | PRO | A | 287 | 49.099 | 59.490 | 51.390 | 1.00 | 30.38 | A |
| ATOM | 405 | CB | PRO | A | 287 | 47.954 | 60.022 | 52.200 | 1.00 | 30.73 | A |
| ATOM | 406 | CG | PRO | A | 287 | 47.005 | 58.939 | 52.326 | 1.00 | 32.38 | A |
| ATOM | 407 | C | PRO | A | 287 | 50.372 | 59.957 | 51.959 | 1.00 | 30.36 | A |
| ATOM | 408 | O | PRO | A | 287 | 50.662 | 59.690 | 53.102 | 1.00 | 30.78 | A |
| ATOM | 409 | N | GLY | A | 288 | 51.152 | 60.590 | 51.101 | 1.00 | 31.06 | A |
| ATOM | 410 | CA | GLY | A | 288 | 52.373 | 61.199 | 51.497 | 1.00 | 30.88 | A |
| ATOM | 411 | C | GLY | A | 288 | 53.625 | 60.450 | 51.014 | 1.00 | 32.35 | A |
| ATOM | 412 | O | GLY | A | 288 | 54.732 | 60.973 | 50.981 | 1.00 | 32.27 | A |
| ATOM | 413 | N | PHE | A | 289 | 53.475 | 59.172 | 50.762 | 1.00 | 32.71 | A |
| ATOM | 414 | CA | PHE | A | 289 | 54.635 | 58.319 | 50.522 | 1.00 | 33.50 | A |
| ATOM | 415 | CB | PHE | A | 289 | 54.225 | 56.865 | 50.698 | 1.00 | 31.42 | A |
| ATOM | 416 | CG | PHE | A | 289 | 55.353 | 55.884 | 50.580 | 1.00 | 30.51 | A |
| ATOM | 417 | CD1 | PHE | A | 289 | 56.254 | 55.724 | 51.633 | 1.00 | 29.29 | A |
| ATOM | 418 | CD2 | PHE | A | 289 | 55.542 | 55.139 | 49.430 | 1.00 | 29.41 | A |
| ATOM | 419 | CE1 | PHE | A | 289 | 57.266 | 54.837 | 51.537 | 1.00 | 29.24 | A |
| ATOM | 420 | CE2 | PHE | A | 289 | 56.542 | 54.234 | 49.367 | 1.00 | 28.37 | A |
| ATOM | 421 | CZ | PHE | A | 289 | 57.425 | 54.099 | 50.487 | 1.00 | 28.60 | A |
| ATOM | 422 | C | PHE | A | 289 | 55.333 | 58.487 | 49.163 | 1.00 | 35.72 | A |
| ATOM | 423 | O | PHE | A | 289 | 56.605 | 58.400 | 49.073 | 1.00 | 36.16 | A |
| ATOM | 424 | N | SER | A | 290 | 54.545 | 58.600 | 48.101 | 1.00 | 36.89 | A |
| ATOM | 425 | CA | SER | A | 290 | 55.061 | 58.448 | 46.768 | 1.00 | 39.02 | A |
| ATOM | 426 | CB | SER | A | 290 | 53.927 | 58.041 | 45.756 | 1.00 | 40.26 | A |
| ATOM | 427 | OG | SER | A | 290 | 53.091 | 59.186 | 45.422 | 1.00 | 42.06 | A |
| ATOM | 428 | C | SER | A | 290 | 55.799 | 59.743 | 46.376 | 1.00 | 39.63 | A |
| ATOM | 429 | O | SER | A | 290 | 56.497 | 59.774 | 45.411 | 1.00 | 38.87 | A |
| ATOM | 430 | N | THR | A | 291 | 55.685 | 60.796 | 47.150 | 1.00 | 39.89 | A |
| ATOM | 431 | CA | THR | A | 291 | 56.498 | 61.944 | 46.909 | 1.00 | 39.85 | A |
| ATOM | 432 | CB | THR | A | 291 | 55.746 | 63.161 | 47.277 | 1.00 | 41.00 | A |
| ATOM | 433 | OG1 | THR | A | 291 | 55.150 | 62.975 | 48.536 | 1.00 | 40.67 | A |
| ATOM | 434 | CG2 | THR | A | 291 | 54.541 | 63.311 | 46.383 | 1.00 | 41.09 | A |
| ATOM | 435 | C | THR | A | 291 | 57.884 | 61.938 | 47.624 | 1.00 | 40.87 | A |
| ATOM | 436 | O | THR | A | 291 | 58.718 | 62.907 | 47.376 | 1.00 | 40.33 | A |
| ATOM | 437 | N | LEU | A | 292 | 58.196 | 60.860 | 48.387 | 1.00 | 38.55 | A |
| ATOM | 438 | CA | LEU | A | 292 | 59.540 | 60.708 | 48.862 | 1.00 | 37.49 | A |
| ATOM | 439 | CB | LEU | A | 292 | 59.735 | 59.564 | 49.856 | 1.00 | 36.05 | A |
| ATOM | 440 | CG | LEU | A | 292 | 58.901 | 59.593 | 51.153 | 1.00 | 36.03 | A |
| ATOM | 441 | CD1 | LEU | A | 292 | 59.194 | 58.407 | 52.123 | 1.00 | 34.22 | A |
| ATOM | 442 | CD2 | LEU | A | 292 | 59.169 | 60.841 | 51.865 | 1.00 | 34.77 | A |
| ATOM | 443 | C | LEU | A | 292 | 60.348 | 60.389 | 47.618 | 1.00 | 38.17 | A |
| ATOM | 444 | O | LEU | A | 292 | 59.881 | 59.814 | 46.676 | 1.00 | 37.71 | A |
| ATOM | 445 | N | SER | A | 293 | 61.619 | 60.672 | 47.677 | 1.00 | 37.88 | A |
| ATOM | 446 | CA | SER | A | 293 | 62.466 | 60.108 | 46.664 | 1.00 | 37.78 | A |
| ATOM | 447 | CB | SER | A | 293 | 63.873 | 60.547 | 46.928 | 1.00 | 37.79 | A |
| ATOM | 448 | OG | SER | A | 293 | 64.295 | 59.991 | 48.194 | 1.00 | 39.77 | A |
| ATOM | 449 | C | SER | A | 293 | 62.447 | 58.599 | 46.726 | 1.00 | 37.30 | A |

TABLE 2-continued

ATOMIC COORDINATES OF THE ERR3 LBD/
DIETHYLSTILBESTROL COMPLEX

| ATOM | 450 | O   | SER | A | 293 | 62.139 | 57.966 | 47.710 | 1.00 | 35.46 | A |
| --- | --- | --- | --- | --- | --- | --- | --- | --- | --- | --- | --- |
| ATOM | 451 | N   | LEU | A | 294 | 62.836 | 58.033 | 45.602 | 1.00 | 36.82 | A |
| ATOM | 452 | CA  | LEU | A | 294 | 62.868 | 56.674 | 45.382 | 1.00 | 36.54 | A |
| ATOM | 453 | CB  | LEU | A | 294 | 63.283 | 56.437 | 43.974 | 1.00 | 38.24 | A |
| ATOM | 454 | CG  | LEU | A | 294 | 62.098 | 56.273 | 42.945 | 1.00 | 40.35 | A |
| ATOM | 455 | CD1 | LEU | A | 294 | 60.704 | 57.104 | 43.011 | 1.00 | 40.11 | A |
| ATOM | 456 | CD2 | LEU | A | 294 | 62.686 | 56.331 | 41.498 | 1.00 | 41.43 | A |
| ATOM | 457 | C   | LEU | A | 294 | 63.825 | 56.013 | 46.363 | 1.00 | 36.33 | A |
| ATOM | 458 | O   | LEU | A | 294 | 63.462 | 54.930 | 46.892 | 1.00 | 36.48 | A |
| ATOM | 459 | N   | ALA | A | 295 | 64.986 | 56.639 | 46.652 | 1.00 | 34.35 | A |
| ATOM | 460 | CA  | ALA | A | 295 | 65.878 | 56.055 | 47.587 | 1.00 | 34.33 | A |
| ATOM | 461 | CB  | ALA | A | 295 | 67.135 | 56.822 | 47.743 | 1.00 | 33.38 | A |
| ATOM | 462 | C   | ALA | A | 295 | 65.176 | 55.970 | 48.940 | 1.00 | 34.62 | A |
| ATOM | 463 | O   | ALA | A | 295 | 65.223 | 54.934 | 49.568 | 1.00 | 35.79 | A |
| ATOM | 464 | N   | ASP | A | 296 | 64.533 | 57.068 | 49.374 | 1.00 | 34.98 | A |
| ATOM | 465 | CA  | ASP | A | 296 | 63.908 | 57.156 | 50.683 | 1.00 | 34.10 | A |
| ATOM | 466 | CB  | ASP | A | 296 | 63.460 | 58.594 | 51.047 | 1.00 | 33.96 | A |
| ATOM | 467 | CG  | ASP | A | 296 | 64.614 | 59.417 | 51.507 | 1.00 | 36.27 | A |
| ATOM | 468 | OD1 | ASP | A | 296 | 65.769 | 58.902 | 51.568 | 1.00 | 34.47 | A |
| ATOM | 469 | OD2 | ASP | A | 296 | 64.464 | 60.588 | 51.867 | 1.00 | 36.47 | A |
| ATOM | 470 | C   | ASP | A | 296 | 62.745 | 56.159 | 50.740 | 1.00 | 33.23 | A |
| ATOM | 471 | O   | ASP | A | 296 | 62.546 | 55.505 | 51.763 | 1.00 | 33.00 | A |
| ATOM | 472 | N   | GLN | A | 297 | 62.013 | 55.999 | 49.640 | 1.00 | 31.69 | A |
| ATOM | 473 | CA  | GLN | A | 297 | 60.939 | 54.985 | 49.623 | 1.00 | 31.00 | A |
| ATOM | 474 | CB  | GLN | A | 297 | 60.315 | 54.847 | 48.278 | 1.00 | 29.80 | A |
| ATOM | 475 | CG  | GLN | A | 297 | 59.355 | 56.038 | 48.078 | 1.00 | 31.63 | A |
| ATOM | 476 | CD  | GLN | A | 297 | 58.644 | 56.077 | 46.698 | 1.00 | 31.57 | A |
| ATOM | 477 | OE1 | GLN | A | 297 | 58.349 | 55.022 | 46.080 | 1.00 | 31.92 | A |
| ATOM | 478 | NE2 | GLN | A | 297 | 58.480 | 57.302 | 46.190 | 1.00 | 31.33 | A |
| ATOM | 479 | C   | GLN | A | 297 | 61.544 | 53.695 | 49.965 | 1.00 | 31.60 | A |
| ATOM | 480 | O   | GLN | A | 297 | 61.118 | 52.965 | 50.844 | 1.00 | 31.08 | A |
| ATOM | 481 | N   | MET | A | 298 | 62.631 | 53.433 | 49.289 | 1.00 | 32.55 | A |
| ATOM | 482 | CA  | MET | A | 298 | 63.275 | 52.167 | 49.451 | 1.00 | 33.36 | A |
| ATOM | 483 | CB  | MET | A | 298 | 64.426 | 52.013 | 48.497 | 1.00 | 37.14 | A |
| ATOM | 484 | CG  | MET | A | 298 | 64.464 | 50.632 | 48.031 | 1.00 | 45.07 | A |
| ATOM | 485 | SD  | MET | A | 298 | 63.283 | 50.641 | 46.740 | 1.00 | 55.31 | A |
| ATOM | 486 | CE  | MET | A | 298 | 61.957 | 49.241 | 47.250 | 1.00 | 51.59 | A |
| ATOM | 487 | C   | MET | A | 298 | 63.818 | 51.930 | 50.817 | 1.00 | 32.13 | A |
| ATOM | 488 | O   | MET | A | 298 | 63.682 | 50.814 | 51.373 | 1.00 | 29.01 | A |
| ATOM | 489 | N   | SER | A | 299 | 64.399 | 52.975 | 51.386 | 1.00 | 31.02 | A |
| ATOM | 490 | CA  | SER | A | 299 | 64.973 | 52.767 | 52.705 | 1.00 | 29.70 | A |
| ATOM | 491 | CB  | SER | A | 299 | 65.780 | 53.971 | 53.126 | 1.00 | 28.26 | A |
| ATOM | 492 | OG  | SER | A | 299 | 66.735 | 54.229 | 52.106 | 1.00 | 31.41 | A |
| ATOM | 493 | C   | SER | A | 299 | 63.860 | 52.492 | 53.682 | 1.00 | 27.49 | A |
| ATOM | 494 | O   | SER | A | 299 | 64.071 | 51.740 | 54.650 | 1.00 | 28.10 | A |
| ATOM | 495 | N   | LEU | A | 300 | 62.698 | 53.087 | 53.518 | 1.00 | 26.32 | A |
| ATOM | 496 | CA  | LEU | A | 300 | 61.638 | 52.887 | 54.604 | 1.00 | 25.94 | A |
| ATOM | 497 | CB  | LEU | A | 300 | 60.479 | 53.867 | 54.487 | 1.00 | 24.42 | A |
| ATOM | 498 | CG  | LEU | A | 300 | 60.721 | 55.365 | 54.801 | 1.00 | 27.60 | A |
| ATOM | 499 | CD1 | LEU | A | 300 | 59.467 | 56.176 | 54.589 | 1.00 | 25.94 | A |
| ATOM | 500 | CD2 | LEU | A | 300 | 61.256 | 55.607 | 56.054 | 1.00 | 29.49 | A |
| ATOM | 501 | C   | LEU | A | 300 | 61.098 | 51.433 | 54.483 | 1.00 | 25.27 | A |
| ATOM | 502 | O   | LEU | A | 300 | 60.857 | 50.795 | 55.438 | 1.00 | 24.81 | A |
| ATOM | 503 | N   | LEU | A | 301 | 60.931 | 50.930 | 53.261 | 1.00 | 23.63 | A |
| ATOM | 504 | CA  | LEU | A | 301 | 60.380 | 49.579 | 53.041 | 1.00 | 25.76 | A |
| ATOM | 505 | CB  | LEU | A | 301 | 60.071 | 49.414 | 51.539 | 1.00 | 26.26 | A |
| ATOM | 506 | CG  | LEU | A | 301 | 58.763 | 50.079 | 50.990 | 1.00 | 26.53 | A |
| ATOM | 507 | CD1 | LEU | A | 301 | 58.882 | 49.997 | 49.430 | 1.00 | 28.58 | A |
| ATOM | 508 | CD2 | LEU | A | 301 | 57.555 | 49.232 | 51.302 | 1.00 | 25.38 | A |
| ATOM | 509 | C   | LEU | A | 301 | 61.328 | 48.483 | 53.469 | 1.00 | 27.04 | A |
| ATOM | 510 | O   | LEU | A | 301 | 60.891 | 47.477 | 54.057 | 1.00 | 24.25 | A |
| ATOM | 511 | N   | GLN | A | 302 | 62.633 | 48.750 | 53.238 | 1.00 | 28.05 | A |
| ATOM | 512 | CA  | GLN | A | 302 | 63.745 | 47.931 | 53.733 | 1.00 | 30.53 | A |
| ATOM | 513 | CB  | GLN | A | 302 | 65.155 | 48.388 | 53.280 | 1.00 | 33.84 | A |
| ATOM | 514 | CG  | GLN | A | 302 | 65.429 | 48.031 | 51.821 | 1.00 | 40.90 | A |
| ATOM | 515 | CD  | GLN | A | 302 | 66.550 | 48.923 | 51.059 | 1.00 | 44.71 | A |
| ATOM | 516 | OE1 | GLN | A | 302 | 67.666 | 48.453 | 50.891 | 1.00 | 49.73 | A |
| ATOM | 517 | NE2 | GLN | A | 302 | 66.186 | 50.121 | 50.524 | 1.00 | 47.76 | A |
| ATOM | 518 | C   | GLN | A | 302 | 63.723 | 47.869 | 55.220 | 1.00 | 29.71 | A |
| ATOM | 519 | O   | GLN | A | 302 | 63.936 | 46.807 | 55.752 | 1.00 | 29.18 | A |
| ATOM | 520 | N   | SER | A | 303 | 63.472 | 48.980 | 55.878 | 1.00 | 29.45 | A |
| ATOM | 521 | CA  | SER | A | 303 | 63.487 | 48.904 | 57.312 | 1.00 | 29.39 | A |
| ATOM | 522 | CB  | SER | A | 303 | 63.627 | 50.301 | 57.894 | 1.00 | 29.88 | A |
| ATOM | 523 | OG  | SER | A | 303 | 64.967 | 50.762 | 57.687 | 1.00 | 34.18 | A |
| ATOM | 524 | C   | SER | A | 303 | 62.223 | 48.299 | 57.916 | 1.00 | 29.14 | A |
| ATOM | 525 | O   | SER | A | 303 | 62.241 | 47.780 | 59.012 | 1.00 | 27.39 | A |

TABLE 2-continued

ATOMIC COORDINATES OF THE ERR3 LBD/
DIETHYLSTILBESTROL COMPLEX

| ATOM | 526 | N | ALA | A | 304 | 61.074 | 48.443 | 57.251 | 1.00 | 28.55 | A |
|---|---|---|---|---|---|---|---|---|---|---|---|
| ATOM | 527 | CA | ALA | A | 304 | 59.829 | 48.130 | 57.935 | 1.00 | 27.70 | A |
| ATOM | 528 | CB | ALA | A | 304 | 58.978 | 49.278 | 57.810 | 1.00 | 27.47 | A |
| ATOM | 529 | C | ALA | A | 304 | 59.075 | 46.929 | 57.391 | 1.00 | 26.82 | A |
| ATOM | 530 | O | ALA | A | 304 | 58.058 | 46.638 | 57.860 | 1.00 | 25.56 | A |
| ATOM | 531 | N | TRP | A | 305 | 59.542 | 46.316 | 56.317 | 1.00 | 27.75 | A |
| ATOM | 532 | CA | TRP | A | 305 | 58.761 | 45.258 | 55.682 | 1.00 | 28.52 | A |
| ATOM | 533 | CB | TRP | A | 305 | 59.353 | 44.573 | 54.388 | 1.00 | 29.64 | A |
| ATOM | 534 | CG | TRP | A | 305 | 60.595 | 43.736 | 54.681 | 1.00 | 32.64 | A |
| ATOM | 535 | CD2 | TRP | A | 305 | 60.694 | 42.393 | 55.090 | 1.00 | 32.77 | A |
| ATOM | 536 | CE2 | TRP | A | 305 | 62.052 | 42.111 | 55.260 | 1.00 | 35.78 | A |
| ATOM | 537 | CE3 | TRP | A | 305 | 59.780 | 41.339 | 55.240 | 1.00 | 33.94 | A |
| ATOM | 538 | CD1 | TRP | A | 305 | 61.857 | 44.226 | 54.656 | 1.00 | 34.91 | A |
| ATOM | 539 | NE1 | TRP | A | 305 | 62.730 | 43.266 | 55.034 | 1.00 | 35.82 | A |
| ATOM | 540 | CZ2 | TRP | A | 305 | 62.547 | 40.818 | 55.614 | 1.00 | 35.85 | A |
| ATOM | 541 | CZ3 | TRP | A | 305 | 60.242 | 40.093 | 55.581 | 1.00 | 33.95 | A |
| ATOM | 542 | CH2 | TRP | A | 305 | 61.632 | 39.832 | 55.747 | 1.00 | 35.86 | A |
| ATOM | 543 | C | TRP | A | 305 | 58.380 | 44.245 | 56.739 | 1.00 | 27.77 | A |
| ATOM | 544 | O | TRP | A | 305 | 57.214 | 43.793 | 56.720 | 1.00 | 28.25 | A |
| ATOM | 545 | N | MET | A | 306 | 59.276 | 43.881 | 57.650 | 1.00 | 26.35 | A |
| ATOM | 546 | CA | MET | A | 306 | 58.892 | 42.801 | 58.517 | 1.00 | 25.93 | A |
| ATOM | 547 | CB | MET | A | 306 | 60.110 | 42.275 | 59.171 | 1.00 | 26.24 | A |
| ATOM | 548 | CG | MET | A | 306 | 59.728 | 41.110 | 60.155 | 1.00 | 27.93 | A |
| ATOM | 549 | SD | MET | A | 306 | 59.015 | 39.496 | 59.368 | 1.00 | 31.10 | A |
| ATOM | 550 | CE | MET | A | 306 | 60.369 | 38.778 | 58.901 | 1.00 | 29.03 | A |
| ATOM | 551 | C | MET | A | 306 | 57.823 | 43.237 | 59.541 | 1.00 | 26.14 | A |
| ATOM | 552 | O | MET | A | 306 | 56.998 | 42.487 | 59.979 | 1.00 | 25.66 | A |
| ATOM | 553 | N | GLU | A | 307 | 57.871 | 44.473 | 59.987 | 1.00 | 25.52 | A |
| ATOM | 554 | CA | GLU | A | 307 | 56.822 | 45.012 | 60.833 | 1.00 | 25.95 | A |
| ATOM | 555 | CB | GLU | A | 307 | 57.148 | 46.441 | 61.306 | 1.00 | 24.81 | A |
| ATOM | 556 | CG | GLU | A | 307 | 58.384 | 46.561 | 62.118 | 1.00 | 25.11 | A |
| ATOM | 557 | CD | GLU | A | 307 | 58.612 | 47.902 | 62.792 | 1.00 | 27.08 | A |
| ATOM | 558 | OE1 | GLU | A | 307 | 57.631 | 48.660 | 63.088 | 1.00 | 27.07 | A |
| ATOM | 559 | OE2 | GLU | A | 307 | 59.812 | 48.167 | 63.095 | 1.00 | 27.52 | A |
| ATOM | 560 | C | GLU | A | 307 | 55.417 | 44.963 | 60.117 | 1.00 | 25.37 | A |
| ATOM | 561 | O | GLU | A | 307 | 54.423 | 44.739 | 60.793 | 1.00 | 24.84 | A |
| ATOM | 562 | N | ILE | A | 308 | 55.377 | 45.326 | 58.847 | 1.00 | 25.32 | A |
| ATOM | 563 | CA | ILE | A | 308 | 54.148 | 45.389 | 58.072 | 1.00 | 27.08 | A |
| ATOM | 564 | CB | ILE | A | 308 | 54.391 | 46.072 | 56.707 | 1.00 | 27.70 | A |
| ATOM | 565 | CG2 | ILE | A | 308 | 53.223 | 45.959 | 55.707 | 1.00 | 27.02 | A |
| ATOM | 566 | CG1 | ILE | A | 308 | 54.781 | 47.564 | 56.877 | 1.00 | 29.53 | A |
| ATOM | 567 | CD1 | ILE | A | 308 | 55.404 | 48.107 | 55.610 | 1.00 | 28.15 | A |
| ATOM | 568 | C | ILE | A | 308 | 53.643 | 43.960 | 57.918 | 1.00 | 26.74 | A |
| ATOM | 569 | O | ILE | A | 308 | 52.486 | 43.704 | 58.122 | 1.00 | 28.08 | A |
| ATOM | 570 | N | LEU | A | 309 | 54.482 | 43.004 | 57.599 | 1.00 | 26.03 | A |
| ATOM | 571 | CA | LEU | A | 309 | 54.073 | 41.578 | 57.553 | 1.00 | 26.47 | A |
| ATOM | 572 | CB | LEU | A | 309 | 55.214 | 40.730 | 57.058 | 1.00 | 26.29 | A |
| ATOM | 573 | CG | LEU | A | 309 | 55.797 | 40.822 | 55.687 | 1.00 | 28.45 | A |
| ATOM | 574 | CD1 | LEU | A | 309 | 56.920 | 39.711 | 55.442 | 1.00 | 26.61 | A |
| ATOM | 575 | CD2 | LEU | A | 309 | 54.758 | 40.504 | 54.768 | 1.00 | 28.99 | A |
| ATOM | 576 | C | LEU | A | 309 | 53.579 | 41.086 | 58.887 | 1.00 | 25.73 | A |
| ATOM | 577 | O | LEU | A | 309 | 52.483 | 40.577 | 58.997 | 1.00 | 25.72 | A |
| ATOM | 578 | N | ILE | A | 310 | 54.327 | 41.332 | 59.960 | 1.00 | 26.93 | A |
| ATOM | 579 | CA | ILE | A | 310 | 53.921 | 40.808 | 61.283 | 1.00 | 26.61 | A |
| ATOM | 580 | CB | ILE | A | 310 | 54.966 | 41.056 | 62.303 | 1.00 | 28.21 | A |
| ATOM | 581 | CG2 | ILE | A | 310 | 54.431 | 40.820 | 63.682 | 1.00 | 26.03 | A |
| ATOM | 582 | CG1 | ILE | A | 310 | 56.233 | 40.207 | 62.120 | 1.00 | 29.61 | A |
| ATOM | 583 | CD1 | ILE | A | 310 | 55.985 | 38.799 | 62.389 | 1.00 | 31.29 | A |
| ATOM | 584 | C | ILE | A | 310 | 52.634 | 41.457 | 61.744 | 1.00 | 27.13 | A |
| ATOM | 585 | O | ILE | A | 310 | 51.703 | 40.765 | 62.236 | 1.00 | 26.75 | A |
| ATOM | 586 | N | LEU | A | 311 | 52.505 | 42.784 | 61.651 | 1.00 | 26.83 | A |
| ATOM | 587 | CA | LEU | A | 311 | 51.204 | 43.372 | 61.964 | 1.00 | 26.95 | A |
| ATOM | 588 | CB | LEU | A | 311 | 51.179 | 44.841 | 61.702 | 1.00 | 28.09 | A |
| ATOM | 589 | CG | LEU | A | 311 | 50.318 | 45.777 | 62.389 | 1.00 | 29.72 | A |
| ATOM | 590 | CD1 | LEU | A | 311 | 50.084 | 45.505 | 63.871 | 1.00 | 29.97 | A |
| ATOM | 591 | CD2 | LEU | A | 311 | 50.928 | 47.139 | 62.192 | 1.00 | 31.37 | A |
| ATOM | 592 | C | LEU | A | 311 | 50.018 | 42.723 | 61.249 | 1.00 | 26.47 | A |
| ATOM | 593 | O | LEU | A | 311 | 48.985 | 42.512 | 61.832 | 1.00 | 25.99 | A |
| ATOM | 594 | N | GLY | A | 312 | 50.127 | 42.464 | 59.972 | 1.00 | 26.55 | A |
| ATOM | 595 | CA | GLY | A | 312 | 49.042 | 41.762 | 59.227 | 1.00 | 26.99 | A |
| ATOM | 596 | C | GLY | A | 312 | 48.763 | 40.383 | 59.819 | 1.00 | 26.88 | A |
| ATOM | 597 | O | GLY | A | 312 | 47.606 | 40.038 | 60.069 | 1.00 | 26.18 | A |
| ATOM | 598 | N | VAL | A | 313 | 49.805 | 39.622 | 60.147 | 1.00 | 27.84 | A |
| ATOM | 599 | CA | VAL | A | 313 | 49.553 | 38.305 | 60.815 | 1.00 | 28.57 | A |
| ATOM | 600 | CB | VAL | A | 313 | 50.753 | 37.543 | 61.050 | 1.00 | 27.93 | A |
| ATOM | 601 | CG1 | VAL | A | 313 | 50.461 | 36.257 | 61.645 | 1.00 | 31.19 | A |

TABLE 2-continued

ATOMIC COORDINATES OF THE ERR3 LBD/
DIETHYLSTILBESTROL COMPLEX

| ATOM | 602 | CG2 | VAL | A | 313 | 51.342 | 37.225 | 59.728 | 1.00 | 29.40 | A |
|------|-----|-----|-----|---|-----|--------|--------|--------|------|-------|---|
| ATOM | 603 | C | VAL | A | 313 | 48.811 | 38.490 | 62.109 | 1.00 | 28.37 | A |
| ATOM | 604 | O | VAL | A | 313 | 47.847 | 37.814 | 62.389 | 1.00 | 28.40 | A |
| ATOM | 605 | N | VAL | A | 314 | 49.117 | 39.534 | 62.826 | 1.00 | 28.51 | A |
| ATOM | 606 | CA | VAL | A | 314 | 48.535 | 39.716 | 64.100 | 1.00 | 27.11 | A |
| ATOM | 607 | CB | VAL | A | 314 | 49.289 | 40.853 | 64.848 | 1.00 | 27.92 | A |
| ATOM | 608 | CG1 | VAL | A | 314 | 48.571 | 41.320 | 66.021 | 1.00 | 25.00 | A |
| ATOM | 609 | CG2 | VAL | A | 314 | 50.690 | 40.416 | 65.311 | 1.00 | 24.86 | A |
| ATOM | 610 | C | VAL | A | 314 | 47.121 | 40.051 | 63.942 | 1.00 | 28.06 | A |
| ATOM | 611 | O | VAL | A | 314 | 46.307 | 39.563 | 64.694 | 1.00 | 29.12 | A |
| ATOM | 612 | N | TYR | A | 315 | 46.814 | 41.070 | 63.158 | 1.00 | 29.39 | A |
| ATOM | 613 | CA | TYR | A | 315 | 45.478 | 41.527 | 62.946 | 1.00 | 30.27 | A |
| ATOM | 614 | CB | TYR | A | 315 | 45.454 | 42.578 | 61.830 | 1.00 | 31.14 | A |
| ATOM | 615 | CG | TYR | A | 315 | 44.075 | 43.061 | 61.673 | 1.00 | 33.40 | A |
| ATOM | 616 | CD1 | TYR | A | 315 | 43.501 | 43.855 | 62.680 | 1.00 | 32.38 | A |
| ATOM | 617 | CE1 | TYR | A | 315 | 42.207 | 44.270 | 62.628 | 1.00 | 33.98 | A |
| ATOM | 618 | CD2 | TYR | A | 315 | 43.313 | 42.693 | 60.599 | 1.00 | 32.20 | A |
| ATOM | 619 | CE2 | TYR | A | 315 | 41.990 | 43.063 | 60.548 | 1.00 | 34.52 | A |
| ATOM | 620 | CZ | TYR | A | 315 | 41.417 | 43.828 | 61.578 | 1.00 | 34.70 | A |
| ATOM | 621 | OH | TYR | A | 315 | 40.088 | 44.242 | 61.547 | 1.00 | 36.38 | A |
| ATOM | 622 | C | TYR | A | 315 | 44.577 | 40.317 | 62.496 | 1.00 | 31.70 | A |
| ATOM | 623 | O | TYR | A | 315 | 43.456 | 40.136 | 62.986 | 1.00 | 32.02 | A |
| ATOM | 624 | N | ARG | A | 316 | 45.090 | 39.471 | 61.583 | 1.00 | 32.39 | A |
| ATOM | 625 | CA | ARG | A | 316 | 44.328 | 38.368 | 61.077 | 1.00 | 32.50 | A |
| ATOM | 626 | CB | ARG | A | 316 | 44.982 | 37.672 | 59.888 | 1.00 | 31.37 | A |
| ATOM | 627 | CG | ARG | A | 316 | 44.864 | 38.447 | 58.544 | 1.00 | 30.11 | A |
| ATOM | 628 | CD | ARG | A | 316 | 45.525 | 37.791 | 57.451 | 1.00 | 28.86 | A |
| ATOM | 629 | NE | ARG | A | 316 | 46.951 | 37.287 | 57.647 | 1.00 | 31.32 | A |
| ATOM | 630 | CZ | ARG | A | 316 | 48.046 | 37.982 | 57.194 | 1.00 | 31.46 | A |
| ATOM | 631 | NH1 | ARG | A | 316 | 47.866 | 39.162 | 56.713 | 1.00 | 32.06 | A |
| ATOM | 632 | NH2 | ARG | A | 316 | 49.267 | 37.546 | 57.277 | 1.00 | 30.36 | A |
| ATOM | 633 | C | ARG | A | 316 | 44.028 | 37.327 | 62.201 | 1.00 | 32.87 | A |
| ATOM | 634 | O | ARG | A | 316 | 43.170 | 36.453 | 61.987 | 1.00 | 33.44 | A |
| ATOM | 635 | N | SER | A | 317 | 44.692 | 37.440 | 63.347 | 1.00 | 31.30 | A |
| ATOM | 636 | CA | SER | A | 317 | 44.706 | 36.401 | 64.410 | 1.00 | 31.36 | A |
| ATOM | 637 | CB | SER | A | 317 | 46.180 | 36.174 | 64.861 | 1.00 | 29.82 | A |
| ATOM | 638 | OG | SER | A | 317 | 46.895 | 35.666 | 63.711 | 1.00 | 30.59 | A |
| ATOM | 639 | C | SER | A | 317 | 43.897 | 36.773 | 65.616 | 1.00 | 32.10 | A |
| ATOM | 640 | O | SER | A | 317 | 43.877 | 36.019 | 66.607 | 1.00 | 31.68 | A |
| ATOM | 641 | N | LEU | A | 318 | 43.312 | 37.987 | 65.585 | 1.00 | 32.55 | A |
| ATOM | 642 | CA | LEU | A | 318 | 42.750 | 38.609 | 66.769 | 1.00 | 35.31 | A |
| ATOM | 643 | CB | LEU | A | 318 | 42.268 | 40.039 | 66.483 | 1.00 | 34.51 | A |
| ATOM | 644 | CG | LEU | A | 318 | 43.363 | 41.044 | 66.385 | 1.00 | 36.16 | A |
| ATOM | 645 | CD1 | LEU | A | 318 | 42.807 | 42.423 | 66.100 | 1.00 | 37.82 | A |
| ATOM | 646 | CD2 | LEU | A | 318 | 44.176 | 41.033 | 67.623 | 1.00 | 34.50 | A |
| ATOM | 647 | C | LEU | A | 318 | 41.537 | 37.875 | 67.278 | 1.00 | 36.42 | A |
| ATOM | 648 | O | LEU | A | 318 | 41.263 | 37.936 | 68.501 | 1.00 | 37.97 | A |
| ATOM | 649 | N | SER | A | 319 | 40.727 | 37.306 | 66.381 | 1.00 | 37.07 | A |
| ATOM | 650 | CA | SER | A | 319 | 39.562 | 36.507 | 66.882 | 1.00 | 38.81 | A |
| ATOM | 651 | CB | SER | A | 319 | 38.375 | 36.509 | 65.933 | 1.00 | 38.72 | A |
| ATOM | 652 | OG | SER | A | 319 | 38.174 | 37.744 | 65.260 | 1.00 | 40.86 | A |
| ATOM | 653 | C | SER | A | 319 | 39.972 | 35.044 | 67.106 | 1.00 | 39.62 | A |
| ATOM | 654 | O | SER | A | 319 | 39.142 | 34.183 | 67.376 | 1.00 | 40.75 | A |
| ATOM | 655 | N | PHE | A | 320 | 41.242 | 34.711 | 66.905 | 1.00 | 39.71 | A |
| ATOM | 656 | CA | PHE | A | 320 | 41.674 | 33.337 | 67.191 | 1.00 | 39.65 | A |
| ATOM | 657 | CB | PHE | A | 320 | 42.616 | 32.842 | 66.138 | 1.00 | 38.74 | A |
| ATOM | 658 | CG | PHE | A | 320 | 41.996 | 32.614 | 64.836 | 1.00 | 36.44 | A |
| ATOM | 659 | CD1 | PHE | A | 320 | 41.801 | 31.293 | 64.361 | 1.00 | 36.91 | A |
| ATOM | 660 | CD2 | PHE | A | 320 | 41.646 | 33.674 | 64.057 | 1.00 | 36.82 | A |
| ATOM | 661 | CE1 | PHE | A | 320 | 41.281 | 31.012 | 63.092 | 1.00 | 35.54 | A |
| ATOM | 662 | CE2 | PHE | A | 320 | 41.103 | 33.489 | 62.772 | 1.00 | 35.91 | A |
| ATOM | 663 | CZ | PHE | A | 320 | 40.864 | 32.138 | 62.258 | 1.00 | 34.67 | A |
| ATOM | 664 | C | PHE | A | 320 | 42.258 | 33.270 | 68.580 | 1.00 | 40.55 | A |
| ATOM | 665 | O | PHE | A | 320 | 42.336 | 34.295 | 69.276 | 1.00 | 40.10 | A |
| ATOM | 666 | N | GLU | A | 321 | 42.588 | 32.074 | 69.046 | 1.00 | 42.31 | A |
| ATOM | 667 | CA | GLU | A | 321 | 43.191 | 31.873 | 70.393 | 1.00 | 45.46 | A |
| ATOM | 668 | CB | GLU | A | 321 | 42.225 | 31.165 | 71.385 | 1.00 | 49.67 | A |
| ATOM | 669 | CG | GLU | A | 321 | 41.584 | 32.038 | 72.515 | 1.00 | 56.77 | A |
| ATOM | 670 | CD | GLU | A | 321 | 42.621 | 32.668 | 73.424 | 1.00 | 61.80 | A |
| ATOM | 671 | OE1 | GLU | A | 321 | 43.463 | 33.439 | 72.920 | 1.00 | 65.27 | A |
| ATOM | 672 | OE2 | GLU | A | 321 | 42.593 | 32.390 | 74.640 | 1.00 | 65.27 | A |
| ATOM | 673 | C | GLU | A | 321 | 44.371 | 30.949 | 70.197 | 1.00 | 44.86 | A |
| ATOM | 674 | O | GLU | A | 321 | 44.200 | 29.857 | 69.680 | 1.00 | 46.11 | A |
| ATOM | 675 | N | ASP | A | 322 | 45.552 | 31.368 | 70.625 | 1.00 | 42.97 | A |
| ATOM | 676 | CA | ASP | A | 322 | 46.820 | 30.620 | 70.490 | 1.00 | 40.75 | A |
| ATOM | 677 | CB | ASP | A | 322 | 46.893 | 29.412 | 71.448 | 1.00 | 42.38 | A |

TABLE 2-continued

ATOMIC COORDINATES OF THE ERR3 LBD/
DIETHYLSTILBESTROL COMPLEX

| ATOM | 678 | CG | ASP | A | 322 | 46.778 | 29.846 | 72.937 | 1.00 | 42.20 | A |
|---|---|---|---|---|---|---|---|---|---|---|---|
| ATOM | 679 | OD1 | ASP | A | 322 | 46.934 | 31.099 | 72.969 | 1.00 | 41.17 | A |
| ATOM | 680 | OD2 | ASP | A | 322 | 47.933 | 29.404 | 73.634 | 0.00 | 41.91 | A |
| ATOM | 681 | C | ASP | A | 322 | 47.079 | 30.235 | 69.097 | 1.00 | 39.49 | A |
| ATOM | 682 | O | ASP | A | 322 | 47.743 | 29.242 | 68.834 | 1.00 | 37.66 | A |
| ATOM | 683 | N | GLU | A | 323 | 46.551 | 30.954 | 68.135 | 1.00 | 38.11 | A |
| ATOM | 684 | CA | GLU | A | 323 | 46.889 | 30.506 | 66.771 | 1.00 | 38.44 | A |
| ATOM | 685 | CB | GLU | A | 323 | 45.729 | 29.700 | 66.107 | 1.00 | 40.07 | A |
| ATOM | 686 | CG | GLU | A | 323 | 45.394 | 28.265 | 66.596 | 1.00 | 44.01 | A |
| ATOM | 687 | CD | GLU | A | 323 | 44.192 | 27.647 | 65.809 | 1.00 | 46.48 | A |
| ATOM | 688 | OE1 | GLU | A | 323 | 43.164 | 28.371 | 65.580 | 1.00 | 46.07 | A |
| ATOM | 689 | OE2 | GLU | A | 323 | 44.321 | 26.462 | 65.373 | 1.00 | 48.69 | A |
| ATOM | 690 | C | GLU | A | 323 | 47.140 | 31.663 | 65.909 | 1.00 | 36.38 | A |
| ATOM | 691 | O | GLU | A | 323 | 46.553 | 32.750 | 66.150 | 1.00 | 36.55 | A |
| ATOM | 692 | N | LEU | A | 324 | 47.900 | 31.435 | 64.849 | 1.00 | 34.67 | A |
| ATOM | 693 | CA | LEU | A | 324 | 48.225 | 32.492 | 63.935 | 1.00 | 33.72 | A |
| ATOM | 694 | CB | LEU | A | 324 | 49.743 | 32.808 | 64.045 | 1.00 | 32.72 | A |
| ATOM | 695 | CG | LEU | A | 324 | 50.322 | 33.331 | 65.406 | 1.00 | 33.28 | A |
| ATOM | 696 | CD1 | LEU | A | 324 | 51.864 | 33.414 | 65.322 | 1.00 | 30.66 | A |
| ATOM | 697 | CD2 | LEU | A | 324 | 49.773 | 34.702 | 65.802 | 1.00 | 31.28 | A |
| ATOM | 698 | C | LEU | A | 324 | 47.873 | 32.242 | 62.528 | 1.00 | 33.93 | A |
| ATOM | 699 | O | LEU | A | 324 | 48.234 | 31.265 | 61.969 | 1.00 | 34.54 | A |
| ATOM | 700 | N | VAL | A | 325 | 47.163 | 33.206 | 61.958 | 1.00 | 33.62 | A |
| ATOM | 701 | CA | VAL | A | 325 | 46.664 | 33.181 | 60.658 | 1.00 | 32.84 | A |
| ATOM | 702 | CB | VAL | A | 325 | 45.323 | 34.004 | 60.664 | 1.00 | 33.53 | A |
| ATOM | 703 | CG1 | VAL | A | 325 | 44.474 | 33.947 | 59.286 | 1.00 | 32.27 | A |
| ATOM | 704 | CG2 | VAL | A | 325 | 44.484 | 33.549 | 61.806 | 1.00 | 33.63 | A |
| ATOM | 705 | C | VAL | A | 325 | 47.618 | 33.849 | 59.723 | 1.00 | 33.25 | A |
| ATOM | 706 | O | VAL | A | 325 | 47.412 | 34.987 | 59.384 | 1.00 | 32.08 | A |
| ATOM | 707 | N | TYR | A | 326 | 48.645 | 33.092 | 59.270 | 1.00 | 32.48 | A |
| ATOM | 708 | CA | TYR | A | 326 | 49.533 | 33.554 | 58.293 | 1.00 | 32.76 | A |
| ATOM | 709 | CB | TYR | A | 326 | 50.706 | 32.596 | 58.100 | 1.00 | 31.40 | A |
| ATOM | 710 | CG | TYR | A | 326 | 51.760 | 32.820 | 59.134 | 1.00 | 31.66 | A |
| ATOM | 711 | CD1 | TYR | A | 326 | 52.636 | 33.876 | 59.028 | 1.00 | 31.98 | A |
| ATOM | 712 | CE1 | TYR | A | 326 | 53.647 | 34.150 | 60.138 | 1.00 | 33.15 | A |
| ATOM | 713 | CD2 | TYR | A | 326 | 51.780 | 32.090 | 60.338 | 1.00 | 30.98 | A |
| ATOM | 714 | CE2 | TYR | A | 326 | 52.692 | 32.360 | 61.395 | 1.00 | 31.56 | A |
| ATOM | 715 | CZ | TYR | A | 326 | 53.620 | 33.388 | 61.273 | 1.00 | 33.38 | A |
| ATOM | 716 | OH | TYR | A | 326 | 54.559 | 33.572 | 62.260 | 1.00 | 34.72 | A |
| ATOM | 717 | C | TYR | A | 326 | 48.759 | 33.884 | 57.014 | 1.00 | 34.79 | A |
| ATOM | 718 | O | TYR | A | 326 | 48.985 | 34.901 | 56.366 | 1.00 | 32.94 | A |
| ATOM | 719 | N | ALA | A | 327 | 47.869 | 32.947 | 56.658 | 1.00 | 34.74 | A |
| ATOM | 720 | CA | ALA | A | 327 | 46.926 | 33.111 | 55.581 | 1.00 | 35.88 | A |
| ATOM | 721 | CB | ALA | A | 327 | 47.598 | 32.737 | 54.141 | 1.00 | 32.85 | A |
| ATOM | 722 | C | ALA | A | 327 | 45.687 | 32.221 | 55.918 | 1.00 | 37.25 | A |
| ATOM | 723 | O | ALA | A | 327 | 45.734 | 31.369 | 56.808 | 1.00 | 36.30 | A |
| ATOM | 724 | N | ASP | A | 328 | 44.591 | 32.409 | 55.187 | 1.00 | 39.78 | A |
| ATOM | 725 | CA | ASP | A | 328 | 43.382 | 31.625 | 55.455 | 1.00 | 42.13 | A |
| ATOM | 726 | CB | ASP | A | 328 | 42.255 | 31.905 | 54.470 | 1.00 | 43.64 | A |
| ATOM | 727 | CG | ASP | A | 328 | 41.552 | 33.178 | 54.759 | 1.00 | 46.91 | A |
| ATOM | 728 | OD1 | ASP | A | 328 | 41.437 | 33.569 | 55.953 | 1.00 | 48.80 | A |
| ATOM | 729 | OD2 | ASP | A | 328 | 41.049 | 33.841 | 53.810 | 1.00 | 50.03 | A |
| ATOM | 730 | C | ASP | A | 328 | 43.653 | 30.180 | 55.346 | 1.00 | 42.47 | A |
| ATOM | 731 | O | ASP | A | 328 | 43.061 | 29.473 | 56.109 | 1.00 | 43.63 | A |
| ATOM | 732 | N | ASP | A | 329 | 44.483 | 29.754 | 54.383 | 1.00 | 43.07 | A |
| ATOM | 733 | CA | ASP | A | 329 | 44.865 | 28.368 | 54.158 | 1.00 | 44.32 | A |
| ATOM | 734 | CB | ASP | A | 329 | 45.087 | 28.102 | 52.658 | 1.00 | 45.38 | A |
| ATOM | 735 | CG | ASP | A | 329 | 46.090 | 29.075 | 52.020 | 1.00 | 47.23 | A |
| ATOM | 736 | OD1 | ASP | A | 329 | 46.478 | 30.130 | 52.672 | 1.00 | 47.30 | A |
| ATOM | 737 | OD2 | ASP | A | 329 | 46.600 | 28.865 | 50.881 | 1.00 | 46.53 | A |
| ATOM | 738 | C | ASP | A | 329 | 46.176 | 27.978 | 54.910 | 1.00 | 44.55 | A |
| ATOM | 739 | O | ASP | A | 329 | 46.740 | 26.952 | 54.634 | 1.00 | 44.61 | A |
| ATOM | 740 | N | TYR | A | 330 | 46.647 | 28.793 | 55.855 | 1.00 | 44.96 | A |
| ATOM | 741 | CA | TYR | A | 330 | 47.868 | 28.492 | 56.622 | 1.00 | 44.05 | A |
| ATOM | 742 | CB | TYR | A | 330 | 49.111 | 28.878 | 55.861 | 1.00 | 44.37 | A |
| ATOM | 743 | CG | TYR | A | 330 | 50.293 | 28.022 | 56.218 | 1.00 | 45.15 | A |
| ATOM | 744 | CD1 | TYR | A | 330 | 50.336 | 26.680 | 55.859 | 1.00 | 45.92 | A |
| ATOM | 745 | CE1 | TYR | A | 330 | 51.422 | 25.872 | 56.153 | 1.00 | 45.81 | A |
| ATOM | 746 | CD2 | TYR | A | 330 | 51.361 | 28.520 | 56.940 | 1.00 | 44.94 | A |
| ATOM | 747 | CE2 | TYR | A | 330 | 52.443 | 27.700 | 57.286 | 1.00 | 45.12 | A |
| ATOM | 748 | CZ | TYR | A | 330 | 52.468 | 26.387 | 56.891 | 1.00 | 45.22 | A |
| ATOM | 749 | OH | TYR | A | 330 | 53.500 | 25.577 | 57.219 | 1.00 | 45.12 | A |
| ATOM | 750 | C | TYR | A | 330 | 47.784 | 29.152 | 57.946 | 1.00 | 44.48 | A |
| ATOM | 751 | O | TYR | A | 330 | 48.143 | 30.328 | 58.129 | 1.00 | 45.43 | A |
| ATOM | 752 | N | ILE | A | 331 | 47.250 | 28.390 | 58.866 | 1.00 | 43.73 | A |
| ATOM | 753 | CA | ILE | A | 331 | 46.998 | 28.787 | 60.196 | 1.00 | 43.98 | A |

TABLE 2-continued

ATOMIC COORDINATES OF THE ERR3 LBD/
DIETHYLSTILBESTROL COMPLEX

| ATOM | 754 | CB  | ILE | A | 331 | 45.444 | 28.655 | 60.519 | 1.00 | 43.06 | A |
|------|-----|-----|-----|---|-----|--------|--------|--------|------|-------|---|
| ATOM | 755 | CG2 | ILE | A | 331 | 45.202 | 28.913 | 61.928 | 1.00 | 41.84 | A |
| ATOM | 756 | CG1 | ILE | A | 331 | 44.673 | 29.634 | 59.634 | 1.00 | 43.34 | A |
| ATOM | 757 | CD1 | ILE | A | 331 | 43.114 | 29.561 | 59.579 | 1.00 | 43.39 | A |
| ATOM | 758 | C   | ILE | A | 331 | 47.798 | 27.888 | 61.136 | 1.00 | 44.73 | A |
| ATOM | 759 | O   | ILE | A | 331 | 47.618 | 26.716 | 61.120 | 1.00 | 45.00 | A |
| ATOM | 760 | N   | MET | A | 332 | 48.632 | 28.455 | 62.025 | 1.00 | 45.70 | A |
| ATOM | 761 | CA  | MET | A | 332 | 49.648 | 27.659 | 62.718 | 1.00 | 46.50 | A |
| ATOM | 762 | CB  | MET | A | 332 | 51.058 | 28.302 | 62.512 | 1.00 | 45.95 | A |
| ATOM | 763 | CG  | MET | A | 332 | 51.642 | 28.136 | 61.130 | 1.00 | 46.76 | A |
| ATOM | 764 | SD  | MET | A | 332 | 53.373 | 28.569 | 61.019 | 1.00 | 46.39 | A |
| ATOM | 765 | CE  | MET | A | 332 | 54.023 | 27.212 | 62.019 | 1.00 | 46.80 | A |
| ATOM | 766 | C   | MET | A | 332 | 49.230 | 27.587 | 64.178 | 1.00 | 47.16 | A |
| ATOM | 767 | O   | MET | A | 332 | 49.072 | 28.606 | 64.882 | 1.00 | 47.69 | A |
| ATOM | 768 | N   | ASP | A | 333 | 48.970 | 26.396 | 64.649 | 1.00 | 48.19 | A |
| ATOM | 769 | CA  | ASP | A | 333 | 48.818 | 26.164 | 66.089 | 1.00 | 49.55 | A |
| ATOM | 770 | CB  | ASP | A | 333 | 47.705 | 25.095 | 66.444 | 1.00 | 50.95 | A |
| ATOM | 771 | CG  | ASP | A | 333 | 47.926 | 23.703 | 65.793 | 1.00 | 52.59 | A |
| ATOM | 772 | OD1 | ASP | A | 333 | 48.836 | 23.506 | 64.945 | 1.00 | 52.54 | A |
| ATOM | 773 | OD2 | ASP | A | 333 | 47.175 | 22.733 | 66.143 | 1.00 | 55.05 | A |
| ATOM | 774 | C   | ASP | A | 333 | 50.144 | 25.792 | 66.686 | 1.00 | 50.04 | A |
| ATOM | 775 | O   | ASP | A | 333 | 51.148 | 25.714 | 65.989 | 1.00 | 49.72 | A |
| ATOM | 776 | N   | GLU | A | 334 | 50.162 | 25.564 | 67.970 | 1.00 | 51.15 | A |
| ATOM | 777 | CA  | GLU | A | 334 | 51.392 | 25.131 | 68.622 | 1.00 | 53.08 | A |
| ATOM | 778 | CB  | GLU | A | 334 | 51.108 | 24.807 | 70.046 | 1.00 | 53.97 | A |
| ATOM | 779 | CG  | GLU | A | 334 | 52.250 | 25.188 | 70.958 | 1.00 | 57.26 | A |
| ATOM | 780 | CD  | GLU | A | 334 | 51.846 | 25.265 | 72.453 | 1.00 | 58.10 | A |
| ATOM | 781 | OE1 | GLU | A | 334 | 50.752 | 25.819 | 72.739 | 1.00 | 58.81 | A |
| ATOM | 782 | OE2 | GLU | A | 334 | 52.629 | 24.766 | 73.304 | 1.00 | 58.46 | A |
| ATOM | 783 | C   | GLU | A | 334 | 52.090 | 23.954 | 68.005 | 1.00 | 53.98 | A |
| ATOM | 784 | O   | GLU | A | 334 | 53.317 | 23.968 | 67.735 | 1.00 | 54.60 | A |
| ATOM | 785 | N   | ASP | A | 335 | 51.351 | 22.908 | 67.790 | 1.00 | 54.04 | A |
| ATOM | 786 | CA  | ASP | A | 335 | 52.004 | 21.683 | 67.379 | 1.00 | 54.59 | A |
| ATOM | 787 | CB  | ASP | A | 335 | 51.048 | 20.422 | 67.407 | 1.00 | 54.41 | A |
| ATOM | 788 | CG  | ASP | A | 335 | 50.370 | 20.203 | 68.819 | 1.00 | 55.03 | A |
| ATOM | 789 | OD1 | ASP | A | 335 | 50.738 | 20.857 | 69.782 | 0.00 | 54.81 | A |
| ATOM | 790 | OD2 | ASP | A | 335 | 49.220 | 19.601 | 68.782 | 0.00 | 54.81 | A |
| ATOM | 791 | C   | ASP | A | 335 | 52.636 | 21.939 | 66.027 | 1.00 | 54.47 | A |
| ATOM | 792 | O   | ASP | A | 335 | 53.707 | 21.466 | 65.761 | 1.00 | 54.67 | A |
| ATOM | 793 | N   | GLN | A | 336 | 51.985 | 22.709 | 65.179 | 1.00 | 54.71 | A |
| ATOM | 794 | CA  | GLN | A | 336 | 52.474 | 22.955 | 63.810 | 1.00 | 54.99 | A |
| ATOM | 795 | CB  | GLN | A | 336 | 51.342 | 23.626 | 62.977 | 1.00 | 56.99 | A |
| ATOM | 796 | CG  | GLN | A | 336 | 50.648 | 22.776 | 61.805 | 1.00 | 60.25 | A |
| ATOM | 797 | CD  | GLN | A | 336 | 50.841 | 23.493 | 60.407 | 1.00 | 62.13 | A |
| ATOM | 798 | OE1 | GLN | A | 336 | 50.027 | 24.410 | 60.018 | 1.00 | 63.43 | A |
| ATOM | 799 | NE2 | GLN | A | 336 | 51.934 | 23.102 | 59.661 | 1.00 | 63.30 | A |
| ATOM | 800 | C   | GLN | A | 336 | 53.733 | 23.880 | 63.905 | 1.00 | 53.86 | A |
| ATOM | 801 | O   | GLN | A | 336 | 54.651 | 23.815 | 63.051 | 1.00 | 53.31 | A |
| ATOM | 802 | N   | SER | A | 337 | 53.719 | 24.711 | 64.962 | 1.00 | 52.12 | A |
| ATOM | 803 | CA  | SER | A | 337 | 54.802 | 25.620 | 65.325 | 1.00 | 51.50 | A |
| ATOM | 804 | CB  | SER | A | 337 | 54.331 | 26.614 | 66.416 | 1.00 | 50.03 | A |
| ATOM | 805 | OG  | SER | A | 337 | 53.703 | 27.726 | 65.819 | 1.00 | 49.19 | A |
| ATOM | 806 | C   | SER | A | 337 | 56.064 | 24.880 | 65.783 | 1.00 | 51.77 | A |
| ATOM | 807 | O   | SER | A | 337 | 57.143 | 25.097 | 65.216 | 1.00 | 52.15 | A |
| ATOM | 808 | N   | LYS | A | 338 | 55.936 | 24.019 | 66.780 | 1.00 | 51.83 | A |
| ATOM | 809 | CA  | LYS | A | 338 | 57.050 | 23.113 | 67.179 | 1.00 | 52.30 | A |
| ATOM | 810 | CB  | LYS | A | 338 | 56.609 | 22.257 | 68.328 | 1.00 | 51.20 | A |
| ATOM | 811 | CG  | LYS | A | 338 | 55.324 | 22.465 | 69.191 | 0.00 | 51.39 | A |
| ATOM | 812 | CD  | LYS | A | 338 | 54.872 | 21.749 | 70.291 | 1.00 | 51.14 | A |
| ATOM | 813 | CE  | LYS | A | 338 | 54.289 | 21.599 | 71.719 | 1.00 | 50.85 | A |
| ATOM | 814 | NZ  | LYS | A | 338 | 54.833 | 22.647 | 72.643 | 1.00 | 52.02 | A |
| ATOM | 815 | C   | LYS | A | 338 | 57.490 | 22.237 | 65.985 | 1.00 | 53.17 | A |
| ATOM | 816 | O   | LYS | A | 338 | 58.673 | 22.129 | 65.629 | 1.00 | 52.74 | A |
| ATOM | 817 | N   | LEU | A | 339 | 56.504 | 21.681 | 65.287 | 1.00 | 53.64 | A |
| ATOM | 818 | CA  | LEU | A | 339 | 56.813 | 20.961 | 64.086 | 1.00 | 53.94 | A |
| ATOM | 819 | CB  | LEU | A | 339 | 55.498 | 20.509 | 63.393 | 1.00 | 54.62 | A |
| ATOM | 820 | CG  | LEU | A | 339 | 55.117 | 18.991 | 63.401 | 1.00 | 56.29 | A |
| ATOM | 821 | CD1 | LEU | A | 339 | 54.056 | 18.425 | 64.440 | 1.00 | 55.80 | A |
| ATOM | 822 | CD2 | LEU | A | 339 | 54.713 | 18.619 | 61.968 | 1.00 | 55.95 | A |
| ATOM | 823 | C   | LEU | A | 339 | 57.677 | 21.770 | 63.091 | 1.00 | 53.73 | A |
| ATOM | 824 | O   | LEU | A | 339 | 58.288 | 21.144 | 62.201 | 1.00 | 54.55 | A |
| ATOM | 825 | N   | ALA | A | 340 | 57.665 | 23.128 | 63.143 | 1.00 | 51.98 | A |
| ATOM | 826 | CA  | ALA | A | 340 | 58.391 | 23.922 | 62.159 | 1.00 | 51.09 | A |
| ATOM | 827 | CB  | ALA | A | 340 | 57.465 | 24.972 | 61.434 | 1.00 | 50.93 | A |
| ATOM | 828 | C   | ALA | A | 340 | 59.581 | 24.643 | 62.710 | 1.00 | 50.53 | A |
| ATOM | 829 | O   | ALA | A | 340 | 60.323 | 25.256 | 61.915 | 1.00 | 50.85 | A |

TABLE 2-continued

ATOMIC COORDINATES OF THE ERR3 LBD/
DIETHYLSTILBESTROL COMPLEX

| ATOM | 830 | N | GLY | A | 341 | 59.755 | 24.599 | 64.033 | 1.00 | 49.63 | A |
| --- | --- | --- | --- | --- | --- | --- | --- | --- | --- | --- | --- |
| ATOM | 831 | CA | GLY | A | 341 | 60.842 | 25.288 | 64.714 | 1.00 | 49.20 | A |
| ATOM | 832 | C | GLY | A | 341 | 60.499 | 26.760 | 64.883 | 1.00 | 49.50 | A |
| ATOM | 833 | O | GLY | A | 341 | 61.406 | 27.622 | 64.899 | 1.00 | 49.80 | A |
| ATOM | 834 | N | LEU | A | 342 | 59.192 | 27.064 | 65.012 | 1.00 | 48.99 | A |
| ATOM | 835 | CA | LEU | A | 342 | 58.751 | 28.457 | 65.127 | 1.00 | 48.63 | A |
| ATOM | 836 | CB | LEU | A | 342 | 57.852 | 28.812 | 63.941 | 1.00 | 47.35 | A |
| ATOM | 837 | CG | LEU | A | 342 | 58.707 | 29.061 | 62.736 | 1.00 | 46.32 | A |
| ATOM | 838 | CD1 | LEU | A | 342 | 57.953 | 28.858 | 61.498 | 1.00 | 45.56 | A |
| ATOM | 839 | CD2 | LEU | A | 342 | 59.244 | 30.495 | 62.820 | 1.00 | 45.83 | A |
| ATOM | 840 | C | LEU | A | 342 | 58.113 | 28.843 | 66.422 | 1.00 | 48.52 | A |
| ATOM | 841 | O | LEU | A | 342 | 57.567 | 29.959 | 66.540 | 1.00 | 49.73 | A |
| ATOM | 842 | N | LEU | A | 343 | 58.292 | 28.046 | 67.451 | 1.00 | 47.92 | A |
| ATOM | 843 | CA | LEU | A | 343 | 57.526 | 28.225 | 68.695 | 1.00 | 47.81 | A |
| ATOM | 844 | CB | LEU | A | 343 | 57.667 | 26.996 | 69.661 | 1.00 | 49.51 | A |
| ATOM | 845 | CG | LEU | A | 343 | 56.492 | 26.801 | 70.649 | 1.00 | 50.55 | A |
| ATOM | 846 | CD1 | LEU | A | 343 | 56.565 | 25.513 | 71.395 | 1.00 | 50.80 | A |
| ATOM | 847 | CD2 | LEU | A | 343 | 56.400 | 27.963 | 71.696 | 1.00 | 52.23 | A |
| ATOM | 848 | C | LEU | A | 343 | 57.826 | 29.481 | 69.459 | 1.00 | 46.79 | A |
| ATOM | 849 | O | LEU | A | 343 | 56.921 | 30.147 | 69.919 | 1.00 | 47.71 | A |
| ATOM | 850 | N | ASP | A | 344 | 59.086 | 29.757 | 69.685 | 1.00 | 45.36 | A |
| ATOM | 851 | CA | ASP | A | 344 | 59.458 | 30.999 | 70.285 | 1.00 | 43.66 | A |
| ATOM | 852 | CB | ASP | A | 344 | 60.986 | 31.085 | 70.175 | 1.00 | 46.76 | A |
| ATOM | 853 | CG | ASP | A | 344 | 61.697 | 30.803 | 71.426 | 1.00 | 47.93 | A |
| ATOM | 854 | OD1 | ASP | A | 344 | 61.156 | 31.148 | 72.541 | 1.00 | 49.84 | A |
| ATOM | 855 | OD2 | ASP | A | 344 | 62.855 | 30.300 | 71.330 | 1.00 | 49.29 | A |
| ATOM | 856 | C | ASP | A | 344 | 58.993 | 32.179 | 69.529 | 1.00 | 41.87 | A |
| ATOM | 857 | O | ASP | A | 344 | 58.464 | 33.089 | 70.044 | 1.00 | 42.30 | A |
| ATOM | 858 | N | LEU | A | 345 | 59.276 | 32.239 | 68.238 | 1.00 | 39.91 | A |
| ATOM | 859 | CA | LEU | A | 345 | 58.904 | 33.454 | 67.485 | 1.00 | 38.44 | A |
| ATOM | 860 | CB | LEU | A | 345 | 59.544 | 33.360 | 66.111 | 1.00 | 36.99 | A |
| ATOM | 861 | CG | LEU | A | 345 | 59.094 | 34.405 | 65.160 | 1.00 | 38.38 | A |
| ATOM | 862 | CD1 | LEU | A | 345 | 59.465 | 35.808 | 65.638 | 1.00 | 37.49 | A |
| ATOM | 863 | CD2 | LEU | A | 345 | 59.699 | 34.117 | 63.843 | 1.00 | 35.28 | A |
| ATOM | 864 | C | LEU | A | 345 | 57.369 | 33.533 | 67.446 | 1.00 | 37.65 | A |
| ATOM | 865 | O | LEU | A | 345 | 56.805 | 34.611 | 67.592 | 1.00 | 37.36 | A |
| ATOM | 866 | N | ASN | A | 346 | 56.668 | 32.366 | 67.311 | 1.00 | 37.18 | A |
| ATOM | 867 | CA | ASN | A | 346 | 55.174 | 32.403 | 67.167 | 1.00 | 36.62 | A |
| ATOM | 868 | CB | ASN | A | 346 | 54.508 | 31.215 | 66.523 | 1.00 | 35.33 | A |
| ATOM | 869 | CG | ASN | A | 346 | 54.679 | 31.217 | 65.033 | 1.00 | 36.30 | A |
| ATOM | 870 | OD1 | ASN | A | 346 | 55.154 | 32.229 | 64.445 | 1.00 | 35.73 | A |
| ATOM | 871 | ND2 | ASN | A | 346 | 54.278 | 30.125 | 64.380 | 1.00 | 33.69 | A |
| ATOM | 872 | C | ASN | A | 346 | 54.606 | 32.808 | 68.462 | 1.00 | 36.86 | A |
| ATOM | 873 | O | ASN | A | 346 | 53.774 | 33.703 | 68.454 | 1.00 | 37.26 | A |
| ATOM | 874 | N | ASN | A | 347 | 55.200 | 32.359 | 69.569 | 1.00 | 36.61 | A |
| ATOM | 875 | CA | ASN | A | 347 | 54.826 | 32.909 | 70.877 | 1.00 | 37.64 | A |
| ATOM | 876 | CB | ASN | A | 347 | 55.535 | 32.159 | 71.995 | 1.00 | 40.39 | A |
| ATOM | 877 | CG | ASN | A | 347 | 54.834 | 30.832 | 72.336 | 1.00 | 44.47 | A |
| ATOM | 878 | OD1 | ASN | A | 347 | 53.675 | 30.555 | 71.873 | 1.00 | 44.24 | A |
| ATOM | 879 | ND2 | ASN | A | 347 | 55.538 | 29.961 | 73.112 | 1.00 | 46.42 | A |
| ATOM | 880 | C | ASN | A | 347 | 55.055 | 34.342 | 71.126 | 1.00 | 36.35 | A |
| ATOM | 881 | O | ASN | A | 347 | 54.190 | 35.085 | 71.738 | 1.00 | 37.45 | A |
| ATOM | 882 | N | ALA | A | 348 | 56.184 | 34.859 | 70.648 | 1.00 | 35.35 | A |
| ATOM | 883 | CA | ALA | A | 348 | 56.374 | 36.359 | 70.720 | 1.00 | 34.51 | A |
| ATOM | 884 | CB | ALA | A | 348 | 57.816 | 36.671 | 70.192 | 1.00 | 32.00 | A |
| ATOM | 885 | C | ALA | A | 348 | 55.289 | 37.055 | 69.824 | 1.00 | 33.71 | A |
| ATOM | 886 | O | ALA | A | 348 | 54.672 | 38.083 | 70.152 | 1.00 | 33.98 | A |
| ATOM | 887 | N | ILE | A | 349 | 55.023 | 36.510 | 68.654 | 1.00 | 33.71 | A |
| ATOM | 888 | CA | ILE | A | 349 | 53.905 | 37.173 | 67.842 | 1.00 | 33.04 | A |
| ATOM | 889 | CB | ILE | A | 349 | 53.884 | 36.614 | 66.413 | 1.00 | 31.90 | A |
| ATOM | 890 | CG2 | ILE | A | 349 | 52.725 | 37.102 | 65.664 | 1.00 | 30.47 | A |
| ATOM | 891 | CG1 | ILE | A | 349 | 55.140 | 37.018 | 65.666 | 1.00 | 32.30 | A |
| ATOM | 892 | CD1 | ILE | A | 349 | 55.376 | 36.111 | 64.461 | 1.00 | 32.51 | A |
| ATOM | 893 | C | ILE | A | 349 | 52.510 | 37.139 | 68.558 | 1.00 | 33.29 | A |
| ATOM | 894 | O | ILE | A | 349 | 51.709 | 38.121 | 68.508 | 1.00 | 33.41 | A |
| ATOM | 895 | N | LEU | A | 350 | 52.246 | 36.033 | 69.274 | 1.00 | 32.21 | A |
| ATOM | 896 | CA | LEU | A | 350 | 51.034 | 35.981 | 70.058 | 1.00 | 33.58 | A |
| ATOM | 897 | CB | LEU | A | 350 | 50.871 | 34.592 | 70.699 | 1.00 | 35.15 | A |
| ATOM | 898 | CG | LEU | A | 350 | 50.392 | 33.477 | 69.761 | 1.00 | 36.64 | A |
| ATOM | 899 | CD1 | LEU | A | 350 | 50.513 | 31.982 | 70.456 | 1.00 | 35.64 | A |
| ATOM | 900 | CD2 | LEU | A | 350 | 48.890 | 33.769 | 69.178 | 1.00 | 35.90 | A |
| ATOM | 901 | C | LEU | A | 350 | 50.933 | 37.028 | 71.144 | 1.00 | 33.28 | A |
| ATOM | 902 | O | LEU | A | 350 | 49.844 | 37.467 | 71.524 | 1.00 | 33.63 | A |
| ATOM | 903 | N | GLN | A | 351 | 52.064 | 37.426 | 71.693 | 1.00 | 34.36 | A |
| ATOM | 904 | CA | GLN | A | 351 | 52.107 | 38.480 | 72.732 | 1.00 | 34.99 | A |
| ATOM | 905 | CB | GLN | A | 351 | 53.540 | 38.640 | 73.301 | 1.00 | 35.66 | A |

TABLE 2-continued

ATOMIC COORDINATES OF THE ERR3 LBD/
DIETHYLSTILBESTROL COMPLEX

| ATOM | 906 | CG | GLN | A | 351 | 53.571 | 39.440 | 74.579 | 1.00 | 38.96 | A |
|---|---|---|---|---|---|---|---|---|---|---|---|
| ATOM | 907 | CD | GLN | A | 351 | 54.988 | 39.524 | 75.285 | 1.00 | 40.64 | A |
| ATOM | 908 | OE1 | GLN | A | 351 | 55.755 | 38.555 | 75.253 | 1.00 | 43.49 | A |
| ATOM | 909 | NE2 | GLN | A | 351 | 55.321 | 40.670 | 75.863 | 1.00 | 38.53 | A |
| ATOM | 910 | C | GLN | A | 351 | 51.620 | 39.779 | 72.111 | 1.00 | 34.65 | A |
| ATOM | 911 | O | GLN | A | 351 | 50.914 | 40.514 | 72.733 | 1.00 | 34.56 | A |
| ATOM | 912 | N | LEU | A | 352 | 51.975 | 40.065 | 70.863 | 1.00 | 34.33 | A |
| ATOM | 913 | CA | LEU | A | 352 | 51.378 | 41.267 | 70.237 | 1.00 | 34.30 | A |
| ATOM | 914 | CB | LEU | A | 352 | 51.947 | 41.483 | 68.822 | 1.00 | 34.71 | A |
| ATOM | 915 | CG | LEU | A | 352 | 53.233 | 42.173 | 68.659 | 1.00 | 35.91 | A |
| ATOM | 916 | CD1 | LEU | A | 352 | 53.648 | 42.201 | 67.287 | 1.00 | 34.63 | A |
| ATOM | 917 | CD2 | LEU | A | 352 | 52.918 | 43.599 | 69.136 | 1.00 | 35.37 | A |
| ATOM | 918 | C | LEU | A | 352 | 49.888 | 41.118 | 70.108 | 1.00 | 33.50 | A |
| ATOM | 919 | O | LEU | A | 352 | 49.133 | 42.062 | 70.290 | 1.00 | 31.82 | A |
| ATOM | 920 | N | VAL | A | 353 | 49.478 | 39.886 | 69.692 | 1.00 | 33.35 | A |
| ATOM | 921 | CA | VAL | A | 353 | 48.055 | 39.570 | 69.439 | 1.00 | 32.71 | A |
| ATOM | 922 | CB | VAL | A | 353 | 47.834 | 38.111 | 69.035 | 1.00 | 32.06 | A |
| ATOM | 923 | CG1 | VAL | A | 353 | 46.299 | 37.886 | 68.956 | 1.00 | 30.52 | A |
| ATOM | 924 | CG2 | VAL | A | 353 | 48.445 | 37.826 | 67.689 | 1.00 | 31.44 | A |
| ATOM | 925 | C | VAL | A | 353 | 47.264 | 39.755 | 70.696 | 1.00 | 33.64 | A |
| ATOM | 926 | O | VAL | A | 353 | 46.251 | 40.468 | 70.721 | 1.00 | 34.53 | A |
| ATOM | 927 | N | LYS | A | 354 | 47.793 | 39.278 | 71.778 | 1.00 | 34.55 | A |
| ATOM | 928 | CA | LYS | A | 354 | 47.149 | 39.576 | 73.076 | 1.00 | 37.58 | A |
| ATOM | 929 | CB | LYS | A | 354 | 47.834 | 38.787 | 74.217 | 1.00 | 38.52 | A |
| ATOM | 930 | CG | LYS | A | 354 | 47.293 | 39.209 | 75.651 | 1.00 | 42.97 | A |
| ATOM | 931 | CD | LYS | A | 354 | 47.881 | 38.371 | 76.895 | 1.00 | 46.41 | A |
| ATOM | 932 | CE | LYS | A | 354 | 48.579 | 37.080 | 76.415 | 1.00 | 47.65 | A |
| ATOM | 933 | NZ | LYS | A | 354 | 47.674 | 35.913 | 76.039 | 1.00 | 50.51 | A |
| ATOM | 934 | C | LYS | A | 354 | 47.048 | 40.998 | 73.486 | 1.00 | 37.45 | A |
| ATOM | 935 | O | LYS | A | 354 | 46.012 | 41.407 | 74.082 | 1.00 | 38.31 | A |
| ATOM | 936 | N | LYS | A | 355 | 48.053 | 41.846 | 73.225 | 1.00 | 37.08 | A |
| ATOM | 937 | CA | LYS | A | 355 | 47.842 | 43.248 | 73.619 | 1.00 | 36.53 | A |
| ATOM | 938 | CB | LYS | A | 355 | 49.115 | 44.140 | 73.586 | 1.00 | 39.12 | A |
| ATOM | 939 | CG | LYS | A | 355 | 48.795 | 45.553 | 74.244 | 1.00 | 40.15 | A |
| ATOM | 940 | CD | LYS | A | 355 | 49.760 | 46.100 | 75.285 | 1.00 | 43.08 | A |
| ATOM | 941 | CE | LYS | A | 355 | 49.092 | 47.180 | 76.315 | 1.00 | 43.78 | A |
| ATOM | 942 | NZ | LYS | A | 355 | 50.170 | 47.832 | 77.282 | 1.00 | 42.62 | A |
| ATOM | 943 | C | LYS | A | 355 | 46.792 | 43.871 | 72.765 | 1.00 | 36.12 | A |
| ATOM | 944 | O | LYS | A | 355 | 45.941 | 44.534 | 73.308 | 1.00 | 35.96 | A |
| ATOM | 945 | N | TYR | A | 356 | 46.801 | 43.616 | 71.437 | 1.00 | 34.85 | A |
| ATOM | 946 | CA | TYR | A | 356 | 45.795 | 44.283 | 70.615 | 1.00 | 34.66 | A |
| ATOM | 947 | CB | TYR | A | 356 | 46.098 | 44.141 | 69.130 | 1.00 | 32.89 | A |
| ATOM | 948 | CG | TYR | A | 356 | 47.262 | 45.002 | 68.608 | 1.00 | 29.98 | A |
| ATOM | 949 | CD1 | TYR | A | 356 | 47.309 | 46.391 | 68.879 | 1.00 | 29.91 | A |
| ATOM | 950 | CE1 | TYR | A | 356 | 48.315 | 47.178 | 68.396 | 1.00 | 28.92 | A |
| ATOM | 951 | CD2 | TYR | A | 356 | 48.299 | 44.453 | 67.965 | 1.00 | 28.73 | A |
| ATOM | 952 | CE2 | TYR | A | 356 | 49.319 | 45.278 | 67.409 | 1.00 | 28.80 | A |
| ATOM | 953 | CZ | TYR | A | 356 | 49.287 | 46.622 | 67.625 | 1.00 | 28.08 | A |
| ATOM | 954 | OH | TYR | A | 356 | 50.258 | 47.391 | 67.190 | 1.00 | 30.18 | A |
| ATOM | 955 | C | TYR | A | 356 | 44.405 | 43.742 | 70.913 | 1.00 | 35.72 | A |
| ATOM | 956 | O | TYR | A | 356 | 43.441 | 44.483 | 70.813 | 1.00 | 35.48 | A |
| ATOM | 957 | N | LYS | A | 357 | 44.270 | 42.490 | 71.294 | 1.00 | 36.99 | A |
| ATOM | 958 | CA | LYS | A | 357 | 42.901 | 41.970 | 71.681 | 1.00 | 39.30 | A |
| ATOM | 959 | CB | LYS | A | 357 | 42.887 | 40.525 | 72.142 | 1.00 | 40.11 | A |
| ATOM | 960 | CG | LYS | A | 357 | 42.786 | 39.590 | 71.060 | 1.00 | 41.12 | A |
| ATOM | 961 | CD | LYS | A | 357 | 43.112 | 38.213 | 71.599 | 1.00 | 43.89 | A |
| ATOM | 962 | CE | LYS | A | 357 | 42.510 | 37.052 | 70.799 | 1.00 | 43.71 | A |
| ATOM | 963 | NZ | LYS | A | 357 | 42.843 | 35.746 | 71.414 | 1.00 | 47.00 | A |
| ATOM | 964 | C | LYS | A | 357 | 42.318 | 42.714 | 72.839 | 1.00 | 40.19 | A |
| ATOM | 965 | O | LYS | A | 357 | 41.179 | 43.180 | 72.773 | 1.00 | 40.72 | A |
| ATOM | 966 | N | SER | A | 358 | 43.095 | 42.860 | 73.890 | 1.00 | 40.28 | A |
| ATOM | 967 | CA | SER | A | 358 | 42.635 | 43.556 | 75.075 | 1.00 | 40.45 | A |
| ATOM | 968 | CB | SER | A | 358 | 43.737 | 43.505 | 76.186 | 1.00 | 40.48 | A |
| ATOM | 969 | OG | SER | A | 358 | 44.701 | 44.512 | 75.866 | 1.00 | 44.11 | A |
| ATOM | 970 | C | SER | A | 358 | 42.247 | 45.022 | 74.787 | 1.00 | 40.67 | A |
| ATOM | 971 | O | SER | A | 358 | 41.349 | 45.617 | 75.455 | 1.00 | 40.76 | A |
| ATOM | 972 | N | MET | A | 359 | 42.930 | 45.629 | 73.810 | 1.00 | 39.45 | A |
| ATOM | 973 | CA | MET | A | 359 | 42.555 | 46.965 | 73.377 | 1.00 | 39.05 | A |
| ATOM | 974 | CB | MET | A | 359 | 43.752 | 47.575 | 72.653 | 1.00 | 40.40 | A |
| ATOM | 975 | CG | MET | A | 359 | 44.911 | 47.876 | 73.587 | 1.00 | 43.36 | A |
| ATOM | 976 | SD | MET | A | 359 | 46.139 | 48.716 | 72.548 | 1.00 | 45.99 | A |
| ATOM | 977 | CE | MET | A | 359 | 46.914 | 47.506 | 72.593 | 1.00 | 42.42 | A |
| ATOM | 978 | C | MET | A | 359 | 41.323 | 47.038 | 72.388 | 1.00 | 37.51 | A |
| ATOM | 979 | O | MET | A | 359 | 40.802 | 48.084 | 72.127 | 1.00 | 37.89 | A |
| ATOM | 980 | N | LYS | A | 360 | 40.993 | 45.939 | 71.800 | 1.00 | 35.91 | A |
| ATOM | 981 | CA | LYS | A | 360 | 40.014 | 45.791 | 70.716 | 1.00 | 36.39 | A |

TABLE 2-continued

ATOMIC COORDINATES OF THE ERR3 LBD/
DIETHYLSTILBESTROL COMPLEX

| ATOM | 982 | CB | LYS | A | 360 | 38.547 | 46.103 | 71.210 | 1.00 | 39.10 | A |
|---|---|---|---|---|---|---|---|---|---|---|---|
| ATOM | 983 | CG | LYS | A | 360 | 38.005 | 44.990 | 72.253 | 1.00 | 40.56 | A |
| ATOM | 984 | CD | LYS | A | 360 | 37.156 | 45.628 | 73.420 | 1.00 | 43.99 | A |
| ATOM | 985 | CE | LYS | A | 360 | 36.382 | 44.530 | 74.402 | 1.00 | 45.86 | A |
| ATOM | 986 | NZ | LYS | A | 360 | 34.949 | 44.946 | 74.897 | 1.00 | 47.09 | A |
| ATOM | 987 | C | LYS | A | 360 | 40.335 | 46.515 | 69.439 | 1.00 | 34.89 | A |
| ATOM | 988 | O | LYS | A | 360 | 39.572 | 47.323 | 68.953 | 1.00 | 33.96 | A |
| ATOM | 989 | N | LEU | A | 361 | 41.516 | 46.217 | 68.909 | 1.00 | 33.39 | A |
| ATOM | 990 | CA | LEU | A | 361 | 41.975 | 46.916 | 67.766 | 1.00 | 31.38 | A |
| ATOM | 991 | CB | LEU | A | 361 | 43.281 | 46.229 | 67.308 | 1.00 | 31.66 | A |
| ATOM | 992 | CG | LEU | A | 361 | 43.940 | 46.916 | 66.146 | 1.00 | 29.90 | A |
| ATOM | 993 | CD1 | LEU | A | 361 | 44.367 | 48.268 | 66.632 | 1.00 | 28.29 | A |
| ATOM | 994 | CD2 | LEU | A | 361 | 45.171 | 46.146 | 65.800 | 1.00 | 31.30 | A |
| ATOM | 995 | C | LEU | A | 361 | 40.956 | 46.804 | 66.638 | 1.00 | 31.52 | A |
| ATOM | 996 | O | LEU | A | 361 | 40.502 | 45.734 | 66.288 | 1.00 | 29.34 | A |
| ATOM | 997 | N | GLU | A | 362 | 40.617 | 47.933 | 66.049 | 1.00 | 32.12 | A |
| ATOM | 998 | CA | GLU | A | 362 | 39.728 | 47.972 | 64.941 | 1.00 | 32.86 | A |
| ATOM | 999 | CB | GLU | A | 362 | 38.968 | 49.292 | 65.099 | 1.00 | 34.53 | A |
| ATOM | 1000 | CG | GLU | A | 362 | 37.897 | 49.326 | 66.190 | 1.00 | 37.28 | A |
| ATOM | 1001 | CD | GLU | A | 362 | 37.569 | 50.756 | 66.640 | 1.00 | 39.67 | A |
| ATOM | 1002 | OE1 | GLU | A | 362 | 38.045 | 51.812 | 66.057 | 1.00 | 39.34 | A |
| ATOM | 1003 | OE2 | GLU | A | 362 | 36.833 | 50.795 | 67.612 | 1.00 | 41.26 | A |
| ATOM | 1004 | C | GLU | A | 362 | 40.490 | 48.000 | 63.572 | 1.00 | 32.70 | A |
| ATOM | 1005 | O | GLU | A | 362 | 41.625 | 48.398 | 63.516 | 1.00 | 31.52 | A |
| ATOM | 1006 | N | LYS | A | 363 | 39.846 | 47.587 | 62.485 | 1.00 | 32.35 | A |
| ATOM | 1007 | CA | LYS | A | 363 | 40.471 | 47.538 | 61.236 | 1.00 | 32.91 | A |
| ATOM | 1008 | CB | LYS | A | 363 | 39.485 | 47.045 | 60.196 | 1.00 | 34.26 | A |
| ATOM | 1009 | CG | LYS | A | 363 | 40.188 | 46.858 | 58.877 | 1.00 | 37.93 | A |
| ATOM | 1010 | CD | LYS | A | 363 | 39.500 | 45.753 | 57.983 | 1.00 | 41.62 | A |
| ATOM | 1011 | CE | LYS | A | 363 | 40.166 | 45.758 | 56.619 | 1.00 | 43.58 | A |
| ATOM | 1012 | N2 | LYS | A | 363 | 40.284 | 44.505 | 55.847 | 1.00 | 45.92 | A |
| ATOM | 1013 | C | LYS | A | 363 | 41.017 | 48.940 | 60.856 | 1.00 | 32.37 | A |
| ATOM | 1014 | O | LYS | A | 363 | 42.118 | 49.042 | 60.255 | 1.00 | 31.74 | A |
| ATOM | 1015 | N | GLU | A | 364 | 40.312 | 49.981 | 61.240 | 1.00 | 30.55 | A |
| ATOM | 1016 | CA | GLU | A | 364 | 40.777 | 51.312 | 60.945 | 1.00 | 30.65 | A |
| ATOM | 1017 | CB | GLU | A | 364 | 39.830 | 52.407 | 61.551 | 1.00 | 31.69 | A |
| ATOM | 1018 | CG | GLU | A | 364 | 38.492 | 52.569 | 60.761 | 1.00 | 34.47 | A |
| ATOM | 1019 | CD | GLU | A | 364 | 37.460 | 51.425 | 60.954 | 1.00 | 37.22 | A |
| ATOM | 1020 | OE1 | GLU | A | 364 | 37.653 | 50.473 | 61.733 | 1.00 | 38.40 | A |
| ATOM | 1021 | OE2 | GLU | A | 364 | 36.401 | 51.517 | 60.330 | 1.00 | 40.16 | A |
| ATOM | 1022 | C | GLU | A | 364 | 42.086 | 51.582 | 61.533 | 1.00 | 30.15 | A |
| ATOM | 1023 | O | GLU | A | 364 | 42.846 | 52.393 | 60.966 | 1.00 | 30.26 | A |
| ATOM | 1024 | N | GLU | A | 365 | 42.320 | 51.057 | 62.727 | 1.00 | 28.81 | A |
| ATOM | 1025 | CA | GLU | A | 365 | 43.508 | 51.403 | 63.514 | 1.00 | 27.48 | A |
| ATOM | 1026 | CB | GLU | A | 365 | 43.262 | 51.143 | 65.032 | 1.00 | 28.20 | A |
| ATOM | 1027 | CG | GLU | A | 365 | 42.346 | 52.260 | 65.617 | 1.00 | 28.91 | A |
| ATOM | 1028 | CD | GLU | A | 365 | 41.509 | 51.763 | 66.874 | 1.00 | 30.81 | A |
| ATOM | 1029 | OE1 | GLU | A | 365 | 41.416 | 50.498 | 67.118 | 1.00 | 30.69 | A |
| ATOM | 1030 | OE2 | GLU | A | 365 | 41.032 | 52.667 | 67.651 | 1.00 | 30.51 | A |
| ATOM | 1031 | C | GLU | A | 365 | 44.692 | 50.591 | 63.034 | 1.00 | 27.08 | A |
| ATOM | 1032 | O | GLU | A | 365 | 45.791 | 51.088 | 62.838 | 1.00 | 26.63 | A |
| ATOM | 1033 | N | PHE | A | 366 | 44.380 | 49.357 | 62.693 | 1.00 | 27.95 | A |
| ATOM | 1034 | CA | PHE | A | 366 | 45.275 | 48.440 | 62.079 | 1.00 | 28.29 | A |
| ATOM | 1035 | CB | PHE | A | 366 | 44.547 | 47.172 | 61.666 | 1.00 | 28.78 | A |
| ATOM | 1036 | CG | PHE | A | 366 | 45.260 | 46.339 | 60.681 | 1.00 | 28.12 | A |
| ATOM | 1037 | CD1 | PHE | A | 366 | 46.524 | 45.851 | 60.937 | 1.00 | 28.46 | A |
| ATOM | 1038 | CD2 | PHE | A | 366 | 44.633 | 45.976 | 59.508 | 1.00 | 28.45 | A |
| ATOM | 1039 | CE1 | PHE | A | 366 | 47.159 | 45.012 | 60.026 | 1.00 | 27.86 | A |
| ATOM | 1040 | CE2 | PHE | A | 366 | 45.249 | 45.200 | 58.601 | 1.00 | 27.04 | A |
| ATOM | 1041 | CZ | PHE | A | 366 | 46.563 | 44.756 | 58.847 | 1.00 | 29.70 | A |
| ATOM | 1042 | C | PHE | A | 366 | 45.900 | 49.100 | 60.852 | 1.00 | 28.59 | A |
| ATOM | 1043 | O | PHE | A | 366 | 47.119 | 49.092 | 60.759 | 1.00 | 26.24 | A |
| ATOM | 1044 | N | VAL | A | 367 | 45.066 | 49.699 | 59.959 | 1.00 | 26.88 | A |
| ATOM | 1045 | CA | VAL | A | 367 | 45.572 | 50.088 | 58.643 | 1.00 | 25.56 | A |
| ATOM | 1046 | CB | VAL | A | 367 | 44.532 | 50.224 | 57.515 | 1.00 | 26.81 | A |
| ATOM | 1047 | CG1 | VAL | A | 367 | 43.948 | 48.943 | 57.211 | 1.00 | 25.26 | A |
| ATOM | 1048 | CG2 | VAL | A | 367 | 43.578 | 51.267 | 57.858 | 1.00 | 24.28 | A |
| ATOM | 1049 | C | VAL | A | 367 | 46.395 | 51.339 | 58.785 | 1.00 | 26.92 | A |
| ATOM | 1050 | O | VAL | A | 367 | 47.449 | 51.443 | 58.185 | 1.00 | 25.78 | A |
| ATOM | 1051 | N | THR | A | 368 | 46.040 | 52.147 | 59.772 | 1.00 | 26.35 | A |
| ATOM | 1052 | CA | THR | A | 368 | 46.778 | 53.340 | 60.094 | 1.00 | 27.72 | A |
| ATOM | 1053 | CB | THR | A | 368 | 45.900 | 54.352 | 60.872 | 1.00 | 28.96 | A |
| ATOM | 1054 | OG1 | THR | A | 368 | 44.692 | 54.570 | 60.107 | 1.00 | 30.02 | A |
| ATOM | 1055 | CG2 | THR | A | 368 | 46.530 | 55.742 | 60.931 | 1.00 | 27.25 | A |
| ATOM | 1056 | C | THR | A | 368 | 48.065 | 53.027 | 60.804 | 1.00 | 28.82 | A |
| ATOM | 1057 | O | THR | A | 368 | 49.097 | 53.682 | 60.542 | 1.00 | 28.27 | A |

TABLE 2-continued

ATOMIC COORDINATES OF THE ERR3 LBD/
DIETHYLSTILBESTROL COMPLEX

| ATOM | 1058 | N   | LEU | A | 369 | 48.077 | 51.929 | 61.570 | 1.00 | 29.83 | A |
|------|------|-----|-----|---|-----|--------|--------|--------|------|-------|---|
| ATOM | 1059 | CA  | LEU | A | 369 | 49.270 | 51.583 | 62.312 | 1.00 | 28.11 | A |
| ATOM | 1060 | CB  | LEU | A | 369 | 48.956 | 50.664 | 63.492 | 1.00 | 27.99 | A |
| ATOM | 1061 | CG  | LEU | A | 369 | 48.599 | 51.383 | 64.749 | 1.00 | 27.75 | A |
| ATOM | 1062 | CD1 | LEU | A | 369 | 48.261 | 50.371 | 65.819 | 1.00 | 29.18 | A |
| ATOM | 1063 | CD2 | LEU | A | 369 | 49.628 | 52.246 | 65.210 | 1.00 | 27.97 | A |
| ATOM | 1064 | C   | LEU | A | 369 | 50.302 | 50.990 | 61.371 | 1.00 | 27.90 | A |
| ATOM | 1065 | O   | LEU | A | 369 | 51.466 | 51.279 | 61.538 | 1.00 | 27.05 | A |
| ATOM | 1066 | N   | LYS | A | 370 | 49.859 | 50.264 | 60.340 | 1.00 | 27.79 | A |
| ATOM | 1067 | CA  | LYS | A | 370 | 50.757 | 49.735 | 59.367 | 1.00 | 28.67 | A |
| ATOM | 1068 | CB  | LYS | A | 370 | 50.057 | 49.044 | 58.274 | 1.00 | 27.49 | A |
| ATOM | 1069 | CG  | LYS | A | 370 | 49.626 | 47.691 | 58.514 | 1.00 | 29.81 | A |
| ATOM | 1070 | CD  | LYS | A | 370 | 49.465 | 46.918 | 57.174 | 1.00 | 29.70 | A |
| ATOM | 1071 | CE  | LYS | A | 370 | 48.033 | 47.163 | 56.561 | 1.00 | 31.12 | A |
| ATOM | 1072 | NZ  | LYS | A | 370 | 47.708 | 46.086 | 55.613 | 1.00 | 32.47 | A |
| ATOM | 1073 | C   | LYS | A | 370 | 51.468 | 50.872 | 58.677 | 1.00 | 29.79 | A |
| ATOM | 1074 | O   | LYS | A | 370 | 52.628 | 50.747 | 58.416 | 1.00 | 29.57 | A |
| ATOM | 1075 | N   | ALA | A | 371 | 50.711 | 51.860 | 58.160 | 1.00 | 27.90 | A |
| ATOM | 1076 | CA  | ALA | A | 371 | 51.304 | 53.009 | 57.480 | 1.00 | 27.87 | A |
| ATOM | 1077 | CB  | ALA | A | 371 | 50.180 | 53.992 | 56.873 | 1.00 | 25.83 | A |
| ATOM | 1078 | C   | ALA | A | 371 | 52.251 | 53.751 | 58.352 | 1.00 | 26.96 | A |
| ATOM | 1079 | O   | ALA | A | 371 | 53.359 | 54.176 | 57.930 | 1.00 | 26.72 | A |
| ATOM | 1080 | N   | ILE | A | 372 | 51.821 | 53.940 | 59.595 | 1.00 | 27.73 | A |
| ATOM | 1081 | CA  | ILE | A | 372 | 52.672 | 54.580 | 60.607 | 1.00 | 26.76 | A |
| ATOM | 1082 | CB  | ILE | A | 372 | 51.947 | 54.833 | 61.944 | 1.00 | 26.08 | A |
| ATOM | 1083 | CG2 | ILE | A | 372 | 52.955 | 55.250 | 63.072 | 1.00 | 24.97 | A |
| ATOM | 1084 | CG1 | ILE | A | 372 | 51.018 | 56.048 | 61.821 | 1.00 | 27.77 | A |
| ATOM | 1085 | CD1 | ILE | A | 372 | 49.959 | 56.170 | 62.923 | 1.00 | 24.58 | A |
| ATOM | 1086 | C   | ILE | A | 372 | 53.950 | 53.834 | 60.830 | 1.00 | 26.47 | A |
| ATOM | 1087 | O   | ILE | A | 372 | 55.016 | 54.471 | 60.933 | 1.00 | 27.35 | A |
| ATOM | 1088 | N   | ALA | A | 373 | 53.873 | 52.506 | 60.846 | 1.00 | 25.31 | A |
| ATOM | 1089 | CA  | ALA | A | 373 | 55.068 | 51.678 | 61.100 | 1.00 | 24.89 | A |
| ATOM | 1090 | CB  | ALA | A | 373 | 54.663 | 50.274 | 61.309 | 1.00 | 24.38 | A |
| ATOM | 1091 | C   | ALA | A | 373 | 56.070 | 51.811 | 59.913 | 1.00 | 24.01 | A |
| ATOM | 1092 | O   | ALA | A | 373 | 57.284 | 51.958 | 60.146 | 1.00 | 22.94 | A |
| ATOM | 1093 | N   | LEU | A | 374 | 55.536 | 51.916 | 58.696 | 1.00 | 23.99 | A |
| ATOM | 1094 | CA  | LEU | A | 374 | 56.307 | 52.234 | 57.494 | 1.00 | 24.86 | A |
| ATOM | 1095 | CB  | LEU | A | 374 | 55.453 | 52.120 | 56.203 | 1.00 | 25.97 | A |
| ATOM | 1096 | CG  | LEU | A | 374 | 56.186 | 52.514 | 54.934 | 1.00 | 27.17 | A |
| ATOM | 1097 | CD1 | LEU | A | 374 | 57.298 | 51.638 | 54.622 | 1.00 | 24.52 | A |
| ATOM | 1098 | CD2 | LEU | A | 374 | 55.257 | 52.557 | 53.676 | 1.00 | 28.16 | A |
| ATOM | 1099 | C   | LEU | A | 374 | 57.028 | 53.594 | 57.637 | 1.00 | 25.52 | A |
| ATOM | 1100 | O   | LEU | A | 374 | 58.269 | 53.675 | 57.558 | 1.00 | 26.20 | A |
| ATOM | 1101 | N   | ALA | A | 375 | 56.290 | 54.648 | 57.939 | 1.00 | 24.39 | A |
| ATOM | 1102 | CA  | ALA | A | 375 | 56.836 | 56.015 | 58.007 | 1.00 | 24.40 | A |
| ATOM | 1103 | CB  | ALA | A | 375 | 55.714 | 57.046 | 58.235 | 1.00 | 22.04 | A |
| ATOM | 1104 | C   | ALA | A | 375 | 57.809 | 56.177 | 59.153 | 1.00 | 24.49 | A |
| ATOM | 1105 | O   | ALA | A | 375 | 58.693 | 57.021 | 59.068 | 1.00 | 25.06 | A |
| ATOM | 1106 | N   | ASN | A | 376 | 57.619 | 55.397 | 60.221 | 1.00 | 24.24 | A |
| ATOM | 1107 | CA  | ASN | A | 376 | 58.367 | 55.598 | 61.450 | 1.00 | 24.60 | A |
| ATOM | 1108 | CB  | ASN | A | 376 | 57.395 | 55.607 | 62.646 | 1.00 | 23.16 | A |
| ATOM | 1109 | CG  | ASN | A | 376 | 58.050 | 56.042 | 63.948 | 1.00 | 23.46 | A |
| ATOM | 1110 | OD1 | ASN | A | 376 | 58.700 | 57.064 | 63.987 | 1.00 | 23.86 | A |
| ATOM | 1111 | ND2 | ASN | A | 376 | 57.838 | 55.266 | 65.037 | 1.00 | 22.43 | A |
| ATOM | 1112 | C   | ASN | A | 376 | 59.453 | 54.530 | 61.658 | 1.00 | 25.42 | A |
| ATOM | 1113 | O   | ASN | A | 376 | 59.929 | 54.322 | 62.808 | 1.00 | 26.80 | A |
| ATOM | 1114 | N   | SER | A | 377 | 59.924 | 53.936 | 60.583 | 1.00 | 25.54 | A |
| ATOM | 1115 | CA  | SER | A | 377 | 60.769 | 52.769 | 60.733 | 1.00 | 27.92 | A |
| ATOM | 1116 | CB  | SER | A | 377 | 60.635 | 51.868 | 59.516 | 1.00 | 28.48 | A |
| ATOM | 1117 | OG  | SER | A | 377 | 60.908 | 52.594 | 58.320 | 1.00 | 29.34 | A |
| ATOM | 1118 | C   | SER | A | 377 | 62.239 | 53.028 | 60.999 | 1.00 | 27.06 | A |
| ATOM | 1119 | O   | SER | A | 377 | 62.962 | 52.101 | 61.158 | 1.00 | 26.82 | A |
| ATOM | 1120 | N   | ASP | A | 378 | 62.654 | 54.273 | 61.115 | 1.00 | 26.46 | A |
| ATOM | 1121 | CA  | ASP | A | 378 | 63.997 | 54.634 | 61.611 | 1.00 | 28.01 | A |
| ATOM | 1122 | CB  | ASP | A | 378 | 64.193 | 54.166 | 63.068 | 1.00 | 26.90 | A |
| ATOM | 1123 | CG  | ASP | A | 378 | 63.200 | 54.837 | 63.977 | 1.00 | 27.45 | A |
| ATOM | 1124 | OD1 | ASP | A | 378 | 63.163 | 56.086 | 63.879 | 1.00 | 29.28 | A |
| ATOM | 1125 | OD2 | ASP | A | 378 | 62.395 | 54.248 | 64.770 | 1.00 | 26.85 | A |
| ATOM | 1126 | C   | ASP | A | 378 | 65.196 | 54.136 | 60.714 | 1.00 | 28.16 | A |
| ATOM | 1127 | O   | ASP | A | 378 | 66.257 | 53.795 | 61.264 | 1.00 | 29.46 | A |
| ATOM | 1128 | N   | SER | A | 379 | 65.010 | 54.085 | 59.396 | 1.00 | 28.58 | A |
| ATOM | 1129 | CA  | SER | A | 379 | 66.143 | 53.778 | 58.488 | 1.00 | 31.13 | A |
| ATOM | 1130 | CB  | SER | A | 379 | 65.785 | 53.927 | 56.999 | 1.00 | 28.95 | A |
| ATOM | 1131 | OG  | SER | A | 379 | 66.887 | 53.458 | 56.262 | 1.00 | 32.31 | A |
| ATOM | 1132 | C   | SER | A | 379 | 67.240 | 54.793 | 58.746 | 1.00 | 32.60 | A |
| ATOM | 1133 | O   | SER | A | 379 | 66.974 | 55.942 | 58.925 | 1.00 | 30.70 | A |

TABLE 2-continued

ATOMIC COORDINATES OF THE ERR3 LBD/
DIETHYLSTILBESTROL COMPLEX

| ATOM | 1134 | N   | MET | A | 380 | 68.457 | 54.368 | 58.725 | 1.00 | 36.34 | A |
|------|------|-----|-----|---|-----|--------|--------|--------|------|-------|---|
| ATOM | 1135 | CA  | MET | A | 380 | 69.561 | 55.314 | 58.892 | 1.00 | 39.93 | A |
| ATOM | 1136 | CB  | MET | A | 380 | 70.801 | 54.640 | 59.310 | 1.00 | 44.35 | A |
| ATOM | 1137 | CG  | MET | A | 380 | 70.910 | 54.349 | 60.797 | 1.00 | 49.85 | A |
| ATOM | 1138 | SD  | MET | A | 380 | 71.380 | 52.551 | 60.805 | 1.00 | 58.72 | A |
| ATOM | 1139 | CE  | MET | A | 380 | 72.894 | 52.460 | 59.386 | 1.00 | 55.47 | A |
| ATOM | 1140 | C   | MET | A | 380 | 69.973 | 55.859 | 57.607 | 1.00 | 40.78 | A |
| ATOM | 1141 | O   | MET | A | 380 | 70.927 | 56.550 | 57.607 | 1.00 | 41.95 | A |
| ATOM | 1142 | N   | HIS | A | 381 | 69.302 | 55.514 | 56.529 | 1.00 | 39.86 | A |
| ATOM | 1143 | CA  | HIS | A | 381 | 69.766 | 55.813 | 55.231 | 1.00 | 40.72 | A |
| ATOM | 1144 | CB  | HIS | A | 381 | 69.678 | 54.523 | 54.364 | 1.00 | 41.96 | A |
| ATOM | 1145 | CG  | HIS | A | 381 | 70.638 | 53.463 | 54.805 | 1.00 | 44.77 | A |
| ATOM | 1146 | CD2 | HIS | A | 381 | 71.929 | 53.574 | 55.239 | 1.00 | 45.41 | A |
| ATOM | 1147 | ND1 | HIS | A | 381 | 70.280 | 52.132 | 54.987 | 1.00 | 45.55 | A |
| ATOM | 1148 | CE1 | HIS | A | 381 | 71.326 | 51.469 | 55.457 | 1.00 | 46.69 | A |
| ATOM | 1149 | NE2 | HIS | A | 381 | 72.315 | 52.333 | 55.670 | 1.00 | 46.30 | A |
| ATOM | 1150 | C   | HIS | A | 381 | 68.912 | 56.898 | 54.594 | 1.00 | 40.10 | A |
| ATOM | 1151 | O   | HIS | A | 381 | 69.037 | 57.078 | 53.417 | 1.00 | 39.51 | A |
| ATOM | 1152 | N   | ILE | A | 382 | 68.042 | 57.555 | 55.349 | 1.00 | 39.35 | A |
| ATOM | 1153 | CA  | ILE | A | 382 | 67.146 | 58.562 | 54.807 | 1.00 | 39.03 | A |
| ATOM | 1154 | CB  | ILE | A | 382 | 66.145 | 59.037 | 55.874 | 1.00 | 38.87 | A |
| ATOM | 1155 | CG2 | ILE | A | 382 | 65.371 | 60.265 | 55.391 | 1.00 | 36.89 | A |
| ATOM | 1156 | CG1 | ILE | A | 382 | 65.225 | 57.930 | 56.355 | 1.00 | 38.69 | A |
| ATOM | 1157 | CD1 | ILE | A | 382 | 64.458 | 57.395 | 55.335 | 1.00 | 39.69 | A |
| ATOM | 1158 | C   | ILE | A | 382 | 67.871 | 59.841 | 54.323 | 1.00 | 39.55 | A |
| ATOM | 1159 | O   | ILE | A | 382 | 68.667 | 60.372 | 55.027 | 1.00 | 39.85 | A |
| ATOM | 1160 | N   | GLU | A | 383 | 67.507 | 60.368 | 53.172 | 1.00 | 40.09 | A |
| ATOM | 1161 | CA  | GLU | A | 383 | 68.154 | 61.569 | 52.635 | 1.00 | 40.27 | A |
| ATOM | 1162 | CB  | GLU | A | 383 | 68.110 | 61.533 | 51.127 | 1.00 | 41.19 | A |
| ATOM | 1163 | CG  | GLU | A | 383 | 68.930 | 60.502 | 50.392 | 1.00 | 42.63 | A |
| ATOM | 1164 | CD  | GLU | A | 383 | 68.490 | 60.352 | 48.922 | 1.00 | 44.69 | A |
| ATOM | 1165 | OE1 | GLU | A | 383 | 67.324 | 60.768 | 48.488 | 1.00 | 44.31 | A |
| ATOM | 1166 | OE2 | GLU | A | 383 | 69.314 | 59.752 | 48.185 | 1.00 | 46.51 | A |
| ATOM | 1167 | C   | GLU | A | 383 | 67.451 | 62.838 | 53.017 | 1.00 | 40.52 | A |
| ATOM | 1168 | O   | GLU | A | 383 | 68.107 | 63.938 | 53.244 | 1.00 | 41.93 | A |
| ATOM | 1169 | N   | ASP | A | 384 | 66.123 | 62.752 | 53.013 | 1.00 | 39.13 | A |
| ATOM | 1170 | CA  | ASP | A | 384 | 65.268 | 63.890 | 53.335 | 1.00 | 39.18 | A |
| ATOM | 1171 | CB  | ASP | A | 384 | 64.416 | 64.213 | 52.116 | 1.00 | 39.65 | A |
| ATOM | 1172 | CG  | ASP | A | 384 | 63.733 | 65.575 | 52.238 | 1.00 | 40.66 | A |
| ATOM | 1173 | OD1 | ASP | A | 384 | 63.786 | 66.204 | 53.334 | 1.00 | 41.10 | A |
| ATOM | 1174 | OD2 | ASP | A | 384 | 63.067 | 66.021 | 51.282 | 1.00 | 42.48 | A |
| ATOM | 1175 | C   | ASP | A | 384 | 64.315 | 63.626 | 54.580 | 1.00 | 38.81 | A |
| ATOM | 1176 | O   | ASP | A | 384 | 63.075 | 63.188 | 54.454 | 1.00 | 36.93 | A |
| ATOM | 1177 | N   | VAL | A | 385 | 64.944 | 63.948 | 55.714 | 1.00 | 38.25 | A |
| ATOM | 1178 | CA  | VAL | A | 385 | 64.478 | 63.689 | 57.014 | 1.00 | 39.14 | A |
| ATOM | 1179 | CB  | VAL | A | 385 | 65.605 | 64.013 | 58.059 | 1.00 | 39.88 | A |
| ATOM | 1180 | CG1 | VAL | A | 385 | 65.067 | 64.074 | 59.552 | 1.00 | 39.96 | A |
| ATOM | 1181 | CG2 | VAL | A | 385 | 66.724 | 63.024 | 57.979 | 1.00 | 40.46 | A |
| ATOM | 1182 | C   | VAL | A | 385 | 63.115 | 64.450 | 57.214 | 1.00 | 39.57 | A |
| ATOM | 1183 | O   | VAL | A | 385 | 62.104 | 63.876 | 57.706 | 1.00 | 38.98 | A |
| ATOM | 1184 | N   | GLU | A | 386 | 63.080 | 65.727 | 56.765 | 1.00 | 40.32 | A |
| ATOM | 1185 | CA  | GLU | A | 386 | 61.917 | 66.511 | 56.947 | 1.00 | 39.59 | A |
| ATOM | 1186 | CB  | GLU | A | 386 | 62.175 | 68.007 | 56.566 | 1.00 | 43.15 | A |
| ATOM | 1187 | CG  | GLU | A | 386 | 61.029 | 68.897 | 56.610 | 0.00 | 48.09 | A |
| ATOM | 1188 | CD  | GLU | A | 386 | 61.306 | 71.132 | 56.709 | 1.00 | 52.41 | A |
| ATOM | 1189 | OE1 | GLU | A | 386 | 62.560 | 71.153 | 56.883 | 1.00 | 54.01 | A |
| ATOM | 1190 | OE2 | GLU | A | 386 | 60.741 | 71.105 | 55.578 | 1.00 | 53.87 | A |
| ATOM | 1191 | C   | GLU | A | 386 | 60.785 | 65.983 | 56.182 | 1.00 | 37.88 | A |
| ATOM | 1192 | O   | GLU | A | 386 | 59.618 | 66.053 | 56.656 | 1.00 | 39.01 | A |
| ATOM | 1193 | N   | ALA | A | 387 | 61.023 | 65.537 | 54.978 | 1.00 | 34.50 | A |
| ATOM | 1194 | CA  | ALA | A | 387 | 59.937 | 64.966 | 54.211 | 1.00 | 33.46 | A |
| ATOM | 1195 | CB  | ALA | A | 387 | 60.346 | 64.654 | 52.884 | 1.00 | 31.94 | A |
| ATOM | 1196 | C   | ALA | A | 387 | 59.395 | 63.675 | 54.841 | 1.00 | 33.66 | A |
| ATOM | 1197 | O   | ALA | A | 387 | 58.194 | 63.388 | 54.792 | 1.00 | 34.36 | A |
| ATOM | 1198 | N   | VAL | A | 388 | 60.264 | 62.865 | 55.410 | 1.00 | 33.14 | A |
| ATOM | 1199 | CA  | VAL | A | 388 | 59.794 | 61.599 | 56.039 | 1.00 | 33.10 | A |
| ATOM | 1200 | CB  | VAL | A | 388 | 60.987 | 60.732 | 56.426 | 1.00 | 32.10 | A |
| ATOM | 1201 | CG1 | VAL | A | 388 | 60.575 | 59.578 | 57.515 | 1.00 | 30.61 | A |
| ATOM | 1202 | CG2 | VAL | A | 388 | 61.576 | 60.116 | 55.078 | 1.00 | 30.56 | A |
| ATOM | 1203 | C   | VAL | A | 388 | 59.019 | 61.944 | 57.315 | 1.00 | 33.26 | A |
| ATOM | 1204 | O   | VAL | A | 388 | 58.024 | 61.356 | 57.626 | 1.00 | 33.12 | A |
| ATOM | 1205 | N   | GLN | A | 389 | 59.537 | 62.879 | 58.097 | 1.00 | 35.45 | A |
| ATOM | 1206 | CA  | GLN | A | 389 | 58.743 | 63.463 | 59.232 | 1.00 | 36.73 | A |
| ATOM | 1207 | CB  | GLN | A | 389 | 59.536 | 64.586 | 59.916 | 1.00 | 40.00 | A |
| ATOM | 1208 | CG  | GLN | A | 389 | 60.797 | 63.917 | 60.732 | 1.00 | 46.22 | A |
| ATOM | 1209 | CD  | GLN | A | 389 | 61.333 | 64.828 | 61.828 | 1.00 | 50.16 | A |

TABLE 2-continued

ATOMIC COORDINATES OF THE ERR3 LBD/
DIETHYLSTILBESTROL COMPLEX

| ATOM | 1210 | OE1 | GLN | A | 389 | 60.960 | 65.996 | 61.870 | 1.00 | 54.51 | A |
|------|------|-----|-----|---|-----|--------|--------|--------|------|-------|---|
| ATOM | 1211 | NE2 | GLN | A | 389 | 62.228 | 64.317 | 62.673 | 1.00 | 52.27 | A |
| ATOM | 1212 | C   | GLN | A | 389 | 57.361 | 63.987 | 58.891 | 1.00 | 35.17 | A |
| ATOM | 1213 | O   | GLN | A | 389 | 56.412 | 63.828 | 59.652 | 1.00 | 34.18 | A |
| ATOM | 1214 | N   | LYS | A | 390 | 57.249 | 64.566 | 57.711 | 1.00 | 34.61 | A |
| ATOM | 1215 | CA  | LYS | A | 390 | 55.982 | 65.057 | 57.210 | 1.00 | 34.79 | A |
| ATOM | 1216 | CB  | LYS | A | 390 | 56.242 | 65.954 | 55.915 | 1.00 | 36.83 | A |
| ATOM | 1217 | CG  | LYS | A | 390 | 55.061 | 66.807 | 55.424 | 1.00 | 40.30 | A |
| ATOM | 1218 | CD  | LYS | A | 390 | 54.320 | 67.623 | 56.648 | 1.00 | 44.01 | A |
| ATOM | 1219 | CE  | LYS | A | 390 | 52.714 | 68.001 | 56.442 | 1.00 | 47.23 | A |
| ATOM | 1220 | NZ  | LYS | A | 390 | 51.961 | 68.070 | 57.871 | 1.00 | 50.28 | A |
| ATOM | 1221 | C   | LYS | A | 390 | 55.031 | 63.836 | 56.896 | 1.00 | 33.90 | A |
| ATOM | 1222 | O   | LYS | A | 390 | 53.835 | 63.860 | 57.183 | 1.00 | 32.06 | A |
| ATOM | 1223 | N   | LEU | A | 391 | 55.566 | 62.776 | 56.284 | 1.00 | 32.97 | A |
| ATOM | 1224 | CA  | LEU | A | 391 | 54.743 | 61.556 | 56.153 | 1.00 | 32.16 | A |
| ATOM | 1225 | CB  | LEU | A | 391 | 55.462 | 60.520 | 55.337 | 1.00 | 29.43 | A |
| ATOM | 1226 | CG  | LEU | A | 391 | 54.916 | 59.125 | 55.290 | 1.00 | 31.30 | A |
| ATOM | 1227 | CD1 | LEU | A | 391 | 53.769 | 58.969 | 54.326 | 1.00 | 30.55 | A |
| ATOM | 1228 | CD2 | LEU | A | 391 | 56.035 | 58.259 | 54.829 | 1.00 | 30.65 | A |
| ATOM | 1229 | C   | LEU | A | 391 | 54.269 | 61.065 | 57.526 | 1.00 | 31.39 | A |
| ATOM | 1230 | O   | LEU | A | 391 | 53.103 | 60.744 | 57.747 | 1.00 | 33.15 | A |
| ATOM | 1231 | N   | GLN | A | 392 | 55.148 | 61.047 | 58.495 | 1.00 | 30.75 | A |
| ATOM | 1232 | CA  | GLN | A | 392 | 54.703 | 60.658 | 59.842 | 1.00 | 31.34 | A |
| ATOM | 1233 | CB  | GLN | A | 392 | 55.924 | 60.695 | 60.825 | 1.00 | 30.09 | A |
| ATOM | 1234 | CG  | GLN | A | 392 | 57.001 | 59.624 | 60.429 | 1.00 | 30.46 | A |
| ATOM | 1235 | CD  | GLN | A | 392 | 58.322 | 59.764 | 61.177 | 1.00 | 31.07 | A |
| ATOM | 1236 | OE1 | GLN | A | 392 | 58.392 | 60.538 | 62.125 | 1.00 | 31.00 | A |
| ATOM | 1237 | NE2 | GLN | A | 392 | 59.373 | 59.090 | 60.697 | 1.00 | 27.90 | A |
| ATOM | 1238 | C   | GLN | A | 392 | 53.538 | 61.508 | 60.349 | 1.00 | 31.03 | A |
| ATOM | 1239 | O   | GLN | A | 392 | 52.578 | 60.994 | 60.892 | 1.00 | 29.96 | A |
| ATOM | 1240 | N   | ASP | A | 393 | 53.692 | 62.830 | 60.252 | 1.00 | 32.67 | A |
| ATOM | 1241 | CA  | ASP | A | 393 | 52.750 | 63.802 | 60.808 | 1.00 | 34.30 | A |
| ATOM | 1242 | CB  | ASP | A | 393 | 53.205 | 65.274 | 60.599 | 1.00 | 38.62 | A |
| ATOM | 1243 | CG  | ASP | A | 393 | 52.364 | 66.320 | 61.477 | 1.00 | 42.54 | A |
| ATOM | 1244 | OD1 | ASP | A | 393 | 52.394 | 66.121 | 62.764 | 1.00 | 46.62 | A |
| ATOM | 1245 | OD2 | ASP | A | 393 | 51.599 | 67.317 | 60.986 | 1.00 | 45.65 | A |
| ATOM | 1246 | C   | ASP | A | 393 | 51.448 | 63.612 | 60.177 | 1.00 | 33.89 | A |
| ATOM | 1247 | O   | ASP | A | 393 | 50.394 | 63.524 | 60.872 | 1.00 | 33.05 | A |
| ATOM | 1248 | N   | VAL | A | 394 | 51.467 | 63.394 | 58.861 | 1.00 | 31.68 | A |
| ATOM | 1249 | CA  | VAL | A | 394 | 50.200 | 63.287 | 58.187 | 1.00 | 32.33 | A |
| ATOM | 1250 | CB  | VAL | A | 394 | 50.437 | 63.130 | 56.597 | 1.00 | 33.30 | A |
| ATOM | 1251 | CG1 | VAL | A | 394 | 49.319 | 62.497 | 56.028 | 1.00 | 33.18 | A |
| ATOM | 1252 | CG2 | VAL | A | 394 | 50.702 | 64.502 | 55.930 | 1.00 | 34.76 | A |
| ATOM | 1253 | C   | VAL | A | 394 | 49.410 | 61.984 | 58.693 | 1.00 | 31.61 | A |
| ATOM | 1254 | O   | VAL | A | 394 | 48.181 | 61.909 | 58.777 | 1.00 | 31.10 | A |
| ATOM | 1255 | N   | LEU | A | 395 | 50.145 | 60.904 | 58.935 | 1.00 | 30.75 | A |
| ATOM | 1256 | CA  | LEU | A | 395 | 49.445 | 59.643 | 59.286 | 1.00 | 28.73 | A |
| ATOM | 1257 | CB  | LEU | A | 395 | 50.341 | 58.519 | 58.889 | 1.00 | 27.62 | A |
| ATOM | 1258 | CG  | LEU | A | 395 | 50.777 | 58.395 | 57.457 | 1.00 | 27.19 | A |
| ATOM | 1259 | CD1 | LEU | A | 395 | 51.949 | 57.330 | 57.312 | 1.00 | 25.83 | A |
| ATOM | 1260 | CD2 | LEU | A | 395 | 49.470 | 57.897 | 56.764 | 1.00 | 24.70 | A |
| ATOM | 1261 | C   | LEU | A | 395 | 49.198 | 59.646 | 60.769 | 1.00 | 30.12 | A |
| ATOM | 1262 | O   | LEU | A | 395 | 48.118 | 59.337 | 61.255 | 1.00 | 30.74 | A |
| ATOM | 1263 | N   | HIS | A | 396 | 50.113 | 60.230 | 61.526 | 1.00 | 29.77 | A |
| ATOM | 1264 | CA  | HIS | A | 396 | 49.859 | 60.434 | 62.935 | 1.00 | 30.13 | A |
| ATOM | 1265 | CB  | HIS | A | 396 | 51.090 | 61.023 | 63.540 | 1.00 | 30.24 | A |
| ATOM | 1266 | CG  | HIS | A | 396 | 51.022 | 61.282 | 65.008 | 1.00 | 30.13 | A |
| ATOM | 1267 | CD2 | HIS | A | 396 | 50.071 | 61.005 | 65.949 | 1.00 | 30.90 | A |
| ATOM | 1268 | ND1 | HIS | A | 396 | 51.950 | 62.033 | 65.633 | 1.00 | 30.56 | A |
| ATOM | 1269 | CE1 | HIS | A | 396 | 51.615 | 62.210 | 66.909 | 1.00 | 29.96 | A |
| ATOM | 1270 | NE2 | HIS | A | 396 | 50.539 | 61.494 | 67.150 | 1.00 | 29.64 | A |
| ATOM | 1271 | C   | HIS | A | 396 | 48.617 | 61.258 | 63.150 | 1.00 | 31.98 | A |
| ATOM | 1272 | O   | HIS | A | 396 | 47.718 | 60.906 | 63.971 | 1.00 | 32.63 | A |
| ATOM | 1273 | N   | GLU | A | 397 | 48.554 | 62.369 | 62.411 | 1.00 | 33.56 | A |
| ATOM | 1274 | CA  | GLU | A | 397 | 47.379 | 63.289 | 62.424 | 1.00 | 34.51 | A |
| ATOM | 1275 | CB  | GLU | A | 397 | 47.520 | 64.537 | 61.482 | 1.00 | 37.17 | A |
| ATOM | 1276 | CG  | GLU | A | 397 | 46.230 | 65.450 | 61.358 | 1.00 | 40.95 | A |
| ATOM | 1277 | CD  | GLU | A | 397 | 46.415 | 66.670 | 60.408 | 1.00 | 43.30 | A |
| ATOM | 1278 | OE1 | GLU | A | 397 | 46.611 | 66.564 | 59.185 | 1.00 | 45.46 | A |
| ATOM | 1279 | OE2 | GLU | A | 397 | 46.434 | 67.772 | 60.890 | 1.00 | 45.28 | A |
| ATOM | 1280 | C   | GLU | A | 397 | 46.162 | 62.550 | 62.172 | 1.00 | 33.88 | A |
| ATOM | 1281 | O   | GLU | A | 397 | 45.237 | 62.653 | 62.972 | 1.00 | 32.75 | A |
| ATOM | 1282 | N   | ALA | A | 398 | 46.166 | 61.660 | 61.172 | 1.00 | 33.76 | A |
| ATOM | 1283 | CA  | ALA | A | 398 | 44.949 | 60.832 | 60.883 | 1.00 | 33.73 | A |
| ATOM | 1284 | CB  | ALA | A | 398 | 45.138 | 59.933 | 59.721 | 1.00 | 31.28 | A |
| ATOM | 1285 | C   | ALA | A | 398 | 44.483 | 59.986 | 62.051 | 1.00 | 33.96 | A |

TABLE 2-continued

ATOMIC COORDINATES OF THE ERR3 LBD/
DIETHYLSTILBESTROL COMPLEX

| ATOM | 1286 | O | ALA | A | 398 | 43.217 | 59.772 | 62.258 | 1.00 | 34.86 | A |
| --- | --- | --- | --- | --- | --- | --- | --- | --- | --- | --- | --- |
| ATOM | 1287 | N | LEU | A | 399 | 45.451 | 59.303 | 62.665 | 1.00 | 32.97 | A |
| ATOM | 1288 | CA | LEU | A | 399 | 45.126 | 58.487 | 63.776 | 1.00 | 31.93 | A |
| ATOM | 1289 | CB | LEU | A | 399 | 46.320 | 57.805 | 64.345 | 1.00 | 30.25 | A |
| ATOM | 1290 | CG | LEU | A | 399 | 46.140 | 56.885 | 65.555 | 1.00 | 29.25 | A |
| ATOM | 1291 | CD1 | LEU | A | 399 | 45.351 | 55.631 | 65.152 | 1.00 | 27.04 | A |
| ATOM | 1292 | CD2 | LEU | A | 399 | 47.614 | 56.543 | 66.301 | 1.00 | 27.00 | A |
| ATOM | 1293 | C | LEU | A | 399 | 44.550 | 59.361 | 64.910 | 1.00 | 32.42 | A |
| ATOM | 1294 | O | LEU | A | 399 | 43.659 | 58.915 | 65.574 | 1.00 | 32.73 | A |
| ATOM | 1295 | N | GLN | A | 400 | 45.185 | 60.463 | 65.260 | 1.00 | 32.59 | A |
| ATOM | 1296 | CA | GLN | A | 400 | 44.747 | 61.188 | 66.385 | 1.00 | 35.03 | A |
| ATOM | 1297 | CB | GLN | A | 400 | 45.554 | 62.412 | 66.624 | 1.00 | 36.20 | A |
| ATOM | 1298 | CG | GLN | A | 400 | 45.126 | 63.653 | 67.355 | 0.00 | 40.51 | A |
| ATOM | 1299 | CD | GLN | A | 400 | 46.271 | 65.205 | 67.603 | 1.00 | 43.57 | A |
| ATOM | 1300 | OE1 | GLN | A | 400 | 46.200 | 65.809 | 66.492 | 1.00 | 43.68 | A |
| ATOM | 1301 | NE2 | GLN | A | 400 | 46.617 | 65.817 | 68.758 | 1.00 | 46.15 | A |
| ATOM | 1302 | C | GLN | A | 400 | 43.274 | 61.659 | 66.105 | 1.00 | 36.26 | A |
| ATOM | 1303 | O | GLN | A | 400 | 42.381 | 61.520 | 66.950 | 1.00 | 36.54 | A |
| ATOM | 1304 | N | ASP | A | 401 | 43.015 | 62.179 | 64.932 | 1.00 | 36.31 | A |
| ATOM | 1305 | CA | ASP | A | 401 | 41.683 | 62.703 | 64.616 | 1.00 | 37.92 | A |
| ATOM | 1306 | CB | ASP | A | 401 | 41.720 | 63.509 | 63.339 | 1.00 | 39.90 | A |
| ATOM | 1307 | CG | ASP | A | 401 | 40.372 | 63.952 | 62.844 | 1.00 | 43.31 | A |
| ATOM | 1308 | OD1 | ASP | A | 401 | 39.887 | 64.992 | 63.350 | 1.00 | 45.75 | A |
| ATOM | 1309 | OD2 | ASP | A | 401 | 39.816 | 63.402 | 61.859 | 1.00 | 45.28 | A |
| ATOM | 1310 | C | ASP | A | 401 | 40.731 | 61.557 | 64.589 | 1.00 | 37.30 | A |
| ATOM | 1311 | O | ASP | A | 401 | 39.566 | 61.657 | 65.108 | 1.00 | 37.43 | A |
| ATOM | 1312 | N | TYR | A | 402 | 41.171 | 60.421 | 64.126 | 1.00 | 36.12 | A |
| ATOM | 1313 | CA | TYR | A | 402 | 40.248 | 59.275 | 64.173 | 1.00 | 34.49 | A |
| ATOM | 1314 | CB | TYR | A | 402 | 40.763 | 58.050 | 63.516 | 1.00 | 33.64 | A |
| ATOM | 1315 | CG | TYR | A | 402 | 39.894 | 56.832 | 63.627 | 1.00 | 32.45 | A |
| ATOM | 1316 | CD1 | TYR | A | 402 | 38.860 | 56.606 | 62.757 | 1.00 | 33.25 | A |
| ATOM | 1317 | CE1 | TYR | A | 402 | 38.017 | 55.427 | 62.888 | 1.00 | 33.92 | A |
| ATOM | 1318 | CD2 | TYR | A | 402 | 40.114 | 55.905 | 64.637 | 1.00 | 31.48 | A |
| ATOM | 1319 | CE2 | TYR | A | 402 | 39.317 | 54.774 | 64.777 | 1.00 | 32.81 | A |
| ATOM | 1320 | CZ | TYR | A | 402 | 38.249 | 54.544 | 63.950 | 1.00 | 33.25 | A |
| ATOM | 1321 | OH | TYR | A | 402 | 37.517 | 53.413 | 64.176 | 1.00 | 34.53 | A |
| ATOM | 1322 | C | TYR | A | 402 | 39.872 | 58.969 | 65.568 | 1.00 | 34.89 | A |
| ATOM | 1323 | O | TYR | A | 402 | 38.748 | 58.647 | 65.797 | 1.00 | 35.35 | A |
| ATOM | 1324 | N | GLU | A | 403 | 40.803 | 58.963 | 66.510 | 1.00 | 34.19 | A |
| ATOM | 1325 | CA | GLU | A | 403 | 40.471 | 58.445 | 67.827 | 1.00 | 33.45 | A |
| ATOM | 1326 | CB | GLU | A | 403 | 41.742 | 58.171 | 68.652 | 1.00 | 33.57 | A |
| ATOM | 1327 | CG | GLU | A | 403 | 42.710 | 57.066 | 68.114 | 1.00 | 31.30 | A |
| ATOM | 1328 | CD | GLU | A | 403 | 42.027 | 55.725 | 68.102 | 1.00 | 31.62 | A |
| ATOM | 1329 | OE1 | GLU | A | 403 | 41.052 | 55.547 | 68.789 | 1.00 | 32.79 | A |
| ATOM | 1330 | OE2 | GLU | A | 403 | 42.458 | 54.801 | 67.429 | 1.00 | 33.15 | A |
| ATOM | 1331 | C | GLU | A | 403 | 39.614 | 59.452 | 68.544 | 1.00 | 34.30 | A |
| ATOM | 1332 | O | GLU | A | 403 | 38.859 | 59.110 | 69.394 | 1.00 | 32.88 | A |
| ATOM | 1333 | N | ALA | A | 404 | 39.872 | 60.707 | 68.271 | 1.00 | 36.28 | A |
| ATOM | 1334 | CA | ALA | A | 404 | 39.142 | 61.849 | 68.847 | 1.00 | 38.80 | A |
| ATOM | 1335 | CB | ALA | A | 404 | 39.643 | 63.224 | 68.290 | 1.00 | 37.44 | A |
| ATOM | 1336 | C | ALA | A | 404 | 37.666 | 61.707 | 68.559 | 1.00 | 40.48 | A |
| ATOM | 1337 | O | ALA | A | 404 | 36.829 | 61.793 | 69.481 | 1.00 | 41.50 | A |
| ATOM | 1338 | N | GLY | A | 405 | 37.400 | 61.395 | 67.312 | 1.00 | 42.31 | A |
| ATOM | 1339 | CA | GLY | A | 405 | 36.077 | 61.281 | 66.755 | 1.00 | 43.95 | A |
| ATOM | 1340 | C | GLY | A | 405 | 35.384 | 59.972 | 67.129 | 1.00 | 44.65 | A |
| ATOM | 1341 | O | GLY | A | 405 | 34.166 | 60.011 | 67.301 | 1.00 | 45.87 | A |
| ATOM | 1342 | N | GLN | A | 406 | 36.050 | 58.818 | 67.178 | 1.00 | 44.03 | A |
| ATOM | 1343 | CA | GLN | A | 406 | 35.329 | 57.551 | 67.411 | 1.00 | 43.50 | A |
| ATOM | 1344 | CB | GLN | A | 406 | 35.757 | 56.425 | 66.411 | 1.00 | 45.52 | A |
| ATOM | 1345 | CG | GLN | A | 406 | 35.649 | 56.798 | 64.910 | 1.00 | 48.55 | A |
| ATOM | 1346 | CD | GLN | A | 406 | 34.157 | 56.929 | 64.446 | 1.00 | 50.22 | A |
| ATOM | 1347 | OE1 | GLN | A | 406 | 33.455 | 55.944 | 64.524 | 1.00 | 50.30 | A |
| ATOM | 1348 | NE2 | GLN | A | 406 | 33.716 | 58.139 | 63.938 | 1.00 | 49.92 | A |
| ATOM | 1349 | C | GLN | A | 406 | 35.509 | 57.000 | 68.785 | 1.00 | 42.85 | A |
| ATOM | 1350 | O | GLN | A | 406 | 34.946 | 55.920 | 69.087 | 1.00 | 42.26 | A |
| ATOM | 1351 | N | HIS | A | 407 | 36.321 | 57.635 | 69.639 | 1.00 | 41.95 | A |
| ATOM | 1352 | CA | HIS | A | 407 | 36.699 | 56.949 | 70.901 | 1.00 | 42.09 | A |
| ATOM | 1353 | CB | HIS | A | 407 | 37.954 | 55.984 | 70.761 | 1.00 | 38.93 | A |
| ATOM | 1354 | CG | HIS | A | 407 | 37.709 | 54.704 | 70.016 | 1.00 | 36.53 | A |
| ATOM | 1355 | CD2 | HIS | A | 407 | 37.746 | 54.425 | 68.681 | 1.00 | 36.07 | A |
| ATOM | 1356 | ND1 | HIS | A | 407 | 37.366 | 53.527 | 70.638 | 1.00 | 36.76 | A |
| ATOM | 1357 | CE1 | HIS | A | 407 | 37.189 | 52.567 | 69.727 | 1.00 | 36.05 | A |
| ATOM | 1358 | NE2 | HIS | A | 407 | 37.446 | 53.080 | 68.528 | 1.00 | 36.24 | A |
| ATOM | 1359 | C | HIS | A | 407 | 36.884 | 58.016 | 72.024 | 1.00 | 43.53 | A |
| ATOM | 1360 | O | HIS | A | 407 | 37.856 | 58.064 | 72.834 | 1.00 | 42.13 | A |
| ATOM | 1361 | N | MET | A | 408 | 35.872 | 58.883 | 72.021 | 1.00 | 46.19 | A |

TABLE 2-continued

ATOMIC COORDINATES OF THE ERR3 LBD/
DIETHYLSTILBESTROL COMPLEX

| ATOM | 1362 | CA | MET | A | 408 | 35.710 | 59.956 | 73.003 | 1.00 | 48.29 | A |
|------|------|-----|-----|---|-----|--------|--------|--------|------|-------|---|
| ATOM | 1363 | CB | MET | A | 408 | 34.368 | 60.720 | 72.769 | 1.00 | 53.57 | A |
| ATOM | 1364 | CG | MET | A | 408 | 34.152 | 61.931 | 73.670 | 1.00 | 62.03 | A |
| ATOM | 1365 | SD | MET | A | 408 | 35.476 | 63.144 | 73.536 | 1.00 | 70.12 | A |
| ATOM | 1366 | CE | MET | A | 408 | 34.846 | 64.195 | 72.233 | 1.00 | 68.52 | A |
| ATOM | 1367 | C | MET | A | 408 | 35.737 | 59.380 | 74.364 | 1.00 | 46.21 | A |
| ATOM | 1368 | O | MET | A | 408 | 36.193 | 60.012 | 75.238 | 1.00 | 46.56 | A |
| ATOM | 1369 | N | GLU | A | 409 | 35.317 | 58.155 | 74.527 | 1.00 | 44.38 | A |
| ATOM | 1370 | CA | GLU | A | 409 | 35.356 | 57.600 | 75.822 | 1.00 | 44.24 | A |
| ATOM | 1371 | CB | GLU | A | 409 | 34.606 | 56.245 | 75.784 | 1.00 | 44.41 | A |
| ATOM | 1372 | CG | GLU | A | 409 | 35.471 | 55.066 | 75.231 | 1.00 | 46.70 | A |
| ATOM | 1373 | CD | GLU | A | 409 | 35.449 | 54.884 | 73.661 | 1.00 | 46.80 | A |
| ATOM | 1374 | OE1 | GLU | A | 409 | 34.537 | 55.412 | 72.938 | 1.00 | 48.23 | A |
| ATOM | 1375 | OE2 | GLU | A | 409 | 36.341 | 54.192 | 73.125 | 1.00 | 47.75 | A |
| ATOM | 1376 | C | GLU | A | 409 | 36.820 | 57.398 | 76.388 | 1.00 | 43.67 | A |
| ATOM | 1377 | O | GLU | A | 409 | 36.980 | 57.216 | 77.600 | 1.00 | 43.83 | A |
| ATOM | 1378 | N | ASP | A | 410 | 37.865 | 57.398 | 75.539 | 1.00 | 41.62 | A |
| ATOM | 1379 | CA | ASP | A | 410 | 39.246 | 57.211 | 76.008 | 1.00 | 39.84 | A |
| ATOM | 1380 | CB | ASP | A | 410 | 39.708 | 55.780 | 75.731 | 1.00 | 39.22 | A |
| ATOM | 1381 | CG | ASP | A | 410 | 41.203 | 55.578 | 76.195 | 1.00 | 39.09 | A |
| ATOM | 1382 | OD1 | ASP | A | 410 | 41.883 | 56.543 | 76.569 | 1.00 | 36.97 | A |
| ATOM | 1383 | OD2 | ASP | A | 410 | 41.765 | 54.528 | 76.203 | 1.00 | 37.94 | A |
| ATOM | 1384 | C | ASP | A | 410 | 40.134 | 58.145 | 75.255 | 1.00 | 38.87 | A |
| ATOM | 1385 | O | ASP | A | 410 | 40.548 | 57.835 | 74.104 | 1.00 | 37.76 | A |
| ATOM | 1386 | N | PRO | A | 411 | 40.379 | 59.309 | 75.857 | 1.00 | 38.43 | A |
| ATOM | 1387 | CD | PRO | A | 411 | 39.955 | 59.611 | 77.249 | 1.00 | 38.35 | A |
| ATOM | 1388 | CA | PRO | A | 411 | 41.087 | 60.393 | 75.199 | 1.00 | 37.92 | A |
| ATOM | 1389 | CB | PRO | A | 411 | 40.909 | 61.569 | 76.142 | 1.00 | 39.09 | A |
| ATOM | 1390 | CG | PRO | A | 411 | 40.630 | 60.847 | 77.584 | 1.00 | 39.61 | A |
| ATOM | 1391 | C | PRO | A | 411 | 42.552 | 60.073 | 75.051 | 1.00 | 37.60 | A |
| ATOM | 1392 | O | PRO | A | 411 | 43.216 | 60.800 | 74.447 | 1.00 | 36.51 | A |
| ATOM | 1393 | N | ARG | A | 412 | 43.014 | 58.931 | 75.573 | 1.00 | 37.07 | A |
| ATOM | 1394 | CA | ARG | A | 412 | 44.375 | 58.457 | 75.326 | 1.00 | 35.84 | A |
| ATOM | 1395 | CB | ARG | A | 412 | 44.994 | 58.157 | 76.712 | 1.00 | 37.12 | A |
| ATOM | 1396 | CG | ARG | A | 412 | 45.315 | 59.453 | 77.485 | 1.00 | 37.59 | A |
| ATOM | 1397 | CD | ARG | A | 412 | 46.045 | 59.253 | 78.739 | 1.00 | 39.60 | A |
| ATOM | 1398 | NE | ARG | A | 412 | 45.238 | 58.564 | 79.716 | 1.00 | 40.70 | A |
| ATOM | 1399 | CZ | ARG | A | 412 | 44.328 | 59.197 | 80.508 | 1.00 | 40.44 | A |
| ATOM | 1400 | NH1 | ARG | A | 412 | 44.105 | 60.496 | 80.394 | 1.00 | 39.96 | A |
| ATOM | 1401 | NH2 | ARG | A | 412 | 43.630 | 58.511 | 81.361 | 1.00 | 41.67 | A |
| ATOM | 1402 | C | ARG | A | 412 | 44.462 | 57.200 | 74.460 | 1.00 | 34.45 | A |
| ATOM | 1403 | O | ARG | A | 412 | 45.506 | 56.542 | 74.420 | 1.00 | 34.76 | A |
| ATOM | 1404 | N | ARG | A | 413 | 43.387 | 56.825 | 73.767 | 1.00 | 32.76 | A |
| ATOM | 1405 | CA | ARG | A | 413 | 43.453 | 55.656 | 72.960 | 1.00 | 31.83 | A |
| ATOM | 1406 | CB | ARG | A | 413 | 42.106 | 55.305 | 72.308 | 1.00 | 31.56 | A |
| ATOM | 1407 | CG | ARG | A | 413 | 41.962 | 53.896 | 71.824 | 1.00 | 30.50 | A |
| ATOM | 1408 | CD | ARG | A | 413 | 40.735 | 53.705 | 71.344 | 1.00 | 32.43 | A |
| ATOM | 1409 | NE | ARG | A | 413 | 40.607 | 52.555 | 70.496 | 1.00 | 31.59 | A |
| ATOM | 1410 | CZ | ARG | A | 413 | 40.624 | 51.359 | 70.919 | 1.00 | 29.89 | A |
| ATOM | 1411 | NH1 | ARG | A | 413 | 40.720 | 51.114 | 72.175 | 1.00 | 30.91 | A |
| ATOM | 1412 | NH2 | ARG | A | 413 | 40.492 | 50.367 | 70.074 | 1.00 | 30.12 | A |
| ATOM | 1413 | C | ARG | A | 413 | 44.580 | 55.890 | 71.853 | 1.00 | 31.79 | A |
| ATOM | 1414 | O | ARG | A | 413 | 45.332 | 54.990 | 71.630 | 1.00 | 32.04 | A |
| ATOM | 1415 | N | ALA | A | 414 | 44.757 | 57.081 | 71.245 | 1.00 | 30.03 | A |
| ATOM | 1416 | CA | ALA | A | 414 | 45.732 | 57.198 | 70.181 | 1.00 | 29.29 | A |
| ATOM | 1417 | CB | ALA | A | 414 | 45.747 | 58.642 | 69.613 | 1.00 | 28.98 | A |
| ATOM | 1418 | C | ALA | A | 414 | 47.165 | 56.832 | 70.733 | 1.00 | 29.59 | A |
| ATOM | 1419 | O | ALA | A | 414 | 47.937 | 56.180 | 70.098 | 1.00 | 28.63 | A |
| ATOM | 1420 | N | GLY | A | 415 | 47.427 | 57.319 | 71.920 | 1.00 | 28.51 | A |
| ATOM | 1421 | CA | GLY | A | 415 | 48.687 | 57.328 | 72.585 | 1.00 | 28.89 | A |
| ATOM | 1422 | C | GLY | A | 415 | 48.907 | 55.816 | 72.914 | 1.00 | 29.06 | A |
| ATOM | 1423 | O | GLY | A | 415 | 49.967 | 55.321 | 72.734 | 1.00 | 30.21 | A |
| ATOM | 1424 | N | LYS | A | 416 | 47.882 | 55.103 | 73.298 | 1.00 | 28.75 | A |
| ATOM | 1425 | CA | LYS | A | 416 | 48.012 | 53.661 | 73.581 | 1.00 | 28.62 | A |
| ATOM | 1426 | CB | LYS | A | 416 | 46.729 | 53.081 | 74.229 | 1.00 | 28.27 | A |
| ATOM | 1427 | CG | LYS | A | 416 | 46.535 | 53.486 | 75.747 | 1.00 | 27.37 | A |
| ATOM | 1428 | CD | LYS | A | 416 | 45.155 | 53.019 | 76.309 | 1.00 | 28.04 | A |
| ATOM | 1429 | CE | LYS | A | 416 | 44.798 | 53.808 | 77.584 | 1.00 | 29.28 | A |
| ATOM | 1430 | NZ | LYS | A | 416 | 43.305 | 53.735 | 77.814 | 1.00 | 31.32 | A |
| ATOM | 1431 | C | LYS | A | 416 | 48.338 | 52.891 | 72.324 | 1.00 | 28.22 | A |
| ATOM | 1432 | O | LYS | A | 416 | 49.137 | 51.958 | 72.425 | 1.00 | 28.18 | A |
| ATOM | 1433 | N | MET | A | 417 | 47.819 | 53.320 | 71.158 | 1.00 | 28.00 | A |
| ATOM | 1434 | CA | MET | A | 417 | 48.125 | 52.610 | 69.865 | 1.00 | 27.97 | A |
| ATOM | 1435 | CB | MET | A | 417 | 47.238 | 53.079 | 68.704 | 1.00 | 28.27 | A |
| ATOM | 1436 | CG | MET | A | 417 | 45.735 | 52.747 | 68.886 | 1.00 | 30.81 | A |
| ATOM | 1437 | SD | MET | A | 417 | 45.559 | 50.974 | 68.955 | 1.00 | 34.69 | A |

TABLE 2-continued

ATOMIC COORDINATES OF THE ERR3 LBD/
DIETHYLSTILBESTROL COMPLEX

| ATOM | 1438 | CE | MET | A | 417 | 43.879 | 50.699 | 69.498 | 1.00 | 33.83 | A |
|---|---|---|---|---|---|---|---|---|---|---|---|
| ATOM | 1439 | C | MET | A | 417 | 49.571 | 52.768 | 69.569 | 1.00 | 26.35 | A |
| ATOM | 1440 | O | MET | A | 417 | 50.269 | 51.819 | 69.200 | 1.00 | 23.94 | A |
| ATOM | 1441 | N | LEU | A | 418 | 50.030 | 53.988 | 69.783 | 1.00 | 26.11 | A |
| ATOM | 1442 | CA | LEU | A | 418 | 51.418 | 54.263 | 69.481 | 1.00 | 25.88 | A |
| ATOM | 1443 | CB | LEU | A | 418 | 51.688 | 55.755 | 69.505 | 1.00 | 25.22 | A |
| ATOM | 1444 | CG | LEU | A | 418 | 50.971 | 56.638 | 68.506 | 1.00 | 24.44 | A |
| ATOM | 1445 | CD1 | LEU | A | 418 | 51.325 | 58.015 | 68.985 | 1.00 | 22.55 | A |
| ATOM | 1446 | CD2 | LEU | A | 418 | 51.397 | 56.420 | 67.117 | 1.00 | 21.92 | A |
| ATOM | 1447 | C | LEU | A | 418 | 52.373 | 53.565 | 70.415 | 1.00 | 24.86 | A |
| ATOM | 1448 | O | LEU | A | 418 | 53.453 | 53.178 | 70.054 | 1.00 | 23.38 | A |
| ATOM | 1449 | N | MET | A | 419 | 51.920 | 53.321 | 71.621 | 1.00 | 24.18 | A |
| ATOM | 1450 | CA | MET | A | 419 | 52.749 | 52.597 | 72.591 | 1.00 | 24.64 | A |
| ATOM | 1451 | CB | MET | A | 419 | 52.343 | 52.828 | 74.055 | 1.00 | 26.01 | A |
| ATOM | 1452 | CG | MET | A | 419 | 52.636 | 54.261 | 74.531 | 1.00 | 30.30 | A |
| ATOM | 1453 | SD | MET | A | 419 | 51.791 | 54.634 | 76.096 | 1.00 | 34.61 | A |
| ATOM | 1454 | CE | MET | A | 419 | 52.841 | 53.640 | 76.985 | 1.00 | 35.10 | A |
| ATOM | 1455 | C | MET | A | 419 | 52.839 | 51.121 | 72.332 | 1.00 | 24.71 | A |
| ATOM | 1456 | O | MET | A | 419 | 53.632 | 50.509 | 73.052 | 1.00 | 25.76 | A |
| ATOM | 1457 | N | THR | A | 420 | 52.132 | 50.570 | 71.327 | 1.00 | 23.45 | A |
| ATOM | 1458 | CA | THR | A | 420 | 52.311 | 49.168 | 70.944 | 1.00 | 22.69 | A |
| ATOM | 1459 | CB | THR | A | 420 | 51.090 | 48.540 | 70.332 | 1.00 | 22.57 | A |
| ATOM | 1460 | OG1 | THR | A | 420 | 50.718 | 49.221 | 69.113 | 1.00 | 21.50 | A |
| ATOM | 1461 | CG2 | THR | A | 420 | 49.791 | 48.664 | 71.242 | 1.00 | 23.35 | A |
| ATOM | 1462 | C | THR | A | 420 | 53.470 | 48.998 | 69.915 | 1.00 | 22.89 | A |
| ATOM | 1463 | O | THR | A | 420 | 53.808 | 47.877 | 69.530 | 1.00 | 22.57 | A |
| ATOM | 1464 | N | LEU | A | 421 | 53.975 | 50.112 | 69.422 | 1.00 | 22.37 | A |
| ATOM | 1465 | CA | LEU | A | 421 | 54.963 | 50.086 | 68.348 | 1.00 | 22.27 | A |
| ATOM | 1466 | CB | LEU | A | 421 | 55.038 | 51.412 | 67.666 | 1.00 | 22.10 | A |
| ATOM | 1467 | CG | LEU | A | 421 | 53.757 | 51.753 | 66.854 | 1.00 | 22.88 | A |
| ATOM | 1468 | CD1 | LEU | A | 421 | 54.008 | 53.123 | 66.301 | 1.00 | 22.64 | A |
| ATOM | 1469 | CD2 | LEU | A | 421 | 53.424 | 50.924 | 65.708 | 1.00 | 23.43 | A |
| ATOM | 1470 | C | LEU | A | 421 | 56.318 | 49.520 | 68.770 | 1.00 | 22.52 | A |
| ATOM | 1471 | O | LEU | A | 421 | 56.941 | 48.855 | 68.009 | 1.00 | 21.53 | A |
| ATOM | 1472 | N | PRO | A | 422 | 56.746 | 49.778 | 69.970 | 1.00 | 20.83 | A |
| ATOM | 1473 | CD | PRO | A | 422 | 56.206 | 50.709 | 70.933 | 1.00 | 19.78 | A |
| ATOM | 1474 | CA | PRO | A | 422 | 57.983 | 49.154 | 70.449 | 1.00 | 21.84 | A |
| ATOM | 1475 | CB | PRO | A | 422 | 58.078 | 49.649 | 71.861 | 1.00 | 18.96 | A |
| ATOM | 1476 | CG | PRO | A | 422 | 57.467 | 51.052 | 71.730 | 1.00 | 20.88 | A |
| ATOM | 1477 | C | PRO | A | 422 | 57.941 | 47.590 | 70.380 | 1.00 | 22.21 | A |
| ATOM | 1478 | O | PRO | A | 422 | 58.869 | 47.048 | 69.864 | 1.00 | 22.40 | A |
| ATOM | 1479 | N | LEU | A | 423 | 56.890 | 46.961 | 70.866 | 1.00 | 21.23 | A |
| ATOM | 1480 | CA | LEU | A | 423 | 56.793 | 45.499 | 70.756 | 1.00 | 22.11 | A |
| ATOM | 1481 | CB | LEU | A | 423 | 55.522 | 44.973 | 71.502 | 1.00 | 21.53 | A |
| ATOM | 1482 | CG | LEU | A | 423 | 55.348 | 43.477 | 71.659 | 1.00 | 23.13 | A |
| ATOM | 1483 | CD1 | LEU | A | 423 | 56.599 | 42.926 | 72.225 | 1.00 | 23.25 | A |
| ATOM | 1484 | CD2 | LEU | A | 423 | 54.223 | 43.176 | 72.630 | 1.00 | 22.05 | A |
| ATOM | 1485 | C | LEU | A | 423 | 56.757 | 45.019 | 69.333 | 1.00 | 22.40 | A |
| ATOM | 1486 | O | LEU | A | 423 | 57.390 | 44.092 | 68.963 | 1.00 | 21.23 | A |
| ATOM | 1487 | N | LEU | A | 424 | 56.077 | 45.753 | 68.478 | 1.00 | 22.32 | A |
| ATOM | 1488 | CA | LEU | A | 424 | 56.101 | 45.377 | 67.062 | 1.00 | 21.29 | A |
| ATOM | 1489 | CB | LEU | A | 424 | 55.143 | 46.319 | 66.323 | 1.00 | 21.19 | A |
| ATOM | 1490 | CG | LEU | A | 424 | 55.236 | 46.145 | 64.804 | 1.00 | 21.68 | A |
| ATOM | 1491 | CD1 | LEU | A | 424 | 54.660 | 44.761 | 64.620 | 1.00 | 20.26 | A |
| ATOM | 1492 | CD2 | LEU | A | 424 | 54.401 | 47.193 | 64.188 | 1.00 | 21.23 | A |
| ATOM | 1493 | C | LEU | A | 424 | 57.535 | 45.367 | 66.519 | 1.00 | 22.52 | A |
| ATOM | 1494 | O | LEU | A | 424 | 57.919 | 44.535 | 65.695 | 1.00 | 21.09 | A |
| ATOM | 1495 | N | ARG | A | 425 | 58.294 | 46.426 | 66.852 | 1.00 | 22.51 | A |
| ATOM | 1496 | CA | ARG | A | 425 | 59.645 | 46.597 | 66.374 | 1.00 | 23.17 | A |
| ATOM | 1497 | CB | ARG | A | 425 | 60.206 | 47.927 | 66.917 | 1.00 | 22.72 | A |
| ATOM | 1498 | CG | ARG | A | 425 | 61.651 | 48.249 | 66.548 | 1.00 | 24.98 | A |
| ATOM | 1499 | CD | ARG | A | 425 | 62.000 | 48.609 | 65.244 | 1.00 | 24.90 | A |
| ATOM | 1500 | NE | ARG | A | 425 | 61.302 | 49.769 | 64.670 | 1.00 | 26.04 | A |
| ATOM | 1501 | CZ | ARG | A | 425 | 61.563 | 51.014 | 64.741 | 1.00 | 24.57 | A |
| ATOM | 1502 | NH1 | ARG | A | 425 | 62.568 | 51.421 | 65.390 | 1.00 | 24.96 | A |
| ATOM | 1503 | NH2 | ARG | A | 425 | 60.713 | 51.917 | 64.167 | 1.00 | 24.98 | A |
| ATOM | 1504 | C | ARG | A | 425 | 60.448 | 45.375 | 66.919 | 1.00 | 24.30 | A |
| ATOM | 1505 | O | ARG | A | 425 | 61.223 | 44.794 | 66.208 | 1.00 | 24.36 | A |
| ATOM | 1506 | N | GLN | A | 426 | 60.296 | 45.098 | 68.216 | 1.00 | 24.09 | A |
| ATOM | 1507 | CA | GLN | A | 426 | 61.045 | 44.113 | 68.937 | 1.00 | 25.88 | A |
| ATOM | 1508 | CB | GLN | A | 426 | 60.752 | 44.172 | 70.443 | 1.00 | 24.94 | A |
| ATOM | 1509 | CG | GLN | A | 426 | 61.392 | 43.074 | 71.306 | 1.00 | 28.77 | A |
| ATOM | 1510 | CD | GLN | A | 426 | 60.863 | 43.012 | 72.679 | 1.00 | 31.19 | A |
| ATOM | 1511 | OE1 | GLN | A | 426 | 60.535 | 44.037 | 73.257 | 1.00 | 32.54 | A |
| ATOM | 1512 | NE2 | GLN | A | 426 | 60.677 | 41.742 | 73.237 | 1.00 | 34.10 | A |
| ATOM | 1513 | C | GLN | A | 426 | 60.766 | 42.739 | 68.300 | 1.00 | 25.48 | A |

TABLE 2-continued

ATOMIC COORDINATES OF THE ERR3 LBD/
DIETHYLSTILBESTROL COMPLEX

| ATOM | 1514 | O   | GLN | A | 426 | 61.644 | 41.988 | 68.112 | 1.00 | 24.93 | A |
|------|------|-----|-----|---|-----|--------|--------|--------|------|-------|---|
| ATOM | 1515 | N   | THR | A | 427 | 59.544 | 42.426 | 67.995 | 1.00 | 26.03 | A |
| ATOM | 1516 | CA  | THR | A | 427 | 59.177 | 41.055 | 67.551 | 1.00 | 24.96 | A |
| ATOM | 1517 | CB  | THR | A | 427 | 57.679 | 40.968 | 67.569 | 1.00 | 24.91 | A |
| ATOM | 1518 | OG1 | THR | A | 427 | 57.168 | 41.236 | 68.868 | 1.00 | 24.39 | A |
| ATOM | 1519 | CG2 | THR | A | 427 | 57.096 | 39.681 | 67.055 | 1.00 | 22.93 | A |
| ATOM | 1520 | C   | THR | A | 427 | 59.622 | 40.957 | 66.074 | 1.00 | 25.17 | A |
| ATOM | 1521 | O   | THR | A | 427 | 59.963 | 39.956 | 65.604 | 1.00 | 24.36 | A |
| ATOM | 1522 | N   | SER | A | 428 | 59.617 | 42.048 | 65.340 | 1.00 | 25.65 | A |
| ATOM | 1523 | CA  | SER | A | 428 | 60.041 | 42.013 | 63.972 | 1.00 | 25.77 | A |
| ATOM | 1524 | CB  | SER | A | 428 | 59.580 | 43.210 | 63.230 | 1.00 | 26.35 | A |
| ATOM | 1525 | OG  | SER | A | 428 | 60.596 | 43.575 | 62.253 | 1.00 | 35.44 | A |
| ATOM | 1526 | C   | SER | A | 428 | 61.502 | 41.784 | 63.808 | 1.00 | 26.02 | A |
| ATOM | 1527 | O   | SER | A | 428 | 61.974 | 41.043 | 62.876 | 1.00 | 27.24 | A |
| ATOM | 1528 | N   | THR | A | 429 | 62.240 | 42.315 | 64.753 | 1.00 | 27.74 | A |
| ATOM | 1529 | CA  | THR | A | 429 | 63.689 | 42.171 | 64.800 | 1.00 | 28.82 | A |
| ATOM | 1530 | CB  | THR | A | 429 | 64.265 | 43.141 | 65.942 | 1.00 | 27.44 | A |
| ATOM | 1531 | OG1 | THR | A | 429 | 64.301 | 44.444 | 65.440 | 1.00 | 27.38 | A |
| ATOM | 1532 | CG2 | THR | A | 429 | 65.747 | 42.850 | 66.151 | 1.00 | 27.15 | A |
| ATOM | 1533 | C   | THR | A | 429 | 64.031 | 40.690 | 65.155 | 1.00 | 30.55 | A |
| ATOM | 1534 | O   | THR | A | 429 | 64.859 | 40.107 | 64.532 | 1.00 | 31.44 | A |
| ATOM | 1535 | N   | LYS | A | 430 | 63.351 | 40.083 | 66.112 | 1.00 | 30.87 | A |
| ATOM | 1536 | CA  | LYS | A | 430 | 63.435 | 38.651 | 66.383 | 1.00 | 32.91 | A |
| ATOM | 1537 | CB  | LYS | A | 430 | 62.693 | 38.383 | 67.680 | 1.00 | 35.01 | A |
| ATOM | 1538 | CG  | LYS | A | 430 | 62.476 | 36.949 | 68.023 | 1.00 | 38.66 | A |
| ATOM | 1539 | CD  | LYS | A | 430 | 61.752 | 36.847 | 69.428 | 1.00 | 42.42 | A |
| ATOM | 1540 | CE  | LYS | A | 430 | 61.777 | 35.392 | 69.962 | 1.00 | 43.74 | A |
| ATOM | 1541 | NZ  | LYS | A | 430 | 63.222 | 34.779 | 70.118 | 1.00 | 46.38 | A |
| ATOM | 1542 | C   | LYS | A | 430 | 63.038 | 37.763 | 65.168 | 1.00 | 33.73 | A |
| ATOM | 1543 | O   | LYS | A | 430 | 63.724 | 36.814 | 64.812 | 1.00 | 34.45 | A |
| ATOM | 1544 | N   | ALA | A | 431 | 62.016 | 38.124 | 64.419 | 1.00 | 32.97 | A |
| ATOM | 1545 | CA  | ALA | A | 431 | 61.711 | 37.364 | 63.246 | 1.00 | 31.97 | A |
| ATOM | 1546 | CB  | ALA | A | 431 | 60.392 | 37.791 | 62.723 | 1.00 | 29.51 | A |
| ATOM | 1547 | C   | ALA | A | 431 | 62.778 | 37.431 | 62.135 | 1.00 | 32.47 | A |
| ATOM | 1548 | O   | ALA | A | 431 | 63.072 | 36.461 | 61.453 | 1.00 | 31.12 | A |
| ATOM | 1549 | N   | VAL | A | 432 | 63.270 | 38.626 | 61.863 | 1.00 | 34.05 | A |
| ATOM | 1550 | CA  | VAL | A | 432 | 64.317 | 38.885 | 60.875 | 1.00 | 34.99 | A |
| ATOM | 1551 | CB  | VAL | A | 432 | 64.690 | 40.377 | 60.840 | 1.00 | 35.69 | A |
| ATOM | 1552 | CG1 | VAL | A | 432 | 65.996 | 40.566 | 60.214 | 1.00 | 36.19 | A |
| ATOM | 1553 | CG2 | VAL | A | 432 | 63.687 | 41.095 | 60.070 | 1.00 | 38.00 | A |
| ATOM | 1554 | C   | VAL | A | 432 | 65.595 | 38.038 | 61.269 | 1.00 | 36.52 | A |
| ATOM | 1555 | O   | VAL | A | 432 | 66.177 | 37.319 | 60.455 | 1.00 | 36.02 | A |
| ATOM | 1556 | N   | GLN | A | 433 | 65.941 | 38.052 | 62.519 | 1.00 | 37.86 | A |
| ATOM | 1557 | CA  | GLN | A | 433 | 67.102 | 37.361 | 62.990 | 1.00 | 40.93 | A |
| ATOM | 1558 | CB  | GLN | A | 433 | 67.484 | 37.662 | 64.441 | 1.00 | 41.37 | A |
| ATOM | 1559 | CG  | GLN | A | 433 | 68.342 | 39.055 | 64.566 | 1.00 | 46.86 | A |
| ATOM | 1560 | CD  | GLN | A | 433 | 68.333 | 39.668 | 66.029 | 1.00 | 48.66 | A |
| ATOM | 1561 | OE1 | GLN | A | 433 | 67.681 | 39.089 | 66.988 | 1.00 | 50.73 | A |
| ATOM | 1562 | NE2 | GLN | A | 433 | 69.009 | 40.825 | 66.192 | 1.00 | 49.68 | A |
| ATOM | 1563 | C   | GLN | A | 433 | 66.822 | 35.840 | 62.906 | 1.00 | 42.31 | A |
| ATOM | 1564 | O   | GLN | A | 433 | 67.820 | 35.085 | 62.777 | 1.00 | 42.02 | A |
| ATOM | 1565 | N   | HIS | A | 434 | 65.556 | 35.402 | 63.034 | 1.00 | 42.86 | A |
| ATOM | 1566 | CA  | HIS | A | 434 | 65.271 | 33.970 | 62.948 | 1.00 | 44.63 | A |
| ATOM | 1567 | CB  | HIS | A | 434 | 63.883 | 33.668 | 63.488 | 1.00 | 43.33 | A |
| ATOM | 1568 | CG  | HIS | A | 434 | 63.512 | 32.214 | 63.535 | 1.00 | 42.63 | A |
| ATOM | 1569 | CD2 | HIS | A | 434 | 63.173 | 31.431 | 64.589 | 1.00 | 42.07 | A |
| ATOM | 1570 | ND1 | HIS | A | 434 | 63.353 | 31.431 | 62.390 | 1.00 | 41.46 | A |
| ATOM | 1571 | CE1 | HIS | A | 434 | 63.029 | 30.203 | 62.774 | 1.00 | 43.22 | A |
| ATOM | 1572 | NE2 | HIS | A | 434 | 62.920 | 30.176 | 64.103 | 1.00 | 43.23 | A |
| ATOM | 1573 | C   | HIS | A | 434 | 65.466 | 33.560 | 61.484 | 1.00 | 46.05 | A |
| ATOM | 1574 | O   | HIS | A | 434 | 66.086 | 32.623 | 61.206 | 1.00 | 45.82 | A |
| ATOM | 1575 | N   | PHE | A | 435 | 64.967 | 34.343 | 60.583 | 1.00 | 48.43 | A |
| ATOM | 1576 | CA  | PHE | A | 435 | 65.072 | 34.183 | 59.178 | 1.00 | 51.58 | A |
| ATOM | 1577 | CB  | PHE | A | 435 | 64.381 | 35.407 | 58.593 | 1.00 | 53.36 | A |
| ATOM | 1578 | CG  | PHE | A | 435 | 64.171 | 35.445 | 57.062 | 1.00 | 55.91 | A |
| ATOM | 1579 | CD1 | PHE | A | 435 | 63.433 | 34.489 | 56.390 | 1.00 | 56.60 | A |
| ATOM | 1580 | CD2 | PHE | A | 435 | 64.655 | 36.584 | 56.300 | 1.00 | 56.58 | A |
| ATOM | 1581 | CE1 | PHE | A | 435 | 63.246 | 34.593 | 54.935 | 1.00 | 56.65 | A |
| ATOM | 1582 | CE2 | PHE | A | 435 | 64.454 | 36.710 | 54.898 | 1.00 | 57.41 | A |
| ATOM | 1583 | CZ  | PHE | A | 435 | 63.713 | 35.699 | 54.218 | 1.00 | 57.05 | A |
| ATOM | 1584 | C   | PHE | A | 435 | 66.510 | 34.107 | 58.700 | 1.00 | 53.52 | A |
| ATOM | 1585 | O   | PHE | A | 435 | 66.704 | 33.572 | 57.592 | 1.00 | 54.46 | A |
| ATOM | 1586 | N   | TYR | A | 436 | 67.458 | 34.741 | 59.430 | 1.00 | 54.45 | A |
| ATOM | 1587 | CA  | TYR | A | 436 | 68.917 | 34.662 | 59.195 | 1.00 | 55.22 | A |
| ATOM | 1588 | CB  | TYR | A | 436 | 69.693 | 35.903 | 59.814 | 1.00 | 55.18 | A |
| ATOM | 1589 | CG  | TYR | A | 436 | 69.770 | 37.201 | 58.901 | 1.00 | 54.94 | A |

TABLE 2-continued

ATOMIC COORDINATES OF THE ERR3 LBD/
DIETHYLSTILBESTROL COMPLEX

| ATOM | 1590 | CD1 | TYR | A | 436 | 69.621 | 37.114 | 57.522 | 1.00 | 54.41 | A |
|------|------|-----|-----|---|-----|--------|--------|--------|------|-------|---|
| ATOM | 1591 | CE1 | TYR | A | 436 | 69.075 | 37.982 | 56.702 | 0.00 | 54.70 | A |
| ATOM | 1592 | CD2 | TYR | A | 436 | 69.853 | 38.518 | 59.479 | 1.00 | 55.03 | A |
| ATOM | 1593 | CE2 | TYR | A | 436 | 69.702 | 39.402 | 58.566 | 0.00 | 54.85 | A |
| ATOM | 1594 | CZ  | TYR | A | 436 | 69.339 | 39.255 | 57.221 | 0.00 | 54.75 | A |
| ATOM | 1595 | OH  | TYR | A | 436 | 69.102 | 40.388 | 56.416 | 0.00 | 54.77 | A |
| ATOM | 1596 | C   | TYR | A | 436 | 69.499 | 33.366 | 59.787 | 1.00 | 56.56 | A |
| ATOM | 1597 | O   | TYR | A | 436 | 70.194 | 32.654 | 59.126 | 1.00 | 56.75 | A |
| ATOM | 1598 | N   | ASN | A | 437 | 69.175 | 33.006 | 61.008 | 1.00 | 58.00 | A |
| ATOM | 1599 | CA  | ASN | A | 437 | 69.683 | 31.750 | 61.562 | 1.00 | 60.99 | A |
| ATOM | 1600 | CB  | ASN | A | 437 | 69.184 | 31.462 | 63.013 | 1.00 | 61.06 | A |
| ATOM | 1601 | CG  | ASN | A | 437 | 70.058 | 32.091 | 64.103 | 1.00 | 61.96 | A |
| ATOM | 1602 | OD1 | ASN | A | 437 | 70.231 | 33.314 | 64.167 | 1.00 | 62.45 | A |
| ATOM | 1603 | ND2 | ASN | A | 437 | 70.391 | 31.284 | 65.145 | 0.00 | 61.74 | A |
| ATOM | 1604 | C   | ASN | A | 437 | 69.364 | 30.508 | 60.676 | 1.00 | 62.93 | A |
| ATOM | 1605 | O   | ASN | A | 437 | 70.146 | 29.518 | 60.750 | 1.00 | 63.46 | A |
| ATOM | 1606 | N   | ILE | A | 438 | 68.232 | 30.544 | 59.912 | 1.00 | 63.49 | A |
| ATOM | 1607 | CA  | ILE | A | 438 | 67.789 | 29.439 | 59.040 | 1.00 | 64.30 | A |
| ATOM | 1608 | CB  | ILE | A | 438 | 66.148 | 29.253 | 58.901 | 1.00 | 63.56 | A |
| ATOM | 1609 | CG2 | ILE | A | 438 | 65.454 | 29.261 | 60.240 | 1.00 | 62.42 | A |
| ATOM | 1610 | CG1 | ILE | A | 438 | 65.503 | 30.267 | 57.922 | 1.00 | 62.79 | A |
| ATOM | 1611 | CD1 | ILE | A | 438 | 65.049 | 29.667 | 56.469 | 1.00 | 62.05 | A |
| ATOM | 1612 | C   | ILE | A | 438 | 68.373 | 29.608 | 57.650 | 1.00 | 65.67 | A |
| ATOM | 1613 | O   | ILE | A | 438 | 68.697 | 28.597 | 56.971 | 1.00 | 65.27 | A |
| ATOM | 1614 | N   | LYS | A | 439 | 68.440 | 30.864 | 57.197 | 1.00 | 67.02 | A |
| ATOM | 1615 | CA  | LYS | A | 439 | 68.846 | 31.161 | 55.802 | 1.00 | 68.65 | A |
| ATOM | 1616 | CB  | LYS | A | 439 | 68.292 | 32.536 | 55.344 | 1.00 | 68.58 | A |
| ATOM | 1617 | CG  | LYS | A | 439 | 69.103 | 33.340 | 54.310 | 1.00 | 68.90 | A |
| ATOM | 1618 | CD  | LYS | A | 439 | 68.154 | 34.173 | 53.377 | 1.00 | 70.29 | A |
| ATOM | 1619 | CE  | LYS | A | 439 | 68.835 | 34.738 | 52.092 | 1.00 | 71.14 | A |
| ATOM | 1620 | NZ  | LYS | A | 439 | 69.546 | 36.047 | 52.247 | 1.00 | 72.03 | A |
| ATOM | 1621 | C   | LYS | A | 439 | 70.359 | 31.176 | 55.721 | 1.00 | 69.76 | A |
| ATOM | 1622 | O   | LYS | A | 439 | 70.913 | 31.246 | 54.633 | 1.00 | 70.56 | A |
| ATOM | 1623 | N   | LEU | A | 440 | 70.996 | 31.236 | 56.904 | 1.00 | 70.37 | A |
| ATOM | 1624 | CA  | LEU | A | 440 | 72.387 | 30.860 | 57.098 | 1.00 | 70.35 | A |
| ATOM | 1625 | CB  | LEU | A | 440 | 72.806 | 30.989 | 58.623 | 1.00 | 69.85 | A |
| ATOM | 1626 | CG  | LEU | A | 440 | 74.225 | 30.892 | 59.248 | 1.00 | 69.10 | A |
| ATOM | 1627 | CD1 | LEU | A | 440 | 74.450 | 31.705 | 60.592 | 1.00 | 67.66 | A |
| ATOM | 1628 | CD2 | LEU | A | 440 | 74.466 | 29.376 | 59.651 | 0.00 | 68.72 | A |
| ATOM | 1629 | C   | LEU | A | 440 | 72.206 | 29.418 | 56.590 | 1.00 | 70.91 | A |
| ATOM | 1630 | O   | LEU | A | 440 | 72.346 | 29.188 | 55.401 | 1.00 | 71.12 | A |
| ATOM | 1631 | N   | GLU | A | 441 | 71.719 | 28.525 | 57.471 | 1.00 | 71.34 | A |
| ATOM | 1632 | CA  | GLU | A | 441 | 71.619 | 27.062 | 57.243 | 1.00 | 71.30 | A |
| ATOM | 1633 | CB  | GLU | A | 441 | 70.770 | 26.406 | 58.353 | 1.00 | 71.38 | A |
| ATOM | 1634 | CG  | GLU | A | 441 | 71.342 | 26.692 | 59.739 | 1.00 | 72.35 | A |
| ATOM | 1635 | CD  | GLU | A | 441 | 70.409 | 26.297 | 60.878 | 1.00 | 73.24 | A |
| ATOM | 1636 | OE1 | GLU | A | 441 | 69.253 | 25.829 | 60.603 | 1.00 | 74.12 | A |
| ATOM | 1637 | OE2 | GLU | A | 441 | 70.833 | 26.458 | 62.055 | 1.00 | 72.59 | A |
| ATOM | 1638 | C   | GLU | A | 441 | 71.126 | 26.592 | 55.868 | 1.00 | 70.93 | A |
| ATOM | 1639 | O   | GLU | A | 441 | 71.224 | 25.402 | 55.588 | 1.00 | 70.75 | A |
| ATOM | 1640 | N   | GLY | A | 442 | 70.985 | 27.084 | 54.905 | 0.00 | 70.98 | A |
| ATOM | 1641 | CA  | GLY | A | 442 | 70.813 | 26.726 | 53.564 | 0.00 | 71.11 | A |
| ATOM | 1642 | C   | GLY | A | 442 | 69.788 | 25.622 | 53.334 | 0.00 | 71.35 | A |
| ATOM | 1643 | O   | GLY | A | 442 | 69.381 | 25.506 | 52.148 | 0.00 | 71.18 | A |
| ATOM | 1644 | N   | LYS | A | 443 | 69.209 | 25.174 | 54.433 | 1.00 | 71.70 | A |
| ATOM | 1645 | CA  | LYS | A | 443 | 68.287 | 24.098 | 54.005 | 1.00 | 72.54 | A |
| ATOM | 1646 | CB  | LYS | A | 443 | 68.057 | 23.053 | 55.162 | 1.00 | 72.51 | A |
| ATOM | 1647 | CG  | LYS | A | 443 | 69.276 | 22.828 | 56.266 | 1.00 | 72.22 | A |
| ATOM | 1648 | CD  | LYS | A | 443 | 70.130 | 21.481 | 56.125 | 1.00 | 71.56 | A |
| ATOM | 1649 | CE  | LYS | A | 443 | 70.152 | 20.383 | 56.676 | 0.00 | 71.16 | A |
| ATOM | 1650 | NZ  | LYS | A | 443 | 68.890 | 20.335 | 58.215 | 0.00 | 70.80 | A |
| ATOM | 1651 | C   | LYS | A | 443 | 66.909 | 24.637 | 53.398 | 1.00 | 73.02 | A |
| ATOM | 1652 | O   | LYS | A | 443 | 66.177 | 23.877 | 52.692 | 1.00 | 73.22 | A |
| ATOM | 1653 | N   | VAL | A | 444 | 66.622 | 25.942 | 53.616 | 1.00 | 73.26 | A |
| ATOM | 1654 | CA  | VAL | A | 444 | 65.418 | 26.601 | 53.096 | 1.00 | 73.71 | A |
| ATOM | 1655 | CB  | VAL | A | 444 | 64.794 | 27.724 | 53.798 | 0.00 | 73.32 | A |
| ATOM | 1656 | CG1 | VAL | A | 444 | 64.752 | 29.121 | 53.125 | 0.00 | 73.07 | A |
| ATOM | 1657 | CG2 | VAL | A | 444 | 63.301 | 27.380 | 54.128 | 0.00 | 73.07 | A |
| ATOM | 1658 | C   | VAL | A | 444 | 65.538 | 27.164 | 51.672 | 1.00 | 74.31 | A |
| ATOM | 1659 | O   | VAL | A | 444 | 64.527 | 27.289 | 50.951 | 1.00 | 74.51 | A |
| ATOM | 1660 | OXT | VAL | A | 444 | 66.675 | 27.453 | 51.282 | 1.00 | 75.10 | A |
| ATOM | 1661 | CB  | ASN | B | 235 | 52.083 | 67.931 | 85.456 | 1.00 | 43.49 | B |
| ATOM | 1662 | CG  | ASN | B | 235 | 51.785 | 66.352 | 85.471 | 1.00 | 42.24 | B |
| ATOM | 1663 | OD1 | ASN | B | 235 | 52.572 | 65.540 | 86.011 | 1.00 | 40.35 | B |
| ATOM | 1664 | ND2 | ASN | B | 235 | 50.599 | 66.014 | 85.089 | 1.00 | 42.99 | B |
| ATOM | 1665 | C   | ASN | B | 235 | 52.664 | 67.797 | 87.904 | 1.00 | 42.50 | B |

TABLE 2-continued

ATOMIC COORDINATES OF THE ERR3 LBD/
DIETHYLSTILBESTROL COMPLEX

| ATOM | 1666 | O | ASN | B | 235 | 53.885 | 67.652 | 87.845 | 1.00 | 42.74 | B |
|------|------|-----|-----|---|-----|--------|--------|--------|------|-------|---|
| ATOM | 1667 | N | ASN | B | 235 | 52.226 | 70.131 | 86.793 | 1.00 | 45.37 | B |
| ATOM | 1668 | CA | ASN | B | 235 | 51.899 | 68.598 | 86.835 | 1.00 | 42.46 | B |
| ATOM | 1669 | N | LYS | B | 236 | 51.907 | 67.192 | 88.846 | 1.00 | 42.33 | B |
| ATOM | 1670 | CA | LYS | B | 236 | 52.470 | 66.573 | 90.059 | 1.00 | 40.83 | B |
| ATOM | 1671 | CB | LYS | B | 236 | 51.340 | 66.009 | 90.904 | 1.00 | 40.40 | B |
| ATOM | 1672 | CG | LYS | B | 236 | 51.739 | 65.206 | 92.177 | 1.00 | 40.69 | B |
| ATOM | 1673 | CD | LYS | B | 236 | 52.536 | 66.095 | 93.108 | 1.00 | 40.75 | B |
| ATOM | 1674 | CE | LYS | B | 236 | 52.880 | 65.372 | 94.370 | 1.00 | 39.82 | B |
| ATOM | 1675 | NZ | LYS | B | 236 | 53.936 | 66.014 | 95.082 | 1.00 | 40.11 | B |
| ATOM | 1676 | C | LYS | B | 236 | 53.424 | 65.389 | 89.734 | 1.00 | 39.53 | B |
| ATOM | 1677 | O | LYS | B | 236 | 54.538 | 65.276 | 90.271 | 1.00 | 39.38 | B |
| ATOM | 1678 | N | ILE | B | 237 | 52.916 | 64.503 | 88.879 | 1.00 | 37.39 | B |
| ATOM | 1679 | CA | ILE | B | 237 | 53.697 | 63.334 | 88.416 | 1.00 | 35.99 | B |
| ATOM | 1680 | CB | ILE | B | 237 | 52.860 | 62.500 | 87.343 | 1.00 | 36.94 | B |
| ATOM | 1681 | CG2 | ILE | B | 237 | 53.690 | 61.249 | 86.944 | 1.00 | 37.44 | B |
| ATOM | 1682 | CG1 | ILE | B | 237 | 51.659 | 61.992 | 88.001 | 1.00 | 37.55 | B |
| ATOM | 1683 | CD1 | ILE | B | 237 | 51.975 | 60.988 | 89.146 | 1.00 | 38.75 | B |
| ATOM | 1684 | C | ILE | B | 237 | 55.003 | 63.789 | 87.833 | 1.00 | 33.92 | B |
| ATOM | 1685 | O | ILE | B | 237 | 56.064 | 63.399 | 88.259 | 1.00 | 31.93 | B |
| ATOM | 1686 | N | VAL | B | 238 | 54.946 | 64.725 | 86.913 | 1.00 | 34.84 | B |
| ATOM | 1687 | CA | VAL | B | 238 | 56.231 | 65.240 | 86.333 | 1.00 | 34.61 | B |
| ATOM | 1688 | CB | VAL | B | 238 | 56.020 | 66.212 | 85.232 | 1.00 | 34.85 | B |
| ATOM | 1689 | CG1 | VAL | B | 238 | 57.352 | 66.722 | 84.726 | 1.00 | 33.36 | B |
| ATOM | 1690 | CG2 | VAL | B | 238 | 55.289 | 65.613 | 84.103 | 1.00 | 34.67 | B |
| ATOM | 1691 | C | VAL | B | 238 | 57.115 | 65.933 | 87.360 | 1.00 | 36.12 | B |
| ATOM | 1692 | O | VAL | B | 238 | 58.346 | 65.852 | 87.319 | 1.00 | 36.89 | B |
| ATOM | 1693 | N | SER | B | 239 | 56.503 | 66.584 | 88.373 | 1.00 | 37.51 | B |
| ATOM | 1694 | CA | SER | B | 239 | 57.334 | 67.317 | 89.351 | 1.00 | 37.39 | B |
| ATOM | 1695 | CB | SER | B | 239 | 56.483 | 68.318 | 90.264 | 1.00 | 38.77 | B |
| ATOM | 1696 | OG | SER | B | 239 | 56.730 | 69.596 | 89.759 | 1.00 | 43.71 | B |
| ATOM | 1697 | C | SER | B | 239 | 58.079 | 66.376 | 90.160 | 1.00 | 35.41 | B |
| ATOM | 1698 | O | SER | B | 239 | 59.297 | 66.499 | 90.459 | 1.00 | 35.25 | B |
| ATOM | 1699 | N | HIS | B | 240 | 57.375 | 65.371 | 90.484 | 1.00 | 33.82 | B |
| ATOM | 1700 | CA | HIS | B | 240 | 57.935 | 64.337 | 91.312 | 1.00 | 34.11 | B |
| ATOM | 1701 | CB | HIS | B | 240 | 56.815 | 63.400 | 91.720 | 1.00 | 32.86 | B |
| ATOM | 1702 | CG | HIS | B | 240 | 57.292 | 62.289 | 92.584 | 1.00 | 33.55 | B |
| ATOM | 1703 | CD2 | HIS | B | 240 | 57.507 | 60.992 | 92.320 | 1.00 | 34.75 | B |
| ATOM | 1704 | ND1 | HIS | B | 240 | 57.792 | 62.516 | 93.846 | 1.00 | 34.16 | B |
| ATOM | 1705 | CE1 | HIS | B | 240 | 58.252 | 61.394 | 94.337 | 1.00 | 34.14 | B |
| ATOM | 1706 | NE2 | HIS | B | 240 | 58.158 | 60.466 | 93.405 | 1.00 | 35.70 | B |
| ATOM | 1707 | C | HIS | B | 240 | 59.064 | 63.546 | 90.580 | 1.00 | 33.80 | B |
| ATOM | 1708 | O | HIS | B | 240 | 60.101 | 63.278 | 91.137 | 1.00 | 34.52 | B |
| ATOM | 1709 | N | LEU | B | 241 | 58.883 | 63.268 | 89.295 | 1.00 | 33.74 | B |
| ATOM | 1710 | CA | LEU | B | 241 | 59.948 | 62.541 | 88.549 | 1.00 | 32.61 | B |
| ATOM | 1711 | CB | LEU | B | 241 | 59.478 | 62.143 | 87.168 | 1.00 | 31.05 | B |
| ATOM | 1712 | CG | LEU | B | 241 | 58.442 | 61.076 | 87.092 | 1.00 | 28.51 | B |
| ATOM | 1713 | CD1 | LEU | B | 241 | 57.825 | 60.954 | 85.678 | 1.00 | 26.21 | B |
| ATOM | 1714 | CD2 | LEU | B | 241 | 58.989 | 59.780 | 87.572 | 1.00 | 26.27 | B |
| ATOM | 1715 | C | LEU | B | 241 | 61.154 | 63.503 | 88.459 | 1.00 | 33.49 | B |
| ATOM | 1716 | O | LEU | B | 241 | 62.250 | 63.039 | 88.584 | 1.00 | 31.55 | B |
| ATOM | 1717 | N | LEU | B | 242 | 60.960 | 64.819 | 88.304 | 1.00 | 34.94 | B |
| ATOM | 1718 | CA | LEU | B | 242 | 62.169 | 65.674 | 88.424 | 1.00 | 36.88 | B |
| ATOM | 1719 | CB | LEU | B | 242 | 61.912 | 67.181 | 88.178 | 1.00 | 37.77 | B |
| ATOM | 1720 | CG | LEU | B | 242 | 61.331 | 67.461 | 86.798 | 1.00 | 38.41 | B |
| ATOM | 1721 | CD1 | LEU | B | 242 | 60.569 | 68.796 | 86.764 | 1.00 | 36.58 | B |
| ATOM | 1722 | CD2 | LEU | B | 242 | 62.384 | 67.314 | 85.703 | 1.00 | 36.72 | B |
| ATOM | 1723 | C | LEU | B | 242 | 62.935 | 65.508 | 89.712 | 1.00 | 38.25 | B |
| ATOM | 1724 | O | LEU | B | 242 | 64.112 | 65.205 | 89.720 | 1.00 | 38.90 | B |
| ATOM | 1725 | N | VAL | B | 243 | 62.281 | 65.614 | 90.842 | 1.00 | 39.81 | B |
| ATOM | 1726 | CA | VAL | B | 243 | 63.065 | 65.616 | 92.050 | 1.00 | 40.26 | B |
| ATOM | 1727 | CB | VAL | B | 243 | 62.238 | 66.135 | 93.236 | 1.00 | 41.11 | B |
| ATOM | 1728 | CG1 | VAL | B | 243 | 61.822 | 67.585 | 93.020 | 1.00 | 40.42 | B |
| ATOM | 1729 | CG2 | VAL | B | 243 | 61.010 | 65.200 | 93.430 | 1.00 | 41.07 | B |
| ATOM | 1730 | C | VAL | B | 243 | 63.536 | 64.217 | 92.347 | 1.00 | 41.25 | B |
| ATOM | 1731 | O | VAL | B | 243 | 64.479 | 64.009 | 93.147 | 1.00 | 41.43 | B |
| ATOM | 1732 | N | ALA | B | 244 | 62.855 | 63.220 | 91.760 | 1.00 | 41.64 | B |
| ATOM | 1733 | CA | ALA | B | 244 | 63.328 | 61.808 | 91.856 | 1.00 | 41.57 | B |
| ATOM | 1734 | CB | ALA | B | 244 | 62.239 | 60.873 | 91.429 | 1.00 | 41.38 | B |
| ATOM | 1735 | C | ALA | B | 244 | 64.624 | 61.521 | 91.027 | 1.00 | 42.19 | B |
| ATOM | 1736 | O | ALA | B | 244 | 65.269 | 60.536 | 91.209 | 1.00 | 42.94 | B |
| ATOM | 1737 | N | GLU | B | 245 | 65.025 | 62.391 | 90.145 | 1.00 | 42.81 | B |
| ATOM | 1738 | CA | GLU | B | 245 | 66.203 | 62.066 | 89.325 | 1.00 | 44.09 | B |
| ATOM | 1739 | CB | GLU | B | 245 | 66.574 | 63.222 | 88.462 | 1.00 | 42.60 | B |
| ATOM | 1740 | CG | GLU | B | 245 | 65.883 | 63.336 | 87.131 | 1.00 | 43.38 | B |
| ATOM | 1741 | CD | GLU | B | 245 | 66.409 | 62.226 | 86.099 | 1.00 | 43.58 | B |

TABLE 2-continued

ATOMIC COORDINATES OF THE ERR3 LBD/
DIETHYLSTILBESTROL COMPLEX

| ATOM | 1742 | OE1 | GLU | B | 245 | 67.514 | 62.316 | 85.490 | 1.00 | 44.49 | B |
|---|---|---|---|---|---|---|---|---|---|---|---|
| ATOM | 1743 | OE2 | GLU | B | 245 | 65.731 | 61.218 | 86.090 | 1.00 | 41.63 | B |
| ATOM | 1744 | C | GLU | B | 245 | 67.465 | 61.820 | 90.159 | 1.00 | 45.74 | B |
| ATOM | 1745 | O | GLU | B | 245 | 67.896 | 62.715 | 90.809 | 1.00 | 46.79 | B |
| ATOM | 1746 | N | PRO | B | 246 | 68.178 | 60.741 | 89.945 | 1.00 | 46.62 | B |
| ATOM | 1747 | CD | PRO | B | 246 | 67.881 | 59.735 | 88.918 | 1.00 | 46.58 | B |
| ATOM | 1748 | CA | PRO | B | 246 | 69.426 | 60.504 | 90.668 | 1.00 | 47.87 | B |
| ATOM | 1749 | CB | PRO | B | 246 | 69.696 | 59.057 | 90.446 | 1.00 | 47.93 | B |
| ATOM | 1750 | CG | PRO | B | 246 | 68.466 | 58.555 | 89.622 | 1.00 | 47.91 | B |
| ATOM | 1751 | C | PRO | B | 246 | 70.562 | 61.406 | 90.237 | 1.00 | 49.18 | B |
| ATOM | 1752 | O | PRO | B | 246 | 70.418 | 62.117 | 89.249 | 1.00 | 48.85 | B |
| ATOM | 1753 | N | GLU | B | 247 | 71.574 | 61.583 | 91.090 | 1.00 | 51.10 | B |
| ATOM | 1754 | CA | GLU | B | 247 | 72.569 | 62.655 | 90.849 | 1.00 | 53.49 | B |
| ATOM | 1755 | CB | GLU | B | 247 | 73.310 | 63.166 | 92.110 | 1.00 | 57.02 | B |
| ATOM | 1756 | CG | GLU | B | 247 | 73.888 | 62.071 | 93.017 | 1.00 | 63.54 | B |
| ATOM | 1757 | CD | GLU | B | 247 | 72.830 | 61.257 | 93.757 | 1.00 | 67.32 | B |
| ATOM | 1758 | OE1 | GLU | B | 247 | 73.213 | 60.280 | 94.435 | 1.00 | 69.88 | B |
| ATOM | 1759 | OE2 | GLU | B | 247 | 71.625 | 61.583 | 93.676 | 1.00 | 69.73 | B |
| ATOM | 1760 | C | GLU | B | 247 | 73.615 | 62.016 | 89.953 | 1.00 | 52.50 | B |
| ATOM | 1761 | O | GLU | B | 247 | 73.773 | 60.815 | 90.020 | 1.00 | 52.38 | B |
| ATOM | 1762 | N | LYS | B | 248 | 74.343 | 62.849 | 89.211 | 1.00 | 52.22 | B |
| ATOM | 1763 | CA | LYS | B | 248 | 75.525 | 62.464 | 88.464 | 1.00 | 52.54 | B |
| ATOM | 1764 | CB | LYS | B | 248 | 76.316 | 63.748 | 88.138 | 1.00 | 55.11 | B |
| ATOM | 1765 | CG | LYS | B | 248 | 76.120 | 64.957 | 89.093 | 1.00 | 60.09 | B |
| ATOM | 1766 | CD | LYS | B | 248 | 76.394 | 64.657 | 90.575 | 1.00 | 62.15 | B |
| ATOM | 1767 | CE | LYS | B | 248 | 77.873 | 64.466 | 90.873 | 1.00 | 63.90 | B |
| ATOM | 1768 | NZ | LYS | B | 248 | 78.113 | 64.173 | 92.313 | 1.00 | 65.03 | B |
| ATOM | 1769 | C | LYS | B | 248 | 76.393 | 61.274 | 89.006 | 1.00 | 51.24 | B |
| ATOM | 1770 | O | LYS | B | 248 | 76.533 | 61.032 | 90.210 | 1.00 | 51.00 | B |
| ATOM | 1771 | N | ILE | B | 249 | 76.818 | 60.396 | 88.097 | 1.00 | 49.12 | B |
| ATOM | 1772 | CA | ILE | B | 249 | 77.632 | 59.210 | 88.444 | 1.00 | 47.11 | B |
| ATOM | 1773 | CB | ILE | B | 249 | 76.906 | 57.881 | 88.248 | 1.00 | 47.08 | B |
| ATOM | 1774 | CG2 | ILE | B | 249 | 77.848 | 56.706 | 88.547 | 1.00 | 46.11 | B |
| ATOM | 1775 | CG1 | ILE | B | 249 | 75.539 | 57.704 | 89.050 | 1.00 | 46.04 | B |
| ATOM | 1776 | CD1 | ILE | B | 249 | 74.945 | 56.574 | 88.754 | 0.00 | 46.44 | B |
| ATOM | 1777 | C | ILE | B | 249 | 78.801 | 59.331 | 87.441 | 1.00 | 46.53 | B |
| ATOM | 1778 | O | ILE | B | 249 | 78.576 | 59.881 | 86.309 | 1.00 | 45.84 | B |
| ATOM | 1779 | N | TYR | B | 250 | 80.031 | 58.934 | 87.848 | 1.00 | 45.09 | B |
| ATOM | 1780 | CA | TYR | B | 250 | 81.238 | 59.293 | 87.114 | 1.00 | 44.76 | B |
| ATOM | 1781 | CB | TYR | B | 250 | 82.260 | 60.095 | 88.051 | 1.00 | 46.27 | B |
| ATOM | 1782 | CG | TYR | B | 250 | 81.773 | 61.473 | 88.313 | 1.00 | 47.10 | B |
| ATOM | 1783 | CD1 | TYR | B | 250 | 81.817 | 62.477 | 87.297 | 1.00 | 48.04 | B |
| ATOM | 1784 | CE1 | TYR | B | 250 | 81.233 | 63.676 | 87.512 | 1.00 | 47.87 | B |
| ATOM | 1785 | CD2 | TYR | B | 250 | 81.086 | 61.745 | 89.508 | 1.00 | 47.77 | B |
| ATOM | 1786 | CE2 | TYR | B | 250 | 80.512 | 62.942 | 89.706 | 1.00 | 47.85 | B |
| ATOM | 1787 | CZ | TYR | B | 250 | 80.573 | 63.885 | 88.717 | 1.00 | 47.98 | B |
| ATOM | 1788 | OH | TYR | B | 250 | 80.034 | 65.077 | 89.000 | 1.00 | 48.86 | B |
| ATOM | 1789 | C | TYR | B | 250 | 81.792 | 57.969 | 86.719 | 1.00 | 43.75 | B |
| ATOM | 1790 | O | TYR | B | 250 | 81.613 | 56.990 | 87.478 | 1.00 | 42.87 | B |
| ATOM | 1791 | N | ALA | B | 251 | 82.476 | 57.887 | 85.581 | 1.00 | 42.98 | B |
| ATOM | 1792 | CA | ALA | B | 251 | 83.102 | 56.590 | 85.219 | 1.00 | 43.73 | B |
| ATOM | 1793 | CB | ALA | B | 251 | 83.278 | 56.489 | 83.776 | 1.00 | 42.94 | B |
| ATOM | 1794 | C | ALA | B | 251 | 84.436 | 56.261 | 85.877 | 1.00 | 44.39 | B |
| ATOM | 1795 | O | ALA | B | 251 | 84.783 | 55.058 | 86.067 | 1.00 | 43.56 | B |
| ATOM | 1796 | N | MET | B | 252 | 85.186 | 57.331 | 86.185 | 1.00 | 45.63 | B |
| ATOM | 1797 | CA | MET | B | 252 | 86.498 | 57.248 | 86.878 | 1.00 | 46.25 | B |
| ATOM | 1798 | CB | MET | B | 252 | 86.283 | 56.734 | 88.298 | 1.00 | 47.51 | B |
| ATOM | 1799 | CG | MET | B | 252 | 85.623 | 57.803 | 89.144 | 1.00 | 50.56 | B |
| ATOM | 1800 | SD | MET | B | 252 | 85.160 | 57.366 | 90.878 | 1.00 | 54.66 | B |
| ATOM | 1801 | CE | MET | B | 252 | 83.430 | 56.226 | 90.903 | 1.00 | 53.11 | B |
| ATOM | 1802 | C | MET | B | 252 | 87.424 | 56.339 | 86.092 | 1.00 | 46.52 | B |
| ATOM | 1803 | O | MET | B | 252 | 87.859 | 55.283 | 86.593 | 1.00 | 44.65 | B |
| ATOM | 1804 | N | PRO | B | 253 | 87.727 | 56.738 | 84.859 | 1.00 | 47.16 | B |
| ATOM | 1805 | CD | PRO | B | 253 | 87.301 | 57.937 | 84.157 | 1.00 | 47.34 | B |
| ATOM | 1806 | CA | PRO | B | 253 | 88.686 | 55.964 | 84.071 | 1.00 | 49.55 | B |
| ATOM | 1807 | CB | PRO | B | 253 | 88.742 | 56.701 | 82.736 | 1.00 | 48.68 | B |
| ATOM | 1808 | CG | PRO | B | 253 | 88.240 | 58.115 | 83.040 | 1.00 | 47.69 | B |
| ATOM | 1809 | C | PRO | B | 253 | 90.051 | 55.990 | 84.819 | 1.00 | 51.67 | B |
| ATOM | 1810 | O | PRO | B | 253 | 90.463 | 57.043 | 85.162 | 1.00 | 51.82 | B |
| ATOM | 1811 | N | ASP | B | 254 | 90.572 | 54.816 | 85.157 | 1.00 | 54.06 | B |
| ATOM | 1812 | CA | ASP | B | 254 | 91.905 | 54.594 | 85.697 | 1.00 | 56.81 | B |
| ATOM | 1813 | CB | ASP | B | 254 | 92.112 | 53.052 | 85.764 | 1.00 | 55.41 | B |
| ATOM | 1814 | CG | ASP | B | 254 | 93.182 | 52.658 | 86.779 | 1.00 | 55.56 | B |
| ATOM | 1815 | OD1 | ASP | B | 254 | 94.076 | 53.461 | 86.976 | 1.00 | 54.85 | B |
| ATOM | 1816 | OD2 | ASP | B | 254 | 93.222 | 51.619 | 87.452 | 1.00 | 53.81 | B |
| ATOM | 1817 | C | ASP | B | 254 | 93.061 | 55.207 | 84.871 | 1.00 | 59.27 | B |

TABLE 2-continued

ATOMIC COORDINATES OF THE ERR3 LBD/
DIETHYLSTILBESTROL COMPLEX

| ATOM | 1818 | O | ASP | B | 254 | 93.419 | 54.637 | 83.817 | 1.00 | 59.29 | B |
|---|---|---|---|---|---|---|---|---|---|---|---|
| ATOM | 1819 | N | PRO | B | 255 | 93.692 | 56.319 | 85.325 | 1.00 | 62.21 | B |
| ATOM | 1820 | CD | PRO | B | 255 | 93.543 | 56.817 | 86.715 | 1.00 | 63.24 | B |
| ATOM | 1821 | CA | PRO | B | 255 | 95.039 | 56.676 | 84.781 | 1.00 | 63.53 | B |
| ATOM | 1822 | CB | PRO | B | 255 | 95.512 | 57.705 | 85.781 | 1.00 | 64.67 | B |
| ATOM | 1823 | CG | PRO | B | 255 | 94.983 | 57.067 | 87.135 | 1.00 | 64.23 | B |
| ATOM | 1824 | C | PRO | B | 255 | 96.195 | 55.563 | 84.730 | 1.00 | 64.62 | B |
| ATOM | 1825 | O | PRO | B | 255 | 96.934 | 55.521 | 83.791 | 1.00 | 64.57 | B |
| ATOM | 1826 | N | THR | B | 256 | 96.408 | 54.718 | 85.722 | 1.00 | 66.37 | B |
| ATOM | 1827 | CA | THR | B | 256 | 97.393 | 53.613 | 85.575 | 1.00 | 68.07 | B |
| ATOM | 1828 | CB | THR | B | 256 | 98.078 | 53.130 | 86.916 | 1.00 | 70.23 | B |
| ATOM | 1829 | OG1 | THR | B | 256 | 98.534 | 54.281 | 87.655 | 1.00 | 71.61 | B |
| ATOM | 1830 | CG2 | THR | B | 256 | 99.365 | 52.262 | 86.598 | 1.00 | 72.04 | B |
| ATOM | 1831 | C | THR | B | 256 | 97.090 | 52.465 | 84.543 | 1.00 | 67.75 | B |
| ATOM | 1832 | O | THR | B | 256 | 98.088 | 52.312 | 83.276 | 0.00 | 67.71 | B |
| ATOM | 1833 | N | VAL | B | 257 | 95.871 | 52.412 | 83.935 | 1.00 | 67.27 | B |
| ATOM | 1834 | CA | VAL | B | 257 | 95.543 | 51.416 | 82.883 | 1.00 | 66.78 | B |
| ATOM | 1835 | CB | VAL | B | 257 | 94.023 | 51.091 | 82.854 | 1.00 | 67.60 | B |
| ATOM | 1836 | CG1 | VAL | B | 257 | 93.721 | 50.037 | 81.789 | 1.00 | 68.19 | B |
| ATOM | 1837 | CG2 | VAL | B | 257 | 93.577 | 50.585 | 84.216 | 1.00 | 68.44 | B |
| ATOM | 1838 | C | VAL | B | 257 | 95.950 | 52.104 | 81.607 | 1.00 | 65.62 | B |
| ATOM | 1839 | O | VAL | B | 257 | 95.530 | 53.227 | 81.413 | 1.00 | 65.61 | B |
| ATOM | 1840 | N | PRO | B | 258 | 96.795 | 51.527 | 80.744 | 1.00 | 64.90 | B |
| ATOM | 1841 | CD | PRO | B | 258 | 98.089 | 50.934 | 81.165 | 1.00 | 65.57 | B |
| ATOM | 1842 | CA | PRO | B | 258 | 96.962 | 52.167 | 79.382 | 1.00 | 63.70 | B |
| ATOM | 1843 | CB | PRO | B | 258 | 98.213 | 51.504 | 78.831 | 1.00 | 65.37 | B |
| ATOM | 1844 | CG | PRO | B | 258 | 99.102 | 51.550 | 80.141 | 1.00 | 66.53 | B |
| ATOM | 1845 | C | PRO | B | 258 | 95.608 | 52.071 | 78.531 | 1.00 | 61.85 | B |
| ATOM | 1846 | O | PRO | B | 258 | 94.923 | 51.054 | 78.679 | 1.00 | 60.48 | B |
| ATOM | 1847 | N | ASP | B | 259 | 95.283 | 53.062 | 77.700 | 1.00 | 60.22 | B |
| ATOM | 1848 | CA | ASP | B | 259 | 94.078 | 53.026 | 76.907 | 1.00 | 59.61 | B |
| ATOM | 1849 | CB | ASP | B | 259 | 93.935 | 54.258 | 76.015 | 1.00 | 60.30 | B |
| ATOM | 1850 | CG | ASP | B | 259 | 93.532 | 55.487 | 76.811 | 1.00 | 61.42 | B |
| ATOM | 1851 | OD1 | ASP | B | 259 | 92.881 | 55.330 | 77.874 | 1.00 | 61.96 | B |
| ATOM | 1852 | OD2 | ASP | B | 259 | 93.847 | 56.654 | 76.490 | 1.00 | 61.62 | B |
| ATOM | 1853 | C | ASP | B | 259 | 94.063 | 51.796 | 76.058 | 1.00 | 58.71 | B |
| ATOM | 1854 | O | ASP | B | 259 | 95.020 | 51.646 | 75.343 | 1.00 | 58.68 | B |
| ATOM | 1855 | N | SER | B | 260 | 93.051 | 50.913 | 76.245 | 1.00 | 56.74 | B |
| ATOM | 1856 | CA | SER | B | 260 | 92.705 | 49.804 | 75.376 | 1.00 | 56.03 | B |
| ATOM | 1857 | CB | SER | B | 260 | 93.279 | 48.484 | 75.909 | 1.00 | 55.10 | B |
| ATOM | 1858 | OG | SER | B | 260 | 92.745 | 48.068 | 77.180 | 1.00 | 53.67 | B |
| ATOM | 1859 | C | SER | B | 260 | 91.168 | 49.550 | 75.206 | 1.00 | 56.49 | B |
| ATOM | 1860 | O | SER | B | 260 | 90.368 | 50.052 | 75.987 | 1.00 | 56.78 | B |
| ATOM | 1861 | N | ASP | B | 261 | 90.782 | 48.732 | 74.205 | 1.00 | 55.31 | B |
| ATOM | 1862 | CA | ASP | B | 261 | 89.415 | 48.250 | 74.088 | 1.00 | 54.22 | B |
| ATOM | 1863 | CB | ASP | B | 261 | 89.292 | 47.182 | 72.963 | 1.00 | 56.59 | B |
| ATOM | 1864 | CG | ASP | B | 261 | 90.133 | 45.946 | 73.238 | 1.00 | 57.59 | B |
| ATOM | 1865 | OD1 | ASP | B | 261 | 89.583 | 44.841 | 73.329 | 1.00 | 60.20 | B |
| ATOM | 1866 | OD2 | ASP | B | 261 | 91.315 | 45.987 | 73.509 | 1.00 | 58.63 | B |
| ATOM | 1867 | C | ASP | B | 261 | 88.978 | 47.688 | 75.453 | 1.00 | 52.32 | B |
| ATOM | 1868 | O | ASP | B | 261 | 87.911 | 48.047 | 75.979 | 1.00 | 52.19 | B |
| ATOM | 1869 | N | ILE | B | 262 | 89.833 | 46.912 | 76.088 | 1.00 | 49.90 | B |
| ATOM | 1870 | CA | ILE | B | 262 | 89.446 | 46.203 | 77.304 | 1.00 | 47.44 | B |
| ATOM | 1871 | CB | ILE | B | 262 | 90.482 | 45.101 | 77.675 | 1.00 | 47.66 | B |
| ATOM | 1872 | CG2 | ILE | B | 262 | 90.093 | 44.296 | 78.924 | 1.00 | 46.57 | B |
| ATOM | 1873 | CG1 | ILE | B | 262 | 90.629 | 44.111 | 76.484 | 1.00 | 47.64 | B |
| ATOM | 1874 | CD1 | ILE | B | 262 | 89.635 | 43.364 | 76.163 | 0.00 | 47.65 | B |
| ATOM | 1875 | C | ILE | B | 262 | 89.195 | 47.229 | 78.431 | 1.00 | 45.93 | B |
| ATOM | 1876 | O | ILE | B | 262 | 88.495 | 46.946 | 79.406 | 1.00 | 45.66 | B |
| ATOM | 1877 | N | LYS | B | 263 | 89.733 | 48.424 | 78.245 | 1.00 | 44.65 | B |
| ATOM | 1878 | CA | LYS | B | 263 | 89.715 | 49.346 | 79.284 | 1.00 | 42.87 | B |
| ATOM | 1879 | CB | LYS | B | 263 | 90.945 | 50.244 | 79.298 | 1.00 | 43.55 | B |
| ATOM | 1880 | CG | LYS | B | 263 | 90.943 | 51.272 | 80.479 | 1.00 | 44.71 | B |
| ATOM | 1881 | CD | LYS | B | 263 | 91.604 | 52.556 | 79.981 | 1.00 | 45.83 | B |
| ATOM | 1882 | CE | LYS | B | 263 | 91.855 | 53.575 | 81.119 | 1.00 | 46.31 | B |
| ATOM | 1883 | NZ | LYS | B | 263 | 92.657 | 54.745 | 80.605 | 1.00 | 49.35 | B |
| ATOM | 1884 | C | LYS | B | 263 | 88.455 | 50.091 | 79.113 | 1.00 | 41.63 | B |
| ATOM | 1885 | O | LYS | B | 263 | 87.755 | 50.335 | 80.108 | 1.00 | 41.13 | B |
| ATOM | 1886 | N | ALA | B | 264 | 88.177 | 50.494 | 77.901 | 1.00 | 39.67 | B |
| ATOM | 1887 | CA | ALA | B | 264 | 86.966 | 51.212 | 77.623 | 1.00 | 38.73 | B |
| ATOM | 1888 | CB | ALA | B | 264 | 86.951 | 51.674 | 76.229 | 1.00 | 37.41 | B |
| ATOM | 1889 | C | ALA | B | 264 | 85.720 | 50.347 | 77.956 | 1.00 | 37.61 | B |
| ATOM | 1890 | O | ALA | B | 264 | 84.859 | 50.823 | 78.605 | 1.00 | 36.76 | B |
| ATOM | 1891 | N | LEU | B | 265 | 85.737 | 49.078 | 77.697 | 1.00 | 37.31 | B |
| ATOM | 1892 | CA | LEU | B | 265 | 84.644 | 48.170 | 78.022 | 1.00 | 39.33 | B |
| ATOM | 1893 | CB | LEU | B | 265 | 84.826 | 46.831 | 77.282 | 1.00 | 39.26 | B |

TABLE 2-continued

ATOMIC COORDINATES OF THE ERR3 LBD/
DIETHYLSTILBESTROL COMPLEX

| ATOM | 1894 | CG | LEU | B | 265 | 84.751 | 46.853 | 75.716 | 1.00 | 40.42 | B |
|------|------|-----|-----|---|-----|--------|--------|--------|------|-------|---|
| ATOM | 1895 | CD1 | LEU | B | 265 | 85.096 | 45.473 | 75.168 | 1.00 | 40.98 | B |
| ATOM | 1896 | CD2 | LEU | B | 265 | 83.377 | 47.228 | 75.190 | 1.00 | 39.72 | B |
| ATOM | 1897 | C | LEU | B | 265 | 84.468 | 47.883 | 79.499 | 1.00 | 40.07 | B |
| ATOM | 1898 | O | LEU | B | 265 | 83.327 | 47.709 | 80.000 | 1.00 | 40.64 | B |
| ATOM | 1899 | N | THR | B | 266 | 85.608 | 47.815 | 80.189 | 1.00 | 39.33 | B |
| ATOM | 1900 | CA | THR | B | 266 | 85.676 | 47.505 | 81.609 | 1.00 | 38.80 | B |
| ATOM | 1901 | CB | THR | B | 266 | 87.160 | 47.347 | 82.035 | 1.00 | 38.15 | B |
| ATOM | 1902 | OG1 | THR | B | 266 | 87.588 | 46.043 | 81.613 | 1.00 | 41.28 | B |
| ATOM | 1903 | CG2 | THR | B | 266 | 87.305 | 47.401 | 83.614 | 1.00 | 38.87 | B |
| ATOM | 1904 | C | THR | B | 266 | 85.067 | 48.715 | 82.271 | 1.00 | 38.26 | B |
| ATOM | 1905 | O | THR | B | 266 | 84.197 | 48.610 | 83.084 | 1.00 | 37.47 | B |
| ATOM | 1906 | N | THR | B | 267 | 85.484 | 49.868 | 81.858 | 1.00 | 37.38 | B |
| ATOM | 1907 | CA | THR | B | 267 | 84.966 | 51.023 | 82.482 | 1.00 | 38.02 | B |
| ATOM | 1908 | CB | THR | B | 267 | 85.628 | 52.196 | 81.830 | 1.00 | 38.19 | B |
| ATOM | 1909 | OG1 | THR | B | 267 | 87.018 | 52.003 | 81.916 | 1.00 | 38.50 | B |
| ATOM | 1910 | CG2 | THR | B | 267 | 85.398 | 53.507 | 82.577 | 1.00 | 36.35 | B |
| ATOM | 1911 | C | THR | B | 267 | 83.473 | 51.180 | 82.288 | 1.00 | 38.47 | B |
| ATOM | 1912 | O | THR | B | 267 | 82.760 | 51.813 | 83.106 | 1.00 | 39.13 | B |
| ATOM | 1913 | N | LEU | B | 268 | 83.006 | 50.793 | 81.103 | 1.00 | 37.68 | B |
| ATOM | 1914 | CA | LEU | B | 268 | 81.684 | 51.233 | 80.705 | 1.00 | 36.18 | B |
| ATOM | 1915 | CB | LEU | B | 268 | 81.575 | 51.152 | 79.202 | 1.00 | 33.60 | B |
| ATOM | 1916 | CG | LEU | B | 268 | 81.906 | 52.334 | 78.327 | 1.00 | 32.41 | B |
| ATOM | 1917 | CD1 | LEU | B | 268 | 81.664 | 51.885 | 76.864 | 1.00 | 33.15 | B |
| ATOM | 1918 | CD2 | LEU | B | 268 | 81.126 | 53.533 | 78.517 | 1.00 | 28.22 | B |
| ATOM | 1919 | C | LEU | B | 268 | 80.813 | 50.248 | 81.469 | 1.00 | 36.07 | B |
| ATOM | 1920 | O | LEU | B | 268 | 79.861 | 50.634 | 81.983 | 1.00 | 35.40 | B |
| ATOM | 1921 | N | CYS | B | 269 | 81.230 | 48.983 | 81.607 | 1.00 | 36.90 | B |
| ATOM | 1922 | CA | CYS | B | 269 | 80.551 | 47.974 | 82.398 | 1.00 | 37.81 | B |
| ATOM | 1923 | CB | CYS | B | 269 | 81.204 | 46.571 | 82.337 | 1.00 | 38.60 | B |
| ATOM | 1924 | SG | CYS | B | 269 | 80.850 | 45.827 | 80.649 | 1.00 | 44.00 | B |
| ATOM | 1925 | C | CYS | B | 269 | 80.413 | 48.343 | 83.828 | 1.00 | 37.94 | B |
| ATOM | 1926 | O | CYS | B | 269 | 79.284 | 48.064 | 84.441 | 1.00 | 37.08 | B |
| ATOM | 1927 | N | ASP | B | 270 | 81.508 | 48.922 | 84.395 | 1.00 | 37.64 | B |
| ATOM | 1928 | CA | ASP | B | 270 | 81.518 | 49.306 | 85.798 | 1.00 | 36.30 | B |
| ATOM | 1929 | CB | ASP | B | 270 | 82.959 | 49.446 | 86.382 | 1.00 | 38.67 | B |
| ATOM | 1930 | CG | ASP | B | 270 | 82.946 | 49.661 | 87.935 | 1.00 | 41.34 | B |
| ATOM | 1931 | OD1 | ASP | B | 270 | 82.644 | 48.669 | 88.723 | 1.00 | 41.64 | B |
| ATOM | 1932 | OD2 | ASP | B | 270 | 83.008 | 50.815 | 88.393 | 1.00 | 45.27 | B |
| ATOM | 1933 | C | ASP | B | 270 | 80.686 | 50.578 | 85.965 | 1.00 | 34.21 | B |
| ATOM | 1934 | O | ASP | B | 270 | 79.987 | 50.761 | 86.919 | 1.00 | 32.82 | B |
| ATOM | 1935 | N | LEU | B | 271 | 80.780 | 51.515 | 85.070 | 1.00 | 32.92 | B |
| ATOM | 1936 | CA | LEU | B | 271 | 79.888 | 52.607 | 85.151 | 1.00 | 33.35 | B |
| ATOM | 1937 | CB | LEU | B | 271 | 80.154 | 53.548 | 84.001 | 1.00 | 32.30 | B |
| ATOM | 1938 | CG | LEU | B | 271 | 79.052 | 54.612 | 83.833 | 1.00 | 32.11 | B |
| ATOM | 1939 | CD1 | LEU | B | 271 | 78.986 | 55.558 | 84.972 | 1.00 | 31.67 | B |
| ATOM | 1940 | CD2 | LEU | B | 271 | 79.183 | 55.360 | 82.552 | 1.00 | 30.28 | B |
| ATOM | 1941 | C | LEU | B | 271 | 78.336 | 52.117 | 85.119 | 1.00 | 34.54 | B |
| ATOM | 1942 | O | LEU | B | 271 | 77.508 | 52.559 | 85.902 | 1.00 | 35.14 | B |
| ATOM | 1943 | N | ALA | B | 272 | 78.017 | 51.151 | 84.288 | 1.00 | 34.64 | B |
| ATOM | 1944 | CA | ALA | B | 272 | 76.651 | 50.687 | 84.120 | 1.00 | 35.77 | B |
| ATOM | 1945 | CB | ALA | B | 272 | 76.564 | 49.633 | 82.982 | 1.00 | 34.55 | B |
| ATOM | 1946 | C | ALA | B | 272 | 76.198 | 50.027 | 85.416 | 1.00 | 37.30 | B |
| ATOM | 1947 | O | ALA | B | 272 | 75.076 | 50.284 | 85.875 | 1.00 | 35.57 | B |
| ATOM | 1948 | N | ASP | B | 273 | 77.031 | 49.166 | 85.963 | 1.00 | 38.75 | B |
| ATOM | 1949 | CA | ASP | B | 273 | 76.673 | 48.508 | 87.233 | 1.00 | 42.23 | B |
| ATOM | 1950 | CB | ASP | B | 273 | 77.703 | 47.504 | 87.804 | 1.00 | 48.40 | B |
| ATOM | 1951 | CG | ASP | B | 273 | 78.804 | 48.172 | 88.625 | 1.00 | 56.16 | B |
| ATOM | 1952 | OD1 | ASP | B | 273 | 79.790 | 48.644 | 88.033 | 1.00 | 60.93 | B |
| ATOM | 1953 | OD2 | ASP | B | 273 | 78.674 | 48.219 | 89.866 | 1.00 | 58.75 | B |
| ATOM | 1954 | C | ASP | B | 273 | 76.344 | 49.502 | 88.356 | 1.00 | 41.21 | B |
| ATOM | 1955 | O | ASP | B | 273 | 75.324 | 49.292 | 89.069 | 1.00 | 41.38 | B |
| ATOM | 1956 | N | ARG | B | 274 | 77.127 | 50.560 | 88.480 | 1.00 | 39.23 | B |
| ATOM | 1957 | CA | ARG | B | 274 | 76.814 | 51.557 | 89.494 | 1.00 | 37.73 | B |
| ATOM | 1958 | CB | ARG | B | 274 | 78.027 | 52.513 | 89.788 | 1.00 | 37.65 | B |
| ATOM | 1959 | CG | ARG | B | 274 | 79.216 | 51.713 | 90.489 | 1.00 | 37.35 | B |
| ATOM | 1960 | CD | ARG | B | 274 | 80.602 | 52.466 | 90.644 | 1.00 | 37.29 | B |
| ATOM | 1961 | NE | ARG | B | 274 | 81.267 | 52.858 | 89.378 | 1.00 | 37.72 | B |
| ATOM | 1962 | CZ | ARG | B | 274 | 81.232 | 54.075 | 88.834 | 1.00 | 38.81 | B |
| ATOM | 1963 | NH1 | ARG | B | 274 | 80.623 | 55.036 | 89.427 | 1.00 | 38.43 | B |
| ATOM | 1964 | NH2 | ARG | B | 274 | 81.903 | 54.364 | 87.714 | 1.00 | 39.20 | B |
| ATOM | 1965 | C | ARG | B | 274 | 75.625 | 52.322 | 89.105 | 1.00 | 36.58 | B |
| ATOM | 1966 | O | ARG | B | 274 | 74.892 | 52.656 | 89.975 | 1.00 | 35.79 | B |
| ATOM | 1967 | N | GLU | B | 275 | 75.394 | 52.635 | 87.794 | 1.00 | 35.25 | B |
| ATOM | 1968 | CA | GLU | B | 275 | 74.214 | 53.372 | 87.418 | 1.00 | 33.68 | B |
| ATOM | 1969 | CB | GLU | B | 275 | 74.202 | 53.768 | 85.978 | 1.00 | 34.01 | B |

TABLE 2-continued

ATOMIC COORDINATES OF THE ERR3 LBD/
DIETHYLSTILBESTROL COMPLEX

| ATOM | 1970 | CG | GLU | B | 275 | 75.217 | 54.794 | 85.459 | 1.00 | 34.20 | B |
|------|------|-----|-----|---|-----|--------|--------|--------|------|-------|---|
| ATOM | 1971 | CD | GLU | B | 275 | 74.954 | 55.143 | 84.014 | 1.00 | 35.35 | B |
| ATOM | 1972 | OE1 | GLU | B | 275 | 73.953 | 55.897 | 83.734 | 1.00 | 36.17 | B |
| ATOM | 1973 | OE2 | GLU | B | 275 | 75.724 | 54.643 | 83.152 | 1.00 | 35.24 | B |
| ATOM | 1974 | C | GLU | B | 275 | 72.967 | 52.471 | 87.726 | 1.00 | 33.77 | B |
| ATOM | 1975 | O | GLU | B | 275 | 71.939 | 52.973 | 88.060 | 1.00 | 32.91 | B |
| ATOM | 1976 | N | LEU | B | 276 | 73.088 | 51.166 | 87.658 | 1.00 | 34.24 | B |
| ATOM | 1977 | CA | LEU | B | 276 | 72.013 | 50.255 | 87.905 | 1.00 | 36.37 | B |
| ATOM | 1978 | CB | LEU | B | 276 | 72.308 | 48.837 | 87.429 | 1.00 | 36.67 | B |
| ATOM | 1979 | CG | LEU | B | 276 | 71.733 | 48.593 | 86.059 | 1.00 | 41.49 | B |
| ATOM | 1980 | CD1 | LEU | B | 276 | 72.495 | 47.337 | 85.513 | 1.00 | 42.98 | B |
| ATOM | 1981 | CD2 | LEU | B | 276 | 70.227 | 48.238 | 86.203 | 1.00 | 41.63 | B |
| ATOM | 1982 | C | LEU | B | 276 | 71.595 | 50.163 | 89.372 | 1.00 | 36.59 | B |
| ATOM | 1983 | O | LEU | B | 276 | 70.440 | 50.055 | 89.636 | 1.00 | 36.99 | B |
| ATOM | 1984 | N | VAL | B | 277 | 72.522 | 50.200 | 90.297 | 1.00 | 36.60 | B |
| ATOM | 1985 | CA | VAL | B | 277 | 72.146 | 50.364 | 91.698 | 1.00 | 37.53 | B |
| ATOM | 1986 | CB | VAL | B | 277 | 73.420 | 50.469 | 92.659 | 1.00 | 37.11 | B |
| ATOM | 1987 | CG1 | VAL | B | 277 | 72.969 | 50.900 | 94.080 | 1.00 | 36.57 | B |
| ATOM | 1988 | CG2 | VAL | B | 277 | 74.152 | 49.209 | 92.606 | 1.00 | 35.46 | B |
| ATOM | 1989 | C | VAL | B | 277 | 71.318 | 51.633 | 91.832 | 1.00 | 37.94 | B |
| ATOM | 1990 | O | VAL | B | 277 | 70.275 | 51.573 | 92.400 | 1.00 | 39.79 | B |
| ATOM | 1991 | N | VAL | B | 278 | 71.724 | 52.741 | 91.253 | 1.00 | 38.09 | B |
| ATOM | 1992 | CA | VAL | B | 278 | 70.884 | 53.943 | 91.350 | 1.00 | 38.49 | B |
| ATOM | 1993 | CB | VAL | B | 278 | 71.589 | 55.256 | 91.003 | 1.00 | 40.25 | B |
| ATOM | 1994 | CG1 | VAL | B | 278 | 70.923 | 56.206 | 91.150 | 0.00 | 39.54 | B |
| ATOM | 1995 | CG2 | VAL | B | 278 | 72.696 | 55.496 | 92.022 | 1.00 | 39.92 | B |
| ATOM | 1996 | C | VAL | B | 278 | 69.571 | 53.866 | 90.584 | 1.00 | 37.41 | B |
| ATOM | 1997 | O | VAL | B | 278 | 68.582 | 54.447 | 91.008 | 1.00 | 37.02 | B |
| ATOM | 1998 | N | ILE | B | 279 | 69.514 | 53.046 | 89.551 | 1.00 | 36.44 | B |
| ATOM | 1999 | CA | ILE | B | 279 | 68.245 | 52.918 | 88.877 | 1.00 | 35.14 | B |
| ATOM | 2000 | CB | ILE | B | 279 | 68.470 | 52.325 | 87.490 | 1.00 | 35.04 | B |
| ATOM | 2001 | CG2 | ILE | B | 279 | 67.208 | 51.566 | 86.873 | 1.00 | 33.13 | B |
| ATOM | 2002 | CG1 | ILE | B | 279 | 68.871 | 53.490 | 86.559 | 1.00 | 34.30 | B |
| ATOM | 2003 | CD1 | ILE | B | 279 | 69.698 | 52.990 | 85.404 | 1.00 | 36.52 | B |
| ATOM | 2004 | C | ILE | B | 279 | 67.210 | 52.181 | 89.692 | 1.00 | 34.84 | B |
| ATOM | 2005 | O | ILE | B | 279 | 66.044 | 52.523 | 89.575 | 1.00 | 33.90 | B |
| ATOM | 2006 | N | ILE | B | 280 | 67.618 | 51.109 | 90.381 | 1.00 | 35.03 | B |
| ATOM | 2007 | CA | ILE | B | 280 | 66.708 | 50.251 | 91.146 | 1.00 | 35.15 | B |
| ATOM | 2008 | CB | ILE | B | 280 | 67.444 | 49.171 | 91.894 | 1.00 | 36.59 | B |
| ATOM | 2009 | CG2 | ILE | B | 280 | 66.618 | 48.597 | 93.048 | 1.00 | 35.32 | B |
| ATOM | 2010 | CG1 | ILE | B | 280 | 67.907 | 48.026 | 91.007 | 1.00 | 37.48 | B |
| ATOM | 2011 | CD1 | ILE | B | 280 | 67.625 | 48.216 | 89.660 | 1.00 | 39.11 | B |
| ATOM | 2012 | C | ILE | B | 280 | 66.068 | 51.147 | 92.187 | 1.00 | 35.48 | B |
| ATOM | 2013 | O | ILE | B | 280 | 64.893 | 51.102 | 92.363 | 1.00 | 35.35 | B |
| ATOM | 2014 | N | GLY | B | 281 | 66.917 | 51.926 | 92.879 | 1.00 | 34.47 | B |
| ATOM | 2015 | CA | GLY | B | 281 | 66.516 | 53.015 | 93.756 | 1.00 | 33.63 | B |
| ATOM | 2016 | C | GLY | B | 281 | 65.549 | 54.034 | 93.214 | 1.00 | 34.61 | B |
| ATOM | 2017 | O | GLY | B | 281 | 64.532 | 54.369 | 93.909 | 1.00 | 35.34 | B |
| ATOM | 2018 | N | TRP | B | 282 | 65.787 | 54.491 | 91.987 | 1.00 | 32.93 | B |
| ATOM | 2019 | CA | TRP | B | 282 | 64.954 | 55.470 | 91.429 | 1.00 | 32.18 | B |
| ATOM | 2020 | CB | TRP | B | 282 | 65.628 | 56.159 | 90.216 | 1.00 | 32.04 | B |
| ATOM | 2021 | CG | TRP | B | 282 | 64.692 | 56.676 | 89.085 | 1.00 | 31.87 | B |
| ATOM | 2022 | CD2 | TRP | B | 282 | 64.171 | 55.996 | 87.911 | 1.00 | 31.20 | B |
| ATOM | 2023 | CE2 | TRP | B | 282 | 63.392 | 56.925 | 87.207 | 1.00 | 31.63 | B |
| ATOM | 2024 | CE3 | TRP | B | 282 | 64.244 | 54.724 | 87.416 | 1.00 | 30.73 | B |
| ATOM | 2025 | CD1 | TRP | B | 282 | 64.312 | 57.944 | 88.962 | 1.00 | 31.81 | B |
| ATOM | 2026 | NE1 | TRP | B | 282 | 63.552 | 58.114 | 87.835 | 1.00 | 32.96 | B |
| ATOM | 2027 | CZ2 | TRP | B | 282 | 62.743 | 56.628 | 86.040 | 1.00 | 30.41 | B |
| ATOM | 2028 | CZ3 | TRP | B | 282 | 63.579 | 54.395 | 86.276 | 1.00 | 30.80 | B |
| ATOM | 2029 | CH2 | TRP | B | 282 | 62.835 | 55.336 | 85.575 | 1.00 | 30.85 | B |
| ATOM | 2030 | C | TRP | B | 282 | 63.586 | 54.857 | 91.060 | 1.00 | 33.09 | B |
| ATOM | 2031 | O | TRP | B | 282 | 62.528 | 55.487 | 91.140 | 1.00 | 32.75 | B |
| ATOM | 2032 | N | ALA | B | 283 | 63.574 | 53.621 | 90.656 | 1.00 | 32.96 | B |
| ATOM | 2033 | CA | ALA | B | 283 | 62.345 | 53.046 | 90.153 | 1.00 | 32.96 | B |
| ATOM | 2034 | CB | ALA | B | 283 | 62.601 | 51.643 | 89.547 | 1.00 | 29.89 | B |
| ATOM | 2035 | C | ALA | B | 283 | 61.333 | 53.008 | 91.349 | 1.00 | 34.07 | B |
| ATOM | 2036 | O | ALA | B | 283 | 60.133 | 53.120 | 91.209 | 1.00 | 32.64 | B |
| ATOM | 2037 | N | LYS | B | 284 | 61.869 | 52.878 | 92.561 | 1.00 | 35.82 | B |
| ATOM | 2038 | CA | LYS | B | 284 | 60.951 | 52.836 | 93.716 | 1.00 | 38.05 | B |
| ATOM | 2039 | CB | LYS | B | 284 | 61.705 | 52.311 | 94.954 | 1.00 | 38.84 | B |
| ATOM | 2040 | CG | LYS | B | 284 | 62.118 | 50.821 | 94.838 | 1.00 | 41.20 | B |
| ATOM | 2041 | CD | LYS | B | 284 | 63.346 | 50.514 | 95.747 | 1.00 | 44.62 | B |
| ATOM | 2042 | CE | LYS | B | 284 | 63.860 | 49.086 | 95.661 | 1.00 | 45.70 | B |
| ATOM | 2043 | NZ | LYS | B | 284 | 64.922 | 48.900 | 96.725 | 1.00 | 48.33 | B |
| ATOM | 2044 | C | LYS | B | 284 | 60.163 | 54.137 | 93.927 | 1.00 | 38.18 | B |
| ATOM | 2045 | O | LYS | B | 284 | 59.174 | 54.118 | 94.535 | 1.00 | 38.21 | B |

TABLE 2-continued

ATOMIC COORDINATES OF THE ERR3 LBD/
DIETHYLSTILBESTROL COMPLEX

| ATOM | 2046 | N | HIS | B | 285 | 60.586 | 55.252 | 93.358 | 1.00 | 37.80 | B |
|---|---|---|---|---|---|---|---|---|---|---|---|
| ATOM | 2047 | CA | HIS | B | 285 | 59.922 | 56.511 | 93.463 | 1.00 | 39.21 | B |
| ATOM | 2048 | CB | HIS | B | 285 | 61.011 | 57.527 | 93.313 | 1.00 | 39.61 | B |
| ATOM | 2049 | CG | HIS | B | 285 | 61.764 | 57.475 | 94.482 | 1.00 | 41.50 | B |
| ATOM | 2050 | CD2 | HIS | B | 285 | 63.036 | 56.780 | 94.862 | 1.00 | 41.88 | B |
| ATOM | 2051 | ND1 | HIS | B | 285 | 60.970 | 57.941 | 95.594 | 1.00 | 43.54 | B |
| ATOM | 2052 | CE1 | HIS | B | 285 | 61.808 | 58.035 | 96.596 | 1.00 | 42.40 | B |
| ATOM | 2053 | NE2 | HIS | B | 285 | 63.144 | 57.557 | 96.276 | 1.00 | 42.96 | B |
| ATOM | 2054 | C | HIS | B | 285 | 58.956 | 56.818 | 92.424 | 1.00 | 40.02 | B |
| ATOM | 2055 | O | HIS | B | 285 | 58.324 | 57.886 | 92.483 | 1.00 | 40.84 | B |
| ATOM | 2056 | N | ILE | B | 286 | 58.716 | 55.865 | 91.539 | 1.00 | 40.00 | B |
| ATOM | 2057 | CA | ILE | B | 286 | 57.818 | 56.119 | 90.482 | 1.00 | 39.46 | B |
| ATOM | 2058 | CB | ILE | B | 286 | 58.150 | 55.263 | 89.168 | 1.00 | 38.31 | B |
| ATOM | 2059 | CG2 | ILE | B | 286 | 57.020 | 55.447 | 88.151 | 1.00 | 36.12 | B |
| ATOM | 2060 | CG1 | ILE | B | 286 | 59.469 | 55.742 | 88.552 | 1.00 | 36.08 | B |
| ATOM | 2061 | CD1 | ILE | B | 286 | 60.083 | 54.835 | 87.504 | 1.00 | 34.38 | B |
| ATOM | 2062 | C | ILE | B | 286 | 56.511 | 55.780 | 91.066 | 1.00 | 40.35 | B |
| ATOM | 2063 | O | ILE | B | 286 | 56.317 | 54.716 | 91.500 | 1.00 | 40.55 | B |
| ATOM | 2064 | N | PRO | B | 287 | 55.575 | 56.685 | 90.929 | 1.00 | 41.92 | B |
| ATOM | 2065 | CD | PRO | B | 287 | 55.672 | 57.956 | 90.158 | 1.00 | 42.01 | B |
| ATOM | 2066 | CA | PRO | B | 287 | 54.241 | 56.494 | 91.507 | 1.00 | 43.31 | B |
| ATOM | 2067 | CB | PRO | B | 287 | 53.512 | 57.695 | 91.000 | 1.00 | 42.52 | B |
| ATOM | 2068 | CG | PRO | B | 287 | 54.442 | 58.638 | 90.606 | 1.00 | 41.59 | B |
| ATOM | 2069 | C | PRO | B | 287 | 53.594 | 55.179 | 90.992 | 1.00 | 44.35 | B |
| ATOM | 2070 | O | PRO | B | 287 | 53.507 | 55.172 | 89.843 | 1.00 | 45.82 | B |
| ATOM | 2071 | N | GLY | B | 288 | 53.281 | 54.154 | 91.785 | 1.00 | 45.82 | B |
| ATOM | 2072 | CA | GLY | B | 288 | 52.744 | 52.830 | 91.358 | 1.00 | 46.39 | B |
| ATOM | 2073 | C | GLY | B | 288 | 53.729 | 51.640 | 91.509 | 1.00 | 47.19 | B |
| ATOM | 2074 | O | GLY | B | 288 | 53.398 | 50.406 | 91.702 | 1.00 | 47.45 | B |
| ATOM | 2075 | N | PHE | B | 289 | 54.997 | 51.976 | 91.360 | 1.00 | 46.94 | B |
| ATOM | 2076 | CA | PHE | B | 289 | 55.943 | 50.916 | 91.064 | 1.00 | 46.57 | B |
| ATOM | 2077 | CB | PHE | B | 289 | 57.256 | 51.545 | 90.450 | 1.00 | 44.03 | B |
| ATOM | 2078 | CG | PHE | B | 289 | 58.255 | 50.536 | 90.033 | 1.00 | 42.34 | B |
| ATOM | 2079 | CD1 | PHE | B | 289 | 58.284 | 50.104 | 88.711 | 1.00 | 40.46 | B |
| ATOM | 2080 | CD2 | PHE | B | 289 | 59.122 | 49.968 | 90.962 | 1.00 | 40.93 | B |
| ATOM | 2081 | CE1 | PHE | B | 289 | 59.198 | 49.250 | 88.308 | 1.00 | 40.21 | B |
| ATOM | 2082 | CE2 | PHE | B | 289 | 59.992 | 49.044 | 90.620 | 1.00 | 40.71 | B |
| ATOM | 2083 | CZ | PHE | B | 289 | 60.048 | 48.626 | 89.218 | 1.00 | 40.86 | B |
| ATOM | 2084 | C | PHE | B | 289 | 56.256 | 49.984 | 92.279 | 1.00 | 47.68 | B |
| ATOM | 2085 | O | PHE | B | 289 | 56.320 | 48.701 | 92.126 | 1.00 | 47.45 | B |
| ATOM | 2086 | N | SER | B | 290 | 56.536 | 50.585 | 93.452 | 1.00 | 48.60 | B |
| ATOM | 2087 | CA | SER | B | 290 | 56.914 | 49.784 | 94.669 | 1.00 | 50.46 | B |
| ATOM | 2088 | CB | SER | B | 290 | 57.455 | 50.674 | 95.787 | 1.00 | 50.77 | B |
| ATOM | 2089 | OG | SER | B | 290 | 58.701 | 50.796 | 95.525 | 0.00 | 50.61 | B |
| ATOM | 2090 | C | SER | B | 290 | 55.751 | 48.980 | 95.224 | 1.00 | 51.54 | B |
| ATOM | 2091 | O | SER | B | 290 | 55.921 | 48.068 | 96.073 | 1.00 | 52.91 | B |
| ATOM | 2092 | N | THR | B | 291 | 54.551 | 49.279 | 94.738 | 1.00 | 51.86 | B |
| ATOM | 2093 | CA | THR | B | 291 | 53.406 | 48.494 | 95.073 | 1.00 | 51.93 | B |
| ATOM | 2094 | CB | THR | B | 291 | 52.157 | 49.436 | 94.917 | 1.00 | 53.03 | B |
| ATOM | 2095 | OG1 | THR | B | 291 | 52.330 | 50.424 | 93.894 | 1.00 | 52.03 | B |
| ATOM | 2096 | CG2 | THR | B | 291 | 52.123 | 50.326 | 96.061 | 1.00 | 54.02 | B |
| ATOM | 2097 | C | THR | B | 291 | 53.179 | 47.208 | 94.282 | 1.00 | 51.82 | B |
| ATOM | 2098 | O | THR | B | 291 | 52.339 | 46.404 | 94.694 | 1.00 | 52.52 | B |
| ATOM | 2099 | N | LEU | B | 292 | 53.802 | 47.006 | 93.113 | 1.00 | 49.96 | B |
| ATOM | 2100 | CA | LEU | B | 292 | 53.442 | 45.862 | 92.284 | 1.00 | 48.56 | B |
| ATOM | 2101 | CB | LEU | B | 292 | 54.058 | 46.001 | 90.842 | 1.00 | 47.19 | B |
| ATOM | 2102 | CG | LEU | B | 292 | 53.672 | 47.111 | 89.837 | 1.00 | 46.27 | B |
| ATOM | 2103 | CD1 | LEU | B | 292 | 54.671 | 47.512 | 88.710 | 1.00 | 44.79 | B |
| ATOM | 2104 | CD2 | LEU | B | 292 | 52.335 | 46.669 | 89.214 | 1.00 | 43.88 | B |
| ATOM | 2105 | C | LEU | B | 292 | 54.148 | 44.723 | 93.005 | 1.00 | 48.86 | B |
| ATOM | 2106 | O | LEU | B | 292 | 55.082 | 44.936 | 93.807 | 1.00 | 48.73 | B |
| ATOM | 2107 | N | SER | B | 293 | 53.780 | 43.487 | 92.728 | 1.00 | 49.21 | B |
| ATOM | 2108 | CA | SER | B | 293 | 54.592 | 42.406 | 93.287 | 1.00 | 50.41 | B |
| ATOM | 2109 | CB | SER | B | 293 | 54.092 | 41.060 | 92.821 | 1.00 | 51.00 | B |
| ATOM | 2110 | OG | SER | B | 293 | 54.723 | 40.724 | 91.646 | 1.00 | 50.73 | B |
| ATOM | 2111 | C | SER | B | 293 | 56.084 | 42.542 | 92.952 | 1.00 | 51.34 | B |
| ATOM | 2112 | O | SER | B | 293 | 56.473 | 43.107 | 91.949 | 1.00 | 51.65 | B |
| ATOM | 2113 | N | LEU | B | 294 | 56.935 | 42.038 | 93.808 | 1.00 | 51.93 | B |
| ATOM | 2114 | CA | LEU | B | 294 | 58.341 | 42.256 | 93.643 | 1.00 | 51.56 | B |
| ATOM | 2115 | CB | LEU | B | 294 | 59.162 | 41.820 | 94.896 | 1.00 | 52.91 | B |
| ATOM | 2116 | CG | LEU | B | 294 | 59.965 | 42.909 | 95.679 | 1.00 | 53.53 | B |
| ATOM | 2117 | CD1 | LEU | B | 294 | 59.371 | 44.270 | 95.504 | 0.00 | 53.36 | B |
| ATOM | 2118 | CD2 | LEU | B | 294 | 60.565 | 42.573 | 96.907 | 0.00 | 53.36 | B |
| ATOM | 2119 | C | LEU | B | 294 | 58.745 | 41.502 | 92.365 | 1.00 | 50.48 | B |
| ATOM | 2120 | O | LEU | B | 294 | 59.649 | 41.913 | 91.645 | 1.00 | 50.54 | B |
| ATOM | 2121 | N | ALA | B | 295 | 58.011 | 40.448 | 92.052 | 1.00 | 49.11 | B |

TABLE 2-continued

ATOMIC COORDINATES OF THE ERR3 LBD/
DIETHYLSTILBESTROL COMPLEX

| ATOM | 2122 | CA | ALA | B | 295 | 58.133 | 39.839 | 90.771 | 1.00 | 47.84 | B |
|---|---|---|---|---|---|---|---|---|---|---|---|
| ATOM | 2123 | CB | ALA | B | 295 | 57.166 | 38.646 | 90.626 | 1.00 | 48.09 | B |
| ATOM | 2124 | C | ALA | B | 295 | 57.945 | 40.867 | 89.588 | 1.00 | 46.63 | B |
| ATOM | 2125 | O | ALA | B | 295 | 58.733 | 40.855 | 88.634 | 1.00 | 46.37 | B |
| ATOM | 2126 | N | ASP | B | 296 | 56.871 | 41.655 | 89.610 | 1.00 | 43.71 | B |
| ATOM | 2127 | CA | ASP | B | 296 | 56.525 | 42.417 | 88.425 | 1.00 | 42.52 | B |
| ATOM | 2128 | CB | ASP | B | 296 | 55.085 | 42.919 | 88.514 | 1.00 | 40.39 | B |
| ATOM | 2129 | CG | ASP | B | 296 | 54.055 | 41.912 | 88.056 | 1.00 | 40.42 | B |
| ATOM | 2130 | OD1 | ASP | B | 296 | 54.404 | 40.728 | 87.641 | 1.00 | 36.76 | B |
| ATOM | 2131 | OD2 | ASP | B | 296 | 52.845 | 42.314 | 88.009 | 1.00 | 38.61 | B |
| ATOM | 2132 | C | ASP | B | 296 | 57.544 | 43.606 | 88.344 | 1.00 | 41.88 | B |
| ATOM | 2133 | O | ASP | B | 296 | 57.974 | 44.012 | 87.255 | 1.00 | 41.99 | B |
| ATOM | 2134 | N | GLN | B | 297 | 57.948 | 44.106 | 89.495 | 1.00 | 41.56 | B |
| ATOM | 2135 | CA | GLN | B | 297 | 58.975 | 45.204 | 89.630 | 1.00 | 42.45 | B |
| ATOM | 2136 | CB | GLN | B | 297 | 59.202 | 45.684 | 91.087 | 1.00 | 43.75 | B |
| ATOM | 2137 | CG | GLN | B | 297 | 58.038 | 45.949 | 91.943 | 0.00 | 46.33 | B |
| ATOM | 2138 | CD | GLN | B | 297 | 58.484 | 46.389 | 93.274 | 1.00 | 48.15 | B |
| ATOM | 2139 | OE1 | GLN | B | 297 | 59.465 | 47.049 | 93.630 | 1.00 | 49.27 | B |
| ATOM | 2140 | NE2 | GLN | B | 297 | 57.407 | 46.242 | 94.047 | 1.00 | 49.57 | B |
| ATOM | 2141 | C | GLN | B | 297 | 60.235 | 44.784 | 89.004 | 1.00 | 41.94 | B |
| ATOM | 2142 | O | GLN | B | 297 | 60.789 | 45.468 | 88.132 | 1.00 | 41.80 | B |
| ATOM | 2143 | N | MET | B | 298 | 60.589 | 43.557 | 89.270 | 1.00 | 42.40 | B |
| ATOM | 2144 | CA | MET | B | 298 | 61.781 | 43.006 | 88.738 | 1.00 | 42.52 | B |
| ATOM | 2145 | CB | MET | B | 298 | 62.114 | 41.756 | 89.473 | 1.00 | 47.68 | B |
| ATOM | 2146 | CG | MET | B | 298 | 63.496 | 41.917 | 90.090 | 1.00 | 53.12 | B |
| ATOM | 2147 | SD | MET | B | 298 | 63.883 | 41.018 | 91.751 | 1.00 | 60.73 | B |
| ATOM | 2148 | CE | MET | B | 298 | 62.209 | 40.624 | 92.700 | 1.00 | 57.05 | B |
| ATOM | 2149 | C | MET | B | 298 | 61.675 | 42.667 | 87.280 | 1.00 | 40.17 | B |
| ATOM | 2150 | O | MET | B | 298 | 62.661 | 42.737 | 86.495 | 1.00 | 38.26 | B |
| ATOM | 2151 | N | SER | B | 299 | 60.499 | 42.242 | 86.908 | 1.00 | 36.41 | B |
| ATOM | 2152 | CA | SER | B | 299 | 60.262 | 41.938 | 85.535 | 1.00 | 34.06 | B |
| ATOM | 2153 | CB | SER | B | 299 | 58.900 | 41.323 | 85.386 | 1.00 | 33.20 | B |
| ATOM | 2154 | OG | SER | B | 299 | 59.018 | 40.014 | 85.733 | 1.00 | 32.03 | B |
| ATOM | 2155 | C | SER | B | 299 | 60.367 | 43.179 | 84.622 | 1.00 | 32.09 | B |
| ATOM | 2156 | O | SER | B | 299 | 60.942 | 43.111 | 83.513 | 1.00 | 30.16 | B |
| ATOM | 2157 | N | LEU | B | 300 | 59.785 | 44.279 | 85.078 | 1.00 | 31.07 | B |
| ATOM | 2158 | CA | LEU | B | 300 | 59.858 | 45.563 | 84.343 | 1.00 | 30.07 | B |
| ATOM | 2159 | CB | LEU | B | 300 | 58.996 | 46.634 | 84.961 | 1.00 | 30.91 | B |
| ATOM | 2160 | CG | LEU | B | 300 | 57.474 | 46.459 | 85.223 | 1.00 | 33.82 | B |
| ATOM | 2161 | CD1 | LEU | B | 300 | 56.766 | 47.743 | 85.535 | 1.00 | 31.12 | B |
| ATOM | 2162 | CD2 | LEU | B | 300 | 56.808 | 45.870 | 84.081 | 1.00 | 32.32 | B |
| ATOM | 2163 | C | LEU | B | 300 | 61.291 | 46.022 | 84.277 | 1.00 | 29.37 | B |
| ATOM | 2164 | O | LEU | B | 300 | 61.755 | 46.360 | 83.227 | 1.00 | 26.71 | B |
| ATOM | 2165 | N | LEU | B | 301 | 62.028 | 45.961 | 85.390 | 1.00 | 28.66 | B |
| ATOM | 2166 | CA | LEU | B | 301 | 63.403 | 46.388 | 85.397 | 1.00 | 29.87 | B |
| ATOM | 2167 | CB | LEU | B | 301 | 64.001 | 46.391 | 86.772 | 1.00 | 29.18 | B |
| ATOM | 2168 | CG | LEU | B | 301 | 63.604 | 47.621 | 87.498 | 1.00 | 31.53 | B |
| ATOM | 2169 | CD1 | LEU | B | 301 | 63.703 | 47.389 | 89.049 | 1.00 | 31.84 | B |
| ATOM | 2170 | CD2 | LEU | B | 301 | 64.412 | 48.834 | 86.975 | 1.00 | 31.36 | B |
| ATOM | 2171 | C | LEU | B | 301 | 64.311 | 45.504 | 84.481 | 1.00 | 30.94 | B |
| ATOM | 2172 | O | LEU | B | 301 | 65.239 | 45.998 | 83.692 | 1.00 | 30.45 | B |
| ATOM | 2173 | N | GLN | B | 302 | 64.051 | 44.235 | 84.536 | 1.00 | 30.59 | B |
| ATOM | 2174 | CA | GLN | B | 302 | 64.837 | 43.309 | 83.747 | 1.00 | 30.86 | B |
| ATOM | 2175 | CB | GLN | B | 302 | 64.333 | 41.945 | 84.013 | 1.00 | 32.05 | B |
| ATOM | 2176 | CG | GLN | B | 302 | 64.991 | 40.877 | 83.143 | 1.00 | 33.88 | B |
| ATOM | 2177 | CD | GLN | B | 302 | 64.508 | 39.525 | 83.584 | 1.00 | 36.75 | B |
| ATOM | 2178 | OE1 | GLN | B | 302 | 63.917 | 39.386 | 84.734 | 1.00 | 37.73 | B |
| ATOM | 2179 | NE2 | GLN | B | 302 | 64.759 | 38.519 | 82.756 | 1.00 | 35.71 | B |
| ATOM | 2180 | C | GLN | B | 302 | 64.638 | 43.546 | 82.189 | 1.00 | 29.87 | B |
| ATOM | 2181 | O | GLN | B | 302 | 65.548 | 43.458 | 81.418 | 1.00 | 29.73 | B |
| ATOM | 2182 | N | SER | B | 303 | 63.466 | 43.926 | 81.796 | 1.00 | 27.03 | B |
| ATOM | 2183 | CA | SER | B | 303 | 63.263 | 44.163 | 80.415 | 1.00 | 28.27 | B |
| ATOM | 2184 | CB | SER | B | 303 | 61.776 | 44.103 | 80.077 | 1.00 | 27.33 | B |
| ATOM | 2185 | OG | SER | B | 303 | 61.311 | 42.707 | 80.203 | 1.00 | 30.11 | B |
| ATOM | 2186 | C | SER | B | 303 | 63.753 | 45.613 | 80.062 | 1.00 | 26.98 | B |
| ATOM | 2187 | O | SER | B | 303 | 64.042 | 45.835 | 78.958 | 1.00 | 27.89 | B |
| ATOM | 2188 | N | ALA | B | 304 | 63.748 | 46.570 | 80.984 | 1.00 | 24.54 | B |
| ATOM | 2189 | CA | ALA | B | 304 | 63.899 | 47.959 | 80.622 | 1.00 | 24.50 | B |
| ATOM | 2190 | CB | ALA | B | 304 | 62.843 | 48.795 | 81.302 | 1.00 | 19.35 | B |
| ATOM | 2191 | C | ALA | B | 304 | 65.320 | 48.521 | 80.881 | 1.00 | 23.09 | B |
| ATOM | 2192 | O | ALA | B | 304 | 65.604 | 49.606 | 80.508 | 1.00 | 24.79 | B |
| ATOM | 2193 | N | TRP | B | 305 | 66.185 | 47.818 | 81.589 | 1.00 | 24.36 | B |
| ATOM | 2194 | CA | TRP | B | 305 | 67.316 | 48.462 | 82.285 | 1.00 | 24.93 | B |
| ATOM | 2195 | CB | TRP | B | 305 | 68.137 | 47.496 | 83.115 | 1.00 | 23.98 | B |
| ATOM | 2196 | CG | TRP | B | 305 | 68.805 | 46.337 | 82.333 | 1.00 | 25.83 | B |
| ATOM | 2197 | CD2 | TRP | B | 305 | 70.119 | 46.279 | 81.745 | 1.00 | 25.60 | B |

TABLE 2-continued

ATOMIC COORDINATES OF THE ERR3 LBD/DIETHYLSTILBESTROL COMPLEX

| ATOM | 2198 | CE2 | TRP | B | 305 | 70.241 | 45.031 | 81.101 | 1.00 | 26.38 | B |
|------|------|-----|-----|---|-----|--------|--------|--------|------|-------|---|
| ATOM | 2199 | CE3 | TRP | B | 305 | 71.206 | 47.083 | 81.778 | 1.00 | 26.11 | B |
| ATOM | 2200 | CD1 | TRP | B | 305 | 68.216 | 45.158 | 82.003 | 1.00 | 27.08 | B |
| ATOM | 2201 | NE1 | TRP | B | 305 | 69.053 | 44.381 | 81.253 | 1.00 | 26.58 | B |
| ATOM | 2202 | CZ2 | TRP | B | 305 | 71.398 | 44.619 | 80.477 | 1.00 | 26.00 | B |
| ATOM | 2203 | CZ3 | TRP | B | 305 | 72.392 | 46.687 | 81.110 | 1.00 | 26.17 | B |
| ATOM | 2204 | CH2 | TRP | B | 305 | 72.483 | 45.489 | 80.509 | 1.00 | 27.08 | B |
| ATOM | 2205 | C | TRP | B | 305 | 68.147 | 49.111 | 81.214 | 1.00 | 24.97 | B |
| ATOM | 2206 | O | TRP | B | 305 | 68.561 | 50.261 | 81.401 | 1.00 | 27.41 | B |
| ATOM | 2207 | N | MET | B | 306 | 68.220 | 48.499 | 80.036 | 1.00 | 24.79 | B |
| ATOM | 2208 | CA | MET | B | 306 | 69.079 | 49.017 | 78.980 | 1.00 | 24.62 | B |
| ATOM | 2209 | CB | MET | B | 306 | 69.657 | 47.985 | 78.082 | 1.00 | 23.79 | B |
| ATOM | 2210 | CG | MET | B | 306 | 70.564 | 48.530 | 77.001 | 1.00 | 26.43 | B |
| ATOM | 2211 | SD | MET | B | 306 | 72.156 | 49.325 | 77.607 | 1.00 | 30.02 | B |
| ATOM | 2212 | CE | MET | B | 306 | 73.042 | 47.949 | 77.638 | 1.00 | 27.20 | B |
| ATOM | 2213 | C | MET | B | 306 | 68.488 | 50.250 | 78.306 | 1.00 | 23.77 | B |
| ATOM | 2214 | O | MET | B | 306 | 69.208 | 51.282 | 78.094 | 1.00 | 24.11 | B |
| ATOM | 2215 | N | GLU | B | 307 | 67.167 | 50.223 | 78.104 | 1.00 | 22.92 | B |
| ATOM | 2216 | CA | GLU | B | 307 | 66.507 | 51.427 | 77.664 | 1.00 | 23.45 | B |
| ATOM | 2217 | CB | GLU | B | 307 | 65.043 | 51.227 | 77.480 | 1.00 | 23.82 | B |
| ATOM | 2218 | CG | GLU | B | 307 | 64.733 | 50.120 | 76.383 | 1.00 | 25.10 | B |
| ATOM | 2219 | CD | GLU | B | 307 | 63.279 | 49.991 | 75.962 | 1.00 | 25.61 | B |
| ATOM | 2220 | OE1 | GLU | B | 307 | 62.508 | 50.998 | 75.992 | 1.00 | 25.11 | B |
| ATOM | 2221 | OE2 | GLU | B | 307 | 62.915 | 48.866 | 75.607 | 1.00 | 26.86 | B |
| ATOM | 2222 | C | GLU | B | 307 | 66.810 | 52.614 | 78.623 | 1.00 | 24.04 | B |
| ATOM | 2223 | O | GLU | B | 307 | 67.031 | 53.704 | 78.163 | 1.00 | 24.19 | B |
| ATOM | 2224 | N | ILE | B | 308 | 66.722 | 52.392 | 79.914 | 1.00 | 24.68 | B |
| ATOM | 2225 | CA | ILE | B | 308 | 66.936 | 53.384 | 80.902 | 1.00 | 27.03 | B |
| ATOM | 2226 | CB | ILE | B | 308 | 66.506 | 52.939 | 82.362 | 1.00 | 26.02 | B |
| ATOM | 2227 | CG2 | ILE | B | 308 | 66.815 | 54.133 | 83.371 | 1.00 | 22.94 | B |
| ATOM | 2228 | CG1 | ILE | B | 308 | 65.003 | 52.614 | 82.417 | 1.00 | 25.67 | B |
| ATOM | 2229 | CD1 | ILE | B | 308 | 64.692 | 51.606 | 83.554 | 1.00 | 26.46 | B |
| ATOM | 2230 | C | ILE | B | 308 | 68.421 | 53.918 | 80.871 | 1.00 | 28.56 | B |
| ATOM | 2231 | O | ILE | B | 308 | 68.660 | 55.087 | 80.799 | 1.00 | 29.27 | B |
| ATOM | 2232 | N | LEU | B | 309 | 69.364 | 53.041 | 80.795 | 1.00 | 30.06 | B |
| ATOM | 2233 | CA | LEU | B | 309 | 70.719 | 53.477 | 80.595 | 1.00 | 31.21 | B |
| ATOM | 2234 | CB | LEU | B | 309 | 71.670 | 52.258 | 80.463 | 1.00 | 30.80 | B |
| ATOM | 2235 | CG | LEU | B | 309 | 71.846 | 51.549 | 81.795 | 1.00 | 32.10 | B |
| ATOM | 2236 | CD1 | LEU | B | 309 | 72.815 | 50.337 | 81.502 | 1.00 | 29.25 | B |
| ATOM | 2237 | CD2 | LEU | B | 309 | 72.312 | 52.542 | 82.845 | 1.00 | 30.06 | B |
| ATOM | 2238 | C | LEU | B | 309 | 70.873 | 54.312 | 79.383 | 1.00 | 31.15 | B |
| ATOM | 2239 | O | LEU | B | 309 | 71.454 | 55.361 | 79.451 | 1.00 | 31.08 | B |
| ATOM | 2240 | N | ILE | B | 310 | 70.351 | 53.852 | 78.273 | 1.00 | 30.66 | B |
| ATOM | 2241 | CA | ILE | B | 310 | 70.659 | 54.480 | 76.954 | 1.00 | 29.37 | B |
| ATOM | 2242 | CB | ILE | B | 310 | 70.220 | 53.582 | 75.820 | 1.00 | 29.53 | B |
| ATOM | 2243 | CG2 | ILE | B | 310 | 70.121 | 54.276 | 74.554 | 1.00 | 26.63 | B |
| ATOM | 2244 | CG1 | ILE | B | 310 | 71.094 | 52.346 | 75.740 | 1.00 | 31.36 | B |
| ATOM | 2245 | CD1 | ILE | B | 310 | 72.310 | 52.453 | 74.935 | 1.00 | 33.55 | B |
| ATOM | 2246 | C | ILE | B | 310 | 69.916 | 55.780 | 76.897 | 1.00 | 29.49 | B |
| ATOM | 2247 | O | ILE | B | 310 | 70.457 | 56.725 | 76.417 | 1.00 | 28.86 | B |
| ATOM | 2248 | N | LEU | B | 311 | 68.688 | 55.860 | 77.410 | 1.00 | 29.18 | B |
| ATOM | 2249 | CA | LEU | B | 311 | 68.030 | 57.171 | 77.436 | 1.00 | 29.01 | B |
| ATOM | 2250 | CB | LEU | B | 311 | 66.643 | 57.075 | 78.057 | 1.00 | 27.70 | B |
| ATOM | 2251 | CG | LEU | B | 311 | 65.524 | 58.014 | 77.613 | 1.00 | 27.95 | B |
| ATOM | 2252 | CD1 | LEU | B | 311 | 65.661 | 58.665 | 76.260 | 1.00 | 25.60 | B |
| ATOM | 2253 | CD2 | LEU | B | 311 | 64.283 | 57.287 | 77.683 | 1.00 | 29.47 | B |
| ATOM | 2254 | C | LEU | B | 311 | 68.905 | 58.291 | 78.251 | 1.00 | 29.48 | B |
| ATOM | 2255 | O | LEU | B | 311 | 69.042 | 59.451 | 77.855 | 1.00 | 28.72 | B |
| ATOM | 2256 | N | GLY | B | 312 | 69.503 | 57.897 | 79.348 | 1.00 | 29.47 | B |
| ATOM | 2257 | CA | GLY | B | 312 | 70.361 | 58.846 | 80.033 | 1.00 | 30.46 | B |
| ATOM | 2258 | C | GLY | B | 312 | 71.556 | 59.319 | 79.171 | 1.00 | 31.33 | B |
| ATOM | 2259 | O | GLY | B | 312 | 71.705 | 60.526 | 78.971 | 1.00 | 32.33 | B |
| ATOM | 2260 | N | VAL | B | 313 | 72.356 | 58.371 | 78.635 | 1.00 | 30.89 | B |
| ATOM | 2261 | CA | VAL | B | 313 | 73.414 | 58.678 | 77.688 | 1.00 | 31.23 | B |
| ATOM | 2262 | CB | VAL | B | 313 | 73.963 | 57.443 | 77.035 | 1.00 | 32.49 | B |
| ATOM | 2263 | CG1 | VAL | B | 313 | 75.186 | 57.795 | 76.203 | 1.00 | 31.94 | B |
| ATOM | 2264 | CG2 | VAL | B | 313 | 74.422 | 56.499 | 78.102 | 1.00 | 32.21 | B |
| ATOM | 2265 | C | VAL | B | 313 | 72.928 | 59.684 | 76.698 | 1.00 | 32.02 | B |
| ATOM | 2266 | O | VAL | B | 313 | 73.500 | 60.732 | 76.543 | 1.00 | 32.76 | B |
| ATOM | 2267 | N | VAL | B | 314 | 71.822 | 59.410 | 76.060 | 1.00 | 31.69 | B |
| ATOM | 2268 | CA | VAL | B | 314 | 71.284 | 60.260 | 75.077 | 1.00 | 30.59 | B |
| ATOM | 2269 | CB | VAL | B | 314 | 69.981 | 59.596 | 74.446 | 1.00 | 29.52 | B |
| ATOM | 2270 | CG1 | VAL | B | 314 | 69.167 | 60.540 | 73.706 | 1.00 | 27.16 | B |
| ATOM | 2271 | CG2 | VAL | B | 314 | 70.348 | 58.382 | 73.565 | 1.00 | 24.81 | B |
| ATOM | 2272 | C | VAL | B | 314 | 70.979 | 61.680 | 75.647 | 1.00 | 33.13 | B |
| ATOM | 2273 | O | VAL | B | 314 | 71.320 | 62.749 | 75.018 | 1.00 | 34.01 | B |

TABLE 2-continued

ATOMIC COORDINATES OF THE ERR3 LBD/
DIETHYLSTILBESTROL COMPLEX

| ATOM | 2274 | N | TYR | B | 315 | 70.260 | 61.744 | 76.747 | 1.00 | 32.81 | B |
|------|------|-----|-----|---|-----|--------|--------|--------|------|-------|---|
| ATOM | 2275 | CA | TYR | B | 315 | 69.855 | 63.000 | 77.226 | 1.00 | 32.25 | B |
| ATOM | 2276 | CB | TYR | B | 315 | 69.031 | 62.872 | 78.477 | 1.00 | 32.50 | B |
| ATOM | 2277 | CG | TYR | B | 315 | 68.533 | 64.260 | 78.923 | 1.00 | 31.80 | B |
| ATOM | 2278 | CD1 | TYR | B | 315 | 67.599 | 64.897 | 78.209 | 1.00 | 32.09 | B |
| ATOM | 2279 | CE1 | TYR | B | 315 | 67.188 | 66.212 | 78.531 | 1.00 | 34.04 | B |
| ATOM | 2280 | CD2 | TYR | B | 315 | 69.080 | 64.910 | 80.081 | 1.00 | 32.95 | B |
| ATOM | 2281 | CE2 | TYR | B | 315 | 68.678 | 66.191 | 80.450 | 1.00 | 32.34 | B |
| ATOM | 2282 | CZ | TYR | B | 315 | 67.762 | 66.846 | 79.659 | 1.00 | 32.92 | B |
| ATOM | 2283 | OH | TYR | B | 315 | 67.300 | 68.055 | 79.995 | 1.00 | 36.08 | B |
| ATOM | 2284 | C | TYR | B | 315 | 71.116 | 63.893 | 77.524 | 1.00 | 33.56 | B |
| ATOM | 2285 | O | TYR | B | 315 | 71.149 | 65.051 | 77.180 | 1.00 | 33.02 | B |
| ATOM | 2286 | N | ARG | B | 316 | 72.125 | 63.301 | 78.160 | 1.00 | 33.10 | B |
| ATOM | 2287 | CA | ARG | B | 316 | 73.365 | 64.000 | 78.463 | 1.00 | 34.32 | B |
| ATOM | 2288 | CB | ARG | B | 316 | 74.287 | 63.122 | 79.353 | 1.00 | 32.72 | B |
| ATOM | 2289 | CG | ARG | B | 316 | 73.803 | 62.824 | 80.758 | 1.00 | 30.34 | B |
| ATOM | 2290 | CD | ARG | B | 316 | 74.738 | 61.943 | 81.520 | 1.00 | 29.36 | B |
| ATOM | 2291 | NE | ARG | B | 316 | 75.059 | 60.607 | 81.018 | 1.00 | 32.17 | B |
| ATOM | 2292 | CZ | ARG | B | 316 | 74.421 | 59.452 | 81.309 | 1.00 | 30.81 | B |
| ATOM | 2293 | NH1 | ARG | B | 316 | 73.385 | 59.412 | 82.047 | 1.00 | 31.43 | B |
| ATOM | 2294 | NH2 | ARG | B | 316 | 74.839 | 58.308 | 80.867 | 1.00 | 31.09 | B |
| ATOM | 2295 | C | ARG | B | 316 | 74.211 | 64.381 | 77.257 | 1.00 | 34.91 | B |
| ATOM | 2296 | O | ARG | B | 316 | 75.236 | 65.068 | 77.439 | 1.00 | 36.52 | B |
| ATOM | 2297 | N | SER | B | 317 | 73.870 | 63.897 | 76.076 | 1.00 | 34.74 | B |
| ATOM | 2298 | CA | SER | B | 317 | 74.641 | 64.073 | 74.853 | 1.00 | 34.16 | B |
| ATOM | 2299 | CB | SER | B | 317 | 74.827 | 62.707 | 74.117 | 1.00 | 32.78 | B |
| ATOM | 2300 | OG | SER | B | 317 | 75.680 | 61.889 | 74.898 | 1.00 | 31.44 | B |
| ATOM | 2301 | C | SER | B | 317 | 73.960 | 65.096 | 73.993 | 1.00 | 34.91 | B |
| ATOM | 2302 | O | SER | B | 317 | 74.440 | 65.383 | 72.883 | 1.00 | 35.72 | B |
| ATOM | 2303 | N | LEU | B | 318 | 72.825 | 65.641 | 74.440 | 1.00 | 35.54 | B |
| ATOM | 2304 | CA | LEU | B | 318 | 72.050 | 66.479 | 73.572 | 1.00 | 37.65 | B |
| ATOM | 2305 | CB | LEU | B | 318 | 70.747 | 66.871 | 74.210 | 1.00 | 37.06 | B |
| ATOM | 2306 | CG | LEU | B | 318 | 69.660 | 65.814 | 74.427 | 1.00 | 38.19 | B |
| ATOM | 2307 | CD1 | LEU | B | 318 | 68.505 | 66.355 | 75.273 | 1.00 | 36.64 | B |
| ATOM | 2308 | CD2 | LEU | B | 318 | 69.120 | 65.321 | 73.143 | 1.00 | 36.56 | B |
| ATOM | 2309 | C | LEU | B | 318 | 72.761 | 67.820 | 73.089 | 1.00 | 39.99 | B |
| ATOM | 2310 | O | LEU | B | 318 | 72.510 | 68.275 | 71.971 | 1.00 | 40.15 | B |
| ATOM | 2311 | N | SER | B | 319 | 73.556 | 68.461 | 73.946 | 1.00 | 40.46 | B |
| ATOM | 2312 | CA | SER | B | 319 | 74.311 | 69.692 | 73.548 | 1.00 | 42.18 | B |
| ATOM | 2313 | CB | SER | B | 319 | 74.784 | 70.430 | 74.803 | 1.00 | 41.10 | B |
| ATOM | 2314 | OG | SER | B | 319 | 73.650 | 70.754 | 75.590 | 1.00 | 40.12 | B |
| ATOM | 2315 | C | SER | B | 319 | 75.585 | 69.410 | 72.798 | 1.00 | 43.68 | B |
| ATOM | 2316 | O | SER | B | 319 | 76.355 | 70.317 | 72.557 | 1.00 | 45.44 | B |
| ATOM | 2317 | N | PHE | B | 320 | 75.923 | 68.154 | 72.594 | 1.00 | 43.12 | B |
| ATOM | 2318 | CA | PHE | B | 320 | 77.212 | 67.813 | 72.035 | 1.00 | 42.35 | B |
| ATOM | 2319 | CB | PHE | B | 320 | 77.881 | 66.700 | 72.747 | 1.00 | 40.98 | B |
| ATOM | 2320 | CG | PHE | B | 320 | 78.322 | 67.061 | 74.090 | 1.00 | 40.50 | B |
| ATOM | 2321 | CD1 | PHE | B | 320 | 79.697 | 67.037 | 74.411 | 1.00 | 40.22 | B |
| ATOM | 2322 | CD2 | PHE | B | 320 | 77.383 | 67.415 | 75.058 | 1.00 | 39.23 | B |
| ATOM | 2323 | CE1 | PHE | B | 320 | 80.116 | 67.409 | 75.723 | 1.00 | 40.99 | B |
| ATOM | 2324 | CE2 | PHE | B | 320 | 77.770 | 67.729 | 76.385 | 1.00 | 39.67 | B |
| ATOM | 2325 | CZ | PHE | B | 320 | 79.117 | 67.746 | 76.694 | 1.00 | 40.54 | B |
| ATOM | 2326 | C | PHE | B | 320 | 76.979 | 67.504 | 70.621 | 1.00 | 43.48 | B |
| ATOM | 2327 | O | PHE | B | 320 | 75.855 | 67.689 | 70.131 | 1.00 | 43.94 | B |
| ATOM | 2328 | N | GLU | B | 321 | 78.054 | 67.093 | 69.937 | 1.00 | 44.29 | B |
| ATOM | 2329 | CA | GLU | B | 321 | 77.990 | 66.821 | 68.493 | 1.00 | 44.97 | B |
| ATOM | 2330 | CB | GLU | B | 321 | 78.285 | 68.062 | 67.601 | 1.00 | 45.34 | B |
| ATOM | 2331 | CG | GLU | B | 321 | 77.118 | 68.284 | 66.612 | 1.00 | 46.77 | B |
| ATOM | 2332 | CD | GLU | B | 321 | 75.879 | 69.171 | 67.542 | 0.00 | 46.47 | B |
| ATOM | 2333 | OE1 | GLU | B | 321 | 76.137 | 70.064 | 68.390 | 0.00 | 46.63 | B |
| ATOM | 2334 | OE2 | GLU | B | 321 | 74.677 | 68.944 | 67.396 | 0.00 | 46.63 | B |
| ATOM | 2335 | C | GLU | B | 321 | 78.857 | 65.688 | 68.125 | 1.00 | 44.20 | B |
| ATOM | 2336 | O | GLU | B | 321 | 80.082 | 65.698 | 68.303 | 1.00 | 43.11 | B |
| ATOM | 2337 | N | ASP | B | 322 | 78.174 | 64.644 | 67.660 | 1.00 | 42.54 | B |
| ATOM | 2338 | CA | ASP | B | 322 | 78.858 | 63.417 | 67.398 | 1.00 | 41.44 | B |
| ATOM | 2339 | CB | ASP | B | 322 | 79.631 | 63.608 | 66.084 | 1.00 | 42.81 | B |
| ATOM | 2340 | CG | ASP | B | 322 | 78.693 | 63.457 | 64.893 | 1.00 | 45.59 | B |
| ATOM | 2341 | OD1 | ASP | B | 322 | 77.437 | 63.517 | 64.960 | 0.00 | 45.52 | B |
| ATOM | 2342 | OD2 | ASP | B | 322 | 78.428 | 64.349 | 64.093 | 1.00 | 48.39 | B |
| ATOM | 2343 | C | ASP | B | 322 | 79.677 | 62.931 | 68.561 | 1.00 | 39.69 | B |
| ATOM | 2344 | O | ASP | B | 322 | 80.640 | 62.166 | 68.427 | 1.00 | 38.51 | B |
| ATOM | 2345 | N | GLU | B | 323 | 79.262 | 63.279 | 69.757 | 1.00 | 39.31 | B |
| ATOM | 2346 | CA | GLU | B | 323 | 79.881 | 62.637 | 70.963 | 1.00 | 39.98 | B |
| ATOM | 2347 | CB | GLU | B | 323 | 80.830 | 63.620 | 71.687 | 1.00 | 42.90 | B |
| ATOM | 2348 | CG | GLU | B | 323 | 81.725 | 64.367 | 70.667 | 1.00 | 52.92 | B |
| ATOM | 2349 | CD | GLU | B | 323 | 81.113 | 65.641 | 70.180 | 1.00 | 59.04 | B |

TABLE 2-continued

ATOMIC COORDINATES OF THE ERR3 LBD/
DIETHYLSTILBESTROL COMPLEX

| ATOM | 2350 | OE1 | GLU | B | 323 | 79.972 | 65.947 | 70.596 | 1.00 | 63.36 | B |
|---|---|---|---|---|---|---|---|---|---|---|---|
| ATOM | 2351 | OE2 | GLU | B | 323 | 81.785 | 66.352 | 69.393 | 1.00 | 64.41 | B |
| ATOM | 2352 | C | GLU | B | 323 | 78.817 | 62.059 | 71.932 | 1.00 | 36.65 | B |
| ATOM | 2353 | O | GLU | B | 323 | 77.755 | 62.563 | 71.954 | 1.00 | 34.31 | B |
| ATOM | 2354 | N | LEU | B | 324 | 79.225 | 61.175 | 72.824 | 1.00 | 35.01 | B |
| ATOM | 2355 | CA | LEU | B | 324 | 78.331 | 60.589 | 73.833 | 1.00 | 34.74 | B |
| ATOM | 2356 | CB | LEU | B | 324 | 78.075 | 59.040 | 73.536 | 1.00 | 33.47 | B |
| ATOM | 2357 | CG | LEU | B | 324 | 77.370 | 58.616 | 72.288 | 1.00 | 32.79 | B |
| ATOM | 2358 | CD1 | LEU | B | 324 | 77.345 | 57.059 | 72.020 | 1.00 | 30.94 | B |
| ATOM | 2359 | CD2 | LEU | B | 324 | 76.064 | 59.231 | 72.205 | 1.00 | 31.72 | B |
| ATOM | 2360 | C | LEU | B | 324 | 78.890 | 60.729 | 75.213 | 1.00 | 34.38 | B |
| ATOM | 2361 | O | LEU | B | 324 | 79.988 | 60.323 | 75.479 | 1.00 | 34.84 | B |
| ATOM | 2362 | N | VAL | B | 325 | 78.105 | 61.325 | 76.106 | 1.00 | 35.25 | B |
| ATOM | 2363 | CA | VAL | B | 325 | 78.540 | 61.622 | 77.425 | 1.00 | 33.68 | B |
| ATOM | 2364 | CB | VAL | B | 325 | 77.929 | 62.930 | 77.879 | 1.00 | 34.23 | B |
| ATOM | 2365 | CG1 | VAL | B | 325 | 78.271 | 63.312 | 79.269 | 1.00 | 31.30 | B |
| ATOM | 2366 | CG2 | VAL | B | 325 | 78.184 | 63.980 | 76.905 | 1.00 | 34.10 | B |
| ATOM | 2367 | C | VAL | B | 325 | 77.995 | 60.467 | 78.171 | 1.00 | 33.34 | B |
| ATOM | 2368 | O | VAL | B | 325 | 76.961 | 60.540 | 78.769 | 1.00 | 32.70 | B |
| ATOM | 2369 | N | TYR | B | 326 | 78.719 | 59.380 | 78.146 | 1.00 | 34.48 | B |
| ATOM | 2370 | CA | TYR | B | 326 | 78.477 | 58.339 | 79.063 | 1.00 | 35.03 | B |
| ATOM | 2371 | CB | TYR | B | 326 | 79.367 | 57.103 | 78.801 | 1.00 | 34.39 | B |
| ATOM | 2372 | CG | TYR | B | 326 | 78.926 | 56.294 | 77.567 | 1.00 | 33.63 | B |
| ATOM | 2373 | CD1 | TYR | B | 326 | 77.834 | 55.390 | 77.636 | 1.00 | 33.31 | B |
| ATOM | 2374 | CE1 | TYR | B | 326 | 77.418 | 54.653 | 76.467 | 1.00 | 34.84 | B |
| ATOM | 2375 | CD2 | TYR | B | 326 | 79.588 | 56.440 | 76.331 | 1.00 | 32.99 | B |
| ATOM | 2376 | CE2 | TYR | B | 326 | 79.174 | 55.753 | 75.159 | 1.00 | 33.38 | B |
| ATOM | 2377 | CZ | TYR | B | 326 | 78.076 | 54.877 | 75.243 | 1.00 | 34.67 | B |
| ATOM | 2378 | OH | TYR | B | 326 | 77.682 | 54.203 | 74.172 | 1.00 | 36.10 | B |
| ATOM | 2379 | C | TYR | B | 326 | 78.453 | 58.837 | 80.553 | 1.00 | 36.71 | B |
| ATOM | 2380 | O | TYR | B | 326 | 77.758 | 58.240 | 81.453 | 1.00 | 35.48 | B |
| ATOM | 2381 | N | ALA | B | 327 | 79.309 | 59.810 | 80.794 | 1.00 | 37.42 | B |
| ATOM | 2382 | CA | ALA | B | 327 | 79.494 | 60.512 | 82.077 | 1.00 | 40.16 | B |
| ATOM | 2383 | CB | ALA | B | 327 | 80.198 | 59.609 | 83.061 | 1.00 | 36.43 | B |
| ATOM | 2384 | C | ALA | B | 327 | 80.309 | 61.797 | 81.767 | 1.00 | 41.92 | B |
| ATOM | 2385 | O | ALA | B | 327 | 80.810 | 61.926 | 80.628 | 1.00 | 43.35 | B |
| ATOM | 2386 | N | ASP | B | 328 | 80.400 | 62.750 | 82.702 | 1.00 | 43.79 | B |
| ATOM | 2387 | CA | ASP | B | 328 | 80.995 | 64.077 | 82.434 | 1.00 | 45.63 | B |
| ATOM | 2388 | CB | ASP | B | 328 | 80.731 | 65.088 | 83.533 | 1.00 | 47.41 | B |
| ATOM | 2389 | CG | ASP | B | 328 | 79.278 | 65.551 | 83.625 | 1.00 | 49.98 | B |
| ATOM | 2390 | OD1 | ASP | B | 328 | 78.494 | 65.650 | 82.641 | 1.00 | 51.76 | B |
| ATOM | 2391 | OD2 | ASP | B | 328 | 78.865 | 65.955 | 84.700 | 1.00 | 51.84 | B |
| ATOM | 2392 | C | ASP | B | 328 | 82.441 | 63.734 | 82.492 | 1.00 | 45.90 | B |
| ATOM | 2393 | O | ASP | B | 328 | 83.257 | 64.254 | 81.867 | 1.00 | 45.94 | B |
| ATOM | 2394 | N | ASP | B | 329 | 82.653 | 62.674 | 83.191 | 1.00 | 46.56 | B |
| ATOM | 2395 | CA | ASP | B | 329 | 83.849 | 61.894 | 83.205 | 1.00 | 46.24 | B |
| ATOM | 2396 | CB | ASP | B | 329 | 83.506 | 60.787 | 84.227 | 1.00 | 46.44 | B |
| ATOM | 2397 | CG | ASP | B | 329 | 84.670 | 60.407 | 85.026 | 1.00 | 48.27 | B |
| ATOM | 2398 | OD1 | ASP | B | 329 | 85.727 | 60.873 | 84.659 | 1.00 | 50.25 | B |
| ATOM | 2399 | OD2 | ASP | B | 329 | 84.706 | 59.607 | 85.947 | 1.00 | 46.54 | B |
| ATOM | 2400 | C | ASP | B | 329 | 84.383 | 61.202 | 81.924 | 1.00 | 45.93 | B |
| ATOM | 2401 | O | ASP | B | 329 | 85.529 | 60.674 | 81.947 | 1.00 | 45.70 | B |
| ATOM | 2402 | N | TYR | B | 330 | 83.547 | 61.000 | 80.884 | 1.00 | 45.49 | B |
| ATOM | 2403 | CA | TYR | B | 330 | 83.815 | 59.900 | 79.896 | 1.00 | 44.13 | B |
| ATOM | 2404 | CB | TYR | B | 330 | 83.505 | 58.581 | 80.566 | 1.00 | 44.52 | B |
| ATOM | 2405 | CG | TYR | B | 330 | 84.246 | 57.505 | 79.978 | 1.00 | 45.53 | B |
| ATOM | 2406 | CD1 | TYR | B | 330 | 85.571 | 57.368 | 80.251 | 1.00 | 45.25 | B |
| ATOM | 2407 | CE1 | TYR | B | 330 | 86.316 | 56.341 | 79.692 | 1.00 | 46.79 | B |
| ATOM | 2408 | CD2 | TYR | B | 330 | 83.629 | 56.664 | 79.034 | 1.00 | 45.86 | B |
| ATOM | 2409 | CE2 | TYR | B | 330 | 84.318 | 55.649 | 78.465 | 1.00 | 47.39 | B |
| ATOM | 2410 | CZ | TYR | B | 330 | 85.689 | 55.461 | 78.775 | 1.00 | 47.46 | B |
| ATOM | 2411 | OH | TYR | B | 330 | 86.398 | 54.442 | 78.179 | 1.00 | 47.00 | B |
| ATOM | 2412 | C | TYR | B | 330 | 82.967 | 60.053 | 78.708 | 1.00 | 43.02 | B |
| ATOM | 2413 | O | TYR | B | 330 | 81.869 | 59.465 | 78.615 | 1.00 | 42.52 | B |
| ATOM | 2414 | N | ILE | B | 331 | 83.416 | 60.972 | 77.871 | 1.00 | 42.51 | B |
| ATOM | 2415 | CA | ILE | B | 331 | 82.769 | 61.439 | 76.644 | 1.00 | 41.81 | B |
| ATOM | 2416 | CB | ILE | B | 331 | 82.882 | 62.878 | 76.492 | 1.00 | 39.50 | B |
| ATOM | 2417 | CG2 | ILE | B | 331 | 82.271 | 63.402 | 75.172 | 1.00 | 38.06 | B |
| ATOM | 2418 | CG1 | ILE | B | 331 | 82.181 | 63.555 | 77.620 | 1.00 | 39.56 | B |
| ATOM | 2419 | CD1 | ILE | B | 331 | 82.493 | 65.181 | 77.664 | 1.00 | 38.15 | B |
| ATOM | 2420 | C | ILE | B | 331 | 83.575 | 60.758 | 75.547 | 1.00 | 43.27 | B |
| ATOM | 2421 | O | ILE | B | 331 | 84.799 | 60.944 | 75.542 | 1.00 | 43.05 | B |
| ATOM | 2422 | N | MET | B | 332 | 82.887 | 59.866 | 74.770 | 1.00 | 43.57 | B |
| ATOM | 2423 | CA | MET | B | 332 | 83.419 | 59.095 | 73.617 | 1.00 | 44.18 | B |
| ATOM | 2424 | CB | MET | B | 332 | 82.806 | 57.694 | 73.489 | 1.00 | 44.56 | B |
| ATOM | 2425 | CG | MET | B | 332 | 83.169 | 56.866 | 74.627 | 1.00 | 46.35 | B |

TABLE 2-continued

ATOMIC COORDINATES OF THE ERR3 LBD/
DIETHYLSTILBESTROL COMPLEX

| ATOM | 2426 | SD | MET | B | 332 | 82.689 | 55.206 | 74.484 | 1.00 | 48.28 | B |
| --- | --- | --- | --- | --- | --- | --- | --- | --- | --- | --- | --- |
| ATOM | 2427 | CE | MET | B | 332 | 83.789 | 54.885 | 73.124 | 1.00 | 46.76 | B |
| ATOM | 2428 | C | MET | B | 332 | 83.126 | 59.778 | 72.351 | 1.00 | 44.54 | B |
| ATOM | 2429 | O | MET | B | 332 | 81.940 | 60.077 | 72.044 | 1.00 | 44.49 | B |
| ATOM | 2430 | N | ASP | B | 333 | 84.223 | 60.101 | 71.642 | 1.00 | 45.57 | B |
| ATOM | 2431 | CA | ASP | B | 333 | 84.129 | 60.547 | 70.267 | 1.00 | 47.05 | B |
| ATOM | 2432 | CB | ASP | B | 333 | 85.058 | 61.772 | 70.010 | 1.00 | 48.43 | B |
| ATOM | 2433 | CG | ASP | B | 333 | 86.600 | 61.436 | 69.904 | 1.00 | 49.92 | B |
| ATOM | 2434 | OD1 | ASP | B | 333 | 87.117 | 60.284 | 70.238 | 1.00 | 51.04 | B |
| ATOM | 2435 | OD2 | ASP | B | 333 | 87.390 | 62.367 | 69.485 | 1.00 | 53.15 | B |
| ATOM | 2436 | C | ASP | B | 333 | 84.320 | 59.381 | 69.267 | 1.00 | 47.01 | B |
| ATOM | 2437 | O | ASP | B | 333 | 84.546 | 58.208 | 69.678 | 1.00 | 47.03 | B |
| ATOM | 2438 | N | GLU | B | 334 | 84.274 | 59.714 | 67.981 | 1.00 | 47.62 | B |
| ATOM | 2439 | CA | GLU | B | 334 | 84.401 | 58.737 | 66.929 | 1.00 | 49.18 | B |
| ATOM | 2440 | CB | GLU | B | 334 | 84.204 | 59.349 | 65.513 | 1.00 | 50.68 | B |
| ATOM | 2441 | CG | GLU | B | 334 | 84.392 | 58.346 | 64.333 | 1.00 | 52.83 | B |
| ATOM | 2442 | CD | GLU | B | 334 | 83.806 | 58.784 | 62.968 | 1.00 | 55.00 | B |
| ATOM | 2443 | OE1 | GLU | B | 334 | 83.054 | 59.812 | 62.908 | 1.00 | 56.52 | B |
| ATOM | 2444 | OE2 | GLU | B | 334 | 84.091 | 58.072 | 61.943 | 1.00 | 55.97 | B |
| ATOM | 2445 | C | GLU | B | 334 | 85.636 | 57.896 | 67.071 | 1.00 | 49.70 | B |
| ATOM | 2446 | O | GLU | B | 334 | 85.529 | 56.668 | 66.861 | 1.00 | 50.15 | B |
| ATOM | 2447 | N | ASP | B | 335 | 86.780 | 58.467 | 67.495 | 1.00 | 50.51 | B |
| ATOM | 2448 | CA | ASP | B | 335 | 88.000 | 57.678 | 67.577 | 1.00 | 50.85 | B |
| ATOM | 2449 | CB | ASP | B | 335 | 89.273 | 58.494 | 67.665 | 1.00 | 53.49 | B |
| ATOM | 2450 | CG | ASP | B | 335 | 89.406 | 59.528 | 66.595 | 1.00 | 55.75 | B |
| ATOM | 2451 | OD1 | ASP | B | 335 | 89.155 | 59.254 | 65.388 | 1.00 | 56.53 | B |
| ATOM | 2452 | OD2 | ASP | B | 335 | 89.776 | 60.684 | 66.930 | 1.00 | 58.99 | B |
| ATOM | 2453 | C | ASP | B | 335 | 88.050 | 56.860 | 68.775 | 1.00 | 50.11 | B |
| ATOM | 2454 | O | ASP | B | 335 | 88.645 | 55.805 | 68.773 | 1.00 | 49.05 | B |
| ATOM | 2455 | N | GLN | B | 336 | 87.458 | 57.301 | 69.848 | 1.00 | 49.27 | B |
| ATOM | 2456 | CA | GLN | B | 336 | 87.327 | 56.376 | 70.982 | 1.00 | 48.88 | B |
| ATOM | 2457 | CB | GLN | B | 336 | 86.838 | 57.151 | 72.176 | 1.00 | 52.18 | B |
| ATOM | 2458 | CG | GLN | B | 336 | 87.653 | 56.895 | 73.433 | 1.00 | 58.65 | B |
| ATOM | 2459 | CD | GLN | B | 336 | 89.082 | 57.396 | 73.328 | 1.00 | 61.58 | B |
| ATOM | 2460 | OE1 | GLN | B | 336 | 89.838 | 56.975 | 72.454 | 1.00 | 64.40 | B |
| ATOM | 2461 | NE2 | GLN | B | 336 | 89.459 | 58.304 | 74.223 | 1.00 | 62.99 | B |
| ATOM | 2462 | C | GLN | B | 336 | 86.418 | 55.167 | 70.764 | 1.00 | 46.60 | B |
| ATOM | 2463 | O | GLN | B | 336 | 86.680 | 54.000 | 71.199 | 1.00 | 44.55 | B |
| ATOM | 2464 | N | SER | B | 337 | 85.345 | 55.417 | 70.062 | 1.00 | 45.28 | B |
| ATOM | 2465 | CA | SER | B | 337 | 84.355 | 54.337 | 69.810 | 1.00 | 44.79 | B |
| ATOM | 2466 | CB | SER | B | 337 | 83.160 | 54.961 | 69.089 | 1.00 | 43.98 | B |
| ATOM | 2467 | OG | SER | B | 337 | 82.474 | 55.912 | 69.875 | 1.00 | 41.90 | B |
| ATOM | 2468 | C | SER | B | 337 | 85.023 | 53.221 | 68.922 | 1.00 | 45.48 | B |
| ATOM | 2469 | O | SER | B | 337 | 84.920 | 51.972 | 69.163 | 1.00 | 44.52 | B |
| ATOM | 2470 | N | LYS | B | 338 | 85.710 | 53.631 | 67.893 | 1.00 | 46.78 | B |
| ATOM | 2471 | CA | LYS | B | 338 | 86.458 | 52.636 | 67.057 | 1.00 | 49.49 | B |
| ATOM | 2472 | CB | LYS | B | 338 | 87.094 | 53.318 | 65.820 | 1.00 | 53.18 | B |
| ATOM | 2473 | CG | LYS | B | 338 | 88.073 | 54.444 | 66.155 | 1.00 | 59.94 | B |
| ATOM | 2474 | CD | LYS | B | 338 | 88.685 | 55.082 | 64.906 | 1.00 | 64.28 | B |
| ATOM | 2475 | CE | LYS | B | 338 | 87.711 | 56.007 | 64.178 | 1.00 | 65.85 | B |
| ATOM | 2476 | NZ | LYS | B | 338 | 86.500 | 55.288 | 63.692 | 1.00 | 67.20 | B |
| ATOM | 2477 | C | LYS | B | 338 | 87.518 | 51.863 | 67.859 | 1.00 | 48.94 | B |
| ATOM | 2478 | O | LYS | B | 338 | 87.590 | 50.600 | 67.787 | 1.00 | 48.51 | B |
| ATOM | 2479 | N | LEU | B | 339 | 88.277 | 52.577 | 68.709 | 1.00 | 48.04 | B |
| ATOM | 2480 | CA | LEU | B | 339 | 89.167 | 51.911 | 69.683 | 1.00 | 47.74 | B |
| ATOM | 2481 | CB | LEU | B | 339 | 89.928 | 52.977 | 70.460 | 1.00 | 48.94 | B |
| ATOM | 2482 | CG | LEU | B | 339 | 91.293 | 53.573 | 69.960 | 1.00 | 50.03 | B |
| ATOM | 2483 | CD1 | LEU | B | 339 | 92.188 | 52.426 | 69.483 | 1.00 | 50.37 | B |
| ATOM | 2484 | CD2 | LEU | B | 339 | 91.261 | 54.615 | 68.842 | 1.00 | 50.21 | B |
| ATOM | 2485 | C | LEU | B | 339 | 88.449 | 50.846 | 70.604 | 1.00 | 47.22 | B |
| ATOM | 2486 | O | LEU | B | 339 | 88.978 | 49.698 | 70.875 | 1.00 | 47.40 | B |
| ATOM | 2487 | N | ALA | B | 340 | 87.217 | 51.145 | 71.007 | 1.00 | 46.34 | B |
| ATOM | 2488 | CA | ALA | B | 340 | 86.519 | 50.268 | 72.021 | 1.00 | 45.49 | B |
| ATOM | 2489 | CB | ALA | B | 340 | 85.482 | 51.044 | 72.837 | 1.00 | 46.18 | B |
| ATOM | 2490 | C | ALA | B | 340 | 85.808 | 49.183 | 71.316 | 1.00 | 44.68 | B |
| ATOM | 2491 | O | ALA | B | 340 | 85.333 | 48.236 | 71.944 | 1.00 | 44.58 | B |
| ATOM | 2492 | N | GLY | B | 341 | 85.714 | 49.319 | 69.999 | 1.00 | 43.64 | B |
| ATOM | 2493 | CA | GLY | B | 341 | 84.971 | 48.356 | 69.211 | 1.00 | 42.84 | B |
| ATOM | 2494 | C | GLY | B | 341 | 83.493 | 48.678 | 69.296 | 1.00 | 42.29 | B |
| ATOM | 2495 | O | GLY | B | 341 | 82.665 | 47.799 | 69.131 | 1.00 | 43.95 | B |
| ATOM | 2496 | N | LEU | B | 342 | 83.204 | 49.960 | 69.407 | 1.00 | 40.77 | B |
| ATOM | 2497 | CA | LEU | B | 342 | 81.850 | 50.498 | 69.672 | 1.00 | 40.11 | B |
| ATOM | 2498 | CB | LEU | B | 342 | 81.750 | 51.224 | 71.068 | 1.00 | 40.41 | B |
| ATOM | 2499 | CG | LEU | B | 342 | 81.893 | 50.270 | 72.294 | 1.00 | 40.96 | B |
| ATOM | 2500 | CD1 | LEU | B | 342 | 81.809 | 51.021 | 73.611 | 1.00 | 41.99 | B |
| ATOM | 2501 | CD2 | LEU | B | 342 | 80.781 | 49.287 | 72.297 | 1.00 | 41.03 | B |

TABLE 2-continued

ATOMIC COORDINATES OF THE ERR3 LBD/
DIETHYLSTILBESTROL COMPLEX

| ATOM | 2502 | C | LEU | B | 342 | 81.390 | 51.442 | 68.658 | 1.00 | 38.32 | B |
|---|---|---|---|---|---|---|---|---|---|---|---|
| ATOM | 2503 | O | LEU | B | 342 | 80.477 | 52.104 | 68.933 | 1.00 | 38.30 | B |
| ATOM | 2504 | N | LEU | B | 343 | 81.942 | 51.462 | 67.446 | 1.00 | 37.08 | B |
| ATOM | 2505 | CA | LEU | B | 343 | 81.514 | 52.480 | 66.471 | 1.00 | 36.56 | B |
| ATOM | 2506 | CB | LEU | B | 343 | 82.431 | 52.455 | 65.254 | 1.00 | 37.72 | B |
| ATOM | 2507 | CG | LEU | B | 343 | 82.184 | 53.506 | 64.184 | 1.00 | 37.45 | B |
| ATOM | 2508 | CD1 | LEU | B | 343 | 82.171 | 54.870 | 64.831 | 1.00 | 38.46 | B |
| ATOM | 2509 | CD2 | LEU | B | 343 | 83.223 | 53.500 | 62.980 | 1.00 | 38.64 | B |
| ATOM | 2510 | C | LEU | B | 343 | 80.037 | 52.342 | 66.022 | 1.00 | 35.33 | B |
| ATOM | 2511 | O | LEU | B | 343 | 79.298 | 53.293 | 65.934 | 1.00 | 34.97 | B |
| ATOM | 2512 | N | ASP | B | 344 | 79.636 | 51.178 | 65.678 | 1.00 | 34.80 | B |
| ATOM | 2513 | CA | ASP | B | 344 | 78.284 | 50.949 | 65.207 | 1.00 | 35.29 | B |
| ATOM | 2514 | CB | ASP | B | 344 | 78.113 | 49.500 | 64.680 | 1.00 | 38.01 | B |
| ATOM | 2515 | CG | ASP | B | 344 | 78.893 | 49.236 | 63.399 | 1.00 | 42.19 | B |
| ATOM | 2516 | OD1 | ASP | B | 344 | 79.317 | 50.182 | 62.709 | 1.00 | 42.92 | B |
| ATOM | 2517 | OD2 | ASP | B | 344 | 79.101 | 48.040 | 63.011 | 1.00 | 45.89 | B |
| ATOM | 2518 | C | ASP | B | 344 | 77.263 | 51.096 | 66.286 | 1.00 | 33.78 | B |
| ATOM | 2519 | O | ASP | B | 344 | 76.191 | 51.584 | 66.079 | 1.00 | 32.78 | B |
| ATOM | 2520 | N | LEU | B | 345 | 77.567 | 50.615 | 67.473 | 1.00 | 34.02 | B |
| ATOM | 2521 | CA | LEU | B | 345 | 76.558 | 50.779 | 68.558 | 1.00 | 32.95 | B |
| ATOM | 2522 | CB | LEU | B | 345 | 76.972 | 49.983 | 69.836 | 1.00 | 32.85 | B |
| ATOM | 2523 | CG | LEU | B | 345 | 76.044 | 50.199 | 71.051 | 1.00 | 34.64 | B |
| ATOM | 2524 | CD1 | LEU | B | 345 | 74.613 | 49.892 | 70.680 | 1.00 | 32.16 | B |
| ATOM | 2525 | CD2 | LEU | B | 345 | 76.579 | 49.245 | 72.094 | 1.00 | 34.86 | B |
| ATOM | 2526 | C | LEU | B | 345 | 76.456 | 52.298 | 68.861 | 1.00 | 30.96 | B |
| ATOM | 2527 | O | LEU | B | 345 | 75.399 | 52.867 | 68.978 | 1.00 | 30.65 | B |
| ATOM | 2528 | N | ASN | B | 346 | 77.577 | 52.980 | 68.957 | 1.00 | 31.70 | B |
| ATOM | 2529 | CA | ASN | B | 346 | 77.527 | 54.404 | 69.375 | 1.00 | 32.17 | B |
| ATOM | 2530 | CB | ASN | B | 346 | 78.944 | 54.836 | 69.812 | 1.00 | 32.63 | B |
| ATOM | 2531 | CG | ASN | B | 346 | 79.306 | 54.412 | 71.253 | 1.00 | 31.81 | B |
| ATOM | 2532 | OD1 | ASN | B | 346 | 78.458 | 53.920 | 72.051 | 1.00 | 31.64 | B |
| ATOM | 2533 | ND2 | ASN | B | 346 | 80.548 | 54.721 | 71.640 | 1.00 | 31.88 | B |
| ATOM | 2534 | C | ASN | B | 346 | 76.939 | 55.226 | 68.272 | 1.00 | 32.54 | B |
| ATOM | 2535 | O | ASN | B | 346 | 76.193 | 56.154 | 68.461 | 1.00 | 32.79 | B |
| ATOM | 2536 | N | ASN | B | 347 | 77.134 | 54.788 | 67.041 | 1.00 | 33.19 | B |
| ATOM | 2537 | CA | ASN | B | 347 | 76.438 | 55.405 | 65.920 | 1.00 | 32.91 | B |
| ATOM | 2538 | CB | ASN | B | 347 | 77.002 | 54.927 | 64.580 | 1.00 | 35.83 | B |
| ATOM | 2539 | CG | ASN | B | 347 | 78.261 | 55.810 | 64.129 | 1.00 | 40.40 | B |
| ATOM | 2540 | OD1 | ASN | B | 347 | 78.547 | 56.884 | 64.704 | 1.00 | 42.01 | B |
| ATOM | 2541 | ND2 | ASN | B | 347 | 79.006 | 55.315 | 63.145 | 1.00 | 42.67 | B |
| ATOM | 2542 | C | ASN | B | 347 | 75.011 | 55.203 | 65.980 | 1.00 | 31.57 | B |
| ATOM | 2543 | O | ASN | B | 347 | 74.206 | 56.120 | 65.628 | 1.00 | 30.93 | B |
| ATOM | 2544 | N | ALA | B | 348 | 74.557 | 54.013 | 66.377 | 1.00 | 30.83 | B |
| ATOM | 2545 | CA | ALA | B | 348 | 73.094 | 53.931 | 66.530 | 1.00 | 30.57 | B |
| ATOM | 2546 | CB | ALA | B | 348 | 72.718 | 52.503 | 66.838 | 1.00 | 30.64 | B |
| ATOM | 2547 | C | ALA | B | 348 | 72.587 | 54.855 | 67.636 | 1.00 | 29.89 | B |
| ATOM | 2548 | O | ALA | B | 348 | 71.501 | 55.385 | 67.576 | 1.00 | 30.19 | B |
| ATOM | 2549 | N | ILE | B | 349 | 73.322 | 54.930 | 68.736 | 1.00 | 29.36 | B |
| ATOM | 2550 | CA | ILE | B | 349 | 72.823 | 55.750 | 69.920 | 1.00 | 29.10 | B |
| ATOM | 2551 | CB | ILE | B | 349 | 73.710 | 55.553 | 71.104 | 1.00 | 28.12 | B |
| ATOM | 2552 | CG2 | ILE | B | 349 | 73.355 | 56.480 | 72.198 | 1.00 | 26.32 | B |
| ATOM | 2553 | CG1 | ILE | B | 349 | 73.618 | 54.084 | 71.519 | 1.00 | 29.69 | B |
| ATOM | 2554 | CD1 | ILE | B | 349 | 74.606 | 53.635 | 72.554 | 1.00 | 28.86 | B |
| ATOM | 2555 | C | ILE | B | 349 | 72.767 | 57.189 | 69.471 | 1.00 | 29.14 | B |
| ATOM | 2556 | O | ILE | B | 349 | 71.751 | 57.894 | 69.713 | 1.00 | 28.81 | B |
| ATOM | 2557 | N | LEU | B | 350 | 73.774 | 57.636 | 68.679 | 1.00 | 29.98 | B |
| ATOM | 2558 | CA | LEU | B | 350 | 73.684 | 59.043 | 68.069 | 1.00 | 30.27 | B |
| ATOM | 2559 | CB | LEU | B | 350 | 74.988 | 59.404 | 67.307 | 1.00 | 31.02 | B |
| ATOM | 2560 | CG | LEU | B | 350 | 76.132 | 59.634 | 68.335 | 1.00 | 30.89 | B |
| ATOM | 2561 | CD1 | LEU | B | 350 | 77.358 | 59.387 | 67.574 | 1.00 | 34.50 | B |
| ATOM | 2562 | CD2 | LEU | B | 350 | 75.953 | 61.182 | 68.929 | 1.00 | 31.94 | B |
| ATOM | 2563 | C | LEU | B | 350 | 72.504 | 59.317 | 67.212 | 1.00 | 31.52 | B |
| ATOM | 2564 | O | LEU | B | 350 | 71.941 | 60.471 | 67.185 | 1.00 | 32.22 | B |
| ATOM | 2565 | N | GLN | B | 351 | 71.993 | 58.271 | 66.572 | 1.00 | 31.37 | B |
| ATOM | 2566 | CA | GLN | B | 351 | 70.785 | 58.469 | 65.767 | 1.00 | 31.93 | B |
| ATOM | 2567 | CB | GLN | B | 351 | 70.524 | 57.222 | 64.925 | 1.00 | 33.56 | B |
| ATOM | 2568 | CG | GLN | B | 351 | 69.334 | 57.267 | 63.892 | 1.00 | 36.14 | B |
| ATOM | 2569 | CD | GLN | B | 351 | 68.727 | 55.795 | 63.417 | 1.00 | 39.74 | B |
| ATOM | 2570 | OE1 | GLN | B | 351 | 69.286 | 54.685 | 63.778 | 1.00 | 42.05 | B |
| ATOM | 2571 | NE2 | GLN | B | 351 | 67.571 | 55.827 | 62.683 | 1.00 | 38.69 | B |
| ATOM | 2572 | C | GLN | B | 351 | 69.615 | 58.907 | 66.659 | 1.00 | 31.91 | B |
| ATOM | 2573 | O | GLN | B | 351 | 68.816 | 59.790 | 66.332 | 1.00 | 32.15 | B |
| ATOM | 2574 | N | LEU | B | 352 | 69.562 | 58.337 | 67.848 | 1.00 | 30.93 | B |
| ATOM | 2575 | CA | LEU | B | 352 | 68.500 | 58.696 | 68.750 | 1.00 | 31.27 | B |
| ATOM | 2576 | CB | LEU | B | 352 | 68.477 | 57.685 | 69.872 | 1.00 | 32.76 | B |
| ATOM | 2577 | CG | LEU | B | 352 | 67.352 | 57.278 | 70.793 | 1.00 | 34.44 | B |

TABLE 2-continued

ATOMIC COORDINATES OF THE ERR3 LBD/
DIETHYLSTILBESTROL COMPLEX

| ATOM | 2578 | CD1 | LEU | B | 352 | 66.191 | 56.782 | 69.972 | 1.00 | 34.13 | B |
|---|---|---|---|---|---|---|---|---|---|---|---|
| ATOM | 2579 | CD2 | LEU | B | 352 | 67.920 | 56.062 | 71.571 | 1.00 | 31.70 | B |
| ATOM | 2580 | C | LEU | B | 352 | 68.824 | 60.062 | 69.333 | 1.00 | 30.75 | B |
| ATOM | 2581 | O | LEU | B | 352 | 67.909 | 60.907 | 69.614 | 1.00 | 29.51 | B |
| ATOM | 2582 | N | VAL | B | 353 | 70.107 | 60.338 | 69.563 | 1.00 | 31.59 | B |
| ATOM | 2583 | CA | VAL | B | 353 | 70.456 | 61.719 | 69.993 | 1.00 | 33.20 | B |
| ATOM | 2584 | CB | VAL | B | 353 | 71.915 | 61.889 | 70.220 | 1.00 | 33.44 | B |
| ATOM | 2585 | CG1 | VAL | B | 353 | 72.199 | 63.391 | 70.440 | 1.00 | 31.87 | B |
| ATOM | 2586 | CG2 | VAL | B | 353 | 72.354 | 61.087 | 71.380 | 1.00 | 30.79 | B |
| ATOM | 2587 | C | VAL | B | 353 | 69.992 | 62.773 | 68.957 | 1.00 | 34.47 | B |
| ATOM | 2588 | O | VAL | B | 353 | 69.374 | 63.788 | 69.274 | 1.00 | 34.38 | B |
| ATOM | 2589 | N | LYS | B | 354 | 70.132 | 62.455 | 67.712 | 1.00 | 35.58 | B |
| ATOM | 2590 | CA | LYS | B | 354 | 69.811 | 63.490 | 66.694 | 1.00 | 39.10 | B |
| ATOM | 2591 | CB | LYS | B | 354 | 70.439 | 63.174 | 65.274 | 1.00 | 42.29 | B |
| ATOM | 2592 | CG | LYS | B | 354 | 69.754 | 63.785 | 64.030 | 1.00 | 49.21 | B |
| ATOM | 2593 | CD | LYS | B | 354 | 70.229 | 65.193 | 63.702 | 1.00 | 55.19 | B |
| ATOM | 2594 | CE | LYS | B | 354 | 69.622 | 66.242 | 64.615 | 1.00 | 56.22 | B |
| ATOM | 2595 | NZ | LYS | B | 354 | 68.168 | 66.375 | 64.364 | 1.00 | 59.78 | B |
| ATOM | 2596 | C | LYS | B | 354 | 68.296 | 63.650 | 66.595 | 1.00 | 39.64 | B |
| ATOM | 2597 | O | LYS | B | 354 | 67.782 | 64.776 | 66.354 | 1.00 | 40.04 | B |
| ATOM | 2598 | N | LYS | B | 355 | 67.525 | 62.579 | 66.837 | 1.00 | 38.31 | B |
| ATOM | 2599 | CA | LYS | B | 355 | 66.034 | 62.747 | 66.790 | 1.00 | 37.38 | B |
| ATOM | 2600 | CB | LYS | B | 355 | 65.264 | 61.408 | 66.735 | 1.00 | 38.95 | B |
| ATOM | 2601 | CG | LYS | B | 355 | 63.685 | 61.492 | 66.879 | 1.00 | 41.68 | B |
| ATOM | 2602 | CD | LYS | B | 355 | 62.938 | 61.871 | 65.646 | 1.00 | 43.74 | B |
| ATOM | 2603 | CE | LYS | B | 355 | 61.877 | 60.817 | 65.209 | 1.00 | 44.60 | B |
| ATOM | 2604 | NZ | LYS | B | 355 | 61.171 | 60.973 | 63.759 | 1.00 | 45.92 | B |
| ATOM | 2605 | C | LYS | B | 355 | 65.631 | 63.621 | 67.936 | 1.00 | 36.01 | B |
| ATOM | 2606 | O | LYS | B | 355 | 64.904 | 64.502 | 67.761 | 1.00 | 36.68 | B |
| ATOM | 2607 | N | TYR | B | 356 | 66.164 | 63.418 | 69.103 | 1.00 | 34.28 | B |
| ATOM | 2608 | CA | TYR | B | 356 | 65.750 | 64.197 | 70.253 | 1.00 | 32.96 | B |
| ATOM | 2609 | CB | TYR | B | 356 | 66.170 | 63.522 | 71.634 | 1.00 | 31.01 | B |
| ATOM | 2610 | CG | TYR | B | 356 | 65.323 | 62.270 | 72.087 | 1.00 | 30.67 | B |
| ATOM | 2611 | CD1 | TYR | B | 356 | 63.939 | 62.306 | 72.087 | 1.00 | 30.56 | B |
| ATOM | 2612 | CE1 | TYR | B | 356 | 63.163 | 61.163 | 72.455 | 1.00 | 31.04 | B |
| ATOM | 2613 | CD2 | TYR | B | 356 | 65.924 | 61.078 | 72.404 | 1.00 | 30.42 | B |
| ATOM | 2614 | CE2 | TYR | B | 356 | 65.197 | 59.958 | 72.816 | 1.00 | 30.57 | B |
| ATOM | 2615 | CZ | TYR | B | 356 | 63.831 | 59.988 | 72.810 | 1.00 | 30.76 | B |
| ATOM | 2616 | OH | TYR | B | 356 | 63.123 | 58.866 | 73.057 | 1.00 | 32.47 | B |
| ATOM | 2617 | C | TYR | B | 356 | 66.279 | 65.685 | 70.136 | 1.00 | 33.93 | B |
| ATOM | 2618 | O | TYR | B | 356 | 65.584 | 66.576 | 70.619 | 1.00 | 32.66 | B |
| ATOM | 2619 | N | LYS | B | 357 | 67.485 | 65.898 | 69.591 | 1.00 | 34.28 | B |
| ATOM | 2620 | CA | LYS | B | 357 | 68.034 | 67.294 | 69.438 | 1.00 | 37.11 | B |
| ATOM | 2621 | CB | LYS | B | 357 | 69.467 | 67.386 | 68.905 | 1.00 | 37.73 | B |
| ATOM | 2622 | CG | LYS | B | 357 | 70.419 | 66.826 | 69.902 | 1.00 | 38.78 | B |
| ATOM | 2623 | CD | LYS | B | 357 | 71.837 | 66.533 | 69.319 | 1.00 | 40.58 | B |
| ATOM | 2624 | CE | LYS | B | 357 | 72.650 | 67.788 | 68.895 | 1.00 | 42.61 | B |
| ATOM | 2625 | NZ | LYS | B | 357 | 73.805 | 67.299 | 68.102 | 1.00 | 46.13 | B |
| ATOM | 2626 | C | LYS | B | 357 | 67.174 | 68.085 | 68.577 | 1.00 | 37.36 | B |
| ATOM | 2627 | O | LYS | B | 357 | 66.794 | 69.149 | 68.949 | 1.00 | 38.58 | B |
| ATOM | 2628 | N | SER | B | 358 | 66.727 | 67.524 | 67.497 | 1.00 | 37.85 | B |
| ATOM | 2629 | CA | SER | B | 358 | 65.758 | 68.200 | 66.643 | 1.00 | 39.55 | B |
| ATOM | 2630 | CB | SER | B | 358 | 65.614 | 67.378 | 65.342 | 1.00 | 40.16 | B |
| ATOM | 2631 | OG | SER | B | 358 | 64.803 | 66.240 | 65.506 | 1.00 | 44.56 | B |
| ATOM | 2632 | C | SER | B | 358 | 64.350 | 68.475 | 67.159 | 1.00 | 39.86 | B |
| ATOM | 2633 | O | SER | B | 358 | 63.638 | 69.337 | 66.617 | 1.00 | 39.55 | B |
| ATOM | 2634 | N | MET | B | 359 | 63.851 | 67.656 | 68.092 | 1.00 | 40.08 | B |
| ATOM | 2635 | CA | MET | B | 359 | 62.536 | 67.955 | 68.725 | 1.00 | 40.43 | B |
| ATOM | 2636 | CB | MET | B | 359 | 61.884 | 66.635 | 69.217 | 1.00 | 42.32 | B |
| ATOM | 2637 | CG | MET | B | 359 | 61.823 | 65.514 | 68.124 | 1.00 | 44.33 | B |
| ATOM | 2638 | SD | MET | B | 359 | 61.388 | 63.825 | 68.812 | 1.00 | 47.39 | B |
| ATOM | 2639 | CE | MET | B | 359 | 59.644 | 64.178 | 69.012 | 1.00 | 42.83 | B |
| ATOM | 2640 | C | MET | B | 359 | 62.819 | 68.854 | 69.965 | 1.00 | 39.17 | B |
| ATOM | 2641 | O | MET | B | 359 | 61.979 | 69.393 | 70.514 | 1.00 | 39.01 | B |
| ATOM | 2642 | N | LYS | B | 360 | 64.036 | 69.011 | 70.374 | 1.00 | 37.87 | B |
| ATOM | 2643 | CA | LYS | B | 360 | 64.383 | 69.833 | 71.525 | 1.00 | 38.70 | B |
| ATOM | 2644 | CB | LYS | B | 360 | 63.996 | 71.338 | 71.365 | 1.00 | 39.09 | B |
| ATOM | 2645 | CG | LYS | B | 360 | 64.418 | 72.027 | 69.970 | 1.00 | 39.00 | B |
| ATOM | 2646 | CD | LYS | B | 360 | 63.959 | 73.611 | 69.973 | 1.00 | 40.73 | B |
| ATOM | 2647 | CE | LYS | B | 360 | 64.539 | 74.192 | 68.716 | 0.00 | 40.20 | B |
| ATOM | 2648 | NZ | LYS | B | 360 | 65.064 | 75.666 | 68.911 | 0.00 | 40.42 | B |
| ATOM | 2649 | C | LYS | B | 360 | 63.756 | 69.226 | 72.737 | 1.00 | 38.41 | B |
| ATOM | 2650 | O | LYS | B | 360 | 62.941 | 69.840 | 73.410 | 1.00 | 39.38 | B |
| ATOM | 2651 | N | LEU | B | 361 | 64.197 | 67.994 | 73.028 | 1.00 | 37.76 | B |
| ATOM | 2652 | CA | LEU | B | 361 | 63.736 | 67.266 | 74.141 | 1.00 | 36.21 | B |
| ATOM | 2653 | CB | LEU | B | 361 | 64.464 | 65.884 | 74.194 | 1.00 | 34.94 | B |

TABLE 2-continued

ATOMIC COORDINATES OF THE ERR3 LBD/
DIETHYLSTILBESTROL COMPLEX

| ATOM | 2654 | CG | LEU | B | 361 | 63.930 | 65.017 | 75.385 | 1.00 | 34.78 | B |
|---|---|---|---|---|---|---|---|---|---|---|---|
| ATOM | 2655 | CD1 | LEU | B | 361 | 62.485 | 64.655 | 75.232 | 1.00 | 31.38 | B |
| ATOM | 2656 | CD2 | LEU | B | 361 | 64.789 | 63.866 | 75.592 | 1.00 | 31.90 | B |
| ATOM | 2657 | C | LEU | B | 361 | 64.073 | 68.090 | 75.389 | 1.00 | 37.31 | B |
| ATOM | 2658 | O | LEU | B | 361 | 65.236 | 68.337 | 75.640 | 1.00 | 36.41 | B |
| ATOM | 2659 | N | GLU | B | 362 | 63.077 | 68.331 | 76.234 | 1.00 | 37.93 | B |
| ATOM | 2660 | CA | GLU | B | 362 | 63.210 | 68.986 | 77.570 | 1.00 | 38.39 | B |
| ATOM | 2661 | CB | GLU | B | 362 | 61.899 | 69.735 | 77.918 | 1.00 | 39.89 | B |
| ATOM | 2662 | CG | GLU | B | 362 | 61.663 | 70.868 | 76.952 | 1.00 | 42.99 | B |
| ATOM | 2663 | CD | GLU | B | 362 | 60.209 | 71.332 | 76.759 | 1.00 | 44.61 | B |
| ATOM | 2664 | OE1 | GLU | B | 362 | 59.311 | 70.838 | 77.417 | 1.00 | 45.79 | B |
| ATOM | 2665 | OE2 | GLU | B | 362 | 59.967 | 72.257 | 75.929 | 1.00 | 46.58 | B |
| ATOM | 2666 | C | GLU | B | 362 | 63.312 | 67.935 | 78.601 | 1.00 | 37.64 | B |
| ATOM | 2667 | O | GLU | B | 362 | 62.891 | 66.723 | 78.439 | 1.00 | 38.13 | B |
| ATOM | 2668 | N | LYS | B | 363 | 63.758 | 68.355 | 79.721 | 1.00 | 37.04 | B |
| ATOM | 2669 | CA | LYS | B | 363 | 64.020 | 67.474 | 80.835 | 1.00 | 36.91 | B |
| ATOM | 2670 | CB | LYS | B | 363 | 64.876 | 68.194 | 81.859 | 1.00 | 38.15 | B |
| ATOM | 2671 | CG | LYS | B | 363 | 65.034 | 67.417 | 83.139 | 1.00 | 40.38 | B |
| ATOM | 2672 | CD | LYS | B | 363 | 66.410 | 67.009 | 83.548 | 1.00 | 40.62 | B |
| ATOM | 2673 | CE | LYS | B | 363 | 66.592 | 67.425 | 84.993 | 1.00 | 41.14 | B |
| ATOM | 2674 | NZ | LYS | B | 363 | 67.883 | 66.933 | 85.530 | 1.00 | 44.16 | B |
| ATOM | 2675 | C | LYS | B | 363 | 62.786 | 66.811 | 81.478 | 1.00 | 35.89 | B |
| ATOM | 2676 | O | LYS | B | 363 | 62.803 | 65.651 | 81.917 | 1.00 | 36.35 | B |
| ATOM | 2677 | N | GLU | B | 364 | 61.724 | 67.575 | 81.477 | 1.00 | 35.72 | B |
| ATOM | 2678 | CA | GLU | B | 364 | 60.419 | 67.122 | 81.833 | 1.00 | 35.96 | B |
| ATOM | 2679 | CB | GLU | B | 364 | 59.381 | 68.229 | 81.718 | 1.00 | 36.45 | B |
| ATOM | 2680 | CG | GLU | B | 364 | 59.456 | 69.280 | 82.833 | 1.00 | 38.47 | B |
| ATOM | 2681 | CD | GLU | B | 364 | 60.508 | 70.372 | 82.605 | 1.00 | 39.13 | B |
| ATOM | 2682 | OE1 | GLU | B | 364 | 61.216 | 70.356 | 81.588 | 1.00 | 39.00 | B |
| ATOM | 2683 | OE2 | GLU | B | 364 | 60.669 | 71.223 | 83.495 | 1.00 | 42.08 | B |
| ATOM | 2684 | C | GLU | B | 364 | 59.984 | 65.879 | 80.968 | 1.00 | 35.28 | B |
| ATOM | 2685 | O | GLU | B | 364 | 59.303 | 64.960 | 81.489 | 1.00 | 34.00 | B |
| ATOM | 2686 | N | GLU | B | 365 | 60.308 | 65.967 | 79.678 | 1.00 | 34.30 | B |
| ATOM | 2687 | CA | GLU | B | 365 | 59.894 | 65.063 | 78.707 | 1.00 | 33.23 | B |
| ATOM | 2688 | CB | GLU | B | 365 | 59.927 | 65.685 | 77.295 | 1.00 | 33.96 | B |
| ATOM | 2689 | CG | GLU | B | 365 | 58.959 | 66.887 | 77.164 | 1.00 | 35.06 | B |
| ATOM | 2690 | CD | GLU | B | 365 | 59.043 | 67.625 | 75.896 | 1.00 | 34.91 | B |
| ATOM | 2691 | OE1 | GLU | B | 365 | 60.179 | 67.683 | 75.418 | 1.00 | 35.59 | B |
| ATOM | 2692 | OE2 | GLU | B | 365 | 57.960 | 67.998 | 75.319 | 1.00 | 35.15 | B |
| ATOM | 2693 | C | GLU | B | 365 | 60.791 | 63.810 | 78.901 | 1.00 | 32.70 | B |
| ATOM | 2694 | O | GLU | B | 365 | 60.264 | 62.728 | 79.051 | 1.00 | 32.76 | B |
| ATOM | 2695 | N | PHE | B | 366 | 62.088 | 64.011 | 79.097 | 1.00 | 31.07 | B |
| ATOM | 2696 | CA | PHE | B | 366 | 63.056 | 62.984 | 79.406 | 1.00 | 29.71 | B |
| ATOM | 2697 | CB | PHE | B | 366 | 64.420 | 63.583 | 79.657 | 1.00 | 26.42 | B |
| ATOM | 2698 | CG | PHE | B | 366 | 65.390 | 62.671 | 80.309 | 1.00 | 26.98 | B |
| ATOM | 2699 | CD1 | PHE | B | 366 | 65.962 | 61.658 | 79.639 | 1.00 | 27.26 | B |
| ATOM | 2700 | CD2 | PHE | B | 366 | 65.939 | 62.958 | 81.536 | 1.00 | 28.03 | B |
| ATOM | 2701 | CE1 | PHE | B | 366 | 66.852 | 60.810 | 80.284 | 1.00 | 27.31 | B |
| ATOM | 2702 | CE2 | PHE | B | 366 | 66.884 | 62.141 | 82.142 | 1.00 | 27.46 | B |
| ATOM | 2703 | CZ | PHE | B | 366 | 67.375 | 61.069 | 81.429 | 1.00 | 26.85 | B |
| ATOM | 2704 | C | PHE | B | 366 | 62.645 | 62.098 | 80.589 | 1.00 | 29.92 | B |
| ATOM | 2705 | O | PHE | B | 366 | 62.587 | 60.834 | 80.469 | 1.00 | 27.79 | B |
| ATOM | 2706 | N | VAL | B | 367 | 62.368 | 62.732 | 81.711 | 1.00 | 29.16 | B |
| ATOM | 2707 | CA | VAL | B | 367 | 62.028 | 62.002 | 82.905 | 1.00 | 28.14 | B |
| ATOM | 2708 | CB | VAL | B | 367 | 62.058 | 62.853 | 84.241 | 1.00 | 27.17 | B |
| ATOM | 2709 | CG1 | VAL | B | 367 | 63.429 | 63.437 | 84.404 | 1.00 | 26.11 | B |
| ATOM | 2710 | CG2 | VAL | B | 367 | 61.068 | 63.968 | 84.278 | 1.00 | 27.67 | B |
| ATOM | 2711 | C | VAL | B | 367 | 60.743 | 61.217 | 82.768 | 1.00 | 28.51 | B |
| ATOM | 2712 | O | VAL | B | 367 | 60.688 | 60.035 | 83.139 | 1.00 | 28.41 | B |
| ATOM | 2713 | N | THR | B | 368 | 59.822 | 61.732 | 82.049 | 1.00 | 29.20 | B |
| ATOM | 2714 | CA | THR | B | 368 | 58.586 | 61.095 | 81.904 | 1.00 | 29.98 | B |
| ATOM | 2715 | CB | THR | B | 368 | 57.625 | 62.041 | 81.380 | 1.00 | 30.37 | B |
| ATOM | 2716 | OG1 | THR | B | 368 | 57.492 | 63.171 | 82.208 | 1.00 | 34.72 | B |
| ATOM | 2717 | CG2 | THR | B | 368 | 56.251 | 61.478 | 81.301 | 1.00 | 30.54 | B |
| ATOM | 2718 | C | THR | B | 368 | 58.750 | 59.911 | 80.878 | 1.00 | 30.16 | B |
| ATOM | 2719 | O | THR | B | 368 | 58.223 | 58.826 | 81.116 | 1.00 | 29.84 | B |
| ATOM | 2720 | N | LEU | B | 369 | 59.418 | 60.135 | 79.726 | 1.00 | 30.51 | B |
| ATOM | 2721 | CA | LEU | B | 369 | 59.615 | 59.067 | 78.773 | 1.00 | 29.83 | B |
| ATOM | 2722 | CB | LEU | B | 369 | 60.343 | 59.502 | 77.570 | 1.00 | 29.74 | B |
| ATOM | 2723 | CG | LEU | B | 369 | 59.566 | 60.085 | 76.485 | 1.00 | 29.34 | B |
| ATOM | 2724 | CD1 | LEU | B | 369 | 60.609 | 60.447 | 75.371 | 1.00 | 33.38 | B |
| ATOM | 2725 | CD2 | LEU | B | 369 | 58.623 | 59.221 | 75.900 | 1.00 | 30.27 | B |
| ATOM | 2726 | C | LEU | B | 369 | 60.410 | 57.929 | 79.400 | 1.00 | 28.92 | B |
| ATOM | 2727 | O | LEU | B | 369 | 60.168 | 56.815 | 79.146 | 1.00 | 28.50 | B |
| ATOM | 2728 | N | LYS | B | 370 | 61.337 | 58.244 | 80.274 | 1.00 | 28.08 | B |
| ATOM | 2729 | CA | LYS | B | 370 | 62.091 | 57.220 | 80.954 | 1.00 | 27.06 | B |

TABLE 2-continued

ATOMIC COORDINATES OF THE ERR3 LBD/
DIETHYLSTILBESTROL COMPLEX

| ATOM | 2730 | CB  | LYS | B | 370 | 63.211 | 57.953 | 81.703 | 1.00 | 26.89 | B |
|------|------|-----|-----|---|-----|--------|--------|--------|------|-------|---|
| ATOM | 2731 | CG  | LYS | B | 370 | 64.277 | 57.173 | 82.134 | 1.00 | 30.21 | B |
| ATOM | 2732 | CD  | LYS | B | 370 | 65.469 | 57.969 | 82.648 | 1.00 | 31.19 | B |
| ATOM | 2733 | CE  | LYS | B | 370 | 65.074 | 59.032 | 83.763 | 1.00 | 31.82 | B |
| ATOM | 2734 | NZ  | LYS | B | 370 | 66.348 | 59.374 | 84.196 | 1.00 | 34.59 | B |
| ATOM | 2735 | C   | LYS | B | 370 | 61.189 | 56.367 | 81.875 | 1.00 | 27.87 | B |
| ATOM | 2736 | O   | LYS | B | 370 | 61.256 | 55.109 | 81.919 | 1.00 | 27.40 | B |
| ATOM | 2737 | N   | ALA | B | 371 | 60.271 | 57.004 | 82.586 | 1.00 | 26.80 | B |
| ATOM | 2738 | CA  | ALA | B | 371 | 59.351 | 56.244 | 83.407 | 1.00 | 26.77 | B |
| ATOM | 2739 | CB  | ALA | B | 371 | 58.534 | 57.125 | 84.329 | 1.00 | 23.51 | B |
| ATOM | 2740 | C   | ALA | B | 371 | 58.423 | 55.344 | 82.553 | 1.00 | 25.32 | B |
| ATOM | 2741 | O   | ALA | B | 371 | 58.113 | 54.227 | 82.931 | 1.00 | 24.57 | B |
| ATOM | 2742 | N   | ILE | B | 372 | 57.931 | 55.913 | 81.506 | 1.00 | 25.18 | B |
| ATOM | 2743 | CA  | ILE | B | 372 | 57.149 | 55.207 | 80.515 | 1.00 | 25.56 | B |
| ATOM | 2744 | CB  | ILE | B | 372 | 56.669 | 56.165 | 79.426 | 1.00 | 23.55 | B |
| ATOM | 2745 | CG2 | ILE | B | 372 | 55.980 | 55.463 | 78.244 | 1.00 | 19.15 | B |
| ATOM | 2746 | CG1 | ILE | B | 372 | 55.688 | 57.092 | 80.032 | 1.00 | 23.93 | B |
| ATOM | 2747 | CD1 | ILE | B | 372 | 55.188 | 58.152 | 79.052 | 1.00 | 25.66 | B |
| ATOM | 2748 | C   | ILE | B | 372 | 57.894 | 54.013 | 79.924 | 1.00 | 25.51 | B |
| ATOM | 2749 | O   | ILE | B | 372 | 57.259 | 53.000 | 79.769 | 1.00 | 26.16 | B |
| ATOM | 2750 | N   | ALA | B | 373 | 59.174 | 54.113 | 79.645 | 1.00 | 26.04 | B |
| ATOM | 2751 | CA  | ALA | B | 373 | 59.954 | 52.996 | 79.023 | 1.00 | 26.62 | B |
| ATOM | 2752 | CB  | ALA | B | 373 | 61.301 | 53.450 | 78.712 | 1.00 | 26.08 | B |
| ATOM | 2753 | C   | ALA | B | 373 | 60.027 | 51.830 | 79.965 | 1.00 | 27.08 | B |
| ATOM | 2754 | O   | ALA | B | 373 | 59.808 | 50.653 | 79.588 | 1.00 | 26.27 | B |
| ATOM | 2755 | N   | LEU | B | 374 | 60.284 | 52.186 | 81.234 | 1.00 | 27.31 | B |
| ATOM | 2756 | CA  | LEU | B | 374 | 60.120 | 51.242 | 82.365 | 1.00 | 26.55 | B |
| ATOM | 2757 | CB  | LEU | B | 374 | 60.498 | 51.827 | 83.716 | 1.00 | 27.48 | B |
| ATOM | 2758 | CG  | LEU | B | 374 | 60.404 | 50.924 | 84.912 | 1.00 | 27.98 | B |
| ATOM | 2759 | CD1 | LEU | B | 374 | 61.296 | 49.648 | 84.578 | 1.00 | 25.75 | B |
| ATOM | 2760 | CD2 | LEU | B | 374 | 60.886 | 51.648 | 86.082 | 1.00 | 26.56 | B |
| ATOM | 2761 | C   | LEU | B | 374 | 58.788 | 50.570 | 82.346 | 1.00 | 26.29 | B |
| ATOM | 2762 | O   | LEU | B | 374 | 58.682 | 49.336 | 82.171 | 1.00 | 26.19 | B |
| ATOM | 2763 | N   | ALA | B | 375 | 57.723 | 51.335 | 82.395 | 1.00 | 26.02 | B |
| ATOM | 2764 | CA  | ALA | B | 375 | 56.404 | 50.718 | 82.478 | 1.00 | 26.20 | B |
| ATOM | 2765 | CB  | ALA | B | 375 | 55.353 | 51.723 | 82.834 | 1.00 | 24.27 | B |
| ATOM | 2766 | C   | ALA | B | 375 | 55.929 | 49.924 | 81.294 | 1.00 | 25.99 | B |
| ATOM | 2767 | O   | ALA | B | 375 | 55.112 | 49.074 | 81.438 | 1.00 | 25.30 | B |
| ATOM | 2768 | N   | ASN | B | 376 | 56.370 | 50.314 | 80.103 | 1.00 | 25.84 | B |
| ATOM | 2769 | CA  | ASN | B | 376 | 55.908 | 49.785 | 78.816 | 1.00 | 26.80 | B |
| ATOM | 2770 | CB  | ASN | B | 376 | 55.719 | 50.976 | 77.843 | 1.00 | 27.30 | B |
| ATOM | 2771 | CG  | ASN | B | 376 | 54.906 | 50.638 | 76.648 | 1.00 | 28.49 | B |
| ATOM | 2772 | OD1 | ASN | B | 376 | 53.840 | 50.016 | 76.752 | 1.00 | 28.80 | B |
| ATOM | 2773 | ND2 | ASN | B | 376 | 55.396 | 51.078 | 75.468 | 1.00 | 30.34 | B |
| ATOM | 2774 | C   | ASN | B | 376 | 56.892 | 48.866 | 78.229 | 1.00 | 25.06 | B |
| ATOM | 2775 | O   | ASN | B | 376 | 56.927 | 48.712 | 77.023 | 1.00 | 25.55 | B |
| ATOM | 2776 | N   | SER | B | 377 | 57.657 | 48.189 | 79.101 | 1.00 | 24.61 | B |
| ATOM | 2777 | CA  | SER | B | 377 | 58.778 | 47.427 | 78.672 | 1.00 | 25.22 | B |
| ATOM | 2778 | CB  | SER | B | 377 | 59.856 | 47.377 | 79.666 | 1.00 | 24.34 | B |
| ATOM | 2779 | OG  | SER | B | 377 | 59.366 | 46.761 | 80.840 | 1.00 | 24.98 | B |
| ATOM | 2780 | C   | SER | B | 377 | 58.471 | 46.076 | 78.110 | 1.00 | 24.57 | B |
| ATOM | 2781 | O   | SER | B | 377 | 59.384 | 45.389 | 77.547 | 1.00 | 24.78 | B |
| ATOM | 2782 | N   | ASP | B | 378 | 57.228 | 45.734 | 78.182 | 1.00 | 23.60 | B |
| ATOM | 2783 | CA  | ASP | B | 378 | 56.751 | 44.526 | 77.532 | 1.00 | 26.22 | B |
| ATOM | 2784 | CB  | ASP | B | 378 | 56.908 | 44.622 | 75.982 | 1.00 | 25.38 | B |
| ATOM | 2785 | CG  | ASP | B | 378 | 56.001 | 45.632 | 75.375 | 1.00 | 25.85 | B |
| ATOM | 2786 | OD1 | ASP | B | 378 | 54.772 | 45.607 | 75.673 | 1.00 | 27.52 | B |
| ATOM | 2787 | OD2 | ASP | B | 378 | 56.422 | 46.594 | 74.677 | 1.00 | 28.38 | B |
| ATOM | 2788 | C   | ASP | B | 378 | 57.336 | 43.189 | 78.041 | 1.00 | 26.00 | B |
| ATOM | 2789 | O   | ASP | B | 378 | 57.449 | 42.260 | 77.284 | 1.00 | 26.99 | B |
| ATOM | 2790 | N   | SER | B | 379 | 57.615 | 43.066 | 79.314 | 1.00 | 25.94 | B |
| ATOM | 2791 | CA  | SER | B | 379 | 58.189 | 41.874 | 79.872 | 1.00 | 27.98 | B |
| ATOM | 2792 | CB  | SER | B | 379 | 58.402 | 41.981 | 81.376 | 1.00 | 28.92 | B |
| ATOM | 2793 | OG  | SER | B | 379 | 58.534 | 40.691 | 81.867 | 1.00 | 31.63 | B |
| ATOM | 2794 | C   | SER | B | 379 | 57.151 | 40.771 | 79.687 | 1.00 | 28.72 | B |
| ATOM | 2795 | O   | SER | B | 379 | 55.964 | 41.007 | 79.833 | 1.00 | 27.56 | B |
| ATOM | 2796 | N   | MET | B | 380 | 57.608 | 39.624 | 79.223 | 1.00 | 30.45 | B |
| ATOM | 2797 | CA  | MET | B | 380 | 56.762 | 38.452 | 79.120 | 1.00 | 32.04 | B |
| ATOM | 2798 | CB  | MET | B | 380 | 57.349 | 37.330 | 78.255 | 1.00 | 32.80 | B |
| ATOM | 2799 | CG  | MET | B | 380 | 58.514 | 36.672 | 78.932 | 1.00 | 34.38 | B |
| ATOM | 2800 | SD  | MET | B | 380 | 59.219 | 35.338 | 77.899 | 1.00 | 37.82 | B |
| ATOM | 2801 | CE  | MET | B | 380 | 60.391 | 36.383 | 76.716 | 1.00 | 37.33 | B |
| ATOM | 2802 | C   | MET | B | 380 | 56.408 | 37.847 | 80.397 | 1.00 | 32.36 | B |
| ATOM | 2803 | O   | MET | B | 380 | 55.573 | 36.988 | 80.402 | 1.00 | 32.93 | B |
| ATOM | 2804 | N   | HIS | B | 381 | 56.904 | 38.301 | 81.511 | 1.00 | 32.10 | B |
| ATOM | 2805 | CA  | HIS | B | 381 | 56.582 | 37.593 | 82.776 | 1.00 | 32.65 | B |

TABLE 2-continued

ATOMIC COORDINATES OF THE ERR3 LBD/DIETHYLSTILBESTROL COMPLEX

| ATOM | 2806 | CB | HIS | B | 381 | 57.841 | 37.358 | 83.596 | 1.00 | 30.39 | B |
|---|---|---|---|---|---|---|---|---|---|---|---|
| ATOM | 2807 | CG | HIS | B | 381 | 58.899 | 36.695 | 82.802 | 1.00 | 31.76 | B |
| ATOM | 2808 | CD2 | HIS | B | 381 | 60.073 | 37.166 | 82.294 | 1.00 | 30.32 | B |
| ATOM | 2809 | ND1 | HIS | B | 381 | 58.767 | 35.411 | 82.329 | 1.00 | 33.18 | B |
| ATOM | 2810 | CE1 | HIS | B | 381 | 59.853 | 35.073 | 81.632 | 1.00 | 33.47 | B |
| ATOM | 2811 | NE2 | HIS | B | 381 | 60.656 | 36.127 | 81.574 | 1.00 | 32.34 | B |
| ATOM | 2812 | C | HIS | B | 381 | 55.635 | 38.304 | 83.698 | 1.00 | 32.97 | B |
| ATOM | 2813 | O | HIS | B | 381 | 55.450 | 37.837 | 84.787 | 1.00 | 32.82 | B |
| ATOM | 2814 | N | ILE | B | 382 | 55.067 | 39.426 | 83.292 | 1.00 | 32.73 | B |
| ATOM | 2815 | CA | ILE | B | 382 | 54.116 | 40.121 | 84.118 | 1.00 | 32.88 | B |
| ATOM | 2816 | CB | ILE | B | 382 | 53.541 | 41.329 | 83.372 | 1.00 | 32.47 | B |
| ATOM | 2817 | CG2 | ILE | B | 382 | 52.489 | 42.074 | 84.290 | 1.00 | 30.99 | B |
| ATOM | 2818 | CG1 | ILE | B | 382 | 54.634 | 42.353 | 82.958 | 1.00 | 31.00 | B |
| ATOM | 2819 | CD1 | ILE | B | 382 | 55.542 | 42.588 | 83.956 | 1.00 | 32.36 | B |
| ATOM | 2820 | C | ILE | B | 382 | 52.907 | 39.223 | 84.617 | 1.00 | 34.00 | B |
| ATOM | 2821 | O | ILE | B | 382 | 52.249 | 38.546 | 83.792 | 1.00 | 32.50 | B |
| ATOM | 2822 | N | GLU | B | 383 | 52.720 | 39.243 | 85.929 | 1.00 | 34.95 | B |
| ATOM | 2823 | CA | GLU | B | 383 | 51.600 | 38.633 | 86.694 | 1.00 | 37.23 | B |
| ATOM | 2824 | CB | GLU | B | 383 | 51.981 | 38.525 | 88.182 | 1.00 | 37.81 | B |
| ATOM | 2825 | CG | GLU | B | 383 | 53.106 | 37.502 | 88.365 | 1.00 | 40.99 | B |
| ATOM | 2826 | CD | GLU | B | 383 | 53.645 | 37.456 | 89.797 | 1.00 | 43.46 | B |
| ATOM | 2827 | OE1 | GLU | B | 383 | 53.313 | 38.378 | 90.591 | 1.00 | 46.34 | B |
| ATOM | 2828 | OE2 | GLU | B | 383 | 54.440 | 36.540 | 90.108 | 1.00 | 46.74 | B |
| ATOM | 2829 | C | GLU | B | 383 | 50.368 | 39.473 | 86.671 | 1.00 | 37.23 | B |
| ATOM | 2830 | O | GLU | B | 383 | 49.305 | 39.010 | 86.314 | 1.00 | 37.96 | B |
| ATOM | 2831 | N | ASP | B | 384 | 50.502 | 40.745 | 87.040 | 1.00 | 36.13 | B |
| ATOM | 2832 | CA | ASP | B | 384 | 49.306 | 41.641 | 87.108 | 1.00 | 35.05 | B |
| ATOM | 2833 | CB | ASP | B | 384 | 49.283 | 42.188 | 88.491 | 1.00 | 34.74 | B |
| ATOM | 2834 | CG | ASP | B | 384 | 48.013 | 42.935 | 88.847 | 1.00 | 34.79 | B |
| ATOM | 2835 | OD1 | ASP | B | 384 | 47.169 | 43.095 | 88.007 | 1.00 | 33.64 | B |
| ATOM | 2836 | OD2 | ASP | B | 384 | 47.878 | 43.448 | 90.002 | 1.00 | 35.30 | B |
| ATOM | 2837 | C | ASP | B | 384 | 49.283 | 42.667 | 85.953 | 1.00 | 34.56 | B |
| ATOM | 2838 | O | ASP | B | 384 | 49.694 | 43.805 | 85.984 | 1.00 | 32.74 | B |
| ATOM | 2839 | N | VAL | B | 385 | 48.802 | 42.192 | 84.869 | 1.00 | 34.17 | B |
| ATOM | 2840 | CA | VAL | B | 385 | 48.876 | 42.942 | 83.681 | 1.00 | 35.26 | B |
| ATOM | 2841 | CB | VAL | B | 385 | 48.421 | 42.081 | 82.568 | 1.00 | 36.63 | B |
| ATOM | 2842 | CG1 | VAL | B | 385 | 48.276 | 42.871 | 81.309 | 1.00 | 34.72 | B |
| ATOM | 2843 | CG2 | VAL | B | 385 | 49.480 | 40.987 | 82.330 | 1.00 | 37.33 | B |
| ATOM | 2844 | C | VAL | B | 385 | 48.082 | 44.283 | 83.827 | 1.00 | 35.70 | B |
| ATOM | 2845 | O | VAL | B | 385 | 48.543 | 45.353 | 83.338 | 1.00 | 33.89 | B |
| ATOM | 2846 | N | GLU | B | 386 | 46.917 | 44.205 | 84.480 | 1.00 | 36.14 | B |
| ATOM | 2847 | CA | GLU | B | 386 | 46.032 | 45.359 | 84.668 | 1.00 | 38.22 | B |
| ATOM | 2848 | CB | GLU | B | 386 | 44.647 | 45.032 | 85.415 | 1.00 | 41.67 | B |
| ATOM | 2849 | CG | GLU | B | 386 | 43.458 | 45.546 | 84.590 | 1.00 | 50.12 | B |
| ATOM | 2850 | CD | GLU | B | 386 | 43.275 | 44.823 | 83.265 | 1.00 | 55.47 | B |
| ATOM | 2851 | OE1 | GLU | B | 386 | 44.230 | 44.787 | 82.462 | 1.00 | 57.39 | B |
| ATOM | 2852 | OE2 | GLU | B | 386 | 42.167 | 44.297 | 83.024 | 1.00 | 59.65 | B |
| ATOM | 2853 | C | GLU | B | 386 | 46.795 | 46.409 | 85.474 | 1.00 | 36.40 | B |
| ATOM | 2854 | O | GLU | B | 386 | 46.729 | 47.501 | 85.167 | 1.00 | 35.75 | B |
| ATOM | 2855 | N | ALA | B | 387 | 47.439 | 46.030 | 86.550 | 1.00 | 34.12 | B |
| ATOM | 2856 | CA | ALA | B | 387 | 48.220 | 46.945 | 87.310 | 1.00 | 32.57 | B |
| ATOM | 2857 | CB | ALA | B | 387 | 48.601 | 46.353 | 88.532 | 1.00 | 30.58 | B |
| ATOM | 2858 | C | ALA | B | 387 | 49.446 | 47.583 | 86.584 | 1.00 | 31.91 | B |
| ATOM | 2859 | O | ALA | B | 387 | 49.741 | 48.760 | 86.754 | 1.00 | 31.98 | B |
| ATOM | 2860 | N | VAL | B | 388 | 50.047 | 46.874 | 85.669 | 1.00 | 30.61 | B |
| ATOM | 2861 | CA | VAL | B | 388 | 51.115 | 47.441 | 84.877 | 1.00 | 28.24 | B |
| ATOM | 2862 | CB | VAL | B | 388 | 51.969 | 46.375 | 84.216 | 1.00 | 27.17 | B |
| ATOM | 2863 | CG1 | VAL | B | 388 | 52.892 | 47.029 | 83.250 | 1.00 | 25.96 | B |
| ATOM | 2864 | CG2 | VAL | B | 388 | 52.776 | 45.708 | 85.311 | 1.00 | 25.35 | B |
| ATOM | 2865 | C | VAL | B | 388 | 50.532 | 48.431 | 83.908 | 1.00 | 29.43 | B |
| ATOM | 2866 | O | VAL | B | 388 | 51.040 | 49.501 | 83.717 | 1.00 | 26.58 | B |
| ATOM | 2867 | N | GLN | B | 389 | 49.414 | 48.097 | 83.354 | 1.00 | 31.24 | B |
| ATOM | 2868 | CA | GLN | B | 389 | 48.756 | 49.009 | 82.419 | 1.00 | 33.46 | B |
| ATOM | 2869 | CB | GLN | B | 389 | 47.524 | 48.381 | 81.828 | 1.00 | 35.82 | B |
| ATOM | 2870 | CG | GLN | B | 389 | 47.853 | 47.499 | 80.581 | 1.00 | 42.20 | B |
| ATOM | 2871 | CD | GLN | B | 389 | 46.599 | 46.598 | 80.097 | 1.00 | 44.39 | B |
| ATOM | 2872 | OE1 | GLN | B | 389 | 45.657 | 46.289 | 80.920 | 1.00 | 46.14 | B |
| ATOM | 2873 | NE2 | GLN | B | 389 | 46.651 | 46.143 | 78.823 | 1.00 | 46.18 | B |
| ATOM | 2874 | C | GLN | B | 389 | 48.319 | 50.273 | 83.089 | 1.00 | 32.10 | B |
| ATOM | 2875 | O | GLN | B | 389 | 48.395 | 51.305 | 82.484 | 1.00 | 31.12 | B |
| ATOM | 2876 | N | LYS | B | 390 | 47.838 | 50.154 | 84.326 | 1.00 | 31.13 | B |
| ATOM | 2877 | CA | LYS | B | 390 | 47.495 | 51.268 | 85.094 | 1.00 | 32.36 | B |
| ATOM | 2878 | CB | LYS | B | 390 | 46.893 | 50.765 | 86.366 | 1.00 | 33.94 | B |
| ATOM | 2879 | CG | LYS | B | 390 | 46.319 | 51.736 | 87.346 | 1.00 | 35.42 | B |
| ATOM | 2880 | CD | LYS | B | 390 | 45.384 | 52.768 | 86.660 | 1.00 | 38.62 | B |
| ATOM | 2881 | CE | LYS | B | 390 | 45.566 | 54.186 | 87.300 | 1.00 | 39.16 | B |

TABLE 2-continued

ATOMIC COORDINATES OF THE ERR3 LBD/DIETHYLSTILBESTROL COMPLEX

| ATOM | 2882 | NZ | LYS | B | 390 | 46.140 | 54.428 | 88.313 | 0.00 | 38.94 | B |
|---|---|---|---|---|---|---|---|---|---|---|---|
| ATOM | 2883 | C | LYS | B | 390 | 48.750 | 52.158 | 85.351 | 1.00 | 32.19 | B |
| ATOM | 2884 | O | LYS | B | 390 | 48.704 | 53.346 | 85.139 | 1.00 | 32.53 | B |
| ATOM | 2885 | N | LEU | B | 391 | 49.858 | 51.587 | 85.769 | 1.00 | 31.17 | B |
| ATOM | 2886 | CA | LEU | B | 391 | 51.063 | 52.356 | 85.822 | 1.00 | 31.01 | B |
| ATOM | 2887 | CB | LEU | B | 391 | 52.208 | 51.466 | 86.301 | 1.00 | 29.17 | B |
| ATOM | 2888 | CG | LEU | B | 391 | 53.605 | 52.002 | 86.190 | 1.00 | 28.74 | B |
| ATOM | 2889 | CD1 | LEU | B | 391 | 53.705 | 53.264 | 87.173 | 1.00 | 28.05 | B |
| ATOM | 2890 | CD2 | LEU | B | 391 | 54.573 | 50.933 | 86.469 | 1.00 | 25.79 | B |
| ATOM | 2891 | C | LEU | B | 391 | 51.409 | 53.132 | 84.478 | 1.00 | 31.61 | B |
| ATOM | 2892 | O | LEU | B | 391 | 51.737 | 54.358 | 84.529 | 1.00 | 31.62 | B |
| ATOM | 2893 | N | GLN | B | 392 | 51.233 | 52.460 | 83.324 | 1.00 | 30.11 | B |
| ATOM | 2894 | CA | GLN | B | 392 | 51.451 | 53.068 | 82.038 | 1.00 | 31.61 | B |
| ATOM | 2895 | CB | GLN | B | 392 | 51.223 | 52.126 | 80.838 | 1.00 | 29.42 | B |
| ATOM | 2896 | CG | GLN | B | 392 | 52.295 | 50.928 | 80.795 | 1.00 | 31.82 | B |
| ATOM | 2897 | CD | GLN | B | 392 | 51.858 | 49.798 | 79.857 | 1.00 | 32.41 | B |
| ATOM | 2898 | OE1 | GLN | B | 392 | 50.919 | 49.970 | 79.037 | 1.00 | 35.61 | B |
| ATOM | 2899 | NE2 | GLN | B | 392 | 52.574 | 48.689 | 79.906 | 1.00 | 32.21 | B |
| ATOM | 2900 | C | GLN | B | 392 | 50.537 | 54.275 | 81.883 | 1.00 | 32.58 | B |
| ATOM | 2901 | O | GLN | B | 392 | 50.993 | 55.300 | 81.330 | 1.00 | 31.94 | B |
| ATOM | 2902 | N | ASP | B | 393 | 49.218 | 54.055 | 82.164 | 1.00 | 32.91 | B |
| ATOM | 2903 | CA | ASP | B | 393 | 48.220 | 55.104 | 81.979 | 1.00 | 34.09 | B |
| ATOM | 2904 | CB | ASP | B | 393 | 46.811 | 54.558 | 82.270 | 1.00 | 36.76 | B |
| ATOM | 2905 | CG | ASP | B | 393 | 45.722 | 55.346 | 81.519 | 1.00 | 39.41 | B |
| ATOM | 2906 | OD1 | ASP | B | 393 | 45.929 | 55.759 | 80.294 | 1.00 | 40.84 | B |
| ATOM | 2907 | OD2 | ASP | B | 393 | 44.616 | 55.640 | 82.057 | 1.00 | 42.71 | B |
| ATOM | 2908 | C | ASP | B | 393 | 48.462 | 56.362 | 82.842 | 1.00 | 33.33 | B |
| ATOM | 2909 | O | ASP | B | 393 | 48.273 | 57.491 | 82.398 | 1.00 | 31.46 | B |
| ATOM | 2910 | N | VAL | B | 394 | 48.944 | 56.154 | 84.054 | 1.00 | 31.90 | B |
| ATOM | 2911 | CA | VAL | B | 394 | 49.316 | 57.244 | 84.885 | 1.00 | 31.96 | B |
| ATOM | 2912 | CB | VAL | B | 394 | 49.695 | 56.754 | 86.299 | 1.00 | 31.88 | B |
| ATOM | 2913 | CG1 | VAL | B | 394 | 50.327 | 57.938 | 87.016 | 1.00 | 30.34 | B |
| ATOM | 2914 | CG2 | VAL | B | 394 | 48.384 | 56.253 | 87.017 | 1.00 | 32.14 | B |
| ATOM | 2915 | C | VAL | B | 394 | 50.455 | 58.093 | 84.354 | 1.00 | 31.11 | B |
| ATOM | 2916 | O | VAL | B | 394 | 50.415 | 59.311 | 84.366 | 1.00 | 31.17 | B |
| ATOM | 2917 | N | LEU | B | 395 | 51.520 | 57.419 | 83.920 | 1.00 | 30.16 | B |
| ATOM | 2918 | CA | LEU | B | 395 | 52.669 | 58.108 | 83.343 | 1.00 | 28.37 | B |
| ATOM | 2919 | CB | LEU | B | 395 | 53.792 | 57.126 | 83.219 | 1.00 | 28.17 | B |
| ATOM | 2920 | CG | LEU | B | 395 | 54.246 | 56.654 | 84.600 | 1.00 | 29.35 | B |
| ATOM | 2921 | CD1 | LEU | B | 395 | 55.206 | 55.455 | 84.451 | 1.00 | 29.19 | B |
| ATOM | 2922 | CD2 | LEU | B | 395 | 54.901 | 57.850 | 85.373 | 1.00 | 28.04 | B |
| ATOM | 2923 | C | LEU | B | 395 | 52.312 | 58.762 | 82.041 | 1.00 | 28.20 | B |
| ATOM | 2924 | O | LEU | B | 395 | 52.738 | 59.861 | 81.775 | 1.00 | 27.22 | B |
| ATOM | 2925 | N | HIS | B | 396 | 51.527 | 58.071 | 81.216 | 1.00 | 28.45 | B |
| ATOM | 2926 | CA | HIS | B | 396 | 51.084 | 58.548 | 79.937 | 1.00 | 29.27 | B |
| ATOM | 2927 | CB | HIS | B | 396 | 50.423 | 57.388 | 79.149 | 1.00 | 28.73 | B |
| ATOM | 2928 | CG | HIS | B | 396 | 49.806 | 57.767 | 77.846 | 1.00 | 27.98 | B |
| ATOM | 2929 | CD2 | HIS | B | 396 | 50.010 | 58.815 | 76.993 | 1.00 | 28.24 | B |
| ATOM | 2930 | ND1 | HIS | B | 396 | 48.881 | 56.979 | 77.248 | 1.00 | 28.63 | B |
| ATOM | 2931 | CE1 | HIS | B | 396 | 48.470 | 57.527 | 76.110 | 1.00 | 26.09 | B |
| ATOM | 2932 | NE2 | HIS | B | 396 | 49.178 | 58.631 | 75.904 | 1.00 | 26.50 | B |
| ATOM | 2933 | C | HIS | B | 396 | 50.126 | 59.808 | 80.018 | 1.00 | 30.37 | B |
| ATOM | 2934 | O | HIS | B | 396 | 50.182 | 60.727 | 79.202 | 1.00 | 30.73 | B |
| ATOM | 2935 | N | GLU | B | 397 | 49.281 | 59.836 | 81.017 | 1.00 | 31.32 | B |
| ATOM | 2936 | CA | GLU | B | 397 | 48.358 | 60.970 | 81.252 | 1.00 | 33.25 | B |
| ATOM | 2937 | CB | GLU | B | 397 | 47.310 | 60.619 | 82.363 | 1.00 | 34.53 | B |
| ATOM | 2938 | CG | GLU | B | 397 | 46.351 | 61.776 | 82.725 | 1.00 | 37.48 | B |
| ATOM | 2939 | CD | GLU | B | 397 | 45.534 | 61.471 | 83.977 | 1.00 | 40.15 | B |
| ATOM | 2940 | OE1 | GLU | B | 397 | 46.102 | 61.023 | 85.014 | 1.00 | 39.87 | B |
| ATOM | 2941 | OE2 | GLU | B | 397 | 44.302 | 61.682 | 83.896 | 1.00 | 43.02 | B |
| ATOM | 2942 | C | GLU | B | 397 | 49.246 | 62.173 | 81.666 | 1.00 | 33.19 | B |
| ATOM | 2943 | O | GLU | B | 397 | 49.106 | 63.254 | 81.167 | 1.00 | 33.05 | B |
| ATOM | 2944 | N | ALA | B | 398 | 50.205 | 61.917 | 82.504 | 1.00 | 33.20 | B |
| ATOM | 2945 | CA | ALA | B | 398 | 51.113 | 62.955 | 82.887 | 1.00 | 33.33 | B |
| ATOM | 2946 | CB | ALA | B | 398 | 52.140 | 62.408 | 83.823 | 1.00 | 33.94 | B |
| ATOM | 2947 | C | ALA | B | 398 | 51.815 | 63.530 | 81.650 | 1.00 | 34.67 | B |
| ATOM | 2948 | O | ALA | B | 398 | 52.040 | 64.790 | 81.587 | 1.00 | 35.55 | B |
| ATOM | 2949 | N | LEU | B | 399 | 52.326 | 62.664 | 80.747 | 1.00 | 33.30 | B |
| ATOM | 2950 | CA | LEU | B | 399 | 53.052 | 63.202 | 79.615 | 1.00 | 32.94 | B |
| ATOM | 2951 | CB | LEU | B | 399 | 53.683 | 62.144 | 78.730 | 1.00 | 31.32 | B |
| ATOM | 2952 | CG | LEU | B | 399 | 54.114 | 62.491 | 77.331 | 1.00 | 30.57 | B |
| ATOM | 2953 | CD1 | LEU | B | 399 | 55.373 | 63.314 | 77.403 | 1.00 | 29.13 | B |
| ATOM | 2954 | CD2 | LEU | B | 399 | 54.450 | 61.227 | 76.442 | 1.00 | 31.99 | B |
| ATOM | 2955 | C | LEU | B | 399 | 52.048 | 64.013 | 78.811 | 1.00 | 33.14 | B |
| ATOM | 2956 | O | LEU | B | 399 | 52.367 | 65.045 | 78.277 | 1.00 | 32.85 | B |
| ATOM | 2957 | N | GLN | B | 400 | 50.892 | 63.500 | 78.620 | 1.00 | 35.11 | B |

TABLE 2-continued

ATOMIC COORDINATES OF THE ERR3 LBD/
DIETHYLSTILBESTROL COMPLEX

| ATOM | 2958 | CA | GLN | B | 400 | 49.936 | 64.172 | 77.734 | 1.00 | 37.60 | B |
|---|---|---|---|---|---|---|---|---|---|---|---|
| ATOM | 2959 | CB | GLN | B | 400 | 48.825 | 63.192 | 77.382 | 1.00 | 39.38 | B |
| ATOM | 2960 | CG | GLN | B | 400 | 48.167 | 63.344 | 75.890 | 1.00 | 45.88 | B |
| ATOM | 2961 | CD | GLN | B | 400 | 48.792 | 62.514 | 74.715 | 1.00 | 47.78 | B |
| ATOM | 2962 | OE1 | GLN | B | 400 | 48.456 | 61.295 | 74.473 | 1.00 | 51.55 | B |
| ATOM | 2963 | NE2 | GLN | B | 400 | 49.928 | 61.975 | 74.979 | 0.00 | 48.22 | B |
| ATOM | 2964 | C | GLN | B | 400 | 49.450 | 65.561 | 78.377 | 1.00 | 38.88 | B |
| ATOM | 2965 | O | GLN | B | 400 | 49.413 | 66.574 | 77.703 | 1.00 | 37.97 | B |
| ATOM | 2966 | N | ASP | B | 401 | 49.164 | 65.572 | 79.675 | 1.00 | 40.30 | B |
| ATOM | 2967 | CA | ASP | B | 401 | 48.868 | 66.810 | 80.414 | 1.00 | 41.86 | B |
| ATOM | 2968 | CB | ASP | B | 401 | 48.513 | 66.498 | 81.905 | 1.00 | 43.85 | B |
| ATOM | 2969 | CG | ASP | B | 401 | 48.452 | 67.765 | 82.768 | 1.00 | 46.71 | B |
| ATOM | 2970 | OD1 | ASP | B | 401 | 47.419 | 68.417 | 82.520 | 1.00 | 49.92 | B |
| ATOM | 2971 | OD2 | ASP | B | 401 | 49.388 | 68.590 | 83.020 | 0.00 | 46.70 | B |
| ATOM | 2972 | C | ASP | B | 401 | 49.998 | 67.849 | 80.319 | 1.00 | 40.95 | B |
| ATOM | 2973 | O | ASP | B | 401 | 49.815 | 68.959 | 79.916 | 1.00 | 41.60 | B |
| ATOM | 2974 | N | TYR | B | 402 | 51.175 | 67.470 | 80.642 | 1.00 | 40.66 | B |
| ATOM | 2975 | CA | TYR | B | 402 | 52.307 | 68.241 | 80.363 | 1.00 | 40.89 | B |
| ATOM | 2976 | CB | TYR | B | 402 | 53.584 | 67.469 | 80.620 | 1.00 | 39.32 | B |
| ATOM | 2977 | CG | TYR | B | 402 | 54.759 | 68.315 | 80.456 | 1.00 | 39.97 | B |
| ATOM | 2978 | CD1 | TYR | B | 402 | 55.161 | 69.253 | 81.475 | 1.00 | 39.69 | B |
| ATOM | 2979 | CE1 | TYR | B | 402 | 56.267 | 70.118 | 81.249 | 1.00 | 39.65 | B |
| ATOM | 2980 | CD2 | TYR | B | 402 | 55.433 | 68.325 | 79.255 | 1.00 | 38.94 | B |
| ATOM | 2981 | CE2 | TYR | B | 402 | 56.521 | 69.203 | 79.041 | 1.00 | 39.27 | B |
| ATOM | 2982 | CZ | TYR | B | 402 | 56.938 | 70.103 | 80.026 | 1.00 | 39.61 | B |
| ATOM | 2983 | OH | TYR | B | 402 | 58.073 | 70.941 | 79.722 | 1.00 | 39.43 | B |
| ATOM | 2984 | C | TYR | B | 402 | 52.374 | 68.835 | 78.981 | 1.00 | 41.72 | B |
| ATOM | 2985 | O | TYR | B | 402 | 52.791 | 69.949 | 78.913 | 1.00 | 41.48 | B |
| ATOM | 2986 | N | GLU | B | 403 | 52.027 | 68.126 | 77.892 | 1.00 | 41.16 | B |
| ATOM | 2987 | CA | GLU | B | 403 | 52.357 | 68.605 | 76.585 | 1.00 | 41.13 | B |
| ATOM | 2988 | CB | GLU | B | 403 | 52.516 | 67.501 | 75.571 | 1.00 | 40.40 | B |
| ATOM | 2989 | CG | GLU | B | 403 | 53.688 | 66.562 | 75.904 | 1.00 | 40.58 | B |
| ATOM | 2990 | CD | GLU | B | 403 | 54.940 | 67.145 | 75.517 | 1.00 | 40.56 | B |
| ATOM | 2991 | OE1 | GLU | B | 403 | 54.897 | 68.177 | 74.859 | 1.00 | 42.95 | B |
| ATOM | 2992 | OE2 | GLU | B | 403 | 55.959 | 66.647 | 75.897 | 1.00 | 39.38 | B |
| ATOM | 2993 | C | GLU | B | 403 | 51.227 | 69.512 | 76.147 | 1.00 | 41.98 | B |
| ATOM | 2994 | O | GLU | B | 403 | 51.456 | 70.415 | 75.292 | 1.00 | 41.23 | B |
| ATOM | 2995 | N | ALA | B | 404 | 50.021 | 69.290 | 76.675 | 1.00 | 42.07 | B |
| ATOM | 2996 | CA | ALA | B | 404 | 48.943 | 70.254 | 76.451 | 1.00 | 42.98 | B |
| ATOM | 2997 | CB | ALA | B | 404 | 47.513 | 69.628 | 76.749 | 1.00 | 41.33 | B |
| ATOM | 2998 | C | ALA | B | 404 | 49.199 | 71.671 | 77.209 | 1.00 | 43.58 | B |
| ATOM | 2999 | O | ALA | B | 404 | 48.680 | 72.622 | 76.825 | 1.00 | 44.38 | B |
| ATOM | 3000 | N | GLY | B | 405 | 50.011 | 71.747 | 78.231 | 1.00 | 44.11 | B |
| ATOM | 3001 | CA | GLY | B | 405 | 50.245 | 72.966 | 78.948 | 1.00 | 45.71 | B |
| ATOM | 3002 | C | GLY | B | 405 | 51.477 | 73.664 | 78.398 | 1.00 | 46.59 | B |
| ATOM | 3003 | O | GLY | B | 405 | 51.450 | 74.861 | 78.120 | 1.00 | 47.92 | B |
| ATOM | 3004 | N | GLN | B | 406 | 52.521 | 72.924 | 78.096 | 1.00 | 45.99 | B |
| ATOM | 3005 | CA | GLN | B | 406 | 53.734 | 73.513 | 77.615 | 1.00 | 45.76 | B |
| ATOM | 3006 | CB | GLN | B | 406 | 54.962 | 72.712 | 78.197 | 1.00 | 47.53 | B |
| ATOM | 3007 | CG | GLN | B | 406 | 55.883 | 75.002 | 78.612 | 0.00 | 49.78 | B |
| ATOM | 3008 | CD | GLN | B | 406 | 56.374 | 75.096 | 78.965 | 1.00 | 51.23 | B |
| ATOM | 3009 | OE1 | GLN | B | 406 | 57.352 | 74.947 | 78.201 | 1.00 | 54.25 | B |
| ATOM | 3010 | NE2 | GLN | B | 406 | 57.619 | 74.161 | 76.934 | 0.00 | 51.61 | B |
| ATOM | 3011 | C | GLN | B | 406 | 53.896 | 73.655 | 76.124 | 1.00 | 45.25 | B |
| ATOM | 3012 | O | GLN | B | 406 | 54.860 | 74.333 | 75.675 | 1.00 | 44.77 | B |
| ATOM | 3013 | N | HIS | B | 407 | 53.000 | 73.053 | 75.338 | 1.00 | 44.42 | B |
| ATOM | 3014 | CA | HIS | B | 407 | 53.299 | 72.884 | 73.938 | 1.00 | 44.25 | B |
| ATOM | 3015 | CB | HIS | B | 407 | 54.103 | 71.591 | 73.632 | 1.00 | 42.28 | B |
| ATOM | 3016 | CG | HIS | B | 407 | 55.538 | 71.648 | 74.088 | 1.00 | 39.61 | B |
| ATOM | 3017 | CD2 | HIS | B | 407 | 56.650 | 72.107 | 73.471 | 1.00 | 39.11 | B |
| ATOM | 3018 | ND1 | HIS | B | 407 | 55.936 | 71.240 | 75.334 | 1.00 | 39.04 | B |
| ATOM | 3019 | CE1 | HIS | B | 407 | 57.242 | 71.430 | 75.457 | 1.00 | 37.86 | B |
| ATOM | 3020 | NE2 | HIS | B | 407 | 57.685 | 71.966 | 74.341 | 1.00 | 37.75 | B |
| ATOM | 3021 | C | HIS | B | 407 | 52.045 | 72.851 | 73.199 | 1.00 | 46.09 | B |
| ATOM | 3022 | O | HIS | B | 407 | 51.905 | 72.090 | 72.253 | 1.00 | 45.35 | B |
| ATOM | 3023 | N | MET | B | 408 | 51.197 | 73.814 | 73.537 | 1.00 | 48.40 | B |
| ATOM | 3024 | CA | MET | B | 408 | 49.981 | 74.101 | 72.810 | 1.00 | 50.61 | B |
| ATOM | 3025 | CB | MET | B | 408 | 49.152 | 75.207 | 73.498 | 1.00 | 54.20 | B |
| ATOM | 3026 | CG | MET | B | 408 | 48.084 | 74.612 | 74.475 | 1.00 | 59.73 | B |
| ATOM | 3027 | SD | MET | B | 408 | 47.446 | 72.710 | 74.323 | 1.00 | 67.34 | B |
| ATOM | 3028 | CE | MET | B | 408 | 46.661 | 72.777 | 72.432 | 1.00 | 63.60 | B |
| ATOM | 3029 | C | MET | B | 408 | 50.245 | 74.403 | 71.362 | 1.00 | 49.79 | B |
| ATOM | 3030 | O | MET | B | 408 | 49.395 | 74.140 | 70.542 | 1.00 | 49.14 | B |
| ATOM | 3031 | N | GLU | B | 409 | 51.414 | 74.895 | 71.060 | 1.00 | 49.72 | B |
| ATOM | 3032 | CA | GLU | B | 409 | 51.876 | 75.038 | 69.656 | 1.00 | 50.34 | B |
| ATOM | 3033 | CB | GLU | B | 409 | 53.365 | 75.463 | 69.675 | 1.00 | 53.98 | B |

TABLE 2-continued

ATOMIC COORDINATES OF THE ERR3 LBD/
DIETHYLSTILBESTROL COMPLEX

| ATOM | 3034 | CG | GLU | B | 409 | 53.634 | 76.828 | 70.311 | 1.00 | 60.58 | B |
|---|---|---|---|---|---|---|---|---|---|---|---|
| ATOM | 3035 | CD | GLU | B | 409 | 53.243 | 76.892 | 71.779 | 1.00 | 64.16 | B |
| ATOM | 3036 | OE1 | GLU | B | 409 | 53.803 | 76.116 | 72.584 | 1.00 | 65.48 | B |
| ATOM | 3037 | OE2 | GLU | B | 409 | 52.375 | 77.720 | 72.127 | 1.00 | 66.32 | B |
| ATOM | 3038 | C | GLU | B | 409 | 51.854 | 73.749 | 68.784 | 1.00 | 48.63 | B |
| ATOM | 3039 | O | GLU | B | 409 | 51.620 | 73.820 | 67.548 | 1.00 | 48.50 | B |
| ATOM | 3040 | N | ASP | B | 410 | 52.182 | 72.565 | 69.393 | 1.00 | 45.72 | B |
| ATOM | 3041 | CA | ASP | B | 410 | 52.224 | 71.326 | 68.637 | 1.00 | 42.42 | B |
| ATOM | 3042 | CB | ASP | B | 410 | 53.664 | 70.810 | 68.604 | 1.00 | 41.55 | B |
| ATOM | 3043 | CG | ASP | B | 410 | 53.787 | 69.403 | 67.935 | 1.00 | 40.67 | B |
| ATOM | 3044 | OD1 | ASP | B | 410 | 52.760 | 68.785 | 67.491 | 1.00 | 38.06 | B |
| ATOM | 3045 | OD2 | ASP | B | 410 | 54.933 | 68.901 | 67.822 | 1.00 | 40.93 | B |
| ATOM | 3046 | C | ASP | B | 410 | 51.296 | 70.369 | 69.368 | 1.00 | 40.51 | B |
| ATOM | 3047 | O | ASP | B | 410 | 51.687 | 69.784 | 70.335 | 1.00 | 39.02 | B |
| ATOM | 3048 | N | PRO | B | 411 | 50.067 | 70.285 | 68.947 | 1.00 | 39.06 | B |
| ATOM | 3049 | CD | PRO | B | 411 | 49.581 | 70.889 | 67.699 | 1.00 | 38.36 | B |
| ATOM | 3050 | CA | PRO | B | 411 | 49.064 | 69.442 | 69.597 | 1.00 | 38.23 | B |
| ATOM | 3051 | CB | PRO | B | 411 | 47.814 | 69.735 | 68.785 | 1.00 | 37.76 | B |
| ATOM | 3052 | CG | PRO | B | 411 | 48.366 | 70.104 | 67.304 | 1.00 | 37.47 | B |
| ATOM | 3053 | C | PRO | B | 411 | 49.387 | 67.885 | 69.383 | 1.00 | 37.90 | B |
| ATOM | 3054 | O | PRO | B | 411 | 48.556 | 67.023 | 69.625 | 1.00 | 37.58 | B |
| ATOM | 3055 | N | ARG | B | 412 | 50.506 | 67.622 | 68.736 | 1.00 | 36.87 | B |
| ATOM | 3056 | CA | ARG | B | 412 | 50.894 | 66.293 | 68.422 | 1.00 | 35.94 | B |
| ATOM | 3057 | CB | ARG | B | 412 | 51.029 | 66.204 | 66.914 | 1.00 | 38.10 | B |
| ATOM | 3058 | CG | ARG | B | 412 | 49.977 | 65.281 | 66.289 | 1.00 | 39.88 | B |
| ATOM | 3059 | CD | ARG | B | 412 | 50.083 | 65.284 | 64.815 | 1.00 | 41.91 | B |
| ATOM | 3060 | NE | ARG | B | 412 | 48.904 | 65.987 | 64.544 | 1.00 | 46.35 | B |
| ATOM | 3061 | CZ | ARG | B | 412 | 48.803 | 67.117 | 63.908 | 1.00 | 46.66 | B |
| ATOM | 3062 | NH1 | ARG | B | 412 | 49.808 | 67.631 | 63.182 | 1.00 | 45.59 | B |
| ATOM | 3063 | NH2 | ARG | B | 412 | 47.599 | 67.617 | 63.888 | 1.00 | 46.64 | B |
| ATOM | 3064 | C | ARG | B | 412 | 52.191 | 65.919 | 69.133 | 1.00 | 33.79 | B |
| ATOM | 3065 | O | ARG | B | 412 | 52.692 | 64.896 | 68.891 | 1.00 | 33.22 | B |
| ATOM | 3066 | N | ARG | B | 413 | 52.689 | 66.746 | 70.055 | 1.00 | 32.19 | B |
| ATOM | 3067 | CA | ARG | B | 413 | 53.999 | 66.591 | 70.543 | 1.00 | 31.11 | B |
| ATOM | 3068 | CB | ARG | B | 413 | 54.363 | 67.796 | 71.417 | 1.00 | 30.00 | B |
| ATOM | 3069 | CG | ARG | B | 413 | 55.805 | 67.804 | 71.916 | 1.00 | 30.53 | B |
| ATOM | 3070 | CD | ARG | B | 413 | 56.460 | 69.110 | 72.055 | 1.00 | 29.77 | B |
| ATOM | 3071 | NE | ARG | B | 413 | 57.757 | 68.986 | 72.780 | 1.00 | 29.87 | B |
| ATOM | 3072 | CZ | ARG | B | 413 | 58.905 | 69.171 | 72.153 | 1.00 | 29.83 | B |
| ATOM | 3073 | NH1 | ARG | B | 413 | 58.880 | 69.508 | 70.889 | 1.00 | 28.65 | B |
| ATOM | 3074 | NH2 | ARG | B | 413 | 60.055 | 69.020 | 72.749 | 1.00 | 29.08 | B |
| ATOM | 3075 | C | ARG | B | 413 | 54.158 | 65.305 | 71.370 | 1.00 | 29.96 | B |
| ATOM | 3076 | O | ARG | B | 413 | 55.231 | 64.734 | 71.451 | 1.00 | 30.54 | B |
| ATOM | 3077 | N | ALA | B | 414 | 53.137 | 65.004 | 72.139 | 1.00 | 28.52 | B |
| ATOM | 3078 | CA | ALA | B | 414 | 53.167 | 63.841 | 73.016 | 1.00 | 28.54 | B |
| ATOM | 3079 | CB | ALA | B | 414 | 51.995 | 63.820 | 73.922 | 1.00 | 27.40 | B |
| ATOM | 3080 | C | ALA | B | 414 | 53.235 | 62.551 | 72.133 | 1.00 | 27.52 | B |
| ATOM | 3081 | O | ALA | B | 414 | 54.009 | 61.726 | 72.401 | 1.00 | 27.72 | B |
| ATOM | 3082 | N | GLY | B | 415 | 52.453 | 62.452 | 71.101 | 1.00 | 27.21 | B |
| ATOM | 3083 | CA | GLY | B | 415 | 52.468 | 61.348 | 70.151 | 1.00 | 29.57 | B |
| ATOM | 3084 | C | GLY | B | 415 | 53.871 | 61.157 | 69.490 | 1.00 | 30.54 | B |
| ATOM | 3085 | O | GLY | B | 415 | 54.376 | 60.022 | 69.364 | 1.00 | 30.87 | B |
| ATOM | 3086 | N | LYS | B | 416 | 54.551 | 62.262 | 69.227 | 1.00 | 30.03 | B |
| ATOM | 3087 | CA | LYS | B | 416 | 55.859 | 62.230 | 68.671 | 1.00 | 30.77 | B |
| ATOM | 3088 | CB | LYS | B | 416 | 56.274 | 63.585 | 68.129 | 1.00 | 31.89 | B |
| ATOM | 3089 | CG | LYS | B | 416 | 55.591 | 64.026 | 66.809 | 1.00 | 33.88 | B |
| ATOM | 3090 | CD | LYS | B | 416 | 55.576 | 65.557 | 66.719 | 1.00 | 36.63 | B |
| ATOM | 3091 | CE | LYS | B | 416 | 54.819 | 66.206 | 65.488 | 1.00 | 39.60 | B |
| ATOM | 3092 | NZ | LYS | B | 416 | 54.865 | 67.737 | 65.530 | 1.00 | 40.39 | B |
| ATOM | 3093 | C | LYS | B | 416 | 56.849 | 61.735 | 69.665 | 1.00 | 29.74 | B |
| ATOM | 3094 | O | LYS | B | 416 | 57.742 | 61.023 | 69.262 | 1.00 | 31.30 | B |
| ATOM | 3095 | N | MET | B | 417 | 56.743 | 62.129 | 70.933 | 1.00 | 28.83 | B |
| ATOM | 3096 | CA | MET | B | 417 | 57.608 | 61.630 | 71.996 | 1.00 | 27.51 | B |
| ATOM | 3097 | CB | MET | B | 417 | 57.291 | 62.275 | 73.266 | 1.00 | 29.42 | B |
| ATOM | 3098 | CG | MET | B | 417 | 57.773 | 63.735 | 73.272 | 1.00 | 31.51 | B |
| ATOM | 3099 | SD | MET | B | 417 | 59.485 | 63.947 | 73.193 | 1.00 | 34.04 | B |
| ATOM | 3100 | CE | MET | B | 417 | 59.704 | 65.813 | 72.650 | 1.00 | 30.27 | B |
| ATOM | 3101 | C | MET | B | 417 | 57.373 | 60.067 | 72.142 | 1.00 | 25.86 | B |
| ATOM | 3102 | O | MET | B | 417 | 58.295 | 59.328 | 72.097 | 1.00 | 24.47 | B |
| ATOM | 3103 | N | LEU | B | 418 | 56.151 | 59.619 | 72.036 | 1.00 | 27.07 | B |
| ATOM | 3104 | CA | LEU | B | 418 | 55.827 | 58.202 | 72.086 | 1.00 | 27.07 | B |
| ATOM | 3105 | CB | LEU | B | 418 | 54.366 | 58.081 | 72.230 | 1.00 | 26.86 | B |
| ATOM | 3106 | CG | LEU | B | 418 | 53.832 | 58.519 | 73.610 | 1.00 | 26.30 | B |
| ATOM | 3107 | CD1 | LEU | B | 418 | 52.367 | 58.284 | 73.547 | 1.00 | 26.40 | B |
| ATOM | 3108 | CD2 | LEU | B | 418 | 54.446 | 57.761 | 74.825 | 1.00 | 24.24 | B |
| ATOM | 3109 | C | LEU | B | 418 | 56.409 | 57.434 | 70.884 | 1.00 | 26.96 | B |

TABLE 2-continued

ATOMIC COORDINATES OF THE ERR3 LBD/
DIETHYLSTILBESTROL COMPLEX

| ATOM | 3110 | O   | LEU | B | 418 | 56.977 | 56.363 | 71.047 | 1.00 | 28.11 | B |
|------|------|-----|-----|---|-----|--------|--------|--------|------|-------|---|
| ATOM | 3111 | N   | MET | B | 419 | 56.523 | 58.120 | 69.770 | 1.00 | 26.02 | B |
| ATOM | 3112 | CA  | MET | B | 419 | 57.025 | 57.555 | 68.553 | 1.00 | 24.89 | B |
| ATOM | 3113 | CB  | MET | B | 419 | 56.469 | 58.271 | 67.318 | 1.00 | 24.58 | B |
| ATOM | 3114 | CG  | MET | B | 419 | 55.050 | 57.861 | 67.007 | 1.00 | 27.12 | B |
| ATOM | 3115 | SD  | MET | B | 419 | 54.243 | 59.072 | 65.834 | 1.00 | 34.28 | B |
| ATOM | 3116 | CE  | MET | B | 419 | 54.962 | 58.375 | 64.501 | 1.00 | 30.36 | B |
| ATOM | 3117 | C   | MET | B | 419 | 58.525 | 57.405 | 68.480 | 1.00 | 24.51 | B |
| ATOM | 3118 | O   | MET | B | 419 | 58.980 | 56.738 | 67.545 | 1.00 | 26.49 | B |
| ATOM | 3119 | N   | THR | B | 420 | 59.267 | 57.965 | 69.432 | 1.00 | 23.16 | B |
| ATOM | 3120 | CA  | THR | B | 420 | 60.682 | 57.674 | 69.626 | 1.00 | 22.06 | B |
| ATOM | 3121 | CB  | THR | B | 420 | 61.452 | 58.782 | 70.345 | 1.00 | 21.78 | B |
| ATOM | 3122 | OG1 | THR | B | 420 | 60.987 | 58.906 | 71.667 | 1.00 | 21.98 | B |
| ATOM | 3123 | CG2 | THR | B | 420 | 61.058 | 60.298 | 69.736 | 1.00 | 20.54 | B |
| ATOM | 3124 | C   | THR | B | 420 | 60.933 | 56.366 | 70.312 | 1.00 | 21.63 | B |
| ATOM | 3125 | O   | THR | B | 420 | 62.047 | 55.867 | 70.298 | 1.00 | 24.20 | B |
| ATOM | 3126 | N   | LEU | B | 421 | 59.941 | 55.792 | 70.940 | 1.00 | 21.85 | B |
| ATOM | 3127 | CA  | LEU | B | 421 | 60.179 | 54.619 | 71.838 | 1.00 | 22.75 | B |
| ATOM | 3128 | CB  | LEU | B | 421 | 58.892 | 54.423 | 72.661 | 1.00 | 21.03 | B |
| ATOM | 3129 | CG  | LEU | B | 421 | 58.656 | 55.397 | 73.817 | 1.00 | 22.30 | B |
| ATOM | 3130 | CD1 | LEU | B | 421 | 57.343 | 54.947 | 74.431 | 1.00 | 21.68 | B |
| ATOM | 3131 | CD2 | LEU | B | 421 | 59.799 | 55.373 | 74.815 | 1.00 | 20.85 | B |
| ATOM | 3132 | C   | LEU | B | 421 | 60.608 | 53.316 | 71.072 | 1.00 | 23.06 | B |
| ATOM | 3133 | O   | LEU | B | 421 | 61.432 | 52.554 | 71.566 | 1.00 | 24.03 | B |
| ATOM | 3134 | N   | PRO | B | 422 | 60.100 | 53.058 | 69.899 | 1.00 | 22.65 | B |
| ATOM | 3135 | CD  | PRO | B | 422 | 59.076 | 53.880 | 69.142 | 1.00 | 21.54 | B |
| ATOM | 3136 | CA  | PRO | B | 422 | 60.607 | 51.923 | 69.065 | 1.00 | 24.07 | B |
| ATOM | 3137 | CB  | PRO | B | 422 | 59.780 | 52.033 | 67.757 | 1.00 | 21.88 | B |
| ATOM | 3138 | CG  | PRO | B | 422 | 58.522 | 52.880 | 68.155 | 1.00 | 22.27 | B |
| ATOM | 3139 | C   | PRO | B | 422 | 62.092 | 52.046 | 68.767 | 1.00 | 24.76 | B |
| ATOM | 3140 | O   | PRO | B | 422 | 62.848 | 51.088 | 68.922 | 1.00 | 28.16 | B |
| ATOM | 3141 | N   | LEU | B | 423 | 62.585 | 53.224 | 68.457 | 1.00 | 24.74 | B |
| ATOM | 3142 | CA  | LEU | B | 423 | 64.067 | 53.338 | 68.196 | 1.00 | 23.24 | B |
| ATOM | 3143 | CB  | LEU | B | 423 | 64.455 | 54.691 | 67.564 | 1.00 | 22.65 | B |
| ATOM | 3144 | CG  | LEU | B | 423 | 65.913 | 54.736 | 67.168 | 1.00 | 24.47 | B |
| ATOM | 3145 | CD1 | LEU | B | 423 | 66.407 | 53.664 | 66.278 | 1.00 | 20.50 | B |
| ATOM | 3146 | CD2 | LEU | B | 423 | 66.100 | 56.021 | 66.515 | 1.00 | 25.54 | B |
| ATOM | 3147 | C   | LEU | B | 423 | 64.785 | 53.164 | 69.418 | 1.00 | 22.53 | B |
| ATOM | 3148 | O   | LEU | B | 423 | 65.910 | 52.594 | 69.421 | 1.00 | 23.90 | B |
| ATOM | 3149 | N   | LEU | B | 424 | 64.243 | 53.709 | 70.486 | 1.00 | 21.27 | B |
| ATOM | 3150 | CA  | LEU | B | 424 | 64.821 | 53.369 | 71.832 | 1.00 | 21.61 | B |
| ATOM | 3151 | CB  | LEU | B | 424 | 64.063 | 54.047 | 72.983 | 1.00 | 20.19 | B |
| ATOM | 3152 | CG  | LEU | B | 424 | 64.682 | 53.847 | 74.386 | 1.00 | 21.78 | B |
| ATOM | 3153 | CD1 | LEU | B | 424 | 66.113 | 54.459 | 74.522 | 1.00 | 18.10 | B |
| ATOM | 3154 | CD2 | LEU | B | 424 | 63.821 | 54.457 | 75.515 | 1.00 | 20.15 | B |
| ATOM | 3155 | C   | LEU | B | 424 | 64.919 | 51.861 | 72.133 | 1.00 | 21.21 | B |
| ATOM | 3156 | O   | LEU | B | 424 | 65.934 | 51.356 | 72.644 | 1.00 | 20.40 | B |
| ATOM | 3157 | N   | ARG | B | 425 | 63.861 | 51.145 | 71.925 | 1.00 | 22.19 | B |
| ATOM | 3158 | CA  | ARG | B | 425 | 63.863 | 49.649 | 72.115 | 1.00 | 22.88 | B |
| ATOM | 3159 | CB  | ARG | B | 425 | 62.435 | 49.111 | 71.831 | 1.00 | 22.71 | B |
| ATOM | 3160 | CG  | ARG | B | 425 | 62.201 | 47.612 | 71.899 | 1.00 | 24.15 | B |
| ATOM | 3161 | CD  | ARG | B | 425 | 61.949 | 46.976 | 73.183 | 1.00 | 22.69 | B |
| ATOM | 3162 | NE  | ARG | B | 425 | 61.027 | 47.659 | 74.037 | 1.00 | 22.05 | B |
| ATOM | 3163 | CZ  | ARG | B | 425 | 59.746 | 47.394 | 74.216 | 1.00 | 24.65 | B |
| ATOM | 3164 | NH1 | ARG | B | 425 | 59.073 | 46.503 | 73.488 | 1.00 | 21.05 | B |
| ATOM | 3165 | NH2 | ARG | B | 425 | 59.095 | 48.115 | 75.082 | 1.00 | 22.58 | B |
| ATOM | 3166 | C   | ARG | B | 425 | 64.952 | 48.995 | 71.226 | 1.00 | 23.31 | B |
| ATOM | 3167 | O   | ARG | B | 425 | 65.723 | 48.121 | 71.683 | 1.00 | 22.39 | B |
| ATOM | 3168 | N   | GLN | B | 426 | 64.951 | 49.342 | 69.948 | 1.00 | 23.22 | B |
| ATOM | 3169 | CA  | GLN | B | 426 | 65.838 | 48.717 | 68.949 | 1.00 | 23.88 | B |
| ATOM | 3170 | CB  | GLN | B | 426 | 65.610 | 49.397 | 67.596 | 1.00 | 24.14 | B |
| ATOM | 3171 | CG  | GLN | B | 426 | 66.529 | 48.912 | 66.426 | 1.00 | 24.64 | B |
| ATOM | 3172 | CD  | GLN | B | 426 | 65.946 | 49.421 | 65.107 | 1.00 | 28.98 | B |
| ATOM | 3173 | OE1 | GLN | B | 426 | 65.267 | 50.365 | 65.107 | 1.00 | 30.03 | B |
| ATOM | 3174 | NE2 | GLN | B | 426 | 65.981 | 48.606 | 64.117 | 1.00 | 31.55 | B |
| ATOM | 3175 | C   | GLN | B | 426 | 67.370 | 48.996 | 69.296 | 1.00 | 24.62 | B |
| ATOM | 3176 | O   | GLN | B | 426 | 68.100 | 48.081 | 69.418 | 1.00 | 24.33 | B |
| ATOM | 3177 | N   | THR | B | 427 | 67.741 | 50.205 | 69.655 | 1.00 | 24.38 | B |
| ATOM | 3178 | CA  | THR | B | 427 | 69.111 | 50.509 | 70.091 | 1.00 | 24.86 | B |
| ATOM | 3179 | CB  | THR | B | 427 | 69.260 | 51.986 | 70.343 | 1.00 | 26.55 | B |
| ATOM | 3180 | OG1 | THR | B | 427 | 68.727 | 52.739 | 69.281 | 1.00 | 27.99 | B |
| ATOM | 3181 | CG2 | THR | B | 427 | 70.657 | 52.412 | 70.427 | 1.00 | 25.05 | B |
| ATOM | 3182 | C   | THR | B | 427 | 69.566 | 49.808 | 71.345 | 1.00 | 23.90 | B |
| ATOM | 3183 | O   | THR | B | 427 | 70.640 | 49.300 | 71.421 | 1.00 | 23.64 | B |
| ATOM | 3184 | N   | SER | B | 428 | 68.704 | 49.696 | 72.308 | 1.00 | 24.03 | B |
| ATOM | 3185 | CA  | SER | B | 428 | 68.898 | 48.952 | 73.523 | 1.00 | 26.29 | B |

TABLE 2-continued

ATOMIC COORDINATES OF THE ERR3 LBD/DIETHYLSTILBESTROL COMPLEX

| ATOM | 3186 | CB  | SER | B | 428 | 67.766 | 49.166 | 74.494 | 1.00 | 27.39 | B |
|------|------|-----|-----|---|-----|--------|--------|--------|------|-------|---|
| ATOM | 3187 | OG  | SER | B | 428 | 67.618 | 50.665 | 74.654 | 1.00 | 31.97 | B |
| ATOM | 3188 | C   | SER | B | 428 | 69.067 | 47.487 | 73.297 | 1.00 | 26.04 | B |
| ATOM | 3189 | O   | SER | B | 428 | 70.039 | 46.895 | 73.765 | 1.00 | 26.80 | B |
| ATOM | 3190 | N   | THR | B | 429 | 68.276 | 46.957 | 72.419 | 1.00 | 26.37 | B |
| ATOM | 3191 | CA  | THR | B | 429 | 68.448 | 45.574 | 72.069 | 1.00 | 26.80 | B |
| ATOM | 3192 | CB  | THR | B | 429 | 67.290 | 45.085 | 71.126 | 1.00 | 26.19 | B |
| ATOM | 3193 | OG1 | THR | B | 429 | 66.082 | 45.093 | 71.906 | 1.00 | 29.17 | B |
| ATOM | 3194 | CG2 | THR | B | 429 | 67.535 | 43.610 | 70.655 | 1.00 | 25.40 | B |
| ATOM | 3195 | C   | THR | B | 429 | 69.824 | 45.360 | 71.404 | 1.00 | 26.22 | B |
| ATOM | 3196 | O   | THR | B | 429 | 70.516 | 44.514 | 71.817 | 1.00 | 27.58 | B |
| ATOM | 3197 | N   | LYS | B | 430 | 70.218 | 46.175 | 70.431 | 1.00 | 26.32 | B |
| ATOM | 3198 | CA  | LYS | B | 430 | 71.541 | 46.207 | 69.902 | 1.00 | 27.27 | B |
| ATOM | 3199 | CB  | LYS | B | 430 | 71.718 | 47.324 | 68.905 | 1.00 | 30.67 | B |
| ATOM | 3200 | CG  | LYS | B | 430 | 70.884 | 47.174 | 67.653 | 1.00 | 34.29 | B |
| ATOM | 3201 | CD  | LYS | B | 430 | 71.244 | 48.243 | 66.602 | 1.00 | 37.89 | B |
| ATOM | 3202 | CE  | LYS | B | 430 | 70.160 | 48.152 | 65.456 | 1.00 | 37.40 | B |
| ATOM | 3203 | NZ  | LYS | B | 430 | 70.733 | 49.063 | 64.595 | 1.00 | 39.19 | B |
| ATOM | 3204 | C   | LYS | B | 430 | 72.644 | 46.399 | 70.995 | 1.00 | 26.68 | B |
| ATOM | 3205 | O   | LYS | B | 430 | 73.677 | 45.670 | 70.941 | 1.00 | 26.71 | B |
| ATOM | 3206 | N   | ALA | B | 431 | 72.439 | 47.235 | 71.985 | 1.00 | 23.86 | B |
| ATOM | 3207 | CA  | ALA | B | 431 | 73.456 | 47.332 | 73.032 | 1.00 | 24.56 | B |
| ATOM | 3208 | CB  | ALA | B | 431 | 73.208 | 48.460 | 73.950 | 1.00 | 22.87 | B |
| ATOM | 3209 | C   | ALA | B | 431 | 73.539 | 46.073 | 73.858 | 1.00 | 26.27 | B |
| ATOM | 3210 | O   | ALA | B | 431 | 74.613 | 45.679 | 74.228 | 1.00 | 23.91 | B |
| ATOM | 3211 | N   | VAL | B | 432 | 72.404 | 45.490 | 74.221 | 1.00 | 27.72 | B |
| ATOM | 3212 | CA  | VAL | B | 432 | 72.401 | 44.304 | 74.995 | 1.00 | 29.49 | B |
| ATOM | 3213 | CB  | VAL | B | 432 | 71.095 | 43.941 | 75.574 | 1.00 | 30.84 | B |
| ATOM | 3214 | CG1 | VAL | B | 432 | 71.240 | 42.622 | 76.322 | 1.00 | 31.56 | B |
| ATOM | 3215 | CG2 | VAL | B | 432 | 70.630 | 45.019 | 76.571 | 1.00 | 30.75 | B |
| ATOM | 3216 | C   | VAL | B | 432 | 72.989 | 43.126 | 74.268 | 1.00 | 30.01 | B |
| ATOM | 3217 | O   | VAL | B | 432 | 73.781 | 42.364 | 74.847 | 1.00 | 31.26 | B |
| ATOM | 3218 | N   | GLN | B | 433 | 72.672 | 42.998 | 73.021 | 1.00 | 31.21 | B |
| ATOM | 3219 | CA  | GLN | B | 433 | 73.364 | 42.039 | 72.268 | 1.00 | 32.11 | B |
| ATOM | 3220 | CB  | GLN | B | 433 | 72.810 | 41.922 | 70.861 | 1.00 | 33.64 | B |
| ATOM | 3221 | CG  | GLN | B | 433 | 73.601 | 40.955 | 69.946 | 1.00 | 40.69 | B |
| ATOM | 3222 | CD  | GLN | B | 433 | 72.973 | 39.579 | 69.652 | 1.00 | 46.05 | B |
| ATOM | 3223 | OE1 | GLN | B | 433 | 73.560 | 38.511 | 70.057 | 1.00 | 49.59 | B |
| ATOM | 3224 | NE2 | GLN | B | 433 | 71.823 | 39.563 | 68.910 | 1.00 | 48.61 | B |
| ATOM | 3225 | C   | GLN | B | 433 | 74.943 | 42.225 | 72.255 | 1.00 | 32.26 | B |
| ATOM | 3226 | O   | GLN | B | 433 | 75.735 | 41.226 | 72.380 | 1.00 | 30.72 | B |
| ATOM | 3227 | N   | HIS | B | 434 | 75.406 | 43.438 | 72.111 | 1.00 | 32.67 | B |
| ATOM | 3228 | CA  | HIS | B | 434 | 76.835 | 43.662 | 72.015 | 1.00 | 33.75 | B |
| ATOM | 3229 | CB  | HIS | B | 434 | 77.079 | 45.153 | 71.781 | 1.00 | 34.09 | B |
| ATOM | 3230 | CG  | HIS | B | 434 | 78.517 | 45.513 | 71.607 | 1.00 | 35.36 | B |
| ATOM | 3231 | CD2 | HIS | B | 434 | 79.204 | 45.947 | 70.527 | 1.00 | 35.69 | B |
| ATOM | 3232 | ND1 | HIS | B | 434 | 79.438 | 45.385 | 72.620 | 1.00 | 36.05 | B |
| ATOM | 3233 | CE1 | HIS | B | 434 | 80.622 | 45.762 | 72.182 | 1.00 | 32.90 | B |
| ATOM | 3234 | NE2 | HIS | B | 434 | 80.516 | 46.065 | 70.914 | 1.00 | 36.04 | B |
| ATOM | 3235 | C   | HIS | B | 434 | 77.387 | 43.275 | 73.391 | 1.00 | 34.51 | B |
| ATOM | 3236 | O   | HIS | B | 434 | 78.457 | 42.698 | 73.533 | 1.00 | 35.38 | B |
| ATOM | 3237 | N   | PHE | B | 435 | 76.664 | 43.626 | 74.441 | 1.00 | 35.05 | B |
| ATOM | 3238 | CA  | PHE | B | 435 | 77.133 | 43.382 | 75.850 | 1.00 | 36.46 | B |
| ATOM | 3239 | CB  | PHE | B | 435 | 76.173 | 44.019 | 76.787 | 1.00 | 37.69 | B |
| ATOM | 3240 | CG  | PHE | B | 435 | 76.400 | 43.730 | 78.189 | 1.00 | 40.36 | B |
| ATOM | 3241 | CD1 | PHE | B | 435 | 77.469 | 44.286 | 78.849 | 1.00 | 41.91 | B |
| ATOM | 3242 | CD2 | PHE | B | 435 | 75.518 | 42.964 | 78.890 | 1.00 | 39.54 | B |
| ATOM | 3243 | CE1 | PHE | B | 435 | 77.672 | 44.035 | 80.196 | 1.00 | 42.66 | B |
| ATOM | 3244 | CE2 | PHE | B | 435 | 75.703 | 42.745 | 80.245 | 1.00 | 41.92 | B |
| ATOM | 3245 | CZ  | PHE | B | 435 | 76.765 | 43.272 | 80.885 | 1.00 | 41.53 | B |
| ATOM | 3246 | C   | PHE | B | 435 | 77.304 | 41.865 | 76.135 | 1.00 | 36.55 | B |
| ATOM | 3247 | O   | PHE | B | 435 | 78.360 | 41.422 | 76.649 | 1.00 | 36.89 | B |
| ATOM | 3248 | N   | TYR | B | 436 | 76.303 | 41.054 | 75.747 | 1.00 | 37.29 | B |
| ATOM | 3249 | CA  | TYR | B | 436 | 76.344 | 39.649 | 76.076 | 1.00 | 38.24 | B |
| ATOM | 3250 | CB  | TYR | B | 436 | 74.962 | 38.996 | 76.047 | 1.00 | 38.31 | B |
| ATOM | 3251 | CG  | TYR | B | 436 | 74.052 | 39.381 | 77.233 | 1.00 | 39.77 | B |
| ATOM | 3252 | CD1 | TYR | B | 436 | 74.515 | 39.376 | 78.496 | 1.00 | 41.81 | B |
| ATOM | 3253 | CE1 | TYR | B | 436 | 73.724 | 39.709 | 79.605 | 1.00 | 41.18 | B |
| ATOM | 3254 | CD2 | TYR | B | 436 | 72.745 | 39.728 | 77.058 | 1.00 | 39.55 | B |
| ATOM | 3255 | CE2 | TYR | B | 436 | 71.910 | 40.052 | 78.182 | 1.00 | 39.53 | B |
| ATOM | 3256 | CZ  | TYR | B | 436 | 72.421 | 40.047 | 79.428 | 1.00 | 40.94 | B |
| ATOM | 3257 | OH  | TYR | B | 436 | 71.689 | 40.368 | 80.537 | 1.00 | 41.29 | B |
| ATOM | 3258 | C   | TYR | B | 436 | 77.355 | 38.962 | 75.169 | 1.00 | 38.67 | B |
| ATOM | 3259 | O   | TYR | B | 436 | 77.901 | 37.935 | 75.532 | 1.00 | 38.05 | B |
| ATOM | 3260 | N   | ASN | B | 437 | 77.599 | 39.510 | 73.974 | 1.00 | 38.47 | B |
| ATOM | 3261 | CA  | ASN | B | 437 | 78.675 | 38.985 | 73.152 | 1.00 | 39.63 | B |

TABLE 2-continued

ATOMIC COORDINATES OF THE ERR3 LBD/DIETHYLSTILBESTROL COMPLEX

| ATOM | | | | | | | | | | |
|---|---|---|---|---|---|---|---|---|---|---|
| ATOM | 3262 | CB | ASN | B | 437 | 78.611 | 39.458 | 71.712 | 1.00 | 40.22 B |
| ATOM | 3263 | CG | ASN | B | 437 | 79.974 | 39.207 | 70.910 | 1.00 | 42.11 B |
| ATOM | 3264 | OD1 | ASN | B | 437 | 80.526 | 40.314 | 70.806 | 0.00 | 42.18 B |
| ATOM | 3265 | ND2 | ASN | B | 437 | 79.969 | 38.068 | 70.189 | 1.00 | 44.60 B |
| ATOM | 3266 | C | ASN | B | 437 | 80.090 | 39.168 | 73.791 | 1.00 | 39.59 B |
| ATOM | 3267 | O | ASN | B | 437 | 80.927 | 38.227 | 73.696 | 1.00 | 37.95 B |
| ATOM | 3268 | N | ILE | B | 438 | 80.305 | 40.317 | 74.414 | 1.00 | 38.72 B |
| ATOM | 3269 | CA | ILE | B | 438 | 81.553 | 40.602 | 75.062 | 1.00 | 39.74 B |
| ATOM | 3270 | CB | ILE | B | 438 | 81.517 | 42.067 | 75.535 | 1.00 | 38.91 B |
| ATOM | 3271 | CG2 | ILE | B | 438 | 82.444 | 42.372 | 76.632 | 1.00 | 39.76 B |
| ATOM | 3272 | CG1 | ILE | B | 438 | 81.858 | 43.041 | 74.381 | 1.00 | 39.37 B |
| ATOM | 3273 | CD1 | ILE | B | 438 | 82.727 | 42.533 | 73.473 | 1.00 | 39.24 B |
| ATOM | 3274 | C | ILE | B | 438 | 81.768 | 39.621 | 76.201 | 1.00 | 40.64 B |
| ATOM | 3275 | O | ILE | B | 438 | 82.806 | 39.055 | 76.358 | 1.00 | 40.16 B |
| ATOM | 3276 | N | LYS | B | 439 | 80.709 | 39.362 | 76.944 | 1.00 | 42.54 B |
| ATOM | 3277 | CA | LYS | B | 439 | 80.732 | 38.434 | 78.036 | 1.00 | 44.19 B |
| ATOM | 3278 | CB | LYS | B | 439 | 79.396 | 38.314 | 78.719 | 1.00 | 43.97 B |
| ATOM | 3279 | CG | LYS | B | 439 | 79.194 | 39.274 | 79.801 | 1.00 | 44.81 B |
| ATOM | 3280 | CD | LYS | B | 439 | 78.164 | 38.777 | 80.796 | 1.00 | 46.86 B |
| ATOM | 3281 | CE | LYS | B | 439 | 78.547 | 40.131 | 82.123 | 0.00 | 47.41 B |
| ATOM | 3282 | NZ | LYS | B | 439 | 78.997 | 41.145 | 81.998 | 1.00 | 49.66 B |
| ATOM | 3283 | C | LYS | B | 439 | 81.126 | 37.104 | 77.482 | 1.00 | 45.72 B |
| ATOM | 3284 | O | LYS | B | 439 | 82.168 | 36.582 | 77.855 | 1.00 | 46.83 B |
| ATOM | 3285 | N | LEU | B | 440 | 80.336 | 36.603 | 76.545 | 1.00 | 46.02 B |
| ATOM | 3286 | CA | LEU | B | 440 | 80.511 | 35.264 | 76.011 | 1.00 | 46.82 B |
| ATOM | 3287 | CB | LEU | B | 440 | 79.516 | 35.015 | 74.880 | 1.00 | 45.70 B |
| ATOM | 3288 | CG | LEU | B | 440 | 79.737 | 33.973 | 73.830 | 1.00 | 46.31 B |
| ATOM | 3289 | CD1 | LEU | B | 440 | 79.568 | 32.517 | 74.504 | 1.00 | 45.49 B |
| ATOM | 3290 | CD2 | LEU | B | 440 | 78.637 | 34.099 | 72.695 | 1.00 | 45.68 B |
| ATOM | 3291 | C | LEU | B | 440 | 81.956 | 35.139 | 75.540 | 1.00 | 47.05 B |
| ATOM | 3292 | O | LEU | B | 440 | 82.533 | 34.102 | 75.724 | 1.00 | 47.76 B |
| ATOM | 3293 | N | GLU | B | 441 | 82.523 | 36.177 | 74.951 | 1.00 | 47.56 B |
| ATOM | 3294 | CA | GLU | B | 441 | 83.808 | 36.134 | 74.445 | 1.00 | 49.26 B |
| ATOM | 3295 | CB | GLU | B | 441 | 84.063 | 37.324 | 73.558 | 1.00 | 51.76 B |
| ATOM | 3296 | CG | GLU | B | 441 | 83.563 | 37.254 | 72.082 | 1.00 | 58.05 B |
| ATOM | 3297 | CD | GLU | B | 441 | 83.895 | 38.506 | 71.295 | 1.00 | 62.84 B |
| ATOM | 3298 | OE1 | GLU | B | 441 | 85.094 | 38.827 | 71.165 | 1.00 | 65.75 B |
| ATOM | 3299 | OE2 | GLU | B | 441 | 82.955 | 39.168 | 70.806 | 1.00 | 66.41 B |
| ATOM | 3300 | C | GLU | B | 441 | 84.727 | 36.220 | 75.696 | 1.00 | 49.86 B |
| ATOM | 3301 | O | GLU | B | 441 | 85.897 | 36.237 | 75.567 | 1.00 | 48.83 B |
| ATOM | 3302 | N | GLY | B | 442 | 84.197 | 36.325 | 76.908 | 1.00 | 50.75 B |
| ATOM | 3303 | CA | GLY | B | 442 | 85.037 | 36.433 | 78.103 | 1.00 | 52.20 B |
| ATOM | 3304 | C | GLY | B | 442 | 85.989 | 37.659 | 78.092 | 1.00 | 53.44 B |
| ATOM | 3305 | O | GLY | B | 442 | 86.876 | 37.771 | 78.973 | 1.00 | 53.24 B |
| ATOM | 3306 | N | LYS | B | 443 | 85.748 | 38.595 | 77.152 | 1.00 | 53.67 B |
| ATOM | 3307 | CA | LYS | B | 443 | 86.640 | 39.718 | 76.940 | 1.00 | 54.78 B |
| ATOM | 3308 | CB | LYS | B | 443 | 86.083 | 40.563 | 75.824 | 1.00 | 54.81 B |
| ATOM | 3309 | CG | LYS | B | 443 | 87.068 | 40.980 | 74.822 | 1.00 | 55.14 B |
| ATOM | 3310 | CD | LYS | B | 443 | 86.335 | 41.654 | 73.686 | 1.00 | 55.61 B |
| ATOM | 3311 | CE | LYS | B | 443 | 86.990 | 42.958 | 73.261 | 1.00 | 56.46 B |
| ATOM | 3312 | NZ | LYS | B | 443 | 86.614 | 43.309 | 71.804 | 1.00 | 56.68 B |
| ATOM | 3313 | C | LYS | B | 443 | 86.974 | 40.655 | 78.122 | 1.00 | 55.26 B |
| ATOM | 3314 | O | LYS | B | 443 | 88.084 | 41.265 | 78.100 | 1.00 | 55.31 B |
| ATOM | 3315 | N | VAL | B | 444 | 86.042 | 40.767 | 79.104 | 1.00 | 56.11 B |
| ATOM | 3316 | CA | VAL | B | 444 | 86.218 | 41.585 | 80.296 | 1.00 | 56.74 B |
| ATOM | 3317 | CB | VAL | B | 444 | 85.066 | 42.559 | 80.614 | 1.00 | 55.51 B |
| ATOM | 3318 | CG1 | VAL | B | 444 | 84.613 | 42.798 | 81.673 | 0.00 | 55.71 B |
| ATOM | 3319 | CG2 | VAL | B | 444 | 85.129 | 43.684 | 79.633 | 1.00 | 54.66 B |
| ATOM | 3320 | C | VAL | B | 444 | 86.271 | 40.680 | 81.487 | 1.00 | 58.50 B |
| ATOM | 3321 | O | VAL | B | 444 | 85.260 | 39.947 | 81.747 | 1.00 | 57.64 B |
| ATOM | 3322 | N | PRO | B | 445 | 87.402 | 40.796 | 82.236 | 1.00 | 60.20 B |
| ATOM | 3323 | CD | PRO | B | 445 | 88.496 | 41.757 | 81.969 | 1.00 | 60.73 B |
| ATOM | 3324 | CA | PRO | B | 445 | 87.670 | 39.951 | 83.419 | 1.00 | 62.00 B |
| ATOM | 3325 | CB | PRO | B | 445 | 88.884 | 40.633 | 84.106 | 1.00 | 61.83 B |
| ATOM | 3326 | CG | PRO | B | 445 | 89.527 | 41.597 | 83.009 | 1.00 | 61.51 B |
| ATOM | 3327 | C | PRO | B | 445 | 86.434 | 39.856 | 84.377 | 1.00 | 63.53 B |
| ATOM | 3328 | O | PRO | B | 445 | 85.595 | 40.804 | 84.397 | 1.00 | 64.32 B |
| ATOM | 3329 | OXT | PRO | B | 445 | 86.403 | 38.830 | 85.096 | 1.00 | 65.74 B |
| ATOM | 3330 | CB | ASN | C | 235 | 34.366 | 47.757 | 2.454 | 1.00 | 61.24 C |
| ATOM | 3331 | CG | ASN | C | 235 | 33.705 | 49.058 | 2.980 | 1.00 | 61.38 C |
| ATOM | 3332 | OD1 | ASN | C | 235 | 33.989 | 50.151 | 2.507 | 1.00 | 62.34 C |
| ATOM | 3333 | ND2 | ASN | C | 235 | 32.825 | 48.924 | 3.945 | 1.00 | 61.27 C |
| ATOM | 3334 | C | ASN | C | 235 | 34.391 | 48.617 | 0.064 | 1.00 | 60.22 C |
| ATOM | 3335 | O | ASN | C | 235 | 35.569 | 48.746 | −0.303 | 1.00 | 60.28 C |
| ATOM | 3336 | N | ASN | C | 235 | 34.611 | 46.120 | 0.621 | 1.00 | 61.00 C |
| ATOM | 3337 | CA | ASN | C | 235 | 33.978 | 47.439 | 0.988 | 1.00 | 60.90 C |

TABLE 2-continued

ATOMIC COORDINATES OF THE ERR3 LBD/
DIETHYLSTILBESTROL COMPLEX

| ATOM | 3338 | N | LYS | C | 236 | 33.464 | 49.535 | −0.213 | 1.00 | 59.72 | C |
|------|------|-----|-----|---|-----|--------|--------|--------|------|-------|---|
| ATOM | 3339 | CA | LYS | C | 236 | 33.691 | 50.558 | −1.263 | 1.00 | 58.69 | C |
| ATOM | 3340 | CB | LYS | C | 236 | 32.396 | 51.204 | −1.748 | 1.00 | 60.95 | C |
| ATOM | 3341 | CG | LYS | C | 236 | 31.255 | 50.201 | −2.020 | 1.00 | 65.46 | C |
| ATOM | 3342 | CD | LYS | C | 236 | 31.335 | 49.530 | −3.399 | 1.00 | 67.04 | C |
| ATOM | 3343 | CE | LYS | C | 236 | 32.472 | 48.514 | −3.531 | 1.00 | 68.64 | C |
| ATOM | 3344 | NZ | LYS | C | 236 | 33.792 | 49.149 | −3.800 | 1.00 | 69.24 | C |
| ATOM | 3345 | C | LYS | C | 236 | 34.628 | 51.672 | −0.856 | 1.00 | 56.03 | C |
| ATOM | 3346 | O | LYS | C | 236 | 35.514 | 52.115 | −1.635 | 1.00 | 54.38 | C |
| ATOM | 3347 | N | ILE | C | 237 | 34.364 | 52.197 | 0.329 | 1.00 | 53.41 | C |
| ATOM | 3348 | CA | ILE | C | 237 | 35.188 | 53.295 | 0.832 | 1.00 | 50.33 | C |
| ATOM | 3349 | CB | ILE | C | 237 | 34.627 | 53.900 | 2.103 | 1.00 | 49.55 | C |
| ATOM | 3350 | CG2 | ILE | C | 237 | 35.339 | 55.247 | 2.451 | 1.00 | 49.76 | C |
| ATOM | 3351 | CG1 | ILE | C | 237 | 33.135 | 54.158 | 1.972 | 1.00 | 47.19 | C |
| ATOM | 3352 | CD1 | ILE | C | 237 | 32.801 | 55.356 | 1.182 | 1.00 | 42.97 | C |
| ATOM | 3353 | C | ILE | C | 237 | 36.604 | 52.821 | 1.029 | 1.00 | 48.82 | C |
| ATOM | 3354 | O | ILE | C | 237 | 37.494 | 53.505 | 0.551 | 1.00 | 47.77 | C |
| ATOM | 3355 | N | VAL | C | 238 | 36.812 | 51.630 | 1.600 | 1.00 | 47.49 | C |
| ATOM | 3356 | CA | VAL | C | 238 | 38.158 | 51.084 | 1.797 | 1.00 | 47.76 | C |
| ATOM | 3357 | CB | VAL | C | 238 | 38.122 | 49.754 | 2.587 | 1.00 | 46.90 | C |
| ATOM | 3358 | CG1 | VAL | C | 238 | 39.502 | 49.300 | 3.110 | 1.00 | 45.20 | C |
| ATOM | 3359 | CG2 | VAL | C | 238 | 37.103 | 49.775 | 3.800 | 1.00 | 44.17 | C |
| ATOM | 3360 | C | VAL | C | 238 | 38.817 | 50.941 | 0.423 | 1.00 | 49.25 | C |
| ATOM | 3361 | O | VAL | C | 238 | 39.984 | 51.390 | 0.174 | 1.00 | 49.58 | C |
| ATOM | 3362 | N | SER | C | 239 | 38.027 | 50.383 | −0.542 | 1.00 | 50.29 | C |
| ATOM | 3363 | CA | SER | C | 239 | 38.529 | 50.150 | −1.872 | 1.00 | 51.18 | C |
| ATOM | 3364 | CB | SER | C | 239 | 37.429 | 49.731 | −2.966 | 1.00 | 52.70 | C |
| ATOM | 3365 | OG | SER | C | 239 | 36.673 | 50.847 | −3.397 | 1.00 | 57.37 | C |
| ATOM | 3366 | C | SER | C | 239 | 39.216 | 51.378 | −2.280 | 1.00 | 50.15 | C |
| ATOM | 3367 | O | SER | C | 239 | 40.355 | 51.324 | −2.647 | 1.00 | 48.45 | C |
| ATOM | 3368 | N | HIS | C | 240 | 38.454 | 52.470 | −2.273 | 1.00 | 50.81 | C |
| ATOM | 3369 | CA | HIS | C | 240 | 38.935 | 53.767 | −2.702 | 1.00 | 52.28 | C |
| ATOM | 3370 | CB | HIS | C | 240 | 37.763 | 54.739 | −2.741 | 1.00 | 56.59 | C |
| ATOM | 3371 | CG | HIS | C | 240 | 38.002 | 55.939 | −3.603 | 1.00 | 62.91 | C |
| ATOM | 3372 | CD2 | HIS | C | 240 | 37.322 | 56.417 | −4.672 | 1.00 | 64.76 | C |
| ATOM | 3373 | ND1 | HIS | C | 240 | 39.060 | 56.801 | −3.406 | 1.00 | 65.16 | C |
| ATOM | 3374 | CE1 | HIS | C | 240 | 39.021 | 57.756 | −4.317 | 1.00 | 66.23 | C |
| ATOM | 3375 | NE2 | HIS | C | 240 | 37.976 | 57.547 | −5.097 | 1.00 | 66.82 | C |
| ATOM | 3376 | C | HIS | C | 240 | 40.156 | 54.336 | −1.810 | 1.00 | 51.18 | C |
| ATOM | 3377 | O | HIS | C | 240 | 41.017 | 54.996 | −2.340 | 1.00 | 51.50 | C |
| ATOM | 3378 | N | LEU | C | 241 | 40.224 | 54.067 | −0.506 | 1.00 | 49.36 | C |
| ATOM | 3379 | CA | LEU | C | 241 | 41.405 | 54.436 | 0.354 | 1.00 | 48.34 | C |
| ATOM | 3380 | CB | LEU | C | 241 | 41.196 | 54.228 | 1.898 | 1.00 | 45.57 | C |
| ATOM | 3381 | CG | LEU | C | 241 | 40.043 | 55.151 | 2.287 | 1.00 | 43.93 | C |
| ATOM | 3382 | CD1 | LEU | C | 241 | 39.427 | 54.947 | 3.619 | 1.00 | 41.89 | C |
| ATOM | 3383 | CD2 | LEU | C | 241 | 40.341 | 56.592 | 2.065 | 1.00 | 42.91 | C |
| ATOM | 3384 | C | LEU | C | 241 | 42.573 | 53.644 | −0.095 | 1.00 | 48.81 | C |
| ATOM | 3385 | O | LEU | C | 241 | 43.687 | 54.200 | −0.128 | 1.00 | 48.11 | C |
| ATOM | 3386 | N | LEU | C | 242 | 42.379 | 52.386 | −0.512 | 1.00 | 49.09 | C |
| ATOM | 3387 | CA | LEU | C | 242 | 43.608 | 51.623 | −0.846 | 1.00 | 49.81 | C |
| ATOM | 3388 | CB | LEU | C | 242 | 43.407 | 50.164 | −1.053 | 1.00 | 49.14 | C |
| ATOM | 3389 | CG | LEU | C | 242 | 42.982 | 49.424 | 0.157 | 1.00 | 49.77 | C |
| ATOM | 3390 | CD1 | LEU | C | 242 | 41.849 | 48.515 | −0.283 | 1.00 | 49.45 | C |
| ATOM | 3391 | CD2 | LEU | C | 242 | 44.188 | 48.687 | 0.720 | 1.00 | 50.37 | C |
| ATOM | 3392 | C | LEU | C | 242 | 44.191 | 52.132 | −2.104 | 1.00 | 50.86 | C |
| ATOM | 3393 | O | LEU | C | 242 | 45.429 | 51.999 | −2.285 | 1.00 | 50.78 | C |
| ATOM | 3394 | N | VAL | C | 243 | 43.338 | 52.694 | −2.989 | 1.00 | 51.56 | C |
| ATOM | 3395 | CA | VAL | C | 243 | 43.838 | 53.083 | −4.306 | 1.00 | 52.45 | C |
| ATOM | 3396 | CB | VAL | C | 243 | 42.691 | 52.979 | −5.527 | 1.00 | 53.78 | C |
| ATOM | 3397 | CG1 | VAL | C | 243 | 41.517 | 53.903 | −5.232 | 1.00 | 54.98 | C |
| ATOM | 3398 | CG2 | VAL | C | 243 | 43.318 | 53.317 | −6.872 | 1.00 | 55.17 | C |
| ATOM | 3399 | C | VAL | C | 243 | 44.423 | 54.491 | −4.180 | 1.00 | 52.01 | C |
| ATOM | 3400 | O | VAL | C | 243 | 45.177 | 54.938 | −5.035 | 1.00 | 51.57 | C |
| ATOM | 3401 | N | ALA | C | 244 | 43.979 | 55.195 | −3.142 | 1.00 | 50.68 | C |
| ATOM | 3402 | CA | ALA | C | 244 | 44.448 | 56.495 | −2.784 | 1.00 | 49.98 | C |
| ATOM | 3403 | CB | ALA | C | 244 | 43.550 | 57.462 | −2.425 | 0.00 | 50.01 | C |
| ATOM | 3404 | C | ALA | C | 244 | 45.842 | 56.394 | −2.104 | 1.00 | 49.44 | C |
| ATOM | 3405 | O | ALA | C | 244 | 46.513 | 57.404 | −1.997 | 1.00 | 49.70 | C |
| ATOM | 3406 | N | GLU | C | 245 | 46.296 | 55.190 | −1.746 | 1.00 | 48.33 | C |
| ATOM | 3407 | CA | GLU | C | 245 | 47.548 | 55.038 | −1.088 | 1.00 | 47.25 | C |
| ATOM | 3408 | CB | GLU | C | 245 | 47.641 | 53.635 | −0.595 | 1.00 | 45.19 | C |
| ATOM | 3409 | CG | GLU | C | 245 | 48.619 | 53.343 | 0.483 | 1.00 | 43.54 | C |
| ATOM | 3410 | CD | GLU | C | 245 | 48.458 | 54.074 | 1.904 | 1.00 | 41.24 | C |
| ATOM | 3411 | OE1 | GLU | C | 245 | 47.517 | 54.838 | 2.278 | 1.00 | 38.33 | C |
| ATOM | 3412 | OE2 | GLU | C | 245 | 49.350 | 53.785 | 2.646 | 1.00 | 40.12 | C |
| ATOM | 3413 | C | GLU | C | 245 | 48.788 | 55.503 | −1.891 | 1.00 | 48.97 | C |

TABLE 2-continued

ATOMIC COORDINATES OF THE ERR3 LBD/
DIETHYLSTILBESTROL COMPLEX

| ATOM | 3414 | O   | GLU | C | 245 | 49.284 | 54.849 | −2.910 | 1.00 | 49.84 | C |
|------|------|-----|-----|---|-----|--------|--------|--------|------|-------|---|
| ATOM | 3415 | N   | PRO | C | 246 | 49.423 | 56.543 | −1.327 | 1.00 | 50.14 | C |
| ATOM | 3416 | CD  | PRO | C | 246 | 49.163 | 57.103 | 0.037  | 1.00 | 49.93 | C |
| ATOM | 3417 | CA  | PRO | C | 246 | 50.542 | 57.239 | −1.977 | 1.00 | 50.28 | C |
| ATOM | 3418 | CB  | PRO | C | 246 | 50.766 | 58.471 | −1.097 | 1.00 | 50.67 | C |
| ATOM | 3419 | CG  | PRO | C | 246 | 50.365 | 57.964 | 0.335  | 1.00 | 49.81 | C |
| ATOM | 3420 | C   | PRO | C | 246 | 51.734 | 56.359 | −2.002 | 1.00 | 50.84 | C |
| ATOM | 3421 | O   | PRO | C | 246 | 51.748 | 55.334 | −1.291 | 1.00 | 51.09 | C |
| ATOM | 3422 | N   | GLU | C | 247 | 52.625 | 56.671 | −2.958 | 1.00 | 51.49 | C |
| ATOM | 3423 | CA  | GLU | C | 247 | 53.838 | 55.928 | −3.144 | 1.00 | 52.87 | C |
| ATOM | 3424 | CB  | GLU | C | 247 | 54.522 | 56.268 | −4.499 | 1.00 | 57.35 | C |
| ATOM | 3425 | CG  | GLU | C | 247 | 54.530 | 57.744 | −4.907 | 1.00 | 64.77 | C |
| ATOM | 3426 | CD  | GLU | C | 247 | 55.692 | 58.530 | −4.329 | 1.00 | 68.98 | C |
| ATOM | 3427 | OE1 | GLU | C | 247 | 55.717 | 58.760 | −3.104 | 1.00 | 72.02 | C |
| ATOM | 3428 | OE2 | GLU | C | 247 | 56.587 | 58.921 | −5.107 | 1.00 | 71.27 | C |
| ATOM | 3429 | C   | GLU | C | 247 | 54.795 | 56.258 | −1.998 | 1.00 | 50.26 | C |
| ATOM | 3430 | O   | GLU | C | 247 | 54.690 | 57.334 | −1.381 | 1.00 | 49.85 | C |
| ATOM | 3431 | N   | LYS | C | 248 | 55.760 | 55.368 | −1.820 | 1.00 | 47.50 | C |
| ATOM | 3432 | CA  | LYS | C | 248 | 56.775 | 55.500 | −0.838 | 1.00 | 46.31 | C |
| ATOM | 3433 | CB  | LYS | C | 248 | 57.826 | 54.401 | −0.956 | 1.00 | 46.58 | C |
| ATOM | 3434 | CG  | LYS | C | 248 | 57.303 | 53.008 | −0.728 | 1.00 | 46.27 | C |
| ATOM | 3435 | CD  | LYS | C | 248 | 58.465 | 52.032 | −0.392 | 1.00 | 48.37 | C |
| ATOM | 3436 | CE  | LYS | C | 248 | 58.031 | 50.594 | −0.203 | 1.00 | 48.57 | C |
| ATOM | 3437 | NZ  | LYS | C | 248 | 58.711 | 50.073 | 1.031  | 1.00 | 49.69 | C |
| ATOM | 3438 | C   | LYS | C | 248 | 57.499 | 56.768 | −0.973 | 1.00 | 45.53 | C |
| ATOM | 3439 | O   | LYS | C | 248 | 57.604 | 57.353 | −2.079 | 1.00 | 45.26 | C |
| ATOM | 3440 | N   | ILE | C | 249 | 58.101 | 57.151 | 0.179  | 1.00 | 43.35 | C |
| ATOM | 3441 | CA  | ILE | C | 249 | 58.796 | 58.408 | 0.290  | 1.00 | 40.44 | C |
| ATOM | 3442 | CB  | ILE | C | 249 | 57.947 | 59.407 | 0.996  | 1.00 | 41.10 | C |
| ATOM | 3443 | CG2 | ILE | C | 249 | 58.838 | 60.595 | 1.424  | 1.00 | 40.37 | C |
| ATOM | 3444 | CG1 | ILE | C | 249 | 56.945 | 59.940 | −0.019 | 1.00 | 39.40 | C |
| ATOM | 3445 | CD1 | ILE | C | 249 | 55.669 | 60.582 | 0.549  | 1.00 | 39.43 | C |
| ATOM | 3446 | C   | ILE | C | 249 | 60.071 | 58.097 | 0.953  | 1.00 | 38.66 | C |
| ATOM | 3447 | O   | ILE | C | 249 | 60.039 | 57.373 | 1.856  | 1.00 | 37.64 | C |
| ATOM | 3448 | N   | TYR | C | 250 | 61.194 | 58.545 | 0.405  | 1.00 | 37.83 | C |
| ATOM | 3449 | CA  | TYR | C | 250 | 62.505 | 58.248 | 1.016  | 1.00 | 37.24 | C |
| ATOM | 3450 | CB  | TYR | C | 250 | 63.563 | 57.751 | −0.029 | 1.00 | 39.12 | C |
| ATOM | 3451 | CG  | TYR | C | 250 | 63.128 | 56.496 | −0.749 | 1.00 | 40.29 | C |
| ATOM | 3452 | CD1 | TYR | C | 250 | 63.462 | 55.294 | −0.277 | 1.00 | 40.95 | C |
| ATOM | 3453 | CE1 | TYR | C | 250 | 62.959 | 54.123 | −0.919 | 1.00 | 42.32 | C |
| ATOM | 3454 | CD2 | TYR | C | 250 | 62.306 | 56.580 | −1.904 | 1.00 | 41.09 | C |
| ATOM | 3455 | CE2 | TYR | C | 250 | 61.886 | 55.429 | −2.615 | 1.00 | 42.56 | C |
| ATOM | 3456 | CZ  | TYR | C | 250 | 62.190 | 54.232 | −2.086 | 1.00 | 42.09 | C |
| ATOM | 3457 | OH  | TYR | C | 250 | 61.719 | 53.078 | −2.675 | 1.00 | 45.48 | C |
| ATOM | 3458 | C   | TYR | C | 250 | 63.083 | 59.436 | 1.816  | 1.00 | 35.57 | C |
| ATOM | 3459 | O   | TYR | C | 250 | 62.933 | 60.499 | 1.412  | 1.00 | 33.87 | C |
| ATOM | 3460 | N   | ALA | C | 251 | 63.723 | 59.127 | 2.932  | 1.00 | 35.04 | C |
| ATOM | 3461 | CA  | ALA | C | 251 | 64.429 | 60.010 | 3.814  | 1.00 | 35.46 | C |
| ATOM | 3462 | CB  | ALA | C | 251 | 64.955 | 59.305 | 4.934  | 1.00 | 33.16 | C |
| ATOM | 3463 | C   | ALA | C | 251 | 65.526 | 60.710 | 3.104  | 1.00 | 36.01 | C |
| ATOM | 3464 | O   | ALA | C | 251 | 65.561 | 61.983 | 3.083  | 1.00 | 36.63 | C |
| ATOM | 3465 | N   | MET | C | 252 | 66.410 | 59.916 | 2.500  | 1.00 | 36.73 | C |
| ATOM | 3466 | CA  | MET | C | 252 | 67.533 | 60.453 | 1.698  | 1.00 | 36.31 | C |
| ATOM | 3467 | CB  | MET | C | 252 | 67.058 | 61.371 | 0.548  | 1.00 | 36.34 | C |
| ATOM | 3468 | CG  | MET | C | 252 | 66.744 | 60.592 | −0.771 | 1.00 | 36.73 | C |
| ATOM | 3469 | SD  | MET | C | 252 | 66.043 | 61.439 | −2.029 | 1.00 | 37.16 | C |
| ATOM | 3470 | CE  | MET | C | 252 | 64.417 | 61.773 | −1.625 | 1.00 | 38.66 | C |
| ATOM | 3471 | C   | MET | C | 252 | 68.478 | 61.261 | 2.618  | 1.00 | 35.84 | C |
| ATOM | 3472 | O   | MET | C | 252 | 68.737 | 62.371 | 2.357  | 1.00 | 34.26 | C |
| ATOM | 3473 | N   | PRO | C | 253 | 68.984 | 60.674 | 3.689  | 1.00 | 35.35 | C |
| ATOM | 3474 | CD  | PRO | C | 253 | 68.874 | 59.316 | 4.171  | 1.00 | 34.41 | C |
| ATOM | 3475 | CA  | PRO | C | 253 | 69.867 | 61.426 | 4.523  | 1.00 | 35.69 | C |
| ATOM | 3476 | CB  | PRO | C | 253 | 70.400 | 60.384 | 5.536  | 1.00 | 34.67 | C |
| ATOM | 3477 | CG  | PRO | C | 253 | 70.138 | 59.084 | 4.977  | 1.00 | 33.87 | C |
| ATOM | 3478 | C   | PRO | C | 253 | 71.056 | 61.896 | 3.737  | 1.00 | 36.10 | C |
| ATOM | 3479 | O   | PRO | C | 253 | 71.679 | 61.050 | 3.019  | 1.00 | 35.44 | C |
| ATOM | 3480 | N   | ASP | C | 254 | 71.548 | 63.072 | 4.112  | 1.00 | 35.27 | C |
| ATOM | 3481 | CA  | ASP | C | 254 | 72.624 | 63.720 | 3.400  | 1.00 | 36.44 | C |
| ATOM | 3482 | CB  | ASP | C | 254 | 72.572 | 65.209 | 3.595  | 1.00 | 36.46 | C |
| ATOM | 3483 | CG  | ASP | C | 254 | 73.672 | 65.991 | 2.772  | 1.00 | 38.13 | C |
| ATOM | 3484 | OD1 | ASP | C | 254 | 74.840 | 65.500 | 2.532  | 1.00 | 36.56 | C |
| ATOM | 3485 | OD2 | ASP | C | 254 | 73.446 | 67.153 | 2.400  | 1.00 | 38.38 | C |
| ATOM | 3486 | C   | ASP | C | 254 | 73.961 | 63.101 | 3.739  | 1.00 | 37.10 | C |
| ATOM | 3487 | O   | ASP | C | 254 | 74.437 | 63.124 | 4.879  | 1.00 | 36.83 | C |
| ATOM | 3488 | N   | PRO | C | 255 | 74.568 | 62.446 | 2.766  | 1.00 | 37.47 | C |
| ATOM | 3489 | CD  | PRO | C | 255 | 74.076 | 62.241 | 1.386  | 1.00 | 36.92 | C |

TABLE 2-continued

ATOMIC COORDINATES OF THE ERR3 LBD/
DIETHYLSTILBESTROL COMPLEX

| ATOM | 3490 | CA  | PRO | C | 255 | 75.791 | 61.721 | 3.121  | 1.00 | 38.10 | C |
|------|------|-----|-----|---|-----|--------|--------|--------|------|-------|---|
| ATOM | 3491 | CB  | PRO | C | 255 | 76.066 | 60.815 | 1.940  | 1.00 | 38.07 | C |
| ATOM | 3492 | CG  | PRO | C | 255 | 75.127 | 61.464 | 0.718  | 1.00 | 38.11 | C |
| ATOM | 3493 | C   | PRO | C | 255 | 76.949 | 62.630 | 3.287  | 1.00 | 39.32 | C |
| ATOM | 3494 | O   | PRO | C | 255 | 77.911 | 62.065 | 3.707  | 1.00 | 40.32 | C |
| ATOM | 3495 | N   | THR | C | 256 | 76.948 | 63.882 | 2.837  | 1.00 | 39.95 | C |
| ATOM | 3496 | CA  | THR | C | 256 | 78.064 | 64.826 | 3.199  | 1.00 | 40.94 | C |
| ATOM | 3497 | CB  | THR | C | 256 | 78.075 | 66.053 | 2.316  | 1.00 | 40.06 | C |
| ATOM | 3498 | OG1 | THR | C | 256 | 76.805 | 66.650 | 2.262  | 1.00 | 40.02 | C |
| ATOM | 3499 | CG2 | THR | C | 256 | 78.393 | 65.697 | 0.823  | 1.00 | 40.81 | C |
| ATOM | 3500 | C   | THR | C | 256 | 78.070 | 65.412 | 4.638  | 1.00 | 41.93 | C |
| ATOM | 3501 | O   | THR | C | 256 | 78.971 | 66.119 | 5.046  | 1.00 | 42.57 | C |
| ATOM | 3502 | N   | VAL | C | 257 | 77.052 | 65.115 | 5.426  | 1.00 | 42.81 | C |
| ATOM | 3503 | CA  | VAL | C | 257 | 76.945 | 65.633 | 6.788  | 1.00 | 42.10 | C |
| ATOM | 3504 | CB  | VAL | C | 257 | 75.488 | 66.111 | 7.033  | 1.00 | 41.74 | C |
| ATOM | 3505 | CG1 | VAL | C | 257 | 75.252 | 66.608 | 8.491  | 1.00 | 39.45 | C |
| ATOM | 3506 | CG2 | VAL | C | 257 | 75.108 | 67.122 | 6.016  | 1.00 | 38.52 | C |
| ATOM | 3507 | C   | VAL | C | 257 | 77.199 | 64.433 | 7.675  | 1.00 | 42.30 | C |
| ATOM | 3508 | O   | VAL | C | 257 | 76.444 | 63.448 | 7.607  | 1.00 | 43.56 | C |
| ATOM | 3509 | N   | PRO | C | 258 | 78.068 | 64.563 | 8.655  | 1.00 | 42.66 | C |
| ATOM | 3510 | CD  | PRO | C | 258 | 78.810 | 65.790 | 8.958  | 1.00 | 42.42 | C |
| ATOM | 3511 | CA  | PRO | C | 258 | 78.283 | 63.468 | 9.635  | 1.00 | 43.56 | C |
| ATOM | 3512 | CB  | PRO | C | 258 | 79.472 | 63.943 | 10.496 | 1.00 | 43.14 | C |
| ATOM | 3513 | CG  | PRO | C | 258 | 79.633 | 65.497 | 10.193 | 1.00 | 42.65 | C |
| ATOM | 3514 | C   | PRO | C | 258 | 77.114 | 63.274 | 10.525 | 1.00 | 44.58 | C |
| ATOM | 3515 | O   | PRO | C | 258 | 76.412 | 64.265 | 10.776 | 1.00 | 44.38 | C |
| ATOM | 3516 | N   | ASP | C | 259 | 76.947 | 62.053 | 11.001 | 1.00 | 45.55 | C |
| ATOM | 3517 | CA  | ASP | C | 259 | 75.829 | 61.650 | 11.805 | 1.00 | 47.73 | C |
| ATOM | 3518 | CB  | ASP | C | 259 | 75.889 | 60.141 | 12.151 | 1.00 | 50.31 | C |
| ATOM | 3519 | CG  | ASP | C | 259 | 75.486 | 59.271 | 11.003 | 1.00 | 53.24 | C |
| ATOM | 3520 | OD1 | ASP | C | 259 | 74.790 | 59.789 | 10.073 | 1.00 | 55.67 | C |
| ATOM | 3521 | OD2 | ASP | C | 259 | 75.866 | 58.058 | 10.892 | 1.00 | 54.76 | C |
| ATOM | 3522 | C   | ASP | C | 259 | 75.784 | 62.484 | 13.056 | 1.00 | 46.97 | C |
| ATOM | 3523 | O   | ASP | C | 259 | 76.742 | 62.618 | 13.761 | 1.00 | 47.51 | C |
| ATOM | 3524 | N   | SER | C | 260 | 74.661 | 63.121 | 13.280 | 1.00 | 45.73 | C |
| ATOM | 3525 | CA  | SER | C | 260 | 74.400 | 63.881 | 14.543 | 1.00 | 44.67 | C |
| ATOM | 3526 | CB  | SER | C | 260 | 74.920 | 65.363 | 14.529 | 1.00 | 42.58 | C |
| ATOM | 3527 | OG  | SER | C | 260 | 74.414 | 66.202 | 13.427 | 1.00 | 41.21 | C |
| ATOM | 3528 | C   | SER | C | 260 | 72.914 | 63.866 | 14.787 | 1.00 | 43.83 | C |
| ATOM | 3529 | O   | SER | C | 260 | 72.126 | 63.616 | 13.895 | 1.00 | 44.34 | C |
| ATOM | 3530 | N   | ASP | C | 261 | 72.578 | 64.195 | 16.023 | 1.00 | 43.32 | C |
| ATOM | 3531 | CA  | ASP | C | 261 | 71.261 | 64.657 | 16.414 | 1.00 | 41.81 | C |
| ATOM | 3532 | CB  | ASP | C | 261 | 71.332 | 65.186 | 17.911 | 1.00 | 43.63 | C |
| ATOM | 3533 | CG  | ASP | C | 261 | 72.274 | 66.439 | 18.082 | 1.00 | 45.73 | C |
| ATOM | 3534 | OD1 | ASP | C | 261 | 73.455 | 66.370 | 17.728 | 1.00 | 48.29 | C |
| ATOM | 3535 | OD2 | ASP | C | 261 | 71.888 | 67.577 | 18.403 | 1.00 | 47.18 | C |
| ATOM | 3536 | C   | ASP | C | 261 | 70.713 | 65.669 | 15.371 | 1.00 | 39.64 | C |
| ATOM | 3537 | O   | ASP | C | 261 | 69.611 | 65.512 | 14.857 | 1.00 | 40.36 | C |
| ATOM | 3538 | N   | ILE | C | 262 | 71.470 | 66.710 | 15.048 | 1.00 | 37.43 | C |
| ATOM | 3539 | CA  | ILE | C | 262 | 71.046 | 67.764 | 14.112 | 1.00 | 35.88 | C |
| ATOM | 3540 | CB  | ILE | C | 262 | 72.174 | 68.850 | 13.937 | 1.00 | 35.51 | C |
| ATOM | 3541 | CG2 | ILE | C | 262 | 71.889 | 69.798 | 12.734 | 1.00 | 32.83 | C |
| ATOM | 3542 | CG1 | ILE | C | 262 | 72.318 | 69.695 | 15.230 | 1.00 | 38.04 | C |
| ATOM | 3543 | CD1 | ILE | C | 262 | 73.671 | 70.544 | 15.356 | 1.00 | 37.65 | C |
| ATOM | 3544 | C   | ILE | C | 262 | 70.661 | 67.087 | 12.702 | 1.00 | 36.05 | C |
| ATOM | 3545 | O   | ILE | C | 262 | 69.688 | 67.515 | 12.024 | 1.00 | 35.19 | C |
| ATOM | 3546 | N   | LYS | C | 263 | 71.475 | 66.097 | 12.296 | 1.00 | 34.91 | C |
| ATOM | 3547 | CA  | LYS | C | 263 | 71.272 | 65.436 | 11.022 | 1.00 | 34.89 | C |
| ATOM | 3548 | CB  | LYS | C | 263 | 72.508 | 64.543 | 10.623 | 1.00 | 34.25 | C |
| ATOM | 3549 | CG  | LYS | C | 263 | 72.389 | 63.995 | 9.166  | 1.00 | 34.14 | C |
| ATOM | 3550 | CD  | LYS | C | 263 | 73.422 | 62.957 | 8.855  | 1.00 | 32.73 | C |
| ATOM | 3551 | CE  | LYS | C | 263 | 73.188 | 62.369 | 7.369  | 1.00 | 33.03 | C |
| ATOM | 3552 | NZ  | LYS | C | 263 | 74.452 | 61.613 | 7.058  | 1.00 | 31.15 | C |
| ATOM | 3553 | C   | LYS | C | 263 | 70.008 | 64.637 | 11.074 | 1.00 | 33.70 | C |
| ATOM | 3554 | O   | LYS | C | 263 | 69.185 | 64.771 | 10.255 | 1.00 | 33.30 | C |
| ATOM | 3555 | N   | ALA | C | 264 | 69.853 | 63.872 | 12.128 | 1.00 | 32.80 | C |
| ATOM | 3556 | CA  | ALA | C | 264 | 68.744 | 63.110 | 12.290 | 1.00 | 31.52 | C |
| ATOM | 3557 | CB  | ALA | C | 264 | 68.869 | 62.336 | 13.556 | 1.00 | 30.91 | C |
| ATOM | 3558 | C   | ALA | C | 264 | 67.433 | 63.949 | 12.241 | 1.00 | 30.96 | C |
| ATOM | 3559 | O   | ALA | C | 264 | 66.501 | 63.699 | 11.462 | 1.00 | 30.86 | C |
| ATOM | 3560 | N   | LEU | C | 265 | 67.387 | 65.006 | 13.019 | 1.00 | 29.80 | C |
| ATOM | 3561 | CA  | LEU | C | 265 | 66.257 | 65.899 | 13.016 | 1.00 | 28.94 | C |
| ATOM | 3562 | CB  | LEU | C | 265 | 66.391 | 67.011 | 14.186 | 1.00 | 26.62 | C |
| ATOM | 3563 | CG  | LEU | C | 265 | 66.523 | 66.352 | 15.597 | 1.00 | 28.42 | C |
| ATOM | 3564 | CD1 | LEU | C | 265 | 67.041 | 67.330 | 16.699 | 1.00 | 26.73 | C |
| ATOM | 3565 | CD2 | LEU | C | 265 | 65.176 | 65.688 | 16.026 | 1.00 | 27.64 | C |

TABLE 2-continued

ATOMIC COORDINATES OF THE ERR3 LBD/
DIETHYLSTILBESTROL COMPLEX

| | | | | | | | | | | |
|---|---|---|---|---|---|---|---|---|---|---|
| ATOM | 3566 | C | LEU | C | 265 | 66.099 | 66.557 | 11.645 | 1.00 | 27.74 C |
| ATOM | 3567 | O | LEU | C | 265 | 65.014 | 66.757 | 11.211 | 1.00 | 28.40 C |
| ATOM | 3568 | N | THR | C | 266 | 67.138 | 67.071 | 11.045 | 1.00 | 27.82 C |
| ATOM | 3569 | CA | THR | C | 266 | 67.054 | 67.637 | 9.706 | 1.00 | 28.65 C |
| ATOM | 3570 | CB | THR | C | 266 | 68.411 | 68.014 | 9.217 | 1.00 | 28.50 C |
| ATOM | 3571 | OG1 | THR | C | 266 | 69.058 | 68.925 | 10.144 | 1.00 | 30.63 C |
| ATOM | 3572 | CG2 | THR | C | 266 | 68.297 | 68.866 | 7.925 | 1.00 | 28.41 C |
| ATOM | 3573 | C | THR | C | 266 | 66.427 | 66.614 | 8.690 | 1.00 | 28.25 C |
| ATOM | 3574 | O | THR | C | 266 | 65.486 | 66.925 | 7.982 | 1.00 | 29.41 C |
| ATOM | 3575 | N | THR | C | 267 | 66.839 | 65.367 | 8.781 | 1.00 | 28.00 C |
| ATOM | 3576 | CA | THR | C | 267 | 66.389 | 64.324 | 7.873 | 1.00 | 28.93 C |
| ATOM | 3577 | CB | THR | C | 267 | 67.231 | 63.042 | 8.133 | 1.00 | 28.36 C |
| ATOM | 3578 | OG1 | THR | C | 267 | 68.592 | 63.309 | 7.870 | 1.00 | 29.26 C |
| ATOM | 3579 | CG2 | THR | C | 267 | 66.756 | 61.963 | 7.142 | 1.00 | 29.25 C |
| ATOM | 3580 | C | THR | C | 267 | 64.937 | 64.072 | 8.168 | 1.00 | 28.82 C |
| ATOM | 3581 | O | THR | C | 267 | 64.108 | 64.114 | 7.270 | 1.00 | 28.43 C |
| ATOM | 3582 | N | LEU | C | 268 | 64.586 | 63.857 | 9.442 | 1.00 | 28.70 C |
| ATOM | 3583 | CA | LEU | C | 268 | 63.172 | 63.729 | 9.759 | 1.00 | 30.14 C |
| ATOM | 3584 | CB | LEU | C | 268 | 62.943 | 63.347 | 11.177 | 1.00 | 30.94 C |
| ATOM | 3585 | CG | LEU | C | 268 | 63.584 | 62.032 | 11.575 | 1.00 | 32.95 C |
| ATOM | 3586 | CD1 | LEU | C | 268 | 63.442 | 61.835 | 13.055 | 1.00 | 34.47 C |
| ATOM | 3587 | CD2 | LEU | C | 268 | 62.814 | 60.880 | 10.884 | 1.00 | 32.62 C |
| ATOM | 3588 | C | LEU | C | 268 | 62.278 | 64.867 | 9.338 | 1.00 | 30.72 C |
| ATOM | 3589 | O | LEU | C | 268 | 61.196 | 64.605 | 8.760 | 1.00 | 30.96 C |
| ATOM | 3590 | N | CYS | C | 269 | 62.687 | 66.111 | 9.508 | 1.00 | 30.40 C |
| ATOM | 3591 | CA | CYS | C | 269 | 61.855 | 67.257 | 9.092 | 1.00 | 30.52 C |
| ATOM | 3592 | CB | CYS | C | 269 | 62.477 | 68.595 | 9.636 | 1.00 | 30.89 C |
| ATOM | 3593 | SG | CYS | C | 269 | 62.365 | 68.684 | 11.464 | 1.00 | 34.31 C |
| ATOM | 3594 | C | CYS | C | 269 | 61.725 | 67.417 | 7.620 | 1.00 | 30.06 C |
| ATOM | 3595 | O | CYS | C | 269 | 60.633 | 67.693 | 7.064 | 1.00 | 29.85 C |
| ATOM | 3596 | N | ASP | C | 270 | 62.818 | 67.205 | 6.908 | 1.00 | 31.02 C |
| ATOM | 3597 | CA | ASP | C | 270 | 62.691 | 67.163 | 5.429 | 1.00 | 31.04 C |
| ATOM | 3598 | CB | ASP | C | 270 | 64.050 | 67.071 | 4.814 | 1.00 | 32.70 C |
| ATOM | 3599 | CG | ASP | C | 270 | 63.970 | 67.066 | 3.303 | 1.00 | 34.59 C |
| ATOM | 3600 | OD1 | ASP | C | 270 | 63.846 | 68.153 | 2.772 | 1.00 | 35.71 C |
| ATOM | 3601 | OD2 | ASP | C | 270 | 63.845 | 66.001 | 2.653 | 1.00 | 34.87 C |
| ATOM | 3602 | C | ASP | C | 270 | 61.754 | 65.960 | 4.928 | 1.00 | 30.84 C |
| ATOM | 3603 | O | ASP | C | 270 | 60.916 | 66.175 | 4.076 | 1.00 | 31.28 C |
| ATOM | 3604 | N | LEU | C | 271 | 61.831 | 64.796 | 5.566 | 1.00 | 30.64 C |
| ATOM | 3605 | CA | LEU | C | 271 | 60.932 | 63.669 | 5.286 | 1.00 | 30.47 C |
| ATOM | 3606 | CB | LEU | C | 271 | 61.187 | 62.498 | 6.221 | 1.00 | 30.89 C |
| ATOM | 3607 | CG | LEU | C | 271 | 60.324 | 61.252 | 6.131 | 1.00 | 31.88 C |
| ATOM | 3608 | CD1 | LEU | C | 271 | 60.214 | 60.805 | 4.696 | 1.00 | 32.21 C |
| ATOM | 3609 | CD2 | LEU | C | 271 | 60.963 | 60.185 | 6.816 | 1.00 | 28.71 C |
| ATOM | 3610 | C | LEU | C | 271 | 59.529 | 64.074 | 5.487 | 1.00 | 30.61 C |
| ATOM | 3611 | O | LEU | C | 271 | 58.706 | 63.973 | 4.556 | 1.00 | 28.91 C |
| ATOM | 3612 | N | ALA | C | 272 | 59.234 | 64.650 | 6.660 | 1.00 | 29.98 C |
| ATOM | 3613 | CA | ALA | C | 272 | 57.893 | 64.923 | 6.952 | 1.00 | 30.03 C |
| ATOM | 3614 | CB | ALA | C | 272 | 57.739 | 65.345 | 8.267 | 1.00 | 28.28 C |
| ATOM | 3615 | C | ALA | C | 272 | 57.407 | 66.006 | 6.039 | 1.00 | 30.84 C |
| ATOM | 3616 | O | ALA | C | 272 | 56.247 | 66.029 | 5.727 | 1.00 | 31.31 C |
| ATOM | 3617 | N | ASP | C | 273 | 58.256 | 66.967 | 5.708 | 1.00 | 32.62 C |
| ATOM | 3618 | CA | ASP | C | 273 | 57.814 | 68.010 | 4.771 | 1.00 | 34.71 C |
| ATOM | 3619 | CB | ASP | C | 273 | 59.016 | 68.910 | 4.437 | 1.00 | 38.27 C |
| ATOM | 3620 | CG | ASP | C | 273 | 58.572 | 70.306 | 3.992 | 1.00 | 43.11 C |
| ATOM | 3621 | OD1 | ASP | C | 273 | 58.261 | 71.247 | 4.472 | 0.00 | 42.33 C |
| ATOM | 3622 | OD2 | ASP | C | 273 | 58.297 | 70.615 | 2.798 | 1.00 | 45.40 C |
| ATOM | 3623 | C | ASP | C | 273 | 57.294 | 67.445 | 3.406 | 1.00 | 33.79 C |
| ATOM | 3624 | O | ASP | C | 273 | 56.326 | 67.908 | 2.842 | 1.00 | 33.88 C |
| ATOM | 3625 | N | ARG | C | 274 | 58.018 | 66.484 | 2.870 | 1.00 | 32.30 C |
| ATOM | 3626 | CA | ARG | C | 274 | 57.668 | 65.936 | 1.576 | 1.00 | 32.23 C |
| ATOM | 3627 | CB | ARG | C | 274 | 58.924 | 65.245 | 0.924 | 1.00 | 31.44 C |
| ATOM | 3628 | CG | ARG | C | 274 | 59.864 | 66.327 | 0.281 | 1.00 | 30.95 C |
| ATOM | 3629 | CD | ARG | C | 274 | 61.150 | 65.739 | −0.250 | 1.00 | 31.33 C |
| ATOM | 3630 | NE | ARG | C | 274 | 61.999 | 65.135 | 0.792 | 1.00 | 33.73 C |
| ATOM | 3631 | CZ | ARG | C | 274 | 62.205 | 63.872 | 1.005 | 1.00 | 31.63 C |
| ATOM | 3632 | NH1 | ARG | C | 274 | 61.614 | 62.955 | 0.278 | 1.00 | 31.02 C |
| ATOM | 3633 | NH2 | ARG | C | 274 | 63.023 | 63.512 | 1.980 | 1.00 | 28.76 C |
| ATOM | 3634 | C | ARG | C | 274 | 56.432 | 65.051 | 1.794 | 1.00 | 32.02 C |
| ATOM | 3635 | O | ARG | C | 274 | 55.623 | 64.941 | 0.927 | 1.00 | 32.67 C |
| ATOM | 3636 | N | GLU | C | 275 | 56.267 | 64.423 | 2.939 | 1.00 | 31.84 C |
| ATOM | 3637 | CA | GLU | C | 275 | 55.162 | 63.532 | 3.217 | 1.00 | 32.64 C |
| ATOM | 3638 | CB | GLU | C | 275 | 55.388 | 62.773 | 4.495 | 1.00 | 32.52 C |
| ATOM | 3639 | CG | GLU | C | 275 | 56.349 | 61.538 | 4.416 | 1.00 | 31.64 C |
| ATOM | 3640 | CD | GLU | C | 275 | 56.345 | 60.644 | 5.664 | 1.00 | 33.08 C |
| ATOM | 3641 | OE1 | GLU | C | 275 | 55.448 | 59.756 | 5.860 | 1.00 | 33.72 C |

TABLE 2-continued

ATOMIC COORDINATES OF THE ERR3 LBD/
DIETHYLSTILBESTROL COMPLEX

| ATOM | 3642 | OE2 | GLU | C | 275 | 57.197 | 60.888 | 6.536 | 1.00 | 33.64 | C |
|------|------|-----|-----|---|-----|--------|--------|-------|------|-------|---|
| ATOM | 3643 | C | GLU | C | 275 | 53.929 | 64.357 | 3.208 | 1.00 | 34.16 | C |
| ATOM | 3644 | O | GLU | C | 275 | 52.847 | 63.935 | 2.752 | 1.00 | 33.55 | C |
| ATOM | 3645 | N | LEU | C | 276 | 54.061 | 65.616 | 3.602 | 1.00 | 35.69 | C |
| ATOM | 3646 | CA | LEU | C | 276 | 52.872 | 66.371 | 3.882 | 1.00 | 37.49 | C |
| ATOM | 3647 | CB | LEU | C | 276 | 53.196 | 67.535 | 4.747 | 1.00 | 38.12 | C |
| ATOM | 3648 | CG | LEU | C | 276 | 52.909 | 67.375 | 6.221 | 1.00 | 40.13 | C |
| ATOM | 3649 | CD1 | LEU | C | 276 | 53.752 | 68.369 | 6.917 | 1.00 | 40.63 | C |
| ATOM | 3650 | CD2 | LEU | C | 276 | 51.371 | 67.625 | 6.471 | 1.00 | 40.92 | C |
| ATOM | 3651 | C | LEU | C | 276 | 52.301 | 66.841 | 2.569 | 1.00 | 38.43 | C |
| ATOM | 3652 | O | LEU | C | 276 | 51.091 | 66.916 | 2.471 | 1.00 | 39.49 | C |
| ATOM | 3653 | N | VAL | C | 277 | 53.165 | 67.169 | 1.597 | 1.00 | 38.84 | C |
| ATOM | 3654 | CA | VAL | C | 277 | 52.754 | 67.519 | 0.174 | 1.00 | 39.88 | C |
| ATOM | 3655 | CB | VAL | C | 277 | 53.967 | 67.713 | −0.760 | 1.00 | 39.89 | C |
| ATOM | 3656 | CG1 | VAL | C | 277 | 53.565 | 68.193 | −2.245 | 1.00 | 39.81 | C |
| ATOM | 3657 | CG2 | VAL | C | 277 | 55.090 | 68.680 | −0.166 | 1.00 | 40.13 | C |
| ATOM | 3658 | C | VAL | C | 277 | 51.845 | 66.431 | −0.363 | 1.00 | 39.40 | C |
| ATOM | 3659 | O | VAL | C | 277 | 50.782 | 66.635 | −0.819 | 1.00 | 40.09 | C |
| ATOM | 3660 | N | VAL | C | 278 | 52.255 | 65.248 | −0.134 | 1.00 | 39.86 | C |
| ATOM | 3661 | CA | VAL | C | 278 | 51.564 | 64.086 | −0.546 | 1.00 | 40.73 | C |
| ATOM | 3662 | CB | VAL | C | 278 | 52.460 | 62.861 | −0.219 | 1.00 | 40.01 | C |
| ATOM | 3663 | CG1 | VAL | C | 278 | 51.780 | 61.634 | −0.496 | 1.00 | 38.68 | C |
| ATOM | 3664 | CG2 | VAL | C | 278 | 53.714 | 63.007 | −1.020 | 1.00 | 39.49 | C |
| ATOM | 3665 | C | VAL | C | 278 | 50.264 | 63.871 | 0.170 | 1.00 | 41.58 | C |
| ATOM | 3666 | O | VAL | C | 278 | 49.283 | 63.460 | −0.475 | 1.00 | 42.40 | C |
| ATOM | 3667 | N | ILE | C | 279 | 50.263 | 64.114 | 1.493 | 1.00 | 41.80 | C |
| ATOM | 3668 | CA | ILE | C | 279 | 49.071 | 63.931 | 2.288 | 1.00 | 41.81 | C |
| ATOM | 3669 | CB | ILE | C | 279 | 49.378 | 64.036 | 3.856 | 1.00 | 40.95 | C |
| ATOM | 3670 | CG2 | ILE | C | 279 | 48.177 | 64.240 | 4.633 | 1.00 | 38.75 | C |
| ATOM | 3671 | CG1 | ILE | C | 279 | 49.980 | 62.691 | 4.291 | 1.00 | 40.90 | C |
| ATOM | 3672 | CD1 | ILE | C | 279 | 50.962 | 62.810 | 5.401 | 1.00 | 40.81 | C |
| ATOM | 3673 | C | ILE | C | 279 | 47.948 | 64.845 | 1.878 | 1.00 | 42.92 | C |
| ATOM | 3674 | O | ILE | C | 279 | 46.793 | 64.409 | 1.901 | 1.00 | 42.12 | C |
| ATOM | 3675 | N | ILE | C | 280 | 48.278 | 66.091 | 1.557 | 1.00 | 43.54 | C |
| ATOM | 3676 | CA | ILE | C | 280 | 47.301 | 67.039 | 1.037 | 1.00 | 45.20 | C |
| ATOM | 3677 | CB | ILE | C | 280 | 47.983 | 68.334 | 0.658 | 1.00 | 44.90 | C |
| ATOM | 3678 | CG2 | ILE | C | 280 | 47.030 | 69.281 | 0.044 | 1.00 | 44.36 | C |
| ATOM | 3679 | CG1 | ILE | C | 280 | 48.531 | 69.051 | 1.937 | 1.00 | 45.83 | C |
| ATOM | 3680 | CD1 | ILE | C | 280 | 49.580 | 69.917 | 1.757 | 0.00 | 45.47 | C |
| ATOM | 3681 | C | ILE | C | 280 | 46.633 | 66.427 | −0.198 | 1.00 | 46.65 | C |
| ATOM | 3682 | O | ILE | C | 280 | 45.403 | 66.383 | −0.318 | 1.00 | 47.80 | C |
| ATOM | 3683 | N | GLY | C | 281 | 47.461 | 65.882 | −1.099 | 1.00 | 47.66 | C |
| ATOM | 3684 | CA | GLY | C | 281 | 46.984 | 65.254 | −2.320 | 1.00 | 47.83 | C |
| ATOM | 3685 | C | GLY | C | 281 | 46.175 | 64.024 | −1.985 | 1.00 | 48.24 | C |
| ATOM | 3686 | O | GLY | C | 281 | 45.102 | 63.777 | −2.572 | 1.00 | 49.25 | C |
| ATOM | 3687 | N | TRP | C | 282 | 46.659 | 63.242 | −1.035 | 1.00 | 47.96 | C |
| ATOM | 3688 | CA | TRP | C | 282 | 45.965 | 62.025 | −0.698 | 1.00 | 47.16 | C |
| ATOM | 3689 | CB | TRP | C | 282 | 46.772 | 61.222 | 0.246 | 1.00 | 45.58 | C |
| ATOM | 3690 | CG | TRP | C | 282 | 46.019 | 60.276 | 1.100 | 1.00 | 45.29 | C |
| ATOM | 3691 | CD2 | TRP | C | 282 | 45.489 | 60.536 | 2.392 | 1.00 | 45.44 | C |
| ATOM | 3692 | CE2 | TRP | C | 282 | 44.930 | 59.334 | 2.860 | 1.00 | 44.77 | C |
| ATOM | 3693 | CE3 | TRP | C | 282 | 45.456 | 61.670 | 3.230 | 1.00 | 45.42 | C |
| ATOM | 3694 | CD1 | TRP | C | 282 | 45.832 | 58.989 | 0.871 | 1.00 | 45.20 | C |
| ATOM | 3695 | NE1 | TRP | C | 282 | 45.170 | 58.397 | 1.911 | 1.00 | 45.04 | C |
| ATOM | 3696 | CZ2 | TRP | C | 282 | 44.372 | 59.211 | 4.114 | 1.00 | 44.48 | C |
| ATOM | 3697 | CZ3 | TRP | C | 282 | 44.839 | 61.559 | 4.508 | 1.00 | 45.32 | C |
| ATOM | 3698 | CH2 | TRP | C | 282 | 44.325 | 60.358 | 4.933 | 1.00 | 44.65 | C |
| ATOM | 3699 | C | TRP | C | 282 | 44.610 | 62.282 | −0.098 | 1.00 | 48.67 | C |
| ATOM | 3700 | O | TRP | C | 282 | 43.688 | 61.480 | −0.340 | 1.00 | 48.72 | C |
| ATOM | 3701 | N | ALA | C | 283 | 44.472 | 63.373 | 0.657 | 1.00 | 49.23 | C |
| ATOM | 3702 | CA | ALA | C | 283 | 43.239 | 63.720 | 1.355 | 1.00 | 50.87 | C |
| ATOM | 3703 | CB | ALA | C | 283 | 43.512 | 64.889 | 2.200 | 1.00 | 49.81 | C |
| ATOM | 3704 | C | ALA | C | 283 | 42.009 | 64.010 | 0.416 | 1.00 | 52.10 | C |
| ATOM | 3705 | O | ALA | C | 283 | 40.874 | 63.658 | 0.718 | 1.00 | 51.21 | C |
| ATOM | 3706 | N | LYS | C | 284 | 42.283 | 64.718 | −0.680 | 1.00 | 53.98 | C |
| ATOM | 3707 | CA | LYS | C | 284 | 41.366 | 64.945 | −1.833 | 1.00 | 55.62 | C |
| ATOM | 3708 | CB | LYS | C | 284 | 42.236 | 65.486 | −2.992 | 1.00 | 55.00 | C |
| ATOM | 3709 | CG | LYS | C | 284 | 42.864 | 66.889 | −2.588 | 1.00 | 55.67 | C |
| ATOM | 3710 | CD | LYS | C | 284 | 43.909 | 67.520 | −3.575 | 1.00 | 55.38 | C |
| ATOM | 3711 | CE | LYS | C | 284 | 43.873 | 69.056 | −3.407 | 1.00 | 55.58 | C |
| ATOM | 3712 | NZ | LYS | C | 284 | 43.897 | 69.895 | −2.859 | 0.00 | 55.48 | C |
| ATOM | 3713 | C | LYS | C | 284 | 40.647 | 63.686 | −2.302 | 1.00 | 56.96 | C |
| ATOM | 3714 | O | LYS | C | 284 | 39.437 | 63.684 | −2.579 | 1.00 | 57.84 | C |
| ATOM | 3715 | N | HIS | C | 285 | 41.384 | 62.586 | −2.361 | 1.00 | 58.23 | C |
| ATOM | 3716 | CA | HIS | C | 285 | 40.871 | 61.298 | −2.780 | 1.00 | 59.18 | C |
| ATOM | 3717 | CB | HIS | C | 285 | 42.013 | 60.494 | −3.350 | 1.00 | 64.05 | C |

TABLE 2-continued

ATOMIC COORDINATES OF THE ERR3 LBD/
DIETHYLSTILBESTROL COMPLEX

| ATOM | 3718 | CG  | HIS | C | 285 | 43.011 | 60.101 | −2.355 | 1.00 | 70.94 | C |
|------|------|-----|-----|---|-----|--------|--------|--------|------|-------|---|
| ATOM | 3719 | CD2 | HIS | C | 285 | 44.359 | 60.054 | −2.414 | 1.00 | 73.26 | C |
| ATOM | 3720 | ND1 | HIS | C | 285 | 42.639 | 59.538 | −1.156 | 1.00 | 73.64 | C |
| ATOM | 3721 | CE1 | HIS | C | 285 | 43.718 | 59.146 | −0.516 | 1.00 | 75.22 | C |
| ATOM | 3722 | NE2 | HIS | C | 285 | 44.776 | 59.446 | −1.259 | 1.00 | 75.47 | C |
| ATOM | 3723 | C   | HIS | C | 285 | 40.120 | 60.500 | −1.698 | 1.00 | 57.88 | C |
| ATOM | 3724 | O   | HIS | C | 285 | 39.781 | 59.287 | −1.956 | 1.00 | 56.92 | C |
| ATOM | 3725 | N   | ILE | C | 286 | 39.878 | 61.132 | −0.500 | 1.00 | 56.40 | C |
| ATOM | 3726 | CA  | ILE | C | 286 | 39.023 | 60.531 | 0.526  | 1.00 | 54.40 | C |
| ATOM | 3727 | CB  | ILE | C | 286 | 39.270 | 61.050 | 2.000  | 1.00 | 53.31 | C |
| ATOM | 3728 | CG2 | ILE | C | 286 | 38.268 | 60.331 | 2.975  | 1.00 | 51.88 | C |
| ATOM | 3729 | CG1 | ILE | C | 286 | 40.668 | 60.722 | 2.458  | 1.00 | 51.87 | C |
| ATOM | 3730 | CD1 | ILE | C | 286 | 41.177 | 61.499 | 3.664  | 1.00 | 49.76 | C |
| ATOM | 3731 | C   | ILE | C | 286 | 37.627 | 60.918 | 0.118  | 1.00 | 53.49 | C |
| ATOM | 3732 | O   | ILE | C | 286 | 37.309 | 62.105 | −0.009 | 1.00 | 53.57 | C |
| ATOM | 3733 | N   | PRO | C | 287 | 36.752 | 59.956 | 0.042  | 1.00 | 53.16 | C |
| ATOM | 3734 | CD  | PRO | C | 287 | 37.041 | 58.544 | 0.306  | 1.00 | 53.30 | C |
| ATOM | 3735 | CA  | PRO | C | 287 | 35.338 | 60.198 | −0.290 | 1.00 | 52.32 | C |
| ATOM | 3736 | CB  | PRO | C | 287 | 34.753 | 58.805 | −0.226 | 1.00 | 52.97 | C |
| ATOM | 3737 | CG  | PRO | C | 287 | 35.916 | 57.879 | −0.324 | 1.00 | 53.46 | C |
| ATOM | 3738 | C   | PRO | C | 287 | 34.593 | 61.077 | 0.699  | 1.00 | 52.24 | C |
| ATOM | 3739 | O   | PRO | C | 287 | 34.376 | 60.720 | 1.858  | 1.00 | 52.88 | C |
| ATOM | 3740 | N   | GLY | C | 288 | 34.134 | 62.214 | 0.251  | 1.00 | 51.65 | C |
| ATOM | 3741 | CA  | GLY | C | 288 | 33.509 | 63.209 | 1.133  | 1.00 | 51.53 | C |
| ATOM | 3742 | C   | GLY | C | 288 | 34.376 | 64.465 | 1.346  | 1.00 | 51.92 | C |
| ATOM | 3743 | O   | GLY | C | 288 | 33.885 | 65.623 | 1.396  | 1.00 | 51.91 | C |
| ATOM | 3744 | N   | PHE | C | 289 | 35.698 | 64.227 | 1.444  | 1.00 | 52.26 | C |
| ATOM | 3745 | CA  | PHE | C | 289 | 36.645 | 65.265 | 1.808  | 1.00 | 52.13 | C |
| ATOM | 3746 | CB  | PHE | C | 289 | 38.096 | 64.720 | 1.824  | 1.00 | 50.81 | C |
| ATOM | 3747 | CG  | PHE | C | 289 | 39.049 | 65.624 | 2.533  | 1.00 | 50.35 | C |
| ATOM | 3748 | CD1 | PHE | C | 289 | 39.018 | 65.697 | 3.962  | 1.00 | 50.21 | C |
| ATOM | 3749 | CD2 | PHE | C | 289 | 39.891 | 66.478 | 1.842  | 1.00 | 49.95 | C |
| ATOM | 3750 | CE1 | PHE | C | 289 | 39.862 | 66.552 | 4.668  | 1.00 | 49.75 | C |
| ATOM | 3751 | CE2 | PHE | C | 289 | 40.773 | 67.329 | 2.569  | 1.00 | 49.63 | C |
| ATOM | 3752 | CZ  | PHE | C | 289 | 40.716 | 67.355 | 4.006  | 1.00 | 48.75 | C |
| ATOM | 3753 | C   | PHE | C | 289 | 36.512 | 66.506 | 0.903  | 1.00 | 52.59 | C |
| ATOM | 3754 | O   | PHE | C | 289 | 36.349 | 67.652 | 1.385  | 1.00 | 52.14 | C |
| ATOM | 3755 | N   | SER | C | 290 | 36.583 | 66.299 | −0.411 | 1.00 | 54.44 | C |
| ATOM | 3756 | CA  | SER | C | 290 | 36.594 | 67.477 | −1.396 | 1.00 | 56.06 | C |
| ATOM | 3757 | CB  | SER | C | 290 | 36.764 | 67.007 | −2.829 | 1.00 | 56.63 | C |
| ATOM | 3758 | OG  | SER | C | 290 | 38.047 | 66.407 | −2.991 | 1.00 | 58.06 | C |
| ATOM | 3759 | C   | SER | C | 290 | 35.391 | 68.404 | −1.372 | 1.00 | 56.07 | C |
| ATOM | 3760 | O   | SER | C | 290 | 35.446 | 69.480 | −1.906 | 1.00 | 56.18 | C |
| ATOM | 3761 | N   | THR | C | 291 | 34.306 | 67.973 | −0.782 | 1.00 | 56.42 | C |
| ATOM | 3762 | CA  | THR | C | 291 | 33.097 | 68.786 | −0.795 | 1.00 | 57.56 | C |
| ATOM | 3763 | CB  | THR | C | 291 | 31.895 | 67.864 | −0.821 | 1.00 | 58.81 | C |
| ATOM | 3764 | OG1 | THR | C | 291 | 31.919 | 67.019 | 0.342  | 1.00 | 59.91 | C |
| ATOM | 3765 | CG2 | THR | C | 291 | 32.020 | 66.854 | −2.058 | 1.00 | 58.78 | C |
| ATOM | 3766 | C   | THR | C | 291 | 33.021 | 69.766 | 0.356  | 1.00 | 57.97 | C |
| ATOM | 3767 | O   | THR | C | 291 | 32.211 | 70.754 | 0.243  | 1.00 | 58.62 | C |
| ATOM | 3768 | N   | LEU | C | 292 | 33.907 | 69.589 | 1.393  | 1.00 | 56.56 | C |
| ATOM | 3769 | CA  | LEU | C | 292 | 33.889 | 70.488 | 2.529  | 1.00 | 55.56 | C |
| ATOM | 3770 | CB  | LEU | C | 292 | 34.782 | 69.966 | 3.721  | 1.00 | 55.52 | C |
| ATOM | 3771 | CG  | LEU | C | 292 | 34.273 | 68.727 | 4.481  | 1.00 | 55.57 | C |
| ATOM | 3772 | CD1 | LEU | C | 292 | 35.458 | 67.865 | 4.967  | 1.00 | 56.44 | C |
| ATOM | 3773 | CD2 | LEU | C | 292 | 33.215 | 69.169 | 5.231  | 0.00 | 55.84 | C |
| ATOM | 3774 | C   | LEU | C | 292 | 34.424 | 71.774 | 1.981  | 1.00 | 55.17 | C |
| ATOM | 3775 | O   | LEU | C | 292 | 35.112 | 71.757 | 0.980  | 1.00 | 55.05 | C |
| ATOM | 3776 | N   | SER | C | 293 | 34.197 | 72.881 | 2.655  | 1.00 | 55.30 | C |
| ATOM | 3777 | CA  | SER | C | 293 | 34.899 | 74.106 | 2.304  | 1.00 | 55.56 | C |
| ATOM | 3778 | CB  | SER | C | 293 | 34.485 | 75.339 | 3.161  | 1.00 | 55.77 | C |
| ATOM | 3779 | OG  | SER | C | 293 | 35.072 | 75.372 | 4.474  | 1.00 | 56.74 | C |
| ATOM | 3780 | C   | SER | C | 293 | 36.398 | 73.933 | 2.340  | 1.00 | 55.40 | C |
| ATOM | 3781 | O   | SER | C | 293 | 36.961 | 73.036 | 2.966  | 1.00 | 56.75 | C |
| ATOM | 3782 | N   | LEU | C | 294 | 37.066 | 74.856 | 1.720  | 1.00 | 54.32 | C |
| ATOM | 3783 | CA  | LEU | C | 294 | 38.470 | 74.770 | 1.576  | 1.00 | 52.51 | C |
| ATOM | 3784 | CB  | LEU | C | 294 | 38.981 | 75.852 | 0.590  | 1.00 | 52.66 | C |
| ATOM | 3785 | CG  | LEU | C | 294 | 40.131 | 75.513 | −0.385 | 1.00 | 52.89 | C |
| ATOM | 3786 | CD1 | LEU | C | 294 | 40.674 | 74.048 | −0.370 | 1.00 | 52.20 | C |
| ATOM | 3787 | CD2 | LEU | C | 294 | 40.230 | 77.091 | −0.802 | 0.00 | 52.66 | C |
| ATOM | 3788 | C   | LEU | C | 294 | 39.035 | 75.012 | 2.963  | 1.00 | 51.45 | C |
| ATOM | 3789 | O   | LEU | C | 294 | 40.037 | 74.405 | 3.356  | 1.00 | 50.57 | C |
| ATOM | 3790 | N   | ALA | C | 295 | 38.397 | 75.951 | 3.664  | 1.00 | 50.10 | C |
| ATOM | 3791 | CA  | ALA | C | 295 | 38.791 | 76.313 | 5.011  | 1.00 | 49.11 | C |
| ATOM | 3792 | CB  | ALA | C | 295 | 37.907 | 77.409 | 5.544  | 1.00 | 48.31 | C |
| ATOM | 3793 | C   | ALA | C | 295 | 38.732 | 75.090 | 5.933  | 1.00 | 48.68 | C |

TABLE 2-continued

ATOMIC COORDINATES OF THE ERR3 LBD/
DIETHYLSTILBESTROL COMPLEX

| ATOM | 3794 | O | ALA | C | 295 | 39.586 | 74.945 | 6.782 | 1.00 | 48.34 | C |
|---|---|---|---|---|---|---|---|---|---|---|---|
| ATOM | 3795 | N | ASP | C | 296 | 37.701 | 74.263 | 5.737 | 1.00 | 48.09 | C |
| ATOM | 3796 | CA | ASP | C | 296 | 37.410 | 73.175 | 6.634 | 1.00 | 47.01 | C |
| ATOM | 3797 | CB | ASP | C | 296 | 35.944 | 72.663 | 6.528 | 1.00 | 47.21 | C |
| ATOM | 3798 | CG | ASP | C | 296 | 35.013 | 73.381 | 7.466 | 1.00 | 48.46 | C |
| ATOM | 3799 | OD1 | ASP | C | 296 | 35.446 | 74.397 | 8.101 | 1.00 | 48.95 | C |
| ATOM | 3800 | OD2 | ASP | C | 296 | 33.832 | 73.002 | 7.623 | 1.00 | 48.37 | C |
| ATOM | 3801 | C | ASP | C | 296 | 38.374 | 72.034 | 6.292 | 1.00 | 45.93 | C |
| ATOM | 3802 | O | ASP | C | 296 | 38.804 | 71.382 | 7.181 | 1.00 | 44.33 | C |
| ATOM | 3803 | N | GLN | C | 297 | 38.708 | 71.809 | 5.019 | 1.00 | 45.29 | C |
| ATOM | 3804 | CA | GLN | C | 297 | 39.674 | 70.775 | 4.651 | 1.00 | 45.39 | C |
| ATOM | 3805 | CB | GLN | C | 297 | 39.899 | 70.668 | 3.139 | 1.00 | 47.27 | C |
| ATOM | 3806 | CG | GLN | C | 297 | 38.726 | 70.012 | 2.300 | 1.00 | 49.42 | C |
| ATOM | 3807 | CD | GLN | C | 297 | 38.920 | 70.256 | 0.792 | 1.00 | 51.64 | C |
| ATOM | 3808 | OE1 | GLN | C | 297 | 39.292 | 69.348 | 0.016 | 1.00 | 52.11 | C |
| ATOM | 3809 | NE2 | GLN | C | 297 | 38.668 | 71.494 | 0.393 | 1.00 | 51.12 | C |
| ATOM | 3810 | C | GLN | C | 297 | 41.033 | 71.119 | 5.299 | 1.00 | 44.76 | C |
| ATOM | 3811 | O | GLN | C | 297 | 41.742 | 70.197 | 5.736 | 1.00 | 42.86 | C |
| ATOM | 3812 | N | MET | C | 298 | 41.346 | 72.430 | 5.362 | 1.00 | 44.50 | C |
| ATOM | 3813 | CA | MET | C | 298 | 42.646 | 72.898 | 5.822 | 1.00 | 45.55 | C |
| ATOM | 3814 | CB | MET | C | 298 | 42.956 | 74.374 | 5.488 | 1.00 | 50.03 | C |
| ATOM | 3815 | CG | MET | C | 298 | 42.156 | 75.452 | 6.204 | 1.00 | 58.35 | C |
| ATOM | 3816 | SD | MET | C | 298 | 42.644 | 77.117 | 5.715 | 1.00 | 68.46 | C |
| ATOM | 3817 | CE | MET | C | 298 | 43.936 | 77.456 | 6.907 | 1.00 | 64.38 | C |
| ATOM | 3818 | C | MET | C | 298 | 42.638 | 72.759 | 7.342 | 1.00 | 43.25 | C |
| ATOM | 3819 | O | MET | C | 298 | 43.658 | 72.559 | 7.960 | 1.00 | 41.30 | C |
| ATOM | 3820 | N | SER | C | 299 | 41.450 | 72.908 | 7.914 | 1.00 | 40.68 | C |
| ATOM | 3821 | CA | SER | C | 299 | 41.272 | 72.867 | 9.341 | 1.00 | 39.29 | C |
| ATOM | 3822 | CB | SER | C | 299 | 39.919 | 73.465 | 9.695 | 1.00 | 39.65 | C |
| ATOM | 3823 | OG | SER | C | 299 | 40.096 | 74.821 | 9.887 | 1.00 | 40.18 | C |
| ATOM | 3824 | C | SER | C | 299 | 41.457 | 71.445 | 9.920 | 1.00 | 37.39 | C |
| ATOM | 3825 | O | SER | C | 299 | 42.056 | 71.293 | 10.998 | 1.00 | 37.28 | C |
| ATOM | 3826 | N | LEU | C | 300 | 40.974 | 70.452 | 9.188 | 1.00 | 35.92 | C |
| ATOM | 3827 | CA | LEU | C | 300 | 41.166 | 69.105 | 9.515 | 1.00 | 34.92 | C |
| ATOM | 3828 | CB | LEU | C | 300 | 40.325 | 68.177 | 8.659 | 1.00 | 34.17 | C |
| ATOM | 3829 | CG | LEU | C | 300 | 38.760 | 68.291 | 8.746 | 1.00 | 37.06 | C |
| ATOM | 3830 | CD1 | LEU | C | 300 | 38.096 | 67.089 | 7.929 | 1.00 | 33.81 | C |
| ATOM | 3831 | CD2 | LEU | C | 300 | 38.179 | 68.290 | 10.148 | 1.00 | 34.44 | C |
| ATOM | 3832 | C | LEU | C | 300 | 42.677 | 68.748 | 9.339 | 1.00 | 35.05 | C |
| ATOM | 3833 | O | LEU | C | 300 | 43.250 | 67.990 | 10.157 | 1.00 | 34.11 | C |
| ATOM | 3834 | N | LEU | C | 301 | 43.274 | 69.188 | 8.254 | 1.00 | 33.82 | C |
| ATOM | 3835 | CA | LEU | C | 301 | 44.694 | 68.881 | 8.035 | 1.00 | 34.46 | C |
| ATOM | 3836 | CB | LEU | C | 301 | 45.163 | 69.361 | 6.659 | 1.00 | 34.12 | C |
| ATOM | 3837 | CG | LEU | C | 301 | 44.638 | 68.299 | 5.628 | 1.00 | 36.08 | C |
| ATOM | 3838 | CD1 | LEU | C | 301 | 44.544 | 68.900 | 4.203 | 1.00 | 37.29 | C |
| ATOM | 3839 | CD2 | LEU | C | 301 | 45.445 | 67.065 | 5.552 | 1.00 | 36.25 | C |
| ATOM | 3840 | C | LEU | C | 301 | 45.554 | 69.526 | 9.068 | 1.00 | 34.07 | C |
| ATOM | 3841 | O | LEU | C | 301 | 46.495 | 68.962 | 9.541 | 1.00 | 34.51 | C |
| ATOM | 3842 | N | GLN | C | 302 | 45.228 | 70.729 | 9.460 | 1.00 | 33.81 | C |
| ATOM | 3843 | CA | GLN | C | 302 | 46.051 | 71.379 | 10.404 | 1.00 | 33.60 | C |
| ATOM | 3844 | CB | GLN | C | 302 | 45.495 | 72.754 | 10.674 | 1.00 | 35.73 | C |
| ATOM | 3845 | CG | GLN | C | 302 | 46.318 | 73.637 | 11.772 | 1.00 | 39.88 | C |
| ATOM | 3846 | CD | GLN | C | 302 | 45.636 | 74.944 | 12.097 | 1.00 | 42.57 | C |
| ATOM | 3847 | OE1 | GLN | C | 302 | 44.545 | 75.224 | 11.544 | 1.00 | 46.78 | C |
| ATOM | 3848 | NE2 | GLN | C | 302 | 46.215 | 75.736 | 13.017 | 1.00 | 43.01 | C |
| ATOM | 3849 | C | GLN | C | 302 | 46.015 | 70.576 | 11.715 | 1.00 | 31.99 | C |
| ATOM | 3850 | O | GLN | C | 302 | 46.959 | 70.493 | 12.422 | 1.00 | 30.39 | C |
| ATOM | 3851 | N | SER | C | 303 | 44.857 | 70.080 | 12.063 | 1.00 | 31.14 | C |
| ATOM | 3852 | CA | SER | C | 303 | 44.640 | 69.373 | 13.311 | 1.00 | 31.30 | C |
| ATOM | 3853 | CB | SER | C | 303 | 43.163 | 69.378 | 13.754 | 1.00 | 32.11 | C |
| ATOM | 3854 | OG | SER | C | 303 | 42.778 | 70.718 | 14.102 | 1.00 | 35.94 | C |
| ATOM | 3855 | C | SER | C | 303 | 45.151 | 67.956 | 13.212 | 1.00 | 30.27 | C |
| ATOM | 3856 | O | SER | C | 303 | 45.630 | 67.509 | 14.168 | 1.00 | 30.81 | C |
| ATOM | 3857 | N | ALA | C | 304 | 45.167 | 67.284 | 12.069 | 1.00 | 28.51 | C |
| ATOM | 3858 | CA | ALA | C | 304 | 45.596 | 65.855 | 11.979 | 1.00 | 28.00 | C |
| ATOM | 3859 | CB | ALA | C | 304 | 44.488 | 65.076 | 11.140 | 1.00 | 27.97 | C |
| ATOM | 3860 | C | ALA | C | 304 | 46.933 | 65.466 | 11.403 | 1.00 | 27.58 | C |
| ATOM | 3861 | O | ALA | C | 304 | 47.276 | 64.229 | 11.356 | 1.00 | 26.72 | C |
| ATOM | 3862 | N | TRP | C | 305 | 47.706 | 66.419 | 10.867 | 1.00 | 27.39 | C |
| ATOM | 3863 | CA | TRP | C | 305 | 48.769 | 66.026 | 9.994 | 1.00 | 27.87 | C |
| ATOM | 3864 | CB | TRP | C | 305 | 49.450 | 67.274 | 9.432 | 1.00 | 29.77 | C |
| ATOM | 3865 | CG | TRP | C | 305 | 50.149 | 68.136 | 10.402 | 1.00 | 31.79 | C |
| ATOM | 3866 | CD2 | TRP | C | 305 | 51.499 | 68.052 | 10.933 | 1.00 | 32.47 | C |
| ATOM | 3867 | CE2 | TRP | C | 305 | 51.658 | 69.148 | 11.826 | 1.00 | 33.02 | C |
| ATOM | 3868 | CE3 | TRP | C | 305 | 52.603 | 67.243 | 10.693 | 1.00 | 33.64 | C |
| ATOM | 3869 | CD1 | TRP | C | 305 | 49.594 | 69.165 | 11.001 | 1.00 | 32.90 | C |

TABLE 2-continued

ATOMIC COORDINATES OF THE ERR3 LBD/ DIETHYLSTILBESTROL COMPLEX

| ATOM | 3870 | NE1 | TRP | C | 305 | 50.470 | 69.789 | 11.838 | 1.00 | 33.47 | C |
|---|---|---|---|---|---|---|---|---|---|---|---|
| ATOM | 3871 | CZ2 | TRP | C | 305 | 52.864 | 69.463 | 12.477 | 1.00 | 34.01 | C |
| ATOM | 3872 | CZ3 | TRP | C | 305 | 53.839 | 67.536 | 11.372 | 1.00 | 34.55 | C |
| ATOM | 3873 | CH2 | TRP | C | 305 | 53.968 | 68.655 | 12.219 | 1.00 | 34.83 | C |
| ATOM | 3874 | C | TRP | C | 305 | 49.758 | 65.084 | 10.733 | 1.00 | 27.90 | C |
| ATOM | 3875 | O | TRP | C | 305 | 50.244 | 64.057 | 10.235 | 1.00 | 27.64 | C |
| ATOM | 3876 | N | MET | C | 306 | 50.036 | 65.380 | 11.990 | 1.00 | 27.30 | C |
| ATOM | 3877 | CA | MET | C | 306 | 50.981 | 64.527 | 12.724 | 1.00 | 25.70 | C |
| ATOM | 3878 | CB | MET | C | 306 | 51.579 | 65.216 | 13.981 | 1.00 | 26.27 | C |
| ATOM | 3879 | CG | MET | C | 306 | 52.523 | 64.391 | 14.732 | 1.00 | 25.30 | C |
| ATOM | 3880 | SD | MET | C | 306 | 54.091 | 64.166 | 13.922 | 1.00 | 30.86 | C |
| ATOM | 3881 | CE | MET | C | 306 | 54.840 | 65.731 | 14.360 | 1.00 | 27.18 | C |
| ATOM | 3882 | C | MET | C | 306 | 50.406 | 63.187 | 13.101 | 1.00 | 25.75 | C |
| ATOM | 3883 | O | MET | C | 306 | 51.140 | 62.148 | 13.029 | 1.00 | 25.72 | C |
| ATOM | 3884 | N | GLU | C | 307 | 49.114 | 63.148 | 13.389 | 1.00 | 25.69 | C |
| ATOM | 3885 | CA | GLU | C | 307 | 48.501 | 61.839 | 13.519 | 1.00 | 27.78 | C |
| ATOM | 3886 | CB | GLU | C | 307 | 46.995 | 61.986 | 13.836 | 1.00 | 28.33 | C |
| ATOM | 3887 | CG | GLU | C | 307 | 46.788 | 62.496 | 15.252 | 1.00 | 30.04 | C |
| ATOM | 3888 | CD | GLU | C | 307 | 45.391 | 62.378 | 15.825 | 1.00 | 32.67 | C |
| ATOM | 3889 | OE1 | GLU | C | 307 | 44.612 | 61.395 | 15.503 | 1.00 | 34.67 | C |
| ATOM | 3890 | OE2 | GLU | C | 307 | 45.050 | 63.317 | 16.545 | 1.00 | 34.48 | C |
| ATOM | 3891 | C | GLU | C | 307 | 48.692 | 60.900 | 12.313 | 1.00 | 28.96 | C |
| ATOM | 3892 | O | GLU | C | 307 | 48.888 | 59.691 | 12.436 | 1.00 | 30.49 | C |
| ATOM | 3893 | N | ILE | C | 308 | 48.490 | 61.467 | 11.123 | 1.00 | 29.67 | C |
| ATOM | 3894 | CA | ILE | C | 308 | 48.542 | 60.774 | 9.846 | 1.00 | 29.34 | C |
| ATOM | 3895 | CB | ILE | C | 308 | 48.009 | 61.710 | 8.733 | 1.00 | 30.07 | C |
| ATOM | 3896 | CG2 | ILE | C | 308 | 48.082 | 60.996 | 7.366 | 1.00 | 31.21 | C |
| ATOM | 3897 | CG1 | ILE | C | 308 | 46.548 | 61.997 | 8.960 | 1.00 | 28.85 | C |
| ATOM | 3898 | CD1 | ILE | C | 308 | 46.175 | 63.100 | 8.264 | 1.00 | 30.45 | C |
| ATOM | 3899 | C | ILE | C | 308 | 50.014 | 60.389 | 9.612 | 1.00 | 28.90 | C |
| ATOM | 3900 | O | ILE | C | 308 | 50.280 | 59.276 | 9.280 | 1.00 | 29.35 | C |
| ATOM | 3901 | N | LEU | C | 309 | 50.981 | 61.302 | 9.791 | 1.00 | 29.23 | C |
| ATOM | 3902 | CA | LEU | C | 309 | 52.396 | 60.869 | 9.732 | 1.00 | 28.57 | C |
| ATOM | 3903 | CB | LEU | C | 309 | 53.423 | 62.017 | 10.103 | 1.00 | 29.22 | C |
| ATOM | 3904 | CG | LEU | C | 309 | 53.372 | 63.256 | 9.174 | 1.00 | 31.01 | C |
| ATOM | 3905 | CD1 | LEU | C | 309 | 54.300 | 64.426 | 9.615 | 1.00 | 27.78 | C |
| ATOM | 3906 | CD2 | LEU | C | 309 | 53.664 | 62.766 | 7.818 | 1.00 | 28.90 | C |
| ATOM | 3907 | C | LEU | C | 309 | 52.688 | 59.760 | 10.632 | 1.00 | 29.37 | C |
| ATOM | 3908 | O | LEU | C | 309 | 53.320 | 58.822 | 10.201 | 1.00 | 29.06 | C |
| ATOM | 3909 | N | ILE | C | 310 | 52.304 | 59.877 | 11.912 | 1.00 | 30.39 | C |
| ATOM | 3910 | CA | ILE | C | 310 | 52.717 | 58.874 | 12.953 | 1.00 | 30.72 | C |
| ATOM | 3911 | CB | ILE | C | 310 | 52.345 | 59.282 | 14.364 | 1.00 | 29.17 | C |
| ATOM | 3912 | CG2 | ILE | C | 310 | 52.439 | 58.148 | 15.349 | 1.00 | 27.89 | C |
| ATOM | 3913 | CG1 | ILE | C | 310 | 53.166 | 60.368 | 14.904 | 1.00 | 28.53 | C |
| ATOM | 3914 | CD1 | ILE | C | 310 | 54.590 | 60.092 | 15.254 | 1.00 | 28.26 | C |
| ATOM | 3915 | C | ILE | C | 310 | 52.071 | 57.545 | 12.660 | 1.00 | 31.54 | C |
| ATOM | 3916 | O | ILE | C | 310 | 52.720 | 56.509 | 12.845 | 1.00 | 32.24 | C |
| ATOM | 3917 | N | LEU | C | 311 | 50.821 | 57.551 | 12.231 | 1.00 | 32.05 | C |
| ATOM | 3918 | CA | LEU | C | 311 | 50.190 | 56.299 | 11.893 | 1.00 | 34.02 | C |
| ATOM | 3919 | CB | LEU | C | 311 | 48.764 | 56.569 | 11.539 | 1.00 | 34.03 | C |
| ATOM | 3920 | CG | LEU | C | 311 | 47.613 | 55.623 | 11.797 | 1.00 | 36.02 | C |
| ATOM | 3921 | CD1 | LEU | C | 311 | 47.622 | 54.904 | 13.096 | 1.00 | 35.46 | C |
| ATOM | 3922 | CD2 | LEU | C | 311 | 46.369 | 56.494 | 11.711 | 1.00 | 36.38 | C |
| ATOM | 3923 | C | LEU | C | 311 | 50.941 | 55.536 | 10.703 | 1.00 | 35.57 | C |
| ATOM | 3924 | O | LEU | C | 311 | 51.185 | 54.283 | 10.719 | 1.00 | 35.27 | C |
| ATOM | 3925 | N | GLY | C | 312 | 51.342 | 56.285 | 9.693 | 1.00 | 35.18 | C |
| ATOM | 3926 | CA | GLY | C | 312 | 52.215 | 55.646 | 8.710 | 1.00 | 35.66 | C |
| ATOM | 3927 | C | GLY | C | 312 | 53.488 | 54.999 | 9.223 | 1.00 | 35.93 | C |
| ATOM | 3928 | O | GLY | C | 312 | 53.836 | 53.912 | 8.842 | 1.00 | 34.82 | C |
| ATOM | 3929 | N | VAL | C | 313 | 54.231 | 55.697 | 10.075 | 1.00 | 36.08 | C |
| ATOM | 3930 | CA | VAL | C | 313 | 55.418 | 55.109 | 10.656 | 1.00 | 35.16 | C |
| ATOM | 3931 | CB | VAL | C | 313 | 56.002 | 56.025 | 11.697 | 1.00 | 35.42 | C |
| ATOM | 3932 | CG1 | VAL | C | 313 | 57.174 | 55.374 | 12.378 | 1.00 | 34.41 | C |
| ATOM | 3933 | CG2 | VAL | C | 313 | 56.410 | 57.328 | 11.045 | 1.00 | 35.03 | C |
| ATOM | 3934 | C | VAL | C | 313 | 55.128 | 53.841 | 11.420 | 1.00 | 35.58 | C |
| ATOM | 3935 | O | VAL | C | 313 | 55.941 | 52.928 | 11.475 | 1.00 | 34.92 | C |
| ATOM | 3936 | N | VAL | C | 314 | 54.062 | 53.876 | 12.179 | 1.00 | 35.90 | C |
| ATOM | 3937 | CA | VAL | C | 314 | 53.621 | 52.759 | 12.970 | 1.00 | 37.05 | C |
| ATOM | 3938 | CB | VAL | C | 314 | 52.385 | 53.230 | 13.818 | 1.00 | 36.74 | C |
| ATOM | 3939 | CG1 | VAL | C | 314 | 51.647 | 52.161 | 14.459 | 1.00 | 36.07 | C |
| ATOM | 3940 | CG2 | VAL | C | 314 | 52.911 | 54.179 | 14.964 | 1.00 | 36.09 | C |
| ATOM | 3941 | C | VAL | C | 314 | 53.345 | 51.540 | 11.991 | 1.00 | 38.36 | C |
| ATOM | 3942 | O | VAL | C | 314 | 53.860 | 50.488 | 12.192 | 1.00 | 38.46 | C |
| ATOM | 3943 | N | TYR | C | 315 | 52.520 | 51.749 | 10.980 | 1.00 | 39.79 | C |
| ATOM | 3944 | CA | TYR | C | 315 | 52.221 | 50.750 | 10.046 | 1.00 | 41.50 | C |
| ATOM | 3945 | CB | TYR | C | 315 | 51.228 | 51.199 | 9.035 | 1.00 | 43.22 | C |

TABLE 2-continued

ATOMIC COORDINATES OF THE ERR3 LBD/
DIETHYLSTILBESTROL COMPLEX

| ATOM | 3946 | CG | TYR | C | 315 | 50.745 | 50.013 | 8.171 | 1.00 | 45.39 | C |
|------|------|-----|-----|---|-----|--------|--------|--------|------|-------|---|
| ATOM | 3947 | CD1 | TYR | C | 315 | 49.785 | 49.137 | 8.652 | 1.00 | 46.51 | C |
| ATOM | 3948 | CE1 | TYR | C | 315 | 49.347 | 48.061 | 7.916 | 1.00 | 47.21 | C |
| ATOM | 3949 | CD2 | TYR | C | 315 | 51.246 | 49.762 | 6.922 | 1.00 | 46.13 | C |
| ATOM | 3950 | CE2 | TYR | C | 315 | 50.793 | 48.655 | 6.157 | 1.00 | 47.16 | C |
| ATOM | 3951 | CZ | TYR | C | 315 | 49.841 | 47.804 | 6.682 | 1.00 | 47.76 | C |
| ATOM | 3952 | OH | TYR | C | 315 | 49.343 | 46.652 | 6.016 | 1.00 | 48.96 | C |
| ATOM | 3953 | C | TYR | C | 315 | 53.449 | 50.227 | 9.338 | 1.00 | 41.55 | C |
| ATOM | 3954 | O | TYR | C | 315 | 53.550 | 49.027 | 9.201 | 1.00 | 42.67 | C |
| ATOM | 3955 | N | ARG | C | 316 | 54.405 | 51.061 | 8.936 | 1.00 | 40.12 | C |
| ATOM | 3956 | CA | ARG | C | 316 | 55.508 | 50.523 | 8.164 | 1.00 | 39.36 | C |
| ATOM | 3957 | CB | ARG | C | 316 | 56.308 | 51.559 | 7.367 | 1.00 | 37.06 | C |
| ATOM | 3958 | CG | ARG | C | 316 | 55.552 | 52.423 | 6.528 | 1.00 | 35.90 | C |
| ATOM | 3959 | CD | ARG | C | 316 | 56.318 | 53.423 | 5.815 | 1.00 | 36.20 | C |
| ATOM | 3960 | NE | ARG | C | 316 | 56.861 | 54.482 | 6.683 | 1.00 | 37.34 | C |
| ATOM | 3961 | CZ | ARG | C | 316 | 56.289 | 55.648 | 6.931 | 1.00 | 37.59 | C |
| ATOM | 3962 | NH1 | ARG | C | 316 | 55.114 | 55.963 | 6.465 | 1.00 | 37.45 | C |
| ATOM | 3963 | NH2 | ARG | C | 316 | 56.896 | 56.514 | 7.699 | 1.00 | 38.92 | C |
| ATOM | 3964 | C | ARG | C | 316 | 56.404 | 49.799 | 9.159 | 1.00 | 39.26 | C |
| ATOM | 3965 | O | ARG | C | 316 | 57.354 | 49.169 | 8.753 | 1.00 | 39.88 | C |
| ATOM | 3966 | N | SER | C | 317 | 56.119 | 49.904 | 10.436 | 1.00 | 39.02 | C |
| ATOM | 3967 | CA | SER | C | 317 | 57.000 | 49.316 | 11.448 | 1.00 | 39.16 | C |
| ATOM | 3968 | CB | SER | C | 317 | 57.194 | 50.258 | 12.599 | 1.00 | 37.55 | C |
| ATOM | 3969 | OG | SER | C | 317 | 58.044 | 51.374 | 12.278 | 1.00 | 38.73 | C |
| ATOM | 3970 | C | SER | C | 317 | 56.463 | 47.988 | 12.046 | 1.00 | 40.20 | C |
| ATOM | 3971 | O | SER | C | 317 | 57.127 | 47.398 | 12.872 | 1.00 | 39.10 | C |
| ATOM | 3972 | N | LEU | C | 318 | 55.256 | 47.582 | 11.683 | 1.00 | 41.57 | C |
| ATOM | 3973 | CA | LEU | C | 318 | 54.615 | 46.381 | 12.284 | 1.00 | 44.13 | C |
| ATOM | 3974 | CB | LEU | C | 318 | 53.331 | 46.091 | 11.600 | 1.00 | 43.61 | C |
| ATOM | 3975 | CG | LEU | C | 318 | 52.249 | 47.103 | 11.869 | 1.00 | 44.44 | C |
| ATOM | 3976 | CD1 | LEU | C | 318 | 51.020 | 46.597 | 11.304 | 1.00 | 44.64 | C |
| ATOM | 3977 | CD2 | LEU | C | 318 | 52.085 | 47.294 | 13.280 | 1.00 | 42.28 | C |
| ATOM | 3978 | C | LEU | C | 318 | 55.392 | 45.103 | 12.139 | 1.00 | 45.42 | C |
| ATOM | 3979 | O | LEU | C | 318 | 55.396 | 44.328 | 13.046 | 1.00 | 46.70 | C |
| ATOM | 3980 | N | SER | C | 319 | 56.094 | 44.950 | 11.029 | 1.00 | 47.01 | C |
| ATOM | 3981 | CA | SER | C | 319 | 56.943 | 43.766 | 10.792 | 1.00 | 49.54 | C |
| ATOM | 3982 | CB | SER | C | 319 | 57.066 | 43.447 | 9.275 | 1.00 | 50.53 | C |
| ATOM | 3983 | OG | SER | C | 319 | 57.835 | 44.430 | 8.604 | 1.00 | 55.29 | C |
| ATOM | 3984 | C | SER | C | 319 | 58.361 | 43.912 | 11.335 | 1.00 | 50.14 | C |
| ATOM | 3985 | O | SER | C | 319 | 59.244 | 43.212 | 10.825 | 1.00 | 50.88 | C |
| ATOM | 3986 | N | PHE | C | 320 | 58.603 | 44.818 | 12.292 | 1.00 | 49.52 | C |
| ATOM | 3987 | CA | PHE | C | 320 | 59.963 | 45.009 | 12.794 | 1.00 | 49.18 | C |
| ATOM | 3988 | CB | PHE | C | 320 | 60.651 | 46.366 | 12.402 | 1.00 | 47.23 | C |
| ATOM | 3989 | CG | PHE | C | 320 | 61.034 | 46.445 | 10.962 | 1.00 | 45.05 | C |
| ATOM | 3990 | CD1 | PHE | C | 320 | 62.359 | 46.500 | 10.578 | 1.00 | 44.37 | C |
| ATOM | 3991 | CD2 | PHE | C | 320 | 60.101 | 46.457 | 10.029 | 1.00 | 44.37 | C |
| ATOM | 3992 | CE1 | PHE | C | 320 | 62.695 | 46.613 | 9.264 | 1.00 | 43.99 | C |
| ATOM | 3993 | CE2 | PHE | C | 320 | 60.430 | 46.540 | 8.713 | 1.00 | 43.92 | C |
| ATOM | 3994 | CZ | PHE | C | 320 | 61.755 | 46.605 | 8.334 | 1.00 | 43.56 | C |
| ATOM | 3995 | C | PHE | C | 320 | 59.853 | 44.905 | 14.261 | 1.00 | 49.91 | C |
| ATOM | 3996 | O | PHE | C | 320 | 58.773 | 44.762 | 14.791 | 1.00 | 49.55 | C |
| ATOM | 3997 | N | GLU | C | 321 | 60.959 | 44.970 | 14.970 | 1.00 | 51.13 | C |
| ATOM | 3998 | CA | GLU | C | 321 | 60.766 | 44.897 | 16.411 | 1.00 | 52.02 | C |
| ATOM | 3999 | CB | GLU | C | 321 | 60.971 | 43.449 | 16.849 | 1.00 | 56.07 | C |
| ATOM | 4000 | CG | GLU | C | 321 | 62.275 | 42.803 | 16.315 | 1.00 | 61.64 | C |
| ATOM | 4001 | CD | GLU | C | 321 | 63.513 | 43.139 | 17.141 | 1.00 | 64.78 | C |
| ATOM | 4002 | OE1 | GLU | C | 321 | 64.625 | 42.777 | 16.701 | 1.00 | 66.42 | C |
| ATOM | 4003 | OE2 | GLU | C | 321 | 63.388 | 43.750 | 18.226 | 1.00 | 65.92 | C |
| ATOM | 4004 | C | GLU | C | 321 | 61.742 | 45.843 | 17.089 | 1.00 | 51.10 | C |
| ATOM | 4005 | O | GLU | C | 321 | 62.942 | 45.833 | 16.835 | 1.00 | 51.98 | C |
| ATOM | 4006 | N | ASP | C | 322 | 61.193 | 46.747 | 17.879 | 1.00 | 50.13 | C |
| ATOM | 4007 | CA | ASP | C | 322 | 61.940 | 47.804 | 18.542 | 1.00 | 48.42 | C |
| ATOM | 4008 | CB | ASP | C | 322 | 62.991 | 47.133 | 19.450 | 1.00 | 50.13 | C |
| ATOM | 4009 | CG | ASP | C | 322 | 62.408 | 46.845 | 20.744 | 1.00 | 51.94 | C |
| ATOM | 4010 | OD1 | ASP | C | 322 | 61.168 | 46.676 | 20.717 | 1.00 | 53.06 | C |
| ATOM | 4011 | OD2 | ASP | C | 322 | 63.016 | 46.885 | 21.829 | 1.00 | 53.89 | C |
| ATOM | 4012 | C | ASP | C | 322 | 62.576 | 48.752 | 17.597 | 1.00 | 46.41 | C |
| ATOM | 4013 | O | ASP | C | 322 | 63.556 | 49.328 | 17.905 | 1.00 | 45.73 | C |
| ATOM | 4014 | N | GLU | C | 323 | 62.054 | 48.866 | 16.402 | 1.00 | 44.57 | C |
| ATOM | 4015 | CA | GLU | C | 323 | 62.657 | 49.793 | 15.495 | 1.00 | 43.44 | C |
| ATOM | 4016 | CB | GLU | C | 323 | 63.603 | 49.083 | 14.518 | 1.00 | 43.78 | C |
| ATOM | 4017 | CG | GLU | C | 323 | 64.714 | 48.678 | 14.824 | 0.00 | 47.45 | C |
| ATOM | 4018 | CD | GLU | C | 323 | 65.670 | 47.656 | 13.938 | 1.00 | 49.10 | C |
| ATOM | 4019 | OE1 | GLU | C | 323 | 65.015 | 46.910 | 13.211 | 1.00 | 51.10 | C |
| ATOM | 4020 | OE2 | GLU | C | 323 | 66.695 | 48.164 | 13.496 | 1.00 | 52.12 | C |
| ATOM | 4021 | C | GLU | C | 323 | 61.551 | 50.535 | 14.737 | 1.00 | 41.24 | C |

TABLE 2-continued

ATOMIC COORDINATES OF THE ERR3 LBD/
DIETHYLSTILBESTROL COMPLEX

| ATOM | 4022 | O   | GLU | C | 323 | 60.411 | 49.997 | 14.512 | 1.00 | 39.12 | C |
|------|------|-----|-----|---|-----|--------|--------|--------|------|-------|---|
| ATOM | 4023 | N   | LEU | C | 324 | 61.853 | 51.757 | 14.345 | 1.00 | 39.00 | C |
| ATOM | 4024 | CA  | LEU | C | 324 | 60.825 | 52.463 | 13.637 | 1.00 | 37.05 | C |
| ATOM | 4025 | CB  | LEU | C | 324 | 60.525 | 53.749 | 14.383 | 1.00 | 35.66 | C |
| ATOM | 4026 | CG  | LEU | C | 324 | 59.936 | 53.716 | 15.800 | 1.00 | 35.38 | C |
| ATOM | 4027 | CD1 | LEU | C | 324 | 59.829 | 55.188 | 16.253 | 1.00 | 32.28 | C |
| ATOM | 4028 | CD2 | LEU | C | 324 | 58.549 | 53.027 | 15.766 | 1.00 | 34.28 | C |
| ATOM | 4029 | C   | LEU | C | 324 | 61.240 | 52.754 | 12.232 | 1.00 | 36.67 | C |
| ATOM | 4030 | O   | LEU | C | 324 | 62.290 | 53.338 | 11.990 | 1.00 | 36.34 | C |
| ATOM | 4031 | N   | VAL | C | 325 | 60.325 | 52.460 | 11.308 | 1.00 | 36.23 | C |
| ATOM | 4032 | CA  | VAL | C | 325 | 60.511 | 52.645 | 9.874  | 1.00 | 34.39 | C |
| ATOM | 4033 | CB  | VAL | C | 325 | 59.966 | 51.390 | 9.130  | 1.00 | 34.91 | C |
| ATOM | 4034 | CG1 | VAL | C | 325 | 60.222 | 51.467 | 7.674  | 1.00 | 32.73 | C |
| ATOM | 4035 | CG2 | VAL | C | 325 | 60.664 | 50.120 | 9.707  | 1.00 | 34.93 | C |
| ATOM | 4036 | C   | VAL | C | 325 | 59.890 | 53.966 | 9.398  | 1.00 | 34.14 | C |
| ATOM | 4037 | O   | VAL | C | 325 | 58.772 | 54.039 | 8.760  | 1.00 | 33.84 | C |
| ATOM | 4038 | N   | TYR | C | 326 | 60.656 | 54.994 | 9.659  | 1.00 | 33.36 | C |
| ATOM | 4039 | CA  | TYR | C | 326 | 60.349 | 56.329 | 9.153  | 1.00 | 32.88 | C |
| ATOM | 4040 | CB  | TYR | C | 326 | 61.245 | 57.457 | 9.741  | 1.00 | 31.86 | C |
| ATOM | 4041 | CG  | TYR | C | 326 | 60.870 | 57.748 | 11.266 | 1.00 | 32.33 | C |
| ATOM | 4042 | CD1 | TYR | C | 326 | 59.807 | 58.502 | 11.583 | 1.00 | 31.29 | C |
| ATOM | 4043 | CE1 | TYR | C | 326 | 59.489 | 58.805 | 12.860 | 1.00 | 31.03 | C |
| ATOM | 4044 | CD2 | TYR | C | 326 | 61.611 | 57.235 | 12.330 | 1.00 | 31.33 | C |
| ATOM | 4045 | CE2 | TYR | C | 326 | 61.316 | 57.508 | 13.600 | 1.00 | 30.52 | C |
| ATOM | 4046 | CZ  | TYR | C | 326 | 60.235 | 58.321 | 13.877 | 1.00 | 31.98 | C |
| ATOM | 4047 | OH  | TYR | C | 326 | 59.791 | 58.556 | 15.152 | 1.00 | 29.17 | C |
| ATOM | 4048 | C   | TYR | C | 326 | 60.288 | 56.348 | 7.671  | 1.00 | 32.72 | C |
| ATOM | 4049 | O   | TYR | C | 326 | 59.409 | 56.932 | 7.067  | 1.00 | 29.98 | C |
| ATOM | 4050 | N   | ALA | C | 327 | 61.235 | 55.643 | 7.094  | 1.00 | 34.81 | C |
| ATOM | 4051 | CA  | ALA | C | 327 | 61.273 | 55.389 | 5.604  | 1.00 | 36.07 | C |
| ATOM | 4052 | CB  | ALA | C | 327 | 61.750 | 56.575 | 4.863  | 1.00 | 33.93 | C |
| ATOM | 4053 | C   | ALA | C | 327 | 62.163 | 54.139 | 5.400  | 1.00 | 37.49 | C |
| ATOM | 4054 | O   | ALA | C | 327 | 62.827 | 53.679 | 6.333  | 1.00 | 38.52 | C |
| ATOM | 4055 | N   | ASP | C | 328 | 62.068 | 53.561 | 4.214  | 1.00 | 39.01 | C |
| ATOM | 4056 | CA  | ASP | C | 328 | 62.724 | 52.318 | 3.845  | 1.00 | 41.16 | C |
| ATOM | 4057 | CB  | ASP | C | 328 | 62.466 | 51.985 | 2.394  | 1.00 | 41.58 | C |
| ATOM | 4058 | CG  | ASP | C | 328 | 61.162 | 51.285 | 2.136  | 1.00 | 43.28 | C |
| ATOM | 4059 | OD1 | ASP | C | 328 | 60.398 | 51.086 | 3.093  | 1.00 | 42.85 | C |
| ATOM | 4060 | OD2 | ASP | C | 328 | 60.828 | 50.909 | 0.943  | 1.00 | 44.85 | C |
| ATOM | 4061 | C   | ASP | C | 328 | 64.168 | 52.539 | 3.991  | 1.00 | 41.23 | C |
| ATOM | 4062 | O   | ASP | C | 328 | 64.827 | 51.626 | 4.409  | 1.00 | 42.54 | C |
| ATOM | 4063 | N   | ASP | C | 329 | 64.617 | 53.806 | 3.779  | 1.00 | 40.91 | C |
| ATOM | 4064 | CA  | ASP | C | 329 | 66.024 | 54.201 | 3.982  | 1.00 | 40.74 | C |
| ATOM | 4065 | CB  | ASP | C | 329 | 66.539 | 55.068 | 2.831  | 1.00 | 39.08 | C |
| ATOM | 4066 | CG  | ASP | C | 329 | 65.814 | 56.340 | 2.666  | 1.00 | 39.01 | C |
| ATOM | 4067 | OD1 | ASP | C | 329 | 64.666 | 56.580 | 3.208  | 1.00 | 38.62 | C |
| ATOM | 4068 | OD2 | ASP | C | 329 | 66.352 | 57.202 | 1.979  | 1.00 | 35.10 | C |
| ATOM | 4069 | C   | ASP | C | 329 | 66.247 | 54.942 | 5.329  | 1.00 | 40.96 | C |
| ATOM | 4070 | O   | ASP | C | 329 | 67.206 | 55.681 | 5.472  | 1.00 | 41.61 | C |
| ATOM | 4071 | N   | TYR | C | 330 | 65.417 | 54.706 | 6.331  | 1.00 | 40.37 | C |
| ATOM | 4072 | CA  | TYR | C | 330 | 65.580 | 55.485 | 7.602  | 1.00 | 39.56 | C |
| ATOM | 4073 | CB  | TYR | C | 330 | 65.091 | 56.985 | 7.539  | 1.00 | 39.14 | C |
| ATOM | 4074 | CG  | TYR | C | 330 | 65.936 | 57.848 | 8.355  | 1.00 | 37.51 | C |
| ATOM | 4075 | CD1 | TYR | C | 330 | 67.259 | 58.091 | 7.999  | 1.00 | 37.52 | C |
| ATOM | 4076 | CE1 | TYR | C | 330 | 68.136 | 58.922 | 8.799  | 1.00 | 37.87 | C |
| ATOM | 4077 | CD2 | TYR | C | 330 | 65.479 | 58.363 | 9.587  | 1.00 | 37.25 | C |
| ATOM | 4078 | CE2 | TYR | C | 330 | 66.328 | 59.151 | 10.412 | 1.00 | 37.39 | C |
| ATOM | 4079 | CZ  | TYR | C | 330 | 67.637 | 59.420 | 10.024 | 1.00 | 37.65 | C |
| ATOM | 4080 | OH  | TYR | C | 330 | 68.467 | 60.135 | 10.819 | 1.00 | 38.45 | C |
| ATOM | 4081 | C   | TYR | C | 330 | 64.790 | 54.732 | 8.678  | 1.00 | 39.91 | C |
| ATOM | 4082 | O   | TYR | C | 330 | 63.652 | 55.064 | 9.014  | 1.00 | 38.05 | C |
| ATOM | 4083 | N   | ILE | C | 331 | 65.504 | 53.770 | 9.229  | 1.00 | 40.63 | C |
| ATOM | 4084 | CA  | ILE | C | 331 | 65.000 | 52.861 | 10.219 | 1.00 | 41.34 | C |
| ATOM | 4085 | CB  | ILE | C | 331 | 65.199 | 51.362 | 9.754  | 1.00 | 41.80 | C |
| ATOM | 4086 | CG2 | ILE | C | 331 | 64.664 | 50.489 | 10.915 | 1.00 | 42.10 | C |
| ATOM | 4087 | CG1 | ILE | C | 331 | 64.507 | 51.164 | 8.400  | 1.00 | 43.06 | C |
| ATOM | 4088 | CD1 | ILE | C | 331 | 64.348 | 49.736 | 7.834  | 1.00 | 44.24 | C |
| ATOM | 4089 | C   | ILE | C | 331 | 65.779 | 53.116 | 11.437 | 1.00 | 41.22 | C |
| ATOM | 4090 | O   | ILE | C | 331 | 66.930 | 52.930 | 11.405 | 1.00 | 40.14 | C |
| ATOM | 4091 | N   | MET | C | 332 | 65.117 | 53.559 | 12.499 | 1.00 | 42.17 | C |
| ATOM | 4092 | CA  | MET | C | 332 | 65.747 | 54.005 | 13.715 | 1.00 | 44.07 | C |
| ATOM | 4093 | CB  | MET | C | 332 | 65.167 | 55.338 | 14.134 | 1.00 | 43.98 | C |
| ATOM | 4094 | CG  | MET | C | 332 | 65.468 | 56.465 | 13.261 | 1.00 | 44.44 | C |
| ATOM | 4095 | SD  | MET | C | 332 | 64.896 | 57.996 | 14.156 | 1.00 | 48.04 | C |
| ATOM | 4096 | CE  | MET | C | 332 | 66.096 | 58.083 | 15.310 | 1.00 | 43.10 | C |
| ATOM | 4097 | C   | MET | C | 332 | 65.488 | 52.995 | 14.840 | 1.00 | 44.31 | C |

TABLE 2-continued

ATOMIC COORDINATES OF THE ERR3 LBD/DIETHYLSTILBESTROL COMPLEX

| ATOM | 4098 | O   | MET | C | 332 | 64.381 | 52.728 | 15.202 | 1.00 | 44.41 | C |
|------|------|-----|-----|---|-----|--------|--------|--------|------|-------|---|
| ATOM | 4099 | N   | ASP | C | 333 | 66.549 | 52.380 | 15.293 | 1.00 | 45.94 | C |
| ATOM | 4100 | CA  | ASP | C | 333 | 66.582 | 51.488 | 16.475 | 1.00 | 48.53 | C |
| ATOM | 4101 | CB  | ASP | C | 333 | 67.623 | 50.268 | 16.347 | 1.00 | 48.27 | C |
| ATOM | 4102 | CG  | ASP | C | 333 | 69.146 | 50.705 | 16.134 | 1.00 | 48.90 | C |
| ATOM | 4103 | OD1 | ASP | C | 333 | 69.937 | 50.093 | 16.164 | 0.00 | 49.27 | C |
| ATOM | 4104 | OD2 | ASP | C | 333 | 69.533 | 51.856 | 16.467 | 1.00 | 51.17 | C |
| ATOM | 4105 | C   | ASP | C | 333 | 66.884 | 52.347 | 17.678 | 1.00 | 49.82 | C |
| ATOM | 4106 | O   | ASP | C | 333 | 67.036 | 53.578 | 17.580 | 1.00 | 50.60 | C |
| ATOM | 4107 | N   | GLU | C | 334 | 67.028 | 51.699 | 18.821 | 1.00 | 52.02 | C |
| ATOM | 4108 | CA  | GLU | C | 334 | 67.160 | 52.429 | 20.053 | 1.00 | 53.73 | C |
| ATOM | 4109 | CB  | GLU | C | 334 | 67.068 | 51.477 | 21.250 | 1.00 | 54.43 | C |
| ATOM | 4110 | CG  | GLU | C | 334 | 66.159 | 51.591 | 22.341 | 0.00 | 55.83 | C |
| ATOM | 4111 | CD  | GLU | C | 334 | 66.527 | 51.155 | 23.973 | 1.00 | 57.16 | C |
| ATOM | 4112 | OE1 | GLU | C | 334 | 67.763 | 51.103 | 23.826 | 1.00 | 56.65 | C |
| ATOM | 4113 | OE2 | GLU | C | 334 | 65.964 | 51.435 | 25.060 | 1.00 | 57.76 | C |
| ATOM | 4114 | C   | GLU | C | 334 | 68.425 | 53.244 | 20.101 | 1.00 | 54.25 | C |
| ATOM | 4115 | O   | GLU | C | 334 | 68.415 | 54.323 | 20.648 | 1.00 | 54.05 | C |
| ATOM | 4116 | N   | ASP | C | 335 | 69.539 | 52.689 | 19.619 | 1.00 | 54.92 | C |
| ATOM | 4117 | CA  | ASP | C | 335 | 70.796 | 53.387 | 19.724 | 1.00 | 55.20 | C |
| ATOM | 4118 | CB  | ASP | C | 335 | 71.962 | 52.535 | 19.199 | 1.00 | 55.84 | C |
| ATOM | 4119 | CG  | ASP | C | 335 | 72.441 | 51.407 | 20.225 | 1.00 | 56.91 | C |
| ATOM | 4120 | OD1 | ASP | C | 335 | 71.867 | 51.191 | 21.339 | 1.00 | 57.05 | C |
| ATOM | 4121 | OD2 | ASP | C | 335 | 73.414 | 50.678 | 19.964 | 1.00 | 56.87 | C |
| ATOM | 4122 | C   | ASP | C | 335 | 70.610 | 54.652 | 18.940 | 1.00 | 55.10 | C |
| ATOM | 4123 | O   | ASP | C | 335 | 71.008 | 55.741 | 19.373 | 1.00 | 53.85 | C |
| ATOM | 4124 | N   | GLN | C | 336 | 69.963 | 54.538 | 17.783 | 1.00 | 55.43 | C |
| ATOM | 4125 | CA  | GLN | C | 336 | 69.837 | 55.734 | 16.930 | 1.00 | 55.34 | C |
| ATOM | 4126 | CB  | GLN | C | 336 | 69.442 | 55.403 | 15.475 | 1.00 | 57.12 | C |
| ATOM | 4127 | CG  | GLN | C | 336 | 70.513 | 54.607 | 14.628 | 1.00 | 60.63 | C |
| ATOM | 4128 | CD  | GLN | C | 336 | 69.873 | 53.874 | 13.394 | 1.00 | 62.69 | C |
| ATOM | 4129 | OE1 | GLN | C | 336 | 69.481 | 54.533 | 12.379 | 1.00 | 65.55 | C |
| ATOM | 4130 | NE2 | GLN | C | 336 | 69.719 | 52.562 | 13.496 | 1.00 | 62.88 | C |
| ATOM | 4131 | C   | GLN | C | 336 | 68.886 | 56.739 | 17.581 | 1.00 | 54.21 | C |
| ATOM | 4132 | O   | GLN | C | 336 | 69.126 | 57.942 | 17.511 | 1.00 | 53.92 | C |
| ATOM | 4133 | N   | SER | C | 337 | 67.835 | 56.268 | 18.263 | 1.00 | 53.32 | C |
| ATOM | 4134 | CA  | SER | C | 337 | 66.895 | 57.218 | 18.863 | 1.00 | 53.37 | C |
| ATOM | 4135 | CB  | SER | C | 337 | 65.697 | 56.463 | 19.404 | 1.00 | 51.72 | C |
| ATOM | 4136 | OG  | SER | C | 337 | 64.984 | 55.848 | 18.321 | 1.00 | 49.59 | C |
| ATOM | 4137 | C   | SER | C | 337 | 67.591 | 58.107 | 19.954 | 1.00 | 53.88 | C |
| ATOM | 4138 | O   | SER | C | 337 | 67.284 | 59.319 | 20.156 | 1.00 | 53.07 | C |
| ATOM | 4139 | N   | LYS | C | 338 | 68.536 | 57.447 | 20.622 | 1.00 | 54.81 | C |
| ATOM | 4140 | CA  | LYS | C | 338 | 69.283 | 57.993 | 21.740 | 1.00 | 56.47 | C |
| ATOM | 4141 | CB  | LYS | C | 338 | 69.959 | 56.858 | 22.597 | 1.00 | 58.02 | C |
| ATOM | 4142 | CG  | LYS | C | 338 | 70.728 | 57.352 | 23.827 | 1.00 | 62.17 | C |
| ATOM | 4143 | CD  | LYS | C | 338 | 69.811 | 57.766 | 24.981 | 1.00 | 64.31 | C |
| ATOM | 4144 | CE  | LYS | C | 338 | 69.174 | 59.134 | 24.769 | 1.00 | 66.13 | C |
| ATOM | 4145 | NZ  | LYS | C | 338 | 68.276 | 59.498 | 25.896 | 1.00 | 66.22 | C |
| ATOM | 4146 | C   | LYS | C | 338 | 70.254 | 59.052 | 21.155 | 1.00 | 55.79 | C |
| ATOM | 4147 | O   | LYS | C | 338 | 70.151 | 60.208 | 21.550 | 1.00 | 56.21 | C |
| ATOM | 4148 | N   | LEU | C | 339 | 71.113 | 58.692 | 20.174 | 1.00 | 55.19 | C |
| ATOM | 4149 | CA  | LEU | C | 339 | 72.026 | 59.669 | 19.503 | 1.00 | 54.32 | C |
| ATOM | 4150 | CB  | LEU | C | 339 | 72.711 | 59.265 | 18.417 | 0.00 | 56.77 | C |
| ATOM | 4151 | CG  | LEU | C | 339 | 73.552 | 60.092 | 17.392 | 1.00 | 59.51 | C |
| ATOM | 4152 | CD1 | LEU | C | 339 | 72.648 | 60.819 | 16.405 | 1.00 | 60.81 | C |
| ATOM | 4153 | CD2 | LEU | C | 339 | 74.499 | 61.056 | 18.109 | 1.00 | 59.76 | C |
| ATOM | 4154 | C   | LEU | C | 339 | 71.271 | 60.935 | 19.052 | 1.00 | 53.10 | C |
| ATOM | 4155 | O   | LEU | C | 339 | 71.900 | 62.028 | 18.963 | 1.00 | 53.28 | C |
| ATOM | 4156 | N   | ALA | C | 340 | 69.940 | 60.815 | 18.805 | 1.00 | 50.52 | C |
| ATOM | 4157 | CA  | ALA | C | 340 | 69.100 | 61.863 | 18.211 | 1.00 | 48.47 | C |
| ATOM | 4158 | CB  | ALA | C | 340 | 68.170 | 61.246 | 17.103 | 1.00 | 48.20 | C |
| ATOM | 4159 | C   | ALA | C | 340 | 68.225 | 62.625 | 19.144 | 1.00 | 47.24 | C |
| ATOM | 4160 | O   | ALA | C | 340 | 67.475 | 63.565 | 18.705 | 1.00 | 46.82 | C |
| ATOM | 4161 | N   | GLY | C | 341 | 68.218 | 62.240 | 20.422 | 1.00 | 45.39 | C |
| ATOM | 4162 | CA  | GLY | C | 341 | 67.365 | 63.001 | 21.333 | 1.00 | 43.08 | C |
| ATOM | 4163 | C   | GLY | C | 341 | 65.897 | 62.646 | 21.190 | 1.00 | 42.32 | C |
| ATOM | 4164 | O   | GLY | C | 341 | 64.949 | 63.416 | 21.628 | 1.00 | 41.28 | C |
| ATOM | 4165 | N   | LEU | C | 342 | 65.686 | 61.438 | 20.654 | 1.00 | 41.58 | C |
| ATOM | 4166 | CA  | LEU | C | 342 | 64.298 | 61.000 | 20.436 | 1.00 | 41.88 | C |
| ATOM | 4167 | CB  | LEU | C | 342 | 64.056 | 60.830 | 18.938 | 1.00 | 40.47 | C |
| ATOM | 4168 | CG  | LEU | C | 342 | 64.158 | 62.106 | 18.058 | 1.00 | 38.56 | C |
| ATOM | 4169 | CD1 | LEU | C | 342 | 64.263 | 61.675 | 16.587 | 1.00 | 35.94 | C |
| ATOM | 4170 | CD2 | LEU | C | 342 | 62.916 | 63.018 | 18.307 | 1.00 | 36.84 | C |
| ATOM | 4171 | C   | LEU | C | 342 | 63.867 | 59.724 | 21.207 | 1.00 | 42.46 | C |
| ATOM | 4172 | O   | LEU | C | 342 | 62.855 | 59.096 | 20.842 | 1.00 | 42.46 | C |
| ATOM | 4173 | N   | LEU | C | 343 | 64.597 | 59.344 | 22.263 | 1.00 | 42.45 | C |

TABLE 2-continued

ATOMIC COORDINATES OF THE ERR3 LBD/DIETHYLSTILBESTROL COMPLEX

| ATOM | 4174 | CA  | LEU | C | 343 | 64.313 | 58.094 | 22.921 | 1.00 | 41.90 | C |
|------|------|-----|-----|---|-----|--------|--------|--------|------|-------|---|
| ATOM | 4175 | CB  | LEU | C | 343 | 65.312 | 57.710 | 23.989 | 1.00 | 42.00 | C |
| ATOM | 4176 | CG  | LEU | C | 343 | 65.072 | 56.300 | 24.597 | 1.00 | 41.99 | C |
| ATOM | 4177 | CD1 | LEU | C | 343 | 65.431 | 55.112 | 23.533 | 1.00 | 39.67 | C |
| ATOM | 4178 | CD2 | LEU | C | 343 | 65.790 | 56.171 | 26.038 | 1.00 | 41.02 | C |
| ATOM | 4179 | C   | LEU | C | 343 | 62.939 | 58.036 | 23.460 | 1.00 | 41.81 | C |
| ATOM | 4180 | O   | LEU | C | 343 | 62.238 | 57.051 | 23.263 | 1.00 | 41.89 | C |
| ATOM | 4181 | N   | ASP | C | 344 | 62.505 | 59.085 | 24.109 | 1.00 | 41.35 | C |
| ATOM | 4182 | CA  | ASP | C | 344 | 61.187 | 59.030 | 24.691 | 1.00 | 41.89 | C |
| ATOM | 4183 | CB  | ASP | C | 344 | 60.950 | 60.199 | 25.686 | 1.00 | 43.02 | C |
| ATOM | 4184 | CG  | ASP | C | 344 | 61.800 | 60.057 | 27.035 | 1.00 | 46.32 | C |
| ATOM | 4185 | OD1 | ASP | C | 344 | 62.583 | 59.039 | 27.219 | 1.00 | 45.85 | C |
| ATOM | 4186 | OD2 | ASP | C | 344 | 61.716 | 60.967 | 27.943 | 1.00 | 47.73 | C |
| ATOM | 4187 | C   | ASP | C | 344 | 60.111 | 59.086 | 23.648 | 1.00 | 40.72 | C |
| ATOM | 4188 | O   | ASP | C | 344 | 59.062 | 58.435 | 23.786 | 1.00 | 40.12 | C |
| ATOM | 4189 | N   | LEU | C | 345 | 60.295 | 59.953 | 22.643 | 1.00 | 40.04 | C |
| ATOM | 4190 | CA  | LEU | C | 345 | 59.264 | 60.060 | 21.613 | 1.00 | 37.17 | C |
| ATOM | 4191 | CB  | LEU | C | 345 | 59.618 | 61.181 | 20.620 | 1.00 | 35.30 | C |
| ATOM | 4192 | CG  | LEU | C | 345 | 58.599 | 61.420 | 19.469 | 1.00 | 35.44 | C |
| ATOM | 4193 | CD1 | LEU | C | 345 | 57.091 | 61.459 | 19.912 | 1.00 | 32.00 | C |
| ATOM | 4194 | CD2 | LEU | C | 345 | 58.995 | 62.743 | 18.721 | 1.00 | 35.28 | C |
| ATOM | 4195 | C   | LEU | C | 345 | 59.120 | 58.729 | 20.867 | 1.00 | 36.53 | C |
| ATOM | 4196 | O   | LEU | C | 345 | 58.022 | 58.259 | 20.669 | 1.00 | 34.24 | C |
| ATOM | 4197 | N   | ASN | C | 346 | 60.237 | 58.156 | 20.457 | 1.00 | 36.16 | C |
| ATOM | 4198 | CA  | ASN | C | 346 | 60.222 | 56.894 | 19.666 | 1.00 | 37.45 | C |
| ATOM | 4199 | CB  | ASN | C | 346 | 61.618 | 56.629 | 19.067 | 1.00 | 36.62 | C |
| ATOM | 4200 | CG  | ASN | C | 346 | 61.879 | 57.439 | 17.814 | 1.00 | 38.62 | C |
| ATOM | 4201 | OD1 | ASN | C | 346 | 60.991 | 58.125 | 17.343 | 1.00 | 41.59 | C |
| ATOM | 4202 | ND2 | ASN | C | 346 | 63.080 | 57.359 | 17.246 | 1.00 | 37.18 | C |
| ATOM | 4203 | C   | ASN | C | 346 | 59.695 | 55.676 | 20.534 | 1.00 | 37.90 | C |
| ATOM | 4204 | O   | ASN | C | 346 | 58.885 | 54.912 | 20.092 | 1.00 | 38.57 | C |
| ATOM | 4205 | N   | ASN | C | 347 | 60.072 | 55.592 | 21.813 | 1.00 | 38.47 | C |
| ATOM | 4206 | CA  | ASN | C | 347 | 59.431 | 54.641 | 22.761 | 1.00 | 39.03 | C |
| ATOM | 4207 | CB  | ASN | C | 347 | 60.040 | 54.719 | 24.189 | 1.00 | 40.58 | C |
| ATOM | 4208 | CG  | ASN | C | 347 | 61.484 | 54.047 | 24.254 | 1.00 | 41.69 | C |
| ATOM | 4209 | OD1 | ASN | C | 347 | 61.904 | 53.437 | 23.272 | 1.00 | 41.43 | C |
| ATOM | 4210 | ND2 | ASN | C | 347 | 62.222 | 54.192 | 25.404 | 1.00 | 43.34 | C |
| ATOM | 4211 | C   | ASN | C | 347 | 58.011 | 54.904 | 22.799 | 1.00 | 38.48 | C |
| ATOM | 4212 | O   | ASN | C | 347 | 57.227 | 53.986 | 22.671 | 1.00 | 39.60 | C |
| ATOM | 4213 | N   | ALA | C | 348 | 57.560 | 56.169 | 22.874 | 1.00 | 37.99 | C |
| ATOM | 4214 | CA  | ALA | C | 348 | 56.106 | 56.295 | 22.881 | 1.00 | 35.48 | C |
| ATOM | 4215 | CB  | ALA | C | 348 | 55.595 | 57.685 | 23.296 | 1.00 | 33.20 | C |
| ATOM | 4216 | C   | ALA | C | 348 | 55.512 | 55.784 | 21.531 | 1.00 | 34.86 | C |
| ATOM | 4217 | O   | ALA | C | 348 | 54.460 | 55.204 | 21.539 | 1.00 | 36.31 | C |
| ATOM | 4218 | N   | ILE | C | 349 | 56.170 | 55.977 | 20.406 | 1.00 | 33.93 | C |
| ATOM | 4219 | CA  | ILE | C | 349 | 55.615 | 55.565 | 19.139 | 1.00 | 33.70 | C |
| ATOM | 4220 | CB  | ILE | C | 349 | 56.390 | 56.160 | 17.972 | 1.00 | 31.97 | C |
| ATOM | 4221 | CG2 | ILE | C | 349 | 55.772 | 55.692 | 16.684 | 1.00 | 31.20 | C |
| ATOM | 4222 | CG1 | ILE | C | 349 | 56.328 | 57.692 | 18.017 | 1.00 | 31.70 | C |
| ATOM | 4223 | CD1 | ILE | C | 349 | 56.963 | 58.415 | 16.889 | 1.00 | 33.26 | C |
| ATOM | 4224 | C   | ILE | C | 349 | 55.603 | 54.042 | 19.096 | 1.00 | 34.98 | C |
| ATOM | 4225 | O   | ILE | C | 349 | 54.693 | 53.394 | 18.503 | 1.00 | 33.89 | C |
| ATOM | 4226 | N   | LEU | C | 350 | 56.625 | 53.462 | 19.698 | 1.00 | 35.98 | C |
| ATOM | 4227 | CA  | LEU | C | 350 | 56.765 | 51.988 | 19.707 | 1.00 | 37.85 | C |
| ATOM | 4228 | CB  | LEU | C | 350 | 58.075 | 51.509 | 20.275 | 1.00 | 37.46 | C |
| ATOM | 4229 | CG  | LEU | C | 350 | 59.202 | 51.558 | 19.312 | 1.00 | 37.77 | C |
| ATOM | 4230 | CD1 | LEU | C | 350 | 60.539 | 51.346 | 20.078 | 1.00 | 38.99 | C |
| ATOM | 4231 | CD2 | LEU | C | 350 | 59.032 | 50.533 | 18.237 | 1.00 | 38.30 | C |
| ATOM | 4232 | C   | LEU | C | 350 | 55.694 | 51.375 | 20.510 | 1.00 | 38.76 | C |
| ATOM | 4233 | O   | LEU | C | 350 | 55.254 | 50.315 | 20.162 | 1.00 | 40.67 | C |
| ATOM | 4234 | N   | GLN | C | 351 | 55.179 | 52.069 | 21.507 | 1.00 | 38.55 | C |
| ATOM | 4235 | CA  | GLN | C | 351 | 54.021 | 51.557 | 22.299 | 1.00 | 39.88 | C |
| ATOM | 4236 | CB  | GLN | C | 351 | 53.817 | 52.439 | 23.572 | 1.00 | 40.09 | C |
| ATOM | 4237 | CG  | GLN | C | 351 | 52.445 | 52.299 | 24.258 | 1.00 | 42.72 | C |
| ATOM | 4238 | CD  | GLN | C | 351 | 52.132 | 53.363 | 25.423 | 1.00 | 43.17 | C |
| ATOM | 4239 | OE1 | GLN | C | 351 | 52.441 | 54.562 | 25.320 | 1.00 | 44.76 | C |
| ATOM | 4240 | NE2 | GLN | C | 351 | 51.552 | 52.886 | 26.494 | 1.00 | 44.13 | C |
| ATOM | 4241 | C   | GLN | C | 351 | 52.758 | 51.380 | 21.368 | 1.00 | 40.04 | C |
| ATOM | 4242 | O   | GLN | C | 351 | 52.047 | 50.355 | 21.333 | 1.00 | 40.07 | C |
| ATOM | 4243 | N   | LEU | C | 352 | 52.481 | 52.397 | 20.568 | 1.00 | 39.94 | C |
| ATOM | 4244 | CA  | LEU | C | 352 | 51.398 | 52.271 | 19.562 | 1.00 | 39.94 | C |
| ATOM | 4245 | CB  | LEU | C | 352 | 51.340 | 53.536 | 18.778 | 1.00 | 39.07 | C |
| ATOM | 4246 | CG  | LEU | C | 352 | 50.139 | 54.048 | 18.158 | 1.00 | 39.14 | C |
| ATOM | 4247 | CD1 | LEU | C | 352 | 49.084 | 54.045 | 19.107 | 1.00 | 40.05 | C |
| ATOM | 4248 | CD2 | LEU | C | 352 | 50.567 | 55.560 | 17.802 | 1.00 | 39.65 | C |
| ATOM | 4249 | C   | LEU | C | 352 | 51.676 | 51.137 | 18.593 | 1.00 | 40.60 | C |

TABLE 2-continued

ATOMIC COORDINATES OF THE ERR3 LBD/ DIETHYLSTILBESTROL COMPLEX

| ATOM | 4250 | O   | LEU | C | 352 | 50.808 | 50.406 | 18.261 | 1.00 | 41.08 | C |
|------|------|-----|-----|---|-----|--------|--------|--------|------|-------|---|
| ATOM | 4251 | N   | VAL | C | 353 | 52.900 | 50.993 | 18.153 | 1.00 | 41.41 | C |
| ATOM | 4252 | CA  | VAL | C | 353 | 53.278 | 49.861 | 17.287 | 1.00 | 43.07 | C |
| ATOM | 4253 | CB  | VAL | C | 353 | 54.753 | 49.869 | 17.023 | 1.00 | 42.51 | C |
| ATOM | 4254 | CG1 | VAL | C | 353 | 55.188 | 48.582 | 16.266 | 1.00 | 41.75 | C |
| ATOM | 4255 | CG2 | VAL | C | 353 | 55.040 | 50.960 | 16.178 | 1.00 | 41.13 | C |
| ATOM | 4256 | C   | VAL | C | 353 | 52.978 | 48.560 | 18.030 | 1.00 | 44.72 | C |
| ATOM | 4257 | O   | VAL | C | 353 | 52.304 | 47.659 | 17.514 | 1.00 | 45.77 | C |
| ATOM | 4258 | N   | LYS | C | 354 | 53.449 | 48.458 | 19.254 | 1.00 | 46.52 | C |
| ATOM | 4259 | CA  | LYS | C | 354 | 53.265 | 47.213 | 19.979 | 1.00 | 48.44 | C |
| ATOM | 4260 | CB  | LYS | C | 354 | 53.817 | 47.231 | 21.397 | 1.00 | 51.74 | C |
| ATOM | 4261 | CG  | LYS | C | 354 | 53.797 | 45.873 | 22.109 | 1.00 | 57.60 | C |
| ATOM | 4262 | CD  | LYS | C | 354 | 54.361 | 45.943 | 23.529 | 1.00 | 61.07 | C |
| ATOM | 4263 | CE  | LYS | C | 354 | 55.881 | 46.083 | 23.551 | 1.00 | 63.56 | C |
| ATOM | 4264 | NZ  | LYS | C | 354 | 56.554 | 44.929 | 22.890 | 1.00 | 66.06 | C |
| ATOM | 4265 | C   | LYS | C | 354 | 51.810 | 46.902 | 19.974 | 1.00 | 47.86 | C |
| ATOM | 4266 | O   | LYS | C | 354 | 51.398 | 45.712 | 19.789 | 1.00 | 48.05 | C |
| ATOM | 4267 | N   | LYS | C | 355 | 50.992 | 47.922 | 20.084 | 1.00 | 45.86 | C |
| ATOM | 4268 | CA  | LYS | C | 355 | 49.568 | 47.627 | 20.260 | 1.00 | 45.62 | C |
| ATOM | 4269 | CB  | LYS | C | 355 | 48.809 | 48.797 | 20.879 | 1.00 | 44.76 | C |
| ATOM | 4270 | CG  | LYS | C | 355 | 47.467 | 48.394 | 21.430 | 1.00 | 45.56 | C |
| ATOM | 4271 | CD  | LYS | C | 355 | 46.420 | 49.545 | 21.518 | 1.00 | 46.22 | C |
| ATOM | 4272 | CE  | LYS | C | 355 | 46.604 | 50.582 | 22.779 | 1.00 | 46.43 | C |
| ATOM | 4273 | NZ  | LYS | C | 355 | 45.766 | 51.912 | 22.680 | 1.00 | 45.30 | C |
| ATOM | 4274 | C   | LYS | C | 355 | 48.967 | 47.183 | 18.922 | 1.00 | 45.39 | C |
| ATOM | 4275 | O   | LYS | C | 355 | 48.249 | 46.142 | 18.794 | 1.00 | 45.77 | C |
| ATOM | 4276 | N   | TYR | C | 356 | 49.219 | 47.904 | 17.881 | 1.00 | 44.20 | C |
| ATOM | 4277 | CA  | TYR | C | 356 | 48.620 | 47.417 | 16.634 | 1.00 | 44.20 | C |
| ATOM | 4278 | CB  | TYR | C | 356 | 48.913 | 48.428 | 15.541 | 1.00 | 41.22 | C |
| ATOM | 4279 | CG  | TYR | C | 356 | 48.097 | 49.717 | 15.654 | 1.00 | 38.91 | C |
| ATOM | 4280 | CD1 | TYR | C | 356 | 46.749 | 49.672 | 15.603 | 1.00 | 37.06 | C |
| ATOM | 4281 | CE1 | TYR | C | 356 | 45.961 | 50.807 | 15.660 | 1.00 | 38.22 | C |
| ATOM | 4282 | CD2 | TYR | C | 356 | 48.701 | 50.953 | 15.729 | 1.00 | 37.67 | C |
| ATOM | 4283 | CE2 | TYR | C | 356 | 47.899 | 52.173 | 15.791 | 1.00 | 36.40 | C |
| ATOM | 4284 | CZ  | TYR | C | 356 | 46.533 | 52.053 | 15.769 | 1.00 | 37.42 | C |
| ATOM | 4285 | OH  | TYR | C | 356 | 45.709 | 53.132 | 15.853 | 1.00 | 37.67 | C |
| ATOM | 4286 | C   | TYR | C | 356 | 49.224 | 46.014 | 16.261 | 1.00 | 46.02 | C |
| ATOM | 4287 | O   | TYR | C | 356 | 48.614 | 45.228 | 15.507 | 1.00 | 47.28 | C |
| ATOM | 4288 | N   | LYS | C | 357 | 50.425 | 45.702 | 16.705 | 1.00 | 47.16 | C |
| ATOM | 4289 | CA  | LYS | C | 357 | 51.067 | 44.415 | 16.261 | 1.00 | 49.40 | C |
| ATOM | 4290 | CB  | LYS | C | 357 | 52.564 | 44.290 | 16.654 | 1.00 | 49.28 | C |
| ATOM | 4291 | CG  | LYS | C | 357 | 53.556 | 44.750 | 15.635 | 1.00 | 49.74 | C |
| ATOM | 4292 | CD  | LYS | C | 357 | 54.955 | 44.945 | 16.223 | 1.00 | 51.15 | C |
| ATOM | 4293 | CE  | LYS | C | 357 | 55.937 | 43.711 | 16.497 | 1.00 | 52.80 | C |
| ATOM | 4294 | NZ  | LYS | C | 357 | 57.173 | 44.185 | 17.363 | 1.00 | 52.98 | C |
| ATOM | 4295 | C   | LYS | C | 357 | 50.301 | 43.319 | 16.960 | 1.00 | 49.76 | C |
| ATOM | 4296 | O   | LYS | C | 357 | 49.824 | 42.416 | 16.400 | 1.00 | 50.49 | C |
| ATOM | 4297 | N   | SER | C | 358 | 50.221 | 43.421 | 18.231 | 1.00 | 50.13 | C |
| ATOM | 4298 | CA  | SER | C | 358 | 49.382 | 42.556 | 18.994 | 1.00 | 51.22 | C |
| ATOM | 4299 | CB  | SER | C | 358 | 49.279 | 43.158 | 20.319 | 1.00 | 51.24 | C |
| ATOM | 4300 | OG  | SER | C | 358 | 47.955 | 43.569 | 20.375 | 1.00 | 52.86 | C |
| ATOM | 4301 | C   | SER | C | 358 | 47.922 | 42.340 | 18.469 | 1.00 | 52.23 | C |
| ATOM | 4302 | O   | SER | C | 358 | 47.218 | 41.332 | 18.792 | 1.00 | 53.57 | C |
| ATOM | 4303 | N   | MET | C | 359 | 47.421 | 43.273 | 17.679 | 1.00 | 52.31 | C |
| ATOM | 4304 | CA  | MET | C | 359 | 46.098 | 43.086 | 17.090 | 1.00 | 52.30 | C |
| ATOM | 4305 | CB  | MET | C | 359 | 45.300 | 44.404 | 17.133 | 1.00 | 52.23 | C |
| ATOM | 4306 | CG  | MET | C | 359 | 44.980 | 44.891 | 18.472 | 1.00 | 53.31 | C |
| ATOM | 4307 | SD  | MET | C | 359 | 44.676 | 46.728 | 18.408 | 1.00 | 53.74 | C |
| ATOM | 4308 | CE  | MET | C | 359 | 42.987 | 46.633 | 18.115 | 1.00 | 51.76 | C |
| ATOM | 4309 | C   | MET | C | 359 | 46.180 | 42.668 | 15.639 | 1.00 | 51.81 | C |
| ATOM | 4310 | O   | MET | C | 359 | 45.166 | 42.558 | 15.005 | 1.00 | 51.04 | C |
| ATOM | 4311 | N   | LYS | C | 360 | 47.383 | 42.564 | 15.110 | 1.00 | 52.21 | C |
| ATOM | 4312 | CA  | LYS | C | 360 | 47.623 | 42.223 | 13.721 | 1.00 | 53.14 | C |
| ATOM | 4313 | CB  | LYS | C | 360 | 47.501 | 40.689 | 13.519 | 1.00 | 56.77 | C |
| ATOM | 4314 | CG  | LYS | C | 360 | 47.804 | 40.186 | 12.102 | 1.00 | 61.96 | C |
| ATOM | 4315 | CD  | LYS | C | 360 | 49.298 | 40.194 | 11.762 | 1.00 | 65.73 | C |
| ATOM | 4316 | CE  | LYS | C | 360 | 49.823 | 41.585 | 11.429 | 1.00 | 67.62 | C |
| ATOM | 4317 | NZ  | LYS | C | 360 | 51.268 | 41.561 | 11.069 | 1.00 | 69.10 | C |
| ATOM | 4318 | C   | LYS | C | 360 | 46.756 | 43.062 | 12.793 | 1.00 | 52.37 | C |
| ATOM | 4319 | O   | LYS | C | 360 | 46.006 | 42.582 | 11.945 | 1.00 | 51.77 | C |
| ATOM | 4320 | N   | LEU | C | 361 | 46.860 | 44.366 | 12.995 | 1.00 | 51.31 | C |
| ATOM | 4321 | CA  | LEU | C | 361 | 46.417 | 45.359 | 12.077 | 1.00 | 50.10 | C |
| ATOM | 4322 | CB  | LEU | C | 361 | 46.969 | 46.737 | 12.542 | 1.00 | 49.35 | C |
| ATOM | 4323 | CG  | LEU | C | 361 | 46.694 | 47.949 | 11.699 | 1.00 | 49.04 | C |
| ATOM | 4324 | CD1 | LEU | C | 361 | 45.246 | 48.375 | 11.904 | 1.00 | 47.40 | C |
| ATOM | 4325 | CD2 | LEU | C | 361 | 47.692 | 49.121 | 12.013 | 1.00 | 48.16 | C |

TABLE 2-continued

ATOMIC COORDINATES OF THE ERR3 LBD/
DIETHYLSTILBESTROL COMPLEX

| ATOM | 4326 | C | LEU | C | 361 | 46.738 | 45.115 | 10.560 | 1.00 | 50.38 | C |
|---|---|---|---|---|---|---|---|---|---|---|---|
| ATOM | 4327 | O | LEU | C | 361 | 47.894 | 44.841 | 10.100 | 1.00 | 48.76 | C |
| ATOM | 4328 | N | GLU | C | 362 | 45.700 | 45.447 | 9.793 | 1.00 | 51.57 | C |
| ATOM | 4329 | CA | GLU | C | 362 | 45.638 | 45.178 | 8.335 | 1.00 | 52.34 | C |
| ATOM | 4330 | CB | GLU | C | 362 | 44.768 | 44.213 | 7.857 | 0.00 | 56.57 | C |
| ATOM | 4331 | CG | GLU | C | 362 | 45.127 | 43.845 | 6.282 | 1.00 | 63.81 | C |
| ATOM | 4332 | CD | GLU | C | 362 | 44.532 | 42.533 | 5.773 | 1.00 | 68.26 | C |
| ATOM | 4333 | OE1 | GLU | C | 362 | 44.563 | 42.314 | 4.544 | 1.00 | 69.53 | C |
| ATOM | 4334 | OE2 | GLU | C | 362 | 44.050 | 41.717 | 6.585 | 1.00 | 71.48 | C |
| ATOM | 4335 | C | GLU | C | 362 | 45.671 | 46.502 | 7.609 | 1.00 | 49.84 | C |
| ATOM | 4336 | O | GLU | C | 362 | 45.162 | 47.484 | 8.102 | 1.00 | 48.02 | C |
| ATOM | 4337 | N | LYS | C | 363 | 46.273 | 46.472 | 6.431 | 1.00 | 48.54 | C |
| ATOM | 4338 | CA | LYS | C | 363 | 46.395 | 47.577 | 5.504 | 1.00 | 47.76 | C |
| ATOM | 4339 | CB | LYS | C | 363 | 46.964 | 47.122 | 4.129 | 1.00 | 48.50 | C |
| ATOM | 4340 | CG | LYS | C | 363 | 47.275 | 48.281 | 3.055 | 1.00 | 51.14 | C |
| ATOM | 4341 | CD | LYS | C | 363 | 48.823 | 48.717 | 2.935 | 1.00 | 54.24 | C |
| ATOM | 4342 | CE | LYS | C | 363 | 49.887 | 47.587 | 2.483 | 1.00 | 55.67 | C |
| ATOM | 4343 | NZ | LYS | C | 363 | 51.343 | 47.582 | 3.066 | 1.00 | 57.54 | C |
| ATOM | 4344 | C | LYS | C | 363 | 45.070 | 48.282 | 5.362 | 1.00 | 46.19 | C |
| ATOM | 4345 | O | LYS | C | 363 | 44.998 | 49.564 | 5.167 | 1.00 | 46.00 | C |
| ATOM | 4346 | N | GLU | C | 364 | 44.020 | 47.457 | 5.415 | 1.00 | 44.81 | C |
| ATOM | 4347 | CA | GLU | C | 364 | 42.622 | 47.927 | 5.167 | 1.00 | 43.75 | C |
| ATOM | 4348 | CB | GLU | C | 364 | 41.636 | 46.714 | 4.906 | 1.00 | 44.91 | C |
| ATOM | 4349 | CG | GLU | C | 364 | 41.632 | 46.209 | 3.420 | 1.00 | 46.74 | C |
| ATOM | 4350 | CD | GLU | C | 364 | 42.769 | 45.193 | 3.195 | 1.00 | 47.69 | C |
| ATOM | 4351 | OE1 | GLU | C | 364 | 43.429 | 44.704 | 4.181 | 1.00 | 49.75 | C |
| ATOM | 4352 | OE2 | GLU | C | 364 | 42.977 | 44.824 | 2.052 | 1.00 | 49.94 | C |
| ATOM | 4353 | C | GLU | C | 364 | 42.147 | 48.774 | 6.352 | 1.00 | 41.18 | C |
| ATOM | 4354 | O | GLU | C | 364 | 41.384 | 49.693 | 6.236 | 1.00 | 40.24 | C |
| ATOM | 4355 | N | GLU | C | 365 | 42.539 | 48.301 | 7.507 | 1.00 | 40.60 | C |
| ATOM | 4356 | CA | GLU | C | 365 | 42.253 | 48.883 | 8.850 | 1.00 | 40.47 | C |
| ATOM | 4357 | CB | GLU | C | 365 | 42.480 | 47.856 | 9.947 | 1.00 | 40.64 | C |
| ATOM | 4358 | CG | GLU | C | 365 | 41.869 | 46.497 | 9.633 | 1.00 | 40.84 | C |
| ATOM | 4359 | CD | GLU | C | 365 | 41.877 | 45.500 | 10.728 | 1.00 | 40.83 | C |
| ATOM | 4360 | OE1 | GLU | C | 365 | 42.974 | 45.079 | 11.104 | 1.00 | 42.44 | C |
| ATOM | 4361 | OE2 | GLU | C | 365 | 40.769 | 45.194 | 11.215 | 1.00 | 41.65 | C |
| ATOM | 4362 | C | GLU | C | 365 | 43.105 | 50.118 | 8.971 | 1.00 | 39.92 | C |
| ATOM | 4363 | O | GLU | C | 365 | 42.580 | 51.174 | 9.024 | 1.00 | 39.71 | C |
| ATOM | 4364 | N | PHE | C | 366 | 44.392 | 50.003 | 8.652 | 1.00 | 41.25 | C |
| ATOM | 4365 | CA | PHE | C | 366 | 45.340 | 51.172 | 8.577 | 1.00 | 39.97 | C |
| ATOM | 4366 | CB | PHE | C | 366 | 46.654 | 50.687 | 8.079 | 1.00 | 40.37 | C |
| ATOM | 4367 | CG | PHE | C | 366 | 47.553 | 51.778 | 7.606 | 1.00 | 41.79 | C |
| ATOM | 4368 | CD1 | PHE | C | 366 | 47.918 | 52.803 | 8.473 | 1.00 | 40.40 | C |
| ATOM | 4369 | CD2 | PHE | C | 366 | 48.085 | 51.775 | 6.298 | 1.00 | 42.27 | C |
| ATOM | 4370 | CE1 | PHE | C | 366 | 48.732 | 53.815 | 8.068 | 1.00 | 39.90 | C |
| ATOM | 4371 | CE2 | PHE | C | 366 | 48.977 | 52.834 | 5.877 | 1.00 | 42.46 | C |
| ATOM | 4372 | CZ | PHE | C | 366 | 49.312 | 53.852 | 6.819 | 1.00 | 40.51 | C |
| ATOM | 4373 | C | PHE | C | 366 | 44.852 | 52.327 | 7.743 | 1.00 | 40.11 | C |
| ATOM | 4374 | O | PHE | C | 366 | 44.669 | 53.482 | 8.263 | 1.00 | 39.44 | C |
| ATOM | 4375 | N | VAL | C | 367 | 44.475 | 52.073 | 6.487 | 1.00 | 39.40 | C |
| ATOM | 4376 | CA | VAL | C | 367 | 44.139 | 53.191 | 5.647 | 1.00 | 39.11 | C |
| ATOM | 4377 | CB | VAL | C | 367 | 44.188 | 52.813 | 4.147 | 1.00 | 40.89 | C |
| ATOM | 4378 | CG1 | VAL | C | 367 | 45.528 | 52.193 | 3.842 | 1.00 | 41.47 | C |
| ATOM | 4379 | CG2 | VAL | C | 367 | 43.032 | 51.843 | 3.752 | 1.00 | 40.60 | C |
| ATOM | 4380 | C | VAL | C | 367 | 42.832 | 53.868 | 6.020 | 1.00 | 38.50 | C |
| ATOM | 4381 | O | VAL | C | 367 | 42.597 | 55.029 | 5.729 | 1.00 | 38.84 | C |
| ATOM | 4382 | N | THR | C | 368 | 41.985 | 53.120 | 6.660 | 1.00 | 37.38 | C |
| ATOM | 4383 | CA | THR | C | 368 | 40.715 | 53.619 | 7.194 | 1.00 | 37.42 | C |
| ATOM | 4384 | CB | THR | C | 368 | 39.748 | 52.392 | 7.356 | 1.00 | 39.16 | C |
| ATOM | 4385 | OG1 | THR | C | 368 | 39.666 | 51.586 | 6.129 | 1.00 | 39.86 | C |
| ATOM | 4386 | CG2 | THR | C | 368 | 38.348 | 52.800 | 7.610 | 1.00 | 39.20 | C |
| ATOM | 4387 | C | THR | C | 368 | 40.850 | 54.343 | 8.517 | 1.00 | 36.53 | C |
| ATOM | 4388 | O | THR | C | 368 | 40.166 | 55.309 | 8.757 | 1.00 | 35.96 | C |
| ATOM | 4389 | N | LEU | C | 369 | 41.789 | 53.940 | 9.352 | 1.00 | 35.91 | C |
| ATOM | 4390 | CA | LEU | C | 369 | 42.110 | 54.721 | 10.597 | 1.00 | 36.38 | C |
| ATOM | 4391 | CB | LEU | C | 369 | 42.922 | 53.923 | 11.594 | 1.00 | 35.33 | C |
| ATOM | 4392 | CG | LEU | C | 369 | 42.146 | 52.812 | 12.226 | 1.00 | 36.91 | C |
| ATOM | 4393 | CD1 | LEU | C | 369 | 43.137 | 51.845 | 12.935 | 1.00 | 37.62 | C |
| ATOM | 4394 | CD2 | LEU | C | 369 | 41.050 | 53.197 | 13.187 | 1.00 | 35.77 | C |
| ATOM | 4395 | C | LEU | C | 369 | 42.729 | 56.038 | 10.303 | 1.00 | 35.05 | C |
| ATOM | 4396 | O | LEU | C | 369 | 42.266 | 57.022 | 10.862 | 1.00 | 34.70 | C |
| ATOM | 4397 | N | LYS | C | 370 | 43.591 | 56.112 | 9.281 | 1.00 | 34.88 | C |
| ATOM | 4398 | CA | LYS | C | 370 | 44.153 | 57.379 | 8.808 | 1.00 | 34.98 | C |
| ATOM | 4399 | CB | LYS | C | 370 | 45.047 | 57.239 | 7.583 | 1.00 | 35.98 | C |
| ATOM | 4400 | CG | LYS | C | 370 | 46.326 | 56.642 | 7.833 | 1.00 | 38.10 | C |
| ATOM | 4401 | CD | LYS | C | 370 | 47.438 | 57.021 | 6.755 | 1.00 | 39.63 | C |

TABLE 2-continued

ATOMIC COORDINATES OF THE ERR3 LBD/
DIETHYLSTILBESTROL COMPLEX

| ATOM | 4402 | CE | LYS | C | 370 | 47.134 | 56.445 | 5.342 | 1.00 | 40.14 | C |
|------|------|-----|-----|---|-----|--------|--------|--------|------|-------|---|
| ATOM | 4403 | NZ | LYS | C | 370 | 48.304 | 56.593 | 4.523 | 1.00 | 40.24 | C |
| ATOM | 4404 | C | LYS | C | 370 | 43.093 | 58.310 | 8.404 | 1.00 | 35.36 | C |
| ATOM | 4405 | O | LYS | C | 370 | 43.129 | 59.461 | 8.710 | 1.00 | 33.97 | C |
| ATOM | 4406 | N | ALA | C | 371 | 42.119 | 57.807 | 7.646 | 1.00 | 35.33 | C |
| ATOM | 4407 | CA | ALA | C | 371 | 41.045 | 58.685 | 7.198 | 1.00 | 34.58 | C |
| ATOM | 4408 | CB | ALA | C | 371 | 40.227 | 57.981 | 5.958 | 1.00 | 35.02 | C |
| ATOM | 4409 | C | ALA | C | 371 | 40.163 | 59.075 | 8.359 | 1.00 | 33.40 | C |
| ATOM | 4410 | O | ALA | C | 371 | 39.672 | 60.186 | 8.483 | 1.00 | 33.30 | C |
| ATOM | 4411 | N | ILE | C | 372 | 39.952 | 58.195 | 9.266 | 1.00 | 33.50 | C |
| ATOM | 4412 | CA | ILE | C | 372 | 39.040 | 58.547 | 10.401 | 1.00 | 32.92 | C |
| ATOM | 4413 | CB | ILE | C | 372 | 38.742 | 57.249 | 11.220 | 1.00 | 33.42 | C |
| ATOM | 4414 | CG2 | ILE | C | 372 | 38.155 | 57.624 | 12.566 | 1.00 | 33.14 | C |
| ATOM | 4415 | CG1 | ILE | C | 372 | 37.782 | 56.364 | 10.470 | 1.00 | 34.03 | C |
| ATOM | 4416 | CD1 | ILE | C | 372 | 37.611 | 54.817 | 10.998 | 1.00 | 32.76 | C |
| ATOM | 4417 | C | ILE | C | 372 | 39.816 | 59.573 | 11.317 | 1.00 | 32.48 | C |
| ATOM | 4418 | O | ILE | C | 372 | 39.295 | 60.577 | 11.831 | 1.00 | 31.26 | C |
| ATOM | 4419 | N | ALA | C | 373 | 41.095 | 59.313 | 11.499 | 1.00 | 31.23 | C |
| ATOM | 4420 | CA | ALA | C | 373 | 41.897 | 60.251 | 12.297 | 1.00 | 31.16 | C |
| ATOM | 4421 | CB | ALA | C | 373 | 43.314 | 59.821 | 12.395 | 1.00 | 30.05 | C |
| ATOM | 4422 | C | ALA | C | 373 | 41.811 | 61.634 | 11.701 | 1.00 | 30.13 | C |
| ATOM | 4423 | O | ALA | C | 373 | 41.706 | 62.642 | 12.454 | 1.00 | 29.16 | C |
| ATOM | 4424 | N | LEU | C | 374 | 41.814 | 61.723 | 10.359 | 1.00 | 30.09 | C |
| ATOM | 4425 | CA | LEU | C | 374 | 41.736 | 63.054 | 9.738 | 1.00 | 29.38 | C |
| ATOM | 4426 | CB | LEU | C | 374 | 42.114 | 62.922 | 8.238 | 1.00 | 30.56 | C |
| ATOM | 4427 | CG | LEU | C | 374 | 41.708 | 64.154 | 7.346 | 1.00 | 32.66 | C |
| ATOM | 4428 | CD1 | LEU | C | 374 | 42.540 | 65.446 | 7.855 | 1.00 | 29.27 | C |
| ATOM | 4429 | CD2 | LEU | C | 374 | 42.052 | 63.954 | 5.927 | 1.00 | 30.07 | C |
| ATOM | 4430 | C | LEU | C | 374 | 40.378 | 63.719 | 10.014 | 1.00 | 30.44 | C |
| ATOM | 4431 | O | LEU | C | 374 | 40.233 | 64.874 | 10.540 | 1.00 | 30.41 | C |
| ATOM | 4432 | N | ALA | C | 375 | 39.314 | 62.936 | 9.778 | 1.00 | 30.21 | C |
| ATOM | 4433 | CA | ALA | C | 375 | 38.000 | 63.465 | 9.914 | 1.00 | 29.46 | C |
| ATOM | 4434 | CB | ALA | C | 375 | 36.978 | 62.429 | 9.251 | 1.00 | 30.27 | C |
| ATOM | 4435 | C | ALA | C | 375 | 37.639 | 63.694 | 11.334 | 1.00 | 28.82 | C |
| ATOM | 4436 | O | ALA | C | 375 | 36.769 | 64.494 | 11.609 | 1.00 | 26.98 | C |
| ATOM | 4437 | N | ASN | C | 376 | 38.183 | 62.914 | 12.265 | 1.00 | 28.83 | C |
| ATOM | 4438 | CA | ASN | C | 376 | 37.819 | 63.115 | 13.728 | 1.00 | 29.51 | C |
| ATOM | 4439 | CB | ASN | C | 376 | 37.612 | 61.756 | 14.319 | 1.00 | 29.31 | C |
| ATOM | 4440 | CG | ASN | C | 376 | 36.913 | 61.798 | 15.637 | 1.00 | 30.07 | C |
| ATOM | 4441 | OD1 | ASN | C | 376 | 35.997 | 62.604 | 15.880 | 1.00 | 33.18 | C |
| ATOM | 4442 | ND2 | ASN | C | 376 | 37.492 | 61.099 | 16.558 | 1.00 | 29.47 | C |
| ATOM | 4443 | C | ASN | C | 376 | 38.852 | 63.941 | 14.600 | 1.00 | 30.39 | C |
| ATOM | 4444 | O | ASN | C | 376 | 38.998 | 63.771 | 15.850 | 1.00 | 28.84 | C |
| ATOM | 4445 | N | SER | C | 377 | 39.541 | 64.883 | 13.934 | 1.00 | 31.15 | C |
| ATOM | 4446 | CA | SER | C | 377 | 40.684 | 65.497 | 14.504 | 1.00 | 29.99 | C |
| ATOM | 4447 | CB | SER | C | 377 | 41.606 | 65.867 | 13.336 | 1.00 | 30.70 | C |
| ATOM | 4448 | OG | SER | C | 377 | 41.054 | 66.819 | 12.439 | 1.00 | 31.39 | C |
| ATOM | 4449 | C | SER | C | 377 | 40.355 | 66.664 | 15.420 | 1.00 | 31.22 | C |
| ATOM | 4450 | O | SER | C | 377 | 41.228 | 67.251 | 16.021 | 1.00 | 31.29 | C |
| ATOM | 4451 | N | ASP | C | 378 | 39.103 | 67.022 | 15.571 | 1.00 | 31.34 | C |
| ATOM | 4452 | CA | ASP | C | 378 | 38.648 | 67.988 | 16.591 | 1.00 | 31.88 | C |
| ATOM | 4453 | CB | ASP | C | 378 | 38.929 | 67.476 | 18.060 | 1.00 | 32.05 | C |
| ATOM | 4454 | CG | ASP | C | 378 | 38.110 | 66.246 | 18.370 | 1.00 | 30.31 | C |
| ATOM | 4455 | OD1 | ASP | C | 378 | 36.878 | 66.178 | 18.146 | 1.00 | 32.43 | C |
| ATOM | 4456 | OD2 | ASP | C | 378 | 38.615 | 65.197 | 18.520 | 1.00 | 29.05 | C |
| ATOM | 4457 | C | ASP | C | 378 | 39.169 | 69.376 | 16.439 | 1.00 | 32.37 | C |
| ATOM | 4458 | O | ASP | C | 378 | 39.238 | 70.095 | 17.415 | 1.00 | 31.12 | C |
| ATOM | 4459 | N | SER | C | 379 | 39.408 | 69.826 | 15.227 | 1.00 | 33.92 | C |
| ATOM | 4460 | CA | SER | C | 379 | 39.683 | 71.248 | 14.995 | 1.00 | 37.04 | C |
| ATOM | 4461 | CB | SER | C | 379 | 39.691 | 71.630 | 13.504 | 1.00 | 35.97 | C |
| ATOM | 4462 | OG | SER | C | 379 | 39.820 | 73.025 | 13.495 | 1.00 | 35.83 | C |
| ATOM | 4463 | C | SER | C | 379 | 38.690 | 72.132 | 15.706 | 1.00 | 40.02 | C |
| ATOM | 4464 | O | SER | C | 379 | 37.506 | 71.867 | 15.741 | 1.00 | 40.33 | C |
| ATOM | 4465 | N | MET | C | 380 | 39.154 | 73.205 | 16.296 | 1.00 | 43.03 | C |
| ATOM | 4466 | CA | MET | C | 380 | 38.214 | 74.185 | 16.873 | 1.00 | 46.25 | C |
| ATOM | 4467 | CB | MET | C | 380 | 38.884 | 74.902 | 18.098 | 1.00 | 52.05 | C |
| ATOM | 4468 | CG | MET | C | 380 | 37.873 | 75.675 | 18.942 | 1.00 | 61.56 | C |
| ATOM | 4469 | SD | MET | C | 380 | 38.509 | 76.361 | 20.483 | 1.00 | 70.97 | C |
| ATOM | 4470 | CE | MET | C | 380 | 38.506 | 78.113 | 20.100 | 1.00 | 69.59 | C |
| ATOM | 4471 | C | MET | C | 380 | 37.657 | 75.168 | 15.804 | 1.00 | 46.07 | C |
| ATOM | 4472 | O | MET | C | 380 | 36.822 | 75.991 | 16.089 | 1.00 | 45.90 | C |
| ATOM | 4473 | N | HIS | C | 381 | 38.028 | 75.044 | 14.544 | 1.00 | 45.07 | C |
| ATOM | 4474 | CA | HIS | C | 381 | 37.694 | 76.105 | 13.625 | 1.00 | 45.19 | C |
| ATOM | 4475 | CB | HIS | C | 381 | 38.942 | 76.642 | 12.820 | 1.00 | 43.51 | C |
| ATOM | 4476 | CG | HIS | C | 381 | 40.036 | 77.071 | 13.709 | 1.00 | 44.72 | C |
| ATOM | 4477 | CD2 | HIS | C | 381 | 41.258 | 76.521 | 13.966 | 1.00 | 44.12 | C |

TABLE 2-continued

ATOMIC COORDINATES OF THE ERR3 LBD/
DIETHYLSTILBESTROL COMPLEX

| ATOM | 4478 | ND1 | HIS | C | 381 | 39.888 | 78.127 | 14.564 | 1.00 | 44.49 | C |
|------|------|-----|-----|---|-----|--------|--------|--------|------|-------|---|
| ATOM | 4479 | CE1 | HIS | C | 381 | 40.962 | 78.224 | 15.325 | 1.00 | 44.38 | C |
| ATOM | 4480 | NE2 | HIS | C | 381 | 41.820 | 77.262 | 14.969 | 1.00 | 43.62 | C |
| ATOM | 4481 | C   | HIS | C | 381 | 36.672 | 75.606 | 12.636 | 1.00 | 45.55 | C |
| ATOM | 4482 | O   | HIS | C | 381 | 36.625 | 76.175 | 11.568 | 1.00 | 44.96 | C |
| ATOM | 4483 | N   | ILE | C | 382 | 35.949 | 74.532 | 12.915 | 1.00 | 46.22 | C |
| ATOM | 4484 | CA  | ILE | C | 382 | 35.160 | 73.971 | 11.846 | 1.00 | 46.98 | C |
| ATOM | 4485 | CB  | ILE | C | 382 | 34.730 | 72.574 | 12.129 | 1.00 | 47.47 | C |
| ATOM | 4486 | CG2 | ILE | C | 382 | 33.768 | 72.061 | 11.049 | 1.00 | 46.83 | C |
| ATOM | 4487 | CG1 | ILE | C | 382 | 35.975 | 71.663 | 12.088 | 1.00 | 47.51 | C |
| ATOM | 4488 | CD1 | ILE | C | 382 | 36.681 | 71.720 | 10.731 | 1.00 | 47.43 | C |
| ATOM | 4489 | C   | ILE | C | 382 | 34.037 | 74.995 | 11.654 | 1.00 | 47.32 | C |
| ATOM | 4490 | O   | ILE | C | 382 | 33.711 | 75.661 | 12.591 | 1.00 | 48.00 | C |
| ATOM | 4491 | N   | GLU | C | 383 | 33.660 | 75.261 | 10.411 | 1.00 | 47.54 | C |
| ATOM | 4492 | CA  | GLU | C | 383 | 32.451 | 76.079 | 10.047 | 1.00 | 48.42 | C |
| ATOM | 4493 | CB  | GLU | C | 383 | 32.565 | 76.764 | 8.659  | 1.00 | 49.79 | C |
| ATOM | 4494 | CG  | GLU | C | 383 | 33.836 | 77.544 | 8.300  | 1.00 | 51.29 | C |
| ATOM | 4495 | CD  | GLU | C | 383 | 33.986 | 77.787 | 6.789  | 1.00 | 52.68 | C |
| ATOM | 4496 | OE1 | GLU | C | 383 | 34.509 | 78.879 | 6.578  | 1.00 | 53.30 | C |
| ATOM | 4497 | OE2 | GLU | C | 383 | 33.654 | 76.911 | 5.838  | 1.00 | 51.89 | C |
| ATOM | 4498 | C   | GLU | C | 383 | 31.274 | 75.169 | 9.904  | 1.00 | 47.87 | C |
| ATOM | 4499 | O   | GLU | C | 383 | 30.269 | 75.331 | 10.553 | 1.00 | 49.11 | C |
| ATOM | 4500 | N   | ASP | C | 384 | 31.412 | 74.199 | 9.029  | 1.00 | 46.81 | C |
| ATOM | 4501 | CA  | ASP | C | 384 | 30.406 | 73.132 | 8.883  | 1.00 | 45.40 | C |
| ATOM | 4502 | CB  | ASP | C | 384 | 30.297 | 72.790 | 7.378  | 1.00 | 46.54 | C |
| ATOM | 4503 | CG  | ASP | C | 384 | 28.893 | 72.212 | 7.020  | 1.00 | 48.56 | C |
| ATOM | 4504 | OD1 | ASP | C | 384 | 28.067 | 72.022 | 7.955  | 1.00 | 48.24 | C |
| ATOM | 4505 | OD2 | ASP | C | 384 | 28.548 | 71.922 | 5.854  | 1.00 | 50.46 | C |
| ATOM | 4506 | C   | ASP | C | 384 | 30.441 | 71.797 | 9.752  | 1.00 | 43.32 | C |
| ATOM | 4507 | O   | ASP | C | 384 | 30.653 | 70.692 | 9.254  | 1.00 | 40.64 | C |
| ATOM | 4508 | N   | VAL | C | 385 | 30.003 | 71.906 | 11.004 | 1.00 | 42.99 | C |
| ATOM | 4509 | CA  | VAL | C | 385 | 30.008 | 70.758 | 11.901 | 1.00 | 42.90 | C |
| ATOM | 4510 | CB  | VAL | C | 385 | 29.535 | 71.145 | 13.286 | 1.00 | 44.04 | C |
| ATOM | 4511 | CG1 | VAL | C | 385 | 29.306 | 69.807 | 14.228 | 1.00 | 44.87 | C |
| ATOM | 4512 | CG2 | VAL | C | 385 | 30.552 | 72.039 | 13.951 | 1.00 | 43.50 | C |
| ATOM | 4513 | C   | VAL | C | 385 | 29.283 | 69.514 | 11.370 | 1.00 | 44.21 | C |
| ATOM | 4514 | O   | VAL | C | 385 | 29.861 | 68.384 | 11.368 | 1.00 | 41.76 | C |
| ATOM | 4515 | N   | GLU | C | 386 | 28.052 | 69.668 | 10.790 | 1.00 | 45.80 | C |
| ATOM | 4516 | CA  | GLU | C | 386 | 27.309 | 68.476 | 10.275 | 1.00 | 46.35 | C |
| ATOM | 4517 | CB  | GLU | C | 386 | 25.762 | 68.829 | 10.141 | 1.00 | 50.84 | C |
| ATOM | 4518 | CG  | GLU | C | 386 | 24.965 | 68.729 | 11.449 | 1.00 | 58.16 | C |
| ATOM | 4519 | CD  | GLU | C | 386 | 25.367 | 69.749 | 12.513 | 1.00 | 62.98 | C |
| ATOM | 4520 | OE1 | GLU | C | 386 | 24.813 | 69.672 | 13.631 | 1.00 | 65.57 | C |
| ATOM | 4521 | OE2 | GLU | C | 386 | 26.218 | 70.626 | 12.251 | 1.00 | 65.22 | C |
| ATOM | 4522 | C   | GLU | C | 386 | 27.949 | 67.847 | 9.038  | 1.00 | 44.57 | C |
| ATOM | 4523 | O   | GLU | C | 386 | 28.115 | 66.624 | 8.945  | 1.00 | 43.75 | C |
| ATOM | 4524 | N   | ALA | C | 387 | 28.474 | 68.619 | 8.104  | 1.00 | 43.75 | C |
| ATOM | 4525 | CA  | ALA | C | 387 | 29.329 | 67.971 | 7.040  | 1.00 | 42.77 | C |
| ATOM | 4526 | CB  | ALA | C | 387 | 29.735 | 68.961 | 5.920  | 1.00 | 42.63 | C |
| ATOM | 4527 | C   | ALA | C | 387 | 30.571 | 67.234 | 7.538  | 1.00 | 42.74 | C |
| ATOM | 4528 | O   | ALA | C | 387 | 30.919 | 66.113 | 7.046  | 1.00 | 43.06 | C |
| ATOM | 4529 | N   | VAL | C | 388 | 31.254 | 67.770 | 8.546  | 1.00 | 41.61 | C |
| ATOM | 4530 | CA  | VAL | C | 388 | 32.364 | 66.978 | 9.075  | 1.00 | 40.92 | C |
| ATOM | 4531 | CB  | VAL | C | 388 | 33.270 | 67.777 | 9.993  | 1.00 | 40.98 | C |
| ATOM | 4532 | CG1 | VAL | C | 388 | 34.349 | 66.799 | 10.603 | 1.00 | 40.52 | C |
| ATOM | 4533 | CG2 | VAL | C | 388 | 33.939 | 68.817 | 9.152  | 1.00 | 40.76 | C |
| ATOM | 4534 | C   | VAL | C | 388 | 31.846 | 65.740 | 9.747  | 1.00 | 41.67 | C |
| ATOM | 4535 | O   | VAL | C | 388 | 32.375 | 64.601 | 9.568  | 1.00 | 40.13 | C |
| ATOM | 4536 | N   | GLN | C | 389 | 30.776 | 65.905 | 10.508 | 1.00 | 42.82 | C |
| ATOM | 4537 | CA  | GLN | C | 389 | 30.225 | 64.688 | 11.208 | 1.00 | 45.45 | C |
| ATOM | 4538 | CB  | GLN | C | 389 | 29.103 | 64.970 | 12.220 | 1.00 | 48.02 | C |
| ATOM | 4539 | CG  | GLN | C | 389 | 28.482 | 63.746 | 12.922 | 1.00 | 54.54 | C |
| ATOM | 4540 | CD  | GLN | C | 389 | 29.361 | 63.132 | 14.004 | 1.00 | 57.73 | C |
| ATOM | 4541 | OE1 | GLN | C | 389 | 29.049 | 62.065 | 14.531 | 1.00 | 60.36 | C |
| ATOM | 4542 | NE2 | GLN | C | 389 | 30.451 | 63.806 | 14.349 | 1.00 | 60.38 | C |
| ATOM | 4543 | C   | GLN | C | 389 | 29.771 | 63.632 | 10.249 | 1.00 | 44.84 | C |
| ATOM | 4544 | O   | GLN | C | 389 | 30.046 | 62.428 | 10.475 | 1.00 | 44.45 | C |
| ATOM | 4545 | N   | LYS | C | 390 | 29.261 | 64.082 | 9.081  | 1.00 | 45.11 | C |
| ATOM | 4546 | CA  | LYS | C | 390 | 28.824 | 63.146 | 8.022  | 1.00 | 45.96 | C |
| ATOM | 4547 | CB  | LYS | C | 390 | 28.069 | 63.888 | 6.816  | 1.00 | 50.06 | C |
| ATOM | 4548 | CG  | LYS | C | 390 | 28.929 | 64.682 | 5.834  | 1.00 | 56.52 | C |
| ATOM | 4549 | CD  | LYS | C | 390 | 28.121 | 65.226 | 4.650  | 1.00 | 60.49 | C |
| ATOM | 4550 | CE  | LYS | C | 390 | 27.237 | 66.416 | 5.029  | 1.00 | 62.26 | C |
| ATOM | 4551 | NZ  | LYS | C | 390 | 26.219 | 66.067 | 6.056  | 1.00 | 64.53 | C |
| ATOM | 4552 | C   | LYS | C | 390 | 29.987 | 62.396 | 7.501  | 1.00 | 44.03 | C |
| ATOM | 4553 | O   | LYS | C | 390 | 29.856 | 61.257 | 7.221  | 1.00 | 44.21 | C |

TABLE 2-continued

ATOMIC COORDINATES OF THE ERR3 LBD/
DIETHYLSTILBESTROL COMPLEX

| ATOM | 4554 | N | LEU | C | 391 | 31.128 | 63.043 | 7.271 | 1.00 | 42.11 | C |
|------|------|------|-----|---|-----|--------|--------|--------|------|-------|---|
| ATOM | 4555 | CA | LEU | C | 391 | 32.331 | 62.376 | 6.801 | 1.00 | 40.86 | C |
| ATOM | 4556 | CB | LEU | C | 391 | 33.384 | 63.459 | 6.508 | 1.00 | 42.37 | C |
| ATOM | 4557 | CG | LEU | C | 391 | 34.757 | 62.898 | 6.136 | 1.00 | 44.03 | C |
| ATOM | 4558 | CD1 | LEU | C | 391 | 34.530 | 62.191 | 4.851 | 1.00 | 43.95 | C |
| ATOM | 4559 | CD2 | LEU | C | 391 | 35.815 | 64.010 | 6.017 | 1.00 | 43.43 | C |
| ATOM | 4560 | C | LEU | C | 391 | 32.849 | 61.431 | 7.832 | 1.00 | 40.06 | C |
| ATOM | 4561 | O | LEU | C | 391 | 33.248 | 60.298 | 7.548 | 1.00 | 40.11 | C |
| ATOM | 4562 | N | GLN | C | 392 | 32.766 | 61.803 | 9.088 | 1.00 | 39.05 | C |
| ATOM | 4563 | CA | GLN | C | 392 | 33.177 | 60.817 | 10.141 | 1.00 | 38.44 | C |
| ATOM | 4564 | CB | GLN | C | 392 | 33.069 | 61.417 | 11.584 | 1.00 | 37.25 | C |
| ATOM | 4565 | CG | GLN | C | 392 | 34.101 | 62.486 | 11.963 | 1.00 | 39.00 | C |
| ATOM | 4566 | CD | GLN | C | 392 | 33.704 | 63.383 | 13.153 | 1.00 | 39.57 | C |
| ATOM | 4567 | OE1 | GLN | C | 392 | 32.811 | 63.020 | 13.894 | 1.00 | 41.73 | C |
| ATOM | 4568 | NE2 | GLN | C | 392 | 34.348 | 64.570 | 13.306 | 1.00 | 38.05 | C |
| ATOM | 4569 | C | GLN | C | 392 | 32.306 | 59.604 | 10.013 | 1.00 | 38.77 | C |
| ATOM | 4570 | O | GLN | C | 392 | 32.719 | 58.456 | 10.093 | 1.00 | 37.64 | C |
| ATOM | 4571 | N | ASP | C | 393 | 31.026 | 59.872 | 9.859 | 1.00 | 40.74 | C |
| ATOM | 4572 | CA | ASP | C | 393 | 30.006 | 58.798 | 9.847 | 1.00 | 42.14 | C |
| ATOM | 4573 | CB | ASP | C | 393 | 28.642 | 59.469 | 9.799 | 1.00 | 44.07 | C |
| ATOM | 4574 | CG | ASP | C | 393 | 27.832 | 59.226 | 11.074 | 1.00 | 46.37 | C |
| ATOM | 4575 | OD1 | ASP | C | 393 | 27.789 | 58.023 | 11.577 | 1.00 | 48.52 | C |
| ATOM | 4576 | OD2 | ASP | C | 393 | 27.489 | 59.975 | 11.974 | 0.00 | 46.28 | C |
| ATOM | 4577 | C | ASP | C | 393 | 30.248 | 57.846 | 8.645 | 1.00 | 41.88 | C |
| ATOM | 4578 | O | ASP | C | 393 | 30.330 | 56.646 | 8.794 | 1.00 | 42.01 | C |
| ATOM | 4579 | N | VAL | C | 394 | 30.531 | 58.364 | 7.452 | 1.00 | 41.50 | C |
| ATOM | 4580 | CA | VAL | C | 394 | 30.806 | 57.385 | 6.385 | 1.00 | 40.50 | C |
| ATOM | 4581 | CB | VAL | C | 394 | 30.655 | 57.987 | 4.904 | 1.00 | 40.77 | C |
| ATOM | 4582 | CG1 | VAL | C | 394 | 30.057 | 59.305 | 4.873 | 1.00 | 39.63 | C |
| ATOM | 4583 | CG2 | VAL | C | 394 | 31.882 | 57.861 | 4.094 | 1.00 | 41.22 | C |
| ATOM | 4584 | C | VAL | C | 394 | 32.061 | 56.576 | 6.571 | 1.00 | 40.25 | C |
| ATOM | 4585 | O | VAL | C | 394 | 32.108 | 55.420 | 6.193 | 1.00 | 38.72 | C |
| ATOM | 4586 | N | LEU | C | 395 | 33.130 | 57.186 | 7.134 | 1.00 | 40.41 | C |
| ATOM | 4587 | CA | LEU | C | 395 | 34.360 | 56.410 | 7.253 | 1.00 | 39.59 | C |
| ATOM | 4588 | CB | LEU | C | 395 | 35.578 | 57.313 | 7.490 | 1.00 | 40.12 | C |
| ATOM | 4589 | CG | LEU | C | 395 | 35.695 | 58.560 | 6.565 | 1.00 | 39.87 | C |
| ATOM | 4590 | CD1 | LEU | C | 395 | 36.686 | 59.642 | 7.082 | 1.00 | 38.09 | C |
| ATOM | 4591 | CD2 | LEU | C | 395 | 36.126 | 58.007 | 5.157 | 1.00 | 38.66 | C |
| ATOM | 4592 | C | LEU | C | 395 | 34.160 | 55.395 | 8.362 | 1.00 | 39.33 | C |
| ATOM | 4593 | O | LEU | C | 395 | 34.632 | 54.304 | 8.236 | 1.00 | 38.76 | C |
| ATOM | 4594 | N | HIS | C | 396 | 33.468 | 55.790 | 9.432 | 1.00 | 38.90 | C |
| ATOM | 4595 | CA | HIS | C | 396 | 33.053 | 54.898 | 10.487 | 1.00 | 40.65 | C |
| ATOM | 4596 | CB | HIS | C | 396 | 32.326 | 55.681 | 11.560 | 1.00 | 38.90 | C |
| ATOM | 4597 | CG | HIS | C | 396 | 31.950 | 54.911 | 12.806 | 1.00 | 36.98 | C |
| ATOM | 4598 | CD2 | HIS | C | 396 | 32.172 | 53.637 | 13.193 | 1.00 | 36.23 | C |
| ATOM | 4599 | ND1 | HIS | C | 396 | 31.139 | 55.471 | 13.783 | 1.00 | 34.70 | C |
| ATOM | 4600 | CE1 | HIS | C | 396 | 30.896 | 54.576 | 14.721 | 1.00 | 33.45 | C |
| ATOM | 4601 | NE2 | HIS | C | 396 | 31.502 | 53.447 | 14.388 | 1.00 | 37.25 | C |
| ATOM | 4602 | C | HIS | C | 396 | 32.173 | 53.697 | 9.970 | 1.00 | 42.43 | C |
| ATOM | 4603 | O | HIS | C | 396 | 32.467 | 52.501 | 10.313 | 1.00 | 41.87 | C |
| ATOM | 4604 | N | GLU | C | 397 | 31.146 | 53.988 | 9.181 | 1.00 | 45.06 | C |
| ATOM | 4605 | CA | GLU | C | 397 | 30.330 | 52.871 | 8.566 | 1.00 | 47.77 | C |
| ATOM | 4606 | CB | GLU | C | 397 | 29.153 | 53.340 | 7.690 | 1.00 | 51.51 | C |
| ATOM | 4607 | CG | GLU | C | 397 | 28.337 | 54.417 | 8.327 | 1.00 | 59.83 | C |
| ATOM | 4608 | CD | GLU | C | 397 | 28.322 | 55.714 | 7.561 | 1.00 | 64.80 | C |
| ATOM | 4609 | OE1 | GLU | C | 397 | 28.766 | 55.746 | 6.396 | 1.00 | 67.48 | C |
| ATOM | 4610 | OE2 | GLU | C | 397 | 27.848 | 56.719 | 8.130 | 1.00 | 67.72 | C |
| ATOM | 4611 | C | GLU | C | 397 | 31.239 | 51.949 | 7.796 | 1.00 | 47.13 | C |
| ATOM | 4612 | O | GLU | C | 397 | 31.160 | 50.777 | 7.955 | 1.00 | 47.62 | C |
| ATOM | 4613 | N | ALA | C | 398 | 32.208 | 52.501 | 7.077 | 1.00 | 46.89 | C |
| ATOM | 4614 | CA | ALA | C | 398 | 33.167 | 51.684 | 6.332 | 1.00 | 47.41 | C |
| ATOM | 4615 | CB | ALA | C | 398 | 34.151 | 52.597 | 5.661 | 1.00 | 47.35 | C |
| ATOM | 4616 | C | ALA | C | 398 | 33.925 | 50.765 | 7.187 | 1.00 | 47.74 | C |
| ATOM | 4617 | O | ALA | C | 398 | 34.206 | 49.625 | 6.848 | 1.00 | 48.04 | C |
| ATOM | 4618 | N | LEU | C | 399 | 34.408 | 51.279 | 8.297 | 1.00 | 48.38 | C |
| ATOM | 4619 | CA | LEU | C | 399 | 35.219 | 50.456 | 9.137 | 1.00 | 48.37 | C |
| ATOM | 4620 | CB | LEU | C | 399 | 35.970 | 51.280 | 10.230 | 1.00 | 47.28 | C |
| ATOM | 4621 | CG | LEU | C | 399 | 36.617 | 50.521 | 11.342 | 1.00 | 46.51 | C |
| ATOM | 4622 | CD1 | LEU | C | 399 | 37.919 | 50.039 | 10.828 | 1.00 | 44.16 | C |
| ATOM | 4623 | CD2 | LEU | C | 399 | 36.742 | 51.542 | 12.631 | 1.00 | 47.25 | C |
| ATOM | 4624 | C | LEU | C | 399 | 34.283 | 49.429 | 9.729 | 1.00 | 49.14 | C |
| ATOM | 4625 | O | LEU | C | 399 | 34.757 | 48.312 | 9.974 | 1.00 | 48.78 | C |
| ATOM | 4626 | N | GLN | C | 400 | 33.029 | 49.803 | 10.066 | 1.00 | 51.16 | C |
| ATOM | 4627 | CA | GLN | C | 400 | 32.131 | 48.773 | 10.673 | 1.00 | 54.04 | C |
| ATOM | 4628 | CB | GLN | C | 400 | 30.831 | 49.320 | 11.301 | 1.00 | 57.93 | C |
| ATOM | 4629 | CG | GLN | C | 400 | 31.116 | 50.739 | 11.953 | 1.00 | 64.33 | C |

TABLE 2-continued

ATOMIC COORDINATES OF THE ERR3 LBD/
DIETHYLSTILBESTROL COMPLEX

| ATOM | 4630 | CD | GLN | C | 400 | 32.570 | 50.885 | 12.543 | 1.00 | 68.09 | C |
|---|---|---|---|---|---|---|---|---|---|---|---|
| ATOM | 4631 | OE1 | GLN | C | 400 | 32.866 | 50.422 | 13.637 | 1.00 | 70.16 | C |
| ATOM | 4632 | NE2 | GLN | C | 400 | 33.458 | 51.512 | 11.791 | 1.00 | 70.55 | C |
| ATOM | 4633 | C | GLN | C | 400 | 31.838 | 47.688 | 9.595 | 1.00 | 53.39 | C |
| ATOM | 4634 | O | GLN | C | 400 | 32.026 | 46.508 | 9.860 | 1.00 | 52.07 | C |
| ATOM | 4635 | N | ASP | C | 401 | 31.582 | 48.084 | 8.354 | 1.00 | 53.14 | C |
| ATOM | 4636 | CA | ASP | C | 401 | 31.318 | 47.050 | 7.345 | 1.00 | 53.31 | C |
| ATOM | 4637 | CB | ASP | C | 401 | 30.853 | 47.675 | 6.039 | 1.00 | 54.64 | C |
| ATOM | 4638 | CG | ASP | C | 401 | 29.478 | 48.377 | 6.176 | 1.00 | 56.36 | C |
| ATOM | 4639 | OD1 | ASP | C | 401 | 28.665 | 47.942 | 7.057 | 1.00 | 58.48 | C |
| ATOM | 4640 | OD2 | ASP | C | 401 | 29.105 | 49.336 | 5.411 | 1.00 | 57.17 | C |
| ATOM | 4641 | C | ASP | C | 401 | 32.531 | 46.127 | 7.147 | 1.00 | 52.94 | C |
| ATOM | 4642 | O | ASP | C | 401 | 32.402 | 44.900 | 7.123 | 1.00 | 53.18 | C |
| ATOM | 4643 | N | TYR | C | 402 | 33.731 | 46.686 | 7.073 | 1.00 | 52.00 | C |
| ATOM | 4644 | CA | TYR | C | 402 | 34.853 | 45.852 | 6.756 | 1.00 | 50.54 | C |
| ATOM | 4645 | CB | TYR | C | 402 | 36.124 | 46.693 | 6.576 | 1.00 | 47.99 | C |
| ATOM | 4646 | CG | TYR | C | 402 | 37.340 | 45.843 | 6.423 | 1.00 | 46.93 | C |
| ATOM | 4647 | CD1 | TYR | C | 402 | 37.796 | 45.446 | 5.145 | 1.00 | 46.05 | C |
| ATOM | 4648 | CE1 | TYR | C | 402 | 38.923 | 44.677 | 5.013 | 1.00 | 46.47 | C |
| ATOM | 4649 | CD2 | TYR | C | 402 | 38.074 | 45.468 | 7.524 | 1.00 | 45.64 | C |
| ATOM | 4650 | CE2 | TYR | C | 402 | 39.205 | 44.693 | 7.391 | 1.00 | 46.25 | C |
| ATOM | 4651 | CZ | TYR | C | 402 | 39.616 | 44.301 | 6.116 | 1.00 | 47.03 | C |
| ATOM | 4652 | OH | TYR | C | 402 | 40.743 | 43.518 | 5.974 | 1.00 | 49.54 | C |
| ATOM | 4653 | C | TYR | C | 402 | 35.056 | 44.753 | 7.825 | 1.00 | 50.76 | C |
| ATOM | 4654 | O | TYR | C | 402 | 35.476 | 43.619 | 7.487 | 1.00 | 50.73 | C |
| ATOM | 4655 | N | GLU | C | 403 | 34.882 | 45.169 | 9.100 | 1.00 | 50.59 | C |
| ATOM | 4656 | CA | GLU | C | 403 | 35.067 | 44.363 | 10.275 | 1.00 | 50.49 | C |
| ATOM | 4657 | CB | GLU | C | 403 | 35.089 | 45.269 | 11.525 | 1.00 | 49.32 | C |
| ATOM | 4658 | CG | GLU | C | 403 | 36.244 | 46.309 | 11.596 | 1.00 | 49.82 | C |
| ATOM | 4659 | CD | GLU | C | 403 | 37.537 | 45.609 | 11.717 | 1.00 | 49.97 | C |
| ATOM | 4660 | OE1 | GLU | C | 403 | 37.466 | 44.425 | 12.106 | 1.00 | 49.86 | C |
| ATOM | 4661 | OE2 | GLU | C | 403 | 38.600 | 46.187 | 11.368 | 1.00 | 49.10 | C |
| ATOM | 4662 | C | GLU | C | 403 | 33.937 | 43.277 | 10.433 | 1.00 | 51.12 | C |
| ATOM | 4663 | O | GLU | C | 403 | 34.216 | 42.140 | 10.852 | 1.00 | 50.12 | C |
| ATOM | 4664 | N | ALA | C | 404 | 32.692 | 43.704 | 10.160 | 1.00 | 52.51 | C |
| ATOM | 4665 | CA | ALA | C | 404 | 31.508 | 42.802 | 9.958 | 1.00 | 54.53 | C |
| ATOM | 4666 | CB | ALA | C | 404 | 30.186 | 43.639 | 9.623 | 1.00 | 53.55 | C |
| ATOM | 4667 | C | ALA | C | 404 | 31.753 | 41.723 | 8.859 | 1.00 | 55.99 | C |
| ATOM | 4668 | O | ALA | C | 404 | 31.449 | 40.548 | 9.116 | 1.00 | 56.30 | C |
| ATOM | 4669 | N | GLY | C | 405 | 32.342 | 42.143 | 7.705 | 1.00 | 57.10 | C |
| ATOM | 4670 | CA | GLY | C | 405 | 32.617 | 41.327 | 6.500 | 1.00 | 58.26 | C |
| ATOM | 4671 | C | GLY | C | 405 | 33.897 | 40.462 | 6.613 | 1.00 | 59.47 | C |
| ATOM | 4672 | O | GLY | C | 405 | 33.903 | 39.255 | 6.301 | 1.00 | 60.05 | C |
| ATOM | 4673 | N | GLN | C | 406 | 34.988 | 41.042 | 7.125 | 1.00 | 59.94 | C |
| ATOM | 4674 | CA | GLN | C | 406 | 36.274 | 40.355 | 7.187 | 1.00 | 60.09 | C |
| ATOM | 4675 | CB | GLN | C | 406 | 37.424 | 41.337 | 6.888 | 1.00 | 60.61 | C |
| ATOM | 4676 | CG | GLN | C | 406 | 38.777 | 40.663 | 6.510 | 1.00 | 60.89 | C |
| ATOM | 4677 | CD | GLN | C | 406 | 38.735 | 40.025 | 5.075 | 1.00 | 61.33 | C |
| ATOM | 4678 | OE1 | GLN | C | 406 | 37.824 | 40.320 | 4.220 | 1.00 | 62.41 | C |
| ATOM | 4679 | NE2 | GLN | C | 406 | 39.674 | 39.127 | 4.837 | 1.00 | 60.02 | C |
| ATOM | 4680 | C | GLN | C | 406 | 36.537 | 39.696 | 8.509 | 1.00 | 60.05 | C |
| ATOM | 4681 | O | GLN | C | 406 | 37.545 | 38.967 | 8.650 | 1.00 | 59.84 | C |
| ATOM | 4682 | N | HIS | C | 407 | 35.696 | 40.024 | 9.501 | 1.00 | 60.50 | C |
| ATOM | 4683 | CA | HIS | C | 407 | 35.975 | 39.648 | 10.888 | 1.00 | 61.60 | C |
| ATOM | 4684 | CB | HIS | C | 407 | 36.793 | 40.758 | 11.663 | 1.00 | 59.60 | C |
| ATOM | 4685 | CG | HIS | C | 407 | 38.211 | 40.924 | 11.177 | 1.00 | 57.10 | C |
| ATOM | 4686 | CD2 | HIS | C | 407 | 38.724 | 41.619 | 10.141 | 1.00 | 55.62 | C |
| ATOM | 4687 | ND1 | HIS | C | 407 | 39.277 | 40.282 | 11.757 | 1.00 | 55.81 | C |
| ATOM | 4688 | CE1 | HIS | C | 407 | 40.381 | 40.537 | 11.078 | 1.00 | 55.07 | C |
| ATOM | 4689 | NE2 | HIS | C | 407 | 40.081 | 41.388 | 10.119 | 1.00 | 55.08 | C |
| ATOM | 4690 | C | HIS | C | 407 | 34.684 | 39.341 | 11.611 | 1.00 | 63.54 | C |
| ATOM | 4691 | O | HIS | C | 407 | 33.929 | 40.177 | 11.928 | 0.00 | 63.71 | C |
| ATOM | 4692 | N | MET | C | 408 | 34.165 | 38.128 | 11.370 | 1.00 | 66.12 | C |
| ATOM | 4693 | CA | MET | C | 408 | 33.024 | 37.631 | 12.193 | 1.00 | 67.86 | C |
| ATOM | 4694 | CB | MET | C | 408 | 32.136 | 36.651 | 11.375 | 1.00 | 70.92 | C |
| ATOM | 4695 | CG | MET | C | 408 | 31.401 | 37.294 | 10.213 | 1.00 | 75.78 | C |
| ATOM | 4696 | SD | MET | C | 408 | 30.201 | 38.528 | 10.747 | 1.00 | 81.55 | C |
| ATOM | 4697 | CE | MET | C | 408 | 28.739 | 37.515 | 10.961 | 1.00 | 79.74 | C |
| ATOM | 4698 | C | MET | C | 408 | 33.503 | 37.049 | 13.525 | 1.00 | 67.27 | C |
| ATOM | 4699 | O | MET | C | 408 | 32.772 | 37.097 | 14.513 | 1.00 | 67.16 | C |
| ATOM | 4700 | N | GLU | C | 409 | 34.744 | 36.559 | 13.599 | 1.00 | 66.62 | C |
| ATOM | 4701 | CA | GLU | C | 409 | 35.275 | 35.940 | 14.842 | 1.00 | 65.94 | C |
| ATOM | 4702 | CB | GLU | C | 409 | 36.592 | 35.349 | 14.577 | 0.00 | 68.30 | C |
| ATOM | 4703 | CG | GLU | C | 409 | 37.117 | 34.360 | 15.630 | 1.00 | 72.09 | C |
| ATOM | 4704 | CD | GLU | C | 409 | 38.085 | 34.982 | 16.635 | 1.00 | 74.33 | C |
| ATOM | 4705 | OE1 | GLU | C | 409 | 38.553 | 34.247 | 17.530 | 1.00 | 75.75 | C |

TABLE 2-continued

ATOMIC COORDINATES OF THE ERR3 LBD/DIETHYLSTILBESTROL COMPLEX

| ATOM | 4706 | OE2 | GLU | C | 409 | 38.383 | 36.194 | 16.540 | 1.00 | 76.28 | C |
|---|---|---|---|---|---|---|---|---|---|---|---|
| ATOM | 4707 | C | GLU | C | 409 | 35.475 | 36.937 | 16.033 | 1.00 | 64.28 | C |
| ATOM | 4708 | O | GLU | C | 409 | 35.899 | 36.530 | 17.123 | 1.00 | 63.46 | C |
| ATOM | 4709 | N | ASP | C | 410 | 35.241 | 38.249 | 15.835 | 1.00 | 62.44 | C |
| ATOM | 4710 | CA | ASP | C | 410 | 35.250 | 39.244 | 16.970 | 1.00 | 60.67 | C |
| ATOM | 4711 | CB | ASP | C | 410 | 36.644 | 39.885 | 17.158 | 1.00 | 60.95 | C |
| ATOM | 4712 | CG | ASP | C | 410 | 36.722 | 40.809 | 18.396 | 1.00 | 61.87 | C |
| ATOM | 4713 | OD1 | ASP | C | 410 | 35.722 | 41.003 | 19.103 | 1.00 | 62.17 | C |
| ATOM | 4714 | OD2 | ASP | C | 410 | 37.768 | 41.387 | 18.737 | 1.00 | 62.36 | C |
| ATOM | 4715 | C | ASP | C | 410 | 34.273 | 40.351 | 16.623 | 1.00 | 59.07 | C |
| ATOM | 4716 | O | ASP | C | 410 | 34.592 | 41.236 | 15.809 | 1.00 | 59.74 | C |
| ATOM | 4717 | N | PRO | C | 411 | 33.086 | 40.336 | 17.203 | 1.00 | 56.85 | C |
| ATOM | 4718 | CD | PRO | C | 411 | 32.600 | 39.526 | 18.335 | 1.00 | 55.34 | C |
| ATOM | 4719 | CA | PRO | C | 411 | 32.114 | 41.383 | 16.851 | 1.00 | 55.50 | C |
| ATOM | 4720 | CB | PRO | C | 411 | 30.847 | 40.947 | 17.604 | 1.00 | 55.26 | C |
| ATOM | 4721 | CG | PRO | C | 411 | 31.478 | 40.647 | 18.928 | 1.00 | 55.44 | C |
| ATOM | 4722 | C | PRO | C | 411 | 32.579 | 42.818 | 17.398 | 1.00 | 54.23 | C |
| ATOM | 4723 | O | PRO | C | 411 | 31.913 | 43.774 | 17.084 | 1.00 | 54.55 | C |
| ATOM | 4724 | N | ARG | C | 412 | 33.663 | 42.887 | 18.156 | 1.00 | 51.94 | C |
| ATOM | 4725 | CA | ARG | C | 412 | 34.173 | 44.097 | 18.705 | 1.00 | 51.17 | C |
| ATOM | 4726 | CB | ARG | C | 412 | 34.258 | 43.878 | 20.217 | 1.00 | 52.84 | C |
| ATOM | 4727 | CG | ARG | C | 412 | 32.763 | 43.897 | 20.804 | 1.00 | 57.01 | C |
| ATOM | 4728 | CD | ARG | C | 412 | 32.761 | 43.946 | 22.316 | 0.00 | 60.26 | C |
| ATOM | 4729 | NE | ARG | C | 412 | 32.644 | 43.996 | 22.716 | 1.00 | 64.51 | C |
| ATOM | 4730 | CZ | ARG | C | 412 | 33.567 | 44.417 | 23.744 | 1.00 | 66.25 | C |
| ATOM | 4731 | NH1 | ARG | C | 412 | 33.642 | 43.934 | 25.871 | 1.00 | 67.85 | C |
| ATOM | 4732 | NH2 | ARG | C | 412 | 33.010 | 43.413 | 22.803 | 1.00 | 67.21 | C |
| ATOM | 4733 | C | ARG | C | 412 | 35.526 | 44.628 | 18.125 | 1.00 | 48.85 | C |
| ATOM | 4734 | O | ARG | C | 412 | 36.102 | 45.500 | 18.728 | 1.00 | 48.09 | C |
| ATOM | 4735 | N | ARG | C | 413 | 36.043 | 44.052 | 17.015 | 1.00 | 46.68 | C |
| ATOM | 4736 | CA | ARG | C | 413 | 37.275 | 44.510 | 16.393 | 1.00 | 43.94 | C |
| ATOM | 4737 | CB | ARG | C | 413 | 37.641 | 43.800 | 15.054 | 1.00 | 44.91 | C |
| ATOM | 4738 | CG | ARG | C | 413 | 39.175 | 43.875 | 14.731 | 1.00 | 45.07 | C |
| ATOM | 4739 | CD | ARG | C | 413 | 39.603 | 42.985 | 13.567 | 1.00 | 45.81 | C |
| ATOM | 4740 | NE | ARG | C | 413 | 40.945 | 43.221 | 13.104 | 1.00 | 46.06 | C |
| ATOM | 4741 | CZ | ARG | C | 413 | 42.052 | 42.854 | 13.752 | 1.00 | 46.82 | C |
| ATOM | 4742 | NH1 | ARG | C | 413 | 42.013 | 42.232 | 14.906 | 1.00 | 46.50 | C |
| ATOM | 4743 | NH2 | ARG | C | 413 | 43.223 | 43.061 | 13.192 | 1.00 | 47.28 | C |
| ATOM | 4744 | C | ARG | C | 413 | 37.161 | 45.992 | 16.065 | 1.00 | 42.47 | C |
| ATOM | 4745 | O | ARG | C | 413 | 38.103 | 46.725 | 16.287 | 1.00 | 42.73 | C |
| ATOM | 4746 | N | ALA | C | 414 | 36.019 | 46.422 | 15.513 | 1.00 | 40.01 | C |
| ATOM | 4747 | CA | ALA | C | 414 | 35.892 | 47.796 | 14.999 | 1.00 | 38.07 | C |
| ATOM | 4748 | CB | ALA | C | 414 | 34.594 | 48.013 | 14.362 | 1.00 | 36.07 | C |
| ATOM | 4749 | C | ALA | C | 414 | 36.068 | 48.793 | 16.175 | 1.00 | 37.85 | C |
| ATOM | 4750 | O | ALA | C | 414 | 36.802 | 49.774 | 16.080 | 1.00 | 37.29 | C |
| ATOM | 4751 | N | GLY | C | 415 | 35.319 | 48.525 | 17.244 | 1.00 | 36.73 | C |
| ATOM | 4752 | CA | GLY | C | 415 | 35.497 | 49.144 | 18.488 | 1.00 | 36.23 | C |
| ATOM | 4753 | C | GLY | C | 415 | 36.918 | 49.202 | 19.062 | 1.00 | 36.55 | C |
| ATOM | 4754 | O | GLY | C | 415 | 37.325 | 50.275 | 19.627 | 1.00 | 36.59 | C |
| ATOM | 4755 | N | LYS | C | 416 | 37.640 | 48.084 | 18.933 | 1.00 | 36.51 | C |
| ATOM | 4756 | CA | LYS | C | 416 | 39.010 | 47.933 | 19.397 | 1.00 | 36.78 | C |
| ATOM | 4757 | CB | LYS | C | 416 | 39.556 | 46.512 | 19.358 | 1.00 | 39.42 | C |
| ATOM | 4758 | CG | LYS | C | 416 | 39.104 | 45.657 | 20.583 | 1.00 | 42.25 | C |
| ATOM | 4759 | CD | LYS | C | 416 | 39.357 | 44.183 | 20.366 | 1.00 | 44.99 | C |
| ATOM | 4760 | CE | LYS | C | 416 | 38.619 | 43.298 | 21.289 | 1.00 | 46.70 | C |
| ATOM | 4761 | NZ | LYS | C | 416 | 38.844 | 41.896 | 20.751 | 1.00 | 48.55 | C |
| ATOM | 4762 | C | LYS | C | 416 | 40.018 | 48.790 | 18.634 | 1.00 | 36.83 | C |
| ATOM | 4763 | O | LYS | C | 416 | 40.981 | 49.262 | 19.269 | 1.00 | 35.22 | C |
| ATOM | 4764 | N | MET | C | 417 | 39.718 | 49.015 | 17.331 | 1.00 | 36.08 | C |
| ATOM | 4765 | CA | MET | C | 417 | 40.474 | 49.868 | 16.449 | 1.00 | 35.06 | C |
| ATOM | 4766 | CB | MET | C | 417 | 40.225 | 49.519 | 14.957 | 1.00 | 36.19 | C |
| ATOM | 4767 | CG | MET | C | 417 | 40.736 | 48.187 | 14.566 | 1.00 | 39.64 | C |
| ATOM | 4768 | SD | MET | C | 417 | 42.380 | 48.095 | 14.375 | 1.00 | 43.20 | C |
| ATOM | 4769 | CE | MET | C | 417 | 42.624 | 46.149 | 14.202 | 1.00 | 43.31 | C |
| ATOM | 4770 | C | MET | C | 417 | 40.143 | 51.326 | 16.839 | 1.00 | 32.89 | C |
| ATOM | 4771 | O | MET | C | 417 | 41.039 | 52.093 | 16.999 | 1.00 | 30.12 | C |
| ATOM | 4772 | N | LEU | C | 418 | 38.876 | 51.658 | 17.113 | 1.00 | 32.54 | C |
| ATOM | 4773 | CA | LEU | C | 418 | 38.597 | 53.014 | 17.455 | 1.00 | 31.77 | C |
| ATOM | 4774 | CB | LEU | C | 418 | 37.138 | 53.312 | 17.537 | 1.00 | 31.64 | C |
| ATOM | 4775 | CG | LEU | C | 418 | 36.384 | 53.192 | 16.193 | 1.00 | 32.27 | C |
| ATOM | 4776 | CD1 | LEU | C | 418 | 34.873 | 53.308 | 16.419 | 1.00 | 30.78 | C |
| ATOM | 4777 | CD2 | LEU | C | 418 | 36.793 | 54.314 | 15.145 | 1.00 | 31.46 | C |
| ATOM | 4778 | C | LEU | C | 418 | 39.301 | 53.385 | 18.787 | 1.00 | 32.96 | C |
| ATOM | 4779 | O | LEU | C | 418 | 39.756 | 54.524 | 18.964 | 1.00 | 33.44 | C |
| ATOM | 4780 | N | MET | C | 419 | 39.389 | 52.414 | 19.707 | 1.00 | 32.71 | C |
| ATOM | 4781 | CA | MET | C | 419 | 40.019 | 52.586 | 20.992 | 1.00 | 31.73 | C |

TABLE 2-continued

ATOMIC COORDINATES OF THE ERR3 LBD/
DIETHYLSTILBESTROL COMPLEX

| ATOM | 4782 | CB | MET | C | 419 | 39.557 | 51.496 | 21.981 | 1.00 | 32.31 | C |
|---|---|---|---|---|---|---|---|---|---|---|---|
| ATOM | 4783 | CG | MET | C | 419 | 38.143 | 51.730 | 22.517 | 1.00 | 33.86 | C |
| ATOM | 4784 | SD | MET | C | 419 | 37.584 | 50.094 | 23.313 | 1.00 | 37.79 | C |
| ATOM | 4785 | CE | MET | C | 419 | 38.394 | 50.144 | 24.825 | 1.00 | 34.97 | C |
| ATOM | 4786 | C | MET | C | 419 | 41.530 | 52.679 | 20.996 | 1.00 | 30.47 | C |
| ATOM | 4787 | O | MET | C | 419 | 42.086 | 52.936 | 22.057 | 1.00 | 30.23 | C |
| ATOM | 4788 | N | THR | C | 420 | 42.180 | 52.614 | 19.831 | 1.00 | 29.39 | C |
| ATOM | 4789 | CA | THR | C | 420 | 43.559 | 53.029 | 19.699 | 1.00 | 29.26 | C |
| ATOM | 4790 | CB | THR | C | 420 | 44.270 | 52.241 | 18.617 | 1.00 | 29.15 | C |
| ATOM | 4791 | OG1 | THR | C | 420 | 43.615 | 52.525 | 17.369 | 1.00 | 29.05 | C |
| ATOM | 4792 | CG2 | THR | C | 420 | 44.151 | 50.651 | 18.891 | 1.00 | 29.60 | C |
| ATOM | 4793 | C | THR | C | 420 | 43.834 | 54.548 | 19.474 | 1.00 | 29.22 | C |
| ATOM | 4794 | O | THR | C | 420 | 44.953 | 54.958 | 19.585 | 1.00 | 28.93 | C |
| ATOM | 4795 | N | LEU | C | 421 | 42.805 | 55.303 | 19.119 | 1.00 | 28.49 | C |
| ATOM | 4796 | CA | LEU | C | 421 | 42.849 | 56.668 | 18.658 | 1.00 | 28.15 | C |
| ATOM | 4797 | CB | LEU | C | 421 | 41.471 | 57.027 | 18.033 | 1.00 | 28.39 | C |
| ATOM | 4798 | CG | LEU | C | 421 | 41.255 | 56.396 | 16.629 | 1.00 | 29.85 | C |
| ATOM | 4799 | CD1 | LEU | C | 421 | 39.833 | 56.732 | 16.212 | 1.00 | 31.15 | C |
| ATOM | 4800 | CD2 | LEU | C | 421 | 42.230 | 56.885 | 15.494 | 1.00 | 29.36 | C |
| ATOM | 4801 | C | LEU | C | 421 | 43.318 | 57.676 | 19.792 | 1.00 | 27.20 | C |
| ATOM | 4802 | O | LEU | C | 421 | 44.055 | 58.557 | 19.539 | 1.00 | 27.55 | C |
| ATOM | 4803 | N | PRO | C | 422 | 42.927 | 57.477 | 21.018 | 1.00 | 26.35 | C |
| ATOM | 4804 | CD | PRO | C | 422 | 41.868 | 56.599 | 21.455 | 1.00 | 25.13 | C |
| ATOM | 4805 | CA | PRO | C | 422 | 43.476 | 58.216 | 22.167 | 1.00 | 26.49 | C |
| ATOM | 4806 | CB | PRO | C | 422 | 42.779 | 57.498 | 23.347 | 1.00 | 24.23 | C |
| ATOM | 4807 | CG | PRO | C | 422 | 41.369 | 57.339 | 22.804 | 1.00 | 25.78 | C |
| ATOM | 4808 | C | PRO | C | 422 | 44.957 | 58.152 | 22.207 | 1.00 | 25.95 | C |
| ATOM | 4809 | O | PRO | C | 422 | 45.566 | 59.191 | 22.231 | 1.00 | 27.77 | C |
| ATOM | 4810 | N | LEU | C | 423 | 45.539 | 56.975 | 22.117 | 1.00 | 26.67 | C |
| ATOM | 4811 | CA | LEU | C | 423 | 46.987 | 56.825 | 22.100 | 1.00 | 27.58 | C |
| ATOM | 4812 | CB | LEU | C | 423 | 47.385 | 55.351 | 22.213 | 1.00 | 26.35 | C |
| ATOM | 4813 | CG | LEU | C | 423 | 48.889 | 55.121 | 22.421 | 1.00 | 29.17 | C |
| ATOM | 4814 | CD1 | LEU | C | 423 | 49.574 | 55.947 | 23.630 | 1.00 | 25.79 | C |
| ATOM | 4815 | CD2 | LEU | C | 423 | 49.080 | 53.700 | 22.608 | 1.00 | 28.97 | C |
| ATOM | 4816 | C | LEU | C | 423 | 47.612 | 57.516 | 20.865 | 1.00 | 28.37 | C |
| ATOM | 4817 | O | LEU | C | 423 | 48.658 | 58.131 | 20.970 | 1.00 | 28.63 | C |
| ATOM | 4818 | N | LEU | C | 424 | 47.013 | 57.323 | 19.685 | 1.00 | 28.87 | C |
| ATOM | 4819 | CA | LEU | C | 424 | 47.524 | 57.995 | 18.459 | 1.00 | 27.92 | C |
| ATOM | 4820 | CB | LEU | C | 424 | 46.653 | 57.693 | 17.209 | 1.00 | 25.26 | C |
| ATOM | 4821 | CG | LEU | C | 424 | 47.016 | 58.499 | 15.962 | 1.00 | 24.24 | C |
| ATOM | 4822 | CD1 | LEU | C | 424 | 48.403 | 58.119 | 15.503 | 1.00 | 21.29 | C |
| ATOM | 4823 | CD2 | LEU | C | 424 | 45.998 | 58.112 | 14.892 | 1.00 | 27.92 | C |
| ATOM | 4824 | C | LEU | C | 424 | 47.543 | 59.470 | 18.723 | 1.00 | 28.01 | C |
| ATOM | 4825 | O | LEU | C | 424 | 48.521 | 60.156 | 18.381 | 1.00 | 26.16 | C |
| ATOM | 4826 | N | ARG | C | 425 | 46.436 | 59.993 | 19.273 | 1.00 | 28.53 | C |
| ATOM | 4827 | CA | ARG | C | 425 | 46.325 | 61.488 | 19.568 | 1.00 | 29.89 | C |
| ATOM | 4828 | CB | ARG | C | 425 | 44.933 | 61.800 | 20.056 | 1.00 | 29.65 | C |
| ATOM | 4829 | CG | ARG | C | 425 | 44.614 | 63.261 | 20.538 | 1.00 | 31.93 | C |
| ATOM | 4830 | CD | ARG | C | 425 | 44.354 | 64.254 | 19.505 | 1.00 | 31.66 | C |
| ATOM | 4831 | NE | ARG | C | 425 | 43.337 | 63.766 | 18.578 | 1.00 | 31.74 | C |
| ATOM | 4832 | CZ | ARG | C | 425 | 42.053 | 64.103 | 18.548 | 1.00 | 30.76 | C |
| ATOM | 4833 | NH1 | ARG | C | 425 | 41.553 | 64.876 | 19.478 | 1.00 | 29.00 | C |
| ATOM | 4834 | NH2 | ARG | C | 425 | 41.259 | 63.639 | 17.536 | 1.00 | 29.08 | C |
| ATOM | 4835 | C | ARG | C | 425 | 47.379 | 61.995 | 20.625 | 1.00 | 29.64 | C |
| ATOM | 4836 | O | ARG | C | 425 | 48.054 | 63.001 | 20.437 | 1.00 | 29.84 | C |
| ATOM | 4837 | N | GLN | C | 426 | 47.493 | 61.280 | 21.729 | 1.00 | 30.06 | C |
| ATOM | 4838 | CA | GLN | C | 426 | 48.490 | 61.587 | 22.734 | 1.00 | 30.48 | C |
| ATOM | 4839 | CB | GLN | C | 426 | 48.352 | 60.616 | 23.878 | 1.00 | 31.45 | C |
| ATOM | 4840 | CG | GLN | C | 426 | 49.352 | 60.692 | 25.078 | 1.00 | 33.90 | C |
| ATOM | 4841 | CD | GLN | C | 426 | 49.289 | 59.375 | 25.906 | 1.00 | 35.37 | C |
| ATOM | 4842 | OE1 | GLN | C | 426 | 48.193 | 58.892 | 26.164 | 1.00 | 34.72 | C |
| ATOM | 4843 | NE2 | GLN | C | 426 | 50.455 | 58.724 | 26.187 | 1.00 | 36.90 | C |
| ATOM | 4844 | C | GLN | C | 426 | 49.907 | 61.492 | 22.187 | 1.00 | 30.45 | C |
| ATOM | 4845 | O | GLN | C | 426 | 50.648 | 62.384 | 22.418 | 1.00 | 29.12 | C |
| ATOM | 4846 | N | THR | C | 427 | 50.262 | 60.443 | 21.451 | 1.00 | 30.37 | C |
| ATOM | 4847 | CA | THR | C | 427 | 51.596 | 60.358 | 20.809 | 1.00 | 30.64 | C |
| ATOM | 4848 | CB | THR | C | 427 | 51.745 | 59.023 | 20.099 | 1.00 | 31.79 | C |
| ATOM | 4849 | OG1 | THR | C | 427 | 51.533 | 57.945 | 21.025 | 1.00 | 32.74 | C |
| ATOM | 4850 | CG2 | THR | C | 427 | 53.184 | 58.816 | 19.602 | 1.00 | 31.64 | C |
| ATOM | 4851 | C | THR | C | 427 | 51.920 | 61.482 | 19.831 | 1.00 | 31.16 | C |
| ATOM | 4852 | O | THR | C | 427 | 52.981 | 62.059 | 19.859 | 1.00 | 30.16 | C |
| ATOM | 4853 | N | SER | C | 428 | 50.917 | 61.885 | 19.062 | 1.00 | 30.30 | C |
| ATOM | 4854 | CA | SER | C | 428 | 51.075 | 62.960 | 18.223 | 1.00 | 29.92 | C |
| ATOM | 4855 | CB | SER | C | 428 | 49.927 | 63.002 | 17.189 | 1.00 | 30.35 | C |
| ATOM | 4856 | OG | SER | C | 428 | 49.967 | 61.641 | 16.601 | 1.00 | 34.11 | C |
| ATOM | 4857 | C | SER | C | 428 | 51.305 | 64.291 | 18.875 | 1.00 | 30.03 | C |

TABLE 2-continued

ATOMIC COORDINATES OF THE ERR3 LBD/
DIETHYLSTILBESTROL COMPLEX

| ATOM | 4858 | O | SER | C | 428 | 51.946 | 65.102 | 18.274 | 1.00 | 29.34 | C |
|---|---|---|---|---|---|---|---|---|---|---|---|
| ATOM | 4859 | N | THR | C | 429 | 50.608 | 64.581 | 19.971 | 1.00 | 30.88 | C |
| ATOM | 4860 | CA | THR | C | 429 | 50.722 | 65.840 | 20.699 | 1.00 | 30.53 | C |
| ATOM | 4861 | CB | THR | C | 429 | 49.646 | 65.901 | 21.775 | 1.00 | 30.85 | C |
| ATOM | 4862 | OG1 | THR | C | 429 | 48.398 | 66.090 | 21.101 | 1.00 | 32.79 | C |
| ATOM | 4863 | CG2 | THR | C | 429 | 49.769 | 67.155 | 22.753 | 1.00 | 30.51 | C |
| ATOM | 4864 | C | THR | C | 429 | 52.108 | 65.865 | 21.286 | 1.00 | 30.47 | C |
| ATOM | 4865 | O | THR | C | 429 | 52.741 | 66.811 | 21.142 | 1.00 | 29.19 | C |
| ATOM | 4866 | N | LYS | C | 430 | 52.640 | 64.737 | 21.716 | 1.00 | 30.80 | C |
| ATOM | 4867 | CA | LYS | C | 430 | 53.986 | 64.683 | 22.153 | 1.00 | 31.99 | C |
| ATOM | 4868 | CB | LYS | C | 430 | 54.232 | 63.303 | 22.655 | 1.00 | 34.84 | C |
| ATOM | 4869 | CG | LYS | C | 430 | 55.237 | 63.205 | 23.696 | 1.00 | 40.48 | C |
| ATOM | 4870 | CD | LYS | C | 430 | 55.160 | 61.802 | 24.507 | 1.00 | 45.05 | C |
| ATOM | 4871 | CE | LYS | C | 430 | 53.734 | 61.307 | 24.974 | 1.00 | 45.82 | C |
| ATOM | 4872 | NZ | LYS | C | 430 | 53.509 | 61.406 | 26.456 | 1.00 | 47.07 | C |
| ATOM | 4873 | C | LYS | C | 430 | 55.001 | 64.981 | 21.014 | 1.00 | 30.37 | C |
| ATOM | 4874 | O | LYS | C | 430 | 55.941 | 65.754 | 21.211 | 1.00 | 29.57 | C |
| ATOM | 4875 | N | ALA | C | 431 | 54.746 | 64.424 | 19.832 | 1.00 | 27.92 | C |
| ATOM | 4876 | CA | ALA | C | 431 | 55.611 | 64.601 | 18.708 | 1.00 | 28.35 | C |
| ATOM | 4877 | CB | ALA | C | 431 | 55.237 | 63.697 | 17.503 | 1.00 | 26.09 | C |
| ATOM | 4878 | C | ALA | C | 431 | 55.576 | 66.065 | 18.283 | 1.00 | 28.87 | C |
| ATOM | 4879 | O | ALA | C | 431 | 56.632 | 66.599 | 17.994 | 1.00 | 28.48 | C |
| ATOM | 4880 | N | VAL | C | 432 | 54.396 | 66.709 | 18.242 | 1.00 | 28.86 | C |
| ATOM | 4881 | CA | VAL | C | 432 | 54.337 | 68.107 | 17.866 | 1.00 | 30.36 | C |
| ATOM | 4882 | CB | VAL | C | 432 | 52.850 | 68.558 | 17.431 | 1.00 | 31.98 | C |
| ATOM | 4883 | CG1 | VAL | C | 432 | 52.866 | 69.984 | 16.848 | 1.00 | 31.53 | C |
| ATOM | 4884 | CG2 | VAL | C | 432 | 52.339 | 67.710 | 16.204 | 1.00 | 31.88 | C |
| ATOM | 4885 | C | VAL | C | 432 | 54.905 | 69.045 | 18.935 | 1.00 | 30.40 | C |
| ATOM | 4886 | O | VAL | C | 432 | 55.554 | 69.971 | 18.661 | 1.00 | 29.72 | C |
| ATOM | 4887 | N | GLN | C | 433 | 54.758 | 68.706 | 20.184 | 1.00 | 30.95 | C |
| ATOM | 4888 | CA | GLN | C | 433 | 55.532 | 69.402 | 21.188 | 1.00 | 32.08 | C |
| ATOM | 4889 | CB | GLN | C | 433 | 55.126 | 68.953 | 22.582 | 1.00 | 33.52 | C |
| ATOM | 4890 | CG | GLN | C | 433 | 53.893 | 69.318 | 23.144 | 0.00 | 39.01 | C |
| ATOM | 4891 | CD | GLN | C | 433 | 53.404 | 68.606 | 24.385 | 1.00 | 42.50 | C |
| ATOM | 4892 | OE1 | GLN | C | 433 | 54.165 | 68.159 | 25.266 | 1.00 | 46.00 | C |
| ATOM | 4893 | NE2 | GLN | C | 433 | 52.351 | 69.332 | 24.660 | 1.00 | 43.83 | C |
| ATOM | 4894 | C | GLN | C | 433 | 57.048 | 69.358 | 20.973 | 1.00 | 30.63 | C |
| ATOM | 4895 | O | GLN | C | 433 | 57.682 | 70.384 | 20.959 | 1.00 | 29.70 | C |
| ATOM | 4896 | N | HIS | C | 434 | 57.586 | 68.185 | 20.675 | 1.00 | 30.64 | C |
| ATOM | 4897 | CA | HIS | C | 434 | 59.017 | 68.017 | 20.545 | 1.00 | 30.89 | C |
| ATOM | 4898 | CB | HIS | C | 434 | 59.265 | 66.538 | 20.353 | 1.00 | 32.95 | C |
| ATOM | 4899 | CG | HIS | C | 434 | 60.702 | 66.151 | 20.341 | 1.00 | 34.57 | C |
| ATOM | 4900 | CD2 | HIS | C | 434 | 61.438 | 65.453 | 21.233 | 1.00 | 34.43 | C |
| ATOM | 4901 | ND1 | HIS | C | 434 | 61.567 | 66.538 | 19.338 | 1.00 | 32.52 | C |
| ATOM | 4902 | CE1 | HIS | C | 434 | 62.780 | 66.095 | 19.623 | 1.00 | 32.70 | C |
| ATOM | 4903 | NE2 | HIS | C | 434 | 62.722 | 65.408 | 20.737 | 1.00 | 34.92 | C |
| ATOM | 4904 | C | HIS | C | 434 | 59.429 | 68.826 | 19.285 | 1.00 | 31.48 | C |
| ATOM | 4905 | O | HIS | C | 434 | 60.336 | 69.622 | 19.299 | 1.00 | 30.69 | C |
| ATOM | 4906 | N | PHE | C | 435 | 58.640 | 68.696 | 18.230 | 1.00 | 31.40 | C |
| ATOM | 4907 | CA | PHE | C | 435 | 58.922 | 69.379 | 17.018 | 1.00 | 32.86 | C |
| ATOM | 4908 | CB | PHE | C | 435 | 57.819 | 69.045 | 15.980 | 1.00 | 34.54 | C |
| ATOM | 4909 | CG | PHE | C | 435 | 57.900 | 69.803 | 14.669 | 1.00 | 34.98 | C |
| ATOM | 4910 | CD1 | PHE | C | 435 | 58.928 | 69.516 | 13.770 | 1.00 | 38.08 | C |
| ATOM | 4911 | CD2 | PHE | C | 435 | 56.907 | 70.742 | 14.334 | 1.00 | 36.94 | C |
| ATOM | 4912 | CE1 | PHE | C | 435 | 58.995 | 70.210 | 12.531 | 1.00 | 39.25 | C |
| ATOM | 4913 | CE2 | PHE | C | 435 | 56.899 | 71.444 | 13.092 | 1.00 | 37.69 | C |
| ATOM | 4914 | CZ | PHE | C | 435 | 57.934 | 71.156 | 12.173 | 1.00 | 38.57 | C |
| ATOM | 4915 | C | PHE | C | 435 | 59.007 | 70.902 | 17.193 | 1.00 | 32.06 | C |
| ATOM | 4916 | O | PHE | C | 435 | 59.962 | 71.470 | 16.757 | 1.00 | 30.53 | C |
| ATOM | 4917 | N | TYR | C | 436 | 57.982 | 71.528 | 17.771 | 1.00 | 32.77 | C |
| ATOM | 4918 | CA | TYR | C | 436 | 57.967 | 72.998 | 17.983 | 1.00 | 32.91 | C |
| ATOM | 4919 | CB | TYR | C | 436 | 56.595 | 73.489 | 18.358 | 1.00 | 34.02 | C |
| ATOM | 4920 | CG | TYR | C | 436 | 55.666 | 73.614 | 17.197 | 1.00 | 37.46 | C |
| ATOM | 4921 | CD1 | TYR | C | 436 | 55.999 | 74.340 | 16.099 | 1.00 | 40.42 | C |
| ATOM | 4922 | CE1 | TYR | C | 436 | 55.160 | 74.438 | 15.039 | 1.00 | 41.90 | C |
| ATOM | 4923 | CD2 | TYR | C | 436 | 54.498 | 73.006 | 17.205 | 1.00 | 38.30 | C |
| ATOM | 4924 | CE2 | TYR | C | 436 | 53.650 | 73.112 | 16.156 | 1.00 | 41.80 | C |
| ATOM | 4925 | CZ | TYR | C | 436 | 53.983 | 73.801 | 15.097 | 1.00 | 42.95 | C |
| ATOM | 4926 | OH | TYR | C | 436 | 53.090 | 73.873 | 14.078 | 1.00 | 47.16 | C |
| ATOM | 4927 | C | TYR | C | 436 | 59.018 | 73.433 | 19.061 | 1.00 | 32.51 | C |
| ATOM | 4928 | O | TYR | C | 436 | 59.524 | 74.511 | 19.006 | 1.00 | 32.46 | C |
| ATOM | 4929 | N | ASN | C | 437 | 59.468 | 72.530 | 19.879 | 1.00 | 31.42 | C |
| ATOM | 4930 | CA | ASN | C | 437 | 60.624 | 72.831 | 20.691 | 1.00 | 33.79 | C |
| ATOM | 4931 | CB | ASN | C | 437 | 60.791 | 71.741 | 21.760 | 1.00 | 36.11 | C |
| ATOM | 4932 | CG | ASN | C | 437 | 60.424 | 72.226 | 23.082 | 1.00 | 40.93 | C |
| ATOM | 4933 | OD1 | ASN | C | 437 | 61.116 | 73.196 | 23.649 | 1.00 | 43.29 | C |

TABLE 2-continued

ATOMIC COORDINATES OF THE ERR3 LBD/
DIETHYLSTILBESTROL COMPLEX

| ATOM | 4934 | ND2 | ASN | C | 437 | 59.331 | 71.597 | 23.670 | 1.00 | 41.36 | C |
|---|---|---|---|---|---|---|---|---|---|---|---|
| ATOM | 4935 | C | ASN | C | 437 | 61.891 | 72.931 | 19.971 | 1.00 | 33.93 | C |
| ATOM | 4936 | O | ASN | C | 437 | 62.688 | 73.867 | 20.156 | 1.00 | 34.39 | C |
| ATOM | 4937 | N | ILE | C | 438 | 62.088 | 71.973 | 19.068 | 1.00 | 34.13 | C |
| ATOM | 4938 | CA | ILE | C | 438 | 63.272 | 71.962 | 18.200 | 1.00 | 33.31 | C |
| ATOM | 4939 | CB | ILE | C | 438 | 63.279 | 70.601 | 17.437 | 1.00 | 33.81 | C |
| ATOM | 4940 | CG2 | ILE | C | 438 | 63.964 | 70.636 | 16.080 | 1.00 | 34.16 | C |
| ATOM | 4941 | CG1 | ILE | C | 438 | 63.752 | 69.495 | 18.326 | 1.00 | 33.61 | C |
| ATOM | 4942 | CD1 | ILE | C | 438 | 65.036 | 69.786 | 18.963 | 1.00 | 33.65 | C |
| ATOM | 4943 | C | ILE | C | 438 | 63.249 | 73.192 | 17.323 | 1.00 | 32.87 | C |
| ATOM | 4944 | O | ILE | C | 438 | 64.229 | 73.856 | 17.140 | 1.00 | 31.74 | C |
| ATOM | 4945 | N | LYS | C | 439 | 62.115 | 73.625 | 16.886 | 1.00 | 32.89 | C |
| ATOM | 4946 | CA | LYS | C | 439 | 62.036 | 74.940 | 16.205 | 1.00 | 35.42 | C |
| ATOM | 4947 | CB | LYS | C | 439 | 60.628 | 75.141 | 15.586 | 1.00 | 36.34 | C |
| ATOM | 4948 | CG | LYS | C | 439 | 60.464 | 74.307 | 14.227 | 1.00 | 40.36 | C |
| ATOM | 4949 | CD | LYS | C | 439 | 59.268 | 74.600 | 13.275 | 1.00 | 43.39 | C |
| ATOM | 4950 | CE | LYS | C | 439 | 58.958 | 76.161 | 12.916 | 1.00 | 45.38 | C |
| ATOM | 4951 | NZ | LYS | C | 439 | 58.760 | 76.489 | 11.439 | 1.00 | 45.78 | C |
| ATOM | 4952 | C | LYS | C | 439 | 62.423 | 76.191 | 17.076 | 1.00 | 35.73 | C |
| ATOM | 4953 | O | LYS | C | 439 | 63.228 | 76.964 | 16.680 | 1.00 | 35.77 | C |
| ATOM | 4954 | N | LEU | C | 440 | 61.842 | 76.365 | 18.240 | 1.00 | 36.63 | C |
| ATOM | 4955 | CA | LEU | C | 440 | 62.256 | 77.405 | 19.188 | 1.00 | 38.46 | C |
| ATOM | 4956 | CB | LEU | C | 440 | 61.590 | 77.137 | 20.529 | 1.00 | 39.42 | C |
| ATOM | 4957 | CG | LEU | C | 440 | 61.971 | 77.962 | 21.721 | 1.00 | 39.82 | C |
| ATOM | 4958 | CD1 | LEU | C | 440 | 61.679 | 79.439 | 21.413 | 1.00 | 41.42 | C |
| ATOM | 4959 | CD2 | LEU | C | 440 | 61.093 | 77.446 | 22.865 | 1.00 | 40.51 | C |
| ATOM | 4960 | C | LEU | C | 440 | 63.746 | 77.279 | 19.465 | 1.00 | 39.34 | C |
| ATOM | 4961 | O | LEU | C | 440 | 64.454 | 78.246 | 19.478 | 1.00 | 39.52 | C |
| ATOM | 4962 | N | GLU | C | 441 | 64.267 | 76.065 | 19.622 | 1.00 | 39.91 | C |
| ATOM | 4963 | CA | GLU | C | 441 | 65.720 | 76.009 | 19.789 | 1.00 | 39.15 | C |
| ATOM | 4964 | CB | GLU | C | 441 | 66.099 | 74.675 | 20.226 | 1.00 | 41.38 | C |
| ATOM | 4965 | CG | GLU | C | 441 | 66.083 | 74.379 | 21.707 | 1.00 | 46.87 | C |
| ATOM | 4966 | CD | GLU | C | 441 | 66.982 | 73.115 | 21.986 | 1.00 | 51.14 | C |
| ATOM | 4967 | OE1 | GLU | C | 441 | 68.290 | 73.187 | 21.793 | 1.00 | 52.99 | C |
| ATOM | 4968 | OE2 | GLU | C | 441 | 66.375 | 72.054 | 22.354 | 1.00 | 52.31 | C |
| ATOM | 4969 | C | GLU | C | 441 | 66.485 | 76.294 | 18.502 | 1.00 | 37.82 | C |
| ATOM | 4970 | O | GLU | C | 441 | 67.651 | 76.473 | 18.556 | 1.00 | 38.10 | C |
| ATOM | 4971 | N | GLY | C | 442 | 65.867 | 76.344 | 17.325 | 1.00 | 36.96 | C |
| ATOM | 4972 | CA | GLY | C | 442 | 66.599 | 76.565 | 16.088 | 1.00 | 36.92 | C |
| ATOM | 4973 | C | GLY | C | 442 | 67.560 | 75.419 | 15.790 | 1.00 | 38.95 | C |
| ATOM | 4974 | O | GLY | C | 442 | 68.567 | 75.624 | 15.203 | 1.00 | 38.44 | C |
| ATOM | 4975 | N | LYS | C | 443 | 67.298 | 74.212 | 16.274 | 1.00 | 39.87 | C |
| ATOM | 4976 | CA | LYS | C | 443 | 68.285 | 73.161 | 16.169 | 1.00 | 41.92 | C |
| ATOM | 4977 | CB | LYS | C | 443 | 67.920 | 72.041 | 17.171 | 1.00 | 42.98 | C |
| ATOM | 4978 | CG | LYS | C | 443 | 69.000 | 71.393 | 17.910 | 1.00 | 44.89 | C |
| ATOM | 4979 | CD | LYS | C | 443 | 68.355 | 70.248 | 18.729 | 1.00 | 46.31 | C |
| ATOM | 4980 | CE | LYS | C | 443 | 69.337 | 69.523 | 19.586 | 1.00 | 48.03 | C |
| ATOM | 4981 | NZ | LYS | C | 443 | 69.505 | 68.024 | 19.483 | 1.00 | 48.83 | C |
| ATOM | 4982 | C | LYS | C | 443 | 68.377 | 72.611 | 14.713 | 1.00 | 42.39 | C |
| ATOM | 4983 | O | LYS | C | 443 | 69.318 | 71.952 | 14.402 | 1.00 | 41.97 | C |
| ATOM | 4984 | N | VAL | C | 444 | 67.423 | 72.931 | 13.872 | 1.00 | 42.93 | C |
| ATOM | 4985 | CA | VAL | C | 444 | 67.322 | 72.469 | 12.522 | 1.00 | 45.23 | C |
| ATOM | 4986 | CB | VAL | C | 444 | 65.960 | 71.785 | 12.159 | 1.00 | 43.72 | C |
| ATOM | 4987 | CG1 | VAL | C | 444 | 65.815 | 71.583 | 10.628 | 1.00 | 43.69 | C |
| ATOM | 4988 | CG2 | VAL | C | 444 | 65.839 | 70.415 | 12.721 | 1.00 | 42.38 | C |
| ATOM | 4989 | C | VAL | C | 444 | 67.542 | 73.590 | 11.503 | 1.00 | 48.71 | C |
| ATOM | 4990 | O | VAL | C | 444 | 66.757 | 74.527 | 11.413 | 1.00 | 48.56 | C |
| ATOM | 4991 | N | PRO | C | 445 | 68.581 | 73.420 | 10.660 | 1.00 | 51.46 | C |
| ATOM | 4992 | CD | PRO | C | 445 | 69.437 | 72.225 | 10.543 | 1.00 | 51.68 | C |
| ATOM | 4993 | CA | PRO | C | 445 | 68.957 | 74.481 | 9.735 | 1.00 | 54.79 | C |
| ATOM | 4994 | CB | PRO | C | 445 | 70.411 | 74.075 | 9.298 | 1.00 | 53.88 | C |
| ATOM | 4995 | CG | PRO | C | 445 | 70.670 | 72.613 | 9.711 | 1.00 | 52.45 | C |
| ATOM | 4996 | C | PRO | C | 445 | 67.941 | 74.619 | 8.577 | 1.00 | 57.79 | C |
| ATOM | 4997 | O | PRO | C | 445 | 67.966 | 73.764 | 7.726 | 1.00 | 57.89 | C |
| ATOM | 4998 | N | MET | C | 446 | 67.012 | 75.591 | 8.615 | 1.00 | 62.16 | C |
| ATOM | 4999 | CA | MET | C | 446 | 65.957 | 75.805 | 7.560 | 1.00 | 66.42 | C |
| ATOM | 5000 | CB | MET | C | 446 | 65.183 | 77.136 | 7.729 | 1.00 | 68.44 | C |
| ATOM | 5001 | CG | MET | C | 446 | 66.041 | 78.325 | 8.115 | 1.00 | 72.62 | C |
| ATOM | 5002 | SD | MET | C | 446 | 65.096 | 79.854 | 8.267 | 1.00 | 78.53 | C |
| ATOM | 5003 | CE | MET | C | 446 | 64.692 | 79.825 | 10.008 | 1.00 | 76.69 | C |
| ATOM | 5004 | C | MET | C | 446 | 66.596 | 75.827 | 6.193 | 1.00 | 68.48 | C |
| ATOM | 5005 | O | MET | C | 446 | 66.004 | 75.336 | 5.155 | 1.00 | 68.09 | C |
| ATOM | 5006 | N | HIS | C | 447 | 67.830 | 76.342 | 6.205 | 1.00 | 71.45 | C |
| ATOM | 5007 | CA | HIS | C | 447 | 68.448 | 76.732 | 4.990 | 1.00 | 75.00 | C |
| ATOM | 5008 | CB | HIS | C | 447 | 67.840 | 78.091 | 4.731 | 1.00 | 77.85 | C |
| ATOM | 5009 | CG | HIS | C | 447 | 68.420 | 79.198 | 5.561 | 1.00 | 81.65 | C |

TABLE 2-continued

ATOMIC COORDINATES OF THE ERR3 LBD/DIETHYLSTILBESTROL COMPLEX

| ATOM | 5010 | CD2 | HIS | C | 447 | 67.829 | 80.212 | 6.236 | 1.00 | 83.13 | C |
|------|------|-----|-----|---|-----|--------|--------|-------|------|-------|---|
| ATOM | 5011 | ND1 | HIS | C | 447 | 69.779 | 79.373 | 5.722 | 1.00 | 83.13 | C |
| ATOM | 5012 | CE1 | HIS | C | 447 | 69.999 | 80.444 | 6.461 | 1.00 | 84.24 | C |
| ATOM | 5013 | NE2 | HIS | C | 447 | 68.832 | 80.972 | 6.787 | 1.00 | 84.71 | C |
| ATOM | 5014 | C | HIS | C | 447 | 69.996 | 76.683 | 4.921 | 1.00 | 75.71 | C |
| ATOM | 5015 | O | HIS | C | 447 | 70.685 | 76.415 | 5.945 | 1.00 | 76.38 | C |
| ATOM | 5016 | OXT | HIS | C | 447 | 70.511 | 76.927 | 3.812 | 1.00 | 77.08 | C |
| ATOM | 5017 | CB | ASN | D | 235 | 23.605 | 46.332 | 30.010 | 1.00 | 52.92 | D |
| ATOM | 5018 | CG | ASN | D | 235 | 25.116 | 45.928 | 30.123 | 1.00 | 52.95 | D |
| ATOM | 5019 | OD1 | ASN | D | 235 | 25.839 | 46.289 | 31.082 | 1.00 | 52.61 | D |
| ATOM | 5020 | ND2 | ASN | D | 235 | 25.558 | 45.159 | 29.184 | 1.00 | 53.28 | D |
| ATOM | 5021 | C | ASN | D | 235 | 23.306 | 45.619 | 32.395 | 1.00 | 52.05 | D |
| ATOM | 5022 | O | ASN | D | 235 | 23.378 | 46.717 | 33.009 | 1.00 | 52.59 | D |
| ATOM | 5023 | N | ASN | D | 235 | 21.169 | 45.674 | 30.676 | 1.00 | 53.05 | D |
| ATOM | 5024 | CA | ASN | D | 235 | 22.710 | 45.503 | 30.945 | 1.00 | 52.95 | D |
| ATOM | 5025 | N | LYS | D | 236 | 23.831 | 44.504 | 32.900 | 1.00 | 50.33 | D |
| ATOM | 5026 | CA | LYS | D | 236 | 24.257 | 44.467 | 34.329 | 1.00 | 49.07 | D |
| ATOM | 5027 | CB | LYS | D | 236 | 24.528 | 43.001 | 34.788 | 1.00 | 50.44 | D |
| ATOM | 5028 | CG | LYS | D | 236 | 25.131 | 42.819 | 36.241 | 1.00 | 52.62 | D |
| ATOM | 5029 | CD | LYS | D | 236 | 25.464 | 41.274 | 36.519 | 1.00 | 54.50 | D |
| ATOM | 5030 | CE | LYS | D | 236 | 25.857 | 40.986 | 37.974 | 1.00 | 56.91 | D |
| ATOM | 5031 | NZ | LYS | D | 236 | 24.966 | 41.468 | 39.081 | 1.00 | 58.20 | D |
| ATOM | 5032 | C | LYS | D | 236 | 25.472 | 45.325 | 34.680 | 1.00 | 47.44 | D |
| ATOM | 5033 | O | LYS | D | 236 | 25.493 | 45.947 | 35.751 | 1.00 | 47.53 | D |
| ATOM | 5034 | N | ILE | D | 237 | 26.522 | 45.267 | 33.859 | 1.00 | 45.75 | D |
| ATOM | 5035 | CA | ILE | D | 237 | 27.746 | 46.143 | 34.035 | 1.00 | 43.80 | D |
| ATOM | 5036 | CB | ILE | D | 237 | 28.732 | 45.963 | 32.904 | 1.00 | 43.93 | D |
| ATOM | 5037 | CG2 | ILE | D | 237 | 29.963 | 47.000 | 32.965 | 1.00 | 43.84 | D |
| ATOM | 5038 | CG1 | ILE | D | 237 | 29.349 | 44.577 | 32.927 | 1.00 | 44.26 | D |
| ATOM | 5039 | CD1 | ILE | D | 237 | 30.116 | 44.276 | 34.224 | 1.00 | 44.78 | D |
| ATOM | 5040 | C | ILE | D | 237 | 27.313 | 47.610 | 34.202 | 1.00 | 42.12 | D |
| ATOM | 5041 | O | ILE | D | 237 | 27.665 | 48.230 | 35.167 | 1.00 | 42.26 | D |
| ATOM | 5042 | N | VAL | D | 238 | 26.438 | 48.102 | 33.351 | 1.00 | 40.71 | D |
| ATOM | 5043 | CA | VAL | D | 238 | 26.108 | 49.504 | 33.380 | 1.00 | 40.40 | D |
| ATOM | 5044 | CB | VAL | D | 238 | 25.275 | 49.869 | 32.169 | 1.00 | 39.22 | D |
| ATOM | 5045 | CG1 | VAL | D | 238 | 24.784 | 51.353 | 32.252 | 1.00 | 37.58 | D |
| ATOM | 5046 | CG2 | VAL | D | 238 | 26.088 | 49.577 | 30.924 | 1.00 | 37.36 | D |
| ATOM | 5047 | C | VAL | D | 238 | 25.355 | 49.762 | 34.622 | 1.00 | 41.02 | D |
| ATOM | 5048 | O | VAL | D | 238 | 25.466 | 50.793 | 35.237 | 1.00 | 40.51 | D |
| ATOM | 5049 | N | SER | D | 239 | 24.605 | 48.767 | 35.086 | 1.00 | 42.24 | D |
| ATOM | 5050 | CA | SER | D | 239 | 23.900 | 48.962 | 36.413 | 1.00 | 42.57 | D |
| ATOM | 5051 | CB | SER | D | 239 | 22.938 | 47.783 | 36.740 | 1.00 | 43.15 | D |
| ATOM | 5052 | OG | SER | D | 239 | 21.775 | 47.862 | 35.966 | 1.00 | 43.80 | D |
| ATOM | 5053 | C | SER | D | 239 | 24.785 | 49.070 | 37.577 | 1.00 | 42.47 | D |
| ATOM | 5054 | O | SER | D | 239 | 24.502 | 49.857 | 38.479 | 1.00 | 43.65 | D |
| ATOM | 5055 | N | HIS | D | 240 | 25.813 | 48.241 | 37.630 | 1.00 | 42.45 | D |
| ATOM | 5056 | CA | HIS | D | 240 | 26.835 | 48.386 | 38.683 | 1.00 | 43.56 | D |
| ATOM | 5057 | CB | HIS | D | 240 | 27.994 | 47.413 | 38.341 | 1.00 | 45.99 | D |
| ATOM | 5058 | CG | HIS | D | 240 | 28.049 | 46.167 | 39.149 | 1.00 | 49.05 | D |
| ATOM | 5059 | CD2 | HIS | D | 240 | 29.005 | 45.685 | 39.981 | 1.00 | 51.33 | D |
| ATOM | 5060 | ND1 | HIS | D | 240 | 27.086 | 45.179 | 39.049 | 1.00 | 51.21 | D |
| ATOM | 5061 | CE1 | HIS | D | 240 | 27.406 | 44.174 | 39.848 | 1.00 | 51.84 | D |
| ATOM | 5062 | NE2 | HIS | D | 240 | 28.586 | 44.432 | 40.389 | 1.00 | 53.26 | D |
| ATOM | 5063 | C | HIS | D | 240 | 27.479 | 49.812 | 38.705 | 1.00 | 42.82 | D |
| ATOM | 5064 | O | HIS | D | 240 | 27.715 | 50.486 | 39.712 | 1.00 | 42.08 | D |
| ATOM | 5065 | N | LEU | D | 241 | 27.810 | 50.250 | 37.501 | 1.00 | 42.07 | D |
| ATOM | 5066 | CA | LEU | D | 241 | 28.445 | 51.546 | 37.377 | 1.00 | 41.40 | D |
| ATOM | 5067 | CB | LEU | D | 241 | 28.948 | 51.713 | 35.961 | 1.00 | 40.38 | D |
| ATOM | 5068 | CG | LEU | D | 241 | 30.128 | 50.794 | 35.703 | 1.00 | 40.84 | D |
| ATOM | 5069 | CD1 | LEU | D | 241 | 30.548 | 50.977 | 34.249 | 1.00 | 41.37 | D |
| ATOM | 5070 | CD2 | LEU | D | 241 | 31.280 | 51.141 | 36.630 | 1.00 | 40.08 | D |
| ATOM | 5071 | C | LEU | D | 241 | 27.512 | 52.595 | 37.824 | 1.00 | 41.04 | D |
| ATOM | 5072 | O | LEU | D | 241 | 27.934 | 53.509 | 38.494 | 1.00 | 40.18 | D |
| ATOM | 5073 | N | LEU | D | 242 | 26.225 | 52.414 | 37.584 | 1.00 | 41.16 | D |
| ATOM | 5074 | CA | LEU | D | 242 | 25.240 | 53.463 | 38.067 | 1.00 | 41.12 | D |
| ATOM | 5075 | CB | LEU | D | 242 | 23.831 | 53.230 | 37.510 | 1.00 | 39.67 | D |
| ATOM | 5076 | CG | LEU | D | 242 | 23.665 | 53.472 | 35.995 | 1.00 | 38.60 | D |
| ATOM | 5077 | CD1 | LEU | D | 242 | 22.220 | 53.006 | 35.620 | 1.00 | 37.32 | D |
| ATOM | 5078 | CD2 | LEU | D | 242 | 23.846 | 55.028 | 35.566 | 1.00 | 35.87 | D |
| ATOM | 5079 | C | LEU | D | 242 | 25.167 | 53.615 | 39.540 | 1.00 | 42.00 | D |
| ATOM | 5080 | O | LEU | D | 242 | 25.120 | 54.736 | 40.054 | 1.00 | 42.61 | D |
| ATOM | 5081 | N | VAL | D | 243 | 25.220 | 52.488 | 40.268 | 1.00 | 43.42 | D |
| ATOM | 5082 | CA | VAL | D | 243 | 25.137 | 52.495 | 41.741 | 1.00 | 44.27 | D |
| ATOM | 5083 | CB | VAL | D | 243 | 25.018 | 51.092 | 42.296 | 1.00 | 44.95 | D |
| ATOM | 5084 | CG1 | VAL | D | 243 | 25.172 | 50.971 | 43.594 | 0.00 | 44.74 | D |
| ATOM | 5085 | CG2 | VAL | D | 243 | 23.626 | 50.542 | 41.836 | 1.00 | 45.10 | D |

TABLE 2-continued

ATOMIC COORDINATES OF THE ERR3 LBD/
DIETHYLSTILBESTROL COMPLEX

| ATOM | 5086 | C | VAL | D | 243 | 26.352 | 53.021 | 42.336 | 1.00 | 45.28 | D |
|------|------|------|-----|---|-----|--------|--------|--------|------|-------|---|
| ATOM | 5087 | O | VAL | D | 243 | 26.329 | 53.607 | 43.428 | 1.00 | 46.21 | D |
| ATOM | 5088 | N | ALA | D | 244 | 27.470 | 52.811 | 41.645 | 1.00 | 45.19 | D |
| ATOM | 5089 | CA | ALA | D | 244 | 28.774 | 53.269 | 42.173 | 1.00 | 44.54 | D |
| ATOM | 5090 | CB | ALA | D | 244 | 29.939 | 52.449 | 41.539 | 1.00 | 44.97 | D |
| ATOM | 5091 | C | ALA | D | 244 | 28.993 | 54.769 | 42.005 | 1.00 | 44.66 | D |
| ATOM | 5092 | O | ALA | D | 244 | 29.991 | 55.320 | 42.522 | 1.00 | 43.99 | D |
| ATOM | 5093 | N | GLU | D | 245 | 28.090 | 55.499 | 41.332 | 1.00 | 44.35 | D |
| ATOM | 5094 | CA | GLU | D | 245 | 28.369 | 56.954 | 41.222 | 1.00 | 43.99 | D |
| ATOM | 5095 | CB | GLU | D | 245 | 27.222 | 57.736 | 40.596 | 1.00 | 42.92 | D |
| ATOM | 5096 | CG | GLU | D | 245 | 27.369 | 57.905 | 39.099 | 1.00 | 42.09 | D |
| ATOM | 5097 | CD | GLU | D | 245 | 28.670 | 58.581 | 38.672 | 1.00 | 41.29 | D |
| ATOM | 5098 | OE1 | GLU | D | 245 | 29.647 | 57.853 | 38.439 | 1.00 | 41.13 | D |
| ATOM | 5099 | OE2 | GLU | D | 245 | 28.716 | 59.798 | 38.719 | 1.00 | 41.19 | D |
| ATOM | 5100 | C | GLU | D | 245 | 28.642 | 57.506 | 42.594 | 1.00 | 44.88 | D |
| ATOM | 5101 | O | GLU | D | 245 | 27.958 | 57.168 | 43.505 | 1.00 | 45.04 | D |
| ATOM | 5102 | N | PRO | D | 246 | 29.672 | 58.299 | 42.793 | 1.00 | 45.47 | D |
| ATOM | 5103 | CD | PRO | D | 246 | 30.719 | 58.594 | 41.833 | 1.00 | 44.52 | D |
| ATOM | 5104 | CA | PRO | D | 246 | 29.914 | 58.899 | 44.115 | 1.00 | 45.21 | D |
| ATOM | 5105 | CB | PRO | D | 246 | 31.289 | 59.573 | 43.976 | 1.00 | 44.87 | D |
| ATOM | 5106 | CG | PRO | D | 246 | 31.634 | 59.528 | 42.597 | 1.00 | 44.60 | D |
| ATOM | 5107 | C | PRO | D | 246 | 28.868 | 59.920 | 44.503 | 1.00 | 45.41 | D |
| ATOM | 5108 | O | PRO | D | 246 | 28.378 | 60.503 | 43.529 | 1.00 | 46.01 | D |
| ATOM | 5109 | N | LYS | D | 248 | 27.790 | 63.661 | 45.412 | 1.00 | 40.89 | D |
| ATOM | 5110 | CA | LYS | D | 248 | 28.181 | 65.048 | 45.088 | 1.00 | 41.92 | D |
| ATOM | 5111 | CB | LYS | D | 248 | 27.014 | 66.083 | 45.124 | 1.00 | 44.22 | D |
| ATOM | 5112 | CG | LYS | D | 248 | 25.758 | 65.810 | 44.149 | 1.00 | 46.64 | D |
| ATOM | 5113 | CD | LYS | D | 248 | 24.933 | 67.107 | 43.801 | 1.00 | 50.59 | D |
| ATOM | 5114 | CE | LYS | D | 248 | 23.888 | 66.935 | 42.613 | 1.00 | 51.53 | D |
| ATOM | 5115 | NZ | LYS | D | 248 | 24.561 | 66.652 | 41.263 | 1.00 | 54.31 | D |
| ATOM | 5116 | C | LYS | D | 248 | 29.315 | 65.534 | 45.945 | 1.00 | 40.98 | D |
| ATOM | 5117 | O | LYS | D | 248 | 29.472 | 65.081 | 47.036 | 1.00 | 41.14 | D |
| ATOM | 5118 | N | ILE | D | 249 | 30.177 | 66.384 | 45.388 | 1.00 | 39.68 | D |
| ATOM | 5119 | CA | ILE | D | 249 | 31.262 | 66.992 | 46.129 | 1.00 | 37.75 | D |
| ATOM | 5120 | CB | ILE | D | 249 | 32.584 | 66.344 | 45.657 | 1.00 | 36.82 | D |
| ATOM | 5121 | CG2 | ILE | D | 249 | 33.805 | 67.128 | 46.220 | 1.00 | 35.49 | D |
| ATOM | 5122 | CG1 | ILE | D | 249 | 32.646 | 64.892 | 46.190 | 1.00 | 37.23 | D |
| ATOM | 5123 | CD1 | ILE | D | 249 | 33.383 | 63.953 | 45.392 | 1.00 | 34.29 | D |
| ATOM | 5124 | C | ILE | D | 249 | 31.293 | 68.466 | 45.866 | 1.00 | 38.24 | D |
| ATOM | 5125 | O | ILE | D | 249 | 31.149 | 68.874 | 44.764 | 1.00 | 38.41 | D |
| ATOM | 5126 | N | TYR | D | 250 | 31.537 | 69.276 | 46.870 | 1.00 | 38.66 | D |
| ATOM | 5127 | CA | TYR | D | 250 | 31.415 | 70.689 | 46.791 | 1.00 | 39.11 | D |
| ATOM | 5128 | CB | TYR | D | 250 | 30.528 | 71.182 | 47.937 | 1.00 | 40.40 | D |
| ATOM | 5129 | CG | TYR | D | 250 | 29.198 | 70.528 | 47.854 | 1.00 | 42.64 | D |
| ATOM | 5130 | CD1 | TYR | D | 250 | 28.166 | 71.139 | 47.121 | 1.00 | 43.39 | D |
| ATOM | 5131 | CE1 | TYR | D | 250 | 26.979 | 70.599 | 46.964 | 1.00 | 45.07 | D |
| ATOM | 5132 | CD2 | TYR | D | 250 | 28.922 | 69.406 | 48.530 | 1.00 | 43.60 | D |
| ATOM | 5133 | CE2 | TYR | D | 250 | 27.606 | 68.780 | 48.376 | 1.00 | 45.51 | D |
| ATOM | 5134 | CZ | TYR | D | 250 | 26.680 | 69.401 | 47.566 | 1.00 | 45.77 | D |
| ATOM | 5135 | OH | TYR | D | 250 | 25.409 | 68.890 | 47.345 | 1.00 | 48.52 | D |
| ATOM | 5136 | C | TYR | D | 250 | 32.766 | 71.313 | 46.916 | 1.00 | 38.87 | D |
| ATOM | 5137 | O | TYR | D | 250 | 33.614 | 70.864 | 47.678 | 1.00 | 39.86 | D |
| ATOM | 5138 | N | ALA | D | 251 | 32.955 | 72.384 | 46.163 | 1.00 | 38.49 | D |
| ATOM | 5139 | CA | ALA | D | 251 | 34.111 | 73.224 | 46.225 | 1.00 | 38.47 | D |
| ATOM | 5140 | CB | ALA | D | 251 | 34.166 | 74.005 | 44.966 | 1.00 | 37.17 | D |
| ATOM | 5141 | C | ALA | D | 251 | 34.347 | 74.175 | 47.412 | 1.00 | 38.77 | D |
| ATOM | 5142 | O | ALA | D | 251 | 35.509 | 74.506 | 47.749 | 1.00 | 38.31 | D |
| ATOM | 5143 | N | MET | D | 252 | 33.261 | 74.638 | 48.051 | 1.00 | 40.67 | D |
| ATOM | 5144 | CA | MET | D | 252 | 33.332 | 75.490 | 49.240 | 1.00 | 41.08 | D |
| ATOM | 5145 | CB | MET | D | 252 | 33.705 | 74.649 | 50.448 | 1.00 | 43.62 | D |
| ATOM | 5146 | CG | MET | D | 252 | 32.510 | 73.751 | 50.867 | 1.00 | 47.05 | D |
| ATOM | 5147 | SD | MET | D | 252 | 33.000 | 72.430 | 51.959 | 1.00 | 54.35 | D |
| ATOM | 5148 | CE | MET | D | 252 | 31.956 | 71.095 | 52.325 | 1.00 | 51.37 | D |
| ATOM | 5149 | C | MET | D | 252 | 34.277 | 76.603 | 49.098 | 1.00 | 40.31 | D |
| ATOM | 5150 | O | MET | D | 252 | 35.160 | 76.762 | 49.865 | 1.00 | 38.67 | D |
| ATOM | 5151 | N | PRO | D | 253 | 34.089 | 77.456 | 48.130 | 1.00 | 40.92 | D |
| ATOM | 5152 | CD | PRO | D | 253 | 32.889 | 77.543 | 47.293 | 1.00 | 40.49 | D |
| ATOM | 5153 | CA | PRO | D | 253 | 35.058 | 78.521 | 47.954 | 1.00 | 42.21 | D |
| ATOM | 5154 | CB | PRO | D | 253 | 34.649 | 79.226 | 46.660 | 1.00 | 41.50 | D |
| ATOM | 5155 | CG | PRO | D | 253 | 32.955 | 78.977 | 46.543 | 1.00 | 41.02 | D |
| ATOM | 5156 | C | PRO | D | 253 | 34.939 | 79.428 | 49.177 | 1.00 | 44.89 | D |
| ATOM | 5157 | O | PRO | D | 253 | 33.944 | 79.476 | 49.848 | 1.00 | 44.43 | D |
| ATOM | 5158 | N | ASP | D | 254 | 36.008 | 80.082 | 49.533 | 1.00 | 47.76 | D |
| ATOM | 5159 | CA | ASP | D | 254 | 36.031 | 80.978 | 50.713 | 1.00 | 50.73 | D |
| ATOM | 5160 | CB | ASP | D | 254 | 37.427 | 80.955 | 51.271 | 1.00 | 51.98 | D |
| ATOM | 5161 | CG | ASP | D | 254 | 37.472 | 81.395 | 52.673 | 1.00 | 53.12 | D |

TABLE 2-continued

ATOMIC COORDINATES OF THE ERR3 LBD/
DIETHYLSTILBESTROL COMPLEX

| ATOM | 5162 | OD1 | ASP | D | 254 | 36.776 | 82.420 | 52.968 | 1.00 | 53.45 | D |
|---|---|---|---|---|---|---|---|---|---|---|---|
| ATOM | 5163 | OD2 | ASP | D | 254 | 38.175 | 80.771 | 53.482 | 1.00 | 52.99 | D |
| ATOM | 5164 | C | ASP | D | 254 | 35.647 | 82.406 | 50.278 | 1.00 | 51.55 | D |
| ATOM | 5165 | O | ASP | D | 254 | 36.421 | 83.021 | 49.560 | 1.00 | 51.08 | D |
| ATOM | 5166 | N | PRO | D | 255 | 34.410 | 82.892 | 50.595 | 1.00 | 53.23 | D |
| ATOM | 5167 | CD | PRO | D | 255 | 33.384 | 82.243 | 51.446 | 1.00 | 53.28 | D |
| ATOM | 5168 | CA | PRO | D | 255 | 33.983 | 84.262 | 50.167 | 1.00 | 54.09 | D |
| ATOM | 5169 | CB | PRO | D | 255 | 32.432 | 84.321 | 50.465 | 1.00 | 53.75 | D |
| ATOM | 5170 | CG | PRO | D | 255 | 32.203 | 83.289 | 51.606 | 1.00 | 53.53 | D |
| ATOM | 5171 | C | PRO | D | 255 | 34.806 | 85.336 | 50.922 | 1.00 | 54.95 | D |
| ATOM | 5172 | O | PRO | D | 255 | 34.837 | 86.485 | 50.469 | 1.00 | 55.07 | D |
| ATOM | 5173 | N | THR | D | 256 | 35.520 | 84.926 | 51.978 | 1.00 | 55.95 | D |
| ATOM | 5174 | CA | THR | D | 256 | 36.480 | 85.781 | 52.644 | 1.00 | 57.16 | D |
| ATOM | 5175 | CB | THR | D | 256 | 36.825 | 85.396 | 54.073 | 1.00 | 57.35 | D |
| ATOM | 5176 | OG1 | THR | D | 256 | 38.018 | 84.644 | 54.150 | 1.00 | 56.68 | D |
| ATOM | 5177 | CG2 | THR | D | 256 | 35.765 | 84.636 | 54.692 | 1.00 | 57.38 | D |
| ATOM | 5178 | C | THR | D | 256 | 37.765 | 86.046 | 51.949 | 1.00 | 58.28 | D |
| ATOM | 5179 | O | THR | D | 256 | 38.521 | 86.910 | 52.458 | 1.00 | 57.88 | D |
| ATOM | 5180 | N | VAL | D | 257 | 37.964 | 85.433 | 50.760 | 1.00 | 58.70 | D |
| ATOM | 5181 | CA | VAL | D | 257 | 39.157 | 85.698 | 49.970 | 1.00 | 58.97 | D |
| ATOM | 5182 | CB | VAL | D | 257 | 40.043 | 84.314 | 49.844 | 1.00 | 58.76 | D |
| ATOM | 5183 | CG1 | VAL | D | 257 | 41.476 | 84.582 | 49.410 | 1.00 | 58.69 | D |
| ATOM | 5184 | CG2 | VAL | D | 257 | 40.079 | 83.497 | 51.122 | 1.00 | 57.43 | D |
| ATOM | 5185 | C | VAL | D | 257 | 38.958 | 86.508 | 48.630 | 1.00 | 59.99 | D |
| ATOM | 5186 | O | VAL | D | 257 | 38.053 | 86.324 | 47.807 | 1.00 | 59.89 | D |
| ATOM | 5187 | N | PRO | D | 258 | 39.864 | 87.425 | 48.442 | 1.00 | 61.04 | D |
| ATOM | 5188 | CD | PRO | D | 258 | 40.846 | 87.866 | 49.462 | 1.00 | 62.62 | D |
| ATOM | 5189 | CA | PRO | D | 258 | 40.086 | 88.169 | 47.204 | 1.00 | 61.43 | D |
| ATOM | 5190 | CB | PRO | D | 258 | 41.548 | 88.681 | 47.431 | 1.00 | 61.78 | D |
| ATOM | 5191 | CG | PRO | D | 258 | 41.494 | 89.077 | 48.826 | 1.00 | 62.07 | D |
| ATOM | 5192 | C | PRO | D | 258 | 39.979 | 87.427 | 45.791 | 1.00 | 61.81 | D |
| ATOM | 5193 | O | PRO | D | 258 | 40.995 | 86.901 | 45.217 | 1.00 | 61.96 | D |
| ATOM | 5194 | N | ASP | D | 259 | 38.798 | 87.424 | 45.187 | 1.00 | 61.47 | D |
| ATOM | 5195 | CA | ASP | D | 259 | 38.693 | 86.659 | 44.024 | 1.00 | 61.46 | D |
| ATOM | 5196 | CB | ASP | D | 259 | 37.288 | 86.760 | 43.416 | 1.00 | 62.77 | D |
| ATOM | 5197 | CG | ASP | D | 259 | 36.246 | 85.870 | 44.161 | 1.00 | 64.06 | D |
| ATOM | 5198 | OD1 | ASP | D | 259 | 36.383 | 85.618 | 45.394 | 1.00 | 65.56 | D |
| ATOM | 5199 | OD2 | ASP | D | 259 | 35.253 | 85.360 | 43.592 | 1.00 | 64.56 | D |
| ATOM | 5200 | C | ASP | D | 259 | 39.874 | 87.012 | 43.075 | 1.00 | 61.17 | D |
| ATOM | 5201 | O | ASP | D | 259 | 40.033 | 88.185 | 42.663 | 1.00 | 61.48 | D |
| ATOM | 5202 | N | SER | D | 260 | 40.725 | 85.983 | 42.797 | 1.00 | 59.98 | D |
| ATOM | 5203 | CA | SER | D | 260 | 41.951 | 86.084 | 41.992 | 1.00 | 59.21 | D |
| ATOM | 5204 | CB | SER | D | 260 | 43.164 | 86.370 | 42.886 | 1.00 | 59.54 | D |
| ATOM | 5205 | OG | SER | D | 260 | 42.973 | 85.843 | 44.210 | 1.00 | 60.61 | D |
| ATOM | 5206 | C | SER | D | 260 | 42.253 | 84.791 | 41.297 | 1.00 | 58.16 | D |
| ATOM | 5207 | O | SER | D | 260 | 41.575 | 83.814 | 41.518 | 1.00 | 58.53 | D |
| ATOM | 5208 | N | ASP | D | 261 | 43.253 | 84.787 | 40.438 | 1.00 | 56.85 | D |
| ATOM | 5209 | CA | ASP | D | 261 | 43.741 | 83.551 | 39.922 | 1.00 | 56.14 | D |
| ATOM | 5210 | CB | ASP | D | 261 | 44.734 | 83.828 | 38.778 | 1.00 | 56.72 | D |
| ATOM | 5211 | CG | ASP | D | 261 | 46.132 | 84.398 | 39.278 | 1.00 | 56.70 | D |
| ATOM | 5212 | OD1 | ASP | D | 261 | 47.204 | 83.885 | 38.797 | 1.00 | 56.70 | D |
| ATOM | 5213 | OD2 | ASP | D | 261 | 46.197 | 85.298 | 40.128 | 1.00 | 56.32 | D |
| ATOM | 5214 | C | ASP | D | 261 | 44.271 | 82.564 | 41.063 | 1.00 | 55.28 | D |
| ATOM | 5215 | O | ASP | D | 261 | 43.938 | 81.386 | 41.024 | 1.00 | 55.22 | D |
| ATOM | 5216 | N | ILE | D | 262 | 45.025 | 83.031 | 42.077 | 1.00 | 53.77 | D |
| ATOM | 5217 | CA | ILE | D | 262 | 45.424 | 82.138 | 43.199 | 1.00 | 52.93 | D |
| ATOM | 5218 | CB | ILE | D | 262 | 46.145 | 82.907 | 44.310 | 1.00 | 53.15 | D |
| ATOM | 5219 | CG2 | ILE | D | 262 | 46.013 | 82.456 | 45.488 | 0.00 | 52.98 | D |
| ATOM | 5220 | CG1 | ILE | D | 262 | 47.433 | 83.525 | 43.742 | 1.00 | 52.73 | D |
| ATOM | 5221 | CD1 | ILE | D | 262 | 47.844 | 83.993 | 42.451 | 0.00 | 52.95 | D |
| ATOM | 5222 | C | ILE | D | 262 | 44.256 | 81.416 | 43.861 | 1.00 | 52.23 | D |
| ATOM | 5223 | O | ILE | D | 262 | 44.358 | 80.255 | 44.254 | 1.00 | 52.27 | D |
| ATOM | 5224 | N | LYS | D | 263 | 43.157 | 82.121 | 44.056 | 1.00 | 50.13 | D |
| ATOM | 5225 | CA | LYS | D | 263 | 42.123 | 81.567 | 44.890 | 1.00 | 48.19 | D |
| ATOM | 5226 | CB | LYS | D | 263 | 41.234 | 82.711 | 45.455 | 1.00 | 49.19 | D |
| ATOM | 5227 | CG | LYS | D | 263 | 39.959 | 82.228 | 46.129 | 1.00 | 49.65 | D |
| ATOM | 5228 | CD | LYS | D | 263 | 39.007 | 83.300 | 46.639 | 1.00 | 51.27 | D |
| ATOM | 5229 | CE | LYS | D | 263 | 37.501 | 83.036 | 46.207 | 1.00 | 51.75 | D |
| ATOM | 5230 | NZ | LYS | D | 263 | 36.379 | 83.578 | 47.125 | 1.00 | 51.55 | D |
| ATOM | 5231 | C | LYS | D | 263 | 41.298 | 80.569 | 44.076 | 1.00 | 46.86 | D |
| ATOM | 5232 | O | LYS | D | 263 | 40.753 | 79.594 | 44.617 | 1.00 | 46.10 | D |
| ATOM | 5233 | N | ALA | D | 264 | 41.127 | 80.866 | 42.804 | 1.00 | 44.95 | D |
| ATOM | 5234 | CA | ALA | D | 264 | 40.499 | 79.932 | 41.895 | 1.00 | 45.00 | D |
| ATOM | 5235 | CB | ALA | D | 264 | 40.383 | 80.521 | 40.444 | 1.00 | 44.58 | D |
| ATOM | 5236 | C | ALA | D | 264 | 41.264 | 78.630 | 41.857 | 1.00 | 44.24 | D |
| ATOM | 5237 | O | ALA | D | 264 | 40.679 | 77.561 | 42.064 | 1.00 | 44.35 | D |

TABLE 2-continued

ATOMIC COORDINATES OF THE ERR3 LBD/ DIETHYLSTILBESTROL COMPLEX

| ATOM | 5238 | N | LEU | D | 265 | 42.565 | 78.794 | 41.586 | 1.00 | 43.24 | D |
|---|---|---|---|---|---|---|---|---|---|---|---|
| ATOM | 5239 | CA | LEU | D | 265 | 43.541 | 77.720 | 41.486 | 1.00 | 42.88 | D |
| ATOM | 5240 | CB | LEU | D | 265 | 44.887 | 78.329 | 41.045 | 1.00 | 43.45 | D |
| ATOM | 5241 | CG | LEU | D | 265 | 44.789 | 78.964 | 39.601 | 1.00 | 44.95 | D |
| ATOM | 5242 | CD1 | LEU | D | 265 | 46.122 | 79.440 | 39.019 | 1.00 | 46.80 | D |
| ATOM | 5243 | CD2 | LEU | D | 265 | 44.171 | 78.086 | 38.585 | 1.00 | 44.37 | D |
| ATOM | 5244 | C | LEU | D | 265 | 43.674 | 76.895 | 42.757 | 1.00 | 41.66 | D |
| ATOM | 5245 | O | LEU | D | 265 | 43.582 | 75.690 | 42.732 | 1.00 | 41.36 | D |
| ATOM | 5246 | N | THR | D | 266 | 43.697 | 77.584 | 43.870 | 1.00 | 40.02 | D |
| ATOM | 5247 | CA | THR | D | 266 | 43.637 | 76.985 | 45.148 | 1.00 | 39.33 | D |
| ATOM | 5248 | CB | THR | D | 266 | 43.719 | 78.068 | 46.187 | 1.00 | 39.43 | D |
| ATOM | 5249 | OG1 | THR | D | 266 | 45.053 | 78.556 | 46.216 | 1.00 | 41.47 | D |
| ATOM | 5250 | CG2 | THR | D | 266 | 43.543 | 77.554 | 47.542 | 1.00 | 39.14 | D |
| ATOM | 5251 | C | THR | D | 266 | 42.391 | 76.202 | 45.342 | 1.00 | 38.11 | D |
| ATOM | 5252 | O | THR | D | 266 | 42.441 | 75.044 | 45.789 | 1.00 | 37.70 | D |
| ATOM | 5253 | N | THR | D | 267 | 41.277 | 76.818 | 44.998 | 1.00 | 35.96 | D |
| ATOM | 5254 | CA | THR | D | 267 | 39.995 | 76.174 | 45.112 | 1.00 | 34.73 | D |
| ATOM | 5255 | CB | THR | D | 267 | 38.816 | 77.242 | 44.793 | 1.00 | 35.48 | D |
| ATOM | 5256 | OG1 | THR | D | 267 | 38.908 | 78.347 | 45.699 | 1.00 | 36.40 | D |
| ATOM | 5257 | CG2 | THR | D | 267 | 37.464 | 76.574 | 44.994 | 1.00 | 34.74 | D |
| ATOM | 5258 | C | THR | D | 267 | 39.785 | 74.929 | 44.234 | 1.00 | 32.82 | D |
| ATOM | 5259 | O | THR | D | 267 | 39.135 | 73.950 | 44.641 | 1.00 | 30.68 | D |
| ATOM | 5260 | N | LEU | D | 268 | 40.281 | 75.006 | 43.036 | 1.00 | 30.76 | D |
| ATOM | 5261 | CA | LEU | D | 268 | 40.140 | 73.840 | 42.137 | 1.00 | 31.05 | D |
| ATOM | 5262 | CB | LEU | D | 268 | 40.369 | 74.281 | 40.707 | 1.00 | 29.91 | D |
| ATOM | 5263 | CG | LEU | D | 268 | 39.229 | 75.145 | 40.163 | 1.00 | 33.14 | D |
| ATOM | 5264 | CD1 | LEU | D | 268 | 39.592 | 75.918 | 38.914 | 1.00 | 31.82 | D |
| ATOM | 5265 | CD2 | LEU | D | 268 | 38.006 | 74.244 | 39.798 | 1.00 | 32.40 | D |
| ATOM | 5266 | C | LEU | D | 268 | 41.032 | 72.672 | 42.580 | 1.00 | 30.60 | D |
| ATOM | 5267 | O | LEU | D | 268 | 40.629 | 71.517 | 42.476 | 1.00 | 30.65 | D |
| ATOM | 5268 | N | CYS | D | 269 | 42.226 | 72.963 | 43.106 | 1.00 | 30.15 | D |
| ATOM | 5269 | CA | CYS | D | 269 | 43.233 | 71.937 | 43.473 | 1.00 | 31.77 | D |
| ATOM | 5270 | CB | CYS | D | 269 | 44.571 | 72.553 | 43.924 | 1.00 | 31.11 | D |
| ATOM | 5271 | SG | CYS | D | 269 | 45.408 | 73.135 | 42.461 | 1.00 | 38.40 | D |
| ATOM | 5272 | C | CYS | D | 269 | 42.708 | 71.215 | 44.639 | 1.00 | 30.89 | D |
| ATOM | 5273 | O | CYS | D | 269 | 42.626 | 69.994 | 44.651 | 1.00 | 30.64 | D |
| ATOM | 5274 | N | ASP | D | 270 | 42.216 | 71.988 | 45.606 | 1.00 | 31.23 | D |
| ATOM | 5275 | CA | ASP | D | 270 | 41.490 | 71.373 | 46.722 | 1.00 | 31.62 | D |
| ATOM | 5276 | CB | ASP | D | 270 | 41.072 | 72.365 | 47.765 | 1.00 | 34.80 | D |
| ATOM | 5277 | CG | ASP | D | 270 | 40.613 | 71.659 | 49.043 | 1.00 | 38.81 | D |
| ATOM | 5278 | OD1 | ASP | D | 270 | 41.477 | 71.001 | 49.639 | 1.00 | 43.80 | D |
| ATOM | 5279 | OD2 | ASP | D | 270 | 39.464 | 71.493 | 49.428 | 1.00 | 39.88 | D |
| ATOM | 5280 | C | ASP | D | 270 | 40.275 | 70.555 | 46.364 | 1.00 | 31.67 | D |
| ATOM | 5281 | O | ASP | D | 270 | 40.099 | 69.420 | 46.832 | 1.00 | 31.05 | D |
| ATOM | 5282 | N | LEU | D | 271 | 39.417 | 71.079 | 45.494 | 1.00 | 30.69 | D |
| ATOM | 5283 | CA | LEU | D | 271 | 38.287 | 70.289 | 45.058 | 1.00 | 30.24 | D |
| ATOM | 5284 | CB | LEU | D | 271 | 37.478 | 71.145 | 44.109 | 1.00 | 29.69 | D |
| ATOM | 5285 | CG | LEU | D | 271 | 36.504 | 70.347 | 43.232 | 1.00 | 29.71 | D |
| ATOM | 5286 | CD1 | LEU | D | 271 | 35.498 | 69.787 | 44.141 | 1.00 | 27.77 | D |
| ATOM | 5287 | CD2 | LEU | D | 271 | 35.877 | 71.319 | 42.247 | 1.00 | 31.56 | D |
| ATOM | 5288 | C | LEU | D | 271 | 38.765 | 68.963 | 44.400 | 1.00 | 30.48 | D |
| ATOM | 5289 | O | LEU | D | 271 | 38.240 | 67.840 | 44.631 | 1.00 | 29.50 | D |
| ATOM | 5290 | N | ALA | D | 272 | 39.769 | 69.120 | 43.505 | 1.00 | 29.17 | D |
| ATOM | 5291 | CA | ALA | D | 272 | 40.312 | 67.925 | 42.771 | 1.00 | 29.38 | D |
| ATOM | 5292 | CB | ALA | D | 272 | 41.397 | 68.345 | 41.784 | 1.00 | 27.76 | D |
| ATOM | 5293 | C | ALA | D | 272 | 40.860 | 66.903 | 43.774 | 1.00 | 28.48 | D |
| ATOM | 5294 | O | ALA | D | 272 | 40.563 | 65.715 | 43.727 | 1.00 | 27.95 | D |
| ATOM | 5295 | N | ASP | D | 273 | 41.620 | 67.406 | 44.712 | 1.00 | 29.66 | D |
| ATOM | 5296 | CA | ASP | D | 273 | 42.214 | 66.557 | 45.759 | 1.00 | 31.43 | D |
| ATOM | 5297 | CB | ASP | D | 273 | 42.946 | 67.409 | 46.733 | 1.00 | 31.80 | D |
| ATOM | 5298 | CG | ASP | D | 273 | 43.901 | 66.560 | 47.609 | 1.00 | 34.26 | D |
| ATOM | 5299 | OD1 | ASP | D | 273 | 44.845 | 65.879 | 47.065 | 1.00 | 33.21 | D |
| ATOM | 5300 | OD2 | ASP | D | 273 | 43.742 | 66.508 | 48.826 | 1.00 | 37.46 | D |
| ATOM | 5301 | C | ASP | D | 273 | 41.157 | 65.732 | 46.515 | 1.00 | 32.63 | D |
| ATOM | 5302 | O | ASP | D | 273 | 41.320 | 64.498 | 46.666 | 1.00 | 33.23 | D |
| ATOM | 5303 | N | ARG | D | 274 | 39.970 | 66.322 | 46.838 | 1.00 | 31.32 | D |
| ATOM | 5304 | CA | ARG | D | 274 | 38.981 | 65.488 | 47.508 | 1.00 | 31.09 | D |
| ATOM | 5305 | CB | ARG | D | 274 | 38.039 | 66.351 | 48.396 | 1.00 | 32.69 | D |
| ATOM | 5306 | CG | ARG | D | 274 | 38.739 | 67.180 | 49.516 | 1.00 | 33.16 | D |
| ATOM | 5307 | CD | ARG | D | 274 | 37.810 | 68.212 | 50.267 | 1.00 | 34.17 | D |
| ATOM | 5308 | NE | ARG | D | 274 | 37.827 | 69.493 | 49.542 | 1.00 | 35.82 | D |
| ATOM | 5309 | CZ | ARG | D | 274 | 36.711 | 69.975 | 48.927 | 1.00 | 36.72 | D |
| ATOM | 5310 | NH1 | ARG | D | 274 | 35.585 | 69.289 | 48.982 | 1.00 | 35.32 | D |
| ATOM | 5311 | NH2 | ARG | D | 274 | 36.737 | 71.103 | 48.195 | 1.00 | 38.02 | D |
| ATOM | 5312 | C | ARG | D | 274 | 38.242 | 64.645 | 46.529 | 1.00 | 31.59 | D |
| ATOM | 5313 | O | ARG | D | 274 | 37.675 | 63.636 | 46.876 | 1.00 | 30.44 | D |

TABLE 2-continued

ATOMIC COORDINATES OF THE ERR3 LBD/
DIETHYLSTILBESTROL COMPLEX

| ATOM | 5314 | N | GLU | D | 275 | 38.225 | 65.029 | 45.269 | 1.00 | 30.89 | D |
|---|---|---|---|---|---|---|---|---|---|---|---|
| ATOM | 5315 | CA | GLU | D | 275 | 37.524 | 64.210 | 44.269 | 1.00 | 30.75 | D |
| ATOM | 5316 | CB | GLU | D | 275 | 37.319 | 64.902 | 42.896 | 1.00 | 30.30 | D |
| ATOM | 5317 | CG | GLU | D | 275 | 36.208 | 66.023 | 42.876 | 1.00 | 31.30 | D |
| ATOM | 5318 | CD | GLU | D | 275 | 36.013 | 66.652 | 41.554 | 1.00 | 33.08 | D |
| ATOM | 5319 | OE1 | GLU | D | 275 | 35.217 | 66.122 | 40.820 | 1.00 | 35.20 | D |
| ATOM | 5320 | OE2 | GLU | D | 275 | 36.715 | 67.685 | 41.188 | 1.00 | 34.43 | D |
| ATOM | 5321 | C | GLU | D | 275 | 38.304 | 62.992 | 44.075 | 1.00 | 29.90 | D |
| ATOM | 5322 | O | GLU | D | 275 | 37.750 | 61.968 | 43.838 | 1.00 | 29.85 | D |
| ATOM | 5323 | N | LEU | D | 276 | 39.611 | 63.145 | 44.081 | 1.00 | 30.23 | D |
| ATOM | 5324 | CA | LEU | D | 276 | 40.496 | 62.034 | 43.673 | 1.00 | 31.58 | D |
| ATOM | 5325 | CB | LEU | D | 276 | 41.927 | 62.563 | 43.490 | 1.00 | 29.20 | D |
| ATOM | 5326 | CG | LEU | D | 276 | 42.034 | 63.372 | 42.183 | 1.00 | 31.09 | D |
| ATOM | 5327 | CD1 | LEU | D | 276 | 43.386 | 63.809 | 42.078 | 1.00 | 31.81 | D |
| ATOM | 5328 | CD2 | LEU | D | 276 | 41.611 | 62.496 | 41.068 | 1.00 | 29.82 | D |
| ATOM | 5329 | C | LEU | D | 276 | 40.456 | 60.899 | 44.715 | 1.00 | 32.50 | D |
| ATOM | 5330 | O | LEU | D | 276 | 40.405 | 59.746 | 44.387 | 1.00 | 32.92 | D |
| ATOM | 5331 | N | VAL | D | 277 | 40.433 | 61.228 | 46.003 | 1.00 | 34.10 | D |
| ATOM | 5332 | CA | VAL | D | 277 | 40.244 | 60.162 | 47.019 | 1.00 | 34.69 | D |
| ATOM | 5333 | CB | VAL | D | 277 | 40.436 | 60.617 | 48.553 | 1.00 | 35.36 | D |
| ATOM | 5334 | CG1 | VAL | D | 277 | 39.338 | 61.379 | 49.011 | 1.00 | 35.44 | D |
| ATOM | 5335 | CG2 | VAL | D | 277 | 40.652 | 59.403 | 49.486 | 1.00 | 35.87 | D |
| ATOM | 5336 | C | VAL | D | 277 | 38.953 | 59.453 | 46.723 | 1.00 | 34.39 | D |
| ATOM | 5337 | O | VAL | D | 277 | 38.916 | 58.221 | 46.801 | 1.00 | 35.02 | D |
| ATOM | 5338 | N | VAL | D | 278 | 37.889 | 60.197 | 46.318 | 1.00 | 33.28 | D |
| ATOM | 5339 | CA | VAL | D | 278 | 36.649 | 59.518 | 45.991 | 1.00 | 31.36 | D |
| ATOM | 5340 | CB | VAL | D | 278 | 35.423 | 60.516 | 46.006 | 1.00 | 32.10 | D |
| ATOM | 5341 | CG1 | VAL | D | 278 | 34.215 | 59.928 | 45.501 | 1.00 | 27.04 | D |
| ATOM | 5342 | CG2 | VAL | D | 278 | 35.037 | 60.833 | 47.538 | 1.00 | 30.90 | D |
| ATOM | 5343 | C | VAL | D | 278 | 36.775 | 58.699 | 44.716 | 1.00 | 31.94 | D |
| ATOM | 5344 | O | VAL | D | 278 | 36.235 | 57.553 | 44.621 | 1.00 | 32.01 | D |
| ATOM | 5345 | N | ILE | D | 279 | 37.522 | 59.217 | 43.718 | 1.00 | 31.71 | D |
| ATOM | 5346 | CA | ILE | D | 279 | 37.709 | 58.417 | 42.528 | 1.00 | 31.53 | D |
| ATOM | 5347 | CB | ILE | D | 279 | 38.435 | 59.238 | 41.378 | 1.00 | 31.56 | D |
| ATOM | 5348 | CG2 | ILE | D | 279 | 39.069 | 58.295 | 40.316 | 1.00 | 30.22 | D |
| ATOM | 5349 | CG1 | ILE | D | 279 | 37.376 | 60.123 | 40.688 | 1.00 | 32.82 | D |
| ATOM | 5350 | CD1 | ILE | D | 279 | 37.904 | 61.570 | 40.443 | 1.00 | 34.45 | D |
| ATOM | 5351 | C | ILE | D | 279 | 38.385 | 57.119 | 42.808 | 1.00 | 31.64 | D |
| ATOM | 5352 | O | ILE | D | 279 | 38.036 | 56.058 | 42.217 | 1.00 | 32.10 | D |
| ATOM | 5353 | N | ILE | D | 280 | 39.350 | 57.151 | 43.703 | 1.00 | 30.96 | D |
| ATOM | 5354 | CA | ILE | D | 280 | 40.096 | 55.924 | 44.028 | 1.00 | 30.63 | D |
| ATOM | 5355 | CB | ILE | D | 280 | 41.333 | 56.178 | 44.949 | 1.00 | 31.19 | D |
| ATOM | 5356 | CG2 | ILE | D | 280 | 41.949 | 54.810 | 45.327 | 1.00 | 29.31 | D |
| ATOM | 5357 | CG1 | ILE | D | 280 | 42.360 | 57.101 | 44.265 | 1.00 | 28.57 | D |
| ATOM | 5358 | CD1 | ILE | D | 280 | 43.414 | 57.763 | 45.189 | 1.00 | 28.39 | D |
| ATOM | 5359 | C | ILE | D | 280 | 39.191 | 54.875 | 44.588 | 1.00 | 30.88 | D |
| ATOM | 5360 | O | ILE | D | 280 | 39.280 | 53.691 | 44.215 | 1.00 | 32.05 | D |
| ATOM | 5361 | N | GLY | D | 281 | 38.235 | 55.268 | 45.412 | 1.00 | 31.97 | D |
| ATOM | 5362 | CA | GLY | D | 281 | 37.247 | 54.317 | 45.977 | 1.00 | 30.30 | D |
| ATOM | 5363 | C | GLY | D | 281 | 36.233 | 53.875 | 44.921 | 1.00 | 32.36 | D |
| ATOM | 5364 | O | GLY | D | 281 | 35.861 | 52.641 | 44.831 | 1.00 | 33.47 | D |
| ATOM | 5365 | N | TRP | D | 282 | 35.782 | 54.826 | 44.084 | 1.00 | 31.71 | D |
| ATOM | 5366 | CA | TRP | D | 282 | 34.892 | 54.467 | 43.028 | 1.00 | 30.96 | D |
| ATOM | 5367 | CB | TRP | D | 282 | 34.590 | 55.761 | 42.194 | 1.00 | 30.40 | D |
| ATOM | 5368 | CG | TRP | D | 282 | 34.080 | 55.503 | 40.745 | 1.00 | 30.38 | D |
| ATOM | 5369 | CD2 | TRP | D | 282 | 34.820 | 55.529 | 39.552 | 1.00 | 29.24 | D |
| ATOM | 5370 | CE2 | TRP | D | 282 | 33.926 | 55.219 | 38.489 | 1.00 | 30.38 | D |
| ATOM | 5371 | CE3 | TRP | D | 282 | 36.097 | 55.888 | 39.239 | 1.00 | 28.26 | D |
| ATOM | 5372 | CD1 | TRP | D | 282 | 32.864 | 55.141 | 40.409 | 1.00 | 30.76 | D |
| ATOM | 5373 | NE1 | TRP | D | 282 | 32.758 | 54.889 | 39.061 | 1.00 | 29.48 | D |
| ATOM | 5374 | CZ2 | TRP | D | 282 | 34.321 | 55.119 | 37.169 | 1.00 | 30.16 | D |
| ATOM | 5375 | CZ3 | TRP | D | 282 | 36.521 | 55.835 | 37.912 | 1.00 | 29.30 | D |
| ATOM | 5376 | CH2 | TRP | D | 282 | 35.624 | 55.489 | 36.889 | 1.00 | 30.63 | D |
| ATOM | 5377 | C | TRP | D | 282 | 35.501 | 53.335 | 42.171 | 1.00 | 31.29 | D |
| ATOM | 5378 | O | TRP | D | 282 | 34.831 | 52.398 | 41.656 | 1.00 | 30.56 | D |
| ATOM | 5379 | N | ALA | D | 283 | 36.783 | 53.434 | 41.876 | 1.00 | 30.14 | D |
| ATOM | 5380 | CA | ALA | D | 283 | 37.278 | 52.498 | 40.889 | 1.00 | 30.66 | D |
| ATOM | 5381 | CB | ALA | D | 283 | 38.720 | 52.782 | 40.551 | 1.00 | 29.89 | D |
| ATOM | 5382 | C | ALA | D | 283 | 37.186 | 51.081 | 41.361 | 1.00 | 31.24 | D |
| ATOM | 5383 | O | ALA | D | 283 | 37.142 | 50.160 | 40.546 | 1.00 | 28.78 | D |
| ATOM | 5384 | N | LYS | D | 284 | 37.354 | 50.909 | 42.677 | 1.00 | 33.41 | D |
| ATOM | 5385 | CA | LYS | D | 284 | 37.234 | 49.580 | 43.278 | 1.00 | 36.19 | D |
| ATOM | 5386 | CB | LYS | D | 284 | 37.250 | 49.643 | 44.794 | 1.00 | 37.48 | D |
| ATOM | 5387 | CG | LYS | D | 284 | 38.437 | 50.293 | 45.347 | 1.00 | 38.67 | D |
| ATOM | 5388 | CD | LYS | D | 284 | 39.729 | 49.783 | 44.760 | 1.00 | 39.28 | D |
| ATOM | 5389 | CE | LYS | D | 284 | 40.835 | 50.311 | 45.731 | 1.00 | 41.26 | D |

TABLE 2-continued

ATOMIC COORDINATES OF THE ERR3 LBD/
DIETHYLSTILBESTROL COMPLEX

| ATOM | 5390 | NZ | LYS | D | 284 | 42.020 | 49.517 | 45.609 | 1.00 | 42.27 | D |
|---|---|---|---|---|---|---|---|---|---|---|---|
| ATOM | 5391 | C | LYS | D | 284 | 35.964 | 48.874 | 42.901 | 1.00 | 37.22 | D |
| ATOM | 5392 | O | LYS | D | 284 | 35.914 | 47.651 | 43.010 | 1.00 | 36.59 | D |
| ATOM | 5393 | N | HIS | D | 285 | 34.924 | 49.637 | 42.598 | 1.00 | 38.50 | D |
| ATOM | 5394 | CA | HIS | D | 285 | 33.654 | 49.058 | 42.255 | 1.00 | 40.72 | D |
| ATOM | 5395 | CB | HIS | D | 285 | 32.477 | 49.924 | 42.768 | 1.00 | 41.58 | D |
| ATOM | 5396 | CG | HIS | D | 285 | 32.455 | 50.095 | 44.249 | 1.00 | 43.92 | D |
| ATOM | 5397 | CD2 | HIS | D | 285 | 33.004 | 51.049 | 45.038 | 1.00 | 44.33 | D |
| ATOM | 5398 | ND1 | HIS | D | 285 | 31.778 | 49.229 | 45.086 | 1.00 | 45.27 | D |
| ATOM | 5399 | CE1 | HIS | D | 285 | 31.903 | 49.652 | 46.324 | 1.00 | 45.54 | D |
| ATOM | 5400 | NE2 | HIS | D | 285 | 32.671 | 50.738 | 46.325 | 1.00 | 46.38 | D |
| ATOM | 5401 | C | HIS | D | 285 | 33.434 | 48.867 | 40.813 | 1.00 | 41.22 | D |
| ATOM | 5402 | O | HIS | D | 285 | 32.328 | 48.462 | 40.437 | 1.00 | 43.42 | D |
| ATOM | 5403 | N | ILE | D | 286 | 34.398 | 49.181 | 39.965 | 1.00 | 39.90 | D |
| ATOM | 5404 | CA | ILE | D | 286 | 34.324 | 48.792 | 38.568 | 1.00 | 38.74 | D |
| ATOM | 5405 | CB | ILE | D | 286 | 35.359 | 49.546 | 37.751 | 1.00 | 37.75 | D |
| ATOM | 5406 | CG2 | ILE | D | 286 | 35.348 | 49.056 | 36.313 | 1.00 | 34.80 | D |
| ATOM | 5407 | CG1 | ILE | D | 286 | 35.050 | 50.988 | 37.830 | 1.00 | 37.84 | D |
| ATOM | 5408 | CD1 | ILE | D | 286 | 36.106 | 51.835 | 37.318 | 1.00 | 38.44 | D |
| ATOM | 5409 | C | ILE | D | 286 | 34.640 | 47.296 | 38.488 | 1.00 | 39.86 | D |
| ATOM | 5410 | O | ILE | D | 286 | 35.683 | 46.925 | 38.881 | 1.00 | 39.11 | D |
| ATOM | 5411 | N | PRO | D | 287 | 33.749 | 46.472 | 37.943 | 1.00 | 40.79 | D |
| ATOM | 5412 | CD | PRO | D | 287 | 32.467 | 46.882 | 37.337 | 1.00 | 40.87 | D |
| ATOM | 5413 | CA | PRO | D | 287 | 33.922 | 45.005 | 37.901 | 1.00 | 40.23 | D |
| ATOM | 5414 | CB | PRO | D | 287 | 32.864 | 44.514 | 36.895 | 1.00 | 39.83 | D |
| ATOM | 5415 | CG | PRO | D | 287 | 31.842 | 45.529 | 36.913 | 1.00 | 41.71 | D |
| ATOM | 5416 | C | PRO | D | 287 | 35.229 | 44.638 | 37.369 | 1.00 | 40.25 | D |
| ATOM | 5417 | O | PRO | D | 287 | 35.510 | 45.213 | 36.315 | 1.00 | 40.63 | D |
| ATOM | 5418 | N | GLY | D | 288 | 35.990 | 43.759 | 38.046 | 1.00 | 38.90 | D |
| ATOM | 5419 | CA | GLY | D | 288 | 37.278 | 43.372 | 37.548 | 1.00 | 37.73 | D |
| ATOM | 5420 | C | GLY | D | 288 | 38.444 | 44.241 | 38.025 | 1.00 | 37.58 | D |
| ATOM | 5421 | O | GLY | D | 288 | 39.604 | 43.809 | 38.021 | 1.00 | 35.79 | D |
| ATOM | 5422 | N | PHE | D | 289 | 38.172 | 45.480 | 38.383 | 1.00 | 36.75 | D |
| ATOM | 5423 | CA | PHE | D | 289 | 39.301 | 46.363 | 38.677 | 1.00 | 36.28 | D |
| ATOM | 5424 | CB | PHE | D | 289 | 38.832 | 47.738 | 38.918 | 1.00 | 34.08 | D |
| ATOM | 5425 | CG | PHE | D | 289 | 39.937 | 48.724 | 39.139 | 1.00 | 31.09 | D |
| ATOM | 5426 | CD1 | PHE | D | 289 | 40.602 | 49.270 | 38.033 | 1.00 | 29.64 | D |
| ATOM | 5427 | CD2 | PHE | D | 289 | 40.242 | 49.162 | 40.383 | 1.00 | 31.12 | D |
| ATOM | 5428 | CE1 | PHE | D | 289 | 41.532 | 50.273 | 38.150 | 1.00 | 31.14 | D |
| ATOM | 5429 | CE2 | PHE | D | 289 | 41.246 | 50.266 | 40.577 | 1.00 | 29.59 | D |
| ATOM | 5430 | CZ | PHE | D | 289 | 41.897 | 50.785 | 39.483 | 1.00 | 29.89 | D |
| ATOM | 5431 | C | PHE | D | 289 | 39.974 | 45.948 | 39.925 | 1.00 | 37.76 | D |
| ATOM | 5432 | O | PHE | D | 289 | 41.171 | 45.970 | 40.031 | 1.00 | 37.73 | D |
| ATOM | 5433 | N | SER | D | 290 | 39.173 | 45.603 | 40.912 | 1.00 | 39.75 | D |
| ATOM | 5434 | CA | SER | D | 290 | 39.793 | 45.239 | 42.181 | 1.00 | 41.03 | D |
| ATOM | 5435 | CB | SER | D | 290 | 38.720 | 45.071 | 43.313 | 1.00 | 42.76 | D |
| ATOM | 5436 | OG | SER | D | 290 | 37.736 | 44.084 | 42.945 | 1.00 | 45.64 | D |
| ATOM | 5437 | C | SER | D | 290 | 40.638 | 43.962 | 42.163 | 1.00 | 41.51 | D |
| ATOM | 5438 | O | SER | D | 290 | 41.352 | 43.699 | 43.173 | 1.00 | 40.60 | D |
| ATOM | 5439 | N | THR | D | 291 | 40.575 | 43.225 | 41.049 | 1.00 | 40.59 | D |
| ATOM | 5440 | CA | THR | D | 291 | 41.360 | 42.044 | 40.927 | 1.00 | 40.75 | D |
| ATOM | 5441 | CB | THR | D | 291 | 40.711 | 41.092 | 39.948 | 1.00 | 41.79 | D |
| ATOM | 5442 | OG1 | THR | D | 291 | 39.465 | 40.773 | 40.553 | 1.00 | 44.55 | D |
| ATOM | 5443 | CG2 | THR | D | 291 | 41.186 | 39.814 | 39.635 | 0.00 | 42.20 | D |
| ATOM | 5444 | C | THR | D | 291 | 42.732 | 42.379 | 40.470 | 1.00 | 39.82 | D |
| ATOM | 5445 | O | THR | D | 291 | 43.651 | 41.546 | 40.632 | 1.00 | 40.87 | D |
| ATOM | 5446 | N | LEU | D | 292 | 42.879 | 43.508 | 39.803 | 1.00 | 36.60 | D |
| ATOM | 5447 | CA | LEU | D | 292 | 44.231 | 43.857 | 39.302 | 1.00 | 36.29 | D |
| ATOM | 5448 | CB | LEU | D | 292 | 44.213 | 45.214 | 38.525 | 1.00 | 33.83 | D |
| ATOM | 5449 | CG | LEU | D | 292 | 43.329 | 45.197 | 37.286 | 1.00 | 33.27 | D |
| ATOM | 5450 | CD1 | LEU | D | 292 | 43.034 | 46.557 | 36.726 | 1.00 | 32.64 | D |
| ATOM | 5451 | CD2 | LEU | D | 292 | 44.121 | 44.257 | 36.300 | 1.00 | 31.17 | D |
| ATOM | 5452 | C | LEU | D | 292 | 45.134 | 44.012 | 40.501 | 1.00 | 34.70 | D |
| ATOM | 5453 | O | LEU | D | 292 | 44.652 | 44.361 | 41.505 | 1.00 | 33.78 | D |
| ATOM | 5454 | N | SER | D | 293 | 46.412 | 43.853 | 40.338 | 1.00 | 34.20 | D |
| ATOM | 5455 | CA | SER | D | 293 | 47.266 | 44.194 | 41.437 | 1.00 | 34.94 | D |
| ATOM | 5456 | CB | SER | D | 293 | 48.714 | 43.900 | 41.082 | 1.00 | 35.30 | D |
| ATOM | 5457 | OG | SER | D | 293 | 49.119 | 44.753 | 39.988 | 1.00 | 36.34 | D |
| ATOM | 5458 | C | SER | D | 293 | 47.137 | 45.674 | 41.827 | 1.00 | 35.15 | D |
| ATOM | 5459 | O | SER | D | 293 | 46.619 | 46.540 | 41.080 | 1.00 | 34.84 | D |
| ATOM | 5460 | N | LEU | D | 294 | 47.598 | 45.967 | 43.030 | 1.00 | 34.96 | D |
| ATOM | 5461 | CA | LEU | D | 294 | 47.546 | 47.305 | 43.494 | 1.00 | 33.87 | D |
| ATOM | 5462 | CB | LEU | D | 294 | 47.763 | 47.394 | 45.016 | 1.00 | 32.92 | D |
| ATOM | 5463 | CG | LEU | D | 294 | 46.647 | 46.965 | 46.001 | 1.00 | 33.65 | D |
| ATOM | 5464 | CD1 | LEU | D | 294 | 47.211 | 46.807 | 47.512 | 1.00 | 33.86 | D |
| ATOM | 5465 | CD2 | LEU | D | 294 | 45.465 | 47.961 | 45.999 | 1.00 | 31.98 | D |

TABLE 2-continued

ATOMIC COORDINATES OF THE ERR3 LBD/
DIETHYLSTILBESTROL COMPLEX

| ATOM | 5466 | C   | LEU | D | 294 | 48.495 | 48.177 | 42.714 | 1.00 | 32.93 | D |
|------|------|-----|-----|---|-----|--------|--------|--------|------|-------|---|
| ATOM | 5467 | O   | LEU | D | 294 | 48.233 | 49.399 | 42.651 | 1.00 | 34.45 | D |
| ATOM | 5468 | N   | ALA | D | 295 | 49.565 | 47.614 | 42.113 | 1.00 | 31.47 | D |
| ATOM | 5469 | CA  | ALA | D | 295 | 50.419 | 48.403 | 41.284 | 1.00 | 30.36 | D |
| ATOM | 5470 | CB  | ALA | D | 295 | 51.861 | 47.807 | 41.059 | 1.00 | 27.04 | D |
| ATOM | 5471 | C   | ALA | D | 295 | 49.772 | 48.746 | 39.959 | 1.00 | 30.03 | D |
| ATOM | 5472 | O   | ALA | D | 295 | 49.975 | 49.846 | 39.499 | 1.00 | 30.56 | D |
| ATOM | 5473 | N   | ASP | D | 296 | 49.101 | 47.800 | 39.334 | 1.00 | 29.98 | D |
| ATOM | 5474 | CA  | ASP | D | 296 | 48.346 | 48.031 | 38.108 | 1.00 | 32.78 | D |
| ATOM | 5475 | CB  | ASP | D | 296 | 47.795 | 46.711 | 37.453 | 1.00 | 32.46 | D |
| ATOM | 5476 | CG  | ASP | D | 296 | 48.831 | 45.976 | 36.699 | 1.00 | 35.32 | D |
| ATOM | 5477 | OD1 | ASP | D | 296 | 49.959 | 46.492 | 36.519 | 1.00 | 34.65 | D |
| ATOM | 5478 | OD2 | ASP | D | 296 | 48.585 | 44.852 | 36.174 | 1.00 | 39.51 | D |
| ATOM | 5479 | C   | ASP | D | 296 | 47.169 | 49.058 | 38.257 | 1.00 | 32.44 | D |
| ATOM | 5480 | O   | ASP | D | 296 | 46.917 | 49.867 | 37.350 | 1.00 | 33.58 | D |
| ATOM | 5481 | N   | GLN | D | 297 | 46.470 | 48.963 | 39.371 | 1.00 | 32.53 | D |
| ATOM | 5482 | CA  | GLN | D | 297 | 45.364 | 49.789 | 39.711 | 1.00 | 32.84 | D |
| ATOM | 5483 | CB  | GLN | D | 297 | 44.781 | 49.452 | 41.083 | 1.00 | 31.92 | D |
| ATOM | 5484 | CG  | GLN | D | 297 | 43.900 | 48.216 | 41.084 | 1.00 | 31.48 | D |
| ATOM | 5485 | CD  | GLN | D | 297 | 43.323 | 47.923 | 42.500 | 1.00 | 32.36 | D |
| ATOM | 5486 | OE1 | GLN | D | 297 | 42.880 | 48.788 | 43.176 | 1.00 | 31.77 | D |
| ATOM | 5487 | NE2 | GLN | D | 297 | 43.271 | 46.679 | 42.857 | 1.00 | 32.11 | D |
| ATOM | 5488 | C   | GLN | D | 297 | 45.879 | 51.227 | 39.773 | 1.00 | 33.40 | D |
| ATOM | 5489 | O   | GLN | D | 297 | 45.241 | 52.162 | 39.195 | 1.00 | 33.25 | D |
| ATOM | 5490 | N   | MET | D | 298 | 46.993 | 51.388 | 40.469 | 1.00 | 32.94 | D |
| ATOM | 5491 | CA  | MET | D | 298 | 47.589 | 52.691 | 40.634 | 1.00 | 32.29 | D |
| ATOM | 5492 | CB  | MET | D | 298 | 48.741 | 52.743 | 41.663 | 1.00 | 32.87 | D |
| ATOM | 5493 | CG  | MET | D | 298 | 49.448 | 54.149 | 41.847 | 1.00 | 33.35 | D |
| ATOM | 5494 | SD  | MET | D | 298 | 48.113 | 55.382 | 42.413 | 1.00 | 36.24 | D |
| ATOM | 5495 | CE  | MET | D | 298 | 47.750 | 54.786 | 44.052 | 1.00 | 37.54 | D |
| ATOM | 5496 | C   | MET | D | 298 | 48.070 | 53.188 | 39.240 | 1.00 | 31.88 | D |
| ATOM | 5497 | O   | MET | D | 298 | 47.878 | 54.333 | 38.943 | 1.00 | 31.61 | D |
| ATOM | 5498 | N   | SER | D | 299 | 48.694 | 52.340 | 38.436 | 1.00 | 30.51 | D |
| ATOM | 5499 | CA  | SER | D | 299 | 49.224 | 52.806 | 37.135 | 1.00 | 31.26 | D |
| ATOM | 5500 | CB  | SER | D | 299 | 50.015 | 51.774 | 36.329 | 1.00 | 29.35 | D |
| ATOM | 5501 | OG  | SER | D | 299 | 51.107 | 51.240 | 37.089 | 1.00 | 33.80 | D |
| ATOM | 5502 | C   | SER | D | 299 | 47.998 | 53.261 | 36.314 | 1.00 | 30.59 | D |
| ATOM | 5503 | O   | SER | D | 299 | 48.120 | 54.289 | 35.618 | 1.00 | 30.32 | D |
| ATOM | 5504 | N   | LEU | D | 300 | 46.862 | 52.569 | 36.358 | 1.00 | 30.18 | D |
| ATOM | 5505 | CA  | LEU | D | 300 | 45.720 | 53.042 | 35.498 | 1.00 | 30.30 | D |
| ATOM | 5506 | CB  | LEU | D | 300 | 44.545 | 52.095 | 35.493 | 1.00 | 29.69 | D |
| ATOM | 5507 | CG  | LEU | D | 300 | 44.740 | 50.668 | 34.972 | 1.00 | 32.89 | D |
| ATOM | 5508 | CD1 | LEU | D | 300 | 43.467 | 49.869 | 34.725 | 1.00 | 28.91 | D |
| ATOM | 5509 | CD2 | LEU | D | 300 | 45.605 | 50.639 | 33.787 | 1.00 | 31.58 | D |
| ATOM | 5510 | C   | LEU | D | 300 | 45.237 | 54.381 | 35.983 | 1.00 | 30.30 | D |
| ATOM | 5511 | O   | LEU | D | 300 | 44.939 | 55.254 | 35.214 | 1.00 | 30.24 | D |
| ATOM | 5512 | N   | LEU | D | 301 | 45.143 | 54.518 | 37.285 | 1.00 | 27.62 | D |
| ATOM | 5513 | CA  | LEU | D | 301 | 44.673 | 55.696 | 37.892 | 1.00 | 26.86 | D |
| ATOM | 5514 | CB  | LEU | D | 301 | 44.514 | 55.489 | 39.422 | 1.00 | 27.30 | D |
| ATOM | 5515 | CG  | LEU | D | 301 | 43.283 | 54.652 | 39.757 | 1.00 | 26.51 | D |
| ATOM | 5516 | CD1 | LEU | D | 301 | 43.537 | 54.235 | 41.208 | 1.00 | 26.48 | D |
| ATOM | 5517 | CD2 | LEU | D | 301 | 41.976 | 55.424 | 39.696 | 1.00 | 23.60 | D |
| ATOM | 5518 | C   | LEU | D | 301 | 45.526 | 56.859 | 37.655 | 1.00 | 27.47 | D |
| ATOM | 5519 | O   | LEU | D | 301 | 45.004 | 58.025 | 37.405 | 1.00 | 26.43 | D |
| ATOM | 5520 | N   | GLN | D | 302 | 46.849 | 56.616 | 37.663 | 1.00 | 27.31 | D |
| ATOM | 5521 | CA  | GLN | D | 302 | 47.790 | 57.732 | 37.411 | 1.00 | 27.69 | D |
| ATOM | 5522 | CB  | GLN | D | 302 | 49.284 | 57.346 | 37.723 | 1.00 | 26.89 | D |
| ATOM | 5523 | CG  | GLN | D | 302 | 49.548 | 57.318 | 39.251 | 1.00 | 28.24 | D |
| ATOM | 5524 | CD  | GLN | D | 302 | 50.894 | 56.785 | 39.679 | 1.00 | 28.62 | D |
| ATOM | 5525 | OE1 | GLN | D | 302 | 51.507 | 56.004 | 38.966 | 1.00 | 29.18 | D |
| ATOM | 5526 | NE2 | GLN | D | 302 | 51.277 | 57.115 | 40.868 | 1.00 | 26.87 | D |
| ATOM | 5527 | C   | GLN | D | 302 | 47.703 | 58.187 | 36.006 | 1.00 | 28.28 | D |
| ATOM | 5528 | O   | GLN | D | 302 | 48.074 | 59.252 | 35.698 | 1.00 | 28.06 | D |
| ATOM | 5529 | N   | SER | D | 303 | 47.299 | 57.319 | 35.097 | 1.00 | 29.80 | D |
| ATOM | 5530 | CA  | SER | D | 303 | 47.294 | 57.704 | 33.690 | 1.00 | 30.58 | D |
| ATOM | 5531 | CB  | SER | D | 303 | 47.451 | 56.546 | 32.825 | 1.00 | 29.22 | D |
| ATOM | 5532 | OG  | SER | D | 303 | 48.858 | 56.346 | 32.647 | 1.00 | 36.11 | D |
| ATOM | 5533 | C   | SER | D | 303 | 45.985 | 58.404 | 33.331 | 1.00 | 30.82 | D |
| ATOM | 5534 | O   | SER | D | 303 | 45.952 | 59.070 | 32.375 | 1.00 | 32.12 | D |
| ATOM | 5535 | N   | ALA | D | 304 | 44.920 | 58.115 | 34.045 | 1.00 | 30.55 | D |
| ATOM | 5536 | CA  | ALA | D | 304 | 43.550 | 58.459 | 33.677 | 1.00 | 30.93 | D |
| ATOM | 5537 | CB  | ALA | D | 304 | 42.686 | 57.201 | 33.766 | 1.00 | 28.45 | D |
| ATOM | 5538 | C   | ALA | D | 304 | 42.921 | 59.483 | 34.552 | 1.00 | 30.72 | D |
| ATOM | 5539 | O   | ALA | D | 304 | 41.846 | 59.951 | 34.265 | 1.00 | 31.53 | D |
| ATOM | 5540 | N   | TRP | D | 305 | 43.572 | 59.880 | 35.632 | 1.00 | 30.66 | D |
| ATOM | 5541 | CA  | TRP | D | 305 | 42.827 | 60.643 | 36.705 | 1.00 | 29.71 | D |

TABLE 2-continued

ATOMIC COORDINATES OF THE ERR3 LBD/
DIETHYLSTILBESTROL COMPLEX

| ATOM | 5542 | CB  | TRP | D | 305 | 43.680 | 60.970 | 37.948 | 1.00 | 28.25 | D |
|------|------|-----|-----|---|-----|--------|--------|--------|------|-------|---|
| ATOM | 5543 | CG  | TRP | D | 305 | 44.847 | 61.789 | 37.747 | 1.00 | 28.62 | D |
| ATOM | 5544 | CD2 | TRP | D | 305 | 44.963 | 63.201 | 37.911 | 1.00 | 29.22 | D |
| ATOM | 5545 | CE2 | TRP | D | 305 | 46.276 | 63.553 | 37.638 | 1.00 | 30.24 | D |
| ATOM | 5546 | CE3 | TRP | D | 305 | 44.069 | 64.237 | 38.267 | 1.00 | 32.01 | D |
| ATOM | 5547 | CD1 | TRP | D | 305 | 46.133 | 61.336 | 37.444 | 1.00 | 28.51 | D |
| ATOM | 5548 | NE1 | TRP | D | 305 | 46.986 | 62.385 | 37.458 | 1.00 | 29.13 | D |
| ATOM | 5549 | CZ2 | TRP | D | 305 | 46.734 | 64.914 | 37.725 | 1.00 | 30.71 | D |
| ATOM | 5550 | CZ3 | TRP | D | 305 | 44.525 | 65.585 | 38.294 | 1.00 | 30.49 | D |
| ATOM | 5551 | CH2 | TRP | D | 305 | 45.836 | 65.876 | 38.100 | 1.00 | 31.92 | D |
| ATOM | 5552 | C   | TRP | D | 305 | 42.223 | 61.940 | 36.153 | 1.00 | 29.83 | D |
| ATOM | 5553 | O   | TRP | D | 305 | 41.053 | 62.243 | 36.426 | 1.00 | 30.34 | D |
| ATOM | 5554 | N   | MET | D | 306 | 42.995 | 62.741 | 35.423 | 1.00 | 29.00 | D |
| ATOM | 5555 | CA  | MET | D | 306 | 42.449 | 64.027 | 34.867 | 1.00 | 29.18 | D |
| ATOM | 5556 | CB  | MET | D | 306 | 43.523 | 64.874 | 34.212 | 1.00 | 28.22 | D |
| ATOM | 5557 | CG  | MET | D | 306 | 43.008 | 66.204 | 33.665 | 1.00 | 30.16 | D |
| ATOM | 5558 | SD  | MET | D | 306 | 42.313 | 67.263 | 34.972 | 1.00 | 31.62 | D |
| ATOM | 5559 | CE  | MET | D | 306 | 43.714 | 68.051 | 35.643 | 1.00 | 29.76 | D |
| ATOM | 5560 | C   | MET | D | 306 | 41.309 | 63.785 | 33.859 | 1.00 | 28.14 | D |
| ATOM | 5561 | O   | MET | D | 306 | 40.375 | 64.525 | 33.827 | 1.00 | 27.52 | D |
| ATOM | 5562 | N   | GLU | D | 307 | 41.369 | 62.671 | 33.118 | 1.00 | 29.25 | D |
| ATOM | 5563 | CA  | GLU | D | 307 | 40.276 | 62.237 | 32.293 | 1.00 | 29.60 | D |
| ATOM | 5564 | CB  | GLU | D | 307 | 40.597 | 61.056 | 31.409 | 1.00 | 28.58 | D |
| ATOM | 5565 | CG  | GLU | D | 307 | 41.510 | 61.378 | 30.315 | 1.00 | 30.64 | D |
| ATOM | 5566 | CD  | GLU | D | 307 | 41.704 | 60.298 | 29.362 | 1.00 | 31.55 | D |
| ATOM | 5567 | OE1 | GLU | D | 307 | 40.803 | 59.470 | 29.076 | 1.00 | 32.09 | D |
| ATOM | 5568 | OE2 | GLU | D | 307 | 42.822 | 60.217 | 28.890 | 1.00 | 34.39 | D |
| ATOM | 5569 | C   | GLU | D | 307 | 38.962 | 61.985 | 33.026 | 1.00 | 29.22 | D |
| ATOM | 5570 | O   | GLU | D | 307 | 37.953 | 62.347 | 32.458 | 1.00 | 28.97 | D |
| ATOM | 5571 | N   | ILE | D | 308 | 39.005 | 61.379 | 34.202 | 1.00 | 28.73 | D |
| ATOM | 5572 | CA  | ILE | D | 308 | 37.862 | 61.073 | 35.119 | 1.00 | 28.70 | D |
| ATOM | 5573 | CB  | ILE | D | 308 | 38.291 | 60.241 | 36.228 | 1.00 | 28.73 | D |
| ATOM | 5574 | CG2 | ILE | D | 308 | 37.125 | 59.762 | 37.134 | 1.00 | 27.20 | D |
| ATOM | 5575 | CG1 | ILE | D | 308 | 39.021 | 58.977 | 35.696 | 1.00 | 30.40 | D |
| ATOM | 5576 | CD1 | ILE | D | 308 | 38.353 | 58.341 | 34.731 | 1.00 | 31.64 | D |
| ATOM | 5577 | C   | ILE | D | 308 | 37.281 | 62.315 | 35.667 | 1.00 | 29.10 | D |
| ATOM | 5578 | O   | ILE | D | 308 | 36.113 | 62.604 | 35.495 | 1.00 | 29.57 | D |
| ATOM | 5579 | N   | LEU | D | 309 | 38.127 | 63.133 | 36.175 | 1.00 | 27.58 | D |
| ATOM | 5580 | CA  | LEU | D | 309 | 37.700 | 64.391 | 36.671 | 1.00 | 28.58 | D |
| ATOM | 5581 | CB  | LEU | D | 309 | 38.891 | 65.188 | 37.231 | 1.00 | 27.75 | D |
| ATOM | 5582 | CG  | LEU | D | 309 | 39.590 | 64.718 | 38.520 | 1.00 | 29.94 | D |
| ATOM | 5583 | CD1 | LEU | D | 309 | 40.665 | 65.716 | 38.737 | 1.00 | 27.83 | D |
| ATOM | 5584 | CD2 | LEU | D | 309 | 38.650 | 64.798 | 39.668 | 1.00 | 29.63 | D |
| ATOM | 5585 | C   | LEU | D | 309 | 37.032 | 65.278 | 35.545 | 1.00 | 29.53 | D |
| ATOM | 5586 | O   | LEU | D | 309 | 35.951 | 65.728 | 35.756 | 1.00 | 30.12 | D |
| ATOM | 5587 | N   | ILE | D | 310 | 37.701 | 65.570 | 34.455 | 1.00 | 29.08 | D |
| ATOM | 5588 | CA  | ILE | D | 310 | 37.149 | 66.305 | 33.379 | 1.00 | 30.11 | D |
| ATOM | 5589 | CB  | ILE | D | 310 | 38.120 | 66.398 | 32.142 | 1.00 | 31.34 | D |
| ATOM | 5590 | CG2 | ILE | D | 310 | 37.464 | 67.106 | 30.988 | 1.00 | 29.17 | D |
| ATOM | 5591 | CG1 | ILE | D | 310 | 39.512 | 67.135 | 32.321 | 1.00 | 32.75 | D |
| ATOM | 5592 | CD1 | ILE | D | 310 | 39.403 | 68.430 | 32.510 | 1.00 | 34.56 | D |
| ATOM | 5593 | C   | ILE | D | 310 | 35.837 | 65.672 | 32.866 | 1.00 | 30.51 | D |
| ATOM | 5594 | O   | ILE | D | 310 | 34.930 | 66.407 | 32.499 | 1.00 | 31.11 | D |
| ATOM | 5595 | N   | LEU | D | 311 | 35.713 | 64.351 | 32.780 | 1.00 | 29.49 | D |
| ATOM | 5596 | CA  | LEU | D | 311 | 34.552 | 63.833 | 32.179 | 1.00 | 29.25 | D |
| ATOM | 5597 | CB  | LEU | D | 311 | 34.676 | 62.362 | 32.083 | 1.00 | 27.80 | D |
| ATOM | 5598 | CG  | LEU | D | 311 | 34.029 | 61.492 | 31.113 | 1.00 | 29.46 | D |
| ATOM | 5599 | CD1 | LEU | D | 311 | 33.628 | 62.157 | 29.798 | 1.00 | 29.25 | D |
| ATOM | 5600 | CD2 | LEU | D | 311 | 34.901 | 60.210 | 30.929 | 1.00 | 29.87 | D |
| ATOM | 5601 | C   | LEU | D | 311 | 33.427 | 64.176 | 33.123 | 1.00 | 29.79 | D |
| ATOM | 5602 | O   | LEU | D | 311 | 32.324 | 64.457 | 32.756 | 1.00 | 29.39 | D |
| ATOM | 5603 | N   | GLY | D | 312 | 33.760 | 64.155 | 34.406 | 1.00 | 30.60 | D |
| ATOM | 5604 | CA  | GLY | D | 312 | 32.945 | 64.685 | 35.472 | 1.00 | 30.57 | D |
| ATOM | 5605 | C   | GLY | D | 312 | 32.433 | 66.106 | 35.223 | 1.00 | 31.27 | D |
| ATOM | 5606 | O   | GLY | D | 312 | 31.245 | 66.341 | 35.258 | 1.00 | 30.29 | D |
| ATOM | 5607 | N   | VAL | D | 313 | 33.310 | 67.073 | 35.201 | 1.00 | 32.19 | D |
| ATOM | 5608 | CA  | VAL | D | 313 | 32.868 | 68.427 | 34.953 | 1.00 | 33.03 | D |
| ATOM | 5609 | CB  | VAL | D | 313 | 34.080 | 69.349 | 34.804 | 1.00 | 33.15 | D |
| ATOM | 5610 | CG1 | VAL | D | 313 | 33.791 | 70.673 | 34.131 | 1.00 | 30.72 | D |
| ATOM | 5611 | CG2 | VAL | D | 313 | 34.612 | 69.592 | 36.073 | 1.00 | 34.93 | D |
| ATOM | 5612 | C   | VAL | D | 313 | 31.989 | 68.484 | 33.679 | 1.00 | 33.95 | D |
| ATOM | 5613 | O   | VAL | D | 313 | 30.997 | 69.144 | 33.704 | 1.00 | 35.01 | D |
| ATOM | 5614 | N   | VAL | D | 314 | 32.396 | 67.888 | 32.567 | 1.00 | 33.49 | D |
| ATOM | 5615 | CA  | VAL | D | 314 | 31.664 | 67.909 | 31.300 | 1.00 | 34.37 | D |
| ATOM | 5616 | CB  | VAL | D | 314 | 32.395 | 67.002 | 30.251 | 1.00 | 35.31 | D |
| ATOM | 5617 | CG1 | VAL | D | 314 | 31.579 | 66.772 | 28.995 | 1.00 | 34.12 | D |

TABLE 2-continued

ATOMIC COORDINATES OF THE ERR3 LBD/
DIETHYLSTILBESTROL COMPLEX

| ATOM | 5618 | CG2 | VAL | D | 314 | 33.828 | 67.609 | 29.851 | 1.00 | 34.06 | D |
| --- | --- | --- | --- | --- | --- | --- | --- | --- | --- | --- | --- |
| ATOM | 5619 | C | VAL | D | 314 | 30.231 | 67.419 | 31.496 | 1.00 | 35.56 | D |
| ATOM | 5620 | O | VAL | D | 314 | 29.244 | 68.052 | 31.083 | 1.00 | 35.71 | D |
| ATOM | 5621 | N | TYR | D | 315 | 30.087 | 66.308 | 32.164 | 1.00 | 35.45 | D |
| ATOM | 5622 | CA | TYR | D | 315 | 28.752 | 65.774 | 32.428 | 1.00 | 36.03 | D |
| ATOM | 5623 | CB | TYR | D | 315 | 28.738 | 64.418 | 33.141 | 1.00 | 36.15 | D |
| ATOM | 5624 | CG | TYR | D | 315 | 27.310 | 63.802 | 33.176 | 1.00 | 37.61 | D |
| ATOM | 5625 | CD1 | TYR | D | 315 | 26.800 | 63.157 | 32.060 | 1.00 | 37.07 | D |
| ATOM | 5626 | CE1 | TYR | D | 315 | 25.550 | 62.561 | 32.078 | 1.00 | 38.69 | D |
| ATOM | 5627 | CD2 | TYR | D | 315 | 26.532 | 63.805 | 34.320 | 1.00 | 35.88 | D |
| ATOM | 5628 | CE2 | TYR | D | 315 | 25.220 | 63.288 | 34.316 | 1.00 | 36.91 | D |
| ATOM | 5629 | CZ | TYR | D | 315 | 24.760 | 62.584 | 33.196 | 1.00 | 38.98 | D |
| ATOM | 5630 | OH | TYR | D | 315 | 23.506 | 61.917 | 33.098 | 1.00 | 40.52 | D |
| ATOM | 5631 | C | TYR | D | 315 | 27.899 | 66.696 | 33.231 | 1.00 | 35.90 | D |
| ATOM | 5632 | O | TYR | D | 315 | 26.733 | 66.866 | 32.936 | 1.00 | 34.44 | D |
| ATOM | 5633 | N | ARG | D | 316 | 28.500 | 67.320 | 34.208 | 1.00 | 36.55 | D |
| ATOM | 5634 | CA | ARG | D | 316 | 27.720 | 68.241 | 34.966 | 1.00 | 36.48 | D |
| ATOM | 5635 | CB | ARG | D | 316 | 28.454 | 68.679 | 36.193 | 1.00 | 35.63 | D |
| ATOM | 5636 | CG | ARG | D | 316 | 28.552 | 67.483 | 37.309 | 1.00 | 34.12 | D |
| ATOM | 5637 | CD | ARG | D | 316 | 29.278 | 67.945 | 38.633 | 1.00 | 33.40 | D |
| ATOM | 5638 | NE | ARG | D | 316 | 30.633 | 68.440 | 38.529 | 1.00 | 34.67 | D |
| ATOM | 5639 | CZ | ARG | D | 316 | 31.717 | 67.595 | 38.558 | 1.00 | 33.42 | D |
| ATOM | 5640 | NH1 | ARG | D | 316 | 31.524 | 66.291 | 38.561 | 1.00 | 31.85 | D |
| ATOM | 5641 | NH2 | ARG | D | 316 | 32.961 | 68.047 | 38.467 | 1.00 | 29.66 | D |
| ATOM | 5642 | C | ARG | D | 316 | 27.333 | 69.448 | 34.199 | 1.00 | 37.82 | D |
| ATOM | 5643 | O | ARG | D | 316 | 26.461 | 70.185 | 34.624 | 1.00 | 38.68 | D |
| ATOM | 5644 | N | SER | D | 317 | 28.023 | 69.700 | 33.111 | 1.00 | 37.89 | D |
| ATOM | 5645 | CA | SER | D | 317 | 27.841 | 70.936 | 32.439 | 1.00 | 38.68 | D |
| ATOM | 5646 | CB | SER | D | 317 | 29.212 | 71.510 | 31.969 | 1.00 | 37.38 | D |
| ATOM | 5647 | OG | SER | D | 317 | 29.977 | 71.716 | 33.112 | 1.00 | 36.60 | D |
| ATOM | 5648 | C | SER | D | 317 | 26.856 | 70.767 | 31.270 | 1.00 | 38.52 | D |
| ATOM | 5649 | O | SER | D | 317 | 26.685 | 71.694 | 30.542 | 1.00 | 39.87 | D |
| ATOM | 5650 | N | LEU | D | 318 | 26.268 | 69.606 | 31.062 | 1.00 | 39.78 | D |
| ATOM | 5651 | CA | LEU | D | 318 | 25.441 | 69.472 | 29.857 | 1.00 | 41.68 | D |
| ATOM | 5652 | CB | LEU | D | 318 | 24.993 | 68.030 | 29.666 | 1.00 | 40.25 | D |
| ATOM | 5653 | CG | LEU | D | 318 | 26.143 | 67.063 | 29.545 | 1.00 | 40.56 | D |
| ATOM | 5654 | CD1 | LEU | D | 318 | 25.619 | 65.693 | 29.486 | 1.00 | 40.10 | D |
| ATOM | 5655 | CD2 | LEU | D | 318 | 26.929 | 67.399 | 28.367 | 1.00 | 37.97 | D |
| ATOM | 5656 | C | LEU | D | 318 | 24.155 | 70.370 | 29.777 | 1.00 | 42.56 | D |
| ATOM | 5657 | O | LEU | D | 318 | 23.672 | 70.584 | 28.731 | 1.00 | 44.57 | D |
| ATOM | 5658 | N | SER | D | 319 | 23.669 | 70.908 | 30.860 | 1.00 | 43.26 | D |
| ATOM | 5659 | CA | SER | D | 319 | 22.380 | 71.559 | 30.865 | 1.00 | 44.69 | D |
| ATOM | 5660 | CB | SER | D | 319 | 21.464 | 70.809 | 31.862 | 1.00 | 45.82 | D |
| ATOM | 5661 | OG | SER | D | 319 | 22.006 | 70.834 | 33.171 | 1.00 | 51.09 | D |
| ATOM | 5662 | C | SER | D | 319 | 22.753 | 72.963 | 31.318 | 1.00 | 44.29 | D |
| ATOM | 5663 | O | SER | D | 319 | 22.033 | 73.634 | 32.105 | 1.00 | 44.79 | D |
| ATOM | 5664 | N | PHE | D | 320 | 23.947 | 73.358 | 30.890 | 1.00 | 42.60 | D |
| ATOM | 5665 | CA | PHE | D | 320 | 24.429 | 74.704 | 31.070 | 1.00 | 41.19 | D |
| ATOM | 5666 | CB | PHE | D | 320 | 25.504 | 74.770 | 32.138 | 1.00 | 39.19 | D |
| ATOM | 5667 | CG | PHE | D | 320 | 24.986 | 74.583 | 33.513 | 1.00 | 37.05 | D |
| ATOM | 5668 | CD1 | PHE | D | 320 | 24.778 | 75.664 | 34.328 | 1.00 | 36.36 | D |
| ATOM | 5669 | CD2 | PHE | D | 320 | 24.596 | 73.337 | 33.931 | 1.00 | 35.63 | D |
| ATOM | 5670 | CE1 | PHE | D | 320 | 24.249 | 75.477 | 35.625 | 1.00 | 36.02 | D |
| ATOM | 5671 | CE2 | PHE | D | 320 | 24.118 | 73.111 | 35.128 | 1.00 | 35.63 | D |
| ATOM | 5672 | CZ | PHE | D | 320 | 23.892 | 74.211 | 36.008 | 1.00 | 36.39 | D |
| ATOM | 5673 | C | PHE | D | 320 | 24.983 | 75.099 | 29.760 | 1.00 | 42.45 | D |
| ATOM | 5674 | O | PHE | D | 320 | 25.189 | 74.230 | 28.897 | 1.00 | 41.97 | D |
| ATOM | 5675 | N | GLU | D | 321 | 25.220 | 76.402 | 29.571 | 1.00 | 44.72 | D |
| ATOM | 5676 | CA | GLU | D | 321 | 25.714 | 76.925 | 28.295 | 1.00 | 47.22 | D |
| ATOM | 5677 | CB | GLU | D | 321 | 24.568 | 77.614 | 27.485 | 1.00 | 51.70 | D |
| ATOM | 5678 | CG | GLU | D | 321 | 23.721 | 78.611 | 28.276 | 1.00 | 60.55 | D |
| ATOM | 5679 | CD | GLU | D | 321 | 22.718 | 77.954 | 29.222 | 1.00 | 66.07 | D |
| ATOM | 5680 | OE1 | GLU | D | 321 | 22.001 | 78.699 | 29.923 | 1.00 | 69.03 | D |
| ATOM | 5681 | OE2 | GLU | D | 321 | 22.637 | 76.707 | 29.273 | 1.00 | 69.84 | D |
| ATOM | 5682 | C | GLU | D | 321 | 26.850 | 77.897 | 28.558 | 1.00 | 46.01 | D |
| ATOM | 5683 | O | GLU | D | 321 | 26.653 | 78.865 | 29.263 | 1.00 | 44.55 | D |
| ATOM | 5684 | N | ASP | D | 322 | 28.034 | 77.604 | 27.984 | 1.00 | 44.77 | D |
| ATOM | 5685 | CA | ASP | D | 322 | 29.279 | 78.410 | 28.197 | 1.00 | 44.42 | D |
| ATOM | 5686 | CB | ASP | D | 322 | 29.099 | 79.829 | 27.641 | 1.00 | 46.27 | D |
| ATOM | 5687 | CG | ASP | D | 322 | 28.754 | 79.773 | 26.228 | 1.00 | 48.70 | D |
| ATOM | 5688 | OD1 | ASP | D | 322 | 29.085 | 78.702 | 25.673 | 1.00 | 50.88 | D |
| ATOM | 5689 | OD2 | ASP | D | 322 | 28.143 | 80.657 | 25.613 | 1.00 | 50.12 | D |
| ATOM | 5690 | C | ASP | D | 322 | 29.645 | 78.479 | 29.614 | 1.00 | 42.84 | D |
| ATOM | 5691 | O | ASP | D | 322 | 30.226 | 79.488 | 30.089 | 1.00 | 43.16 | D |
| ATOM | 5692 | N | GLU | D | 323 | 29.215 | 77.469 | 30.349 | 1.00 | 40.69 | D |
| ATOM | 5693 | CA | GLU | D | 323 | 29.588 | 77.396 | 31.748 | 1.00 | 39.76 | D |

TABLE 2-continued

ATOMIC COORDINATES OF THE ERR3 LBD/
DIETHYLSTILBESTROL COMPLEX

| ATOM | 5694 | CB  | GLU | D | 323 | 28.396 | 77.717 | 32.606 | 1.00 | 39.90 | D |
|------|------|-----|-----|---|-----|--------|--------|--------|------|-------|---|
| ATOM | 5695 | CG  | GLO | D | 323 | 27.826 | 79.073 | 32.283 | 1.00 | 44.37 | D |
| ATOM | 5696 | CD  | GLU | D | 323 | 27.046 | 79.654 | 33.422 | 1.00 | 45.69 | D |
| ATOM | 5697 | OE1 | GLU | D | 323 | 25.999 | 79.059 | 33.778 | 1.00 | 47.46 | D |
| ATOM | 5698 | OE2 | GLU | D | 323 | 27.495 | 80.693 | 33.937 | 1.00 | 48.10 | D |
| ATOM | 5699 | C   | GLU | D | 323 | 30.069 | 76.004 | 32.146 | 1.00 | 37.46 | D |
| ATOM | 5700 | O   | GLU | D | 323 | 29.506 | 74.939 | 31.668 | 1.00 | 36.63 | D |
| ATOM | 5701 | N   | LEU | D | 324 | 30.950 | 75.975 | 33.144 | 1.00 | 35.98 | D |
| ATOM | 5702 | CA  | LEU | D | 324 | 31.415 | 74.671 | 33.619 | 1.00 | 34.16 | D |
| ATOM | 5703 | CB  | LEU | D | 324 | 32.925 | 74.527 | 33.347 | 1.00 | 32.85 | D |
| ATOM | 5704 | CG  | LEU | D | 324 | 33.404 | 74.579 | 31.952 | 1.00 | 30.67 | D |
| ATOM | 5705 | CD1 | LEU | D | 324 | 34.960 | 74.607 | 31.836 | 1.00 | 31.53 | D |
| ATOM | 5706 | CD2 | LEU | D | 324 | 32.819 | 73.441 | 31.206 | 1.00 | 29.90 | D |
| ATOM | 5707 | C   | LEU | D | 324 | 31.116 | 74.516 | 35.070 | 1.00 | 33.82 | D |
| ATOM | 5708 | O   | LEU | D | 324 | 31.561 | 75.295 | 35.851 | 1.00 | 34.44 | D |
| ATOM | 5709 | N   | VAL | D | 325 | 30.417 | 73.420 | 35.389 | 1.00 | 33.70 | D |
| ATOM | 5710 | CA  | VAL | D | 325 | 30.091 | 73.014 | 36.746 | 1.00 | 33.73 | D |
| ATOM | 5711 | CB  | VAL | D | 325 | 28.752 | 72.157 | 36.699 | 1.00 | 35.10 | D |
| ATOM | 5712 | CG1 | VAL | D | 325 | 28.216 | 71.856 | 38.046 | 1.00 | 32.84 | D |
| ATOM | 5713 | CG2 | VAL | D | 325 | 27.617 | 72.915 | 35.912 | 1.00 | 33.91 | D |
| ATOM | 5714 | C   | VAL | D | 325 | 31.230 | 72.147 | 37.333 | 1.00 | 34.24 | D |
| ATOM | 5715 | O   | VAL | D | 325 | 31.209 | 70.904 | 37.324 | 1.00 | 33.27 | D |
| ATOM | 5716 | N   | TYR | D | 326 | 32.213 | 72.841 | 37.867 | 1.00 | 33.89 | D |
| ATOM | 5717 | CA  | TYR | D | 326 | 33.300 | 72.200 | 38.614 | 1.00 | 33.80 | D |
| ATOM | 5718 | CB  | TYR | D | 326 | 34.507 | 73.125 | 38.908 | 1.00 | 33.16 | D |
| ATOM | 5719 | CG  | TYR | D | 326 | 35.345 | 73.314 | 37.692 | 1.00 | 31.71 | D |
| ATOM | 5720 | CD1 | TYR | D | 326 | 36.193 | 72.308 | 37.290 | 1.00 | 33.29 | D |
| ATOM | 5721 | CE1 | TYR | D | 326 | 36.987 | 72.416 | 36.147 | 1.00 | 33.73 | D |
| ATOM | 5722 | CD2 | TYR | D | 326 | 35.279 | 74.456 | 36.919 | 1.00 | 31.94 | D |
| ATOM | 5723 | CE2 | TYR | D | 326 | 36.082 | 74.591 | 35.741 | 1.00 | 31.80 | D |
| ATOM | 5724 | CZ  | TYR | D | 326 | 36.954 | 73.542 | 35.390 | 1.00 | 33.92 | D |
| ATOM | 5725 | OH  | TYR | D | 326 | 37.767 | 73.500 | 34.250 | 1.00 | 33.00 | D |
| ATOM | 5726 | C   | TYR | D | 326 | 32.671 | 71.618 | 39.806 | 1.00 | 35.18 | D |
| ATOM | 5727 | O   | TYR | D | 326 | 32.939 | 70.455 | 40.117 | 1.00 | 35.98 | D |
| ATOM | 5728 | N   | ALA | D | 327 | 31.733 | 72.360 | 40.402 | 1.00 | 36.22 | D |
| ATOM | 5729 | CA  | ALA | D | 327 | 30.879 | 71.785 | 41.439 | 1.00 | 38.67 | D |
| ATOM | 5730 | CB  | ALA | D | 327 | 31.609 | 71.916 | 42.763 | 1.00 | 38.79 | D |
| ATOM | 5731 | C   | ALA | D | 327 | 29.538 | 72.545 | 41.520 | 1.00 | 40.13 | D |
| ATOM | 5732 | O   | ALA | D | 327 | 29.487 | 73.638 | 41.033 | 1.00 | 41.31 | D |
| ATOM | 5733 | N   | ASP | D | 328 | 28.505 | 72.062 | 42.215 | 1.00 | 40.93 | D |
| ATOM | 5734 | CA  | ASP | D | 328 | 27.208 | 72.852 | 42.249 | 1.00 | 42.45 | D |
| ATOM | 5735 | CB  | ASP | D | 328 | 26.114 | 72.215 | 43.135 | 1.00 | 43.69 | D |
| ATOM | 5736 | CG  | ASP | D | 328 | 25.552 | 70.922 | 42.578 | 1.00 | 44.66 | D |
| ATOM | 5737 | OD1 | ASP | D | 328 | 25.778 | 70.573 | 41.344 | 1.00 | 45.19 | D |
| ATOM | 5738 | OD2 | ASP | D | 328 | 24.904 | 70.145 | 43.377 | 1.00 | 47.97 | D |
| ATOM | 5739 | C   | ASP | D | 328 | 27.426 | 74.269 | 42.743 | 1.00 | 43.00 | D |
| ATOM | 5740 | O   | ASP | D | 328 | 26.834 | 75.237 | 42.206 | 1.00 | 44.69 | D |
| ATOM | 5741 | N   | ASP | D | 329 | 28.326 | 74.432 | 43.709 | 1.00 | 41.99 | D |
| ATOM | 5742 | CA  | ASP | D | 329 | 28.668 | 75.743 | 44.229 | 1.00 | 40.54 | D |
| ATOM | 5743 | CB  | ASP | D | 329 | 28.976 | 75.604 | 45.702 | 1.00 | 41.86 | D |
| ATOM | 5744 | CG  | ASP | D | 329 | 30.190 | 74.586 | 46.028 | 1.00 | 43.30 | D |
| ATOM | 5745 | OD1 | ASP | D | 329 | 30.768 | 73.885 | 45.115 | 1.00 | 43.56 | D |
| ATOM | 5746 | OD2 | ASP | D | 329 | 30.588 | 74.464 | 47.210 | 1.00 | 43.42 | D |
| ATOM | 5747 | C   | ASP | D | 329 | 29.883 | 76.344 | 43.568 | 1.00 | 39.78 | D |
| ATOM | 5748 | O   | ASP | D | 329 | 30.559 | 77.198 | 44.192 | 1.00 | 37.57 | D |
| ATOM | 5749 | N   | TYR | D | 330 | 30.229 | 75.896 | 42.340 | 1.00 | 38.60 | D |
| ATOM | 5750 | CA  | TYR | D | 330 | 31.512 | 76.396 | 41.737 | 1.00 | 38.29 | D |
| ATOM | 5751 | CB  | TYR | D | 330 | 32.767 | 75.829 | 42.417 | 1.00 | 37.27 | D |
| ATOM | 5752 | CG  | TYR | D | 330 | 33.943 | 76.775 | 42.231 | 1.00 | 38.27 | D |
| ATOM | 5753 | CD1 | TYR | D | 330 | 34.047 | 77.949 | 42.924 | 1.00 | 37.02 | D |
| ATOM | 5754 | CE1 | TYR | D | 330 | 35.094 | 78.869 | 42.679 | 1.00 | 38.14 | D |
| ATOM | 5755 | CD2 | TYR | D | 330 | 34.925 | 76.533 | 41.259 | 1.00 | 38.35 | D |
| ATOM | 5756 | CE2 | TYR | D | 330 | 35.932 | 77.477 | 41.037 | 1.00 | 39.16 | D |
| ATOM | 5757 | CZ  | TYR | D | 330 | 36.006 | 78.604 | 41.784 | 1.00 | 39.59 | D |
| ATOM | 5758 | OH  | TYR | D | 330 | 37.044 | 79.492 | 41.525 | 1.00 | 41.08 | D |
| ATOM | 5759 | C   | TYR | D | 330 | 31.478 | 76.242 | 40.213 | 1.00 | 38.54 | D |
| ATOM | 5760 | O   | TYR | D | 330 | 31.970 | 75.284 | 39.560 | 1.00 | 38.59 | D |
| ATOM | 5761 | N   | ILE | D | 331 | 30.779 | 77.201 | 39.640 | 1.00 | 39.58 | D |
| ATOM | 5762 | CA  | ILE | D | 331 | 30.381 | 77.159 | 38.256 | 1.00 | 40.92 | D |
| ATOM | 5763 | CB  | ILE | D | 331 | 28.870 | 77.354 | 38.094 | 1.00 | 41.40 | D |
| ATOM | 5764 | CG2 | ILE | D | 331 | 28.530 | 77.353 | 36.574 | 1.00 | 40.03 | D |
| ATOM | 5765 | CG1 | ILE | D | 331 | 28.112 | 76.224 | 38.712 | 1.00 | 40.56 | D |
| ATOM | 5766 | CD1 | ILE | D | 331 | 26.658 | 76.446 | 38.523 | 1.00 | 42.73 | D |
| ATOM | 5767 | C   | ILE | D | 331 | 31.047 | 78.260 | 37.581 | 1.00 | 42.13 | D |
| ATOM | 5768 | O   | ILE | D | 331 | 30.915 | 79.424 | 38.013 | 1.00 | 42.10 | D |
| ATOM | 5769 | N   | MET | D | 332 | 31.772 | 77.978 | 36.513 | 1.00 | 43.29 | D |

TABLE 2-continued

ATOMIC COORDINATES OF THE ERR3 LBD/
DIETHYLSTILBESTROL COMPLEX

| ATOM | 5770 | CA | MET | D | 332 | 32.667 | 79.037 | 36.037 | 1.00 | 46.39 | D |
| --- | --- | --- | --- | --- | --- | --- | --- | --- | --- | --- | --- |
| ATOM | 5771 | CB | MET | D | 332 | 34.118 | 78.507 | 35.939 | 1.00 | 45.93 | D |
| ATOM | 5772 | CG | MET | D | 332 | 34.938 | 78.818 | 37.090 | 1.00 | 47.42 | D |
| ATOM | 5773 | SD | MET | D | 332 | 36.672 | 78.125 | 36.979 | 1.00 | 48.85 | D |
| ATOM | 5774 | CE | MET | D | 332 | 37.380 | 79.564 | 36.480 | 1.00 | 46.22 | D |
| ATOM | 5775 | C | MET | D | 332 | 32.180 | 79.475 | 34.671 | 1.00 | 48.22 | D |
| ATOM | 5776 | O | MET | D | 332 | 32.055 | 78.596 | 33.778 | 1.00 | 48.22 | D |
| ATOM | 5777 | N | ASP | D | 333 | 31.955 | 80.796 | 34.514 | 1.00 | 50.80 | D |
| ATOM | 5778 | CA | ASP | D | 333 | 31.730 | 81.408 | 33.196 | 1.00 | 53.98 | D |
| ATOM | 5779 | CB | ASP | D | 333 | 30.629 | 82.508 | 33.238 | 1.00 | 55.09 | D |
| ATOM | 5780 | CG | ASP | D | 333 | 30.898 | 83.547 | 34.312 | 1.00 | 57.07 | D |
| ATOM | 5781 | OD1 | ASP | D | 333 | 32.103 | 83.712 | 34.665 | 1.00 | 58.06 | D |
| ATOM | 5782 | OD2 | ASP | D | 333 | 30.006 | 84.240 | 34.854 | 1.00 | 58.96 | D |
| ATOM | 5783 | C | ASP | D | 333 | 32.994 | 82.012 | 32.652 | 1.00 | 55.45 | D |
| ATOM | 5784 | O | ASP | D | 333 | 34.034 | 82.054 | 33.330 | 1.00 | 55.05 | D |
| ATOM | 5785 | N | GLU | D | 334 | 32.888 | 82.449 | 31.391 | 1.00 | 57.66 | D |
| ATOM | 5786 | CA | GLU | D | 334 | 33.974 | 83.133 | 30.684 | 1.00 | 60.73 | D |
| ATOM | 5787 | CB | GLU | D | 334 | 33.600 | 83.746 | 29.313 | 1.00 | 62.79 | D |
| ATOM | 5788 | CG | GLU | D | 334 | 34.776 | 84.222 | 28.459 | 1.00 | 68.83 | D |
| ATOM | 5789 | CD | GLU | D | 334 | 35.114 | 85.687 | 28.673 | 1.00 | 71.82 | D |
| ATOM | 5790 | OE1 | GLU | D | 334 | 35.524 | 86.056 | 29.791 | 1.00 | 73.91 | D |
| ATOM | 5791 | OE2 | GLU | D | 334 | 34.966 | 86.474 | 27.715 | 1.00 | 73.56 | D |
| ATOM | 5792 | C | GLU | D | 334 | 34.716 | 84.146 | 31.557 | 1.00 | 60.71 | D |
| ATOM | 5793 | O | GLU | D | 334 | 35.910 | 84.149 | 31.464 | 1.00 | 60.30 | D |
| ATOM | 5794 | N | ASP | D | 335 | 34.037 | 84.949 | 32.379 | 1.00 | 61.17 | D |
| ATOM | 5795 | CA | ASP | D | 335 | 34.718 | 85.998 | 33.155 | 1.00 | 62.58 | D |
| ATOM | 5796 | CB | ASP | D | 335 | 33.752 | 86.964 | 33.835 | 1.00 | 62.55 | D |
| ATOM | 5797 | CG | ASP | D | 335 | 33.068 | 87.931 | 32.841 | 1.00 | 63.54 | D |
| ATOM | 5798 | OD1 | ASP | D | 335 | 33.791 | 88.422 | 31.917 | 1.00 | 64.15 | D |
| ATOM | 5799 | OD2 | ASP | D | 335 | 31.839 | 88.239 | 32.931 | 1.00 | 62.96 | D |
| ATOM | 5800 | C | ASP | D | 335 | 35.604 | 85.410 | 34.269 | 1.00 | 63.24 | D |
| ATOM | 5801 | O | ASP | D | 335 | 36.727 | 85.858 | 34.443 | 1.00 | 63.59 | D |
| ATOM | 5802 | N | GLN | D | 336 | 35.070 | 84.448 | 35.026 | 1.00 | 63.81 | D |
| ATOM | 5803 | CA | GLN | D | 336 | 35.771 | 83.897 | 36.154 | 1.00 | 64.34 | D |
| ATOM | 5804 | CB | GLN | D | 336 | 34.869 | 83.015 | 37.036 | 1.00 | 66.35 | D |
| ATOM | 5805 | CG | GLN | D | 336 | 35.612 | 82.286 | 38.180 | 1.00 | 70.75 | D |
| ATOM | 5806 | CD | GLN | D | 336 | 36.250 | 83.220 | 39.210 | 1.00 | 72.77 | D |
| ATOM | 5807 | OE1 | GLN | D | 336 | 36.898 | 82.760 | 40.150 | 1.00 | 73.19 | D |
| ATOM | 5808 | NE2 | GLN | D | 336 | 36.067 | 84.528 | 39.040 | 1.00 | 74.20 | D |
| ATOM | 5809 | C | GLN | D | 336 | 36.834 | 83.114 | 35.499 | 1.00 | 63.40 | D |
| ATOM | 5810 | O | GLN | D | 336 | 37.969 | 83.095 | 35.979 | 1.00 | 62.57 | D |
| ATOM | 5811 | N | SER | D | 337 | 36.516 | 82.564 | 34.341 | 1.00 | 62.79 | D |
| ATOM | 5812 | CA | SER | D | 337 | 37.520 | 81.813 | 33.711 | 1.00 | 63.40 | D |
| ATOM | 5813 | CB | SER | D | 337 | 37.009 | 81.062 | 32.517 | 1.00 | 62.82 | D |
| ATOM | 5814 | OG | SER | D | 337 | 36.096 | 80.096 | 33.002 | 1.00 | 63.93 | D |
| ATOM | 5815 | C | SER | D | 337 | 38.681 | 82.749 | 33.385 | 1.00 | 64.08 | D |
| ATOM | 5816 | O | SER | D | 337 | 39.874 | 82.406 | 33.662 | 1.00 | 64.15 | D |
| ATOM | 5817 | N | LYS | D | 338 | 38.355 | 83.945 | 32.848 | 1.00 | 64.02 | D |
| ATOM | 5818 | CA | LYS | D | 338 | 39.395 | 84.765 | 32.265 | 1.00 | 64.26 | D |
| ATOM | 5819 | CB | LYS | D | 338 | 38.873 | 85.806 | 31.220 | 1.00 | 66.32 | D |
| ATOM | 5820 | CG | LYS | D | 338 | 39.962 | 86.667 | 30.579 | 1.00 | 70.11 | D |
| ATOM | 5821 | CD | LYS | D | 338 | 39.915 | 88.126 | 31.043 | 1.00 | 72.60 | D |
| ATOM | 5822 | CE | LYS | D | 338 | 40.456 | 88.315 | 32.457 | 1.00 | 74.23 | D |
| ATOM | 5823 | N2 | LYS | D | 338 | 40.410 | 89.741 | 32.884 | 1.00 | 75.51 | D |
| ATOM | 5824 | C | LYS | D | 338 | 40.160 | 85.353 | 33.441 | 1.00 | 62.89 | D |
| ATOM | 5825 | O | LYS | D | 338 | 41.308 | 85.654 | 33.317 | 1.00 | 63.10 | D |
| ATOM | 5826 | N | LEU | D | 339 | 39.547 | 85.422 | 34.590 | 1.00 | 61.34 | D |
| ATOM | 5827 | CA | LEU | D | 339 | 40.208 | 85.861 | 35.789 | 1.00 | 60.76 | D |
| ATOM | 5828 | CB | LEU | D | 339 | 39.139 | 86.178 | 36.809 | 1.00 | 60.54 | D |
| ATOM | 5829 | CG | LEU | D | 339 | 39.651 | 86.469 | 38.235 | 1.00 | 61.21 | D |
| ATOM | 5830 | CD1 | LEU | D | 339 | 40.672 | 87.653 | 38.321 | 1.00 | 60.92 | D |
| ATOM | 5831 | CD2 | LEU | D | 339 | 38.458 | 86.647 | 39.192 | 1.00 | 61.24 | D |
| ATOM | 5832 | C | LEU | D | 339 | 41.186 | 84.848 | 36.397 | 1.00 | 60.30 | D |
| ATOM | 5833 | O | LEU | D | 339 | 42.131 | 85.215 | 37.175 | 1.00 | 61.32 | D |
| ATOM | 5834 | N | ALA | D | 340 | 40.970 | 83.574 | 36.099 | 1.00 | 58.05 | D |
| ATOM | 5835 | CA | ALA | D | 340 | 41.689 | 82.506 | 36.821 | 1.00 | 55.13 | D |
| ATOM | 5836 | CB | ALA | D | 340 | 40.749 | 81.324 | 37.103 | 1.00 | 54.42 | D |
| ATOM | 5837 | C | ALA | D | 340 | 42.766 | 82.108 | 35.887 | 1.00 | 53.77 | D |
| ATOM | 5838 | O | ALA | D | 340 | 43.464 | 81.106 | 36.108 | 1.00 | 53.98 | D |
| ATOM | 5839 | N | GLY | D | 341 | 42.831 | 82.808 | 34.760 | 1.00 | 51.13 | D |
| ATOM | 5840 | CA | GLY | D | 341 | 43.825 | 82.453 | 33.802 | 1.00 | 48.89 | D |
| ATOM | 5841 | C | GLY | D | 341 | 43.554 | 81.090 | 33.190 | 1.00 | 46.97 | D |
| ATOM | 5842 | O | GLY | D | 341 | 44.466 | 80.450 | 32.649 | 1.00 | 45.04 | D |
| ATOM | 5843 | N | LEU | D | 342 | 42.274 | 80.729 | 33.156 | 1.00 | 45.82 | D |
| ATOM | 5844 | CA | LEU | D | 342 | 41.818 | 79.401 | 32.679 | 1.00 | 45.14 | D |
| ATOM | 5845 | CB | LEU | D | 342 | 41.094 | 78.674 | 33.872 | 1.00 | 44.85 | D |

TABLE 2-continued

ATOMIC COORDINATES OF THE ERR3 LBD/DIETHYLSTILBESTROL COMPLEX

| ATOM | 5846 | CG | LEU | D | 342 | 41.928 | 78.015 | 34.978 | 1.00 | 43.53 | D |
|---|---|---|---|---|---|---|---|---|---|---|---|
| ATOM | 5847 | CD1 | LEU | D | 342 | 41.119 | 77.638 | 36.134 | 1.00 | 42.84 | D |
| ATOM | 5848 | CD2 | LEU | D | 342 | 42.605 | 76.810 | 34.455 | 1.00 | 43.42 | D |
| ATOM | 5849 | C | LEU | D | 342 | 40.888 | 79.416 | 31.447 | 1.00 | 45.05 | D |
| ATOM | 5850 | O | LEU | D | 342 | 40.228 | 78.402 | 31.151 | 1.00 | 43.14 | D |
| ATOM | 5851 | N | LEU | D | 343 | 40.940 | 80.538 | 30.695 | 1.00 | 45.39 | D |
| ATOM | 5852 | CA | LED | D | 343 | 40.016 | 80.838 | 29.628 | 1.00 | 45.42 | D |
| ATOM | 5853 | CB | LEU | D | 343 | 40.167 | 82.278 | 29.111 | 1.00 | 46.54 | D |
| ATOM | 5854 | CG | LEU | D | 343 | 39.113 | 82.962 | 28.191 | 1.00 | 48.08 | D |
| ATOM | 5855 | CD1 | LEU | D | 343 | 37.840 | 82.136 | 28.122 | 1.00 | 48.00 | D |
| ATOM | 5856 | CD2 | LEU | D | 343 | 39.176 | 84.116 | 27.734 | 0.00 | 47.59 | D |
| ATOM | 5857 | C | LEU | D | 343 | 40.198 | 79.840 | 28.574 | 1.00 | 45.27 | D |
| ATOM | 5858 | O | LEU | D | 343 | 39.184 | 79.181 | 28.143 | 1.00 | 44.14 | D |
| ATOM | 5859 | N | ASP | D | 344 | 41.459 | 79.608 | 28.184 | 1.00 | 45.05 | D |
| ATOM | 5860 | CA | ASP | D | 344 | 41.672 | 78.677 | 27.107 | 1.00 | 45.25 | D |
| ATOM | 5861 | CB | ASP | D | 344 | 43.106 | 78.777 | 26.592 | 1.00 | 51.21 | D |
| ATOM | 5862 | CG | ASP | D | 344 | 44.089 | 79.388 | 27.603 | 1.00 | 57.87 | D |
| ATOM | 5863 | OD1 | ASP | D | 344 | 45.286 | 79.040 | 27.524 | 1.00 | 62.11 | D |
| ATOM | 5864 | OD2 | ASP | D | 344 | 43.699 | 80.228 | 28.446 | 1.00 | 60.98 | D |
| ATOM | 5865 | C | ASP | D | 344 | 41.470 | 77.262 | 27.505 | 1.00 | 42.38 | D |
| ATOM | 5866 | O | ASP | D | 344 | 41.116 | 76.420 | 26.683 | 1.00 | 42.15 | D |
| ATOM | 5867 | N | LEU | D | 345 | 41.755 | 76.919 | 28.766 | 1.00 | 39.56 | D |
| ATOM | 5868 | CA | LEU | D | 345 | 41.636 | 75.531 | 29.114 | 1.00 | 37.08 | D |
| ATOM | 5869 | CB | LEU | D | 345 | 42.442 | 75.309 | 30.430 | 1.00 | 35.16 | D |
| ATOM | 5870 | CG | LEU | D | 345 | 42.234 | 73.958 | 31.045 | 1.00 | 34.21 | D |
| ATOM | 5871 | CD1 | LEU | D | 345 | 42.478 | 72.819 | 30.052 | 1.00 | 30.45 | D |
| ATOM | 5872 | CD2 | LEU | D | 345 | 43.124 | 73.825 | 32.377 | 1.00 | 33.30 | D |
| ATOM | 5873 | C | LEU | D | 345 | 40.078 | 75.241 | 29.226 | 1.00 | 36.03 | D |
| ATOM | 5874 | O | LEU | D | 345 | 39.542 | 74.276 | 28.731 | 1.00 | 34.56 | D |
| ATOM | 5875 | N | ASN | D | 346 | 39.375 | 76.161 | 29.830 | 1.00 | 35.78 | D |
| ATOM | 5876 | CA | ASN | D | 346 | 37.920 | 76.081 | 29.991 | 1.00 | 37.13 | D |
| ATOM | 5877 | CB | ASN | D | 346 | 37.428 | 77.076 | 31.018 | 1.00 | 36.17 | D |
| ATOM | 5878 | CG | ASN | D | 346 | 37.711 | 76.563 | 32.476 | 1.00 | 36.25 | D |
| ATOM | 5879 | OD1 | ASN | D | 346 | 38.204 | 75.452 | 32.630 | 1.00 | 36.11 | D |
| ATOM | 5880 | ND2 | ASN | D | 346 | 37.412 | 77.347 | 33.484 | 1.00 | 35.67 | D |
| ATOM | 5881 | C | ASN | D | 346 | 37.173 | 76.056 | 28.656 | 1.00 | 38.04 | D |
| ATOM | 5882 | O | ASN | D | 346 | 36.260 | 75.245 | 28.515 | 1.00 | 38.73 | D |
| ATOM | 5883 | N | ASN | D | 347 | 37.783 | 76.666 | 27.609 | 1.00 | 38.79 | D |
| ATOM | 5884 | CA | ASN | D | 347 | 37.179 | 76.701 | 26.315 | 1.00 | 39.46 | D |
| ATOM | 5885 | CB | ASN | D | 347 | 37.829 | 77.713 | 25.342 | 1.00 | 41.14 | D |
| ATOM | 5886 | CG | ASN | D | 347 | 36.850 | 78.148 | 24.243 | 1.00 | 42.54 | D |
| ATOM | 5887 | OD1 | ASN | D | 347 | 36.665 | 79.390 | 23.751 | 0.00 | 42.50 | D |
| ATOM | 5888 | ND2 | ASN | D | 347 | 35.613 | 78.503 | 24.740 | 1.00 | 43.99 | D |
| ATOM | 5889 | C | ASN | D | 347 | 37.371 | 75.414 | 25.776 | 1.00 | 39.05 | D |
| ATOM | 5890 | O | ASN | D | 347 | 36.439 | 74.933 | 25.151 | 1.00 | 40.46 | D |
| ATOM | 5891 | N | ALA | D | 348 | 38.562 | 74.788 | 26.023 | 1.00 | 38.00 | D |
| ATOM | 5892 | CA | ALA | D | 348 | 38.749 | 73.488 | 25.465 | 1.00 | 36.94 | D |
| ATOM | 5893 | CB | ALA | D | 348 | 40.278 | 73.057 | 25.549 | 1.00 | 37.25 | D |
| ATOM | 5894 | C | ALA | D | 348 | 37.799 | 72.471 | 26.051 | 1.00 | 36.06 | D |
| ATOM | 5895 | O | ALA | D | 348 | 37.305 | 71.601 | 25.370 | 1.00 | 36.14 | D |
| ATOM | 5896 | N | ILE | D | 349 | 37.530 | 72.603 | 27.329 | 1.00 | 35.39 | D |
| ATOM | 5897 | CA | ILE | D | 349 | 36.651 | 71.642 | 27.999 | 1.00 | 34.75 | D |
| ATOM | 5898 | CB | ILE | D | 349 | 36.725 | 71.824 | 29.563 | 1.00 | 33.56 | D |
| ATOM | 5899 | CG2 | ILE | D | 349 | 35.602 | 71.001 | 30.152 | 1.00 | 32.60 | D |
| ATOM | 5900 | CG1 | ILE | D | 349 | 38.154 | 71.393 | 30.079 | 1.00 | 34.15 | D |
| ATOM | 5901 | CD1 | ILE | D | 349 | 38.542 | 71.821 | 31.477 | 1.00 | 32.54 | D |
| ATOM | 5902 | C | ILE | D | 349 | 35.166 | 71.778 | 27.483 | 1.00 | 35.01 | D |
| ATOM | 5903 | O | ILE | D | 349 | 34.480 | 70.804 | 27.308 | 1.00 | 34.61 | D |
| ATOM | 5904 | N | LEU | D | 350 | 34.780 | 72.994 | 27.165 | 1.00 | 35.16 | D |
| ATOM | 5905 | CA | LEU | D | 350 | 33.437 | 73.352 | 26.612 | 1.00 | 35.03 | D |
| ATOM | 5906 | CB | LEU | D | 350 | 33.242 | 74.889 | 26.540 | 1.00 | 35.01 | D |
| ATOM | 5907 | CG | LEU | D | 350 | 32.969 | 75.589 | 27.871 | 1.00 | 34.57 | D |
| ATOM | 5908 | CD1 | LEU | D | 350 | 33.043 | 77.136 | 27.699 | 1.00 | 35.28 | D |
| ATOM | 5909 | CD2 | LEU | D | 350 | 31.570 | 75.162 | 28.431 | 1.00 | 33.03 | D |
| ATOM | 5910 | C | LEU | D | 350 | 33.262 | 72.737 | 25.275 | 1.00 | 35.29 | D |
| ATOM | 5911 | O | LEU | D | 350 | 32.183 | 72.316 | 24.936 | 1.00 | 36.11 | D |
| ATOM | 5912 | N | GLN | D | 351 | 34.310 | 72.576 | 24.526 | 1.00 | 34.20 | D |
| ATOM | 5913 | CA | GLN | D | 351 | 34.167 | 71.825 | 23.273 | 1.00 | 35.77 | D |
| ATOM | 5914 | CB | GLN | D | 351 | 35.442 | 72.051 | 22.457 | 1.00 | 37.81 | D |
| ATOM | 5915 | CG | GLN | D | 351 | 35.654 | 71.145 | 21.237 | 1.00 | 41.30 | D |
| ATOM | 5916 | CD | GLN | D | 351 | 36.847 | 71.626 | 20.264 | 1.00 | 43.90 | D |
| ATOM | 5917 | OE1 | GLN | D | 351 | 37.260 | 70.871 | 19.350 | 1.00 | 43.70 | D |
| ATOM | 5918 | NE2 | GLN | D | 351 | 37.267 | 72.914 | 20.388 | 1.00 | 45.99 | D |
| ATOM | 5919 | C | GLN | D | 351 | 33.863 | 70.375 | 23.392 | 1.00 | 36.72 | D |
| ATOM | 5920 | O | GLN | D | 351 | 33.187 | 69.734 | 22.529 | 1.00 | 37.37 | D |
| ATOM | 5921 | N | LEU | D | 352 | 34.310 | 69.809 | 24.527 | 1.00 | 36.67 | D |

TABLE 2-continued

ATOMIC COORDINATES OF THE ERR3 LBD/DIETHYLSTILBESTROL COMPLEX

| ATOM | 5922 | CA | LEU | D | 352 | 34.039 | 68.403 | 24.796 | 1.00 | 35.86 | D |
|---|---|---|---|---|---|---|---|---|---|---|---|
| ATOM | 5923 | CB | LEU | D | 352 | 35.066 | 67.978 | 25.812 | 1.00 | 35.16 | D |
| ATOM | 5924 | CG | LEU | D | 352 | 35.259 | 66.576 | 26.087 | 1.00 | 36.03 | D |
| ATOM | 5925 | CD1 | LEU | D | 352 | 35.489 | 65.627 | 24.906 | 1.00 | 35.36 | D |
| ATOM | 5926 | CD2 | LEU | D | 352 | 36.424 | 66.539 | 27.106 | 1.00 | 35.79 | D |
| ATOM | 5927 | C | LEU | D | 352 | 32.580 | 68.354 | 25.223 | 1.00 | 36.32 | D |
| ATOM | 5928 | O | LEU | D | 352 | 31.824 | 67.460 | 24.853 | 1.00 | 36.14 | D |
| ATOM | 5929 | N | VAL | D | 353 | 32.180 | 69.378 | 25.962 | 1.00 | 35.59 | D |
| ATOM | 5930 | CA | VAL | D | 353 | 30.834 | 69.536 | 26.411 | 1.00 | 37.38 | D |
| ATOM | 5931 | CB | VAL | D | 353 | 30.729 | 70.701 | 27.340 | 1.00 | 36.33 | D |
| ATOM | 5932 | CG1 | VAL | D | 353 | 29.225 | 70.976 | 27.589 | 1.00 | 36.84 | D |
| ATOM | 5933 | CG2 | VAL | D | 353 | 31.371 | 70.397 | 28.598 | 1.00 | 36.07 | D |
| ATOM | 5934 | C | VAL | D | 353 | 29.811 | 69.716 | 25.217 | 1.00 | 38.88 | D |
| ATOM | 5935 | O | VAL | D | 353 | 28.782 | 69.013 | 25.170 | 1.00 | 38.88 | D |
| ATOM | 5936 | N | LYS | D | 354 | 30.191 | 70.480 | 24.191 | 1.00 | 39.43 | D |
| ATOM | 5937 | CA | LYS | D | 354 | 29.331 | 70.693 | 23.045 | 1.00 | 42.08 | D |
| ATOM | 5938 | CB | LYS | D | 354 | 29.754 | 71.881 | 22.186 | 1.00 | 45.02 | D |
| ATOM | 5939 | CG | LYS | D | 354 | 29.636 | 73.246 | 22.861 | 1.00 | 51.44 | D |
| ATOM | 5940 | CD | LYS | D | 354 | 28.228 | 73.844 | 22.763 | 1.00 | 56.24 | D |
| ATOM | 5941 | CE | LYS | D | 354 | 27.208 | 73.113 | 23.630 | 1.00 | 58.41 | D |
| ATOM | 5942 | NZ | LYS | D | 354 | 27.635 | 73.062 | 25.054 | 1.00 | 62.56 | D |
| ATOM | 5943 | C | LYS | D | 354 | 29.193 | 69.397 | 22.280 | 1.00 | 41.12 | D |
| ATOM | 5944 | O | LYS | D | 354 | 28.054 | 69.051 | 21.897 | 1.00 | 39.73 | D |
| ATOM | 5945 | N | LYS | D | 355 | 30.258 | 68.595 | 22.147 | 1.00 | 40.32 | D |
| ATOM | 5946 | CA | LYS | D | 355 | 30.107 | 67.330 | 21.432 | 1.00 | 40.67 | D |
| ATOM | 5947 | CB | LYS | D | 355 | 31.464 | 66.701 | 21.022 | 1.00 | 41.40 | D |
| ATOM | 5948 | CG | LYS | D | 355 | 31.192 | 65.420 | 20.210 | 1.00 | 42.62 | D |
| ATOM | 5949 | CD | LYS | D | 355 | 32.451 | 64.843 | 19.409 | 1.00 | 44.47 | D |
| ATOM | 5950 | CE | LYS | D | 355 | 33.899 | 65.448 | 19.912 | 1.00 | 43.80 | D |
| ATOM | 5951 | NZ | LYS | D | 355 | 35.089 | 64.521 | 19.662 | 1.00 | 40.58 | D |
| ATOM | 5952 | C | LYS | D | 355 | 29.139 | 66.263 | 22.148 | 1.00 | 40.23 | D |
| ATOM | 5953 | O | LYS | D | 355 | 28.304 | 65.641 | 21.555 | 1.00 | 38.85 | D |
| ATOM | 5954 | N | TYR | D | 356 | 29.276 | 66.107 | 23.459 | 1.00 | 39.84 | D |
| ATOM | 5955 | CA | TYR | D | 356 | 28.351 | 65.268 | 24.202 | 1.00 | 38.96 | D |
| ATOM | 5956 | CB | TYR | D | 356 | 28.878 | 65.061 | 25.625 | 1.00 | 37.29 | D |
| ATOM | 5957 | CG | TYR | D | 356 | 30.085 | 64.157 | 25.643 | 1.00 | 35.17 | D |
| ATOM | 5958 | CD1 | TYR | D | 356 | 30.047 | 62.943 | 24.986 | 1.00 | 32.51 | D |
| ATOM | 5959 | CE1 | TYR | D | 356 | 31.112 | 62.072 | 25.084 | 1.00 | 34.58 | D |
| ATOM | 5960 | CD2 | TYR | D | 356 | 31.200 | 64.469 | 26.363 | 1.00 | 33.87 | D |
| ATOM | 5961 | CE2 | TYR | D | 356 | 32.299 | 63.617 | 26.432 | 1.00 | 34.88 | D |
| ATOM | 5962 | CZ | TYR | D | 356 | 32.267 | 62.424 | 25.759 | 1.00 | 34.63 | D |
| ATOM | 5963 | OH | TYR | D | 356 | 33.340 | 61.543 | 25.821 | 1.00 | 34.31 | D |
| ATOM | 5964 | C | TYR | D | 356 | 26.879 | 65.773 | 24.196 | 1.00 | 39.71 | D |
| ATOM | 5965 | O | TYR | D | 356 | 25.923 | 64.964 | 24.185 | 1.00 | 39.03 | D |
| ATOM | 5966 | N | LYS | D | 357 | 26.748 | 67.073 | 24.316 | 1.00 | 40.51 | D |
| ATOM | 5967 | CA | LYS | D | 357 | 25.515 | 67.773 | 24.109 | 1.00 | 41.77 | D |
| ATOM | 5968 | CB | LYS | D | 357 | 25.681 | 69.253 | 24.184 | 1.00 | 41.97 | D |
| ATOM | 5969 | CG | LYS | D | 357 | 24.987 | 69.850 | 25.455 | 1.00 | 42.49 | D |
| ATOM | 5970 | CD | LYS | D | 357 | 25.316 | 71.360 | 25.653 | 1.00 | 42.04 | D |
| ATOM | 5971 | CE | LYS | D | 357 | 24.122 | 72.279 | 25.823 | 1.00 | 43.47 | D |
| ATOM | 5972 | NZ | LYS | D | 357 | 24.692 | 73.606 | 26.261 | 1.00 | 44.47 | D |
| ATOM | 5973 | C | LYS | D | 357 | 24.816 | 67.443 | 22.815 | 1.00 | 42.17 | D |
| ATOM | 5974 | O | LYS | D | 357 | 23.658 | 67.028 | 22.837 | 1.00 | 42.21 | D |
| ATOM | 5975 | N | SER | D | 358 | 25.518 | 67.529 | 21.718 | 1.00 | 42.31 | D |
| ATOM | 5976 | CA | SER | D | 358 | 24.872 | 67.298 | 20.466 | 1.00 | 42.84 | D |
| ATOM | 5977 | CB | SER | D | 358 | 25.821 | 67.664 | 19.278 | 1.00 | 43.96 | D |
| ATOM | 5978 | OG | SER | D | 358 | 27.004 | 66.884 | 19.312 | 1.00 | 49.80 | D |
| ATOM | 5979 | C | SER | D | 358 | 24.476 | 65.812 | 20.447 | 1.00 | 43.38 | D |
| ATOM | 5980 | O | SER | D | 358 | 23.595 | 65.389 | 19.648 | 1.00 | 44.29 | D |
| ATOM | 5981 | N | MET | D | 359 | 25.155 | 64.984 | 21.225 | 1.00 | 42.00 | D |
| ATOM | 5982 | CA | MET | D | 359 | 24.846 | 63.600 | 21.201 | 1.00 | 42.42 | D |
| ATOM | 5983 | CB | MET | D | 359 | 26.139 | 62.751 | 21.428 | 1.00 | 44.28 | D |
| ATOM | 5984 | CG | MET | D | 359 | 26.847 | 62.204 | 20.184 | 1.00 | 45.13 | D |
| ATOM | 5985 | SD | MET | D | 359 | 28.577 | 61.490 | 20.672 | 1.00 | 50.85 | D |
| ATOM | 5986 | CE | MET | D | 359 | 29.225 | 62.849 | 21.044 | 1.00 | 45.51 | D |
| ATOM | 5987 | C | MET | D | 359 | 23.763 | 63.189 | 22.201 | 1.00 | 41.63 | D |
| ATOM | 5988 | O | MET | D | 359 | 23.263 | 62.043 | 22.055 | 1.00 | 42.58 | D |
| ATOM | 5989 | N | LYS | D | 360 | 23.395 | 64.051 | 23.138 | 1.00 | 40.03 | D |
| ATOM | 5990 | CA | LYS | D | 360 | 22.478 | 63.738 | 24.261 | 1.00 | 40.98 | D |
| ATOM | 5991 | CB | LYS | D | 360 | 21.037 | 63.504 | 23.822 | 1.00 | 40.97 | D |
| ATOM | 5992 | CG | LYS | D | 360 | 20.548 | 64.604 | 22.737 | 1.00 | 43.05 | D |
| ATOM | 5993 | CD | LYS | D | 360 | 19.225 | 64.243 | 21.954 | 1.00 | 44.62 | D |
| ATOM | 5994 | CE | LYS | D | 360 | 19.516 | 63.442 | 20.579 | 1.00 | 46.28 | D |
| ATOM | 5995 | NZ | LYS | D | 360 | 19.522 | 61.970 | 20.692 | 0.00 | 45.59 | D |
| ATOM | 5996 | C | LYS | D | 360 | 22.985 | 62.538 | 25.045 | 1.00 | 40.61 | D |
| ATOM | 5997 | O | LYS | D | 360 | 22.324 | 61.524 | 25.239 | 1.00 | 39.79 | D |

TABLE 2-continued

ATOMIC COORDINATES OF THE ERR3 LBD/ DIETHYLSTILBESTROL COMPLEX

| ATOM | 5998 | N | LEU | D | 361 | 24.223 | 62.697 | 25.475 | 1.00 | 40.12 | D |
|---|---|---|---|---|---|---|---|---|---|---|---|
| ATOM | 5999 | CA | LEU | D | 361 | 24.901 | 61.777 | 26.323 | 1.00 | 39.53 | D |
| ATOM | 6000 | CB | LEU | D | 361 | 26.232 | 62.393 | 26.862 | 1.00 | 38.28 | D |
| ATOM | 6001 | CG | LEU | D | 361 | 27.017 | 61.366 | 27.684 | 1.00 | 36.98 | D |
| ATOM | 6002 | CD1 | LEU | D | 361 | 27.440 | 60.227 | 26.766 | 1.00 | 35.83 | D |
| ATOM | 6003 | CD2 | LEU | D | 361 | 28.111 | 62.043 | 28.301 | 1.00 | 37.59 | D |
| ATOM | 6004 | C | LEU | D | 361 | 23.985 | 61.427 | 27.492 | 1.00 | 39.55 | D |
| ATOM | 6005 | O | LEU | D | 361 | 23.600 | 62.272 | 28.196 | 1.00 | 39.70 | D |
| ATOM | 6006 | N | GLU | D | 362 | 23.735 | 60.161 | 27.736 | 1.00 | 39.06 | D |
| ATOM | 6007 | CA | GLU | D | 362 | 22.998 | 59.753 | 28.968 | 1.00 | 39.60 | D |
| ATOM | 6008 | CB | GLU | D | 362 | 22.054 | 58.611 | 28.605 | 1.00 | 39.71 | D |
| ATOM | 6009 | CG | GLU | D | 362 | 21.101 | 58.950 | 27.434 | 1.00 | 42.34 | D |
| ATOM | 6010 | CD | GLU | D | 362 | 20.664 | 57.776 | 26.621 | 1.00 | 45.60 | D |
| ATOM | 6011 | OE1 | GLU | D | 362 | 21.009 | 56.637 | 26.950 | 1.00 | 47.20 | D |
| ATOM | 6012 | OE2 | GLU | D | 362 | 19.901 | 57.989 | 25.633 | 1.00 | 49.12 | D |
| ATOM | 6013 | C | GLU | D | 362 | 23.982 | 59.302 | 30.117 | 1.00 | 39.55 | D |
| ATOM | 6014 | O | GLU | D | 362 | 25.205 | 58.994 | 29.876 | 1.00 | 38.79 | D |
| ATOM | 6015 | N | LYS | D | 363 | 23.430 | 59.261 | 31.321 | 1.00 | 40.02 | D |
| ATOM | 6016 | CA | LYS | D | 363 | 24.105 | 58.907 | 32.555 | 1.00 | 40.99 | D |
| ATOM | 6017 | CB | LYS | D | 363 | 23.154 | 58.976 | 33.730 | 1.00 | 41.54 | D |
| ATOM | 6018 | CG | LYS | D | 363 | 23.855 | 59.395 | 35.046 | 1.00 | 44.09 | D |
| ATOM | 6019 | CD | LYS | D | 363 | 23.213 | 58.701 | 36.213 | 1.00 | 46.04 | D |
| ATOM | 6020 | CE | LYS | D | 363 | 23.502 | 59.472 | 37.502 | 1.00 | 48.68 | D |
| ATOM | 6021 | NZ | LYS | D | 363 | 23.271 | 58.618 | 38.732 | 1.00 | 49.64 | D |
| ATOM | 6022 | C | LYS | D | 363 | 24.668 | 57.500 | 32.390 | 1.00 | 41.06 | D |
| ATOM | 6023 | O | LYS | D | 363 | 25.763 | 57.236 | 32.780 | 1.00 | 40.83 | D |
| ATOM | 6024 | N | GLU | D | 364 | 23.964 | 56.663 | 31.669 | 1.00 | 40.47 | D |
| ATOM | 6025 | CA | GLU | D | 364 | 24.418 | 55.286 | 31.491 | 1.00 | 41.42 | D |
| ATOM | 6026 | CB | GLU | D | 364 | 23.333 | 54.486 | 30.778 | 1.00 | 42.00 | D |
| ATOM | 6027 | CG | GLU | D | 364 | 22.069 | 54.047 | 31.608 | 1.00 | 43.20 | D |
| ATOM | 6028 | CD | GLU | D | 364 | 20.964 | 55.105 | 31.763 | 1.00 | 44.15 | D |
| ATOM | 6029 | OE1 | GLU | D | 364 | 21.088 | 56.242 | 31.231 | 1.00 | 43.56 | D |
| ATOM | 6030 | OE2 | GLU | D | 364 | 20.050 | 54.843 | 32.583 | 1.00 | 44.68 | D |
| ATOM | 6031 | C | GLU | D | 364 | 25.751 | 55.291 | 30.638 | 1.00 | 41.88 | D |
| ATOM | 6032 | O | GLU | D | 364 | 26.738 | 54.530 | 30.873 | 1.00 | 42.01 | D |
| ATOM | 6033 | N | GLU | D | 365 | 25.724 | 56.100 | 29.572 | 1.00 | 40.30 | D |
| ATOM | 6034 | CA | GLU | D | 365 | 26.800 | 56.186 | 28.662 | 1.00 | 37.85 | D |
| ATOM | 6035 | CB | GLU | D | 365 | 26.336 | 56.936 | 27.437 | 1.00 | 37.84 | D |
| ATOM | 6036 | CG | GLU | D | 365 | 25.352 | 56.179 | 26.600 | 1.00 | 39.19 | D |
| ATOM | 6037 | CD | GLU | D | 365 | 24.680 | 56.971 | 25.513 | 1.00 | 39.99 | D |
| ATOM | 6038 | OE1 | GLU | D | 365 | 24.494 | 58.209 | 25.684 | 1.00 | 39.28 | D |
| ATOM | 6039 | OE2 | GLU | D | 365 | 24.339 | 56.312 | 24.456 | 1.00 | 41.42 | D |
| ATOM | 6040 | C | GLU | D | 365 | 27.990 | 56.940 | 29.379 | 1.00 | 36.36 | D |
| ATOM | 6041 | O | GLU | D | 365 | 29.097 | 56.533 | 29.268 | 1.00 | 35.51 | D |
| ATOM | 6042 | N | PHE | D | 366 | 27.716 | 58.004 | 30.086 | 1.00 | 34.67 | D |
| ATOM | 6043 | CA | PHE | D | 366 | 28.665 | 58.661 | 30.896 | 1.00 | 34.73 | D |
| ATOM | 6044 | CB | PHE | D | 366 | 28.018 | 59.714 | 31.715 | 1.00 | 31.09 | D |
| ATOM | 6045 | CG | PHE | D | 366 | 28.829 | 60.183 | 32.870 | 1.00 | 31.75 | D |
| ATOM | 6046 | CD1 | PHE | D | 366 | 29.983 | 60.916 | 32.659 | 1.00 | 31.40 | D |
| ATOM | 6047 | CD2 | PHE | D | 366 | 28.358 | 60.093 | 34.176 | 1.00 | 29.74 | D |
| ATOM | 6048 | CE1 | PHE | D | 366 | 30.695 | 61.465 | 33.714 | 1.00 | 30.88 | D |
| ATOM | 6049 | CE2 | PHE | D | 366 | 29.045 | 60.684 | 35.247 | 1.00 | 31.33 | D |
| ATOM | 6050 | CZ | PHE | D | 366 | 30.248 | 61.359 | 34.997 | 1.00 | 31.45 | D |
| ATOM | 6051 | C | PHE | D | 366 | 29.460 | 57.678 | 31.826 | 1.00 | 35.51 | D |
| ATOM | 6052 | O | PHE | D | 366 | 30.774 | 57.608 | 31.724 | 1.00 | 36.56 | D |
| ATOM | 6053 | N | VAL | D | 367 | 28.741 | 56.858 | 32.635 | 1.00 | 35.69 | D |
| ATOM | 6054 | CA | VAL | D | 367 | 29.449 | 56.087 | 33.675 | 1.00 | 34.02 | D |
| ATOM | 6055 | CB | VAL | D | 367 | 28.622 | 55.527 | 34.786 | 1.00 | 33.85 | D |
| ATOM | 6056 | CG1 | VAL | D | 367 | 27.930 | 56.619 | 35.563 | 1.00 | 33.93 | D |
| ATOM | 6057 | CG2 | VAL | D | 367 | 27.614 | 54.522 | 34.301 | 1.00 | 33.76 | D |
| ATOM | 6058 | C | VAL | D | 367 | 30.218 | 55.044 | 32.941 | 1.00 | 35.41 | D |
| ATOM | 6059 | O | VAL | D | 367 | 31.367 | 54.686 | 33.304 | 1.00 | 36.83 | D |
| ATOM | 6060 | N | THR | D | 368 | 29.692 | 54.579 | 31.843 | 1.00 | 35.05 | D |
| ATOM | 6061 | CA | THR | D | 368 | 30.448 | 53.579 | 31.173 | 1.00 | 35.39 | D |
| ATOM | 6062 | CB | THR | D | 368 | 29.560 | 52.895 | 30.134 | 1.00 | 34.18 | D |
| ATOM | 6063 | OG1 | THR | D | 368 | 28.553 | 52.218 | 30.815 | 1.00 | 33.22 | D |
| ATOM | 6064 | CG2 | THR | D | 368 | 30.258 | 51.877 | 29.452 | 1.00 | 34.34 | D |
| ATOM | 6065 | C | THR | D | 368 | 31.804 | 54.176 | 30.559 | 1.00 | 36.06 | D |
| ATOM | 6066 | O | THR | D | 368 | 32.881 | 53.491 | 30.499 | 1.00 | 35.94 | D |
| ATOM | 6067 | N | LEU | D | 369 | 31.708 | 55.397 | 30.063 | 1.00 | 35.07 | D |
| ATOM | 6068 | CA | LEU | D | 369 | 32.876 | 55.967 | 29.396 | 1.00 | 34.70 | D |
| ATOM | 6069 | CB | LEU | D | 369 | 32.526 | 57.184 | 28.551 | 1.00 | 33.77 | D |
| ATOM | 6070 | CG | LEU | D | 369 | 31.990 | 56.928 | 27.130 | 1.00 | 33.99 | D |
| ATOM | 6071 | CD1 | LEU | D | 369 | 31.583 | 58.284 | 26.514 | 1.00 | 35.81 | D |
| ATOM | 6072 | CD2 | LEU | D | 369 | 32.980 | 56.305 | 26.194 | 1.00 | 34.75 | D |
| ATOM | 6073 | C | LEU | D | 369 | 33.931 | 56.267 | 30.393 | 1.00 | 34.36 | D |

TABLE 2-continued

ATOMIC COORDINATES OF THE ERR3 LBD/
DIETHYLSTILBESTROL COMPLEX

| ATOM | 6074 | O | LEU | D | 369 | 35.091 | 56.199 | 30.100 | 1.00 | 34.85 | D |
|---|---|---|---|---|---|---|---|---|---|---|---|
| ATOM | 6075 | N | LYS | D | 370 | 33.521 | 56.646 | 31.565 | 1.00 | 34.29 | D |
| ATOM | 6076 | CA | LYS | D | 370 | 34.453 | 56.991 | 32.647 | 1.00 | 33.19 | D |
| ATOM | 6077 | CB | LYS | D | 370 | 33.601 | 57.453 | 33.767 | 1.00 | 33.14 | D |
| ATOM | 6078 | CG | LYS | D | 370 | 34.166 | 58.397 | 34.599 | 1.00 | 33.02 | D |
| ATOM | 6079 | CD | LYS | D | 370 | 33.278 | 59.271 | 35.404 | 1.00 | 30.41 | D |
| ATOM | 6080 | CE | LYS | D | 370 | 32.228 | 58.517 | 36.125 | 1.00 | 29.92 | D |
| ATOM | 6081 | NZ | LYS | D | 370 | 31.755 | 59.145 | 37.288 | 1.00 | 31.26 | D |
| ATOM | 6082 | C | LYS | D | 370 | 35.249 | 55.699 | 32.959 | 1.00 | 33.11 | D |
| ATOM | 6083 | O | LYS | D | 370 | 36.464 | 55.729 | 33.103 | 1.00 | 33.12 | D |
| ATOM | 6084 | N | ALA | D | 371 | 34.581 | 54.543 | 32.951 | 1.00 | 32.18 | D |
| ATOM | 6085 | CA | ALA | D | 371 | 35.247 | 53.255 | 33.211 | 1.00 | 32.39 | D |
| ATOM | 6086 | CB | ALA | D | 371 | 34.216 | 52.146 | 33.483 | 1.00 | 30.61 | D |
| ATOM | 6087 | C | ALA | D | 371 | 36.127 | 52.849 | 32.113 | 1.00 | 30.83 | D |
| ATOM | 6088 | O | ALA | D | 371 | 37.263 | 52.496 | 32.327 | 1.00 | 30.10 | D |
| ATOM | 6089 | N | ILE | D | 372 | 35.606 | 52.966 | 30.900 | 1.00 | 31.26 | D |
| ATOM | 6090 | CA | ILE | D | 372 | 36.414 | 52.688 | 29.700 | 1.00 | 30.47 | D |
| ATOM | 6091 | CB | ILE | D | 372 | 35.562 | 52.876 | 28.461 | 1.00 | 31.04 | D |
| ATOM | 6092 | CG2 | ILE | D | 372 | 36.377 | 52.737 | 27.184 | 1.00 | 28.67 | D |
| ATOM | 6093 | CG1 | ILE | D | 372 | 34.511 | 51.813 | 28.352 | 1.00 | 30.92 | D |
| ATOM | 6094 | CD1 | ILE | D | 372 | 33.675 | 51.853 | 27.096 | 1.00 | 27.17 | D |
| ATOM | 6095 | C | ILE | D | 372 | 37.717 | 53.588 | 29.684 | 1.00 | 29.98 | D |
| ATOM | 6096 | O | ILE | D | 372 | 38.774 | 53.088 | 29.390 | 1.00 | 29.48 | D |
| ATOM | 6097 | N | ALA | D | 373 | 37.589 | 54.871 | 30.012 | 1.00 | 29.51 | D |
| ATOM | 6098 | CA | ALA | D | 373 | 38.718 | 55.804 | 30.141 | 1.00 | 29.98 | D |
| ATOM | 6099 | CB | ALA | D | 373 | 38.268 | 57.333 | 30.476 | 1.00 | 27.97 | D |
| ATOM | 6100 | C | ALA | D | 373 | 39.744 | 55.306 | 31.150 | 1.00 | 29.85 | D |
| ATOM | 6101 | O | ALA | D | 373 | 40.941 | 55.221 | 30.805 | 1.00 | 29.99 | D |
| ATOM | 6102 | N | LEU | D | 374 | 39.306 | 54.842 | 32.315 | 1.00 | 29.39 | D |
| ATOM | 6103 | CA | LEU | D | 374 | 40.270 | 54.300 | 33.297 | 1.00 | 29.50 | D |
| ATOM | 6104 | CB | LEU | D | 374 | 39.569 | 53.839 | 34.576 | 1.00 | 29.34 | D |
| ATOM | 6105 | CG | LEU | D | 374 | 40.449 | 53.463 | 35.739 | 1.00 | 31.06 | D |
| ATOM | 6106 | CD1 | LEU | D | 374 | 41.534 | 54.571 | 36.024 | 1.00 | 27.32 | D |
| ATOM | 6107 | CD2 | LEU | D | 374 | 39.641 | 53.257 | 36.886 | 1.00 | 31.94 | D |
| ATOM | 6108 | C | LEU | D | 374 | 40.981 | 53.169 | 32.652 | 1.00 | 29.46 | D |
| ATOM | 6109 | O | LEU | D | 374 | 42.239 | 53.152 | 32.540 | 1.00 | 29.01 | D |
| ATOM | 6110 | N | ALA | D | 375 | 40.178 | 52.257 | 32.140 | 1.00 | 30.35 | D |
| ATOM | 6111 | CA | ALA | D | 375 | 40.700 | 50.966 | 31.619 | 1.00 | 30.92 | D |
| ATOM | 6112 | CB | ALA | D | 375 | 39.554 | 49.982 | 31.361 | 1.00 | 30.24 | D |
| ATOM | 6113 | C | ALA | D | 375 | 41.521 | 51.115 | 30.372 | 1.00 | 31.43 | D |
| ATOM | 6114 | O | ALA | D | 375 | 42.403 | 50.288 | 30.114 | 1.00 | 31.39 | D |
| ATOM | 6115 | N | ASN | D | 376 | 41.259 | 52.168 | 29.598 | 1.00 | 31.49 | D |
| ATOM | 6116 | CA | ASN | D | 376 | 41.906 | 52.379 | 28.278 | 1.00 | 31.80 | D |
| ATOM | 6117 | CB | ASN | D | 376 | 40.824 | 52.743 | 27.196 | 1.00 | 31.27 | D |
| ATOM | 6118 | CG | ASN | D | 376 | 41.356 | 52.732 | 25.770 | 1.00 | 32.55 | D |
| ATOM | 6119 | OD1 | ASN | D | 376 | 42.103 | 51.852 | 25.411 | 1.00 | 33.34 | D |
| ATOM | 6120 | ND2 | ASN | D | 376 | 41.032 | 53.736 | 24.976 | 1.00 | 32.85 | D |
| ATOM | 6121 | C | ASN | D | 376 | 42.898 | 53.447 | 28.425 | 1.00 | 32.29 | D |
| ATOM | 6122 | O | ASN | D | 376 | 43.248 | 54.115 | 27.444 | 1.00 | 33.05 | D |
| ATOM | 6123 | N | SER | D | 377 | 43.491 | 53.593 | 29.623 | 1.00 | 33.09 | D |
| ATOM | 6124 | CA | SER | D | 377 | 44.242 | 54.821 | 29.822 | 1.00 | 32.95 | D |
| ATOM | 6125 | CB | SER | D | 377 | 44.277 | 55.175 | 31.304 | 1.00 | 33.52 | D |
| ATOM | 6126 | OG | SER | D | 377 | 45.034 | 54.123 | 31.937 | 1.00 | 36.38 | D |
| ATOM | 6127 | C | SER | D | 377 | 45.644 | 54.730 | 29.219 | 1.00 | 31.98 | D |
| ATOM | 6128 | O | SER | D | 377 | 46.365 | 55.715 | 29.248 | 1.00 | 31.06 | D |
| ATOM | 6129 | N | ASP | D | 378 | 46.056 | 53.570 | 28.699 | 1.00 | 32.10 | D |
| ATOM | 6130 | CA | ASP | D | 378 | 47.423 | 53.412 | 28.052 | 1.00 | 32.27 | D |
| ATOM | 6131 | CB | ASP | D | 378 | 47.551 | 54.314 | 26.806 | 1.00 | 31.42 | D |
| ATOM | 6132 | CG | ASP | D | 378 | 46.522 | 53.962 | 25.692 | 1.00 | 31.23 | D |
| ATOM | 6133 | OD1 | ASP | D | 378 | 46.507 | 52.800 | 25.379 | 1.00 | 32.03 | D |
| ATOM | 6134 | OD2 | ASP | D | 378 | 45.617 | 54.753 | 25.180 | 1.00 | 29.40 | D |
| ATOM | 6135 | C | ASP | D | 378 | 48.667 | 53.668 | 28.924 | 1.00 | 33.01 | D |
| ATOM | 6136 | O | ASP | D | 378 | 49.739 | 54.131 | 28.450 | 1.00 | 32.32 | D |
| ATOM | 6137 | N | SER | D | 379 | 48.598 | 53.359 | 30.220 | 1.00 | 33.60 | D |
| ATOM | 6138 | CA | SER | D | 379 | 49.781 | 53.498 | 31.047 | 1.00 | 34.71 | D |
| ATOM | 6139 | CB | SER | D | 379 | 49.530 | 52.926 | 32.447 | 1.00 | 34.89 | D |
| ATOM | 6140 | OG | SER | D | 379 | 50.767 | 52.892 | 33.233 | 1.00 | 33.28 | D |
| ATOM | 6141 | C | SER | D | 379 | 50.889 | 52.631 | 30.419 | 1.00 | 36.04 | D |
| ATOM | 6142 | O | SER | D | 379 | 50.656 | 51.545 | 30.035 | 1.00 | 32.47 | D |
| ATOM | 6143 | N | MET | D | 380 | 52.106 | 53.078 | 30.463 | 1.00 | 40.25 | D |
| ATOM | 6144 | CA | MET | D | 380 | 53.198 | 52.219 | 30.014 | 1.00 | 45.10 | D |
| ATOM | 6145 | CB | MET | D | 380 | 54.346 | 53.067 | 29.481 | 1.00 | 50.66 | D |
| ATOM | 6146 | CG | MET | D | 380 | 55.089 | 53.856 | 30.576 | 1.00 | 59.87 | D |
| ATOM | 6147 | SD | MET | D | 380 | 54.025 | 54.983 | 31.503 | 1.00 | 71.28 | D |
| ATOM | 6148 | CE | MET | D | 380 | 54.046 | 56.429 | 30.449 | 1.00 | 69.74 | D |
| ATOM | 6149 | C | MET | D | 380 | 53.713 | 51.232 | 31.104 | 1.00 | 44.45 | D |

TABLE 2-continued

ATOMIC COORDINATES OF THE ERR3 LBD/ DIETHYLSTILBESTROL COMPLEX

| ATOM | 6150 | O | MET | D | 380 | 54.673 | 50.509 | 30.879 | 1.00 | 43.63 | D |
| --- | --- | --- | --- | --- | --- | --- | --- | --- | --- | --- | --- |
| ATOM | 6151 | N | HIS | D | 381 | 53.051 | 51.155 | 32.244 | 1.00 | 43.84 | D |
| ATOM | 6152 | CA | HIS | D | 381 | 53.634 | 50.372 | 33.319 | 1.00 | 43.95 | D |
| ATOM | 6153 | CB | HIS | D | 381 | 53.858 | 51.231 | 34.546 | 1.00 | 44.40 | D |
| ATOM | 6154 | CG | HIS | D | 381 | 54.584 | 52.472 | 34.285 | 1.00 | 46.81 | D |
| ATOM | 6155 | CD2 | HIS | D | 381 | 54.270 | 53.757 | 34.577 | 1.00 | 48.35 | D |
| ATOM | 6156 | ND1 | HIS | D | 381 | 55.826 | 52.501 | 33.691 | 1.00 | 48.53 | D |
| ATOM | 6157 | CE1 | HIS | D | 381 | 56.202 | 53.756 | 33.558 | 1.00 | 47.88 | D |
| ATOM | 6158 | NE2 | HIS | D | 381 | 55.281 | 54.535 | 34.109 | 1.00 | 48.12 | D |
| ATOM | 6159 | C | HIS | D | 381 | 52.837 | 49.223 | 33.768 | 1.00 | 43.24 | D |
| ATOM | 6160 | O | HIS | D | 381 | 53.048 | 48.735 | 34.866 | 1.00 | 44.36 | D |
| ATOM | 6161 | N | ILE | D | 382 | 51.913 | 48.746 | 32.980 | 1.00 | 43.23 | D |
| ATOM | 6162 | CA | ILE | D | 382 | 51.050 | 47.679 | 33.430 | 1.00 | 41.87 | D |
| ATOM | 6163 | CB | ILE | D | 382 | 49.929 | 47.565 | 32.440 | 1.00 | 40.91 | D |
| ATOM | 6164 | CG2 | ILE | D | 382 | 49.060 | 46.291 | 32.678 | 1.00 | 37.94 | D |
| ATOM | 6165 | CG1 | ILE | D | 382 | 49.015 | 48.849 | 32.511 | 1.00 | 40.77 | D |
| ATOM | 6166 | CD1 | ILE | D | 382 | 48.576 | 49.290 | 33.454 | 0.00 | 40.74 | D |
| ATOM | 6167 | C | ILE | D | 382 | 51.814 | 46.351 | 33.578 | 1.00 | 42.44 | D |
| ATOM | 6168 | O | ILE | D | 382 | 52.676 | 46.030 | 32.747 | 1.00 | 42.25 | D |
| ATOM | 6169 | N | GLU | D | 383 | 51.434 | 45.517 | 34.550 | 1.00 | 42.44 | D |
| ATOM | 6170 | CA | GLU | D | 383 | 52.013 | 44.144 | 34.640 | 1.00 | 42.66 | D |
| ATOM | 6171 | CB | GLU | D | 383 | 52.166 | 43.726 | 36.117 | 1.00 | 42.23 | D |
| ATOM | 6172 | CG | GLU | D | 383 | 53.267 | 44.523 | 36.921 | 1.00 | 42.39 | D |
| ATOM | 6173 | CD | GLU | D | 383 | 52.973 | 44.724 | 38.506 | 1.00 | 43.49 | D |
| ATOM | 6174 | OE1 | GLU | D | 383 | 52.033 | 44.034 | 39.094 | 1.00 | 41.68 | D |
| ATOM | 6175 | OE2 | GLU | D | 383 | 53.668 | 45.588 | 39.158 | 1.00 | 43.22 | D |
| ATOM | 6176 | C | GLU | D | 383 | 51.191 | 43.110 | 33.881 | 1.00 | 42.53 | D |
| ATOM | 6177 | O | GLU | D | 383 | 51.670 | 42.353 | 33.038 | 1.00 | 43.41 | D |
| ATOM | 6178 | N | ASP | D | 384 | 49.931 | 43.054 | 34.242 | 1.00 | 41.69 | D |
| ATOM | 6179 | CA | ASP | D | 384 | 49.028 | 42.102 | 33.671 | 1.00 | 41.49 | D |
| ATOM | 6180 | CB | ASP | D | 384 | 48.125 | 41.563 | 34.779 | 1.00 | 41.11 | D |
| ATOM | 6181 | CG | ASP | D | 384 | 47.462 | 40.234 | 34.408 | 1.00 | 42.57 | D |
| ATOM | 6182 | OD1 | ASP | D | 384 | 47.339 | 39.961 | 33.182 | 1.00 | 42.89 | D |
| ATOM | 6183 | OD2 | ASP | D | 384 | 46.990 | 39.458 | 35.265 | 1.00 | 40.97 | D |
| ATOM | 6184 | C | ASP | D | 384 | 48.303 | 42.756 | 32.467 | 1.00 | 41.43 | D |
| ATOM | 6185 | O | ASP | D | 384 | 47.179 | 43.197 | 32.537 | 1.00 | 39.92 | D |
| ATOM | 6186 | N | VAL | D | 385 | 49.006 | 42.763 | 31.344 | 1.00 | 41.80 | D |
| ATOM | 6187 | CA | VAL | D | 385 | 48.476 | 43.354 | 30.156 | 1.00 | 43.44 | D |
| ATOM | 6188 | CB | VAL | D | 385 | 49.587 | 43.352 | 29.052 | 1.00 | 44.29 | D |
| ATOM | 6189 | CG1 | VAL | D | 385 | 48.996 | 43.466 | 27.610 | 1.00 | 45.02 | D |
| ATOM | 6190 | CG2 | VAL | D | 385 | 50.614 | 44.463 | 29.358 | 1.00 | 43.48 | D |
| ATOM | 6191 | C | VAL | D | 385 | 47.165 | 42.649 | 29.768 | 1.00 | 44.15 | D |
| ATOM | 6192 | O | VAL | D | 385 | 46.138 | 43.259 | 29.450 | 1.00 | 42.84 | D |
| ATOM | 6193 | N | GLU | D | 386 | 47.175 | 41.343 | 29.810 | 1.00 | 45.73 | D |
| ATOM | 6194 | CA | GLU | D | 386 | 45.987 | 40.563 | 29.423 | 1.00 | 47.43 | D |
| ATOM | 6195 | CB | GLU | D | 386 | 46.252 | 39.018 | 29.439 | 1.00 | 50.59 | D |
| ATOM | 6196 | CG | GLU | D | 386 | 47.196 | 38.507 | 28.352 | 1.00 | 58.10 | D |
| ATOM | 6197 | CD | GLU | D | 386 | 48.623 | 39.003 | 28.512 | 1.00 | 62.20 | D |
| ATOM | 6198 | OE1 | GLU | D | 386 | 48.870 | 40.209 | 28.303 | 1.00 | 65.57 | D |
| ATOM | 6199 | OE2 | GLU | D | 386 | 49.502 | 38.182 | 28.850 | 1.00 | 65.00 | D |
| ATOM | 6200 | C | GLU | D | 386 | 44.785 | 40.922 | 30.332 | 1.00 | 46.27 | D |
| ATOM | 6201 | O | GLU | D | 386 | 43.673 | 41.096 | 29.862 | 1.00 | 45.81 | D |
| ATOM | 6202 | N | ALA | D | 387 | 44.995 | 41.085 | 31.617 | 1.00 | 44.43 | D |
| ATOM | 6203 | CA | ALA | D | 387 | 43.807 | 41.332 | 32.426 | 1.00 | 43.84 | D |
| ATOM | 6204 | CB | ALA | D | 387 | 44.062 | 41.119 | 33.910 | 1.00 | 42.10 | D |
| ATOM | 6205 | C | ALA | D | 387 | 43.275 | 42.775 | 32.157 | 1.00 | 42.80 | D |
| ATOM | 6206 | O | ALA | D | 387 | 42.104 | 43.010 | 32.265 | 1.00 | 43.35 | D |
| ATOM | 6207 | N | VAL | D | 388 | 44.131 | 43.722 | 31.785 | 1.00 | 42.11 | D |
| ATOM | 6208 | CA | VAL | D | 388 | 43.658 | 45.067 | 31.554 | 1.00 | 41.50 | D |
| ATOM | 6209 | CB | VAL | D | 388 | 44.759 | 46.071 | 31.541 | 1.00 | 41.56 | D |
| ATOM | 6210 | CG1 | VAL | D | 388 | 44.218 | 47.443 | 31.085 | 1.00 | 40.10 | D |
| ATOM | 6211 | CG2 | VAL | D | 388 | 45.376 | 46.215 | 32.935 | 1.00 | 41.64 | D |
| ATOM | 6212 | C | VAL | D | 388 | 42.905 | 45.085 | 30.291 | 1.00 | 41.36 | D |
| ATOM | 6213 | O | VAL | D | 388 | 41.893 | 45.718 | 30.234 | 1.00 | 42.23 | D |
| ATOM | 6214 | N | GLN | D | 389 | 43.408 | 44.411 | 29.267 | 1.00 | 41.07 | D |
| ATOM | 6215 | CA | GLN | D | 389 | 42.623 | 44.128 | 28.014 | 1.00 | 41.76 | D |
| ATOM | 6216 | CB | GLN | D | 389 | 43.372 | 43.206 | 27.056 | 1.00 | 41.93 | D |
| ATOM | 6217 | CG | GLN | D | 389 | 42.950 | 43.129 | 25.704 | 0.00 | 46.30 | D |
| ATOM | 6218 | CD | GLN | D | 389 | 43.710 | 44.181 | 24.760 | 1.00 | 48.91 | D |
| ATOM | 6219 | OE1 | GLN | D | 389 | 44.712 | 44.450 | 25.416 | 1.00 | 51.53 | D |
| ATOM | 6220 | NE2 | GLN | D | 389 | 42.611 | 44.872 | 24.842 | 1.00 | 49.59 | D |
| ATOM | 6221 | C | GLN | D | 389 | 41.267 | 43.491 | 28.251 | 1.00 | 40.52 | D |
| ATOM | 6222 | O | GLN | D | 389 | 40.285 | 43.871 | 27.606 | 1.00 | 39.99 | D |
| ATOM | 6223 | N | LYS | D | 390 | 41.202 | 42.502 | 29.135 | 1.00 | 40.02 | D |
| ATOM | 6224 | CA | LYS | D | 390 | 39.949 | 41.867 | 29.376 | 1.00 | 39.52 | D |
| ATOM | 6225 | CB | LYS | D | 390 | 40.126 | 40.561 | 30.159 | 1.00 | 42.23 | D |

TABLE 2-continued

ATOMIC COORDINATES OF THE ERR3 LBD/
DIETHYLSTILBESTROL COMPLEX

| ATOM | 6226 | CG | LYS | D | 390 | 38.894 | 40.070 | 31.017 | 1.00 | 43.38 | D |
|---|---|---|---|---|---|---|---|---|---|---|---|
| ATOM | 6227 | CD | LYS | D | 390 | 37.774 | 39.496 | 30.092 | 1.00 | 48.03 | D |
| ATOM | 6228 | CE | LYS | D | 390 | 36.687 | 38.623 | 30.924 | 1.00 | 48.58 | D |
| ATOM | 6229 | NZ | LYS | D | 390 | 36.789 | 38.948 | 32.454 | 1.00 | 49.94 | D |
| ATOM | 6230 | C | LYS | D | 390 | 39.046 | 42.814 | 30.059 | 1.00 | 38.94 | D |
| ATOM | 6231 | O | LYS | D | 390 | 37.847 | 42.910 | 29.748 | 1.00 | 38.47 | D |
| ATOM | 6232 | N | LEU | D | 391 | 39.616 | 43.626 | 30.944 | 1.00 | 37.99 | D |
| ATOM | 6233 | CA | LEU | D | 391 | 38.822 | 44.652 | 31.574 | 1.00 | 37.81 | D |
| ATOM | 6234 | CB | LEU | D | 391 | 39.656 | 45.319 | 32.717 | 1.00 | 37.16 | D |
| ATOM | 6235 | CG | LEU | D | 391 | 39.098 | 46.668 | 33.241 | 1.00 | 37.97 | D |
| ATOM | 6236 | CD1 | LEU | D | 391 | 37.833 | 46.404 | 34.030 | 1.00 | 39.01 | D |
| ATOM | 6237 | CD2 | LEU | D | 391 | 40.009 | 47.456 | 34.085 | 1.00 | 35.25 | D |
| ATOM | 6238 | C | LEU | D | 391 | 38.278 | 45.679 | 30.529 | 1.00 | 37.55 | D |
| ATOM | 6239 | O | LEU | D | 391 | 37.127 | 46.075 | 30.603 | 1.00 | 37.27 | D |
| ATOM | 6240 | N | GLN | D | 392 | 39.076 | 46.076 | 29.546 | 1.00 | 37.67 | D |
| ATOM | 6241 | CA | GLN | D | 392 | 38.573 | 46.950 | 28.494 | 1.00 | 37.90 | D |
| ATOM | 6242 | CB | GLN | D | 392 | 39.662 | 47.295 | 27.495 | 1.00 | 37.55 | D |
| ATOM | 6243 | CG | GLN | D | 392 | 40.703 | 48.157 | 28.044 | 1.00 | 37.42 | D |
| ATOM | 6244 | CD | GLN | D | 392 | 41.929 | 48.208 | 27.125 | 1.00 | 38.58 | D |
| ATOM | 6245 | OE1 | GLN | D | 392 | 41.884 | 47.779 | 25.966 | 1.00 | 39.24 | D |
| ATOM | 6246 | NE2 | GLN | D | 392 | 43.034 | 48.729 | 27.665 | 1.00 | 37.35 | D |
| ATOM | 6247 | C | GLN | D | 392 | 37.476 | 46.206 | 27.739 | 1.00 | 37.97 | D |
| ATOM | 6248 | O | GLN | D | 392 | 36.424 | 46.725 | 27.484 | 1.00 | 36.87 | D |
| ATOM | 6249 | N | ASP | D | 393 | 37.718 | 44.956 | 27.424 | 1.00 | 39.83 | D |
| ATOM | 6250 | CA | ASP | D | 393 | 36.761 | 44.199 | 26.575 | 1.00 | 41.18 | D |
| ATOM | 6251 | CB | ASP | D | 393 | 37.220 | 42.825 | 26.158 | 1.00 | 43.45 | D |
| ATOM | 6252 | CG | ASP | D | 393 | 38.514 | 42.839 | 25.314 | 1.00 | 48.42 | D |
| ATOM | 6253 | OD1 | ASP | D | 393 | 38.961 | 43.938 | 24.825 | 1.00 | 50.34 | D |
| ATOM | 6254 | OD2 | ASP | D | 393 | 39.199 | 41.745 | 25.102 | 1.00 | 51.85 | D |
| ATOM | 6255 | C | ASP | D | 393 | 35.485 | 44.044 | 27.305 | 1.00 | 40.12 | D |
| ATOM | 6256 | O | ASP | D | 393 | 34.419 | 44.117 | 26.729 | 1.00 | 41.40 | D |
| ATOM | 6257 | N | VAL | D | 394 | 35.535 | 43.884 | 28.606 | 1.00 | 39.10 | D |
| ATOM | 6258 | CA | VAL | D | 394 | 34.246 | 43.704 | 29.315 | 1.00 | 37.60 | D |
| ATOM | 6259 | CB | VAL | D | 394 | 34.505 | 43.383 | 30.770 | 1.00 | 37.45 | D |
| ATOM | 6260 | CG1 | VAL | D | 394 | 33.298 | 43.746 | 31.609 | 1.00 | 36.15 | D |
| ATOM | 6261 | CG2 | VAL | D | 394 | 34.848 | 41.870 | 30.916 | 1.00 | 35.77 | D |
| ATOM | 6262 | C | VAL | D | 394 | 33.451 | 45.036 | 29.306 | 1.00 | 37.70 | D |
| ATOM | 6263 | O | VAL | D | 394 | 32.196 | 45.080 | 29.285 | 1.00 | 36.75 | D |
| ATOM | 6264 | N | LEU | D | 395 | 34.149 | 46.172 | 29.439 | 1.00 | 37.24 | D |
| ATOM | 6265 | CA | LEU | D | 395 | 33.390 | 47.425 | 29.547 | 1.00 | 36.45 | D |
| ATOM | 6266 | CB | LEU | D | 395 | 34.276 | 48.452 | 30.177 | 1.00 | 36.95 | D |
| ATOM | 6267 | CG | LEU | D | 395 | 34.726 | 48.181 | 31.612 | 1.00 | 34.42 | D |
| ATOM | 6268 | CD1 | LEU | D | 395 | 35.902 | 49.008 | 31.954 | 1.00 | 34.17 | D |
| ATOM | 6269 | CD2 | LEU | D | 395 | 33.579 | 48.466 | 32.556 | 1.00 | 34.64 | D |
| ATOM | 6270 | C | LEU | D | 395 | 32.972 | 47.864 | 28.166 | 1.00 | 36.77 | D |
| ATOM | 6271 | O | LEU | D | 395 | 31.922 | 48.305 | 27.936 | 1.00 | 35.02 | D |
| ATOM | 6272 | N | HIS | D | 396 | 33.805 | 47.649 | 27.173 | 1.00 | 37.49 | D |
| ATOM | 6273 | CA | HIS | D | 396 | 33.378 | 47.874 | 25.809 | 1.00 | 37.52 | D |
| ATOM | 6274 | CB | HIS | D | 396 | 34.520 | 47.546 | 24.949 | 1.00 | 37.19 | D |
| ATOM | 6275 | CG | HIS | D | 396 | 34.262 | 47.687 | 23.514 | 1.00 | 36.93 | D |
| ATOM | 6276 | CD2 | HIS | D | 396 | 33.246 | 48.272 | 22.807 | 1.00 | 37.66 | D |
| ATOM | 6277 | ND1 | HIS | D | 396 | 35.167 | 47.232 | 22.603 | 1.00 | 36.78 | D |
| ATOM | 6278 | CE1 | HIS | D | 396 | 34.718 | 47.516 | 21.378 | 1.00 | 37.68 | D |
| ATOM | 6279 | NE2 | HIS | D | 396 | 33.555 | 48.144 | 21.467 | 1.00 | 37.09 | D |
| ATOM | 6280 | C | HIS | D | 396 | 32.126 | 47.032 | 25.416 | 1.00 | 38.78 | D |
| ATOM | 6281 | O | HIS | D | 396 | 31.148 | 47.510 | 24.929 | 1.00 | 37.70 | D |
| ATOM | 6282 | N | GLU | D | 397 | 32.173 | 45.762 | 25.582 | 1.00 | 39.78 | D |
| ATOM | 6283 | CA | GLU | D | 397 | 30.982 | 44.984 | 25.421 | 1.00 | 41.42 | D |
| ATOM | 6284 | CB | GLU | D | 397 | 31.134 | 43.629 | 26.087 | 1.00 | 43.56 | D |
| ATOM | 6285 | CG | GLU | D | 397 | 29.838 | 42.770 | 25.974 | 1.00 | 45.47 | D |
| ATOM | 6286 | CD | GLU | D | 397 | 30.026 | 41.272 | 26.436 | 1.00 | 48.73 | D |
| ATOM | 6287 | OE1 | GLU | D | 397 | 30.843 | 40.931 | 27.361 | 1.00 | 49.48 | D |
| ATOM | 6288 | OE2 | GLU | D | 397 | 29.356 | 40.386 | 25.830 | 1.00 | 50.49 | D |
| ATOM | 6289 | C | GLU | D | 397 | 29.747 | 45.551 | 26.097 | 1.00 | 41.60 | D |
| ATOM | 6290 | O | GLU | D | 397 | 28.695 | 45.583 | 25.487 | 1.00 | 41.85 | D |
| ATOM | 6291 | N | ALA | D | 398 | 29.885 | 45.975 | 27.339 | 1.00 | 39.29 | D |
| ATOM | 6292 | CA | ALA | D | 398 | 28.797 | 46.654 | 27.972 | 1.00 | 39.47 | D |
| ATOM | 6293 | CB | ALA | D | 398 | 29.134 | 47.039 | 29.354 | 1.00 | 37.32 | D |
| ATOM | 6294 | C | ALA | D | 398 | 28.292 | 47.845 | 27.202 | 1.00 | 40.49 | D |
| ATOM | 6295 | O | ALA | D | 398 | 27.091 | 48.080 | 27.085 | 1.00 | 40.23 | D |
| ATOM | 6296 | N | LEU | D | 399 | 29.188 | 48.647 | 26.712 | 1.00 | 41.37 | D |
| ATOM | 6297 | CA | LEU | D | 399 | 28.729 | 49.815 | 25.974 | 1.00 | 41.92 | D |
| ATOM | 6298 | CB | LEU | D | 399 | 29.935 | 50.674 | 25.601 | 1.00 | 39.71 | D |
| ATOM | 6299 | CG | LEU | D | 399 | 29.554 | 51.914 | 24.792 | 1.00 | 40.57 | D |
| ATOM | 6300 | CD1 | LEU | D | 399 | 28.822 | 52.908 | 25.722 | 1.00 | 38.24 | D |
| ATOM | 6301 | CD2 | LEU | D | 399 | 30.844 | 52.490 | 24.130 | 1.00 | 39.09 | D |

TABLE 2-continued

ATOMIC COORDINATES OF THE ERR3 LBD/
DIETHYLSTILBESTROL COMPLEX

| ATOM | 6302 | C | LEU | D | 399 | 27.962 | 49.355 | 24.714 | 1.00 | 43.04 | D |
|------|------|------|-----|---|-----|--------|--------|--------|------|-------|---|
| ATOM | 6303 | O | LEU | D | 399 | 26.936 | 49.890 | 24.407 | 1.00 | 42.10 | D |
| ATOM | 6304 | N | GLN | D | 400 | 28.517 | 48.382 | 23.977 | 1.00 | 45.11 | D |
| ATOM | 6305 | CA | GLN | D | 400 | 27.979 | 47.937 | 22.703 | 1.00 | 47.78 | D |
| ATOM | 6306 | CB | GLN | D | 400 | 28.977 | 47.006 | 22.043 | 1.00 | 48.87 | D |
| ATOM | 6307 | CG | GLN | D | 400 | 28.528 | 46.110 | 20.867 | 1.00 | 51.37 | D |
| ATOM | 6308 | CD | GLN | D | 400 | 29.395 | 44.791 | 20.576 | 1.00 | 53.54 | D |
| ATOM | 6309 | OE1 | GLN | D | 400 | 29.867 | 44.605 | 19.411 | 1.00 | 55.32 | D |
| ATOM | 6310 | NE2 | GLN | D | 400 | 29.582 | 43.895 | 21.607 | 1.00 | 54.11 | D |
| ATOM | 6311 | C | GLN | D | 400 | 26.575 | 47.320 | 22.986 | 1.00 | 49.17 | D |
| ATOM | 6312 | O | GLN | D | 400 | 25.589 | 47.614 | 22.260 | 1.00 | 48.62 | D |
| ATOM | 6313 | N | ASP | D | 401 | 26.468 | 46.500 | 24.058 | 1.00 | 51.18 | D |
| ATOM | 6314 | CA | ASP | D | 401 | 25.169 | 45.797 | 24.405 | 1.00 | 53.06 | D |
| ATOM | 6315 | CB | ASP | D | 401 | 25.257 | 44.608 | 25.446 | 1.00 | 57.21 | D |
| ATOM | 6316 | CG | ASP | D | 401 | 26.241 | 44.880 | 26.539 | 1.00 | 62.59 | D |
| ATOM | 6317 | OD1 | ASP | D | 401 | 26.142 | 45.967 | 27.136 | 1.00 | 66.23 | D |
| ATOM | 6318 | OD2 | ASP | D | 401 | 27.106 | 44.021 | 26.807 | 1.00 | 66.02 | D |
| ATOM | 6319 | C | ASP | D | 401 | 24.104 | 46.812 | 24.829 | 1.00 | 51.85 | D |
| ATOM | 6320 | O | ASP | D | 401 | 22.984 | 46.708 | 24.333 | 1.00 | 52.43 | D |
| ATOM | 6321 | N | TYR | D | 402 | 24.466 | 47.815 | 25.643 | 1.00 | 50.04 | D |
| ATOM | 6322 | CA | TYR | D | 402 | 23.554 | 48.860 | 26.024 | 1.00 | 48.08 | D |
| ATOM | 6323 | CB | TYR | D | 402 | 24.170 | 49.802 | 26.999 | 1.00 | 47.09 | D |
| ATOM | 6324 | CG | TYR | D | 402 | 23.315 | 50.972 | 27.325 | 1.00 | 45.41 | D |
| ATOM | 6325 | CD1 | TYR | D | 402 | 22.433 | 50.923 | 28.368 | 1.00 | 45.38 | D |
| ATOM | 6326 | CE1 | TYR | D | 402 | 21.672 | 52.021 | 28.695 | 1.00 | 44.49 | D |
| ATOM | 6327 | CD2 | TYR | D | 402 | 23.431 | 52.159 | 26.639 | 1.00 | 44.82 | D |
| ATOM | 6328 | CE2 | TYR | D | 402 | 22.677 | 53.207 | 26.944 | 1.00 | 43.60 | D |
| ATOM | 6329 | CZ | TYR | D | 402 | 21.761 | 53.124 | 27.951 | 1.00 | 44.96 | D |
| ATOM | 6330 | OH | TYR | D | 402 | 20.961 | 54.221 | 28.272 | 1.00 | 45.41 | D |
| ATOM | 6331 | C | TYR | D | 402 | 23.149 | 49.650 | 24.843 | 1.00 | 48.48 | D |
| ATOM | 6332 | O | TYR | D | 402 | 21.954 | 50.061 | 24.725 | 1.00 | 49.46 | D |
| ATOM | 6333 | N | GLU | D | 403 | 24.075 | 49.931 | 23.918 | 1.00 | 47.19 | D |
| ATOM | 6334 | CA | GLU | D | 403 | 23.625 | 50.811 | 22.847 | 1.00 | 46.53 | D |
| ATOM | 6335 | CB | GLU | D | 403 | 24.811 | 51.436 | 22.085 | 1.00 | 45.54 | D |
| ATOM | 6336 | CG | GLU | D | 403 | 25.683 | 52.397 | 22.853 | 1.00 | 43.65 | D |
| ATOM | 6337 | CD | GLU | D | 403 | 24.982 | 53.636 | 23.203 | 1.00 | 43.03 | D |
| ATOM | 6338 | OE1 | GLU | D | 403 | 23.927 | 53.892 | 22.574 | 1.00 | 44.02 | D |
| ATOM | 6339 | OE2 | GLU | D | 403 | 25.496 | 54.379 | 24.080 | 1.00 | 43.44 | D |
| ATOM | 6340 | C | GLU | D | 403 | 22.694 | 50.025 | 21.869 | 1.00 | 47.09 | D |
| ATOM | 6341 | O | GLU | D | 403 | 21.806 | 50.596 | 21.254 | 1.00 | 47.52 | D |
| ATOM | 6342 | N | ALA | D | 404 | 22.941 | 48.724 | 21.712 | 1.00 | 47.19 | D |
| ATOM | 6343 | CA | ALA | D | 404 | 22.188 | 47.862 | 20.776 | 1.00 | 47.22 | D |
| ATOM | 6344 | CB | ALA | D | 404 | 22.772 | 46.366 | 20.707 | 1.00 | 46.90 | D |
| ATOM | 6345 | C | ALA | D | 404 | 20.753 | 47.813 | 21.201 | 1.00 | 48.18 | D |
| ATOM | 6346 | O | ALA | D | 404 | 19.899 | 47.693 | 20.343 | 1.00 | 48.18 | D |
| ATOM | 6347 | N | GLY | D | 405 | 20.510 | 47.896 | 22.521 | 1.00 | 49.18 | D |
| ATOM | 6348 | CA | GLY | D | 405 | 19.193 | 47.753 | 23.120 | 1.00 | 50.07 | D |
| ATOM | 6349 | C | GLY | D | 405 | 18.532 | 49.111 | 23.248 | 1.00 | 50.98 | D |
| ATOM | 6350 | O | GLY | D | 405 | 17.334 | 49.250 | 22.944 | 1.00 | 52.52 | D |
| ATOM | 6351 | N | GLN | D | 406 | 19.274 | 50.144 | 23.640 | 1.00 | 50.39 | D |
| ATOM | 6352 | CA | GLN | D | 406 | 18.638 | 51.403 | 23.885 | 1.00 | 49.78 | D |
| ATOM | 6353 | CB | GLN | D | 406 | 19.272 | 52.131 | 25.080 | 1.00 | 50.94 | D |
| ATOM | 6354 | CG | GLN | D | 406 | 18.401 | 53.247 | 25.681 | 1.00 | 52.48 | D |
| ATOM | 6355 | CD | GLN | D | 406 | 17.320 | 52.725 | 26.663 | 1.00 | 53.37 | D |
| ATOM | 6356 | OE1 | GLN | D | 406 | 17.371 | 51.537 | 27.101 | 1.00 | 53.57 | D |
| ATOM | 6357 | NE2 | GLN | D | 406 | 17.186 | 52.943 | 28.054 | 0.00 | 53.19 | D |
| ATOM | 6358 | C | GLN | D | 406 | 18.617 | 52.291 | 22.739 | 1.00 | 49.43 | D |
| ATOM | 6359 | O | GLN | D | 406 | 17.920 | 53.255 | 22.829 | 1.00 | 49.37 | D |
| ATOM | 6360 | N | HIS | D | 407 | 19.402 | 52.082 | 21.685 | 1.00 | 49.47 | D |
| ATOM | 6361 | CA | HIS | D | 407 | 19.471 | 53.049 | 20.568 | 1.00 | 50.16 | D |
| ATOM | 6362 | CB | HIS | D | 407 | 20.632 | 54.118 | 20.681 | 1.00 | 48.69 | D |
| ATOM | 6363 | CG | HIS | D | 407 | 20.554 | 55.039 | 21.878 | 1.00 | 45.72 | D |
| ATOM | 6364 | CD2 | HIS | D | 407 | 21.102 | 54.962 | 23.111 | 1.00 | 44.41 | D |
| ATOM | 6365 | ND1 | HIS | D | 407 | 19.863 | 56.229 | 21.850 | 1.00 | 45.95 | D |
| ATOM | 6366 | CE1 | HIS | D | 407 | 19.939 | 56.826 | 23.024 | 1.00 | 44.60 | D |
| ATOM | 6367 | NE2 | HIS | D | 407 | 20.686 | 56.084 | 23.817 | 1.00 | 45.34 | D |
| ATOM | 6368 | C | HIS | D | 407 | 19.628 | 52.327 | 19.212 | 1.00 | 52.27 | D |
| ATOM | 6369 | O | HIS | D | 407 | 20.567 | 52.614 | 18.407 | 1.00 | 52.11 | D |
| ATOM | 6370 | N | MET | D | 408 | 18.656 | 51.439 | 18.916 | 1.00 | 55.03 | D |
| ATOM | 6371 | CA | MET | D | 408 | 18.512 | 50.737 | 17.611 | 1.00 | 57.26 | D |
| ATOM | 6372 | CB | MET | D | 408 | 17.155 | 49.890 | 17.798 | 0.00 | 61.51 | D |
| ATOM | 6373 | CG | MET | D | 408 | 16.740 | 49.111 | 16.516 | 1.00 | 67.54 | D |
| ATOM | 6374 | SD | MET | D | 408 | 15.168 | 48.245 | 16.697 | 1.00 | 75.30 | D |
| ATOM | 6375 | CE | MET | D | 408 | 14.027 | 49.470 | 16.058 | 1.00 | 72.87 | D |
| ATOM | 6376 | C | MET | D | 408 | 18.412 | 51.626 | 16.372 | 1.00 | 55.99 | D |
| ATOM | 6377 | O | MET | D | 408 | 18.797 | 51.204 | 15.317 | 1.00 | 56.00 | D |

TABLE 2-continued

ATOMIC COORDINATES OF THE ERR3 LBD/
DIETHYLSTILBESTROL COMPLEX

| ATOM | 6378 | N   | GLU | D | 409 | 17.943 | 52.853 | 16.495 | 1.00 | 54.95 | D |
|------|------|-----|-----|---|-----|--------|--------|--------|------|-------|---|
| ATOM | 6379 | CA  | GLU | D | 409 | 17.946 | 53.839 | 15.363 | 1.00 | 54.65 | D |
| ATOM | 6380 | CB  | GLU | D | 409 | 17.198 | 55.158 | 15.713 | 1.00 | 56.03 | D |
| ATOM | 6381 | CG  | GLU | D | 409 | 16.598 | 55.263 | 17.130 | 1.00 | 59.42 | D |
| ATOM | 6382 | CD  | GLU | D | 409 | 17.633 | 55.378 | 18.305 | 1.00 | 61.03 | D |
| ATOM | 6383 | OE1 | GLU | D | 409 | 18.298 | 56.429 | 18.520 | 1.00 | 61.47 | D |
| ATOM | 6384 | OE2 | GLU | D | 409 | 17.742 | 54.376 | 19.046 | 1.00 | 61.73 | D |
| ATOM | 6385 | C   | GLU | D | 409 | 19.327 | 54.213 | 14.817 | 1.00 | 53.66 | D |
| ATOM | 6386 | O   | GLU | D | 409 | 19.458 | 54.422 | 13.581 | 1.00 | 53.98 | D |
| ATOM | 6387 | N   | ASP | D | 410 | 20.329 | 54.238 | 15.728 | 1.00 | 52.20 | D |
| ATOM | 6388 | CA  | ASP | D | 410 | 21.735 | 54.600 | 15.478 | 1.00 | 49.61 | D |
| ATOM | 6389 | CB  | ASP | D | 410 | 22.104 | 55.806 | 16.320 | 1.00 | 48.24 | D |
| ATOM | 6390 | CG  | ASP | D | 410 | 23.471 | 56.465 | 15.878 | 1.00 | 48.05 | D |
| ATOM | 6391 | OD1 | ASP | D | 410 | 24.168 | 55.902 | 15.041 | 1.00 | 45.61 | D |
| ATOM | 6392 | OD2 | ASP | D | 410 | 23.895 | 57.535 | 16.391 | 1.00 | 48.14 | D |
| ATOM | 6393 | C   | ASP | D | 410 | 22.664 | 53.429 | 15.835 | 1.00 | 48.74 | D |
| ATOM | 6394 | O   | ASP | D | 410 | 23.117 | 53.275 | 16.938 | 1.00 | 49.10 | D |
| ATOM | 6395 | N   | PRO | D | 411 | 22.808 | 52.529 | 14.917 | 1.00 | 47.60 | D |
| ATOM | 6396 | CD  | PRO | D | 411 | 22.099 | 52.622 | 13.629 | 1.00 | 48.12 | D |
| ATOM | 6397 | CA  | PRO | D | 411 | 23.644 | 51.332 | 15.080 | 1.00 | 46.88 | D |
| ATOM | 6398 | CB  | PRO | D | 411 | 23.497 | 50.597 | 13.723 | 1.00 | 46.91 | D |
| ATOM | 6399 | CG  | PRO | D | 411 | 22.991 | 51.756 | 12.741 | 1.00 | 48.09 | D |
| ATOM | 6400 | C   | PRO | D | 411 | 25.153 | 51.690 | 15.255 | 1.00 | 46.10 | D |
| ATOM | 6401 | O   | PRO | D | 411 | 26.016 | 50.842 | 15.538 | 1.00 | 45.66 | D |
| ATOM | 6402 | N   | ARG | D | 412 | 25.438 | 52.936 | 15.026 | 1.00 | 44.76 | D |
| ATOM | 6403 | CA  | ARG | D | 412 | 26.795 | 53.424 | 15.168 | 1.00 | 45.04 | D |
| ATOM | 6404 | CB  | ARG | D | 412 | 27.086 | 54.430 | 14.076 | 1.00 | 44.99 | D |
| ATOM | 6405 | CG  | ARG | D | 412 | 28.099 | 53.946 | 13.201 | 1.00 | 48.66 | D |
| ATOM | 6406 | CD  | ARG | D | 412 | 28.022 | 54.497 | 11.763 | 1.00 | 50.68 | D |
| ATOM | 6407 | NE  | ARG | D | 412 | 27.416 | 53.387 | 11.057 | 1.00 | 53.08 | D |
| ATOM | 6408 | CZ  | ARG | D | 412 | 26.424 | 53.471 | 10.190 | 1.00 | 52.52 | D |
| ATOM | 6409 | NH1 | ARG | D | 412 | 25.947 | 54.661 | 9.755  | 1.00 | 53.13 | D |
| ATOM | 6410 | NH2 | ARG | D | 412 | 25.977 | 52.317 | 9.749  | 1.00 | 52.39 | D |
| ATOM | 6411 | C   | ARG | D | 412 | 27.055 | 54.156 | 16.497 | 1.00 | 43.35 | D |
| ATOM | 6412 | O   | ARG | D | 412 | 28.122 | 54.758 | 16.653 | 1.00 | 43.88 | D |
| ATOM | 6413 | N   | ARG | D | 413 | 26.072 | 54.224 | 17.364 | 1.00 | 40.17 | D |
| ATOM | 6414 | CA  | ARG | D | 413 | 26.196 | 55.137 | 18.522 | 1.00 | 39.05 | D |
| ATOM | 6415 | CB  | ARG | D | 413 | 24.893 | 55.217 | 19.319 | 1.00 | 37.81 | D |
| ATOM | 6416 | CG  | ARG | D | 413 | 24.845 | 56.334 | 20.313 | 1.00 | 36.98 | D |
| ATOM | 6417 | CD  | ARG | D | 413 | 23.531 | 56.486 | 21.042 | 1.00 | 37.25 | D |
| ATOM | 6418 | NE  | ARG | D | 413 | 23.477 | 57.414 | 22.222 | 1.00 | 36.33 | D |
| ATOM | 6419 | CZ  | ARG | D | 413 | 23.291 | 58.730 | 22.117 | 1.00 | 36.23 | D |
| ATOM | 6420 | NH1 | ARG | D | 413 | 23.141 | 59.277 | 20.936 | 1.00 | 33.79 | D |
| ATOM | 6421 | NH2 | ARG | D | 413 | 23.248 | 59.518 | 23.169 | 1.00 | 33.73 | D |
| ATOM | 6422 | C   | ARG | D | 413 | 27.391 | 54.760 | 19.459 | 1.00 | 37.03 | D |
| ATOM | 6423 | O   | ARG | D | 413 | 28.123 | 55.619 | 19.887 | 1.00 | 36.42 | D |
| ATOM | 6424 | N   | ALA | D | 414 | 27.609 | 53.482 | 19.678 | 1.00 | 35.83 | D |
| ATOM | 6425 | CA  | ALA | D | 414 | 28.734 | 53.024 | 20.458 | 1.00 | 35.85 | D |
| ATOM | 6426 | CB  | ALA | D | 414 | 28.750 | 51.471 | 20.528 | 1.00 | 33.83 | D |
| ATOM | 6427 | C   | ALA | D | 414 | 30.125 | 53.570 | 19.938 | 1.00 | 35.61 | D |
| ATOM | 6428 | O   | ALA | D | 414 | 30.917 | 54.088 | 20.700 | 1.00 | 35.85 | D |
| ATOM | 6429 | N   | GLY | D | 415 | 30.363 | 53.317 | 18.677 | 1.00 | 35.23 | D |
| ATOM | 6430 | CA  | GLY | D | 415 | 31.520 | 53.665 | 17.887 | 1.00 | 35.06 | D |
| ATOM | 6431 | C   | GLY | D | 415 | 31.660 | 55.199 | 17.965 | 1.00 | 35.15 | D |
| ATOM | 6432 | O   | GLY | D | 415 | 32.735 | 55.680 | 18.243 | 1.00 | 35.52 | D |
| ATOM | 6433 | N   | LYS | D | 416 | 30.581 | 55.930 | 17.966 | 1.00 | 34.76 | D |
| ATOM | 6434 | CA  | LYS | D | 416 | 30.684 | 57.381 | 18.101 | 1.00 | 36.26 | D |
| ATOM | 6435 | CB  | LYS | D | 416 | 29.361 | 58.101 | 17.814 | 1.00 | 36.71 | D |
| ATOM | 6436 | CG  | LYS | D | 416 | 28.946 | 58.322 | 16.375 | 1.00 | 38.15 | D |
| ATOM | 6437 | CD  | LYS | D | 416 | 27.481 | 58.605 | 16.218 | 1.00 | 39.78 | D |
| ATOM | 6438 | CE  | LYS | D | 416 | 27.044 | 58.293 | 14.756 | 1.00 | 41.83 | D |
| ATOM | 6439 | NZ  | LYS | D | 416 | 25.598 | 58.540 | 14.490 | 1.00 | 43.62 | D |
| ATOM | 6440 | C   | LYS | D | 416 | 31.132 | 57.816 | 19.503 | 1.00 | 36.75 | D |
| ATOM | 6441 | O   | LYS | D | 416 | 31.833 | 58.793 | 19.645 | 1.00 | 37.37 | D |
| ATOM | 6442 | N   | MET | D | 417 | 30.623 | 57.144 | 20.504 | 1.00 | 35.48 | D |
| ATOM | 6443 | CA  | MET | D | 417 | 30.984 | 57.418 | 21.854 | 1.00 | 35.01 | D |
| ATOM | 6444 | CB  | MET | D | 417 | 30.188 | 56.501 | 22.803 | 1.00 | 36.46 | D |
| ATOM | 6445 | CG  | MET | D | 417 | 28.771 | 56.903 | 23.278 | 1.00 | 37.46 | D |
| ATOM | 6446 | SD  | MET | D | 417 | 28.504 | 58.560 | 23.653 | 1.00 | 40.22 | D |
| ATOM | 6447 | CE  | MET | D | 417 | 26.748 | 58.866 | 23.475 | 1.00 | 39.43 | D |
| ATOM | 6448 | C   | MET | D | 417 | 32.483 | 57.210 | 22.021 | 1.00 | 33.22 | D |
| ATOM | 6449 | O   | MET | D | 417 | 33.222 | 58.023 | 22.625 | 1.00 | 32.96 | D |
| ATOM | 6450 | N   | LEU | D | 418 | 32.936 | 56.104 | 21.520 | 1.00 | 33.14 | D |
| ATOM | 6451 | CA  | LEU | D | 418 | 34.358 | 55.803 | 21.577 | 1.00 | 33.42 | D |
| ATOM | 6452 | CB  | LEU | D | 418 | 34.614 | 54.322 | 21.108 | 1.00 | 33.42 | D |
| ATOM | 6453 | CG  | LEU | D | 418 | 33.963 | 53.181 | 21.897 | 1.00 | 32.47 | D |

TABLE 2-continued

ATOMIC COORDINATES OF THE ERR3 LBD/DIETHYLSTILBESTROL COMPLEX

| ATOM | 6454 | CD1 | LEU | D | 418 | 33.983 | 52.013 | 21.130 | 1.00 | 32.30 | D |
|------|------|-----|-----|---|-----|--------|--------|--------|------|-------|---|
| ATOM | 6455 | CD2 | LEU | D | 418 | 34.671 | 52.987 | 23.244 | 1.00 | 29.46 | D |
| ATOM | 6456 | C | LEU | D | 418 | 35.261 | 56.873 | 20.788 | 1.00 | 32.98 | D |
| ATOM | 6457 | O | LEU | D | 418 | 36.333 | 57.236 | 21.242 | 1.00 | 33.45 | D |
| ATOM | 6458 | N | MET | D | 419 | 34.754 | 57.423 | 19.698 | 1.00 | 32.96 | D |
| ATOM | 6459 | CA | MET | D | 419 | 35.387 | 58.479 | 18.932 | 1.00 | 31.68 | D |
| ATOM | 6460 | CB | MET | D | 419 | 34.771 | 58.741 | 17.506 | 1.00 | 32.16 | D |
| ATOM | 6461 | CG | MET | D | 419 | 35.157 | 57.581 | 16.586 | 1.00 | 35.46 | D |
| ATOM | 6462 | SD | MET | D | 419 | 34.094 | 57.406 | 15.105 | 1.00 | 39.58 | D |
| ATOM | 6463 | CE | MET | D | 419 | 34.195 | 58.931 | 14.507 | 1.00 | 38.46 | D |
| ATOM | 6464 | C | MET | D | 419 | 35.467 | 59.798 | 19.709 | 1.00 | 30.36 | D |
| ATOM | 6465 | O | MET | D | 419 | 36.116 | 60.721 | 19.162 | 1.00 | 30.35 | D |
| ATOM | 6466 | N | THR | D | 420 | 34.837 | 59.910 | 20.887 | 1.00 | 28.81 | D |
| ATOM | 6467 | CA | THR | D | 420 | 34.961 | 61.134 | 21.673 | 1.00 | 28.99 | D |
| ATOM | 6468 | CB | THR | D | 420 | 33.793 | 61.394 | 22.641 | 1.00 | 30.12 | D |
| ATOM | 6469 | OG1 | THR | D | 420 | 33.574 | 60.254 | 23.497 | 1.00 | 29.68 | D |
| ATOM | 6470 | CG2 | THR | D | 420 | 32.394 | 61.514 | 21.829 | 1.00 | 32.16 | D |
| ATOM | 6471 | C | THR | D | 420 | 36.197 | 61.045 | 22.581 | 1.00 | 28.45 | D |
| ATOM | 6472 | O | THR | D | 420 | 36.601 | 62.048 | 23.204 | 1.00 | 28.97 | D |
| ATOM | 6473 | N | LEU | D | 421 | 36.750 | 59.853 | 22.673 | 1.00 | 25.91 | D |
| ATOM | 6474 | CA | LEU | D | 421 | 37.771 | 59.624 | 23.663 | 1.00 | 26.62 | D |
| ATOM | 6475 | CB | LEU | D | 421 | 37.947 | 58.116 | 23.971 | 1.00 | 25.87 | D |
| ATOM | 6476 | CG | LEU | D | 421 | 36.786 | 57.378 | 24.688 | 1.00 | 25.02 | D |
| ATOM | 6477 | CD1 | LEU | D | 421 | 37.096 | 55.941 | 24.637 | 1.00 | 24.62 | D |
| ATOM | 6478 | CD2 | LEU | D | 421 | 36.701 | 57.832 | 26.044 | 1.00 | 23.81 | D |
| ATOM | 6479 | C | LEU | D | 421 | 39.098 | 60.344 | 23.375 | 1.00 | 25.86 | D |
| ATOM | 6480 | O | LEU | D | 421 | 39.766 | 60.747 | 24.312 | 1.00 | 25.25 | D |
| ATOM | 6481 | N | PRO | D | 422 | 39.491 | 60.517 | 22.118 | 1.00 | 25.72 | D |
| ATOM | 6482 | CD | PRO | D | 422 | 38.892 | 59.849 | 20.964 | 1.00 | 23.66 | D |
| ATOM | 6483 | CA | PRO | D | 422 | 40.790 | 61.264 | 21.769 | 1.00 | 25.80 | D |
| ATOM | 6484 | CB | PRO | D | 422 | 40.789 | 61.318 | 20.308 | 1.00 | 24.65 | D |
| ATOM | 6485 | CG | PRO | D | 422 | 40.049 | 59.996 | 19.897 | 1.00 | 25.59 | D |
| ATOM | 6486 | C | PRO | D | 422 | 40.730 | 62.632 | 22.280 | 1.00 | 27.16 | D |
| ATOM | 6487 | O | PRO | D | 422 | 41.697 | 63.123 | 22.922 | 1.00 | 27.51 | D |
| ATOM | 6488 | N | LEU | D | 423 | 39.525 | 63.232 | 22.178 | 1.00 | 28.15 | D |
| ATOM | 6489 | CA | LEU | D | 423 | 39.411 | 64.633 | 22.568 | 1.00 | 27.60 | D |
| ATOM | 6490 | CB | LEU | D | 423 | 38.162 | 65.304 | 21.969 | 1.00 | 26.24 | D |
| ATOM | 6491 | CG | LEU | D | 423 | 38.024 | 66.731 | 22.486 | 1.00 | 26.69 | D |
| ATOM | 6492 | CD1 | LEU | D | 423 | 39.123 | 67.690 | 22.024 | 1.00 | 25.52 | D |
| ATOM | 6493 | CD2 | LEU | D | 423 | 36.669 | 67.277 | 22.050 | 1.00 | 28.90 | D |
| ATOM | 6494 | C | LEU | D | 423 | 39.480 | 64.709 | 24.110 | 1.00 | 28.29 | D |
| ATOM | 6495 | O | LEU | D | 423 | 39.934 | 65.755 | 24.728 | 1.00 | 28.33 | D |
| ATOM | 6496 | N | LEU | D | 424 | 38.983 | 63.655 | 24.764 | 1.00 | 28.85 | D |
| ATOM | 6497 | CA | LEU | D | 424 | 38.957 | 63.619 | 26.228 | 1.00 | 28.52 | D |
| ATOM | 6498 | CB | LEU | D | 424 | 38.160 | 62.460 | 26.726 | 1.00 | 26.76 | D |
| ATOM | 6499 | CG | LEU | D | 424 | 38.219 | 62.204 | 28.266 | 1.00 | 28.25 | D |
| ATOM | 6500 | CD1 | LEU | D | 424 | 37.590 | 63.306 | 29.097 | 1.00 | 25.90 | D |
| ATOM | 6501 | CD2 | LEU | D | 424 | 37.571 | 60.822 | 28.704 | 1.00 | 26.01 | D |
| ATOM | 6502 | C | LEU | D | 424 | 40.408 | 63.572 | 26.693 | 1.00 | 29.34 | D |
| ATOM | 6503 | O | LEU | D | 424 | 40.750 | 64.313 | 27.622 | 1.00 | 30.47 | D |
| ATOM | 6504 | N | ARG | D | 425 | 41.227 | 62.710 | 26.072 | 1.00 | 28.87 | D |
| ATOM | 6505 | CA | ARG | D | 425 | 42.680 | 62.561 | 26.343 | 1.00 | 29.65 | D |
| ATOM | 6506 | CB | ARG | D | 425 | 43.158 | 61.399 | 25.604 | 1.00 | 29.92 | D |
| ATOM | 6507 | CG | ARG | D | 425 | 44.656 | 61.090 | 25.473 | 1.00 | 31.54 | D |
| ATOM | 6508 | CD | ARG | D | 425 | 45.205 | 60.325 | 26.528 | 1.00 | 29.46 | D |
| ATOM | 6509 | NE | ARG | D | 425 | 44.419 | 59.131 | 26.885 | 1.00 | 26.64 | D |
| ATOM | 6510 | CZ | ARG | D | 425 | 44.692 | 57.928 | 26.477 | 1.00 | 26.28 | D |
| ATOM | 6511 | NH1 | ARG | D | 425 | 45.660 | 57.674 | 25.603 | 1.00 | 26.07 | D |
| ATOM | 6512 | NH2 | ARG | D | 425 | 43.897 | 56.981 | 26.825 | 1.00 | 25.94 | D |
| ATOM | 6513 | C | ARG | D | 425 | 43.454 | 63.872 | 26.058 | 1.00 | 30.60 | D |
| ATOM | 6514 | O | ARG | D | 425 | 44.171 | 64.420 | 26.952 | 1.00 | 31.43 | D |
| ATOM | 6515 | N | GLN | D | 426 | 43.193 | 64.464 | 24.885 | 1.00 | 30.84 | D |
| ATOM | 6516 | CA | GLN | D | 426 | 43.792 | 65.732 | 24.522 | 1.00 | 31.06 | D |
| ATOM | 6517 | CB | GLN | D | 426 | 43.241 | 66.178 | 23.149 | 1.00 | 31.15 | D |
| ATOM | 6518 | CG | GLN | D | 426 | 43.784 | 67.503 | 22.703 | 1.00 | 35.23 | D |
| ATOM | 6519 | CD | GLN | D | 426 | 43.102 | 68.019 | 21.395 | 1.00 | 38.17 | D |
| ATOM | 6520 | OE1 | GLN | D | 426 | 42.775 | 67.230 | 20.545 | 1.00 | 39.25 | D |
| ATOM | 6521 | NE2 | GLN | D | 426 | 42.791 | 69.339 | 21.331 | 1.00 | 40.54 | D |
| ATOM | 6522 | C | GLN | D | 426 | 43.514 | 66.798 | 25.584 | 1.00 | 30.36 | D |
| ATOM | 6523 | O | GLN | D | 426 | 44.372 | 67.468 | 25.994 | 1.00 | 31.18 | D |
| ATOM | 6524 | N | THR | D | 427 | 42.256 | 66.998 | 25.961 | 1.00 | 30.15 | D |
| ATOM | 6525 | CA | THR | D | 427 | 41.892 | 68.083 | 26.800 | 1.00 | 29.42 | D |
| ATOM | 6526 | CB | THR | D | 427 | 40.394 | 68.173 | 26.858 | 1.00 | 29.82 | D |
| ATOM | 6527 | OG1 | THR | D | 427 | 39.772 | 68.382 | 25.562 | 1.00 | 30.96 | D |
| ATOM | 6528 | CG2 | THR | D | 427 | 40.011 | 69.345 | 27.767 | 1.00 | 29.85 | D |
| ATOM | 6529 | C | THR | D | 427 | 42.504 | 67.819 | 28.275 | 1.00 | 30.06 | D |

TABLE 2-continued

ATOMIC COORDINATES OF THE ERR3 LBD/
DIETHYLSTILBESTROL COMPLEX

| ATOM | 6530 | O | THR | D | 427 | 42.917 | 68.713 | 29.013 | 1.00 | 28.33 | D |
|---|---|---|---|---|---|---|---|---|---|---|---|
| ATOM | 6531 | N | SER | D | 428 | 42.558 | 66.548 | 28.655 | 1.00 | 29.78 | D |
| ATOM | 6532 | CA | SER | D | 428 | 43.140 | 66.209 | 29.964 | 1.00 | 30.45 | D |
| ATOM | 6533 | CB | SER | D | 428 | 42.827 | 64.797 | 30.220 | 1.00 | 30.13 | D |
| ATOM | 6534 | OG | SER | D | 428 | 41.355 | 64.796 | 30.398 | 1.00 | 34.07 | D |
| ATOM | 6535 | C | SER | D | 428 | 44.619 | 66.519 | 30.065 | 1.00 | 30.92 | D |
| ATOM | 6536 | O | SER | D | 428 | 45.106 | 67.070 | 31.081 | 1.00 | 29.51 | D |
| ATOM | 6537 | N | THR | D | 429 | 45.322 | 66.215 | 28.976 | 1.00 | 30.66 | D |
| ATOM | 6538 | CA | THR | D | 429 | 46.763 | 66.423 | 28.871 | 1.00 | 32.11 | D |
| ATOM | 6539 | CB | THR | D | 429 | 47.262 | 65.892 | 27.556 | 1.00 | 30.50 | D |
| ATOM | 6540 | OG1 | THR | D | 429 | 47.117 | 64.494 | 27.592 | 1.00 | 32.23 | D |
| ATOM | 6541 | CG2 | THR | D | 429 | 48.665 | 66.160 | 27.438 | 1.00 | 30.47 | D |
| ATOM | 6542 | C | THR | D | 429 | 47.032 | 67.931 | 28.949 | 1.00 | 32.32 | D |
| ATOM | 6543 | O | THR | D | 429 | 47.909 | 68.346 | 29.604 | 1.00 | 30.82 | D |
| ATOM | 6544 | N | LYS | D | 430 | 46.184 | 68.706 | 28.317 | 1.00 | 33.80 | D |
| ATOM | 6545 | CA | LYS | D | 430 | 46.272 | 70.119 | 28.474 | 1.00 | 34.77 | D |
| ATOM | 6546 | CB | LYS | D | 430 | 45.344 | 70.734 | 27.472 | 1.00 | 37.73 | D |
| ATOM | 6547 | CG | LYS | D | 430 | 45.281 | 72.220 | 27.448 | 1.00 | 41.85 | D |
| ATOM | 6548 | CD | LYS | D | 430 | 44.253 | 72.841 | 26.444 | 1.00 | 45.29 | D |
| ATOM | 6549 | CE | LYS | D | 430 | 44.451 | 74.435 | 26.401 | 1.00 | 46.71 | D |
| ATOM | 6550 | NZ | LYS | D | 430 | 44.687 | 75.007 | 25.060 | 1.00 | 48.27 | D |
| ATOM | 6551 | C | LYS | D | 430 | 46.093 | 70.684 | 29.882 | 1.00 | 34.17 | D |
| ATOM | 6552 | O | LYS | D | 430 | 46.829 | 71.593 | 30.308 | 1.00 | 34.19 | D |
| ATOM | 6553 | N | ALA | D | 431 | 45.073 | 70.224 | 30.543 | 1.00 | 33.01 | D |
| ATOM | 6554 | CA | ALA | D | 431 | 44.791 | 70.506 | 31.935 | 1.00 | 32.77 | D |
| ATOM | 6555 | CB | ALA | D | 431 | 43.464 | 69.793 | 32.346 | 1.00 | 31.31 | D |
| ATOM | 6556 | C | ALA | D | 431 | 45.959 | 70.075 | 32.873 | 1.00 | 33.52 | D |
| ATOM | 6557 | O | ALA | D | 431 | 46.415 | 70.869 | 33.717 | 1.00 | 33.58 | D |
| ATOM | 6558 | N | VAL | D | 432 | 46.549 | 68.923 | 32.635 | 1.00 | 33.85 | D |
| ATOM | 6559 | CA | VAL | D | 432 | 47.696 | 68.519 | 33.423 | 1.00 | 35.12 | D |
| ATOM | 6560 | CB | VAL | D | 432 | 47.963 | 67.042 | 33.223 | 1.00 | 35.27 | D |
| ATOM | 6561 | CG1 | VAL | D | 432 | 49.232 | 66.637 | 33.918 | 1.00 | 38.04 | D |
| ATOM | 6562 | CG2 | VAL | D | 432 | 46.883 | 66.222 | 33.786 | 1.00 | 33.69 | D |
| ATOM | 6563 | C | VAL | D | 432 | 48.959 | 69.395 | 33.125 | 1.00 | 35.83 | D |
| ATOM | 6564 | O | VAL | D | 432 | 49.726 | 69.690 | 33.954 | 1.00 | 34.13 | D |
| ATOM | 6565 | N | GLN | D | 433 | 49.151 | 69.827 | 31.909 | 1.00 | 37.52 | D |
| ATOM | 6566 | CA | GLN | D | 433 | 50.305 | 70.645 | 31.637 | 1.00 | 39.10 | D |
| ATOM | 6567 | CB | GLN | D | 433 | 50.552 | 70.764 | 30.140 | 1.00 | 41.11 | D |
| ATOM | 6568 | CG | GLN | D | 433 | 51.253 | 69.450 | 29.571 | 1.00 | 45.69 | D |
| ATOM | 6569 | CD | GLN | D | 433 | 51.459 | 69.331 | 27.992 | 1.00 | 47.66 | D |
| ATOM | 6570 | OE1 | GLN | D | 433 | 51.047 | 70.244 | 27.221 | 1.00 | 48.65 | D |
| ATOM | 6571 | NE2 | GLN | D | 433 | 52.127 | 68.200 | 27.539 | 1.00 | 49.64 | D |
| ATOM | 6572 | C | GLN | D | 433 | 50.091 | 72.044 | 32.237 | 1.00 | 39.38 | D |
| ATOM | 6573 | O | GLN | D | 433 | 51.041 | 72.699 | 32.712 | 1.00 | 39.96 | D |
| ATOM | 6574 | N | HIS | D | 434 | 48.859 | 72.529 | 32.197 | 1.00 | 38.68 | D |
| ATOM | 6575 | CA | HIS | D | 434 | 48.559 | 73.855 | 32.752 | 1.00 | 39.38 | D |
| ATOM | 6576 | CB | HIS | D | 434 | 47.146 | 74.279 | 32.373 | 1.00 | 40.25 | D |
| ATOM | 6577 | CG | HIS | D | 434 | 46.755 | 75.610 | 32.870 | 1.00 | 41.82 | D |
| ATOM | 6578 | CD2 | HIS | D | 434 | 46.411 | 76.740 | 32.208 | 1.00 | 43.57 | D |
| ATOM | 6579 | ND1 | HIS | D | 434 | 46.618 | 75.891 | 34.208 | 1.00 | 42.16 | D |
| ATOM | 6580 | CE1 | HIS | D | 434 | 46.224 | 77.144 | 34.346 | 1.00 | 42.72 | D |
| ATOM | 6581 | NE2 | HIS | D | 434 | 46.062 | 77.677 | 33.150 | 1.00 | 43.58 | D |
| ATOM | 6582 | C | HIS | D | 434 | 48.741 | 73.835 | 34.290 | 1.00 | 39.19 | D |
| ATOM | 6583 | O | HIS | D | 434 | 49.326 | 74.737 | 34.834 | 1.00 | 37.86 | D |
| ATOM | 6584 | N | PHE | D | 435 | 48.218 | 72.798 | 34.932 | 1.00 | 39.59 | D |
| ATOM | 6585 | CA | PHE | D | 435 | 48.519 | 72.540 | 36.289 | 1.00 | 41.49 | D |
| ATOM | 6586 | CB | PHE | D | 435 | 47.826 | 71.282 | 36.729 | 1.00 | 41.10 | D |
| ATOM | 6587 | CG | PHE | D | 435 | 48.131 | 70.831 | 38.171 | 1.00 | 42.13 | D |
| ATOM | 6588 | CD1 | PHE | D | 435 | 47.678 | 71.501 | 39.253 | 1.00 | 42.45 | D |
| ATOM | 6589 | CD2 | PHE | D | 435 | 48.820 | 69.654 | 38.412 | 1.00 | 43.25 | D |
| ATOM | 6590 | CE1 | PHE | D | 435 | 47.916 | 71.076 | 40.551 | 1.00 | 42.92 | D |
| ATOM | 6591 | CE2 | PHE | D | 435 | 49.018 | 69.188 | 39.727 | 1.00 | 44.34 | D |
| ATOM | 6592 | CZ | PHE | D | 435 | 48.569 | 69.936 | 40.781 | 1.00 | 44.14 | D |
| ATOM | 6593 | C | PHE | D | 435 | 50.037 | 72.548 | 36.595 | 1.00 | 43.38 | D |
| ATOM | 6594 | O | PHE | D | 435 | 50.458 | 73.176 | 37.572 | 1.00 | 42.72 | D |
| ATOM | 6595 | N | TYR | D | 436 | 50.865 | 71.905 | 35.782 | 1.00 | 46.05 | D |
| ATOM | 6596 | CA | TYR | D | 436 | 52.294 | 71.702 | 36.111 | 1.00 | 48.06 | D |
| ATOM | 6597 | CB | TYR | D | 436 | 52.938 | 70.506 | 35.340 | 1.00 | 49.24 | D |
| ATOM | 6598 | CG | TYR | D | 436 | 52.550 | 69.005 | 35.745 | 1.00 | 51.18 | D |
| ATOM | 6599 | CD1 | TYR | D | 436 | 51.946 | 68.708 | 36.932 | 1.00 | 52.70 | D |
| ATOM | 6600 | CE1 | TYR | D | 436 | 51.568 | 67.381 | 37.304 | 1.00 | 53.78 | D |
| ATOM | 6601 | CD2 | TYR | D | 436 | 52.837 | 67.884 | 34.902 | 1.00 | 52.76 | D |
| ATOM | 6602 | CE2 | TYR | D | 436 | 52.532 | 66.513 | 35.301 | 1.00 | 53.05 | D |
| ATOM | 6603 | CZ | TYR | D | 436 | 51.857 | 66.286 | 36.525 | 1.00 | 53.99 | D |
| ATOM | 6604 | OH | TYR | D | 436 | 51.385 | 65.020 | 37.052 | 1.00 | 54.12 | D |
| ATOM | 6605 | C | TYR | D | 436 | 52.999 | 73.056 | 35.910 | 1.00 | 49.20 | D |

TABLE 2-continued

ATOMIC COORDINATES OF THE ERR3 LBD/
DIETHYLSTILBESTROL COMPLEX

| ATOM | 6606 | O | TYR | D | 436 | 53.903 | 73.379 | 36.619 | 1.00 | 49.26 | D |
| --- | --- | --- | --- | --- | --- | --- | --- | --- | --- | --- | --- |
| ATOM | 6607 | N | ASN | D | 437 | 52.516 | 73.910 | 35.034 | 1.00 | 50.56 | D |
| ATOM | 6608 | CA | ASN | D | 437 | 53.063 | 75.265 | 34.925 | 1.00 | 53.00 | D |
| ATOM | 6609 | CB | ASN | D | 437 | 52.584 | 76.019 | 33.674 | 1.00 | 55.42 | D |
| ATOM | 6610 | CG | ASN | D | 437 | 53.309 | 77.337 | 33.469 | 1.00 | 59.33 | D |
| ATOM | 6611 | OD1 | ASN | D | 437 | 54.531 | 77.369 | 33.318 | 1.00 | 61.15 | D |
| ATOM | 6612 | ND2 | ASN | D | 437 | 52.558 | 78.431 | 33.464 | 1.00 | 59.05 | D |
| ATOM | 6613 | C | ASN | D | 437 | 52.696 | 76.121 | 36.098 | 1.00 | 53.39 | D |
| ATOM | 6614 | O | ASN | D | 437 | 53.451 | 77.024 | 36.471 | 1.00 | 54.17 | D |
| ATOM | 6615 | N | ILE | D | 438 | 51.529 | 75.883 | 36.672 | 1.00 | 52.88 | D |
| ATOM | 6616 | CA | ILE | D | 438 | 51.106 | 76.657 | 37.818 | 1.00 | 53.13 | D |
| ATOM | 6617 | CB | ILE | D | 438 | 49.618 | 76.520 | 38.035 | 1.00 | 52.03 | D |
| ATOM | 6618 | CG2 | ILE | D | 438 | 49.231 | 76.978 | 39.317 | 1.00 | 51.53 | D |
| ATOM | 6619 | CG1 | ILE | D | 438 | 48.909 | 77.383 | 37.002 | 1.00 | 52.94 | D |
| ATOM | 6620 | CD1 | ILE | D | 438 | 49.564 | 78.717 | 36.752 | 1.00 | 53.40 | D |
| ATOM | 6621 | C | ILE | D | 438 | 51.886 | 76.259 | 39.025 | 1.00 | 52.95 | D |
| ATOM | 6622 | O | ILE | D | 438 | 52.068 | 77.064 | 39.890 | 1.00 | 52.88 | D |
| ATOM | 6623 | N | LYS | D | 439 | 52.313 | 74.998 | 39.032 | 1.00 | 53.10 | D |
| ATOM | 6624 | CA | LYS | D | 439 | 53.026 | 74.385 | 40.149 | 1.00 | 53.31 | D |
| ATOM | 6625 | CB | LYS | D | 439 | 52.984 | 72.875 | 40.073 | 1.00 | 53.51 | D |
| ATOM | 6626 | CG | LYS | D | 439 | 53.907 | 72.129 | 40.972 | 1.00 | 54.17 | D |
| ATOM | 6627 | CD | LYS | D | 439 | 53.193 | 70.916 | 41.506 | 1.00 | 55.99 | D |
| ATOM | 6628 | CE | LYS | D | 439 | 53.952 | 70.238 | 42.710 | 1.00 | 57.02 | D |
| ATOM | 6629 | NZ | LYS | D | 439 | 55.494 | 70.178 | 42.660 | 1.00 | 56.36 | D |
| ATOM | 6630 | C | LYS | D | 439 | 54.461 | 74.862 | 40.112 | 1.00 | 54.32 | D |
| ATOM | 6631 | O | LYS | D | 439 | 55.009 | 75.144 | 41.171 | 1.00 | 53.34 | D |
| ATOM | 6632 | N | LEU | D | 440 | 55.058 | 75.027 | 38.915 | 1.00 | 55.61 | D |
| ATOM | 6633 | CA | LEU | D | 440 | 56.401 | 75.617 | 38.928 | 1.00 | 57.32 | D |
| ATOM | 6634 | CB | LEU | D | 440 | 57.068 | 75.705 | 37.550 | 1.00 | 57.31 | D |
| ATOM | 6635 | CG | LEU | D | 440 | 57.396 | 74.395 | 36.883 | 1.00 | 57.38 | D |
| ATOM | 6636 | CD1 | LEU | D | 440 | 58.159 | 74.721 | 35.484 | 1.00 | 57.76 | D |
| ATOM | 6637 | CD2 | LEU | D | 440 | 58.117 | 73.519 | 37.959 | 1.00 | 58.19 | D |
| ATOM | 6638 | C | LEU | D | 440 | 56.404 | 77.029 | 39.463 | 1.00 | 58.14 | D |
| ATOM | 6639 | O | LEU | D | 440 | 57.438 | 77.469 | 39.907 | 1.00 | 58.54 | D |
| ATOM | 6640 | N | GLU | D | 441 | 55.292 | 77.748 | 39.330 | 1.00 | 58.75 | D |
| ATOM | 6641 | CA | GLU | D | 441 | 55.203 | 79.162 | 39.728 | 1.00 | 59.66 | D |
| ATOM | 6642 | CB | GLU | D | 441 | 54.131 | 79.851 | 38.855 | 1.00 | 62.44 | D |
| ATOM | 6643 | CG | GLU | D | 441 | 53.915 | 81.344 | 39.200 | 1.00 | 68.52 | D |
| ATOM | 6644 | CD | GLU | D | 441 | 55.145 | 82.194 | 38.937 | 1.00 | 72.05 | D |
| ATOM | 6645 | OE1 | GLU | D | 441 | 55.610 | 82.229 | 37.778 | 1.00 | 73.51 | D |
| ATOM | 6646 | OE2 | GLU | D | 441 | 55.645 | 82.829 | 39.889 | 1.00 | 74.01 | D |
| ATOM | 6647 | C | GLU | D | 441 | 54.919 | 79.363 | 41.231 | 1.00 | 58.43 | D |
| ATOM | 6648 | O | GLU | D | 441 | 54.734 | 80.503 | 41.694 | 1.00 | 57.53 | D |
| ATOM | 6649 | N | GLY | D | 442 | 54.878 | 78.267 | 41.993 | 1.00 | 57.46 | D |
| ATOM | 6650 | CA | GLY | D | 442 | 54.431 | 78.312 | 43.339 | 1.00 | 58.07 | D |
| ATOM | 6651 | C | GLY | D | 442 | 52.963 | 78.697 | 43.540 | 1.00 | 58.83 | D |
| ATOM | 6652 | O | GLY | D | 442 | 52.640 | 79.008 | 44.686 | 1.00 | 58.54 | D |
| ATOM | 6653 | N | LYS | D | 443 | 52.074 | 78.676 | 42.516 | 1.00 | 59.07 | D |
| ATOM | 6654 | CA | LYS | D | 443 | 50.621 | 79.060 | 42.728 | 1.00 | 59.64 | D |
| ATOM | 6655 | CB | LYS | D | 443 | 49.989 | 79.887 | 41.536 | 1.00 | 60.06 | D |
| ATOM | 6656 | CG | LYS | D | 443 | 51.031 | 80.649 | 40.603 | 1.00 | 60.92 | D |
| ATOM | 6657 | CD | LYS | D | 443 | 50.627 | 82.123 | 40.176 | 1.00 | 61.53 | D |
| ATOM | 6658 | CE | LYS | D | 443 | 50.864 | 82.396 | 38.669 | 1.00 | 61.97 | D |
| ATOM | 6659 | NZ | LYS | D | 443 | 49.517 | 82.396 | 37.947 | 1.00 | 62.02 | D |
| ATOM | 6660 | C | LYS | D | 443 | 49.681 | 77.885 | 43.189 | 1.00 | 59.34 | D |
| ATOM | 6661 | O | LYS | D | 443 | 48.431 | 77.957 | 43.040 | 1.00 | 59.44 | D |
| ATOM | 6662 | N | VAL | D | 444 | 50.322 | 76.846 | 43.733 | 1.00 | 58.68 | D |
| ATOM | 6663 | CA | VAL | D | 444 | 49.695 | 75.550 | 43.990 | 1.00 | 58.10 | D |
| ATOM | 6664 | CB | VAL | D | 444 | 50.305 | 74.395 | 43.071 | 1.00 | 57.43 | D |
| ATOM | 6665 | CG1 | VAL | D | 444 | 49.764 | 72.987 | 43.443 | 1.00 | 57.12 | D |
| ATOM | 6666 | CG2 | VAL | D | 444 | 50.054 | 74.574 | 41.826 | 0.00 | 57.58 | D |
| ATOM | 6667 | C | VAL | D | 444 | 49.832 | 75.293 | 45.499 | 1.00 | 57.65 | D |
| ATOM | 6668 | O | VAL | D | 444 | 50.919 | 75.297 | 46.040 | 1.00 | 57.59 | D |
| ATOM | 6669 | N | PRO | D | 445 | 48.720 | 75.085 | 46.195 | 1.00 | 57.56 | D |
| ATOM | 6670 | CD | PRO | D | 445 | 47.369 | 74.874 | 45.680 | 1.00 | 57.80 | D |
| ATOM | 6671 | CA | PRO | D | 445 | 48.785 | 74.864 | 47.633 | 1.00 | 57.34 | D |
| ATOM | 6672 | CB | PRO | D | 445 | 47.330 | 74.788 | 48.042 | 1.00 | 57.13 | D |
| ATOM | 6673 | CG | PRO | D | 445 | 46.648 | 74.243 | 46.821 | 1.00 | 57.55 | D |
| ATOM | 6674 | C | PRO | D | 445 | 49.516 | 73.535 | 47.818 | 1.00 | 57.00 | D |
| ATOM | 6675 | O | PRO | D | 445 | 49.375 | 72.644 | 46.988 | 1.00 | 56.38 | D |
| ATOM | 6676 | N | MET | D | 446 | 50.303 | 73.454 | 48.884 | 1.00 | 56.34 | D |
| ATOM | 6677 | CA | MET | D | 446 | 51.258 | 72.368 | 49.098 | 1.00 | 54.93 | D |
| ATOM | 6678 | CB | MET | D | 446 | 52.491 | 72.800 | 49.954 | 1.00 | 58.31 | D |
| ATOM | 6679 | CG | MET | D | 446 | 52.285 | 73.942 | 51.020 | 1.00 | 62.29 | D |
| ATOM | 6680 | SD | MET | D | 446 | 50.961 | 75.241 | 50.623 | 1.00 | 68.68 | D |
| ATOM | 6681 | CE | MET | D | 446 | 51.850 | 76.891 | 49.905 | 0.00 | 66.14 | D |

TABLE 2-continued

ATOMIC COORDINATES OF THE ERR3 LBD/
DIETHYLSTILBESTROL COMPLEX

| ATOM | 6682 | C   | MET | D | 446 | 50.414 | 71.315 | 49.752 | 1.00 | 52.18 | D |
|------|------|-----|-----|---|-----|--------|--------|--------|------|-------|---|
| ATOM | 6683 | O   | MET | D | 446 | 49.283 | 71.582 | 50.147 | 1.00 | 50.45 | D |
| ATOM | 6684 | N   | HIS | D | 447 | 50.957 | 70.090 | 49.727 | 1.00 | 50.10 | D |
| ATOM | 6685 | CA  | HIS | D | 447 | 50.413 | 68.876 | 50.376 | 1.00 | 48.30 | D |
| ATOM | 6686 | CB  | HIS | D | 447 | 50.727 | 68.908 | 51.889 | 1.00 | 49.07 | D |
| ATOM | 6687 | CG  | HIS | D | 447 | 52.149 | 69.323 | 52.156 | 1.00 | 50.54 | D |
| ATOM | 6688 | CD2 | HIS | D | 447 | 53.311 | 68.884 | 51.593 | 1.00 | 50.94 | D |
| ATOM | 6689 | ND1 | HIS | D | 447 | 52.493 | 70.348 | 53.029 | 1.00 | 50.95 | D |
| ATOM | 6690 | CE1 | HIS | D | 447 | 53.806 | 70.505 | 53.009 | 1.00 | 50.68 | D |
| ATOM | 6691 | NE2 | HIS | D | 447 | 54.326 | 69.634 | 52.141 | 1.00 | 51.91 | D |
| ATOM | 6692 | C   | HIS | D | 447 | 48.970 | 68.470 | 50.090 | 1.00 | 45.97 | D |
| ATOM | 6693 | O   | HIS | D | 447 | 48.295 | 67.831 | 50.963 | 1.00 | 46.21 | D |
| ATOM | 6694 | N   | LYS | D | 448 | 48.548 | 68.674 | 48.842 | 1.00 | 43.07 | D |
| ATOM | 6695 | CA  | LYS | D | 448 | 47.408 | 67.924 | 48.329 | 1.00 | 41.13 | D |
| ATOM | 6696 | CB  | LYS | D | 448 | 46.822 | 68.533 | 47.074 | 1.00 | 40.15 | D |
| ATOM | 6697 | CG  | LYS | D | 448 | 46.583 | 70.017 | 47.180 | 1.00 | 41.09 | D |
| ATOM | 6698 | CD  | LYS | D | 448 | 46.172 | 70.473 | 48.605 | 1.00 | 41.23 | D |
| ATOM | 6699 | CE  | LYS | D | 448 | 44.800 | 70.431 | 48.936 | 1.00 | 41.82 | D |
| ATOM | 6700 | NZ  | LYS | D | 448 | 44.459 | 71.545 | 49.990 | 1.00 | 44.34 | D |
| ATOM | 6701 | C   | LYS | D | 448 | 47.878 | 66.503 | 48.039 | 1.00 | 39.83 | D |
| ATOM | 6702 | O   | LYS | D | 448 | 48.421 | 66.215 | 46.929 | 1.00 | 39.63 | D |
| ATOM | 6703 | N   | LEU | D | 449 | 47.643 | 65.644 | 49.013 | 1.00 | 37.61 | D |
| ATOM | 6704 | CA  | LEU | D | 449 | 48.268 | 64.322 | 49.092 | 1.00 | 37.17 | D |
| ATOM | 6705 | CB  | LEU | D | 449 | 47.852 | 63.609 | 50.437 | 1.00 | 35.74 | D |
| ATOM | 6706 | CG  | LEU | D | 449 | 48.425 | 64.371 | 51.655 | 1.00 | 35.56 | D |
| ATOM | 6707 | CD1 | LEU | D | 449 | 48.146 | 63.691 | 52.911 | 1.00 | 34.47 | D |
| ATOM | 6708 | CD2 | LEU | D | 449 | 49.888 | 64.644 | 51.580 | 1.00 | 33.16 | D |
| ATOM | 6709 | C   | LEU | D | 449 | 47.759 | 63.476 | 47.954 | 1.00 | 36.84 | D |
| ATOM | 6710 | O   | LEU | D | 449 | 48.464 | 62.647 | 47.420 | 1.00 | 36.94 | D |
| ATOM | 6711 | N   | PHE | D | 450 | 46.466 | 63.672 | 47.596 | 1.00 | 36.47 | D |
| ATOM | 6712 | CA  | PHE | D | 450 | 45.877 | 62.901 | 46.544 | 1.00 | 34.30 | D |
| ATOM | 6713 | CB  | PHE | D | 450 | 44.443 | 62.599 | 46.823 | 1.00 | 33.58 | D |
| ATOM | 6714 | CG  | PHE | D | 450 | 44.262 | 61.876 | 48.117 | 1.00 | 34.03 | D |
| ATOM | 6715 | CD1 | PHE | D | 450 | 44.398 | 60.511 | 48.162 | 1.00 | 34.09 | D |
| ATOM | 6716 | CD2 | PHE | D | 450 | 43.900 | 62.543 | 49.255 | 1.00 | 34.34 | D |
| ATOM | 6717 | CE1 | PHE | D | 450 | 44.186 | 59.808 | 49.289 | 1.00 | 33.19 | D |
| ATOM | 6718 | CE2 | PHE | D | 450 | 43.710 | 61.856 | 50.421 | 1.00 | 34.67 | D |
| ATOM | 6719 | CZ  | PHE | D | 450 | 43.897 | 60.462 | 50.442 | 1.00 | 34.16 | D |
| ATOM | 6720 | C   | PHE | D | 450 | 46.246 | 63.304 | 45.169 | 1.00 | 33.54 | D |
| ATOM | 6721 | O   | PHE | D | 450 | 46.553 | 62.407 | 44.424 | 1.00 | 33.23 | D |
| ATOM | 6722 | N   | LEU | D | 451 | 46.294 | 64.607 | 44.808 | 1.00 | 32.43 | D |
| ATOM | 6723 | CA  | LEU | D | 451 | 46.838 | 64.988 | 43.562 | 1.00 | 31.77 | D |
| ATOM | 6724 | CB  | LEU | D | 451 | 46.954 | 66.496 | 43.431 | 1.00 | 31.37 | D |
| ATOM | 6725 | CG  | LEU | D | 451 | 45.697 | 67.237 | 42.981 | 1.00 | 29.95 | D |
| ATOM | 6726 | CD1 | LEU | D | 451 | 45.630 | 68.697 | 43.412 | 1.00 | 29.92 | D |
| ATOM | 6727 | CD2 | LEU | D | 451 | 45.558 | 66.955 | 41.449 | 1.00 | 29.42 | D |
| ATOM | 6728 | C   | LEU | D | 451 | 48.282 | 64.460 | 43.534 | 1.00 | 33.10 | D |
| ATOM | 6729 | O   | LEU | D | 451 | 48.746 | 63.991 | 42.509 | 1.00 | 33.77 | D |
| ATOM | 6730 | N   | GLU | D | 452 | 48.976 | 64.476 | 44.683 | 1.00 | 33.31 | D |
| ATOM | 6731 | CA  | GLU | D | 452 | 50.390 | 64.021 | 44.737 | 1.00 | 34.39 | D |
| ATOM | 6732 | CB  | GLU | D | 452 | 51.118 | 64.484 | 45.999 | 1.00 | 34.32 | D |
| ATOM | 6733 | CG  | GLU | D | 452 | 51.406 | 66.027 | 45.993 | 1.00 | 37.51 | D |
| ATOM | 6734 | CD  | GLU | D | 452 | 51.964 | 66.605 | 47.306 | 1.00 | 39.36 | D |
| ATOM | 6735 | OE1 | GLU | D | 452 | 51.932 | 65.807 | 48.288 | 1.00 | 39.90 | D |
| ATOM | 6736 | OE2 | GLU | D | 452 | 52.639 | 67.511 | 47.339 | 0.00 | 38.97 | D |
| ATOM | 6737 | C   | GLU | D | 452 | 50.524 | 62.525 | 44.520 | 1.00 | 34.30 | D |
| ATOM | 6738 | O   | GLU | D | 452 | 51.327 | 62.107 | 43.772 | 1.00 | 34.72 | D |
| ATOM | 6739 | N   | MET | D | 453 | 49.606 | 61.749 | 45.046 | 1.00 | 33.39 | D |
| ATOM | 6740 | CA  | MET | D | 453 | 49.735 | 60.391 | 44.940 | 1.00 | 33.65 | D |
| ATOM | 6741 | CB  | MET | D | 453 | 48.598 | 59.804 | 45.773 | 1.00 | 32.70 | D |
| ATOM | 6742 | CG  | MET | D | 453 | 48.528 | 58.225 | 45.858 | 1.00 | 30.04 | D |
| ATOM | 6743 | SD  | MET | D | 453 | 47.125 | 57.644 | 46.683 | 1.00 | 32.64 | D |
| ATOM | 6744 | CE  | MET | D | 453 | 47.555 | 58.466 | 48.212 | 1.00 | 30.06 | D |
| ATOM | 6745 | C   | MET | D | 453 | 49.528 | 60.045 | 43.458 | 1.00 | 34.86 | D |
| ATOM | 6746 | O   | MET | D | 453 | 49.877 | 58.919 | 43.031 | 1.00 | 35.41 | D |
| ATOM | 6747 | N   | LEU | D | 454 | 48.715 | 60.850 | 42.743 | 1.00 | 35.33 | D |
| ATOM | 6748 | CA  | LEU | D | 454 | 48.259 | 60.414 | 41.466 | 1.00 | 36.48 | D |
| ATOM | 6749 | CB  | LEU | D | 454 | 46.713 | 60.610 | 41.231 | 1.00 | 35.76 | D |
| ATOM | 6750 | CG  | LEU | D | 454 | 45.701 | 59.837 | 42.067 | 1.00 | 35.86 | D |
| ATOM | 6751 | CD1 | LEU | D | 454 | 44.354 | 60.057 | 41.580 | 1.00 | 35.53 | D |
| ATOM | 6752 | CD2 | LEU | D | 454 | 45.942 | 58.377 | 41.805 | 1.00 | 37.92 | D |
| ATOM | 6753 | C   | LEU | D | 454 | 49.145 | 60.996 | 40.377 | 1.00 | 38.67 | D |
| ATOM | 6754 | O   | LEU | D | 454 | 49.020 | 60.574 | 39.242 | 1.00 | 36.83 | D |
| ATOM | 6755 | N   | GLU | D | 455 | 50.074 | 61.873 | 40.725 | 1.00 | 43.25 | D |
| ATOM | 6756 | CA  | GLU | D | 455 | 51.045 | 62.375 | 39.762 | 1.00 | 49.81 | D |
| ATOM | 6757 | CB  | GLU | D | 455 | 51.681 | 63.740 | 40.184 | 1.00 | 53.44 | D |

TABLE 2-continued

ATOMIC COORDINATES OF THE ERR3 LBD/
DIETHYLSTILBESTROL COMPLEX

| ATOM | 6758 | CG | GLU | D | 455 | 52.048 | 63.714 | 41.673 | 1.00 | 61.61 | D |
|---|---|---|---|---|---|---|---|---|---|---|---|
| ATOM | 6759 | CD | GLU | D | 455 | 53.059 | 62.589 | 42.051 | 1.00 | 65.79 | D |
| ATOM | 6760 | OE1 | GLU | D | 455 | 54.273 | 62.869 | 42.187 | 1.00 | 67.94 | D |
| ATOM | 6761 | OE2 | GLU | D | 455 | 52.640 | 61.420 | 42.193 | 1.00 | 68.76 | D |
| ATOM | 6762 | C | GLU | D | 455 | 52.111 | 61.297 | 39.326 | 1.00 | 51.44 | D |
| ATOM | 6763 | O | GLU | D | 455 | 52.396 | 60.256 | 40.032 | 1.00 | 52.39 | D |
| ATOM | 6764 | OXT | GLU | D | 455 | 52.754 | 61.635 | 38.304 | 1.00 | 55.75 | D |
| ATOM | 6765 | CP9 | DES | $ | 600 | 59.583 | 35.283 | 56.086 | 1.00 | 44.29 | $ |
| ATOM | 6766 | CP8 | DES | $ | 600 | 59.152 | 35.876 | 57.378 | 1.00 | 44.56 | $ |
| ATOM | 6767 | CP7 | DES | $ | 600 | 58.707 | 34.844 | 58.420 | 1.00 | 41.65 | $ |
| ATOM | 6768 | CP6 | DES | $ | 600 | 59.818 | 33.910 | 58.847 | 1.00 | 42.04 | $ |
| ATOM | 6769 | CP1 | DES | $ | 600 | 60.754 | 34.296 | 59.814 | 1.00 | 40.79 | $ |
| ATOM | 6770 | CP2 | DES | $ | 600 | 61.814 | 33.450 | 60.155 | 1.00 | 41.03 | $ |
| ATOM | 6771 | CP3 | DES | $ | 600 | 61.939 | 32.211 | 59.531 | 1.00 | 42.34 | $ |
| ATOM | 6772 | OP3 | DES | $ | 600 | 62.998 | 31.356 | 59.808 | 1.00 | 45.22 | $ |
| ATOM | 6773 | CP4 | DES | $ | 600 | 61.021 | 31.806 | 58.575 | 1.00 | 43.48 | $ |
| ATOM | 6774 | CP5 | DES | $ | 600 | 59.963 | 32.663 | 58.244 | 1.00 | 43.33 | $ |
| ATOM | 6775 | C7 | DES | $ | 600 | 57.479 | 34.735 | 58.890 | 1.00 | 40.39 | $ |
| ATOM | 6776 | C6 | DES | $ | 600 | 56.312 | 35.476 | 58.298 | 1.00 | 38.80 | $ |
| ATOM | 6777 | C5 | DES | $ | 600 | 55.779 | 35.091 | 57.063 | 1.00 | 37.33 | $ |
| ATOM | 6778 | C4 | DES | $ | 600 | 54.680 | 35.758 | 56.510 | 1.00 | 37.34 | $ |
| ATOM | 6779 | C3 | DES | $ | 600 | 54.109 | 36.835 | 57.192 | 1.00 | 36.60 | $ |
| ATOM | 6780 | O3 | DES | $ | 600 | 53.021 | 37.531 | 56.673 | 1.00 | 34.89 | $ |
| ATOM | 6781 | C2 | DES | $ | 600 | 54.623 | 37.247 | 58.437 | 1.00 | 38.03 | $ |
| ATOM | 6782 | C1 | DES | $ | 600 | 55.729 | 36.561 | 58.973 | 1.00 | 37.81 | $ |
| ATOM | 6783 | C8 | DES | $ | 600 | 57.086 | 33.816 | 60.032 | 1.00 | 38.59 | $ |
| ATOM | 6784 | C9 | DES | $ | 600 | 57.175 | 34.471 | 61.377 | 1.00 | 37.94 | $ |
| ATOM | 6785 | CP9 | DES | $ | 700 | 76.983 | 48.154 | 80.257 | 1.00 | 36.10 | $ |
| ATOM | 6786 | CP8 | DES | $ | 700 | 76.145 | 48.785 | 79.205 | 1.00 | 38.05 | $ |
| ATOM | 6787 | CP7 | DES | $ | 700 | 76.949 | 49.433 | 78.073 | 1.00 | 37.86 | $ |
| ATOM | 6788 | CP6 | DES | $ | 700 | 77.771 | 48.441 | 77.280 | 1.00 | 38.66 | $ |
| ATOM | 6789 | CP1 | DES | $ | 700 | 77.192 | 47.676 | 76.261 | 1.00 | 38.79 | $ |
| ATOM | 6790 | CP2 | DES | $ | 700 | 77.945 | 46.716 | 75.577 | 1.00 | 37.65 | $ |
| ATOM | 6791 | CP3 | DES | $ | 700 | 79.283 | 46.521 | 75.910 | 1.00 | 39.13 | $ |
| ATOM | 6792 | OP3 | DES | $ | 700 | 80.058 | 45.551 | 75.286 | 1.00 | 38.33 | $ |
| ATOM | 6793 | CP4 | DES | $ | 700 | 79.878 | 47.270 | 76.912 | 1.00 | 38.69 | $ |
| ATOM | 6794 | CP5 | DES | $ | 700 | 79.113 | 48.230 | 77.587 | 1.00 | 39.91 | $ |
| ATOM | 6795 | C7 | DES | $ | 700 | 76.969 | 50.727 | 77.814 | 1.00 | 36.78 | $ |
| ATOM | 6796 | C6 | DES | $ | 700 | 76.370 | 5.752 | 78.737 | 1.00 | 34.94 | $ |
| ATOM | 6797 | C5 | DES | $ | 700 | 77.000 | 52.073 | 79.945 | 1.00 | 32.84 | $ |
| ATOM | 6798 | C4 | DES | $ | 700 | 76.465 | 53.040 | 80.804 | 1.00 | 32.73 | $ |
| ATOM | 6799 | C3 | DES | $ | 700 | 75.276 | 53.689 | 80.461 | 1.00 | 30.96 | $ |
| ATOM | 6800 | O3 | DES | $ | 700 | 74.706 | 54.650 | 81.291 | 1.00 | 37.03 | $ |
| ATOM | 6801 | C2 | DES | $ | 700 | 74.619 | 53.387 | 79.253 | 1.00 | 33.54 | $ |
| ATOM | 6802 | C1 | DES | $ | 700 | 75.175 | 52.411 | 78.405 | 1.00 | 32.19 | $ |
| ATOM | 6803 | C8 | DES | $ | 700 | 77.642 | 51.338 | 76.599 | 1.00 | 37.27 | $ |
| ATOM | 6804 | C9 | DES | $ | 700 | 76.729 | 51.465 | 75.417 | 1.00 | 36.87 | $ |
| ATOM | 6805 | CP9 | DES | $ | 800 | 58.392 | 66.470 | 11.787 | 1.00 | 36.89 | $ |
| ATOM | 6806 | CP8 | DES | $ | 800 | 57.835 | 65.322 | 12.574 | 1.00 | 37.57 | $ |
| ATOM | 6807 | CP7 | DES | $ | 800 | 58.885 | 64.476 | 13.285 | 1.00 | 36.68 | $ |
| ATOM | 6808 | CP6 | DES | $ | 800 | 59.741 | 65.265 | 14.257 | 1.00 | 37.00 | $ |
| ATOM | 6809 | CP1 | DES | $ | 800 | 59.295 | 65.550 | 15.558 | 1.00 | 37.96 | $ |
| ATOM | 6810 | CP2 | DES | $ | 800 | 60.093 | 66.313 | 16.440 | 1.00 | 38.77 | $ |
| ATOM | 6811 | CP3 | DES | $ | 800 | 61.332 | 66.785 | 16.009 | 1.00 | 37.48 | $ |
| ATOM | 6812 | OP3 | DES | $ | 800 | 62.142 | 67.562 | 16.819 | 1.00 | 40.48 | $ |
| ATOM | 6813 | CP4 | DES | $ | 800 | 61.789 | 66.507 | 14.719 | 1.00 | 38.44 | $ |
| ATOM | 6814 | CP5 | DES | $ | 800 | 60.989 | 65.753 | 13.863 | 1.00 | 37.77 | $ |
| ATOM | 6815 | C7 | DES | $ | 800 | 59.061 | 63.184 | 13.072 | 1.00 | 35.87 | $ |
| ATOM | 6816 | C6 | DES | $ | 800 | 58.342 | 62.442 | 11.949 | 1.00 | 33.58 | $ |
| ATOM | 6817 | C5 | DES | $ | 800 | 58.794 | 62.538 | 10.627 | 1.00 | 33.31 | $ |
| ATOM | 6818 | C4 | DES | $ | 800 | 58.153 | 61.842 | 9.592 | 1.00 | 34.15 | $ |
| ATOM | 6819 | C3 | DES | $ | 800 | 57.049 | 61.045 | 9.876 | 1.00 | 34.29 | $ |
| ATOM | 6820 | O3 | DES | $ | 800 | 56.380 | 60.355 | 8.883 | 1.00 | 31.98 | $ |
| ATOM | 6821 | C2 | DES | $ | 800 | 56.574 | 60.928 | 11.187 | 1.00 | 31.26 | $ |
| ATOM | 6822 | C1 | DES | $ | 800 | 57.231 | 61.636 | 12.210 | 1.00 | 30.97 | $ |
| ATOM | 6823 | C8 | DES | $ | 800 | 60.027 | 62.301 | 13.866 | 1.00 | 36.20 | $ |
| ATOM | 6824 | C9 | DES | $ | 800 | 59.396 | 61.568 | 15.024 | 1.00 | 35.80 | $ |
| ATOM | 6825 | CP9 | DES | $ | 900 | 43.420 | 70.380 | 39.573 | 1.00 | 35.28 | $ |
| ATOM | 6826 | CP8 | DES | $ | 900 | 42.991 | 70.170 | 38.166 | 1.00 | 38.99 | $ |
| ATOM | 6827 | CP7 | DES | $ | 900 | 42.425 | 71.426 | 37.493 | 1.00 | 35.89 | $ |
| ATOM | 6828 | CP6 | DES | $ | 900 | 43.439 | 72.540 | 37.360 | 1.00 | 35.70 | $ |
| ATOM | 6829 | CP1 | DES | $ | 900 | 44.367 | 72.549 | 36.311 | 1.00 | 34.80 | $ |
| ATOM | 6830 | CP2 | DES | $ | 900 | 45.341 | 73.549 | 36.232 | 1.00 | 35.39 | $ |
| ATOM | 6831 | CP3 | DES | $ | 900 | 45.388 | 74.547 | 37.203 | 1.00 | 35.89 | $ |
| ATOM | 6832 | OP3 | DES | $ | 900 | 46.363 | 75.536 | 37.189 | 1.00 | 37.60 | $ |
| ATOM | 6833 | CP4 | DES | $ | 900 | 44.477 | 74.561 | 38.247 | 1.00 | 35.22 | $ |

TABLE 2-continued

ATOMIC COORDINATES OF THE ERR3 LBD/
DIETHYLSTILBESTROL COMPLEX

| ATOM | 6834 | CP5 | DES | $ | 900 | 43.505 | 73.553 | 38.312 | 1.00 | 35.61 | $ |
|------|------|-----|-----|---|-----|--------|--------|--------|------|-------|---|
| ATOM | 6835 | C7  | DES | $ | 900 | 41.175 | 71.562 | 37.092 | 1.00 | 33.83 | $ |
| ATOM | 6836 | C6  | DES | $ | 900 | 40.095 | 70.576 | 37.443 | 1.00 | 29.81 | $ |
| ATOM | 6837 | C5  | DES | $ | 900 | 39.579 | 70.520 | 38.742 | 1.00 | 28.05 | $ |
| ATOM | 6838 | C4  | DES | $ | 900 | 38.559 | 69.623 | 39.077 | 1.00 | 27.31 | $ |
| ATOM | 6839 | C3  | DES | $ | 900 | 38.053 | 68.757 | 38.106 | 1.00 | 26.98 | $ |
| ATOM | 6840 | O3  | DES | $ | 900 | 37.045 | 67.842 | 38.399 | 1.00 | 26.16 | $ |
| ATOM | 6841 | C2  | DES | $ | 900 | 38.551 | 68.788 | 36.789 | 1.00 | 25.97 | $ |
| ATOM | 6842 | C1  | DES | $ | 900 | 39.577 | 69.700 | 36.476 | 1.00 | 30.05 | $ |
| ATOM | 6843 | C8  | DES | $ | 900 | 40.666 | 72.745 | 36.289 | 1.00 | 32.06 | $ |
| ATOM | 6844 | C9  | DES | $ | 900 | 40.758 | 72.539 | 34.808 | 1.00 | 32.46 | $ |
| ATOM | 6845 | OH2 | WAT | W | 1   | 60.065 | 50.128 | 76.974 | 1.00 | 19.69 | W |
| ATOM | 6846 | OH2 | WAT | W | 2   | 49.515 | 41.120 | 53.629 | 1.00 | 34.56 | W |
| ATOM | 6847 | OH2 | WAT | W | 3   | 58.463 | 51.034 | 62.316 | 1.00 | 25.79 | W |
| ATOM | 6848 | OH2 | WAT | W | 4   | 61.236 | 55.483 | 67.115 | 1.00 | 22.33 | W |
| ATOM | 6849 | OH2 | WAT | W | 5   | 45.569 | 34.296 | 67.928 | 1.00 | 28.73 | W |
| ATOM | 6850 | OH2 | WAT | W | 6   | 43.152 | 60.334 | 17.405 | 1.00 | 30.15 | W |
| ATOM | 6851 | OH2 | WAT | W | 7   | 51.476 | 56.833 | 44.180 | 1.00 | 25.75 | W |
| ATOM | 6852 | OH2 | WAT | W | 8   | 42.249 | 62.523 | 15.058 | 1.00 | 28.13 | W |
| ATOM | 6853 | OH2 | WAT | W | 9   | 79.795 | 48.406 | 67.983 | 1.00 | 37.37 | W |
| ATOM | 6854 | OH2 | WAT | W | 10  | 62.749 | 61.659 | 50.118 | 1.00 | 34.52 | W |
| ATOM | 6855 | OH2 | WAT | W | 11  | 66.133 | 47.262 | 78.187 | 1.00 | 27.25 | W |
| ATOM | 6856 | OH2 | WAT | W | 12  | 50.641 | 66.724 | 72.757 | 1.00 | 36.36 | W |
| ATOM | 6857 | OH2 | WAT | W | 13  | 61.158 | 40.609 | 82.155 | 1.00 | 29.61 | W |
| ATOM | 6858 | OH2 | WAT | W | 14  | 72.468 | 56.602 | 81.841 | 1.00 | 31.73 | W |
| ATOM | 6859 | OH2 | WAT | W | 15  | 51.041 | 43.740 | 53.456 | 1.00 | 37.39 | W |
| ATOM | 6860 | OH2 | WAT | W | 16  | 72.640 | 34.548 | 49.985 | 1.00 | 87.09 | W |
| ATOM | 6861 | OH2 | WAT | W | 17  | 58.434 | 51.611 | 75.429 | 1.00 | 25.48 | W |
| ATOM | 6862 | OH2 | WAT | W | 18  | 49.600 | 45.996 | 53.402 | 1.00 | 39.91 | W |
| ATOM | 6863 | OH2 | WAT | W | 19  | 57.167 | 52.628 | 64.642 | 1.00 | 30.10 | W |
| ATOM | 6864 | OH2 | WAT | W | 20  | 81.954 | 39.524 | 90.215 | 1.00 | 57.88 | W |
| ATOM | 6865 | OH2 | WAT | W | 21  | 62.587 | 57.751 | 66.106 | 1.00 | 28.96 | W |
| ATOM | 6866 | OH2 | WAT | W | 22  | 70.475 | 71.067 |  5.918 | 1.00 | 52.84 | W |
| ATOM | 6867 | OH2 | WAT | W | 23  | 51.127 | 39.902 | 56.333 | 1.00 | 29.28 | W |
| ATOM | 6868 | OH2 | WAT | W | 24  | 57.349 | 49.954 | 65.431 | 1.00 | 24.75 | W |
| ATOM | 6869 | OH2 | WAT | W | 25  | 60.757 | 51.561 | 74.093 | 1.00 | 18.84 | W |
| ATOM | 6870 | OH2 | WAT | W | 26  | 49.282 | 74.089 |  9.405 | 0.00 | 38.16 | W |
| ATOM | 6871 | OH2 | WAT | W | 27  | 68.679 | 71.908 |  4.877 | 1.00 | 57.34 | W |
| ATOM | 6872 | OH2 | WAT | W | 28  | 50.840 | 42.631 | 55.978 | 1.00 | 33.83 | W |
| ATOM | 6873 | OH2 | WAT | W | 29  | 55.059 | 48.075 | 72.959 | 1.00 | 23.99 | W |
| ATOM | 6874 | OH2 | WAT | W | 30  | 86.175 | 39.236 | 87.951 | 0.00 | 38.16 | W |
| ATOM | 6875 | OH2 | WAT | W | 31  | 53.583 | 47.371 | 77.202 | 1.00 | 33.93 | W |
| ATOM | 6876 | OH2 | WAT | W | 32  | 45.638 | 34.229 | 70.544 | 1.00 | 35.25 | W |
| ATOM | 6877 | OH2 | WAT | W | 33  | 69.737 | 56.596 | 82.801 | 1.00 | 27.89 | W |
| ATOM | 6878 | OH2 | WAT | W | 34  | 40.169 | 56.128 | 48.430 | 1.00 | 27.24 | W |
| ATOM | 6879 | OH2 | WAT | W | 35  | 51.463 | 58.910 |  6.782 | 1.00 | 29.71 | W |
| ATOM | 6880 | OH2 | WAT | W | 36  | 49.550 | 50.449 | 74.658 | 1.00 | 24.27 | W |
| ATOM | 6881 | OH2 | WAT | W | 37  | 59.987 | 58.933 | 65.531 | 1.00 | 37.41 | W |
| ATOM | 6882 | OH2 | WAT | W | 38  | 50.070 | 64.157 | 70.808 | 1.00 | 36.31 | W |
| ATOM | 6883 | OH2 | WAT | W | 39  | 32.898 | 61.139 | 60.166 | 1.00 | 48.61 | W |
| ATOM | 6884 | OH2 | WAT | W | 40  | 42.367 | 73.185 | 12.790 | 1.00 | 29.07 | W |
| ATOM | 6885 | OH2 | WAT | W | 41  | 36.861 | 63.721 | 49.629 | 1.00 | 48.64 | W |
| ATOM | 6886 | OH2 | WAT | W | 42  | 75.498 | 64.377 | 68.011 | 1.00 | 34.25 | W |
| ATOM | 6887 | OH2 | WAT | W | 43  | 53.265 | 59.430 |  3.655 | 1.00 | 36.08 | W |
| ATOM | 6888 | OH2 | WAT | W | 44  | 47.845 | 43.686 | 56.096 | 1.00 | 39.30 | W |
| ATOM | 6889 | OH2 | WAT | W | 45  | 58.707 | 61.107 | 66.652 | 1.00 | 33.12 | W |
| ATOM | 6890 | 0H2 | WAT | W | 46  | 51.959 | 48.897 | 75.277 | 1.00 | 40.17 | W |
| ATOM | 6891 | OH2 | WAT | W | 47  | 52.612 | 46.777 | 73.974 | 1.00 | 39.59 | W |
| ATOM | 6892 | OH2 | WAT | W | 48  | 69.207 | 56.665 | 85.482 | 1.00 | 43.40 | W |
| ATOM | 6893 | OH2 | WAT | W | 49  | 35.541 | 64.963 | 16.013 | 1.00 | 32.99 | W |
| ATOM | 6894 | OH2 | WAT | W | 50  | 65.383 | 57.437 | 62.945 | 1.00 | 40.64 | W |
| ATOM | 6895 | OH2 | WAT | W | 51  | 56.146 | 46.303 |  8.710 | 1.00 | 33.97 | W |
| ATOM | 6896 | OH2 | WAT | W | 52  | 48.439 | 61.787 | 69.239 | 1.00 | 45.31 | W |
| ATOM | 6897 | OH2 | WAT | W | 53  | 45.890 | 59.849 | 72.763 | 1.00 | 37.35 | W |
| ATOM | 6898 | OH2 | WAT | W | 54  | 66.785 | 69.750 |  4.381 | 1.00 | 61.80 | W |
| ATOM | 6899 | OH2 | WAT | W | 55  | 76.764 | 46.848 | 67.323 | 1.00 | 54.70 | W |
| ATOM | 6900 | OH2 | WAT | W | 56  | 66.890 | 51.381 | 55.509 | 1.00 | 29.87 | W |
| ATOM | 6901 | OH2 | WAT | W | 57  | 29.180 | 41.824 | 36.521 | 1.00 | 61.15 | W |
| ATOM | 6902 | OH2 | WAT | W | 58  | 50.811 | 59.801 |  4.432 | 1.00 | 40.69 | W |
| ATOM | 6903 | OH2 | WAT | W | 59  | 37.353 | 63.027 | 19.971 | 1.00 | 31.61 | W |
| ATOM | 6904 | OH2 | WAT | W | 60  | 45.717 | 49.673 | 53.962 | 1.00 | 27.05 | W |
| ATOM | 6905 | OH2 | WAT | W | 61  | 52.653 | 42.594 | 90.755 | 1.00 | 42.41 | W |
| ATOM | 6906 | OH2 | WAT | W | 62  | 61.287 | 38.583 | 86.083 | 1.00 | 63.33 | W |
| ATOM | 6907 | OH2 | WAT | W | 63  | 61.186 | 44.555 | 75.894 | 1.00 | 33.25 | W |
| ATOM | 6908 | OH2 | WAT | W | 64  | 48.532 | 60.883 | 85.843 | 1.00 | 41.56 | W |
| ATOM | 6909 | OH2 | WAT | W | 65  | 64.122 | 49.966 | 62.189 | 1.00 | 35.45 | W |

TABLE 2-continued

ATOMIC COORDINATES OF THE ERR3 LBD/DIETHYLSTILBESTROL COMPLEX

| ATOM | 6910 | OH2 | WAT | W | 66  | 58.672 | 47.939 | 15.173 | 1.00 | 39.58 | W |
|------|------|-----|-----|---|-----|--------|--------|--------|------|-------|---|
| ATOM | 6911 | OH2 | WAT | W | 67  | 64.556 | 46.732 | 75.837 | 1.00 | 36.99 | W |
| ATOM | 6912 | OH2 | WAT | W | 68  | 48.506 | 58.903 | 3.735  | 1.00 | 37.28 | W |
| ATOM | 6913 | OH2 | WAT | W | 69  | 72.174 | 57.507 | 84.953 | 1.00 | 46.68 | W |
| ATOM | 6914 | OH2 | WAT | W | 70  | 71.083 | 61.908 | 83.015 | 0.00 | 38.16 | W |
| ATOM | 6915 | OH2 | WAT | W | 71  | 64.679 | 53.834 | 96.847 | 1.00 | 42.56 | W |
| ATOM | 6916 | OH2 | WAT | W | 72  | 58.586 | 47.049 | 17.685 | 1.00 | 40.97 | W |
| ATOM | 6917 | OH2 | WAT | W | 73  | 73.926 | 67.605 | 76.605 | 1.00 | 34.88 | W |
| ATOM | 6918 | OH2 | WAT | W | 74  | 56.936 | 61.321 | 64.369 | 1.00 | 36.16 | W |
| ATOM | 6919 | OH2 | WAT | W | 75  | 48.863 | 60.986 | 71.767 | 1.00 | 39.07 | W |
| ATOM | 6920 | OH2 | WAT | W | 76  | 61.227 | 57.469 | 63.009 | 1.00 | 37.81 | W |
| ATOM | 6921 | OH2 | WAT | W | 77  | 51.929 | 28.227 | 68.237 | 1.00 | 43.12 | W |
| ATOM | 6922 | OH2 | WAT | W | 78  | 63.291 | 44.525 | 13.124 | 1.00 | 42.57 | W |
| ATOM | 6923 | OH2 | WAT | W | 79  | 46.742 | 67.908 | 24.701 | 1.00 | 34.47 | W |
| ATOM | 6924 | OH2 | WAT | W | 80  | 73.815 | 63.184 | 66.521 | 1.00 | 52.81 | W |
| ATOM | 6925 | OH2 | WAT | W | 81  | 42.072 | 62.811 | 56.407 | 1.00 | 43.54 | W |
| ATOM | 6926 | OH2 | WAT | W | 82  | 45.689 | 41.199 | 56.595 | 1.00 | 42.22 | W |
| ATOM | 6927 | OH2 | WAT | W | 83  | 51.179 | 29.727 | 66.925 | 1.00 | 42.33 | W |
| ATOM | 6928 | OH2 | WAT | W | 84  | 43.175 | 41.963 | 57.013 | 1.00 | 44.15 | W |
| ATOM | 6929 | OH2 | WAT | W | 85  | 86.925 | 55.211 | 75.521 | 1.00 | 54.40 | W |
| ATOM | 6930 | OH2 | WAT | W | 86  | 75.208 | 44.701 | 68.555 | 1.00 | 41.28 | W |
| ATOM | 6931 | OH2 | WAT | W | 87  | 62.290 | 62.197 | 23.038 | 1.00 | 42.26 | W |
| ATOM | 6932 | OH2 | WAT | W | 88  | 71.125 | 58.720 | 1.387  | 1.00 | 34.62 | W |
| ATOM | 6933 | OH2 | WAT | W | 89  | 62.676 | 68.632 | 21.665 | 1.00 | 47.69 | W |
| ATOM | 6934 | OH2 | WAT | W | 90  | 62.641 | 60.800 | 61.695 | 1.00 | 50.91 | W |
| ATOM | 6935 | OH2 | WAT | W | 91  | 86.796 | 61.965 | 66.620 | 1.00 | 61.36 | W |
| ATOM | 6936 | OH2 | WAT | W | 92  | 63.096 | 53.419 | 17.820 | 1.00 | 41.07 | W |
| ATOM | 6937 | OH2 | WAT | W | 93  | 33.733 | 42.223 | 13.544 | 1.00 | 48.59 | W |
| ATOM | 6938 | OH2 | WAT | W | 94  | 49.099 | 63.859 | 85.472 | 1.00 | 35.05 | W |
| ATOM | 6939 | OH2 | WAT | W | 95  | 50.390 | 64.064 | 24.806 | 1.00 | 32.54 | W |
| ATOM | 6940 | OH2 | WAT | W | 96  | 61.015 | 30.333 | 67.096 | 1.00 | 55.59 | W |
| ATOM | 6941 | OH2 | WAT | W | 97  | 62.076 | 47.175 | 61.995 | 1.00 | 49.11 | W |
| ATOM | 6942 | OH2 | WAT | W | 98  | 73.405 | 44.051 | 66.816 | 1.00 | 47.80 | W |
| ATOM | 6943 | OH2 | WAT | W | 99  | 36.726 | 66.610 | 13.748 | 1.00 | 42.75 | W |
| ATOM | 6944 | OH2 | WAT | W | 100 | 68.179 | 65.931 | 4.577  | 1.00 | 42.64 | W |
| ATOM | 6945 | OH2 | WAT | W | 101 | 47.703 | 63.811 | 24.832 | 1.00 | 38.23 | W |
| ATOM | 6946 | OH2 | WAT | W | 102 | 52.599 | 34.953 | 74.263 | 1.00 | 40.15 | W |
| ATOM | 6947 | OH2 | WAT | W | 103 | 66.818 | 73.217 | 4.060  | 1.00 | 59.21 | W |
| ATOM | 6948 | OH2 | WAT | W | 104 | 50.894 | 56.352 | 5.239  | 1.00 | 53.49 | W |
| ATOM | 6949 | OH2 | WAT | W | 105 | 45.150 | 55.624 | 1.788  | 1.00 | 32.94 | W |
| ATOM | 6950 | OH2 | WAT | W | 106 | 72.777 | 32.246 | 52.140 | 1.00 | 61.76 | W |
| ATOM | 6951 | OH2 | WAT | W | 107 | 61.810 | 41.859 | 77.434 | 1.00 | 46.79 | W |
| ATOM | 6952 | OH2 | WAT | W | 108 | 74.485 | 47.853 | 65.053 | 0.00 | 38.16 | W |
| ATOM | 6953 | OH2 | WAT | W | 109 | 82.363 | 38.939 | 88.282 | 1.00 | 65.49 | W |
| ATOM | 6954 | OH2 | WAT | W | 110 | 80.660 | 42.857 | 71.148 | 1.00 | 57.20 | W |
| ATOM | 6955 | OH2 | WAT | W | 111 | 41.566 | 36.474 | 59.558 | 1.00 | 41.30 | W |
| ATOM | 6956 | OH2 | WAT | W | 112 | 61.726 | 72.445 | 74.044 | 1.00 | 60.94 | W |
| ATOM | 6957 | OH2 | WAT | W | 113 | 57.627 | 45.006 | 81.278 | 1.00 | 37.73 | W |
| ATOM | 6958 | OH2 | WAT | W | 114 | 35.382 | 51.706 | 47.612 | 1.00 | 42.01 | W |
| ATOM | 6959 | OH2 | WAT | W | 115 | 84.916 | 45.620 | 71.192 | 1.00 | 37.40 | W |
| ATOM | 6960 | OH2 | WAT | W | 116 | 66.389 | 49.596 | 18.920 | 0.00 | 38.16 | W |
| ATOM | 6961 | OH2 | WAT | W | 117 | 78.215 | 67.148 | 80.930 | 1.00 | 63.22 | W |
| ATOM | 6962 | OH2 | WAT | W | 118 | 61.283 | 36.695 | 51.423 | 1.00 | 55.85 | W |
| ATOM | 6963 | OH2 | WAT | W | 119 | 84.820 | 39.586 | 85.685 | 1.00 | 50.66 | W |
| ATOM | 6964 | OH2 | WAT | W | 120 | 65.656 | 47.575 | 13.495 | 0.00 | 38.16 | W |
| ATOM | 6965 | OH2 | WAT | W | 121 | 76.000 | 63.944 | 70.649 | 1.00 | 38.97 | W |
| ATOM | 6966 | OH2 | WAT | W | 122 | 48.848 | 66.032 | 75.076 | 1.00 | 37.92 | W |
| ATOM | 6967 | OH2 | WAT | W | 123 | 31.028 | 61.145 | 58.829 | 1.00 | 56.78 | W |
| ATOM | 6968 | OH2 | WAT | W | 124 | 66.093 | 58.727 | 44.612 | 1.00 | 35.31 | W |
| ATOM | 6969 | OH2 | WAT | W | 125 | 34.134 | 62.390 | 17.959 | 1.00 | 43.67 | W |
| ATOM | 6970 | OH2 | WAT | W | 126 | 73.478 | 60.047 | 4.503  | 1.00 | 41.11 | W |
| ATOM | 6971 | OH2 | WAT | W | 127 | 50.608 | 42.086 | 52.533 | 1.00 | 51.79 | W |
| ATOM | 6972 | OH2 | WAT | W | 128 | 19.295 | 44.833 | 33.599 | 0.00 | 38.16 | W |
| ATOM | 6973 | OH2 | WAT | W | 129 | 74.216 | 58.090 | 18.902 | 1.00 | 56.37 | W |
| ATOM | 6974 | OH2 | WAT | W | 130 | 78.435 | 62.185 | 85.058 | 1.00 | 44.39 | W |
| ATOM | 6975 | OH2 | WAT | W | 131 | 30.775 | 67.186 | 2.591  | 1.00 | 53.02 | W |
| ATOM | 6976 | OH2 | WAT | W | 132 | 88.012 | 53.697 | 73.560 | 1.00 | 55.63 | W |
| ATOM | 6977 | OH2 | WAT | W | 133 | 68.987 | 59.490 | 84.320 | 1.00 | 69.86 | W |
| ATOM | 6978 | OH2 | WAT | W | 134 | 53.421 | 64.907 | 42.645 | 1.00 | 50.77 | W |
| ATOM | 6979 | OH2 | WAT | W | 135 | 72.377 | 65.688 | 65.437 | 1.00 | 70.46 | W |
| ATOM | 6980 | OH2 | WAT | W | 136 | 71.861 | 68.612 | 9.250  | 1.00 | 30.60 | W |
| ATOM | 6981 | OH2 | WAT | W | 137 | 65.083 | 31.778 | 53.107 | 0.00 | 38.16 | W |
| ATOM | 6982 | OH2 | WAT | W | 138 | 68.082 | 59.989 | 45.508 | 1.00 | 53.74 | W |
| ATOM | 6983 | OH2 | WAT | W | 139 | 56.498 | 66.430 | 93.954 | 1.00 | 45.13 | W |
| ATOM | 6984 | OH2 | WAT | W | 140 | 37.974 | 56.481 | 50.591 | 1.00 | 41.98 | W |
| ATOM | 6985 | OH2 | WAT | W | 141 | 54.304 | 62.702 | 64.175 | 1.00 | 44.28 | W |

TABLE 2-continued

ATOMIC COORDINATES OF THE ERR3 LBD/
DIETHYLSTILBESTROL COMPLEX

| ATOM | 6986 | OH2 | WAT | W | 142 | 75.695 | 66.284 | 80.234 | 1.00 | 43.04 | W |
|------|------|-----|-----|---|-----|--------|--------|--------|------|-------|---|
| ATOM | 6987 | OH2 | WAT | W | 143 | 37.823 | 63.083 | 52.947 | 1.00 | 61.53 | W |
| ATOM | 6988 | OH2 | WAT | W | 144 | 74.063 | 70.159 | 9.589 | 1.00 | 52.88 | W |
| ATOM | 6989 | OH2 | WAT | W | 145 | 52.334 | 16.618 | 47.228 | 1.00 | 67.31 | W |
| ATOM | 6990 | OH2 | WAT | W | 146 | 55.040 | 60.852 | 37.198 | 0.00 | 38.16 | W |
| ATOM | 6991 | OH2 | WAT | W | 147 | 52.756 | 60.409 | 36.945 | 0.00 | 38.16 | W |
| ATOM | 6992 | OH2 | WAT | W | 148 | 67.161 | 21.128 | 51.562 | 1.00 | 50.79 | W |
| ATOM | 6993 | OH2 | WAT | W | 149 | 37.467 | 82.885 | 55.981 | 1.00 | 55.70 | W |
| ATOM | 6994 | OH2 | WAT | W | 150 | 18.131 | 47.170 | 30.048 | 0.00 | 38.16 | W |
| ATOM | 6995 | OH2 | WAT | W | 151 | 71.374 | 66.961 | 6.887 | 1.00 | 34.30 | W |
| ATOM | 6996 | OH2 | WAT | W | 152 | 34.700 | 44.150 | 1.306 | 1.00 | 55.30 | W |
| ATOM | 6997 | OH2 | WAT | W | 153 | 61.304 | 27.342 | 68.517 | 1.00 | 48.90 | W |
| ATOM | 6998 | OH2 | WAT | W | 154 | 53.617 | 66.033 | 50.782 | 1.00 | 45.70 | W |
| ATOM | 6999 | OH2 | WAT | W | 155 | 66.855 | 33.006 | 49.864 | 1.00 | 62.93 | W |
| ATOM | 7000 | OH2 | WAT | W | 156 | 63.789 | 29.562 | 49.449 | 1.00 | 54.09 | W |
| ATOM | 7001 | OH2 | WAT | W | 157 | 70.044 | 64.807 | 6.047 | 1.00 | 37.20 | W |
| ATOM | 7002 | OH2 | WAT | W | 158 | 59.463 | 27.994 | 47.317 | 0.00 | 38.16 | W |
| ATOM | 7003 | OH2 | WAT | W | 159 | 52.542 | 62.990 | 48.764 | 1.00 | 54.00 | W |
| ATOM | 7004 | OH2 | WAT | W | 160 | 68.331 | 33.664 | 48.034 | 1.00 | 69.83 | W |
| ATOM | 7005 | OH2 | WAT | W | 161 | 65.593 | 57.543 | 60.488 | 1.00 | 45.90 | W |
| ATOM | 7006 | OH2 | WAT | W | 162 | 36.835 | 60.997 | 51.054 | 1.00 | 49.61 | W |
| ATOM | 7007 | OH2 | WAT | W | 163 | 57.347 | 65.950 | 23.580 | 1.00 | 39.07 | W |
| ATOM | 7008 | OH2 | WAT | W | 164 | 31.162 | 72.206 | 1.082 | 0.00 | 38.16 | W |
| ATOM | 7009 | OH2 | WAT | W | 165 | 72.959 | 70.660 | 5.350 | 1.00 | 47.01 | W |
| ATOM | 7010 | OH2 | WAT | W | 166 | 68.178 | 68.025 | 3.708 | 1.00 | 51.79 | W |
| ATOM | 7011 | OH2 | WAT | W | 167 | 42.039 | 45.478 | 45.086 | 1.00 | 41.14 | W |
| ATOM | 7012 | OH2 | WAT | W | 168 | 58.018 | 49.067 | 6.313 | 1.00 | 45.34 | W |
| ATOM | 7013 | OH2 | WAT | W | 169 | 30.030 | 55.199 | 38.025 | 1.00 | 43.64 | W |
| ATOM | 7014 | OH2 | WAT | W | 170 | 68.608 | 29.380 | 51.252 | 0.00 | 38.16 | W |
| ATOM | 7015 | OH2 | WAT | W | 171 | 30.518 | 59.966 | 60.542 | 1.00 | 78.17 | W |
| ATOM | 7016 | OH2 | WAT | W | 172 | 58.177 | 57.233 | 4.595 | 1.00 | 50.06 | W |
| ATOM | 7017 | OH2 | WAT | W | 173 | 53.275 | 53.892 | 4.773 | 1.00 | 44.51 | W |
| ATOM | 7018 | OH2 | WAT | W | 174 | 43.830 | 63.531 | 58.587 | 1.00 | 50.27 | W |
| ATOM | 7019 | OH2 | WAT | W | 175 | 69.300 | 50.336 | 19.929 | 0.00 | 38.16 | W |
| ATOM | 7020 | OH2 | WAT | W | 176 | 48.658 | 62.900 | 89.957 | 0.00 | 38.16 | W |
| ATOM | 7021 | OH2 | WAT | W | 177 | 50.637 | 61.444 | 48.585 | 1.00 | 36.53 | W |
| ATOM | 7022 | OH2 | WAT | W | 178 | 52.882 | 51.113 | 3.936 | 1.00 | 48.18 | W |
| ATOM | 7023 | OH2 | WAT | W | 179 | 70.160 | 32.500 | 49.920 | 1.00 | 55.07 | W |
| ATOM | 7024 | OH2 | WAT | W | 180 | 56.900 | 56.283 | 2.679 | 1.00 | 49.22 | W |
| ATOM | 7025 | OH2 | WAT | W | 181 | 37.080 | 60.769 | 63.072 | 1.00 | 63.49 | W |
| ATOM | 7026 | OH2 | WAT | W | 182 | 80.050 | 58.325 | 90.946 | 1.00 | 50.71 | W |
| ATOM | 7027 | OH2 | WAT | W | 183 | 32.872 | 72.258 | 4.863 | 1.00 | 70.86 | W |
| ATOM | 7028 | OH2 | WAT | W | 184 | 42.355 | 47.238 | 47.588 | 1.00 | 60.36 | W |
| ATOM | 7029 | OH2 | WAT | W | 185 | 34.380 | 44.796 | −2.127 | 1.00 | 45.09 | W |
| ATOM | 7030 | OH2 | WAT | W | 186 | 59.506 | 23.081 | 49.786 | 1.00 | 60.74 | W |
| ATOM | 7031 | OH2 | WAT | W | 187 | 60.938 | 42.281 | 18.593 | 1.00 | 62.40 | W |
| ATOM | 7032 | OH2 | WAT | W | 188 | 51.307 | 76.605 | 4.197 | 1.00 | 54.40 | W |
| ATOM | 7033 | OH2 | WAT | W | 189 | 49.707 | 74.932 | 3.784 | 1.00 | 66.50 | W |
| ATOM | 7034 | OH2 | WAT | W | 190 | 48.908 | 75.525 | 1.636 | 1.00 | 57.86 | W |
| ATOM | 7035 | OH2 | WAT | W | 191 | 49.509 | 73.399 | 7.294 | 1.00 | 77.24 | W |
| ATOM | 7036 | OH2 | WAT | W | 192 | 49.491 | 71.385 | 5.943 | 1.00 | 66.91 | W |
| ATOM | 7037 | OH2 | WAT | W | 193 | 48.144 | 72.862 | 5.115 | 1.00 | 56.51 | W |
| ATOM | 7038 | OH2 | WAT | W | 194 | 78.631 | 38.219 | 88.447 | 1.00 | 55.67 | W |
| ATOM | 7039 | OH2 | WAT | W | 195 | 52.806 | 75.340 | 5.018 | 1.00 | 69.46 | W |
| ATOM | 7040 | OH2 | WAT | W | 196 | 29.394 | 62.830 | 45.218 | 1.00 | 31.95 | W |
| ATOM | 7041 | OH2 | WAT | W | 197 | 54.032 | 58.648 | 7.581 | 1.00 | 26.16 | W |
| ATOM | 7042 | OH2 | WAT | W | 198 | 41.681 | 57.056 | 28.737 | 1.00 | 28.67 | W |
| ATOM | 7043 | OH2 | WAT | W | 199 | 83.161 | 65.341 | 71.846 | 1.00 | 36.88 | W |
| ATOM | 7044 | OH2 | WAT | W | 200 | 40.485 | 58.930 | 26.253 | 1.00 | 26.74 | W |
| ATOM | 7045 | OH2 | WAT | W | 201 | 37.304 | 56.568 | 54.685 | 1.00 | 75.97 | W |
| ATOM | 7046 | OH2 | WAT | W | 202 | 37.355 | 81.206 | 43.482 | 1.00 | 47.32 | W |
| ATOM | 7047 | OH2 | WAT | W | 203 | 64.865 | 45.872 | 67.638 | 1.00 | 30.48 | W |
| ATOM | 7048 | OH2 | WAT | W | 204 | 40.554 | 60.500 | 16.204 | 1.00 | 30.51 | W |
| ATOM | 7049 | OH2 | WAT | W | 205 | 44.339 | 54.491 | 22.987 | 1.00 | 29.29 | W |
| ATOM | 7050 | OH2 | WAT | W | 206 | 34.937 | 65.777 | 38.293 | 1.00 | 31.71 | W |
| ATOM | 7051 | OH2 | WAT | W | 207 | 50.724 | 55.142 | 34.414 | 1.00 | 28.68 | W |
| ATOM | 7052 | OH2 | WAT | W | 208 | 60.733 | 45.518 | 59.597 | 1.00 | 34.79 | W |
| ATOM | 7053 | OH2 | WAT | W | 209 | 40.370 | 56.117 | 26.221 | 1.00 | 30.25 | W |
| ATOM | 7054 | OH2 | WAT | W | 210 | 71.336 | 61.758 | 82.908 | 1.00 | 33.59 | W |
| ATOM | 7055 | OH2 | WAT | W | 211 | 27.880 | 53.915 | 5.505 | 1.00 | 56.73 | W |
| ATOM | 7056 | OH2 | WAT | W | 212 | 69.119 | 74.485 | 3.352 | 1.00 | 45.35 | W |
| ATOM | 7057 | OH2 | WAT | W | 213 | 53.712 | 43.323 | 76.422 | 1.00 | 37.47 | W |
| ATOM | 7058 | OH2 | WAT | W | 214 | 57.242 | 62.070 | 25.474 | 1.00 | 53.97 | W |
| ATOM | 7059 | OH2 | WAT | W | 215 | 62.445 | 54.420 | 58.061 | 1.00 | 39.43 | W |
| ATOM | 7060 | OH2 | WAT | W | 216 | 42.894 | 61.859 | −6.259 | 1.00 | 43.82 | W |
| ATOM | 7061 | OH2 | WAT | W | 217 | 20.952 | 75.583 | 32.898 | 1.00 | 42.67 | W |

TABLE 2-continued

ATOMIC COORDINATES OF THE ERR3 LBD/
DIETHYLSTILBESTROL COMPLEX

| ATOM | 7062 | OH2 | WAT | W | 218 | 64.188 | 44.869 | 69.729 | 1.00 | 33.69 | W |
|---|---|---|---|---|---|---|---|---|---|---|---|
| ATOM | 7063 | OH2 | WAT | W | 219 | 94.895 | 58.604 | 85.573 | 1.00 | 46.80 | W |
| ATOM | 7064 | OH2 | WAT | W | 220 | 67.569 | 56.910 | 51.618 | 1.00 | 37.43 | W |
| ATOM | 7065 | OH2 | WAT | W | 221 | 55.071 | 65.944 | 61.681 | 1.00 | 59.78 | W |
| ATOM | 7066 | OH2 | WAT | W | 222 | 55.124 | 46.321 | 79.947 | 1.00 | 39.65 | W |
| ATOM | 7067 | OH2 | WAT | W | 223 | 66.806 | 46.568 | 75.805 | 1.00 | 51.19 | W |
| ATOM | 7068 | OH2 | WAT | W | 224 | 79.355 | 45.893 | 87.409 | 1.00 | 48.06 | W |
| ATOM | 7069 | OH2 | WAT | W | 225 | 50.292 | 67.139 | 58.822 | 1.00 | 41.92 | W |
| ATOM | 7070 | OH2 | WAT | W | 226 | 42.811 | 42.549 | 8.515 | 1.00 | 53.02 | W |
| ATOM | 7071 | OH2 | WAT | W | 227 | 43.522 | 80.551 | 25.610 | 1.00 | 67.11 | W |
| ATOM | 7072 | OH2 | WAT | W | 228 | 53.186 | 20.202 | 46.440 | 1.00 | 51.88 | W |
| ATOM | 7073 | OH2 | WAT | W | 229 | 33.642 | 44.754 | 14.732 | 1.00 | 42.87 | W |
| ATOM | 7074 | OH2 | WAT | W | 230 | 35.611 | 39.166 | 13.300 | 1.00 | 55.82 | W |
| ATOM | 7075 | OH2 | WAT | W | 231 | 61.269 | 60.010 | −1.747 | 1.00 | 35.80 | W |
| ATOM | 7076 | OH2 | WAT | W | 232 | 56.947 | 69.803 | 68.704 | 1.00 | 41.90 | W |
| ATOM | 7077 | OH2 | WAT | W | 233 | 35.977 | 42.679 | 24.346 | 1.00 | 50.54 | W |
| ATOM | 7078 | OH2 | WAT | W | 234 | 55.461 | 74.124 | 70.945 | 1.00 | 49.52 | W |
| ATOM | 7079 | OH2 | WAT | W | 235 | 33.788 | 58.665 | 39.307 | 1.00 | 38.18 | W |
| ATOM | 7080 | OH2 | WAT | W | 236 | 29.271 | 79.464 | 41.383 | 1.00 | 40.62 | W |
| ATOM | 7081 | OH2 | WAT | W | 237 | 97.248 | 53.103 | 87.261 | 1.00 | 70.97 | W |
| ATOM | 7082 | OH2 | WAT | W | 238 | 50.063 | 15.872 | 51.822 | 1.00 | 70.18 | W |
| ATOM | 7083 | OH2 | WAT | W | 239 | 43.427 | 70.983 | 17.092 | 1.00 | 46.72 | W |
| ATOM | 7084 | OH2 | WAT | W | 240 | 46.718 | 41.123 | 47.611 | 1.00 | 45.26 | W |
| ATOM | 7085 | OH2 | WAT | W | 241 | 46.581 | 65.678 | 23.138 | 1.00 | 43.92 | W |
| ATOM | 7086 | OH2 | WAT | W | 242 | 70.632 | 60.786 | 10.035 | 1.00 | 32.56 | W |
| ATOM | 7087 | OH2 | WAT | W | 243 | 42.046 | 73.323 | 16.635 | 1.00 | 46.48 | W |
| ATOM | 7088 | OH2 | WAT | W | 244 | 40.627 | 37.674 | 63.213 | 1.00 | 39.67 | W |
| ATOM | 7089 | OH2 | WAT | W | 245 | 70.385 | 63.612 | 83.468 | 1.00 | 54.37 | W |
| ATOM | 7090 | OH2 | WAT | W | 246 | 28.046 | 61.350 | 45.452 | 1.00 | 45.61 | W |
| ATOM | 7091 | OH2 | WAT | W | 247 | 33.964 | 60.751 | 39.968 | 1.00 | 45.77 | W |
| ATOM | 7092 | OH2 | WAT | W | 248 | 63.905 | 42.155 | 69.129 | 1.00 | 36.41 | W |
| ATOM | 7093 | OH2 | WAT | W | 249 | 30.239 | 53.772 | 4.419 | 1.00 | 46.36 | W |
| ATOM | 7094 | OH2 | WAT | W | 250 | 67.985 | 28.517 | 51.103 | 1.00 | 64.68 | W |
| ATOM | 7095 | OH2 | WAT | W | 251 | 62.995 | 33.677 | 68.131 | 1.00 | 55.52 | W |
| ATOM | 7096 | OH2 | WAT | W | 252 | 45.354 | 66.164 | 50.974 | 1.00 | 35.88 | W |
| ATOM | 7097 | OH2 | WAT | W | 253 | 37.496 | 36.979 | 12.380 | 1.00 | 72.46 | W |
| ATOM | 7098 | OH2 | WAT | W | 254 | 67.600 | 45.970 | 67.708 | 1.00 | 34.30 | W |
| ATOM | 7099 | OH2 | WAT | W | 255 | 28.583 | 69.654 | 43.335 | 1.00 | 45.58 | W |
| ATOM | 7100 | OH2 | WAT | W | 256 | 53.479 | 80.927 | 36.825 | 1.00 | 62.94 | W |
| ATOM | 7101 | OH2 | WAT | W | 257 | 47.872 | 65.959 | 14.443 | 1.00 | 33.77 | W |
| ATOM | 7102 | OH2 | WAT | W | 258 | 61.462 | 56.746 | 59.450 | 1.00 | 48.20 | W |
| ATOM | 7103 | OH2 | WAT | W | 259 | 36.577 | 45.776 | 41.112 | 1.00 | 37.44 | W |
| ATOM | 7104 | OH2 | WAT | W | 260 | 51.730 | 48.338 | 36.965 | 1.00 | 45.92 | W |
| ATOM | 7105 | OH2 | WAT | W | 261 | 55.943 | 67.715 | 60.121 | 1.00 | 59.11 | W |
| ATOM | 7106 | OH2 | WAT | W | 262 | 68.764 | 51.769 | 58.892 | 1.00 | 39.39 | W |
| ATOM | 7107 | OH2 | WAT | W | 263 | 47.459 | 43.193 | 37.901 | 1.00 | 38.90 | W |
| ATOM | 7108 | OH2 | WAT | W | 264 | 41.782 | 70.360 | 19.100 | 1.00 | 60.60 | W |
| ATOM | 7109 | OH2 | WAT | W | 265 | 36.627 | 86.422 | 41.601 | 1.00 | 66.24 | W |
| ATOM | 7110 | OH2 | WAT | W | 266 | 48.064 | 60.625 | 88.636 | 1.00 | 38.73 | W |
| ATOM | 7111 | OH2 | WAT | W | 267 | 20.528 | 74.306 | 35.081 | 1.00 | 43.97 | W |
| ATOM | 7112 | OH2 | WAT | W | 268 | 30.494 | 42.896 | 29.419 | 1.00 | 42.32 | W |
| ATOM | 7113 | OH2 | WAT | W | 269 | 41.946 | 48.692 | 21.710 | 1.00 | 35.28 | W |
| ATOM | 7114 | OH2 | WAT | W | 270 | 25.888 | 52.685 | 6.354 | 1.00 | 67.90 | W |
| ATOM | 7115 | OH2 | WAT | W | 271 | 28.168 | 74.176 | 29.463 | 1.00 | 38.83 | W |
| ATOM | 7116 | OH2 | WAT | W | 272 | 84.996 | 62.559 | 83.915 | 1.00 | 59.83 | W |
| ATOM | 7117 | OH2 | WAT | W | 273 | 54.898 | 54.732 | 28.230 | 1.00 | 52.17 | W |
| ATOM | 7118 | OH2 | WAT | W | 274 | 33.272 | 83.814 | 37.937 | 1.00 | 58.73 | W |
| ATOM | 7119 | OH2 | WAT | W | 275 | 43.162 | 59.469 | 71.421 | 1.00 | 29.05 | W |
| ATOM | 7120 | OH2 | WAT | W | 276 | 28.958 | 48.294 | 19.469 | 1.00 | 49.53 | W |
| ATOM | 7121 | OH2 | WAT | W | 277 | 53.630 | 54.016 | −6.229 | 1.00 | 62.95 | W |
| ATOM | 7122 | OH2 | WAT | W | 278 | 44.191 | 40.829 | 9.672 | 1.00 | 62.06 | W |
| ATOM | 7123 | OH2 | WAT | W | 279 | 61.770 | 69.921 | 9.888 | 1.00 | 58.91 | W |
| ATOM | 7124 | OH2 | WAT | W | 280 | 16.552 | 49.147 | 19.061 | 1.00 | 64.75 | W |
| ATOM | 7125 | OH2 | WAT | W | 281 | 98.018 | 50.414 | 79.526 | 1.00 | 64.78 | W |
| ATOM | 7126 | OH2 | WAT | W | 282 | 34.053 | 84.265 | 52.790 | 1.00 | 51.34 | W |
| ATOM | 7127 | OH2 | WAT | W | 283 | 31.455 | 50.626 | 15.229 | 1.00 | 50.47 | W |
| ATOM | 7128 | OH2 | WAT | W | 284 | 37.414 | 76.087 | 9.303 | 1.00 | 50.83 | W |
| ATOM | 7129 | OH2 | WAT | W | 285 | 22.310 | 63.146 | 30.686 | 1.00 | 42.96 | W |
| ATOM | 7130 | OH2 | WAT | W | 286 | 47.753 | 26.259 | 69.408 | 1.00 | 49.07 | W |
| ATOM | 7131 | OH2 | WAT | W | 287 | 43.876 | 75.751 | 3.284 | 1.00 | 57.11 | W |
| ATOM | 7132 | OH2 | WAT | W | 288 | 47.971 | 66.082 | 17.691 | 1.00 | 50.38 | W |
| ATOM | 7133 | OH2 | WAT | W | 289 | 42.236 | 45.425 | 86.735 | 1.00 | 50.85 | W |
| ATOM | 7134 | OH2 | WAT | W | 290 | 31.920 | 49.694 | 17.362 | 1.00 | 49.76 | W |
| ATOM | 7135 | OH2 | WAT | W | 291 | 34.673 | 62.772 | 37.881 | 1.00 | 34.66 | W |
| ATOM | 7136 | OH2 | WAT | W | 292 | 28.258 | 74.782 | 26.844 | 1.00 | 44.72 | W |
| ATOM | 7137 | OH2 | WAT | W | 293 | 39.334 | 33.233 | 58.968 | 1.00 | 57.38 | W |

TABLE 2-continued

ATOMIC COORDINATES OF THE ERR3 LBD/
DIETHYLSTILBESTROL COMPLEX

| ATOM | 7138 | OH2 | WAT | W | 294 | 43.332 | 61.659 | 69.429 | 1.00 | 41.43 | W |
|---|---|---|---|---|---|---|---|---|---|---|---|
| ATOM | 7139 | OH2 | WAT | W | 295 | 46.040 | 65.738 | 16.589 | 1.00 | 49.17 | W |
| ATOM | 7140 | OH2 | WAT | W | 296 | 40.761 | 39.977 | 62.793 | 1.00 | 41.38 | W |
| ATOM | 7141 | OH2 | WAT | W | 297 | 43.224 | 50.597 | 23.584 | 1.00 | 42.92 | W |
| ATOM | 7142 | OH2 | WAT | W | 298 | 34.002 | 62.834 | 41.188 | 1.00 | 50.78 | W |
| ATOM | 7143 | OH2 | WAT | W | 299 | 38.259 | 83.426 | 42.629 | 1.00 | 65.93 | W |
| ATOM | 7144 | OH2 | WAT | W | 300 | 38.148 | 73.583 | 47.066 | 1.00 | 36.41 | W |
| ATOM | 7145 | OH2 | WAT | W | 301 | 43.857 | 83.552 | 43.085 | 1.00 | 76.82 | W |
| ATOM | 7146 | OH2 | WAT | W | 302 | 23.198 | 51.415 | 18.628 | 1.00 | 41.41 | W |
| ATOM | 7147 | OH2 | WAT | W | 303 | 90.464 | 53.366 | 76.307 | 1.00 | 50.89 | W |
| ATOM | 7148 | OH2 | WAT | W | 304 | 51.293 | 19.361 | 45.677 | 1.00 | 61.33 | W |
| ATOM | 7149 | OH2 | WAT | W | 305 | 34.040 | 78.014 | 31.845 | 1.00 | 51.55 | W |
| ATOM | 7150 | OH2 | WAT | W | 306 | 50.429 | 47.077 | 93.109 | 1.00 | 52.21 | W |
| ATOM | 7151 | OH2 | WAT | W | 307 | 63.008 | 45.404 | 62.554 | 1.00 | 52.97 | W |
| ATOM | 7152 | OH2 | WAT | W | 308 | 48.257 | 76.873 | 75.775 | 1.00 | 58.76 | W |
| ATOM | 7153 | OH2 | WAT | W | 309 | 69.613 | 53.781 | 66.731 | 1.00 | 57.47 | W |
| ATOM | 7154 | OH2 | WAT | W | 310 | 37.123 | 46.634 | 62.572 | 1.00 | 39.83 | W |
| ATOM | 7155 | OH2 | WAT | W | 311 | 54.376 | 64.802 | 97.596 | 1.00 | 40.11 | W |
| ATOM | 7156 | OH2 | WAT | W | 312 | 35.256 | 53.810 | 58.985 | 1.00 | 51.32 | W |
| ATOM | 7157 | OH2 | WAT | W | 313 | 76.738 | 58.939 | 84.026 | 1.00 | 44.49 | W |
| ATOM | 7158 | OH2 | WAT | W | 314 | 81.894 | 66.769 | 71.697 | 1.00 | 47.57 | W |
| ATOM | 7159 | OH2 | WAT | W | 315 | 66.217 | 49.691 | 59.727 | 1.00 | 54.14 | W |
| ATOM | 7160 | OH2 | WAT | W | 316 | 44.426 | 43.836 | 8.180 | 0.00 | 38.16 | W |
| ATOM | 7161 | OH2 | WAT | W | 317 | 26.482 | 48.010 | 19.587 | 1.00 | 52.99 | W |
| ATOM | 7162 | OH2 | WAT | W | 318 | 31.980 | 61.008 | 17.927 | 1.00 | 34.82 | W |
| ATOM | 7163 | OH2 | WAT | W | 319 | 24.375 | 78.395 | 31.364 | 1.00 | 43.27 | W |
| ATOM | 7164 | OH2 | WAT | W | 320 | 33.218 | 46.522 | 17.307 | 1.00 | 43.01 | W |
| ATOM | 7165 | OH2 | WAT | W | 321 | 56.008 | 54.855 | 26.093 | 1.00 | 63.20 | W |
| ATOM | 7166 | OH2 | WAT | W | 322 | 30.648 | 59.501 | 47.495 | 1.00 | 51.65 | W |
| ATOM | 7167 | OH2 | WAT | W | 323 | 38.580 | 56.072 | 20.847 | 1.00 | 51.01 | W |
| ATOM | 7168 | OH2 | WAT | W | 324 | 62.089 | 51.063 | −1.667 | 1.00 | 52.62 | W |
| ATOM | 7169 | OH2 | WAT | W | 325 | 40.731 | 47.389 | 23.826 | 1.00 | 42.01 | W |
| ATOM | 7170 | OH2 | WAT | W | 326 | 52.927 | 24.724 | 59.159 | 1.00 | 72.80 | W |
| ATOM | 7171 | OH2 | WAT | W | 327 | 32.136 | 52.367 | −3.520 | 1.00 | 65.98 | W |
| ATOM | 7172 | OH2 | WAT | W | 328 | 62.039 | 59.147 | 85.226 | 1.00 | 45.50 | W |
| ATOM | 7173 | OH2 | WAT | W | 329 | 48.758 | 67.935 | 13.995 | 1.00 | 45.03 | W |
| ATOM | 7174 | OH2 | WAT | W | 330 | 67.450 | 25.415 | 57.032 | 1.00 | 57.04 | W |
| ATOM | 7175 | OH2 | WAT | W | 331 | 52.695 | 76.057 | 43.174 | 0.00 | 38.16 | W |
| ATOM | 7176 | OH2 | WAT | W | 332 | 50.852 | 45.914 | 78.758 | 1.00 | 44.94 | W |
| ATOM | 7177 | OH2 | WAT | W | 333 | 44.472 | 60.755 | −5.777 | 1.00 | 63.04 | W |
| ATOM | 7178 | OH2 | WAT | W | 334 | 42.610 | 45.995 | 22.031 | 1.00 | 49.28 | W |
| ATOM | 7179 | OH2 | WAT | W | 335 | 84.008 | 49.271 | 66.014 | 1.00 | 56.57 | W |
| ATOM | 7180 | OH2 | WAT | W | 336 | 41.517 | 29.629 | 67.529 | 1.00 | 41.28 | W |
| ATOM | 7181 | OH2 | WAT | W | 337 | 40.806 | 41.885 | 36.538 | 1.00 | 46.43 | W |
| ATOM | 7182 | OH2 | WAT | W | 338 | 39.140 | 75.137 | 49.035 | 1.00 | 43.25 | W |
| ATOM | 7183 | OH2 | WAT | W | 339 | 44.505 | 50.965 | 26.086 | 1.00 | 42.16 | W |
| ATOM | 7184 | OH2 | WAT | W | 340 | 33.797 | 79.130 | 30.270 | 1.00 | 55.91 | W |
| ATOM | 7185 | OH2 | WAT | W | 341 | 67.154 | 24.697 | 59.317 | 1.00 | 66.29 | W |
| ATOM | 7186 | OH2 | WAT | W | 342 | 52.679 | 45.081 | 79.987 | 1.00 | 49.09 | W |
| ATOM | 7187 | OH2 | WAT | W | 343 | 28.777 | 51.313 | 16.768 | 1.00 | 44.10 | W |
| ATOM | 7188 | OH2 | WAT | W | 344 | 63.420 | 60.874 | 87.286 | 1.00 | 46.03 | W |
| ATOM | 7189 | OH2 | WAT | W | 345 | 90.747 | 51.860 | 74.642 | 1.00 | 64.06 | W |
| ATOM | 7190 | OH2 | WAT | W | 346 | 83.951 | 67.731 | 74.332 | 1.00 | 41.85 | W |
| ATOM | 7191 | OH2 | WAT | W | 347 | 69.453 | 50.779 | 65.765 | 1.00 | 51.48 | W |
| ATOM | 7192 | OH2 | WAT | W | 348 | 51.919 | 73.124 | 85.937 | 1.00 | 54.96 | W |
| ATOM | 7193 | OH2 | WAT | W | 349 | 26.070 | 51.144 | 18.399 | 1.00 | 45.53 | W |
| ATOM | 7194 | OH2 | WAT | W | 350 | 81.395 | 48.736 | 65.679 | 1.00 | 53.33 | W |
| ATOM | 7195 | OH2 | WAT | W | 351 | 60.160 | 50.538 | 46.049 | 1.00 | 64.14 | W |
| ATOM | 7196 | OH2 | WAT | W | 352 | 44.117 | 48.511 | 24.493 | 1.00 | 47.83 | W |
| ATOM | 7197 | OH2 | WAT | W | 353 | 28.468 | 74.415 | 12.102 | 1.00 | 57.13 | W |
| ATOM | 7198 | OH2 | WAT | W | 354 | 66.390 | 39.568 | 68.885 | 1.00 | 56.53 | W |
| ATOM | 7199 | OH2 | WAT | W | 355 | 97.123 | 50.539 | 86.794 | 1.00 | 63.32 | W |
| ATOM | 7200 | OH2 | WAT | W | 356 | 80.698 | 68.323 | 70.685 | 1.00 | 43.09 | W |
| ATOM | 7201 | OH2 | WAT | W | 357 | 51.519 | 60.289 | 37.818 | 1.00 | 47.37 | W |
| ATOM | 7202 | OH2 | WAT | W | 358 | 44.264 | 78.275 | 29.844 | 1.00 | 55.75 | W |
| ATOM | 7203 | OH2 | WAT | W | 359 | 71.034 | 24.300 | 59.037 | 1.00 | 72.22 | W |
| ATOM | 7204 | OH2 | WAT | W | 360 | 41.550 | 53.569 | 48.789 | 0.00 | 38.16 | W |
| ATOM | 7205 | OH2 | WAT | W | 361 | 44.382 | 34.750 | 53.629 | 1.00 | 46.69 | W |
| ATOM | 7206 | OH2 | WAT | W | 362 | 50.334 | 63.243 | 36.431 | 1.00 | 48.97 | W |
| ATOM | 7207 | OH2 | WAT | W | 363 | 47.914 | 57.536 | 28.569 | 1.00 | 46.34 | W |
| ATOM | 7208 | OH2 | WAT | W | 364 | 45.631 | 25.828 | 58.017 | 1.00 | 42.47 | W |
| ATOM | 7209 | OH2 | WAT | W | 365 | 53.979 | 42.833 | 78.961 | 1.00 | 38.54 | W |
| ATOM | 7210 | OH2 | WAT | W | 366 | 44.609 | 61.711 | 32.809 | 1.00 | 44.44 | W |
| ATOM | 7211 | OH2 | WAT | W | 367 | 43.458 | 67.534 | 17.625 | 1.00 | 43.38 | W |
| ATOM | 7212 | OH2 | WAT | W | 368 | 54.613 | 73.627 | 50.069 | 1.00 | 67.91 | W |
| ATOM | 7213 | OH2 | WAT | W | 369 | 55.527 | 18.069 | 49.255 | 1.00 | 75.93 | W |

TABLE 2-continued

ATOMIC COORDINATES OF THE ERR3 LBD/
DIETHYLSTILBESTROL COMPLEX

| ATOM | 7214 | OH2 | WAT | W | 370 | 47.585 | 49.366 | 76.342 | 1.00 | 61.95 | W |
|---|---|---|---|---|---|---|---|---|---|---|---|
| ATOM | 7215 | OH2 | WAT | W | 371 | 33.126 | 62.361 | 70.719 | 1.00 | 51.25 | W |
| ATOM | 7216 | OH2 | WAT | W | 372 | 72.572 | 74.356 | 5.187 | 1.00 | 68.16 | W |
| ATOM | 7217 | OH2 | WAT | W | 373 | 52.308 | 55.881 | 36.582 | 1.00 | 42.83 | W |
| ATOM | 7218 | OH2 | WAT | W | 374 | 32.440 | 68.437 | 41.794 | 1.00 | 46.55 | W |
| ATOM | 7219 | OH2 | WAT | W | 375 | 60.300 | 39.479 | 78.574 | 1.00 | 44.44 | W |
| ATOM | 7220 | OH2 | WAT | W | 376 | 87.207 | 59.674 | 73.560 | 1.00 | 55.43 | W |
| ATOM | 7221 | OH2 | WAT | W | 377 | 39.296 | 48.092 | −3.788 | 1.00 | 62.95 | W |
| ATOM | 7222 | OH2 | WAT | W | 378 | 31.121 | 51.322 | 3.057 | 1.00 | 56.55 | W |
| ATOM | 7223 | OH2 | WAT | W | 379 | 51.454 | 57.646 | 48.142 | 0.00 | 38.16 | W |
| ATOM | 7224 | OH2 | WAT | W | 380 | 76.936 | 39.297 | 69.485 | 1.00 | 53.46 | W |
| ATOM | 7225 | OH2 | WAT | W | 381 | 26.330 | 57.604 | 9.933 | 1.00 | 61.03 | W |
| ATOM | 7226 | OH2 | WAT | W | 382 | 27.521 | 50.512 | 11.045 | 1.00 | 56.53 | W |
| ATOM | 7227 | OH2 | WAT | W | 383 | 50.522 | 49.398 | 91.231 | 1.00 | 46.03 | W |
| ATOM | 7228 | OH2 | WAT | W | 384 | 60.440 | 61.868 | −2.180 | 1.00 | 45.71 | W |
| ATOM | 7229 | OH2 | WAT | W | 385 | 31.930 | 64.230 | 16.398 | 1.00 | 46.93 | W |
| ATOM | 7230 | OH2 | WAT | W | 386 | 49.637 | 50.201 | 89.167 | 1.00 | 44.55 | W |
| ATOM | 7231 | OH2 | WAT | W | 387 | 45.906 | 76.905 | 28.685 | 1.00 | 52.32 | W |
| ATOM | 7232 | OH2 | WAT | W | 388 | 44.446 | 43.858 | 8.177 | 0.00 | 38.16 | W |
| ATOM | 7233 | OH2 | WAT | W | 389 | 32.581 | 67.215 | 15.752 | 1.00 | 49.75 | W |
| ATOM | 7234 | OH2 | WAT | W | 390 | 50.060 | 57.911 | 30.610 | 1.00 | 44.13 | W |
| ATOM | 7235 | OH2 | WAT | W | 391 | 59.435 | 63.617 | 65.246 | 1.00 | 50.31 | W |
| ATOM | 7236 | OH2 | WAT | W | 392 | 69.035 | 78.314 | 14.966 | 1.00 | 47.26 | W |
| ATOM | 7237 | OH2 | WAT | W | 393 | 49.225 | 62.015 | 35.203 | 1.00 | 62.60 | W |
| ATOM | 7238 | OH2 | WAT | W | 394 | 40.227 | 59.483 | 71.707 | 1.00 | 46.58 | W |
| ATOM | 7239 | OH2 | WAT | W | 395 | 57.159 | 19.063 | 59.611 | 1.00 | 63.72 | W |
| ATOM | 7240 | OH2 | WAT | W | 396 | 45.195 | 60.542 | 30.215 | 1.00 | 42.19 | W |
| ATOM | 7241 | OH2 | WAT | W | 397 | 45.635 | 37.456 | 53.308 | 1.00 | 49.99 | W |
| ATOM | 7242 | OH2 | WAT | W | 398 | 63.619 | 76.012 | 8.771 | 1.00 | 66.57 | W |
| ATOM | 7243 | OH2 | WAT | W | 399 | 70.298 | 41.185 | 68.786 | 1.00 | 58.52 | W |
| ATOM | 7244 | OH2 | WAT | W | 400 | 26.709 | 72.653 | 10.791 | 1.00 | 61.63 | W |
| ATOM | 7245 | OH2 | WAT | W | 401 | 52.694 | 76.022 | 43.185 | 0.00 | 38.16 | W |
| ATOM | 7246 | OH2 | WAT | W | 402 | 44.957 | 57.060 | 85.016 | 1.00 | 51.37 | W |
| ATOM | 7247 | OH2 | WAT | W | 403 | 38.380 | 78.899 | 48.211 | 1.00 | 55.63 | W |
| ATOM | 7248 | OH2 | WAT | W | 404 | 31.533 | 48.891 | 13.362 | 1.00 | 60.40 | W |
| ATOM | 7249 | OH2 | WAT | W | 405 | 31.011 | 48.639 | 19.885 | 1.00 | 48.60 | W |
| ATOM | 7250 | OH2 | WAT | W | 406 | 93.674 | 56.414 | 73.494 | 1.00 | 66.05 | W |
| ATOM | 7251 | OH2 | WAT | W | 407 | 65.641 | 51.825 | 45.414 | 1.00 | 50.70 | W |
| ATOM | 7252 | OH2 | WAT | W | 408 | 37.633 | 73.946 | 50.984 | 1.00 | 50.22 | W |
| ATOM | 7253 | OH2 | WAT | W | 409 | 44.879 | 69.019 | 52.707 | 1.00 | 60.20 | W |
| ATOM | 7254 | OH2 | WAT | W | 410 | 26.729 | 56.823 | 5.907 | 1.00 | 58.68 | W |
| ATOM | 7255 | OH2 | WAT | W | 411 | 51.494 | 72.327 | 88.709 | 1.00 | 66.22 | W |
| ATOM | 7256 | OH2 | WAT | W | 412 | 45.624 | 63.049 | 30.324 | 1.00 | 57.06 | W |
| ATOM | 7257 | OH2 | WAT | W | 413 | 39.049 | 44.768 | 64.649 | 1.00 | 39.54 | W |
| ATOM | 7258 | OH2 | WAT | W | 414 | 58.036 | 39.219 | 73.881 | 1.00 | 51.60 | W |
| ATOM | 7259 | OH2 | WAT | W | 415 | 31.579 | 50.636 | 0.858 | 1.00 | 72.06 | W |
| ATOM | 7260 | OH2 | WAT | W | 416 | 40.196 | 41.650 | 33.790 | 1.00 | 64.47 | W |
| ATOM | 7261 | OH2 | WAT | W | 417 | 77.323 | 45.965 | 83.600 | 1.00 | 56.30 | W |
| ATOM | 7262 | OH2 | WAT | W | 418 | 72.788 | 35.864 | 71.287 | 1.00 | 54.07 | W |
| ATOM | 7263 | OH2 | WAT | W | 419 | 56.099 | 54.602 | −4.579 | 1.00 | 72.97 | W |
| ATOM | 7264 | OH2 | WAT | W | 420 | 31.828 | 62.128 | 47.818 | 1.00 | 66.69 | W |
| ATOM | 7265 | OH2 | WAT | W | 421 | 50.260 | 69.403 | 73.245 | 1.00 | 43.12 | W |
| ATOM | 7266 | OH2 | WAT | W | 422 | 40.971 | 76.857 | 19.188 | 1.00 | 55.24 | W |
| ATOM | 7267 | OH2 | WAT | W | 423 | 50.817 | 45.598 | 43.726 | 1.00 | 47.39 | W |
| ATOM | 7268 | OH2 | WAT | W | 424 | 57.893 | 63.491 | −2.284 | 1.00 | 45.27 | W |
| ATOM | 7269 | OH2 | WAT | W | 425 | 48.545 | 68.827 | 17.802 | 1.00 | 51.36 | W |
| ATOM | 7270 | OH2 | WAT | W | 426 | 87.746 | 34.844 | 79.915 | 1.00 | 70.98 | W |
| ATOM | 7271 | OH2 | WAT | W | 427 | 38.045 | 76.649 | 50.020 | 1.00 | 62.16 | W |
| ATOM | 7272 | OH2 | WAT | W | 428 | 41.601 | 65.721 | 50.599 | 1.00 | 58.66 | W |
| ATOM | 7273 | OH2 | WAT | W | 429 | 48.691 | 22.663 | 68.713 | 1.00 | 57.83 | W |
| ATOM | 7274 | OH2 | WAT | W | 430 | 79.536 | 56.369 | 92.190 | 1.00 | 50.03 | W |
| ATOM | 7275 | OH2 | WAT | W | 431 | 40.308 | 70.305 | 52.457 | 1.00 | 45.57 | W |
| ATOM | 7276 | OH2 | WAT | W | 432 | 45.196 | 50.967 | 29.344 | 1.00 | 52.17 | W |
| ATOM | 7277 | OH2 | WAT | W | 433 | 66.890 | 56.850 | 86.068 | 1.00 | 44.50 | W |
| ATOM | 7278 | OH2 | WAT | W | 434 | 74.523 | 37.125 | 72.065 | 1.00 | 69.64 | W |
| ATOM | 7279 | OH2 | WAT | W | 435 | 51.504 | 57.806 | 48.099 | 1.00 | 41.70 | W |
| ATOM | 7280 | OH2 | WAT | W | 436 | 48.110 | 62.324 | 33.287 | 1.00 | 57.55 | W |
| ATOM | 7281 | OH2 | WAT | W | 437 | 52.404 | 70.658 | 90.991 | 1.00 | 56.05 | W |
| ATOM | 7282 | OH2 | WAT | W | 438 | 62.104 | 52.853 | −5.702 | 1.00 | 58.68 | W |
| ATOM | 7283 | OH2 | WAT | W | 439 | 42.160 | 68.312 | 50.323 | 1.00 | 65.88 | W |
| ATOM | 7284 | OH2 | WAT | W | 440 | 56.786 | 72.830 | 69.417 | 1.00 | 50.97 | W |
| ATOM | 7285 | OH2 | WAT | W | 441 | 47.733 | 69.238 | 73.317 | 1.00 | 59.72 | W |
| ATOM | 7286 | OH2 | WAT | W | 442 | 62.918 | 75.563 | 11.602 | 1.00 | 69.84 | W |
| ATOM | 7287 | OH2 | WAT | W | 443 | 41.121 | 64.515 | 51.932 | 1.00 | 69.70 | W |
| ATOM | 7288 | OH2 | WAT | W | 444 | 47.328 | 59.429 | 29.446 | 1.00 | 58.33 | W |
| ATOM | 7289 | OH2 | WAT | W | 445 | 46.646 | 54.756 | 90.011 | 1.00 | 57.90 | W |

TABLE 2-continued

ATOMIC COORDINATES OF THE ERR3 LBD/
DIETHYLSTILBESTROL COMPLEX

| ATOM | 7290 | OH2 | WAT | W | 446 | 56.289 | 65.305 | -1.919 | 1.00 | 53.58 | W |
|------|------|-----|-----|---|-----|--------|--------|--------|------|-------|---|
| ATOM | 7291 | OH2 | WAT | W | 447 | 49.952 | 75.371 | 84.886 | 1.00 | 63.07 | W |
| ATOM | 7292 | OH2 | WAT | W | 448 | 48.561 | 63.172 | 89.973 | 1.00 | 58.71 | W |
| ATOM | 7293 | OH2 | WAT | W | 449 | 35.370 | 88.326 | 40.037 | 1.00 | 78.57 | W |
| ATOM | 7294 | OH2 | WAT | W | 450 | 59.380 | 41.199 | 75.492 | 1.00 | 66.52 | W |
| ATOM | 7295 | OH2 | WAT | W | 451 | 89.074 | 54.147 | 78.587 | 1.00 | 47.71 | W |
| ATOM | 7296 | OH2 | WAT | W | 452 | 38.377 | 39.524 | 36.929 | 1.00 | 54.34 | W |
| ATOM | 7297 | OH2 | WAT | W | 453 | 64.397 | 31.908 | 50.701 | 1.00 | 61.83 | W |
| ATOM | 7298 | OH2 | WAT | W | 454 | 62.755 | 58.728 | 60.556 | 1.00 | 64.21 | W |
| ATOM | 7299 | OH2 | WAT | W | 455 | 37.395 | 80.235 | 25.592 | 1.00 | 55.29 | W |
| ATOM | 7300 | OH2 | WAT | W | 456 | 38.851 | 37.110 | 14.193 | 1.00 | 64.08 | W |
| ATOM | 7301 | OH2 | WAT | W | 457 | 41.941 | 57.764 | 79.081 | 1.00 | 51.60 | W |
| ATOM | 7302 | OH2 | WAT | W | 458 | 80.758 | 58.348 | 68.927 | 1.00 | 51.59 | W |
| ATOM | 7303 | OH2 | WAT | W | 459 | 53.695 | 67.181 | 32.352 | 1.00 | 57.79 | W |
| ATOM | 7304 | OH2 | WAT | W | 460 | 29.525 | 64.330 | 38.203 | 1.00 | 46.46 | W |
| ATOM | 7305 | OH2 | WAT | W | 461 | 41.650 | 53.303 | 48.743 | 1.00 | 63.37 | W |
| ATOM | 7306 | OH2 | WAT | W | 462 | 76.118 | 67.254 | 11.735 | 1.00 | 43.66 | W |
| ATOM | 7307 | OH2 | WAT | W | 463 | 39.305 | 68.514 | 12.733 | 1.00 | 54.63 | W |
| ATOM | 7308 | OH2 | WAT | W | 464 | 28.249 | 66.311 | 14.570 | 1.00 | 73.17 | W |
| ATOM | 7309 | OH2 | WAT | W | 465 | 82.531 | 51.099 | 66.091 | 1.00 | 75.14 | W |
| ATOM | 7310 | OH2 | WAT | W | 466 | 72.967 | 47.479 | 68.112 | 1.00 | 64.67 | W |
| ATOM | 7311 | OH2 | WAT | W | 467 | 44.819 | 49.109 | 76.892 | 1.00 | 60.24 | W |
| ATOM | 7312 | OH2 | WAT | W | 468 | 40.657 | 47.097 | 87.479 | 1.00 | 64.57 | W |
| ATOM | 7313 | OH2 | WAT | W | 469 | 62.808 | 71.803 | 23.113 | 1.00 | 59.73 | W |
| ATOM | 7314 | OH2 | WAT | W | 470 | 42.170 | 36.668 | 56.977 | 1.00 | 49.65 | W |
| ATOM | 7315 | OH2 | WAT | W | 471 | 30.555 | 57.956 | 13.257 | 1.00 | 62.89 | W |
| ATOM | 7316 | OH2 | WAT | W | 472 | 52.903 | 52.468 | 46.037 | 1.00 | 70.45 | W |
| ATOM | 7317 | OH2 | WAT | W | 473 | 29.640 | 82.417 | 30.229 | 1.00 | 54.78 | W |
| ATOM | 7318 | OH2 | WAT | W | 474 | 42.409 | 76.178 | 10.747 | 1.00 | 58.43 | W |
| ATOM | 7319 | OH2 | WAT | W | 475 | 33.120 | 69.665 | 19.637 | 1.00 | 60.70 | W |
| ATOM | 7320 | OH2 | WAT | W | 476 | 20.945 | 49.604 | 32.268 | 1.00 | 62.62 | W |
| ATOM | 7321 | OH2 | WAT | W | 477 | 51.494 | 44.055 | 77.166 | 1.00 | 66.25 | W |
| ATOM | 7322 | OH2 | WAT | W | 478 | 36.577 | 35.462 | 51.571 | 1.00 | 50.05 | W |
| ATOM | 7323 | OH2 | WAT | W | 479 | 58.813 | 52.157 | 46.216 | 1.00 | 60.42 | W |
| ATOM | 7324 | OH2 | WAT | W | 480 | 44.090 | 73.001 | 2.251  | 1.00 | 58.35 | W |
| ATOM | 7325 | OH2 | WAT | W | 481 | 53.405 | 62.288 | 40.016 | 1.00 | 61.21 | W |
| END  |      |     |     |   |     |        |        |        |      |       |   |

REFERENCES

Ausubel et al., 1989. Current Protocols in Molecular Biology, Green Publishing Associates and Wiley Interscience, N.Y.

Bartlett et al., 1989, Molecular Recognition in Chemical and Biological Problems Special Publication, Royal Chem. Soc., Vol. 78, (00): 182-196.

Beddell, 1985, Chem. Soc. Reviews, 279.

Billas, I. M. L., Moulinier, L., Rochel, N., and Moras, D. (2000). Crystal structure of the ligand-binding domain of the ultraspiracle protein USP, the ortholog of retinoid X receptors in insects. J. Biol. Chem. 276, 7465-7474.

Blumberg, B., Kang, H., Bolado, J. Jr., Chen, H., Craig, A. G., Moreno, T. A., Umesono, K., Perlmann, T., De Robertis, E. M., and Evans, R. M. (1998). BXR, an embryonic orphan nuclear receptor activated by a novel class of endogenous benzoate metabolites. Genes Dev. 12, 1269-1277.

Blundell et al., 1987, Nature, Vol. 326:347.

Bohm H-J, 1992, J. Comp. Aid. Molec. Design Vol. 6: 61-78.

Bourguet, W., Vivat, V., Wurtz, J. M., Chambon, P., Gronemeyer, H., and Moras, D. (2000). Crystal structure of a heterodimeric complex of RAR and RXR ligand-binding domains. Mol. Cell 5, 289-298.

Brünger, A. T., Adams, P. D., Clore, G. M., Delano, W. L., Gros, P., Grosse-Kunstleve, R W., Jiang, J.-S., Kuszewski, J., Nilges, M., Pannu, N. S., Read, R. J., Rice, L. M., Simonson, T., and Warren, G. L. (1998). Crystallography & NMR system: a new software for macromolecular structure determination. Acta Crystallogr. D54, 905-921.

Brzozowski, A. M., Pike, A. C., Dauter, Z., Hubbard, R. E., Bonn, T., Engström, O., Ohman, L., Greene, G. L., and Gustafsson, J. A. (1997). Molecular basis of agonism and antagonism in the oestrogen receptor. Nature 389, 753-758.

Chen F. et al., 1999, Gene, Vol. 228(1-2): 101-109.

Chen, S., Zhou, D., Yang, C., and Sherman, M. (2001). Molecular basis for the constitutive activity of estrogen-related receptor a-1. J. Biol. Chem. 276, 28465-28470.

Choi, H. S., Chung, M., Tzameli, I., Simha, D., Lee, Y. K., Seol, W., and Moore, D. D. (1997). Differential transactivation by two isoforms of the orphan nuclear hormone receptor CAR. J. Biol. Chem. 272, 23565-23571.

Coward, P., Lee, D., Hull, M. V., and Lehmann, J. (2001). 4-Hydroxytamoxifen binds to and deactivates the estrogen-related receptor g. Proc. Natl. Acad. Sci. USA 98, 8880-8884.

Ducruix, A. and Giegé, R., Eds., 1999, *Crystallization of Nucleic Acids and Proteins. A Practical Approach* (second edition). UK: IRL Press, 1-16.

Dunbrack, R. L. Jr, and Cohen, F. E. (1997). Bayesian statistical analysis of protein side chain rotamer preferences. Protein Sci. 6, 1661-1681.

Eudy J. D. et al., 1998, Genomics, Vol. 50: 382-384.

Forman, B. M., Tzameli, I., Choi, H. S., Chen, J., Simha, D., Seol, W., Evans, R. M., and Moore D. D. (1998). Androstane metabolites bind to and deactivate the nuclear receptor CAR-beta. Nature 395, 612-615.

Freshney (ed.), 1986. *Immobilized Cells And Enzymes*, IRL Press.

Gait (ed.), 1984. *Nucleic Acid Hybridization*.

Giguère, V. (1999). *Orphan nuclear receptors: from gene to function*. Endocrine Rev. 20, 689-725.

Giniger et al. (1985) *Specific DNA binding of GAL4, a positive regulatory protein of yeast*. Cell 40:767-774.

Glover (ed.), 1985. *DNA Cloning: A Practical Approach, Volumes I and II Oligonucleotide Synthesis*, MRL Press, Ltd., Oxford, U.K.

Goodford, 1984, J. Med. Chem., Vol. 27: 557.

Goodford, P. J. J., 1985, Med. Chem., Vol. 28: 849-857

Goodsell, D. S. and Olsen, A. J., 1990, Proteins, Structure, Functions, and Genetics Vol. 8: 195-202

Greiner, E. F., Kirfel, J., Greschik, H., Dorflinger, U., Becker, P., Mercep, A., and Schüle, R. (1996). Functional analysis of retinoid Z receptor b, a brain-specific nuclear orphan receptor. Proc. Natl. Acad. Sci. USA 93, 10105-10110.

Hames and Higgins (eds.), 1984. *Animal Cell Culture*.

Hames and Higgins (eds.), 1985. *Transcription And Translation*.

Hames B D and Higgins S J, 1985. *Nucleic acid hybridization a practical approach*, Hames and Higgins Ed., IRL Press, Oxford.

Heard D. J. et al., 2000, Mol. Endocrinol., Estrogen-Related Receptor 3 (ERR3).ol. 14: 382-392.

Hol, 1986, Angew. Chem., Vol. 25: 767.

Hong, H., Yang, L., and Stallcup, M. R. (1999). Hormone-independent transcriptional activation and coactivator binding by novel orphan receptor ERR3. J. Biol. Chem. 274, 22618-22626.

Jones, T. A., Zou, J. Y., Cowan, S. W., and Kjeldgaard, M. (1991). Improved methods for building protein models in electron density maps and the location of errors in theses models. Acta Cryst. A47, 110-119

Kleywegt, G. J., and Jones, T. A. (1994). Detection, delineation, measurement and display of cavities in macromolecular structures. Acta Crystallogr. D50, 178-185.

Kliewer, S. A., Lehmann, J. M., Milburn, M. V., and Willson, T. M. (1999). The PPARs and PXRs: nuclear xenobiotic receptors that define novel hormone signaling pathways. Recent Prog. Horm. Res. 54, 345-367.

Klinge, C. M. (2000). Estrogen receptor interaction with co-activators and co-repressors. Steroids 65, 227-251.

Kunts et al., 1982, J. Mol. Biol., Vol. 161:269-288

Laskowski, R. A., Mc Arthur, M. W., Moss, D. S., and Thornton, J. M. (1993). Procheck. A program to produce both detailed plots and schematic plots of protein structures. J. Appl. Crystallogr. 26, 283-291.

Martin, Y. C., 1992, J. Med. Chem., Vol. 35:2145-2154.

Mc Ree, D. E. 1993. *Practical protein crystallography*. Academic Press.

Nagase T. et al., 1998, DNA Res., Vol. 5(6): 355-364.

Navaza, J. (1994). AMoRe: an automated package for molecular replacement. Acta Crystallogr. A50, 157-163.

Nolte, R. T., Wisely, G. B., Westin, B., Cobbs, J. E., Lambert, M. H., Kurokawa, R., Rosenfeld, M. G., Willson, T., Glass, C. K., and Millburn, M. V. (1998). Ligand binding and co-activator assembly of the peroxisome proliferator-activated receptor-g. Nature 395, 137-143.

Otwinowski, Z., and Minor, W. (1997). Processing of X-ray diffraction data collected in oscillation mode. Methods Enzymol. 276, 307-326.

Perbal, 1984. *A Practical Guide To Molecular Cloning*.

Pettersson, K., Svensson, K., Mattsson, R., Carlsson, B., Ohlsson, R., and Berkenstam, A. (1996). Expression of a novel member of estrogen response element-binding nuclear receptors is restricted to the early stages of chorion formation during mouse embryogenesis. Mech. Dev. 54, 211-223.

Renaud et al., 1995, Nature 378, 681-689.

Sali, A., and Blundell, T. L. (1993). Comparative protein modelling by satisfaction of spatial restraints. J. Mol. Biol. 234, 779-815.

Sambrook, J. Fritsch, E. F., and T. Maniatis, 1989. *Molecular cloning: a laboratory manual*. 2ed. Cold Spring Harbor Laboratory, Cold spring Harbor, N.Y.

Sheridan and Venkataraghavan, 1987, Acc. Chem. Res., Vol. 20: 322

Shiau, A. K, Barstad, D., Loria, P. M., Cheng, L., Agard, D. A., and Greene, G. L. (1998). The structural basis of estrogen receptor/coactivator recognition and the antagonism of his interaction with tamoxifen. Cell 95, 927-937.

Stehlin, C., Wurtz, J. M., Steinmetz, A., Greiner, E., Schüle, R., Moras, D., and Renaud, J. P. (2001). X-ray structure of the orphan nuclear receptor ROR$\beta$ ligand-binding domain in the active conformation. EMBO J. 20, 5822-5831.

Tremblay, G. B., Kunath, T., Bergeron, D., Lapointe, L., Champigny, C., Bader, J. A., Rossant, J., and Giguere, V. (2001). Diethylstilbestrol regulates trophoblast stem cell differentiation as a ligand of orphan nuclear receptor ERR beta. Genes Dev. 15, 833-838.

Tzameli, I, Pissios, P., Schuetz, E. G., and Moore, D. D. (2000). The xenobiotic compound 1,4-bis[2-(3,5-dichloropyridyloxy)]benzene is an agonist ligand for the nuclear receptor CAR. Mol. Cell. Biol. 20, 2951-2958.

Tzameli, I., and Moore, D. D. (2001). Role reversal: new insights from new ligands for the xenobiotic receptor CAR. Trends Endocrinol. Metabol. 12, 7-10.

Vanacker J. M. et al., 1999, Mol. Endocrinol., Vol. 13:764-773.

Vanacker, J. M., Petterson, K., Gustafsson, J. A., and Laudet, V. (1999b). Transcriptional targets shared by estrogen-related receptor receptors (ERRs) and estrogen receptor (ER) alpha, but not ERbeta. EMBO J. 18, 4270-4279.

Verlinde C. L. M. J. & Hol, W. G. J., 1994, Structure, Vol. 2, :577.

Willy, P. J. and Mangelsdorf, D. J. (1998). Nuclear orphan receptors: the search for novel ligands and signaling pathways. In: Hormones and signaling, Vol. 1, pp 307-358, O'Malley B. W. (ed.), Academic Press.

Wurtz, J. M., Bourguet, W., Renaud, J. P., Vivat, V., Chambon, P., Moras, D., and Gronemeyer, H. (1996). A canonical structure for the ligand-binding domain of nuclear receptors. Nature Struct. Biol. 3, 87-94.

Xie, W., Hong, H., Yang, N. N., Lin, R. J., Simon, C. M., Stallcup, M. R., and Evans, R. M. (1999). Constitutive activation of transcription and binding of coactivator by estrogen-related receptors 1 and 2. Mol. Endocrinol. 13, 1594-1604.

Yang C. and Chen S., 1999, Cancer Res., Vol. 59:4519-4524.

Yang C. et al., 1998, Cancer Res., Vol. 58: 5695-5700.

Yang N. et al., 1996, J. Biol. Chem., Vol. 271: 5795-5804.

The invention claimed is:

1. A method for identifying a compound that potentially interacts with a Ligand Binding Pocket (LBP) of Estrogen-Related Receptor 3 (ERR3), comprising the steps of:
   a) employing the structural coordinates of Table 1, ±1.5 Å a root mean square deviation from the backbone atoms, to generate a three-dimensional (3-D) model;
   b) employing the 3-D model from (a) to generate a specific ERR3 LBP three-dimensional model that consists of residues Leu 268, Cys 269, Ala 272, Glu 275, Trp 305, Leu 309, Ile 310, Arg 316, Val 313, Tyr 326, Leu 342, Leu 345, Ala 431, Val 432, His 434, Phe 435, Phe 450 and Leu 454;
   c) employing said 3-D model of (b) to design or select a potential compound that interacts with the LBP of ERR3;
   d) providing said potential compound; and
   e) contacting said potential compound in vitro with a complex of ERR3 and steroid receptor coactivator-1 (SRC-1) and monitoring the binding activity of the ERR3 and SRC-1 to determine the ability of said potential compound to interact with ERR3.

2. The method according to claim 1, wherein ERR3 comprises amino acids 229 to 458 of SEQ ID NO: 1 and SRC-1 comprises the Receptor Interaction Domain (RID) of the SRC-1 coactivator starting from the amino acid residue in position 614 to the amino acid residue in position 764 of SEQ ID NO: 2, or amino acids 686 to amino acid 704 of SEQ ID NO: 2.

3. The method according to claim 1, wherein ERR3 comprises SEQ ID NO: 1 and SRC-1 comprises SEQ ID NO: 2.

4. The method of claim 1, wherein step c) consists of using said compound as a candidate agonist or antagonist compound.

5. The method according to claim 1, wherein said compound is selected from a library of compounds.

6. The method according to claim 1, wherein said compound is selected from a database.

7. The method according to claim 1, wherein said compound is designed de novo.

8. The method according to claim 1, wherein said compound is selected from the group consisting of estradiol (E2), diethylstilbestrol (DES) and 4-hydroxytamoxifen (4-OHT).

* * * * *

SEQUENCE LISTING

<160> NUMBER OF SEQ ID NOS: 10

<210> SEQ ID NO 1
<211> LENGTH: 458
<212> TYPE: PRT
<213> ORGANISM: Homo sapiens

<400> SEQUENCE: 1

```
Met Asp Ser Val Glu Leu Cys Leu Pro Glu Ser Phe Ser Leu His Tyr
 1               5                  10                  15

Glu Glu Glu Leu Leu Cys Arg Met Ser Asn Lys Asp Arg His Ile Asp
            20                  25                  30

Ser Ser Cys Ser Ser Phe Ile Lys Thr Glu Pro Ser Ser Pro Ala Ser
        35                  40                  45

Leu Thr Asp Ser Val Asn His His Ser Pro Gly Gly Ser Ser Asp Ala
    50                  55                  60

Ser Gly Ser Tyr Ser Ser Thr Met Asn Gly His Gln Asn Gly Leu Asp
65                  70                  75                  80

Ser Pro Pro Leu Tyr Pro Ser Ala Pro Ile Leu Gly Gly Ser Gly Pro
                85                  90                  95

Val Arg Lys Leu Tyr Asp Asp Cys Ser Ser Thr Ile Val Glu Asp Pro
            100                 105                 110

Gln Thr Lys Cys Glu Tyr Met Leu Asn Ser Met Pro Lys Arg Leu Cys
        115                 120                 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
    210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
        275                 280                 285

Phe Ser Thr Leu Ser Leu Ala Asp Gln Met Ser Leu Leu Gln Ser Ala
    290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
```

```
                355                 360                 365
Leu Lys Ala Ile Ala Leu Ala Asn Ser Asp Ser Met His Ile Glu Asp
        370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Ala Gly Lys
                405                 410                 415

Met Leu Met Thr Leu Pro Leu Arg Gln Thr Ser Thr Lys Ala Val
                420                 425                 430

Gln His Phe Tyr Asn Ile Lys Leu Glu Gly Lys Val Pro Met His Lys
                435                 440                 445

Leu Phe Leu Glu Met Leu Glu Ala Lys Val
        450                 455

<210> SEQ ID NO 2
<211> LENGTH: 1441
<212> TYPE: PRT
<213> ORGANISM: Homo sapiens

<400> SEQUENCE: 2

Met Ser Gly Leu Gly Asp Ser Ser Asp Pro Ala Asn Pro Asp Ser
 1               5                  10                  15

His Lys Arg Lys Gly Ser Pro Cys Asp Thr Leu Ala Ser Ser Thr Glu
                20                  25                  30

Lys Arg Arg Arg Glu Gln Glu Asn Lys Tyr Leu Glu Glu Leu Ala Glu
        35                  40                  45

Leu Leu Ser Ala Asn Ile Ser Asp Ile Asp Ser Leu Ser Val Lys Pro
    50                  55                  60

Asp Lys Cys Lys Ile Leu Lys Lys Thr Val Asp Gln Ile Gln Leu Met
65                  70                  75                  80

Lys Arg Met Glu Gln Glu Lys Ser Thr Thr Asp Asp Asp Val Gln Lys
                85                  90                  95

Ser Asp Ile Ser Ser Ser Ser Gln Gly Val Ile Glu Lys Glu Ser Leu
                100                 105                 110

Gly Pro Leu Leu Leu Glu Ala Leu Asp Gly Phe Phe Val Val Asn
        115                 120                 125

Cys Glu Gly Arg Ile Val Phe Val Ser Glu Asn Val Thr Ser Tyr Leu
    130                 135                 140

Gly Tyr Asn Gln Glu Glu Leu Met Asn Thr Ser Val Tyr Ser Ile Leu
145                 150                 155                 160

His Val Gly Asp His Ala Glu Phe Val Lys Asn Leu Leu Pro Lys Ser
                165                 170                 175

Leu Val Asn Gly Val Pro Trp Pro Gln Glu Ala Thr Arg Arg Asn Ser
                180                 185                 190

His Thr Phe Asn Cys Arg Met Leu Ile His Pro Pro Asp Glu Pro Gly
                195                 200                 205

Thr Glu Asn Gln Glu Ala Cys Gln Arg Tyr Glu Val Met Gln Cys Phe
        210                 215                 220

Thr Val Ser Gln Pro Lys Ser Ile Gln Glu Asp Gly Glu Asp Phe Gln
225                 230                 235                 240

Ser Cys Leu Ile Cys Ile Ala Arg Arg Leu Pro Arg Pro Pro Ala Ile
                245                 250                 255

Thr Gly Val Glu Ser Phe Met Thr Lys Gln Asp Thr Thr Gly Lys Ile
                260                 265                 270
```

-continued

```
Ile Ser Ile Asp Thr Ser Ser Leu Arg Ala Ala Gly Arg Thr Gly Trp
        275                 280                 285

Glu Asp Leu Val Arg Lys Cys Ile Tyr Ala Phe Phe Gln Pro Gln Gly
    290                 295                 300

Arg Glu Pro Ser Tyr Ala Arg Gln Leu Phe Gln Glu Val Met Thr Arg
305                 310                 315                 320

Gly Thr Ala Ser Pro Ser Tyr Arg Phe Ile Leu Asn Asp Gly Thr
                325                 330                 335

Met Leu Ser Ala His Thr Lys Cys Lys Leu Cys Tyr Pro Gln Ser Pro
            340                 345                 350

Asp Met Gln Pro Phe Ile Met Gly Ile His Ile Asp Arg Glu His
            355                 360                 365

Ser Gly Leu Ser Pro Gln Asp Asp Thr Asn Ser Gly Met Ser Ile Pro
    370                 375                 380

Arg Val Asn Pro Ser Val Asn Pro Ser Ile Ser Pro Ala His Gly Val
385                 390                 395                 400

Ala Arg Ser Ser Thr Leu Pro Pro Ser Asn Ser Asn Met Val Ser Thr
                405                 410                 415

Arg Ile Asn Arg Gln Gln Ser Ser Asp Leu His Ser Ser His Ser
            420                 425                 430

Asn Ser Ser Asn Ser Gln Gly Ser Phe Gly Cys Ser Pro Gly Ser Gln
    435                 440                 445

Ile Val Ala Asn Val Ala Leu Asn Gln Gly Gln Ala Ser Ser Gln Ser
    450                 455                 460

Ser Asn Pro Ser Leu Asn Leu Asn Asn Ser Pro Met Glu Gly Thr Gly
465                 470                 475                 480

Ile Ser Leu Ala Gln Phe Met Ser Pro Arg Arg Gln Val Thr Ser Gly
                485                 490                 495

Leu Ala Thr Arg Pro Arg Met Pro Asn Asn Ser Phe Pro Pro Asn Ile
            500                 505                 510

Ser Thr Leu Ser Ser Pro Val Gly Met Thr Ser Ser Ala Cys Asn Asn
            515                 520                 525

Asn Asn Arg Ser Tyr Ser Asn Ile Pro Val Thr Ser Leu Gln Gly Met
    530                 535                 540

Asn Glu Gly Pro Asn Asn Ser Val Gly Phe Ser Ala Ser Ser Pro Val
545                 550                 555                 560

Leu Arg Gln Met Ser Ser Gln Asn Ser Pro Ser Arg Leu Asn Ile Gln
                565                 570                 575

Pro Ala Lys Ala Glu Ser Lys Asp Asn Lys Glu Ile Ala Ser Ile Leu
            580                 585                 590

Asn Glu Met Ile Gln Ser Asp Asn Ser Ser Asp Gly Lys Pro Leu
            595                 600                 605

Asp Ser Gly Leu Leu His Asn Asn Asp Arg Leu Ser Asp Gly Asp Ser
    610                 615                 620

Lys Tyr Ser Gln Thr Ser His Lys Leu Val Gln Leu Thr Thr Thr
625                 630                 635                 640

Ala Glu Gln Gln Leu Arg His Ala Asp Ile Asp Thr Ser Cys Lys Asp
                645                 650                 655

Val Leu Ser Cys Thr Gly Thr Ser Asn Ser Ala Ser Ala Asn Ser Ser
            660                 665                 670

Gly Gly Ser Cys Pro Ser Ser His Ser Ser Leu Thr Glu Arg His Lys
    675                 680                 685

Ile Leu His Arg Leu Leu Gln Glu Gly Ser Pro Ser Asp Ile Thr Thr
```

-continued

```
                690                 695                 700
Leu Ser Val Glu Pro Asp Lys Lys Asp Ser Ala Ser Thr Ser Val Ser
705                 710                 715                 720

Val Thr Gly Gln Val Gln Gly Asn Ser Ser Ile Lys Leu Glu Leu Asp
                725                 730                 735

Ala Ser Lys Lys Lys Glu Ser Lys Asp His Gln Leu Leu Arg Tyr Leu
                740                 745                 750

Leu Asp Lys Asp Glu Lys Asp Leu Arg Ser Thr Pro Asn Leu Ser Leu
                755                 760                 765

Asp Asp Val Lys Val Lys Val Glu Lys Gln Met Asp Pro Cys
770                 775                 780

Asn Thr Asn Pro Thr Pro Met Thr Lys Pro Thr Pro Glu Glu Ile Lys
785                 790                 795                 800

Leu Glu Ala Gln Ser Gln Phe Thr Ala Asp Leu Asp Gln Phe Asp Gln
                805                 810                 815

Leu Leu Pro Thr Leu Glu Lys Ala Ala Gln Leu Pro Gly Leu Cys Glu
                820                 825                 830

Thr Asp Arg Met Asp Gly Ala Val Thr Ser Val Thr Ile Lys Ser Glu
                835                 840                 845

Ile Leu Pro Ala Ser Leu Gln Ser Ala Thr Ala Arg Pro Thr Ser Arg
850                 855                 860

Leu Asn Arg Leu Pro Glu Leu Glu Leu Glu Ala Ile Asp Asn Gln Phe
865                 870                 875                 880

Gly Gln Pro Gly Thr Gly Asp Gln Ile Pro Trp Thr Asn Asn Thr Val
                885                 890                 895

Thr Ala Ile Asn Gln Ser Lys Ser Glu Asp Gln Cys Ile Ser Ser Gln
                900                 905                 910

Leu Asp Glu Leu Leu Cys Pro Pro Thr Thr Val Glu Gly Arg Asn Asp
                915                 920                 925

Glu Lys Ala Leu Leu Glu Gln Leu Val Ser Phe Leu Ser Gly Lys Asp
                930                 935                 940

Glu Thr Glu Leu Ala Glu Leu Asp Arg Ala Leu Gly Ile Asp Lys Leu
945                 950                 955                 960

Val Gln Gly Gly Gly Leu Asp Val Leu Ser Glu Arg Phe Pro Pro Gln
                965                 970                 975

Gln Ala Thr Pro Pro Leu Ile Met Glu Glu Arg Pro Asn Leu Tyr Ser
                980                 985                 990

Gln Pro Tyr Ser Ser Pro Ser Pro Thr Ala Asn Leu Pro Ser Pro Phe
                995                 1000                1005

Gln Gly Met Val Arg Gln Lys Pro Ser Leu Gly Thr Met Pro Val Gln
     1010                1015                1020

Val Thr Pro Pro Arg Gly Ala Phe Ser Pro Gly Met Gly Met Gln Pro
1025                1030                1035                1040

Arg Gln Thr Leu Asn Arg Pro Pro Ala Ala Pro Asn Gln Leu Arg Leu
                1045                1050                1055

Gln Leu Gln Gln Arg Leu Gln Gly Gln Gln Leu Ile His Gln Asn
          1060                1065                1070

Arg Gln Ala Ile Leu Asn Gln Phe Ala Ala Thr Ala Pro Val Gly Ile
          1075                1080                1085

Asn Met Arg Ser Gly Met Gln Gln Ile Thr Pro Gln Pro Pro Leu
          1090                1095                1100

Asn Ala Gln Met Leu Ala Gln Arg Gln Arg Glu Leu Tyr Ser Gln Gln
1105                1110                1115                1120
```

His Arg Gln Arg Gln Leu Ile Gln Gln Gln Arg Ala Met Leu Met Arg
            1125                1130                1135
Gln Gln Ser Phe Gly Asn Asn Leu Pro Pro Ser Ser Gly Leu Pro Val
        1140                1145                1150
Gln Met Gly Asn Pro Arg Leu Pro Gln Gly Ala Pro Gln Gln Phe Pro
    1155                1160                1165
Tyr Pro Pro Asn Tyr Gly Thr Asn Pro Gly Thr Pro Pro Ala Ser Thr
1170                1175                1180
Ser Pro Phe Ser Gln Leu Ala Ala Asn Pro Glu Ala Ser Leu Ala Asn
1185                1190                1195                1200
Arg Asn Ser Met Val Ser Arg Gly Met Thr Gly Asn Ile Gly Gly Gln
            1205                1210                1215
Phe Gly Thr Gly Ile Asn Pro Gln Met Gln Gln Asn Val Phe Gln Tyr
        1220                1225                1230
Pro Gly Ala Gly Met Val Pro Gln Gly Glu Ala Asn Phe Ala Pro Ser
    1235                1240                1245
Leu Ser Pro Gly Ser Ser Met Val Pro Met Pro Ile Pro Pro Pro Gln
1250                1255                1260
Ser Ser Leu Leu Gln Gln Thr Pro Pro Ala Ser Gly Tyr Gln Ser Pro
1265                1270                1275                1280
Asp Met Lys Ala Trp Gln Gln Gly Ala Ile Gly Asn Asn Asn Val Phe
            1285                1290                1295
Ser Gln Ala Val Gln Asn Gln Pro Thr Pro Ala Gln Pro Gly Val Tyr
        1300                1305                1310
Asn Asn Met Ser Ile Thr Val Ser Met Ala Gly Gly Asn Thr Asn Val
    1315                1320                1325
Gln Asn Met Asn Pro Met Met Ala Gln Met Gln Met Ser Ser Leu Gln
1330                1335                1340
Met Pro Gly Met Asn Thr Val Cys Pro Glu Gln Ile Asn Asp Pro Ala
1345                1350                1355                1360
Leu Arg His Thr Gly Leu Tyr Cys Asn Gln Leu Ser Ser Thr Asp Leu
            1365                1370                1375
Leu Lys Thr Glu Ala Asp Gly Thr Gln Gln Val Gln Gln Val Gln Val
        1380                1385                1390
Phe Ala Asp Val Gln Cys Thr Val Asn Leu Val Gly Gly Asp Pro Tyr
    1395                1400                1405
Leu Asn Gln Pro Gly Pro Leu Gly Thr Gln Lys Pro Thr Ser Gly Pro
    1410                1415                1420
Gln Thr Pro Gln Ala Gln Gln Lys Ser Leu Leu Gln Gln Leu Leu Thr
1425                1430                1435                1440
Glu

<210> SEQ ID NO 3
<211> LENGTH: 1377
<212> TYPE: DNA
<213> ORGANISM: Homo sapiens

<400> SEQUENCE: 3
atggattcgg tagaactttg ccttcctgaa tctttttccc tgcactacga ggaagagctt      60
ctctgcagaa tgtcaaacaa agatcgacac attgattcca gctgttcgtc cttcatcaag     120
acggaacctt ccagcccagc ctccctgacg gacagcgtca accaccacag ccctggtggc     180
tcttcagacg ccagtgggag ctacagttca accatgaatg ccatcagaa cggacttgac      240

-continued

| | |
|---|---|
| tcgccacctc tctacccttc tgctcctatc ctgggaggta gtgggcctgt caggaaactg | 300 |
| tatgatgact gctccagcac cattgttgaa gatcccaga ccaagtgtga atacatgctc | 360 |
| aactcgatgc ccaagagact gtgtttagtg tgtggtgaca tcgcttctgg gtaccactat | 420 |
| ggggtagcat catgtgaagc ctgcaaggca ttcttcaaga ggacaattca aggcaatata | 480 |
| gaatacagct gccctgccac gaatgaatgt gaaatcacaa agcgcagacg taaatcctgc | 540 |
| caggcttgcc gcttcatgaa gtgtttaaaa gtgggcatgc tgaaagaagg ggtgcgtctt | 600 |
| gacagagtac gtggaggtcg gcagaagtac aagcgcagga tagatgcgga aacagccca | 660 |
| tacctgaacc ctcagctggt tcagccagcc aaaaagccat ataacaagat tgtctcacat | 720 |
| ttgttggtgg ctgaaccgga aagatctat gccatgcctg accctactgt ccccgacagt | 780 |
| gacatcaaag ccctcactac actgtgtgac ttggccgacc gagagttggt ggttatcatt | 840 |
| ggatgggcga agcatattcc aggcttctcc acgctgtccc tggcggacca gatgagcctt | 900 |
| ctgcagagtg cttggatgga aattttgatc cttggtgtcg tataccggtc tctttcattt | 960 |
| gaggatgaac ttgtctatgc agacgattat ataatggacg aagaccagtc caaattagca | 1020 |
| ggccttcttg atctaaataa tgctatcctg cagctggtaa agaaatacaa gagcatgaag | 1080 |
| ctggaaaaag aagaatttgt caccctcaaa gctatagctc ttgctaattc agactccatg | 1140 |
| cacatagaag atgttgaagc cgttcagaag cttcaggatg tcttacatga agcgctgcag | 1200 |
| gattatgaag ctggccagca catggaagac cctcgtcgag ctggcaagat gctgatgaca | 1260 |
| ctgccactcc tgaggcagac ctctaccaag gccgtgcagc atttctacaa catcaaacta | 1320 |
| gaaggcaaag tcccaatgca caaacttttt ttggaaatgt tggaggccaa ggtctga | 1377 |

<210> SEQ ID NO 4
<211> LENGTH: 4326
<212> TYPE: DNA
<213> ORGANISM: Homo sapiens

<400> SEQUENCE: 4

| | |
|---|---|
| atgagtggcc tcggggacag ttcatccgac cctgctaacc cagactcaca taagaggaaa | 60 |
| ggatcgccat gtgacacact ggcatcaagc acggaaaaga ggcgcaggga gcaagaaaat | 120 |
| aaatatttag aagaactagc tgagttactg tctgccaaca ttagtgacat tgacagcttg | 180 |
| agtgtaaaac cagacaaatg caagattttg aagaaaacag tcgatcagat acagctaatg | 240 |
| aagagaatgg aacaagagaa atcaacaact gatgacgatg tacagaaatc agacatctca | 300 |
| tcaagtagtc aaggagtgat agaaaaggaa tccttgggac ctcttctttt ggaggctttg | 360 |
| gatggatttt tctttgttgt gaactgtgaa gggagaattg tatttgtgtc agagaatgta | 420 |
| accagctact taggttacaa tcaggaggaa ttaatgaata ccagcgtcta cagcatactg | 480 |
| cacgtggggg atcatgcaga atttgtgaag aatctgctac caaaatcact agtaaatgga | 540 |
| gttccttggc ctcaagagc aacacgacga atagccata cctttaactg caggatgcta | 600 |
| attcaccctc cagatgagcc agggaccgag aaccaagaag cttgccagcg ttatgaagta | 660 |
| atgcagtgtt tcactgtgtc acagccaaaa tcaattcaag aggatggaga agatttccag | 720 |
| tcatgtctga tttgtattgc acggcgatta cctcggcctc cagctattac gggtgtagaa | 780 |
| tcctttatga ccaagcaaga tactacaggt aaaatcatct ctattgatac tagttccctg | 840 |
| agagctgctg gcagaactgg ttgggaagat ttagtgagga agtgcattta tgcttttttc | 900 |
| caacctcagg gcagagaacc atcttatgcc agacagctgt tccaagaagt gatgactcgt | 960 |
| ggcactgcct ccagccctc ctatagattc atattgaatg atgggacaat gcttagcgcc | 1020 |

-continued

```
cacaccaagt gtaaactttg ctaccctcaa agtccagaca tgcaaccttt catcatggga    1080
attcatatca tcgacaggga gcacagtggg ctttctcctc aagatgacac taattctgga    1140
atgtcaattc cccgagtaaa tccctcggtc aatcctagta tctctccagc tcatggtgtg    1200
gctcgttcat ccacattgcc accatccaac agcaacatgg tatccaccag aataaaccgc    1260
cagcagagct cagaccttca tagcagcagt catagtaatt ctagcaacag ccaaggaagt    1320
ttcggatgct cacccggaag tcagattgta gccaatgttg ccttaaacca aggacaggcc    1380
agttcacaga gcagtaatcc ctctttaaac ctcaataatt ctcctatgga aggtacagga    1440
atatccctag cacagttcat gtctccaagg agacaggtta cttctggatt ggcaacaagg    1500
cccaggatgc caaacaattc ctttcctcct aatatttcga cattaagctc cccgttggc    1560 atgacaagta gtgcctgtaa taataataac cgatcttatt caaacatccc agtaacatct    1620
ttacagggta tgaatgaagg acccaataac tccgttggct tctctgccag ttctccagtc    1680
ctcaggcaga tgagctcaca gaattcacct agcagattaa atatacaacc agcaaaagct    1740
gagtccaaag ataacaaaga gattgcctca attttaaatg aaatgattca atctgacaac    1800
agctctagtg atggcaaacc tctggattca gggcttctgc ataacaatga cagactttca    1860
gatggagaca gtaaatactc tcaaaccagt cacaaactag tgcagctttt gacaacaact    1920
gccgaacagc agttacggca tgctgatata gacacaagct gcaaagatgt cctgtcttgc    1980
acaggcactt ccaactctgc ctctgctaac tcttcaggag gttcttgtcc ctcttctcat    2040
agctcattga cagaacggca taaaattcta caccggctct tacaggaggg tagcccctca    2100
gatatcacca ctttgtctgt cgagcctgat aaaaaggaca gtgcatctac ttctgtgtca    2160
gtgactggac aggtacaagg aaactccagt ataaaactag aactggatgc ttcaaagaaa    2220
aaagaatcaa aagaccatca gctcctacgc tatcttttag ataaagatga gaaagattta    2280
agatcaactc caaacctgag cctggatgat gtaaaggtga agtgaaaa gaagaacag     2340 atggatccat gtaatacaaa cccaaccccca atgaccaaac ccactcctga ggaaataaaa    2400
ctggaggccc agagccagtt tacagctgac cttgaccagt ttgatcagtt actgccacg    2460 ctggagaagg cagcacagtt gccaggctta tgtgagacag acaggatgga tggtgcggtc    2520
accagtgtaa ccatcaaatc ggagatcctg ccagcttcac ttcagtccgc cactgccaga    2580
cccacttcca ggctaaatag attacctgag ctggaattgg aagcaattga taaccaattt    2640
ggacaaccag gaacaggcga tcagattcca tggacaaata atacagtgac agctataaat    2700
cagagtaaat cagaagacca gtgtattagc tcacaattag atgagcttct ctgtccaccc    2760
acaacagtag aagggagaaa tgatgagaag gctcttcttg aacagctggt atccttcctt    2820
agtggcaaag atgaaactga gctagctgaa ctagacagag ctctgggaat tgacaaactt    2880
gttcaggggg gtggattaga tgtattatca gagagatttc caccacaaca agcaacgcca    2940
cctttgatca tggaagaaag acccaacctt tattcccagc cttactcttc tccttctcct    3000
actgccaatc tccctagccc tttccaaggc atggtcaggc aaaaaccttc actggggacg    3060
atgcctgttc aagtaacacc tccccgaggt gctttttcac ctggcatggg catgcagccc    3120
aggcaaactc taaacagacc tccggctgca cctaaccagc ttcgacttca actacagcag    3180
cgattacagg gacaacagca gttgatacac caaaatcggc aagctatctt aaaccagttt    3240
gcagcaactg ctcctgttgg catcaatatg agatcaggca tgcaacagca aattacacct    3300
cagccacccc tgaatgctca aatgttggca caacgtcagc gggaactgta cagtcaacag    3360
```

-continued

```
caccgacaga ggcagctaat acagcagcaa agagccatgc ttatgaggca gcaaagcttt      3420
gggaacaacc tccctccctc atctggacta ccagttcaaa tggggaaccc ccgtcttcct      3480
cagggtgctc cacagcaatt ccctatcca ccaaactatg gtacaaatcc aggaacccca      3540
cctgcttcta ccagcccgtt ttcacaacta gcagcaaatc ctgaagcatc cttggccaac      3600
cgcaacagca tggtgagcag aggcatgaca ggaaacatag gaggacagtt tggcactgga      3660
atcaatcctc agatgcagca gaatgtcttc cagtatccag gagcaggaat ggttccccaa      3720
ggtgaggcca actttgctcc atctctaagc cctgggagct ccatggtgcc gatgccaatc      3780
cctcctcctc agagttctct gctccagcaa actccacctg cctccgggta tcagtcacca      3840
gacatgaagg cctggcagca aggagcgata ggaaacaaca atgtgttcag tcaagctgtc      3900
cagaaccagc ccacgcctgc acagccagga gtatacaaca acatgagcat caccgtttcc      3960
atggcaggtg gaaatacgaa tgttcagaac atgaacccaa tgatggccca gatgcagatg      4020
agctctttgc agatgccagg aatgaacact gtgtgccctg agcagataaa tgatcccgca      4080
ctgagacaca caggcctcta ctgcaaccag ctctcatcca ctgaccttct caaaacagaa      4140
gcagatggaa cccagcaggt gcaacaggtt caggtgtttg ctgacgtcca gtgtacagtg      4200
aatctggtag gcggggaccc ttacctgaac cagcctggtc cactgggaac tcaaaagccc      4260
acgtcaggac cacagacccc ccaggcccag cagaagagcc tccttcagca gctactgact      4320
gaataa                                                                 4326
```

```
<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
ggcggatcca tatgccagcc aaaaagccat                                         30

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 6
gcggatcctc agaccttggc ctccagcatt tccaa                                   35

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 7

His His His His His His
  1               5

<210> SEQ ID NO 8
<211> LENGTH: 230
<212> TYPE: PRT
<213> ORGANISM: Homo sapiens

<400> SEQUENCE: 8
```

-continued

```
Ala Lys Lys Pro Leu Thr Lys Ile Val Ser Tyr Leu Val Ala Glu
 1               5                  10                  15

Pro Asp Lys Leu Tyr Ala Met Pro Pro Gly Met Pro Glu Gly Asp
             20                  25                  30

Ile Lys Ala Leu Thr Thr Leu Cys Asp Leu Ala Asp Arg Glu Leu Val
         35                  40                  45

Val Ile Ile Gly Trp Ala Lys His Ile Pro Gly Phe Ser Ser Leu Ser
     50                  55                  60

Leu Gly Asp Gln Met Ser Leu Leu Gln Ser Ala Trp Met Glu Ile Leu
 65                  70                  75                  80

Ile Leu Gly Ile Val Tyr Arg Ser Leu Pro Tyr Asp Asp Lys Leu Val
                 85                  90                  95

Tyr Ala Glu Asp Tyr Ile Met Asp Glu Glu His Ser Arg Leu Ala Gly
             100                 105                 110

Leu Leu Glu Leu Tyr Arg Ala Ile Leu Gln Leu Val Arg Arg Tyr Lys
         115                 120                 125

Lys Leu Lys Val Glu Lys Glu Glu Phe Val Thr Leu Lys Ala Leu Ala
130                 135                 140

Leu Ala Asn Ser Asp Ser Met Tyr Ile Glu Asp Leu Glu Ala Val Gln
145                 150                 155                 160

Lys Leu Gln Asp Leu Leu His Glu Ala Leu Gln Asp Tyr Glu Leu Ser
             165                 170                 175

Gln Arg His Glu Glu Pro Trp Arg Thr Gly Lys Leu Leu Thr Leu
         180                 185                 190

Pro Leu Leu Arg Gln Thr Ala Ala Lys Ala Val Gln His Phe Tyr Ser
         195                 200                 205

Val Lys Leu Gln Gly Lys Val Pro Met His Lys Leu Phe Leu Glu Met
210                 215                 220

Leu Glu Ala Lys Ala Trp
225                 230

<210> SEQ ID NO 9
<211> LENGTH: 234
<212> TYPE: PRT
<213> ORGANISM: Homo sapiens

<400> SEQUENCE: 9

Lys Thr Ala Pro Val Asn Ala Leu Val Ser His Leu Leu Val Val Glu
 1               5                  10                  15

Pro Glu Lys Leu Tyr Ala Met Pro Asp Pro Ala Gly Pro Asp Gly His
             20                  25                  30

Leu Pro Ala Val Ala Thr Leu Cys Asp Leu Phe Asp Arg Glu Ile Val
         35                  40                  45

Val Thr Ile Ser Trp Ala Lys Ser Ile Pro Gly Phe Ser Ser Leu Ser
     50                  55                  60

Leu Ser Asp Gln Met Ser Val Leu Gln Ser Val Trp Met Glu Val Leu
 65                  70                  75                  80

Val Leu Gly Val Ala Gln Arg Ser Leu Pro Leu Gln Asp Glu Leu Ala
                 85                  90                  95

Phe Ala Glu Asp Leu Val Leu Asp Glu Glu Gly Ala Arg Ala Ala Gly
             100                 105                 110

Leu Gly Glu Leu Gly Ala Ala Leu Leu Gln Leu Val Arg Arg Leu Gln
         115                 120                 125

Ala Leu Arg Leu Glu Arg Glu Glu Tyr Val Leu Leu Lys Ala Leu Ala
130                 135                 140
```

```
Leu Ala Asn Ser Asp Ser Val His Ile Glu Asp Ala Glu Ala Val Glu
145                 150                 155                 160

Gln Leu Arg Glu Ala Leu His Glu Ala Leu Leu Glu Tyr Glu Ala Gly
                165                 170                 175

Arg Ala Gly Pro Gly Gly Ala Glu Arg Arg Arg Ala Gly Arg Leu
            180                 185                 190

Leu Leu Thr Leu Pro Leu Leu Arg Gln Thr Ala Gly Lys Val Leu Ala
            195                 200                 205

His Phe Tyr Gly Val Lys Leu Glu Gly Lys Val Pro Met His Lys Leu
210                 215                 220

Phe Leu Glu Met Leu Glu Ala Met Met Asp
225                 230

<210> SEQ ID NO 10
<211> LENGTH: 242
<212> TYPE: PRT
<213> ORGANISM: Homo sapiens

<400> SEQUENCE: 10

Leu Ser Leu Thr Ala Asp Gln Met Val Ser Ala Leu Leu Asp Ala Glu
 1               5                  10                  15

Pro Pro Ile Leu Tyr Ser Glu Tyr Asp Pro Thr Arg Pro Phe Ser Glu
                20                  25                  30

Ala Ser Met Met Gly Leu Leu Thr Asn Leu Ala Asp Arg Glu Leu Val
            35                  40                  45

His Met Ile Asn Trp Ala Lys Arg Val Pro Gly Phe Val Asp Leu Thr
    50                  55                  60

Leu His Asp Gln Val His Leu Leu Glu Cys Ala Trp Leu Glu Ile Leu
 65                 70                  75                  80

Met Ile Gly Leu Val Trp Arg Ser Met Glu His Pro Gly Lys Leu Leu
                85                  90                  95

Phe Ala Pro Asn Leu Leu Leu Asp Arg Asn Gln Gly Lys Cys Val Glu
            100                 105                 110

Gly Met Val Glu Ile Phe Asp Met Leu Leu Ala Thr Ser Ser Arg Phe
        115                 120                 125

Arg Met Met Asn Leu Gln Gly Glu Glu Phe Val Cys Leu Lys Ser Ile
130                 135                 140

Ile Leu Leu Asn Ser Gly Val Tyr Thr Phe Leu Ser Ser Thr Leu Lys
145                 150                 155                 160

Ser Leu Glu Glu Lys Asp His Ile His Arg Val Leu Asp Lys Ile Thr
                165                 170                 175

Asp Thr Leu Ile His Leu Met Ala Lys Ala Gly Leu Thr Leu Gln Gln
            180                 185                 190

Gln His Gln Arg Leu Ala Gln Leu Leu Leu Ile Leu Ser His Ile Arg
        195                 200                 205

His Met Ser Asn Lys Gly Met Glu His Leu Tyr Ser Met Lys Cys Lys
210                 215                 220

Asn Val Val Pro Leu Tyr Asp Leu Leu Leu Glu Met Leu Asp Ala His
225                 230                 235                 240

Arg Leu
```